US012589101B2

(12) United States Patent
Han et al.

(10) Patent No.: US 12,589,101 B2
(45) Date of Patent: Mar. 31, 2026

(54) CYCLODEXTRIN PROTEIN DRUG CONJUGATES

(71) Applicant: Regeneron Pharmaceuticals, Inc., Tarrytown, NY (US)

(72) Inventors: Amy Han, Hockessin, DE (US); William Olson, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 785 days.

(21) Appl. No.: 17/837,598

(22) Filed: Jun. 10, 2022

(65) Prior Publication Data

US 2023/0035898 A1 Feb. 2, 2023

Related U.S. Application Data

(62) Division of application No. 15/975,191, filed on May 9, 2018, now Pat. No. 11,491,237.

(60) Provisional application No. 62/508,315, filed on May 18, 2017.

(51) Int. Cl.

| | |
|---|---|
| ***A61K 31/573*** | (2006.01) |
| ***A61K 31/724*** | (2006.01) |
| ***A61K 47/61*** | (2017.01) |
| ***A61K 47/68*** | (2017.01) |
| ***A61P 3/00*** | (2006.01) |
| ***A61P 25/00*** | (2006.01) |
| ***A61P 29/00*** | (2006.01) |
| ***A61P 35/00*** | (2006.01) |
| ***A61P 35/04*** | (2006.01) |
| ***C07J 43/00*** | (2006.01) |
| ***C07J 71/00*** | (2006.01) |

(52) U.S. Cl.

CPC .......... *A61K 31/573* (2013.01); *A61K 31/724* (2013.01); *A61K 47/61* (2017.08); *A61K 47/6803* (2017.08); *A61K 47/68031* (2023.08); *A61K 47/6807* (2017.08); *A61K 47/6817* (2017.08); *A61K 47/6849* (2017.08); *A61K 47/6851* (2017.08); *A61K 47/6889* (2017.08); *A61P 3/00* (2018.01); *A61P 25/00* (2018.01); *A61P 29/00* (2018.01); *A61P 35/00* (2018.01); *A61P 35/04* (2018.01); *C07J 43/003* (2013.01); *C07J 71/0031* (2013.01)

(58) Field of Classification Search

CPC .. A61K 31/573; A61K 47/61; A61K 47/6889; A61K 47/6807; A61K 47/6851; A61K 47/6803; A61K 47/6817; A61K 47/6849; A61K 47/68031; A61K 31/724; A61P 3/00; A61P 25/00; A61P 29/00; A61P 35/00; A61P 35/04; C07J 43/003; C07J 71/0031

USPC .......................................................... 514/58

See application file for complete search history.

(56) References Cited

U.S. PATENT DOCUMENTS

| | | | |
|---|---|---|---|
| 2,920,999 | A | 1/1960 | Agnello et al. |
| 3,007,923 | A | 11/1961 | Muller et al. |
| 3,020,275 | A | 2/1962 | Marx et al. |
| 3,033,873 | A | 5/1962 | Pinson et al. |
| 3,033,874 | A | 5/1962 | Pinson et al. |
| 3,047,468 | A | 7/1962 | Origoni et al. |
| 3,197,469 | A | 7/1965 | Fried |
| 3,232,839 | A | 2/1966 | Kieslich et al. |
| 3,383,394 | A | 5/1968 | Weber et al. |
| 3,723,484 | A | 3/1973 | Laurant et al. |
| 3,798,216 | A | 3/1974 | Boissier et al. |
| 3,886,145 | A | 5/1975 | Diamanti |
| 3,928,326 | A | 12/1975 | Brattsand et al. |
| 3,929,768 | A | 12/1975 | Brattsand et al. |
| 4,076,737 | A | 2/1978 | Anner et al. |
| 4,925,933 | A | 5/1990 | Jakupovic et al. |
| 5,116,829 | A | 5/1992 | Hori et al. |
| 5,183,815 | A | 2/1993 | Saari et al. |
| 5,208,020 | A | 5/1993 | Chari et al. |
| 5,500,362 | A | 3/1996 | Robinson et al. |
| 5,714,586 | A | 2/1998 | Kunstmann et al. |
| 5,821,337 | A | 10/1998 | Carter et al. |
| 5,837,698 | A | 11/1998 | Tjoeng et al. |
| 5,908,833 | A | 6/1999 | Brattsand et al. |

(Continued)

FOREIGN PATENT DOCUMENTS

| | | | |
|---|---|---|---|
| AU | 2018270784 | A1 | 12/2019 |
| CN | 1414008 | A | 4/2003 |
| CN | 101397328 | A | 4/2009 |
| CN | 103694375 | A | 4/2014 |
| CN | 104302664 | A | 1/2015 |
| CN | 107849131 | A | 3/2018 |
| CN | 108 853 514 | A | 11/2018 |
| CN | 109 106 951 | A | 1/2019 |
| DE | 1165595 | B | 3/1964 |
| EP | 1625854 | A1 | 2/2006 |
| ES | 544825 | A1 | 7/1985 |
| GB | 889766 | A | 2/1962 |
| GB | 898295 | A | 6/1962 |
| GB | 1428416 | | 3/1976 |

(Continued)

OTHER PUBLICATIONS

Patani et al., "Bioisosterism: A Rational Approach in Drug Design", Chem. Rev. 96, 1996, pp. 3147-3176.

(Continued)

*Primary Examiner* — Yih-Horng Shiao

(74) *Attorney, Agent, or Firm* — Schwegman, Lundberg & Woessner, P.A.

(57) ABSTRACT

Provided herein are compounds, compositions, conjugates and methods for the treatment of diseases, and/or conditions such as, but not limited to, proliferative diseases. In certain embodiments, compounds, compositions, and conjugates are provided, which include cyclodextrin-based linker-payloads and protein conjugates thereof, and/or in combination with other agents. By administering these compounds, compositions, and conjugates as described herein to specific target cells, side-effects due to non-specific binding phenomena, for example, to non-target cells are reduced.

41 Claims, 23 Drawing Sheets

(56) References Cited

U.S. PATENT DOCUMENTS

| | | | |
|---|---|---|---|
| 6,596,541 | B2 | 7/2003 | Murphy et al. |
| 6,908,934 | B2 | 6/2005 | Adams et al. |
| 7,750,116 | B1 | 7/2010 | Doronina et al. |
| 8,524,697 | B2 | 9/2013 | Anthes et al. |
| 8,703,714 | B2 | 4/2014 | Doronina et al. |
| 9,375,473 | B2 | 6/2016 | Latov et al. |
| 10,711,032 | B2 | 7/2020 | Han et al. |
| 11,129,903 | B2 | 9/2021 | Andreev et al. |
| 11,491,237 | B2 | 11/2022 | Han et al. |
| 11,578,135 | B2 | 2/2023 | Papadopoulos et al. |
| 11,760,775 | B2 | 9/2023 | Han et al. |
| 12,070,506 | B2 | 8/2024 | Han et al. |
| 2003/0125357 | A1 | 7/2003 | Adams et al. |
| 2003/0199529 | A1 | 10/2003 | Garvey et al. |
| 2004/0077595 | A1 | 4/2004 | Cheng et al. |
| 2004/0157810 | A1 | 8/2004 | Teicher et al. |
| 2004/0192778 | A1 | 9/2004 | Jardien et al. |
| 2005/0009798 | A1 | 1/2005 | Currie et al. |
| 2005/0192257 | A1 | 9/2005 | Peyman |
| 2005/0287155 | A1 | 12/2005 | Santi et al. |
| 2006/0046967 | A1 | 3/2006 | Satyam |
| 2006/0074008 | A1 | 4/2006 | Senter et al. |
| 2007/0258987 | A1 | 11/2007 | Francisco et al. |
| 2008/0171040 | A1 | 7/2008 | Ebens et al. |
| 2008/0305044 | A1 | 12/2008 | McDonagh et al. |
| 2008/0305497 | A1 | 12/2008 | Kosmeder et al. |
| 2009/0221543 | A1 | 9/2009 | Soldato et al. |
| 2009/0318396 | A1 | 12/2009 | Baker et al. |
| 2010/0041633 | A1 | 2/2010 | Benedini et al. |
| 2010/0093685 | A1 | 4/2010 | Benedini et al. |
| 2010/0129314 | A1 | 5/2010 | Singh et al. |
| 2010/0209508 | A1 | 8/2010 | Baker et al. |
| 2010/0226987 | A1 | 9/2010 | Gnaim et al. |
| 2010/0323973 | A1 | 12/2010 | Leamon et al. |
| 2011/0178287 | A1 | 7/2011 | Glucksmann et al. |
| 2011/0182828 | A1 | 7/2011 | Anthes et al. |
| 2011/0262368 | A1 | 10/2011 | Anthes et al. |
| 2012/0058892 | A1 | 3/2012 | Braun et al. |
| 2012/0059158 | A1 | 3/2012 | Ishii |
| 2012/0096572 | A1 | 4/2012 | Macdonald et al. |
| 2012/0258107 | A1 | 10/2012 | Graversen et al. |
| 2012/0276193 | A1 | 11/2012 | Graversen et al. |
| 2012/0302505 | A1* | 11/2012 | Fetzer .................... A61P 37/00 514/19.3 |
| 2013/0101546 | A1 | 4/2013 | Yurkovetskiy et al. |
| 2014/0227294 | A1 | 8/2014 | Anderson et al. |
| 2015/0152187 | A1 | 6/2015 | Sun et al. |
| 2015/0165064 | A1 | 6/2015 | Bregeon et al. |
| 2015/0258203 | A1 | 9/2015 | Vlahov et al. |
| 2015/0290337 | A1 | 10/2015 | Vetter et al. |
| 2015/0291563 | A1 | 10/2015 | Park et al. |
| 2016/0082119 | A1 | 3/2016 | Gonzalez et al. |
| 2016/0158369 | A1 | 6/2016 | Sato et al. |
| 2016/0279054 | A1 | 9/2016 | Rangaramanujam et al. |
| 2016/0310612 | A1 | 10/2016 | Lyon et al. |
| 2016/0340445 | A1 | 11/2016 | Bouckaert et al. |
| 2017/0182181 | A1 | 6/2017 | Garbaccio et al. |
| 2018/0002372 | A1 | 1/2018 | Tripathi et al. |
| 2018/0126000 | A1 | 5/2018 | Mcpherson et al. |
| 2018/0155389 | A1 | 6/2018 | Han et al. |
| 2018/0334426 | A1 | 11/2018 | Han et al. |
| 2018/0360979 | A1 | 12/2018 | Mejia Oneto et al. |
| 2019/0030171 | A1 | 1/2019 | Garbaccio et al. |
| 2019/0134220 | A1 | 5/2019 | Godwin |
| 2019/0167804 | A1 | 6/2019 | Hobson et al. |
| 2019/0209702 | A1 | 7/2019 | Han |
| 2019/0367631 | A1* | 12/2019 | Gromada ........... A61K 31/4985 |
| 2020/0115326 | A1 | 4/2020 | Tsuchikama et al. |
| 2020/0368361 | A1 | 11/2020 | Nittoli et al. |
| 2021/0040144 | A1 | 2/2021 | Han et al. |
| 2022/0080052 | A1 | 3/2022 | Gromada et al. |
| 2023/0079407 | A1 | 3/2023 | Gromada et al. |
| 2023/0119539 | A1 | 4/2023 | Han |

FOREIGN PATENT DOCUMENTS

| | | | |
|---|---|---|---|
| IL | 73337 | A | 9/1988 |
| JP | 7617974 | B2 | 1/2025 |
| KR | 20250008984 | A | 1/2025 |
| WO | WO 94/22898 | A1 | 10/1994 |
| WO | WO 2000/049993 | A2 | 8/2000 |
| WO | WO 2002/080931 | A1 | 10/2002 |
| WO | WO 2004/017904 | A2 | 3/2004 |
| WO | WO 2004/022099 | A2 | 3/2004 |
| WO | WO 2005/063777 | A1 | 7/2005 |
| WO | WO 2005/079523 | A2 | 9/2005 |
| WO | WO 2005/089808 | | 9/2005 |
| WO | WO 2005/119266 | A1 | 12/2005 |
| WO | WO 2006/135371 | A1 | 12/2006 |
| WO | WO 2008/122039 | A2 | 10/2008 |
| WO | WO 2008/127347 | A1 | 10/2008 |
| WO | WO 2009/001364 | A2 | 12/2008 |
| WO | WO 2009/085879 | A2 | 7/2009 |
| WO | WO 2009/085880 | A2 | 7/2009 |
| WO | WO 2010/010119 | A1 | 1/2010 |
| WO | WO 2010/010324 | A1 | 1/2010 |
| WO | WO 2010/126953 | A1 | 11/2010 |
| WO | WO 2010/132743 | A1 | 11/2010 |
| WO | WO 2011/018611 | A1 | 2/2011 |
| WO | WO 2011/020107 | A2 | 2/2011 |
| WO | WO 2011/039511 | A2 | 4/2011 |
| WO | WO 2011/081937 | A1 | 7/2011 |
| WO | WO 2011/103389 | A1 | 8/2011 |
| WO | WO 2011/130598 | | 10/2011 |
| WO | WO 2012/011591 | A1 | 1/2012 |
| WO | WO 2012/058592 | | 5/2012 |
| WO | WO 2012/145632 | | 10/2012 |
| WO | WO 2012/166559 | | 12/2012 |
| WO | WO 2013/053872 | | 4/2013 |
| WO | WO 2013/053873 | | 4/2013 |
| WO | WO 2013/055990 | | 4/2013 |
| WO | WO 2013/055993 | | 4/2013 |
| WO | WO 2013/068874 | | 5/2013 |
| WO | WO 2013/085925 | | 6/2013 |
| WO | WO 2013/093465 | A2 | 6/2013 |
| WO | WO 2014/065661 | | 5/2014 |
| WO | WO 2014/165119 | | 10/2014 |
| WO | WO 2014/177771 | A1 | 11/2014 |
| WO | WO 2014/197854 | | 12/2014 |
| WO | WO 2015/026907 | | 2/2015 |
| WO | WO 2015/153401 | A1 | 10/2015 |
| WO | WO 2015/155998 | A1 | 10/2015 |
| WO | WO 2015/189478 | A1 | 12/2015 |
| WO | WO 2016/090038 | A1 | 6/2016 |
| WO | WO 2016/090040 | A1 | 6/2016 |
| WO | WO 2016/094509 | A1 | 6/2016 |
| WO | WO 2016/094517 | A1 | 6/2016 |
| WO | WO 2016127081 | A1 | 8/2016 |
| WO | WO 2017006279 | A1 | 1/2017 |
| WO | WO 2017/062271 | A1 | 4/2017 |
| WO | WO 2017/132103 | A2 | 8/2017 |
| WO | WO 2017/147542 | | 8/2017 |
| WO | WO 2017/165851 | A1 | 9/2017 |
| WO | WO 2017/199046 | A1 | 11/2017 |
| WO | WO 2017/210471 | A1 | 12/2017 |
| WO | WO 2017/214458 | A2 | 12/2017 |
| WO | WO 2018/058001 | | 3/2018 |
| WO | WO 2018/089373 | A2 | 5/2018 |
| WO | WO 2018/160539 | A1 | 9/2018 |
| WO | WO 2018/213077 | A1 | 11/2018 |
| WO | WO 2018/213082 | A1 | 11/2018 |
| WO | WO 2019/094395 | A2 | 5/2019 |
| WO | WO 2019/136487 | A2 | 7/2019 |
| WO | WO 2019/195665 | A1 | 10/2019 |
| WO | WO 2020/146541 | A2 | 7/2020 |

OTHER PUBLICATIONS

Thalen et al., "6a-Fluoro- and 6a,9a-difluoro-11b,21-dihydroxy-16a,17a-propylmethylenedioxypregn-4-ene-3,20-dione: Synthesis and evaluation of activity and kinetics of their C-22 epimers", Steroids 63:37-43, 1998.

(56) References Cited

OTHER PUBLICATIONS

Gonzales et al., "Minimizing the Immunogenicity of Antibodies for Clinical Application", Tumor Biol. 2005; vol. 26, pp. 31-43; doi: 10.1159/000084184.
Kunik, Vered et al: "Structural consensus among antibodies defines the antigen binding site", PLoS Comput Biol 8(2): e1002388. https://doi.org/10.1371/journal.pcbi.1002388; Published Feb. 23, 2012.
Kussie et al., "A Single Engineered Amino Acid Substitution Changes Antibody Fine Specificity", Journal of Immunology, 1994, pp. 146-152.
Opalinski et al., "High Affinity Promotes Internalization of Engineered Antibodies Targeting FGFR1", International Journal of Molecular Sciences, 2018, vol. 19, 1435; Published online May 10, 2018. doi: 10.3390/ijms19051435.
Panka et al., "Variable region framework differences result in decreased or increased affinity of variant anti-digoxin antibodies", Proc. Natl. Acad. Scl. USA, vol. 85, May 1988, pp. 3080-30844, Immunology; doi: 10.1073/pnas.85.9.3080.
Rudikoff, Stuart el al., "Single amino acid substitution altering antigen-binding specificity", Proc. Nat. Acad. Sci., USA, vol. 79, Mar. 1982, pp. 1979-1983; DOI: 10.1073/pnas.79.6.1979.
Sela-Culang et al., "The Structural Basis of Antibody-Antigen Recognition", Frontiers in Immunology, vol. 4, article 302, Oct. 2013; doi: 10.3389/fimmu.2013.00302.
Wark et al., "Latest technologies for the enhancement of antibody affinity", Advanced Drug Delivery Reviews, 2006, vol. 58, pp. 657-670; doi:10.1016/j.addr.2006.01.025.
Besret et al., "Thiocarbamate-Linked Polysulfonate-Peptide Conjugates as Selective Hepatocyte Growth Factor Receptor Binders", dx.doi.org/10.1021/bc500137j | Bioconjugate Chem. 2014, 25, pp. 1000-1010.
Reyna et al., "Targeted Delivery of LXR Agonist Using a Site-Specific Antibody-Drug Conjugate", Bioconjugate Chem. 2015, 26, pp. 2216-2222; DOI: 10.1021/acs.bioconjchem.5b00203.
Millan et al., "Design and synthesis of long acting inhaled corticosteroids for the treatment of asthma", Bioorganic & Medicinal Chemistry Letters 21 (2011) 5826-5830.
Makinen et al., "Silencing of either SR-A or CD36 reduces at herosclerosis in hyperlipidaemic mice and reveals reciprocal upregulation of these receptors", Cardiovascular Research, 2010, vol. 88, No. 3, pp. 530-538.
Ozment et al., "Blood Monocyte Scavenger Receptor A (Cd204) Expression Is Increased in Septic Patients", SHOCK, 2016, vol. 45, No. 6S, p. 129.
Bak et al., "Scavenger Receptor-A—Targeted Leukocyte Depletion Inhibits Peritoneal Ovarian Tumor Progression", Cancer Res 2007; 67: (10). May 15, 2007; doi:10.1158/0008-5472.CAN-06-44-10.
CAS RN 91748-21-8 (entered into STN on 1/116/2007).
Mark Frigerio et al., "The Chemical Design and Synthesis of Linkers Used in Antibody Drug Conjugates", Current Topics in Medicinal Chemistry, 2017, 17(32), pp. 3393-3424.
Everts et al., "Selective Intracellular Delivery of Dexamethasone into Activated Endothelial Cells Using an E-Selectin-Directed Immunoconjugate", J Immunol (2002) 168 (2): 883-889; https://doi.org/10.4049/jimmunol.168.2.883.
Han et al., "Development of Novel Glucocorticoids for Use in Antibody-Drug Conjugates for the Treatment of Inflammatory Diseases", J. Med. Chem. 2021, 64, pp. 11958-11971.
Pang et al., "Synthesis of an enzyme-dependent prodrug and evaluation of its potential for colon targeting", World J Gastroenterol., Oct. 15, 2002; 8(5): 913-917; doi: 10.3748/wjg.v8.i5.913.
Varshosaz et al. "Synthesis and evaluation of dextran-budesonide conjugates as colon specific prodrugs for treatment of ulcerative colitis", International Journal of Pharmaceutics, Jan. 5, 2009;365(1-2):69-76; doi:10.1016/j.ijpharm.2008.08.034.
International Search Report and the Written Opinion of PCT/US2018/031839 mailed Jul. 26, 2018; 20 pages.
Agard et al., "A Strain-Promoted [3+2] Azide-Alkyne Cycloaddition for Covalent Modification of Biomolecules in Living Systems", J. Am. Chem. Soc., Nov. 24, 2004, vol. 126, No. 46, pp. 15046-15047.
Agarwal et al. (Bioconjugate Chem. 2015, 26, 176-192).
Agarwal et al., "A Pictet-Spengler ligation for protein chemical modification", PNAS, Jan. 2, 2013, vol. 110, No. 1, pp. 46-51.
Aherne et al., "A sensitive radioimmunoassay for budesonide in plasma", Journal of Steroid Biochemistry, vol. 17, No. 5, Nov. 1982, pp. 559-565.
Angal et al., "A Single Amino Acid Substitution Abolishes the Heterogeneity of Chimeric Mouse/Human (lgG4) Antibody", Molecular Immunology, Jan. 1993, vol. 30, No. 1, pp. 105-108.
Bajaj et al., "Topochemical model for prediction of anti-HIV activity of HEPT analogs", Bioorganic & Medicinal Chemistry Letters, vol. 15, No. 2, Jan. 17, 2005, pp. 467-469.
Baskin et al., "Copper-free click chemistry for dynamic in vivo imaging", PNAS, Oct. 23, 2007, vol. 104, No. 43, pp. 16793-16797.
Beck et al., "Strategies and challenges for the next generation of antibody-drug conjugates", Nature Reviews/Drug Discovery, vol. 16, May 2017, pp. 315-337.
Berge et al., "Pharmaceutical Salts", Review Article, Jan. 1977, vol. 66, No. 1, pp. 1-19.
Berlin M., "Recent advances in the development of novel glucocorticoid receptor modulators", Review, Expert Opinion on Therapeutic Patents (2010) 20(7), pp. 855-873; DOI: 10.1517/13543776.2010.493876.
Biju et al., "Synthesis of novel anti-inflammatory steroidal macrocycles using ring closing metathesis reaction", Tetrahedron Letters, Jan. 2015, vol. 56, issue 4, pp. 636-638.
Boersma et al., "DARPins and other repeat protein scaffolds: advances in engineering and applications", 2011, Current Opinion in Biotechnology, 2011, vol. 22, pp. 849-857.
Bogan et al., "Liver X Receptor Modulation of Gene Expression Leading to Proluteolytic Effects in Primate Luteal Cells", Biology Of Reproduction, (2012) 86(3):89, 1-9.
Cannon et al., "The liver X receptor agonist AZ876 protects against pathological cardiac hypertrophy and fibrosis without lipogenic side effects", European Journal of Heart Failure, 2015, vol. 17, pp. 273-282.
Carrico et al., "Introducing genetically enclosed aldehydes into proteins", Nature Chemical Biology, Jun. 2007, vol. 3, No. 6, pp. 321-322.
CAS Registry No. 803648-23-9; STN Entry Date Dec. 29, 2004; 21-(Diethylamino)-11,17-dihydroxy-(11β)-(9Cl)pregna-1,4-diene-3,20-dione [2] Category: X Claims: 1, 2, 4, 14; SciFinder"®.
CAS Registry Compounds, accessed Jul. 16, 2019; 355 pages.
CAS RN 2341-08-4, 1984 (entered into STN Nov. 16, 1984).
CAS RN 3859-14-1, 1984 (entered into STN Nov. 16, 1984).
CAS RN 57-86-3, 1984 (entered into STN Nov. 16, 1984).
Casati et al., "Unraveling Unidirectional Threading of α-Cyclodextrin in a [2]Rotaxane through Spin Labeling Approach", Journal of the American Chemical Society, Oct. 29, 2012, vol. 134, pp. 19108-19117.
Cho et al., "Regioselective Synthesis of Heterocycles Containing Nitrogen Neighboring an Aromatic Ring by Reductive Ring Expansion Using Diisobutylaluminum Hydride and Studies on the Reaction Mechanism", J. Org. Chem., 2010, vol. 75, pp. 627-636; published online Dec. 29, 2009.
Cho et al., "The first preparation of alpha-functionalized benzylamine", Tetrahedron Letters, vol. 40, No. 47, Nov. 19, 1999, p. 8215.
Chuu (Medical Hypotheses 76 (2011) 697-699).
Clynes et al., "Fc receptors are required in passive and active immunity to melanoma", Proc. Natl. Acad. Sci. USA, Jan. 1998, vol. 95, pp. 652-656.
Compounds from CAS Registry database, accessed May 20, 2019; 16 pages.
Compounds retrieved on Nov. 18, 2017 from SciFinder, Set 1; 4 pages.
Compounds retrieved on Nov. 18, 2017 from SciFinder, Set 2; 1 page.
Compounds retrieved on Nov. 18, 2017 from SciFinder, Set 3; 3 pages.

(56) References Cited

OTHER PUBLICATIONS

Czerkies et al., "An interplay between scavenger receptor A and CD14 during activation of J774 cells by high concentrations of LPS", Immunobiology, Apr. 12, 2013, vol. 218, pp. 1217-1226.
Dai et al., Regulation of MSR-1 and CD36 in macrophages by LOX-1 mediated through PPAR-c, Biochemical and Biophysical Research Communications, 431, pp. 496-500, Publication Date: Jan. 16, 2013.
Database Registry [Online] Chemical Abstracts Service Retrieved from STN on Aug. 11, 2020; Compounds with CAS Registry Numbers of 23640-98-4 (Entered STN: Nov. 16, 1984); 23640-97-3 (Entered STN: Nov. 16, 1984); 6477-56-1 (Entered STN: Nov. 16, 1984); 5514-61-4 (Entered STN: Nov. 16, 1984); 2353-16-4 (Entered STN: Nov. 16, 1984).
Database Registry: Compounds with CAS Registry No. of 23640-98-4; 23640-97-3; 6477-56-1; 5514-61-4; 2353-16-4.
Dennler et al. (Antibodies 2015, 4, 197-224).
Dennler et al., "Transglutaminase-Based Chemo-Enzymatic Conjugation Approach Yields Homogeneous Antibody-Drug Conjugates", Bioconjugate Chem., Feb. 3, 2014, vol. 25, pp. 569-578.
Diamantis et al. (British Journal of Cancer (2016) 114, 362-367).
Doi et al., "The Histidine Interruption of An □-Helical Coiled Coil Allosterically Mediates A pH-Dependent Ligand Dissociation From Macrophage Scavenger Receptors", The Journal of Biological Chemistry, vol. 269, No. 41, Oct. 14, 1994, pp. 25598-25604.
Doronina et al., "Novel Peptide Linkers for Highly Potent Antibody-Auristatin Conjugate", Bioconjugate Chem., 2008, vol. 19, No. 10, pp. 1960-1963.
Doronina et al., "Development of potent monoclonal antibody auristatin conjugates for cancer therapy", Nature Biotechnology, Jul. 2003, vol. 21, No. 7, pp. 778-941.
Dubois-Camacho et al., "Glucocorticosteroid therapy in inflammatory bowel diseases: From clinical practice to molecular biology", World J Gastroenterol, Sep. 28, 2017, vol. 23(36), pp. 6628-6638; DOI: 10.3748/wjg.v23.i36.6628.
Effenberger et al., "Trifluormethansulfonate von [alpha]-Hydroxycarbonsaureestern—Edukte zur racemisierungsfreien Synthese N-substituierter [alpha]-Aminosauren", Angewandte Chemie, vol. 95, No. 1, Jan. 1, 1983, p. 50.
Fellier et al., "Bindung von Cortisol, Fluocortolon und Difluocortolon a Humanplasmaproteine", J. Clin. Chem. Clin. Biochem., 1977, vol. 15, pp. 545-548.
Ferraboschi et al., "Estimation and characterisation of budesonide tablets impurities", Journal of Pharmaceutical and Biomedical Analysis, 2008, 47(3), pp. 636-640.
Friedman et al. (Curr Pharm Des. 2013; 19(35): 6315-6329).
Gidwani et al., "A Comprehensive Review on Cyclodextrin-Based Carriers for Delivery of Chemotherapeutic Cytotoxic Anticancer Drugs", Hindawi Publishing Corporation, BioMed Research International, vol. 2015, article ID 198268, 15 pages.
Graversen et al., "Targeting the Hemoglobin Scavenger receptor CD163 in Macrophages Highly Increases the Anti-inflammatory Potency of Dexamethasone", Molecular Therapy, vol. 20, No. 8, Aug. 2012, pp. 1550-1558.
Hamasaki et al., "Fluorescent sensors of molecular recognition. Modified cyclodextrins capable of exhibiting guest-responsive twisted intramolecular charge transfer fluorescence", J. Am. Chem. Soc., Jun. 1993, vol. 115, No. 12, pp. 5035-5040.
Hein et al., "The Synthesis of a Multiblock Osteotropic Polyrotaxane by Copper(I)-Catalyzed Huisgen 1,3-Dipolar Cycloaddition", Macromolecular Bioscience, Dec. 8, 2010, vol. 10, No. 12, pp. 1544-1556, XP055052204.
Hofer et al., "An engineered selenocysteine defines a unique class of antibody derivatives", PNAS, Aug. 26, 2008, vol. 105, No. 34, pp. 12451-12456.
Hollander et al., "Selection of Reaction Additives Used in the Preparetion of Monomeric Antibody-Calicheamicin Conjugates", Bioconjugate Chem., 2008, vol. 19, pp. 358-361; published online Nov. 10, 2007.
Huisgen, "1,3-Dipolar Cycloadditions", Proceedings of the Chemical Society, Oct. 1961, pp. 357-369.
Jain et al., "Current ADC Linker Chemistry", Pharm Res, 2015, vol. 32, pp. 3526-3540; DOI 10.1007/s11095-015-1657-7.
Jain R. A., "The manufacturing techniques of various drug loaded biodegradable poly(lactide-co-glycolide) (PLGA) devices", Biomaterials 21(23), 2000, pp. 2475-2490.
Jeger: "Site-specific conjugation of tumour-targeting, antibodies using transglutaminase", Ph.D. thesis, 2009, XP055208841, ETH Zurich, CH; 140 pages. DOI: 10.3929/ethz-a-005963273; pp. 41-46.
Kapp et al., "Studies on the Pharmacology of 6alpha,9-difluoro-11beta-hydroxy-16alpha-methyl-21-valeryloxy-1,4-pregnadiene-3,20-dione", Arzneimittel-Forschung Drug Reserch, 1976;26(7b):1463-1475; with an English summary.
Kern et al., "Discovery of Pyrophosphate Diesters as Tunable, Soluble, and Bioorthogonal Linkers for Site-Specific Antibody-Drug Conjugates", J. Am. Chem. Soc. (JACS), Jan. 25, 2016, vol. 138, No. 4, pp. 1430-1445.
Kern et al., "Novel Phosphate Modified Cathepsin B Linkers: Improving Aqueous Solubility and Enhancing Payload Scope of ADCs", Bioconjugate Chem. Bioconjugate Chem., Jul. 28, 2016, vol. 27, No. 9, pp. 2081-2088.
Kovtun et al., "Antibody-Maytansinoid Conjugates Designed to Bypass Multidrug Resistance", Cancer Research, vol. 70, No. 6, Mar. 15, 2010, pp. 2528-2537.
Krajcsi et al., "Novel Synthesis of 21-Aminopregnanes", J. Chem. Research (S), Nov. 1987, issue 11, pp. 382-383.
Kronkvist et al., "Determination of Drugs in Biosamples at Picomolar Concentrations Using Competitive Elisa With Electrochemical Detection: Application to Steroids", Journal of Pharmaceutical and Biomedical Analysis, vol. 11, No. 6, 1993, pp. 459-463.
Lehar et al., "Novel antibody-antibiotic conjugate eliminates intracellular *S. aureus*", Nature, Nov. 19, 2015, vol. 527, No. 7578, pp. 323-328.
Lemke et al., Foye's Principles of Medicinal Chemistry, Chapter 44, pp. 1253, Publication Year: 2008.
Lhospice et al. "Site-Specific Conjugation of Monomethyl Auristatin E to Anti-CD30 Antibodies Improves Their Pharmacokinetics and Therapeutic Index in Rodent Models", Mol. Pharmaceutics, 2015, vol. 12, pp. 1863-1871.
Lichtenecker R. J., "Synthesis of aromatic $^{13}C/^{2}H$-α-ketoacid precursors to be used in selective phenylalanine and tyrosine protein labelling", Organic & Biomolecular Chemistry, Jul. 31, 2014, vol. 12, pp. 7551-7560.
Lim et al., "Targeted Delivery of LXR Agonist Using a Site-Specific Antibody-Drug Conjugate", Bioconjugate Chemistry, 2015, vol. 26, No. 11, pp. 2216-2222.
Lu et al., "Linkers Having a Crucial Role in Antibody-Drug Conjugates", Int. J. Mol. Sci., Apr. 14, 2016, vol. 17, No. 561, 22 pages.
Lyon et al., Reducing hydrophobicity of homogeneous antibody-drug conjugates improves pharmacokinetics and therapeutic index, Nature Biotechnology, Jul. 2015, vol. 33, No. 7, pp. 733-735.
McCombs et al., "Antibody Drug Conjugates: Design and Selection of Linker, Payload and Conjugation Chemistry", The AAPS Journal, Mar. 2015, vol. 17, No. 2, pp. 339-351.
Miller-Larsson et al., "Reversible Fatty Acid Conjugation of Budesonide—Novel Mechanism for Prolonged Retention of Topically Applied Steroid in Airway Tissue", Drug Metab. Dispos. 1998, vol. 26, pp. 623-630.
Mori et al., "Endocytic Pathway of Scavenger Receptors Via Trans-Golgi System In Bovine Alveolar Macrophages", Laboratory Investigation, vol. 71, No. 3, 1994, pp. 409-417.
Muck et al., "High pressure liquid chromatography of some triamcinolone derivatives", Bollettino chimico farmaceutica, Italy, Apr. 1981, 120(4), pp. 240-247; with an English abstract.
Papachristos et al., "Antibody-drug conjugates: a mini-review. The synopsis of two approved medicines", Drug Delivery, 2016, vol. 23, No. 5, pp. 1662-1666; published online Jan. 27, 2015.
Park T. G., "Degradation of poly(lactic-co-glycolic acid) microspheres: effect of copolymer composition", Biomaterials 16(15), 1995, pp. 1123-1130.

(56) References Cited

OTHER PUBLICATIONS

Paul-Clark et al., "Glucocorticoid Receptor Nitration Leads to Enhanced Anti-Inflammatory Effects of Novel Steroid Ligands", The Journal of Immunology, 2003, vol. 171, pp. 3245-3252; doi: 10.4049/jimmunol.171.6.3245.
Peng, J., et al. "Chemoselective reduction of 21-azidocorticosteroids to primary 21-primary aminocorticosteroids." Chemical Research In Chinese Universities (2004), 25(5), pp. 866-869.
Pufall (Adv Exp Med Biol. 2015; 872: 315-333).
Rabuka et al., "Site-specific chemical protein conjugation using genetically encoded aldehyde tags", Nat Protoc., vol. 7, No. 6, pp. 1052-1067, Dec. 1, 2012, doi:10.1038/nprot.2012.04.
Reggelin et al., "Asymmetric Synthesis of Highly Substituted Azapolycyclic Compounds via 2-Alkenyl Sulfoximines: Potential Scaffolds for Peptide Mimetics", J. American Chemical Society, Mar. 8, 2006, vol. 128, pp. 4023-4034.
Romero-Hernandez et al., "Diosgenin-based thio (seleno) ureas and triazolyl glycoconjugates as hybrid drugs. Antioxidant and antiproliferative profile", European Journal Of Medicinal Chemistry, Editions Scientifique Elsevier, Paris, FR, May 14, 2015, vol. 99, pp. 67-81, XP029222662.
Romero-Hernández et al., "Diosgenin-based thio(seleno)ureas and triazolyl glycoconjugates as hybrid drugs, Antioxidant and antiproliferative profile", European Journal of Medicinal Chemistry, May 14, 2015, vol. 99, pp. 67-82.
Ryan et al., "Polyclonal Antibody Production Against Chito-Oligosaccharides", Food and Agricultural Immunology, 2001, vol. 13, pp. 127-130.
Sagar S. et al., Bifidobacterium breve and Lactobacillus rhamnosus treatment is as effective as budesonide at reducing inflammation in a murine model for chronic asthma, Respiratory Research, Apr. 16, 2014, vol. 15, No. 1, article No. 46; Abstract.
Samal et al., "The First Synthesis of Water-Soluble Cyclodextrinazafullerenes", Synthetic Communications, 2002, vol. 32, No. 21, pp. 3367-3372.
Samant et al., "Synthesis of 3-hydroxypyrid-2-ones from furfural for treatment against iron overload and iron deficiency", European Journal Of Medicinal Chemistry, vol. 43, No. 9 , Sep. 1, 2008, pp. 1978-1982.
Sehgal et al., "Desoxymethasone: a new topical corticosteroid", International Journal of Dermatology, Dec. 1976, vol. 15, pp. 770-773; with an English abstract.
Shaunak et al., "Site-specific PEGylation of native disulfide bonds in therapeutic proteins", Nature Chemical Biology, Jun. 2006, vol. 2, No. 6, pp. 312-313.
Simons S. Jr. et al., "Alpha Keto Mesylate: a Reactive Thiol Specific Functional Group", Journal of Organic Chemistry, American Chemical Society, Washington, vol. 45, No. 15, Jan. 1, 1980, pp. 3084-3088, XP008100022.
Singh et al., "Polymer Drug Conjugates: Recent Advancements in Various Diseases", Current Pharmaceutical Design, May 10, 2016, vol. 22, No. 19, pp. 2821-2843, XP055490895.
Svendsen et al., "Antibody-Directed Glucocorticoid Targeting to CD163 M2-type Macrophages Attenuates Fructose-Induced Liver Inflammatory Changes", Molecular Therapy—Methods & Clinical Develop, vol. 4, Mar. 2017, pp. 50-61.
Tang et al., Org Biomol Chem 14:9501-9518, Oct. 28, 2016.
Taylor et al., "A transgenic mouse that expresses a diversity of human sequence heavy and light chain immunoglobulins", Nucleic Acids Research, 1992, vol. 20, No. 23, pp. 6287-6295.
Thalen et al., "Epimers of budesonide and related corticosteroids. I. Preparative resolution by chromatography on Sephadex LH-20", Acta Pharmaceutica Suecica, 1982, 19(4), pp. 247-266.
Thalen et al., "Synthesis and pharmacological properties of some 16α,17α-acetals of 16α hydroxyhydrocortisone, 16α-hydroxyprednisolone and fluorinated 16α-hydroxyprednisolones", Acta Pharmaceutical Suecica, 1984, 21(2), pp. 109-124.
Thalen, "Epimers of budesonide and related corticosteroids. II. Structure elucidation by mass spectrometry", Acta Pharmaceutica Suecica, 1982, 19(5), pp. 327-354.
Tian et al., "Inhibition of influenza virus infection by multivalent pentacyclic triterpene-functionalized per-0-methylated cyclodextrin conjugates", European Journal Of Medicinal Chemistry, Editions Scientifique Elsevier, Paris, FR, Apr. 2, 2017, vol. 134, pp. 133-139, XP029995979.
Toth et al., "Amino-derivatives of 11,17,21-Trihydroxy-3,20-Dioxo-1,4-Pregnadiene", Nature 191, Aug. 5, 1961, p. 607.
Tumey et al., "ADME Considerations for the Development of Biopharmaceutical Conjugates Using Cleavable Linkers", Current Topics In Medicinal Chemistry, vol. 17, No. 32, 2017, pp. 3444-3462.
Tunek et al., "Reversible Formation of Fatty Acid Esters of Budesonide, an Antiasthma Glucgcorticoid, In Human Lung and Liver Microsomes", Drug Metab. Dispos. 1997, vol. 25, No. 11, pp. 1311-1317.
Uekama et al., "$6^A$-O-[(4-Biphenylyl)acetyl]-α-, -β-, and -γ-cyclodextrins and 6 $^A$-Deoxy-6 $^A$-[[(4-biphenylyl)acetyl]amino]-α-, -β-, and -γ-cyclodextrins: Potential Prodrugs for Colon-Specific Delivery", J. Med. Chem., 1997, vol. 40, pp. 2755-2761.
Uhrich et al., "Polymeric Systems for Controlled Drug Release", Chemical Reviews, 1999, vol. 11, pp. 3181-3198.
Vert et al., "Something new in the field of PLA/GA bioresorbable polymers?" Journal of Controlled Release 53, 1998, pp. 85-92.
Wang et al., "Bioconjugation by Copper(I)-Catalyzed Azide-Alkyne [3+2] Cycloaddition", J. Am. Chem. Soc., 2003, vol. 125, pp. 3192-3193.
Wikby et al., "Separation of epimers of budesonide and related corticosteroids by high-performance liquid chromatography. A comparison between straight- and reversed-phase systems", Journal of Chromatography, 1978, 157(1), pp. 65-74.
Wikby et al., "Separation of epimers of budesonide and related corticosteroids by reversed bonded-phase liquid chromatography", Journal of Chromatography, 1978, 157(1), pp. 51-64.
Williams et al., (Foye's Principles of Medicinal Chemistry, 5th Ed, pp. 59-63, 2002.
Xiao et al., "Synthesis and biological evaluation of novel pentacyclic triterpene [alpha]-cyclodextrin conjugates as HCV entry inhibitors", European Journal Of Medicinal Chemistry, Nov. 1, 2016, vol. 124, pp. 1-9, XP055490888.
Yano et al., "Preparation of prednisolone-appended [alpha]-, [beta]- and [gamma]-cyclodextrins: Substitution at secondary hydroxyl groups and in vitro hydrolysis behavior", Journal of Pharmaceutical Sciences, American Chemical Society and American Pharmaceutical Association, US, Apr. 1, 2001, vol. 90, No. 4, pp. 493-503, XP009506679.
Zoltan, T., et al. "Synthesis of biologically active amino and aza steroids and some of their new chemical reactions", Int. Conf. Chem. Biotechnol. Biol. Act. Nat. Prod., 1981, 2, pp. 135-149.
"European Application Serial No. 18729847.6, Communication Pursuant to Article 94(3) EPC mailed Apr. 10, 2025", 4 pgs.
"Indian Application Serial No. 201917047055, First Examination Report mailed Jun. 30, 2025", 7 pgs.
"Australian Application Serial No. 2024205046, First Examination Report mailed Aug. 5, 2025", 5 pgs.

* cited by examiner

MMAE
1a

1b: 22rac-
1c: 22R-

1d: R = $NH_2$
1e: R =
1f: R =
1g: R =

1h

1i

P2
Fluocinolone acetonide

P3

P4

1i

P5

1h

P15 + P11 → P16 → P17 → 1d

13 n=1, α-Cyclodextrin
n=2, β-Cyclodextrin
n=3, γ-Cyclodextrin

14

6b 10c
16
15a: m = 0
15b: m = 1
17
7a: m = 0
7b: m = 1

2a 3a,e-i 3a payload
3e payload
3f payload
3g payload
3H payload
3I payload

2b 3b-d 3a, e-g,H,I

2c

3J 7a (m = 0) or 7b (m = 1)

3b payload
3c payload
3d payload 8a-i,J 8a-o
m = 0, 8a-f, J-L
m = 1, 8g-i

9a-L

8j, R = $(CH_2)_3$
8k, R = $PEG_4$

Ex37, R = $(CH_2)_3$
Ex40, R = $PEG_4$

8j

Ex38

8a

Ex39-Int

Ex39

Ab-MC-CD-Linker-MMAE

ETF

POF

PCK

CCK

CEK

ACK

AHA

AZF

ACF

AON

MFF

TEF

NOK

MCK

STCOK

TCOK

BlocLys

OAY

ACRK

CRTK

CPK

TZF

*p*IF

CYCLODEXTRIN PROTEIN DRUG CONJUGATES

CROSS-REFERENCE

This application is a divisional of U.S. patent application Ser. No. 15/975,191, filed May 9, 2018, which claims the benefit of U.S. provisional application No. 62/508,315, filed May 18, 2017. The contents of both are hereby incorporated in their entirety.

FIELD

Provided herein are novel, cyclodextrin-including protein-drug conjugates, and methods for treating a variety of diseases, disorders, and conditions including administering the cyclodextrin-including protein-drug conjugates. Also set forth herein are methods of making cyclodextrin-including protein-drug conjugates.

BACKGROUND

Antibody-drug conjugates (ADCs) use antibodies to deliver a potent drug selectively to target-expressing cells, leading to a potential reduction of off-target side effects and/or toxicity, and therefore, increasing therapeutic index.

The lipophilic nature of many payloads (i.e., drugs) can adversely affect the properties of the ADC to the extent that the payloads are not efficiently delivered to the target cells. Modulating ADC properties by affixing polar groups in linkers may reduce aggregation during conjugation, and improve physiochemical properties of the ADCs leading to improved pharmacokinetics (PK) and an improved therapeutic index of the ADC (see, for example, Nature Biotechnology, 2015, 33, 733-735). Modulation of the linker to effect a change in the polarity or charge of the final metabolite may improve activity toward multidrug resistant (MDR) cells owing to better retention of the payloads inside the cells (see, for example, *Cancer Res;* 70(6) Mar. 15, 2010, p2528). The chemical moieties on linkers, e.g., polyethylene glycol (PEG), sugar, or sulfuric acid groups (See, for example, WO2014062697, US20100323973), not only affect the conjugation efficiency and the ease of production of ADCs, but also often remain as part of the metabolites and thus affect the ADC's activity and safety. Various strategies have been employed to improve ADCs (See, for example, *Bioconjugate Chem.,* 2008, 19 (10), pp 1960-1963).

Cyclodextrins (CDs) are biodegradable soluble dietary fiber and food ingredients, and are also used as drug carriers. Their safety has been documented. CDs are more soluble than PEGs, and they have no charge like sulfonates, which allows them to be easily handled during processing. In addition, since the glucose units are covalently attached end-to-end via α-1, 4 linkages, every unit should have the same chemical property and also form a unique hydrophilic exterior surface and hydrophobic interior core.

Low bioavailability of lipophilic payloads can exacerbate therapeutic windows for ADC treatment. The development of cyclodextrin-including protein conjugates, e.g., ADCs, would allow for improved modulation of biological targets, improved bioavailability, and improved therapeutic windows, particularly when lipophilic payloads are included in the ADC. Therefore, there is a continuing need for effective treatments of, for example, diseases using agents in cyclodextrin protein drug conjugates.

SUMMARY

Provided herein are compounds useful, for example, for the treatment of diseases, conditions, and disorders including, without limitation, metabolic diseases, proliferative diseases, and other diseases and conditions.

In one embodiment, set forth herein, is a compound or a pharmaceutically acceptable salt thereof, including: a protein linked to at least one payload moiety and linked to at least one cyclodextrin moiety via a covalent linker, wherein said covalent linker is bonded directly or indirectly to each of the binding agent, the payload moiety, and the cyclodextrin moiety.

In one embodiment, set forth herein, is a compound or a pharmaceutically acceptable salt thereof, including: a binding agent linked to at least one payload moiety and linked to at least one cyclodextrin moiety via a covalent linker, wherein said covalent linker is bonded directly or indirectly to each of the binding agent, the payload moiety, and the cyclodextrin moiety.

In another embodiment, set forth herein, is a compound, including: a reactive group linked to at least one payload moiety and linked to at least one cyclodextrin moiety via a covalent linker, wherein said covalent linker is bonded directly or indirectly to each of the reactive group, the payload moiety, and the cyclodextrin moiety.

In another embodiment, set forth herein is an antibody-drug conjugate having a compound, above, bonded to an antibody or an antigen binding fragment thereof.

In another embodiment, set forth herein is a method of treating a disease, condition, or disorder in a patient in need thereof including administering to the patient a compound set forth herein.

In another embodiment, set forth herein is a method of preparing an antibody-drug conjugate including the step of contacting a binding agent with a linker-payload compound set forth herein under conditions suitable for forming a bond between the binding agent and the linker-payload compound.

BRIEF DESCRIPTIONS OF THE DRAWINGS

Figure 5:
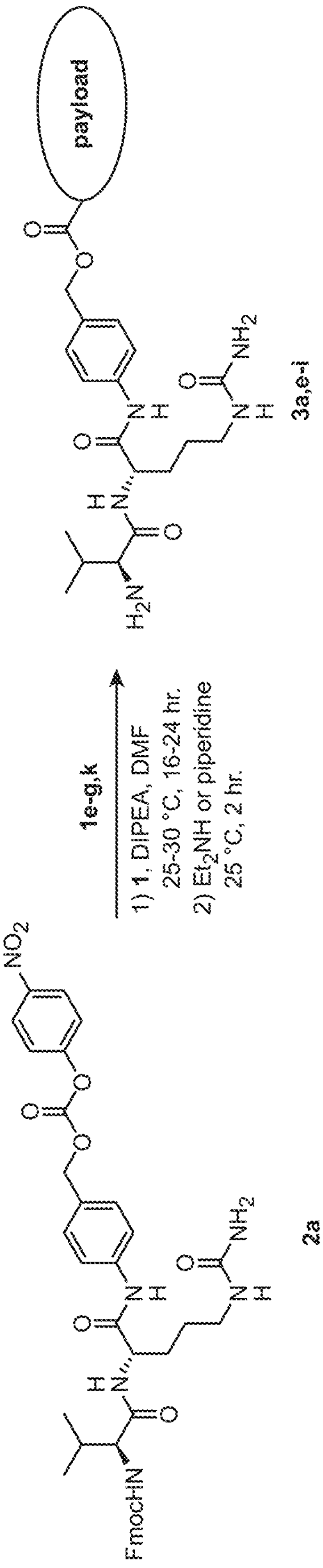

FIG. 5 shows a general synthetic process describing procedure A for preparing compound 3 (3e, 3f, and 3g) from 2a.

Figure 6:
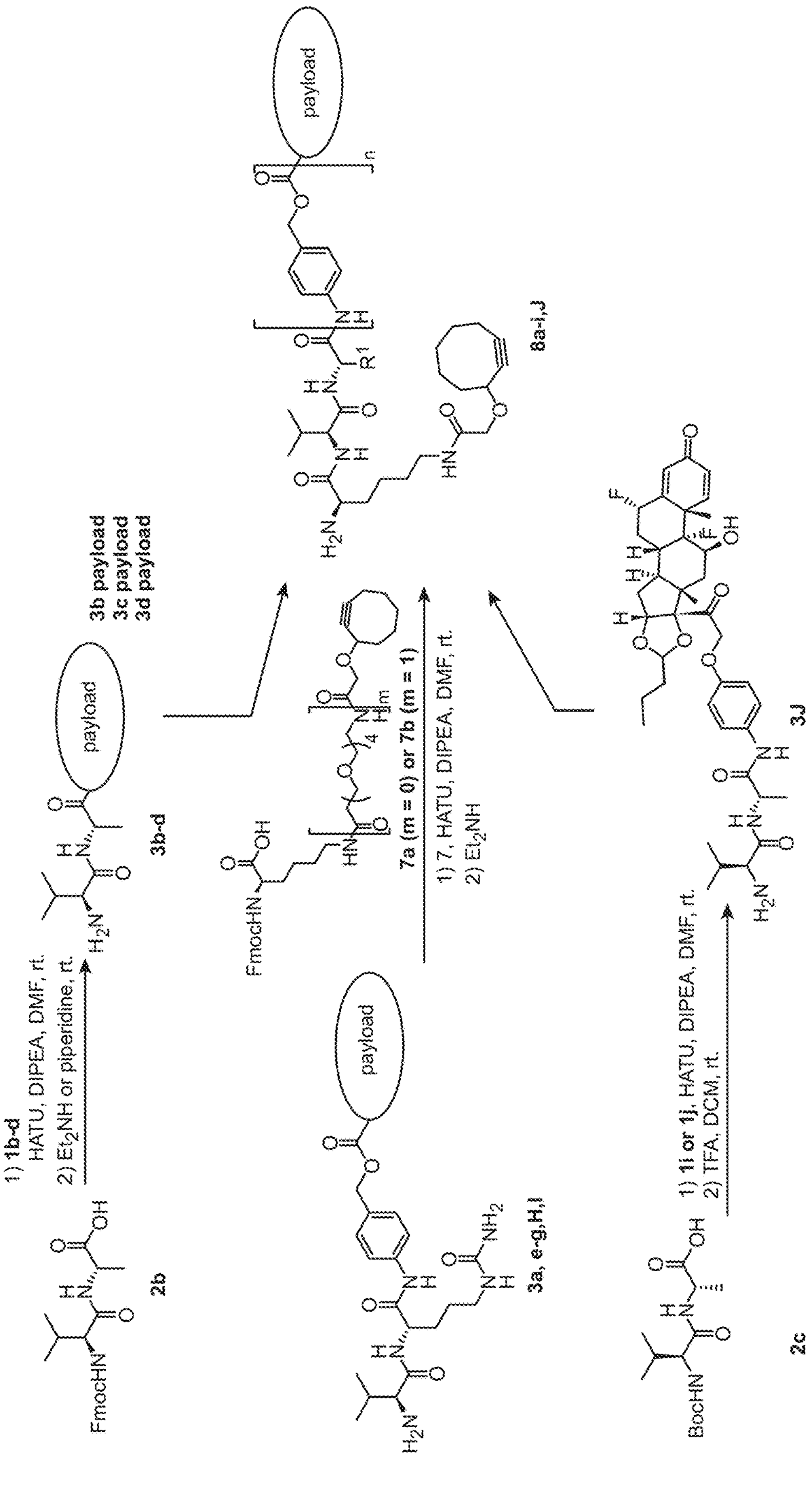

FIG. 6 shows a general synthetic process describing procedure B for preparing compound 3 from compound 2 and also for making compound 8 from compound 3.

Figure 7:
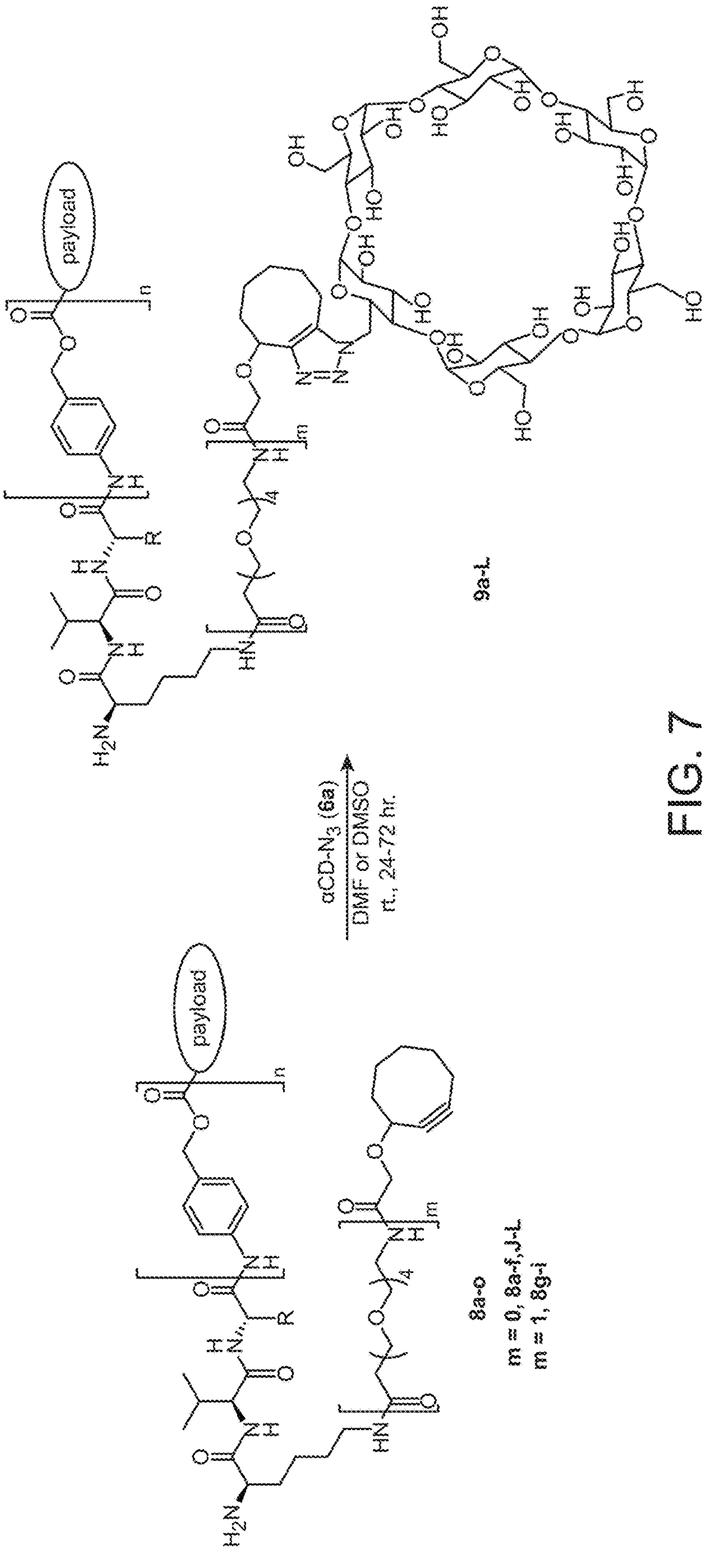

FIG. 7 shows a general synthetic process describing procedure C for making compounds 9a-L.

Figure 8:
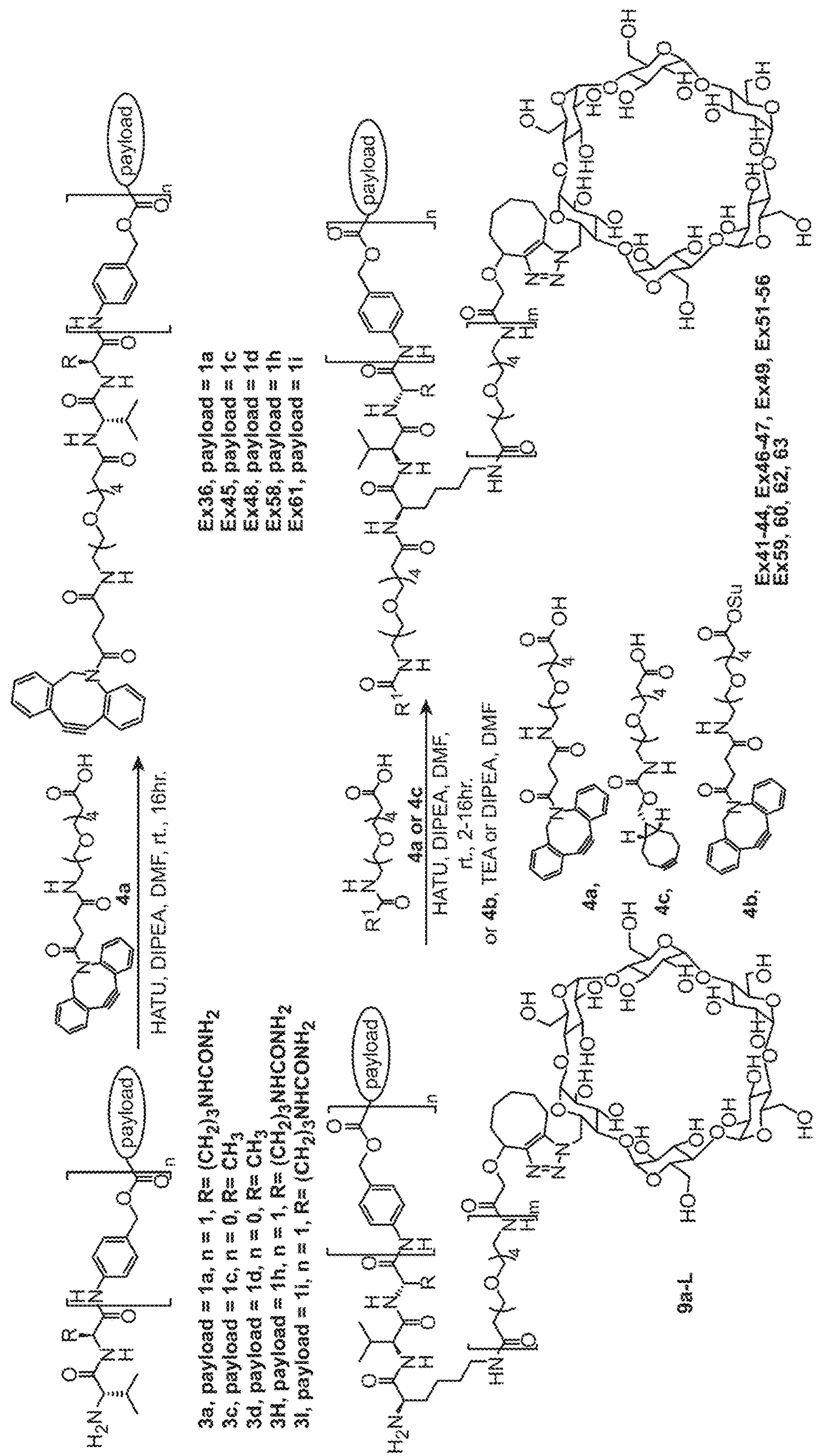

FIG. 8 shows a general synthetic process describing procedure D for making linker-payloads.

Figure 9:
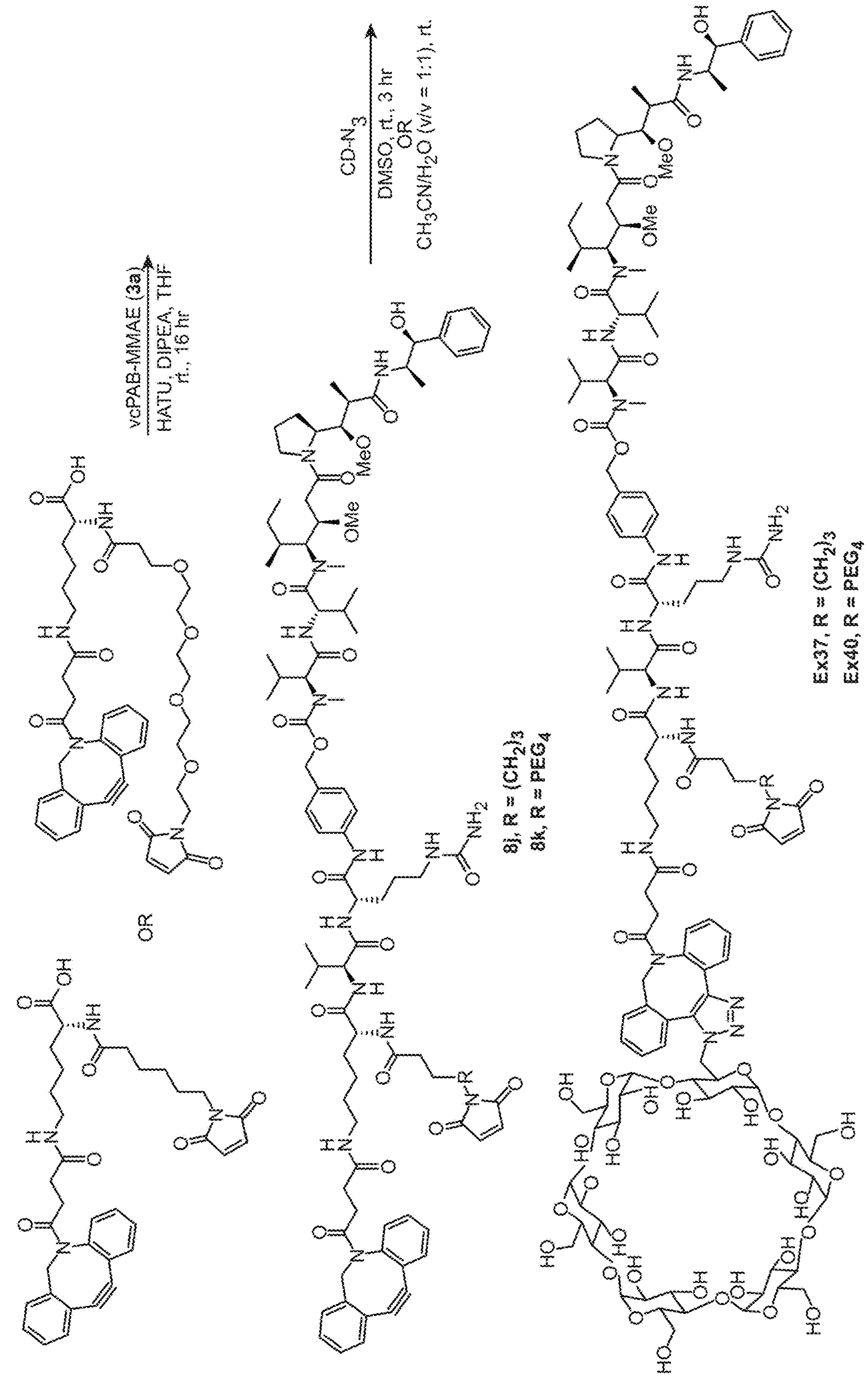

FIG. 9 shows a synthetic process describing a procedure for making linker-payloads.

Figure 10:
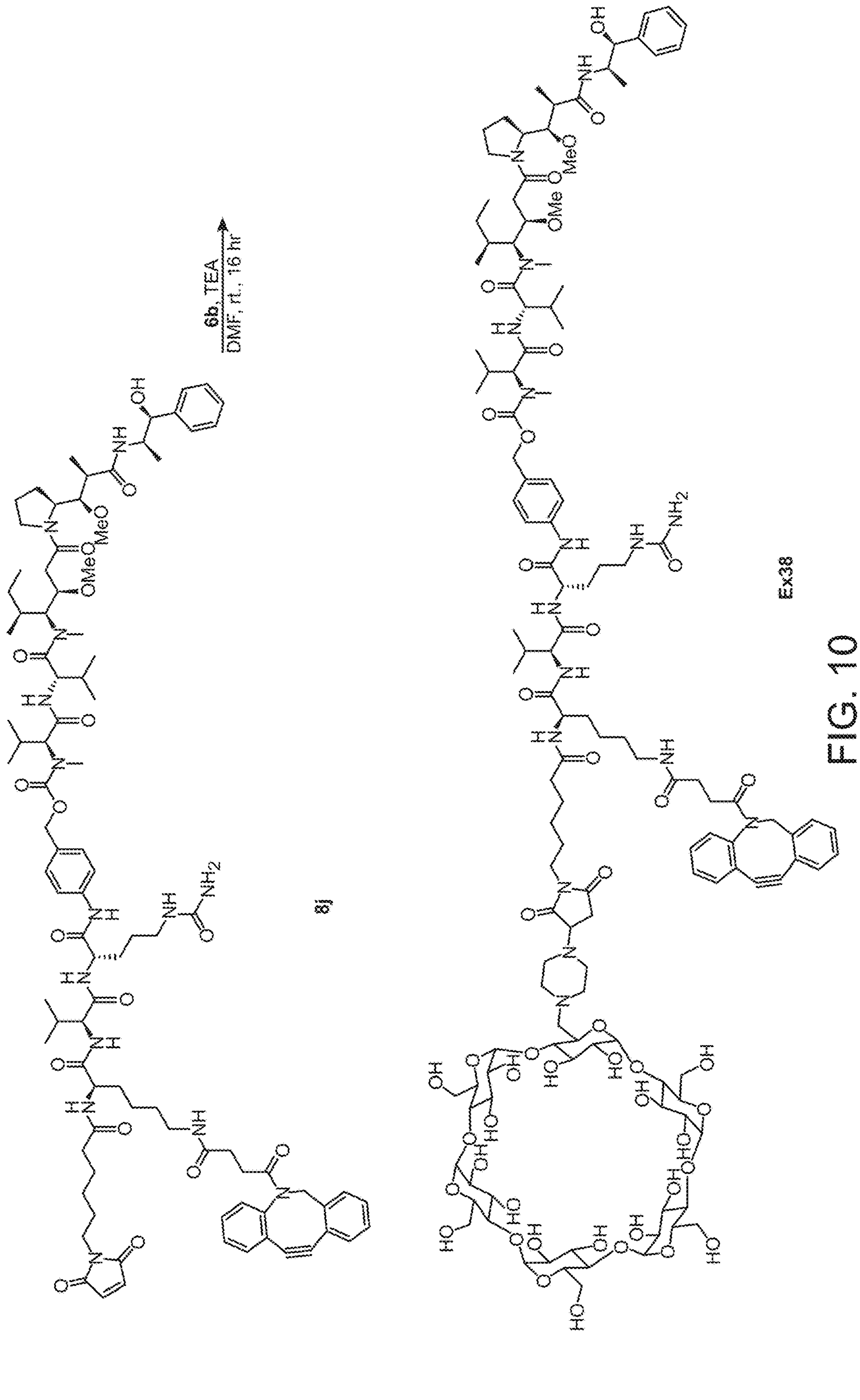

FIG. 10 shows a synthetic process describing a procedure for making the linker-payloads in Example 38.

Figure 11:
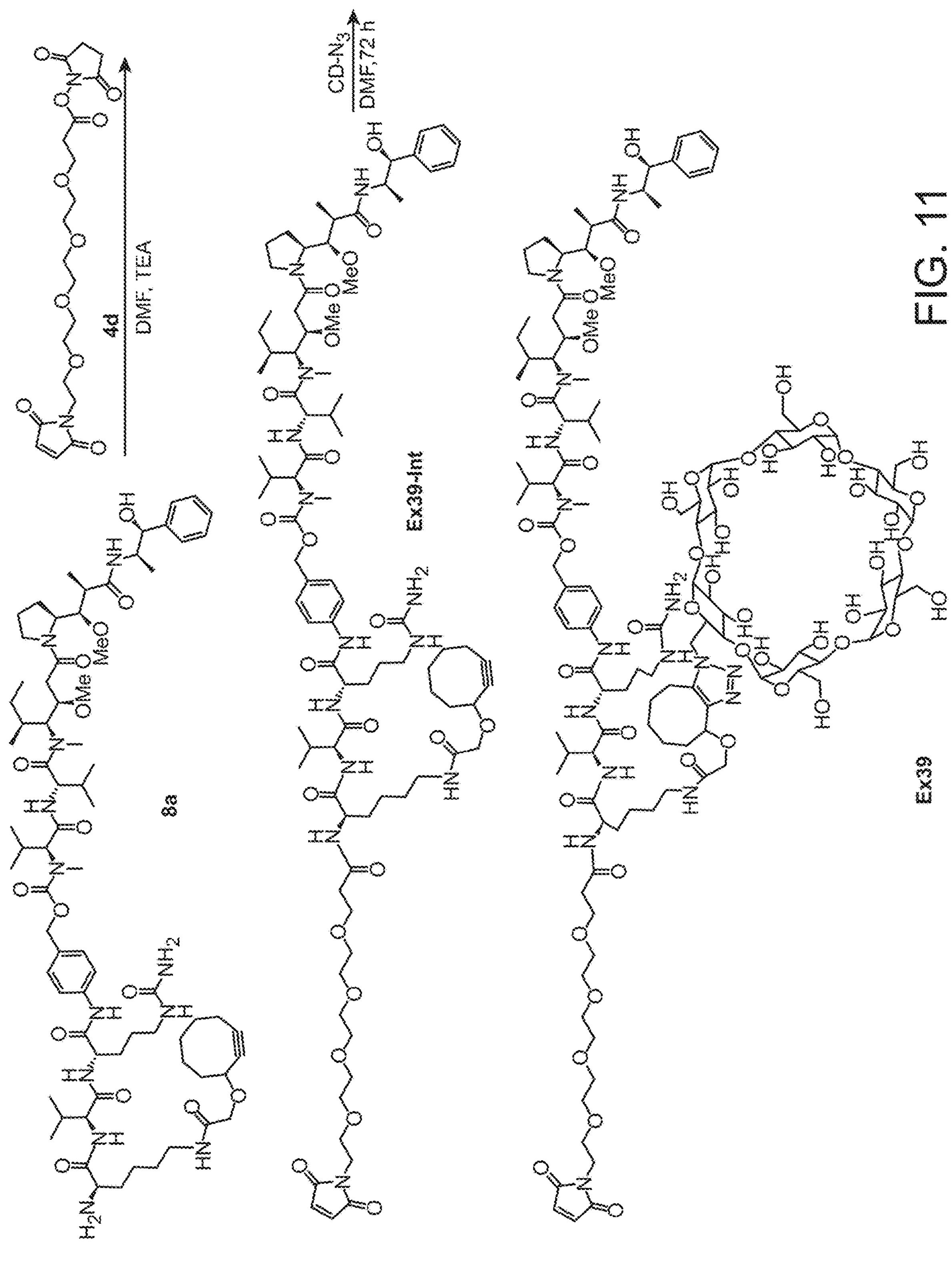

FIG. 11 shows a synthetic process describing a procedure for making the linker-payloads in Example 39.

Figure 12:
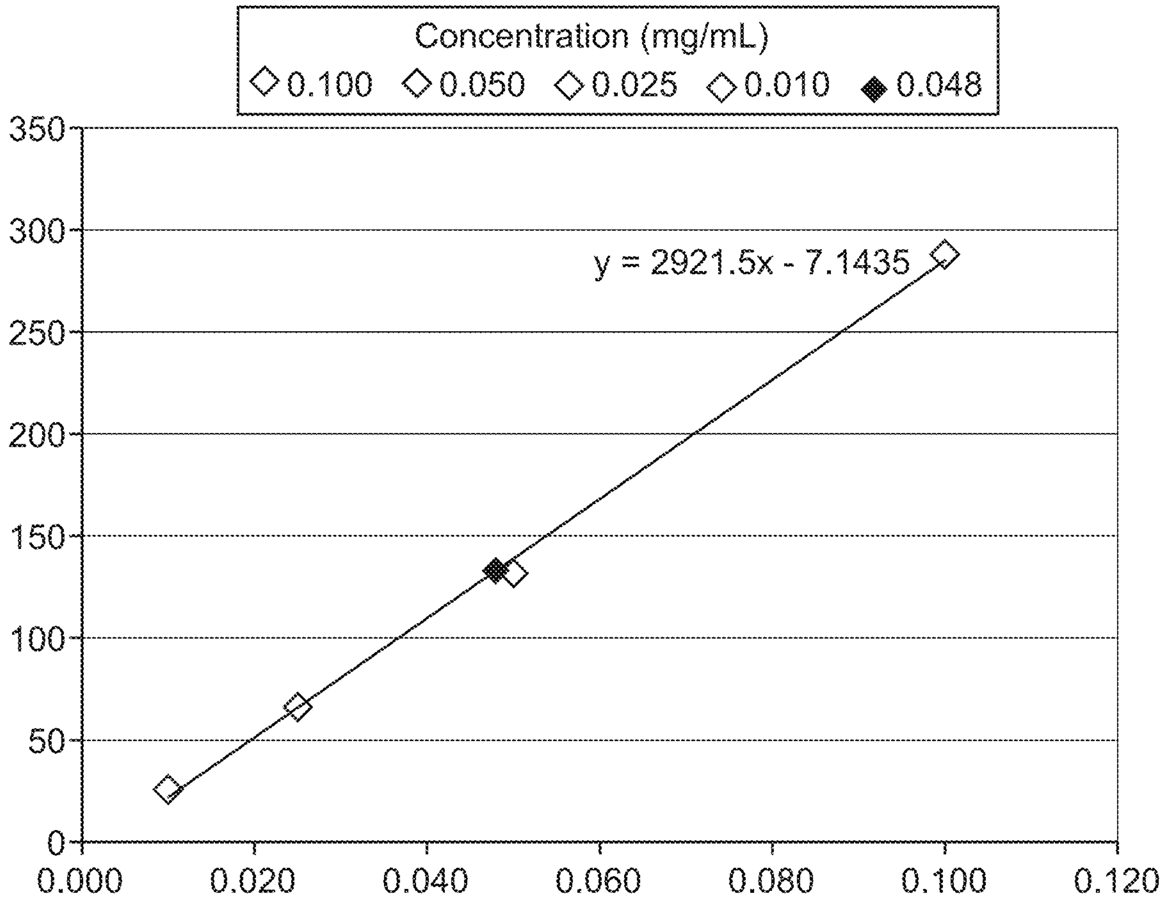

FIG. 12 shows a solubility plot for Example 49.

Figure 13:
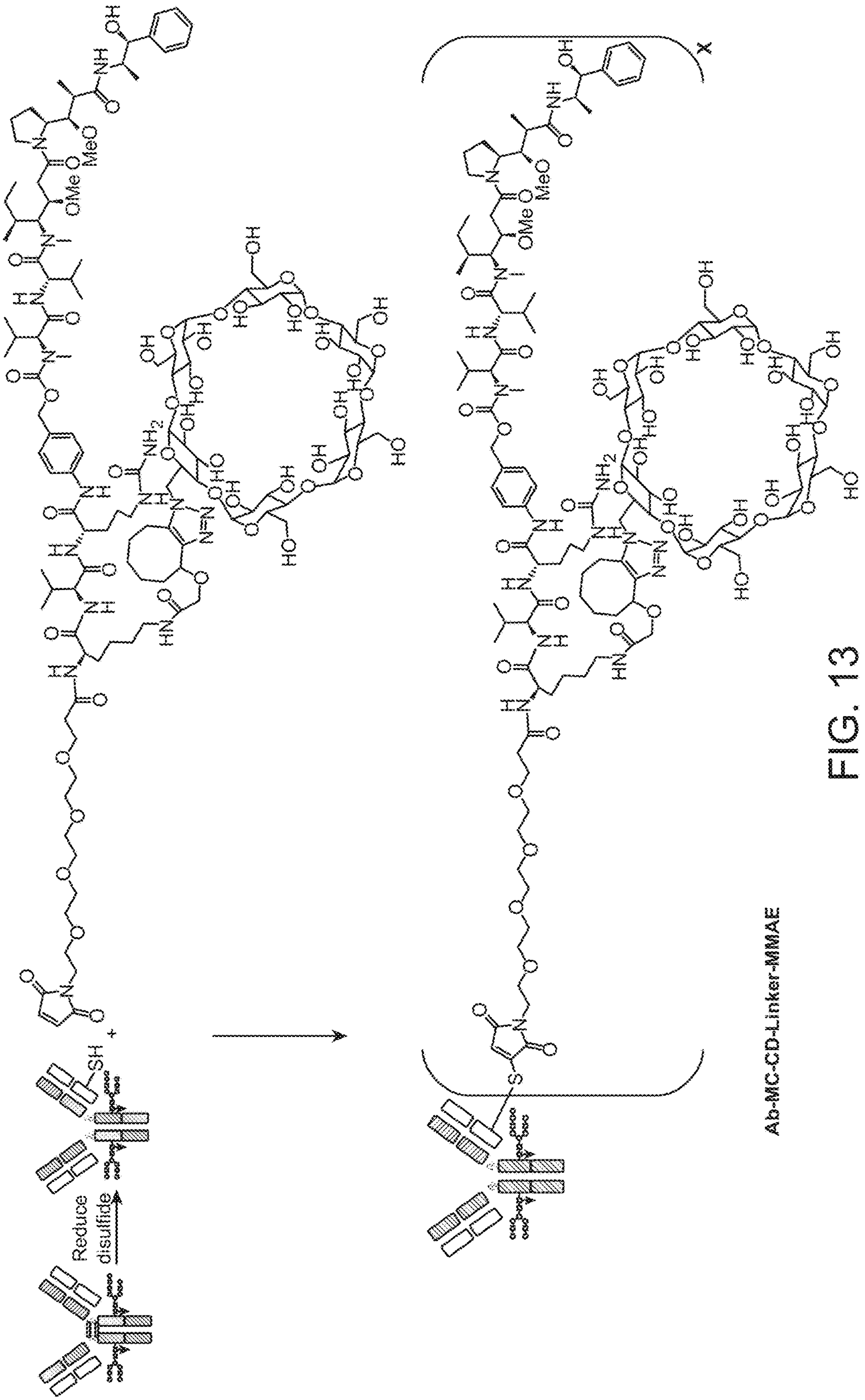

FIG. 13 shows a general synthetic process for Conjugation via Michael addition.

Figure 14:
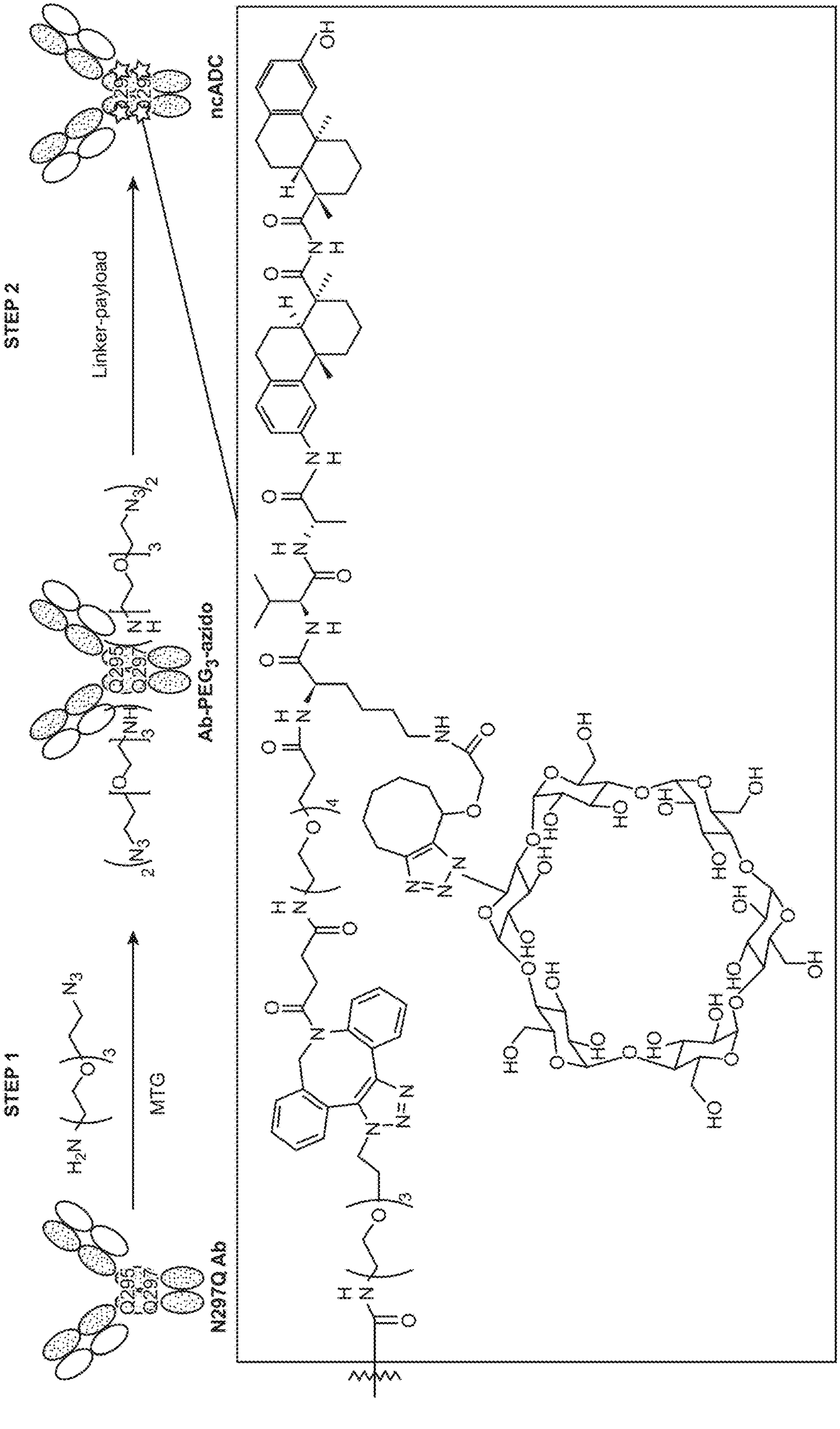

FIG. 14 shows a general synthetic process for an ADC conjugation via [2+3] click reaction represent by Ab-Ex49.

Figure 15:
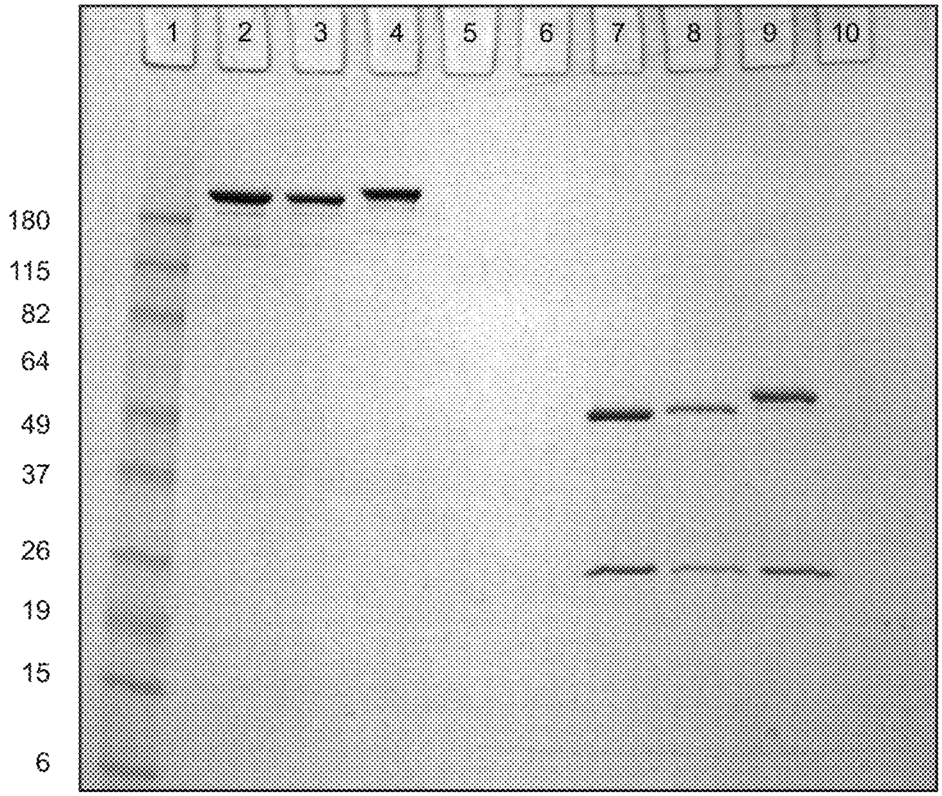

FIG. 15 shows a Coomassie-stained SDS-PAGE Gel of anti-Her2 antibody, anti-Her2-$PEG_3$-$N_3$, and anti-Her2-Ex49.

Figure 16:
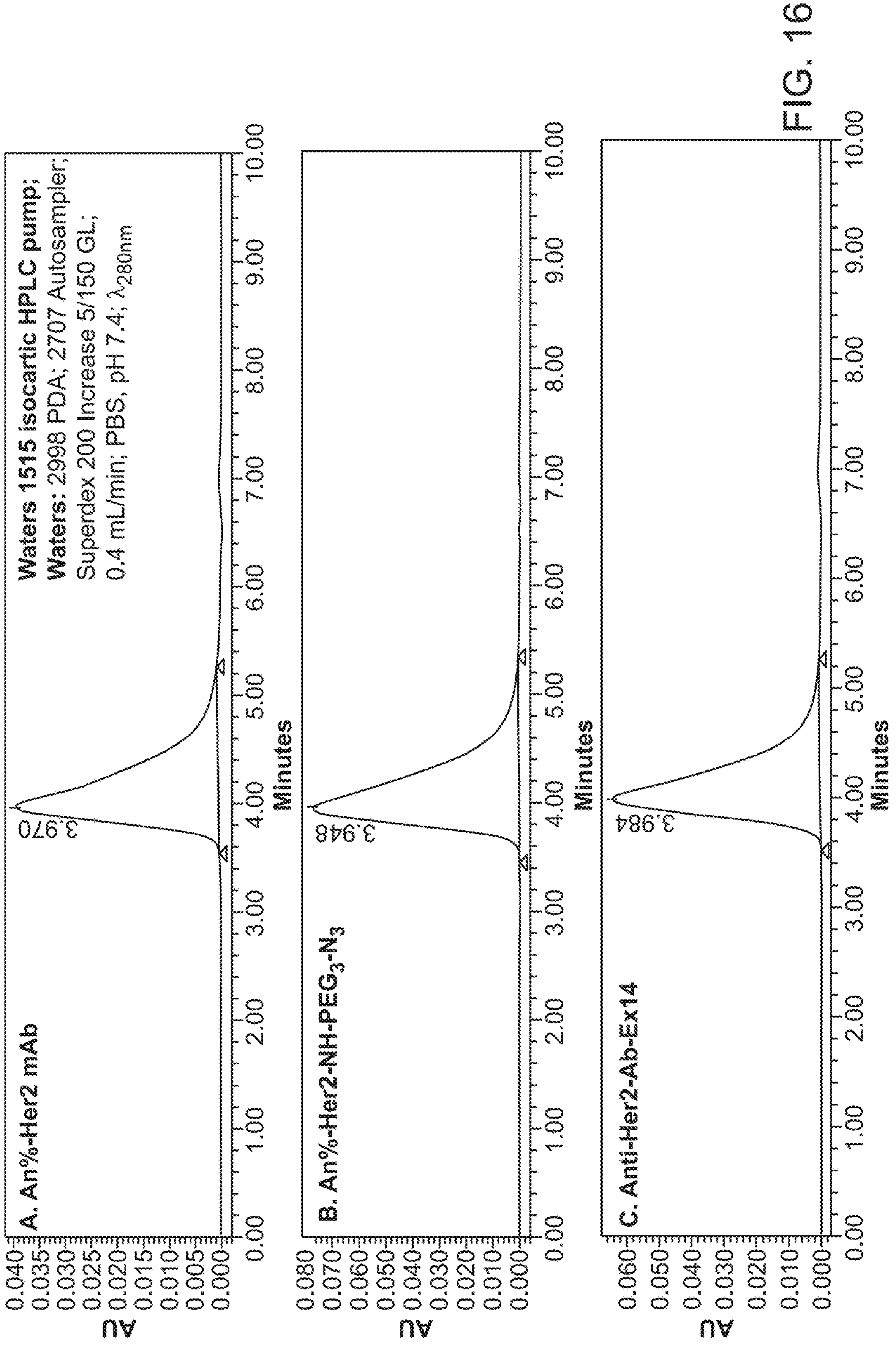

FIG. 16 shows a Size Exclusion Chromatography (SEC) of anti-Her2 Ab, anti-Her2-$PEG_3$-$N_3$, and anti-Her2-Ex49.

Figure 17:
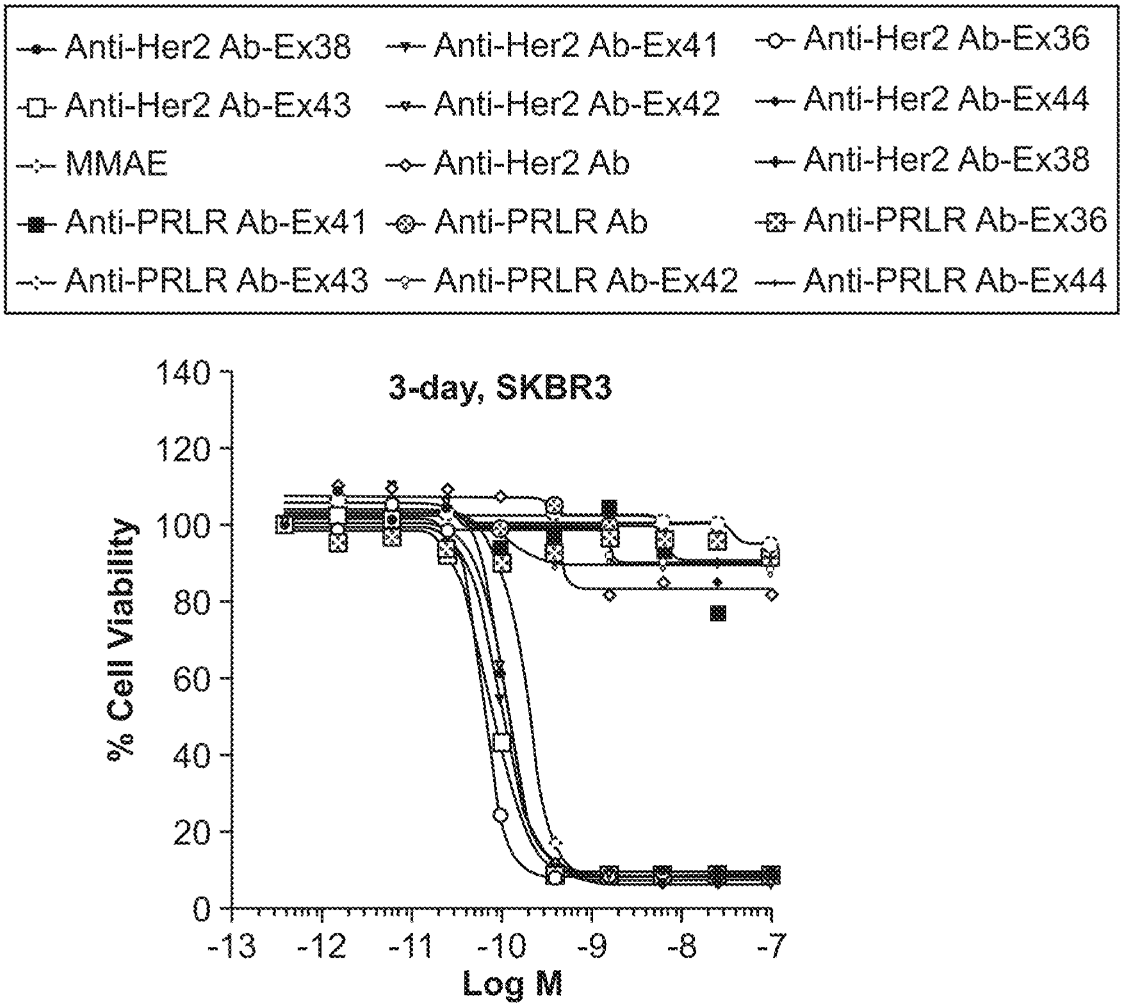

FIG. 17 shows the plot of % Cell viability vs. $Log_{10}$ [M] of certain compounds tested in Example 72.

Figure 18:
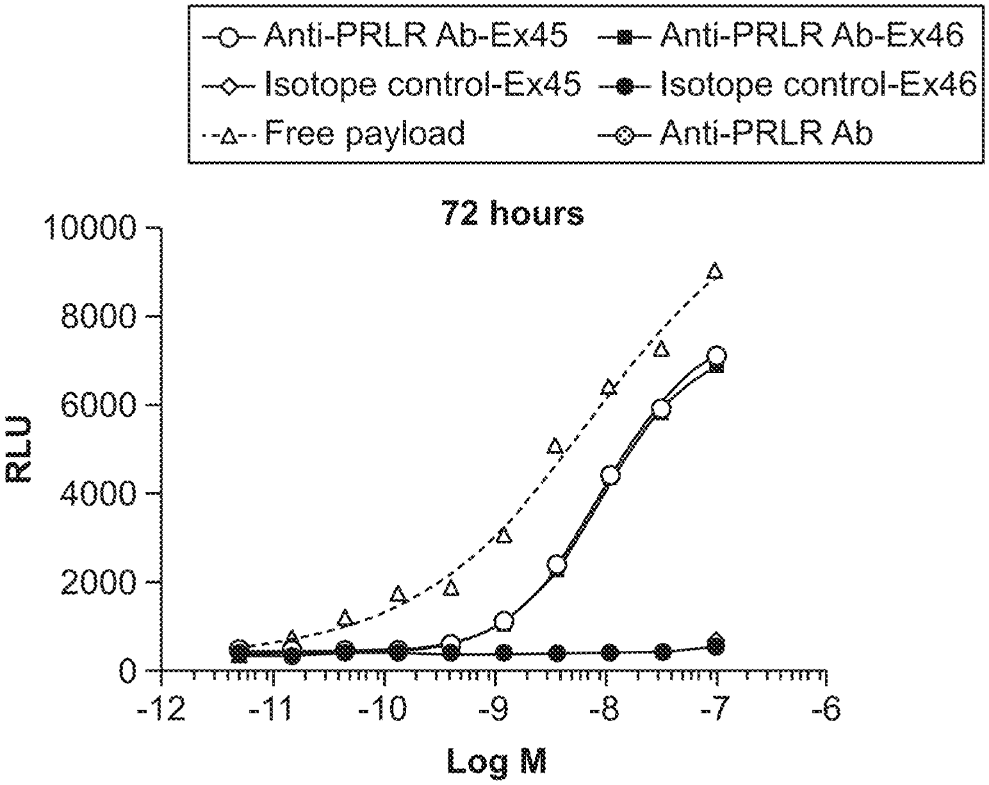

FIG. 18 shows bioactivity of LXR agonist ADCs with and without cyclodextrin linkers in a plot of relative light units (RLU) vs. $Log_{10}$ [M].

Figure 19:
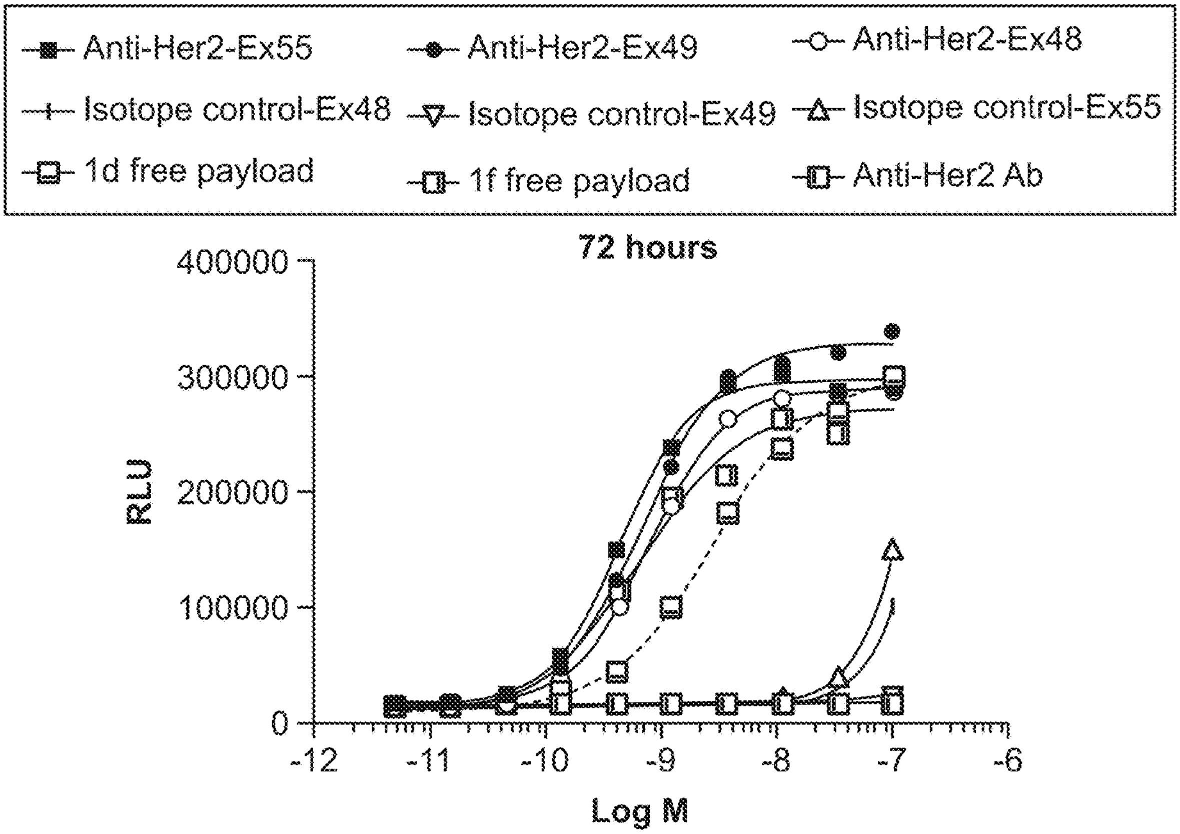

FIG. 19 shows bioactivity of LXR agonist ADCs with and without cyclodextrin linkers in a plot of relative light units (RLU) vs. $Log_{10}$ [M].

Figure 20:
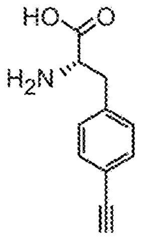
Figure 20:
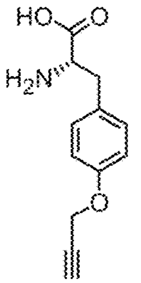
Figure 20:
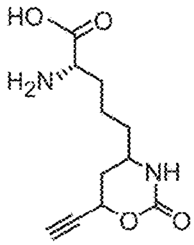
Figure 20:
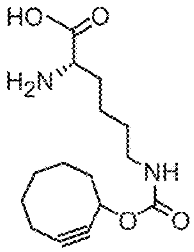
Figure 20:
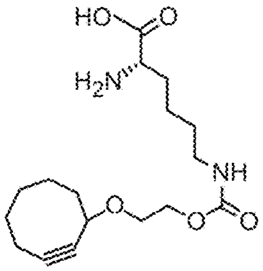
Figure 20:
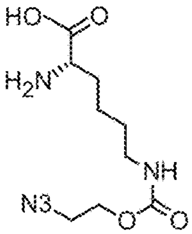
Figure 20:
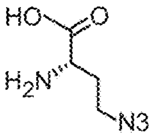
Figure 20:
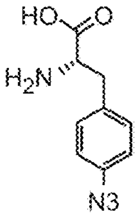
Figure 20:
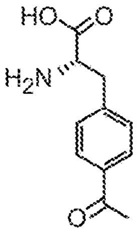
Figure 20:
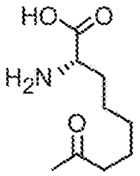
Figure 20:
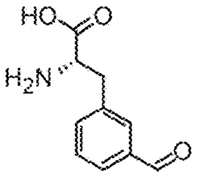
Figure 20:
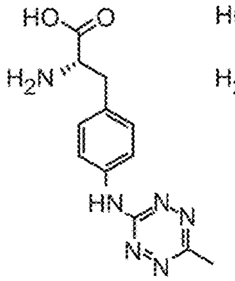
Figure 20:
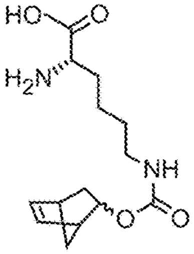
Figure 20:
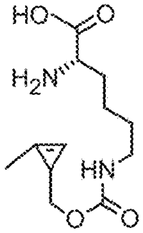
Figure 20:
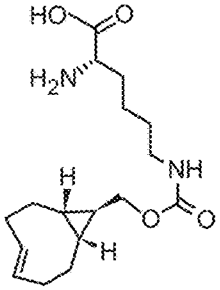
Figure 20:
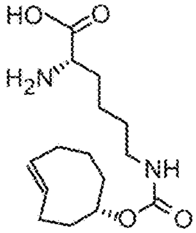
Figure 20:
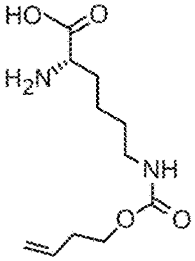
Figure 20:
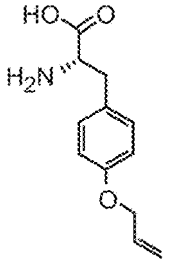
Figure 20:
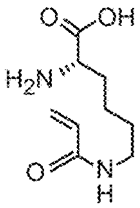
Figure 20:
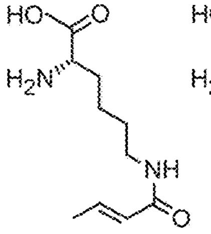
Figure 20:
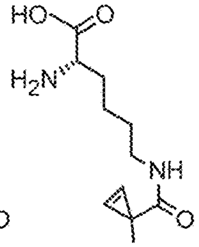
Figure 20:
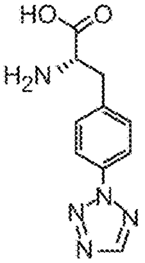
Figure 20:
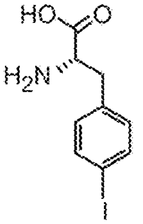

FIG. 20 shows reagents that may be used in place of D-Lys in the methods set forth herein.

DESCRIPTION OF EXEMPLARY EMBODIMENTS

Provided herein are compounds, compositions, and methods useful for treating, for example, dyslipidemia, a metabolic disease, inflammation, or a neurodegenerative disease, in a subject.

Definitions

When referring to the compounds provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term provided herein, these Definitions prevail unless stated otherwise.

As used herein, "alkyl" refers to a monovalent and saturated hydrocarbon radical moiety. Alkyl is optionally substituted and can be linear, branched, or cyclic, i.e., cycloalkyl. Alkyl includes, but is not limited to, those radicals having 1-20 carbon atoms, i.e., $C_{1-20}$ alkyl; 1-12 carbon atoms, i.e., $C_{1-12}$ alkyl; 1-8 carbon atoms, i.e., $C_{1-8}$ alkyl; 1-6 carbon atoms, i.e., $C_{1-6}$ alkyl; and 1-3 carbon atoms, i.e., $C_{1-3}$ alkyl. Examples of alkyl moieties include, but are not limited to methyl, ethyl, n-propyl, i-propyl, n-butyl, s-butyl, t-butyl, i-butyl, a pentyl moiety, a hexyl moiety, cyclopropyl, cyclobutyl, cyclopentyl, and cyclohexyl. A pentyl moiety includes, but is not limited to, n-pentyl and i-pentyl. A hexyl moiety includes, but is not limited to, n-hexyl.

As used herein, "alkylene" refers to a divalent alkyl group. Unless specified otherwise, alkylene includes, but is not limited to, 1-20 carbon atoms. The alkylene group is optionally substituted as described herein for alkyl. In some embodiments, alkylene is unsubstituted.

Designation of an amino acid or amino acid residue without specifying its stereochemistry is intended to encompass the L form of the amino acid, the D form of the amino acid, or a racemic mixture thereof.

As used herein, "haloalkyl" refers to alkyl, as defined above, wherein the alkyl includes at least one substituent selected from a halogen, for example, fluorine (F), chlorine (Cl), bromine (Br), or iodine (1). Examples of haloalkyl include, but are not limited to, $—CF_3$, $—CH_2CF_3$, $—CCl_2F$, and $—CCl_3$.

As used herein, "alkenyl" refers to a monovalent hydrocarbon radical moiety containing at least two carbon atoms and one or more non-aromatic carbon-carbon double bonds. Alkenyl is optionally substituted and can be linear, branched, or cyclic. Alkenyl includes, but is not limited to, those radicals having 2-20 carbon atoms, i.e., $C_{2-20}$ alkenyl; 2-12 carbon atoms, i.e., $C_{2-12}$ alkenyl; 2-8 carbon atoms, i.e., $C_{2-8}$ alkenyl; 2-6 carbon atoms, i.e., $C_{2-6}$ alkenyl; and 2-4 carbon atoms, i.e., $C_{2-4}$ alkenyl. Examples of alkenyl moieties include, but are not limited to vinyl, propenyl, butenyl, and cyclohexenyl.

As used herein, "alkynyl" refers to a monovalent hydrocarbon radical moiety containing at least two carbon atoms and one or more carbon-carbon triple bonds. Alkynyl is optionally substituted and can be linear, branched, or cyclic. Alkynyl includes, but is not limited to, those radicals having 2-20 carbon atoms, i.e., $C_{2-20}$ alkynyl; 2-12 carbon atoms, i.e., $C_{2-12}$ alkynyl; 2-8 carbon atoms, i.e., $C_{2-8}$ alkynyl; 2-6 carbon atoms, i.e., $C_{2-8}$ alkynyl; and 2-4 carbon atoms, i.e., $C_{2-4}$ alkynyl. Examples of alkynyl moieties include, but are not limited to ethynyl, propynyl, and butynyl.

As used herein, "alkoxy" refers to a monovalent and saturated hydrocarbon radical moiety wherein the hydrocarbon includes a single bond to an oxygen atom and wherein the radical is localized on the oxygen atom, e.g., $CH_3CH_2$—O. for ethoxy. Alkoxy substituents bond to the compound which they substitute through this oxygen atom of the alkoxy substituent. Alkoxy is optionally substituted and can be linear, branched, or cyclic, i.e., cycloalkoxy. Alkoxy includes, but is not limited to, those having 1-20 carbon atoms, i.e., $C_{1-20}$ alkoxy; 1-12 carbon atoms, i.e., $C_{1-12}$ alkoxy; 1-8 carbon atoms, i.e., $C_{1-8}$ alkoxy; 1-6 carbon atoms, i.e., $C_{1-6}$ alkoxy; and 1-3 carbon atoms, i.e., $C_{1-3}$ alkoxy. Examples of alkoxy moieties include, but are not limited to methoxy, ethoxy, n-propoxy, i-propoxy, n-butoxy, s-butoxy, t-butoxy, i-butoxy, a pentoxy moiety, a hexoxy moiety, cyclopropoxy, cyclobutoxy, cyclopentoxy, and cyclohexoxy.

As used herein, "haloalkoxy" refers to alkoxy, as defined above, wherein the alkoxy includes at least one substituent selected from a halogen, e.g., F, Cl, Br, or I.

As used herein, "aryl" refers to a monovalent moiety that is a radical of an aromatic compound wherein the ring atoms are carbon atoms. Aryl is optionally substituted and can be monocyclic or polycyclic, e.g., bicyclic or tricyclic. Examples of aryl moieties include, but are not limited to, those having 6 to 20 ring carbon atoms, i.e., $C_{6-20}$ aryl; 6 to 15 ring carbon atoms, i.e., $C_{6-15}$ aryl, and 6 to 10 ring carbon atoms, i.e., $C_{6-10}$ aryl. Examples of aryl moieties include, but are not limited to phenyl, naphthyl, fluorenyl, azulenyl, anthryl, phenanthryl, and pyrenyl.

As used herein, "arylalkyl" refers to a monovalent moiety that is a radical of an alkyl compound, wherein the alkyl compound is substituted with an aromatic substituent, i.e., the aromatic compound includes a single bond to an alkyl group and wherein the radical is localized on the alkyl group. An arylalkyl group bonds to the illustrated chemical structure via the alkyl group. An arylalkyl can be represented by the structure, e.g.,

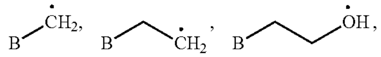

-continued

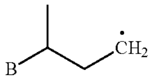 or 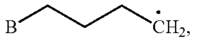, wherein B is an aromatic moiety, e.g., phenyl. Arylalkyl is optionally substituted, i.e., the aryl group and/or the alkyl group, can be substituted as disclosed herein. Examples of arylalkyl include, but are not limited to, benzyl.

As used herein, "alkylaryl" refers to a monovalent moiety that is a radical of an aryl compound, wherein the aryl compound is substituted with an alkyl substituent, i.e., the aryl compound includes a single bond to an alkyl group and wherein the radical is localized on the aryl group. An alkylaryl group bonds to the illustrated chemical structure via the aryl group. An alkylaryl can be represented by the structure, e.g.,

, , 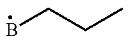,

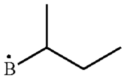 or 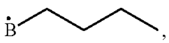, wherein B is an aromatic moiety, e.g., phenyl. Alkylaryl is optionally substituted, i.e., the aryl group and/or the alkyl group, can be substituted as disclosed herein. Examples of alkylaryl include, but are not limited to, toluyl.

As used herein, "aryloxy" refers to a monovalent moiety that is a radical of an aromatic compound wherein the ring atoms are carbon atoms and wherein the ring is substituted with an oxygen radical, i.e., the aromatic compound includes a single bond to an oxygen atom and wherein the radical is localized on the oxygen atom, e.g.,

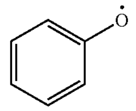

for phenoxy. Aryloxy substituents bond to the compound which they substitute through this oxygen atom. Aryloxy is optionally substituted. Aryloxy includes, but is not limited to, those radicals having 6 to 20 ring carbon atoms, i.e., $C_{6-20}$ aryloxy; 6 to 15 ring carbon atoms, i.e., $C_{6-15}$ aryloxy, and 6 to 10 ring carbon atoms, i.e., $C_{6-10}$ aryloxy. Examples of aryloxy moieties include, but are not limited to phenoxy, naphthoxy, and anthroxy.

As used herein, "$R^aR^bN$-aryloxy" refers to a monovalent moiety that is a radical of an aromatic compound wherein the ring atoms are carbon atoms and wherein the ring is substituted with at least one $R^aR^bN$— substituent and at least one oxygen radical, i.e., the aromatic compound includes a single bond to an $R^aR^bN$— substituent and a single bond to an oxygen atom and wherein the radical is localized on the oxygen atom, e.g.,

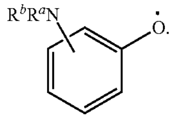

$R^aR^bN$-aryloxy substituents bond to the compound which they substitute through this oxygen atom. $R^aR^bN$— aryloxy is optionally substituted. $R^aR^bN$-aryloxy includes, but is not limited to, those having 6 to 20 ring carbon atoms, for example, $C_{6-20}$ $(R^aR^bN)_n$-aryloxy, 6 to 15 ring carbon atoms, for example, $C_{6-15}$ $(R^aR^bN)_n$-aryloxy, and 6 to 10 ring carbon atoms, for example, $C_{6-10}$ $(R^aR^bN)_n$-aryloxy, wherein n represents the number of $R^aR^bN$— substituents. An example of an $R^aR^bN$-aryloxy moiety includes, but is not limited to 4-(dimethylamino)-phenoxy,

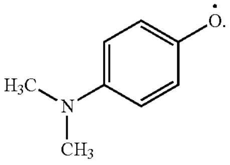

As used herein, "arylene" refers to a divalent moiety of an aromatic compound wherein the ring atoms are only carbon atoms. Arylene is optionally substituted and can be monocyclic or polycyclic, e.g., bicyclic or tricyclic. Examples of arylene moieties include, but are not limited to those having 6 to 20 ring carbon atoms, i.e., $C_{6-20}$ arylene; 6 to 15 ring carbon atoms, i.e., $C_{6-15}$ arylene, and 6 to 10 ring carbon atoms, i.e., $C_{6-10}$ arylene.

As used herein, "heteroalkyl" refers to an alkyl in which one or more carbon atoms are replaced by heteroatoms. As used herein, "heteroalkenyl" refers to an alkenyl in which one or more carbon atoms are replaced by heteroatoms. As used herein, "heteroalkynyl" refers to an alkynyl in which one or more carbon atoms are replaced by heteroatoms. Suitable heteroatoms include, but are not limited to, nitrogen, oxygen, and sulfur atoms. Heteroalkyl is optionally substituted. Examples of heteroalkyl moieties include, but are not limited to, aminoalkyl, sulfonylalkyl, and sulfinylalkyl. Examples of heteroalkyl moieties also include, but are not limited to, methylamino, methylsulfonyl, and methylsulfinyl.

As used herein, "heteroaryl" refers to a monovalent moiety that is a radical of an aromatic compound wherein the ring atoms contain carbon atoms and at least one oxygen, sulfur, nitrogen, or phosphorus atom. Examples of heteroaryl moieties include, but are not limited to those having 5 to 20 ring atoms; 5 to 15 ring atoms; and 5 to 10 ring atoms. Heteroaryl is optionally substituted.

As used herein, "heteroarylene" refers to an arylene in which one or more ring atoms of the aromatic ring are replaced with an oxygen, sulfur, nitrogen, or phosphorus atom. Heteroarylene is optionally substituted.

As used herein, "heterocycloalkyl" refers to a cycloalkyl in which one or more carbon atoms are replaced by heteroatoms. Suitable heteroatoms include, but are not limited to, nitrogen, oxygen, and sulfur atoms. Heterocycloalkyl is optionally substituted. Examples of heterocycloalkyl moieties include, but are not limited to, morpholinyl, piperidinyl, tetrahydropyranyl, pyrrolidinyl, imidazolidinyl, oxazolidinyl, thiazolidinyl, dioxolanyl, dithiolanyl, oxanyl, or thianyl.

As used herein, "Lewis acid" refers to a molecule or ion that accepts an electron lone pair. The Lewis acids used in the methods described herein are those other than protons. Lewis acids include, but are not limited to, non-metal acids, metal acids, hard Lewis acids, and soft Lewis acids. Lewis acids include, but are not limited to, Lewis acids of aluminum, boron, iron, tin, titanium, magnesium, copper, antimony, phosphorus, silver, ytterbium, scandium, nickel, and zinc. Illustrative Lewis acids include, but are not limited to, $AlBr_3$, $AlCl_3$, $BCl_3$, boron trichloride methyl sulfide, $BF_3$, boron trifluoride methyl etherate, boron trifluoride methyl sulfide, boron trifluoride tetrahydrofuran, dicyclohexylboron trifluoromethanesulfonate, iron (Ill) bromide, iron (Ill) chloride, tin (IV) chloride, titanium (IV) chloride, titanium (IV) isopropoxide, $Cu(OTf)_2$, $CuCl_2$, $CuBr_2$, zinc chloride, alkylaluminum halides ($R_nAlX_{3-n}$, wherein R is hydrocarbyl, X is a halide, and subscript n is an integer from 0 to 3), $Zn(OTf)_2$, $ZnCl_2$, $Yb(OTf)_3$, $Sc(OTf)_3$, $MgBr_2$, $NiCl_2$, $Sn(OTf)_2$, $Ni(OTf)_2$, and $Mg(OTf)_2$.

As used herein, "N-containing heterocycloalkyl," refers to a cycloalkyl in which one or more carbon atoms are replaced by heteroatoms and wherein at least one heteroatom is a nitrogen atom. Suitable heteroatoms in addition to nitrogen, include, but are not limited to oxygen and sulfur atoms. N-containing heterocycloalkyl is optionally substituted. Examples of N— containing heterocycloalkyl moieties include, but are not limited to, morpholinyl, piperidinyl, pyrrolidinyl, imidazolidinyl, oxazolidinyl, or thiazolidinyl.

As used herein, "optionally substituted," when used to describe a radical moiety, for example, optionally substituted alkyl, means that such moiety is optionally bonded to one or more substituents. Examples of such substituents include, but are not limited to, halo, cyano, nitro, optionally substituted haloalkyl, azido, epoxy, optionally substituted heteroaryl, optionally substituted heterocycloalkyl,

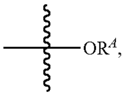, 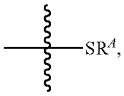, 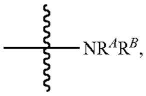,
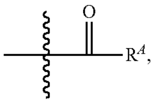, 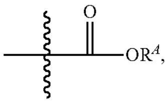, 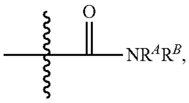,
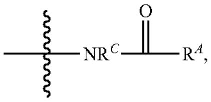, 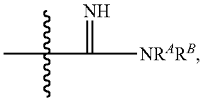,
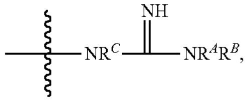, 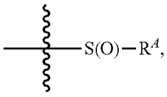,
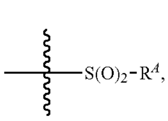, 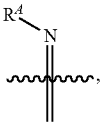,
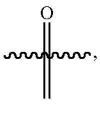, or 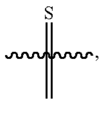, wherein $R^A$, $R^B$, and $R^C$ are, independently at each occurrence, a hydrogen atom, alkyl, alkenyl, alkynyl, aryl, alkylaryl, arylalkyl, heteroalkyl, heteroaryl, or heterocycloalkyl, or $R^A$ and $R^B$ together with the atoms to which they are bonded, form a saturated or unsaturated carbocyclic ring, wherein the ring is optionally substituted, and wherein one or more ring atoms is optionally replaced with a heteroatom. In certain embodiments, when a radical moiety is optionally substituted with an optionally substituted heteroaryl, optionally substituted heterocycloalkyl, or optionally substituted saturated or unsaturated carbocyclic ring, the substituents on the optionally substituted heteroaryl, optionally substituted heterocycloalkyl, or optionally substituted saturated or unsaturated carbocyclic ring, if they are substituted, are not substituted with substituents which are further optionally substituted with additional substituents. In some embodiments, when a group described herein is optionally substituted, the substituent bonded to the group is unsubstituted unless otherwise specified.

As used herein, "binding agent" refers to any molecule, e.g., protein, capable of binding with specificity to a given binding partner, e.g., antigen.

As used herein, "linker" refers to a divalent, trivalent, or multivalent moiety that covalently links the binding agent to one or more compounds described herein, for instance payload compounds and a cyclodextrin group, as described herein.

As used herein, "amide synthesis conditions" refers to reaction conditions suitable to effect the formation of an amide, e.g., by the reaction of a carboxylic acid, activated carboxylic acid, or acyl halide with an amine. In some examples, amide synthesis conditions refer to reaction conditions suitable to effect the formation of an amide bond between a carboxylic acid and an amine. In some of these examples, the carboxylic acid is first converted to an activated carboxylic acid before the activated carboxylic acid reacts with an amine to form an amide. Suitable conditions to effect the formation of an amide include, but are not limited to, those utilizing reagents to effect the reaction between a carboxylic acid and an amine, including, but not limited to, dicyclohexylcarbodiimide (DCC), diisopropylcarbodiimide (DIC), (benzotriazol-1-yloxy)tris(dimethylamino)phosphonium hexafluorophosphate (BOP), (benzotriazol-1-yloxy)tripyrrolidinophosphonium hexafluorophosphate (PyBOP), (7-azabenzotriazol-1-yloxy) tripyrrolidinophosphonium hexafluorophosphate (PyAOP), bromotripyrrolidinophosphonium hexafluorophosphate (PyBrOP), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), 1-[Bis(dimethylamino)methylene]-1H-1,2,3-triazolo[4,5-b] pyridinium 3-oxid hexafluorophosphate (HATU), N-ethoxycarbonyl-2-ethoxy-1,2-dihydroquinoline (EEDQ), N-ethyl-N'-(3-dimethylaminopropyl)carbodiimide (EDC), 2-chloro-1,3-dimethylimidazolidinium hexafluorophosphate (CIP), 2-chloro-4,6-dimethoxy-1,3,5-triazine (CDMT), and carbonyldiimidazole (CDI). In some examples, a carboxylic acid is first converted to an activated carboxylic ester before treating the activated carboxylic ester with an amine to form an amide bond. In certain embodiments, the carboxylic acid is treated with a reagent. The reagent activates the carboxylic acid by deprotonating the carboxylic acid and then forming a product complex with the deprotonated carboxylic acid as a result of nucleophilic attack by the deprotonated carboxylic acid onto the protonated reagent. The activated carboxylic esters for certain carboxylic acids are subsequently more susceptible to nucleophilic attack by an amine than the carboxylic acid is before it is activated. This results in amide bond formation. As such, the carboxylic acid is described as activated. Exemplary reagents include DCC and DIC.

As used herein, "regioisomer," "regioisomers," or "mixture of regioisomers" refers to the product(s) of 1,3-cycloadditions or strain-promoted alkyne-azide cycloadditions (SPAACs)—otherwise known as click reactions—that derive from suitable azides (e.g., $—N_3$, or PEG-$N_3$ derivitized antibodies) treated with suitable alkynes. In certain embodiments, for example, regioisomers and mixtures of regioisomers are characterized by the click reaction products shown below:

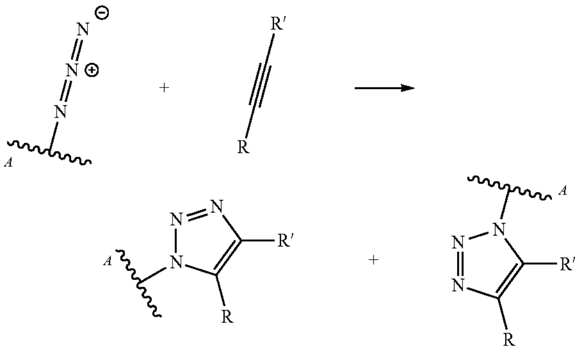

In certain embodiments, more than one suitable azide and more than one suitable alkyne can be utilized within a synthetic process en route to a product, where each pair of azide-alkyne can participate in one or more independent click reactions to generate a mixture of regioisomeric click reaction products. For example, a person of skill will recognize that a first suitable azide may independently react with a first suitable alkyne, and a second suitable azide may independently react with a second suitable alkyne, en route to a product, resulting in the generation of four possible click reaction regioisomers or a mixture of the four possible click reaction regioisomers.

As used herein, the term "residue" refers to the chemical moiety within a compound that remains after a chemical reaction. For example, the term "amino acid residue" or "N-alkyl amino acid residue" refers to the product of an amide coupling or peptide coupling of an amino acid or a N-alkyl amino acid to a suitable coupling partner; wherein, for example, a water molecule is expelled after the amide or peptide coupling of the amino acid or the N-alkylamino acid, resulting in the product having the amino acid residue or N-alkyl amino acid residue incorporated therein.

As used herein, "therapeutically effective amount" refers to an amount (e.g., of a compound) that is sufficient to provide a therapeutic benefit to a patient in the treatment or management of a disease or disorder, or to delay or minimize one or more symptoms associated with the disease or disorder.

Certain groups, moieties, substituents, and atoms are depicted with a wiggly line that intersects a bond or bonds to indicate the atom through which the groups, moieties, substituents, atoms are bonded. For example, a phenyl group that is substituted with a propyl group depicted as:

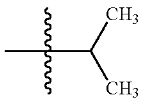 or 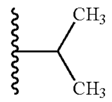

has the following structure:

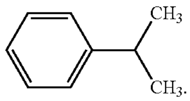

As used herein, illustrations showing substituents bonded to a cyclic group (e.g., aromatic, heteroaromatic, fused ring, and saturated or unsaturated cycloalkyl or heterocycloalkyl) through a bond between ring atoms are meant to indicate, unless specified otherwise, that the cyclic group may be substituted with that substituent at any ring position in the cyclic group or on any ring in the fused ring group, according to techniques set forth herein or which are known in the field to which the instant disclosure pertains. For example, the group,

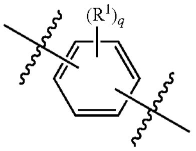 or 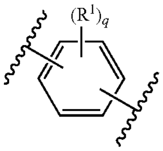 , wherein subscript q is an integer from 0 to 4 and in which the positions of substituent $R^1$ are described generically, i.e., not directly attached to any vertex of the bond line structure, i.e., specific ring carbon atom, includes the following, non-limiting examples of groups in which the substituent $R^1$ is bonded to a specific ring carbon atom:

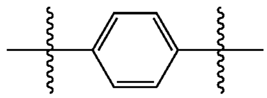, 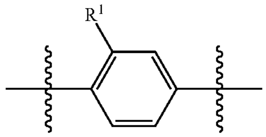,

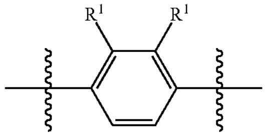, 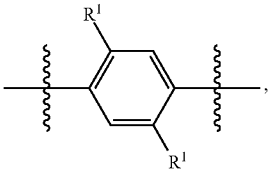,

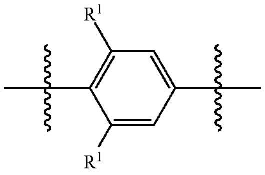, 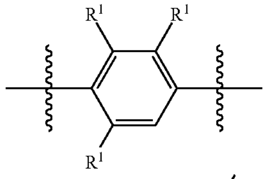,

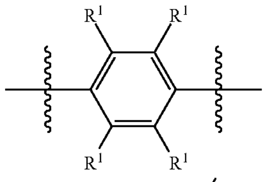, 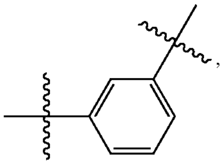,

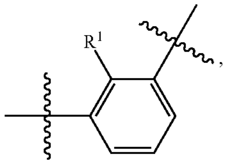, 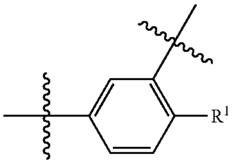,

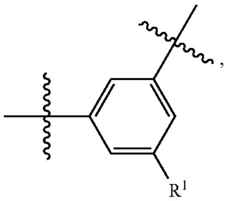, 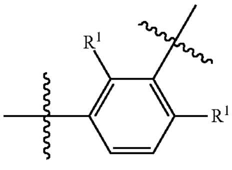,

-continued

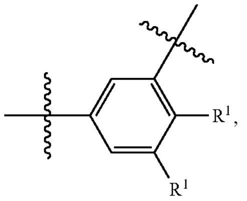
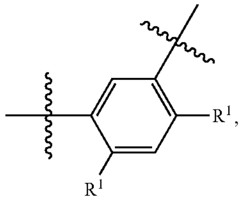
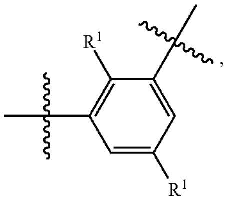
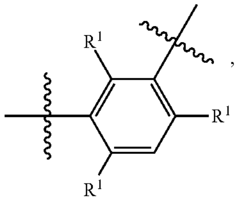
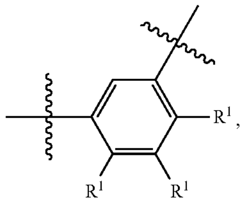
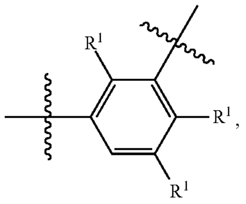
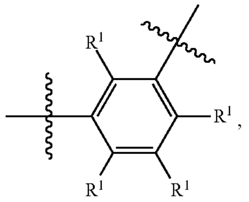
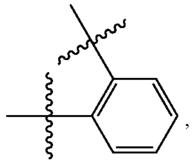
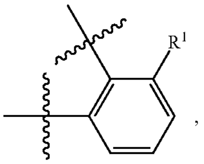
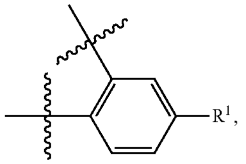
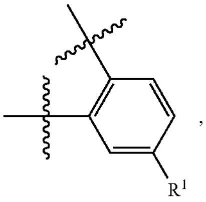
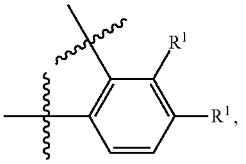
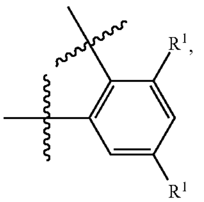
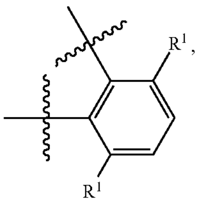
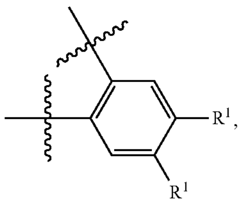
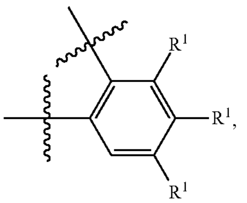

-continued

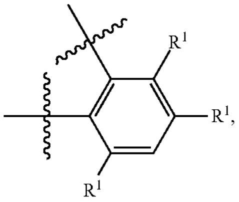
and
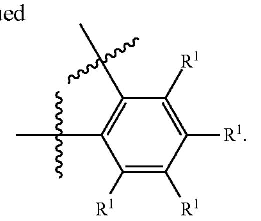

As used herein, the phrase "react linker" refers to a monovalent group that includes a reactive group and spacer group, depicted for example as

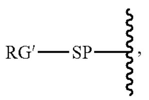

wherein RG' is the reactive group and SP is the spacer group. As described herein, a reactive linker may include more than one reactive group and more than one spacer group. The spacer group is any divalent or trivalent moiety that bridges the reactive group to another group, such as a payload or also to a binding agent. The reactive linkers (RL), together with the payloads to which they are bonded, provide intermediates ("linker-payloads") useful as synthetic precursors for the preparation of the antibody conjugates described herein. The reactive linker contains a reactive group (RG'), which is a functional group or moiety that is capable of reacting with a reactive portion of another group, for instance, an antibody, modified antibody, or antigen binding fragment thereof, or a cyclodextrin group, as described herein. The moiety resulting from the reaction of the reactive group with the antibody, modified antibody, or antigen binding fragment thereof, together with the linking group, includes the "binding agent linker" ("BL") portion of the conjugate, described herein. In certain embodiments, the "reactive group" is a functional group or moiety (e.g., maleimide or N— hydroxysuccinimide (NHS) ester) that reacts with a cysteine or lysine residue of an antibody or antigen-binding fragment thereof. In certain embodiments, the "reactive group" is a functional group or moiety that is capable of undergoing a click chemistry reaction (see, e.g., click chemistry, Huisgen Proc. Chem. Soc. 1961, Wang et al. *J. Am. Chem. Soc.* 2003, and Agard et al. *J. Am. Chem. Soc.* 2004). In some embodiments of said click chemistry reaction, the reactive group is an alkyne that is capable of undergoing a 1,3-cycloaddition reaction with an azide. Such suitable reactive groups include, but are not limited to, strained alkynes, e.g., those suitable for strain-promoted alkyne-azide cycloadditions (SPAAC), cycloalkynes, e.g., cyclooctynes, benzannulated alkynes, and alkynes capable of undergoing 1,3-cycloaddition reactions with alkynes in the absence of copper catalysts. Suitable alkynes also include, but are not limited to, dibenzoazacyclooctyne or

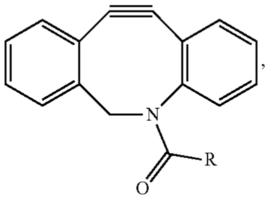
(DIBAC)
for example,
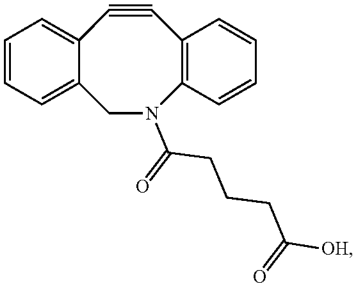 [SMILES: O=C(O)CCCC(=O)N1Cc2ccccc2C#Cc2ccccc21]
dibenzocyclooctyne or
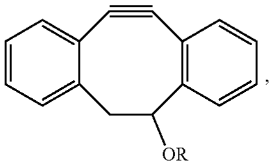
(DIBO)
for example,
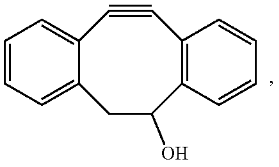 [SMILES: OC1Cc2ccccc2C#Cc2ccccc21]
biarylazacyclooctynone or
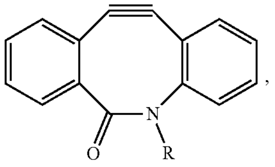
(BARAC)
for example,
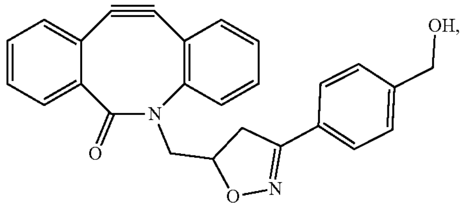 [SMILES: O=C1c2ccccc2C#Cc2ccccc2N1CC1CC(c2ccc(CO)cc2)=NO1]
difluorinated cyclooctyne
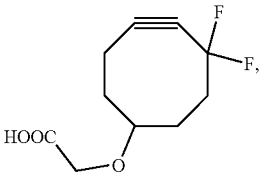
or
(DIFO)
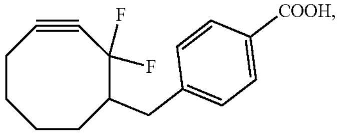
or
(DIFO2)
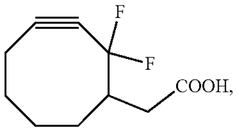
(DIFO3)
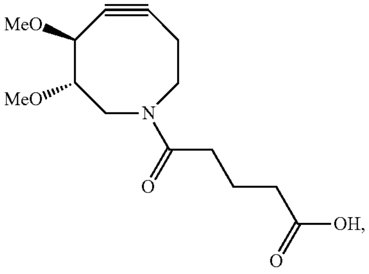
(DIMAC)
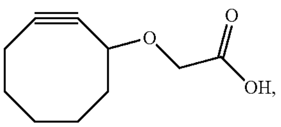
(ALO)
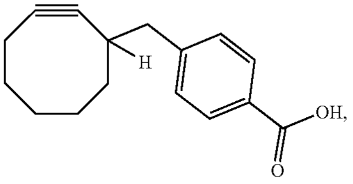
(NOFO)

-continued

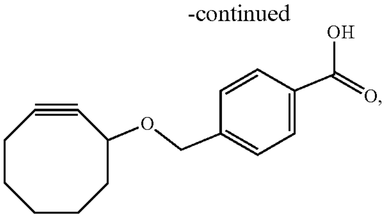

and (OCT)

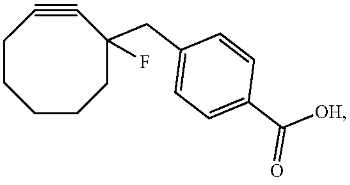

(MOFO)

substituted, e.g., fluorinated alkynes, aza-cycloalkynes, bicycle[6.1.0]nonyne or

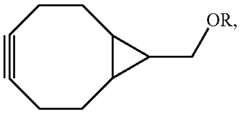

(BCN)

where R is alkyl, alkoxy, or acyl, and derivatives thereof, for example,

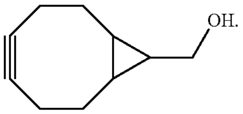 [SMILES: OCC1C2CCC#CCCC12]

Particularly useful alkynes include

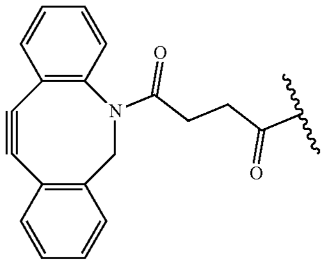

and

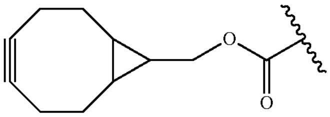

.

Linker-payloads including such reactive groups are useful for conjugating antibodies that have been functionalized with azido groups. Such functionalized antibodies include antibodies functionalized with azido-polyethylene glycol groups. In certain embodiments, such a functionalized antibody is derived by treating an antibody having at least one glutamine residue, e.g., Gln295, Asn297Gln, and/or Gln55, with a compound bearing an amino group and an azide group, in the presence of the enzyme transglutaminase.

In some examples, the alkyne used in the bioconjugation reaction is useful for Cu(I) click-chemistry conjugation reaction. In some examples, the alkyne used in the conjugation reaction reacts with 1,2 aminothiol in the CBT reaction. In some examples, the alkyne used is BCN, derivative of BCN, or trans-cyclooctene (TCOs) in an inverse electron demand Diels Alder reactions. See, for example, *J. Am. Chem. Soc.*; (Article), 2012, 134 (6), 2950-2953.

In some examples, the reactive group is an alkyne, e.g.,

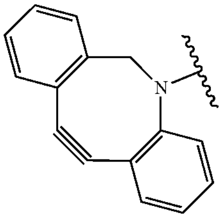

, which can react via click chemistry with an azide, e.g.,

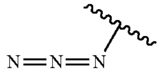

, to form a click chemistry product, e.g.,

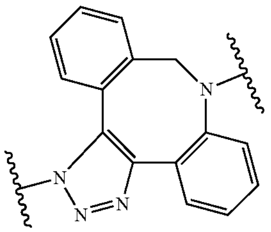

or

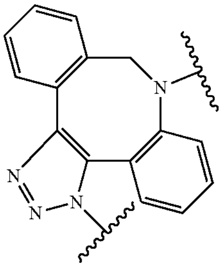

.

In some examples, the group reacts with an azide on a modified antibody or antigen binding fragment thereof. In some examples, the reactive group is an alkyne, e.g.,

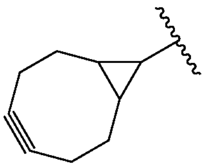

, which can react via click chemistry with an azide, e.g.,

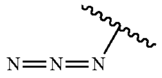

to form a click chemistry product, e.g.,

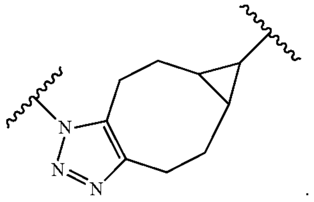 [SMILES: *C1C2CCc3nnn(*)c3CCC12 ; "."]

In some examples, the reactive group is an alkyne, e.g.,

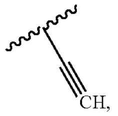 [SMILES: *C#C]

which can react via click chemistry with an azide, e.g.,

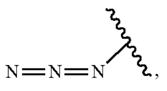

to form a click chemistry product, e.g.,

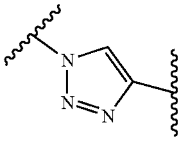 or 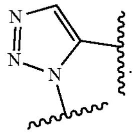

In some examples, the reactive group is a functional group, e.g.,

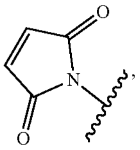

which reacts with a cysteine residue on an antibody or antigen-binding fragment thereof, to form a bond thereto, e.g.,

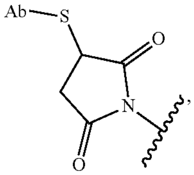

wherein Ab refers to an antibody or antigen-binding fragment thereof and S refers to the S atom on a cysteine residue through which the functional group bonds to the Ab. In some examples, the reactive group is a functional group, e.g.

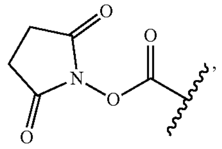 [SMILES: *C(=O)ON1C(=O)CCC1=O]

which reacts with a lysine residue on an antibody or antigen-binding fragment thereof, to form a bond thereto, e.g.,

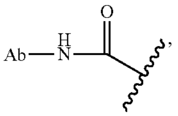

wherein Ab refers to an antibody or antigen-binding fragment thereof and NH refers to the NH atom on a lysine side chain residue through which the functional group bonds to the Ab.

As used herein, the phrase "binding agent linker," or "BL" refers to any divalent, trivalent, or multi-valent group or moiety that links, connects, or bonds a binding agent (e.g., an antibody or an antigen-binding fragment thereof) with a payload compound set forth herein (e.g., MMAE, bis-octahydrophenanthrene carboxamides) and, optionally, with one or more side chain compounds. Generally, suitable binding agent linkers for the antibody conjugates described herein are those that are sufficiently stable to exploit the circulating half-life of the antibody and, at the same time, capable of releasing its payload after antigen-mediated internalization of the conjugate. Linkers can be cleavable or non-cleavable. Cleavable linkers are linkers that are cleaved by intracellular metabolism following internalization, e.g., cleavage via hydrolysis, reduction, or enzymatic reaction. Non-cleavable linkers are linkers that release an attached payload via lysosomal degradation of the antibody following internalization. Suitable linkers include, but are not limited to, acid-labile linkers, hydrolysis-labile linkers, enzymatically cleavable linkers, reduction labile linkers, self-immolative linkers, and non-cleavable linkers. Suitable linkers also include, but are not limited to, those that are or comprise peptides, glucuronides, succinimide-thioethers, polyethylene glycol (PEG) units, hydrazones, mal-caproyl units, dipeptide units, valine-citrulline units, and para-aminobenzyl (PAB) units. In some embodiments, the binding agent linker (BL) includes a moiety that is formed by the reaction of the reactive group (RG) of a reactive linker (RL) and reactive portion of the binding agent, e.g., antibody, modified antibody, or antigen binding fragment thereof.

In some examples, the BL includes the following moiety:

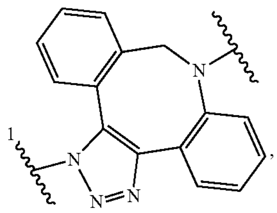, wherein  is the bond to the binding agent. In some examples, the BL includes the following moiety:

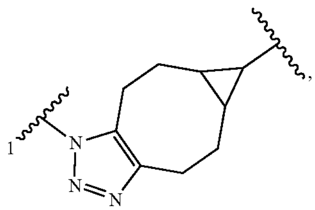, wherein 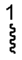 is the bond to the binding agent. In some examples, the BL includes the following moiety:

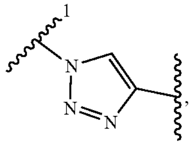, wherein  is the bond to the binding agent. In some examples, the BL includes the following moiety:

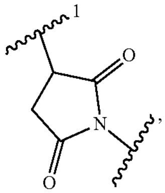, wherein  is the bond to the cysteine of the antibody or antigen-binding fragment thereof. In some examples, the BL includes the following moiety:

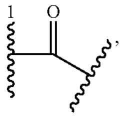, wherein  is the bond to the lysine of the antibody or antigen-binding fragment thereof.

Compounds and Payloads

In some examples, set forth herein is a compound, or a pharmaceutically acceptable salt thereof, comprising: a binding agent linked to at least one payload moiety and linked to at least one cyclodextrin moiety via a covalent linker, wherein said covalent linker is bonded directly or indirectly to each of the binding agent, the payload moiety, and the cyclodextrin moiety.

In some other examples, set forth herein is a compound, or a pharmaceutically acceptable salt thereof, comprising: a protein linked to at least one payload moiety and linked to at least one cyclodextrin moiety via a covalent linker, wherein said covalent linker is bonded directly or indirectly to each of the binding agent, the payload moiety, and the cyclodextrin moiety.

As illustrated herein, in some examples, the binding agent is bonded directly to a covalent linker, such as a lysine amino acid. This means that the binding agent is one bond position away from the lysine amino acid covalent linker. In some of these examples, the covalent linker is also bonded directly to a payload moiety. This means that the covalent linker is one bond position away from a payload such as, but not limited to, MMAE, a steroid, or any payload set forth herein. In some of these examples, the covalent linker is also bonded directly to a cyclodextrin moiety. This means that the covalent linker is one bond position away from a cyclodextrin, such as the cyclodextrins set forth herein. In some of these examples, the covalent linker is a lysine amino acid or a derivative thereof.

In other examples, the binding agent is bonded indirectly to a covalent linker. This means that the binding agent is more than one bond position away from the covalent linker. This also means that the binding agent is bonded through another moiety to the covalent linker. For example, the binding agent may be bonded to a maleimide group which is bonded to a polyethylene glycol group which is bonded to the covalent linker. In some of these examples, the covalent linker is also bonded indirectly to a payload moiety. This means that the covalent linker is more than one bond position away from a payload such as, but not limited to, MMAE, or a steroid, or any payload set forth herein. This also means that the covalent linker is bonded through another moiety to the payload. For example, the covalent linker may be bonded to a dipeptide, such as but not limited to Val-Ala or Val-Cit, which may be bonded to PAB which may be bonded to the payload. In some of these examples, the covalent linker is also bonded indirectly to a cyclodextrin moiety. This means that the covalent linker is more than one bond position away from a cyclodextrin, such as the cyclodextrins set forth herein. This also means that the covalent linker is bonded through another moiety to the cyclodextrin. For example, the covalent linker may be bonded to a polyethylene glycol group which may be bonded to reactive group which may be bonded to the cyclodextrin. In some of these examples, the covalent linker is a lysine amino acid or a derivative thereof.

In one example, set forth herein is a compound according to Formula (I):

(I)

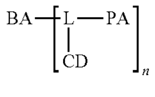

In Formula (I), BA is a binding agent, L is a trivalent linker, CD is a cyclodextrin residue, subscript n is an integer from 1 to 30, and PA is a payload residue. In some examples, more than one trivalent linker, L, may be present. In certain embodiments, n is from 1 to 4. In certain embodiments, n is 4. In certain embodiments, n is 2. In certain embodiments, n is 1. In certain embodiments, n is 3.

In some examples, the compound according to Formula (I) is a compound according to Formula (Ia):

(Ia)

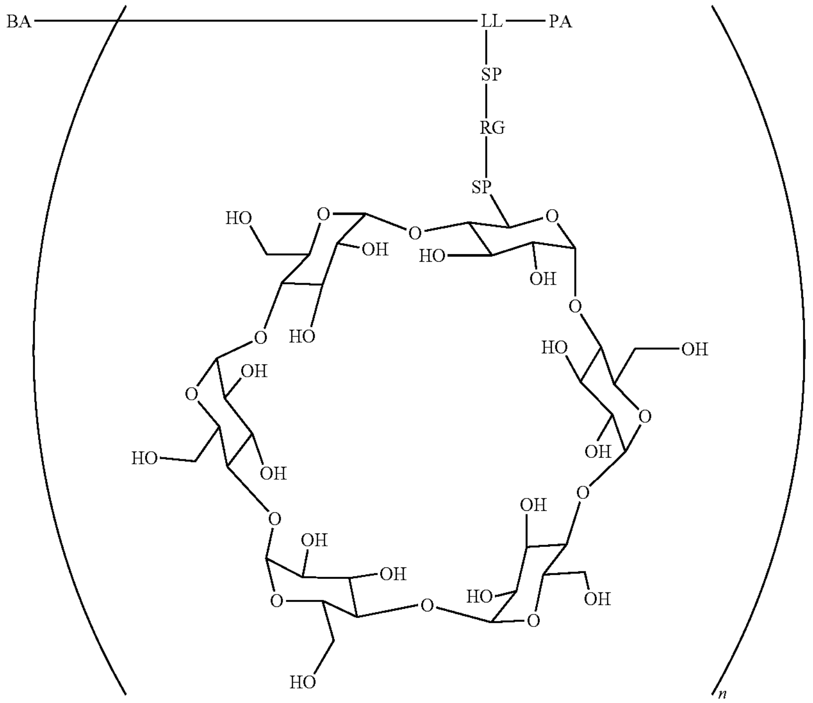

In Formula (Ia), BA is a binding agent, LL is a trivalent linker, RG is a reactive linker residue, SP is, independently in each instance, absent or a spacer group, subscript n is an integer from 1 to 30; and PA is a payload. In certain embodiments, n is from 1 to 4. In certain embodiments, n is 4. In certain embodiments, n is 2. In certain embodiments, n is 1. In certain embodiments, n is 3.

In some examples, the compound according to Formula (I) is a compound according to Formula (Ib) or (Ic):

(Ib)

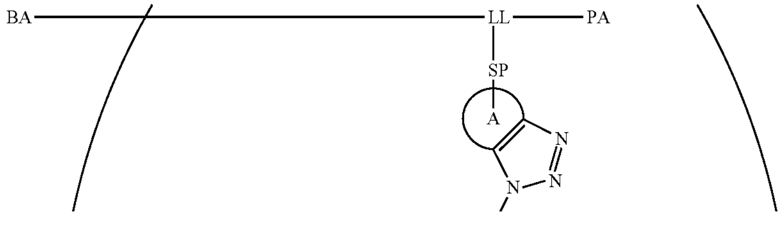

-continued

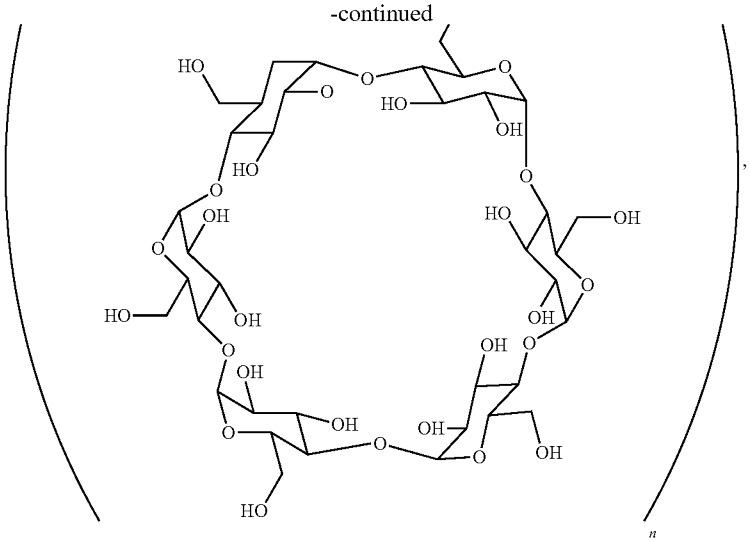

, (Ia)

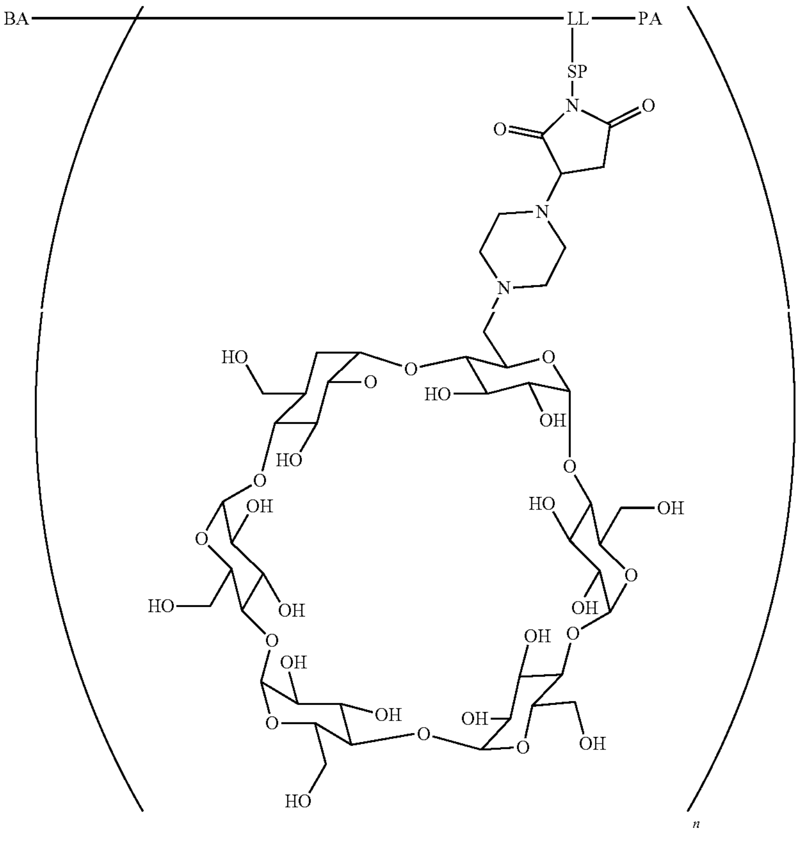

.

In either Formula (Ib) or (Ic), BA is a binding agent, LL is a trivalent linker. SP is, independently in each instance, absent or is a spacer, ring A is fused to the triazole and is selected from the group consisting of cycloalkyl, cycloalkenyl, heterocycloalkyl, and heterocycloalkenyl, wherein cycloalkyl, cycloalkenyl, heterocycloalkyl, and heterocycloalkenyl, are optionally substituted with alkyl, OH, or $NR^aR^b$, where each of $R^a$ and $R^b$ is alkyl or H, n is an integer from 1 to 30, and PA is a payload. In some examples, ring A is an optionally substituted cycloalkyl. In some examples, ring A is an optionally substituted cylcoalkenyl. In some examples, ring A is an optionally substituted cycloalkynyl. In some examples, ring A is an optionally substituted heterocycloalkyl. In some examples, ring A is an optionally substituted heterocycloalkynyl. In some examples, included in either Formula (Ib) or (Ic) are the regioisomers, stereoisomers, and mixtures thereof of the compounds of either Formula (Ib) or (Ic).

In some examples, the compound according to Formula (I) is a compound according to Formula (Ib). In certain of these examples, the compound according to Formula (Ib), is a compound according to Formula (Ib1), (Ib2), (Ib3), (Ib4), (Ib5), or (b6). In some of these examples, to Formula (Ib), is a compound according to Formula (Ib1):

(Ib1)

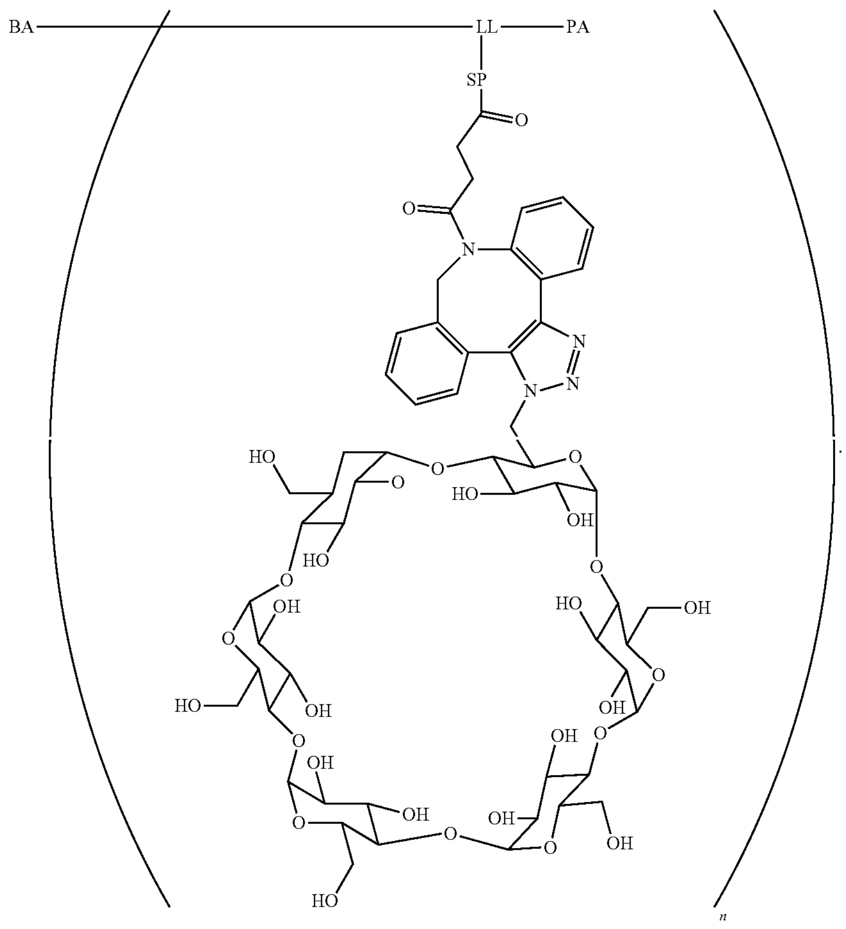

In Formula (Ib1), BA is a binding agent, LL is a trivalent linker, SP is, independently in each instance, absent or is a spacer, n is an integer from 1 to 30, and PA is a payload. Also included in Formula (Ib1) are regioisomers (e.g., with respect to the triazole linkage), stereoisomers, and mixtures thereof. In certain embodiments, n is from 1 to 4. In certain embodiments, n is 4. In certain embodiments, n is 2. In certain embodiments, n is 1. In certain embodiments, n is 3.

In some of these examples, to Formula (Ib), is a compound according to Formula formula (Ib2):

(Ib2)

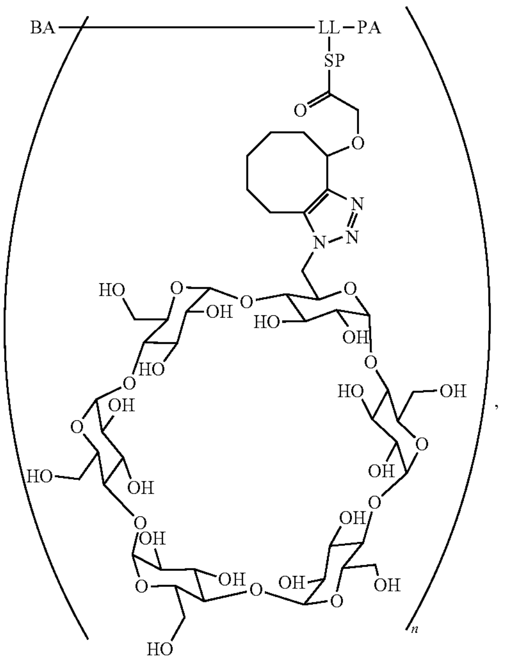

In Formula (Ib2), BA is a binding agent, LL is a trivalent linker, SP is, independently in each instance, absent or is a spacer, n is an integer from 1 to 30, and PA is a payload. Also included in Formula (Ib2) are regioisomers (e.g., with respect to the triazole linkage), stereoisomers, and mixtures thereof. In certain embodiments, n is from 1 to 4. In certain embodiments, n is 4. In certain embodiments, n is 2. In certain embodiments, n is 1. In certain embodiments, n is 3.

In some of these examples, to Formula (Ib), is a compound according to Formula formula (Ib3):

(Ib3)

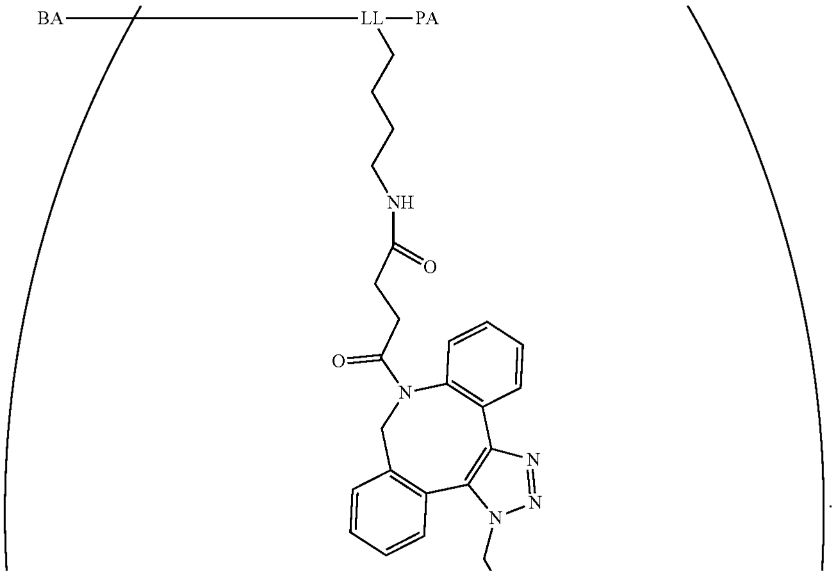

-continued

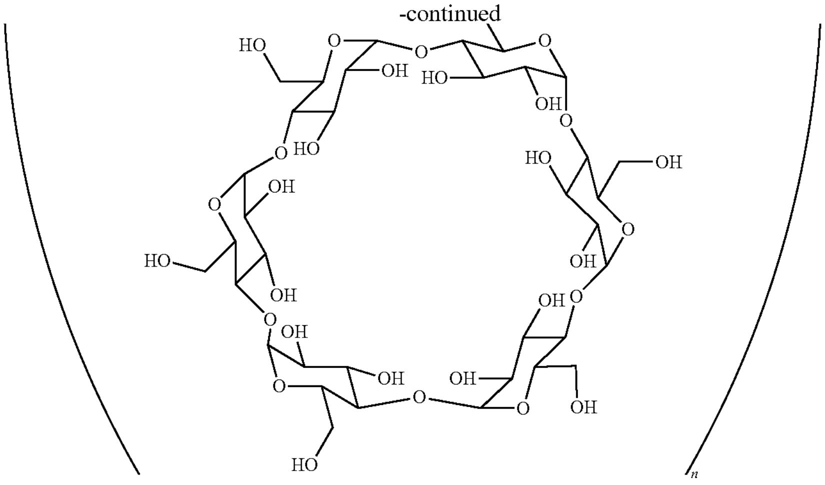

In Formula (Ib3), BA is a binding agent, LL is a trivalent linker, n is an integer from 1 to 30, and PA is a payload. Also included in Formula (Ib3) are regioisomers (e.g., with respect to the triazole linkage), stereoisomers, and mixtures thereof. In certain embodiments, n is from 1 to 4. In certain embodiments, n is 4. In certain embodiments, n is 2. In certain embodiments, n is 1. In certain embodiments, n is 3.

In some of these examples, to Formula (Ib), is a compound according to Formula (Ib4):

(Ib4)

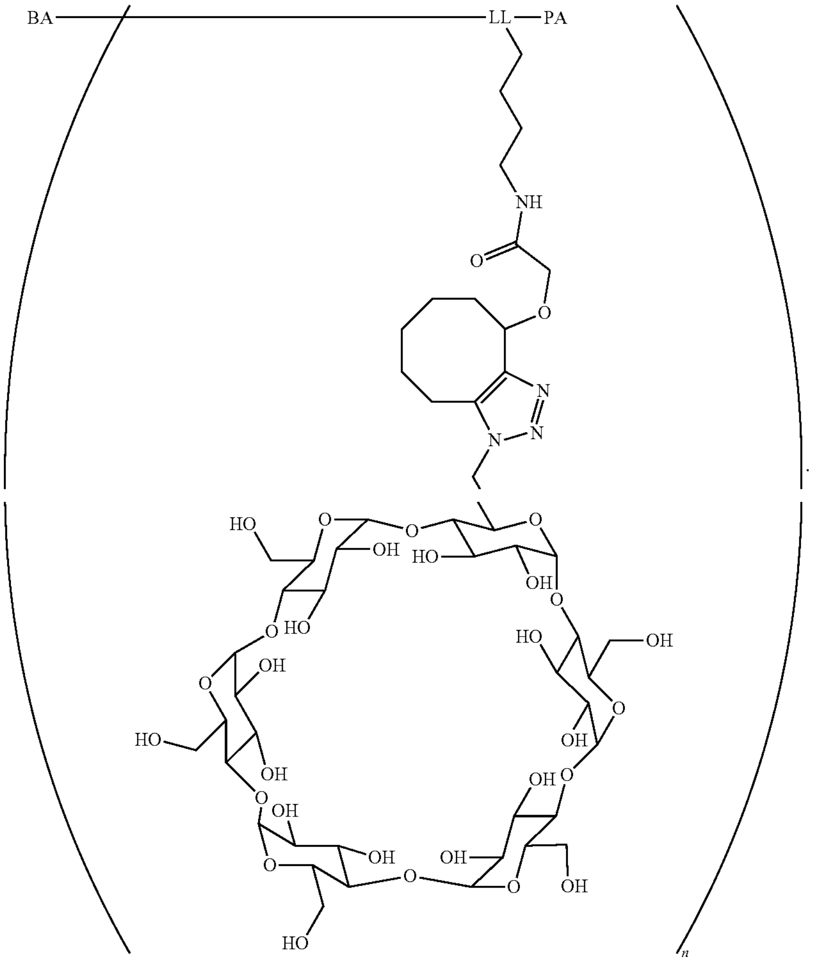

In Formula (Ib4), BA is a binding agent, LL is a trivalent linker, n is an integer from 1 to 30, and PA is a payload. Also included in Formula (Ib4) are regioisomers (e.g., with respect to the triazole linkage), stereoisomers, and mixtures thereof. In certain embodiments, n is from 1 to 4. In certain embodiments, n is 4. In certain embodiments, n is 2. In certain embodiments, n is 1. In certain embodiments, n is 3

In some of these examples, to Formula (Ib), is a compound according to Formula (Ib5):

(Ib5)

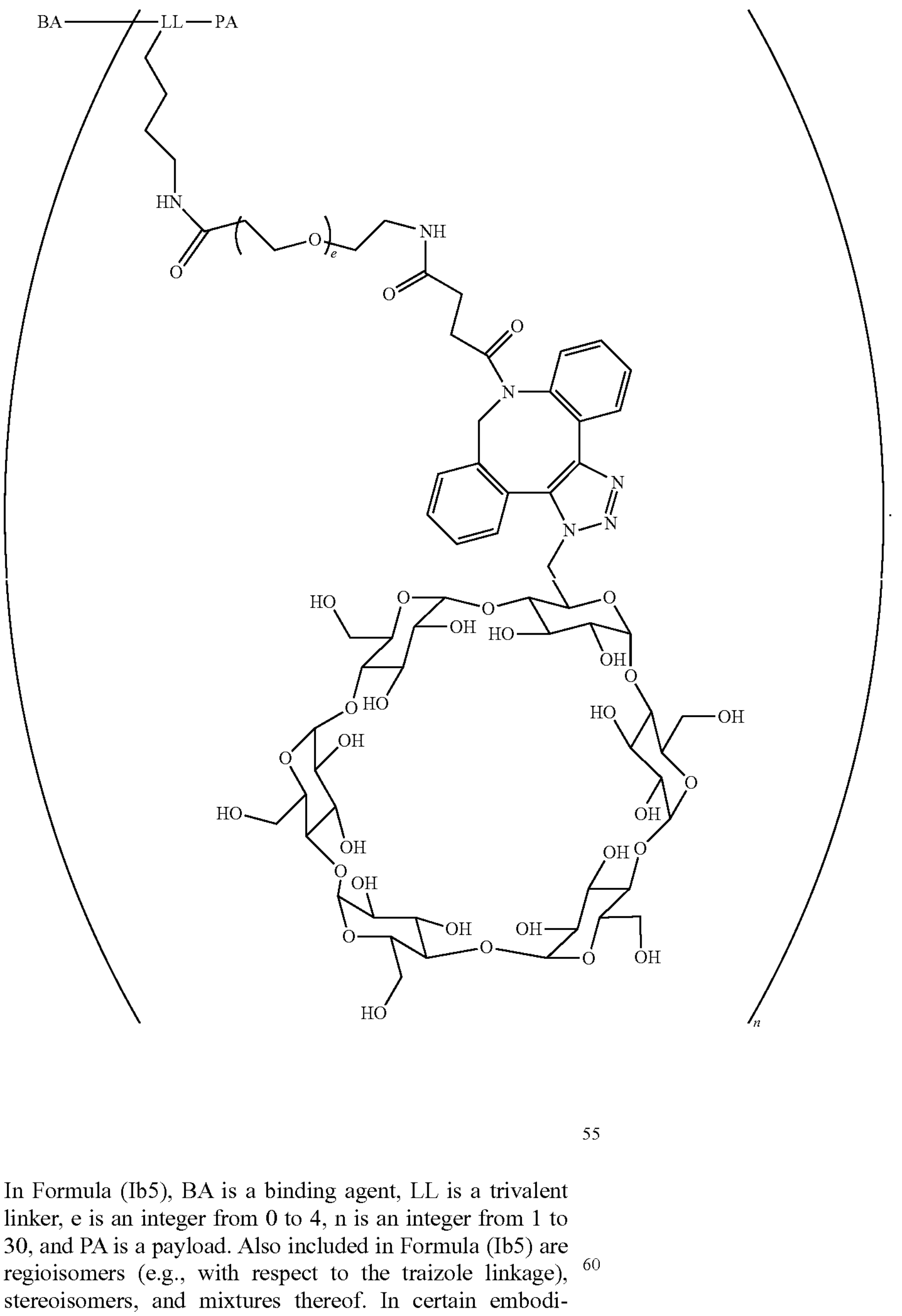

In Formula (Ib5), BA is a binding agent, LL is a trivalent linker, e is an integer from 0 to 4, n is an integer from 1 to 30, and PA is a payload. Also included in Formula (Ib5) are regioisomers (e.g., with respect to the traizole linkage), stereoisomers, and mixtures thereof. In certain embodiments, n is from 1 to 4. In certain embodiments, n is 4. In certain embodiments, n is 2. In certain embodiments, n is 1. In certain embodiments, n is 3.

In some of these examples, to Formula (Ib), is a compound according to Formula (Ib6):

(Ib6)

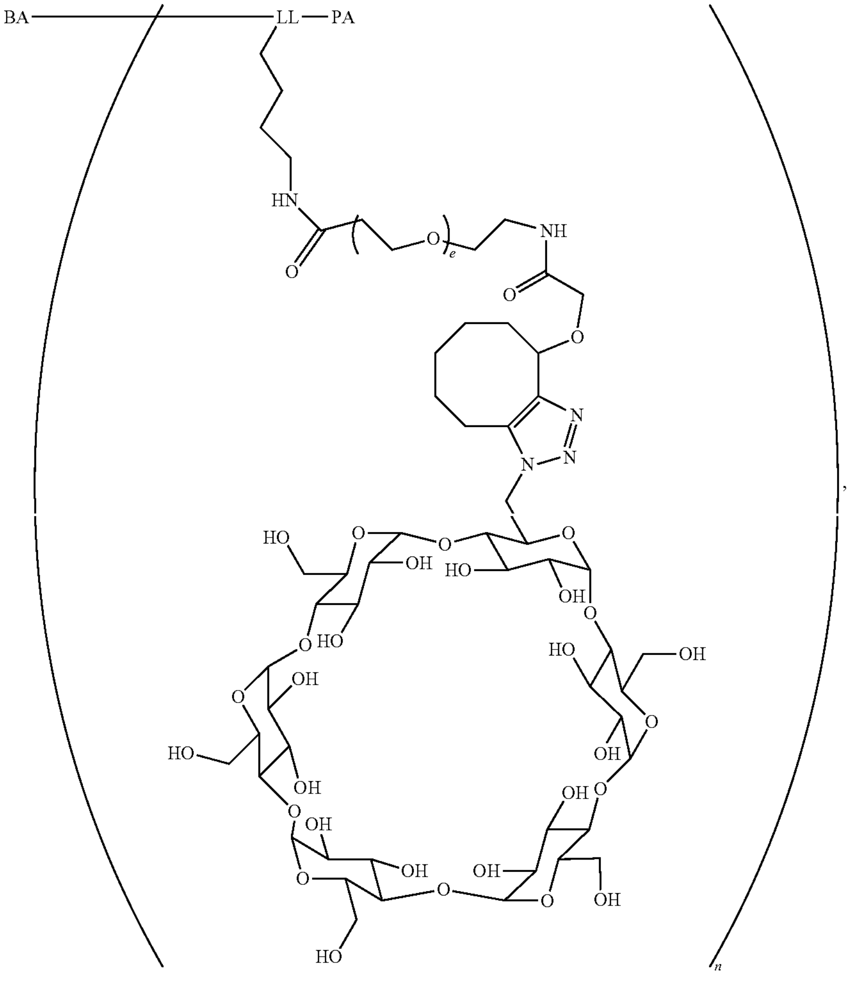

In Formula (b6), BA is a binding agent, LL is a trivalent linker, e is an integer from 0 to 4, n is an integer from 1 to 30, and PA is a payload. Also included in Formula (b6) are regioisomers (e.g., with respect to the traizole linkage), stereoisomers, and mixtures thereof. In certain embodiments, n is from 1 to 4. In certain embodiments, n is 4. In certain embodiments, n is 2. In certain embodiments, n is 1. In certain embodiments, n is 3.

In some examples, the compound according to Formula (I) is a compound according to Formula (Ic). In some of these examples, the compound according to Formula (Ic) is a compound according to Formula (Ic1):

(Ic1)

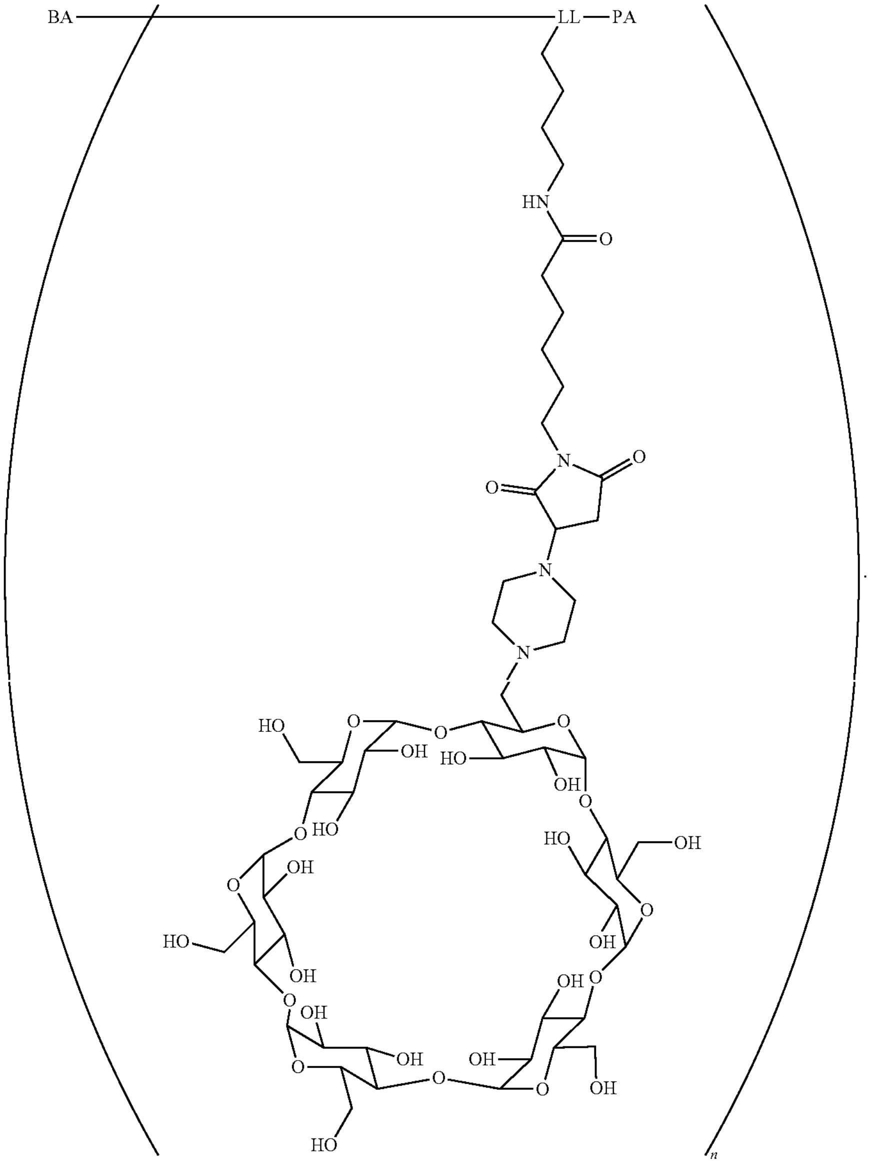

In Formula (I1), BA is a binding agent, LL is a trivalent linker, n is an integer from 1 to 30, and PA is a payload. Also included in Formula (Ic1) are regioisomers, stereoisomers, and mixtures thereof. In certain embodiments, n is from 1 to 4. In certain embodiments, n is 4. In certain embodiments, n is 2. In certain embodiments, n is 1. In certain embodiments, n is 3.

In some examples, set forth herein is a compound according to Formula (Id):

(Id)

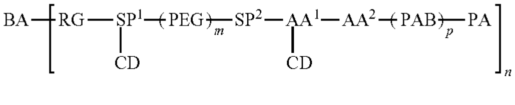

In Formula (Id), BA is a binding agent; RG is a reactive group residue; $SP^1$ and $SP^2$ are each, independently in each instance, absent or a spacer group residue, and wherein $SP^1$ comprises a trivalent linker; $AA^1$ is a trivalent linker comprising an amino acid residue; $AA^2$ is a di-peptide residue; PEG is a polyethylene glycol residue; PAB is

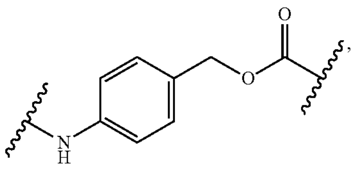 [SMILES: *Nc1ccc(COC(*)=O)cc1]

wherein the

indicates the atom through which the PAB is bonded to the adjacent groups in the formula, CD is, independently in each instance, absent or a cyclodextrin residue, wherein at least one CD is present, subscript n is an integer from 1 to 30; subscript m is an integer from 0 to 5; subscript p is 0 or 1; and PA is a payload moiety. In these examples, subscript m is 0, 1, 2, 3, 4, or 5. In some examples, subscript m is 0. In some examples, subscript m is 1. In some examples, subscript m is 2. In some examples, subscript m is 3. In some examples, subscript m is 4. In some examples, subscript m is 5. In some examples, subscript p is 0. In some examples, subscript p is 1. In some examples, any one of $AA^1$ or $AA^2$ comprises, independently in each instance, an amino acid selected from alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or a combination thereof. In certain embodiments, $AA^1$ is an amino acid selected from alanine, valine, leucine, isoleucine, methionine, tryptophan, phenylalanine, proline, glycine, serine, threonine, cysteine, tyrosine, asparagine, glutamine, aspartic acid, glutamic acid, lysine, arginine, histidine, or citrulline, a derivative thereof, or a combination thereof. In certain embodiments, $AA^1$ is lysine. In certain embodiments, $AA^1$ is lysine or a derivative of lysine. In certain embodiments, the $AA^2$ is valine-citrulline. In some embodiments, the $AA^2$ is citrulline-valine. In some embodiments, the $AA^2$ is valine-alanine. In some embodiments, the $AA^2$ is alanine-valine. In some embodiments, the $AA^2$ is valine-glycine. In some embodiments, the $AA^2$ is glycine-valine. In some embodiments, the $AA^1$-$AA^2$ glutamine-valine-citrulline. In some embodiments, the $AA^1$-$AA^2$ is glutamine-valine-citrulline. In some embodiments, the $AA^1$-$AA^2$ is lysine-valine-alanine. In some embodiments, the $AA^1$-$AA^2$ is lysine-valine-citrulline. In some embodiments, the $AA^1$-$AA^2$ is glutamine-valine-citrulline. In certain embodiments, the lysine is L-lysine. In certain embodiments, the lysine is D-lysine. In some examples, $SP^1$ is independently in each instance, selected from the group consisting of $C_{1-6}$ alkylene, —NH—, —C(O)—, $(—CH_2—CH_2—O)_e$, $—NH—CH_2—CH_2—(—O—CH_2—CH_2)_e—C(O)—$, $—C(O)—(CH_2)$, —C(O)—, $—C(O)—NH—(CH_2)_b—$, and combinations thereof, wherein subscript e is an integer from 0 to 4, subscript u is an integer from 1 to 8, and subscript v is an integer from 1 to 8. In some examples, $SP^2$ is independently in each instance, selected from the group consisting of $C_{1-6}$ alkylene, —NH—, —C(O)—, $(—CH_2—CH_2—O)_e$, $—NH—CH_2—CH_2—(—O—CH_2—CH_2)_e—C(O)—$, $—C(O)—(CH_2)_u—C(O)—$, $—C(O)—NH—(CH_2)_v—$, and combinations thereof, wherein subscript e is an integer from 0 to 4, subscript u is an integer from 1 to 8, and subscript v is an integer from 1 to 8.

In some instances of Formula (Id), CD is a modified-CD group according to the structure:

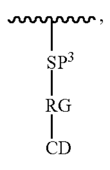

wherein RG is, independently in each instance; a reactive linker residue, $SP^3$ is, independently in each instance, absent or a spacer group residue selected from the group consisting of $C_{1-6}$ alkylene, —NH—, —C(O)—, $(—CH_2—CH_2—O)_e$, $—NH—CH_2—CH_2—(—O—CH_2—CH_2)_e—C(O)—$, $—C(O)—(CH_2)_u—C(O)—$, $—C(O)—NH—(CH_2)—$, and combinations thereof, wherein subscript e is an integer from 0 to 4, subscript u in integer from 1 to 8, and subscript v is an integer from 1 to 8; q is an integer from 0 to 5, and

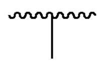

represents the atom through which the modified-CD group is attached to $SP^1$ or $AA^1$.

In some examples, set forth herein is a compound according to Formula (Ie):

(Ie)

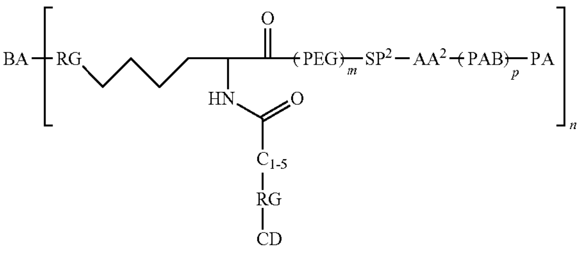

In Formula (Ie), BA is a binding agent; RG is, independently in each instance, a reactive linker residue; $SP^2$ is, independently in each instance, absent or a spacer group residue; $AA^2$ is a di-peptide residue; PEG is a polyethylene glycol residue; PAB is

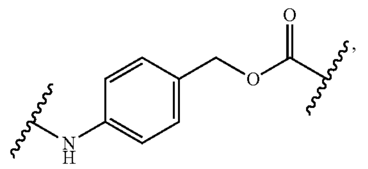 [SMILES: *Nc1ccc(COC(*)=O)cc1]

wherein the

indicates the atom through which the PAB is bonded to the adjacent groups in the formula, CD is a cyclodextrin residue; subscript n is an integer from 1 to 30; subscript m is an integer from 0 to 5; subscript p is 0 or 1; and PA is a payload moiety. In these examples, subscript m is 0, 1, 2, 3, 4, or 5. In some examples, subscript m is 0. In some examples, subscript m is 1. In some examples, subscript m is 2. In some examples, subscript m is 3. In some examples, subscript m is 4. In some examples, subscript m is 5. In some examples, subscript p is 0. In some examples, subscript p is 1. In some examples, any one of $AA^1$ or $AA^2$ comprises, independently in each instance, an amino acid selected from alanine, valine, leucine, isoleucine, methionine, tryptophan, phenylalanine, proline, glycine, serine, threonine, cysteine, tyrosine, asparagine, glutamine, aspartic acid, glutamic acid, lysine, arginine, histidine, or citrulline, a derivative thereof, or a combination thereof. In certain embodiments, the $AA^2$ is valine-citrulline. In some embodiments, the $AA^2$ is citrulline-valine. In some embodiments, the $AA^2$ is valine-alanine. In some embodiments, the $AA^2$ is alanine-valine. In some embodiments, the $AA^2$ is valine-glycine. In some embodiments, the $AA^2$ is glycine-valine. In some embodiments, the $AA^2$ is glutamine-valine-citrulline. In some embodiments, the $AA^2$ is glutamine-valine-citrulline. In some embodiments, the $AA^2$ is lysine-valine-alanine. In some embodiments, the $AA^2$ is lysine-valine-citrulline. In some embodiments, the $AA^2$ is glutamine-valine-citrulline. In some examples, $SP^2$ is independently in each instance, selected from the group consisting of $C_{1-6}$ alkylene, $—NH—$, $—C(O)—$, $(—CH_2—CH_2—O)_e$, $—NH—CH_2—CH_2—(—O—CH_2—CH_2)_e—C(O)—$, $—C(O)—(CH_2)_u—C(O)—$, $—C(O)—NH—(CH_2)_v—$, and combinations thereof, wherein subscript e is an integer from 0 to 4, subscript u is an integer from 1 to 8, and subscript v is an integer from 1 to 8.

In some examples, the compound according to Formula (Ie) is a compound according to Formula (Ie1):

(Ie1)

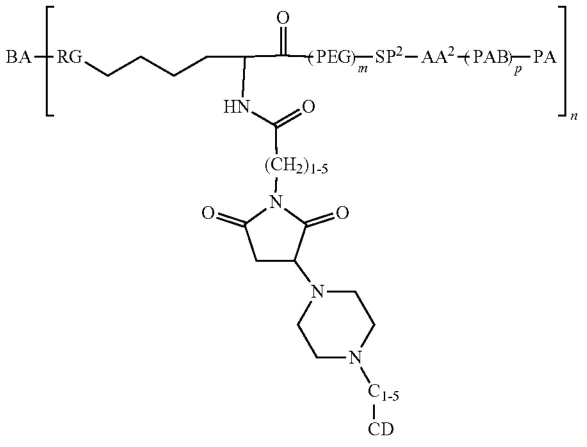

In Formula (Ie1) BA is a binding agent; RG is a reactive linker residue; $SP^2$ is, independently in each instance, absent or a spacer group residue; $AA^2$ is a di-peptide residue; PEG is a polyethylene glycol residue; PAB is

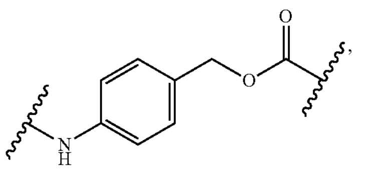 [SMILES: *Nc1ccc(COC(*)=O)cc1]

wherein the

indicates the atom through which the PAB is bonded to the adjacent groups in the formula; CD is a cyclodextrin residue; subscript n is an integer from 1 to 30, subscript m is an integer from 0 to 5, subscript p is 0 or 1, and PA is a payload moiety. In these examples, subscript m is 0, 1, 2, 3, 4, or 5. In some examples, subscript m is 0. In some examples, subscript m is 1. In some examples, subscript m is 2. In some examples, subscript m is 3. In some examples, subscript m is 4. In some examples, subscript m is 5. In some examples, subscript p is 0. In some examples, subscript p is 1. In some examples, $AA^2$ comprises an amino acid selected from alanine, valine, leucine, isoleucine, methionine, tryptophan, phenylalanine, proline, glycine, serine, threonine, cysteine, tyrosine, asparagine, glutamine, aspartic acid, glutamic acid, lysine, arginine, histidine, or citrulline, a derivative thereof, or a combination thereof. In certain embodiments, the $AA^2$ is valine-citrulline. In some embodiments, the $AA^2$ is citrulline-valine. In some embodiments, the $AA^2$ is valine-alanine. In some embodiments, the $AA^2$ is alanine-valine. In some embodiments, the $AA^2$ is valine-glycine. In some embodiments, the $AA^2$ is glycine-valine.

In some examples, the compound according to Formula (Ie) is a compound according to Formula (Ie2):

(Ie2)

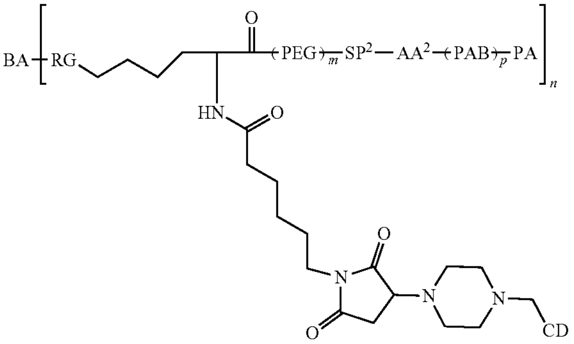

In Formula (Ie2), BA is a binding agent; RG is a reactive linker residue; $SP^2$ is, independently in each instance, absent or a spacer group residue; $AA^2$ is a di-peptide residue; PEG is a polyethylene glycol residue; PAB is

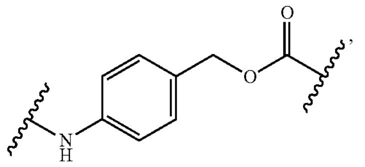 [SMILES: *Nc1ccc(COC(*)=O)cc1]

wherein the

indicates the atom through which the PAB is bonded to the adjacent groups in the formula; CD is a cyclodextrin residue; subscript n is an integer from 1 to 30; subscript m is an integer from 0 to 5; subscript p is 0 or 1; and PA is a payload moiety. In these examples, subscript m is 0, 1, 2, 3, 4, or 5.

In some examples, subscript m is 0. In some examples, subscript m is 1. In some examples, subscript m is 2. In some examples, subscript m is 3. In some examples, subscript m is 4. In some examples, subscript m is 5. In some examples, subscript p is 0. In some examples, subscript p is 1. In some examples, $AA^2$ comprises an amino acid selected from alanine, valine, leucine, isoleucine, methionine, tryptophan, phenylalanine, proline, glycine, serine, threonine, cysteine, tyrosine, asparagine, glutamine, aspartic acid, glutamic acid, lysine, arginine, histidine, or citrulline, a derivative thereof, or a combination thereof. In certain embodiments, the $AA^2$ is valine-citrulline. In some embodiments, the $AA^2$ is citrulline-valine. In some embodiments, the $AA^2$ is valine-alanine. In some embodiments, the $AA^2$ is alanine-valine. In some embodiments, the $AA^2$ is valine-glycine. In some embodiments, the $AA^2$ is glycine-valine.

In some examples, set forth herein is a compound of Formula (If):

(If)

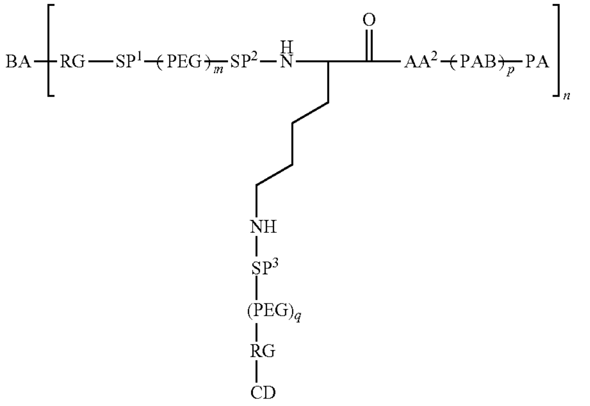

In Formula (If), BA is a binding agent; RG is, independently in each instance; a reactive linker residue, $SP^1$, $SP^2$, and $SP^3$ are each, independently in each instance, absent or a spacer group residue; $AA^2$ is a di-peptide residue; PEG is a polyethylene glycol residue; PAB is

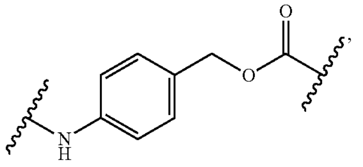 [SMILES: *Nc1ccc(COC(*)=O)cc1]

wherein the

indicates the atom through which the PAB is bonded to the adjacent groups in the formula; CD is a cyclodextrin residue; subscript n is an integer from 1 to 30, subscript m is an integer from 0 to 5, subscript p is 0 or 1, subscript q is an integer from 0 to 5; and PA is a payload moiety. In some examples of Formula (If), $SP^1$ is absent, and $SP^2$ is independently in each instance, selected from the group consisting of $C_{1-6}$ alkylene, —NH—, —C(O)—, $(—CH_2—CH_2—O)_e$, $—NH—CH_2—CH_2—(—O—CH_2—CH_2)_e—C(O)—$, $—C(O)—(CH_2)_u—C(O)—$, $—C(O)—NH—(CH_2)_v—$, and combinations thereof, wherein subscript e is an integer from 0 to 4, subscript u is an integer from 1 to 8, and subscript v is an integer from 1 to 8. In some examples, $AA^2$ comprises an amino acid selected from alanine, valine, leucine, isoleucine, methionine, tryptophan, phenylalanine, proline, glycine, serine, threonine, cysteine, tyrosine, asparagine, glutamine, aspartic acid, glutamic acid, lysine, arginine, histidine, or citrulline, a derivative thereof, or a combination thereof. In certain embodiments, the $AA^2$ is valine-citrulline. In some embodiments, the $AA^2$ is citrulline-valine. In some embodiments, the $AA^2$ is valine-alanine. In some embodiments, the $AA^2$ is alanine-valine. In some embodiments, the $AA^2$ is valine-glycine. In some embodiments, the $AA^2$ is glycine-valine.

In some examples, including any of the foregoing, the compound of Formula (I) comprises at least one CD group. In a specific example, a compound of Formula (I) is a compound of Formula (Ie), Formula (Ie1) or Formula (Ie2) as described herein and comprises one CD group. In another specific example, a compound of Formula (I) is a compound of Formula (If) as described herein and comprises one CD group.

In some examples, including any of the foregoing, CD is, independently in each instance, a cyclodextrin. In some examples, the CD is an α-cyclodextrin. In some examples, the CD is a β-cyclodextrin. In some examples, the CD is a γ-cyclodextrin. In any of these examples, the α-, β-, or γ-cyclodextrin is optionally substituted.

In some examples, including any of the foregoing, CD is, independently in each instance, selected from the group consisting of α-cyclodextrin, β-cyclodextrin, and γ-cyclodextrin. In some examples, CD is α-cyclodextrin. In some examples, CD is β-cyclodextrin. In some examples, CD is γ-cyclodextrin.

In some examples, including any of the foregoing, CD is, independently in each instance, selected from:

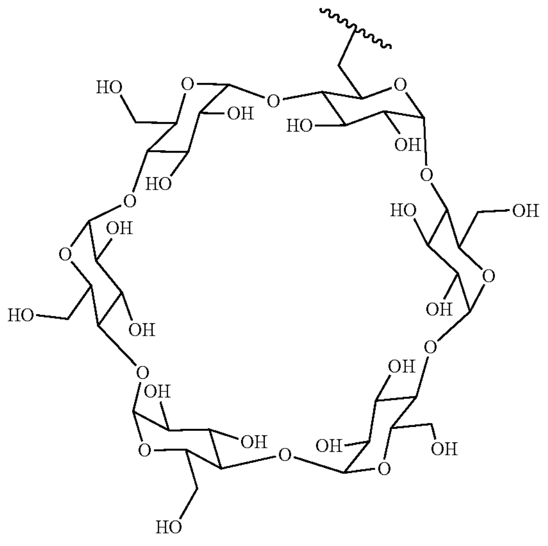 [SMILES: *CC1OC2OC3C(CO)OC(OC4C(CO)OC(OC5C(CO)OC(OC6C(CO)OC(OC7C(CO)OC(OC1C(O)C2O)C(O)C7O)C(O)C6O)C(O)C5O)C(O)C4O)C(O)C3O]

and

-continued
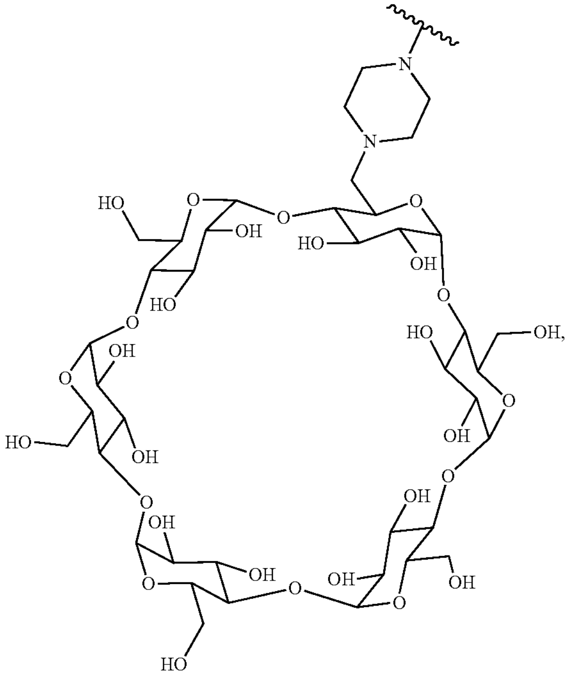 [SMILES: *N1CCN(CC2OC3OC4C(CO)OC(OC5C(CO)OC(OC6C(CO)OC(OC7C(CO)OC(OC8C(CO)OC(OC2C(O)C3O)C(O)C8O)C(O)C7O)C(O)C6O)C(O)C5O)C(O)C4O)CC1]
wherein the
indicates the atom through which the CD is bonded to the adjacent groups in the formula. In certain examples, the CD is
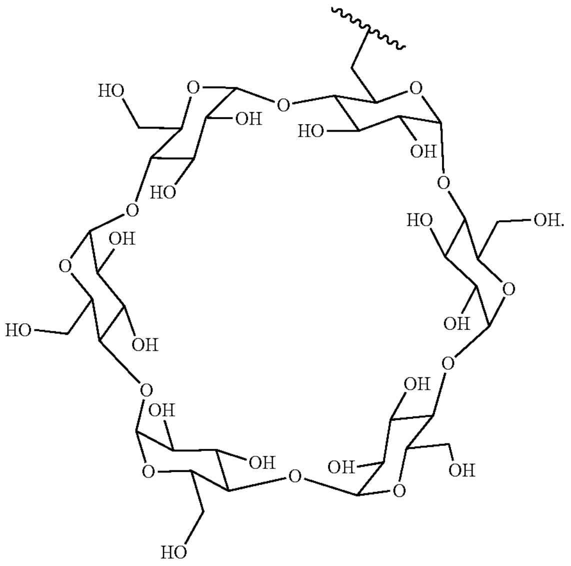 [SMILES: *CC1OC2OC3C(CO)OC(OC4C(CO)OC(OC5C(CO)OC(OC6C(CO)OC(OC7C(CO)OC(OC1C(O)C2O)C(O)C7O)C(O)C6O)C(O)C5O)C(O)C4O)C(O)C3O]
In certain examples, the CD is
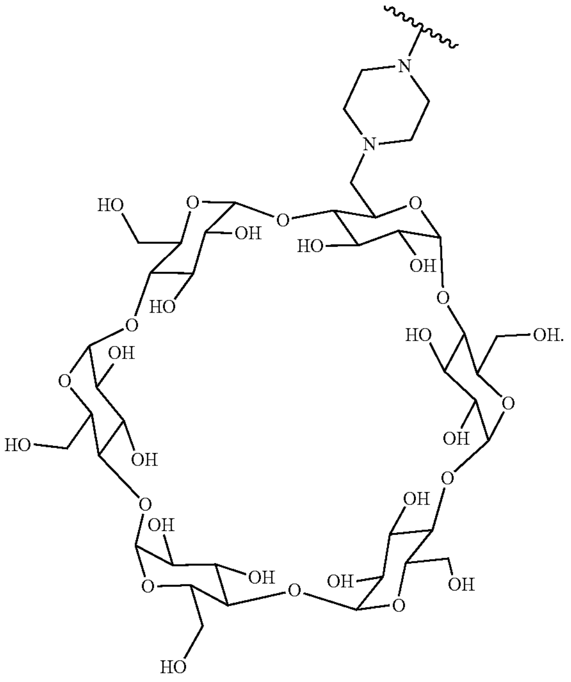 [SMILES: *N1CCN(CC2OC3OC4C(CO)OC(OC5C(CO)OC(OC6C(CO)OC(OC7C(CO)OC(OC8C(CO)OC(OC2C(O)C3O)C(O)C8O)C(O)C7O)C(O)C6O)C(O)C5O)C(O)C4O)CC1]
In some examples, including any of the foregoing, CD is, independently in each instance, selected from
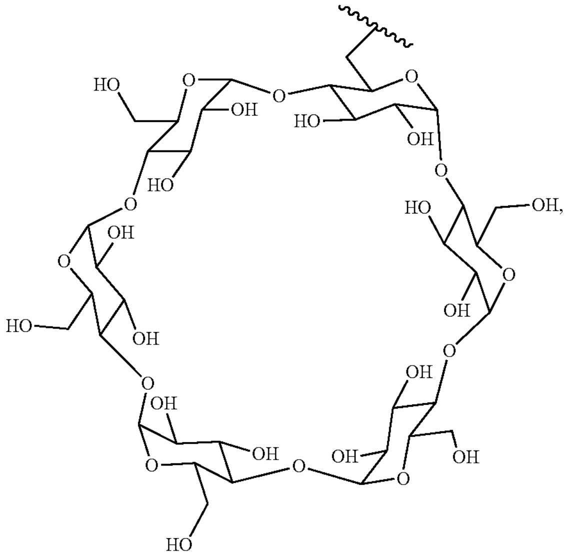

-continued
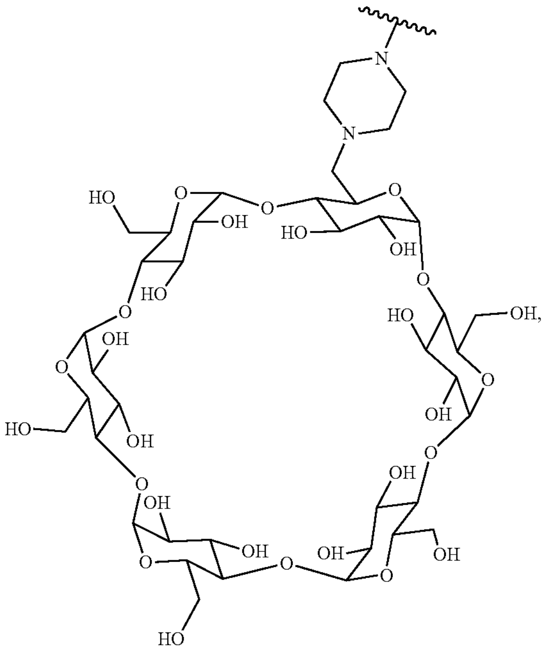
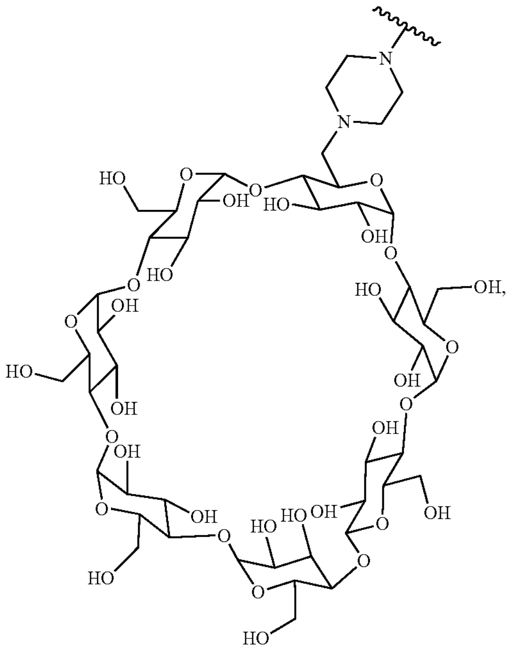
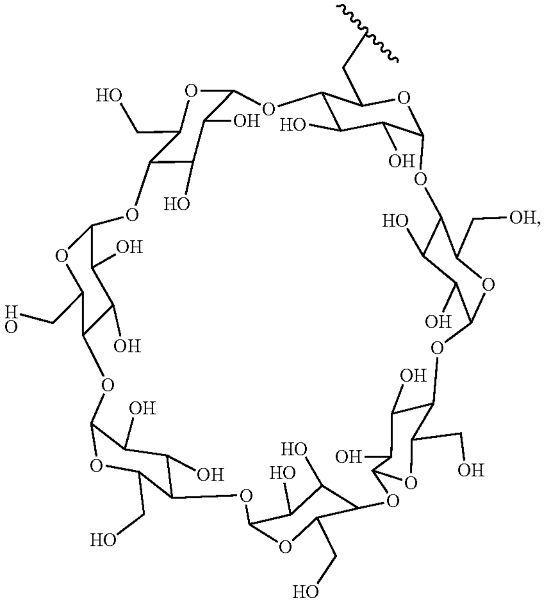
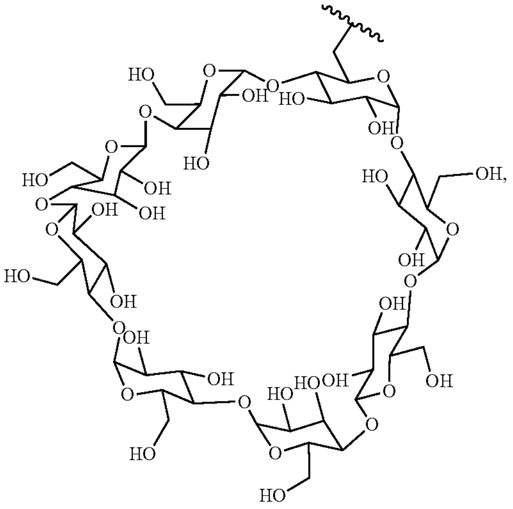
and
-continued

-continued
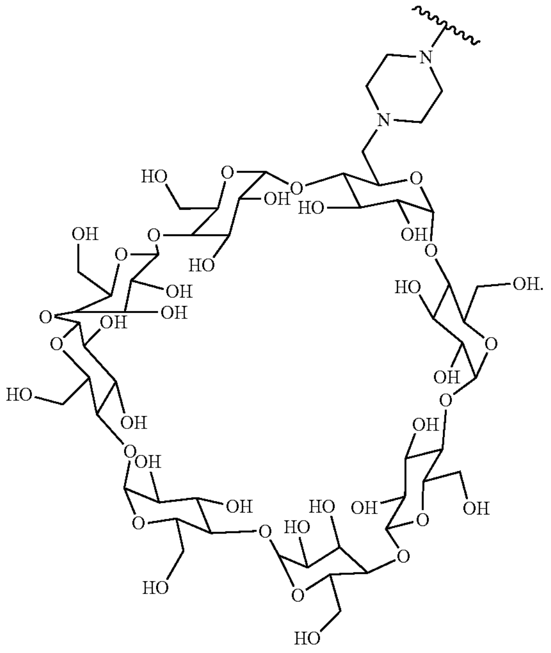
In some examples, the CD
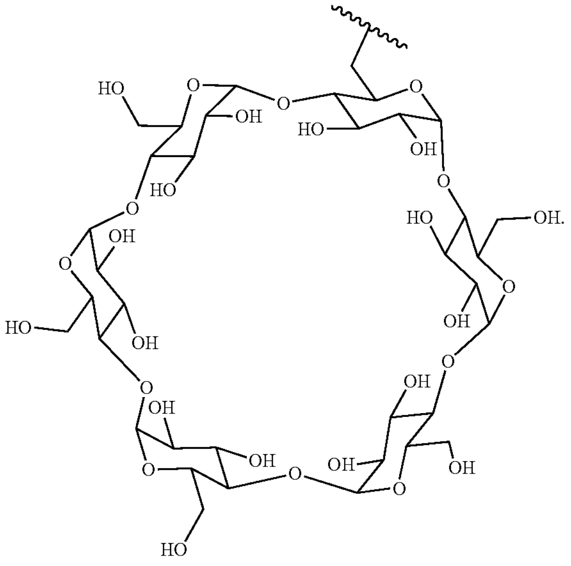
In some examples, the CD is
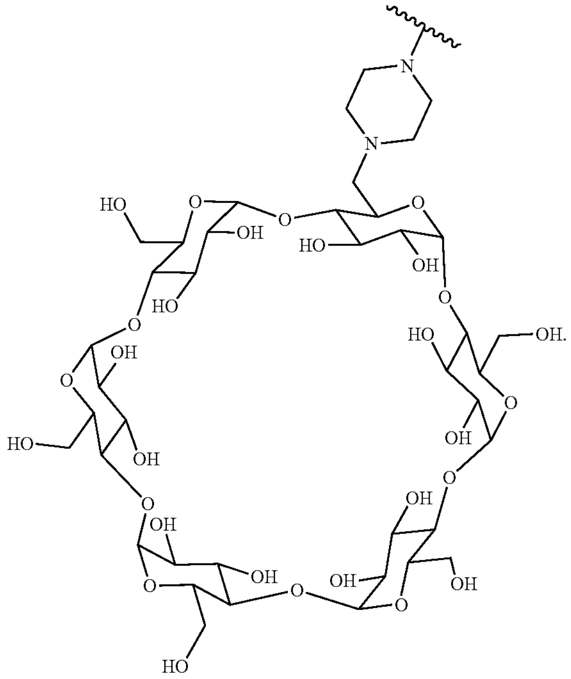
In some examples, the CD is
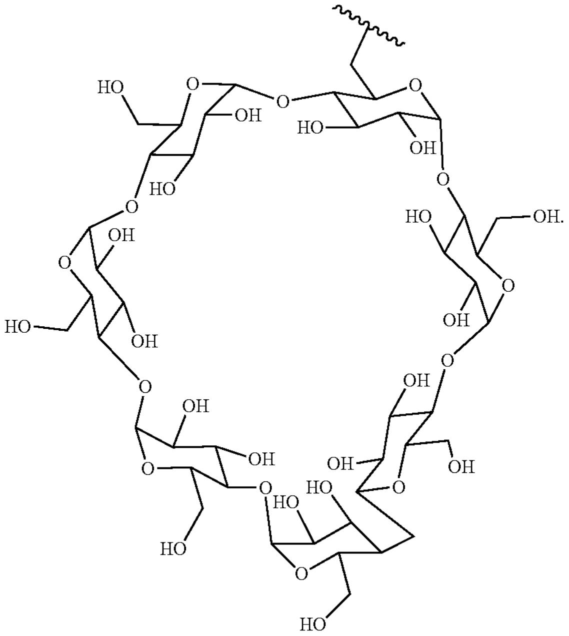 [SMILES: *CC1OC2OC3C(CO)OC(OC4C(CO)OC(CC5C(CO)OC(OC6C(CO)OC(OC7C(CO)OC(OC8C(CO)OC(OC1C(O)C2O)C(O)C8O)C(O)C7O)C(O)C6O)C(O)C5O)C(O)C4O)C(O)C3O]

In some examples, the CD is

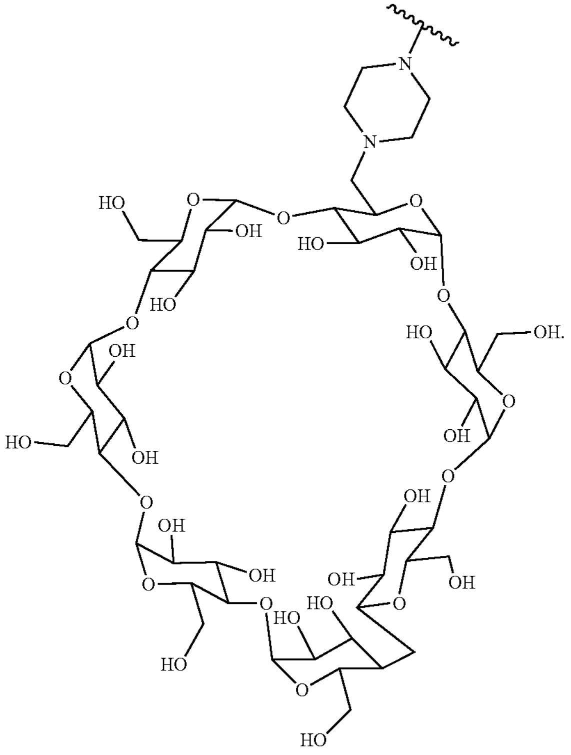 [SMILES: *N1CCN(CC2OC3OC4C(CO)OC(OC5C(CO)OC(CC6C(CO)OC(OC7C(CO)OC(OC8C(CO)OC(OC9C(CO)OC(OC2C(O)C3O)C(O)C9O)C(O)C8O)C(O)C7O)C(O)C6O)C(O)C5O)C(O)C4O)CC1]

In some examples, the CD is

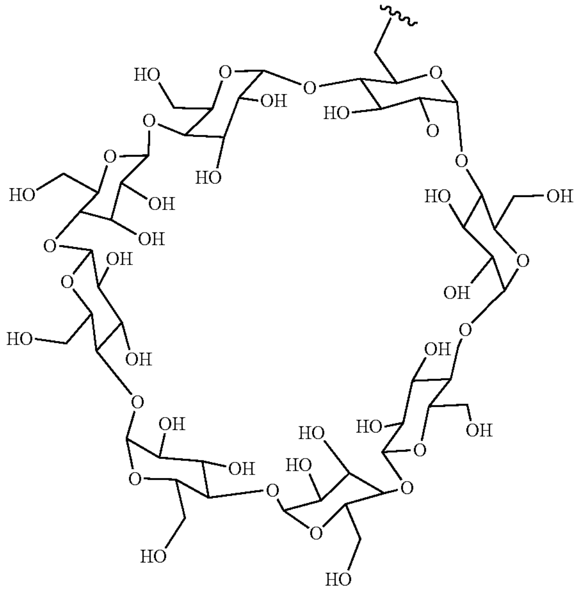

In some examples, the CD is

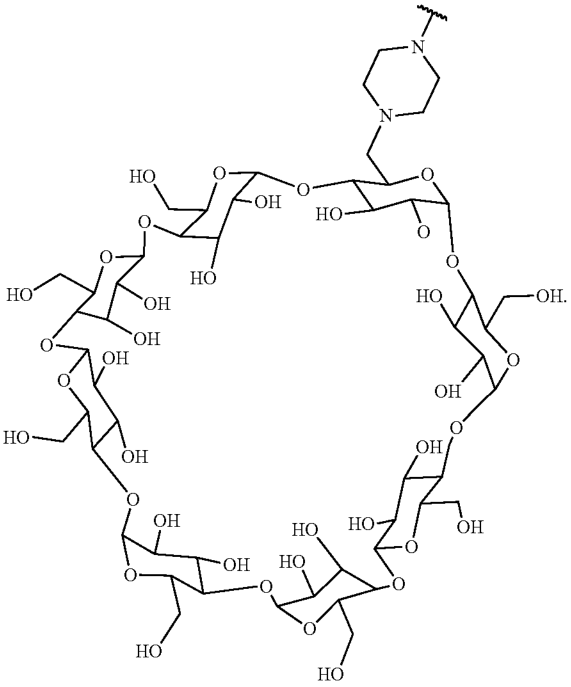

In some examples, including any of the foregoing, RG is, independently in each instance, a click chemistry residue. In some examples, including any of the foregoing, RG, independently in each instance, comprises a triazole or a fused triazole.

In some examples, including any of the foregoing, RG is, independently in each instance, selected from the group consisting of

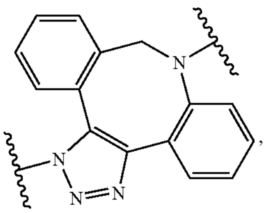

,

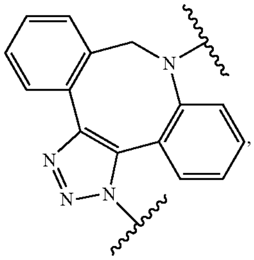

,

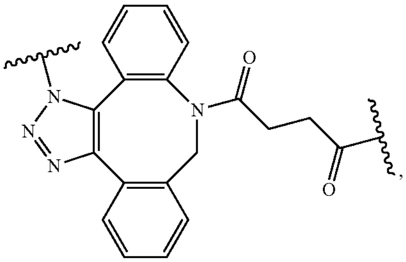

,

-continued
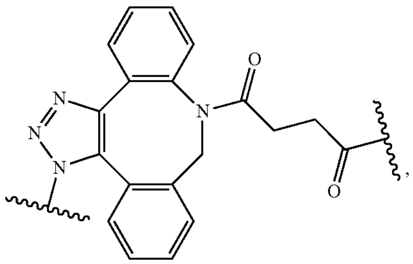,
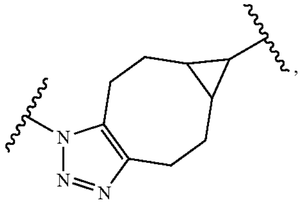,
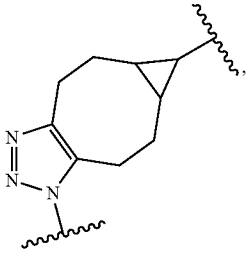,
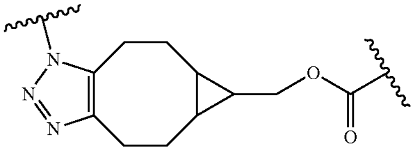,
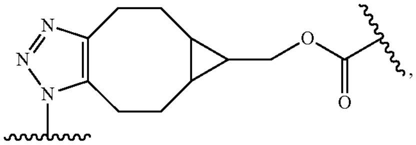,
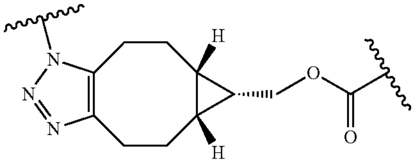,
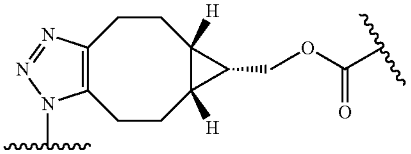,
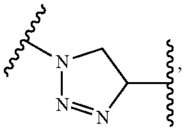,
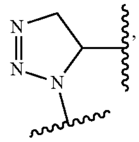,
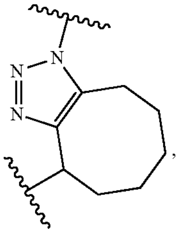,
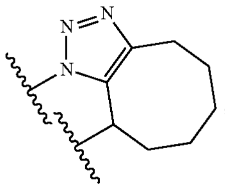,
-continued
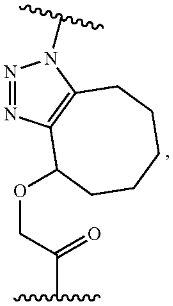,
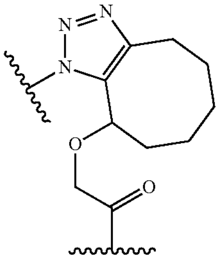, and
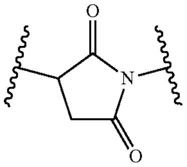,
wherein the
indicates the atom through which the RG is bonded to the adjacent groups in the formula. In certain of these examples, RG, independently in each instance, is
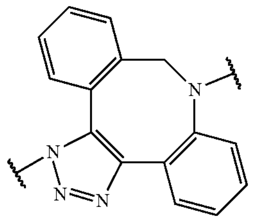.
In certain of these examples, RG, independently in each instance, is
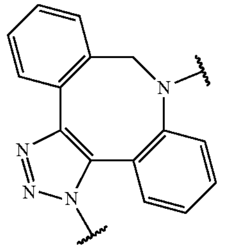.
In certain of these examples, RG, independently in each instance, is

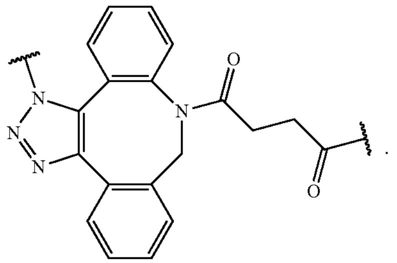

In certain of these examples, RG, independently in each instance, is

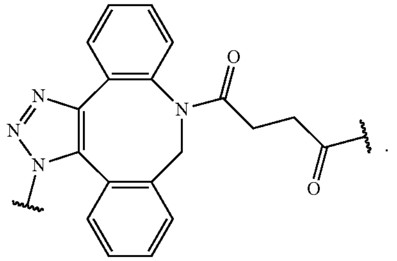

In certain of these examples, RG, independently in each instance, is

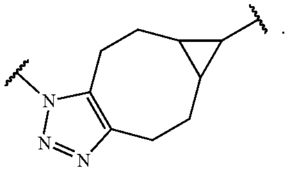

In certain of these examples, RG, independently in each instance, is

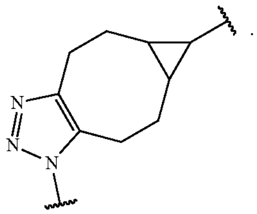

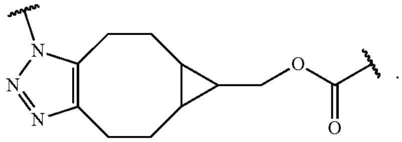

In certain of these examples, RG, independently in each instance, is

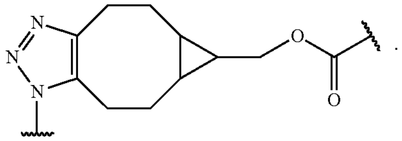

In certain of these examples, RG, independently in each instance, is

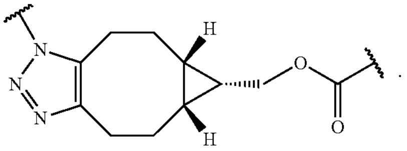

In certain of these examples, RG, independently in each instance, is

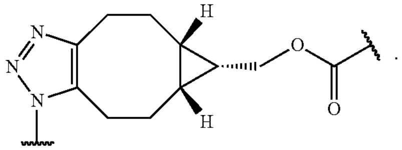

In certain of these examples, RG, independently in each instance, is

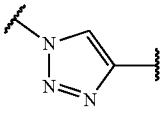
,
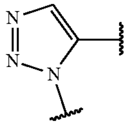
,

In certain of these examples, RG, independently in each instance, is

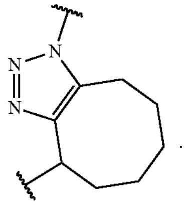

In certain of these examples, RG, independently in each instance, is

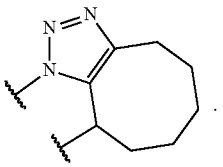

In certain of these examples, RG, independently in each instance, is

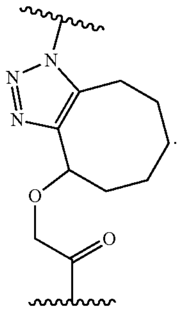 [SMILES: *C(=O)COC1CCCCCc2c1nnn2*]
In certain of these examples, RG, independently in each instance, is
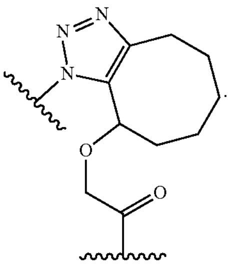 [SMILES: *C(=O)COC1CCCCCc2nnn(*)c21]
In certain of these examples, RG, independently in each instance, is
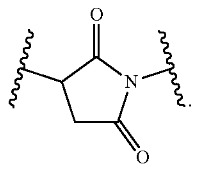 [SMILES: *C1CC(=O)N(*)C1=O]
In some examples, including any of the foregoing, the compound of Formula (I) includes the group,
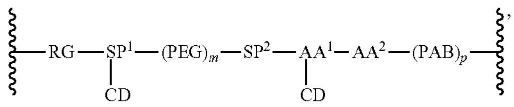
which is selected from the group consisting of
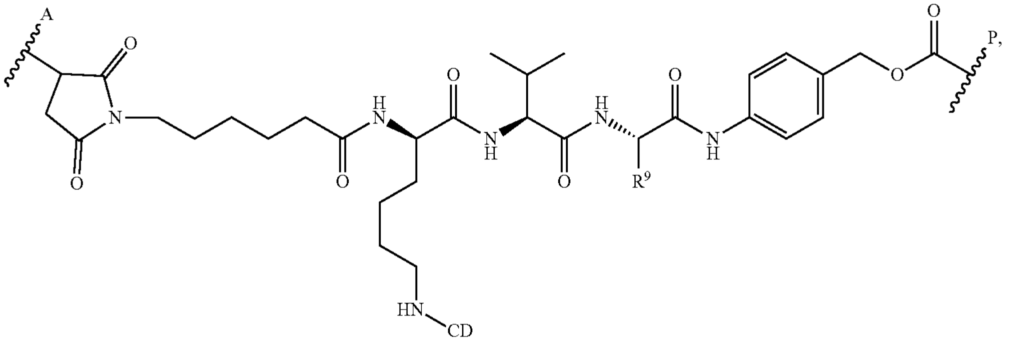
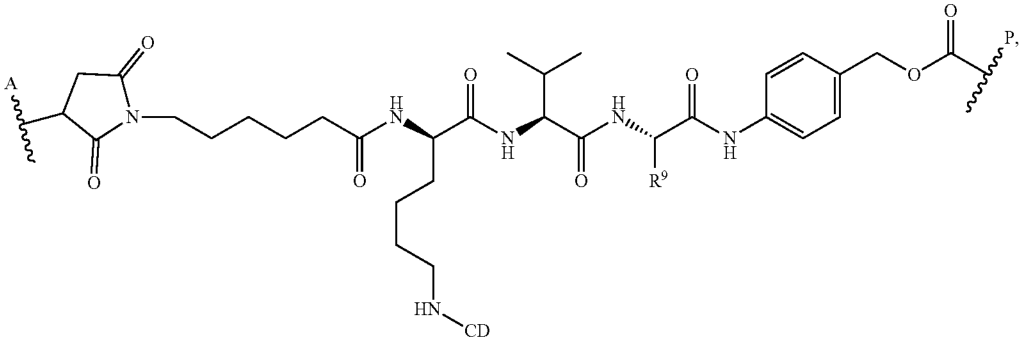

-continued
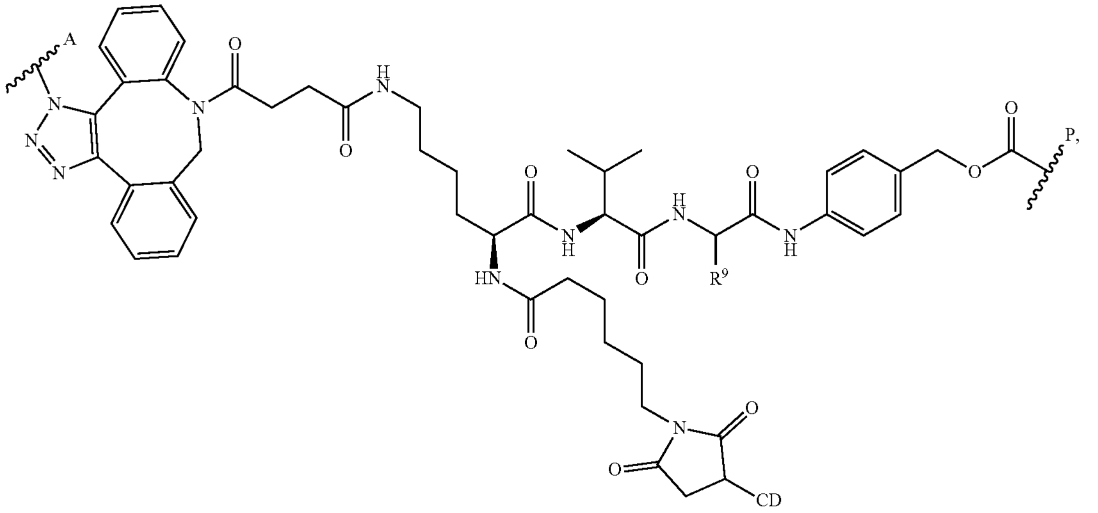
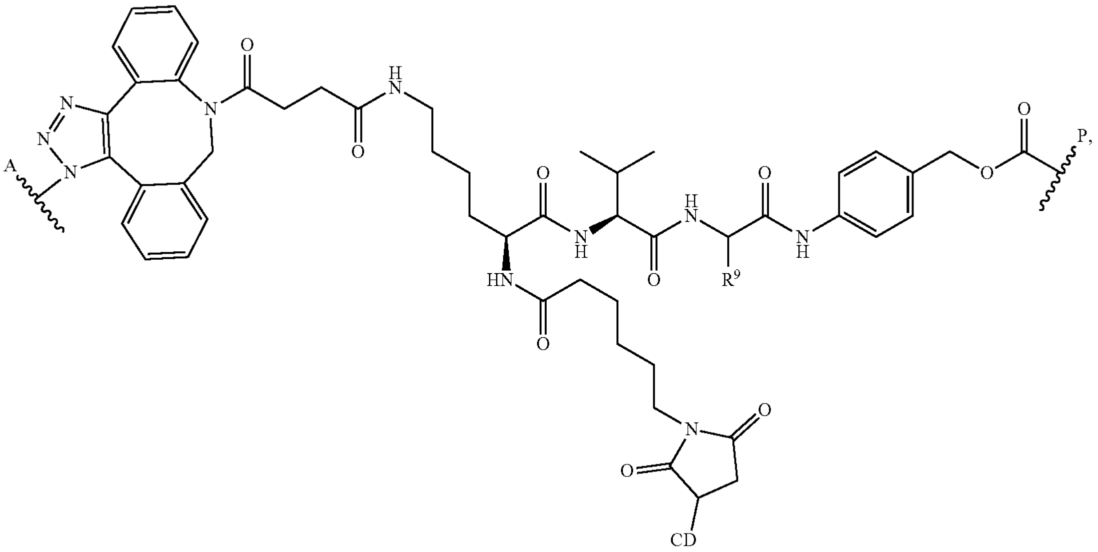
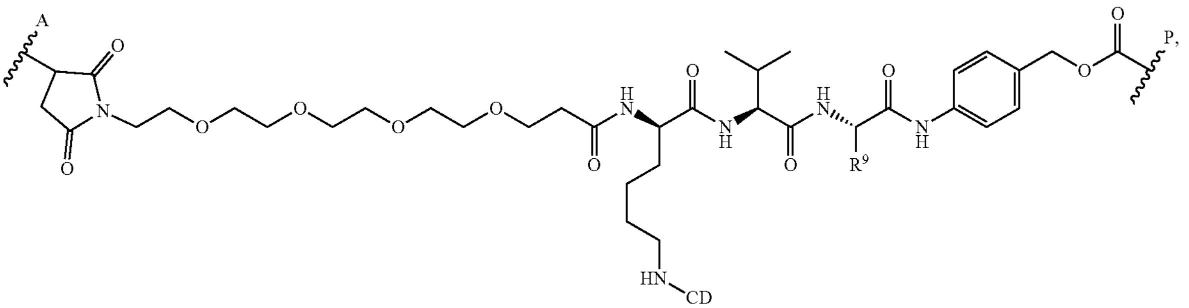
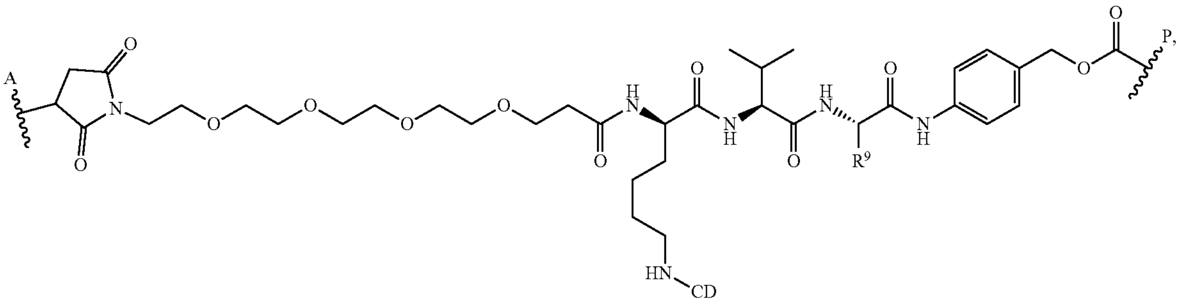

-continued
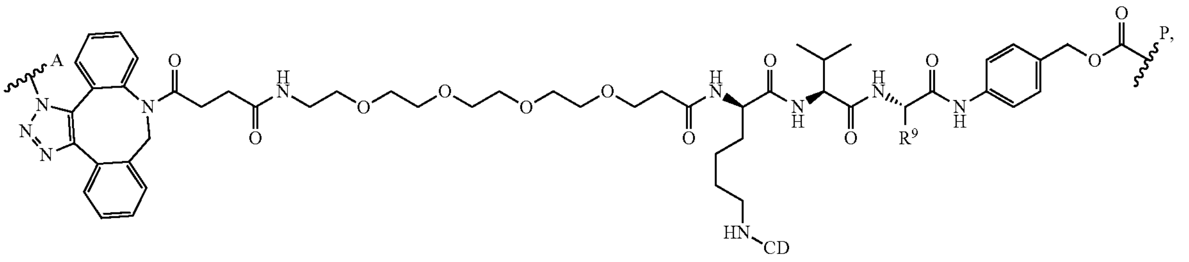
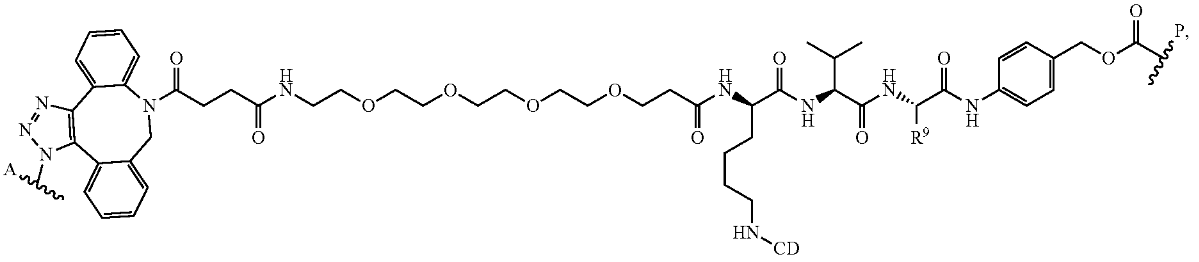
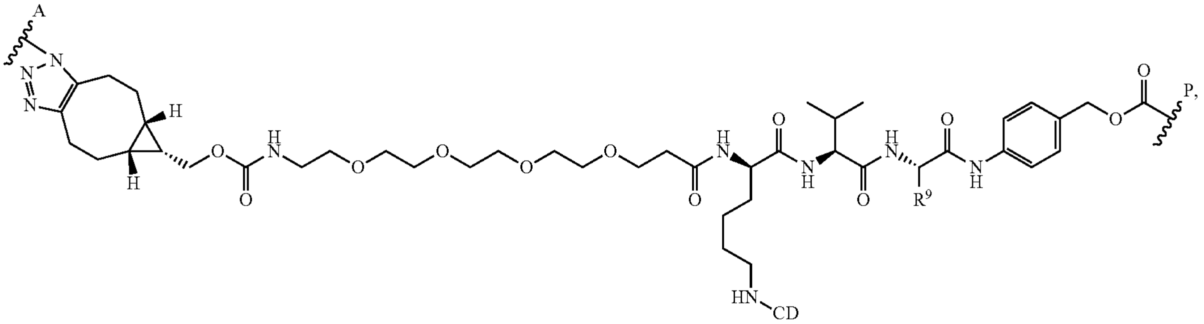
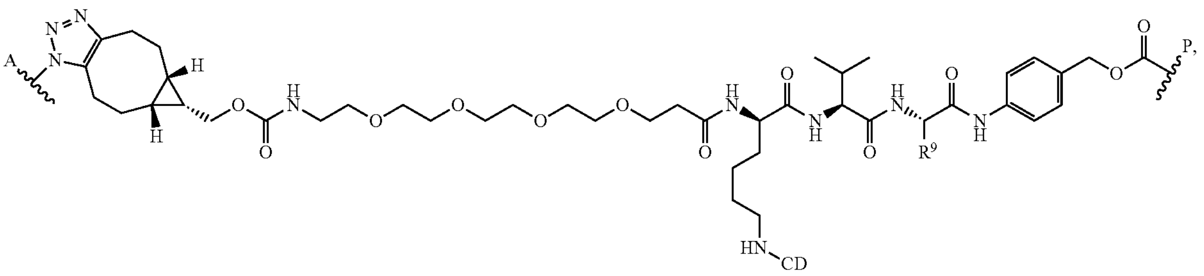
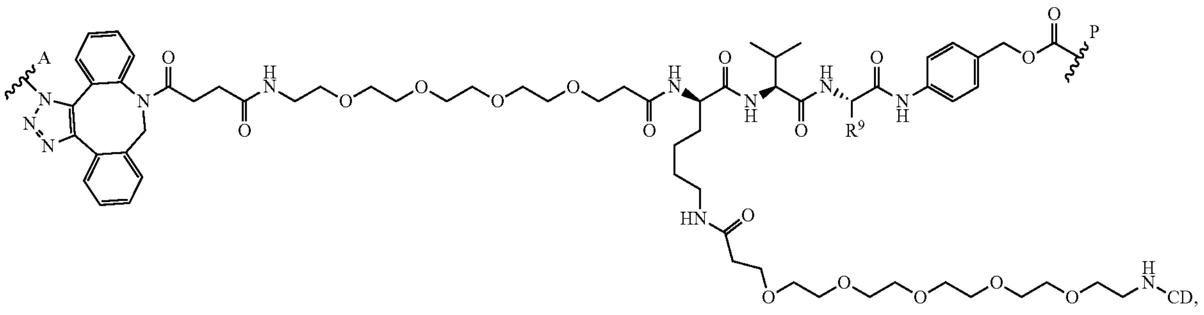

-continued
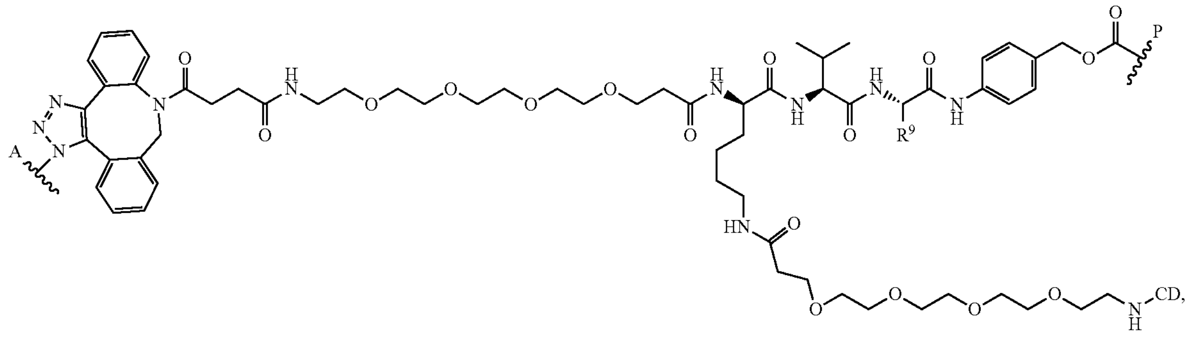
,
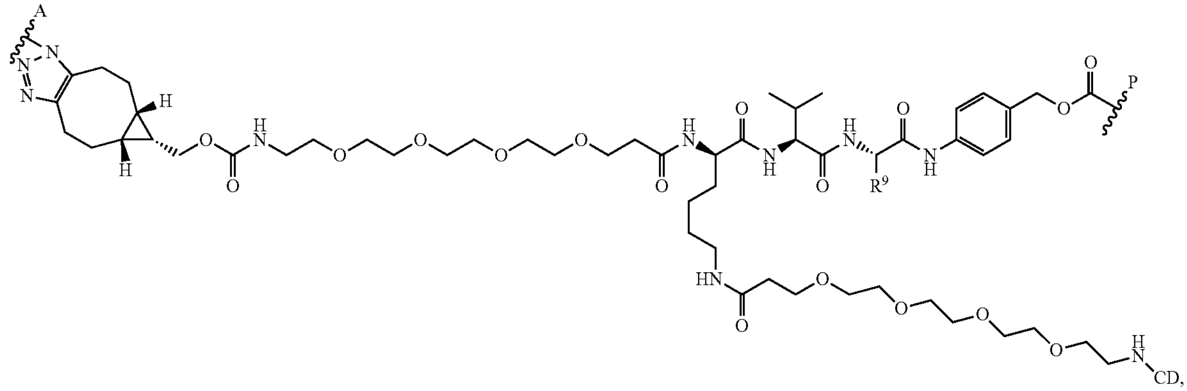
,
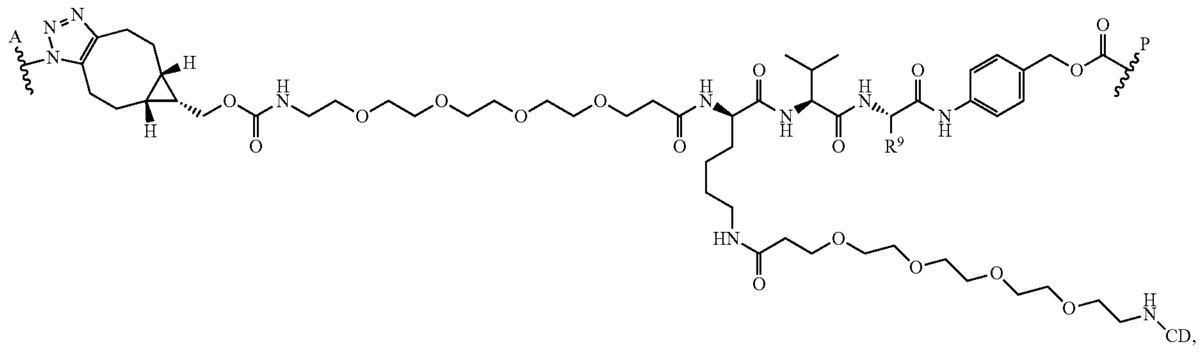
,
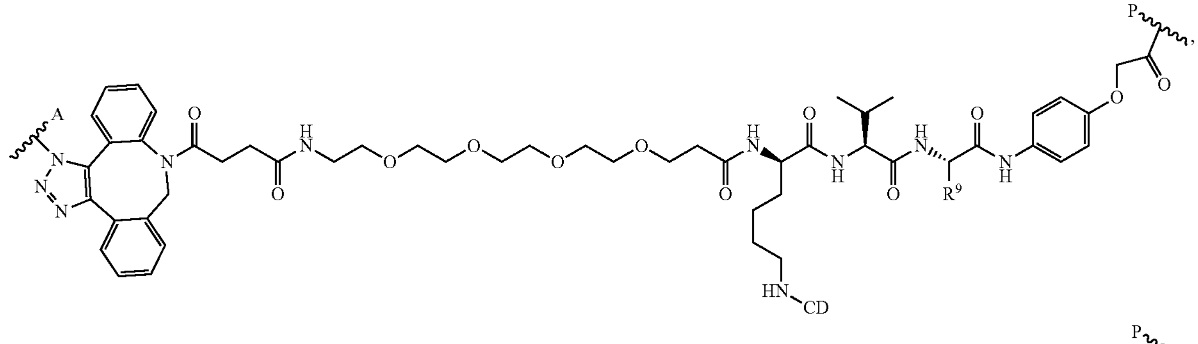
,
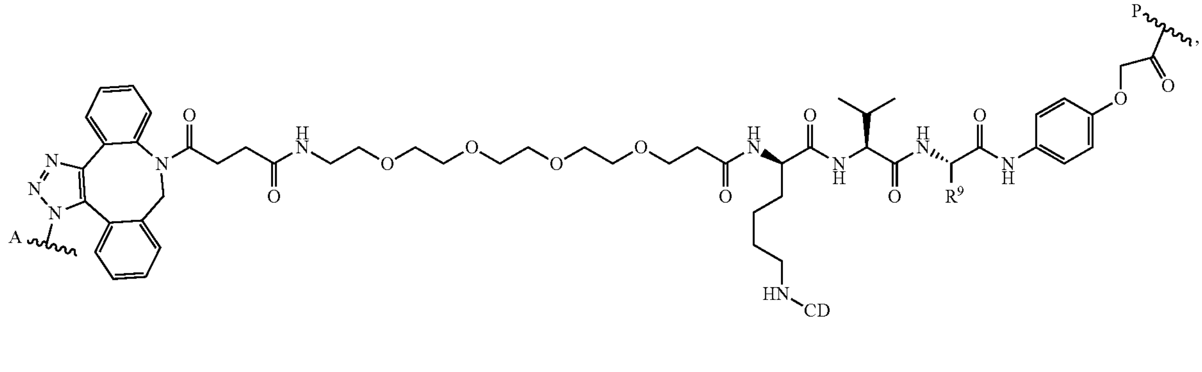
, -continued
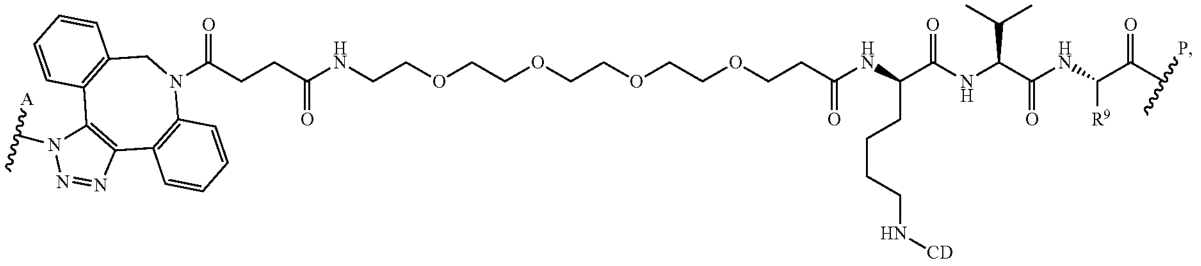
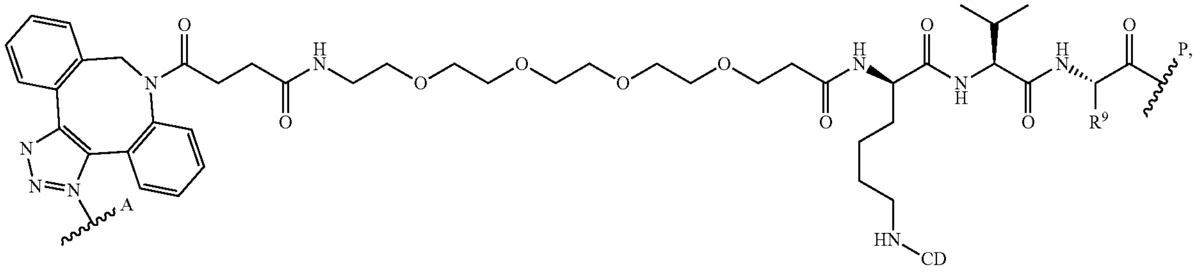
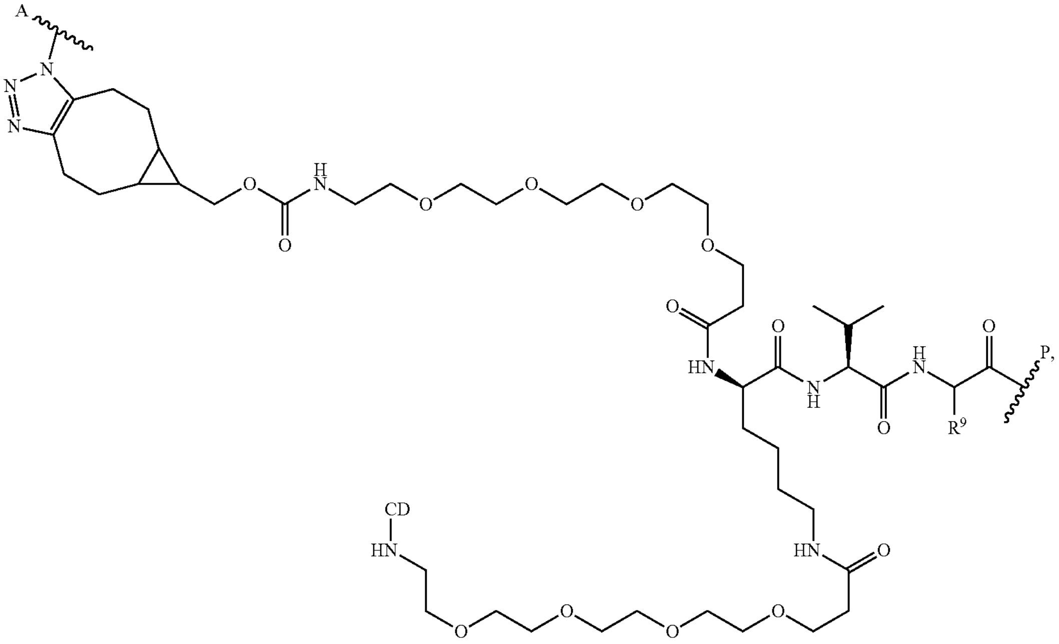

-continued
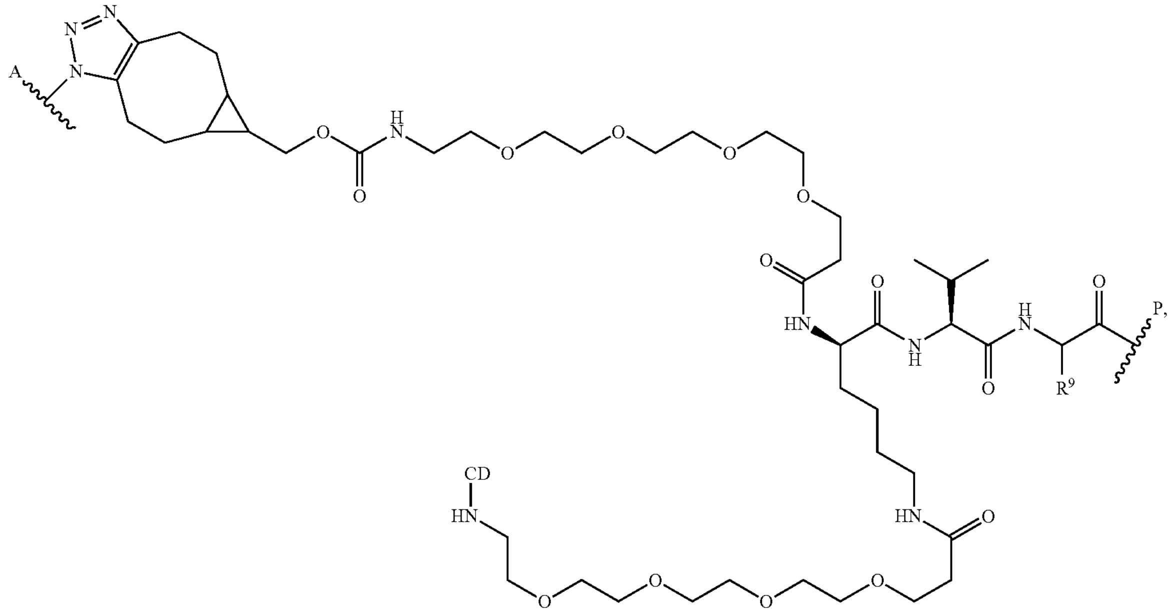
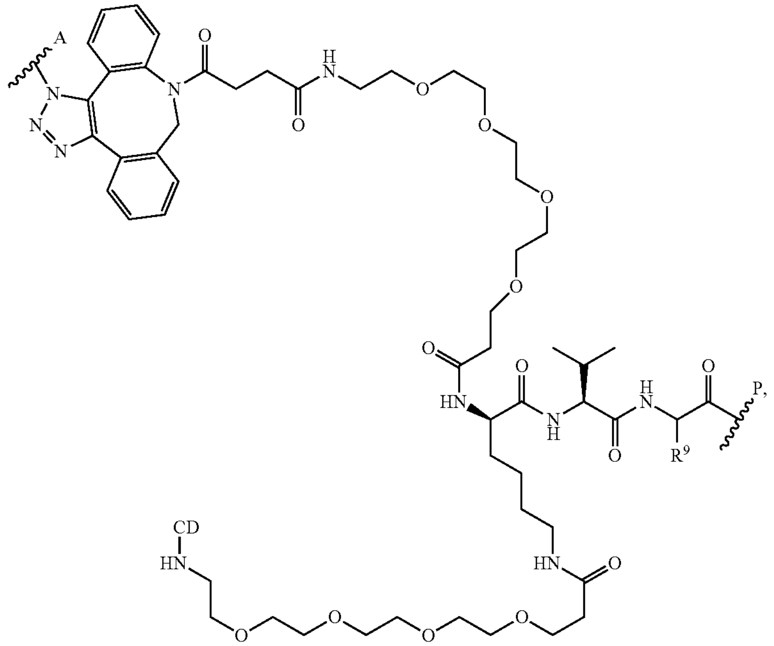

-continued
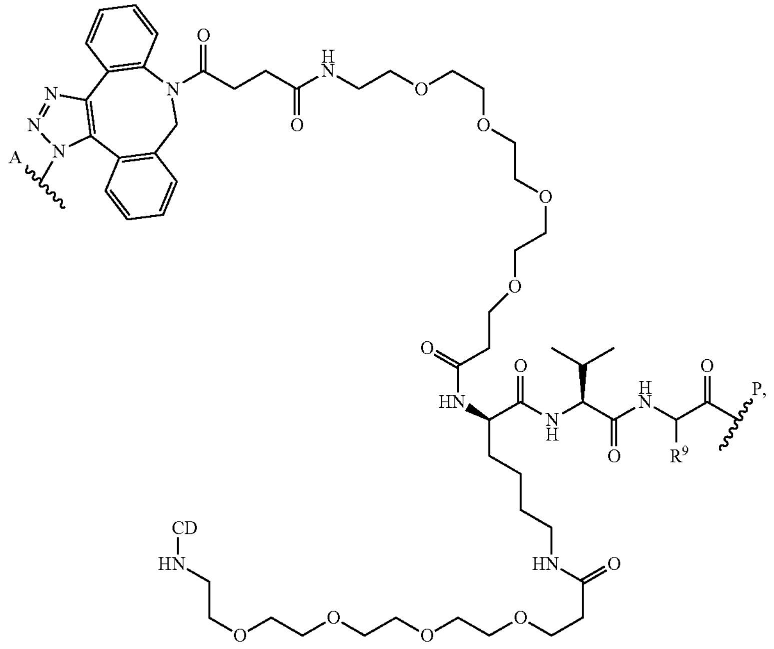
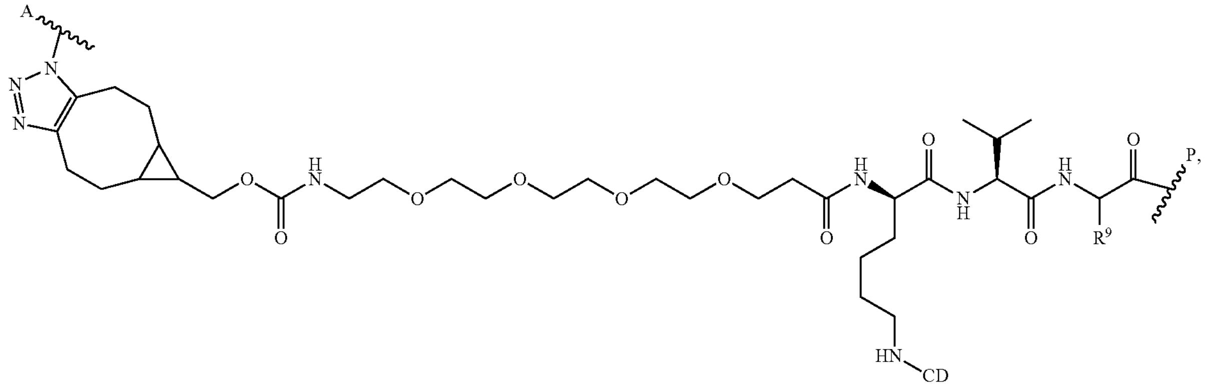
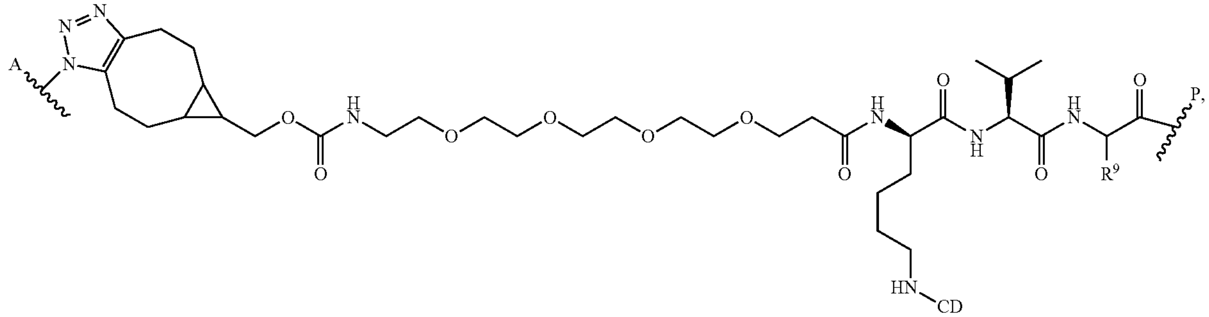
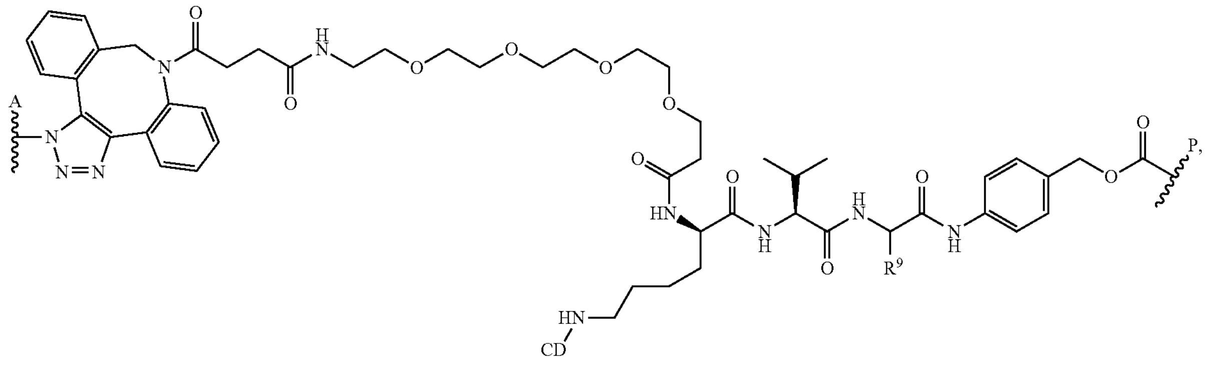

-continued

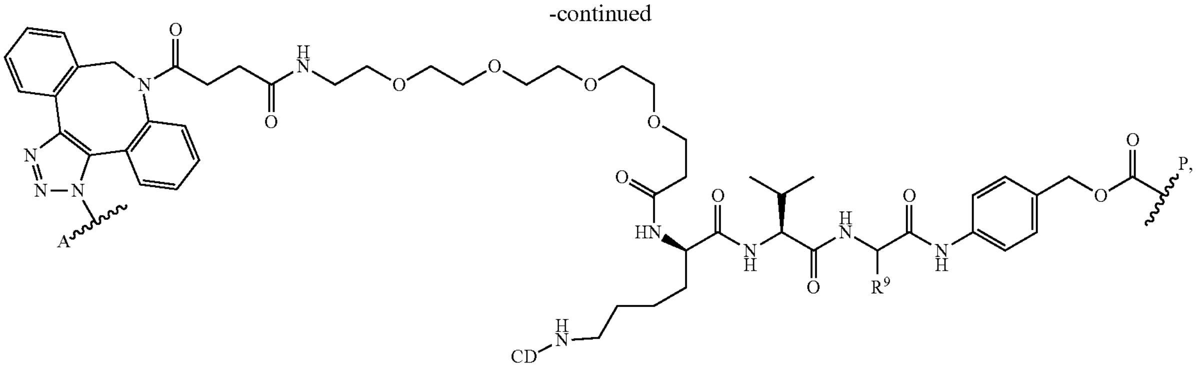

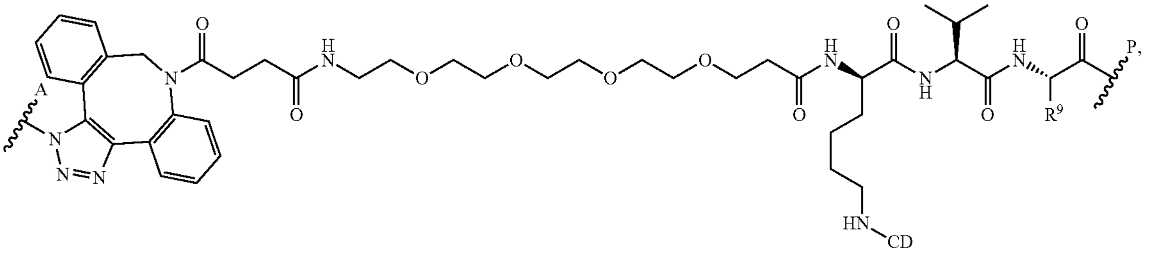

and

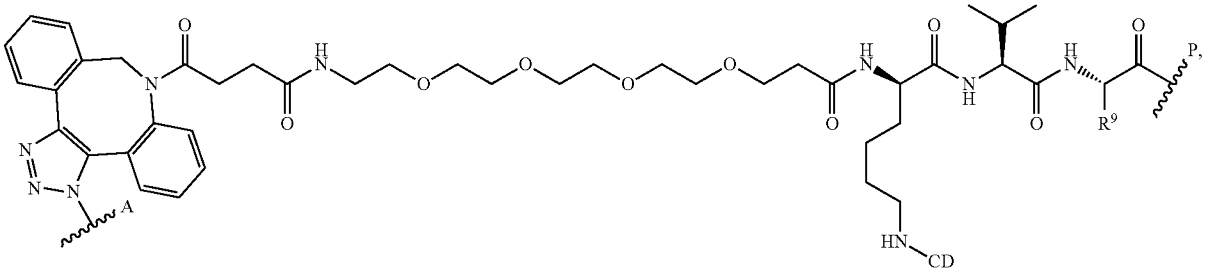

wherein

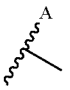

indicates a bond to a binding agent such as an antibody or antigen-binding fragment thereof, and wherein $R^9$ is $-CH_3$, or $-(CH_2)_3N(H)C(O)NH_2$.

indicates a bond to a cyclodextrin.

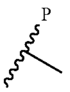

indicates a bond to a payload. In certain examples $R^9$ is $-CH_3$. In certain examples $R^9$ is $-(CH_2)_3N(H)C(O)NH_2$. In these examples, the antibody or antigen-binding fragment thereof may be directly or indirectly bonded to the group to which the

is bonded. In some examples, when the antibody or antigen-binding fragment thereof is indirectly bonded to the group to which

is bonded. In some examples wherein the antibody or antigen-binding fragment thereof is indirectly bonded to the group to which

is bonded, then

is

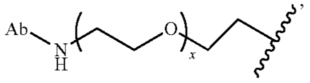

wherein subscript x is an integer from 1 to 4. In some examples, subscript x is 1. In some examples, subscript x is 2. In some examples, subscript x is 3. In some examples, subscript x is 4. Herein, Ab is an antibody or an antigen-binding fragment thereof. In some examples, the illustrated PEG group, i.e.,

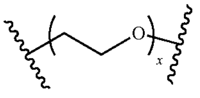

is bonded to a glutamine on the Ab. In some examples depicted in this paragraph, and described or depicted in other embodiments herein, the lysine side chain within the linker is from a L-lysine or D-lysine. In some examples depicted in this paragraph, and described or depicted in other embodiments herein, the stereochemistry of the lysine side chain within the linker is (R). In some examples depicted in this paragraph, and described or depicted in other embodiments herein, the stereochemistry of the lysine side chain within the linker is (S).

In some examples, including any of the foregoing, the compound of Formula (I) includes the group,

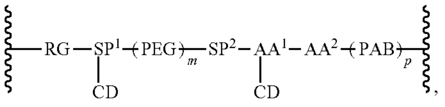

which is selected from the group consisting of

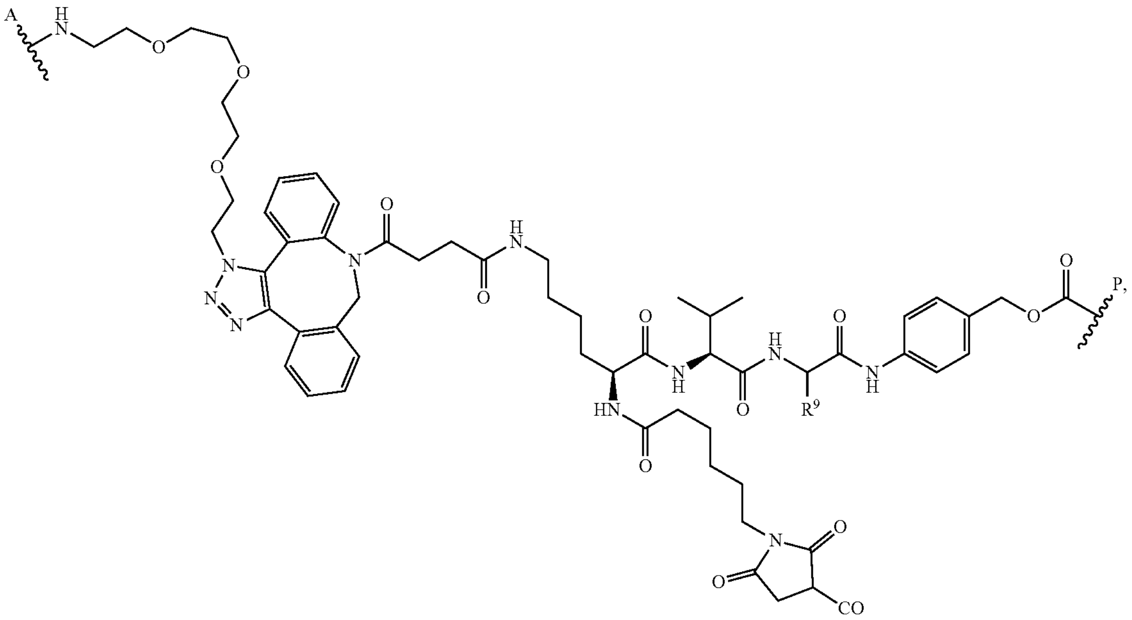

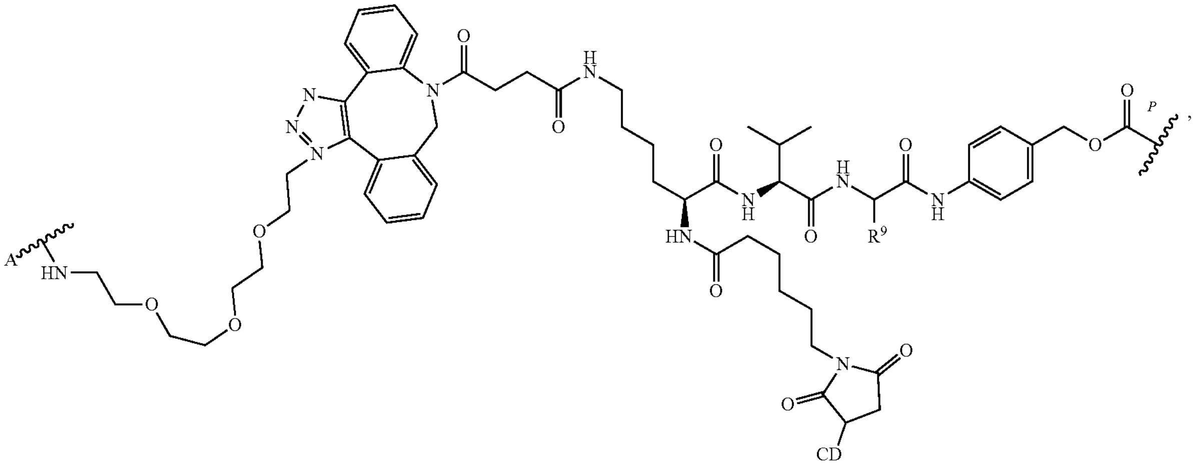

-continued
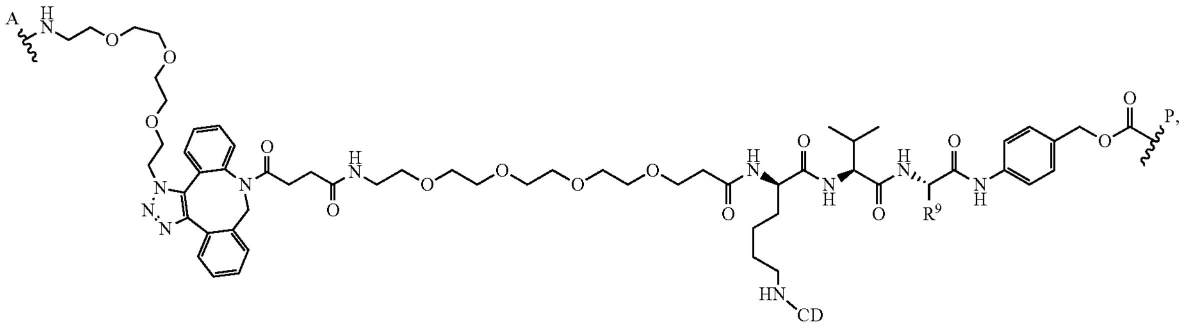
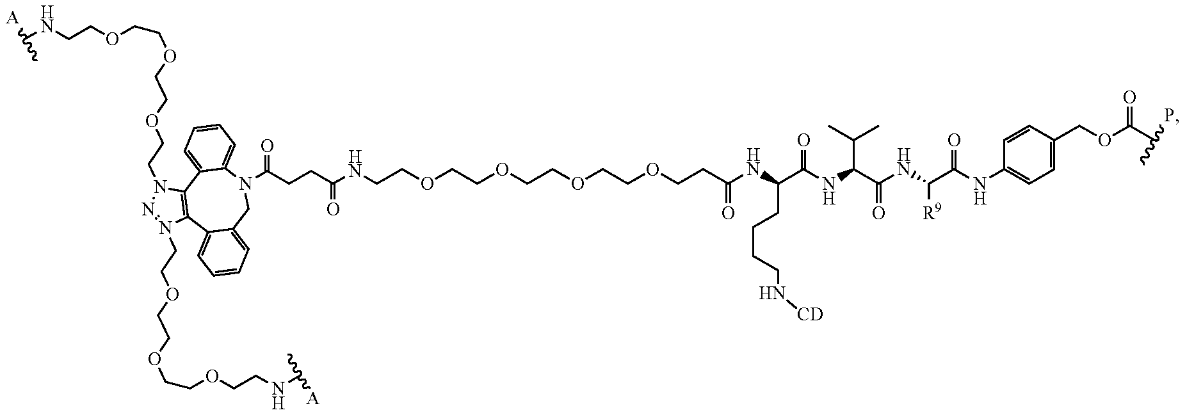
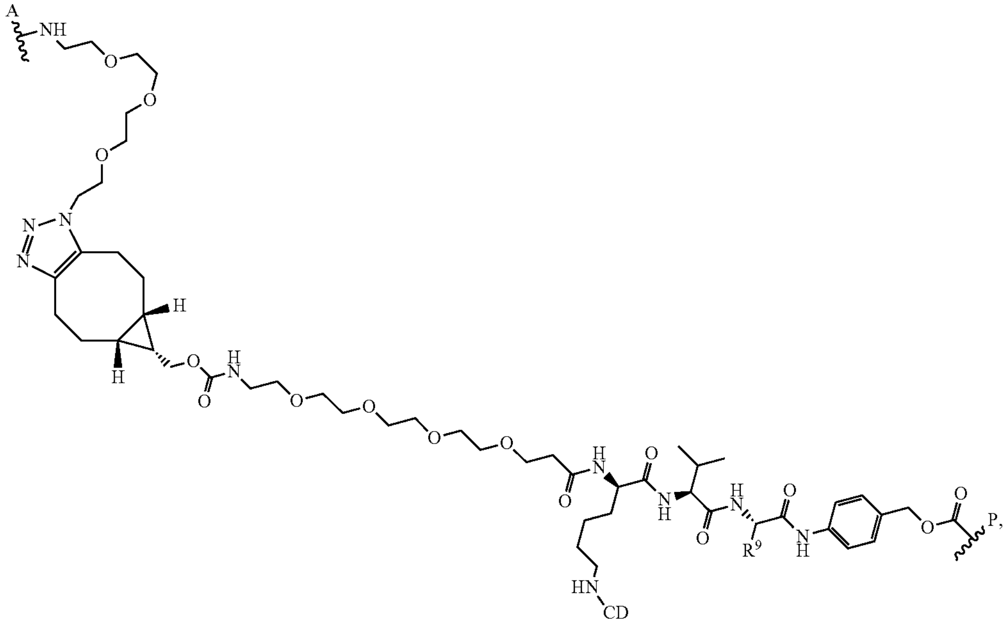
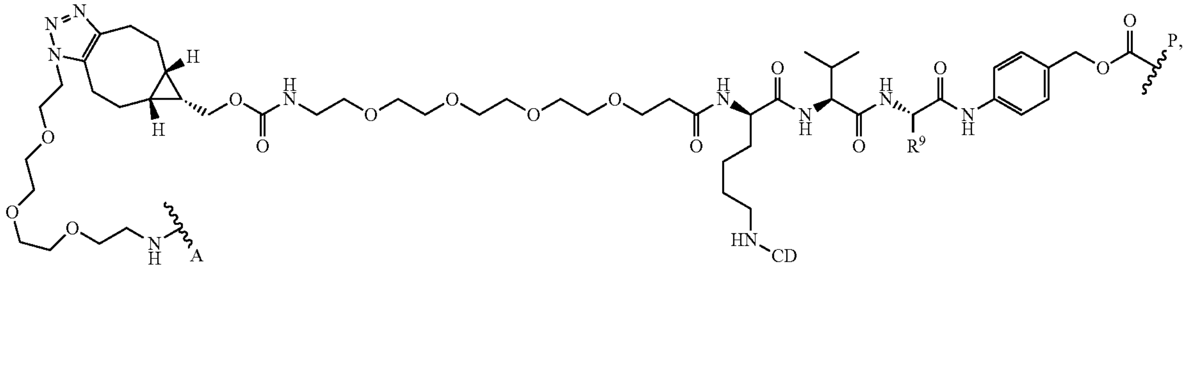

-continued
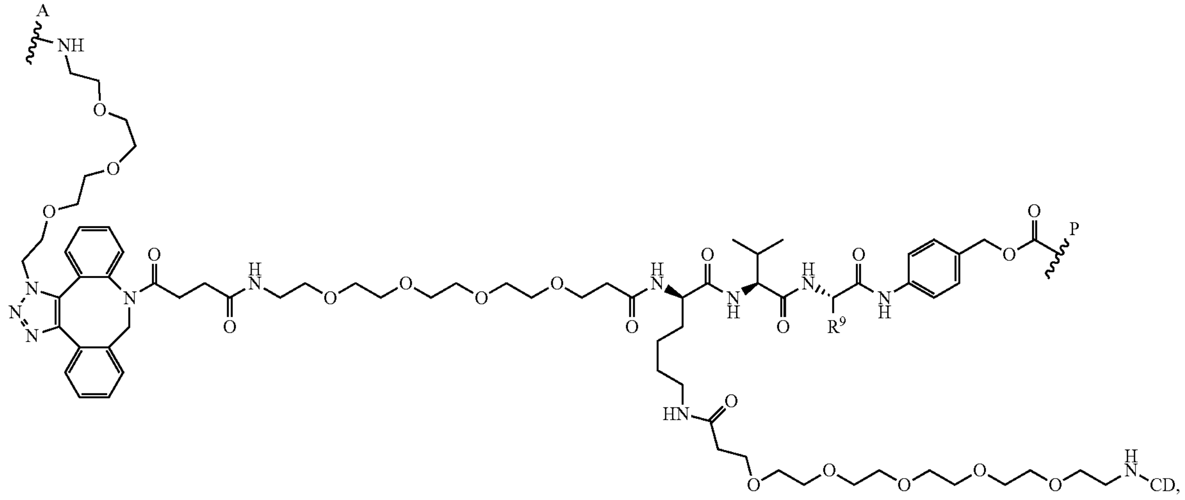
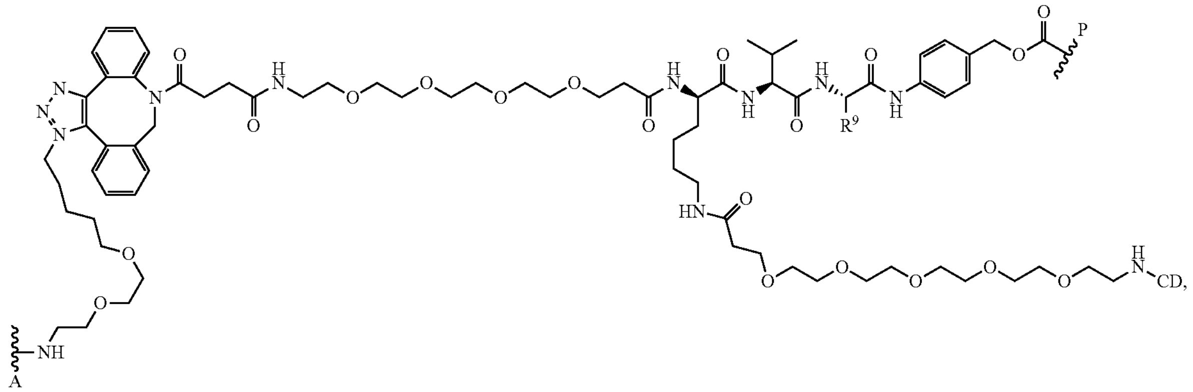
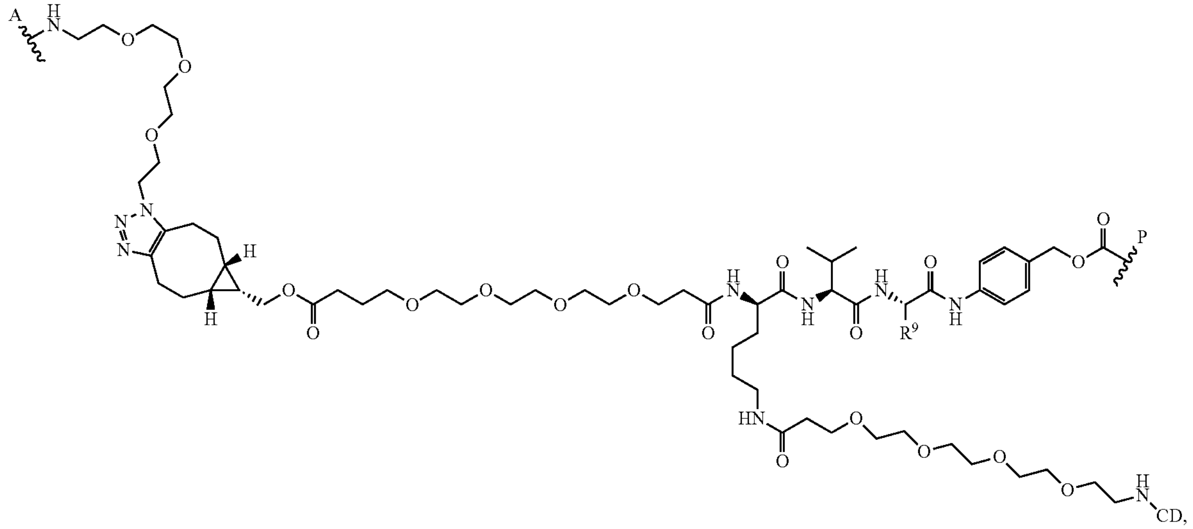

-continued
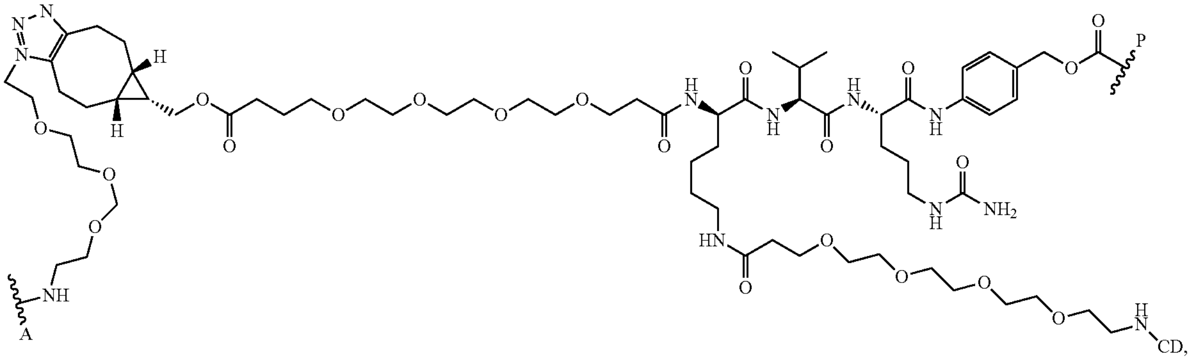
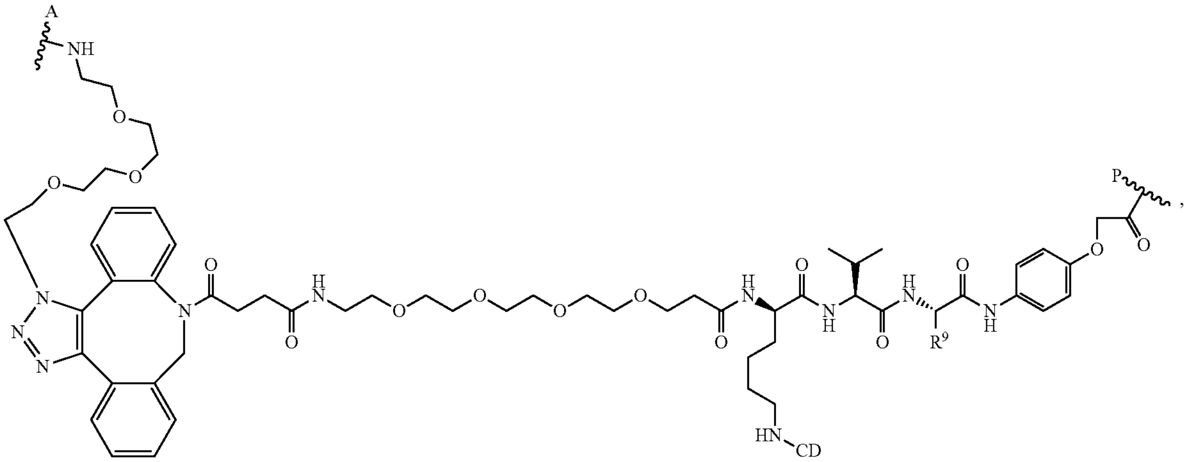
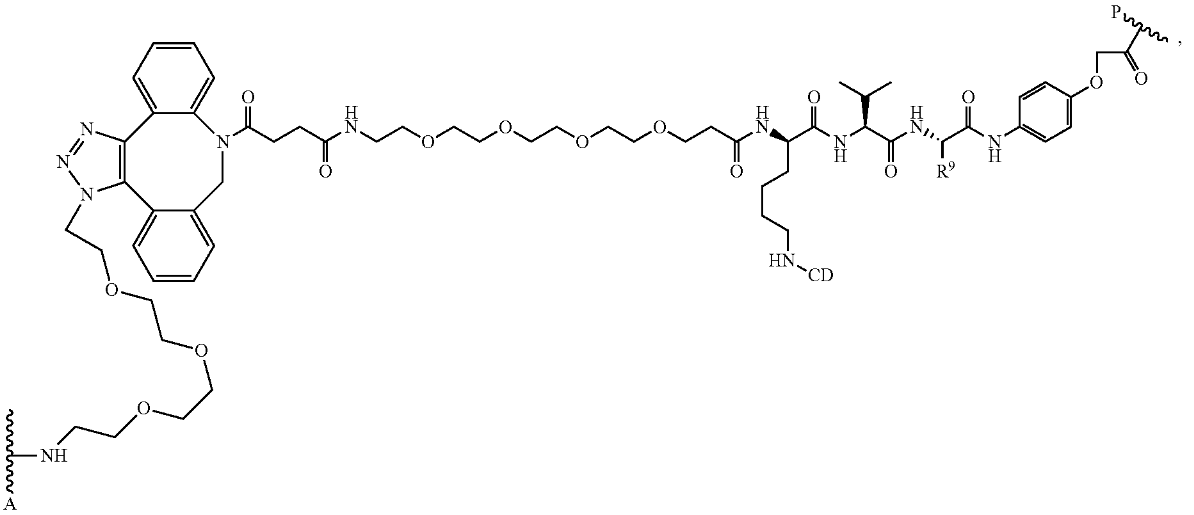
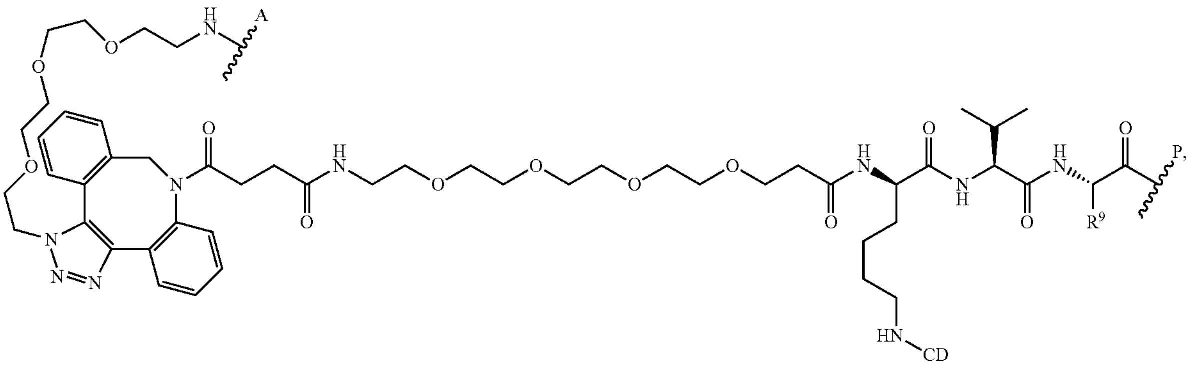

-continued
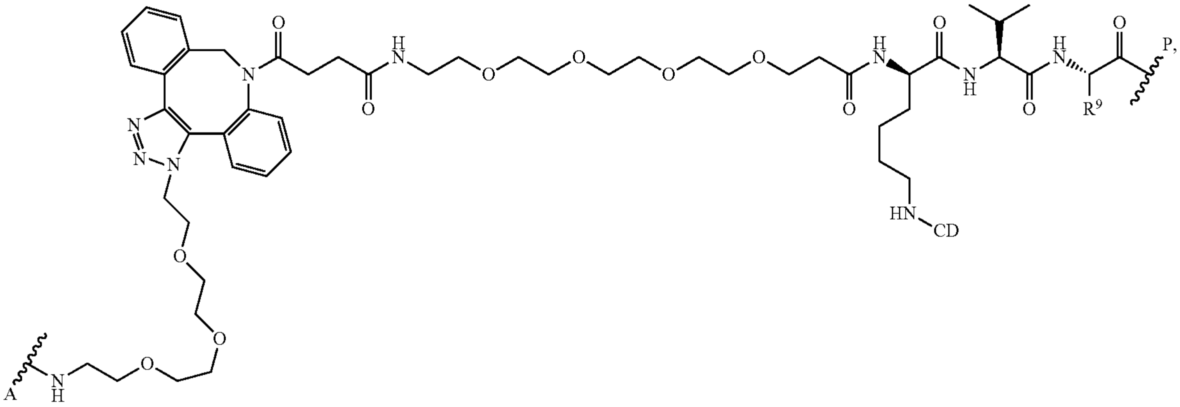
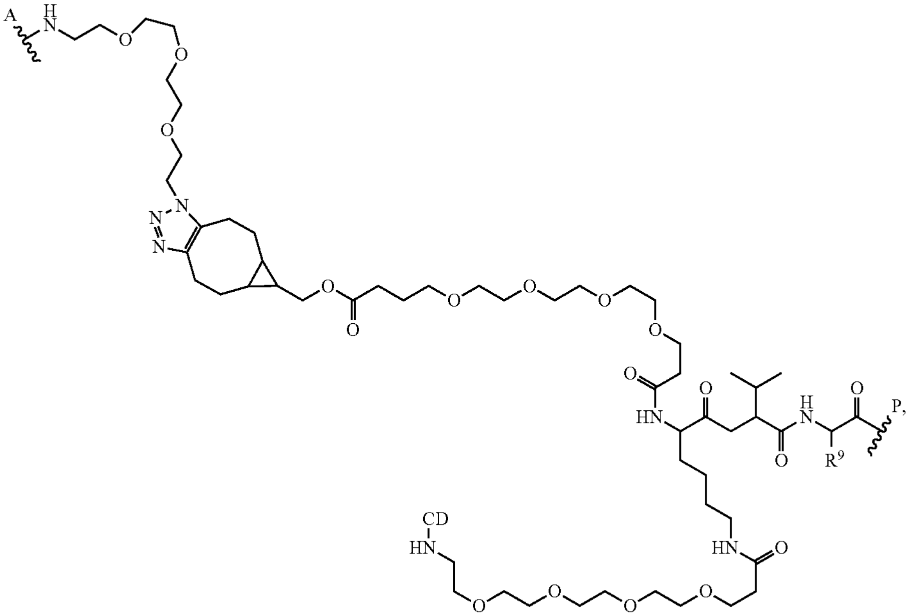
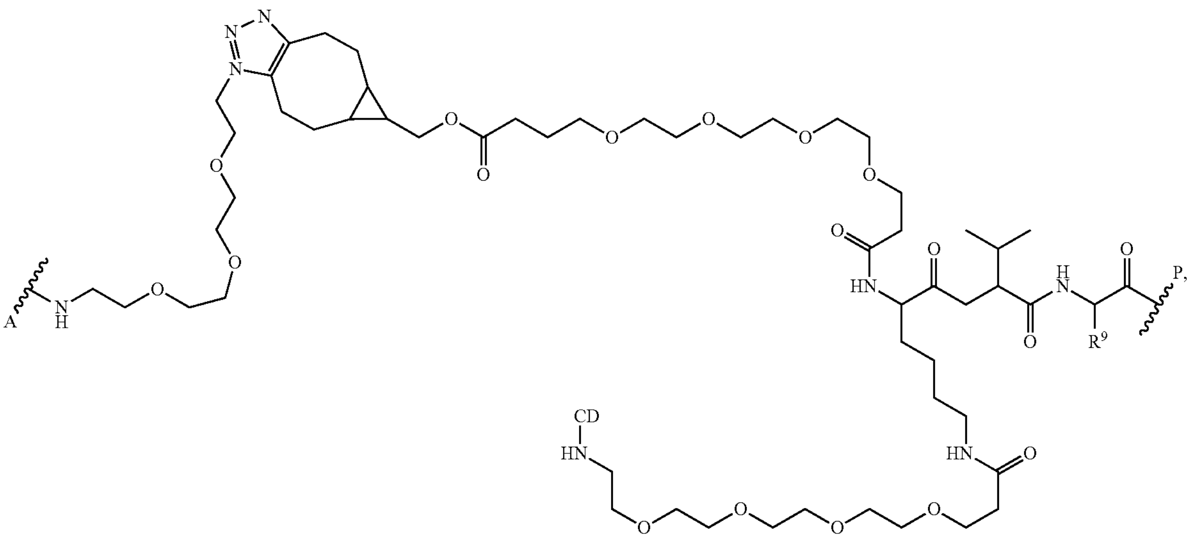

-continued
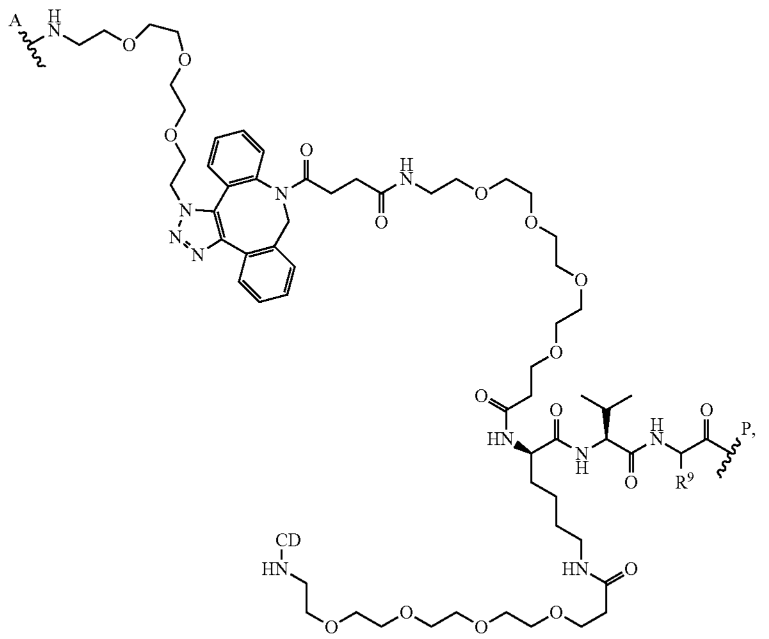
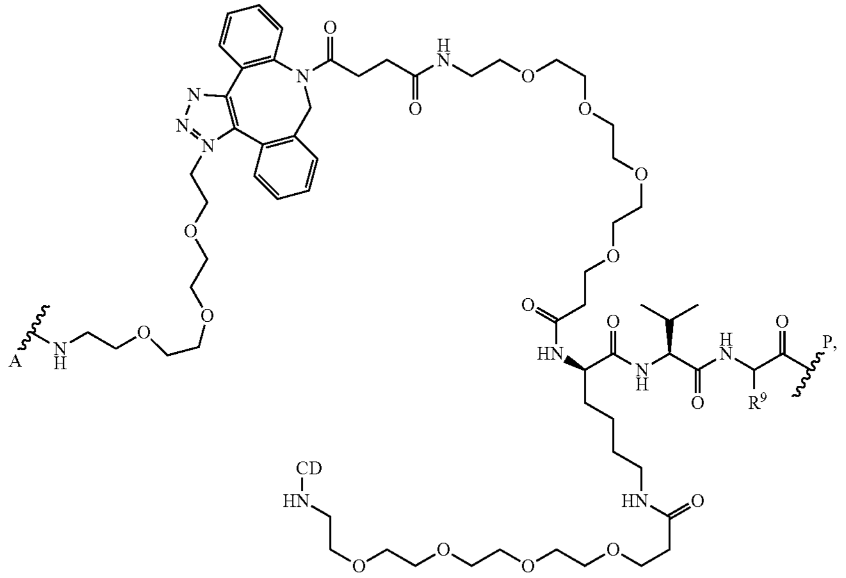
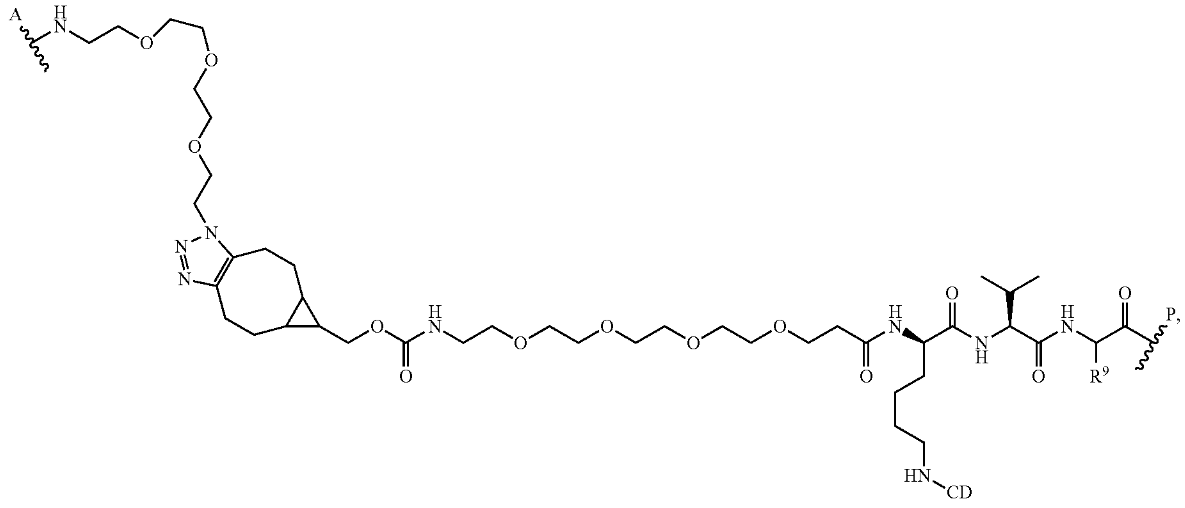

-continued
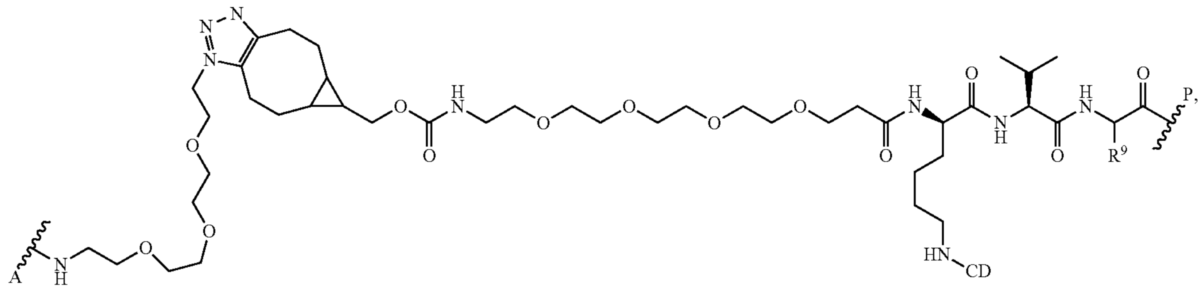
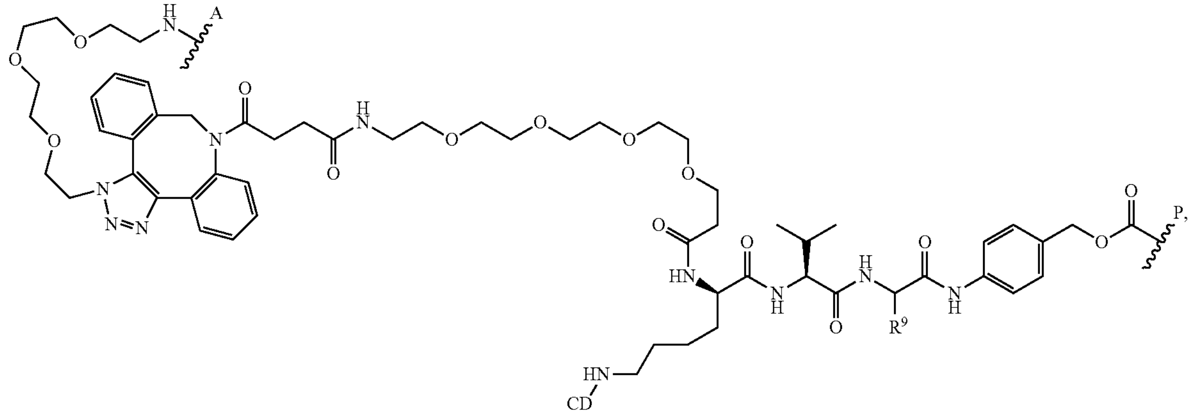
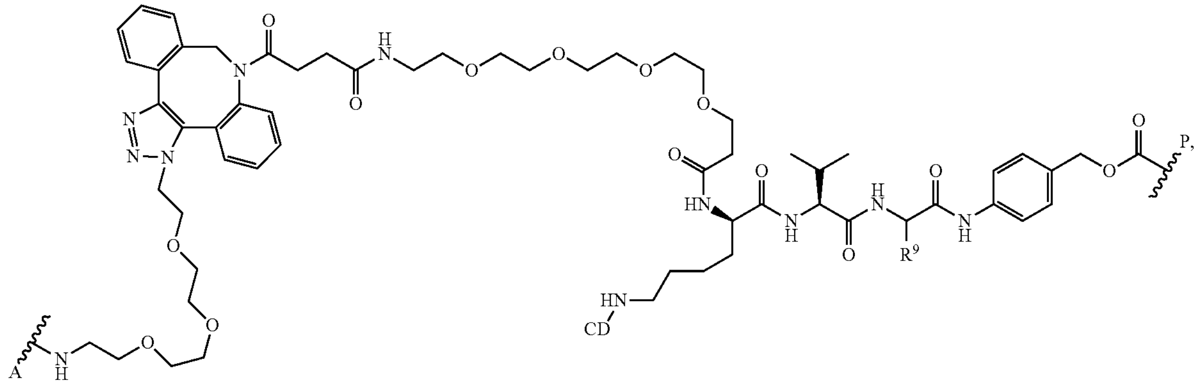
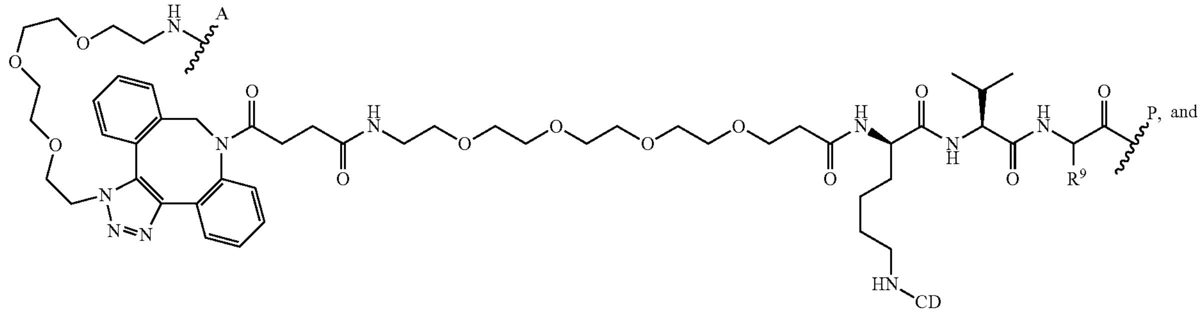
and

-continued

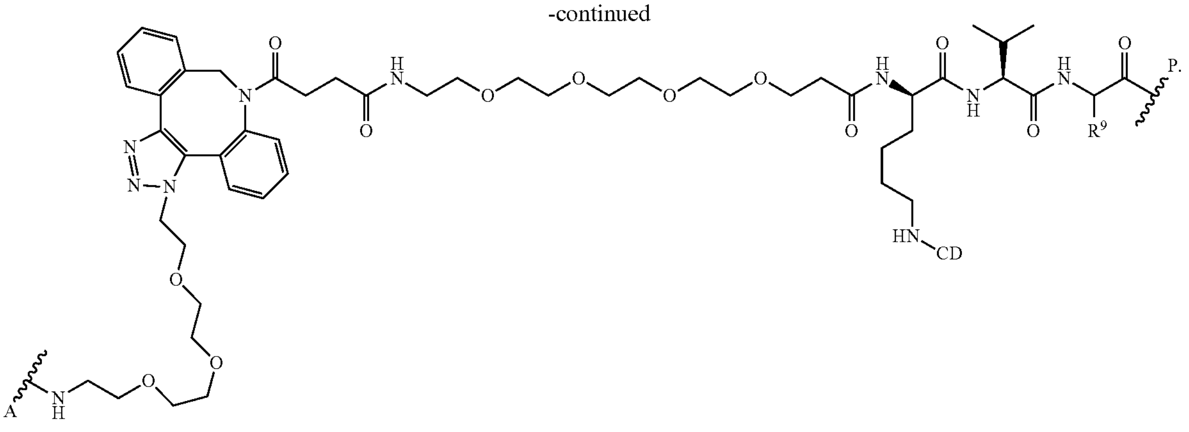

Also included in these examples, is a pharmaceutically acceptable salt, solvate, or stereoisomeric form thereof, a regioisomer thereof, or mixture of regioisomers thereof, wherein each

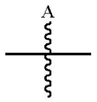

is a bond to the binding agent; each

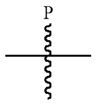

is a bond to the payload; and $R^9$ is —$CH_3$ or —$(CH_2)_3N(H)C(O)NH_2$. In certain examples $R^9$ is —$CH_3$. In certain examples $R^9$ is —$(CH_2)_3N(H)C(O)NH_2$. In some examples, including any of the foregoing,

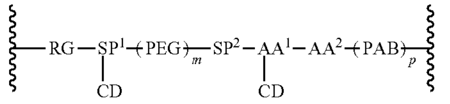

is

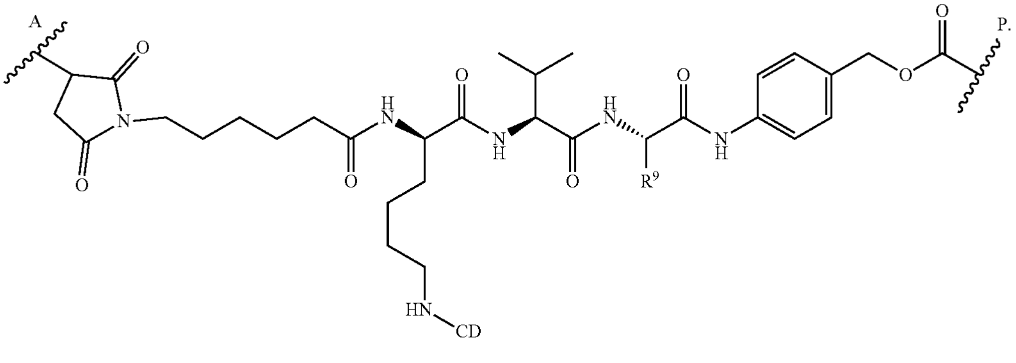

In some examples, including any of the foregoing,

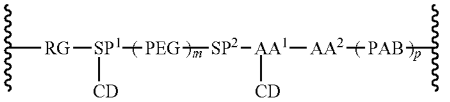

is
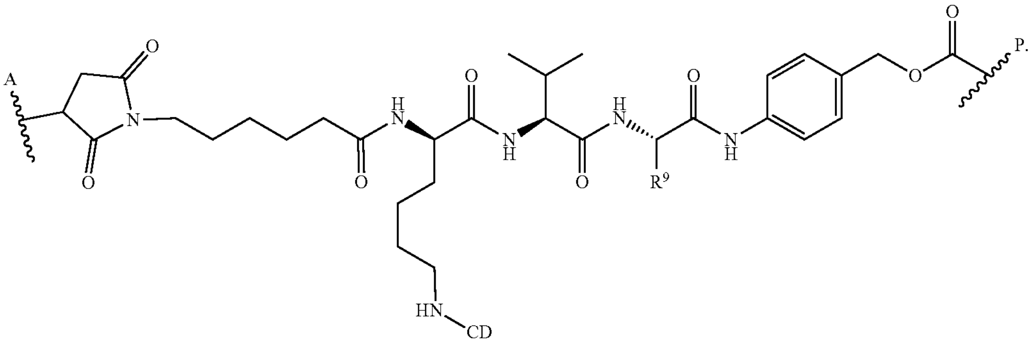
In some examples, including any of the foregoing,
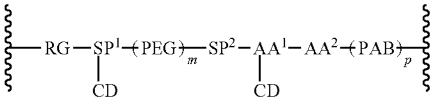
is
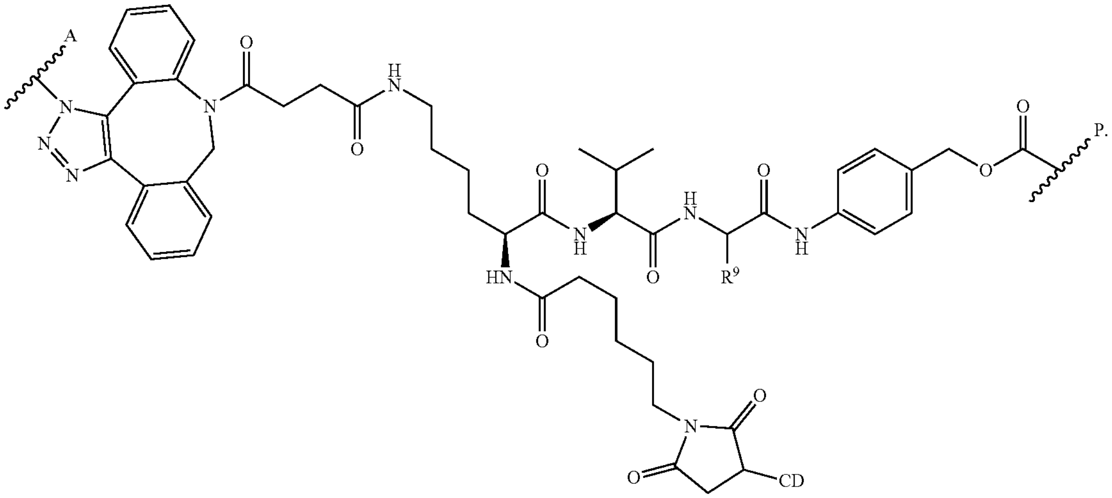
In some examples, including any of the foregoing,
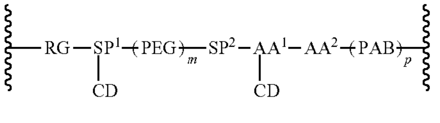

is
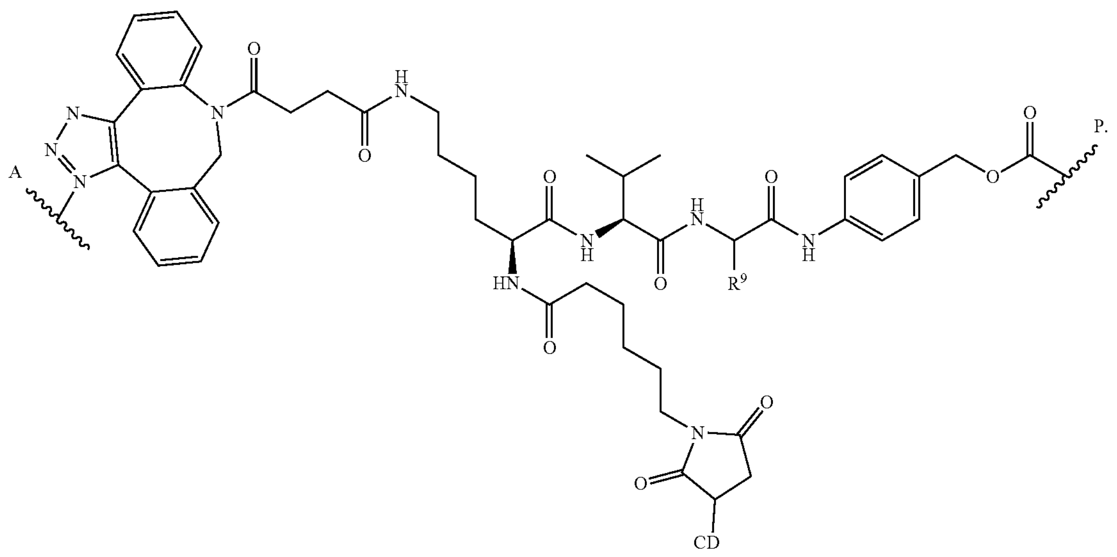
In some examples, including any of the foregoing,
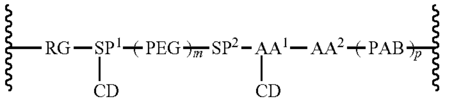
is
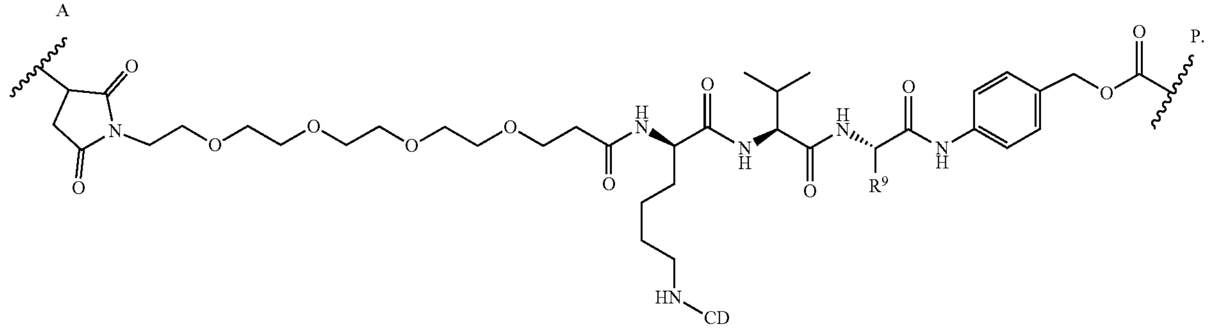
In some examples, including any of the foregoing,
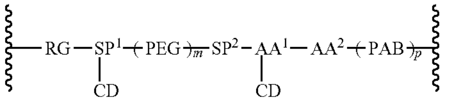

is
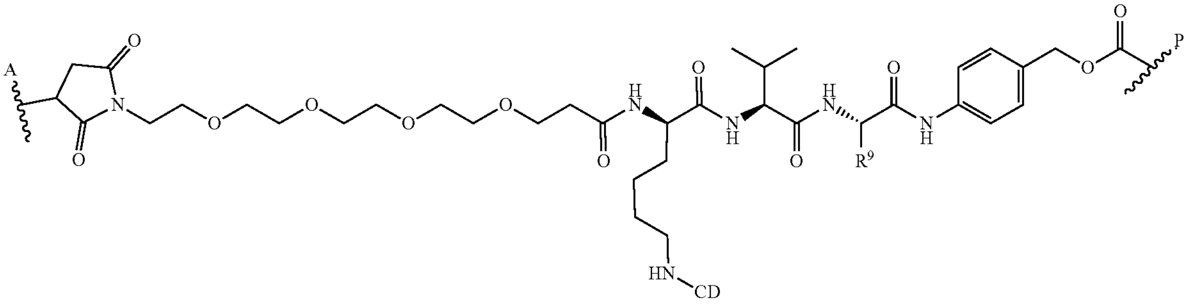
In some examples, including any of the foregoing
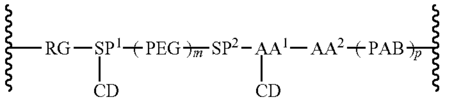
is
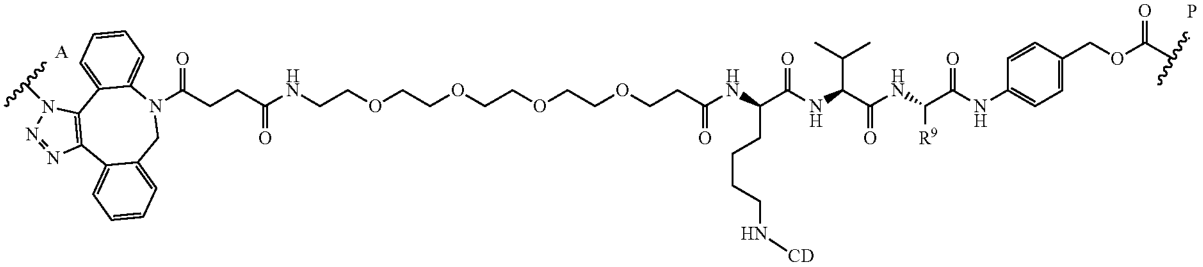
In some examples, including any of the foregoing,
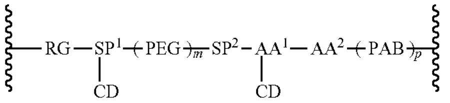
is
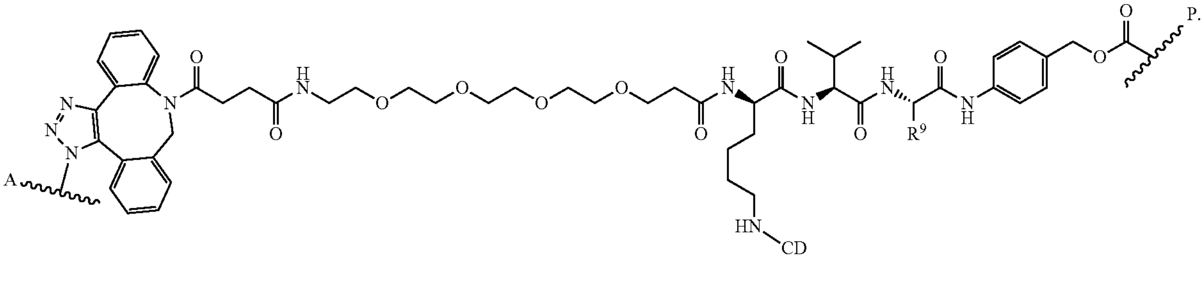
In some examples, including any of the foregoing,
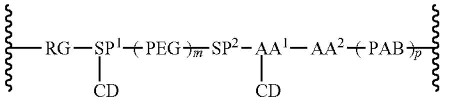

is
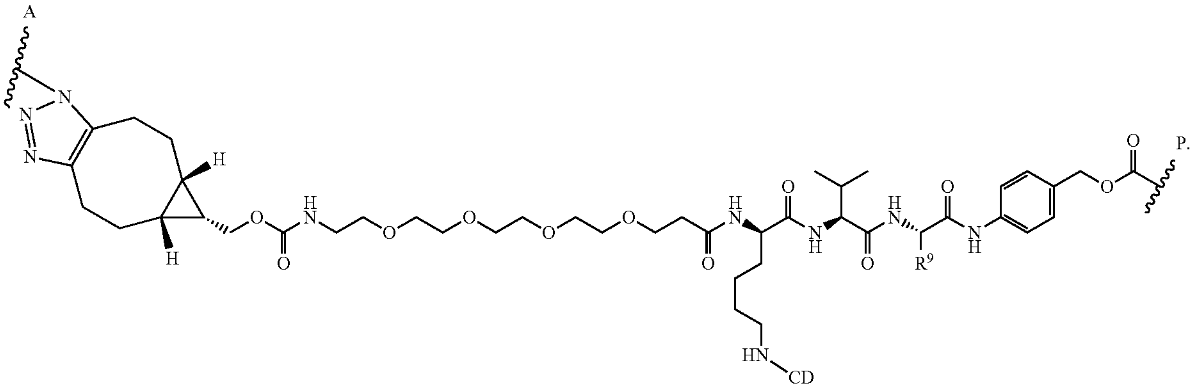
In some examples, including any of the foregoing,
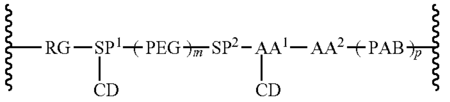
is
In some examples, including any of the foregoing,
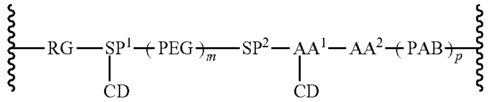
is
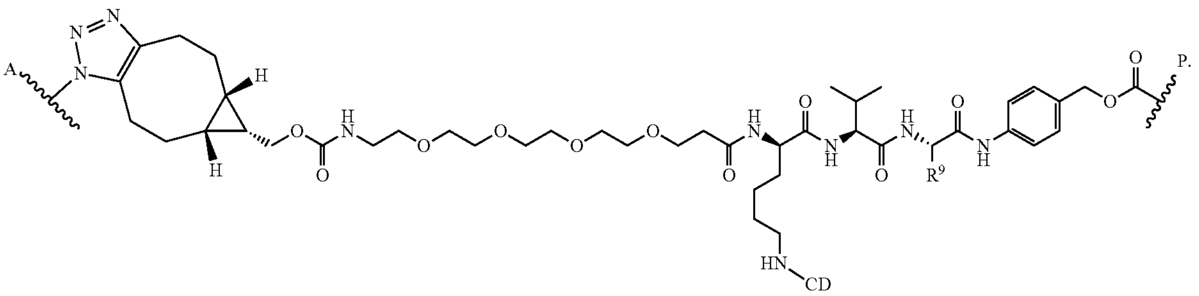
In some examples, including any of the foregoing,
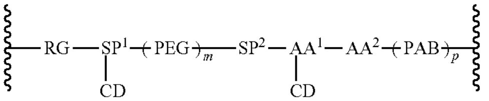
is
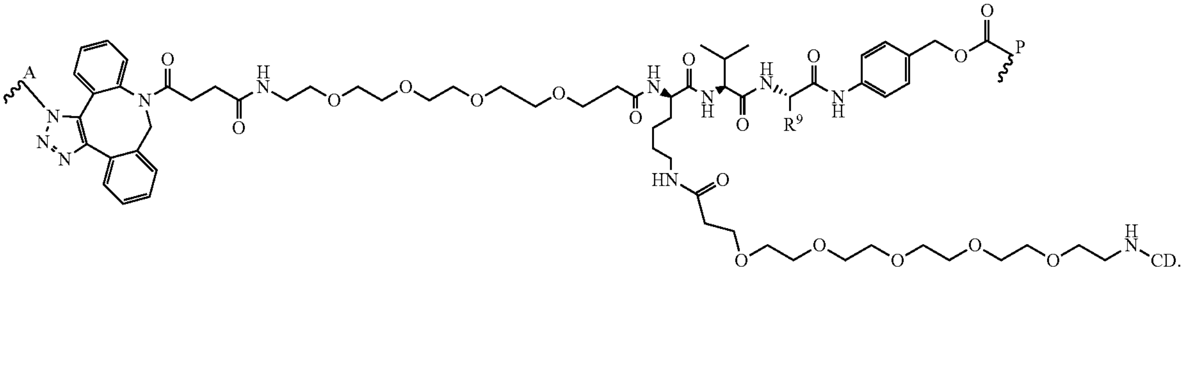

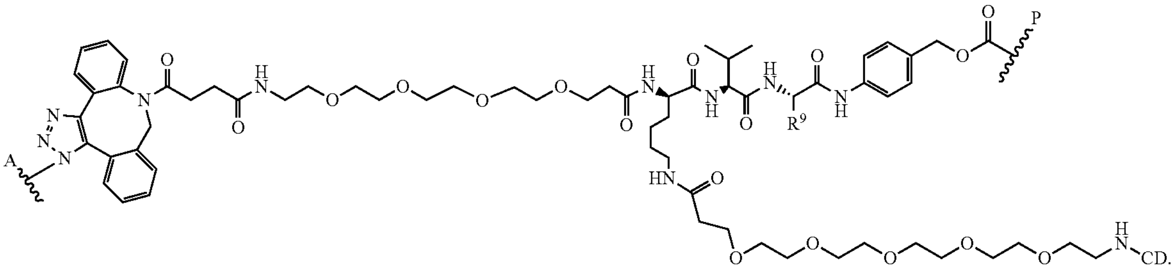
In some examples, including any of the foregoing,
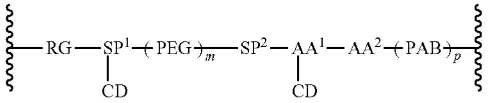
is
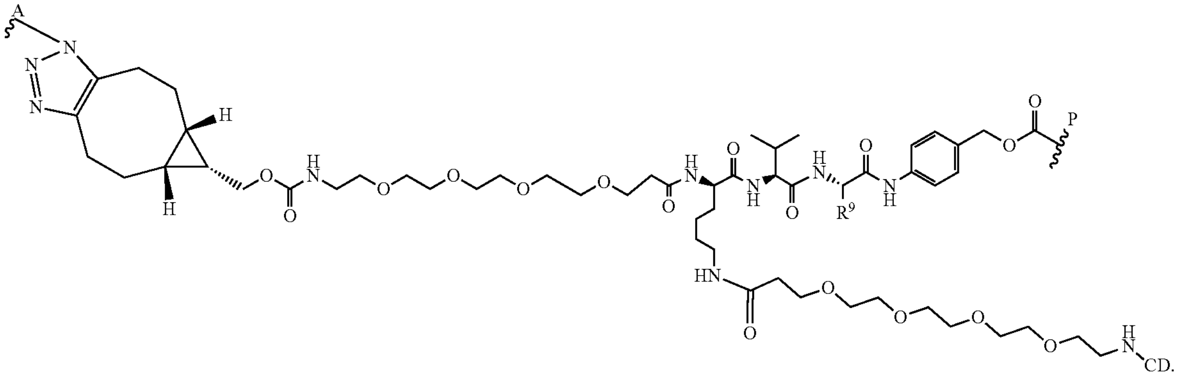
In some examples, including any of the foregoing,
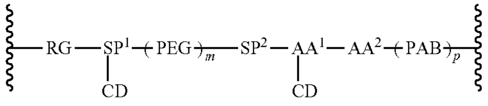
is
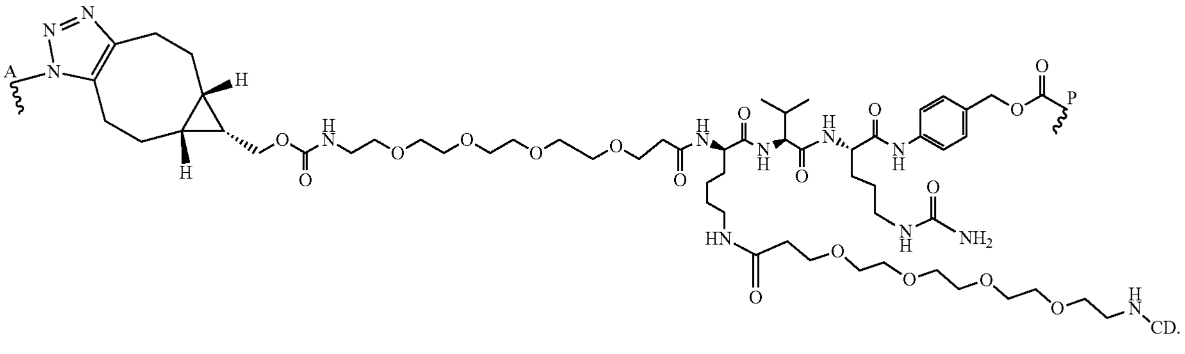

In some examples, including any of the foregoing,
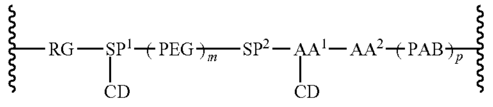
is
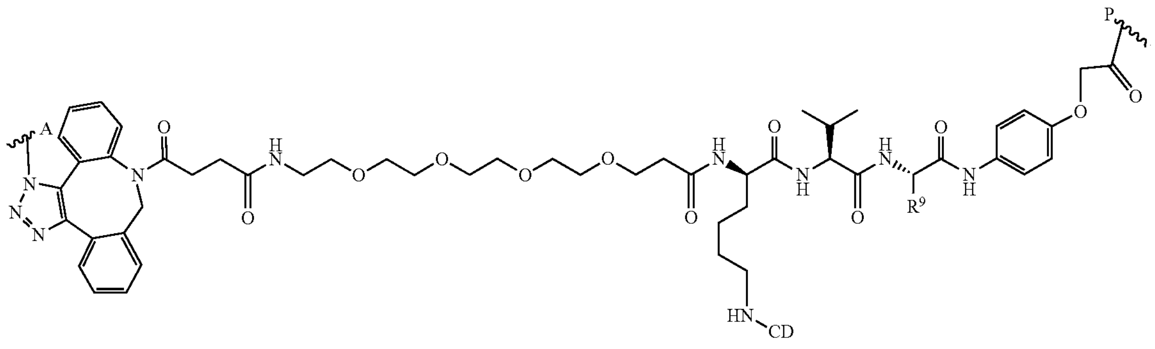
In some examples, including any of the foregoing,
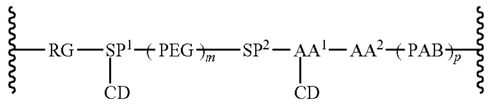
is
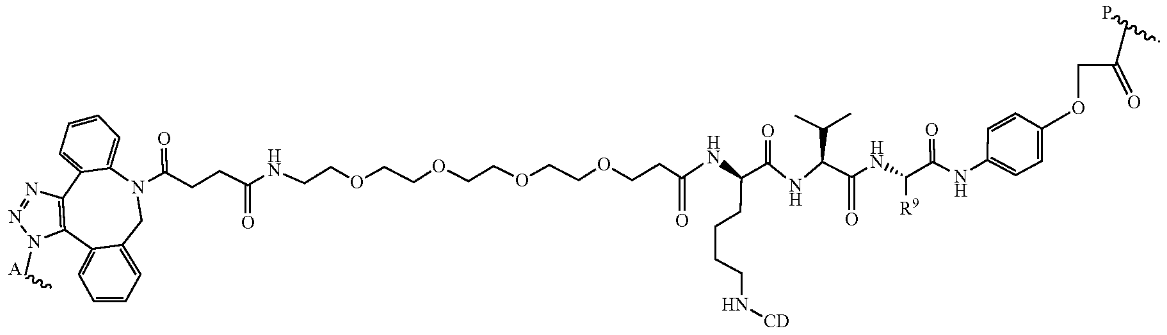
In some examples, including any of the foregoing,
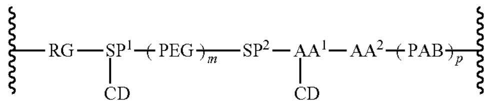

is
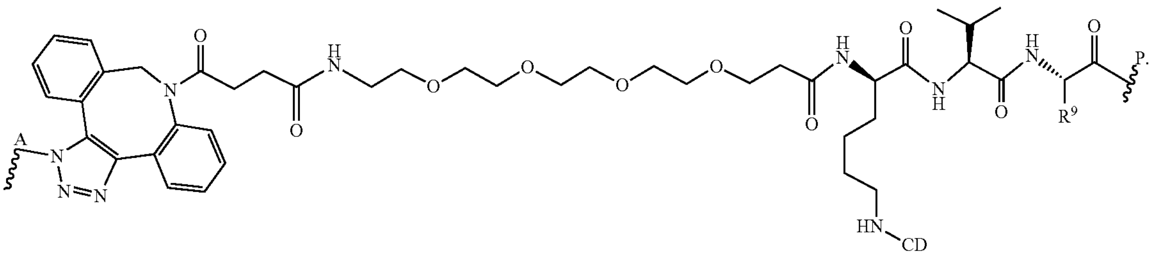
In some examples, including any of the foregoing,
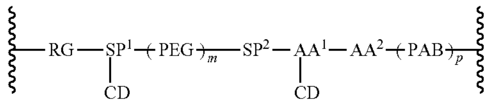
is
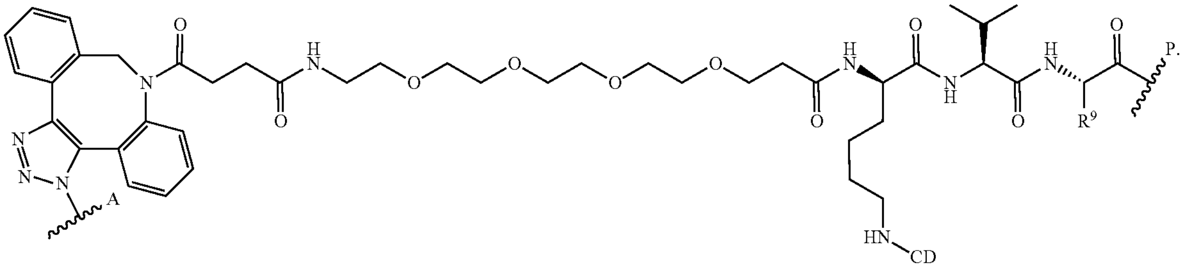
In some examples, including any of the foregoing,
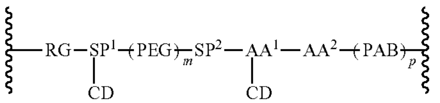

is
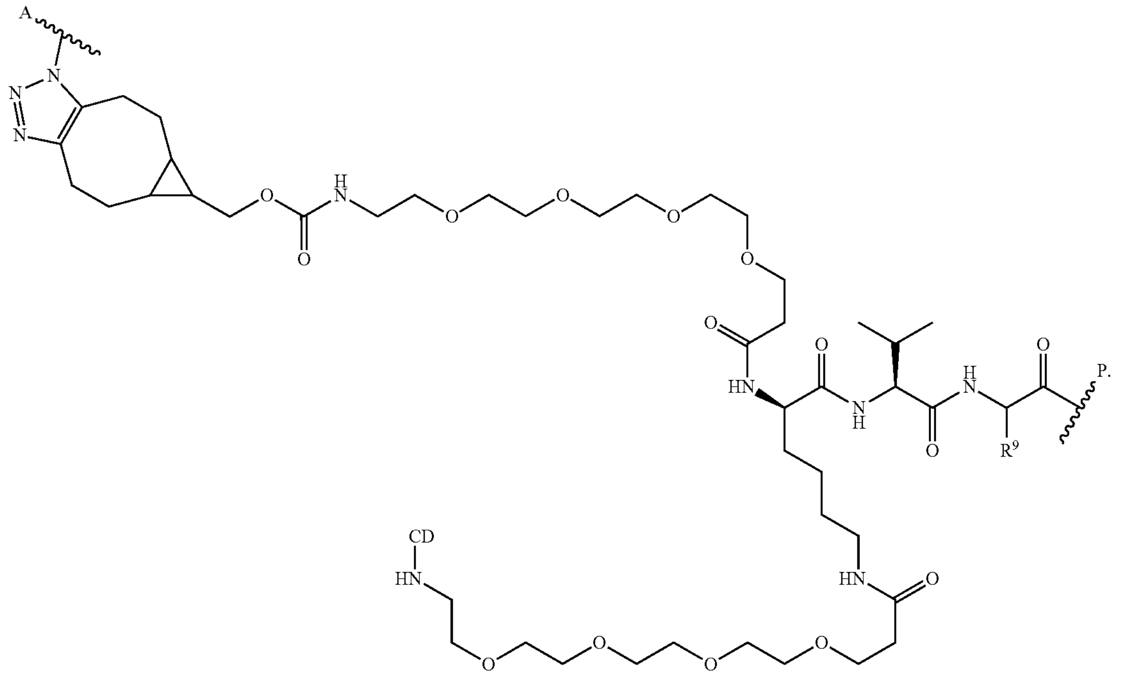
In some examples, including any of the foregoing,
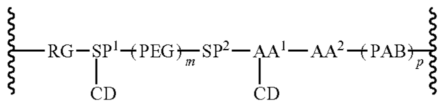
is
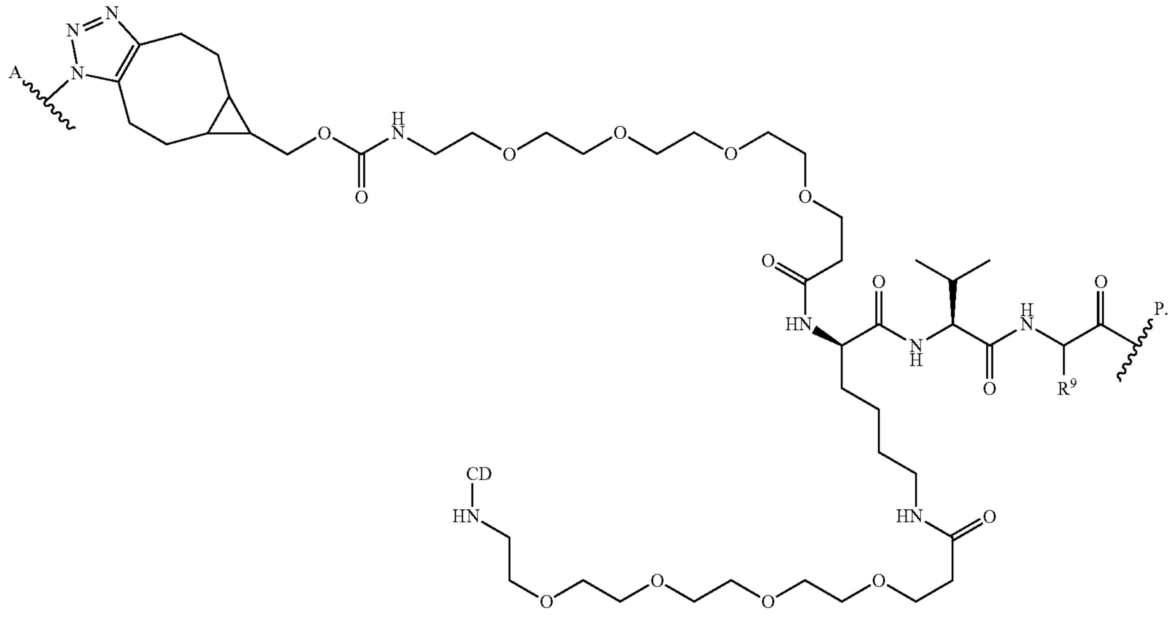

In some examples, including any of the foregoing,
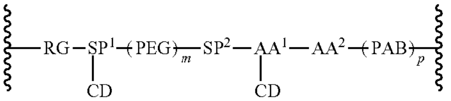
is
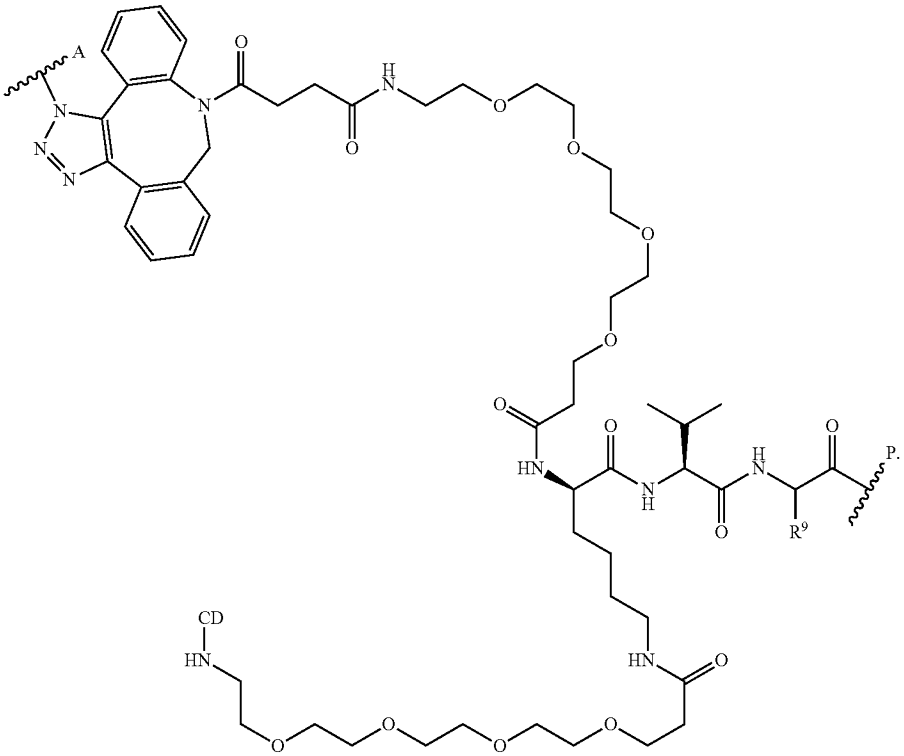
In some examples, including any of the foregoing,
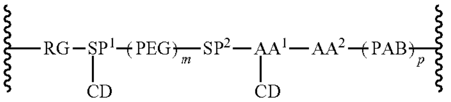

is
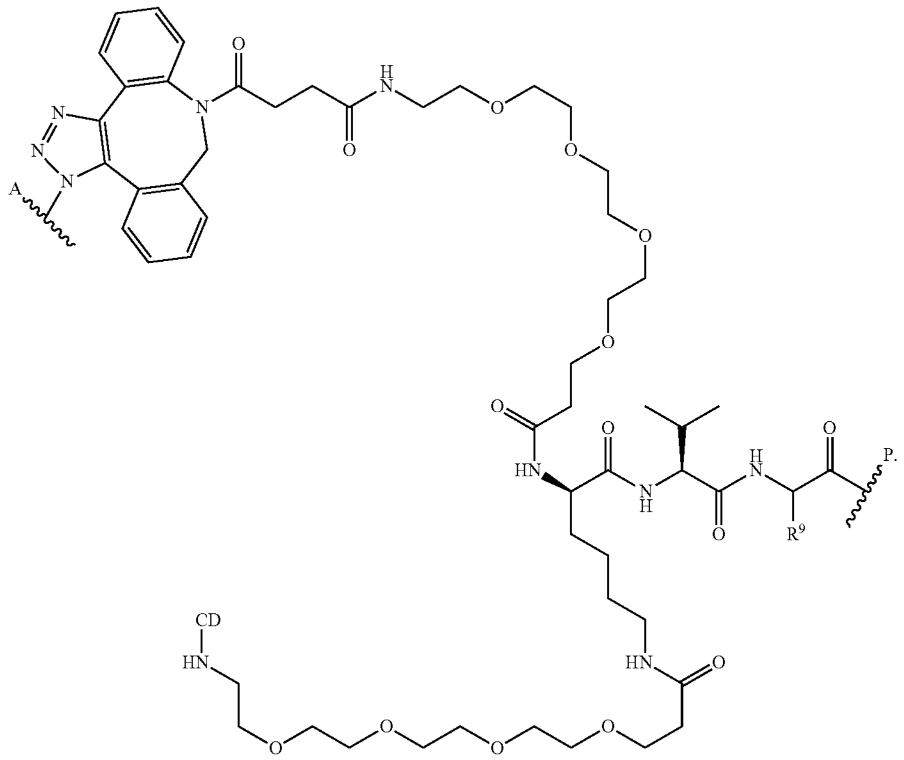
In some examples, including any of the foregoing,
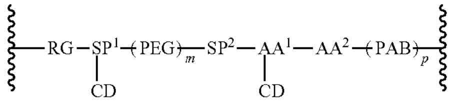
is
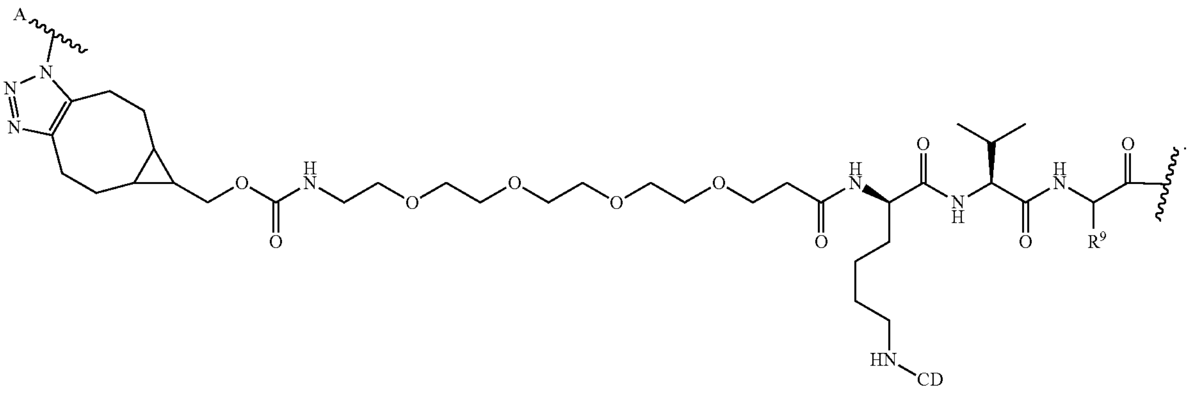
In some examples, including any of the foregoing,
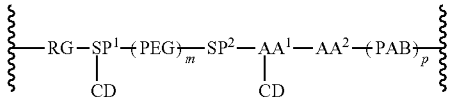

is
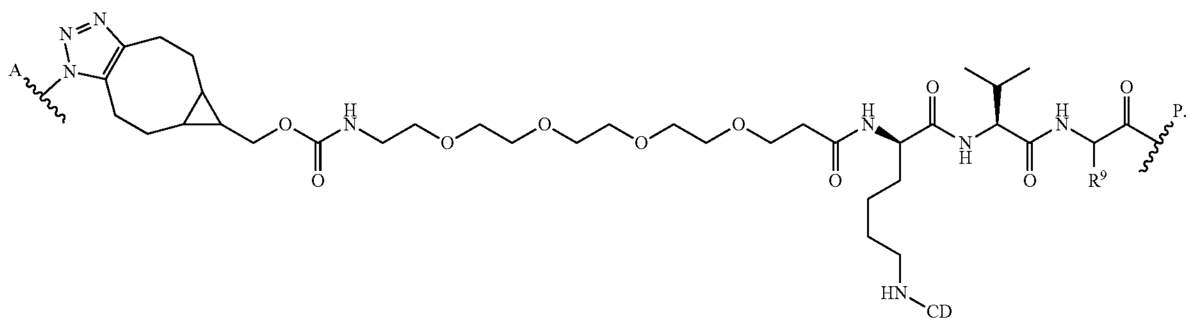
In some examples, including any of the foregoing,
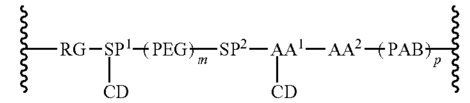
is
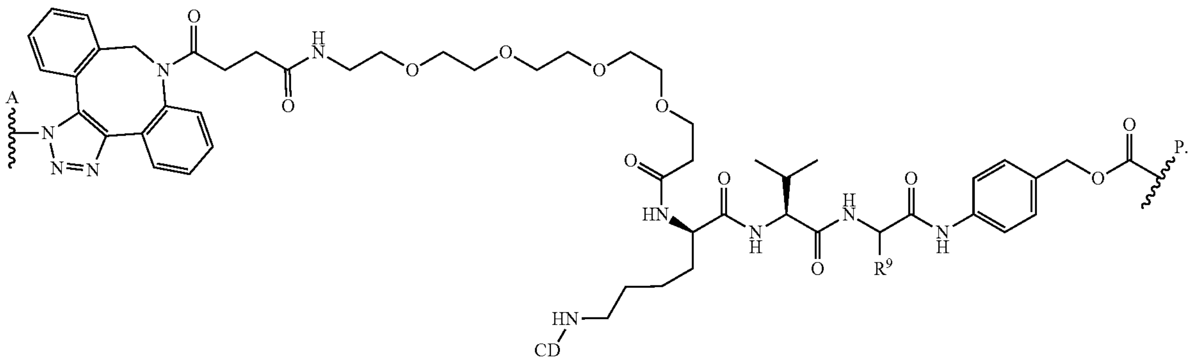
In some examples, including any of the foregoing,
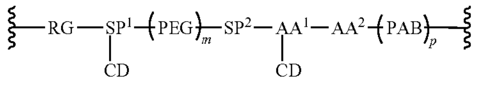
is
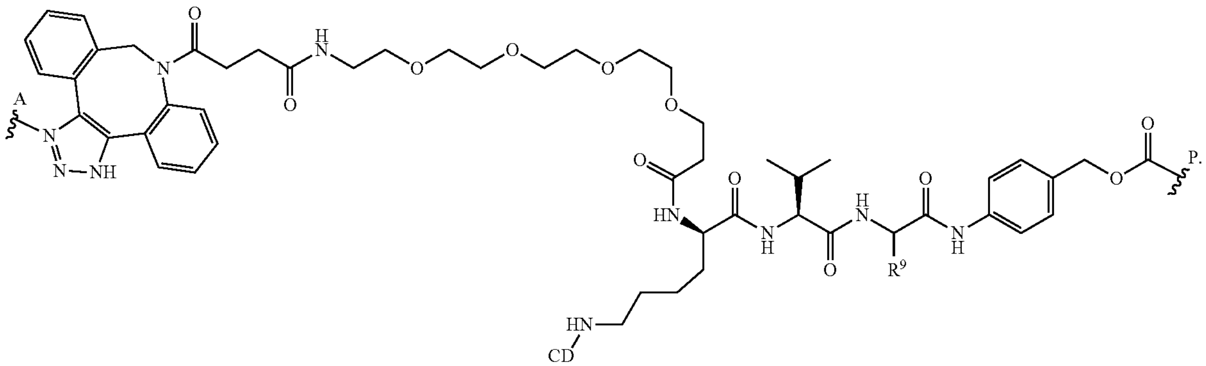

In some examples, including any of the foregoing,
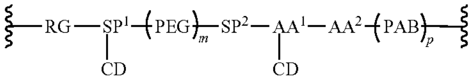
is
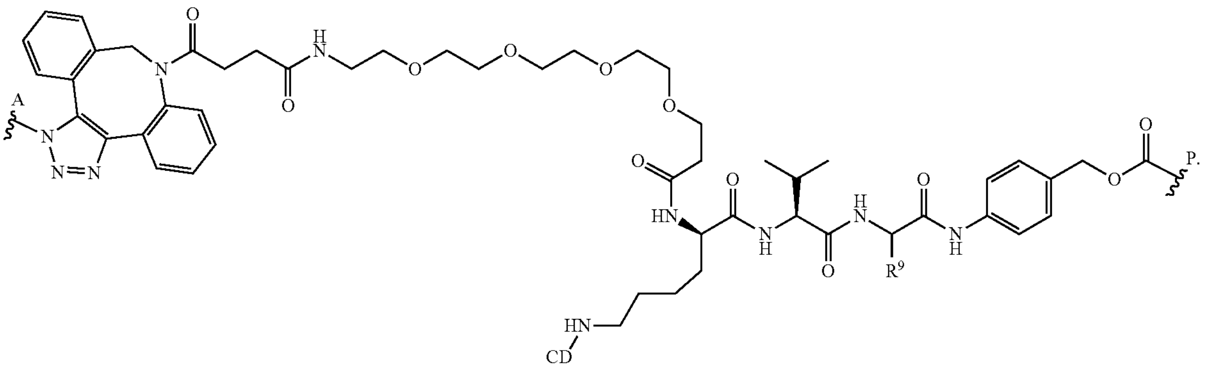
In some examples, including any of the foregoing,
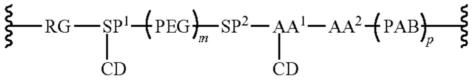
is
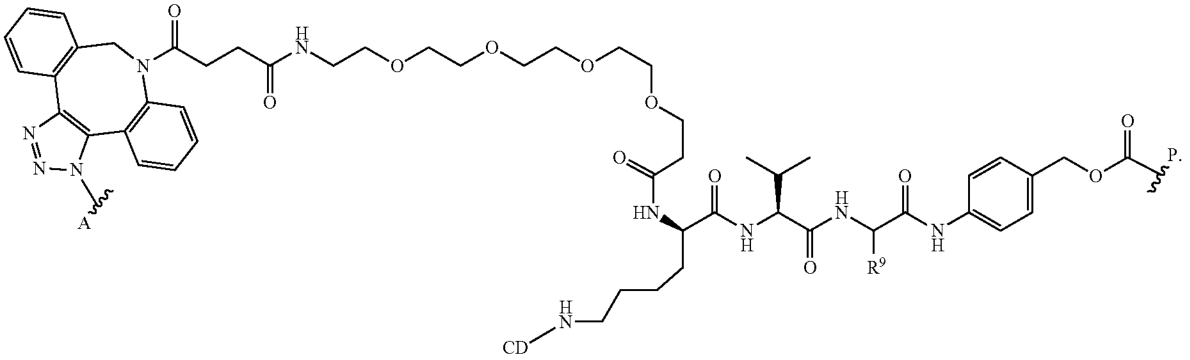
In some examples, including any of the foregoing,
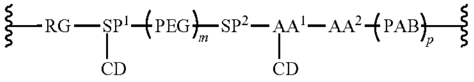

is

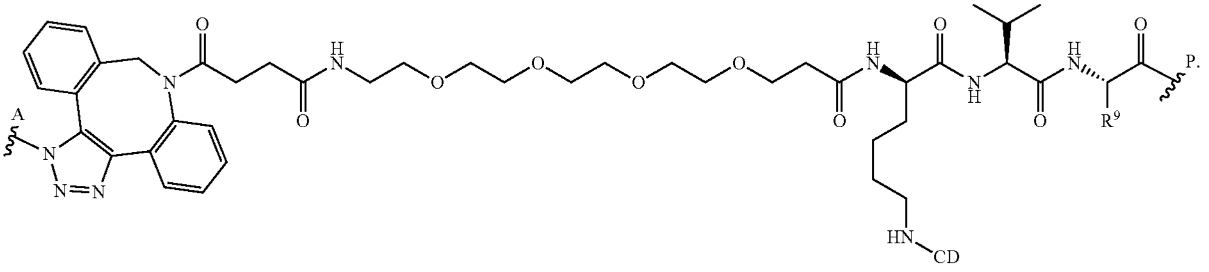

In some examples, including any of the foregoing,

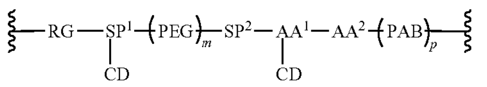

is

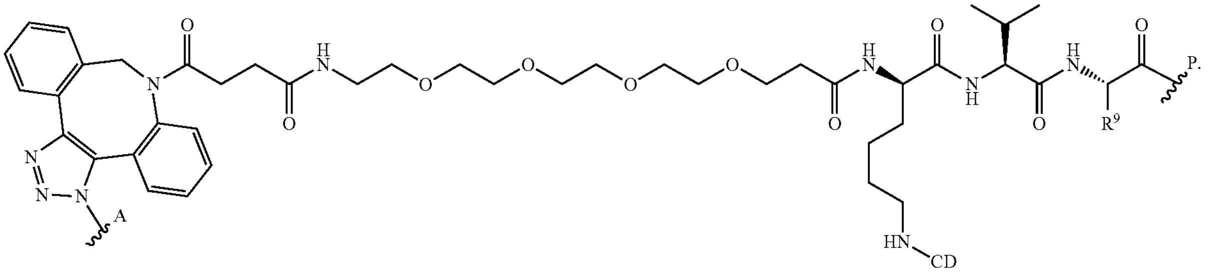

In some examples, including any of the foregoing, CD is, independently in each instance, a cyclodextrin. In some examples, the CD is an α-cyclodextrin. In some examples, the CD is a β-cyclodextrin. In some examples, the CD is a γ-cyclodextrin. In any of these examples, the α-, β-, or γ-cyclodextrin is optionally substituted.

In some examples, including any of the foregoing, CD is, independently in each instance, selected from the group consisting of α-cyclodextrin, β-cyclodextrin, and γ-cyclodextrin. In some examples, CD is α-cyclodextrin. In some examples, CD is β-cyclodextrin. In some examples, CD is γ-cyclodextrin.

In some examples, including any of the foregoing, CD is, independently in each instance, selected from:

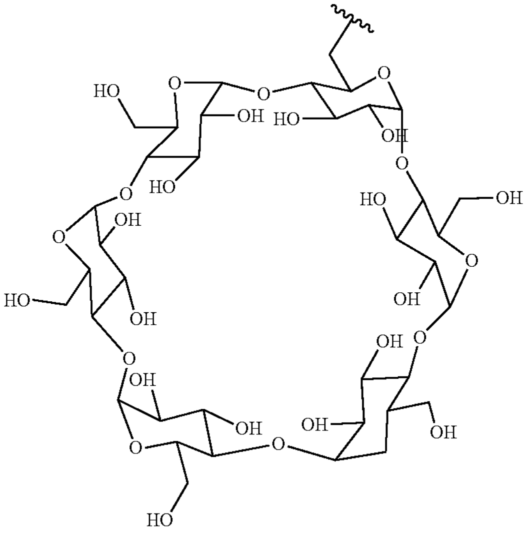 [SMILES: *CC1OC2OC3C(CO)OC(OC4C(CO)CC(OC5C(CO)OC(OC6C(CO)OC(OC7C(CO)OC(OC1C(O)C2O)C(O)C7O)C(O)C6O)C(O)C5O)C(O)C4O)C(O)C3O]
and
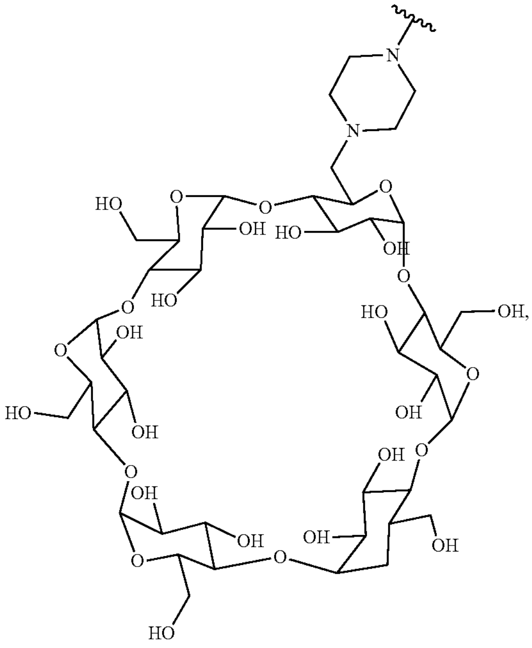
wherein the
indicates the atom through which the CD is bonded to the adjacent groups in the formula. In certain examples, the CD is
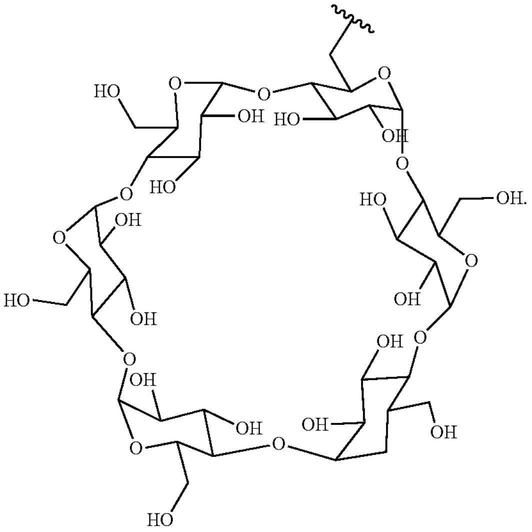
In certain examples, the CD is
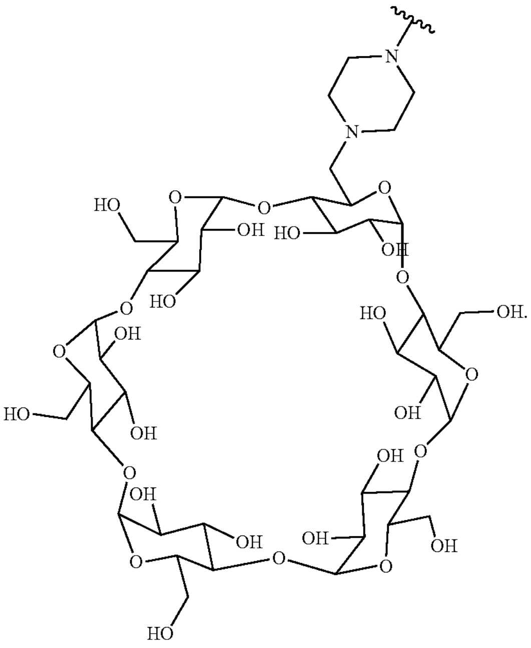 [SMILES: *N1CCN(CC2OC3OC4C(CO)OC(OC5C(CO)OC(OC6C(CO)OC(OC7C(CO)OC(OC8C(CO)OC(OC2C(O)C3O)C(O)C8O)C(O)C7O)C(O)C6O)C(O)C5O)C(O)C4O)CC1]
In some examples, including any of the foregoing, the compound of Formula (I) includes a group selected from

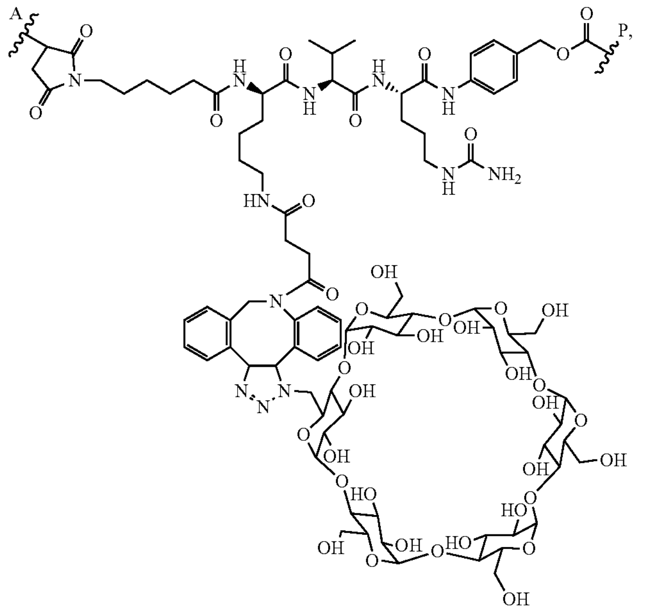
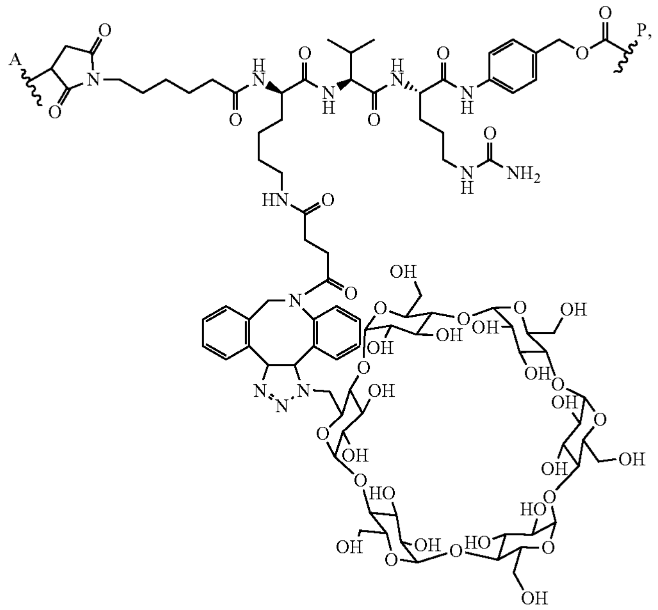

-continued
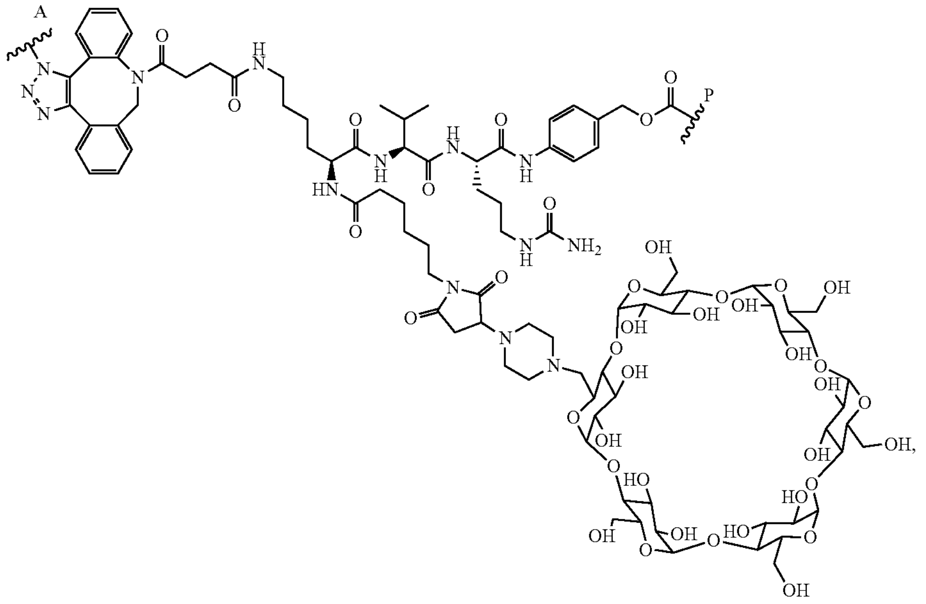
,
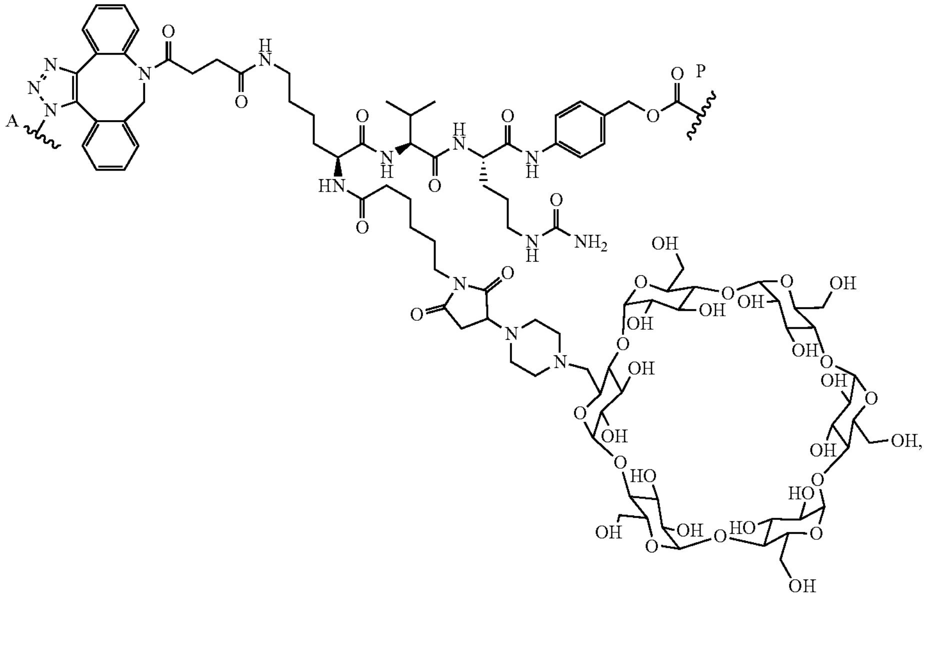
,

-continued
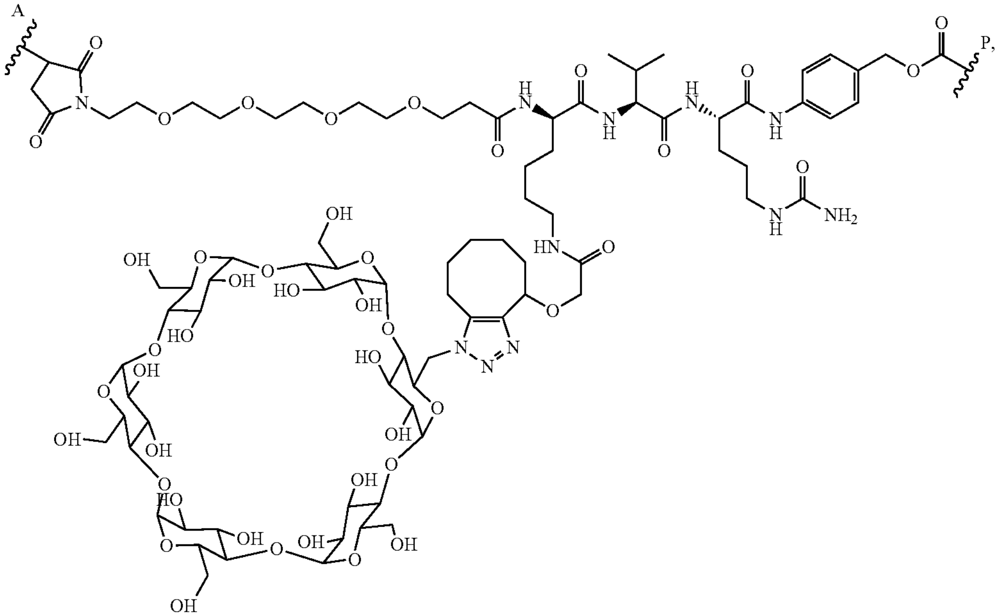
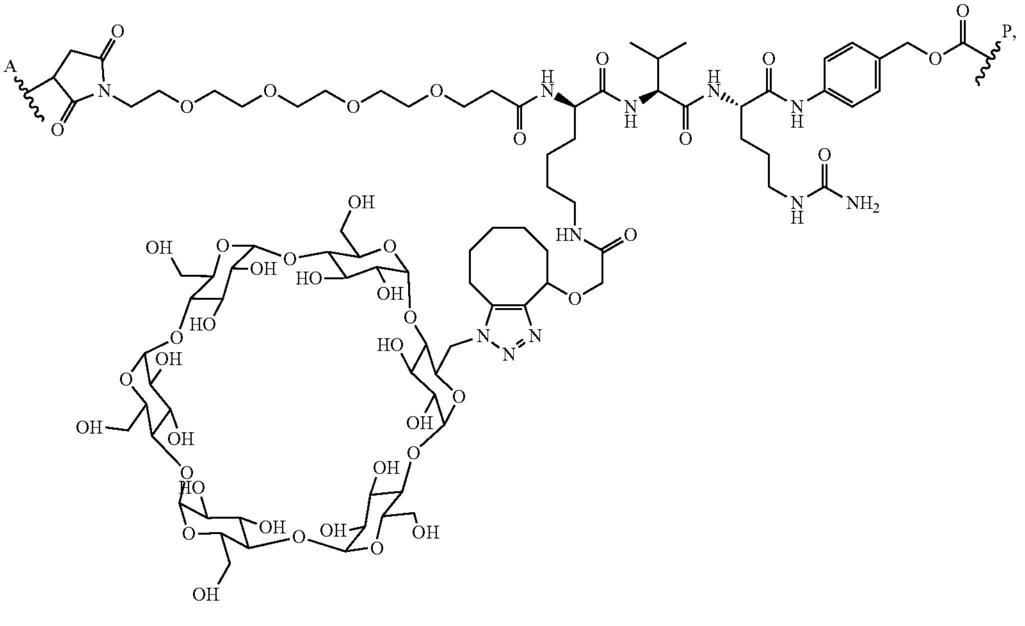

-continued
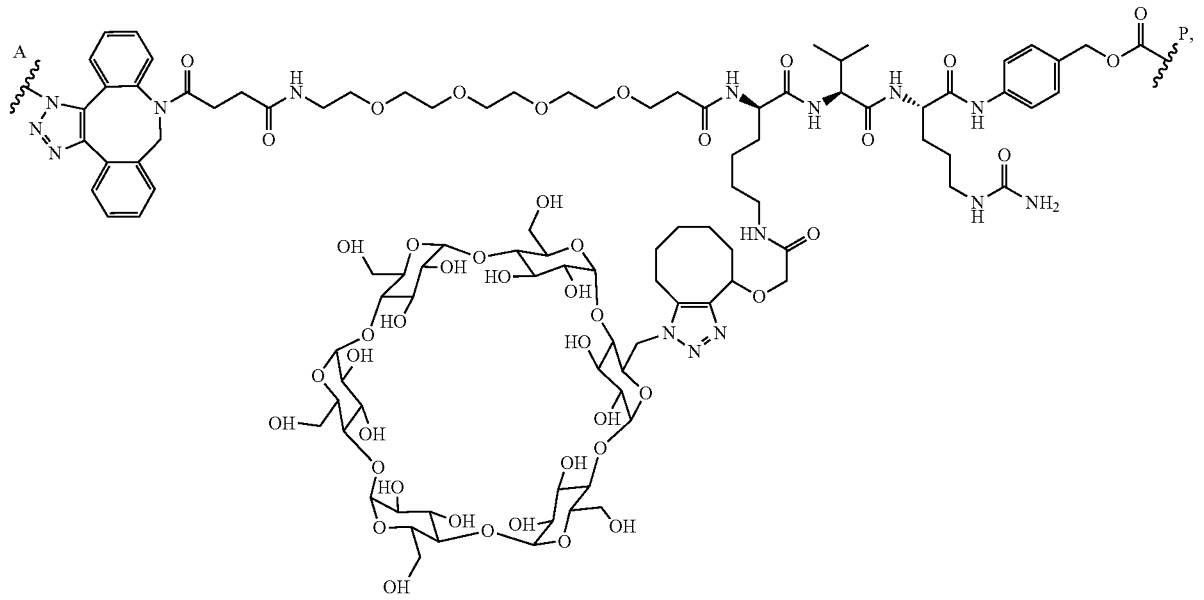
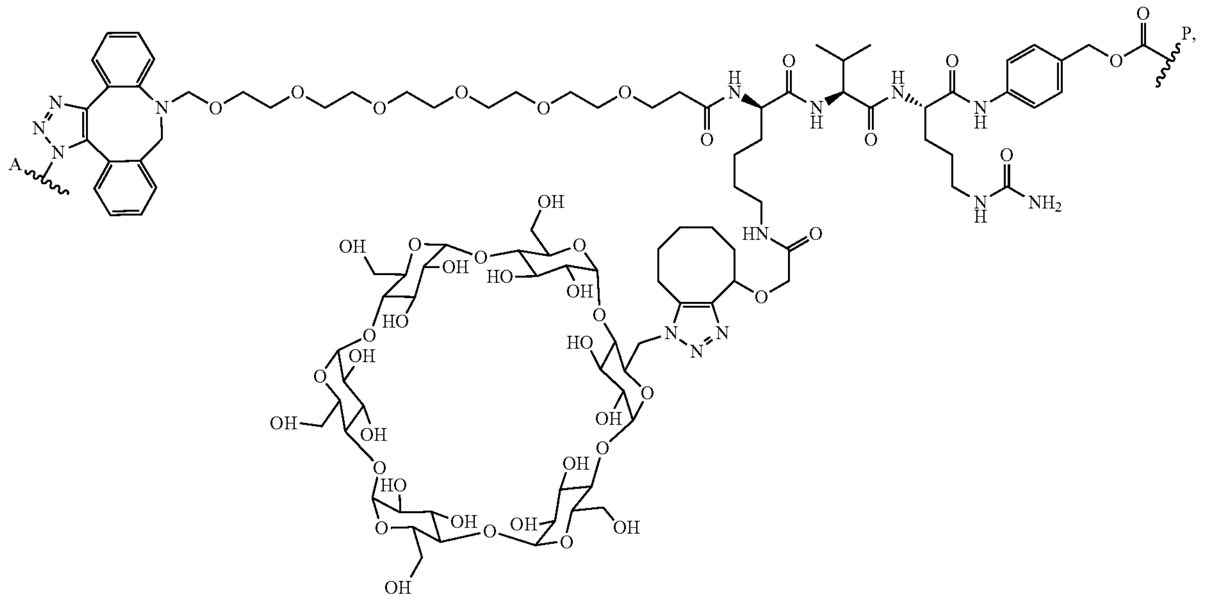

-continued
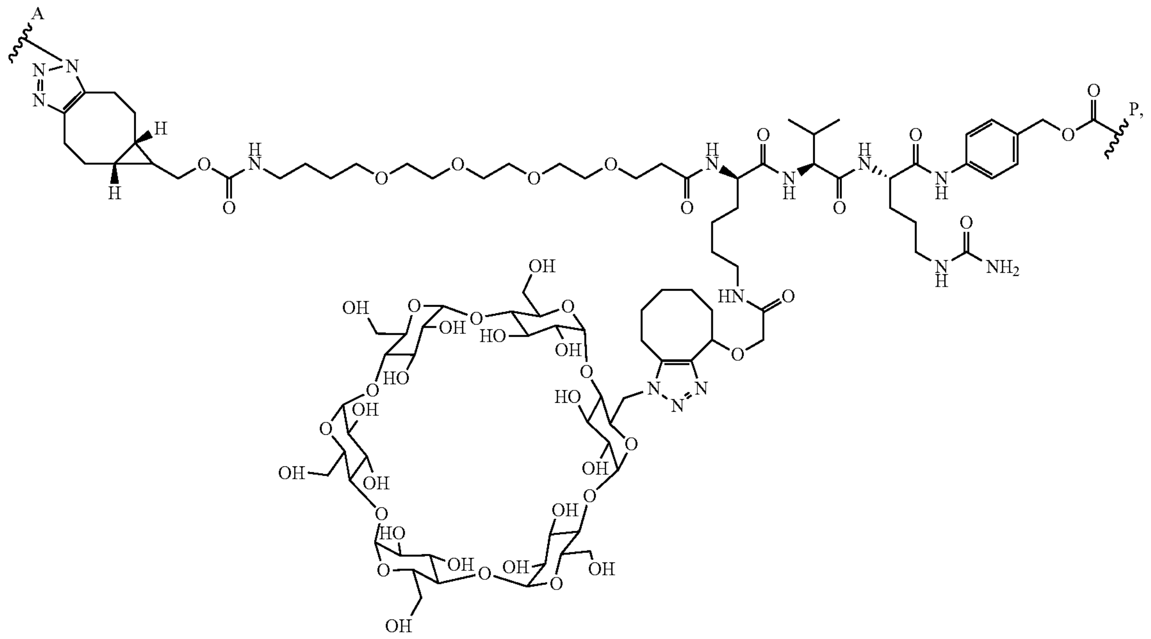
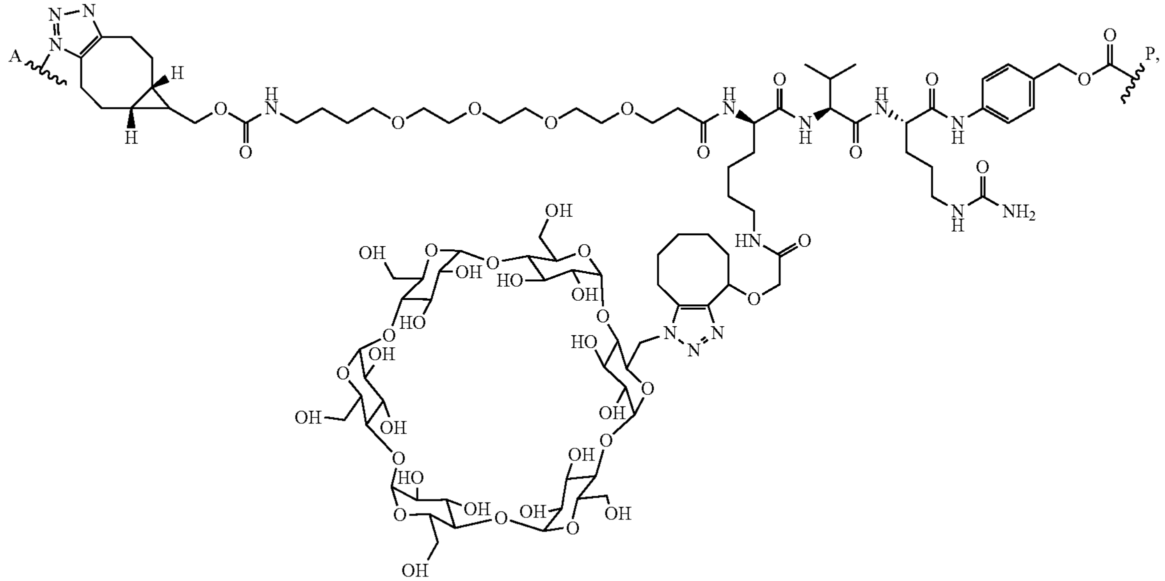
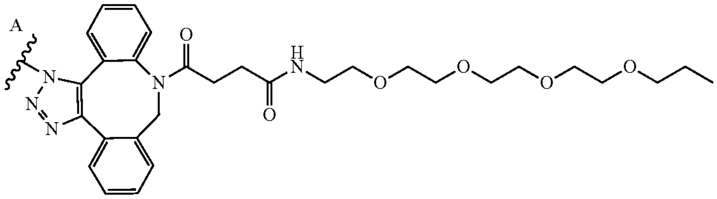

-continued
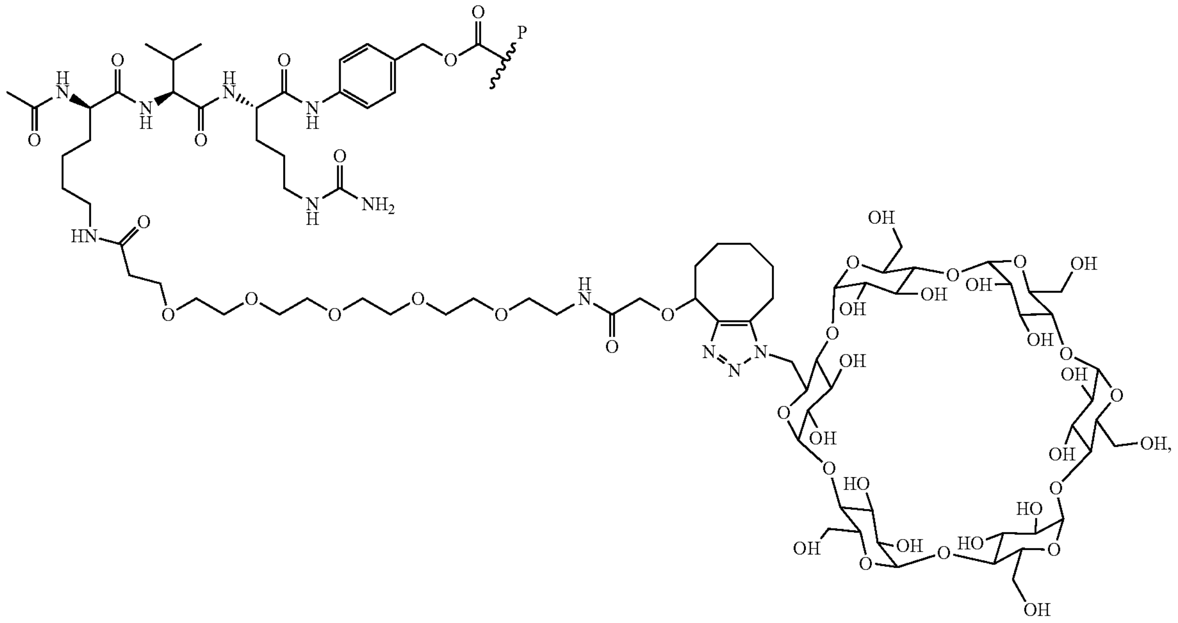
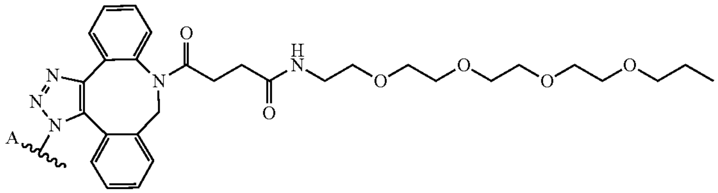
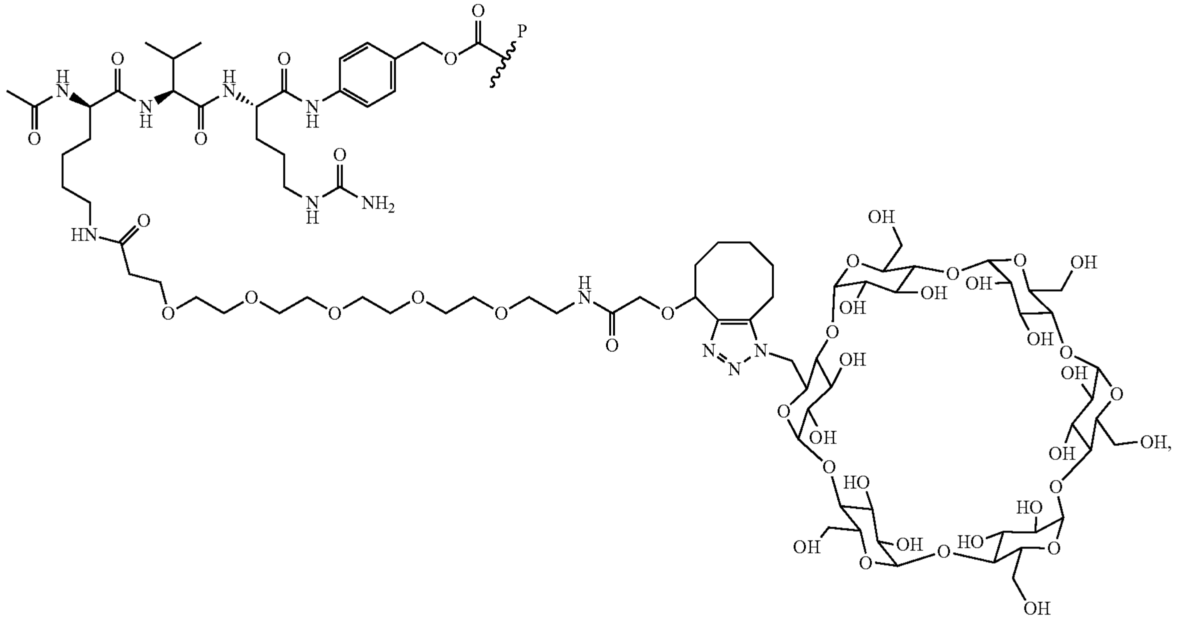
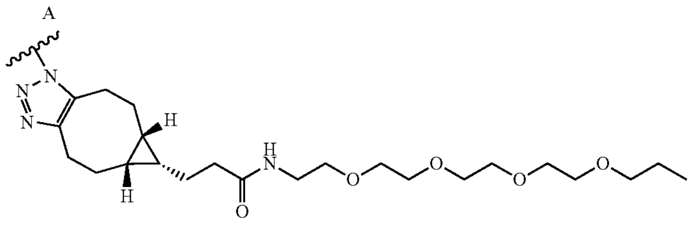

-continued
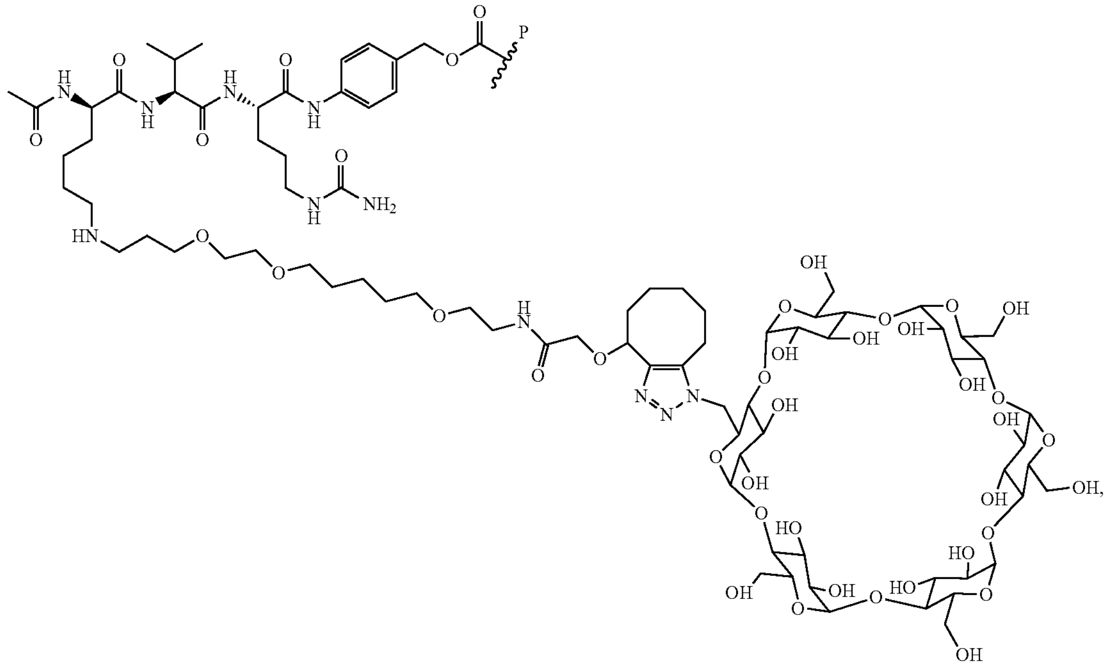
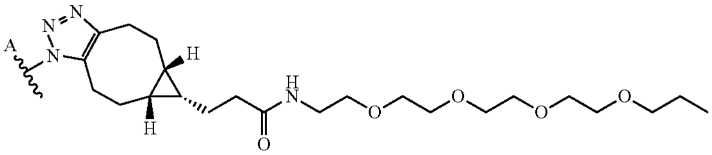
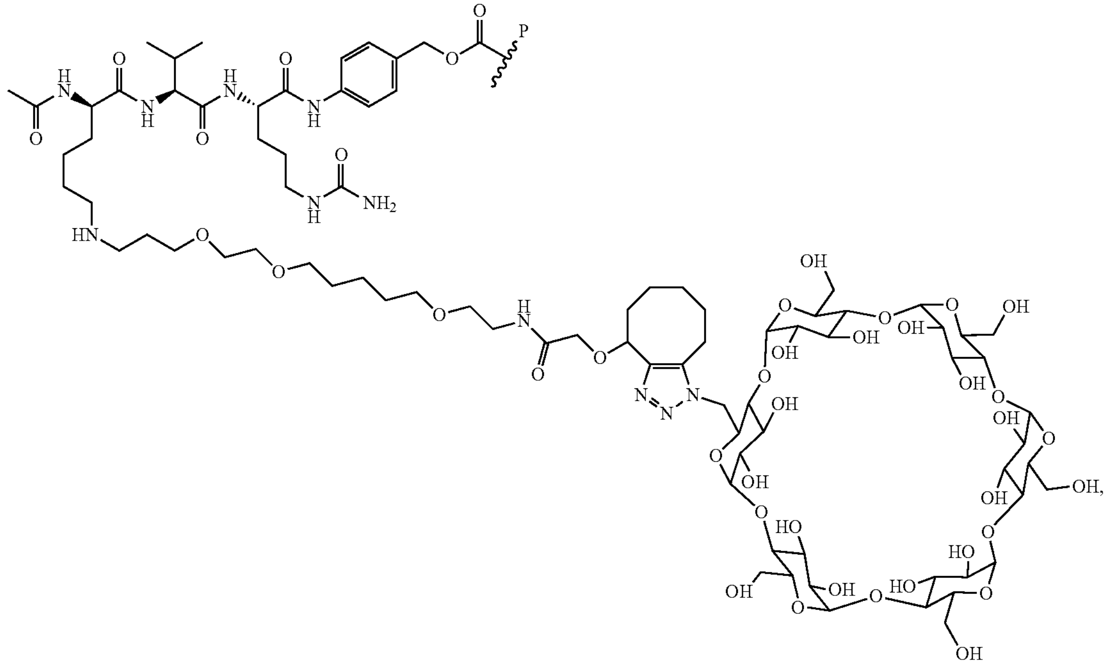

-continued
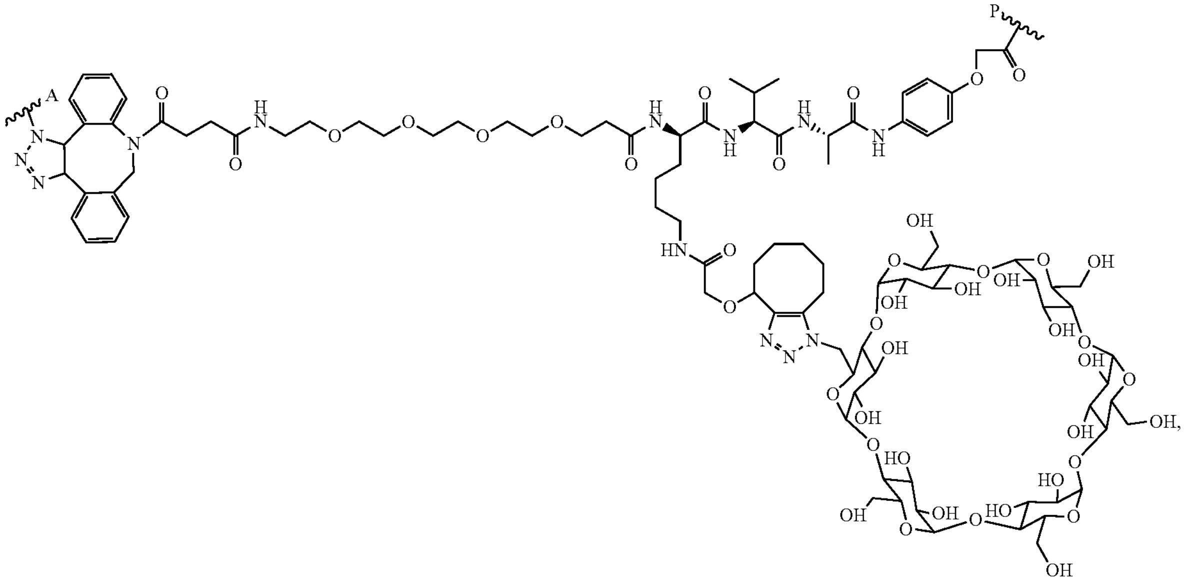
,
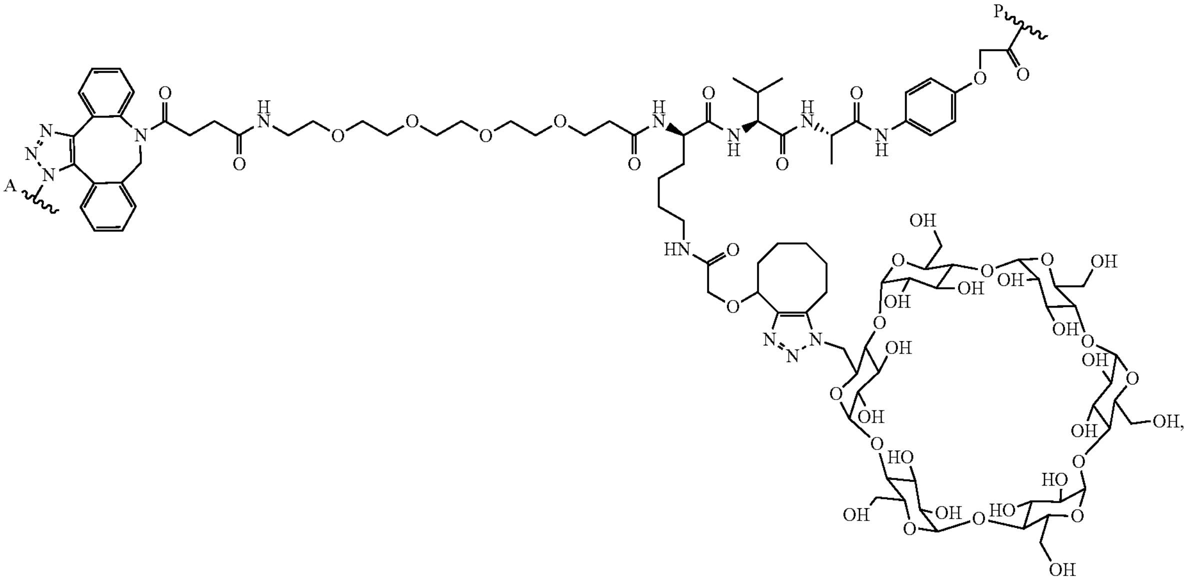
,
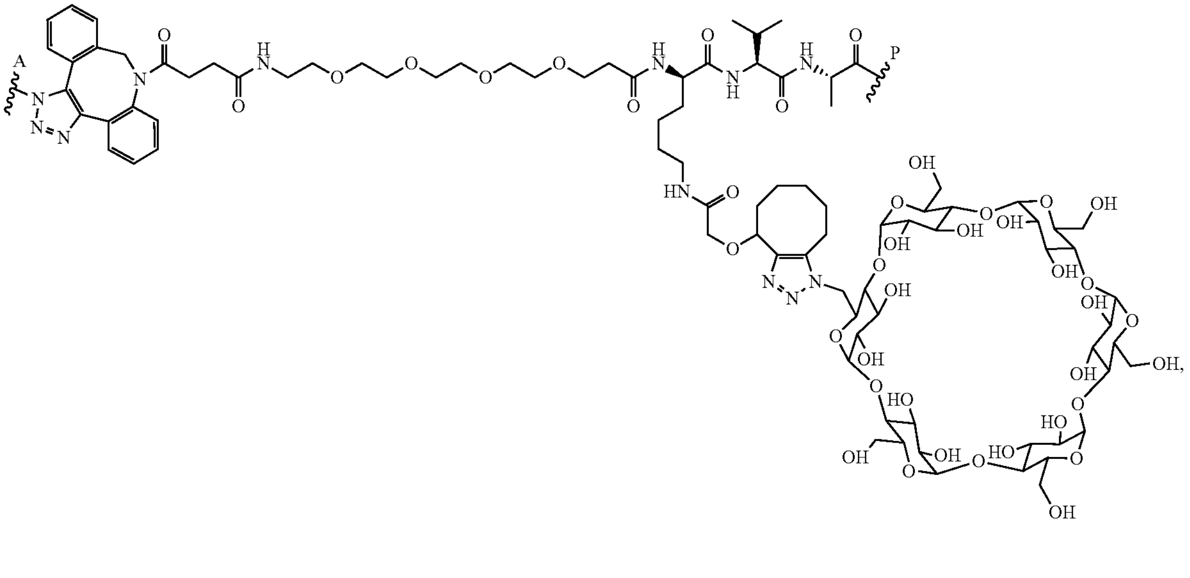
,

-continued
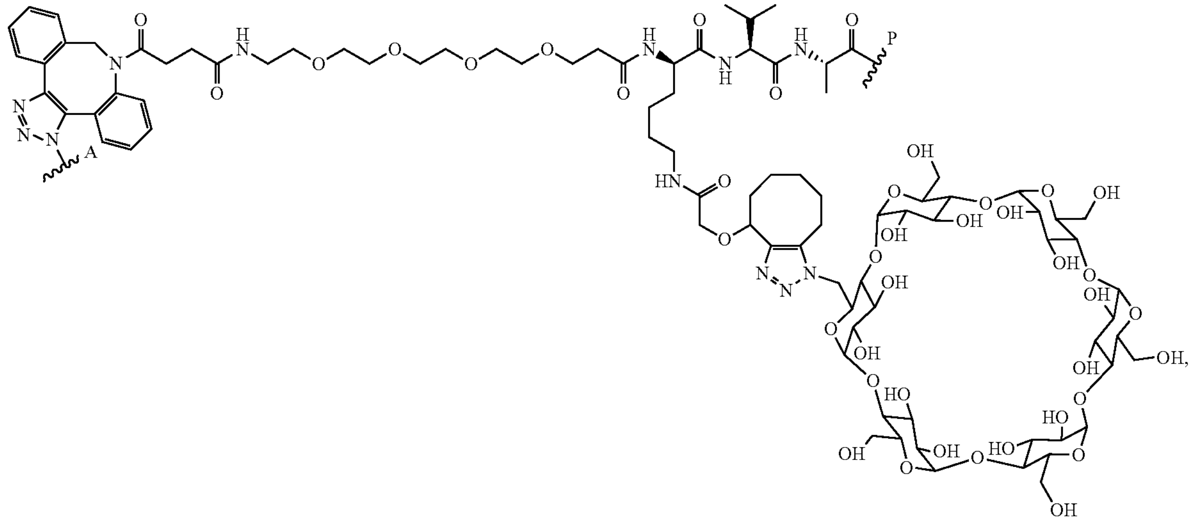
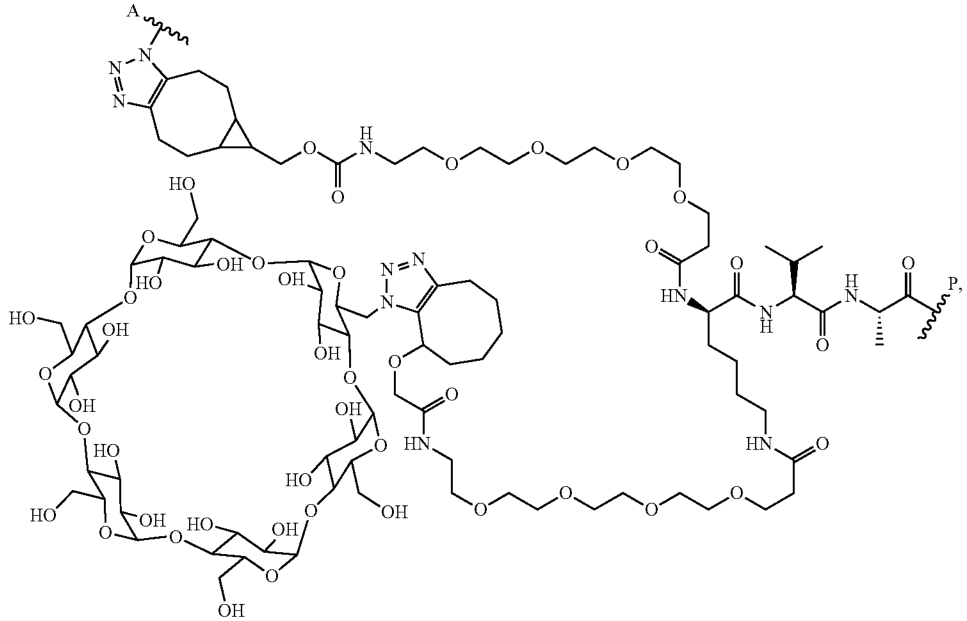
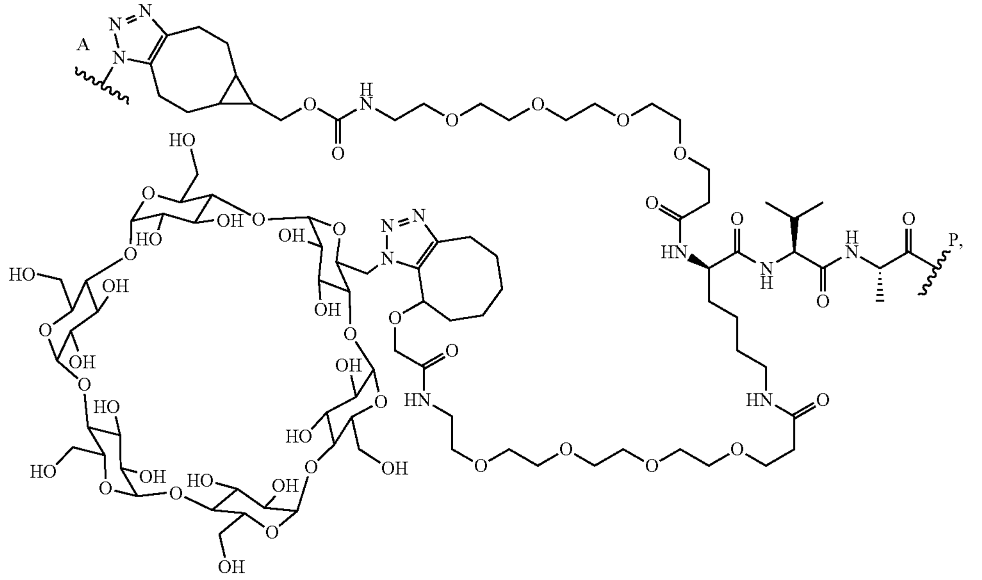

-continued
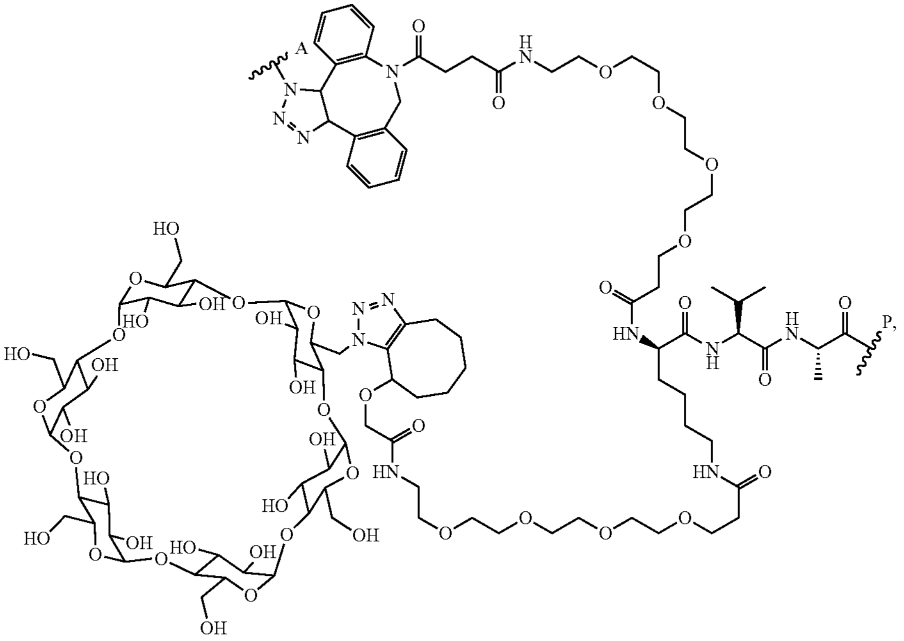
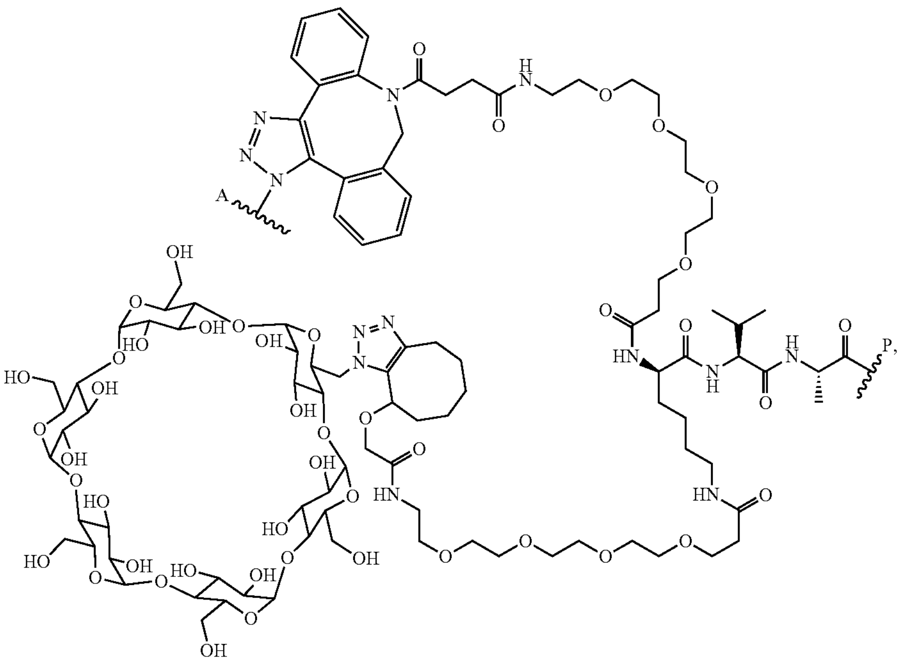

-continued
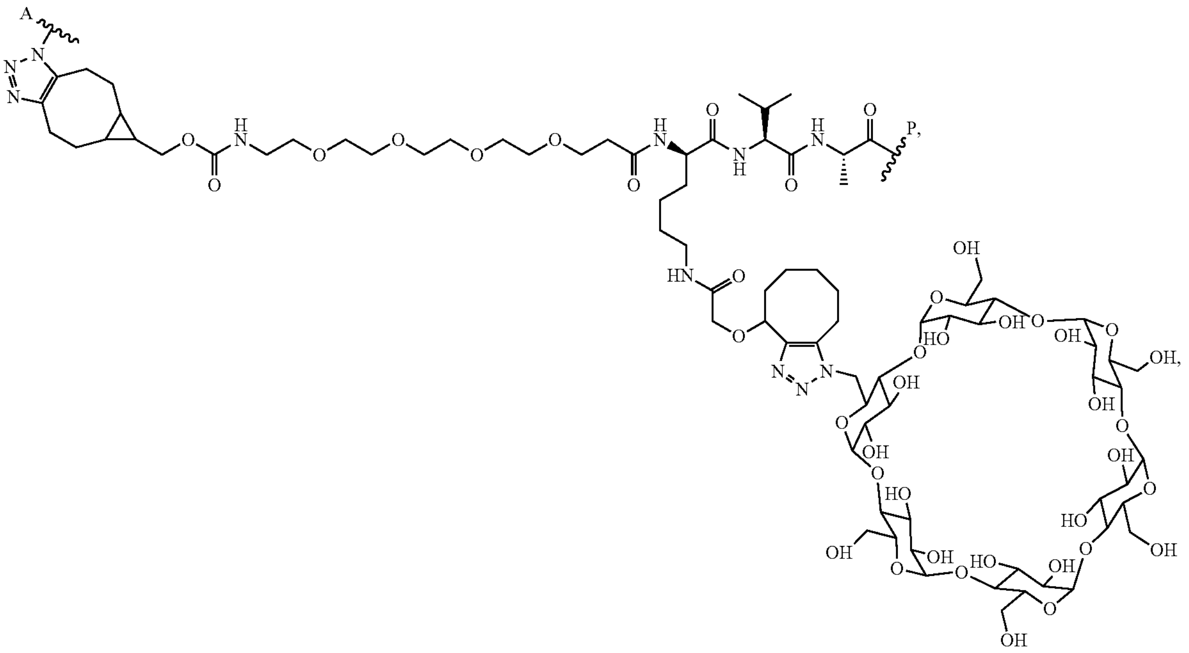
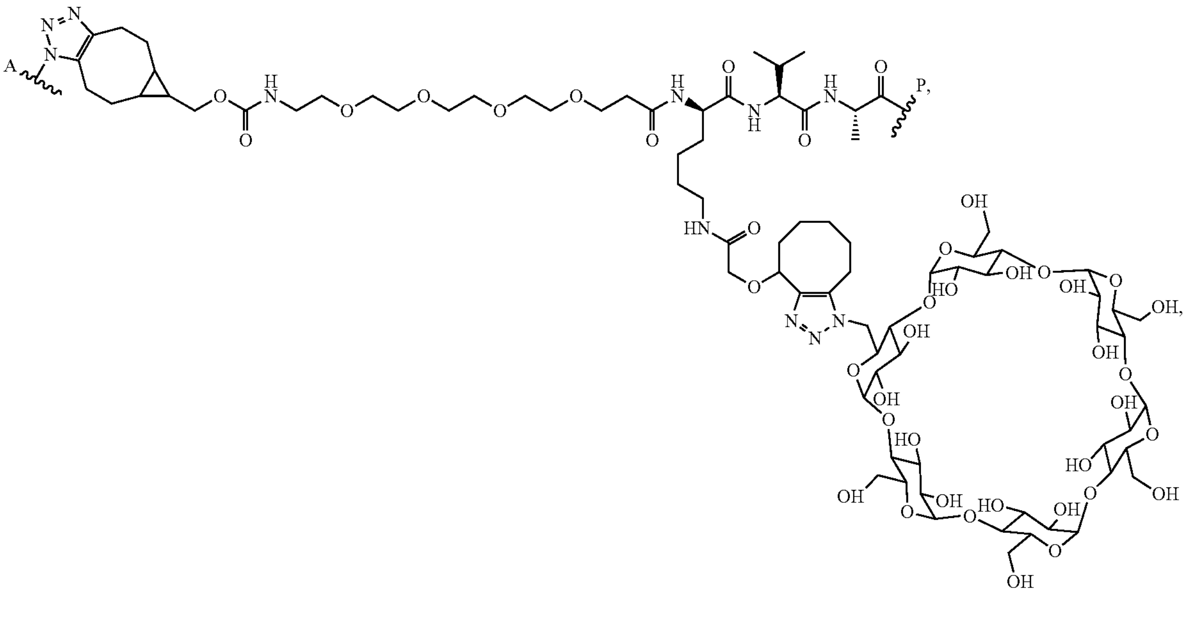

-continued
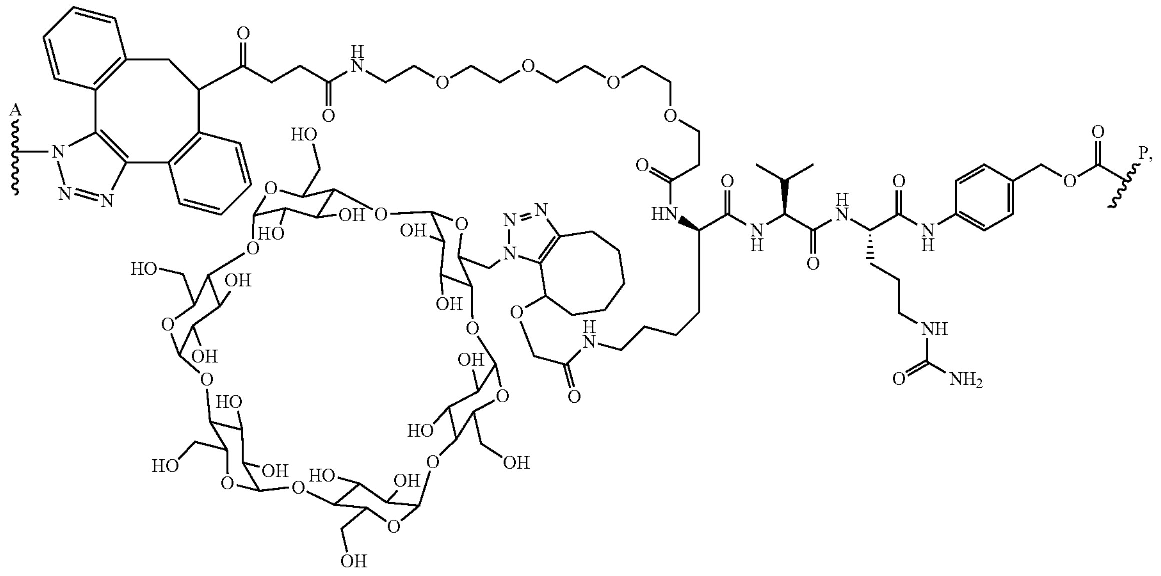
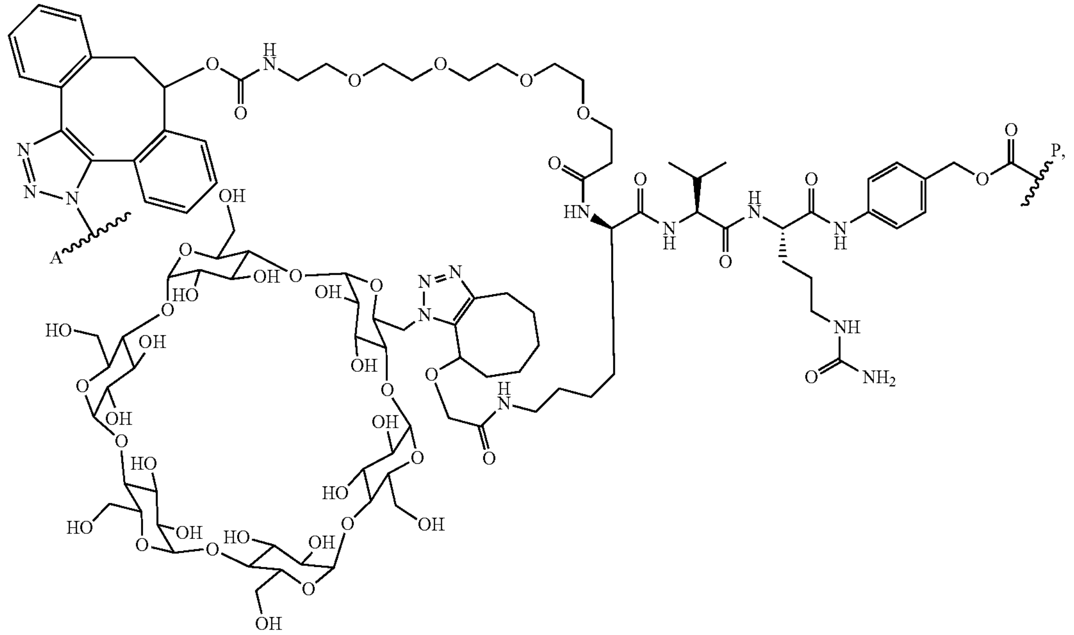

-continued

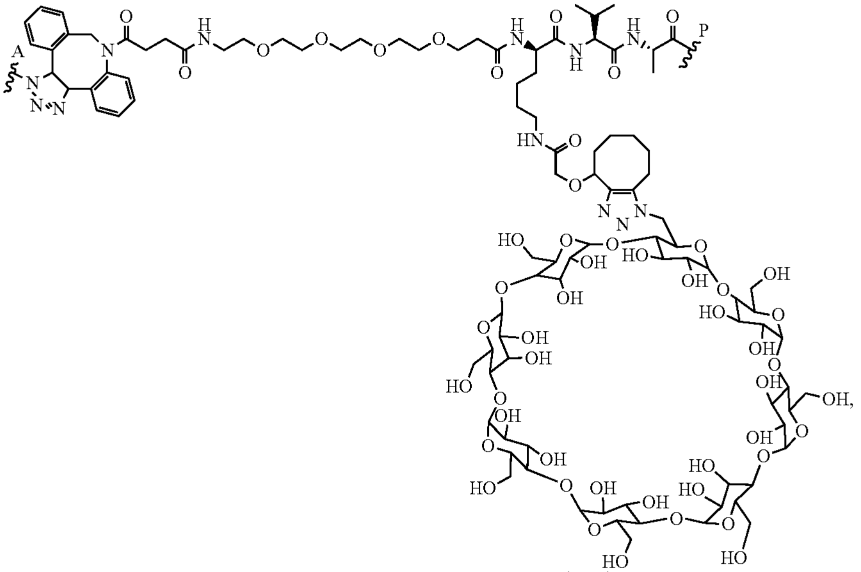

and

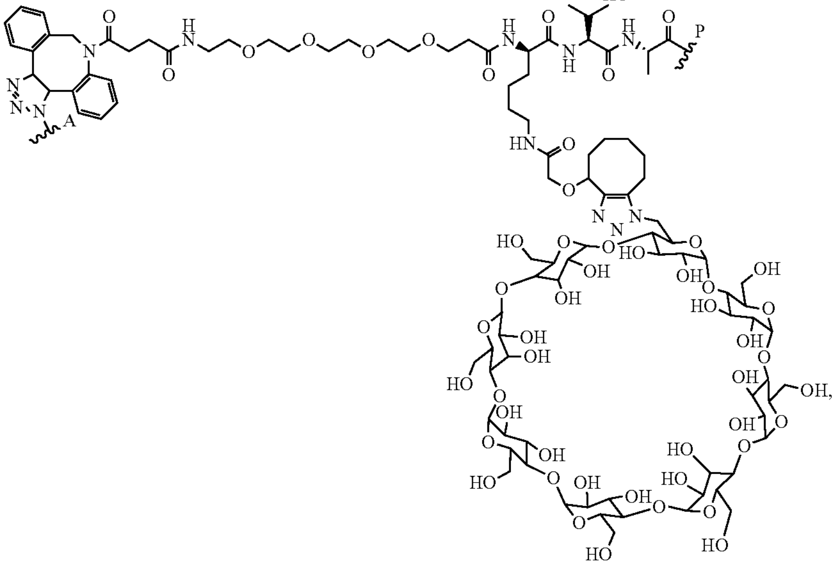

Also included in these examples, is a pharmaceutically acceptable salt, solvate, stereoisomeric form thereof, a regioisomer thereof, or mixture of regioisomers thereof, wherein each

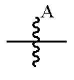

is a bond to the binding agent; and each

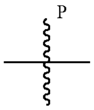

is a bond to the payload.

In some examples, including any of the foregoing, -LL- is according to the Formula (LL1):

(LL1)

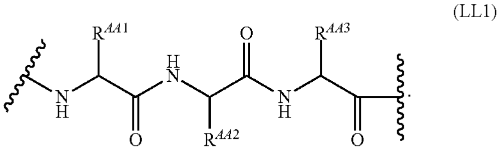

In Formula (LL1), $R^{AA1}$, $R^{AA2}$, and $R^{AA3}$ are each, independently, amino acid side chains, at least one of which is bonded directly or indirectly to —SP-RG-SP-CD. In some examples, SP may be absent. In some examples, SP is not absent. In some examples, in Formula (LL1), $R^{AA1}$, $R^{AA2}$, and $R^{AA3}$ are each, independently, amino acid side chains, at least one of which is bonded directly or indirectly to -RG-CD. In some examples, $R^{AA1}$ is a lysine amino acid side chain. In some examples, $R^{AA1}$ is an L-lysine amino acid side chain. In some examples, $R^{AA1}$ is a D-lysine amino acid side chain. In some examples, $R^{AA2}$ is a valine amino acid side chain. In some examples, $R^{AA3}$ is an alanine amino acid side chain. In some examples, $R^{AA3}$ is a citrulline amino acid side chain. In certain examples, $R^{AA1}$ is a lysine amino acid side chain bonded directly or indirectly to CD and $R^{AA2}$ and $R^{AA3}$ are, independently, valine and alanine amino acid side chains. In certain examples, $R^{AA1}$ is a lysine amino acid side chain bonded directly or indirectly to CD and $R^{AA2}$ and $R^{AA3}$ are, independently, valine and citrulline amino acid side chains.

In some examples, LL includes

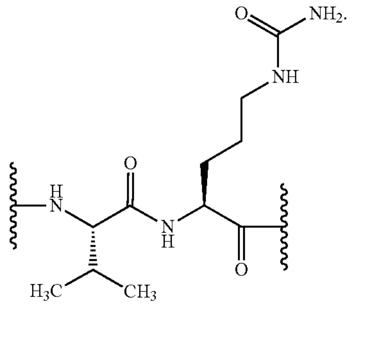 [SMILES: *N[C@H](C(=O)N[C@@H](CCCNC(N)=O)C(*)=O)C(C)C]

In some examples, LL includes

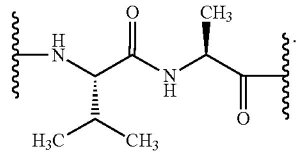 [SMILES: *N[C@H](C(=O)N[C@@H](C)C(*)=O)C(C)C]

In some examples, LL includes

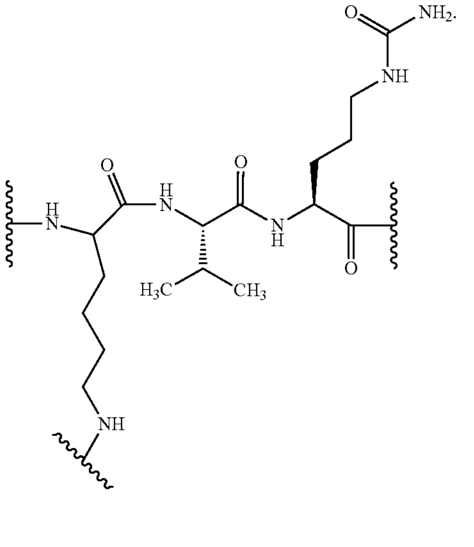 [SMILES: *NCCCCC(N*)C(=O)N[C@H](C(=O)N[C@@H](CCCNC(N)=O)C(*)=O)C(C)C]

In some examples, LL includes

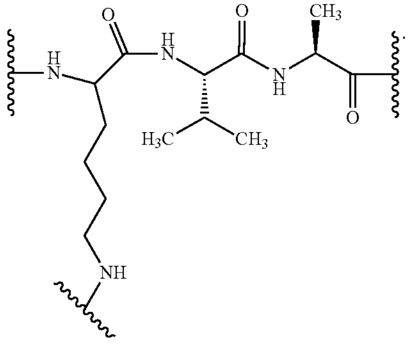 [SMILES: *NCCCCC(N*)C(=O)N[C@H](C(=O)N[C@@H](C)C(*)=O)C(C)C]

In some examples, SP, $SP^1$, $SP^2$, or a combination thereof is a spacer group. In some examples, SP is independently in each instance, selected from the group consisting of $C_{1-6}$ alkylene, —NH—, —C(O)—, $(—CH_2—CH_2—O)_e$, $—NH—CH_2—CH_2—(—O—CH_2—CH_2)_e—C(O)—$, $—C(O)—(CH_2)_u—C(O)—$, $—C(O)—NH—(CH_2)_v—$, and combinations thereof, wherein subscript e is an integer from 0 to 4, subscript u is an integer from 1 to 8, and subscript v is an integer from 1 to 8. In some examples, $SP^1$ is independently in each instance, selected from the group consisting of $C_{1-6}$ alkylene, —NH—, —C(O)—, $(—CH_2—CH_2—O)_e$, $—NH—CH_2—CH_2—(—O—CH_2—CH_2)_e—C(O)—$, $—C(O)—(CH_2)_u—C(O)—$, $—C(O)—NH—(CH_2)_v—$, and combinations thereof, wherein subscript e is an integer from 0 to 4, subscript u is an integer from 1 to 8, and subscript v is an integer from 1 to 8. In some examples, $SP^2$ is independently in each instance, selected from the group consisting of $C_{1-6}$ alkylene, —NH—, —C(O)—, $(—CH_2—CH_2—O)_e$, $—NH—CH_2—CH_2—(—O—CH_2—CH_2)_e—C(O)—$, $—C(O)—(CH_2)_u—C(O)—$, $—C(O)—NH—(CH_2)_v—$, and combinations thereof, wherein subscript e is an integer from 0 to 4, subscript u is an integer from 1 to 8, and subscript v is an integer from 1 to 8.

In some examples, including any of the foregoing, subscript m, q, ore is 1. In some examples, including any of the foregoing, subscript m is 1. In some examples, including any of the foregoing, subscript q is 1. In some examples, including any of the foregoing, subscript e is 1.

In some examples, including any of the foregoing, subscript m, q, or e is 2. In some examples, including any of the foregoing, subscript m is 2. In some examples, including any of the foregoing, subscript q is 2. In some examples, including any of the foregoing, subscript e is 2.

In some examples, including any of the foregoing, subscript m, q, or e is 3. In some examples, including any of the foregoing, subscript m is 3. In some examples, including any of the foregoing, subscript q is 3. In some examples, including any of the foregoing, subscript e is 3.

In some examples, including any of the foregoing, subscript m, q, or e is 4. In some examples, including any of the foregoing, subscript m is 4. In some examples, including any of the foregoing, subscript q is 4. In some examples, including any of the foregoing, subscript e is 4.

In some examples, including any of the foregoing, subscript p is 1.

In some examples, including any of the foregoing, subscript n is 2-4.

In some examples, including any of the foregoing, subscript n is 2.

In some examples, including any of the foregoing, subscript n is 3.

In some examples, including any of the foregoing, subscript n is 4.

In some examples, including any of the foregoing, the binding agent (BA) is selected from any polypeptide. Example polypeptides include, but are not limited to, natural polypeptides and unnatural polypeptides. Example polypeptides include, but are not limited to, those produced from genetically modified organisms.

Polypeptides herein include, but are not limited to, receptors, proteins, enzymes, binding agents, milk peptides, ribosomal peptides, nonribosomal peptides, peptones, and peptide fragments. Polypeptides herein include, but are not limited to, antimicrobial peptides, tachykinin peptides, vasoactive intestinal peptides, pancreatic polypeptide-related peptides, opiod peptides, and calcitonin peptides. Other peptides included in the instant disclosure include, but are not limited to, B-type natriuretic peptide (BNP), lactotripeptides, neuropeptides, lipopeptides, proteases, or hormones.

Polypeptides further include, but are not limited to, short amino acid chains comprising two or more amino acids bonded together. Polypeptides include, but are not limited to, dipeptides (Val-Cit), tripeptides, and tetrapeptides (e.g., Val-Gly-Ser-Ala) having two, three, or four amino acids bonded together, respectively. Polypeptides include longer chains comprising five or more amino acids. Polypeptides include long chains comprising fifty or more amino acids (e.g., proteins). In some exanples, polypeptides herein are selected from dipeptides, tripeptides, tetrapeptides, pentapeptides, hexapeptides, heptapeptides, octapeptides, nonapeptides, decapeptides, undecapeptides, and icosapeptides.

Polypeptides include proteins. In some examples, the proteins include only natural amino acids. In some examples, the proteins further include non-natural amino acids.

In some examples, including any of the foregoing, the binding agent (BA) is an antibody or antigen-binding fragment thereof. In certain examples, the binding agent is an antibody, or an antigen-binding fragment thereof, selective for an antigen selected from the group consisting of AXL, BAFFR, BCMA, BCR-list components, BDCA2, BDCA4, BTLA, BTNL2, BTNL3, BTNL8, BTNL9, 010 or f54, CCR1, CCR3, CCR4, CCR5, CCR6, CCR7, CCR9, CCR10, CD11c, CD137, CD138, CD14, CD168, CD177, CD19, CD20, CD209, CD209L, CD22, CD226, CD248, CD25, CD27, CD274, CD276, CD28, CD30, CD300A, CD33, CD37, CD38, CD4, CD40, CD44, CD45, CD46, CD48, CD5, CD52, CD55, CD56, CD59, CD62E, CD68, CD69, CD70, CD74, CD79a, CD79b, CD8, CD80, CD86, CD90.2, CD96, CLEC12A, CLEC12B, CLEC7A, CLEC9A, CR1, CR3, CRTAM, CSF1R, CTLA4, CXCR1/2, CXCR4, CXCR5, DDR1, DDR2, DEC-205, DLL4, DR6, FAP, FCamR, FCMR, FcR's, FELD1, Fire, GITR, HER2, HHLA2, HLA class II, HVEM, ICOSLG, IFNLR1, MOR1, IL10R2, IL12R, IL13RA1, IL13RA2, IL15R, IL17RA, IL17RB, IL17RC, IL17RE, IL20R1, IL20R2, IL21R, IL22R1, IL22RA, IL23R, IL27R, IL29R, IL2Rg, IL31R, IL36R, IL3RA, IL4R, IL6R, IL5R, IL7R, IL9R, Integrins, LAG3, LIFR, MAG/Siglec-4, MMR, MSR1, NCR3LG1, NKG2D, NKp30, NKp46, PDCD1, PRLR, PROKR1, PVR, PVRIG, PVRL2, PVRL3, RELT, SIGIRR, Siglec-1, Siglec-10, Siglec-5, Siglec-6, Siglec-7, Siglec-8, Siglec-9, SIRPA, SLAMF7, TACI, TCR-list components/assoc, PTCRA, TCRb, CD3z, CD3, TEK, TGFBR1, TGFBR2, TGFBR3, TIGIT, TLR2, TLR4, TROY, TSLPR, TYRO, VLDLR, VSIG4, and VTCN1.

In some examples, including any of the foregoing, PA is the residue of a group selected from the group consisting of a dolastatin, an auristatin, a maytansinoid, a plant alkaloid, a taxane, a vinca alkaloid, a steroid, and an LXR modulator. In some cases, PA is a dolastatin. In some cases, PA is an auristatin. In some cases, PA is a maytansinoid. In some cases, PA is a plant alkaloid. In some cases, PA is a taxane. In some cases, PA is a *vinca* alkalod. In some cases, PA is a steroid. In some cases, PA is a LXR modulator. In some cases, a LXR modulator is a LXR agonist. In some embodiments, a LXR modulator is a LXR antagonist. Other suitable payloads include those that are highly hydrophobic, e.g., those that are not amenable to Ab conjugation conditions due to their hydrophobic nature, e.g., payloads such as pyrrolobenzodiazepines (PBDs), SN38 (7-Ethyl-10-hydroxy-camptothecin), etc. In certain embodiments, provided herein are antibody-drug conjugates wherein PA is a hydrophobic payload moiety.

In some examples, PA is any compound set forth in any one of FIG. 1.

In certain embodiments, PA is an auristatin. In certain embodiments, PA is auristatin E, auristatin F, monomethyl auristatin-D (MMAD), monomethyl auristatin-E (MMAE), or monomethyl auristatin F (MMAF).

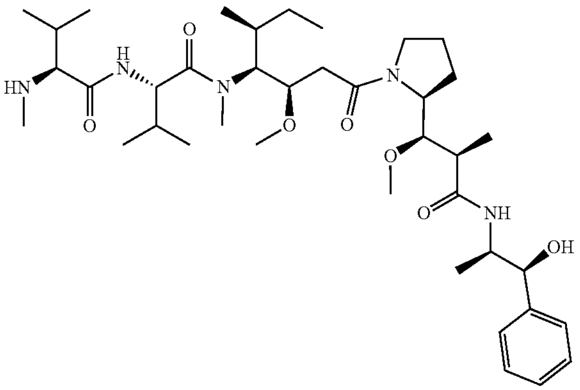

MMAE

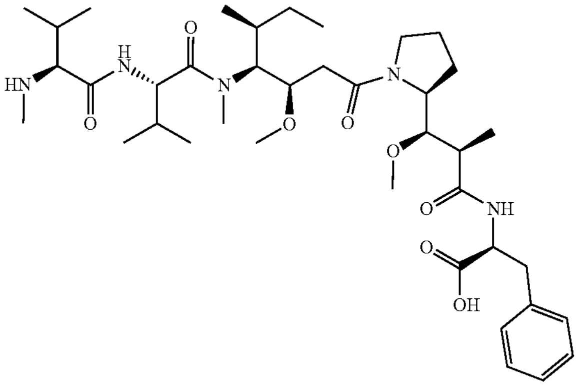

MMAF

In certain embodiments, PA is a maytansinoid. The maytansinoid can be any maytansinoid payload deemed suitable by the practitioner of skill. Maytansinoid payloads disclosed in U.S. Non-Provisional application Ser. No. 15/081,759 filed on Mar. 25, 2016, titled "MAYTANSINOID DERIVATIVES, CONJUGATES THEREOF, AND METHODS OF USE," published as U.S. Patent Application Publication No. 2016/0375147, and in U.S. Non-Provisional application Ser. No. 15/414,537 filed on Jan. 24, 2017, titled "MAYTANSINOID DERIVATIVES, CONJUGATES THEREOF, AND METHODS OF USE," issued as U.S. Pat. No. 9,950,076, are incorporated herein by reference. In certain embodiments, PA is DM1, DM3, or DM4. In certain embodiments, PA is

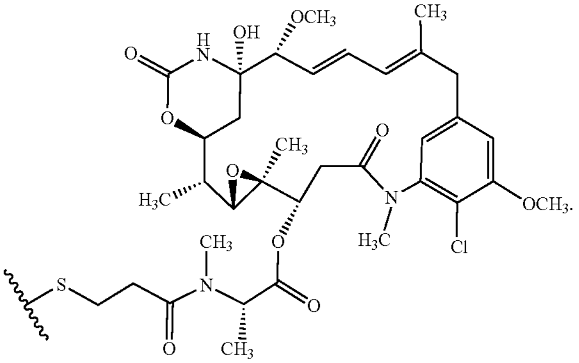 [SMILES: *SCCC(=O)N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

In certain embodiments, PA is

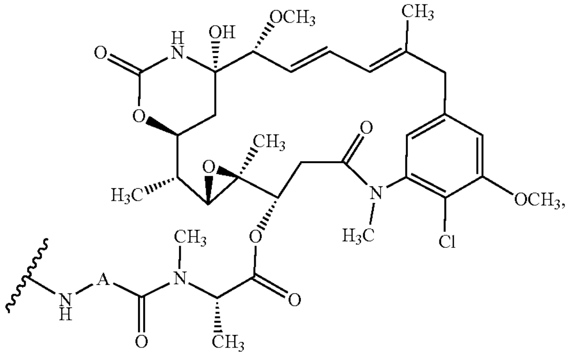

where A is optionally substituted arylene or heteroarylene. In certain embodiments, PA is

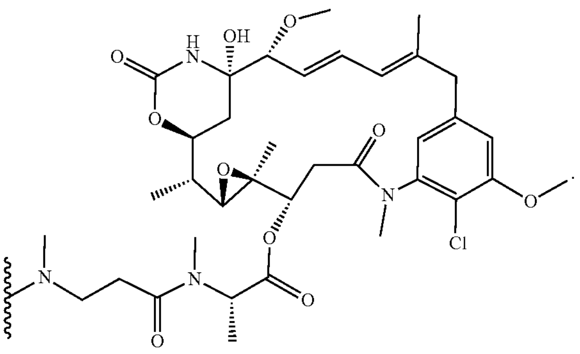 [SMILES: *N(C)CCC(=O)N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

In particular embodiments, the wavy line indicates a bond to LL.

In certain embodiments, the payloads in compounds of Formula (I) are glucocorticoids that have the structure of Formula (A):

(A)

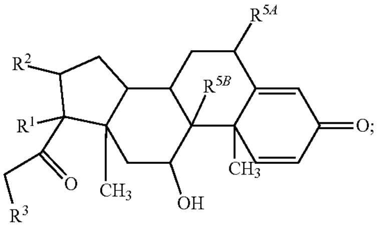

or a pharmaceutically acceptable stereoisomer, or derivative thereof, wherein:

$R^1$ and $R^2$ are, independently, —H, alkyl, alkyl-C(O)—O—, —OH, or halo; or $R^1$ and $R^2$ together form

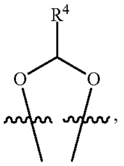

wherein $R^4$ is alkyl, aryl, arylalkyl, or an N-containing heterocycloalkyl, wherein the alkyl, aryl, arylalkyl, and N-containing heterocycloalkyl are, independently in each instance, optionally substituted with $—NR^{Aa}R^{Ab}$;

$R^3$ is —OH, $R^z$—C(O)—X—, heteroalkyl, piperidinyl, $—NR^{Aa}R^{Ab}$, -oxyaryl-$NR^{Aa}R^{Ab}$ or $—Z\text{-}A'(R^P)_t$;

$R^5$ is, independently in each instance, —OH, halo, alkyl, or arylalkyl;

$R^z$ is alkyl;

X is O or $NR^{Aa}$;

Z is S, S(O), $S(O)_2$, $SO_2NR^{Aa}$, O, $C(O)NR^{Aa}$, C(O), or $NR^{Aa}$;

A' is aryl, arylalkyl, or heteroaryl;

$R^P$ is, independently in each instance, halo, optionally substituted alkyl, —OH, or $—NR^{Aa}R^{Ab}$;

$R^{Aa}$ and $R^{Ab}$ are, independently in each instance, —H, optionally substituted alkyl, or optionally substituted aryl;

subscript a is an integer from 0-19; and t is an integer from 1-3;

with the proviso that:

(1) $R^3$ is not —OH (a) when $R^1$ is —OH or (b) when $R^1$ and $R^2$ together form

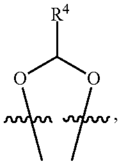

wherein $R^4$ is $C_{1-9}$alkyl or

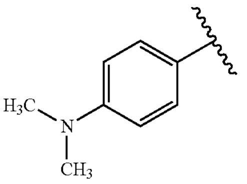 [SMILES: *c1ccc(N(C)C)cc1]

and (2) $R^3$ is not

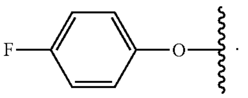 [SMILES: *Oc1ccc(F)cc1]

In some embodiments, $R^3$ is $NH_2$. In some of such embodiments, $R^3$ is

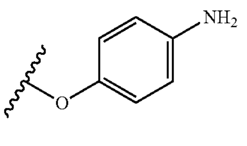 [SMILES: *Oc1ccc(N)cc1]

wherein  indicates the atom through which $R^3$ is attached to the adjacent groups in Formula (I).

In certain embodiments, PA is a steroid. In certain embodiments, PA is selected from

1110

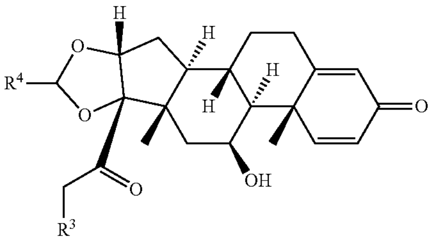

1120

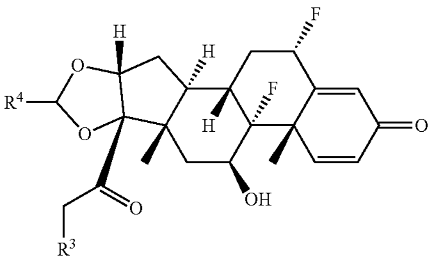

1130

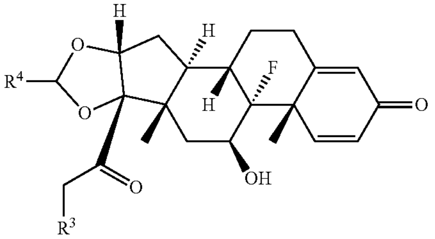

-continued

1140

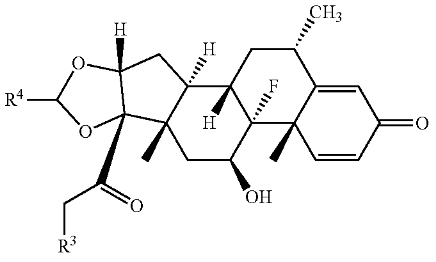

or a pharmaceutically acceptable salt, solvate, or stereoisomer thereof. In certain embodiments according to any of Formulas 1110-1140, $R^3$ is —O-aryl, —$NR^{Aa}R^{Ab}$, -alkylene-$NR^{Aa}R^{Ab}$, —X-arylene-Y—$NR^{Aa}R^{Ab}$, —X-heteroarylene-Y—$NR^{Aa}R^{Ab}$, or N-containing heterocycloalkyl; wherein X is absent, —N—, —$CH_2$—, or —O—; wherein Y is absent or —$CH_2$—; and $R^4$ is alkyl, aryl, alkylaryl, or arylalkyl. In certain embodiments, $R^3$ is —O-arylene-$NR^{Aa}R^{Ab}$, —O-heteroarylene-$NR^{Aa}R^{Ab}$; wherein aryl or heteroaryl is optionally substituted with halogen, deuterium, hydroxyl, or methoxyl. In certain embodiments, $R^3$ is —O-phenyl-$NR^{Aa}R^{Ab}$, —O-heteroarylene-$NR^{Aa}R^{Ab}$; wherein phenyl or heteroaryl is optionally substituted with halogen or deuterium. In certain embodiments, $R^4$ is n-propyl. In certain embodiments, $R^{Aa}$ and $R^{Ab}$ are each independently hydrogen or alkyl. In particular embodiments, one of $R^{Aa}$ and $R^{A}$b is substituted with a bond to LL. In certain embodiments, PA is

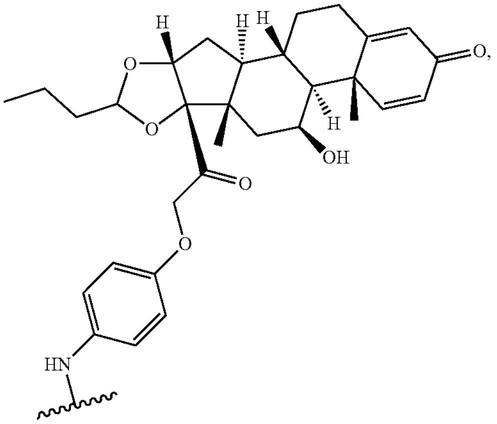 [SMILES: *Nc1ccc(OCC(=O)[C@@]23OC(CCC)O[C@@H]2C[C@H]2[C@@H]4CCC5=CC(=O)C=C[C@]5(C)[C@H]4[C@@H](O)C[C@@]23C)cc1]

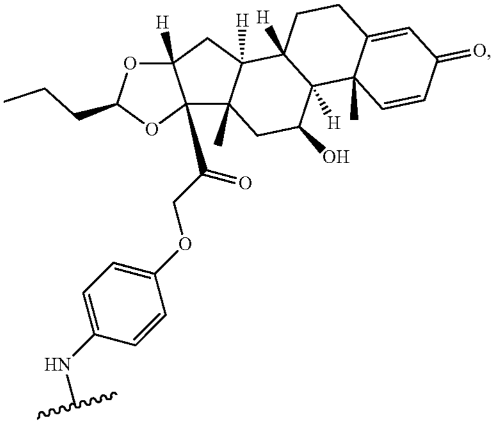 [SMILES: *Nc1ccc(OCC(=O)[C@@]23O[C@@H](CCC)O[C@@H]2C[C@H]2[C@@H]4CCC5=CC(=O)C=C[C@]5(C)[C@H]4[C@@H](O)C[C@@]23C)cc1]

-continued

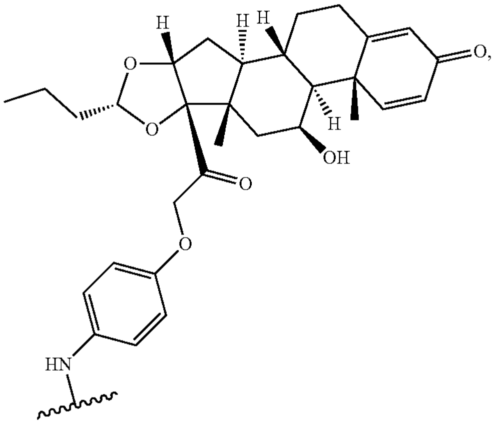

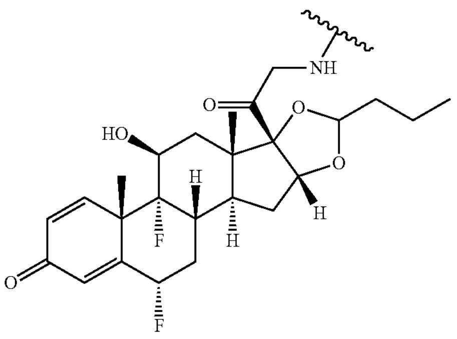

, or

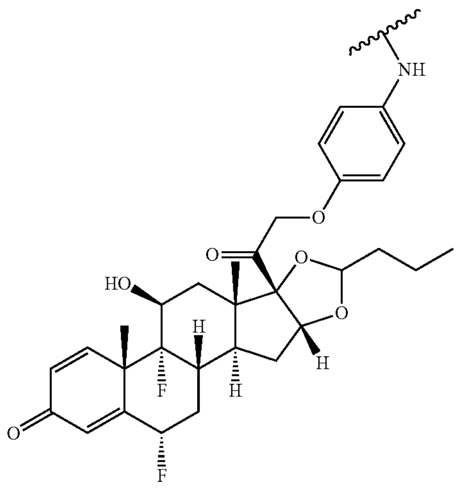

, or a pharmaceutically acceptable salt, solvate, or stereoisomer thereof. In certain embodiments, PA is

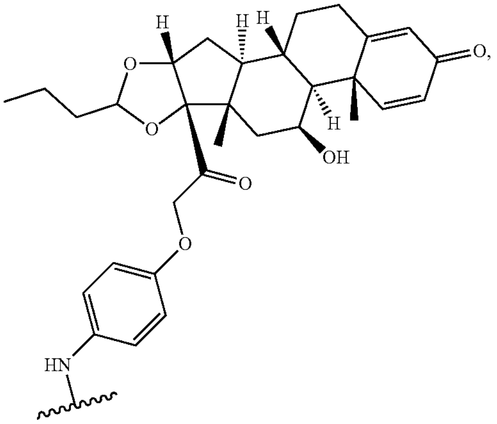

or a pharmaceutically acceptable salt, solvate, or stereoisomer thereof In certain embodiments, PA is

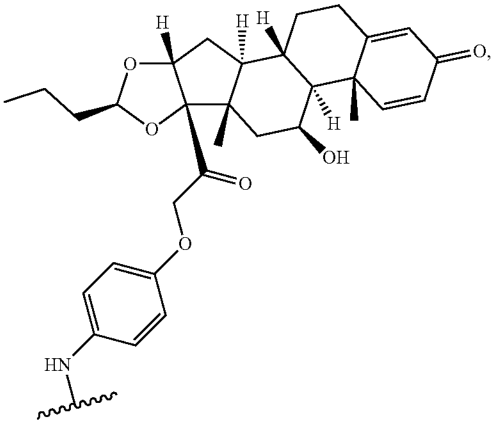

or a pharmaceutically acceptable salt, solvate, or stereoisomer thereof. In certain embodiments, PA is

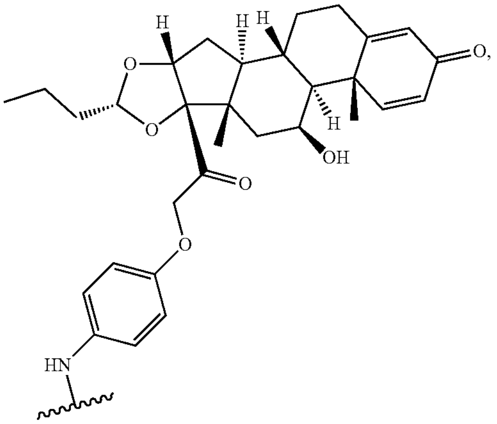 [SMILES: *Nc1ccc(OCC(=O)[C@@]23O[C@H](CCC)O[C@@H]2C[C@H]2[C@@H]4CCC5=CC(=O)C=C[C@]5(C)[C@H]4[C@@H](O)C[C@@]23C)cc1]

or a pharmaceutically acceptable salt, solvate, or stereoisomer thereof. In certain embodiments, PA is

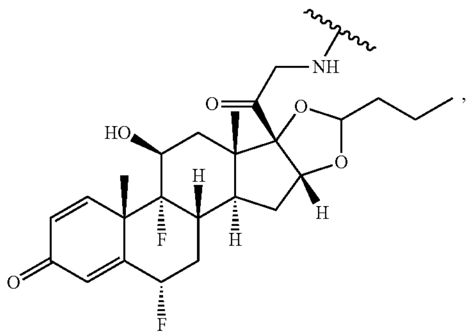
or a pharmaceutically acceptable salt, solvate, or stereoisomer thereof. In
certain embodiments, PA is
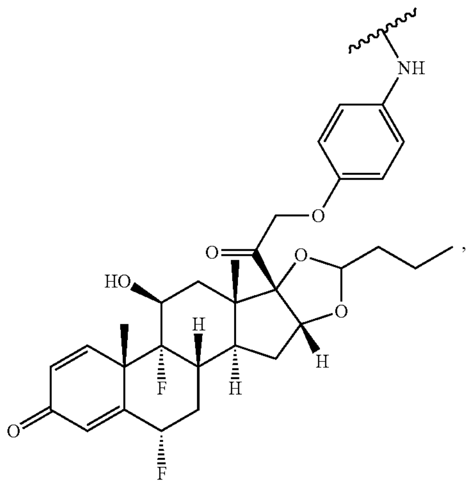
or a pharmaceutically acceptable salt, solvate, or stereoisomer thereof. In such embodiments, the wavy line indicates a bond to LL.
Set forth herein are also payloads of Formula (A) having the following structures:
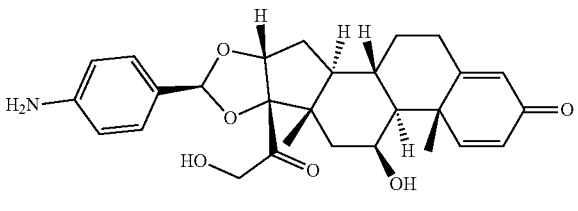
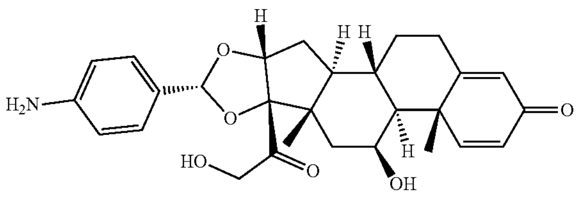
-continued
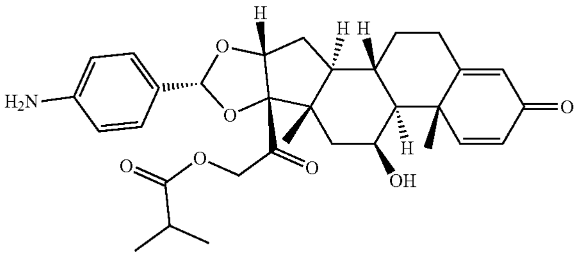
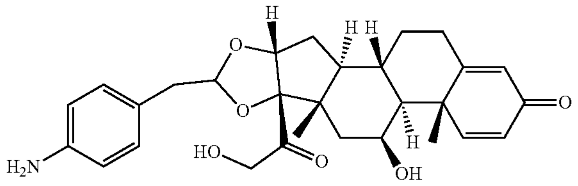
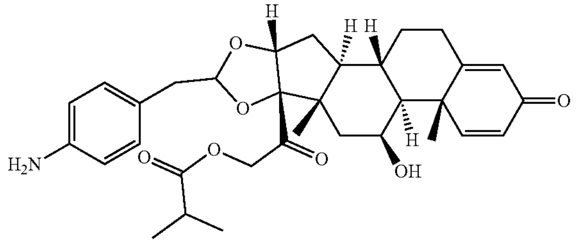
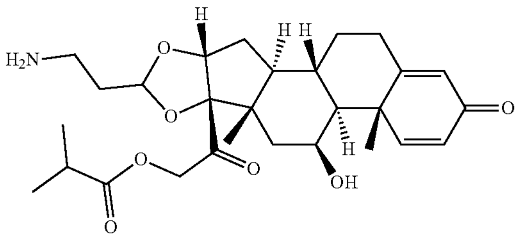
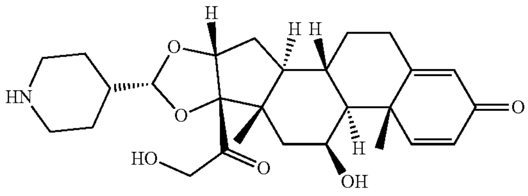
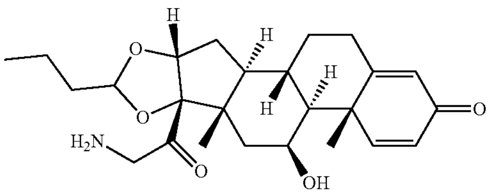
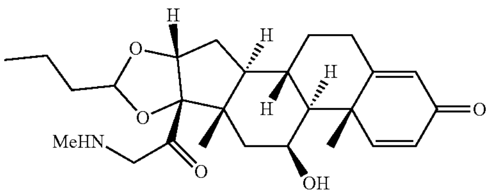
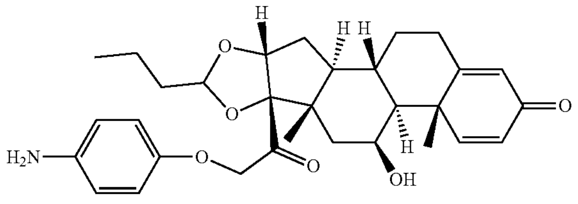

-continued
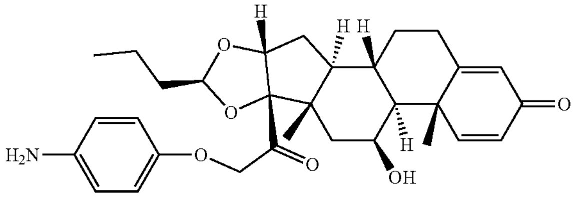
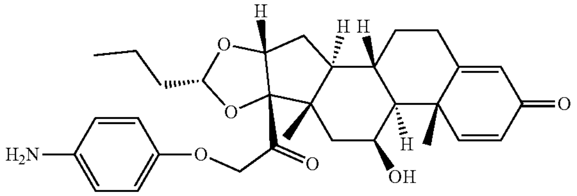
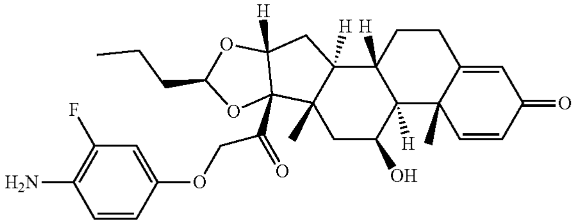
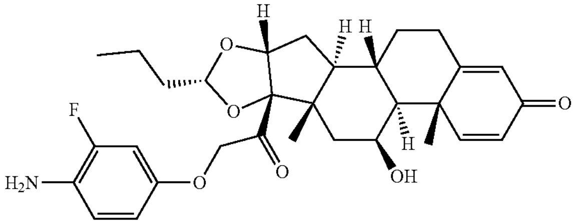
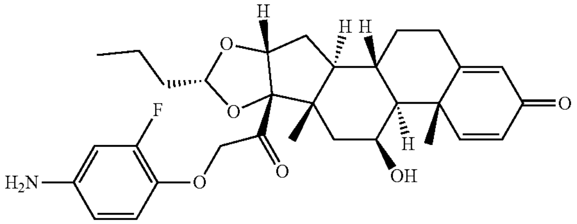
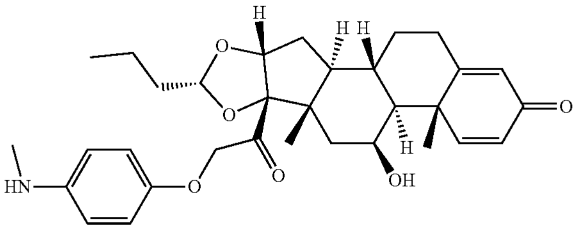
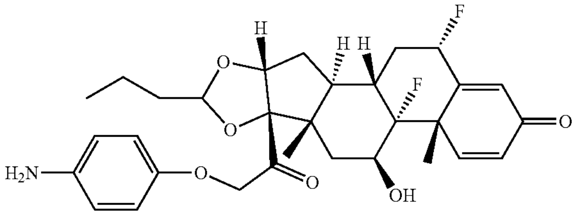
-continued
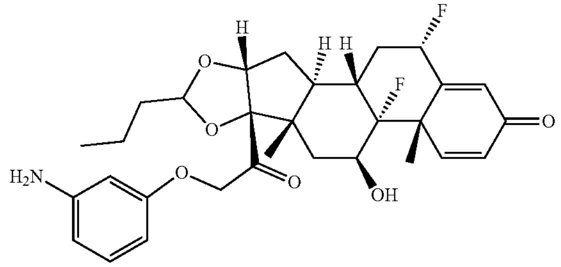
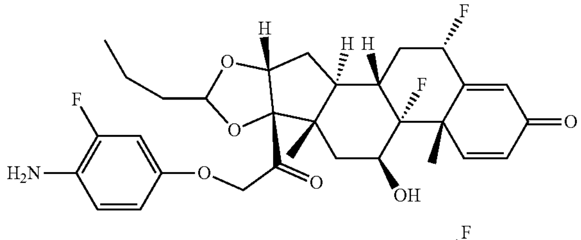
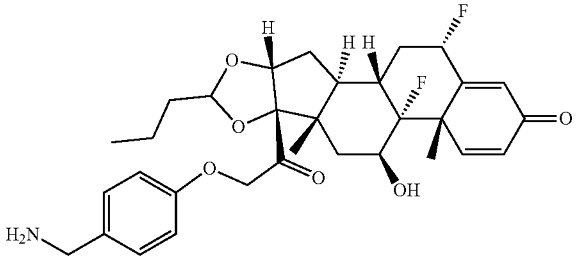
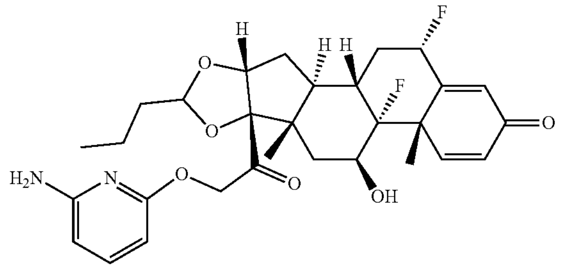
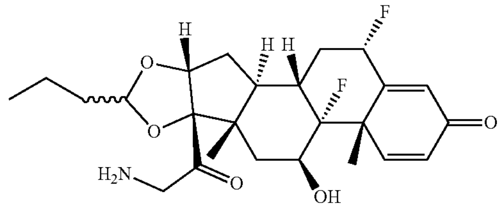
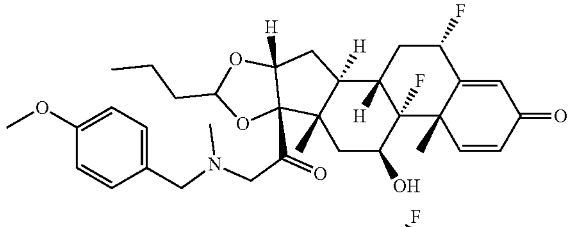
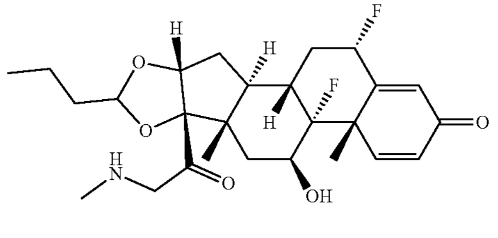

-continued
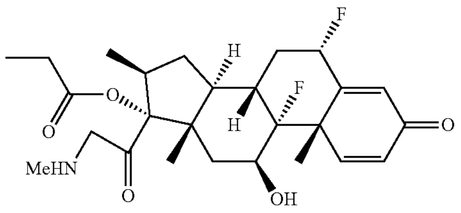
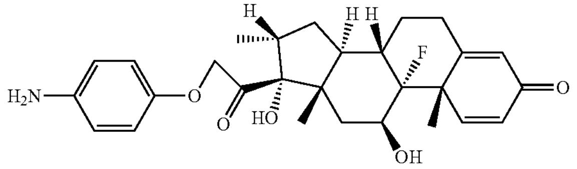
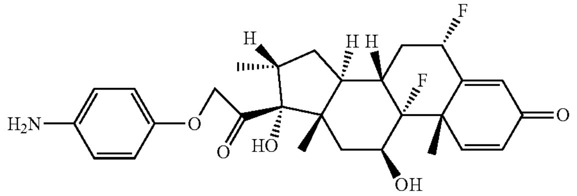
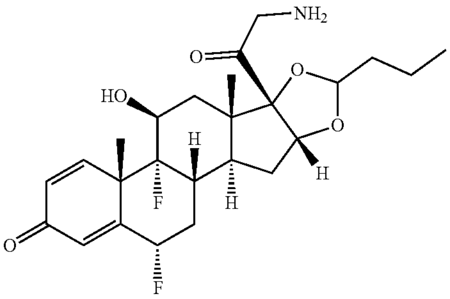
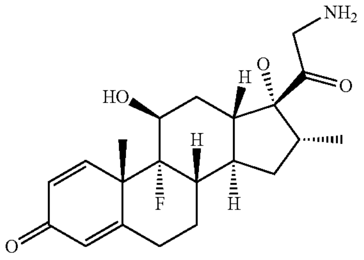
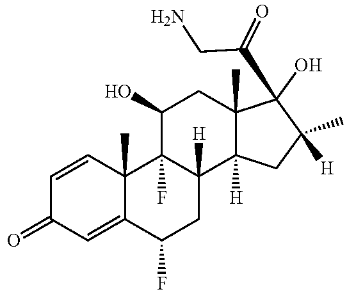
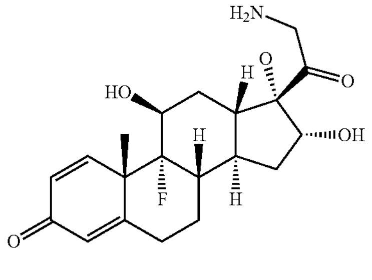
-continued
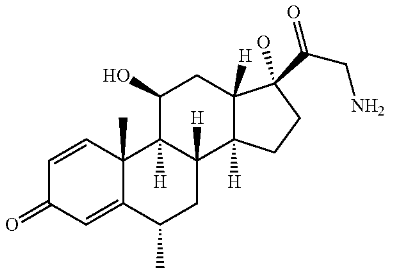
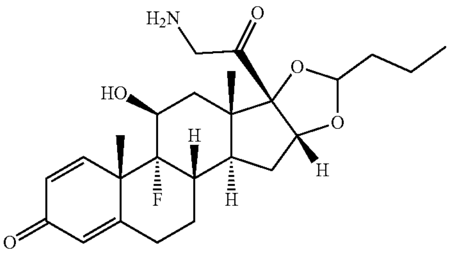
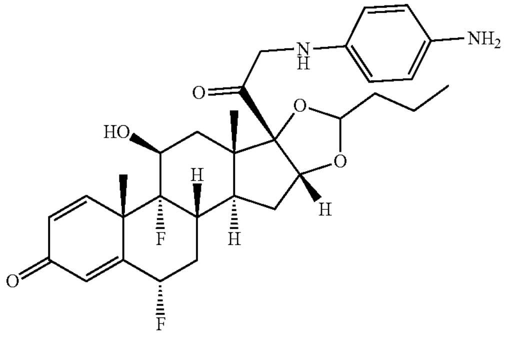
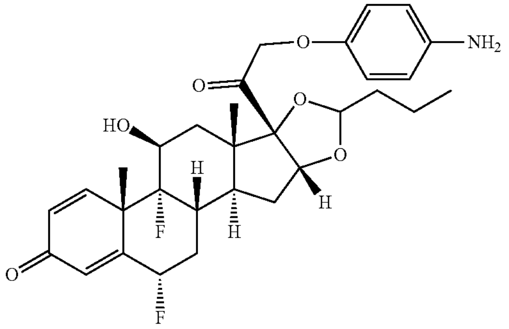
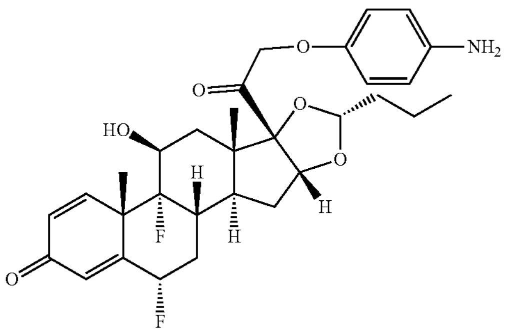

-continued

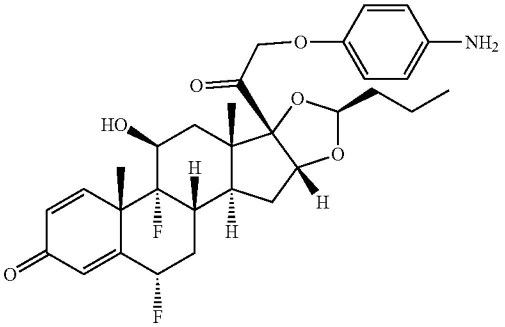

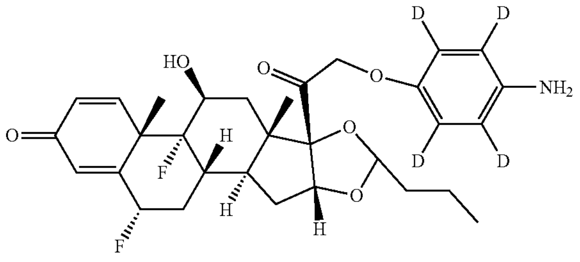

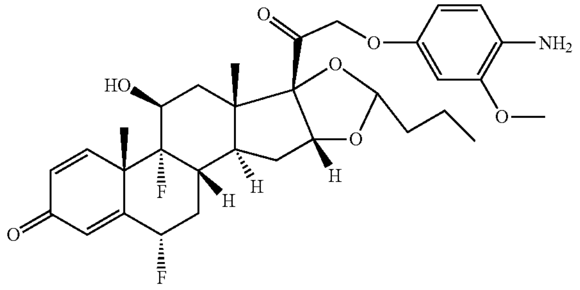

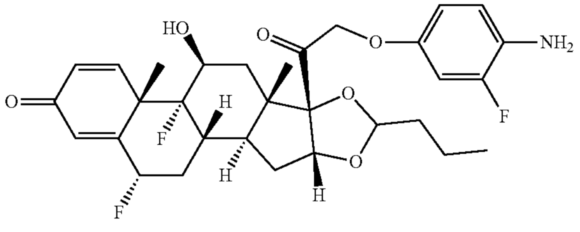

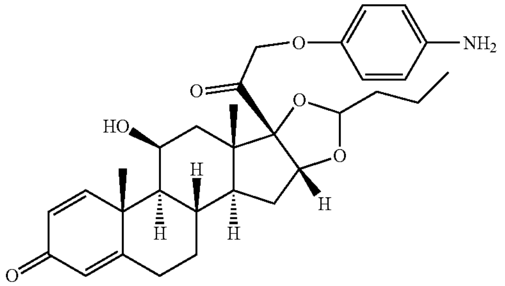

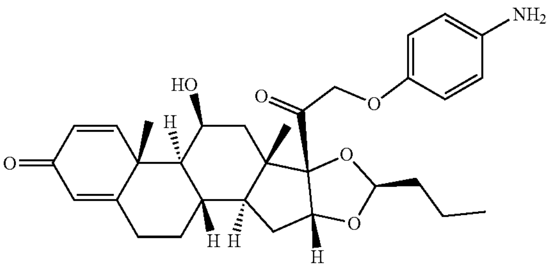

-continued

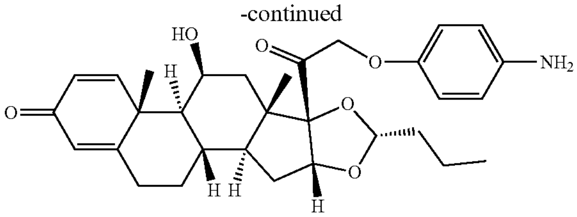

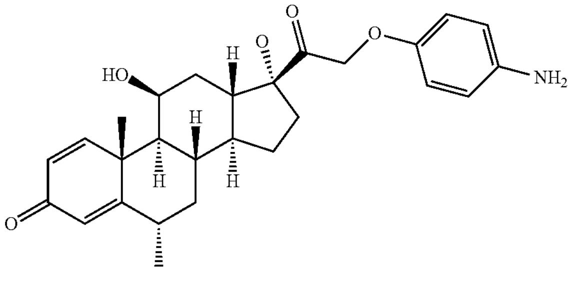

or a pharmaceutically acceptable stereoisomer thereof. In certain embodiments, the conjugates comprise a payload above linked to a linker via a bond to a residue of a primary or secondary amine of the payload. Steroid payloads disclosed in U.S. Non-Provisional application Ser. No. 15/806,197 filed on Nov. 7, 2017, titled "STEROIDS AND PROTEIN-CONJUGATES THEREOF" are incorporated herein by reference.

In certain embodiments, PA is a liver X receptor (LXR) modulator. In certain embodiments, PA is according to Formula B:

Formula B

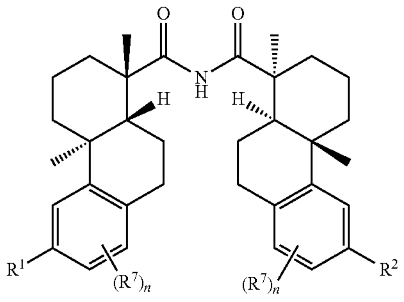

or a pharmaceutically acceptable salt, solvate, or stereoisomeric form, wherein

W is —$CH_2$—, —N(H)—, or —O—;

$R^{B1}$ is —H, —OH, —$NH_2$, alkyl, or —OP(O)($OR^6$)$_2$;

$R^{B2}$ is —H, —OH, —$CH_2NH_2$, $R^{B3}$, $R^{B4}$, $R^{B5}$, or —O—$R^{B5}$, wherein $R_{B1}$ and $R^{B2}$ are not simultaneously —H;

$R^{B3}$ is —N($R^6$)$_2$;

$R^{B4}$ is —X—Y—Z;

X is selected from the group consisting of —O— and —N(H)—;

Y is selected from the group consisting of alkylene, substituted alkylene (including, without limitation, oxo substitution, i.e., =O)), heteroalkylene, and substituted heteroalkylene (including, without limitation, oxo substitution (i.e., =O));

Z is selected from the group consisting of —OH and —$NH_2$;

$R^{B5}$ is alkyl, heterocycloalkyl, or substituted heterocycloalkyl, wherein each heterocycloalkyl or substituted heterocycloalkyl includes one, two, or three heteroatoms selected from nitrogen and oxygen, and includes at least one —OH and —$CH_2OH$ substituent, or at least one primary or secondary nitrogen, for instance, O-glucose;

each $R^6$ is in each instance, —H, an amino acid residue, an N-alkyl amino acid residue, a peptide, or alkyl; and each $R^7$ is, independently, halo, $C_{1-6}$ s alkyl, $C_{1-6}$ alkoxy, —CN, O-glucose, O-amino acid residue, and O—$PEG_b$, wherein each subscript b is an integer from 0-3. In particular embodiments, $R^{B1}$ or $R^{B2}$ is substituted with a bond to LL. In certain embodiments, PA is selected from:

-continued

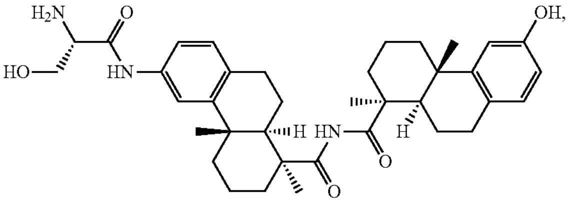

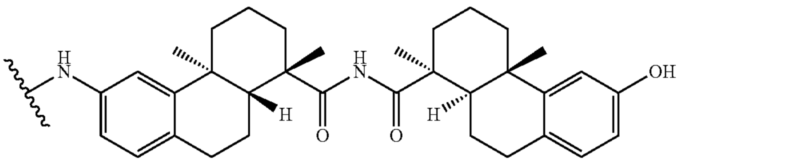

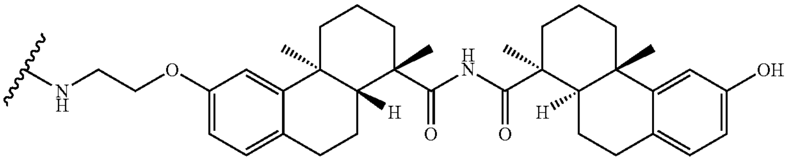

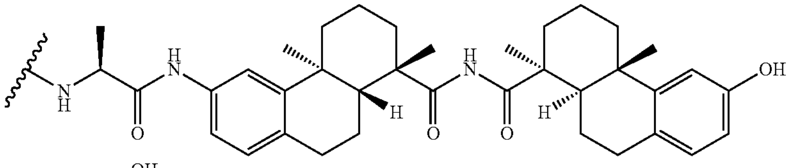

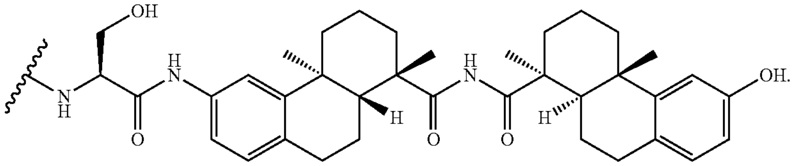

In particular embodiments, the wavy line indicates a bond to LL.

In certain embodiments, the payload of Formula (B) is selected from the group consisting of:

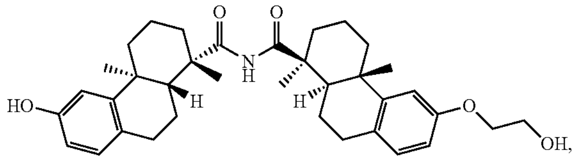

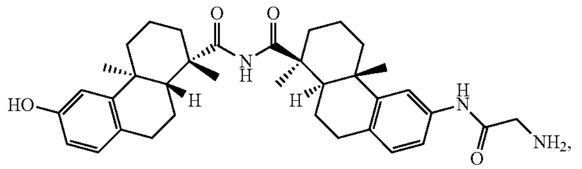

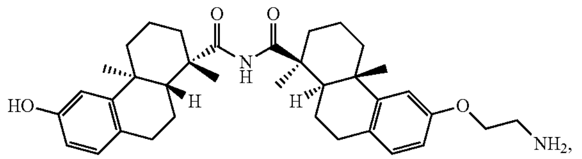

-continued

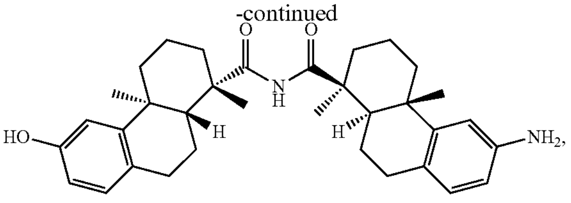

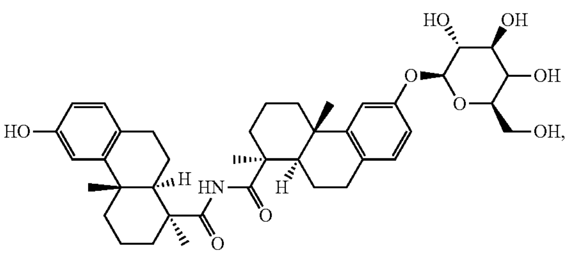

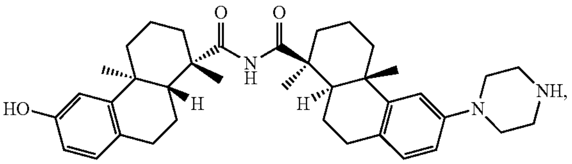

-continued

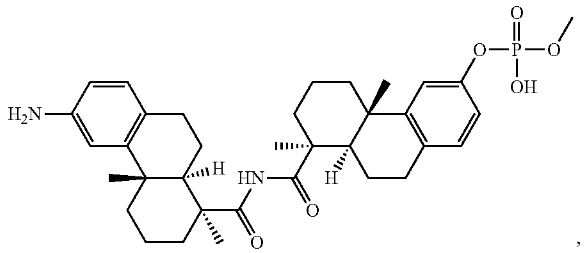

,

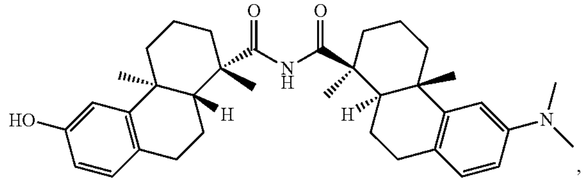

,

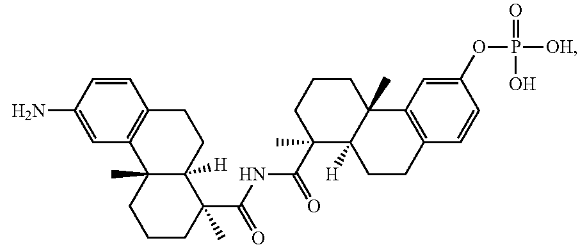

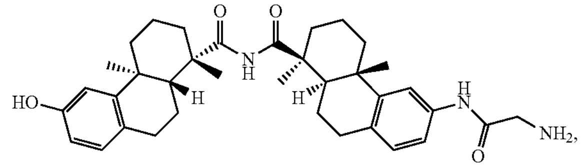

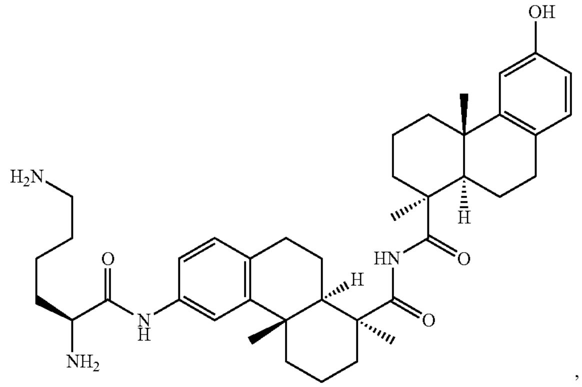

,

-continued

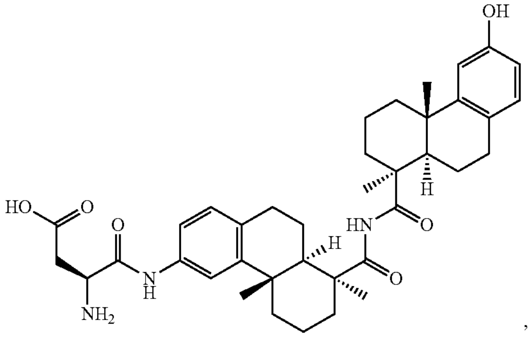

, and

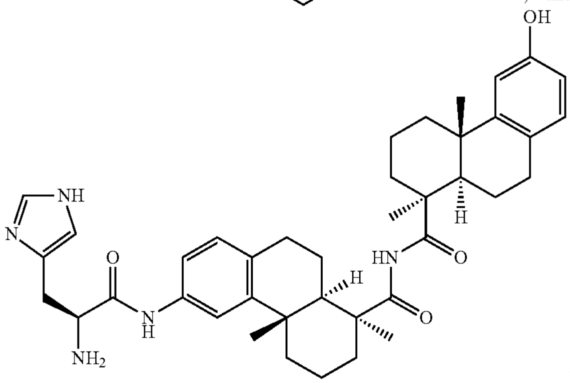

, or a pharmaceutically acceptable stereoisomeric form thereof. In certain embodiments, the conjugates comprise a payload above linked to a linker via a bond to a residue of a primary or secondary amine of the payload. LXR modulator payloads disclosed in U.S. Provisional Application No. 62/508,327 filed on May 18, 2017, titled "BIS-OCTAHYDROPHENANTHRENE CARBOXAMIDES AND PROTEIN CONJUGATES THEREOF" are incorporated herein by reference.

Also contemplated within the scope of embodiments presented herein are payloads disclosed in U.S. Non-Provisional application Ser. No. 14/776,668 filed on Sep. 14, 2015, titled "BIOLOGICALLY ACTIVE MOLECULES, CONJUGATES THEREOF, AND THERAPEUTIC USES," published as U.S. Patent Application Publication No. 2016/0030591, and U.S. Non-Provisional application Ser. No. 14/913,965 filed on Feb. 23, 2016, titled "PHARMACEUTICAL COMPOSITIONS COMPRISING MACROLIDE DIASTEREOMERS, METHODS OF THEIR SYNTHESIS AND THERAPEUTIC USES," published as U.S. Patent Application Publication No. 2016/0354482, the disclosure of said payloads is incorporated herein by reference.

In some examples, the compound of Formula (I) is selected from:

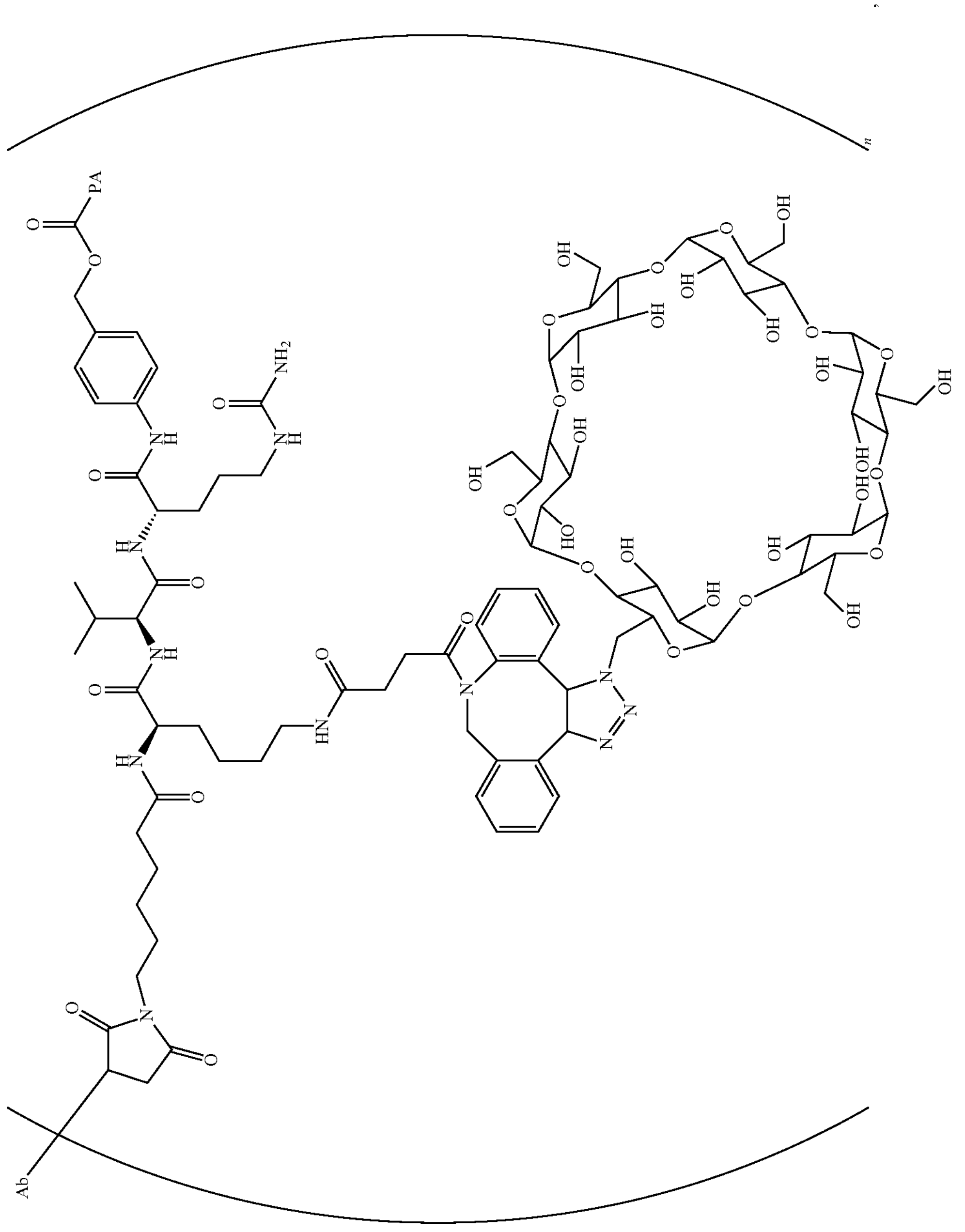

-continued
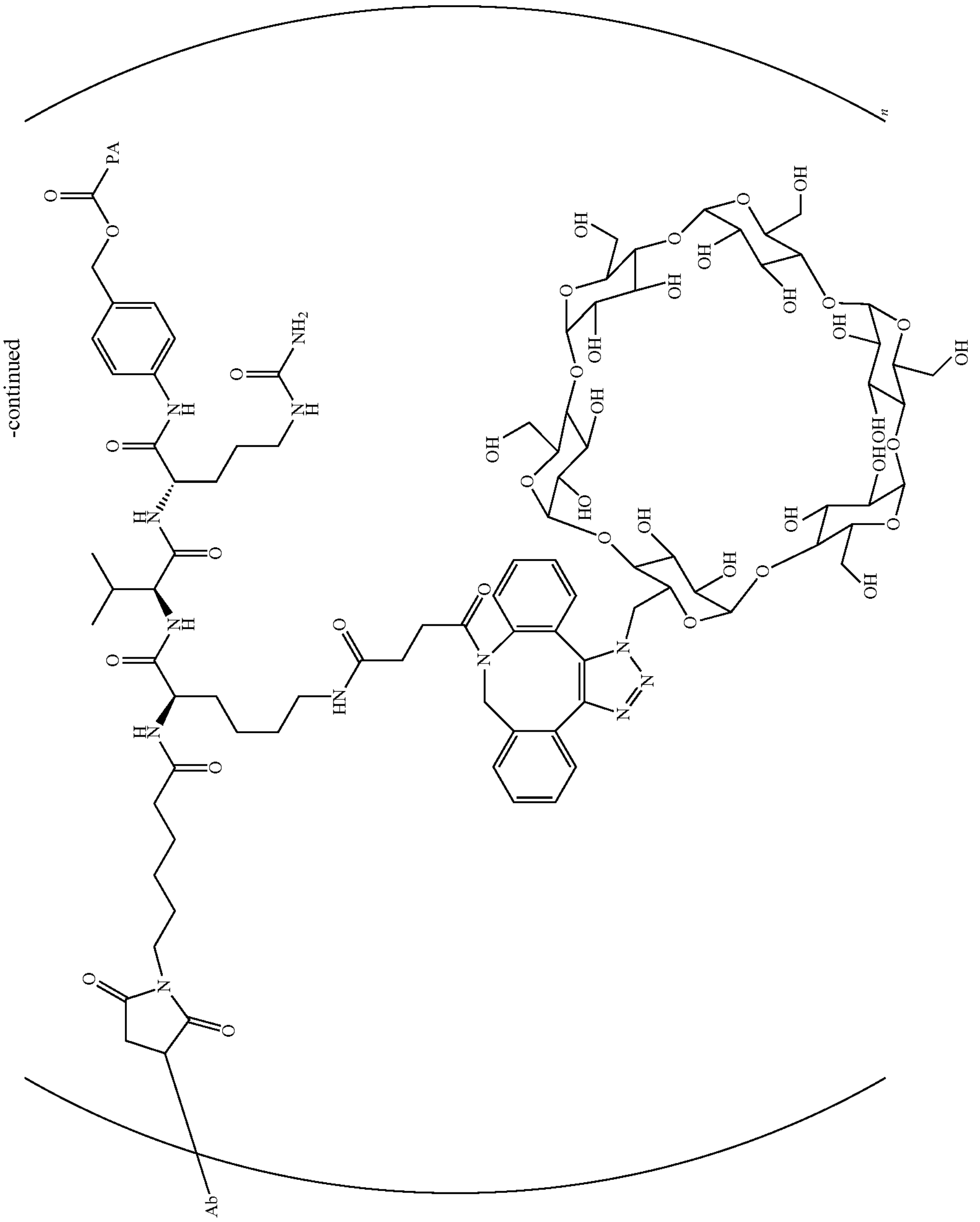
,

-continued
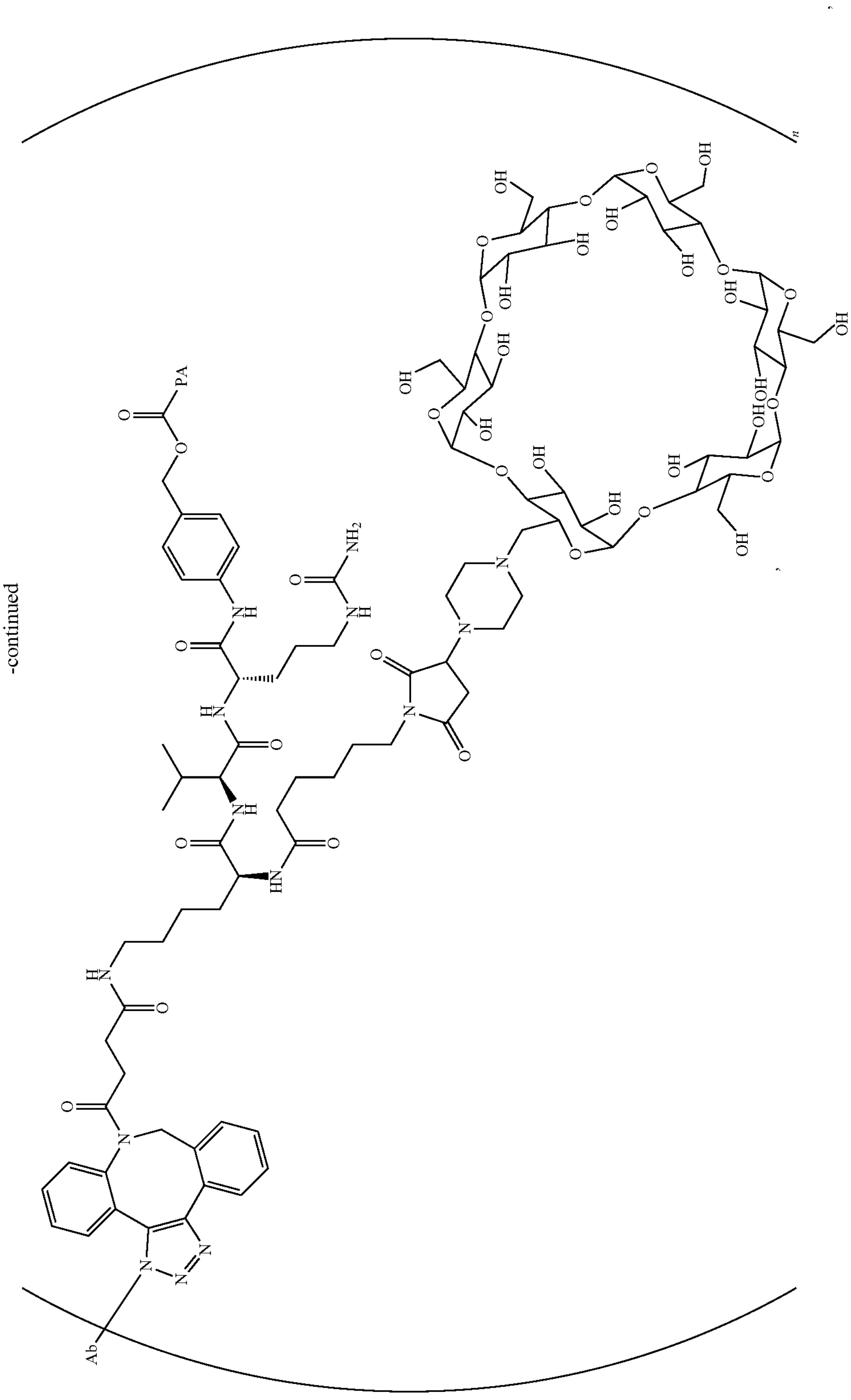

-continued
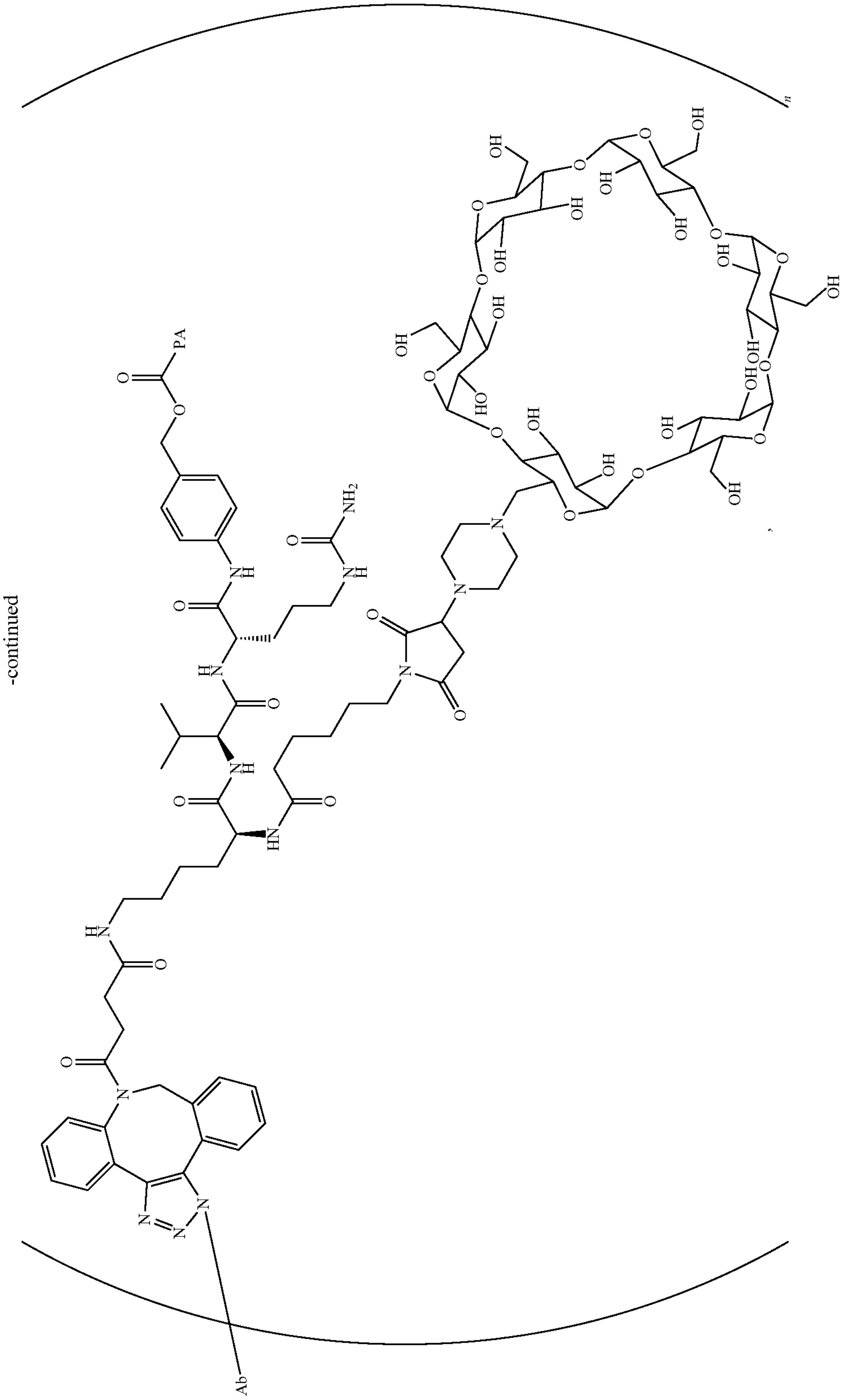
,

-continued
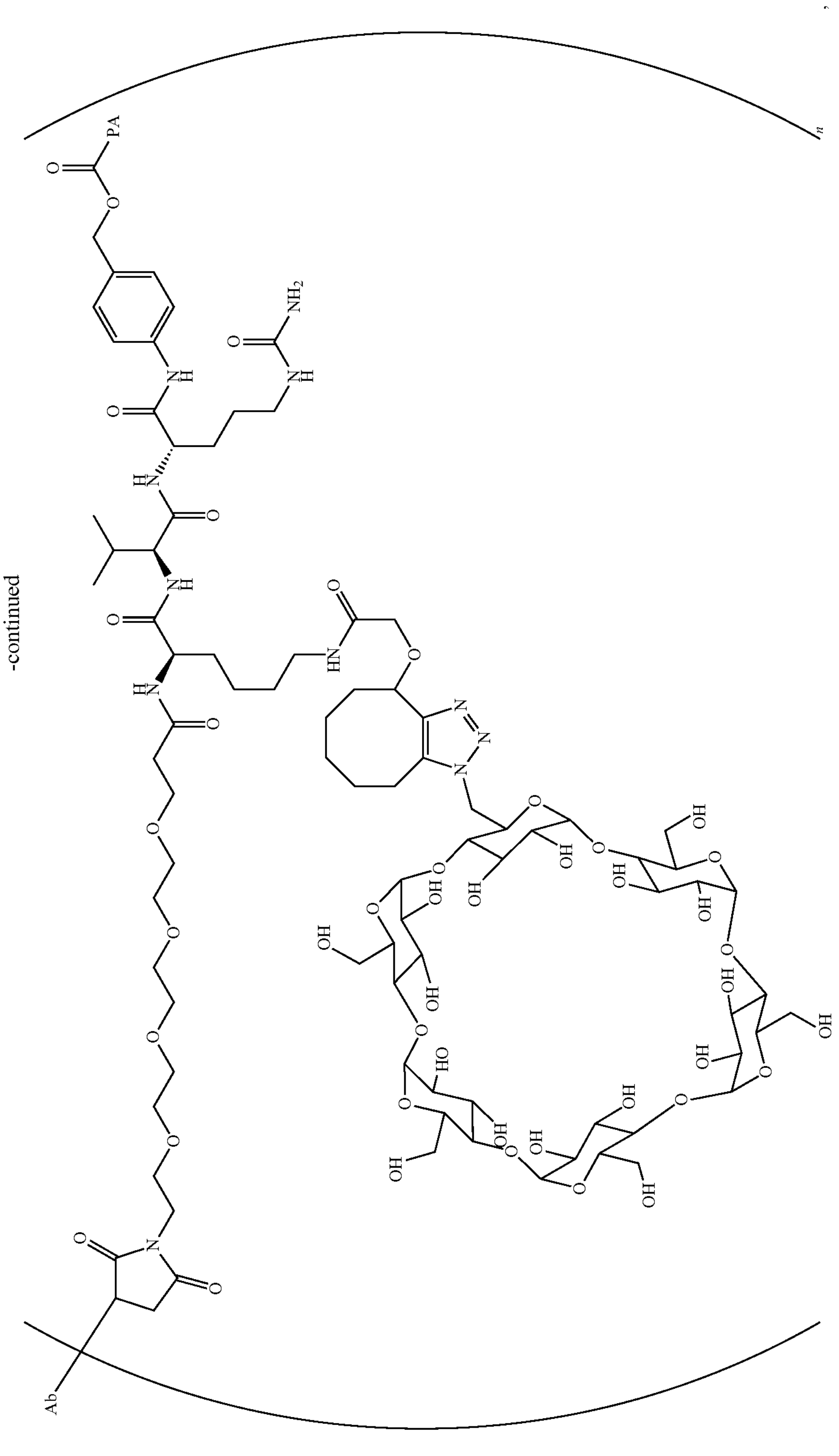

-continued
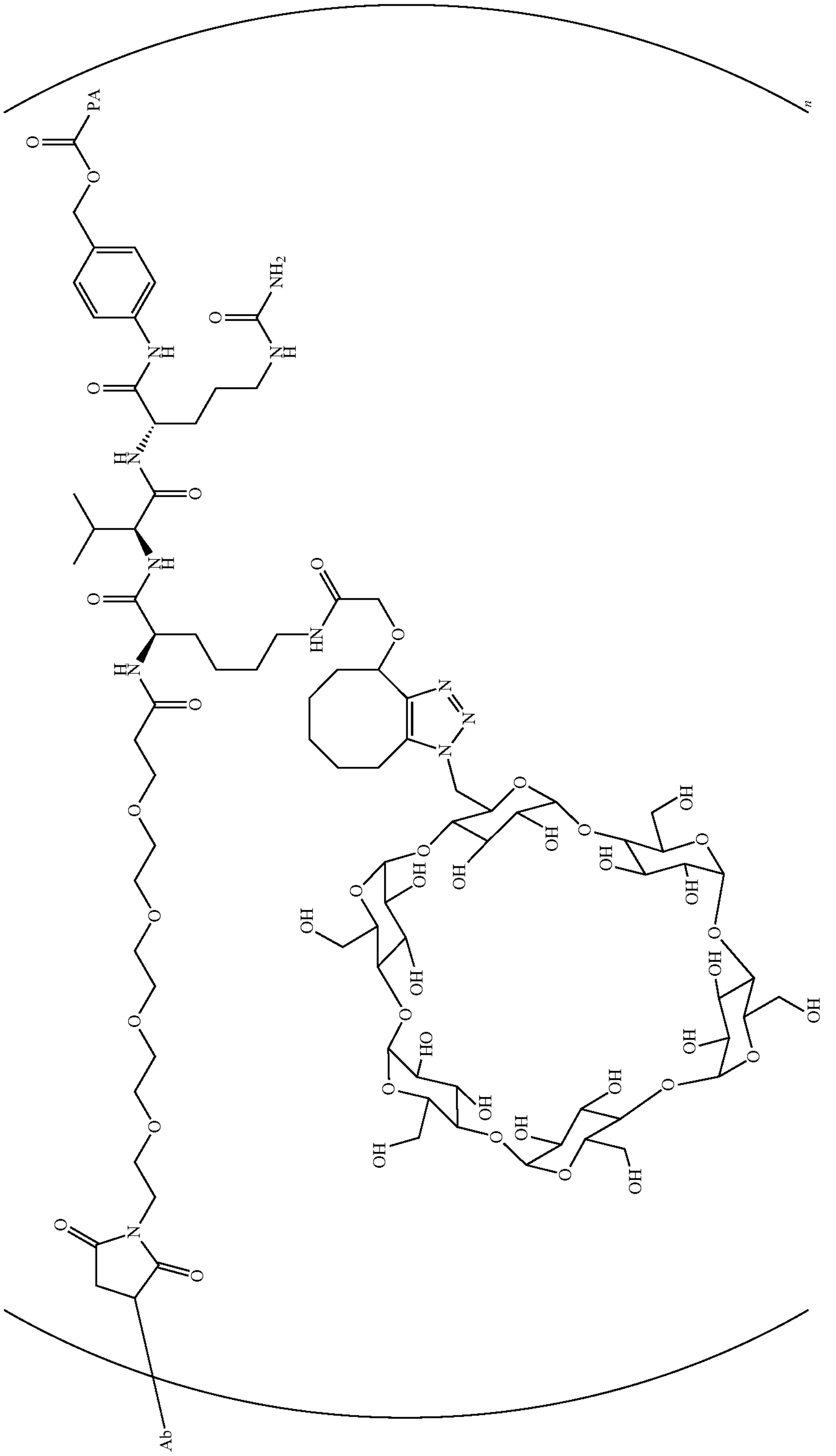
,

-continued
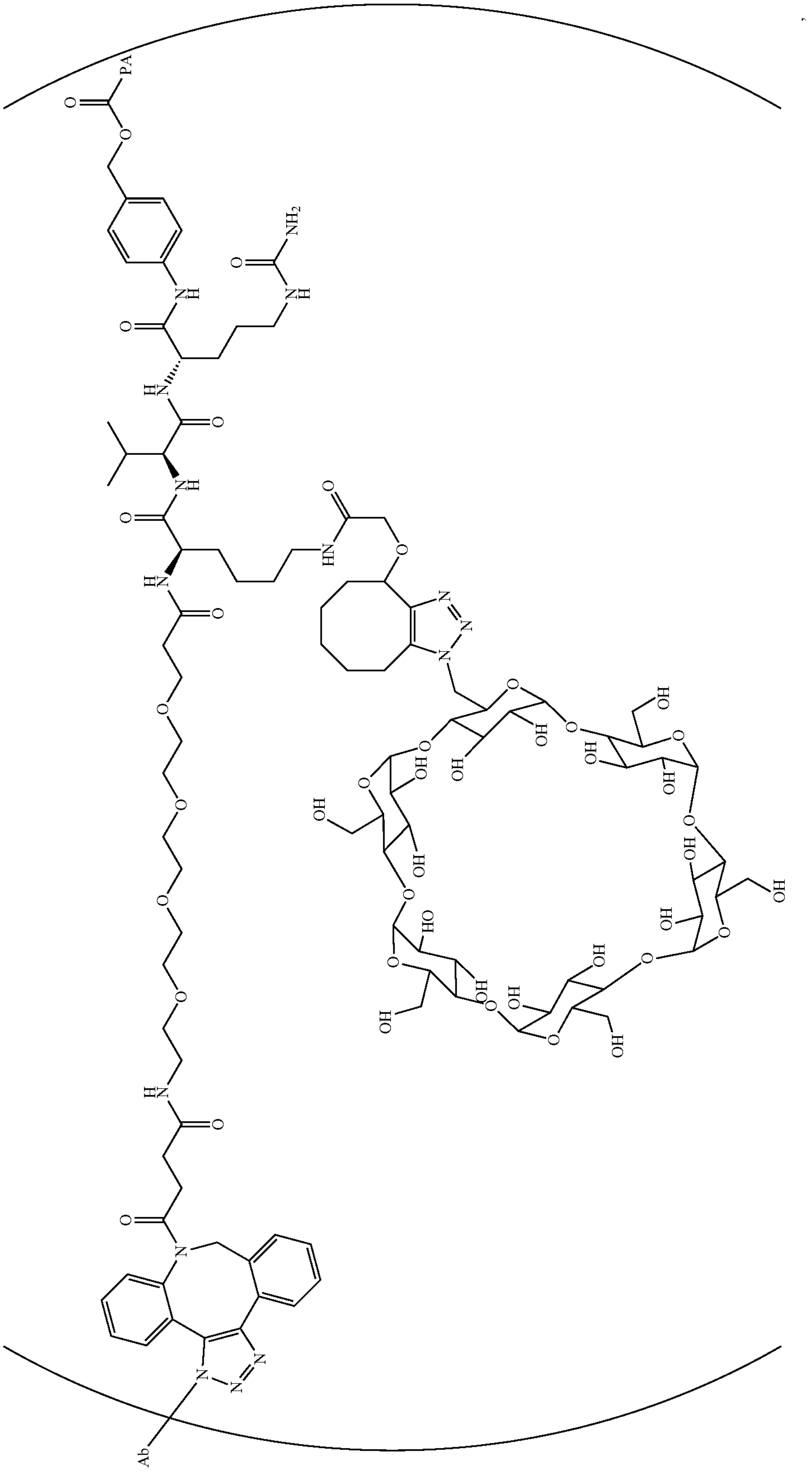

-continued
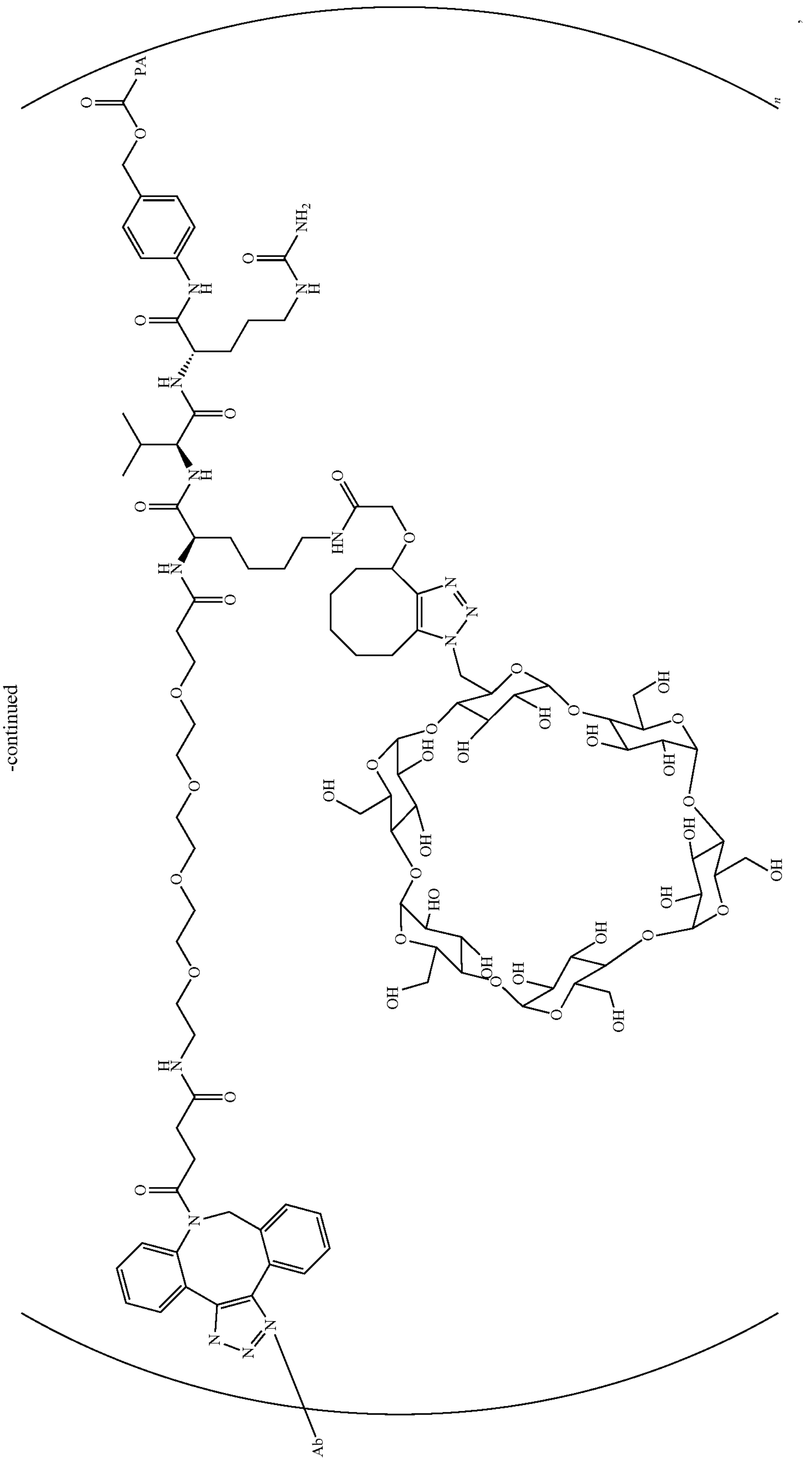

-continued
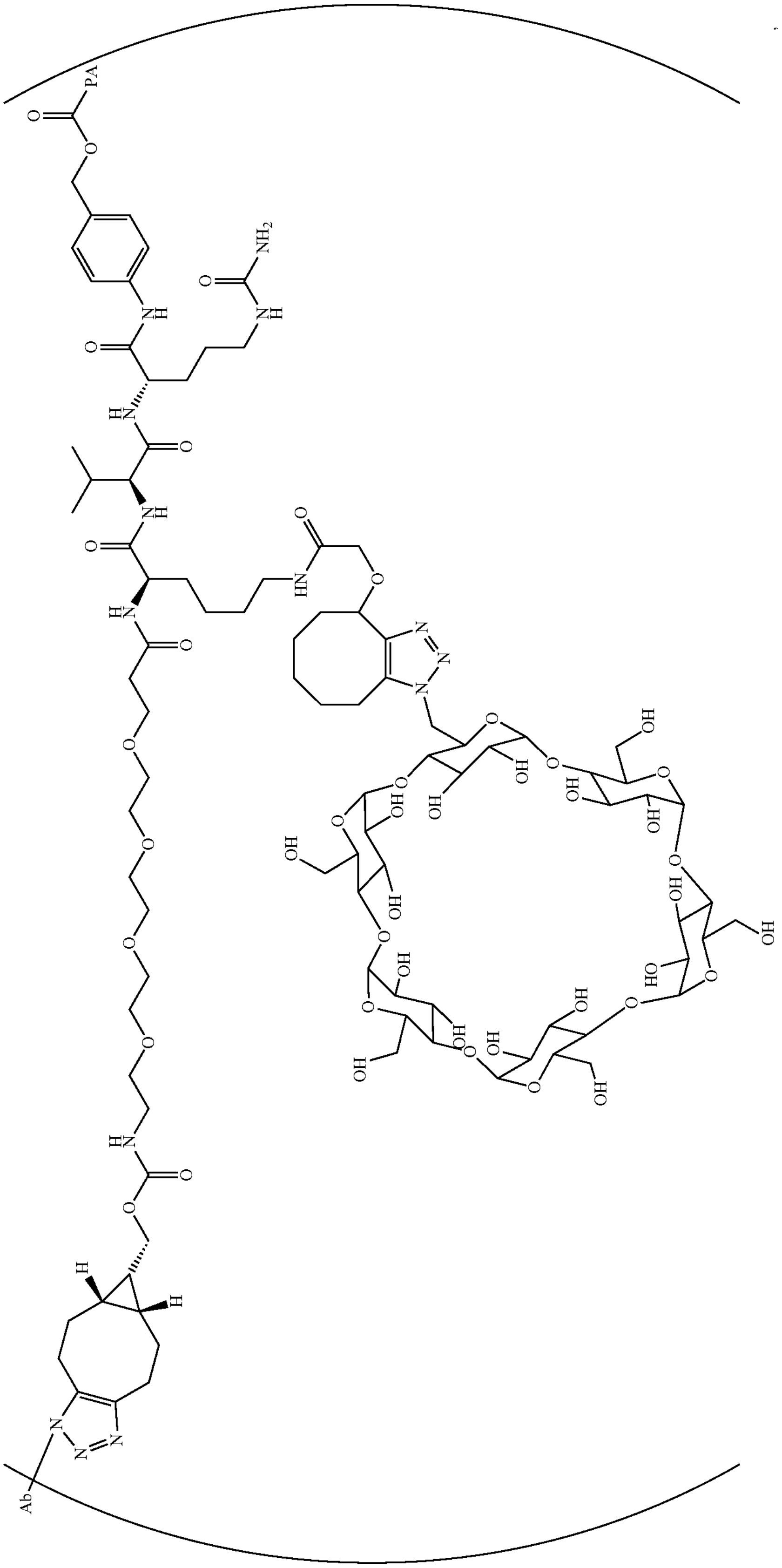

-continued
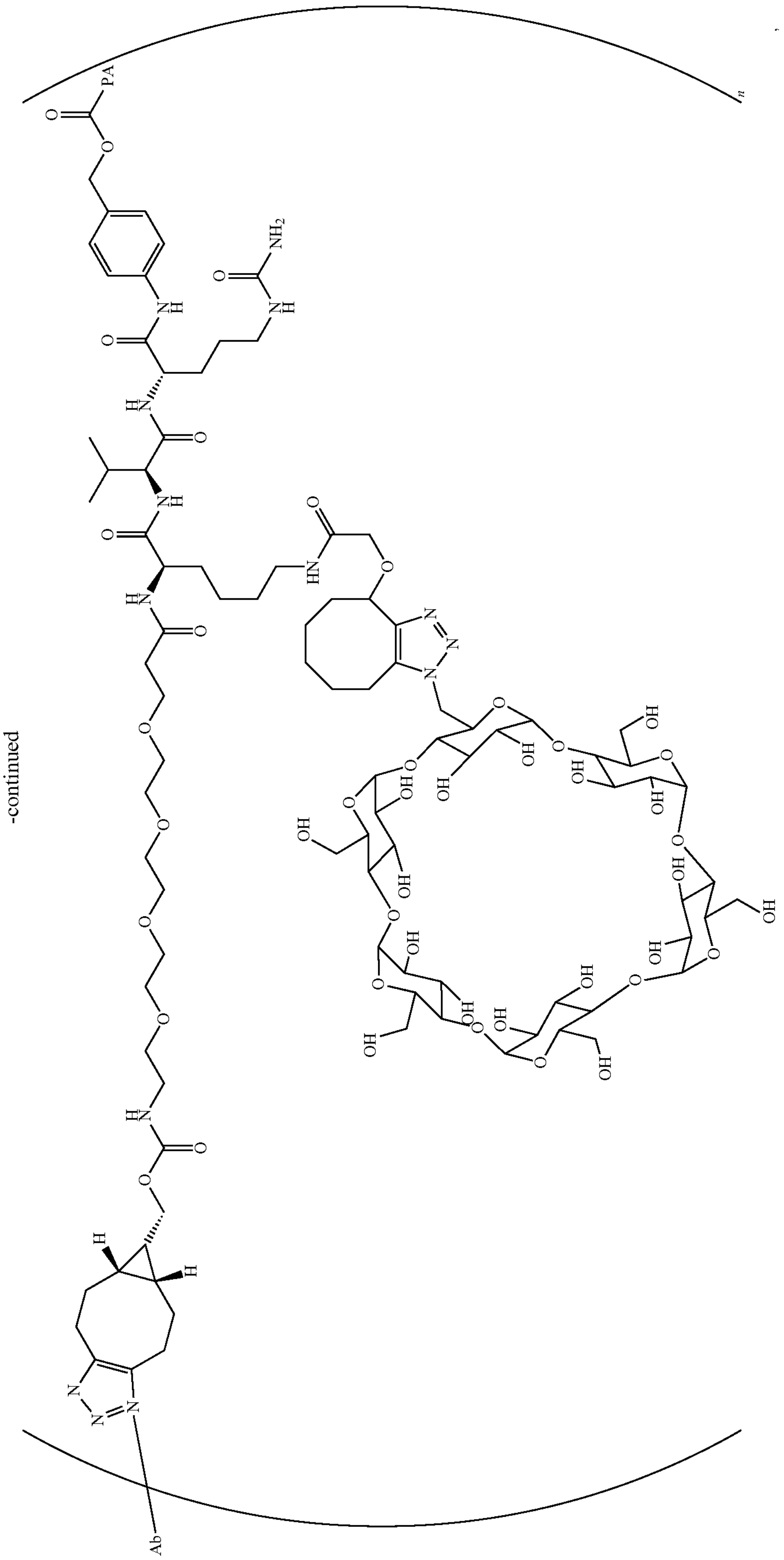

-continued
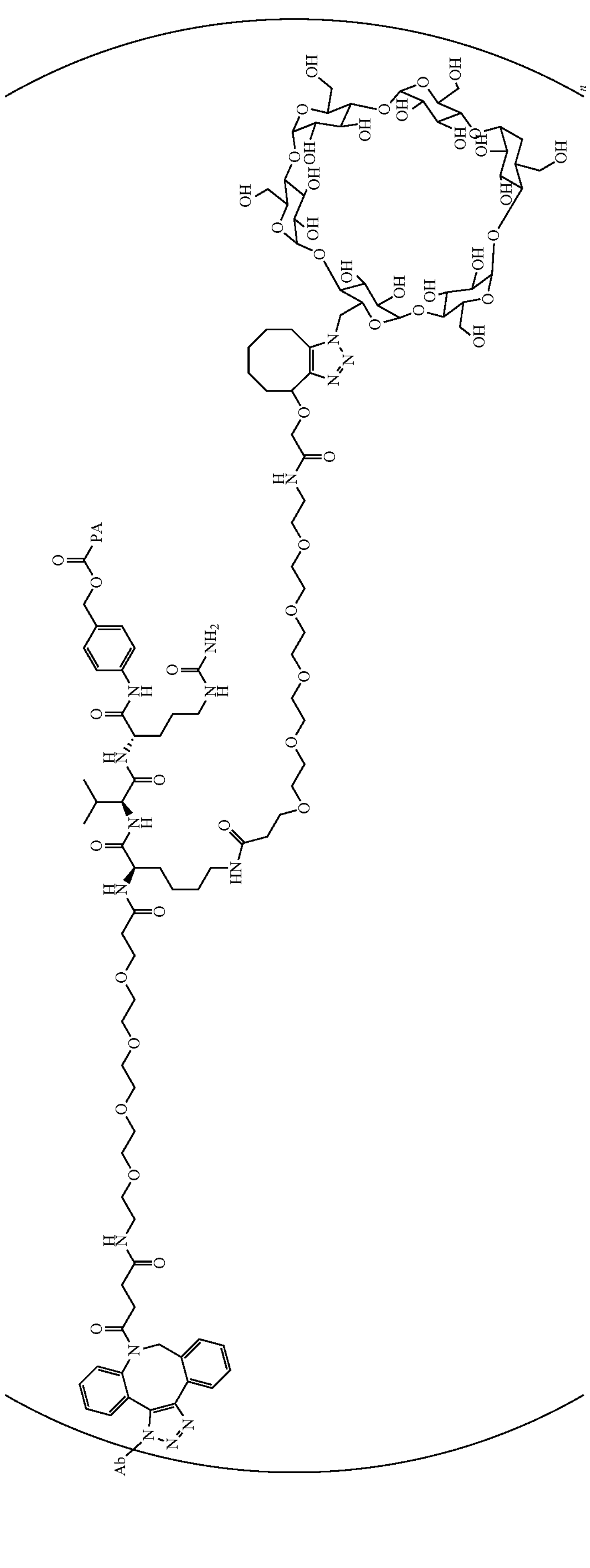

-continued
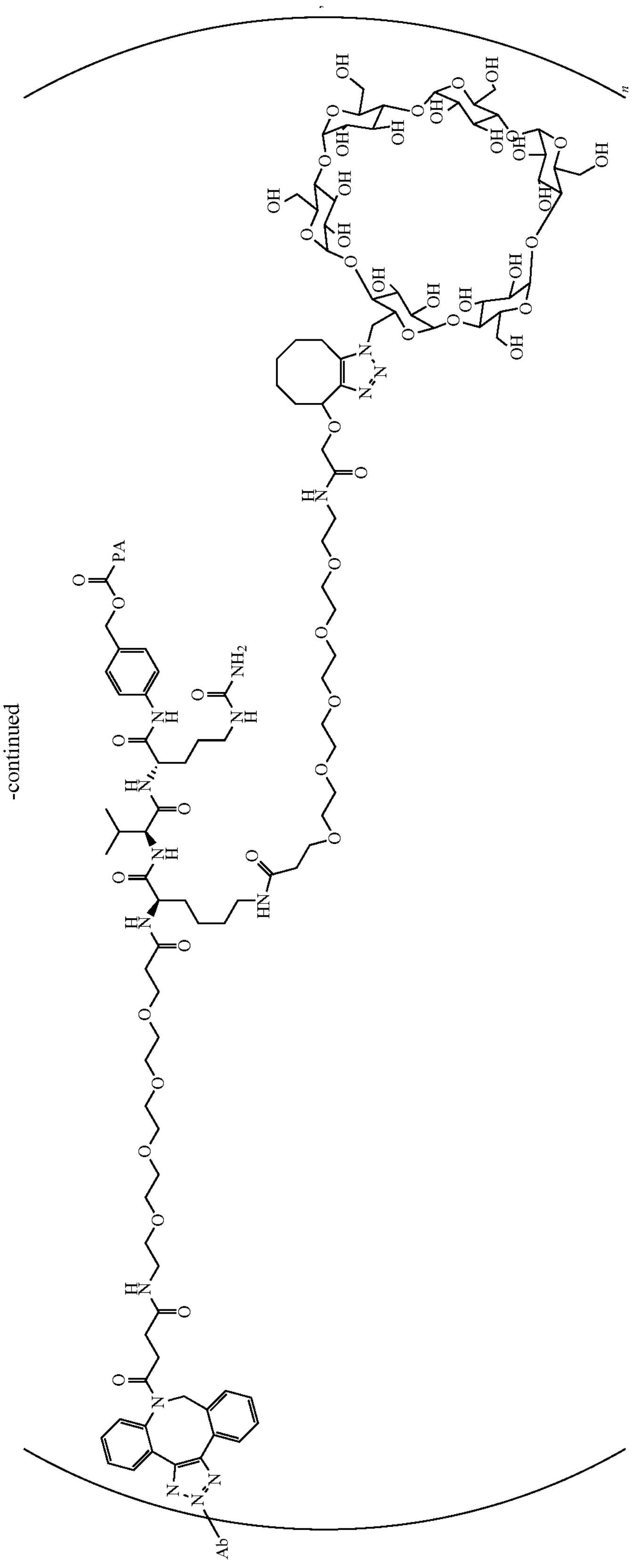

-continued
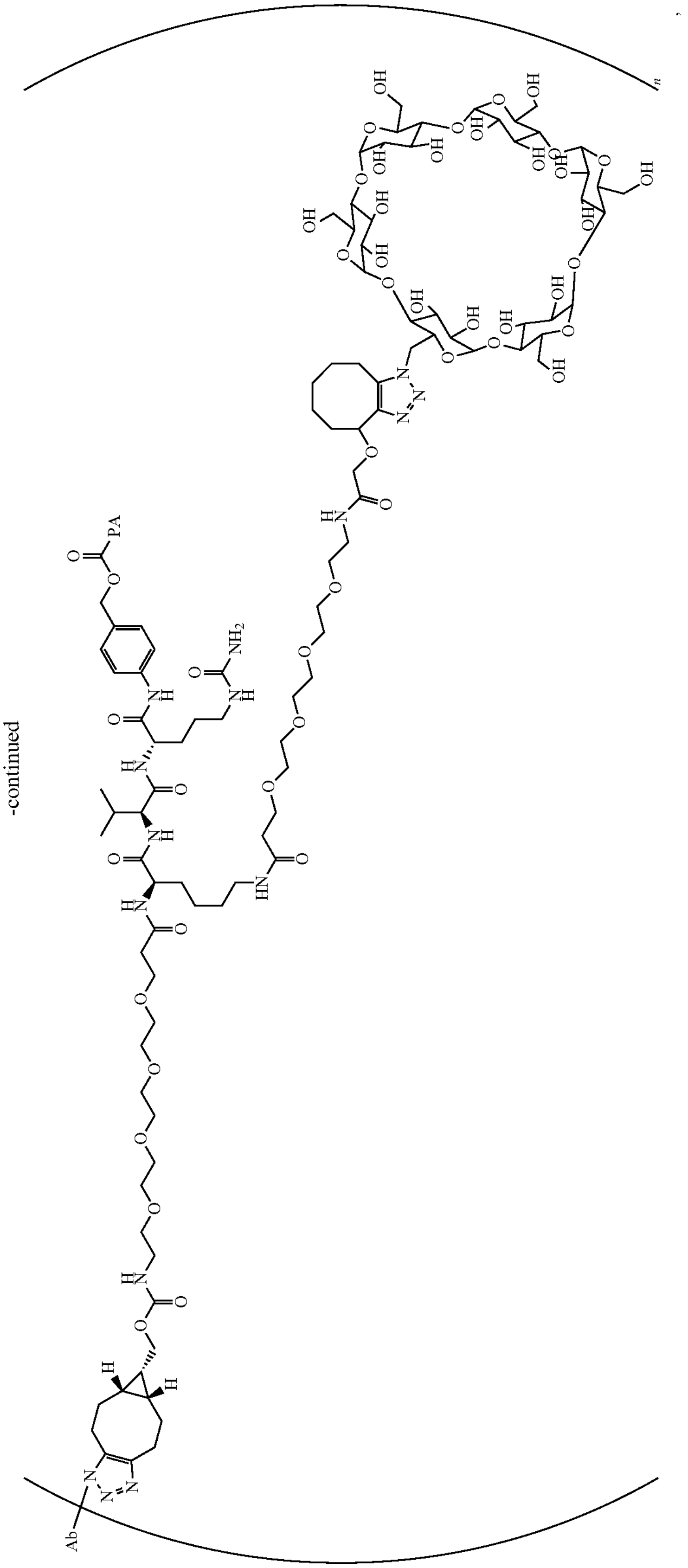

-continued
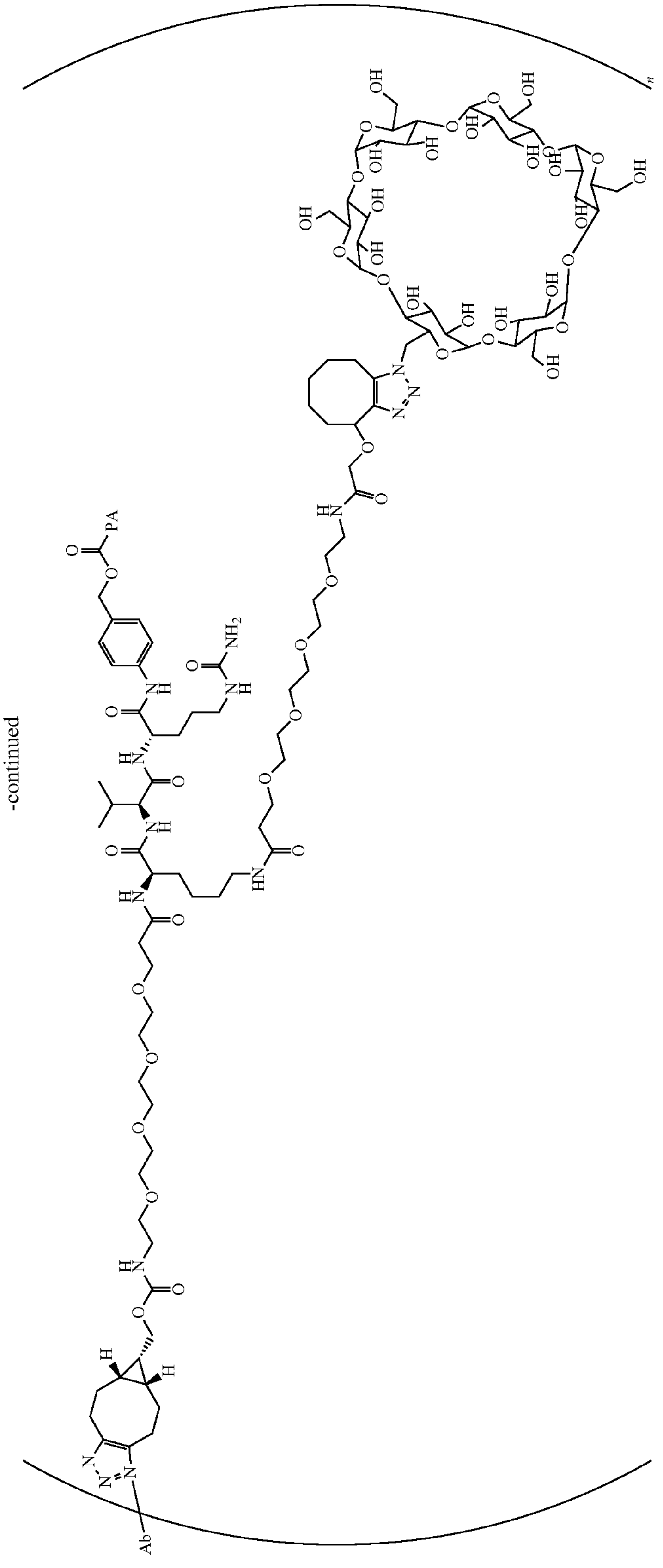
,

-continued
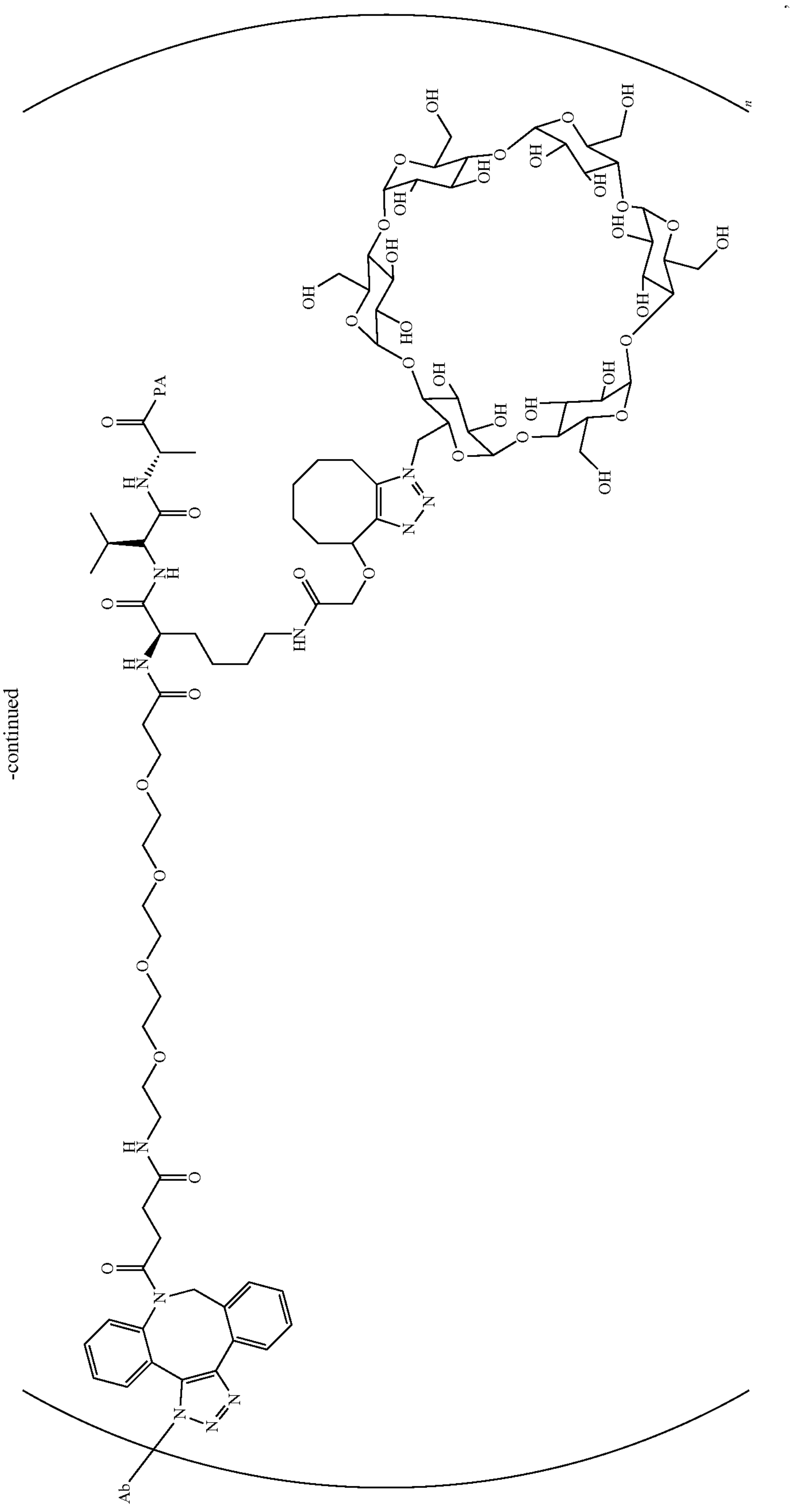

-continued
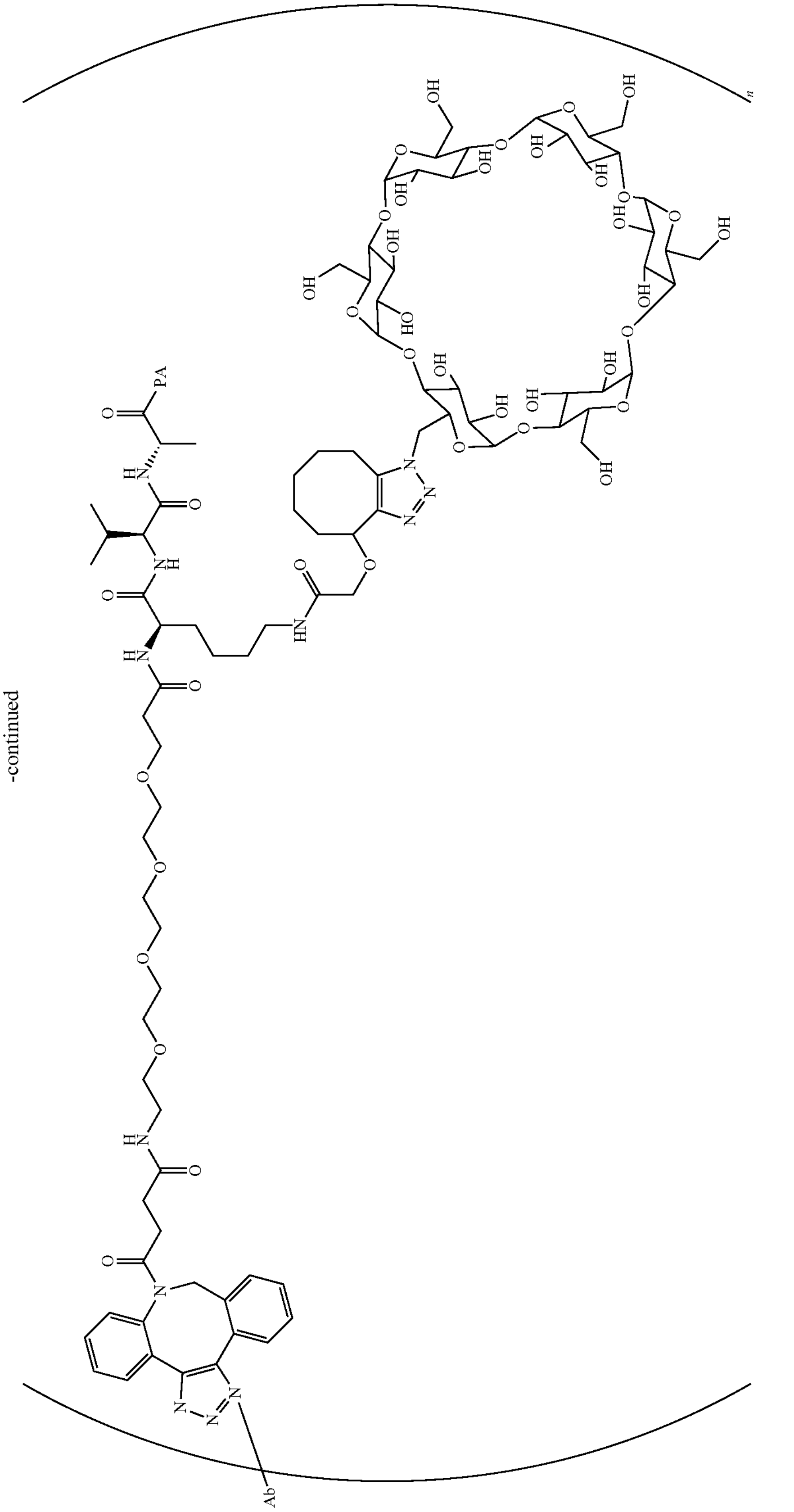

-continued
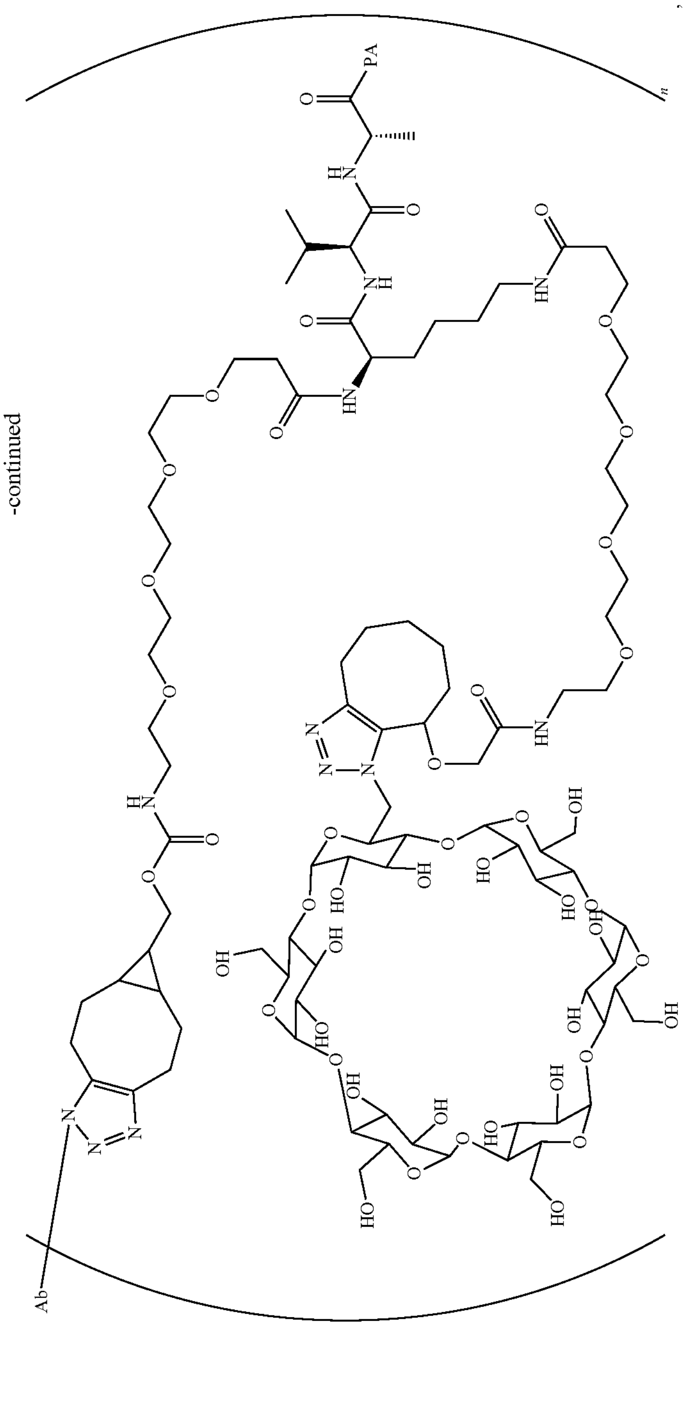
,

-continued
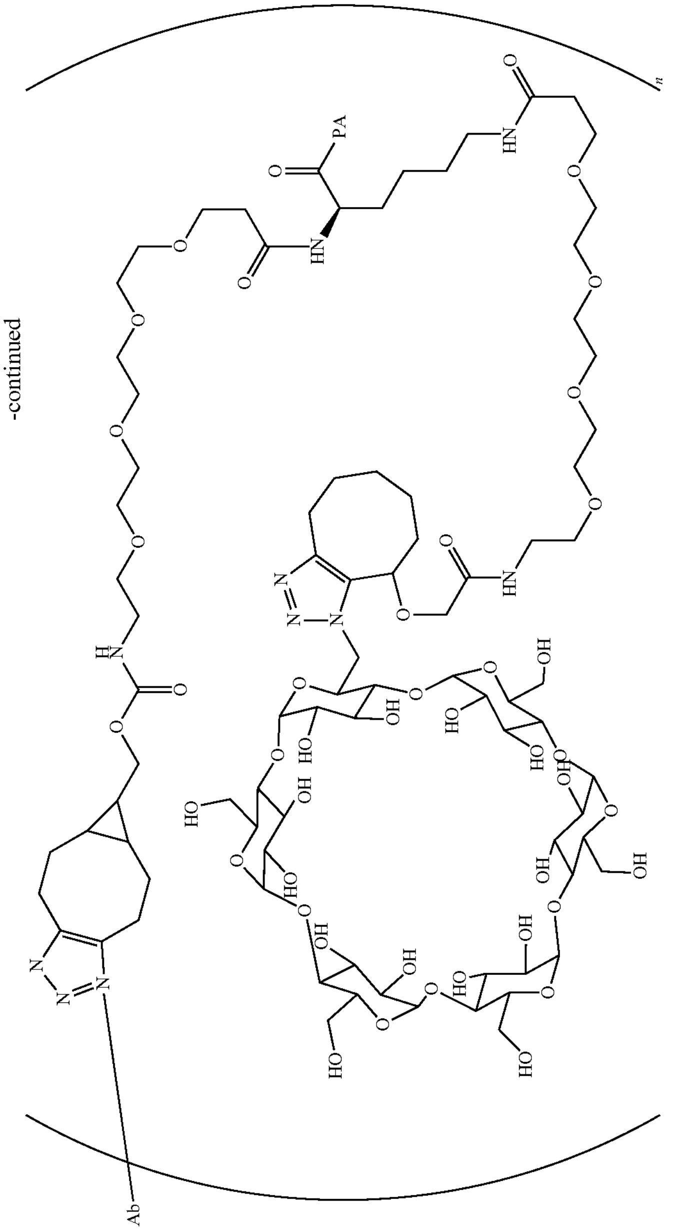
,
,

-continued
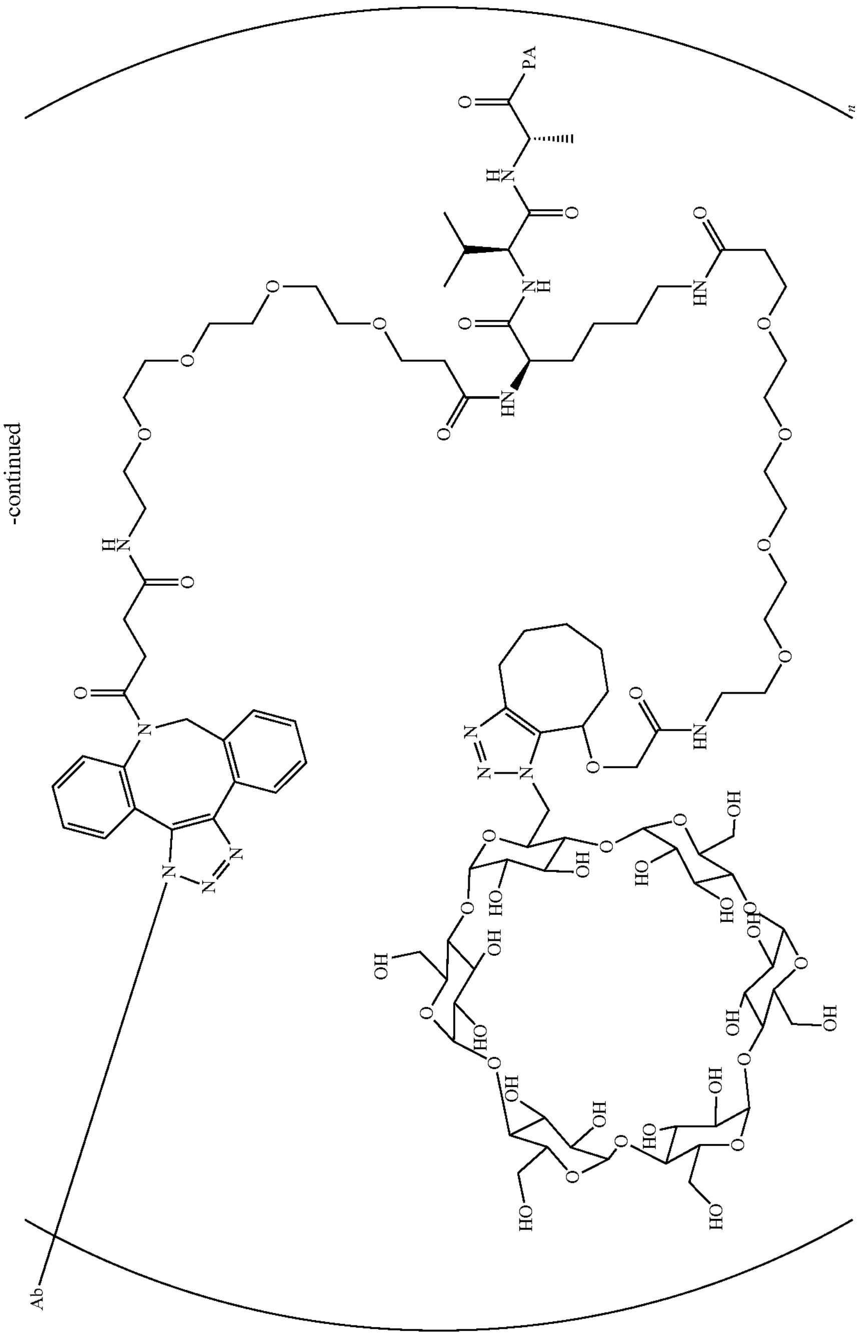
,

-continued
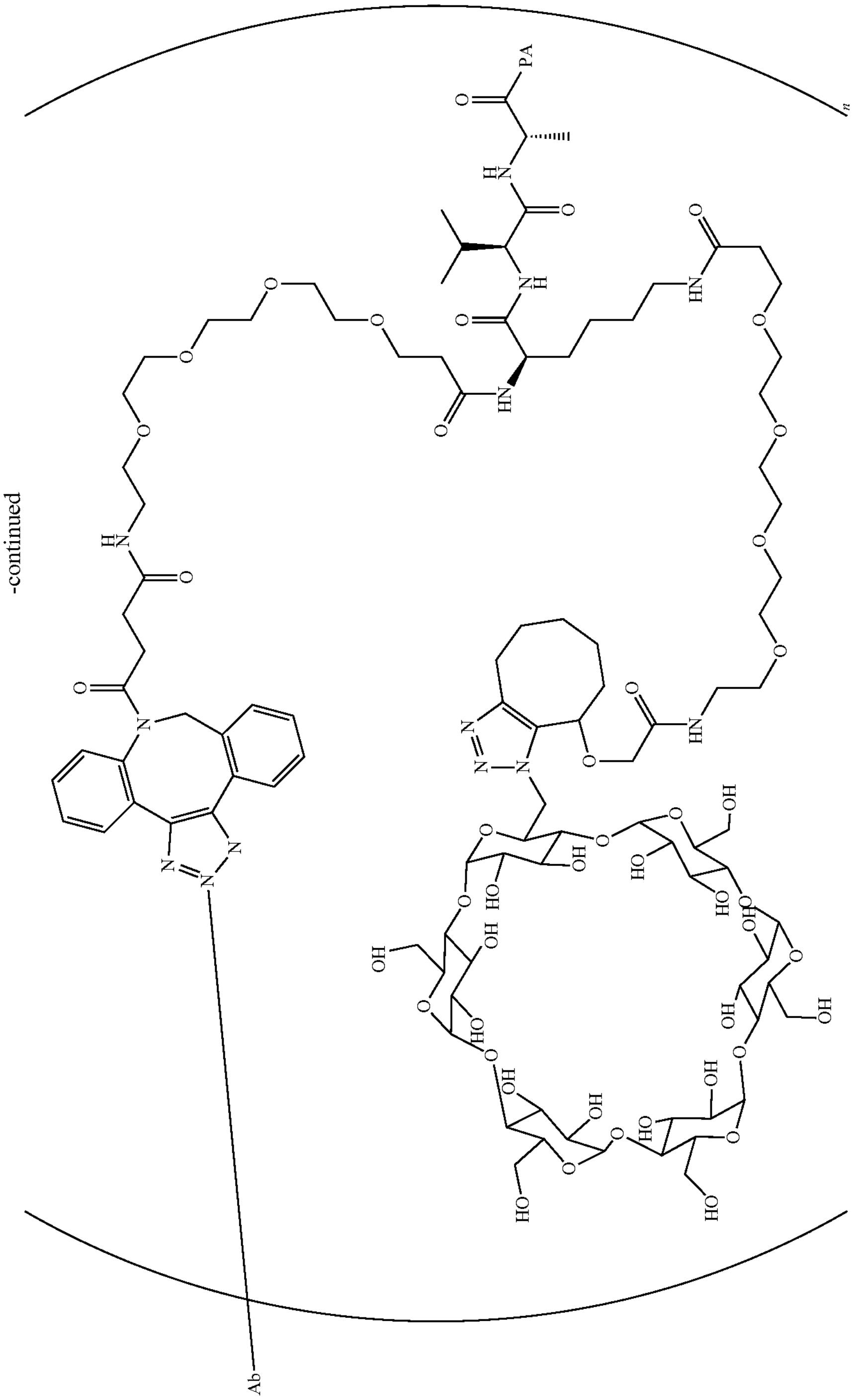
,
,

-continued
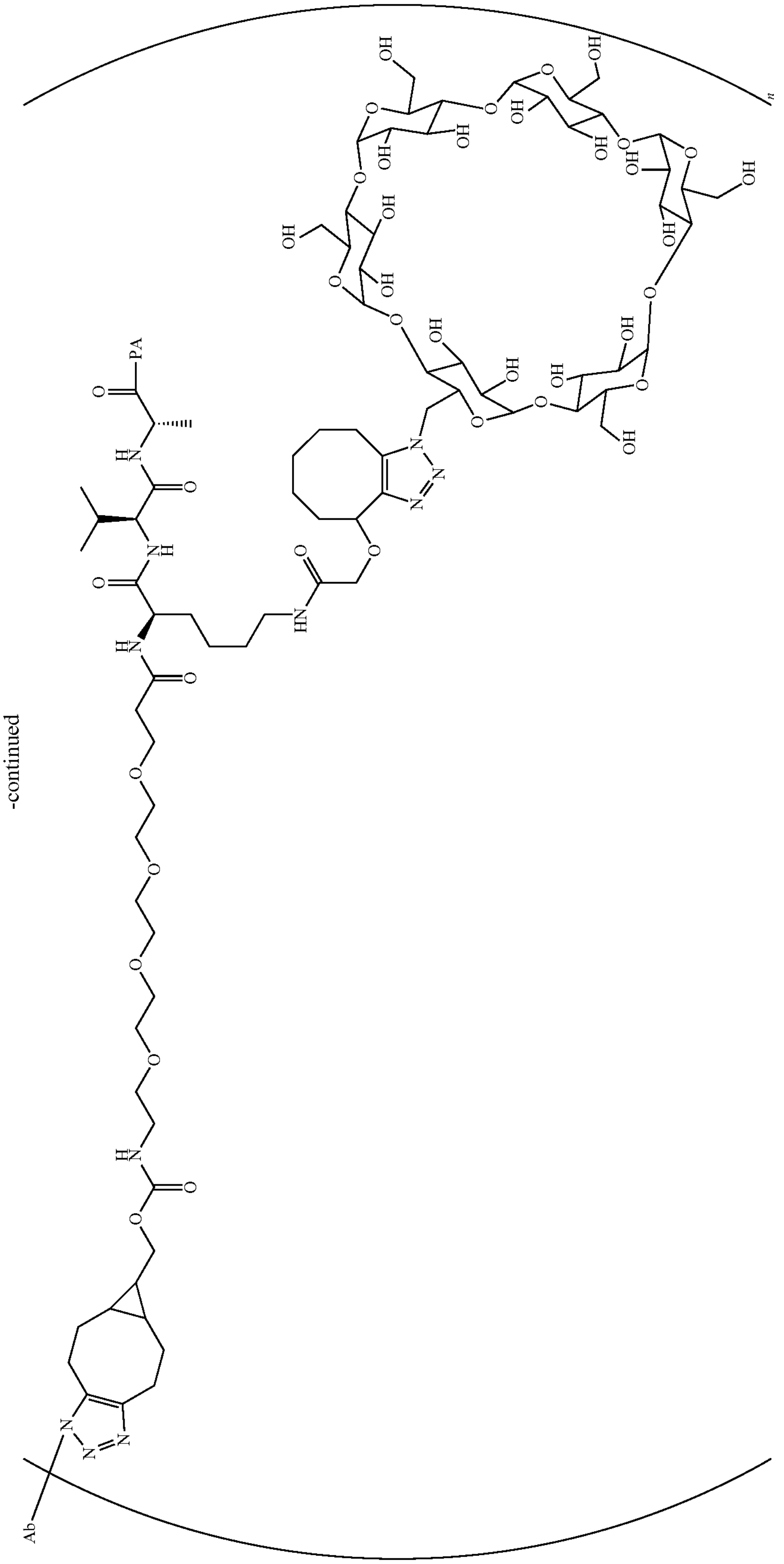

-continued
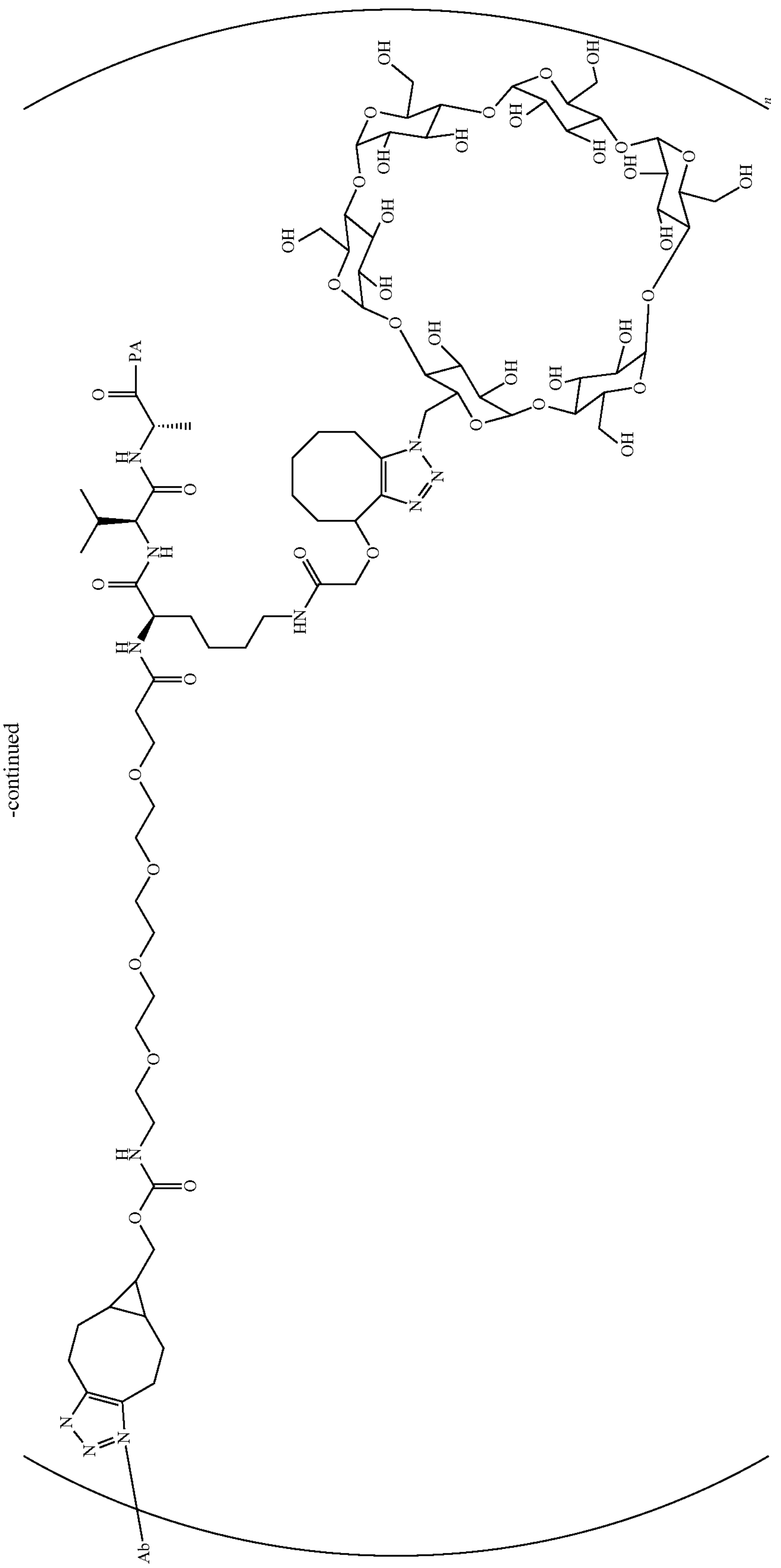

or a regioisomer, stereoisomeric form, pharmaceutically acceptable salt, solvate thereof, or mixture thereof, wherein Ab is an antibody or antigen-binding fragment thereof. In these examples, Ab may be directly or indirectly bonded to the linked-payload. In some examples, when Ab is indirectly bonded to the linker-payload, then

is

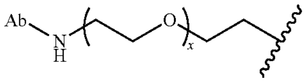

, wherein subscript x is an integer from 1 to 4. In some examples, subscript x is 1. In some examples, subscript x is 2. In some examples, subscript x is 3. In some examples, subscript x is 4. Herein, Ab is an antibody or an antigen-binding fragment thereof. In some examples, the illustrated PEG
group, i.e.,

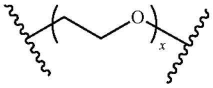

is bonded to a glutamine on the Ab. In certain embodiments, n is an integer from 1 to 30, for instance from 1 to 4, for instance 1, 2, 3, or 4.

In some examples, the compound of Formula (I) is selected from:

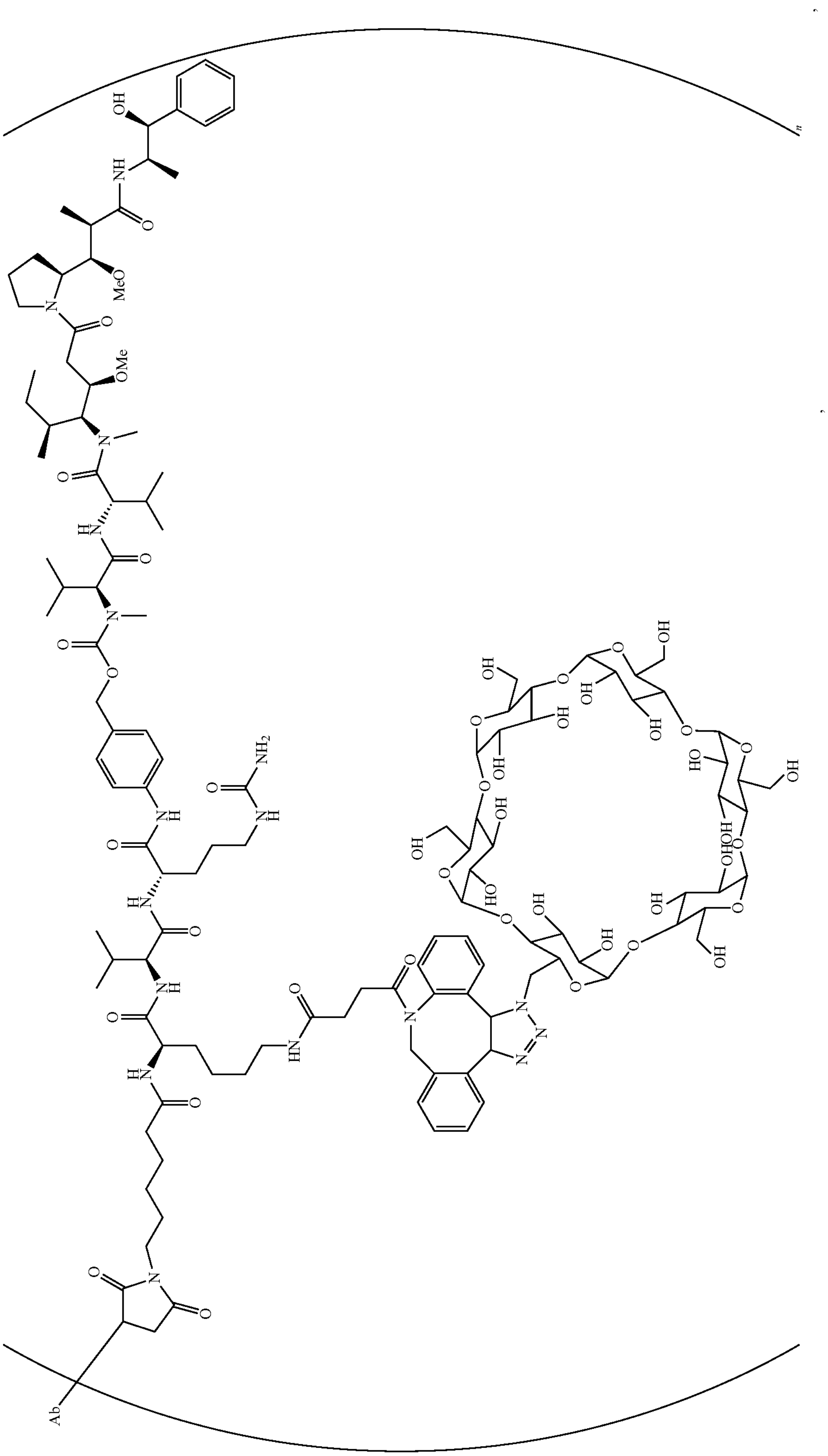

-continued
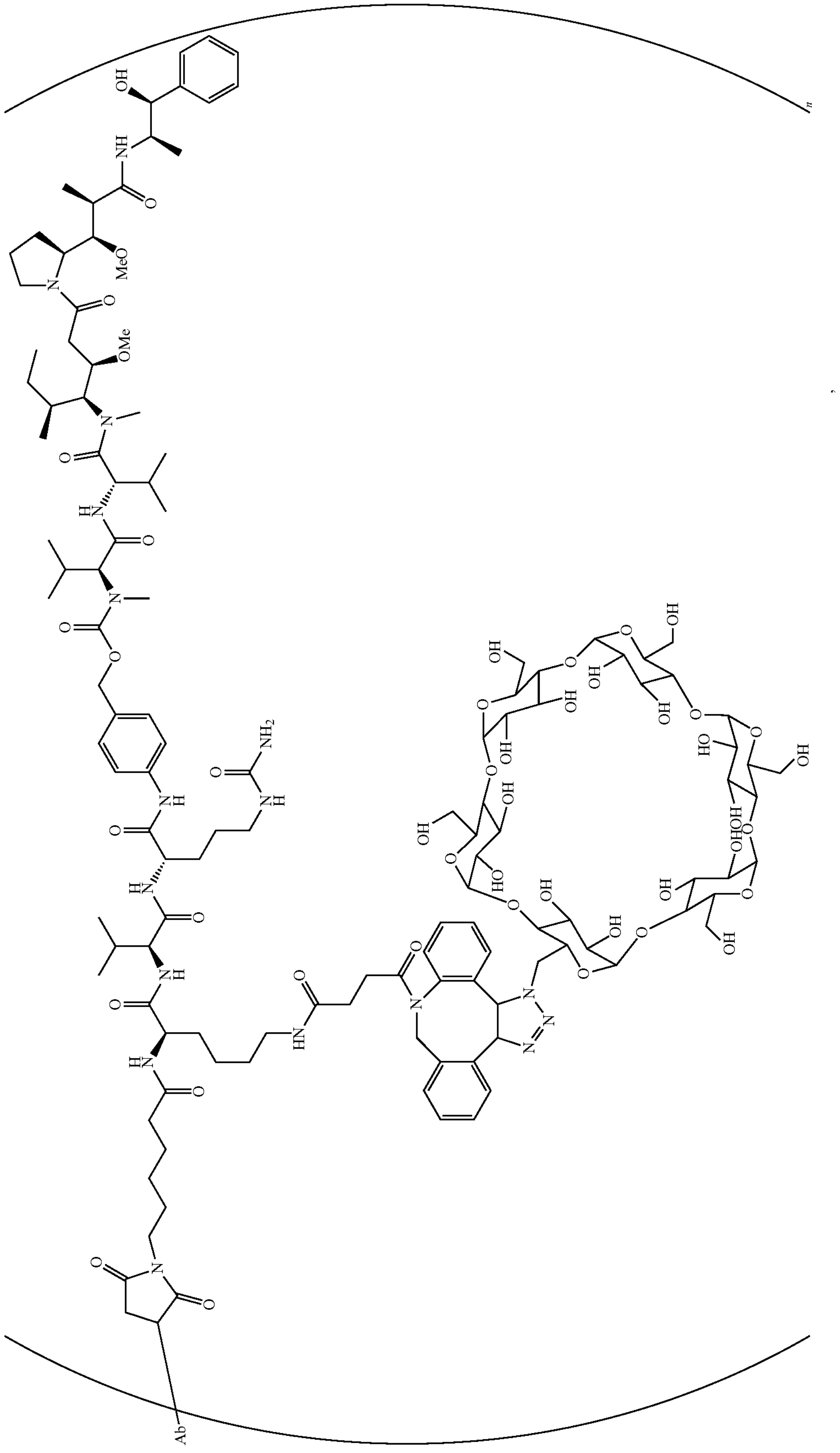

-continued
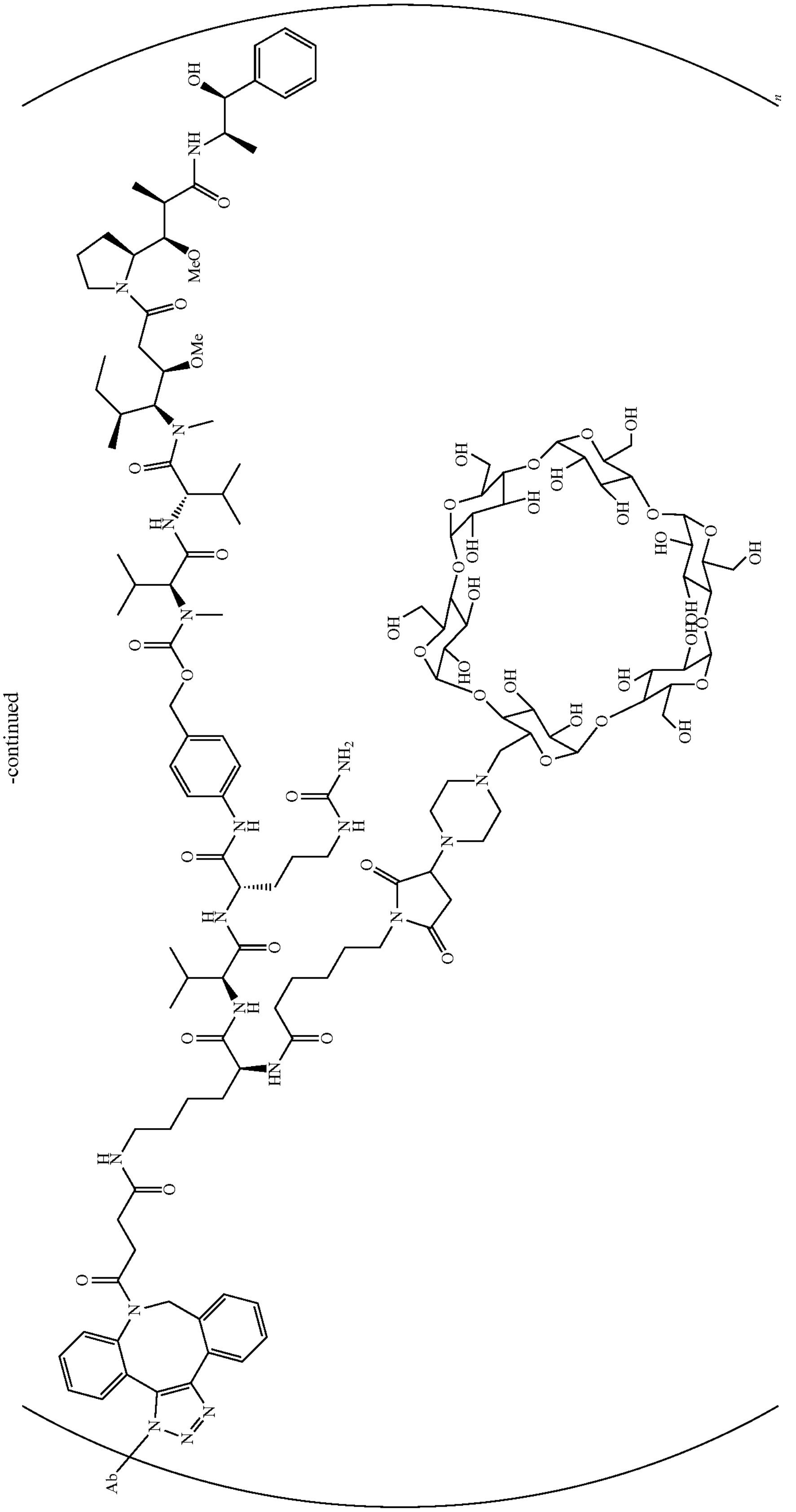

-continued
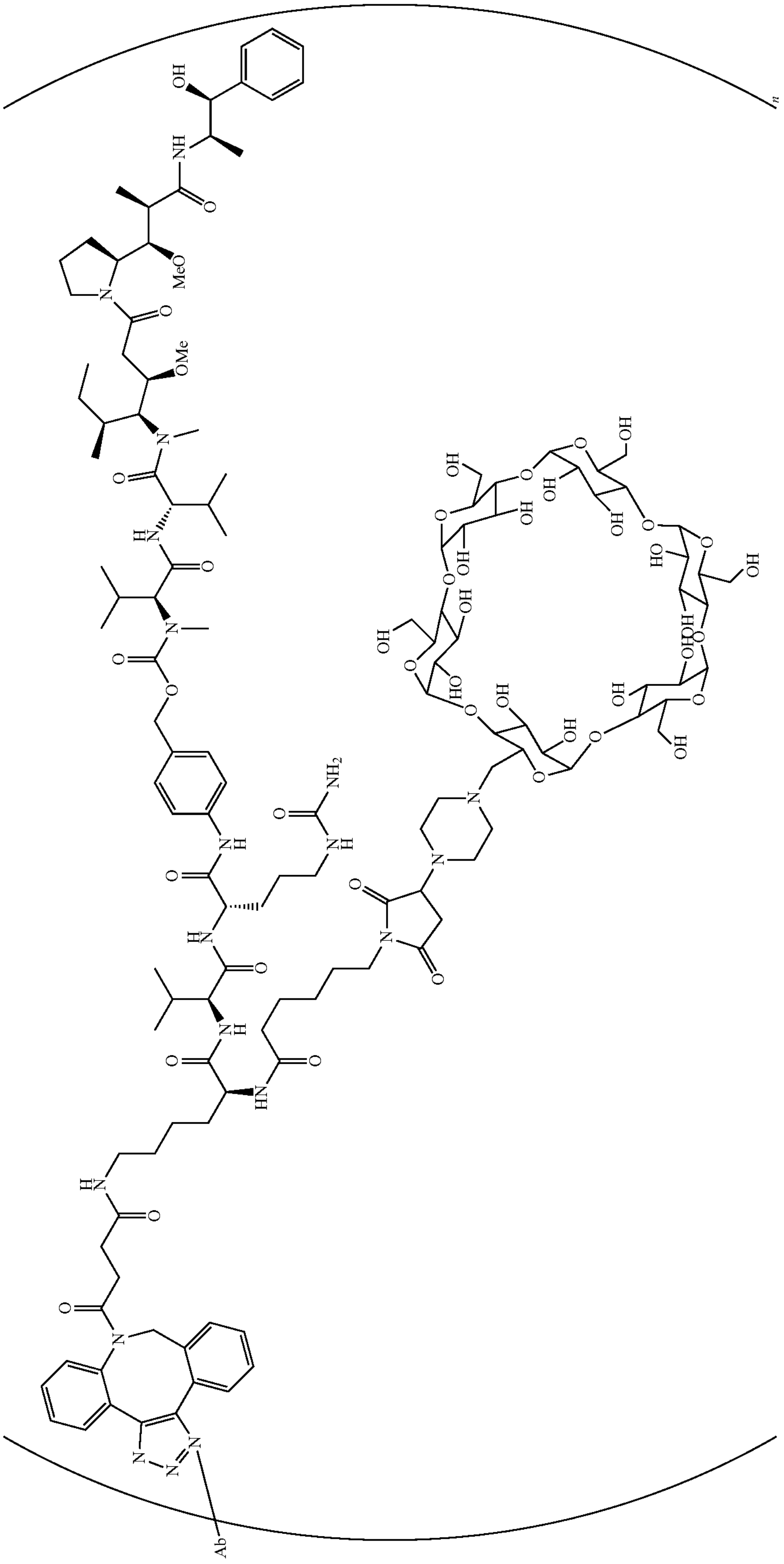

-continued
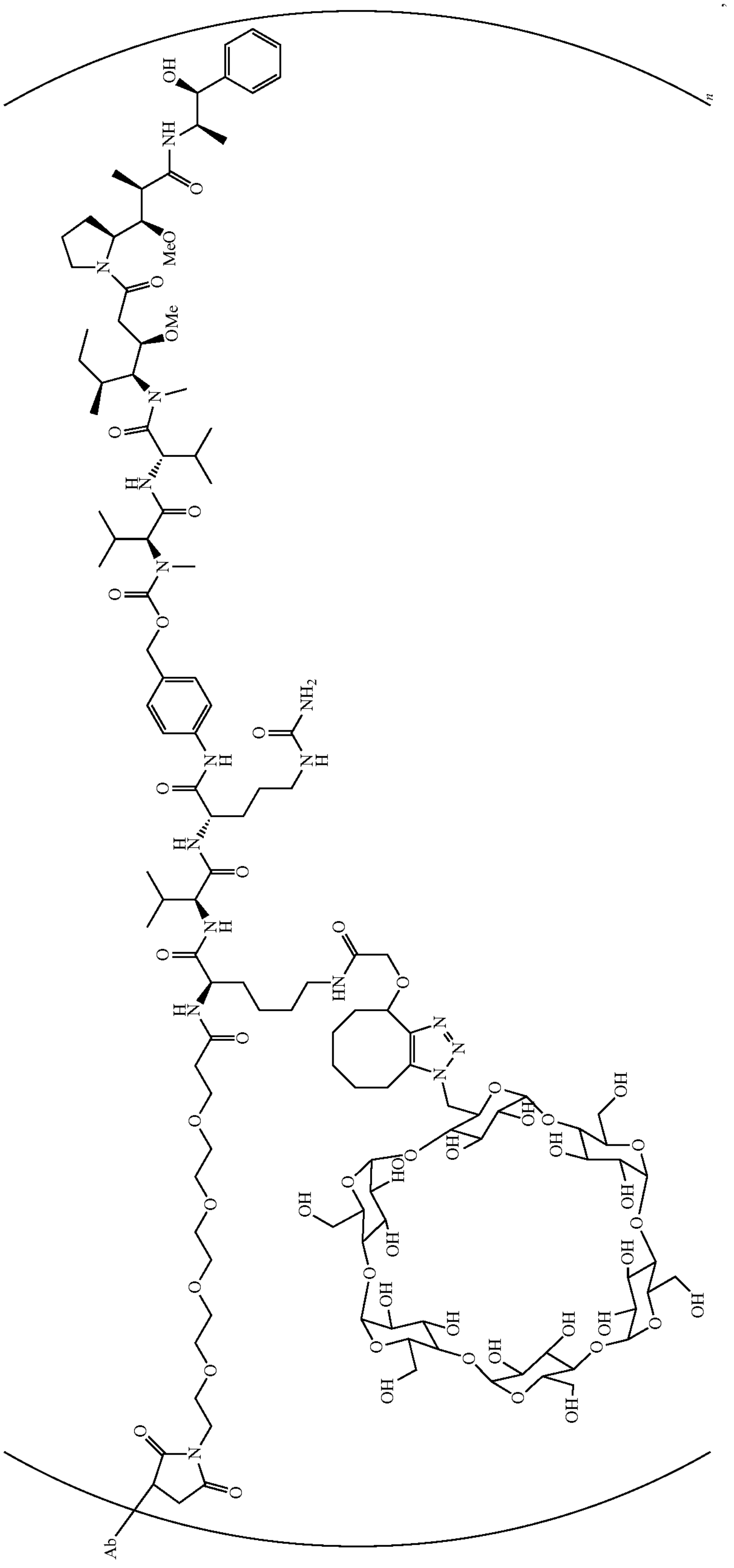

-continued
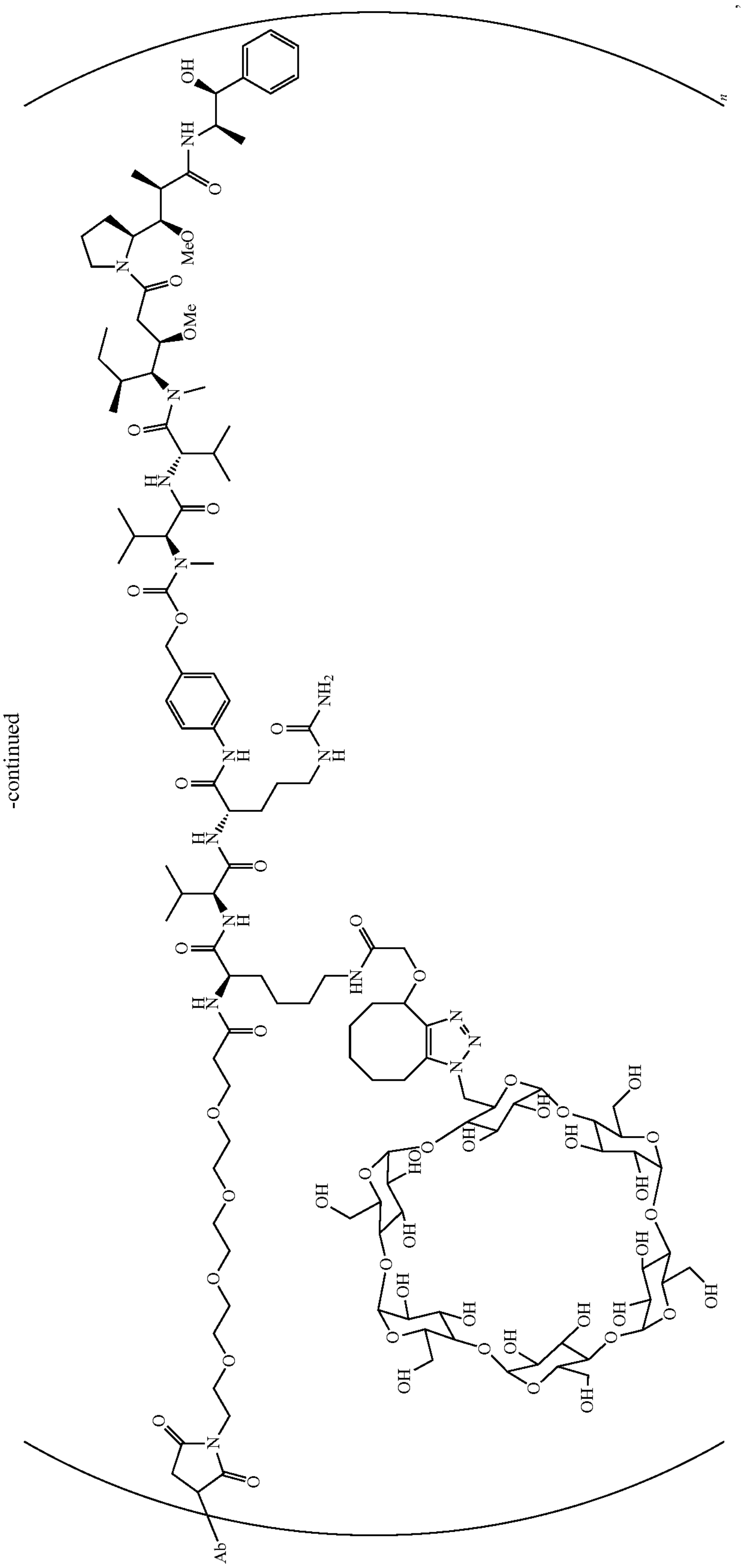

-continued
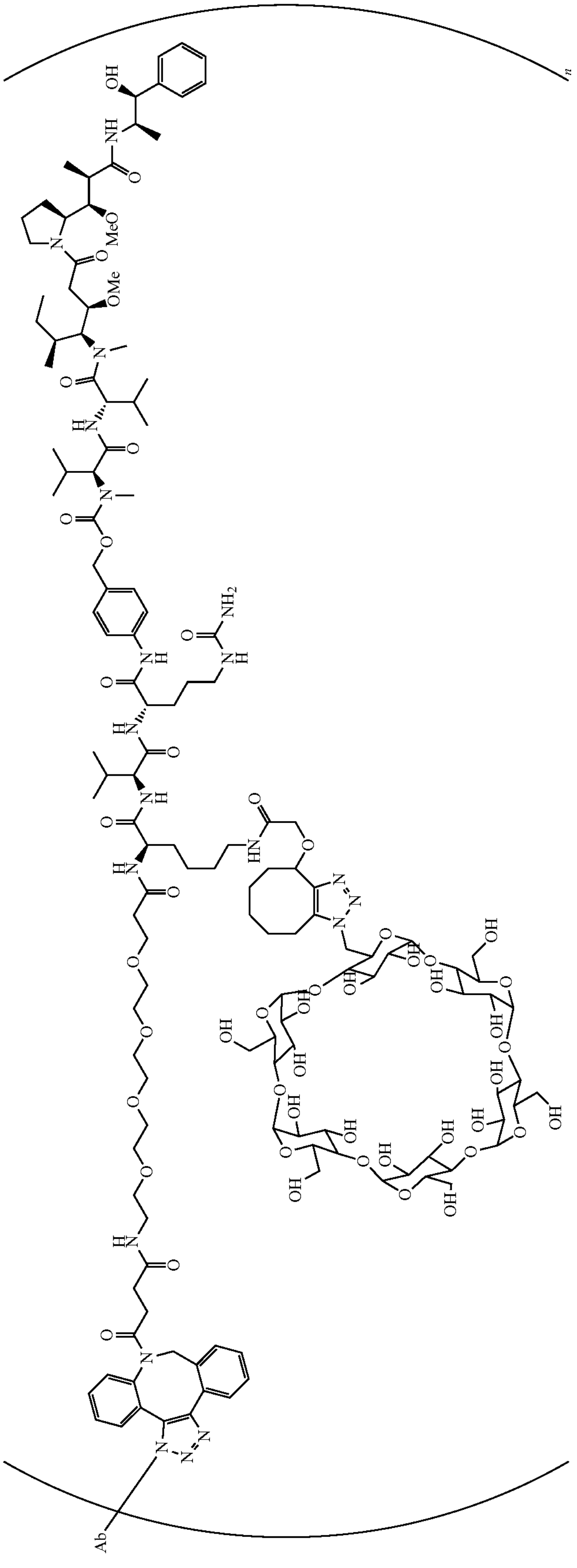
,

-continued
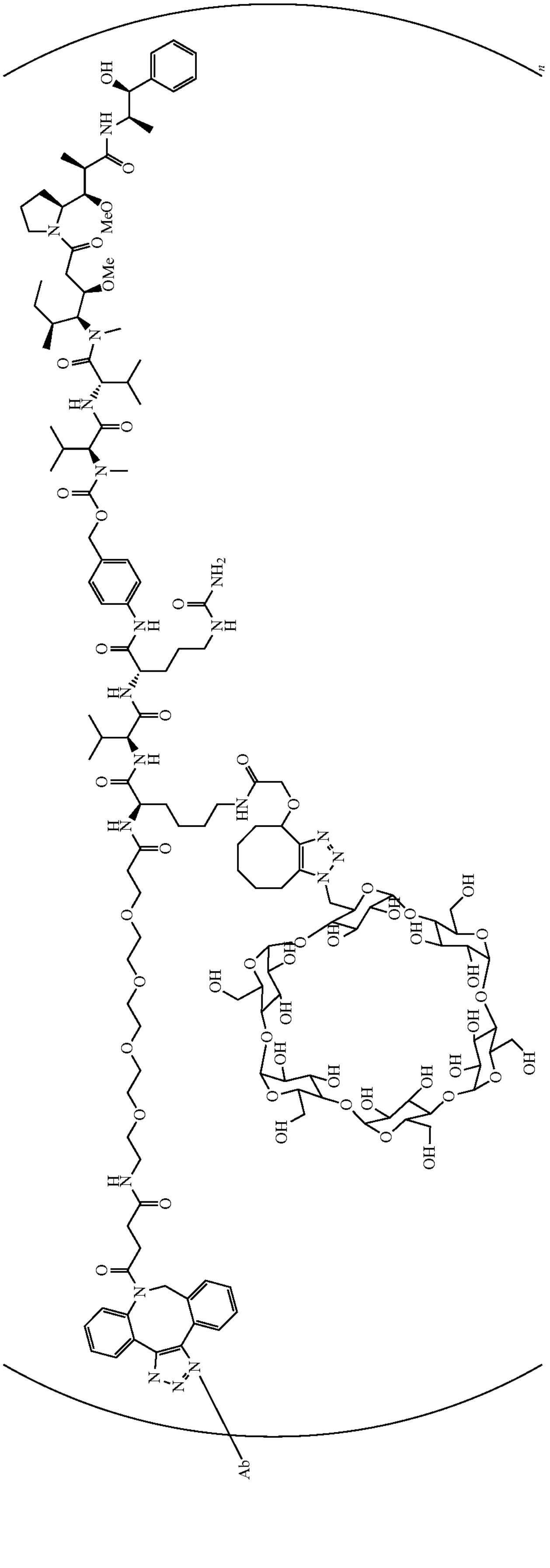

-continued
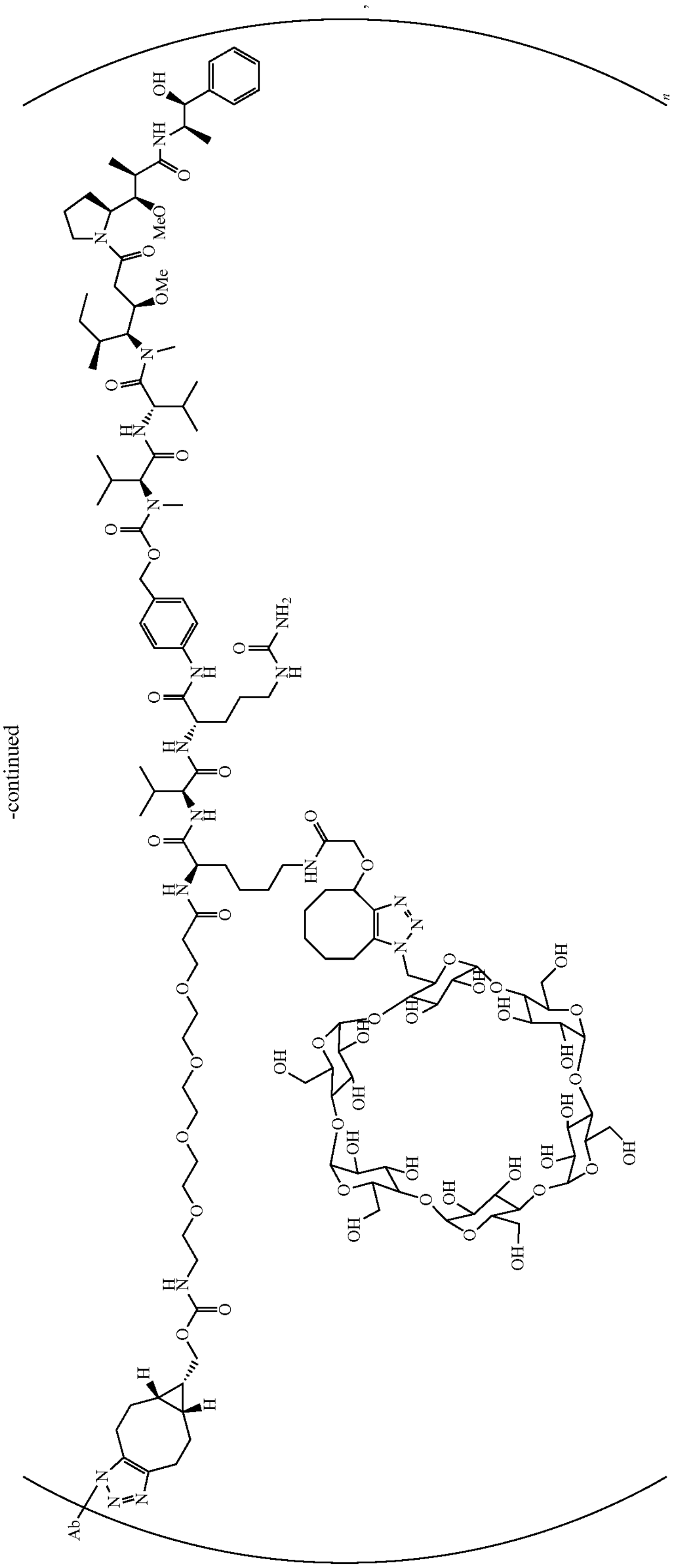

-continued
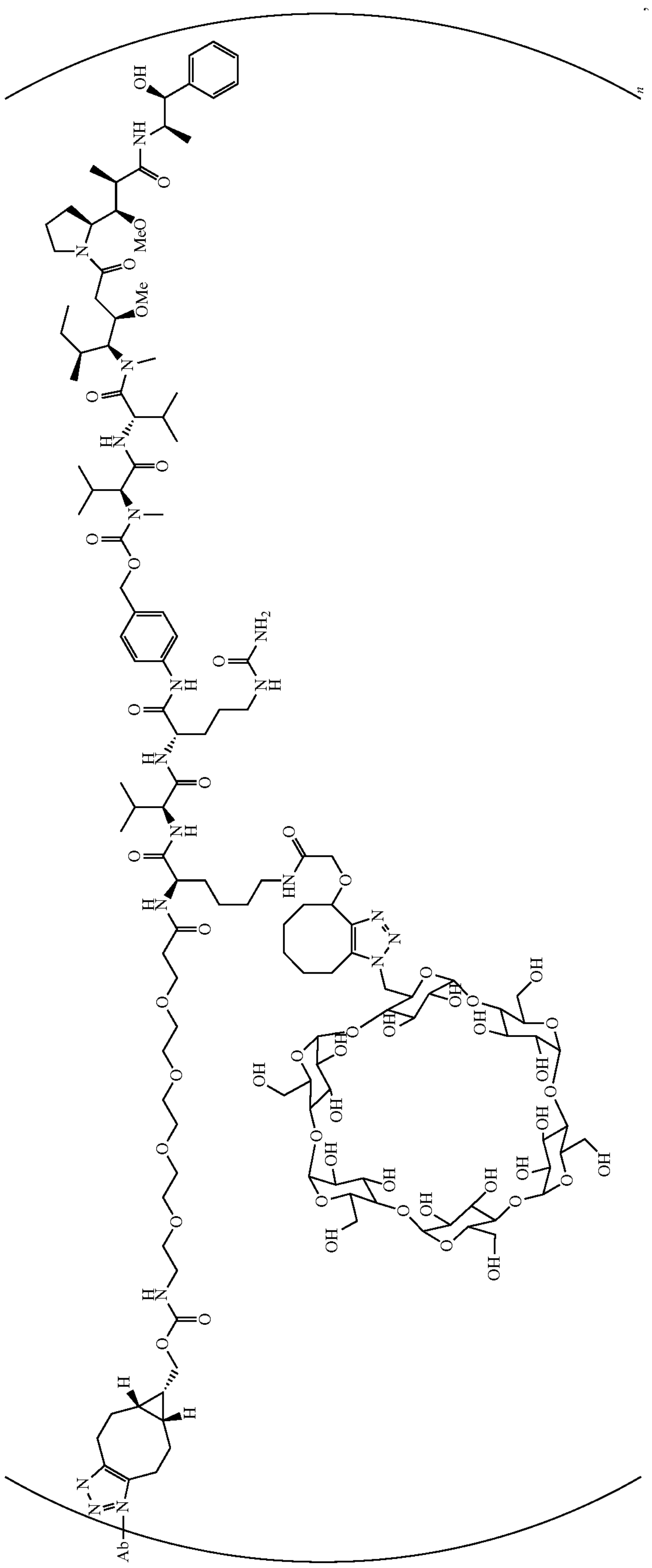

-continued
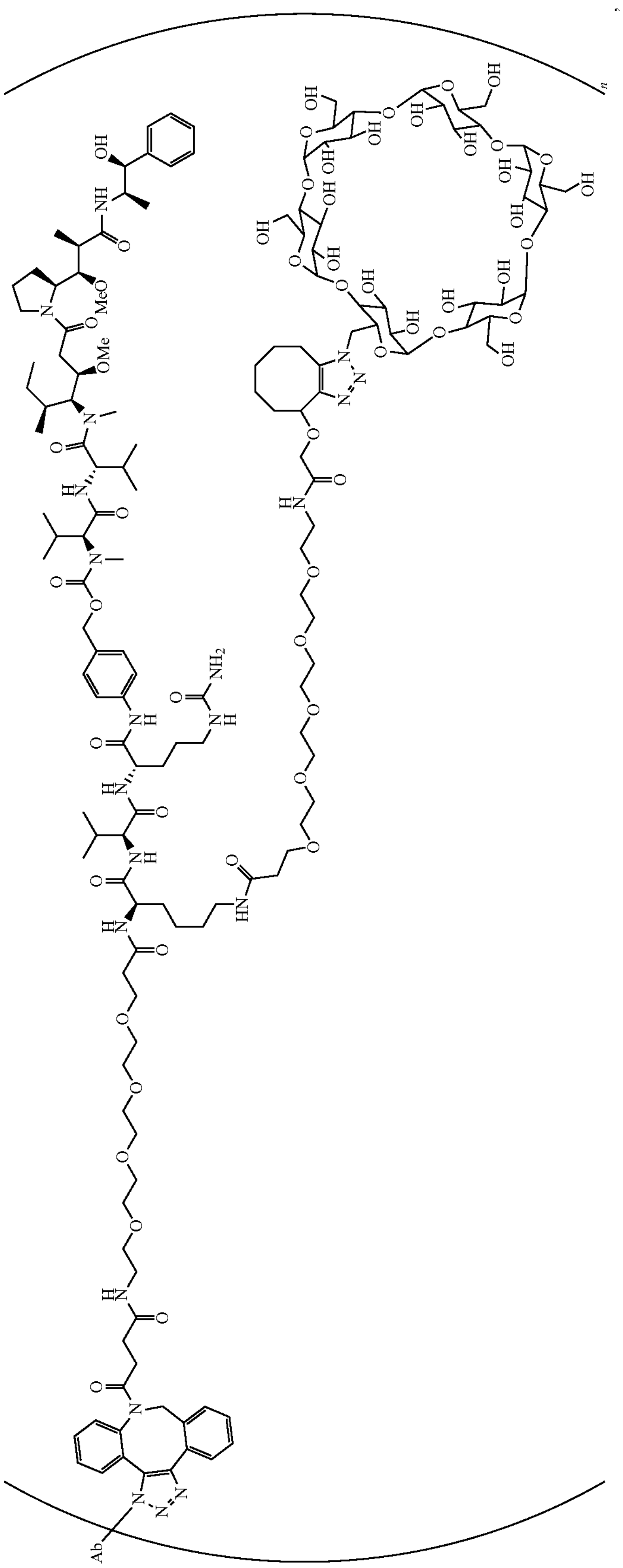

-continued
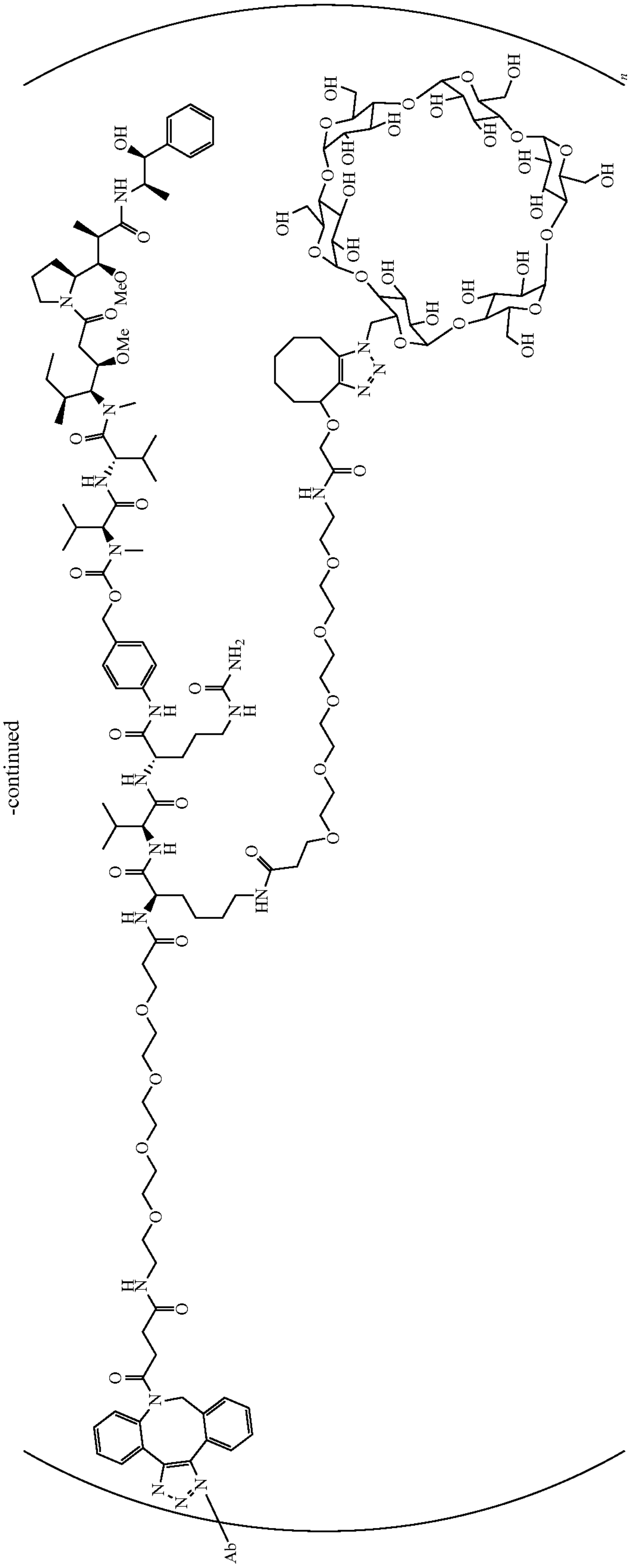
,

-continued
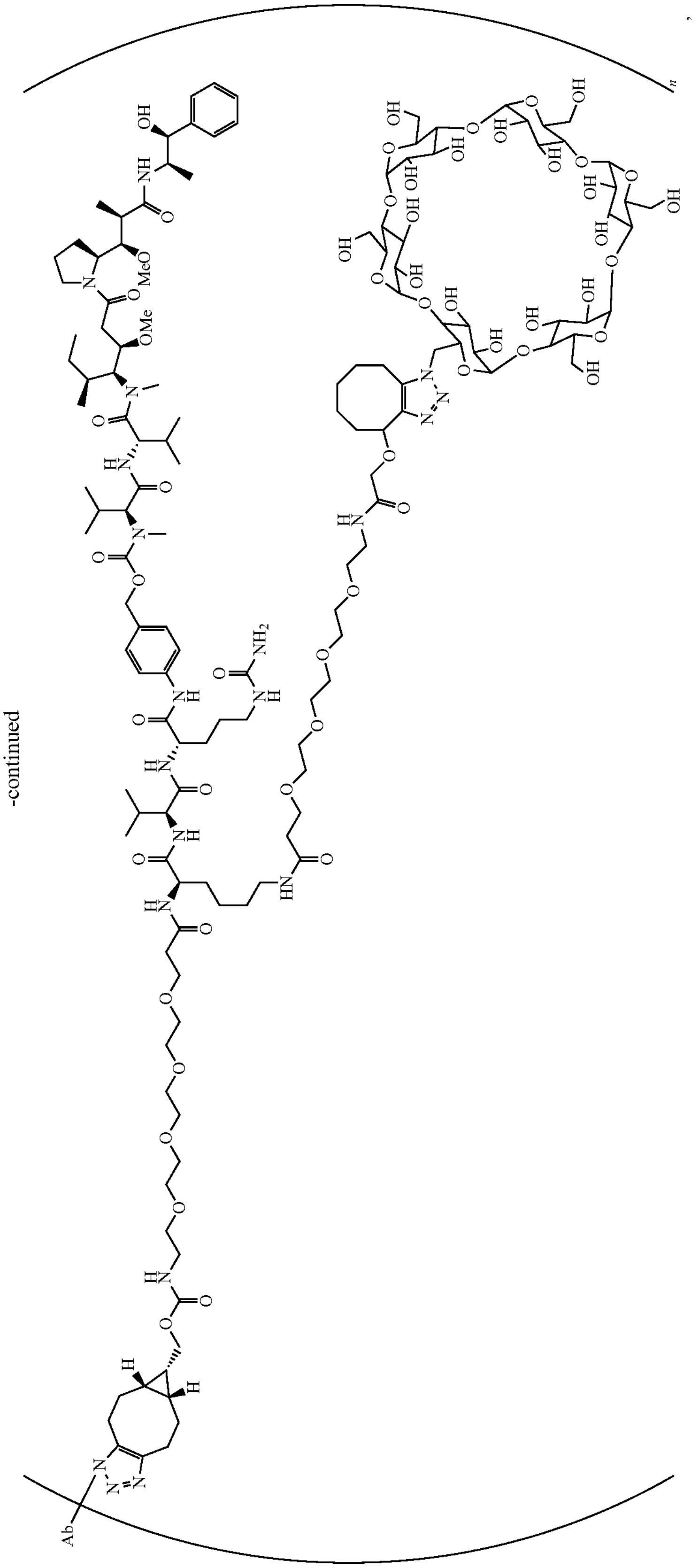

-continued
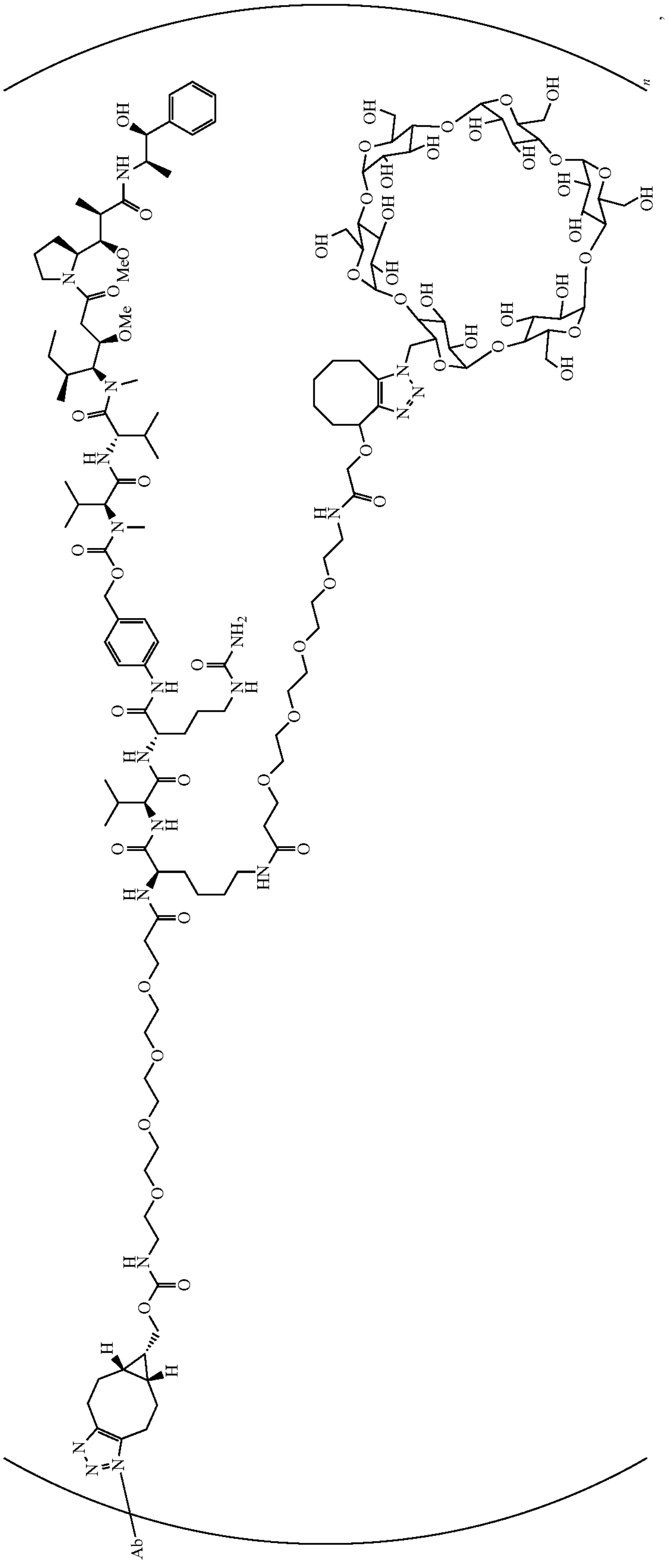

-continued
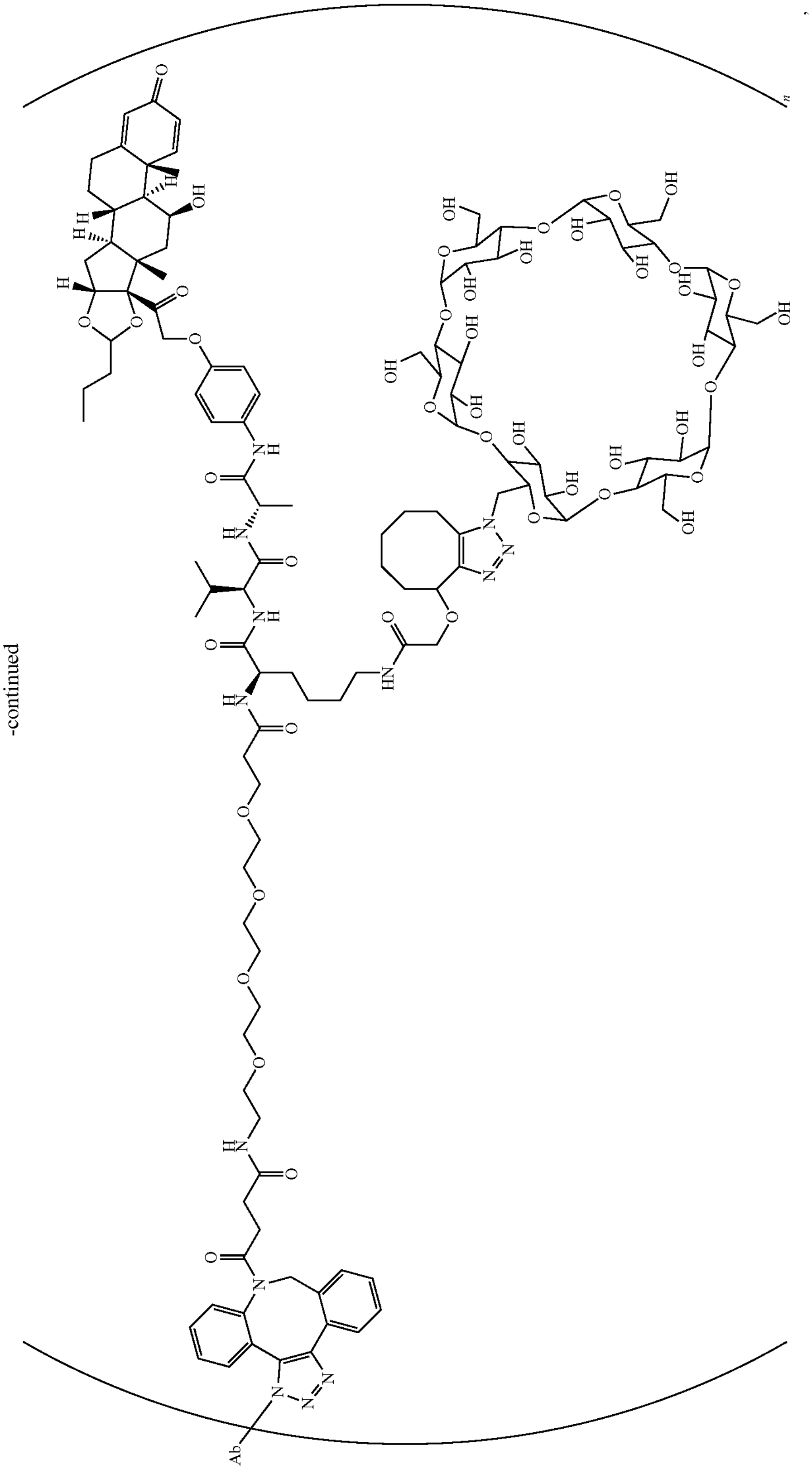

-continued
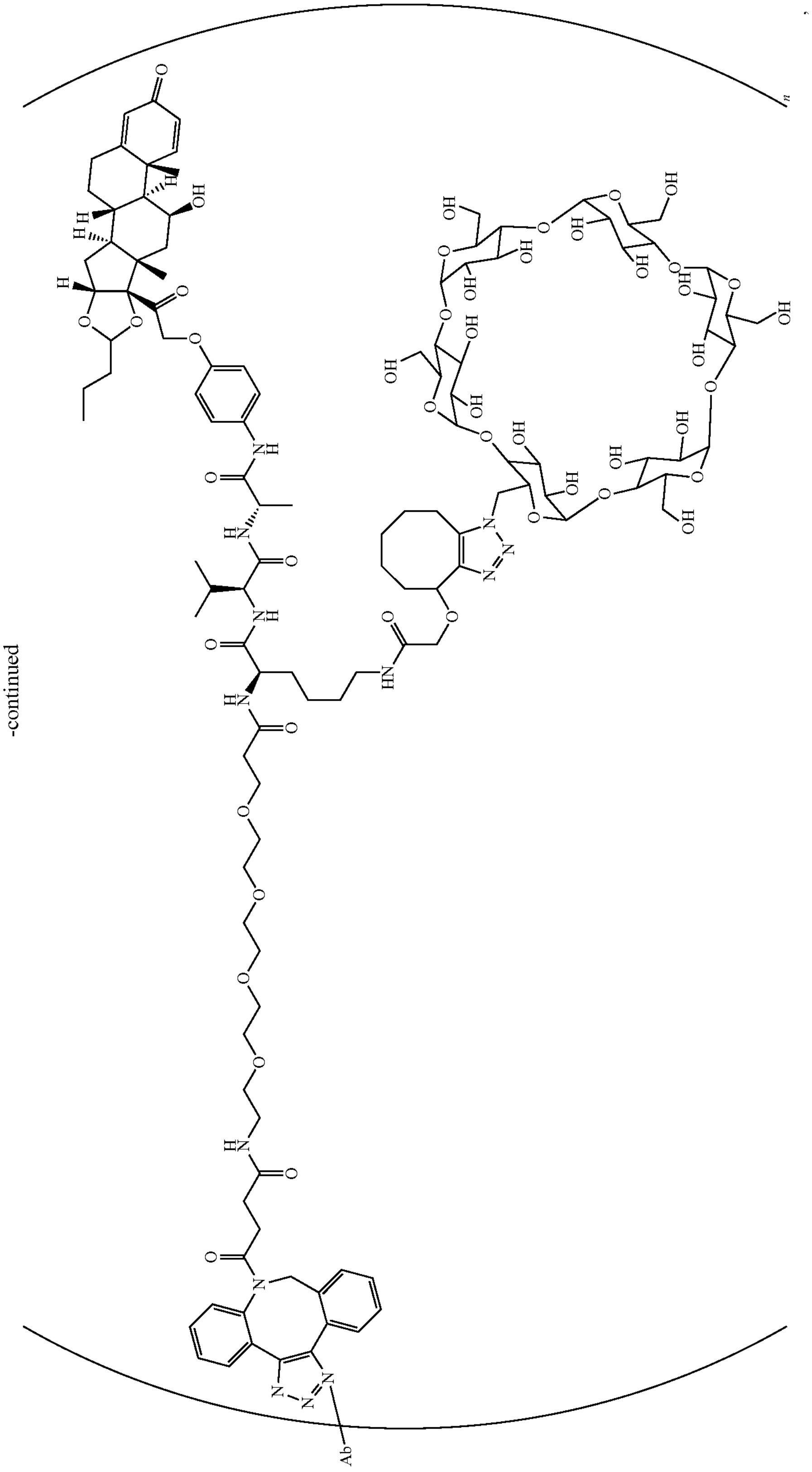

-continued
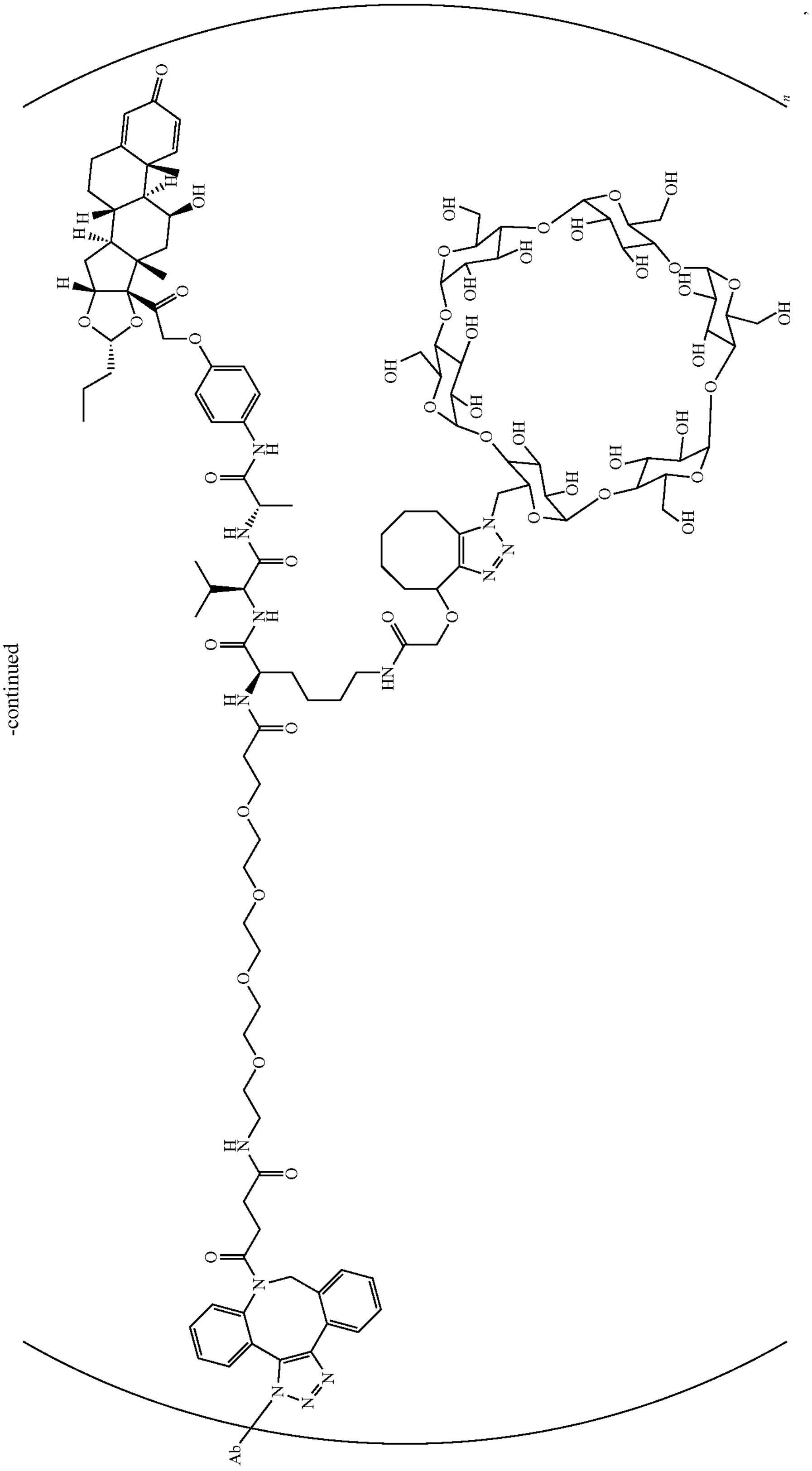

-continued
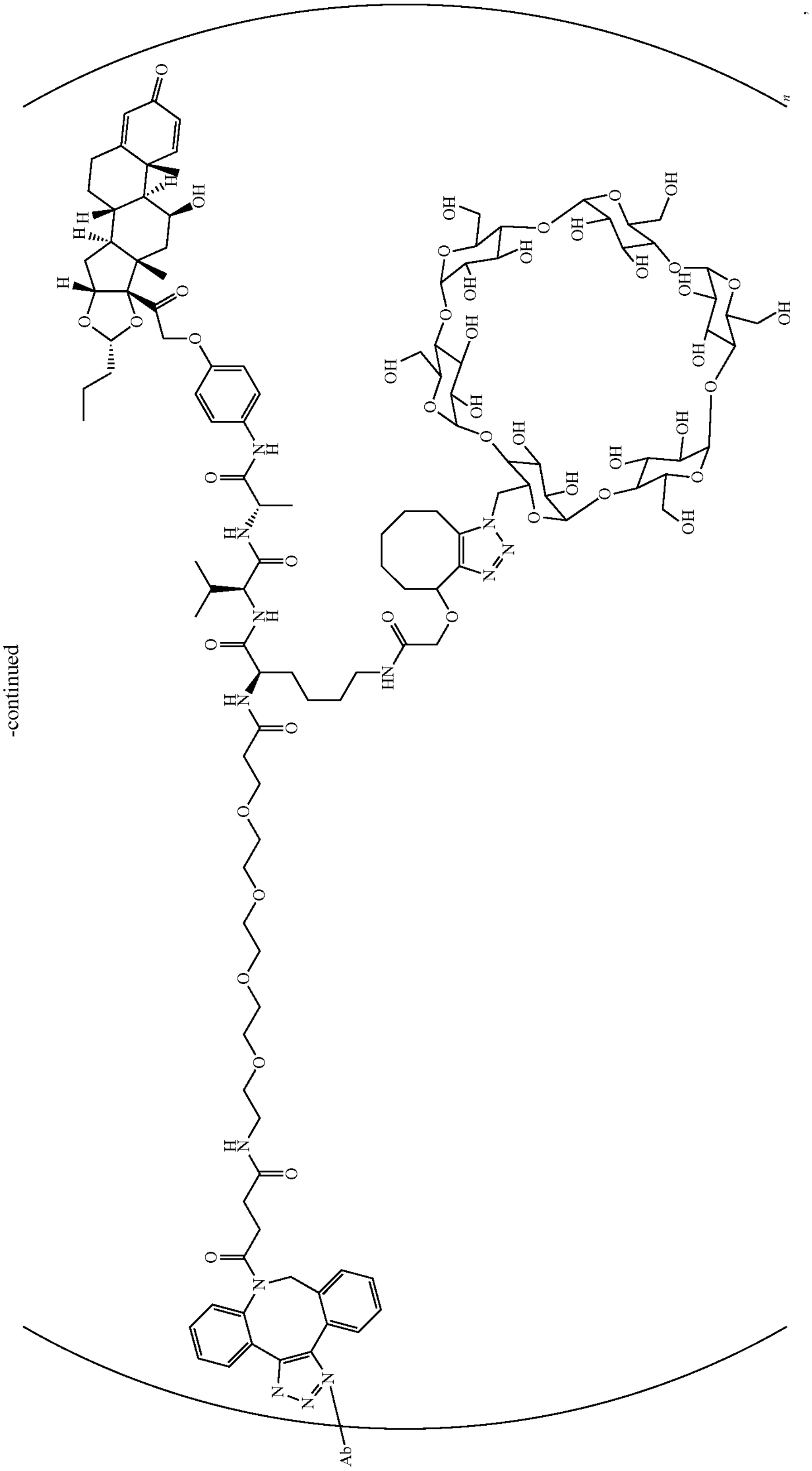

-continued
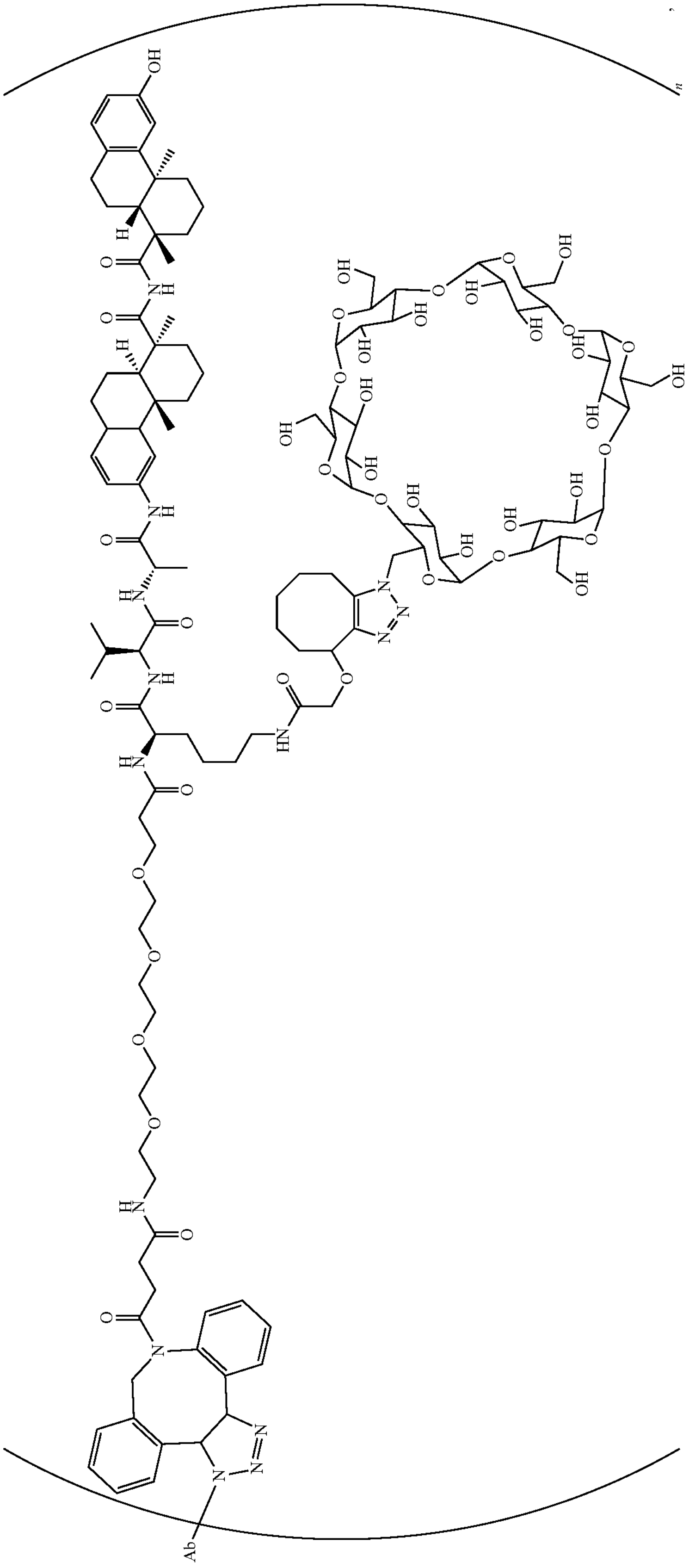

-continued
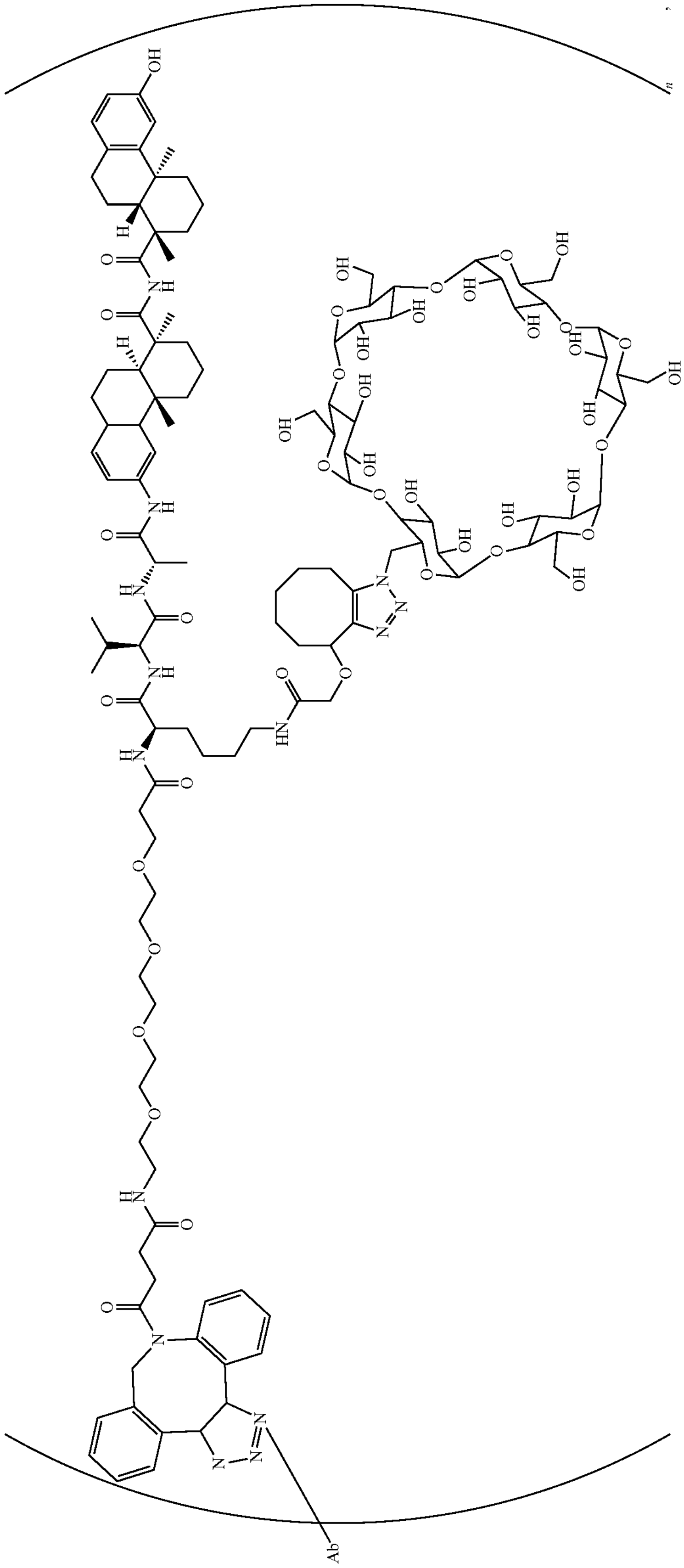
,

-continued
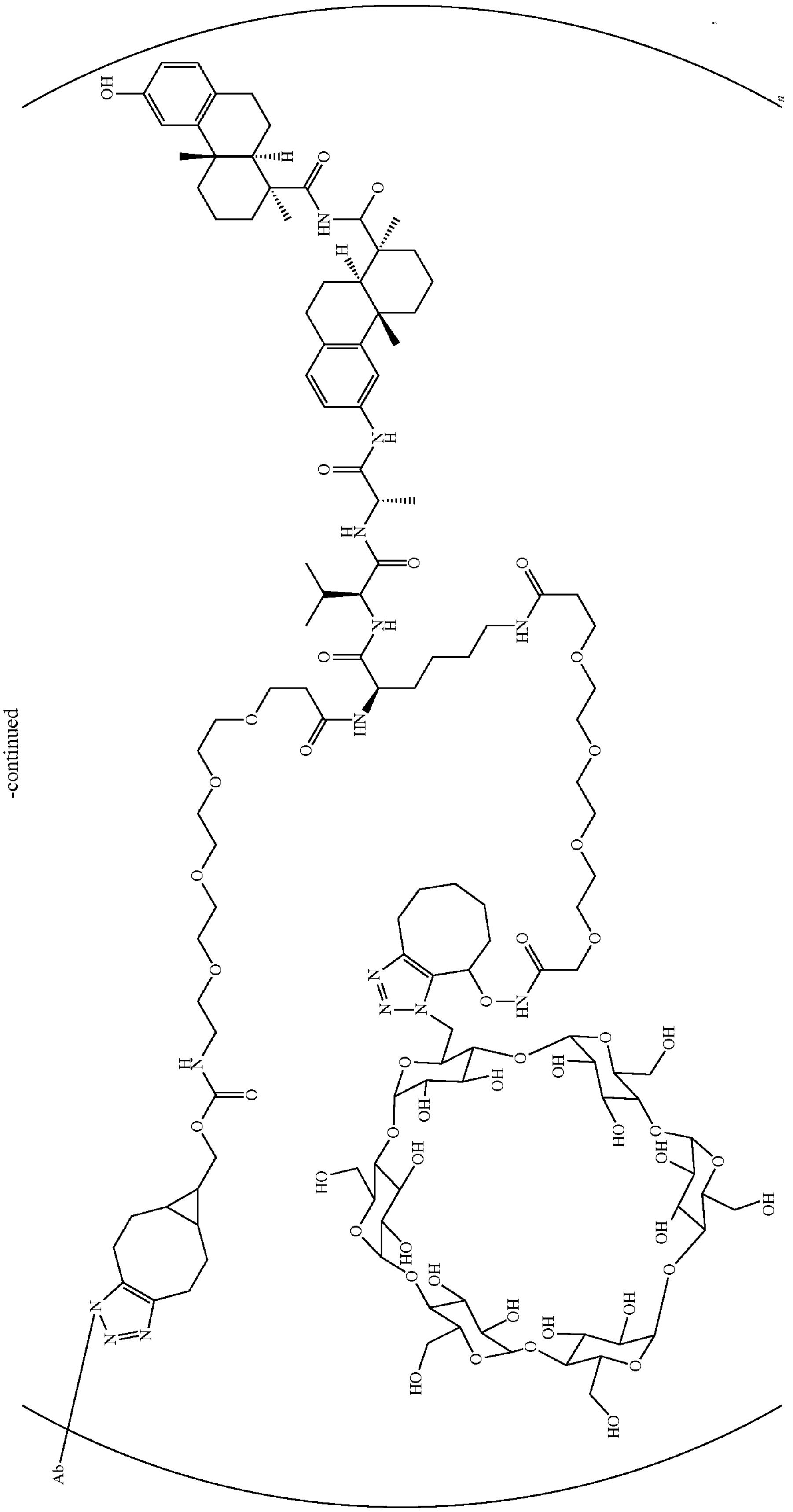

-continued
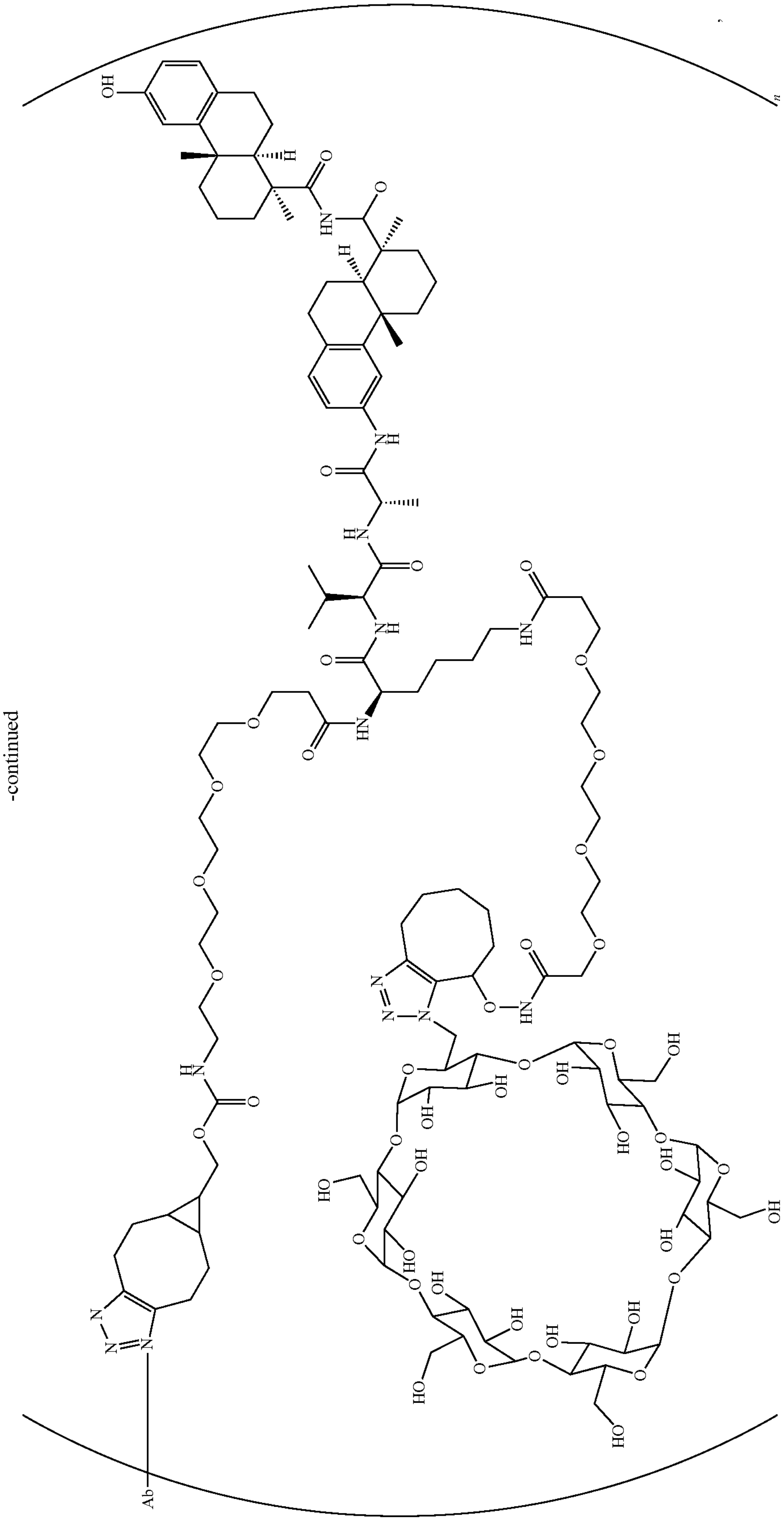

-continued
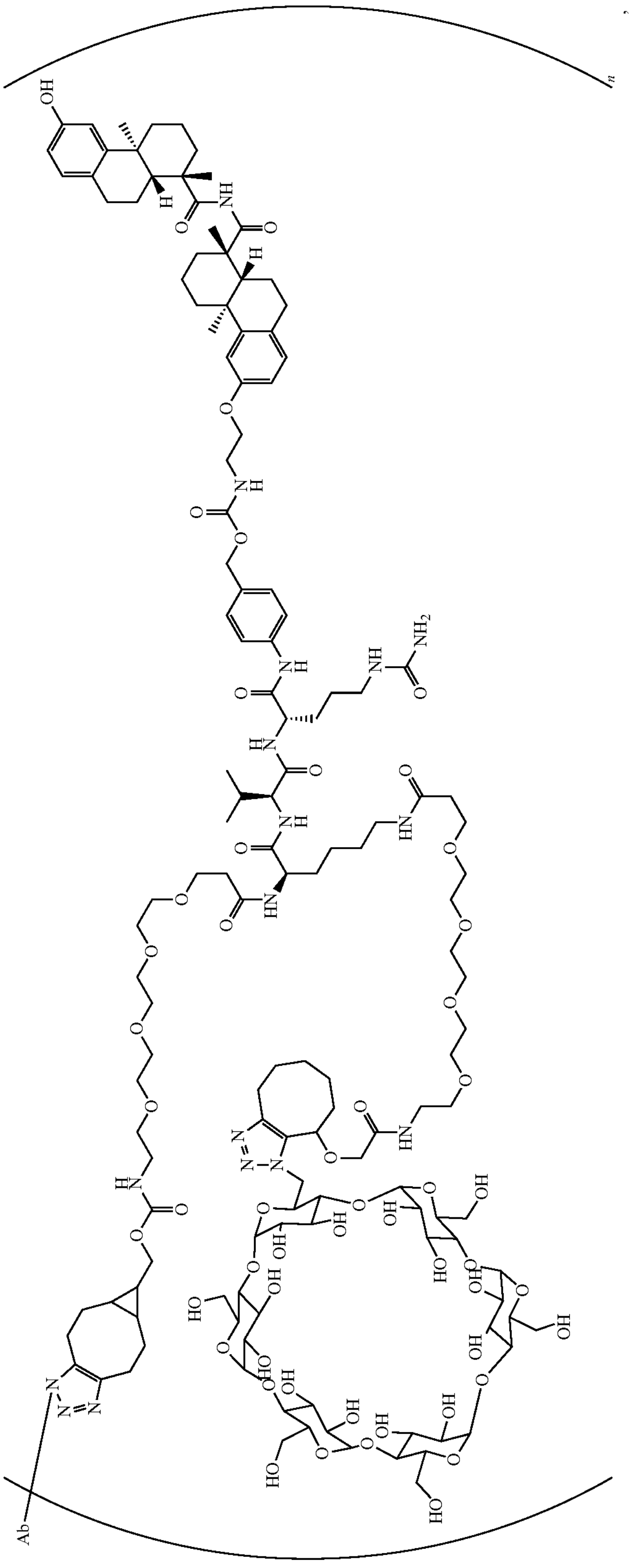

-continued
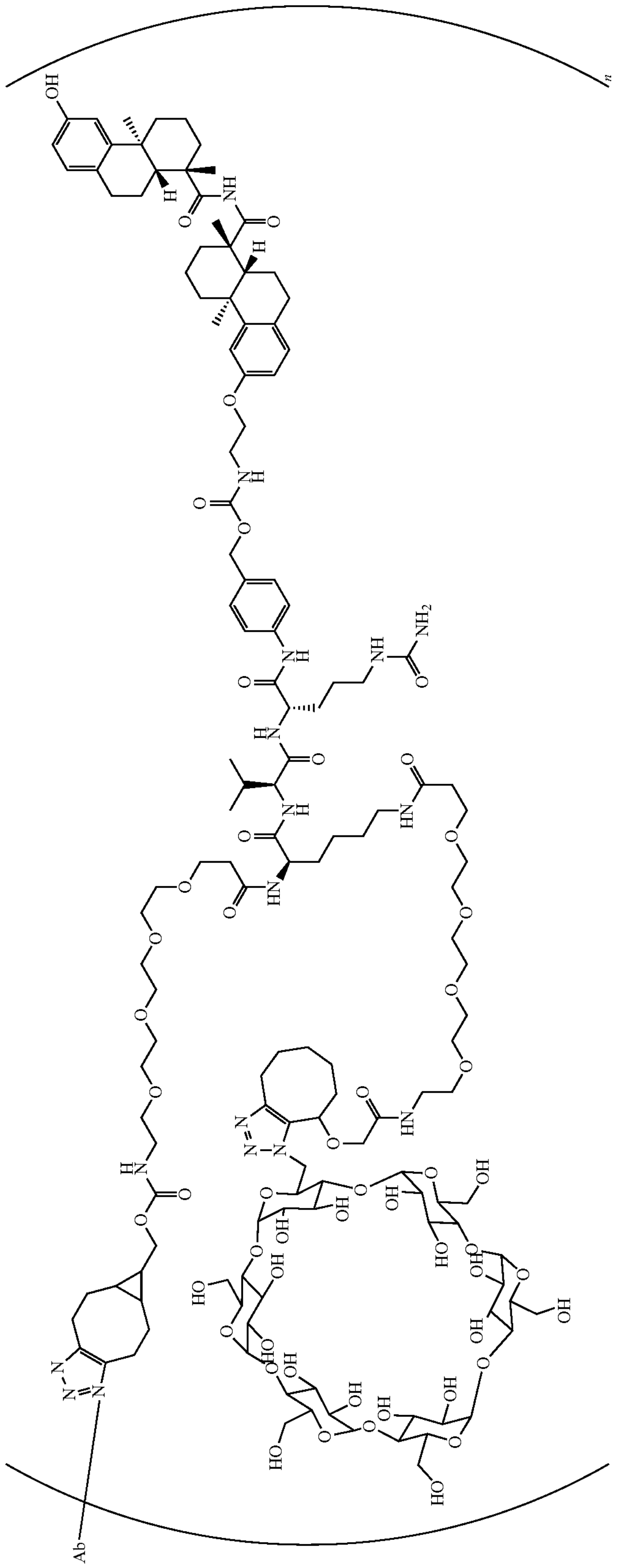
,

-continued
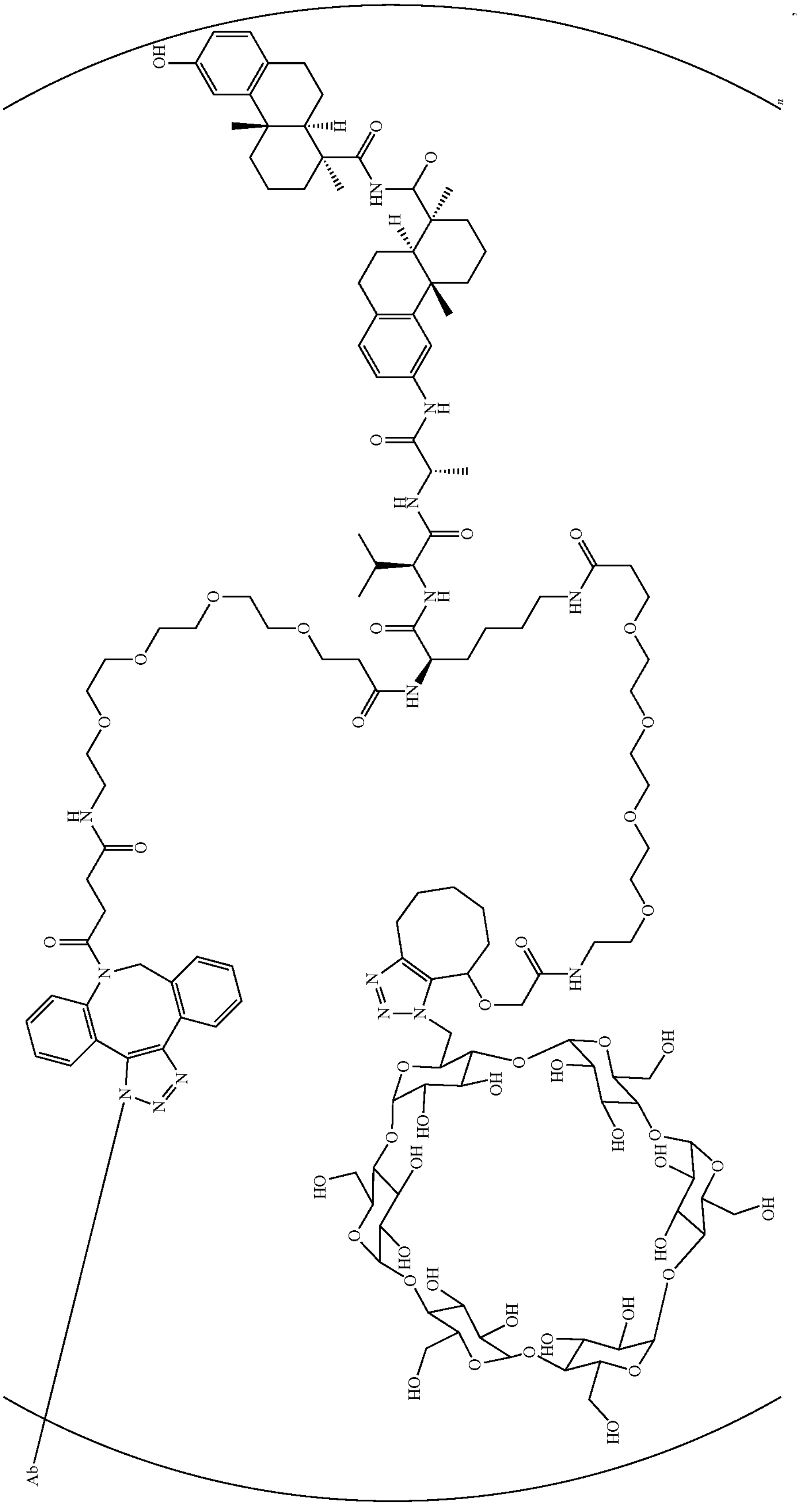

-continued
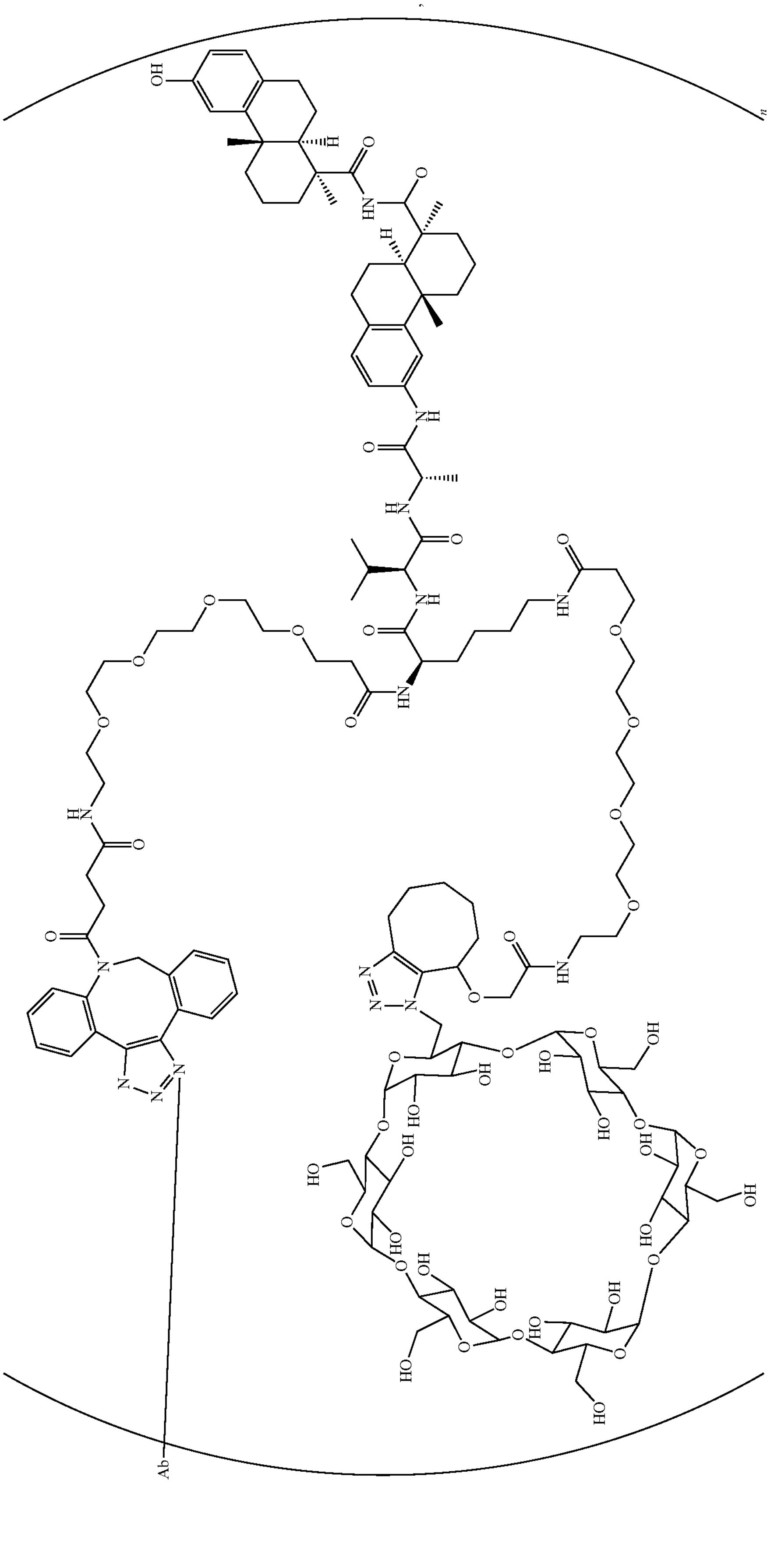

-continued
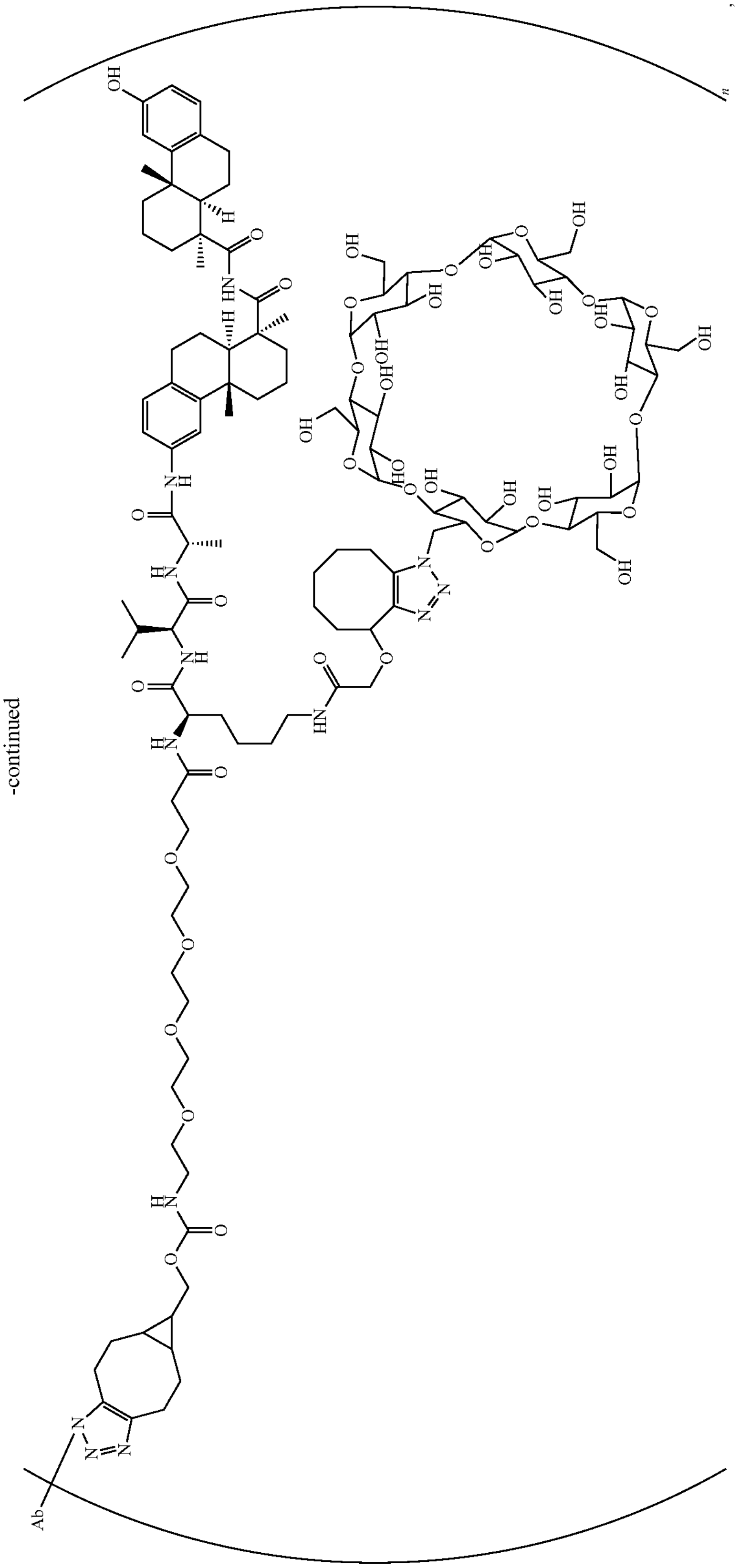

-continued
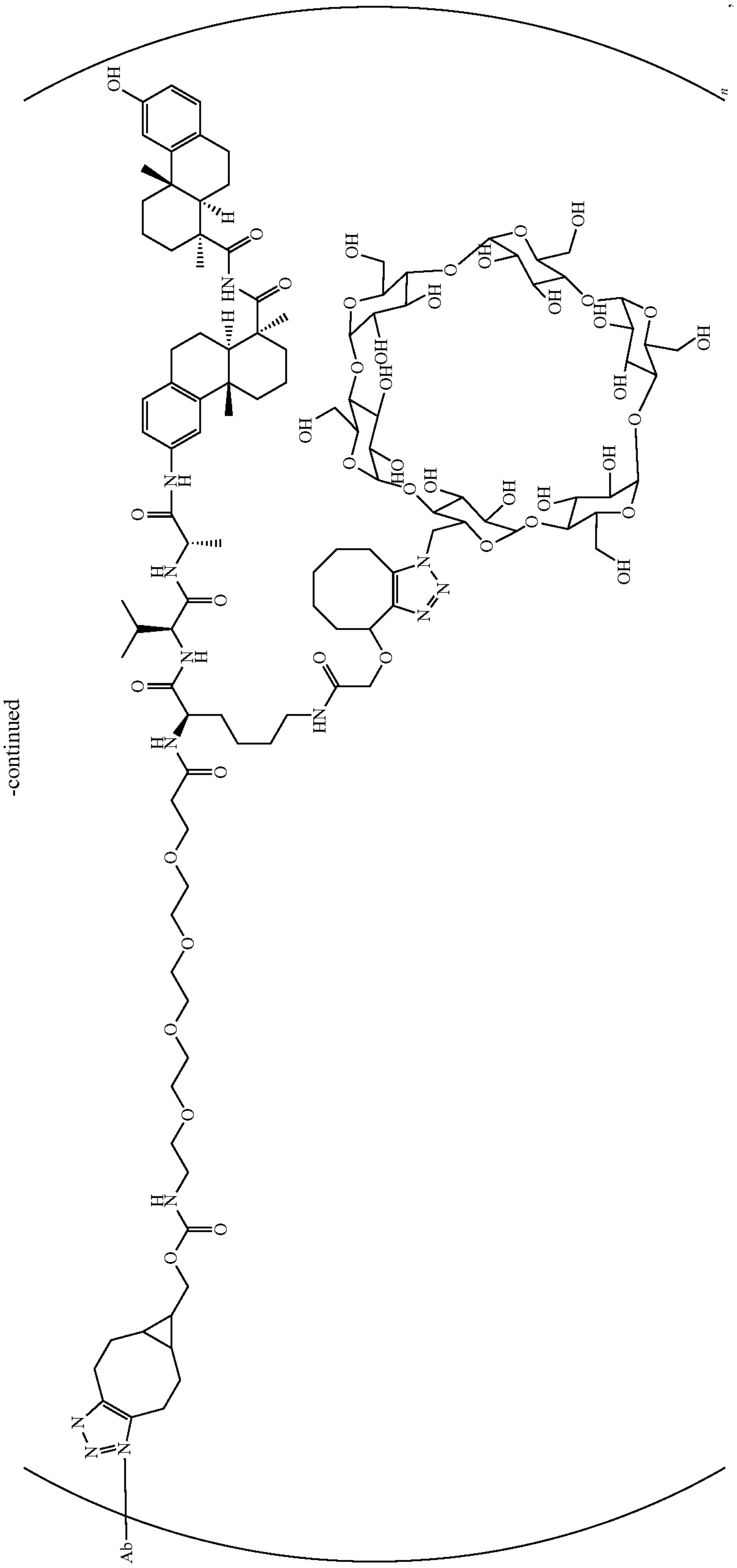

-continued
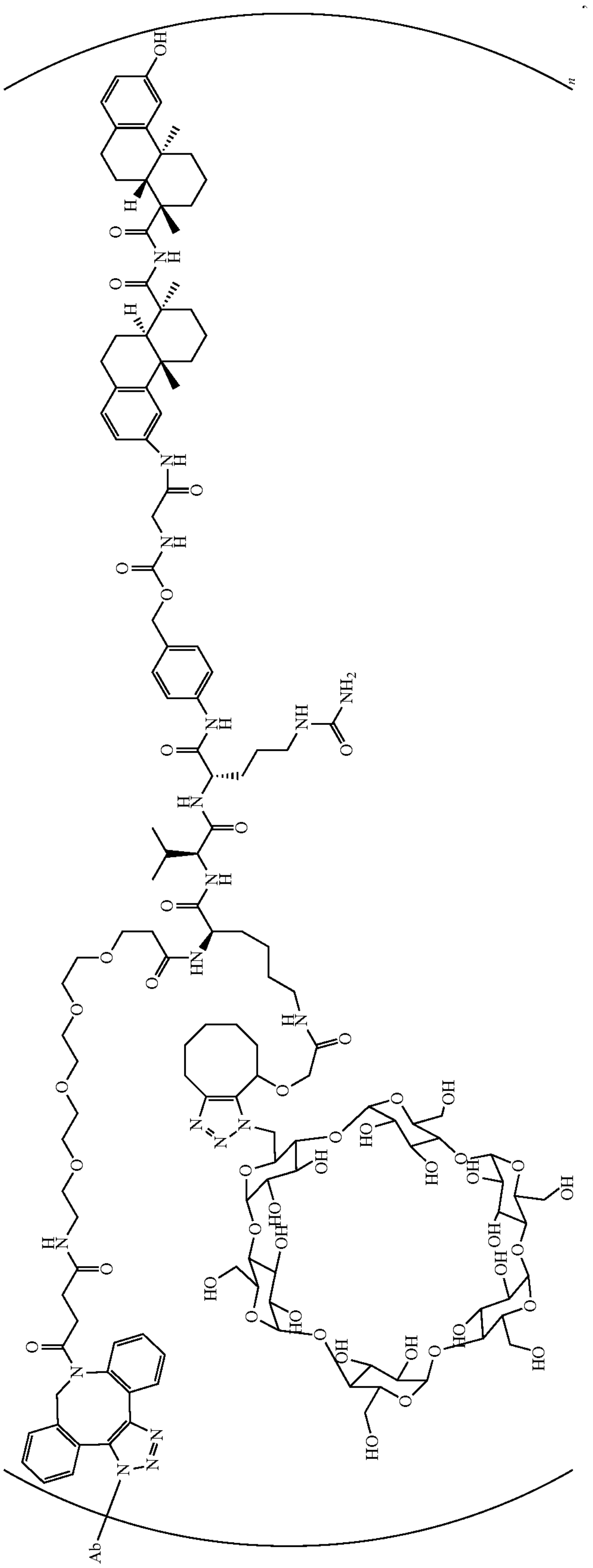

-continued
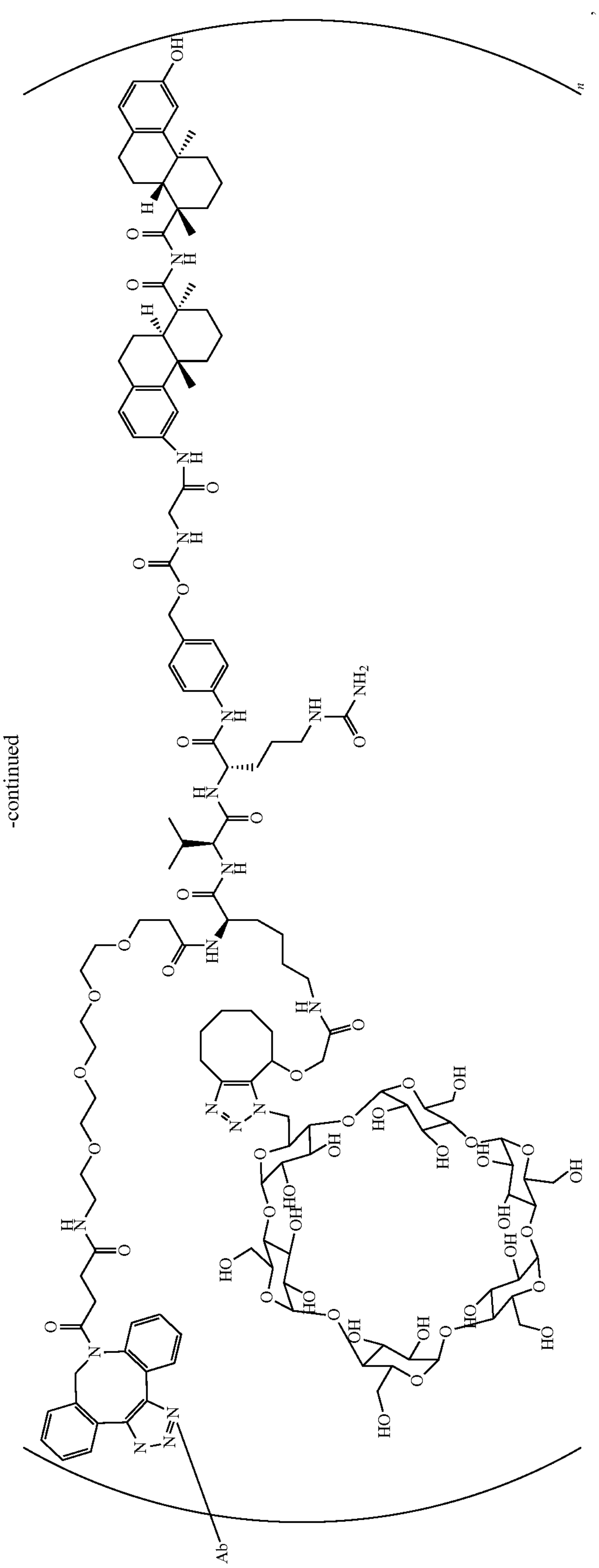

-continued
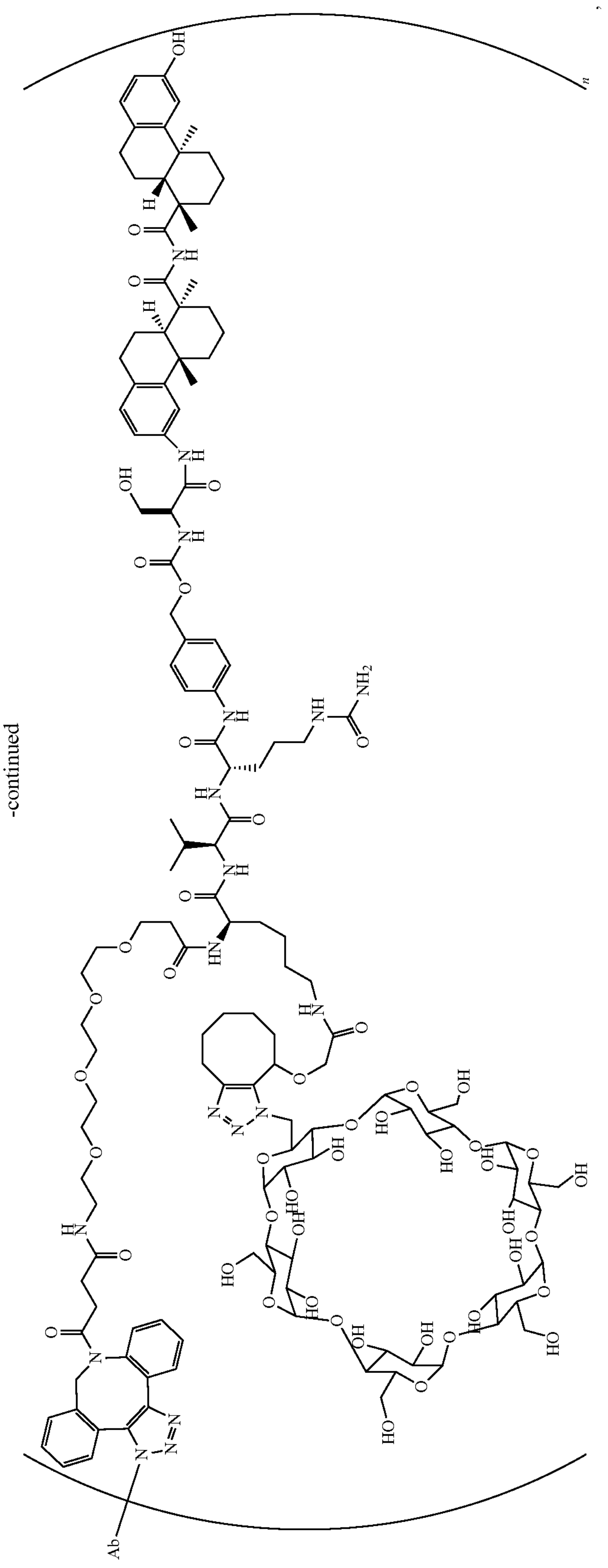

-continued
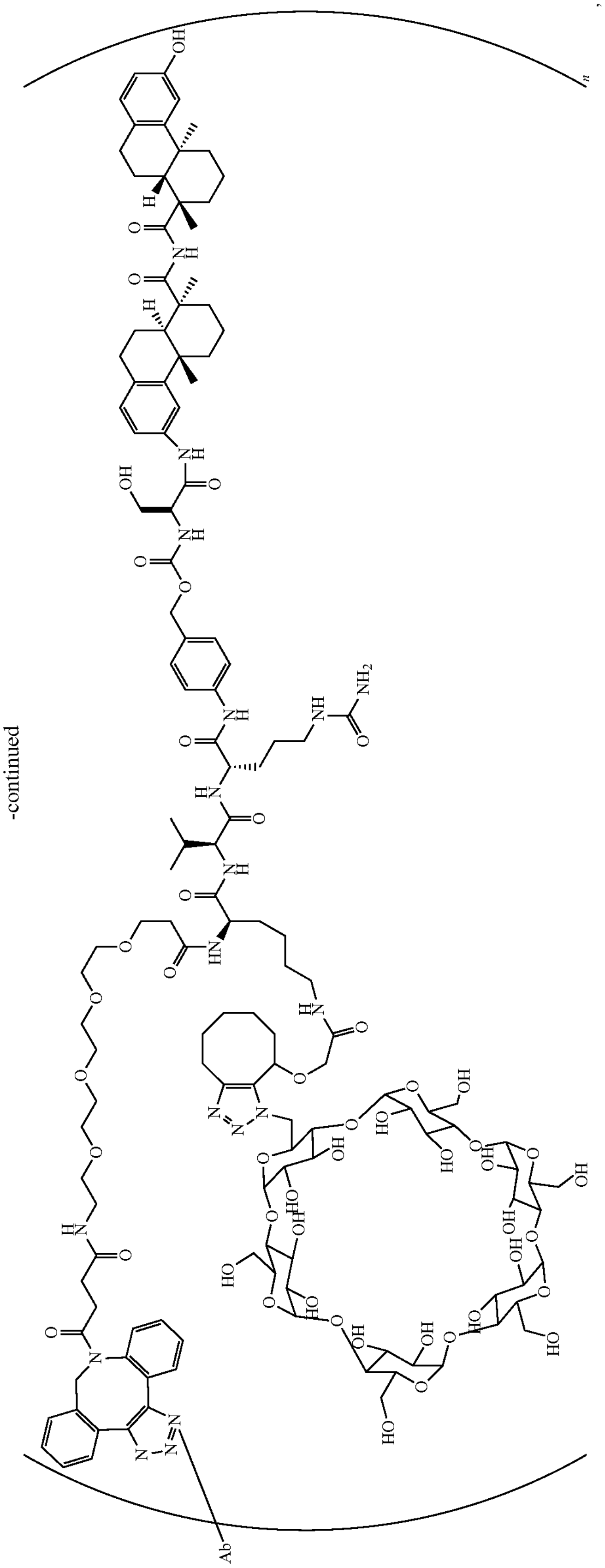

-continued
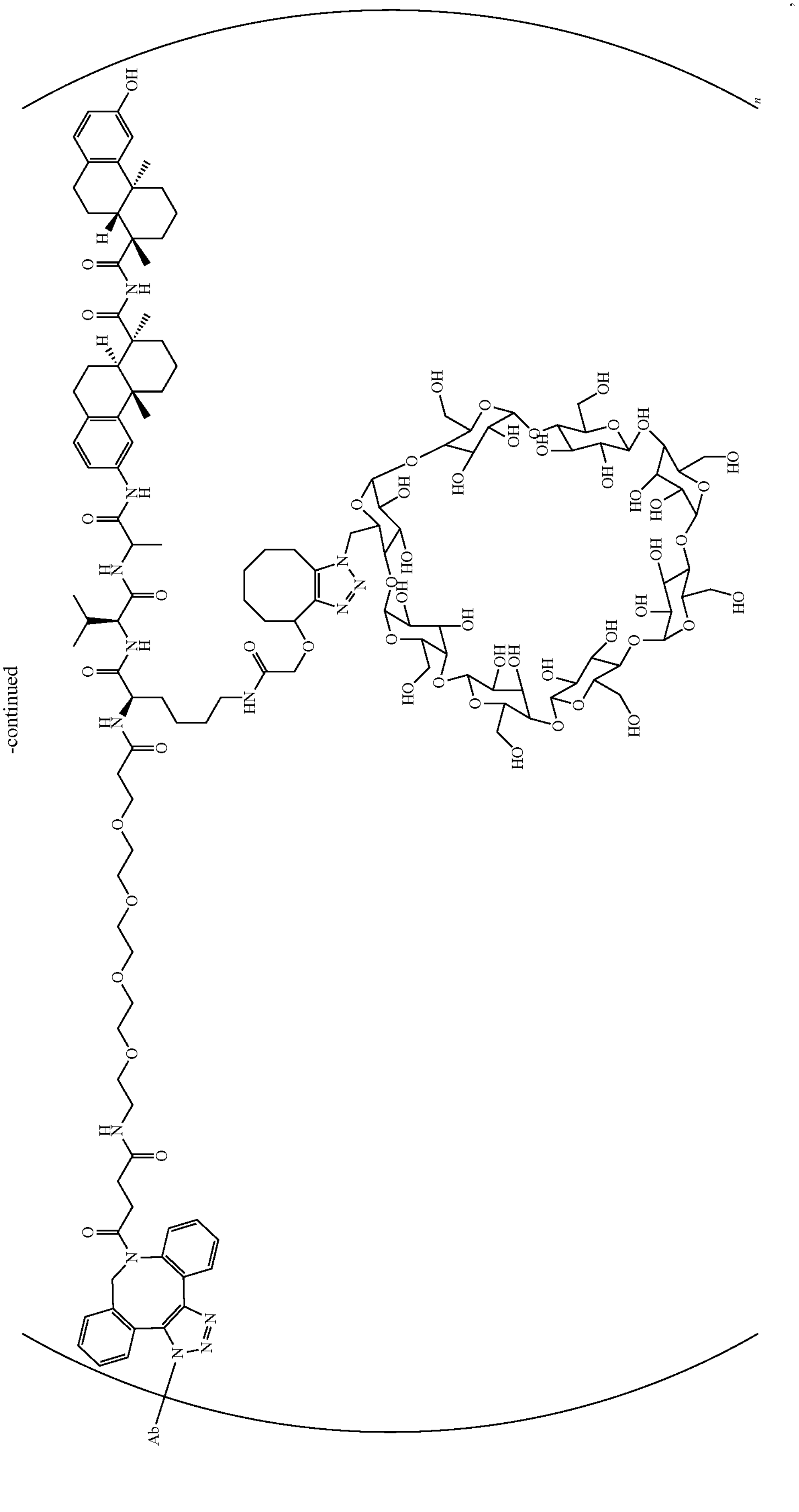

-continued
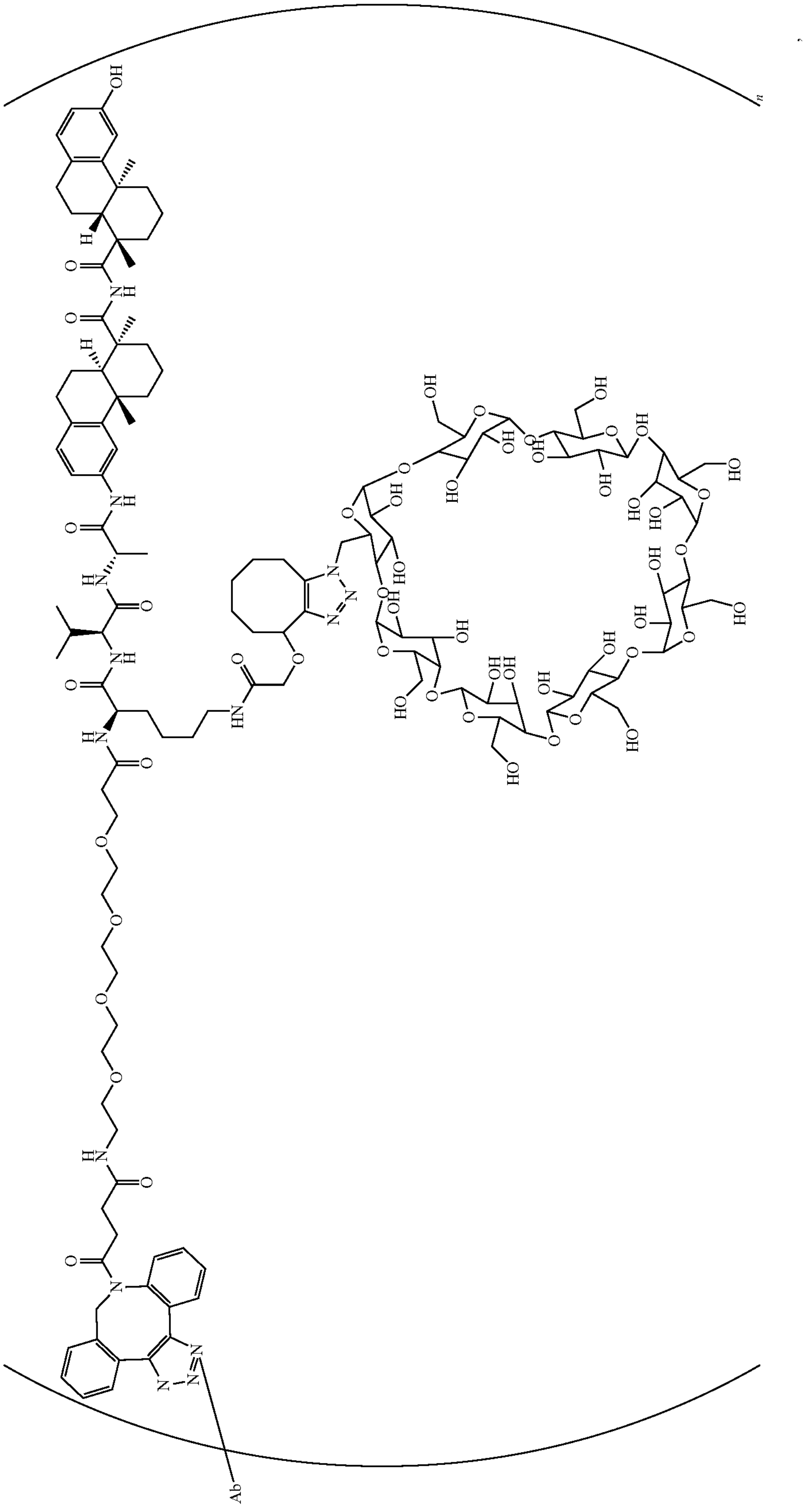

-continued
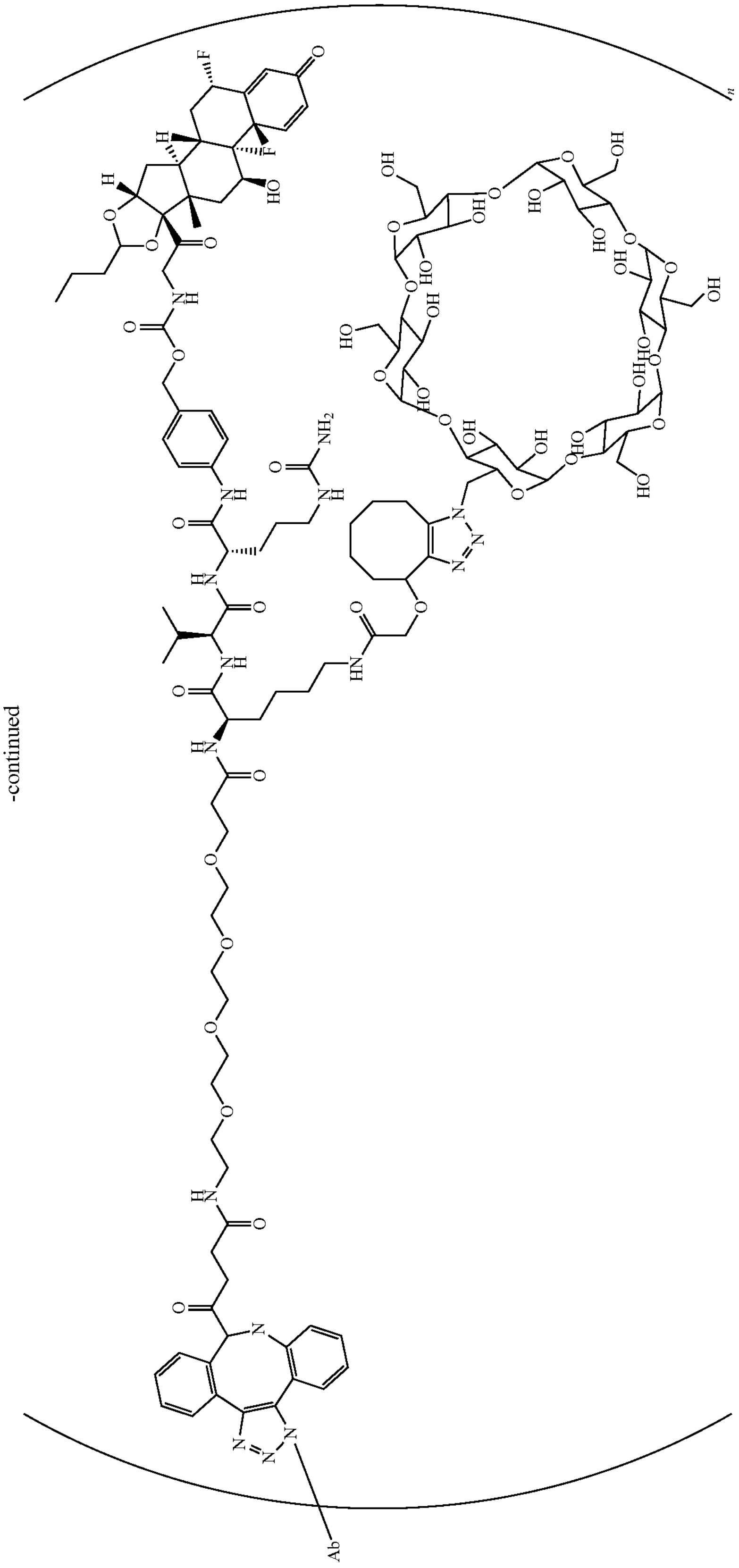

-continued
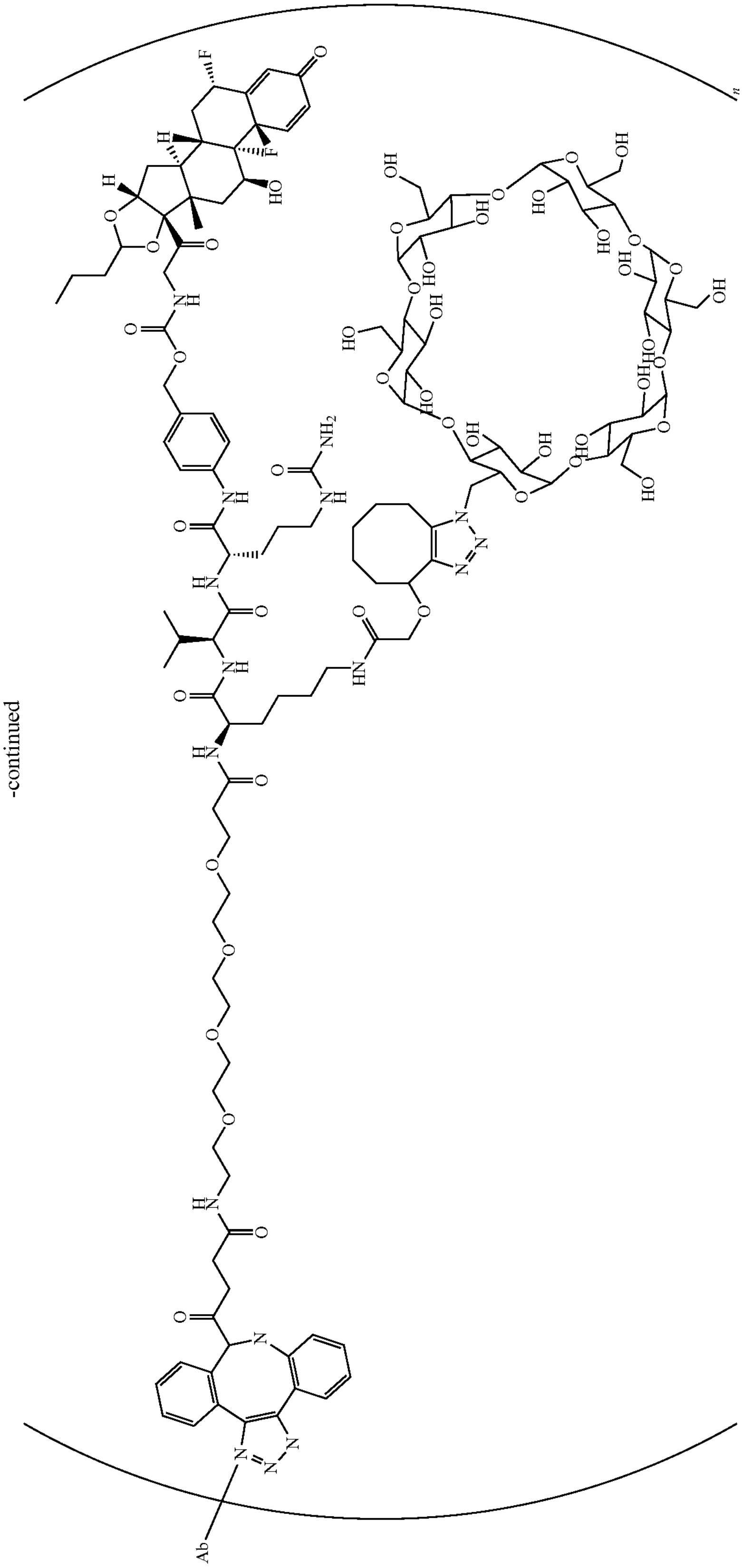

-continued
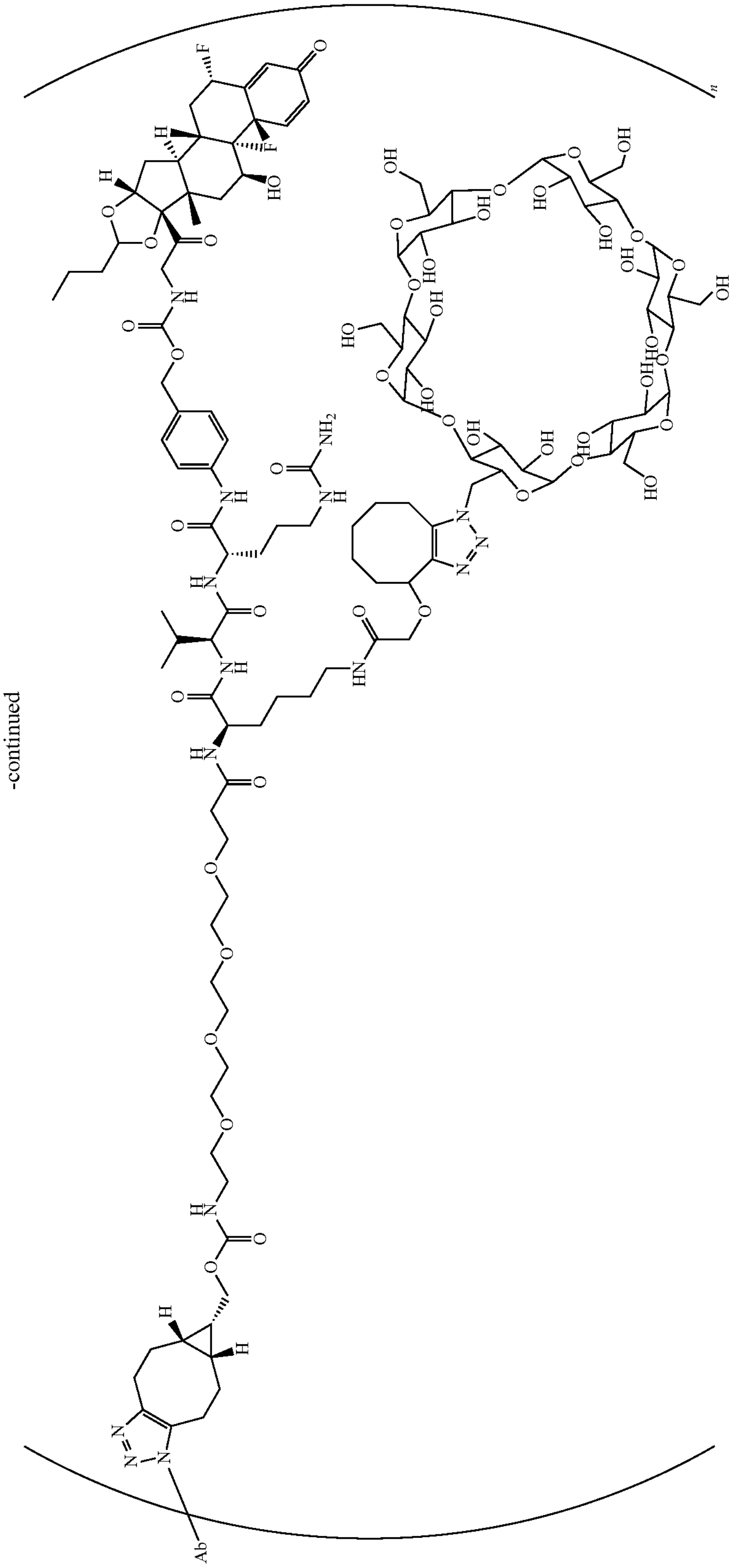

-continued
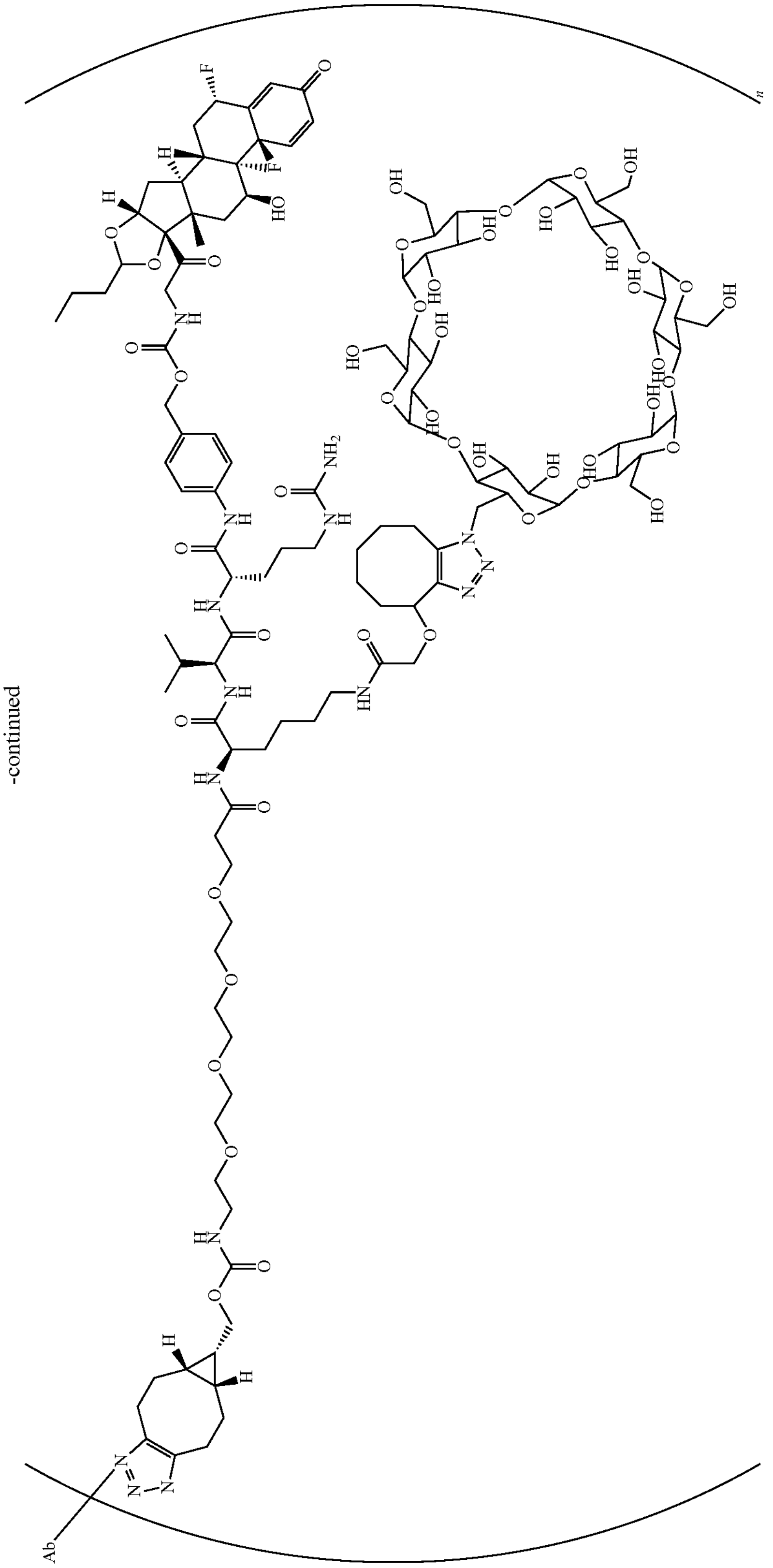

-continued
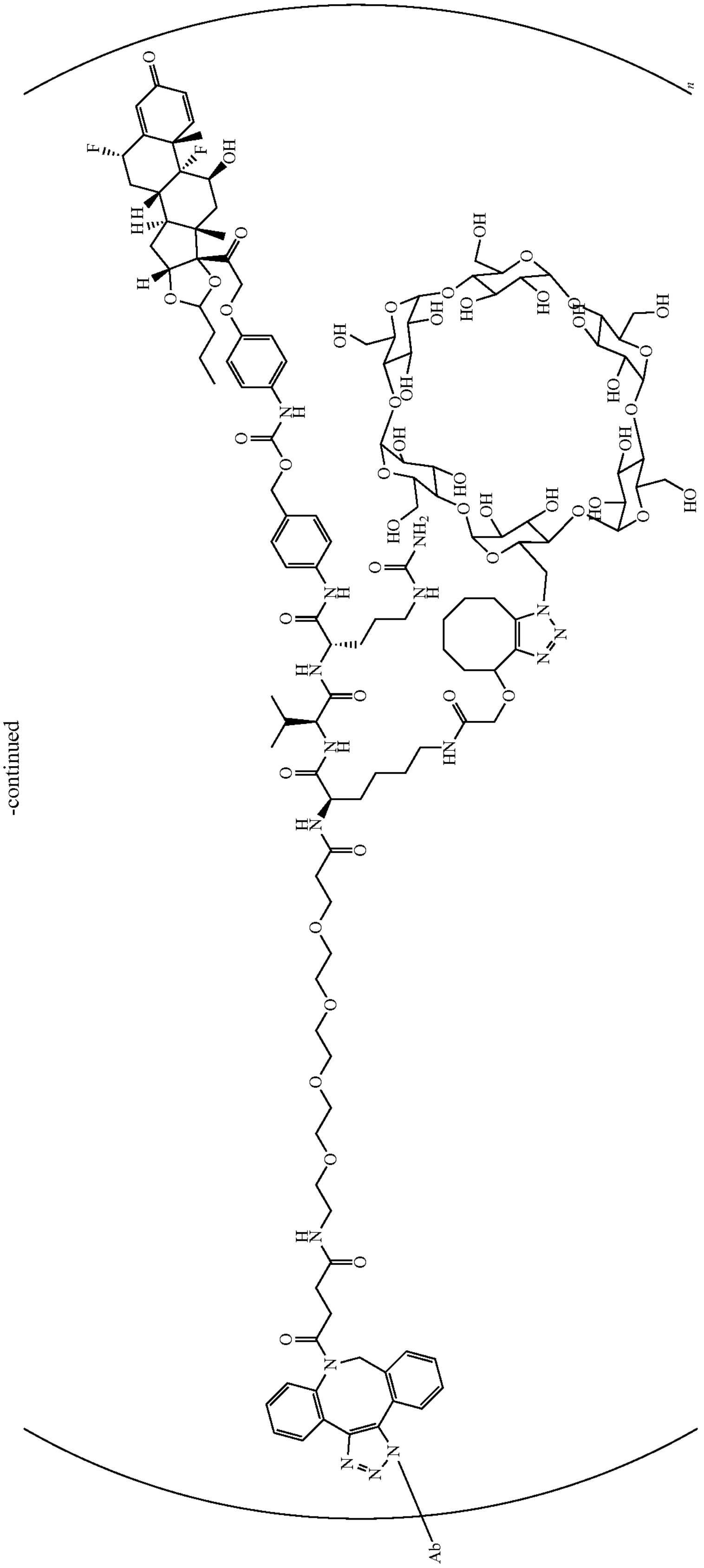

-continued
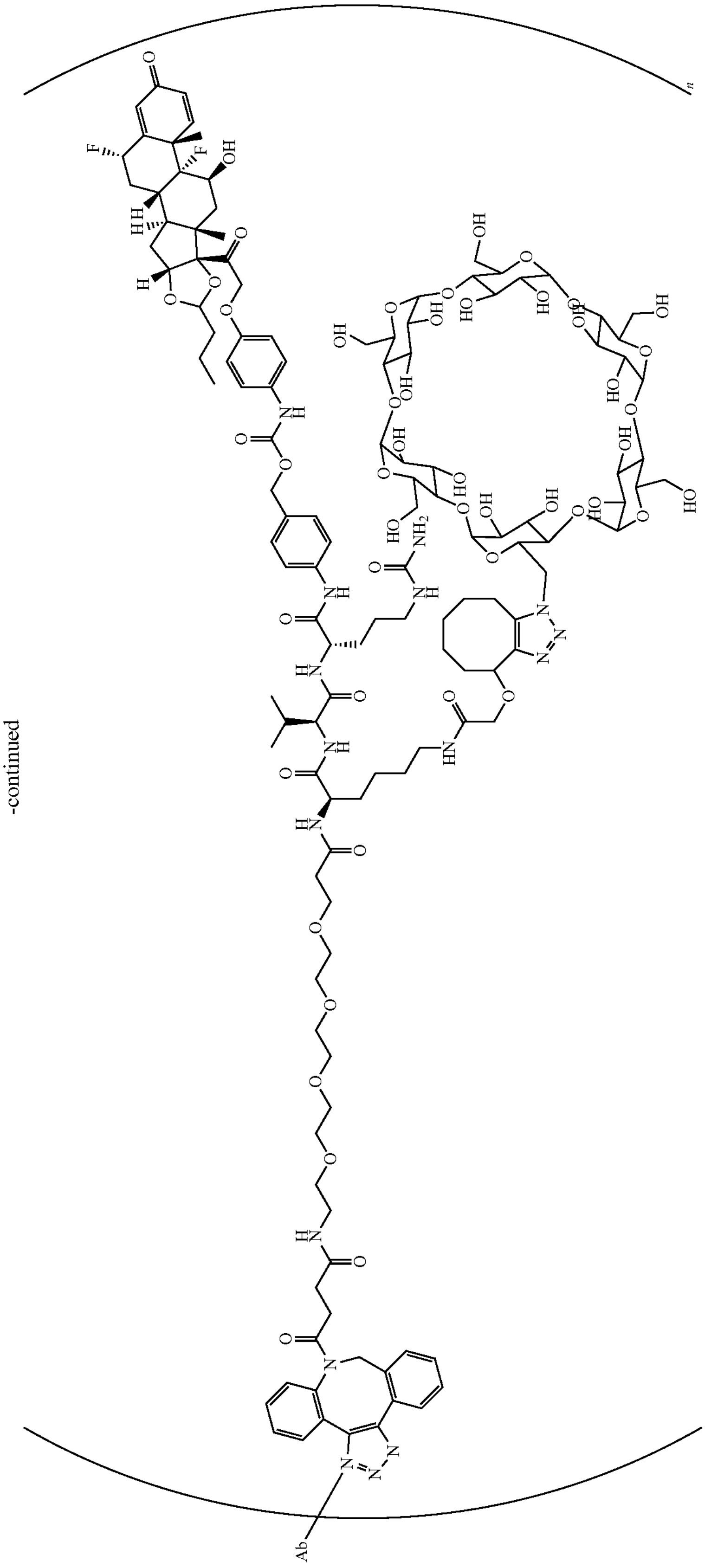

-continued
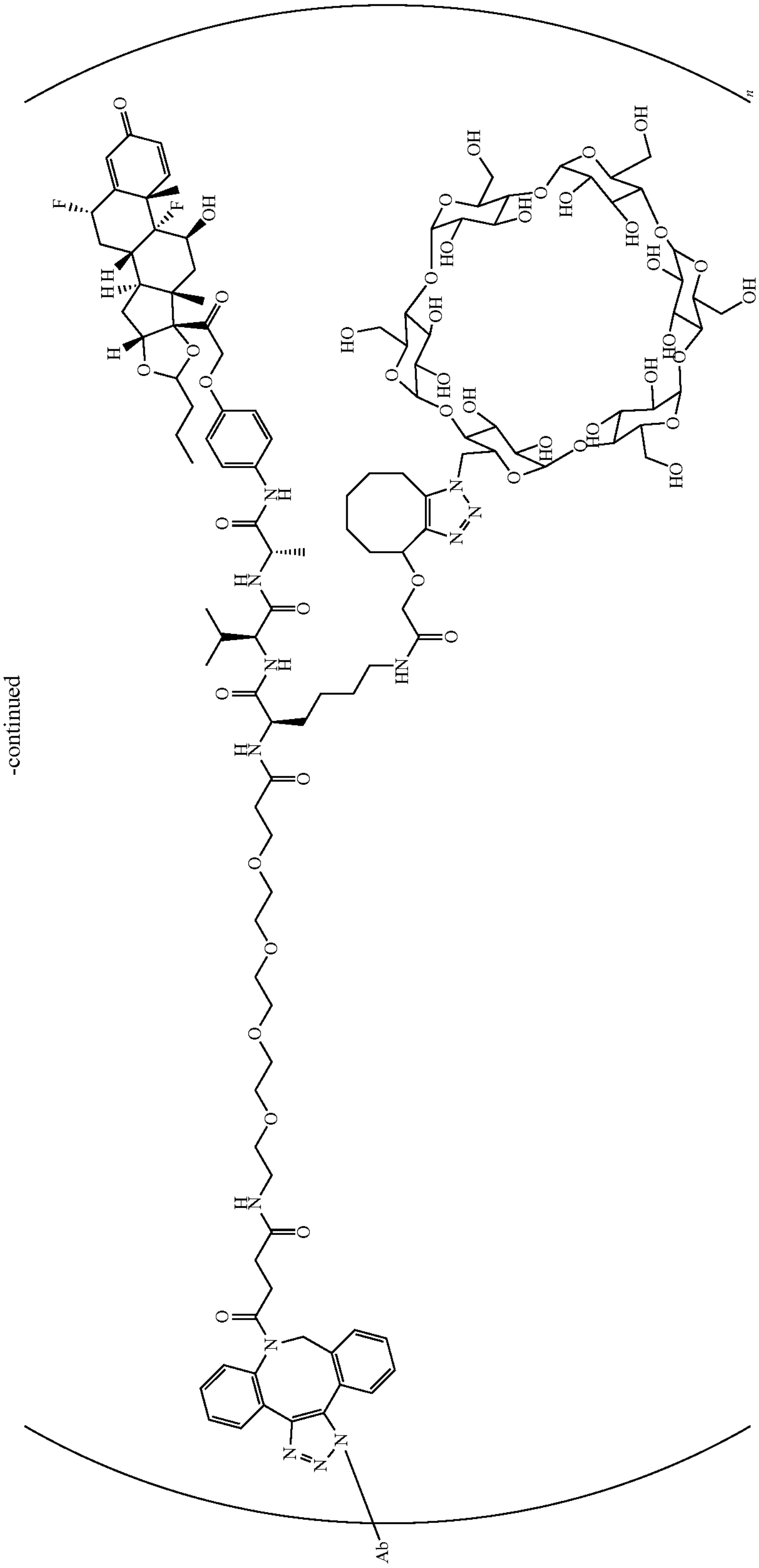

-continued
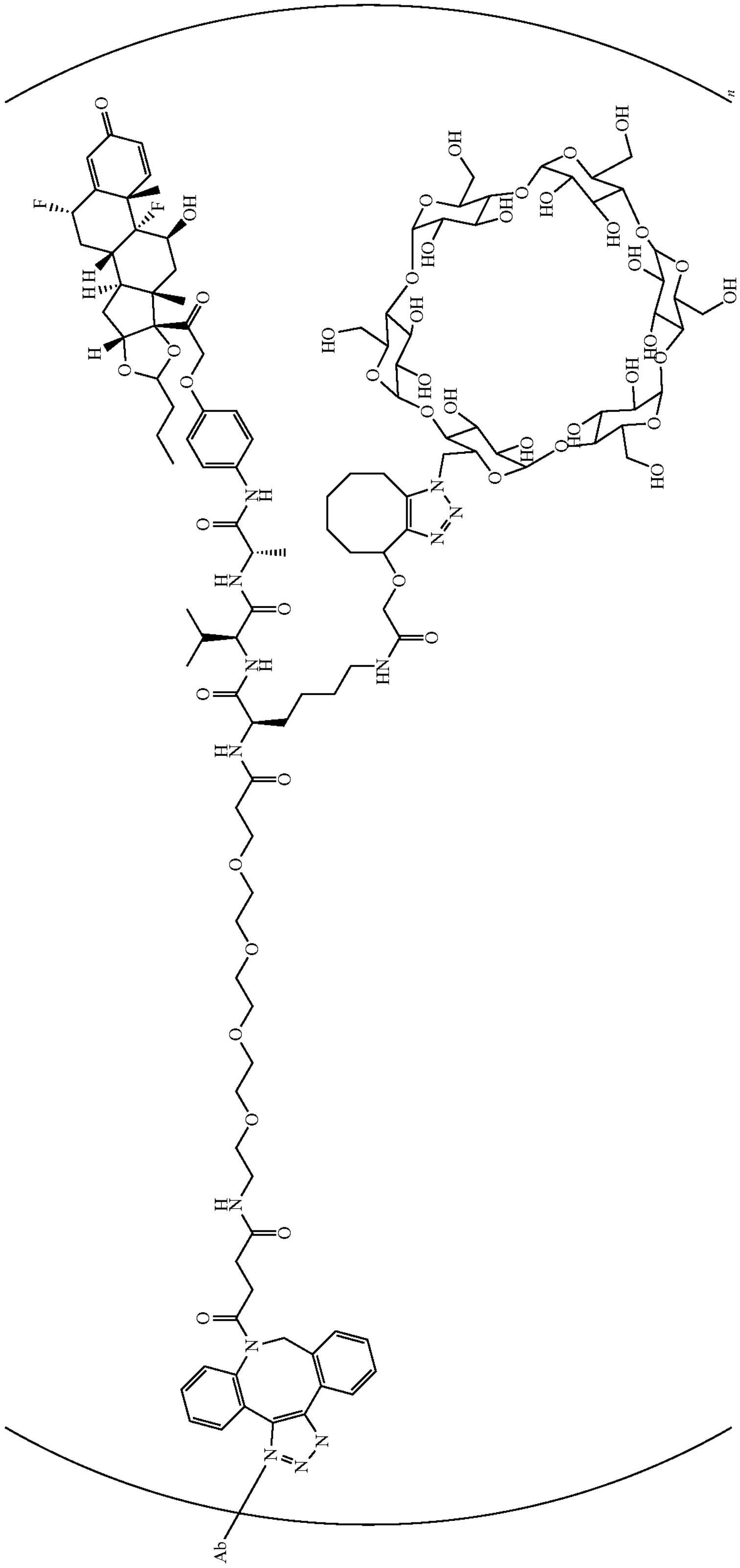

or a regioisomer, stereoisomeric form, pharmaceutically acceptable salt, solvate thereof, or mixture thereof, wherein Ab is an antibody or antigen-binding fragment thereof. In these examples, Ab may be directly or indirectly bonded to the linked-payload. In some examples, when Ab is indirectly bonded to the linker-payload, then

is

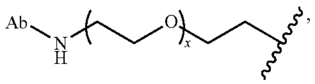

wherein subscript x is an integer from 1 to 4. In some examples, subscript x is 1. In some examples, subscript x is 2. In some examples, subscript x is 3. In some examples, subscript x is 4. Herein, Ab is an antibody or an antigen-binding fragment thereof. In some examples, the illustrated PEG group, i.e.,

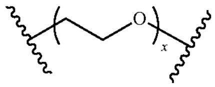

is bonded to a glutamine on the Ab. In certain embodiments, n is an integer from 1 to 30, for instance from 1 to 4, for instance 1, 2, 3, or 4.

In some examples, the compound of Formula (I) is selected from:

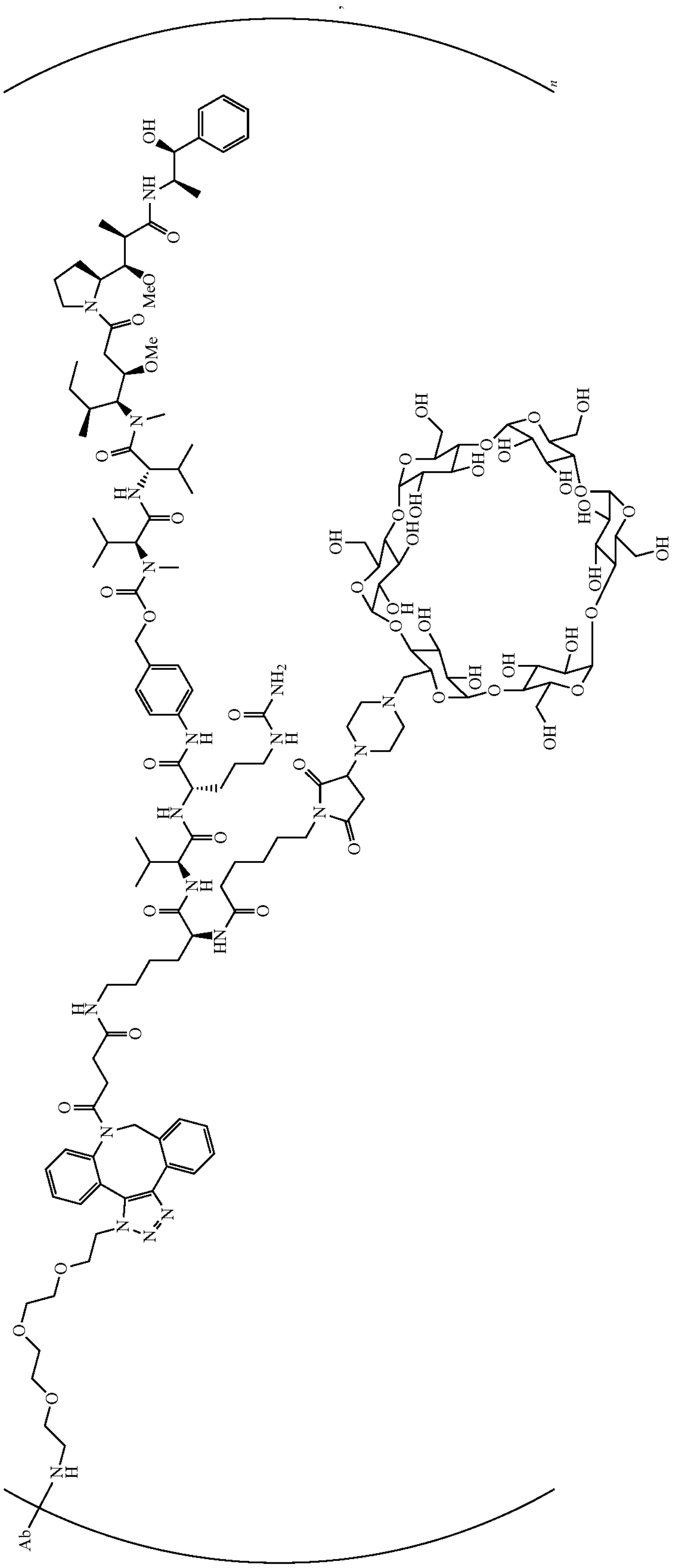

-continued
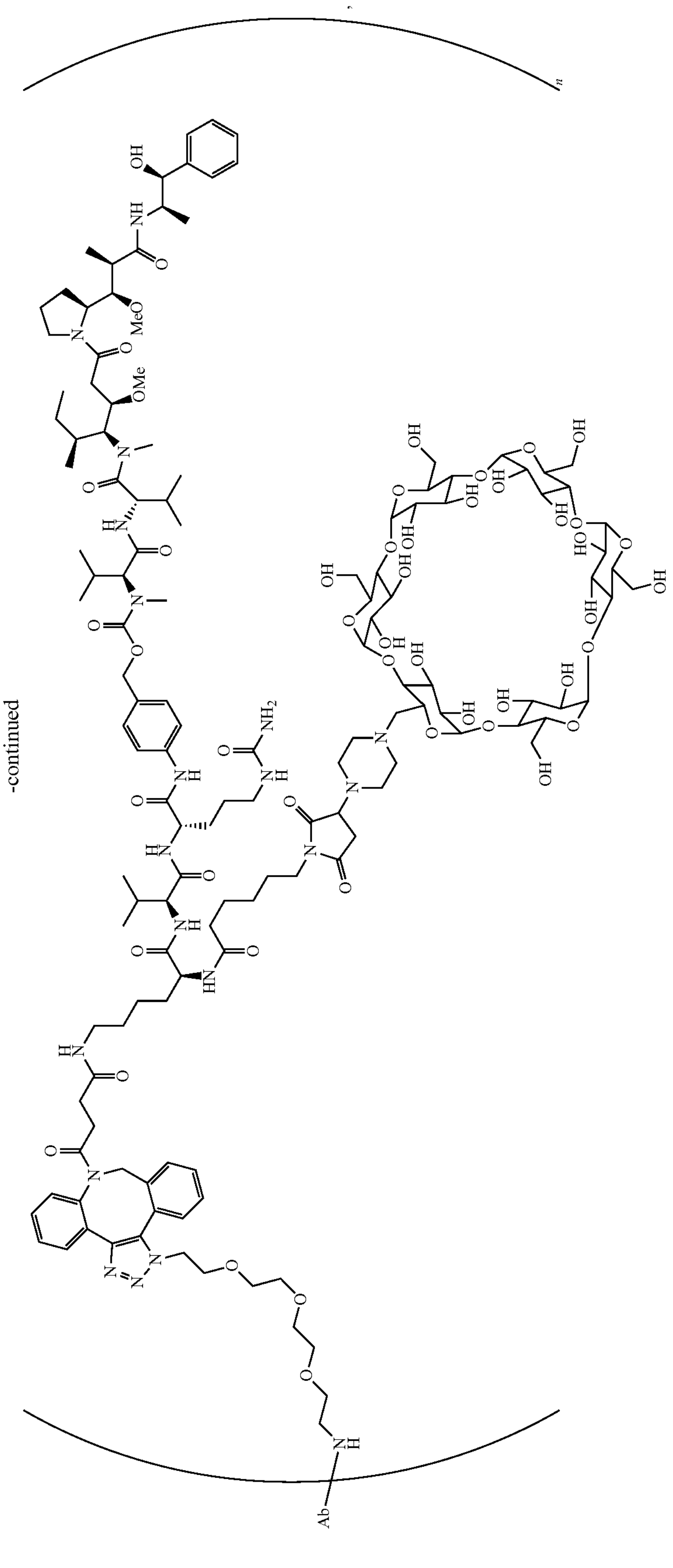

-continued
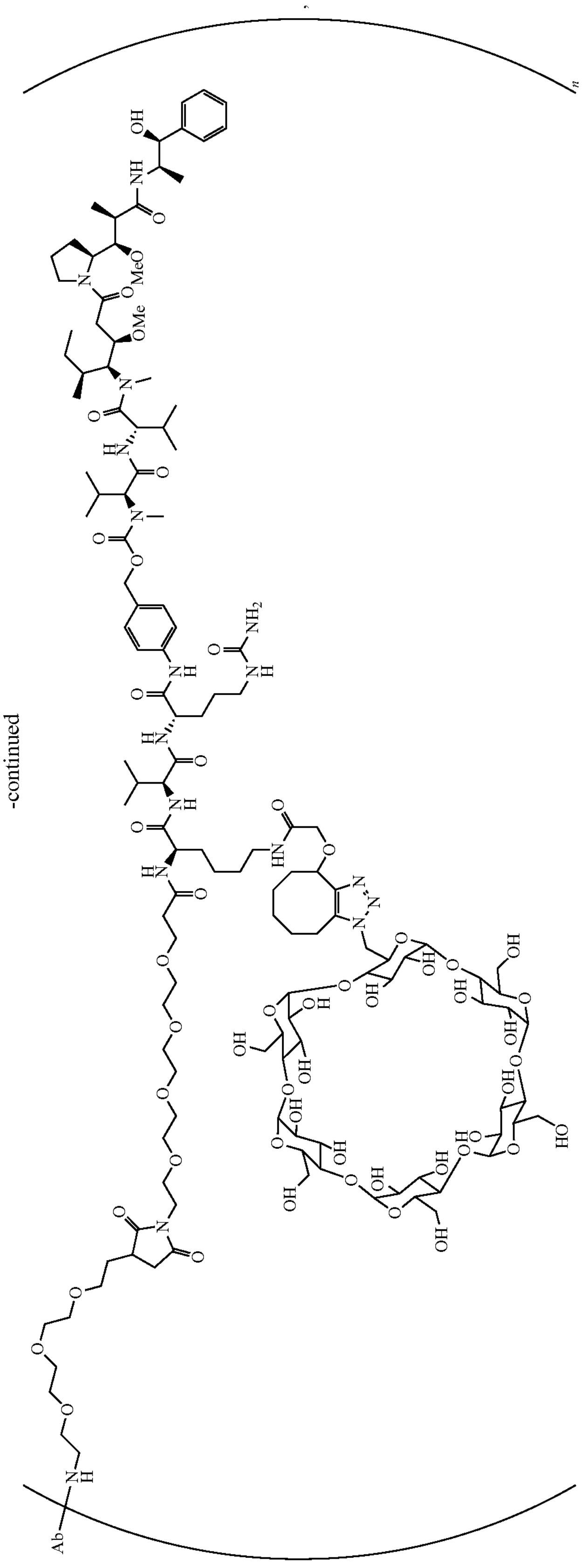
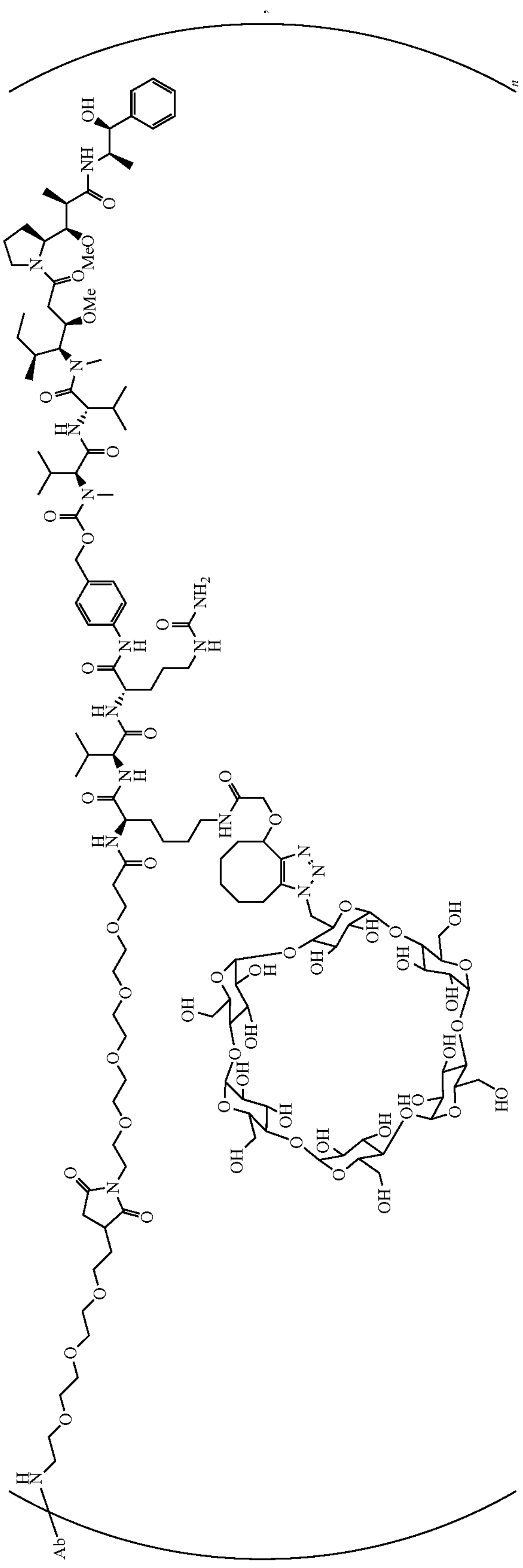

-continued
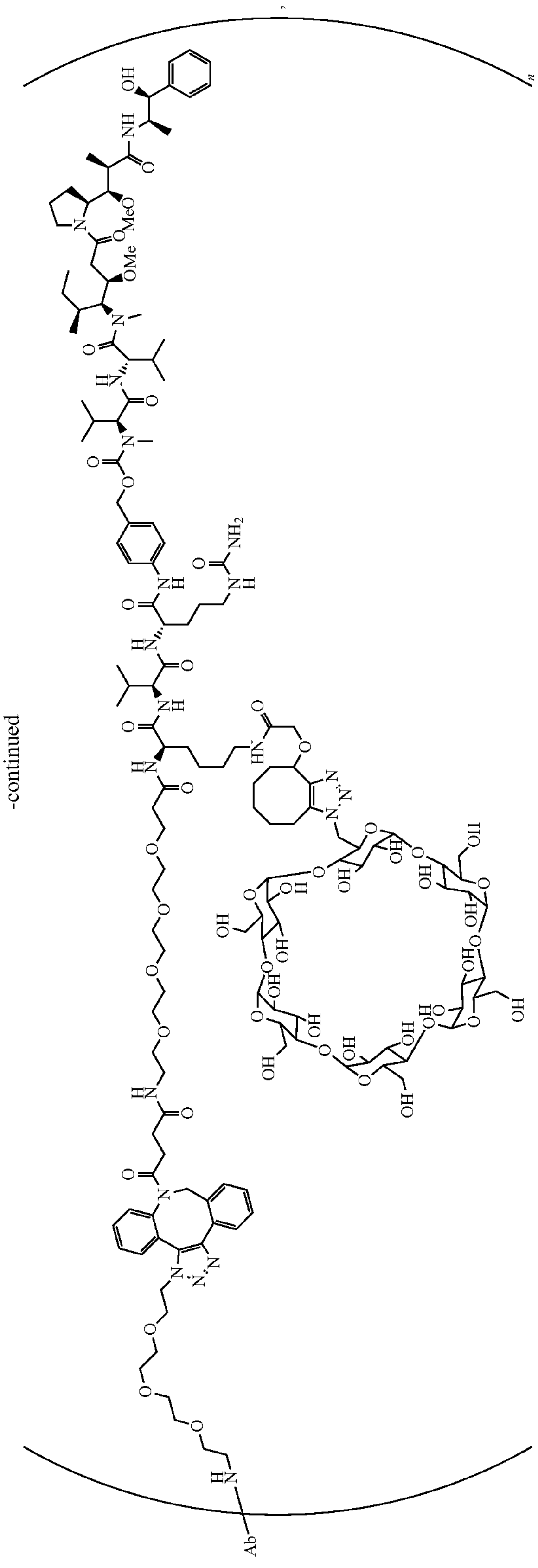
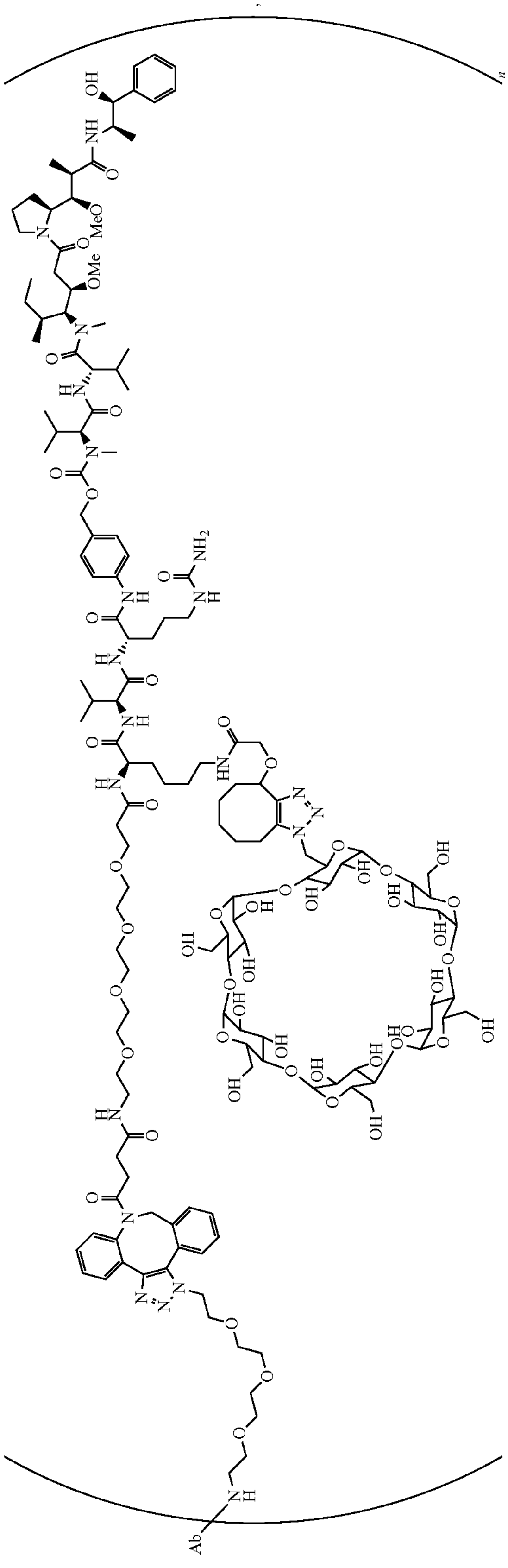

-continued
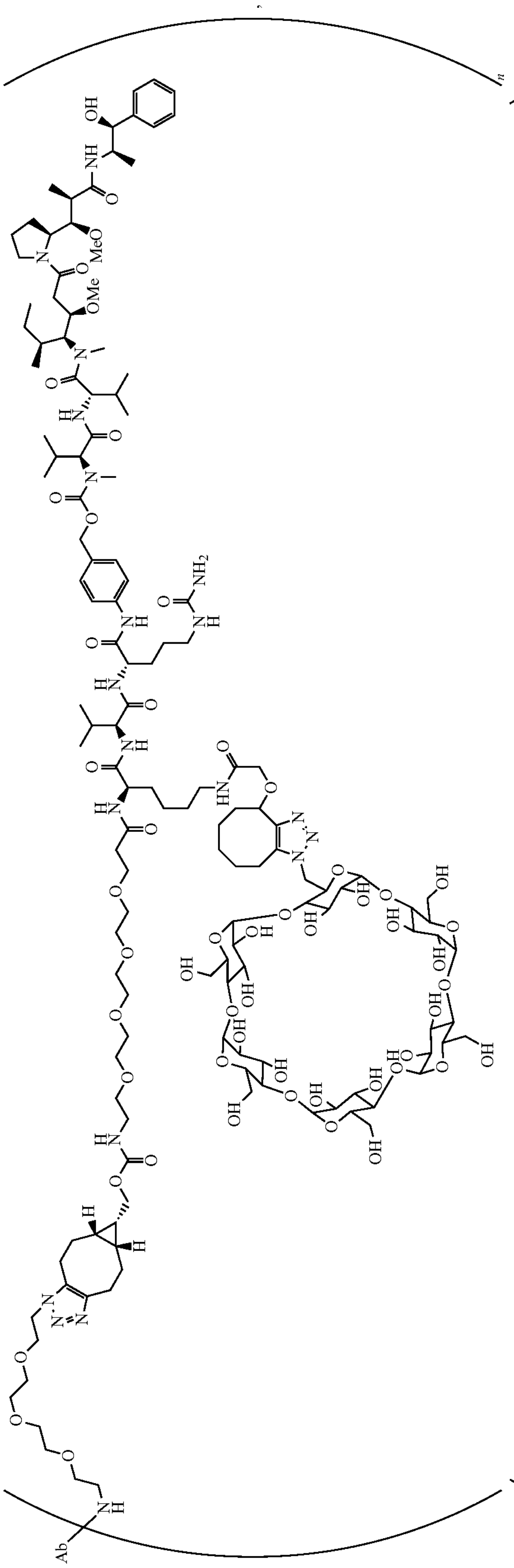
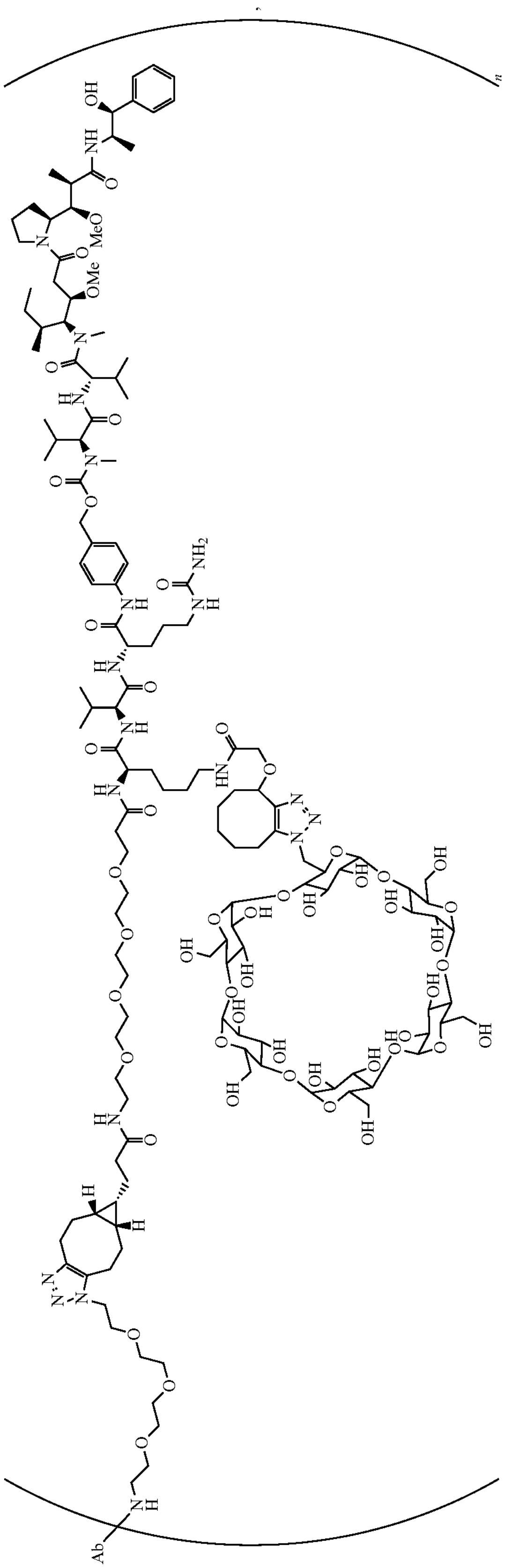

-continued
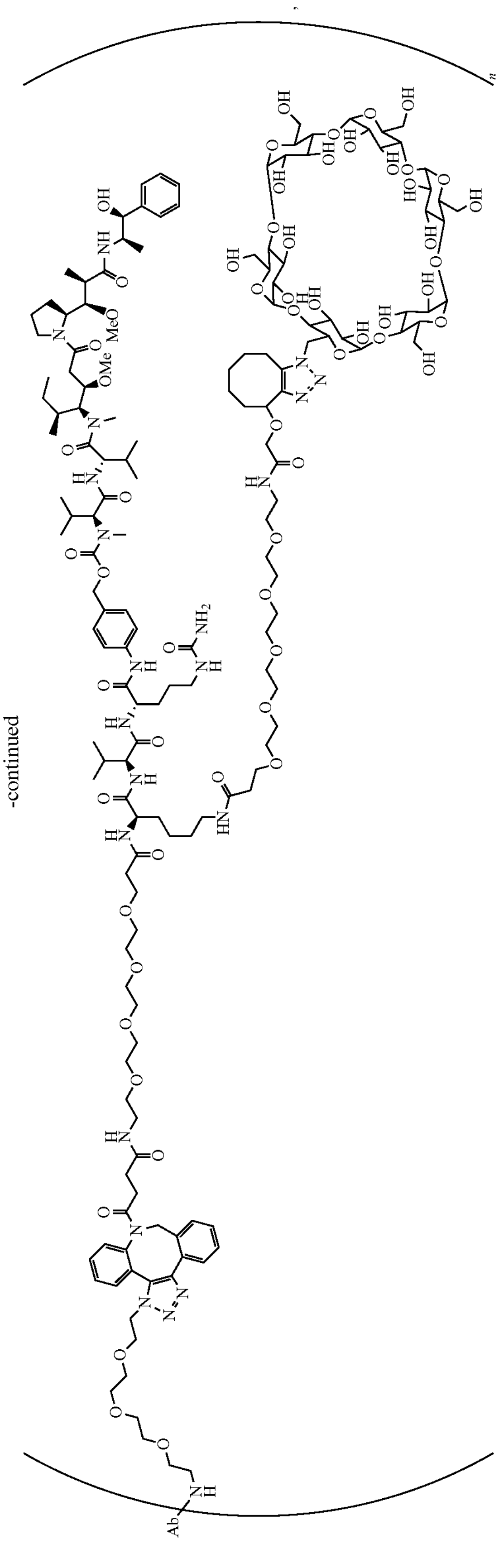
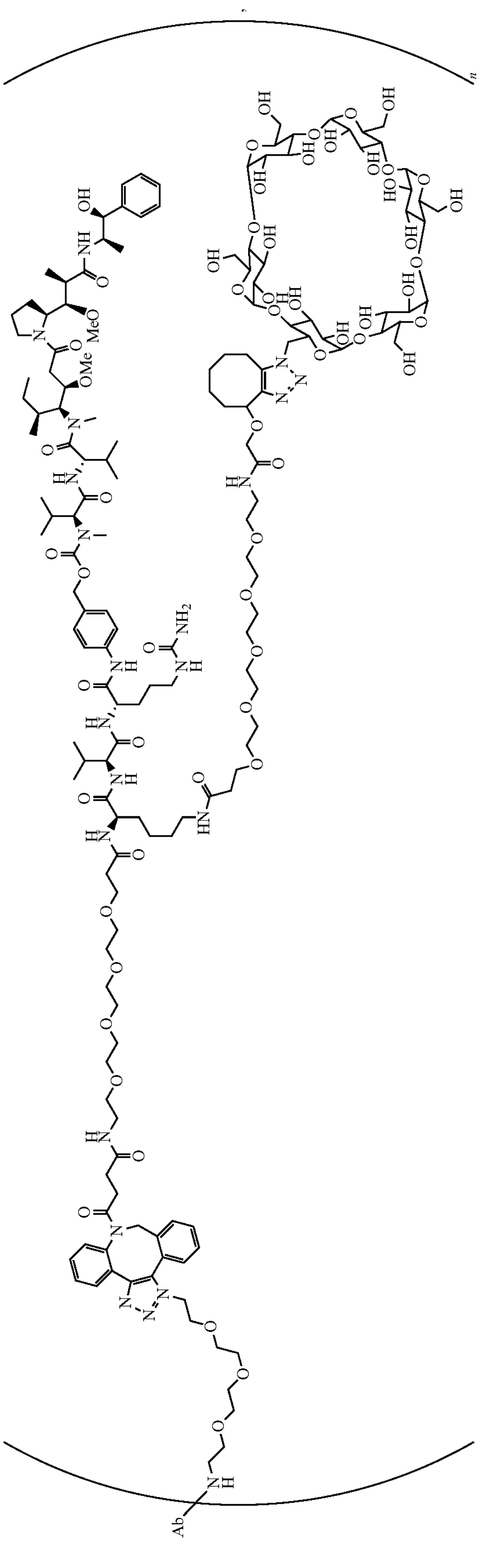

-continued
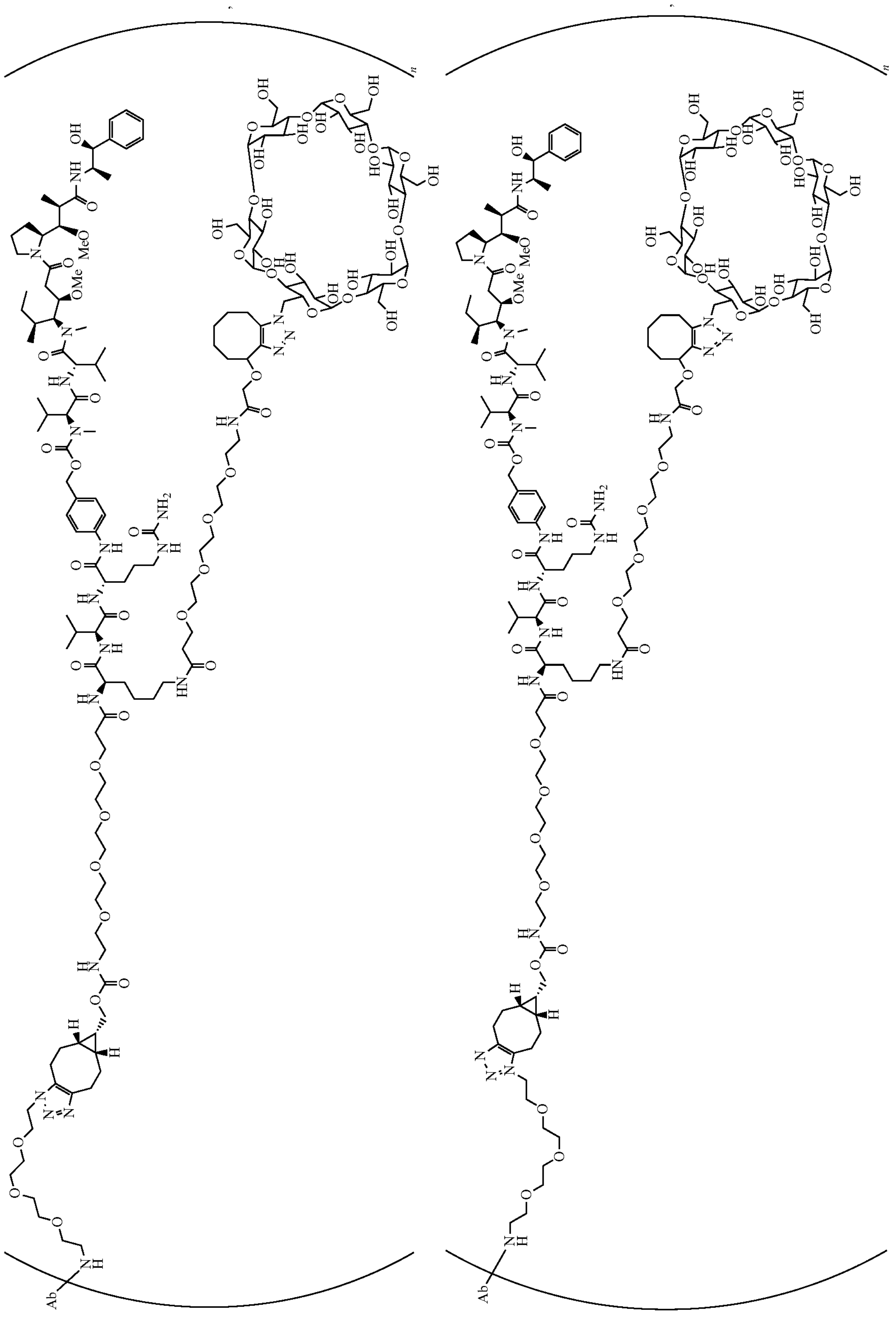

-continued
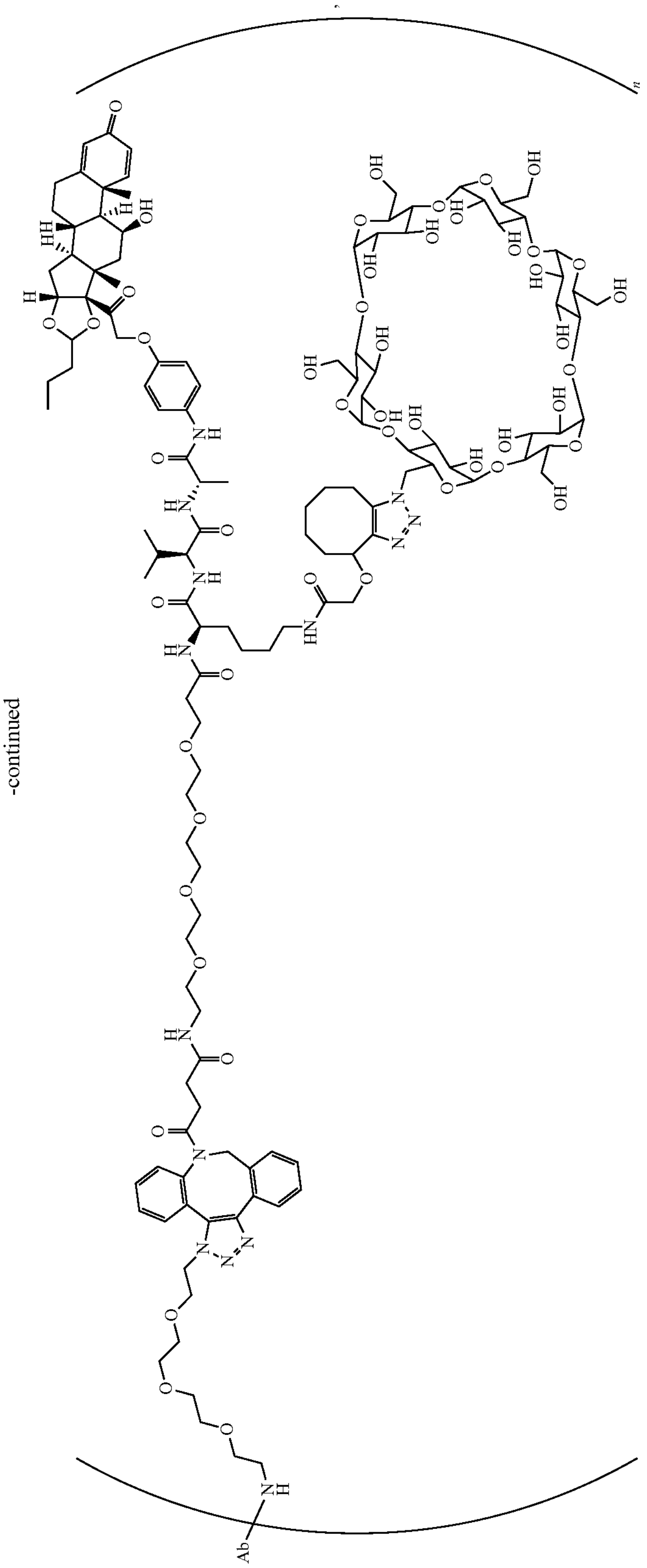

-continued
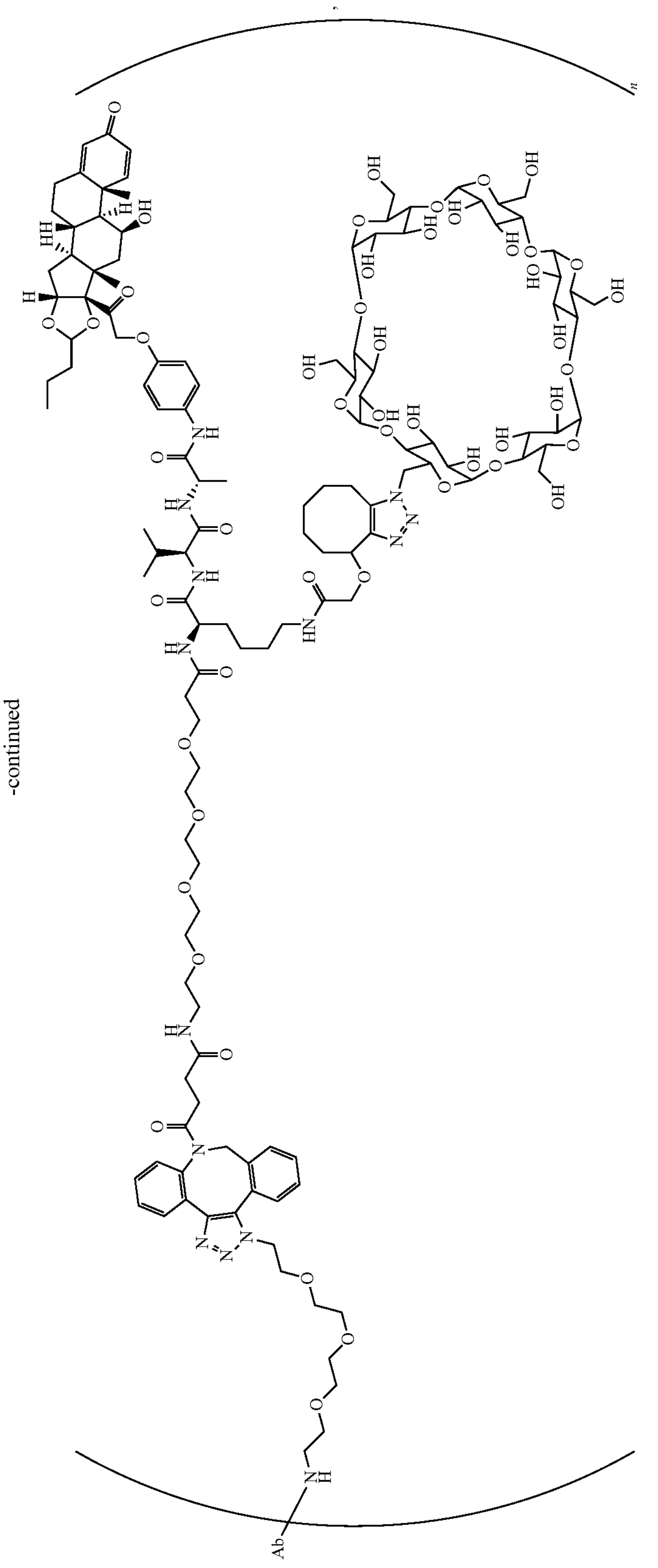

-continued
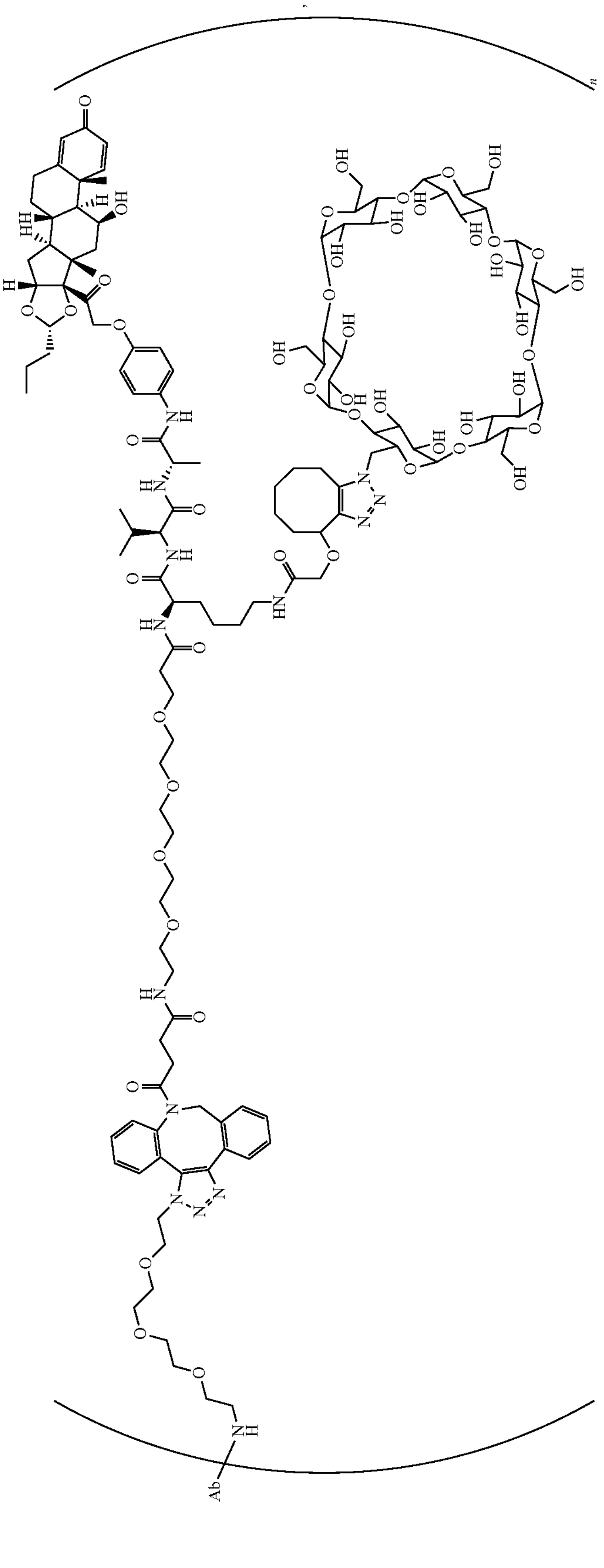

-continued
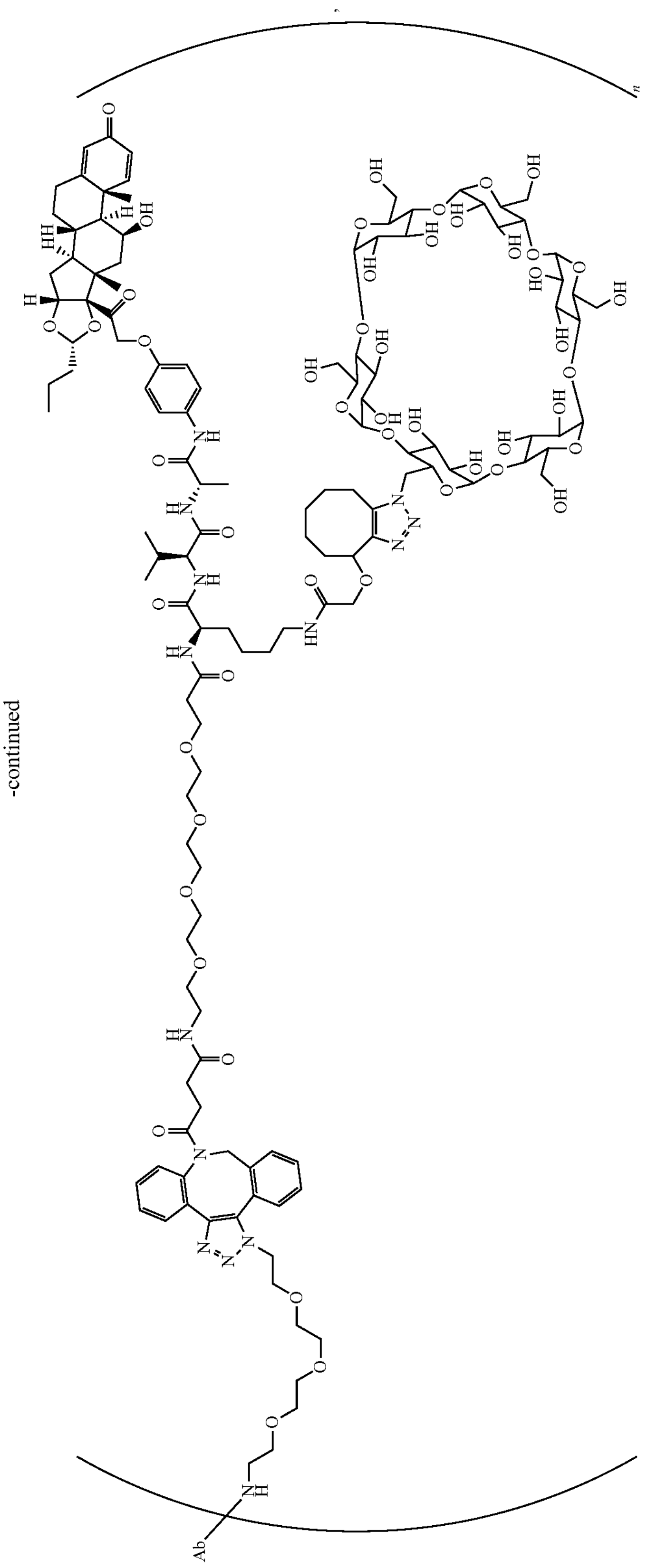

-continued
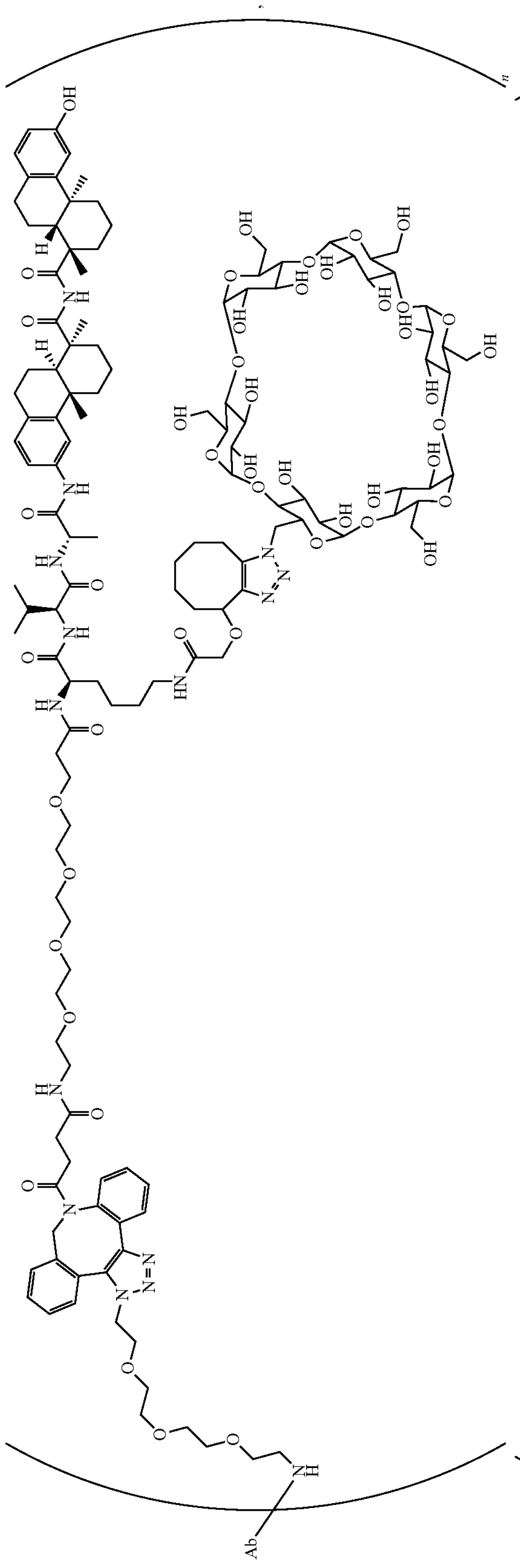
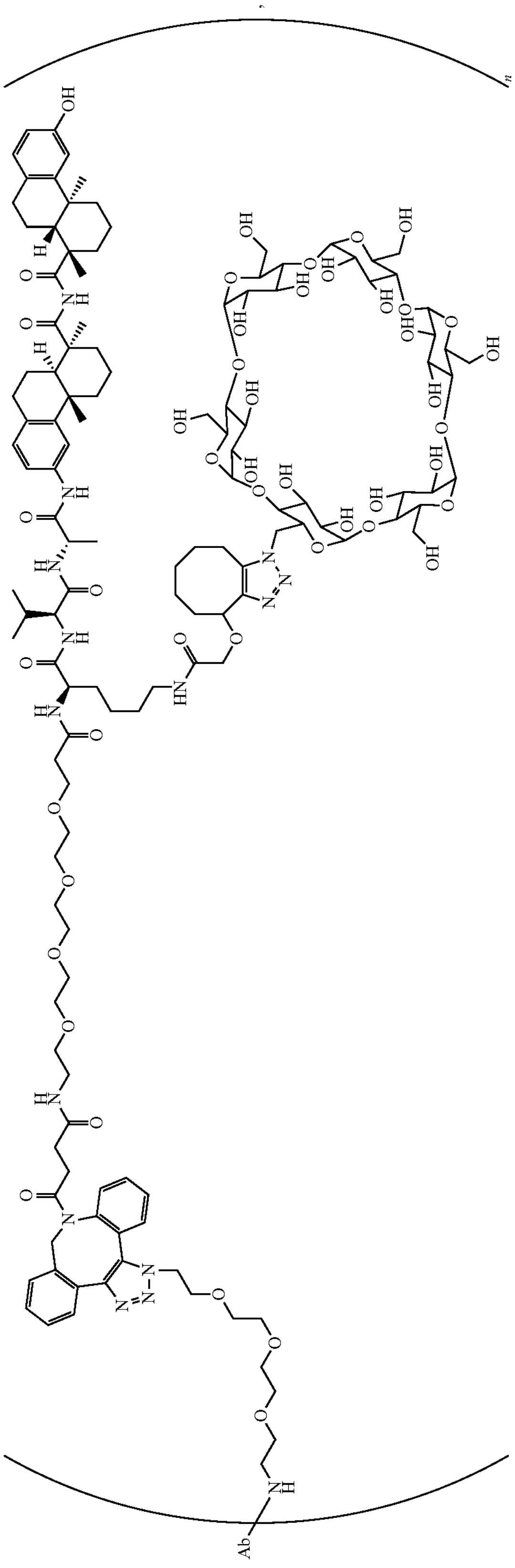

-continued
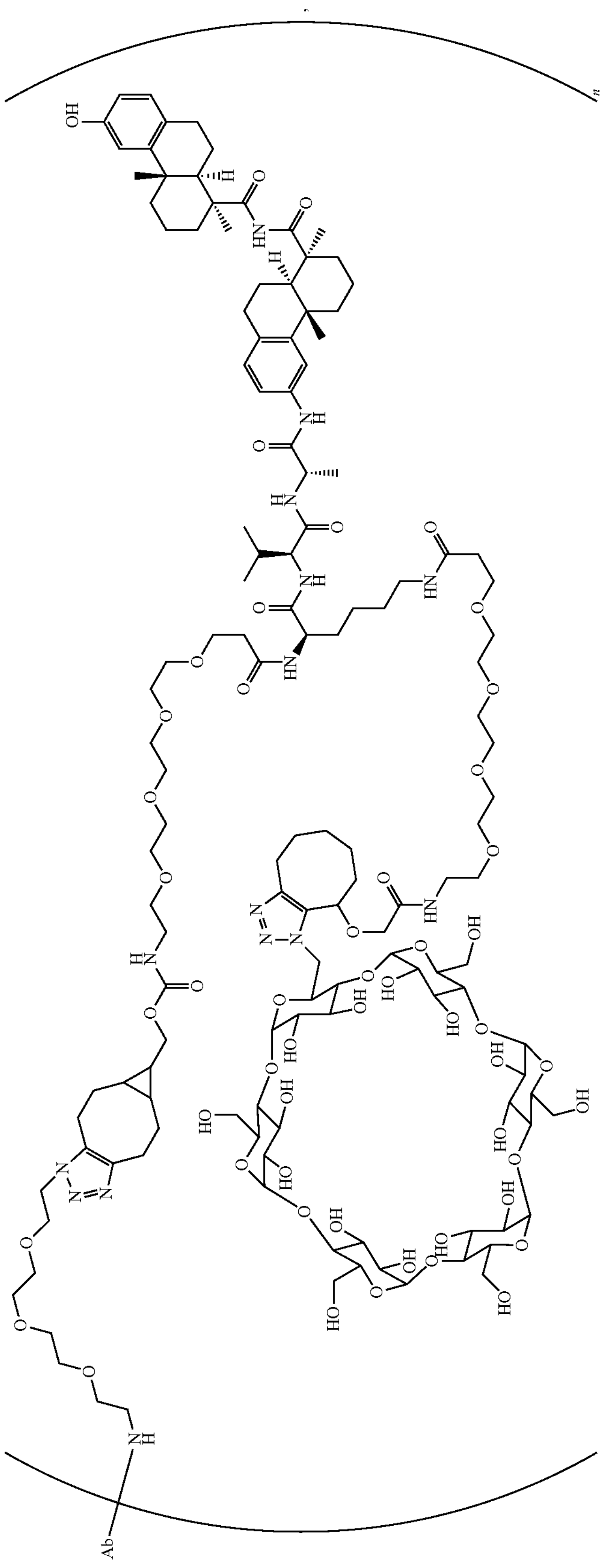

-continued
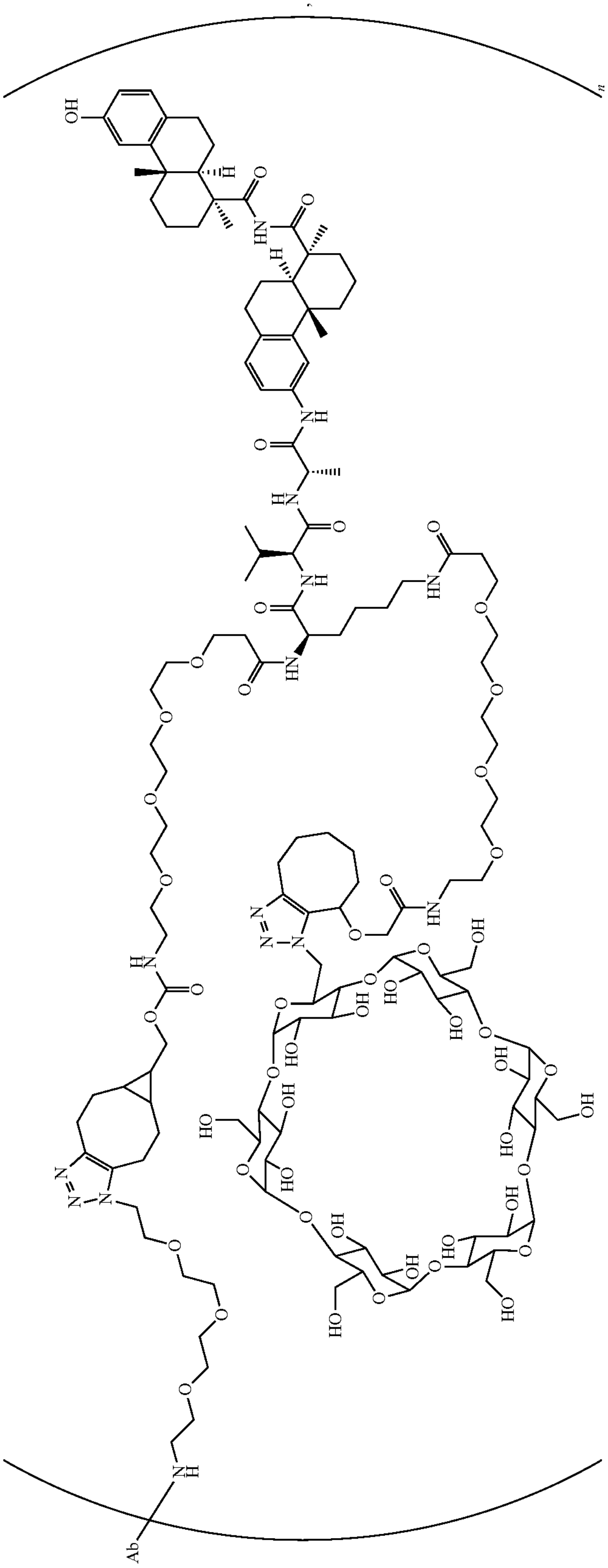

-continued
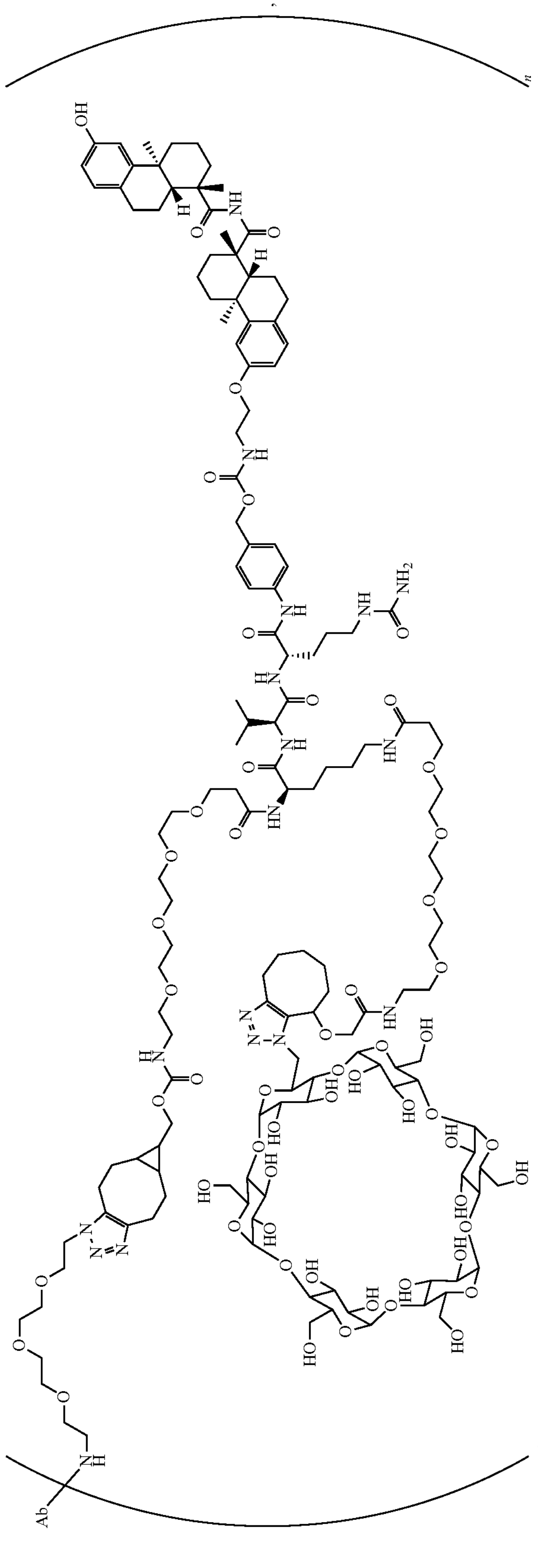
,
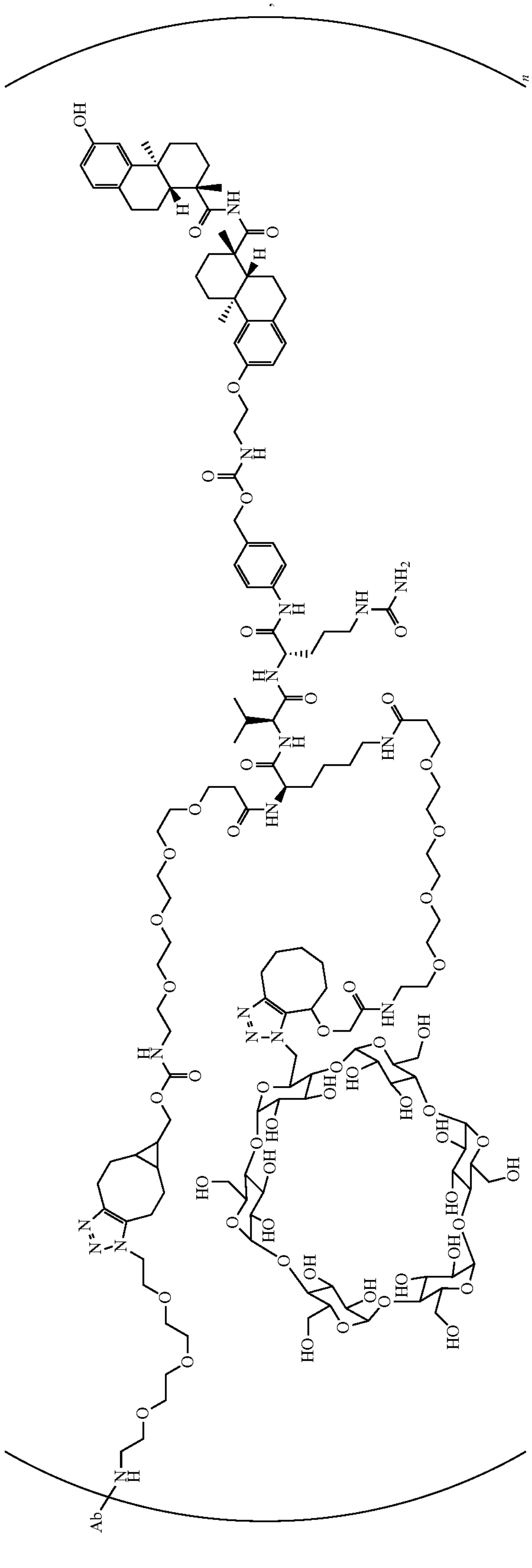
,

-continued
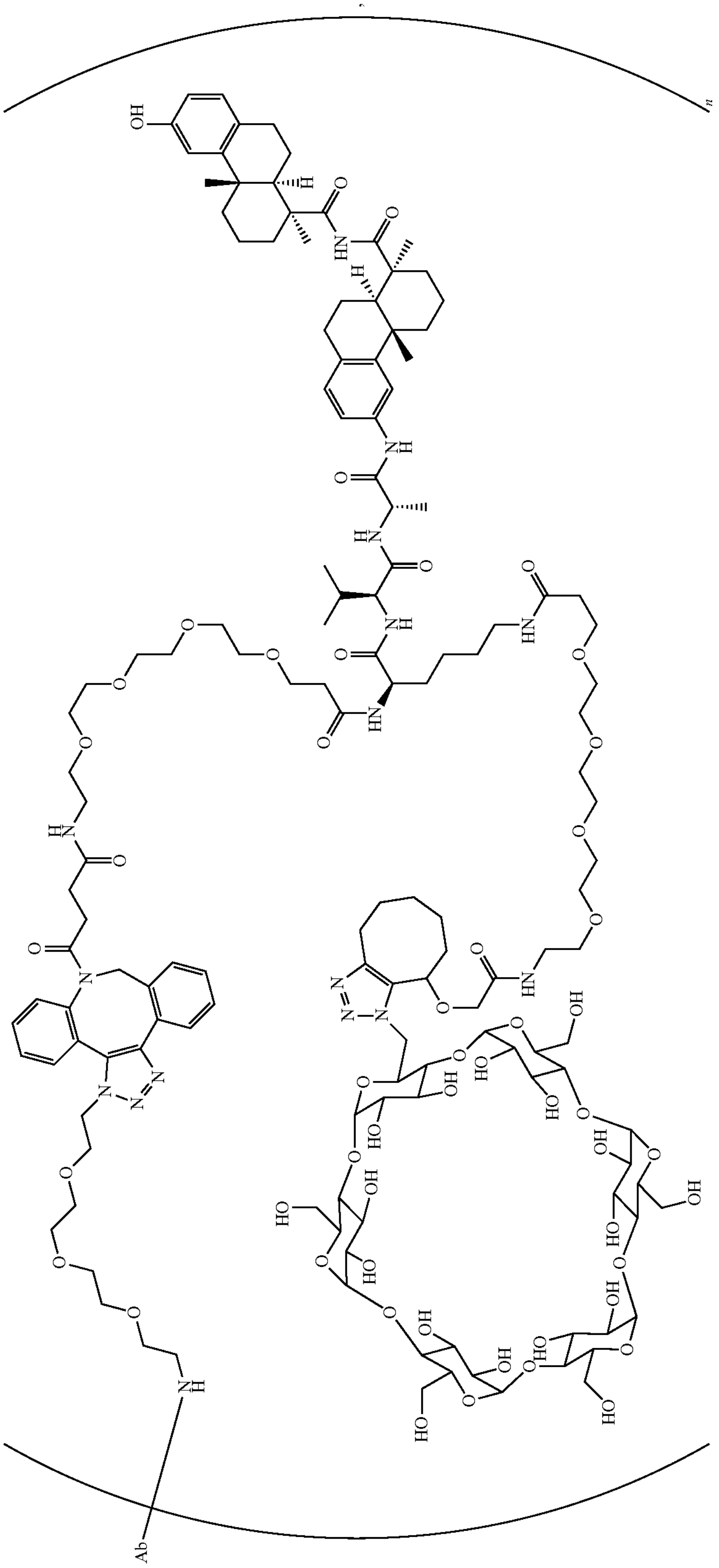

-continued
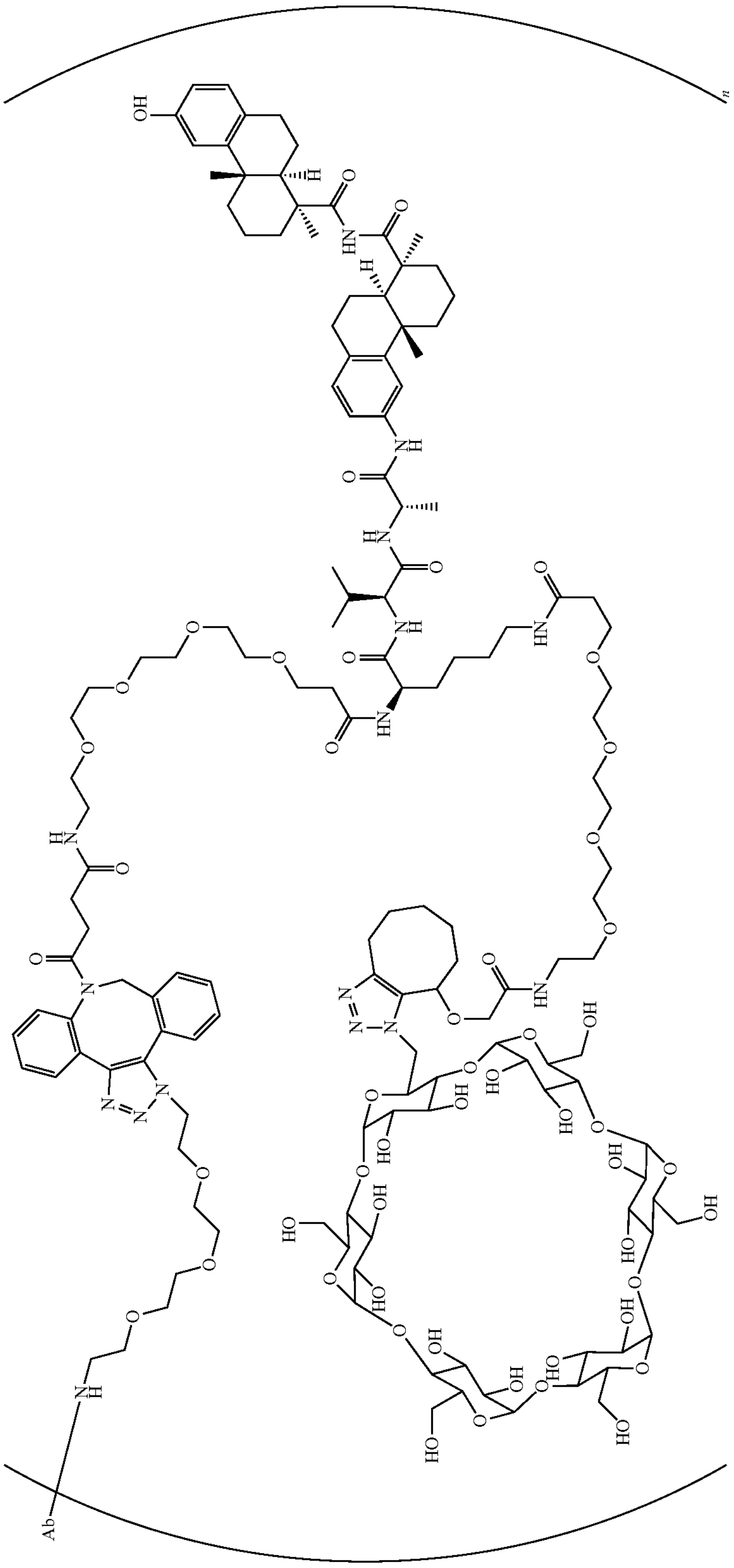

-continued
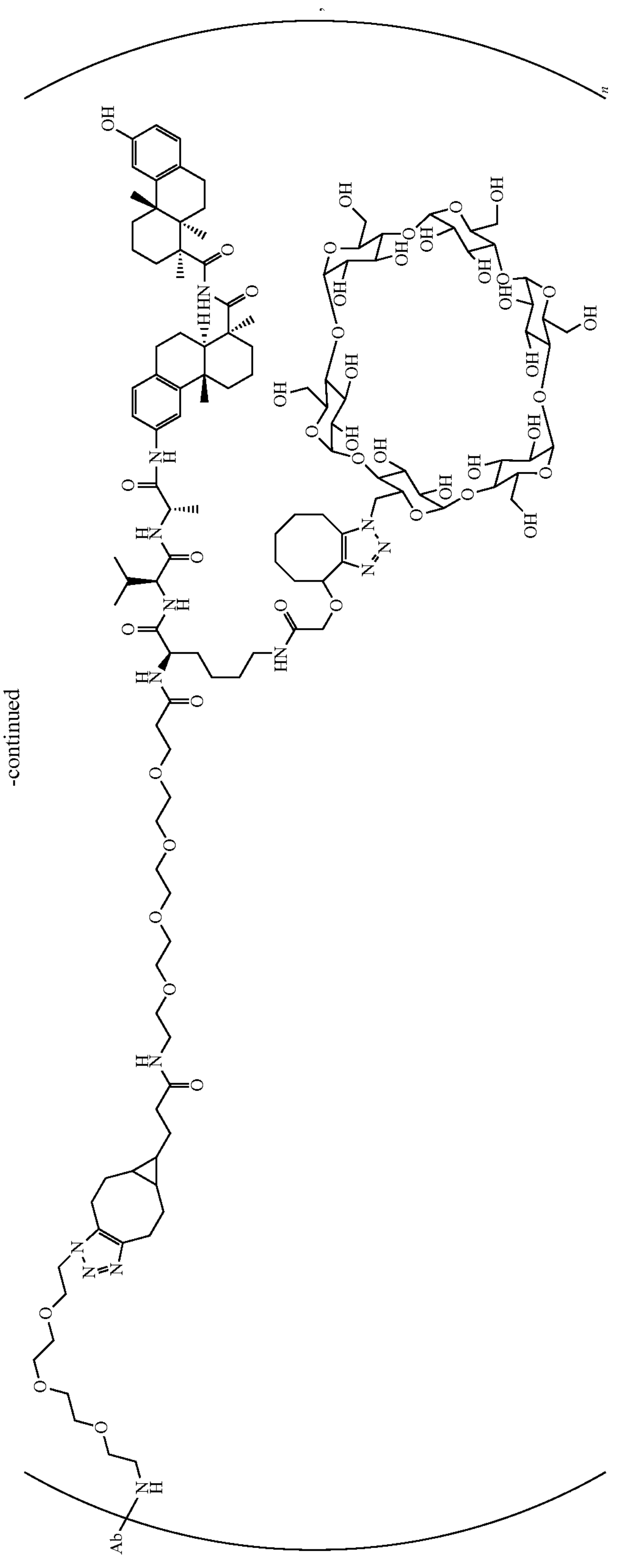

-continued
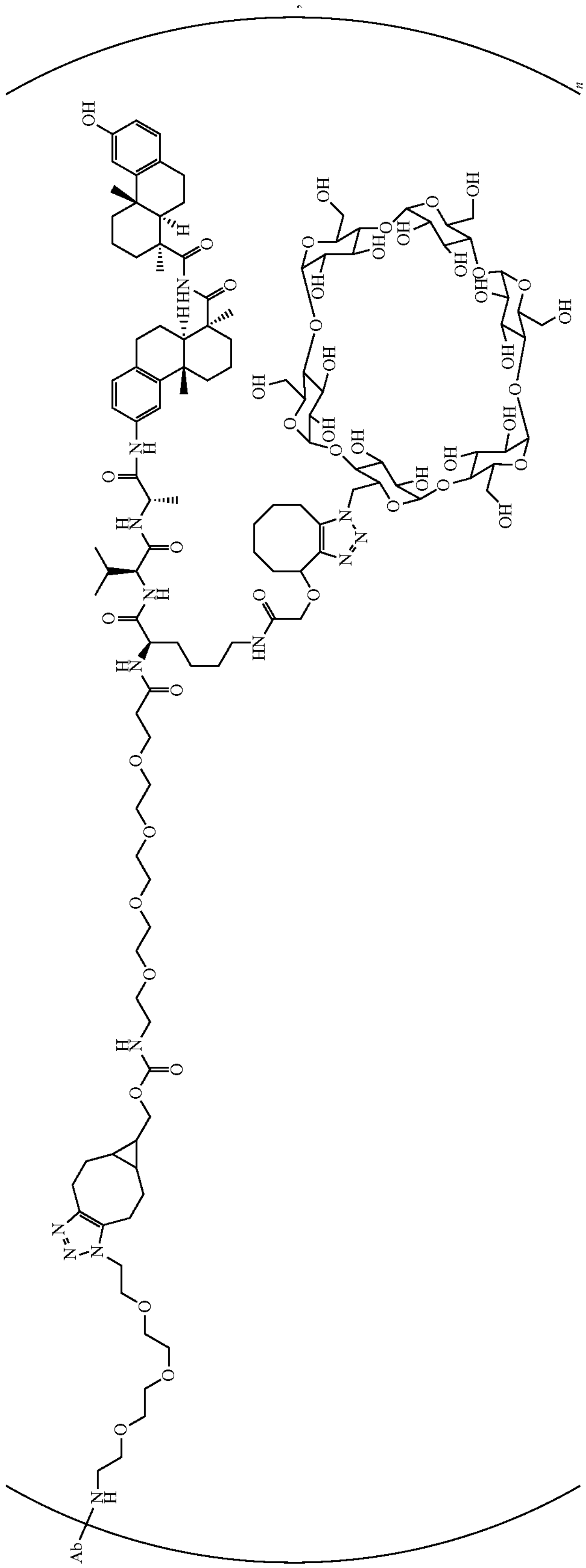
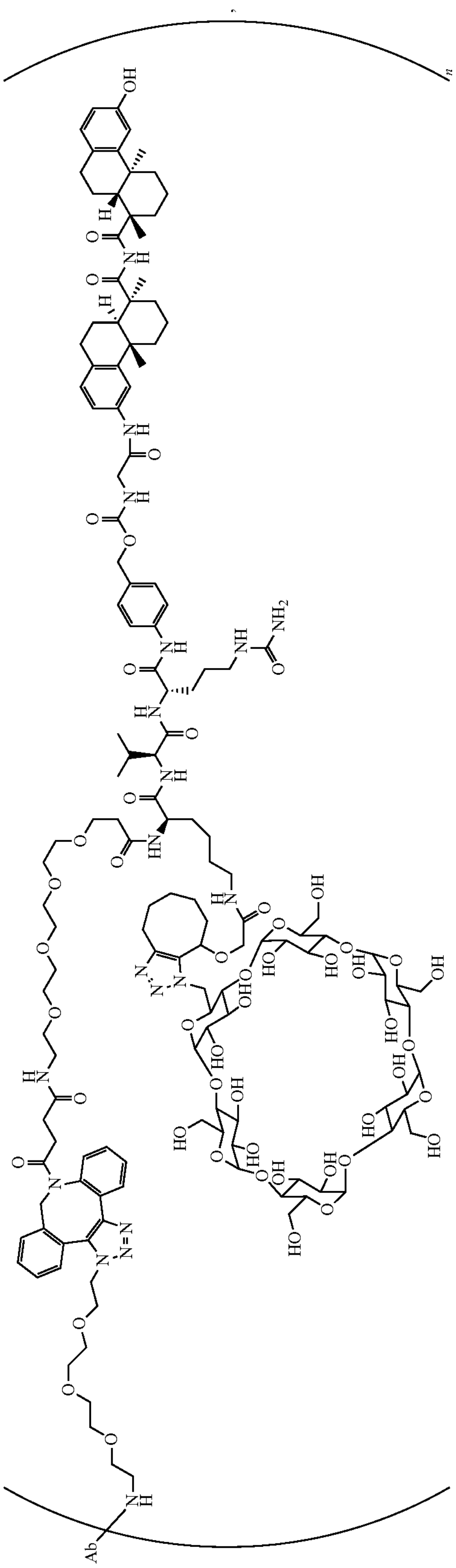

-continued
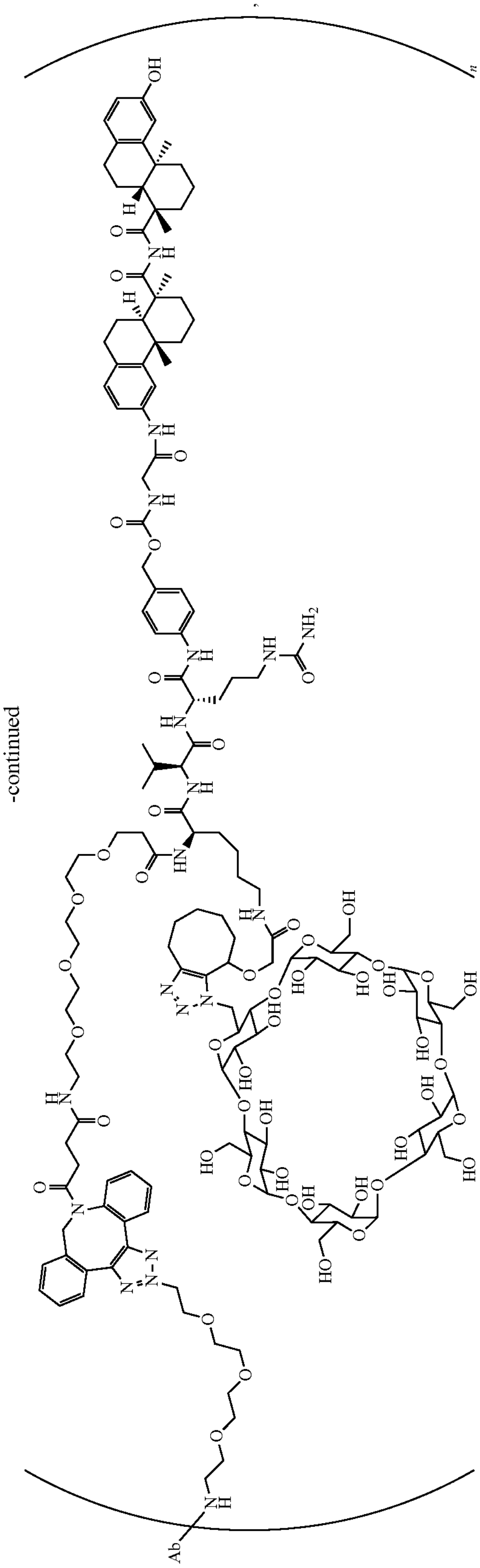
,
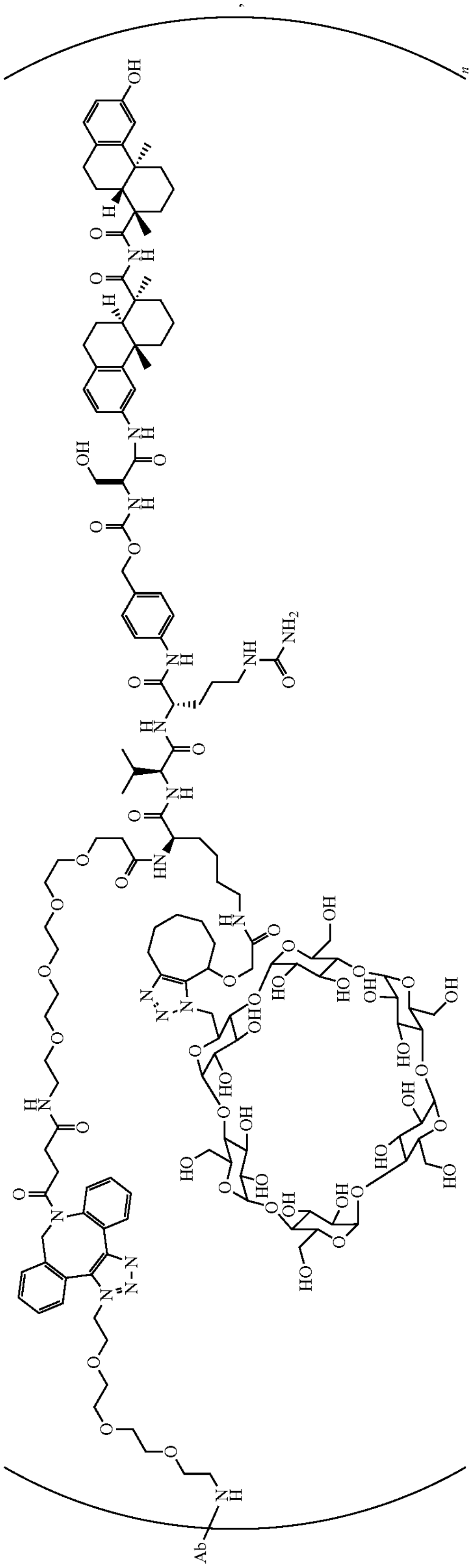
,

-continued
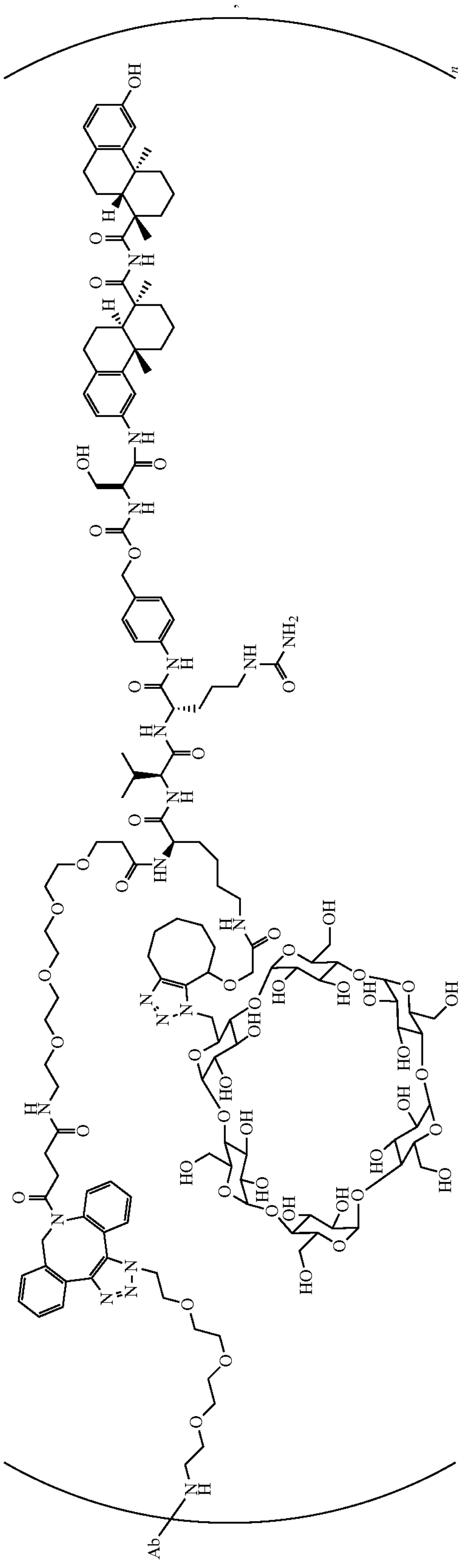

-continued
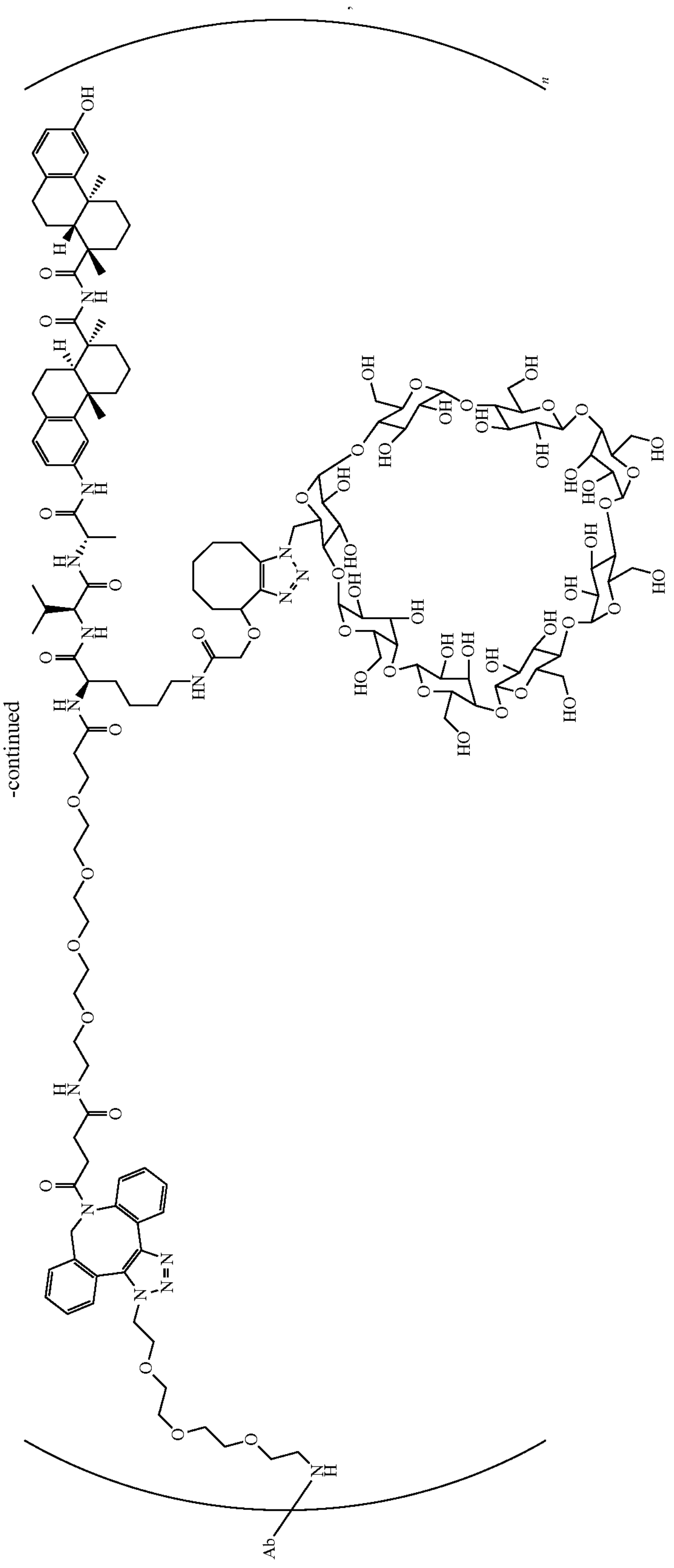

-continued
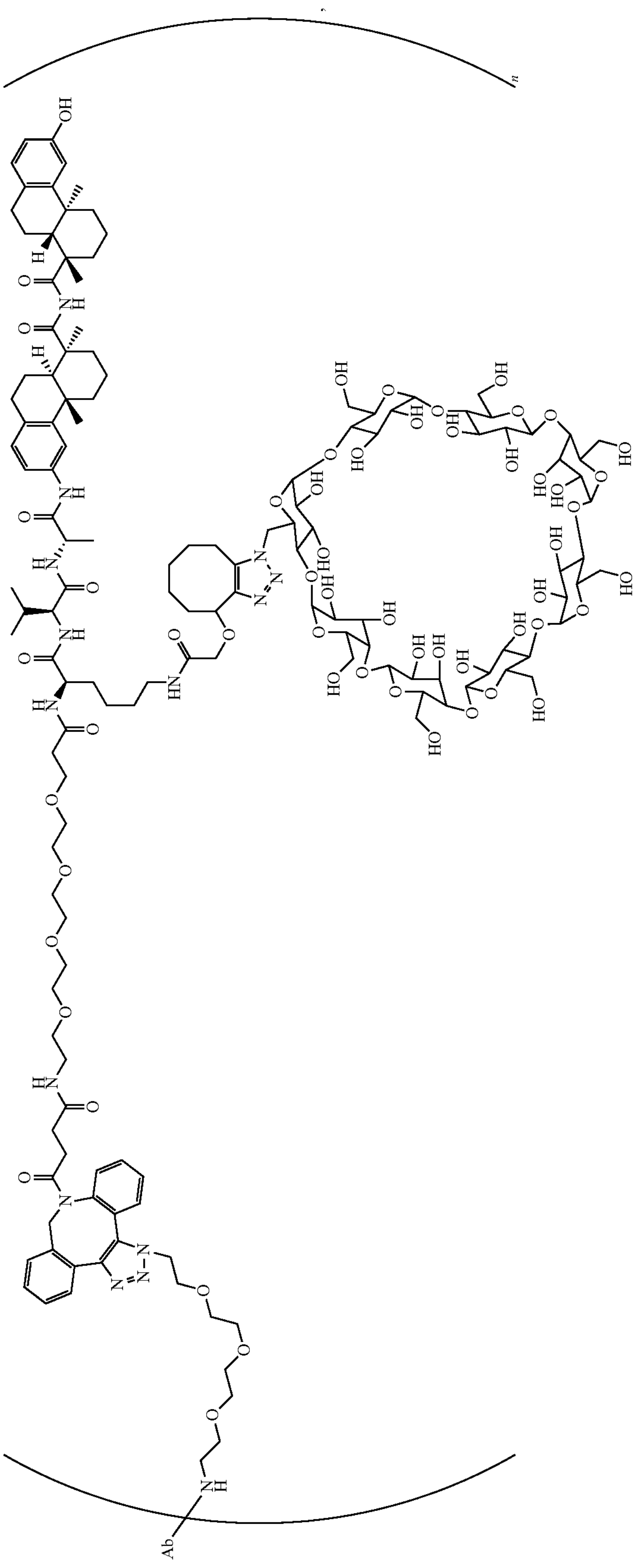

-continued
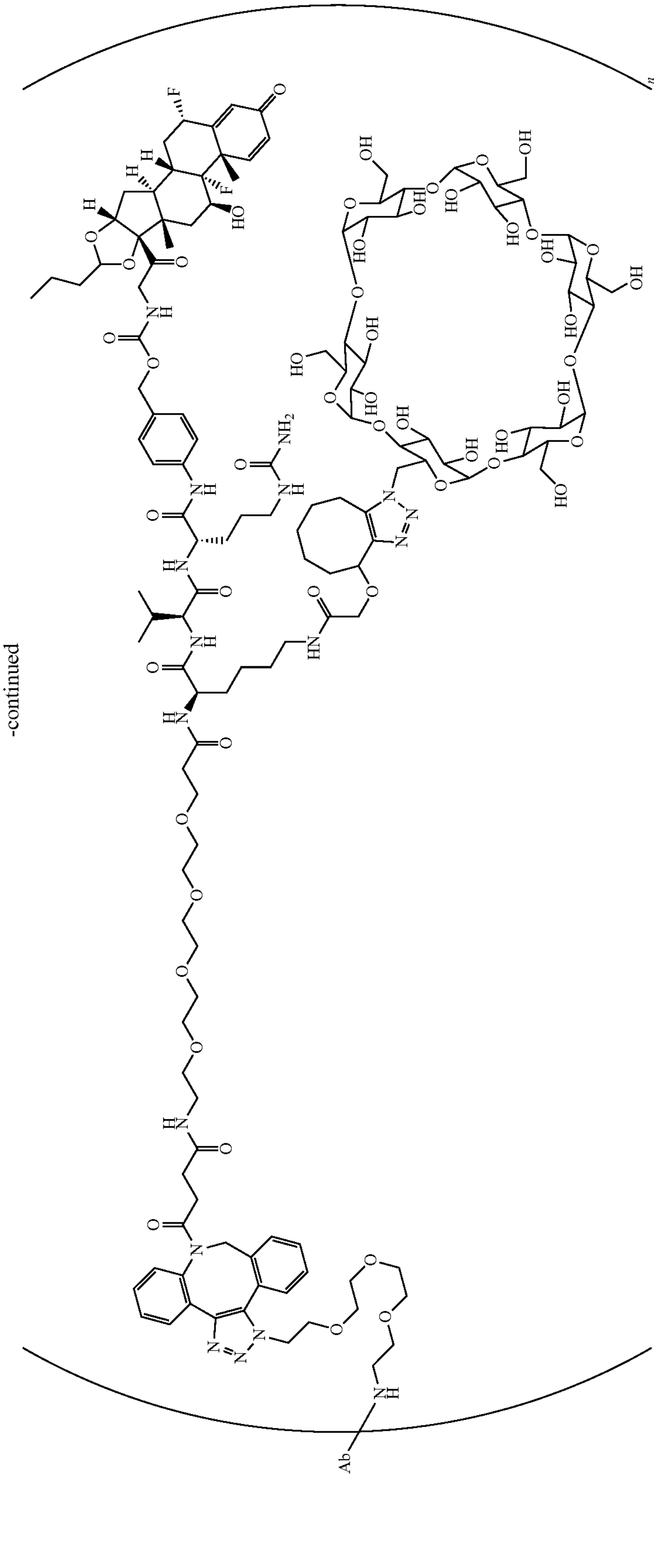

-continued
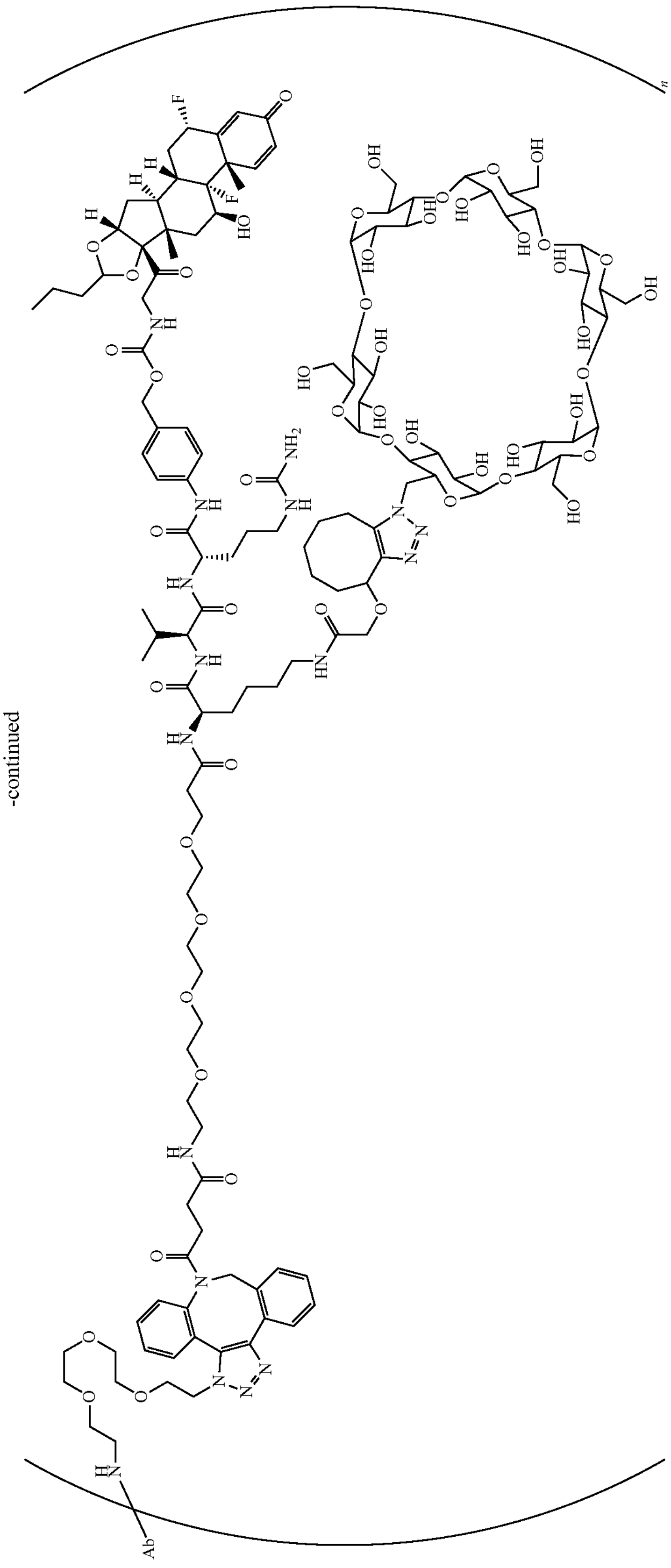

-continued
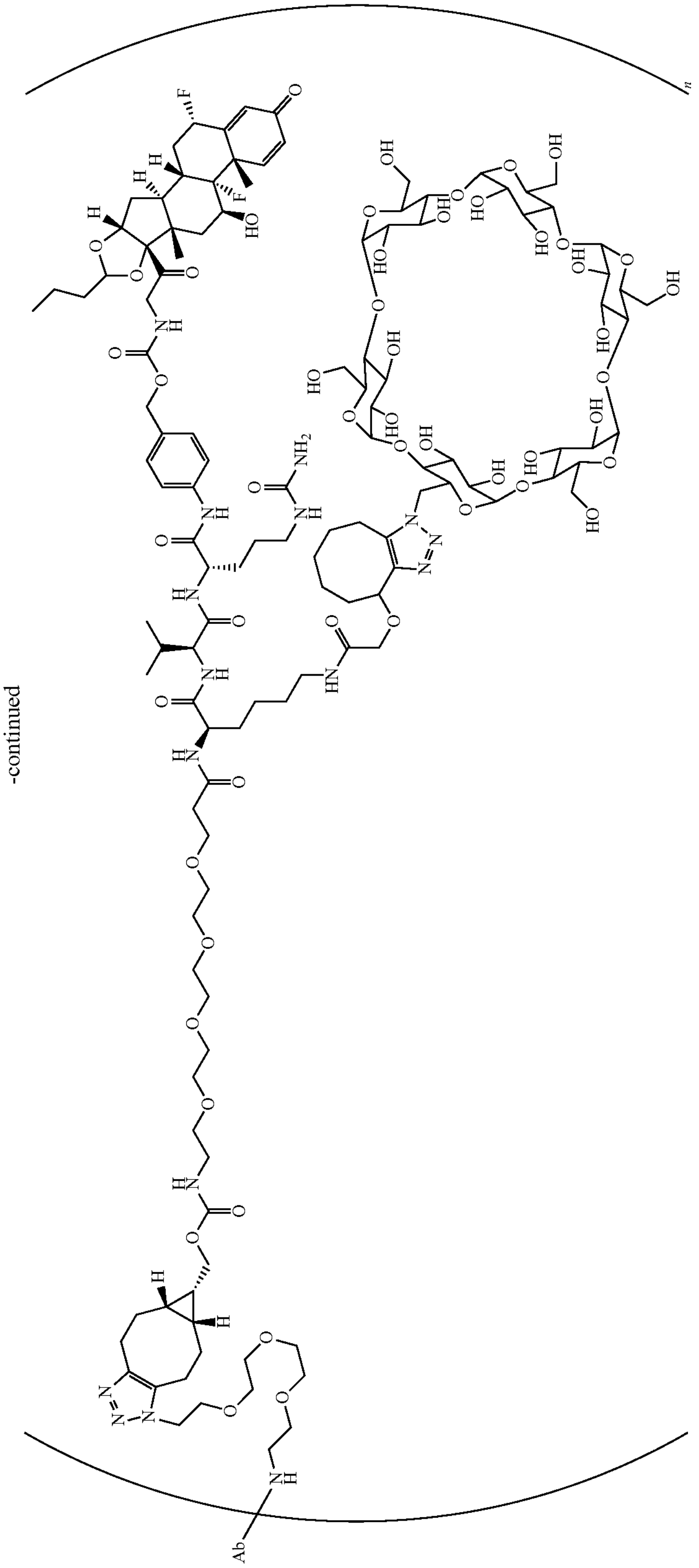

-continued
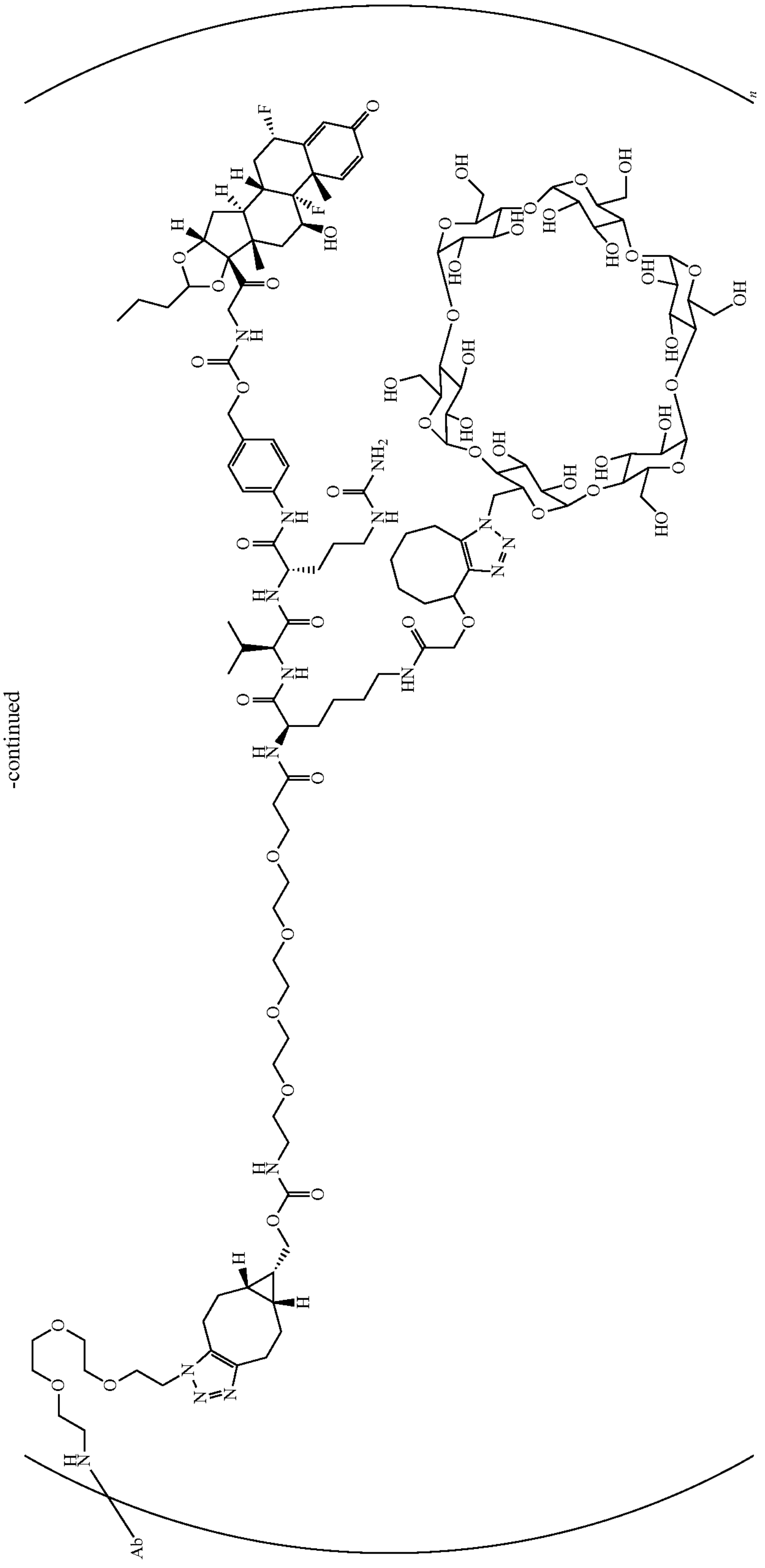

-continued
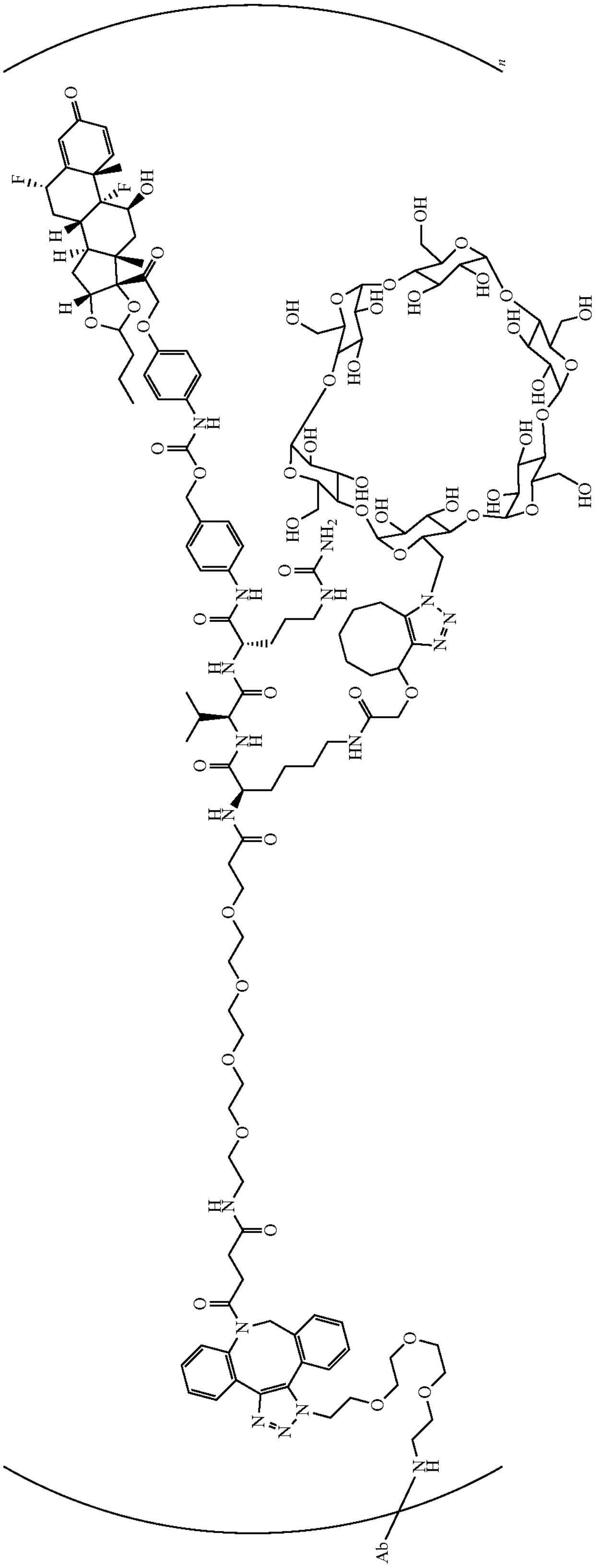

-continued
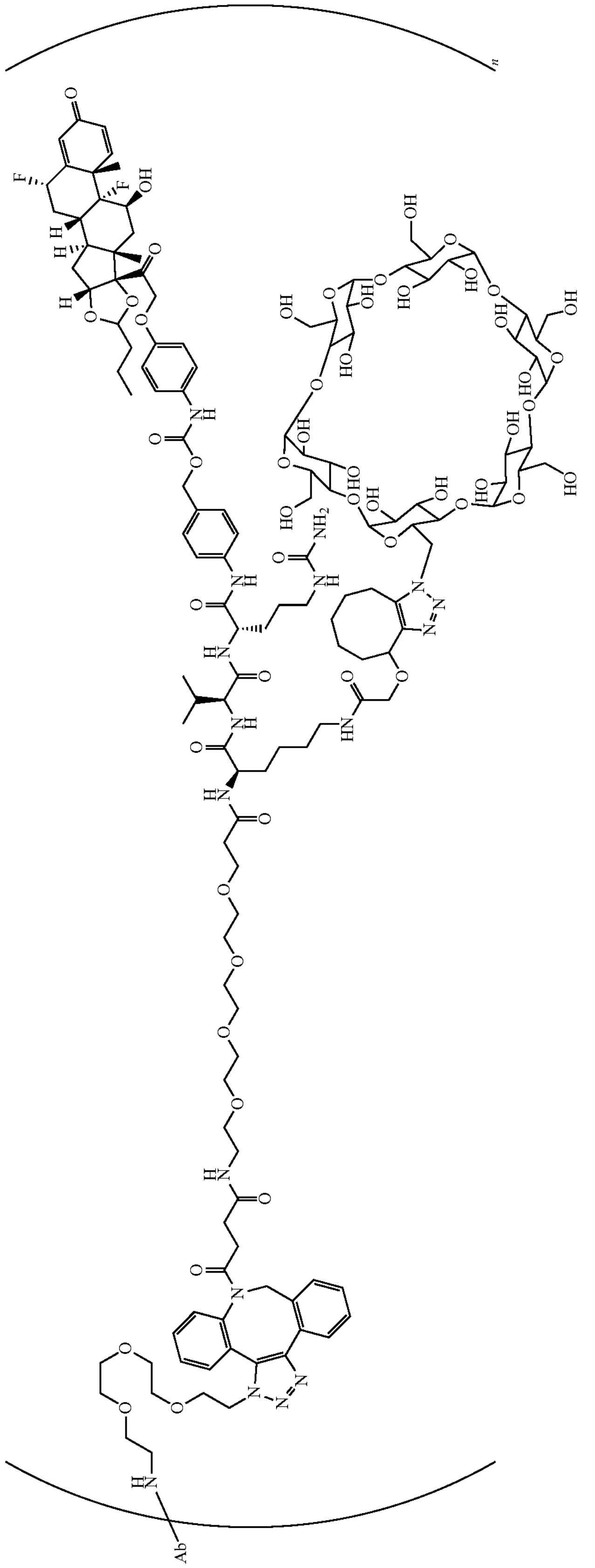

-continued
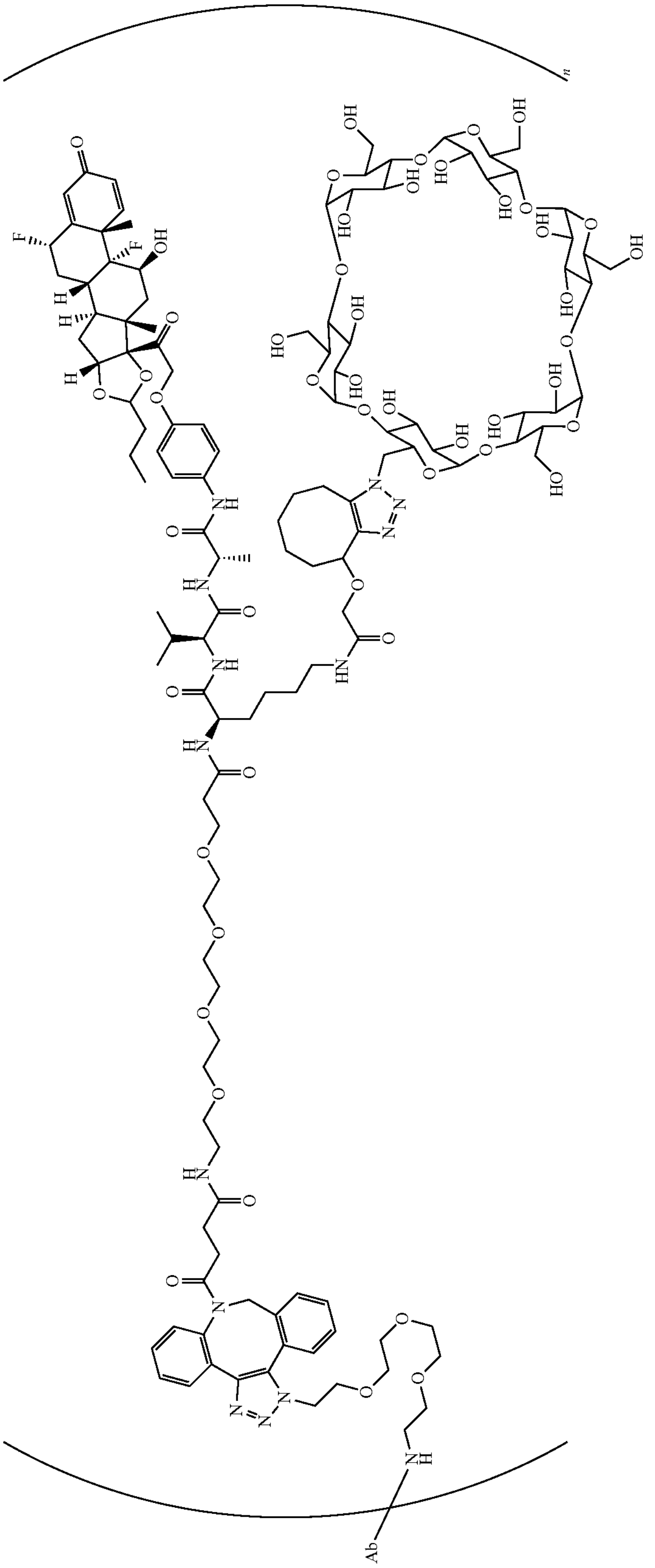

-continued
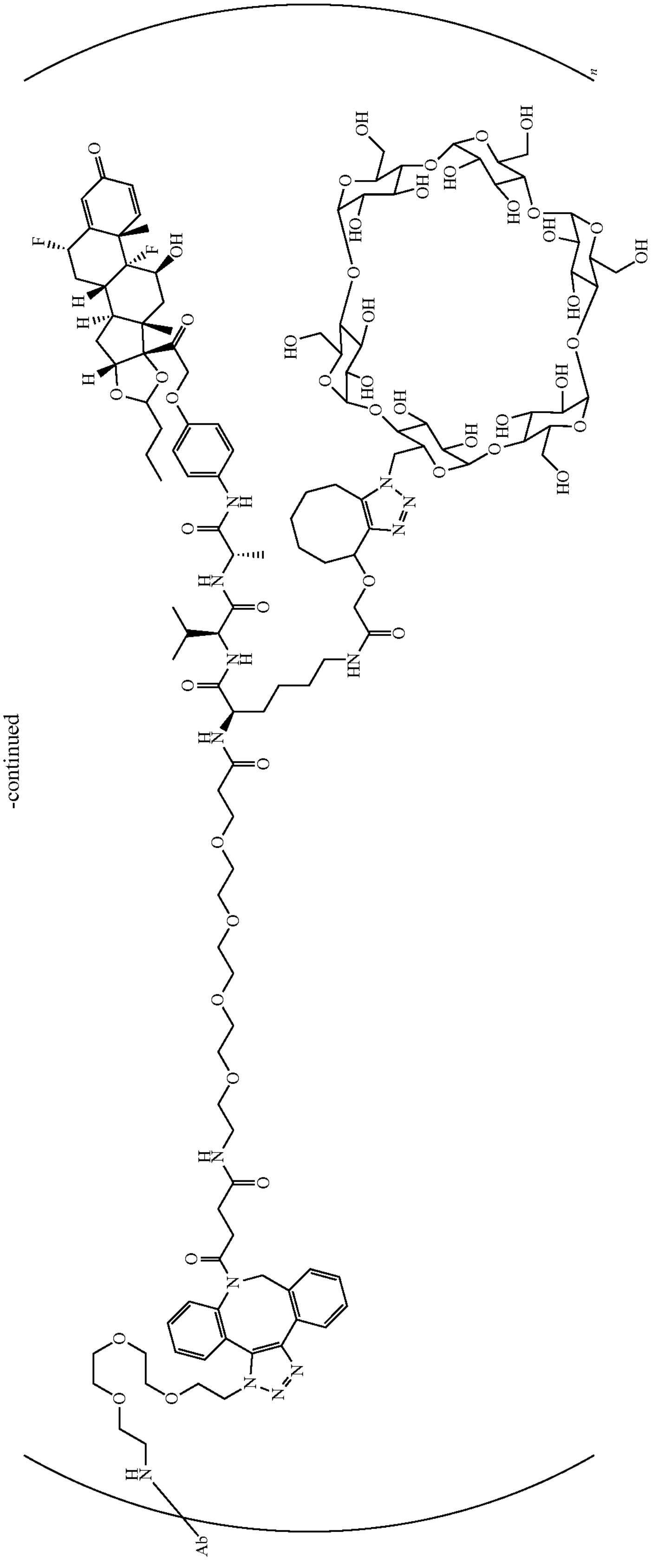

or a regioisomer, or a stereoisomeric form, pharmaceutically acceptable salt thereof, or solvate thereof, wherein Ab is an antibody or antigen-binding fragment thereof.

In some examples, set forth herein is a pharmaceutical composition comprising a compound set forth herein, including any of the foregoing compounds, or a pharmaceutically acceptable salt thereof, and a pharmaceutically acceptable excipient.

Those of skill in the art will recognize that the amino acid residue may be achiral or chiral, for example, an L-amino acid or D-amino acid. The amino acids generally include an amino acid side chain. The side chain can be the side chain of any amino acids known to those of skill. In certain embodiments, the side chain is the side chain of histidine, alanine, isoleucine, arginine, leucine, asparagine, lysine, aspartic acid, methionine, cysteine, phenylalanine, glutamic acid, threonine, glutamine, tryptophan, valine, ornithine, selenocysteine, serine, glycine, homoglycine (e.g., β-homoglycine), or tyrosine. Those of skill in the art will recognize that the peptide may be achiral or chiral, for example, including racemic DL-amino acids or non-racemic D- or L-amino acids and diastereomeric mixtures thereof. The side chains of the peptides are as described in the context of amino acids, above. Those of skill in the art will recognize that the N-alkyl amino acid residue includes an alkyl substituent, as defined herein, at the terminal amino group of the amino acid or the terminal amino group of the peptide.

In some examples, including any of the foregoing, subscript n is an integer from 0 to 30. In some examples, including any of the foregoing, subscript n is 0. In some examples, including any of the foregoing, subscript n is 1. In some examples, including any of the foregoing, subscript n is 2. In some examples, including any of the foregoing, subscript n is 3. In some examples, including any of the foregoing, subscript n is 4. In some examples, including any of the foregoing, subscript n is 5. In some examples, including any of the foregoing, subscript n is 6. In some examples, including any of the foregoing, subscript n is 7. In some examples, including any of the foregoing, subscript n is 8. In some examples, including any of the foregoing, subscript n is 9. In some examples, including any of the foregoing, subscript n is 10. In some examples, including any of the foregoing, subscript n is 11. In some examples, including any of the foregoing, subscript n is 12. In some examples, including any of the foregoing, subscript n is 13. In some examples, including any of the foregoing, subscript n is 14. In some examples, including any of the foregoing, subscript n is 15. In some examples, including any of the foregoing, subscript n is 16. In some examples, including any of the foregoing, subscript n is 17. In some examples, including any of the foregoing, subscript n is 18. In some examples, including any of the foregoing, subscript n is 19. In some examples, including any of the foregoing, subscript n is 20. In some examples, including any of the foregoing, subscript n is 21. In some examples, including any of the foregoing, subscript n is 22. In some examples, including any of the foregoing, subscript n is 23. In some examples, including any of the foregoing, subscript n is 24. In some examples, including any of the foregoing, subscript n is 25. In some examples, including any of the foregoing, subscript n is 26. In some examples, including any of the foregoing, subscript n is 27. In some examples, including any of the foregoing, subscript n is 28. In some examples, including any of the foregoing, subscript n is 29. In some examples, including any of the foregoing, subscript n is 30.

Binding Agents

Suitable binding agents for any of the conjugates provided in the instant disclosure include, but are not limited to, antibodies, lymphokines, hormones, growth factors, viral receptors, interleukins, or any other cell binding or peptide binding molecules or substances. Suitable binding agents also include polypeptides.

In some examples, including any of the foregoing, the binding agent (BA) is selected from any polypeptide. Example polypeptides include, but are not limited to, natural polypeptides and unnatural polypeptides. Example polypeptides include, but are not limited to, those produced from genetically modified organisms.

In some examples, including any of the foregoing, the BA is selected from receptors, cytokines, proteins, enzymes, binding agents, milk peptides, ribosomal peptides, nonribosomal peptides, peptones, and peptide fragments. In some examples, including any of the foregoing, the BA is selected selected from antimicrobial peptides, tachykinin peptides, vasoactive intestinal peptides, pancreatic polypeptide-related peptides, opiod peptides, and calcitonin peptides. In some examples, including any of the foregoing, the BA is selected B-type natriuretic peptide (BNP), lactotripeptides, neuropeptides, lipopeptides, proteoses, or hormones.

In some examples, including any of the foregoing, the BA is selected from short amino acid chains comprising two or more amino acids bonded together. In some examples, including any of the foregoing, the BA is selected from dipeptides (Val-Cit), tripeptides, and tetrapeptides (e.g., Val-Gly-Ser-Ala) having two, three, or four amino acids bonded together, respectively. In some examples, including any of the foregoing, the BA is selected from dipeptides, tripeptides, tetrapeptides, pentapeptides, hexapeptides, heptapeptides, octapeptides, nonapeptides, decapeptides, undecapeptides, and icosapeptides.

In some examples, including any of the foregoing, the BA is selected from any proteins. In some examples, the proteins include only natural amino acids. In some examples, the proteins further include non-natural amino acids. In some embodiments, the binding agent is an antibody of an antigen-binding fragment thereof. The antibody can be in any form known to those of skill in the art. The term "antibody", as used herein, means any antigen-binding molecule or molecular complex comprising at least one complementarity determining region (CDR) that specifically binds to or interacts with a particular antigen. The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the antibodies suitable for the compounds herein (or antigen-binding portion thereof) may be identical to the human germline sequences, or may be naturally or artificially modified. An amino acid consensus sequence may be defined based on a side-by-side analysis of two or more CDRs. The term “antibody”, as used herein, also includes antigen-binding fragments of full antibody molecules. The terms “antigen-binding portion” of an antibody, “antigen-binding fragment” of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc. Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression “antigen-binding fragment,” as used herein. An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain. In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$, (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art. In certain embodiments of the invention, antibodies of the invention are human antibodies. The term “human antibody”, as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term “human antibody”, as used herein, is not intended to include antibodies in which CDR sequences derived from the germline of another mammalian species, such as a mouse, have been grafted onto human framework sequences. The term “human antibody” does not include naturally occurring molecules that normally exist without modification or human intervention/manipulation, in a naturally occurring, unmodified living organism. The antibodies of the invention may, in some embodiments, be recombinant human antibodies. The term “recombinant human antibody”, as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo. Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification. The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form. The antibodies of the invention may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals. The antibodies used herein can comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention. Antibodies useful for the compounds herein also include antibodies comprising variants of any of the HCVR, LCVR, and/or CDR amino acid sequences disclosed herein having one or more conservative substitutions. The term "epitope" refers to an antigenic determinant that interacts with a specific antigen-binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstances, an epitope may include moieties of saccharides, phosphoryl groups, or sulfonyl groups on the antigen.

In certain embodiments, the antibody comprises a light chain. In certain embodiments, the light chain is a kappa light chain. In certain embodiments, the light chain is a lambda light chain. In certain embodiments, the antibody comprises a heavy chain. In some aspects, the heavy chain is an IgA. In some aspects, the heavy chain is an IgD. In some aspects, the heavy chain is an IgE. In some aspects, the heavy chain is an IgG. In some aspects, the heavy chain is an IgM. In some aspects, the heavy chain is an IgG1. In some aspects, the heavy chain is an IgG2. In some aspects, the heavy chain is an IgG3. In some aspects, the heavy chain is an IgG4. In some aspects, the heavy chain is an IgA1. In some aspects, the heavy chain is an IgA2.

In some embodiments, the antibody is an antibody fragment. In some aspects, the antibody fragment is an Fv fragment. In some aspects, the antibody fragment is a Fab fragment. In some aspects, the antibody fragment is a $F(ab')_2$ fragment. In some aspects, the antibody fragment is a Fab' fragment. In some aspects, the antibody fragment is an scFv (sFv) fragment. In some aspects, the antibody fragment is an scFv-Fc fragment.

In some embodiments, the antibody is a monoclonal antibody. In some embodiments, the antibody is a polyclonal antibody.

In some embodiments, the antibody is a chimeric antibody. In some embodiments, the antibody is a humanized antibody. In some embodiments, the antibody is a human antibody.

The antibody can have binding specificity for any antigen deemed suitable to those of skill in the art. In certain embodiments, the antigen is a transmembrane molecule (e.g., receptor) or a growth factor. Exemplary antigens include, but are not limited to, molecules such as renin; a growth hormone, including human growth hormone and bovine growth hormone; growth hormone releasing factor; parathyroid hormone; thyroid stimulating hormone; lipoproteins; alphal-antitrypsin; insulin A-chain; insulin B-chain; proinsulin; follicle stimulating hormone; calcitonin; luteinizing hormone; glucagon; clotting factors such as factor vmc, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta;

enkephalinase; RANTES (regulated on activation normally T-cell expressed and secreted); human macrophage inflammatory protein (MIP-I-alpha); a serum albumin, such as human serum albumin; Muellerian-inhibiting substance; relaxin A-chain; relaxin B-chain; prorelaxin; mouse gonadotropin-associated peptide; a microbial protein, such as beta-lactamase; DNase; 19E; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor such as aFGF and bFGF; fibroblast growth factor receptor 2 (FGFR2), epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(I-3)-IGF-I (brain IGF-I), insulin-like growth factor binding proteins, EpCAM, GD3, FLT3, PSMA, PSCA, MUCI, MUCI6, STEAP, CEA, TENB2, EphA receptors, EphB receptors, folate receptor, FOLRI, mesothelin, cripto, alphavbeta6, integrins, VEGF, VEGFR, EGFR, transferrin receptor, IRTA1, IRTA2, IRTA3, IRTA4, IRTA5; CD proteins such as CD2, CD3, CD4, CD5, CD6, CD8, CD11, CD14, CD19, CD20, CD21, CD22, CD25, CD26, CD28, CD30, CD33, CD36, CD37, CD38, CD40, CD44, CD52, CD55, CD56, CD59, CD70, CD79, CD80. CD81, CD103, CD105, CD134, CD137, CD138, CDI52, or an antibody which binds to one or more tumor-associated antigens or cell-surface receptors disclosed in US Publication No. 2008/0171040 or US Publication No. 2008/0305044 and incorporated in their entirety by reference; erythropoietin; osteoinductive factors; immunotoxins; a bone morphogenetic protein (BMP); an interferon, such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV envelope; transport proteins; homing receptors; addressins; regulatory proteins; integrins, such as CDIIa, CDIIb, CDIIc, CDI8, an ICAM, VLA-4 and VCAM; a tumor associated antigen such as AFP, ALK, B7H4, BAGE proteins, β-catenin, brc-abl, BRCA1, BORIS, CA9 (carbonic anhydrase IX), caspase-8, CD20, CD40, CD123, CDK4, CEA, CLEC12A, c-kit, cMET, CTLA4, cyclin-B1, CYP1B1, EGFR, EGFRvIII, endoglin, Epcam, EphA2, ErbB2/Her2, ErbB3/Her3, ErbB4/Her4, ETV6-AML, Fra-1, FOLR1, GAGE proteins (e.g., GAGE-1, -2), GD2, GD3, GloboH, glypican-3, GM3, gp100, Her2, HLA/B-raf, HLA/EBNA1, HLA/k-ras, HLA/MAGE-A3, hTERT, IGF1R, LGRS, LMP2, MAGE proteins (e.g., MAGE-1, -2, -3, -4, -6, and -12), MART-1, mesothelin, ML-IAP, Muc1, Muc16 (CA-125), MUM1, NA17, NGEP, NY-BR1, NY-BR62, NY-BR85, NY-ESO1, OX40, p15, p53, PAP, PAX3, PAXS, PCTA-1, PDGFR-α, PDGFR-β, PDGF-A, PDGF-B, PDGF-C, PDGF-D, PLAC1, PRLR, PRAME, PSCA, PSGR, PSMA (FOLH1), RAGE proteins, Ras, RGSS, Rho, SART-1, SART-3, Steap-1, Steap-2, STn, survivin, TAG-72, TGF-β, TMPRSS2, Tn, TNFRSF17, TRP-1, TRP-2, tyrosinase, and uroplakin-3, and fragments of any of the above-listed polypeptides. In some embodiments, the antigen is a tumor antigen, including antigens specific for a type of tumor or antigens that are shared, overexpressed or modified on a particular type of tumor. Examples include, but are not limited to: alpha-actinin-4 with lung cancer, ARTC1 with melanoma, BCR-ABL fusion protein with chronic myeloid leukemia, B-RAF, CLPP or Cdc27 with melanoma, CASP-8 with squamous cell carcinoma, and hsp70-2 with renal cell carcinoma as well as the following shared tumor-specific antigens, for example: BAGE-1, GAGE, GnTV, KK-LC-1, MAGE-A2, NA88-A, TRP2-INT2. In some embodiments, the antigen is PRLR or HER2. In some embodiments, the antibody is an anti-PRLR or anti HER2 antibody.

The binding agent linkers can be bonded to the binding agent, e.g., antibody or antigen-binding molecule, through an attachment at a particular amino acid within the antibody or antigen-binding molecule. Exemplary amino acid attachments that can be used in the context of this aspect of the disclosure include, e.g., lysine (see, e.g., U.S. Pat. No. 5,208,020; US 2010/0129314; Hollander et al., *Bioconjugate Chem.*, 2008, 19:358-361; WO 2005/089808; U.S. Pat. No. 5,714,586; US 2013/0101546; and US 2012/0585592), cysteine (see, e.g., US 2007/0258987; WO 2013/055993; WO 2013/055990; WO 2013/053873; WO 2013/053872; WO 2011/130598; US 2013/0101546; and U.S. Pat. No. 7,750,116), selenocysteine (see, e.g., WO 2008/122039; and Hofer et al., *Proc. Natl. Acad. Sci., USA,* 2008, 105:12451-12456), formyl glycine (see, e.g., Carrico et al., Nat. Chem. Biol., 2007, 3:321-322; Agarwal et al., Proc. *Natl. Acad. Sci., USA,* 2013, 110:46-51, and Rabuka et al., *Nat. Protocols,* 2012, 10:1052-1067), non-natural amino acids (see, e.g., WO 2013/068874, and WO 2012/166559), and acidic amino acids (see, e.g., WO 2012/05982). Linkers can also be conjugated to an antigen-binding protein via attachment to carbohydrates (see, e.g., US 2008/0305497, WO 2014/065661, and Ryan et al., *Food & Agriculture Immunol.,* 2001, 13:127-130).

In some examples, the binding agent is an antibody or antigen binding molecule, and the antibody is bonded to the linker through a lysine residue. In some embodiments, the antibody or antigen binding molecule is bonded to the linker through a cysteine residue.

Linkers can also be conjugated to one or more glutamine residues via transglutaminase-based chemo-enzymatic conjugation (see, e.g., Dennler et al., *Bioconjugate Chem.* 2014, 25, 569-578). For example, in the presence of transglutaminase, one or more glutamine residues of an antibody can coupled to a primary amine compound. Primary amine compounds include payloads or linker-payloads, which directly provide antibody drug conjugates via transglutaminase-mediated coupling. Primary amine compounds also include linkers and spacers that are functionalized with reactive groups that can be subsequently reacted with further compounds towards the synthesis of antibody drug conjugates. Antibodies comprising glutamine residues can be isolated from natural sources or engineered to comprise one or more glutamine residues. Techniques for engineering glutamine residues into an antibody polypeptide chain (glutaminyl-modified antibodies or antigen binding molecules) are within the skill of the practitioners in the art. In certain embodiments, the antibody is aglycosylated.

In certain embodiments, the antibody or a glutaminyl-modified antibody or antigen binding molecule comprises at least one glutamine residue in at least one polypeptide chain sequence. In certain embodiments, the antibody or a glutaminyl-modified antibody or antigen binding molecule comprises two heavy chain polypeptides, each with one Gln295 residue. In further embodiments, the antibody or a glutaminyl-modified antibody or antigen binding molecule comprises one or more glutamine residues at a site other than a heavy chain Gln 295. Included herein are antibodies bearing N297Q mutation(s) described herein. Briefly, in some embodiments, an antibody including a glutamine residue is treated with a primary amine compound, described in more detail below, in the presence of the enzyme transglutaminase. In some embodiments, an antibody including a Asn297Gln (N297Q) mutation is treated with a primary amine compound, described in more detail below, in the presence of the enzyme transglutaminase. In some embodiments, an antibody including a Gln295 (Q295) residue is treated with a primary amine compound, described in more detail below, in the presence of the enzyme transglutaminase. In some embodiments, an antibody including a Gln55 (Q55) residue is treated with a primary amine compound, described in more detail below, in the presence of the enzyme transglutaminase. For example, in some embodiments, such an antibody can be prepared by site-directed mutagenesis to remove or disable a sequence or to insert a glutamine residue at a site apart from any interfering structure. Such an antibody also can be isolated from natural or artificial sources.

Primary Amine Compounds

The primary amine compound useful for the transglutaminase mediated coupling of an antibody (or antigen binding compound) comprising a glutamine can be any primary amine compound deemed useful by the practitioner of ordinary skill. Generally, the primary amine compound has the formula $H_2N—R$, where R can be any group compatible with the antibody and reaction conditions. In certain embodiments, R is alkyl, substituted alkyl, heteroalkyl, or substituted heteroalkyl.

In some embodiments, the primary amine compound comprises a reactive group or protected reactive group. Useful reactive groups include azides, alkynes, cycloalkynes, thiols, alcohols, ketones, aldehydes, acids, esters, hydrozides, analines, and amines. In certain embodiments, the reactive group is selected from the group consisting of azide, alkyne, sulfhydryl, cycloalkyne, aldehyde, and carboxyl.

In certain embodiments, the primary amine compound is according to the formula $H_2N$-LL-X, where LL is a divalent spacer and X is a reactive group or protected reactive group. In particular embodiments, LL is a divalent polyethylene glycol (PEG) group. In certain embodiments, X is selected from the group consisting of —SH, —$N_3$, alkyne, aldehyde, and tetrazole. In particular embodiments, X is —$N_3$.

In certain embodiments, the primary amine compound is according to one of the following formulas:

$H_2N—(CH_2)_n—X$;

$H_2N—(CH_2CH_2O)_n—(CH_2)_p—X$;

$H_2N—(CH_2)_n—N(H)C(O)—CH_2)_m—X$;

$H_2N—(CH_2CH_2O)_n—N(H)C(O)—CH_2CH_2O)_m—(CH_2)_p—X$;

$H_2N—(CH_2)_n—C(O)N(H)—(CH_2)_p—X$;

$H_2N—(CH_2CH_2O)_n—C(O)N(H)—(CH_2CH_2O)_m—(CH_2)_p—X$;

$H_2N—(CH_2)_n—N(H)C(O)—(CH_2CH_2O)_m—(CH_2)_p—X$;

$H_2N—(CH_2CH_2O)_n—N(H)C(O)—CH_2)_m—X$;

$H_2N—(CH_2)_n—C(O)N(H)—(CH_2CH_2O)_m—(CH_2)_p—X$; and $H_2N—(CH_2CH_2O)_n—C(O)N(H)—(CH_2)_m—X$;

where n is an integer selected from 1 to 12;

m is an integer selected from 0 to 12;

p is an integer selected from 0 to 2;

and X is selected from the group consisting of —SH, —$N_3$, —CECH, —C(O)H, tetrazole, and any of

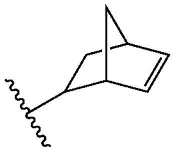

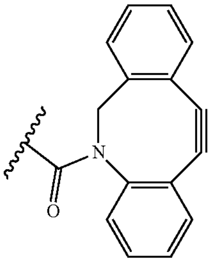

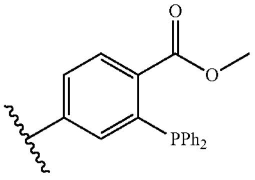

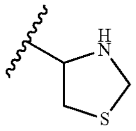

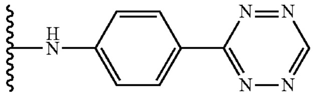
.

In the above, any of the alkyl or alkylene (i.e., —$CH_2$—) groups can optionally be substituted, for example with $C_{1-6}$ alkyl, methylformyl, or —$SO_3H$. In certain embodiments, the alkyl groups are unsubstituted.

In certain embodiments, the primary amine compound is selected from the group consisting of:

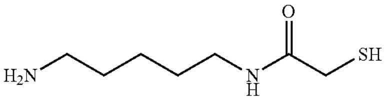

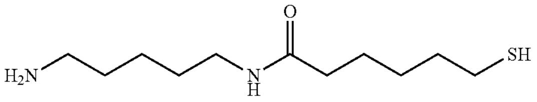

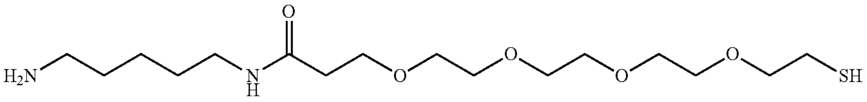

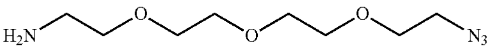

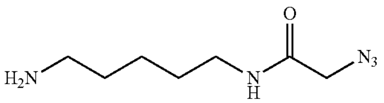

and

-continued

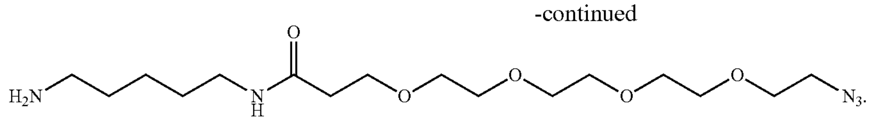

In particular embodiments, the primary amine compound is

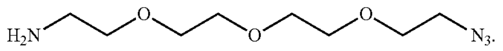

Exemplary conditions for the above reactions are provided in the Examples below.

Linkers

The linker LL portion of the conjugates described herein is a moiety, for instance a divalent moiety, that covalently links a binding agent to a payload compound described herein. In other instances, the linker LL is a trivalent or multivalent moiety that covalently links a binding agent to a payload compound described herein. Suitable linkers may be found, for example, in *Antibody-Drug Conjugates and Immunotoxins*; Phillips, G. L., Ed.; Springer Verlag: New York, 2013; Antibody-Drug Conjugates; Ducry, L., Ed.; Humana Press, 2013*; Antibody-Drug Conjugates*; Wang, J., Shen, W.-C., and Zaro, J. L., Eds.; Springer International Publishing, 2015, the contents of each incorporated herein in their entirety by reference. Payload compounds include compounds of FIG. 1, and their residues following bonding or incorporation with linker LL. Those of skill in the art will recognize that certain functional groups of the payload moieties are convenient for linking or bonding to linkers and/or binding agents. Those groups include amines, hydroxyls, phosphates, and sugars.

In certain embodiments, the linkers are stable in physiological conditions. In certain embodiments, the linkers are cleavable, for instance, able to release at least the payload portion in the presence of an enzyme or at a particular pH range or value. In some embodiments, a linker comprises an enzyme-cleavable moiety. Illustrative enzyme-cleavable moieties include, but are not limited to, peptide bonds, ester linkages, hydrazones, and disulfide linkages. In some embodiments, the linker comprises a cathepsin-cleavable linker.

In some embodiments, the linker comprises a non-cleavable moiety. In some embodiments, the non-cleavable linker is derived from

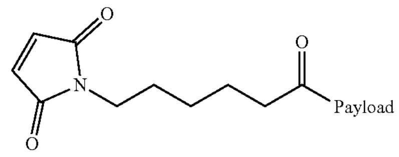

or a residue thereof. In some embodiments, the non-cleavable linker-payload is

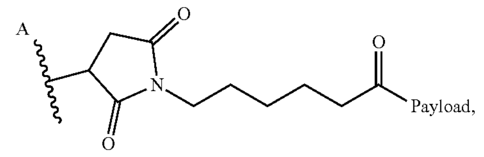

or a regioisomer thereof. In some embodiments, the non-cleavable linker is derived from

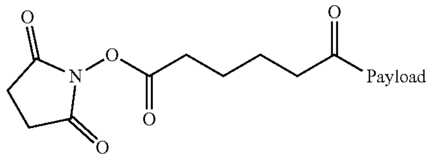

or a residue thereof. In some embodiments, the non-cleavable linker-payload is

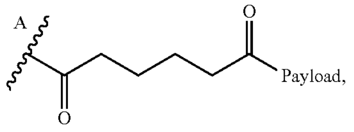

or a regioisomer thereof. In one embodiment, the linker is maleimide cyclohexane carboxylate or 4-(N-maleimidomethyl)cyclohexanecarboxylic acid (MCC). In the structures,  indicates a bond to a binding agent. In the structures, in some examples, 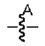 indicates a click chemistry residue which results from the reaction of, for example, a binding agent and a linker payload.

In some embodiments, suitable linkers include, but are not limited to, those that are chemically bonded to two cysteine residues of a single binding agent, e.g., antibody. Such linkers can serve to mimic the antibody's disulfide bonds that are disrupted as a result of the conjugation process.

In some embodiments, the linker comprises one or more amino acids. Suitable amino acids include natural, non-natural, standard, non-standard, proteinogenic, non-proteinogenic, and L-, or D-α-amino acids. In some embodiments, the linker comprises alanine, valine, leucine, isoleucine, methionine, tryptophan, phenylalanine, proline, glycine, serine, threonine, cysteine, tyrosine, asparagine, glutamine, aspartic acid, glutamic acid, lysine, arginine, histidine, or citrulline, a derivative thereof, or combination thereof. In certain embodiments, one or more side chains of the amino acids is linked to a side chain group, described below. In some embodiments, the linker comprises valine and citrulline. In some embodiments, the linker comprises lysine, valine, and citrulline. In some embodiments, the linker comprises lysine, valine, and alanine. In some embodiments, the linker comprises valine and alanine.

In some embodiments, the linker comprises a self-immolative group. The self-immolative group can be any such group known to those of skill. In particular embodiments, the self-immolative group is p-aminobenzyl (PAB), or a derivative thereof. Useful derivatives include p-aminobenzyloxycarbonyl (PABC). Those of skill will recognize that a self-immolative group is capable of carrying out a chemical reaction which releases the remaining atoms of a linker from a payload.

In some embodiments, the reactive group RG' can be any reactive group known to those of skill in the art to be capable of forming one or more bonds to the binding agent. The reactive group RG' is a moiety comprising a portion in its structure that is capable of reacting with the binding agent (e.g., reacting with an antibody at its cysteine or lysine residues, or at an azide moiety, for example, a PEG-$N_3$ functionalized antibody at one or more glutamine residues) to form a compound of Formula A, Aa, or Ab. Following conjugation to the binding agent, the reactive group becomes the reactive group (RG) or linker residue. Illustrative reactive groups include, but are not limited to, those that comprise haloacetyl, isothiocyanate, succinimide, N—hydroxysuccinimide, or maleimide portions that are capable of reacting with the binding agent.

In certain embodiments, reactive groups include, but are not limited to, alkynes. In certain embodiments, the alkynes are alkynes capable of undergoing 1,3-cycloaddition reactions with alkynes in the absence of copper catalysts such as strained alkynes. Strained alkynes are suitable for strain-promoted alkyne-azide cycloadditions (SPAAC), cycloalkynes, e.g., cyclooctynes, ane benzannulated alkynes. Suitable alkynes include, but are not limited to, dibenzoazacyclooctyne or

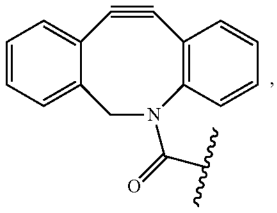

(DIBAC)

dibenzocyclooctyne or

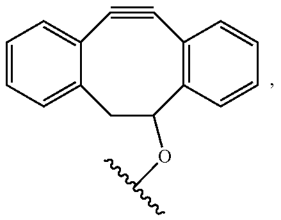

(DIBO)

biarylazacyclooctynone or

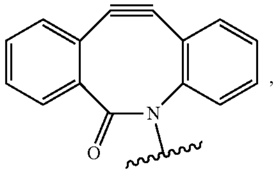

(BARAC)

difluorinated cyclooctyne or

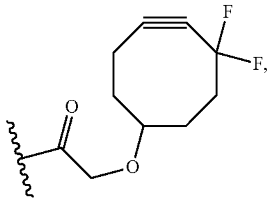

or

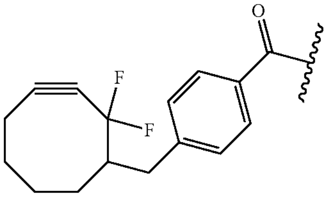

or

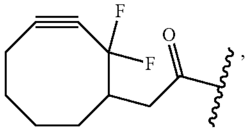

(DIFO)

substituted, e.g., fluorinated alkynes, aza-cycloalkynes, bicycle[6.1.0]nonyne or

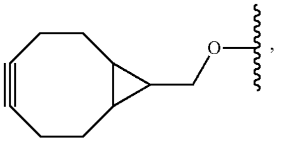

(BCN)

and derivatives thereof. Particularly useful alkynes include

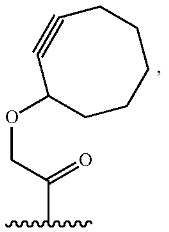

-continued

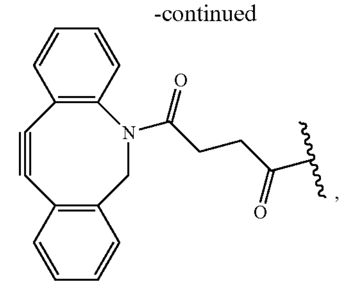

, and

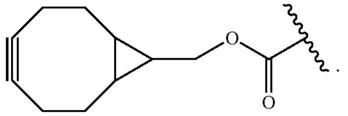

In certain embodiments, the binding agent is bonded directly to RG. In certain embodiments, the binding agent is bonded to RG via a spacer. In particular embodiments, the binding agent is bonded to RG via a PEG spacer. In certain embodiments, the binding agent is prepared by functionalizing with one or more azido groups. Each azido group is capable of reacting with RG' to form RG. In particular embodiments, the binding agent is derivatized with -PEG-$N_3$ linked to a glutamine residue. Exemplary —$N_3$ derivatized binding agents, methods for their preparation, and methods for their use in reacting with RG' are provided herein. In certain embodiments, RG' is an alkyne suitable for participation in 1,3-cycloadditions, and RG' is a 1,2,3-triazolyl moiety formed from the reaction of RG' with an azido-functionalized binding agent. By way of further example, in certain embodiments, RG is linked to the binding agent as shown in

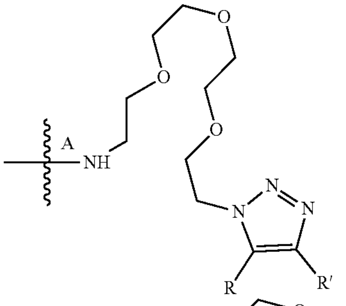

or

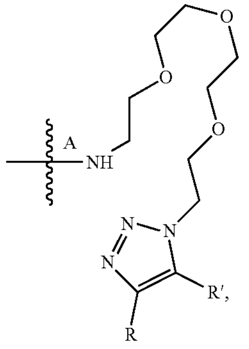

or a mixture of each regioisomer. Each R and R' is as described herein.

In the formulas, herein, each $AA^1$ is an amino acid. In some examples in the formulas, herein, each $AA^2$ is an amino acid. In some examples in the formulas, herein, each $AA^2$ is a di-peptide. In some examples in the formulas, herein, each $AA^2$ is a tri-peptide. Suitable amino acids for each $AA^1$ or $AA^2$ include natural, non-natural, standard, non-standard, proteinogenic, non-proteinogenic, and L-, or D-amino acids. In some embodiments, the linker comprises alanine, valine, leucine, isoleucine, methionine, tryptophan, phenylalanine, proline, glycine, serine, threonine, cysteine, tyrosine, asparagine, glutamine, aspartic acid, glutamic acid, lysine, arginine, histidine, or citrulline, a derivative thereof, or a combination thereof. In certain embodiments, one or more side chains of the amino acids are linked to a side chain group, described below. In some embodiments, the $AA^2$ is valine-citrulline. In some embodiments, the $AA^2$ is citrulline-valine. In some embodiments, the $AA^2$ is valine-alanine. In some embodiments, the $AA^2$ is alanine-valine. In some embodiments, the $AA^2$ is valine-glycine. In some embodiments, the $AA^2$ is glycine-valine. In some embodiments, the $AA^2$ is valine-citrulline. In some embodiments, the $AA^2$ is citrulline-valine. In some embodiments, the $AA^2$ glutamate-valine-citrulline. In some embodiments, the $AA^2$ is glutamine-valine-citrulline. In some embodiments, the $AA^2$ is lysine-valine-alanine. In some embodiments, the $AA^2$ is lysine-valine-citrulline. In some embodiments, the $AA^2$ is glutamate-valine-citrulline. In some embodiments, the $AA^2$ is glutamine-valine-citrulline-PABC.

Those of skill will recognize PABC as a residue of p-aminobenzyloxycarbonyl with the following structure:

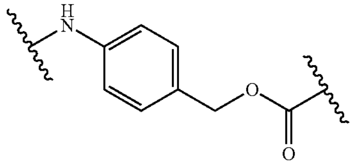

or

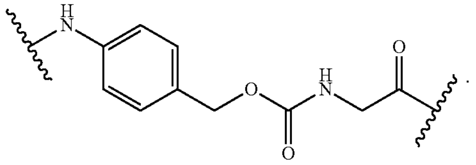

The PABC residue has been shown to facilitate cleavage of certain linkers in vitro and in vivo.

In some examples, the linker is MC-Suc-PEG$_m$-vc-PAB. Subscript m is an integer from 0 to 4. In some examples subscript m is 0. In some examples subscript m is 1. In some examples subscript m is 2. In some examples subscript m is 3. In some examples subscript m is 4.

In some examples, the linker is DIBAC-suc-PEG$_m$-vc-PAB. Subscript m is an integer from 0 to 4. In some examples subscript m is 0. In some examples subscript m is 1. In some examples subscript m is 2. In some examples subscript m is 3. In some examples subscript m is 4.

In some examples, the linker is MAL-PEG$_m$-Lys(COT-CD)-vc-PAB. Subscript m is an integer from 0 to 4. In some examples subscript m is 0. In some examples subscript m is 1. In some examples subscript m is 2. In some examples subscript m is 3. In some examples subscript m is 4. In some examples, the linker is MAL-PEG$_m$-N(suc-DIBAC-CD) Lys-vc-PAB. Subscript m is an integer from 0 to 4. In some examples subscript m is 0. In some examples subscript m is 1. In some examples subscript m is 2. In some examples subscript m is 3. In some examples subscript m is 4.

In some examples, the linker is DIBAC-suc-Lys(mc-pip-CD)-vc-PAB. Subscript m is an integer from 0 to 4. In some examples subscript m is 0. In some examples subscript m is 1. In some examples subscript m is 2. In some examples subscript m is 3. In some examples subscript m is 4.

In some examples, the linker is DIBAC-Suc-$PEG_m$-N(CD-COT)Lys-vc-PAB. Subscript m is an integer from 0 to 4. In some examples subscript m is 0. In some examples subscript m is 1. In some examples subscript m is 2. In some examples subscript m is 3. In some examples subscript m is 4.

In some examples, the linker is BCN-$PEG_m$-Lys(COT-CD)-vc-PAB. Subscript m is an integer from 0 to 4. In some examples subscript m is 0. In some examples subscript m is 1. In some examples subscript m is 2. In some examples subscript m is 3. In some examples subscript m is 4.

In some examples, the linker is DIBAC-Suc-$PEG_m$-D-Lys(PEG4-COT-CD)-vc-PAB. Subscript m is an integer from 0 to 4. In some examples subscript m is 0. In some examples subscript m is 1. In some examples subscript m is 2. In some examples subscript m is 3. In some examples subscript m is 4.

In some examples, the linker is BCN-$PEG_4$-D-Lys-($PEG_m$-COT-CD)-vc-PAB. Subscript m is an integer from 0 to 4. In some examples subscript m is 0. In some examples subscript m is 1. In some examples subscript m is 2. In some examples subscript m is 3. In some examples subscript m is 4.

In some examples, the linker is DIBAC-suc-$PEG_m$-Val-Ala. Subscript m is an integer from 0 to 4. In some examples subscript m is 0. In some examples subscript m is 1. In some examples subscript m is 2. In some examples subscript m is 3. In some examples subscript m is 4.

In some examples, the linker is $PEG_m$-D-Lys-Val-Ala. Subscript m is an integer from 0 to 4. In some examples subscript m is 0. In some examples subscript m is 1. In some examples subscript m is 2. In some examples subscript m is 3. In some examples subscript m is 4.

In some examples, the linker is DIBAC-suc-$PEG_m$-D-Lys($PEG_m$)-vcPAB. Subscript m is an integer from 0 to 4. In some examples subscript m is 0. In some examples subscript m is 1. In some examples subscript m is 2. In some examples subscript m is 3. In some examples subscript m is 4.

In some examples, the linker is BCN-$PEG_m$-D-Lys($PEG_m$)-Val-Ala. Subscript m is an integer from 0 to 4. In some examples subscript m is 0. In some examples subscript m is 1. In some examples subscript m is 2. In some examples subscript m is 3. In some examples subscript m is 4.

In some examples, the linker is BCN-$PEG_m$-D-Lys($PEG_m$)-vcPAB. Subscript m is an integer from 0 to 4. In some examples subscript m is 0. In some examples subscript m is 1. In some examples subscript m is 2. In some examples subscript m is 3. In some examples subscript m is 4.

In some examples, the linker is BCN-$PEG_4$-D-Lys-Val-Ala. Subscript m is an integer from 0 to 4. In some examples subscript m is 0. In some examples subscript m is 1. In some examples subscript m is 2. In some examples subscript m is 3. In some examples subscript m is 4.

In some examples, the linker is DIBAC-suc-$PEG_m$-D-Lys-vcPAB. Subscript m is an integer from 0 to 4. In some examples subscript m is 0. In some examples subscript m is 1. In some examples subscript m is 2. In some examples subscript m is 3. In some examples subscript m is 4.

In some examples, the linker is MC-Suc-$PEG_4$-vc-PAB.

In some examples, the linker is DIBAC-suc-$PEG_4$-vc-PAB.

In some examples, the linker is MAL-Lys(suc-DIBAC-CD)-vc-PAB.

In some examples, the linker is MAL-$PEG_4$-Lys(COT-CD)-vc-PAB.

In some examples, the linker is MAL-$PEG_4$-N(suc-DIBAC-CD)Lys-vc-PAB.

In some examples, the linker is DIBAC-suc-Lys(mc-pip-CD)-vc-PAB.

In some examples, the linker is DIBAC-Suc-$PEG_4$-N(CD-COT)Lys-vc-PAB.

In some examples, the linker is BCN-$PEG_4$-Lys(COT-CD)-vc-PAB.

In some examples, the linker is DIBAC-Suc-$PEG_4$-D-Lys(PEG4-COT-CD)-vc-PAB.

In some examples, the linker is BCN-PEG4-D-Lys($PEG_4$-COT-CD)-vc-PAB.

In some examples, the linker is DIBAC-suc-$PEG_4$-Val-Ala.

In some examples, the linker is DIBAC-suc-$PEG_4$-D-Lys(COT-CD)-Val-Ala.

In some examples, the linker is DIBAC-suc-$PEG_4$-Val-Ala.

In some examples, the linker is DIBAC-suc-$PEG_4$-D-Lys(COT-CD)-Val-Ala.

In some examples, the linker is DIBAC-suc-$PEG_4$-D-Lys(PEG4-COT-CD)-vcPAB.

In some examples, the linker is BCN-$PEG_4$-D-Lys($PEG_4$-COT-CD)-Val-Ala.

In some examples, the linker is BCN-$PEG_4$-D-Lys($PEG_4$-COT-CD)-vcPAB.

In some examples, the linker is DIBAC-suc-$PEG_4$-D-Lys($PEG_4$-COT-CD)-Val-Ala.

In some examples, the linker is BCN-$PEG_4$-D-Lys(COT-CD)-Val-Ala.

In some examples, the linker is DIBAC-suc-$PEG_4$-D-Lys(COT-CD)-vc-PAB.

Reactive Linker-Paylaods

Conjugates provided herein can be prepared from reactive linker-payloads with reactive groups RG' as described above. The reactive linker payloads can be linked to cyclodextrin groups, as described herein, and/or binding agents according to the methods described below.

In some embodiments, set forth herein is a reactive linker-payload which comprises a reactive group linked to at least one payload moiety and linked to at least one cyclodextrin moiety via a covalent linker, wherein said covalent linker is bonded directly or indirectly to each of the reactive group, the payload moiety, the cyclodextrin moiety.

As illustrated herein, in some examples, the reactive group is bonded directly to a covalent linker, such as a lysine amino acid. This means that the reactive group is one bond position away from the covalent linker. In some of these examples, the covalent linker is also bonded directly to a payload moiety. This means that the covalent linker is one bond position away from a payload such as, but not limited to, MMAE, a steroid, or any payload set forth herein. In some of these examples, the covalent linker is also bonded directly to a cyclodextrin moiety. This means that the covalent linker is one bond position away from a cyclodextrin, such as the cyclodextrins set forth herein. In some of these examples, the covalent linker is a lysine amino acid or a derivative thereof.

In other examples, the reactive group is bonded indirectly to a covalent linker. This means that the reactive group is more than one bond position away from the covalent linker. This also means that the reactive group is bonded through another moiety to the covalent linker. For example, the reactive group may be bonded to a polyethylene glycol group which is bonded to the covalent linker. In some of these examples, the covalent linker is also bonded indirectly to a payload moiety. This means that the covalent linker is more than one bond position away from a payload such as, but not limited to, MMAE, or a steroid, or any payload set forth herein. This also means that the covalent linker is bonded through another moiety to the payload. For example, the covalent linker may be bonded to a dipeptide, such as but not limited to Val-Ala or Val-Cit, which may be bonded to PAB which may be bonded to the payload. In some of these examples, the covalent linker is also bonded indirectly to a cyclodextrin moiety. This means that the covalent linker is more than one bond position away from a cyclodextrin, such as the cyclodextrins set forth herein. This also means that the covalent linker is bonded through another moiety to the cyclodextrin. For example, the covalent linker may be bonded to a polyethylene glycol group which may be bonded to reactive group which may be bonded to the cyclodextrin. In some of these examples, the covalent linker is a lysine amino acid or a derivative thereof.

In some embodiments, set forth herein is a reactive linker-payload according to Formula (II):

(II)

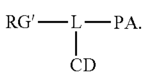

In Formula (II), RG' is a reactive group, L is a trivalent linker, CD is a cyclodextrin residue; and PA is a payload residue.

In some examples, the compound according to Formula (II) is a compound according to Formula (IIa):

(IIa)

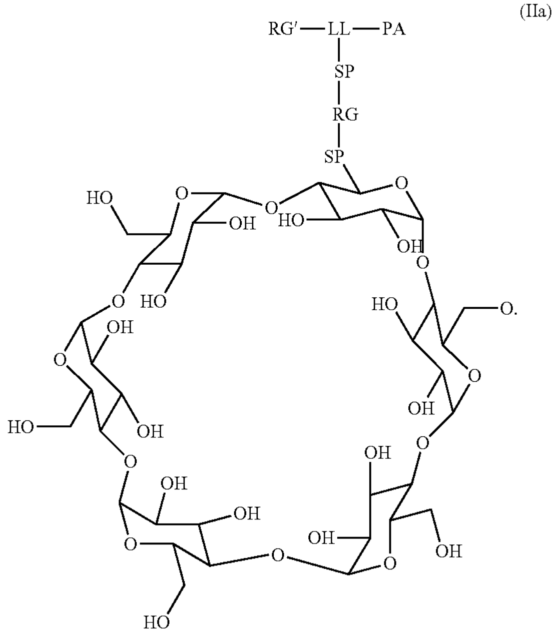

In Formula (IIa), RG' is a reactive group, RG is a reactive linker residue, LL is a trivalent linker, SP is, independently in each instance, absent or a spacer group; and PA is a payload.

In some examples, the compound according to Formula (II) is a compound according to Formula (IIb) or (IIc). In some examples, the compound according to Formula (II) is a compound according to Formula (IIb):

(IIb)

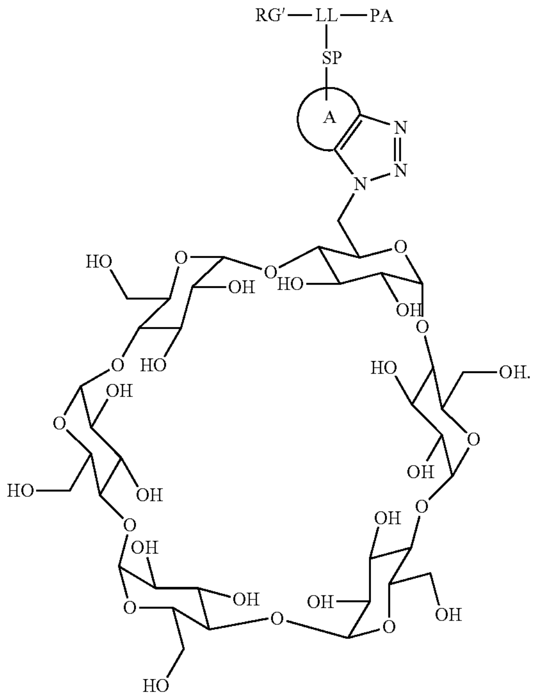

In either Formula (IIb) or (IIc), RG' is a reactive group, LL is a trivalent linker. SP is, independently in each instance, absent or is a spacer, ring A is fused to the triazole and is selected from the group consisting of cycloalkyl, cycloalkenyl, cycloalkynyl, heterocycloalkyl, heterocycloalkenyl, and heterocycloalkynyl, wherein cycloalkyl, cycloalkenyl, cycloalkynyl, heterocycloalkyl, heterocycloalkenyl, and heterocycloalkynyl are optionally substituted with alkyl, OH, or $NR^aR^b$, where each of $R^a$ and $R^b$ is alkyl or H, and PA is a payload. In some examples, ring A is an optionally substituted cycloalkyl. In some examples, ring A is an optionally substituted cylcoalkenyl. In some examples, ring A is an optionally substituted cycloalkynyl. In some examples, ring A is an optionally substituted heterocycloalkyl. In some examples, ring A is an optionally substituted heterocycloalkynyl. In some examples, included in either Formula (IIb) or (IIc) are the regioisomers (e.g., with respect to the triazole linkage), stereoisomers, and mixtures thereof of the compounds of either Formula (IIb) or (IIc).

In some examples, the compound according to Formula (II) is a compound according to Formula (IIc):

(IIc)

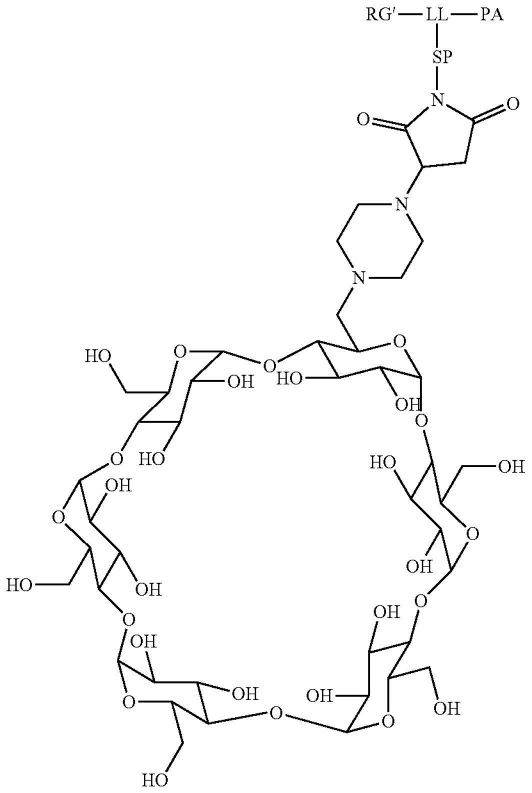

In Formula (IIc), RG' is a reactive group, LL is a trivalent linker. SP is absent or is a spacer, and PA is a payload. In some examples, included in Formula (IIb) (IIc) are the regioisomers (e.g., with respect to the succinimide linkage), stereoisomers, and mixtures thereof of Formula (IIc).

In some examples, the compound according to Formula (II) is a compound according to Formula (IIb1), (IIb2), (IIb3), (IIb4), (IIb5), or (IIb6). In some examples, the compound according to Formula (II) is a compound according to Formula (IIb1):

(IIb1)

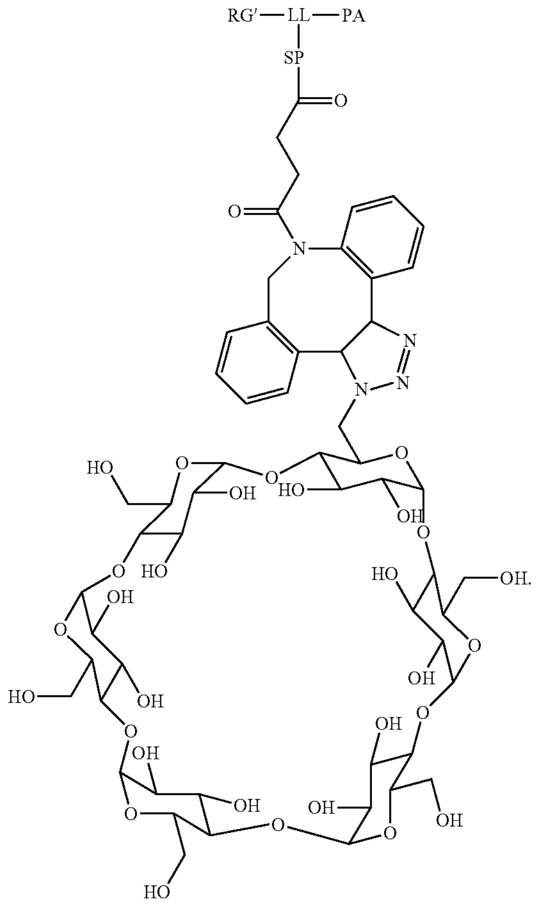

In Formula (IIb1), RG' is a reactive group, LL is a trivalent linker. SP is absent or is a spacer, and PA is a payload. In some examples, included in Formula (IIb1) are the regioisomers (e.g., with respect to the triazole linkage), stereoisomers, and mixtures thereof of the compounds of Formula (IIb1).

In some examples, the compound according to Formula (II) is a compound according to Formula (IIb2):

(IIb2)

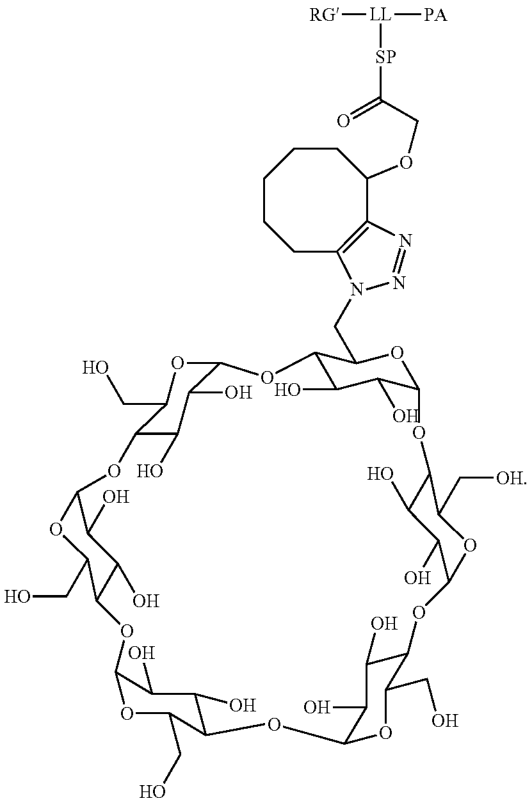

(IIb3)

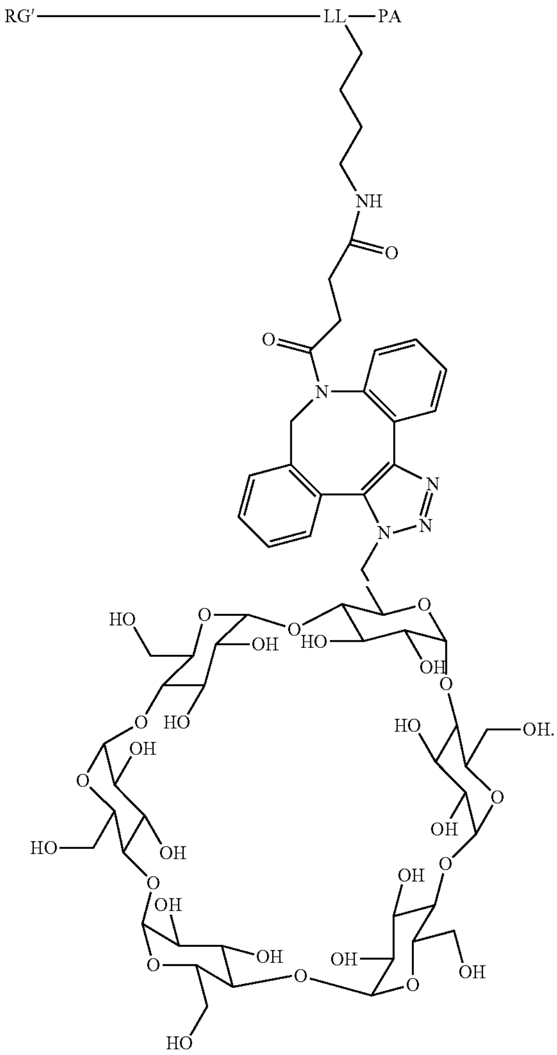

In Formula (IIb2), RG' is a reactive group, LL is a trivalent linker, SP is absent or is a spacer, and PA is a payload. In some examples, included in Formula (IIb2) are the regioisomers (e.g., with respect to the triazole linkage), stereoisomers, and mixtures thereof of the compounds of Formula (IIb2).

In some examples, the compound according to Formula (II) is a compound according to Formula (IIb3):

In Formula (IIb3), RG' is a reactive group, LL is a trivalent linker, and PA is a payload. In some examples, included in Formula (IIb3) are the regioisomers (e.g., with respect to the triazole linkage), stereoisomers, and mixtures thereof of the compounds of Formula (IIb3).

In some examples, the compound according to Formula (II) is a compound according to Formula (IIb4):

(IIb4)

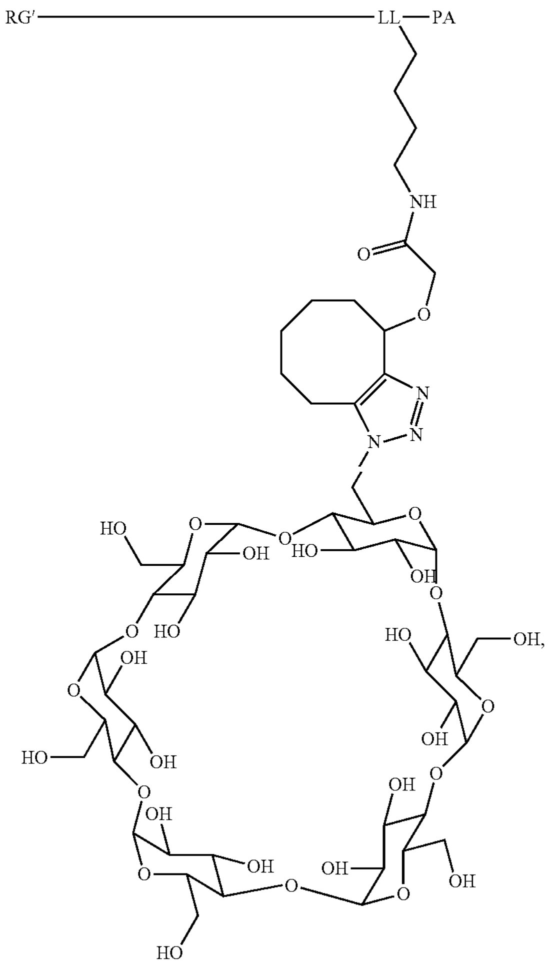

In Formula (IIb4), RG' is a reactive group, LL is a trivalent linker, and PA is a payload. In some examples, included in Formula (IIb4) are the regioisomers (e.g., with respect to the triazole linkage), stereoisomers, and mixtures thereof of the compounds of Formula (IIb4).

In some examples, the compound according to Formula (II) is a compound according to Formula (IIb5):

(IIb5)

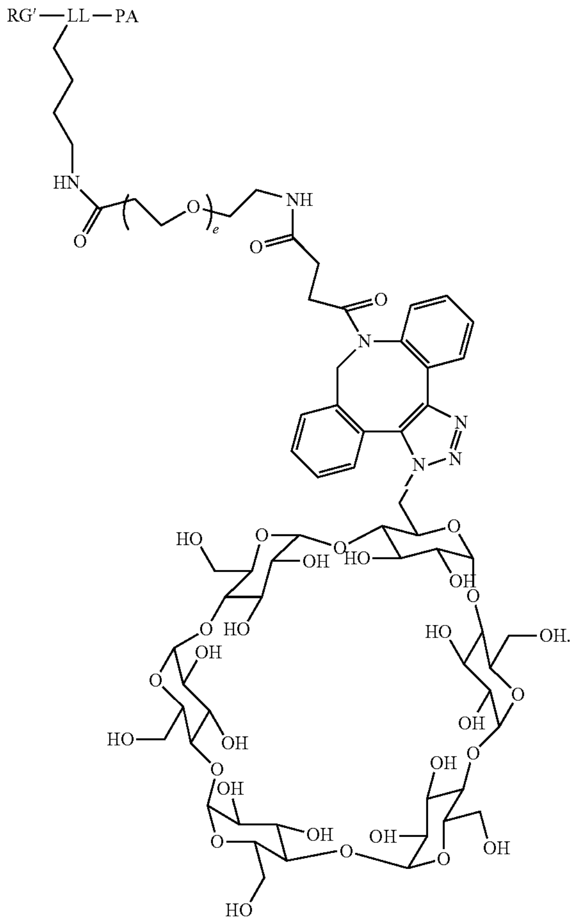

In Formula (IIb5), RG' is a reactive group, LL is a trivalent linker, ne is an integer from 0 to 4, and PA is a payload. In some examples, e is 0. In some examples, e is 1. In some examples, e is 2. In some examples, e is 3. In some examples, e is 4. In some examples, included in Formula (IIb5) are the regioisomers (e.g., with respect to the triazole linkage), stereoisomers, and mixtures thereof of the compounds of Formula (IIb5).

In some examples, the compound according to Formula (II) is a compound according to Formula (IIb6):

(IIb6)

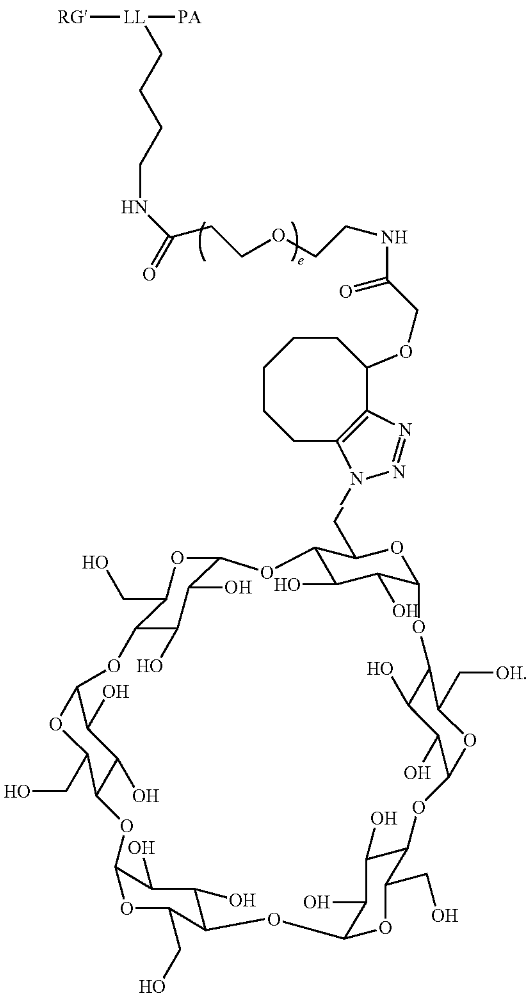

In Formula (IIb6), RG' is a reactive group, LL is a trivalent linker, ne is an integer from 0 to 4, and PA is a payload. In some examples, e is 0. In some examples, e is 1. In some examples, e is 2. In some examples, e is 3. In some examples, e is 4. In some examples, included in Formula (IIb6) are the regioisomers (e.g., with respect to the triazole linkage), stereoisomers, and mixtures thereof of the compounds of Formula (IIb6).

In some examples, the compound according to Formula (II) is a compound according to formula (IIc1):

(IIc1)

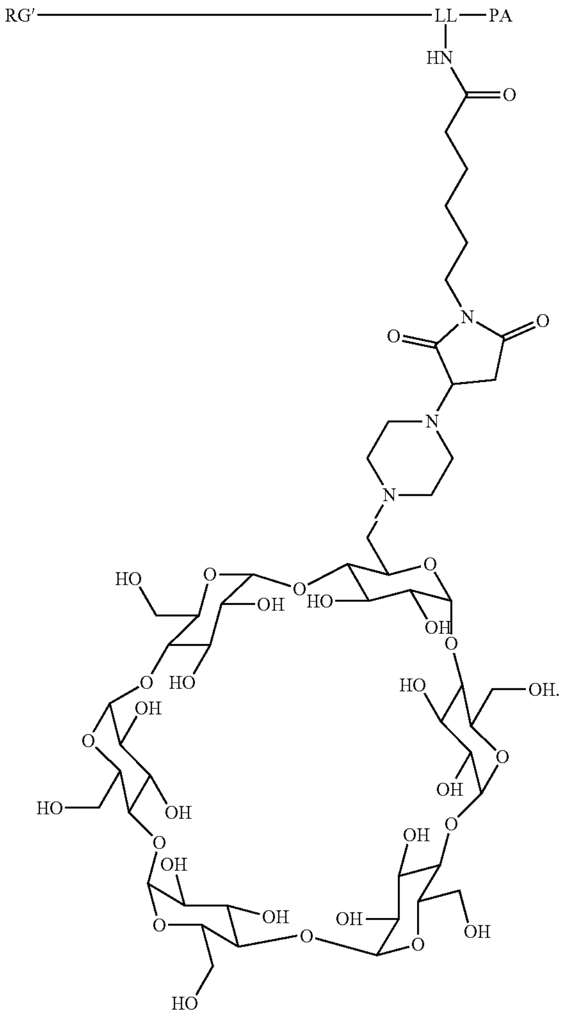

In Formula (IIc1), RG' is a binding agent, LL is a trivalent linker, and PA is a payload. Also included in Formula (IIc1) are regioisomers (e.g., with respect to the succinimide linkage), stereoisomers, and mixtures thereof.

In some examples, the compound according to Formula (II) is a compound according to Formula (IId):

(IId)

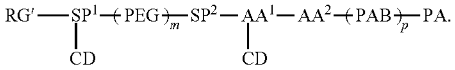

In Formula (IId), RG' is a reactive group, $SP^1$ and $SP^2$ are each, independently in each instance, absent or a spacer group residue, and wherein $SP^1$ comprises a trivalent linker, $AA^1$ is a trivalent linker comprising an amino acid residue; $AA^2$ is a di-peptide residue, PEG is a polyethylene glycol residue, PAB is

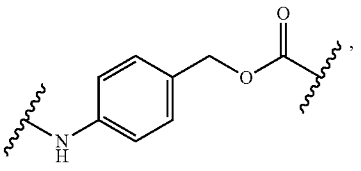 [SMILES: *Nc1ccc(COC(*)=O)cc1]

wherein the

indicates the atom through which the PAB is bonded to the adjacent groups in the formula, CD is, independently in each instance, absent or a cyclodextrin residue, wherein at least one CD is present, subscript m is an integer from 0 to 5, subscript p is 0 or 1; and PA is a payload moiety. In these examples, subscript m is 0, 1, 2, 3, 4, or 5. In some examples, subscript m is 0. In some examples, subscript m is 1. In some examples, subscript m is 2. In some examples, subscript m is 3. In some examples, subscript m is 4. In some examples, subscript m is 5. In some examples, subscript p is 0. In some examples, subscript p is 1.

In some instances of Formula (IId), CD is a modified-CD group according to the structure:

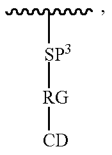

wherein RG is, independently in each instance; a reactive linker residue, $SP^3$ is, independently in each instance, absent or a spacer group residue selected from the group consisting of $C_{1-6}$ alkylene, $-NH-$, $-C(O)-$, $(-CH_2-CH_2-O)_e$, $-NH-CH_2-CH_2-(-O-CH_2-CH_2)_e-C(O)-$, $-C(O)-(CH_2)-C(O)-$, $-C(O)-NH-(CH_2)-$, and combinations thereof, wherein subscript e is an integer from 0 to 4, subscript u is an integer from 1 to 8, and subscript v is an integer from 1 to 8; q is an integer from 0 to 5, and

represents the atom through which the modified-CD group is attached to $SP^1$ or $AA^1$.

In some examples, the compound according to Formula (II) is a compound according to Formula (IIe):

(IIe)

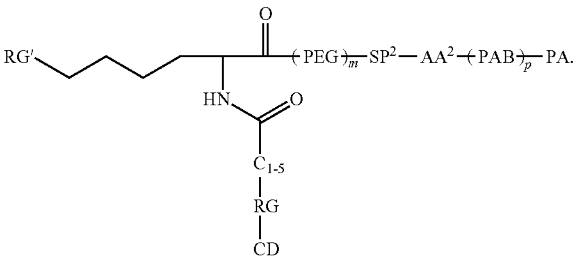

In Formula (IIe), RG' is a reactive group, RG is a reactive group residue; $SP^2$ is, independently in each instance, absent or a spacer group residue, and wherein $AA^2$ is a di-peptide residue, PEG is a polyethylene glycol residue, PAB is

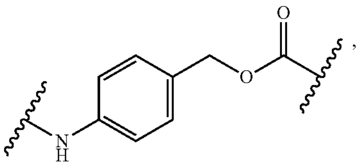 [SMILES: *Nc1ccc(COC(*)=O)cc1]

wherein the

indicates the atom through which the PAB is bonded to the adjacent groups in the formula, CD is absent or a cyclodextrin residue, subscript m is an integer from 0 to 5, subscript p is 0 or 1; and PA is a payload moiety. In these examples, subscript m is 0, 1, 2, 3, 4, or 5. In some examples, subscript m is 0. In some examples, subscript m is 1. In some examples, subscript m is 2. In some examples, subscript m is 3. In some examples, subscript m is 4. In some examples, subscript m is 5. In some examples, subscript p is 0. In some examples, subscript p is 1.

In some examples, the compound according to Formula (II) is a compound according to Formula (IIe1):

(IIe1)

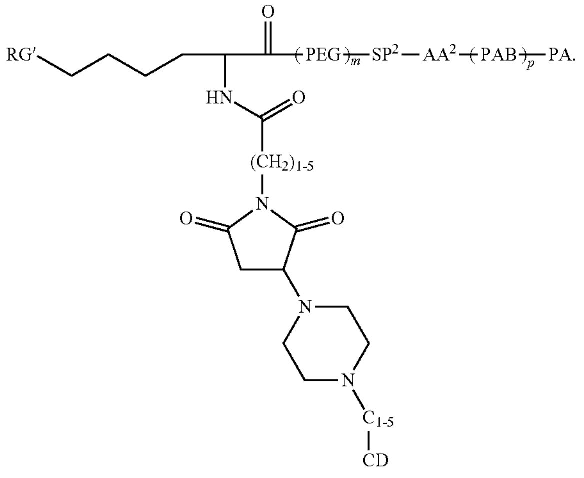

In Formula (IIe1), RG' is a reactive group, $SP^2$ is, independently in each instance, absent or a spacer group residue, and wherein $AA^2$ is a di-peptide residue, PEG is a polyethylene glycol residue, PAB is

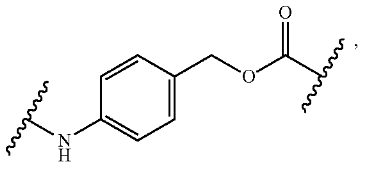 [SMILES: *Nc1ccc(COC(*)=O)cc1]

wherein the

indicates the atom through which the PAB is bonded to the adjacent groups in the formula, CD is absent or a cyclodextrin residue, subscript m is an integer from 0 to 5, subscript p is 0 or 1; and PA is a payload moiety. In these examples, subscript m is 0, 1, 2, 3, 4, or 5. In some examples, subscript m is 0. In some examples, subscript m is 1. In some examples, subscript m is 2. In some examples, subscript m is 3. In some examples, subscript m is 4. In some examples, subscript m is 5. In some examples, subscript p is 0. In some examples, subscript p is 1.

In some examples, the compound according to Formula (II) is a compound according to Formula (IIe2):

(IIe2)

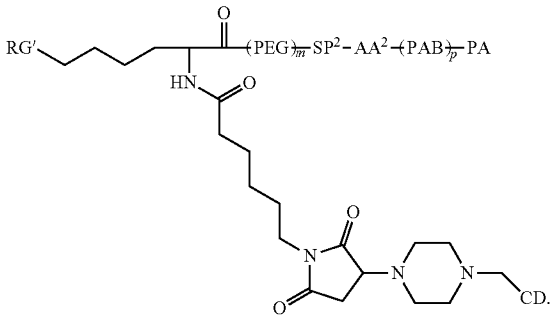

In Formula (IIe), RG' is a reactive group, $SP^2$ is, independently in each instance, absent or a spacer group residue, $AA^2$ is a di-peptide residue, PEG is a polyethylene glycol residue, PAB is

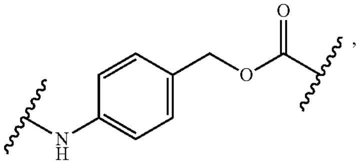 [SMILES: *Nc1ccc(COC(*)=O)cc1]

wherein the

indicates the atom through which the PAB is bonded to the adjacent groups in the formula, CD is a cyclodextrin residue, subscript m is an integer from 0 to 5, subscript p is 0 or 1, and PA is a payload moiety. In these examples, subscript m is 0, 1, 2, 3, 4, or 5. In some examples, subscript m is 0. In some examples, subscript m is 1. In some examples, subscript m is 2. In some examples, subscript m is 3. In some examples, subscript m is 4. In some examples, subscript m is 5. In some examples, subscript p is 0. In some examples, subscript p is 1.

In some examples, the compound according to Formula (II) is a compound according to Formula (IIf):

(IIf)

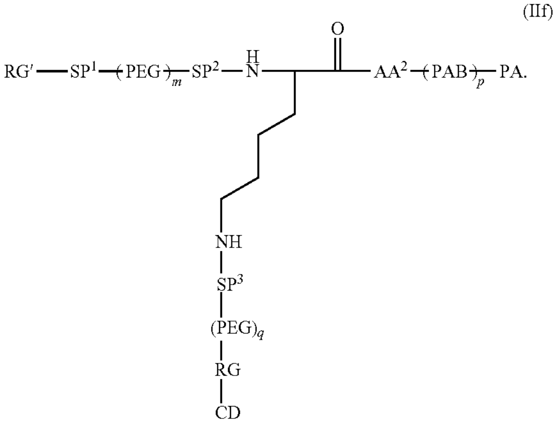

In Formula (IIf), RG' is a binding agent, RG is a reactive group residue, $SP^1$, $SP^2$, and $SP^3$ are, independently in each instance, absent or a spacer group residue, $AA^2$ is a dipeptide residue, PEG is a polyethylene glycol residue, PAB is

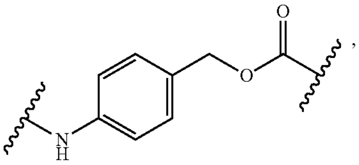 [SMILES: *Nc1ccc(COC(*)=O)cc1]

, wherein the

indicates the atom through which the PAB is bonded to the adjacent groups in the formula, CD is a cyclodextrin residue, subscript q is an integer from 0 to 5, subscript m is an integer from 0 to 5, subscript p is 0 or 1; and PA is a payload moiety. In some examples, m is 0. In some examples, m is 1. In some examples, m is 2. In some examples, m is 3. In some examples, m is 4. In some examples, m is 5. In some examples, p is 0. In some examples, p is 1. In some examples, q is 0. In some examples, q is 1. In some examples, q is 2. In some examples, q is 3. In some examples, q is 4. In some examples, q is 5. In some examples of Formula (IIf), $SP^1$ is absent, and $SP^2$ is independently in each instance, selected from the group consisting of $C_{1-6}$ alkylene, —NH—, —C(O)—, $(—CH_2—CH_2—O)_e$, $—NH—CH_2—CH_2—(—O—CH_2—CH_2)_e—C(O)—$, $—C(O)—(CH_2)_u—C(O)—$, $—C(O)—NH—(CH_2)_v—$, and combinations thereof, wherein subscript e is an integer from 0 to 4, subscript u is an integer from 1 to 8, and subscript v is an integer from 1 to 8.

In some examples, including any of the foregoing, the compound of Formula (II) comprises at least one CD group. In a specific example, a compound of Formula (I) is a compound of Formula (IIe), Formula (IIe1) or Formula (IIe2) as described herein and comprises one CD group. In another specific example, a compound of Formula (II) is a compound of Formula (IIf) as described herein and comprises one CD group.

In some examples, including any of the foregoing, CD is, independently in each instance, a cyclodextrin. In some examples, the CD is an α-cyclodextrin. In some examples, the CD is a β-cyclodextrin. In some examples, the CD is a γ-cyclodextrin. In any of these examples, the α-, β-, or γ-cyclodextrin is optionally substituted.

In some examples, including any of the foregoing, CD is, independently in each instance, selected from:

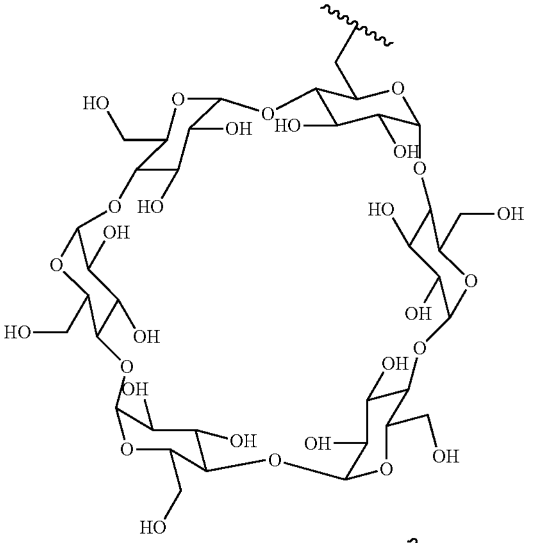

and

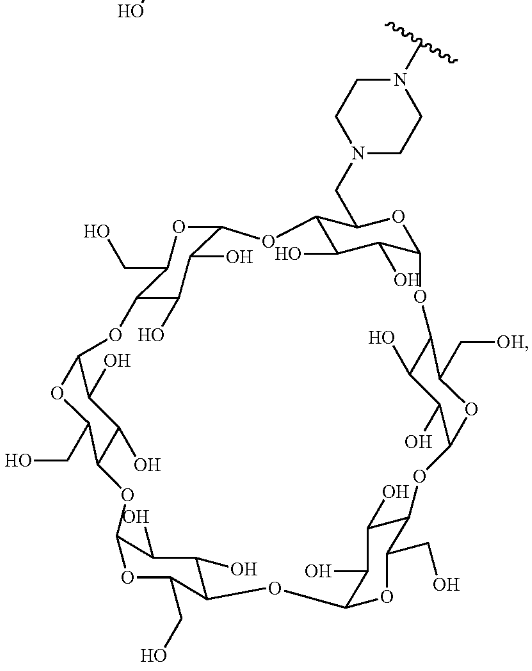

, wherein the

indicates the atom through which the CD is bonded to the adjacent groups in the formula. In certain examples, the CD is

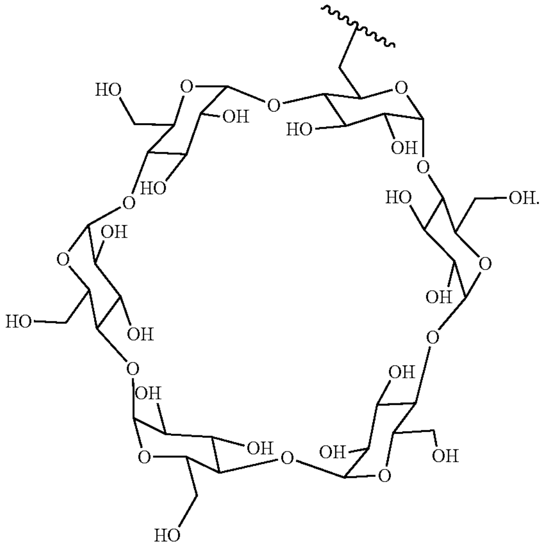 [SMILES: *CC1OC2OC3C(CO)OC(OC4C(CO)OC(OC5C(CO)OC(OC6C(CO)OC(OC7C(CO)OC(OC1C(O)C2O)C(O)C7O)C(O)C6O)C(O)C5O)C(O)C4O)C(O)C3O]

In certain examples, the CD is

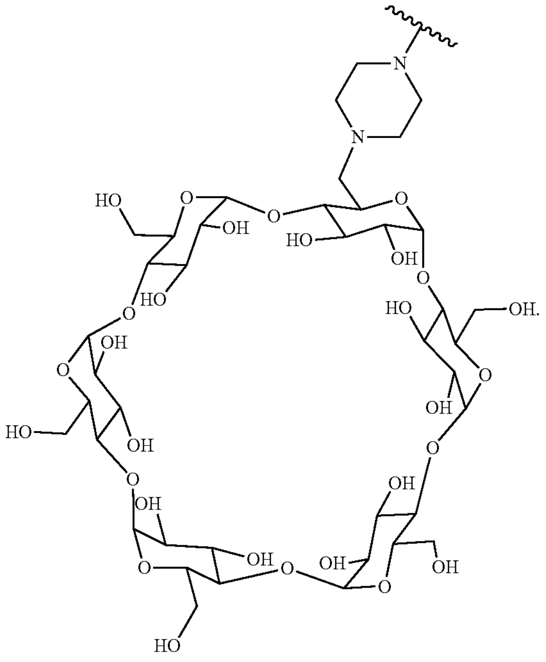 [SMILES: *N1CCN(CC2OC3OC4C(CO)OC(OC5C(CO)OC(OC6C(CO)OC(OC7C(CO)OC(OC8C(CO)OC(OC2C(O)C3O)C(O)C8O)C(O)C7O)C(O)C6O)C(O)C5O)C(O)C4O)CC1]

In some examples, including any of the foregoing, RG is, independently in each instance, a residue from a click chemistry reaction. In some examples, including any of the foregoing, RG, independently in each instance, comprises a triazole or a fused triazole.

In some examples, including any of the foregoing, RG' is, independently in each instance, selected from the group consisting of

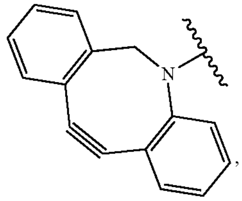,
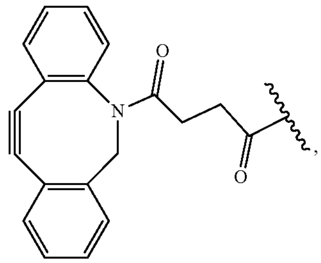,

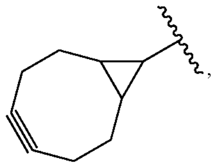,
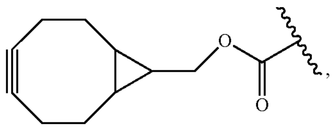,

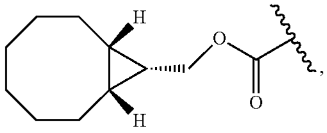,
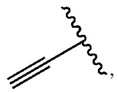,

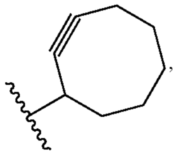,
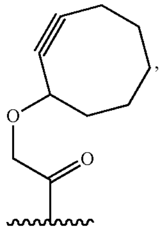, and
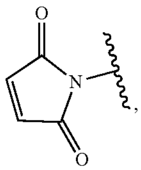, wherein the

indicates the atom through which the RG' is bonded to the adjacent groups in the formula. In certain of these examples, RG', independently in each instance, is

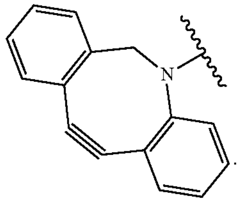 [SMILES: *N1Cc2ccccc2C#Cc2ccccc21].

In certain of these examples, RG', independently in each instance, is

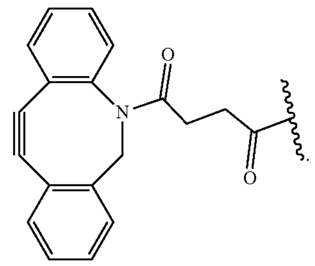 [SMILES: *C(=O)CCC(=O)N1Cc2ccccc2C#Cc2ccccc21]

In certain of these examples, RG', independently in each instance, is

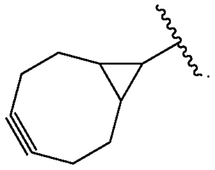 [SMILES: *C1C2CCC#CCCC12]

In certain of these examples, RG', independently in each instance, is

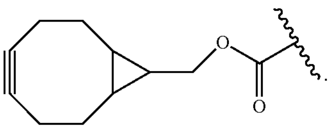 [SMILES: *C(=O)OCC1C2CCC#CCCC21]

In certain of these examples, RG', independently in each instance, is

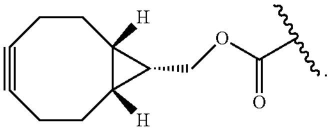 [SMILES: *C(=O)OC[C@@H]1[C@@H]2CCC#CCC[C@@H]21]

In certain of these examples, RG', independently in each instance, is

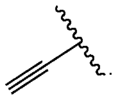 [SMILES: *C#C]

In certain of these examples, RG', independently in each instance, is

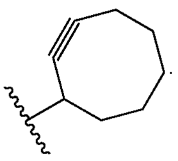 [SMILES: *C1C#CCCCCC1]

In certain of these examples, RG', independently in each instance, is

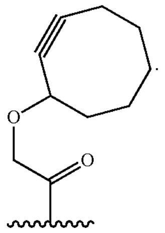 [SMILES: *C(=O)COC1C#CCCCCC1]

In certain of these examples, RG', independently in each instance, is

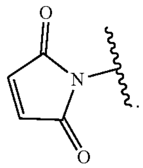 [SMILES: *N1C(=O)C=CC1=O]

In some examples, including any of the foregoing, RG is, independently in each instance, selected from the group consisting of

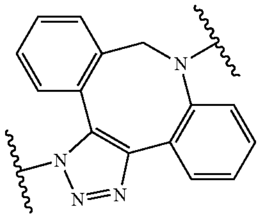,

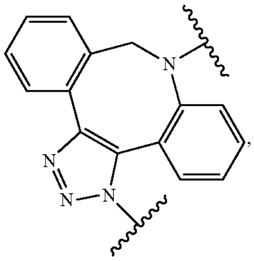,

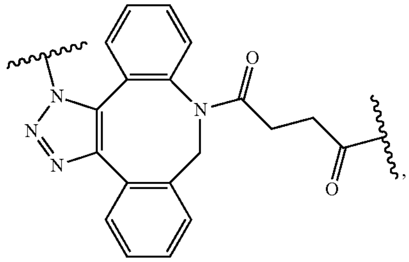,

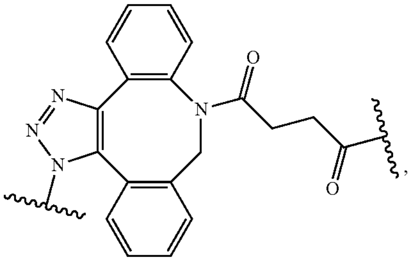,

-continued

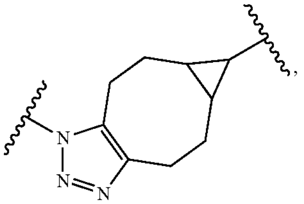

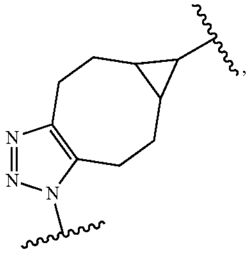

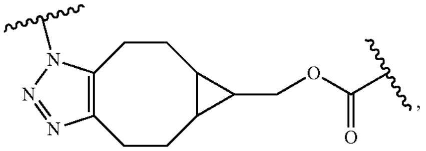

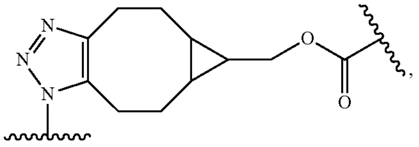

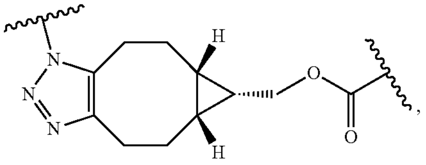

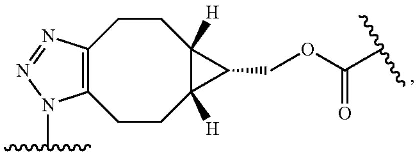

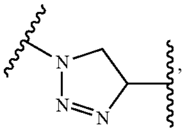

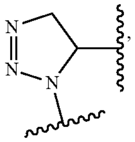

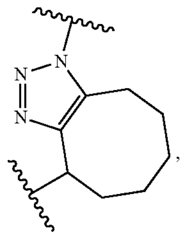

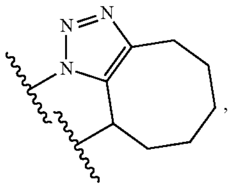

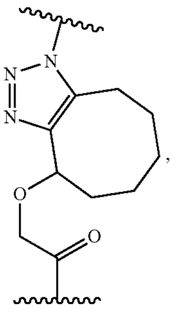

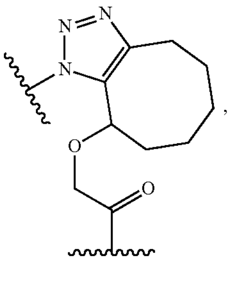

and

-continued

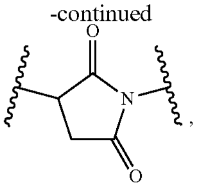

wherein the

indicates the atom through which the RG is bonded to the adjacent groups in the formula. In certain of these examples, RG, independently in each instance, is

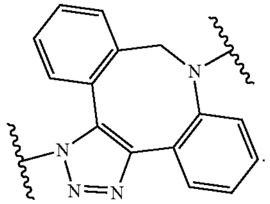 [SMILES: *N1Cc2ccccc2-c2c(nnn2*)-c2ccccc21]

In certain of these examples, RG, independently in each instance, is

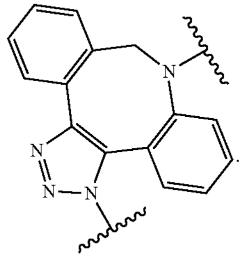 [SMILES: *N1Cc2ccccc2-c2nnn(*)c2-c2ccccc21]

In certain of these examples, RG, independently in each instance, is

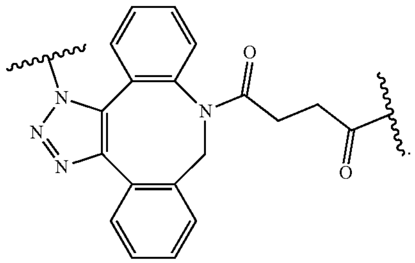 [SMILES: *C(=O)CCC(=O)N1Cc2ccccc2-c2nnn(*)c2-c2ccccc21]

In certain of these examples, RG, independently in each instance, is

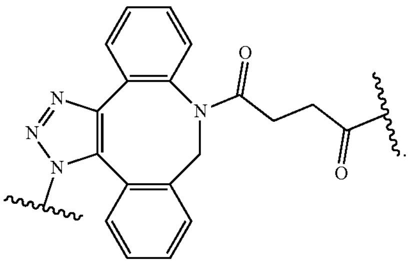 [SMILES: *C(=O)CCC(=O)N1Cc2ccccc2-c2c(nnn2*)-c2ccccc21]

In certain of these examples, RG, independently in each instance, is

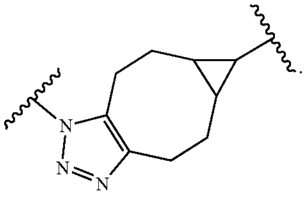 [SMILES: *C1C2CCc3nnn(*)c3CCC12]

In certain of these examples, RG, independently in each instance, is

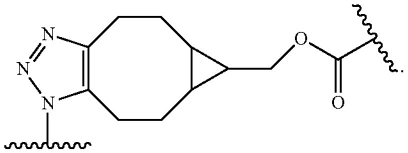 [SMILES: *C(=O)OCC1C2CCc3nnn(*)c3CCC21]

In certain of these examples, RG, independently in each instance, is

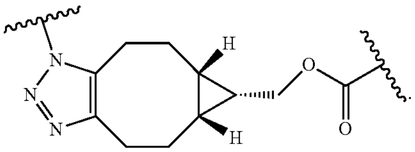 [SMILES: *C(=O)OC[C@@H]1[C@@H]2CCc3nnn(*)c3CC[C@@H]21]

In certain of these examples, RG, independently in each instance, is

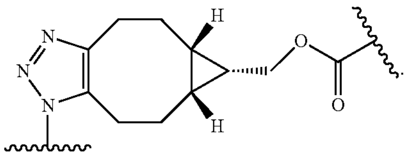 [SMILES: *C(=O)OC[C@@H]1[C@@H]2CCc3c(nnn3*)CC[C@@H]21]

In certain of these examples, RG, independently in each instance, is

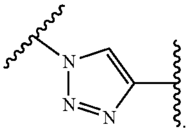 [SMILES: *c1cn(*)nn1]

In certain of these examples, RG, independently in each instance, is

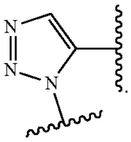

In certain of these examples, RG, independently in each instance, is

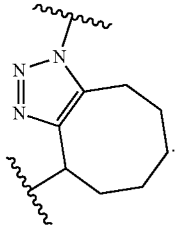 [SMILES: *C1CCCCCc2c1nnn2*]

In certain of these examples, RG, independently in each instance, is

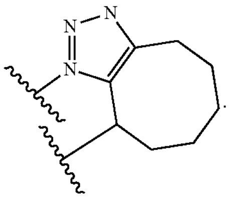

In certain of these examples, RG, independently in each instance, is

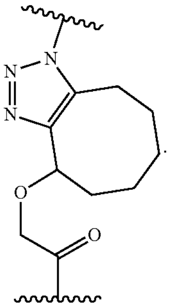 [SMILES: *C(=O)COC1CCCCCc2c1nnn2*]

In certain of these examples, RG, independently in each instance, is

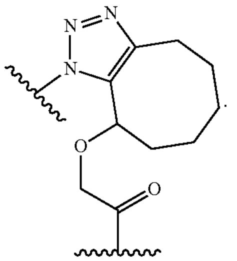 [SMILES: *C(=O)COC1CCCCCc2nnn(*)c21]
In certain of these examples, RG, independently in each instance, is
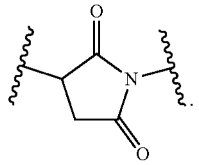 [SMILES: *C1CC(=O)N(*)C1=O]
In some examples,
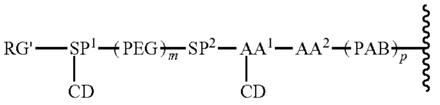
is selected from
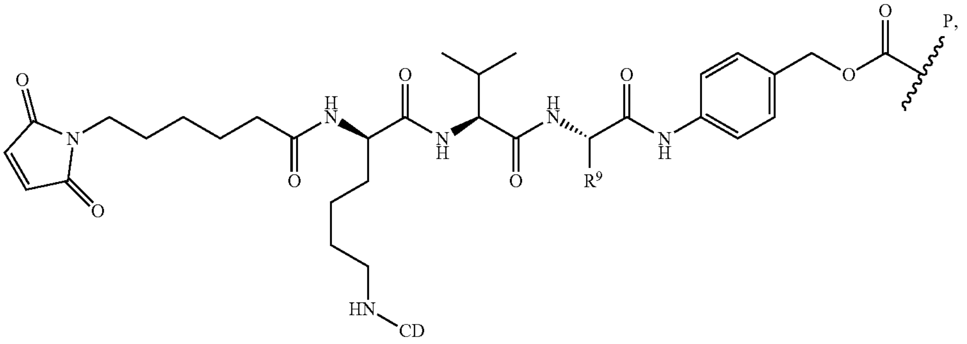
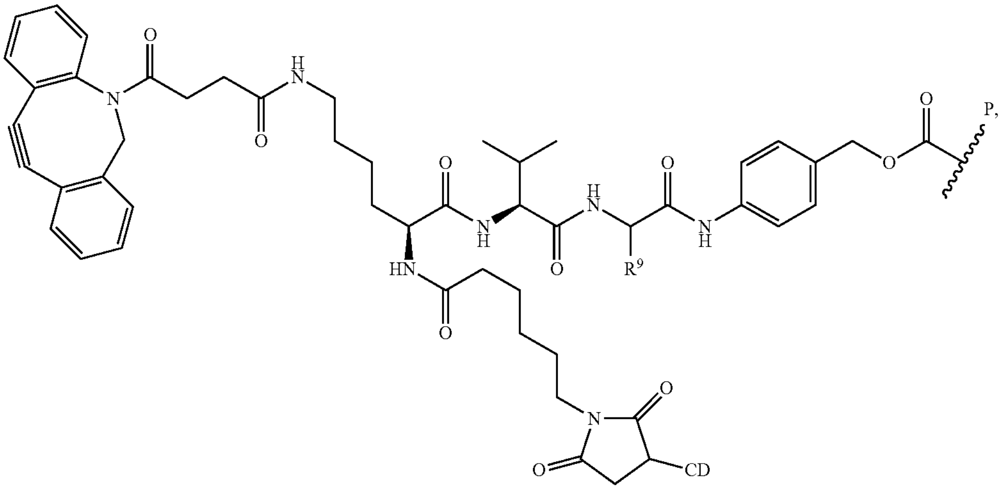

-continued
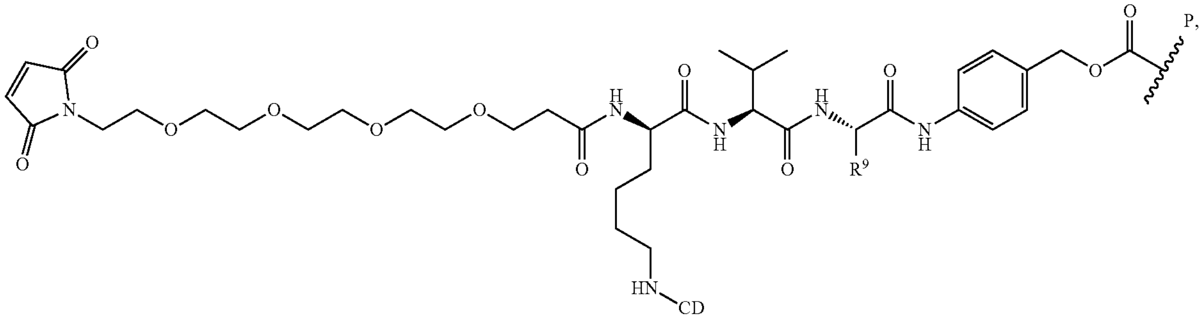
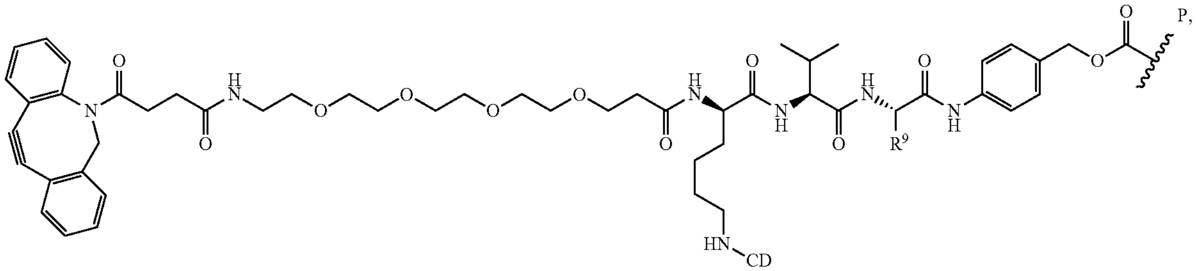
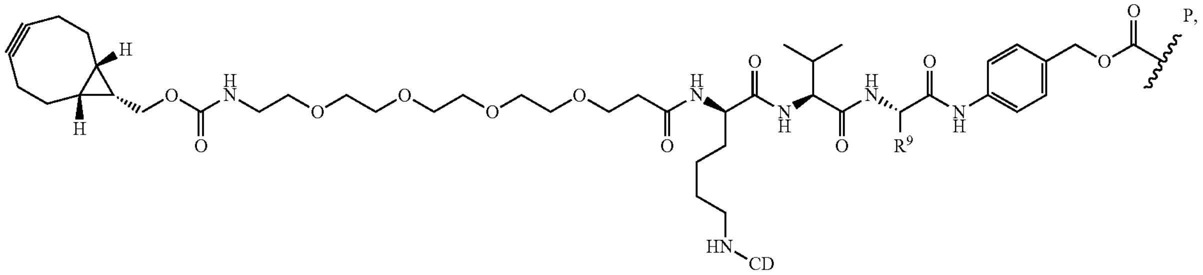
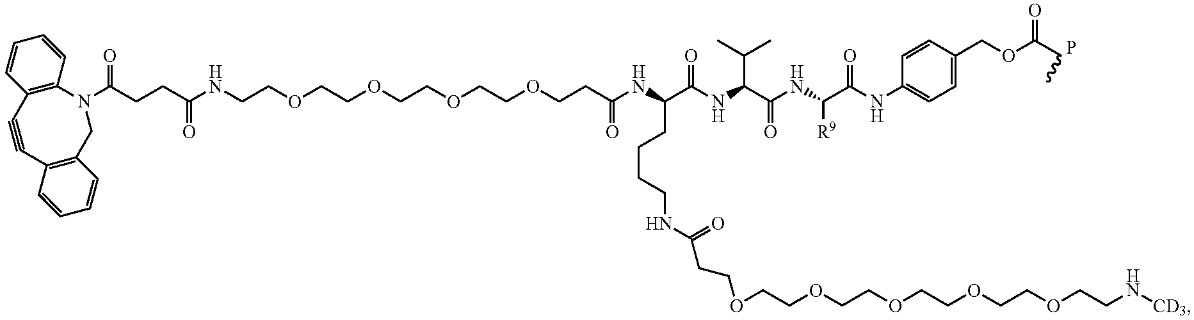
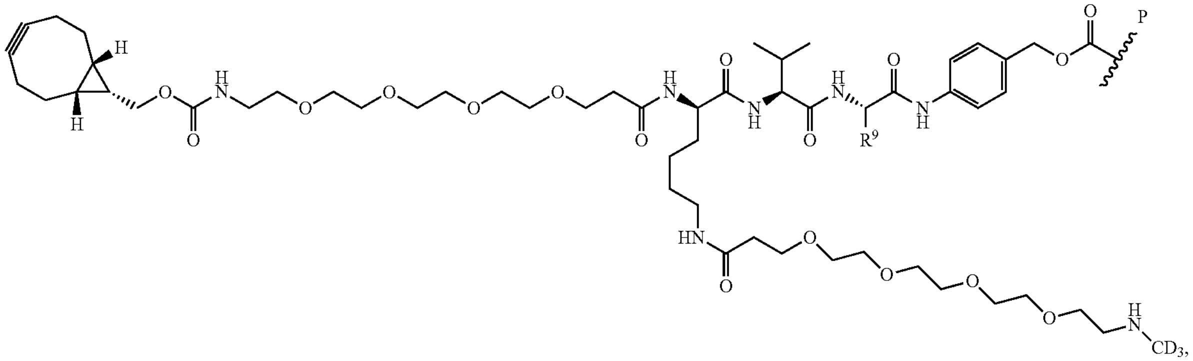

-continued
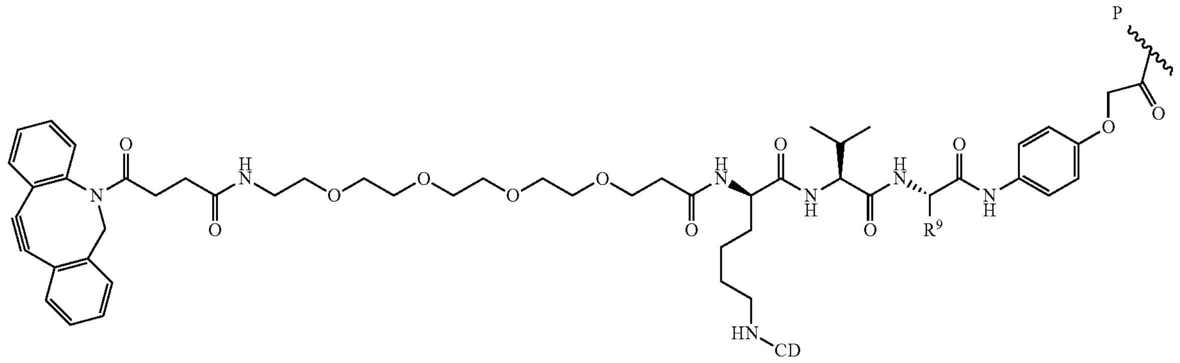
,
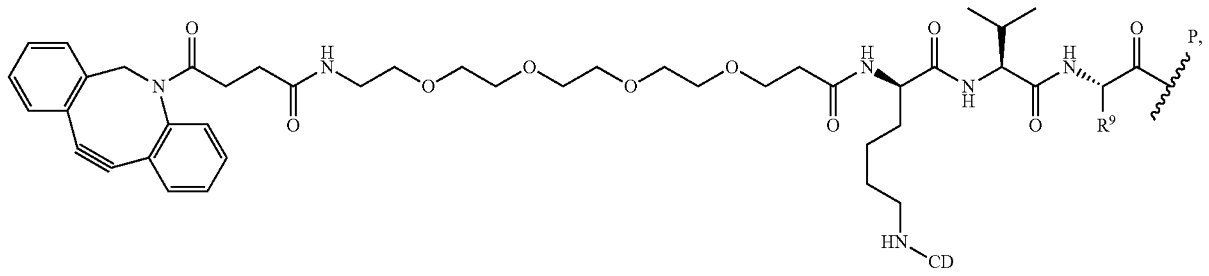
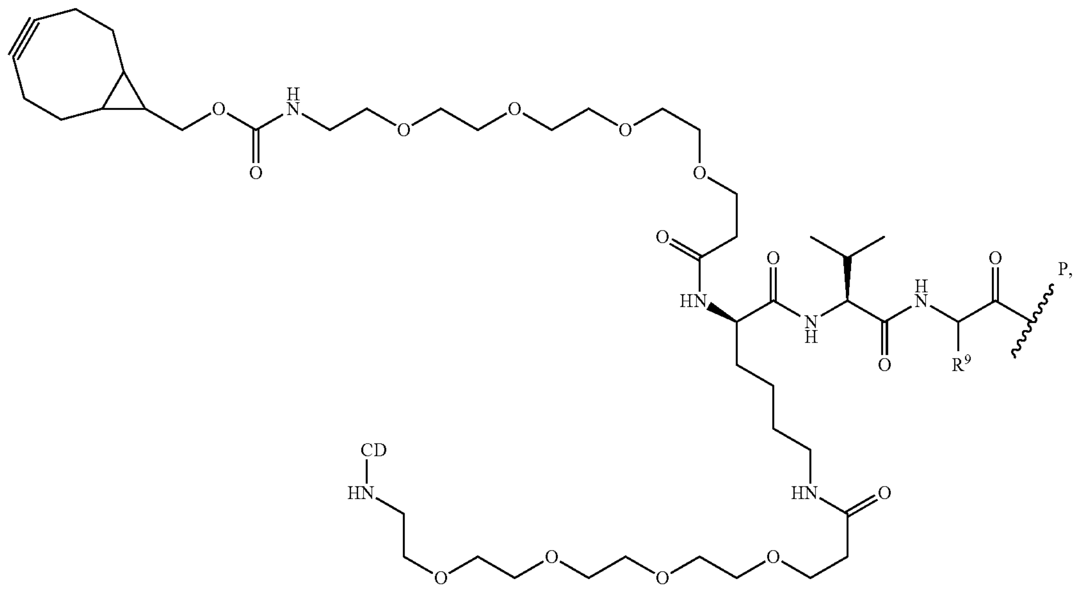

-continued
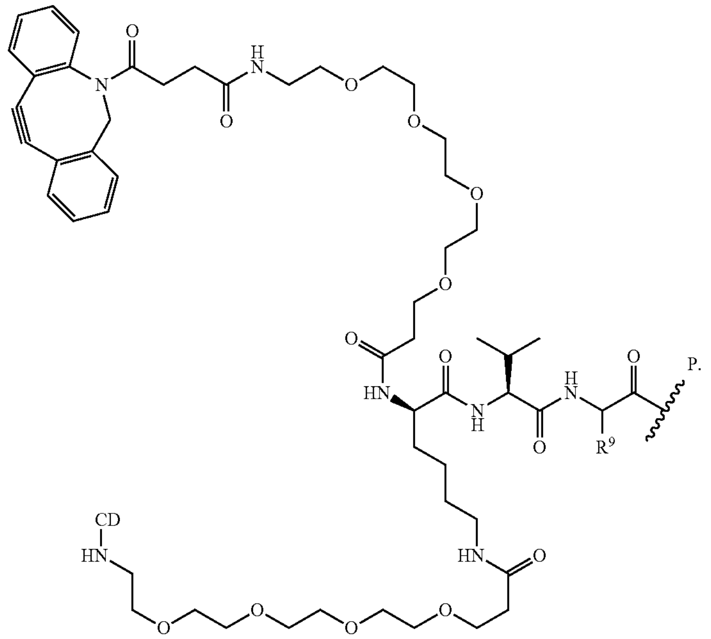
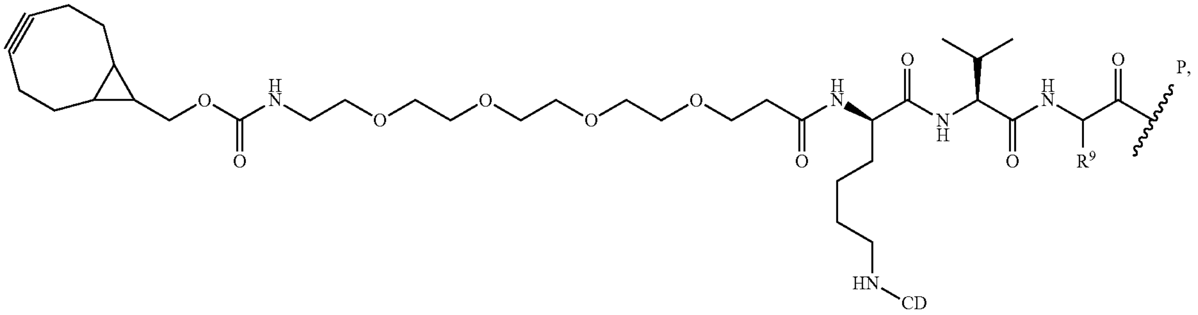
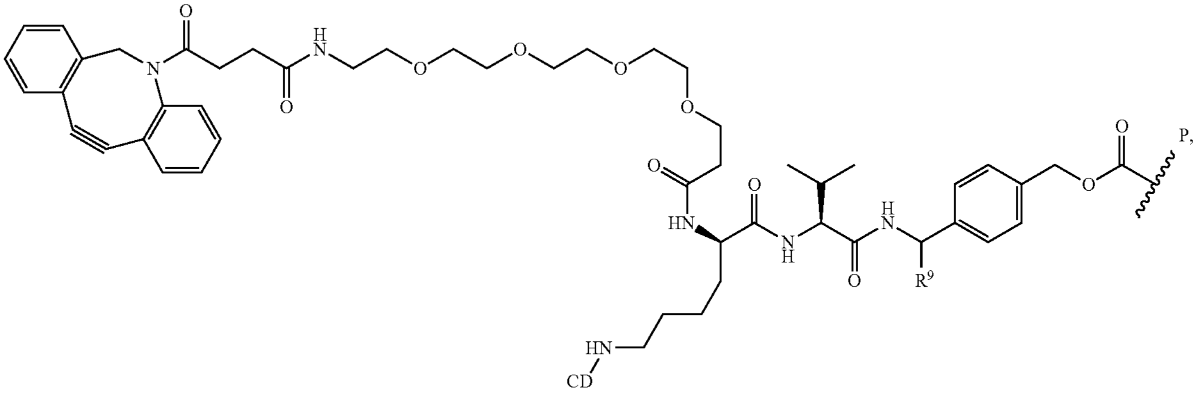
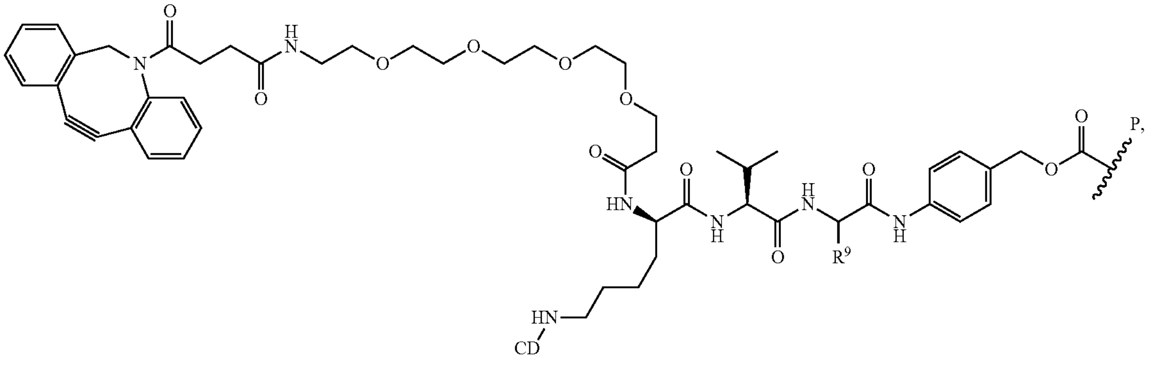
and

-continued
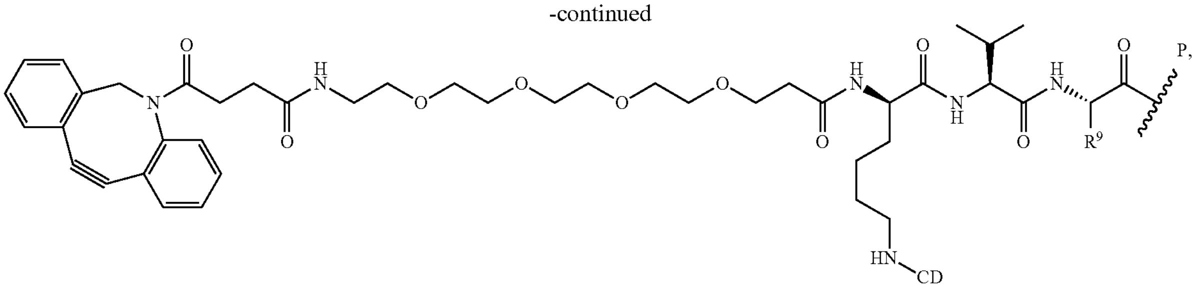
Also included are salts, solvates, stereoisomeric forms thereof, regioisomers thereof, or mixture of regioisomers thereof, wherein each
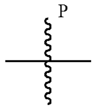
is a bond to the payload; and $R^9$ is $-CH_3$ or $-(CH_2)_3N(H)C(O)NH_2$. In some examples, $R^9$ is $-CH_3$. In some examples, $R^9$ is $-(CH_2)_3N(H)C(O)NH_2$.
In some examples, a compound of Formula (II) comprises a group selected from

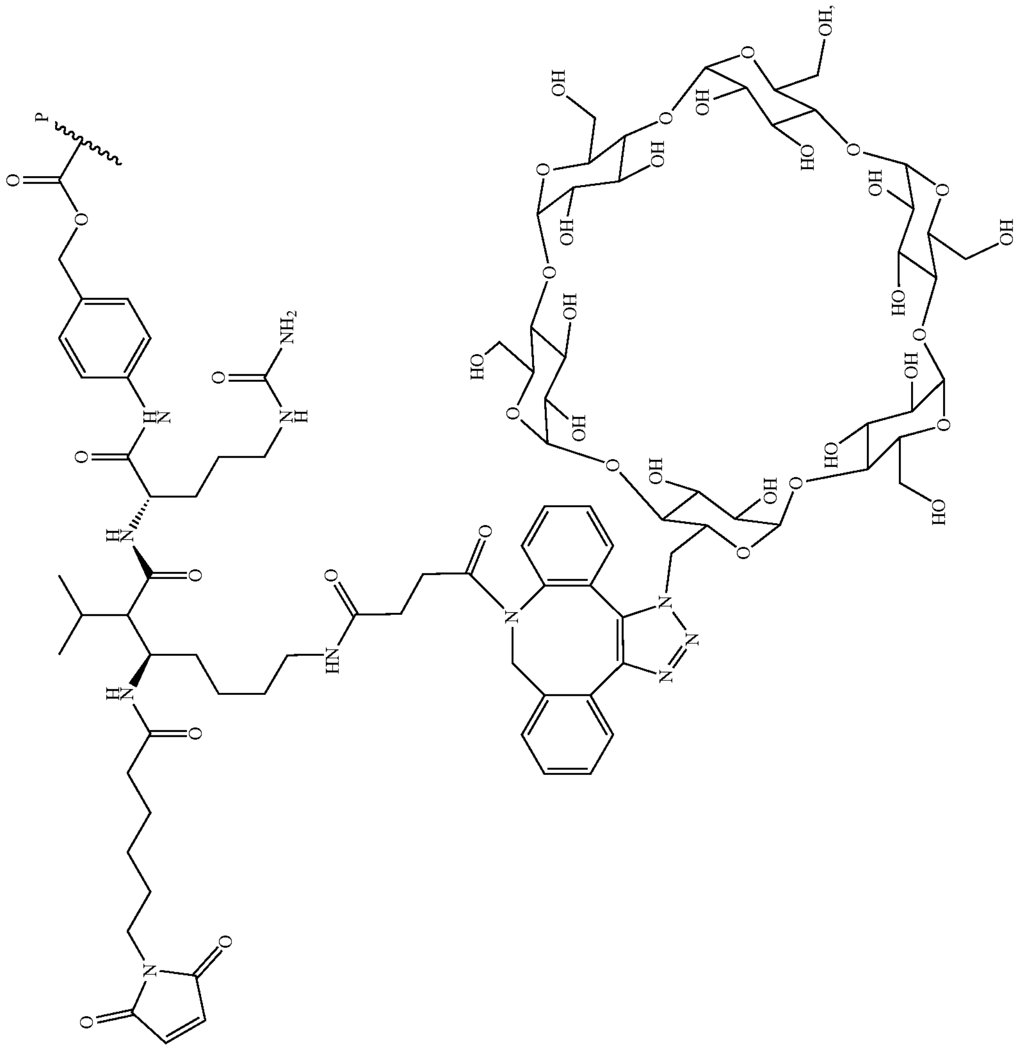

-continued
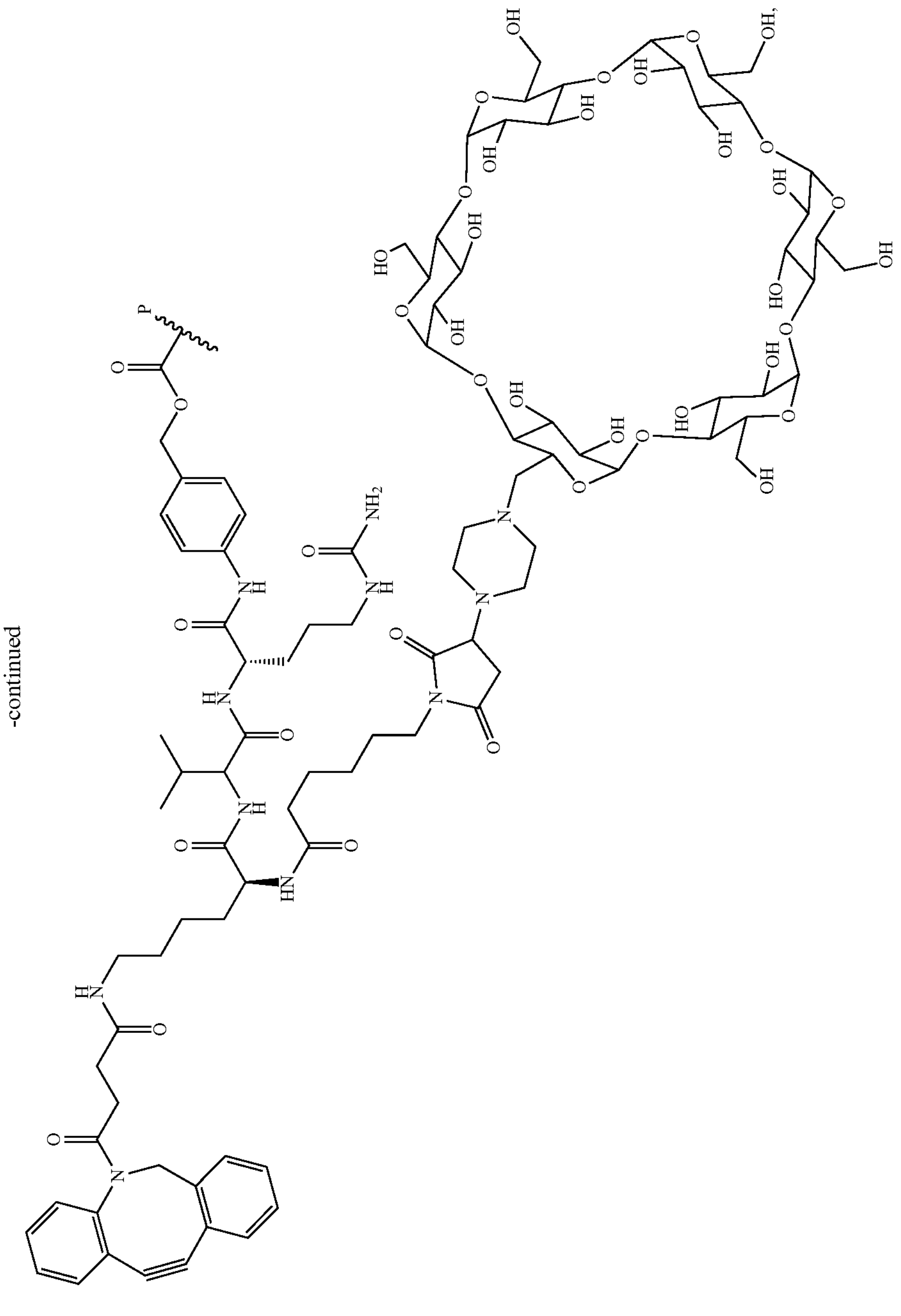

-continued
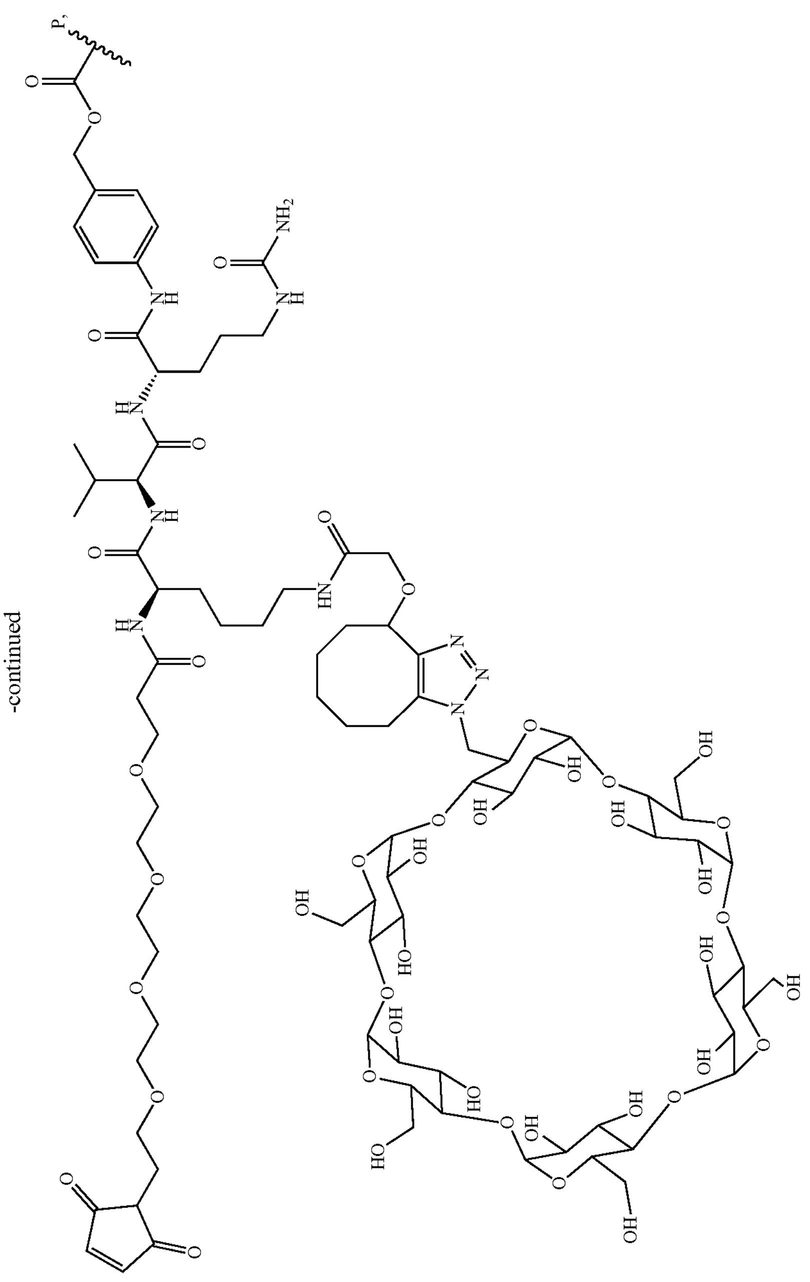

-continued
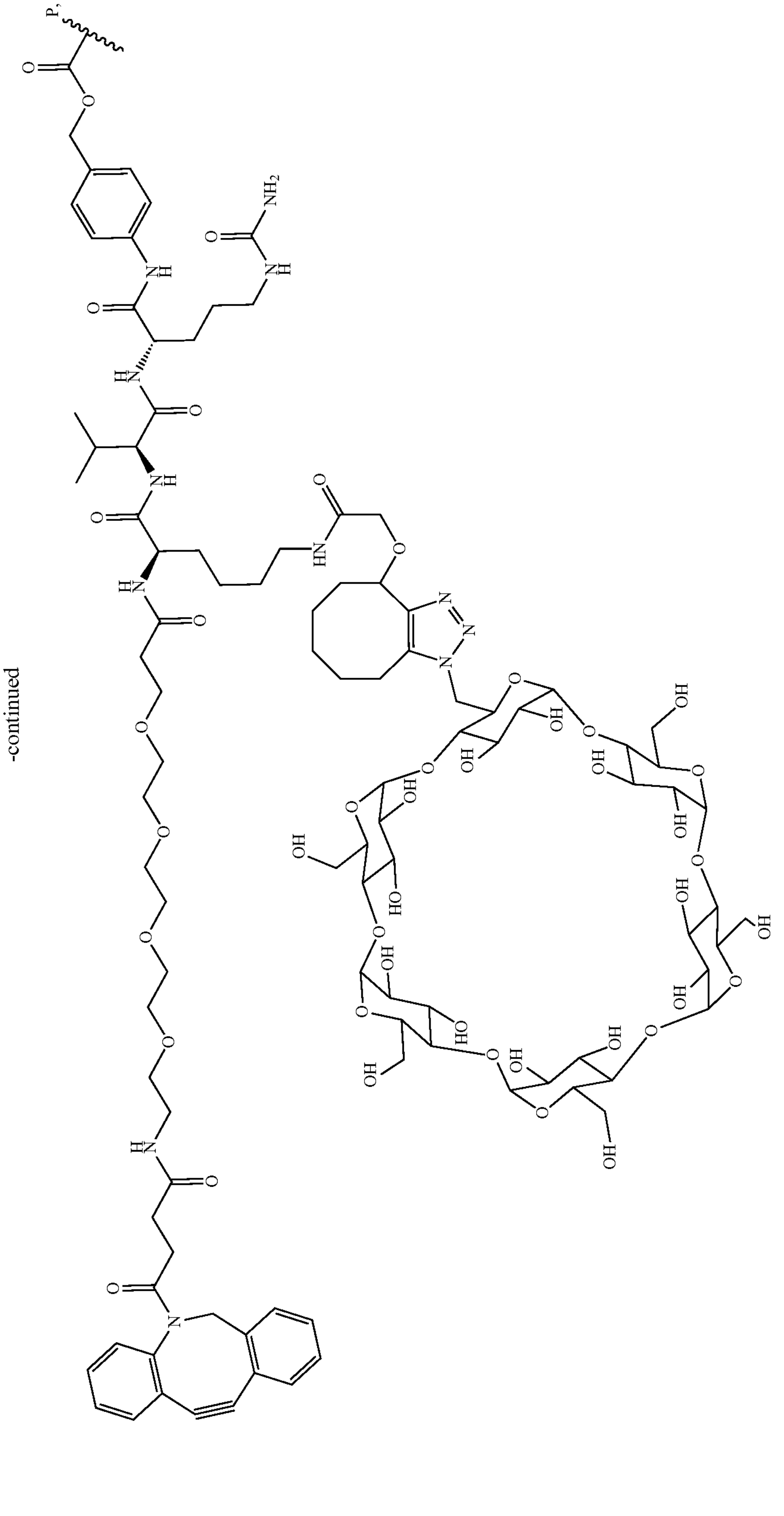

-continued
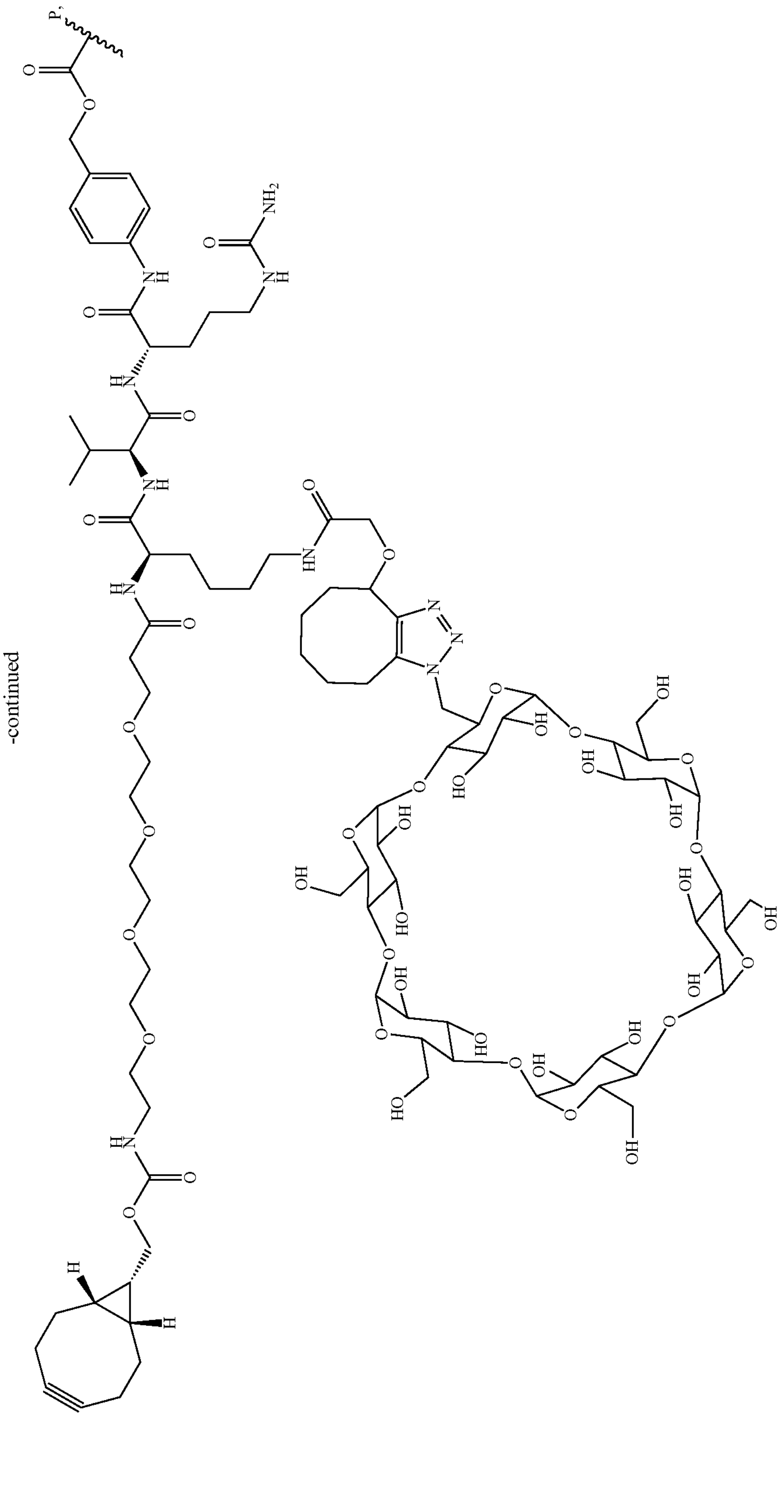

-continued
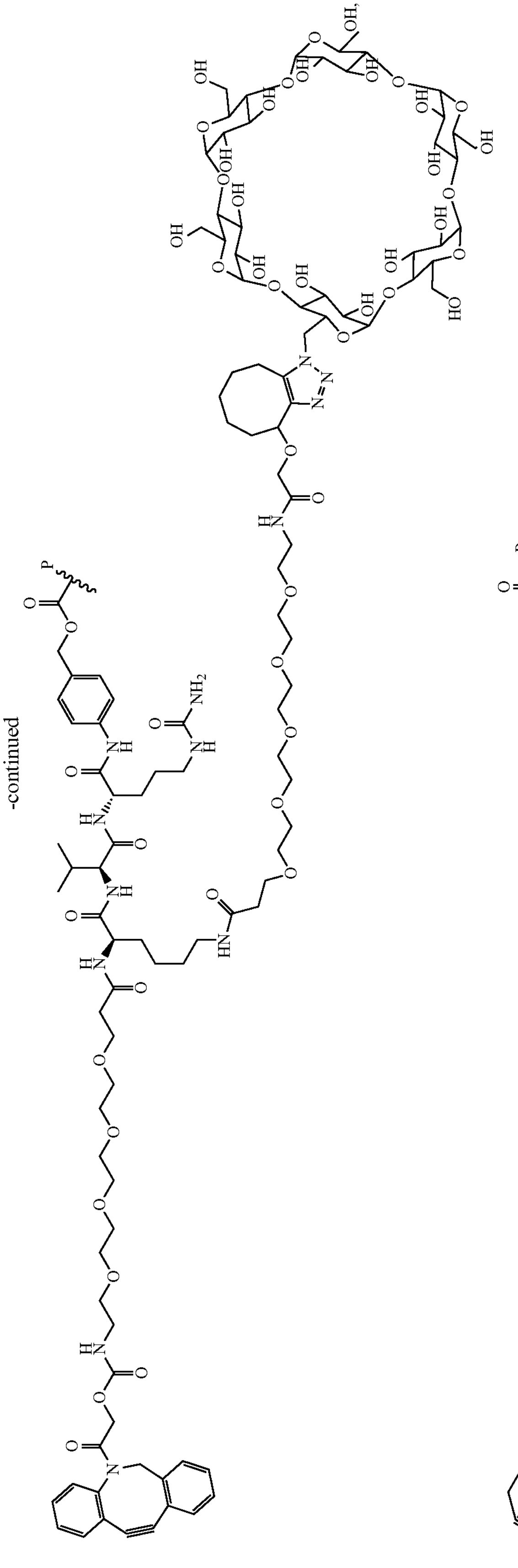
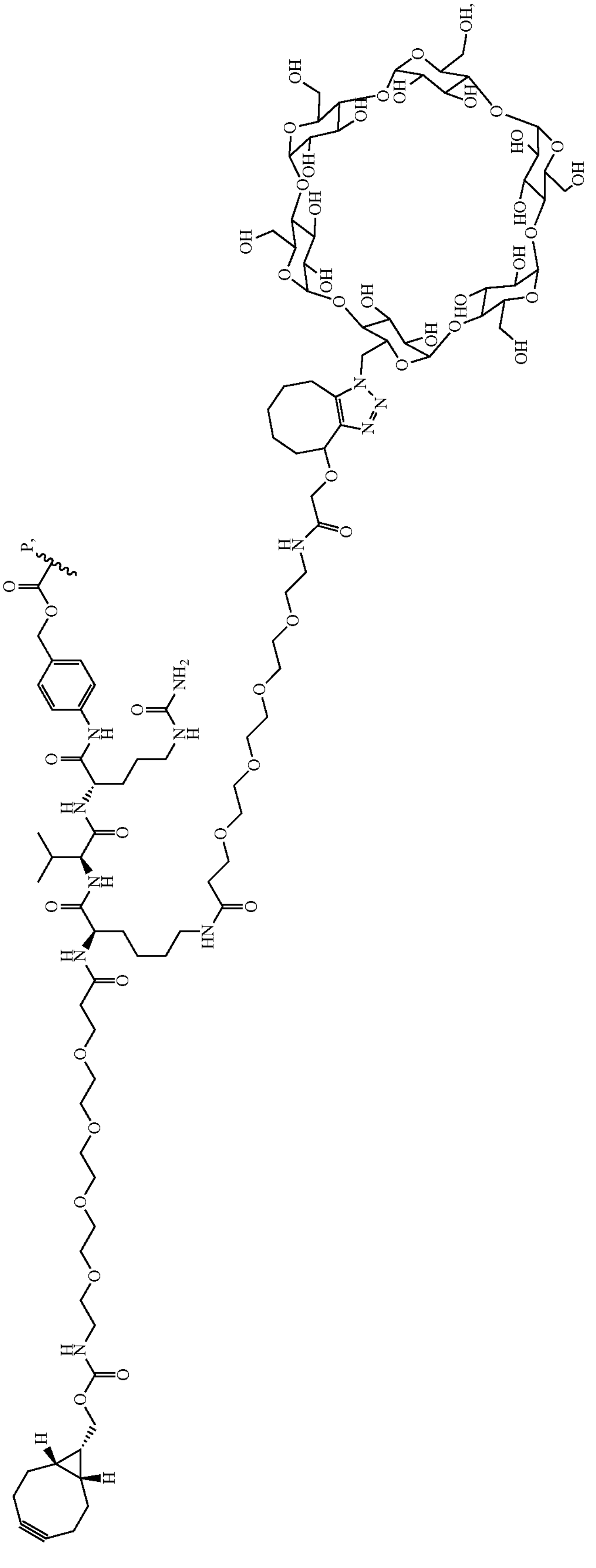

-continued
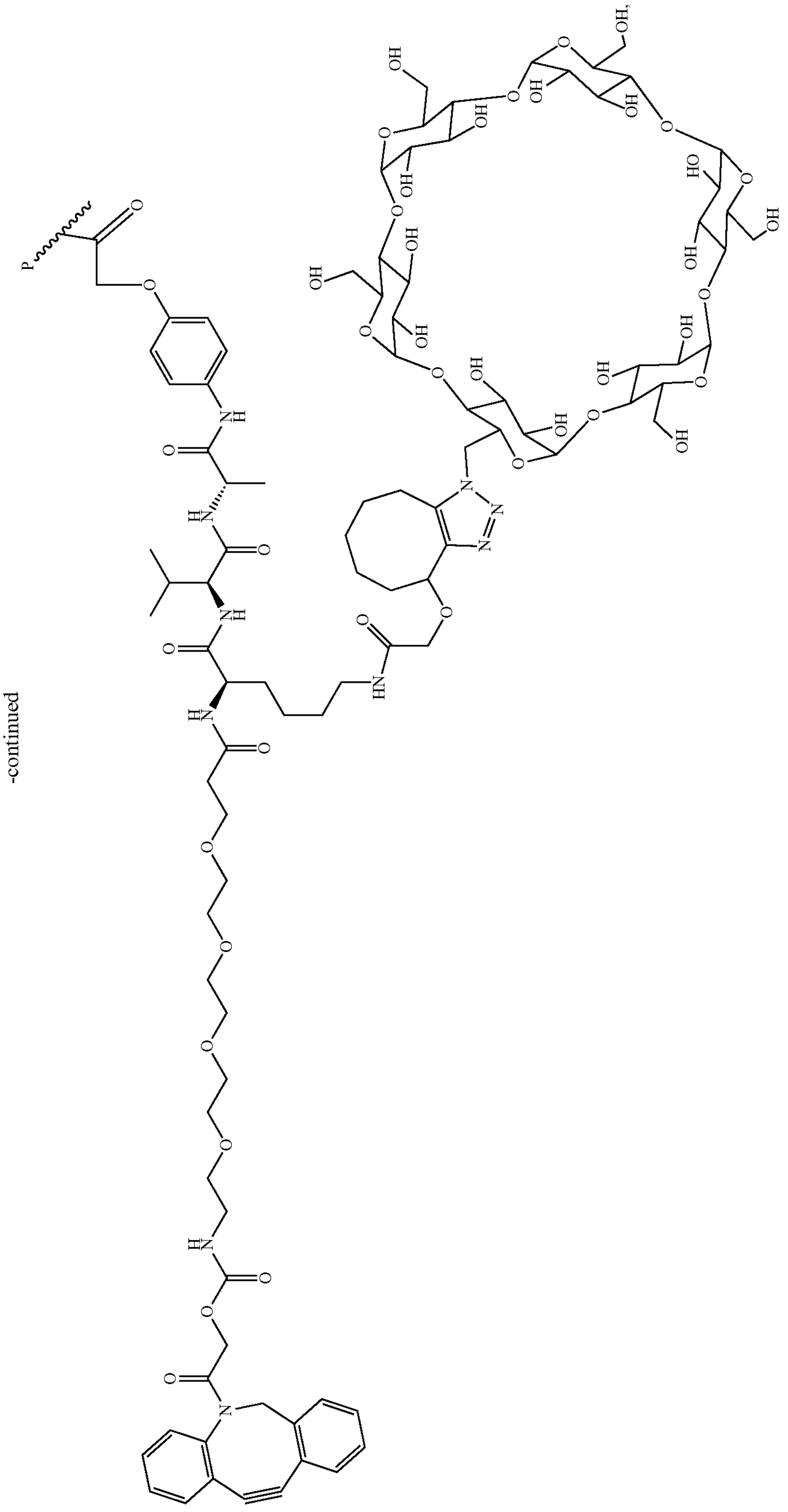

-continued
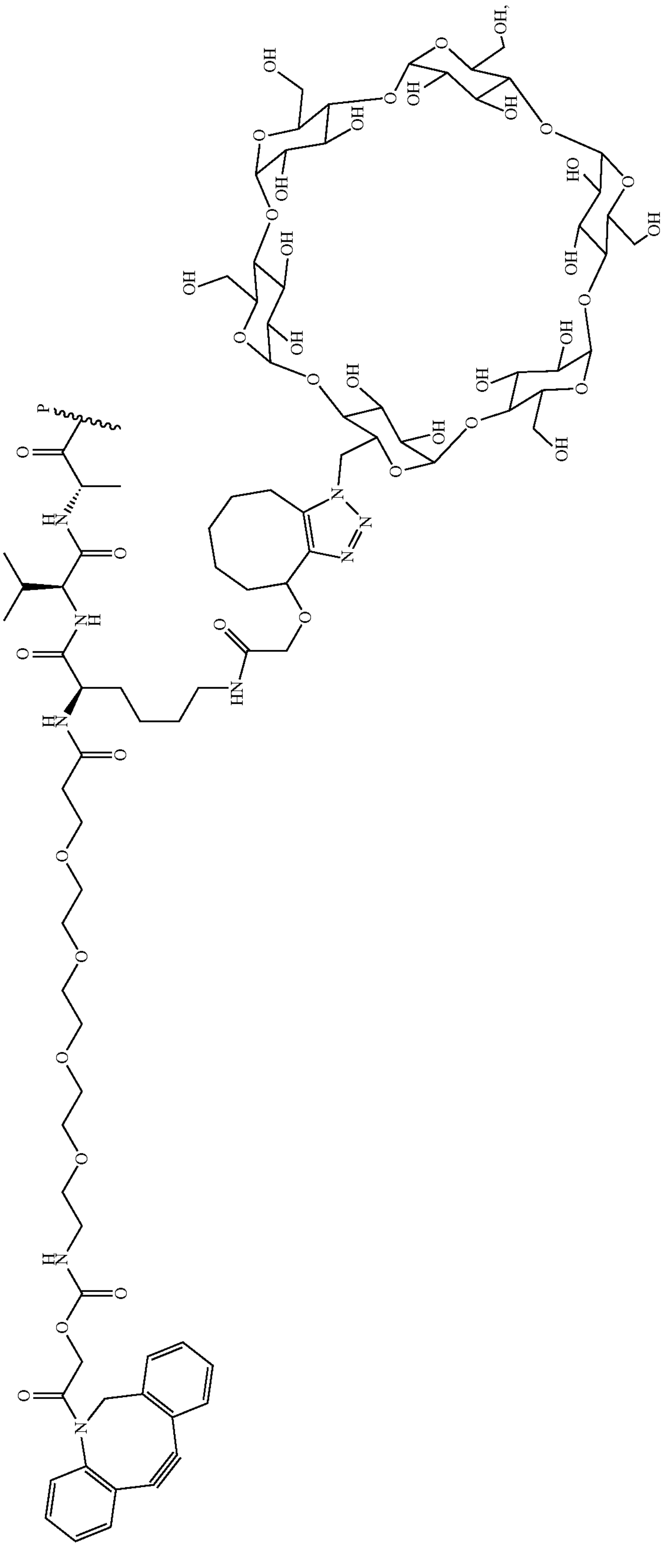

-continued
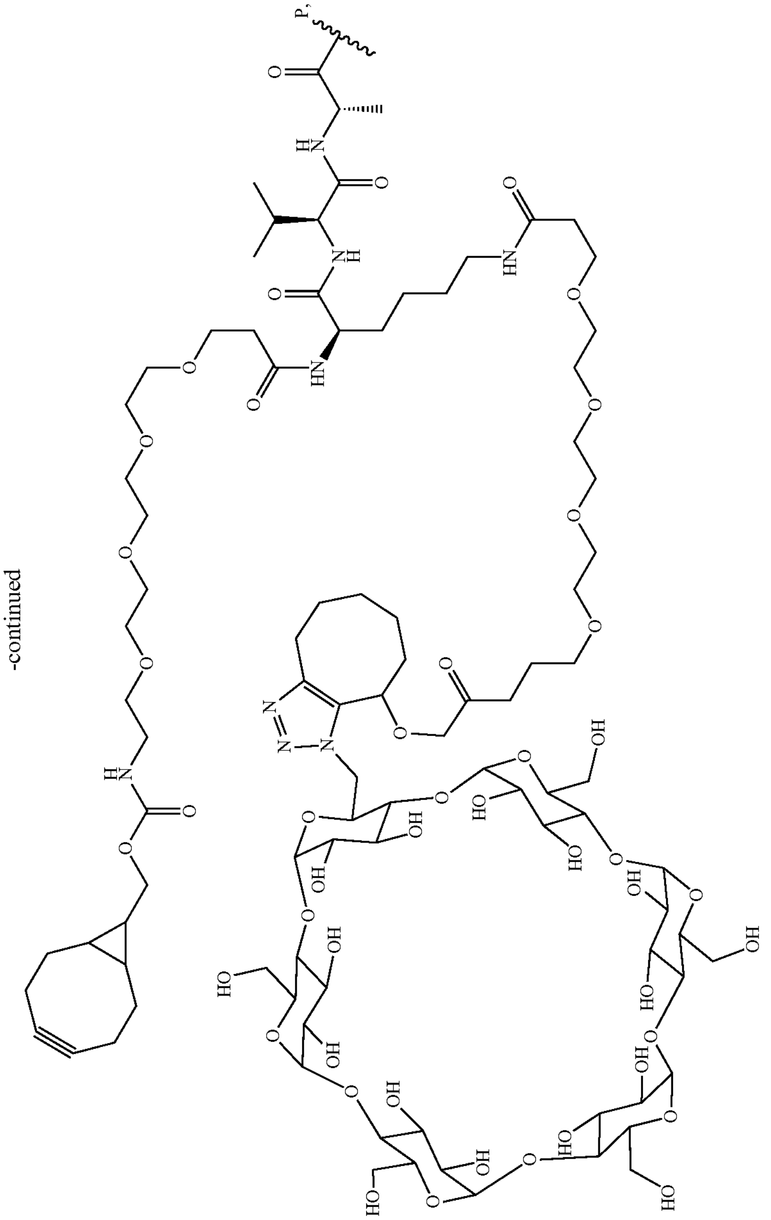

-continued
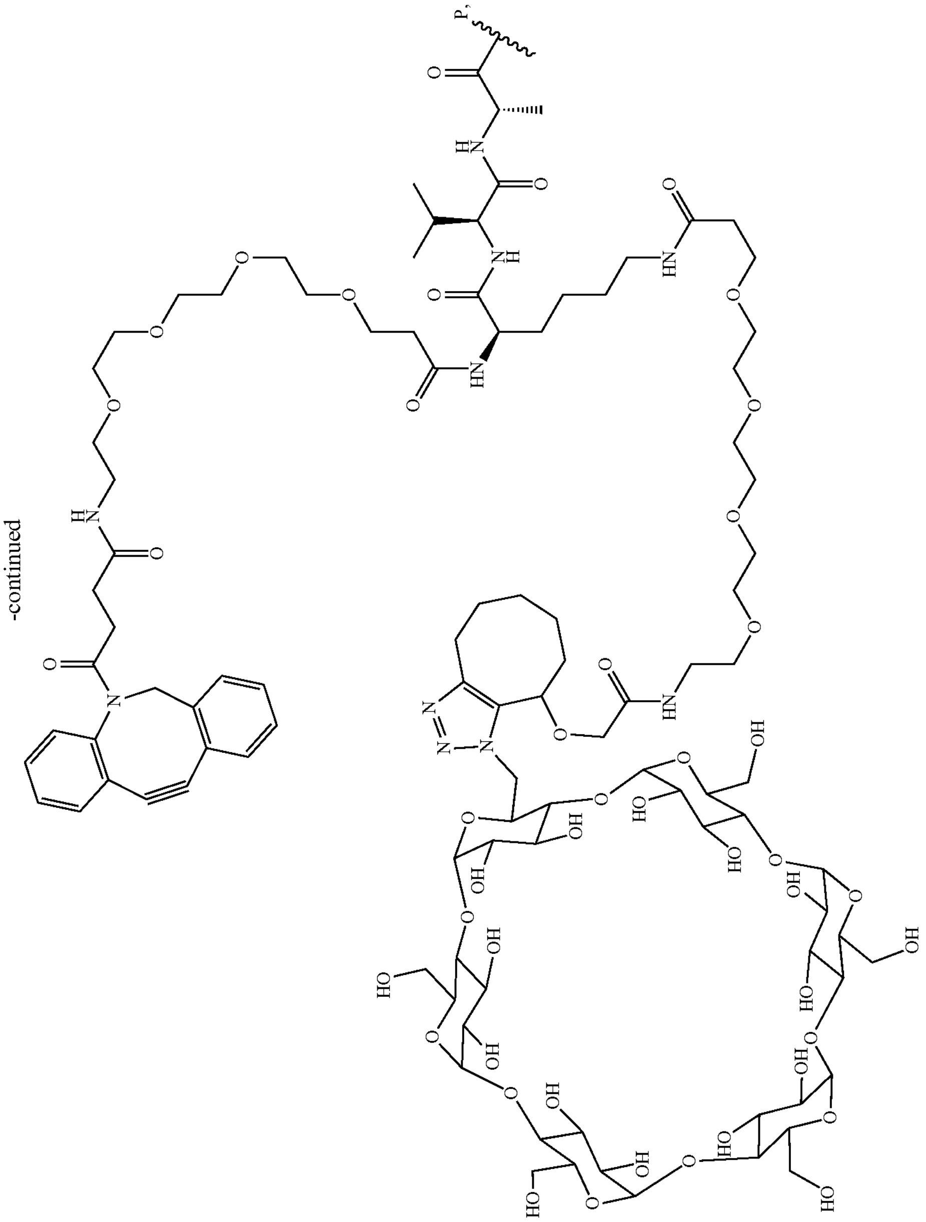

-continued
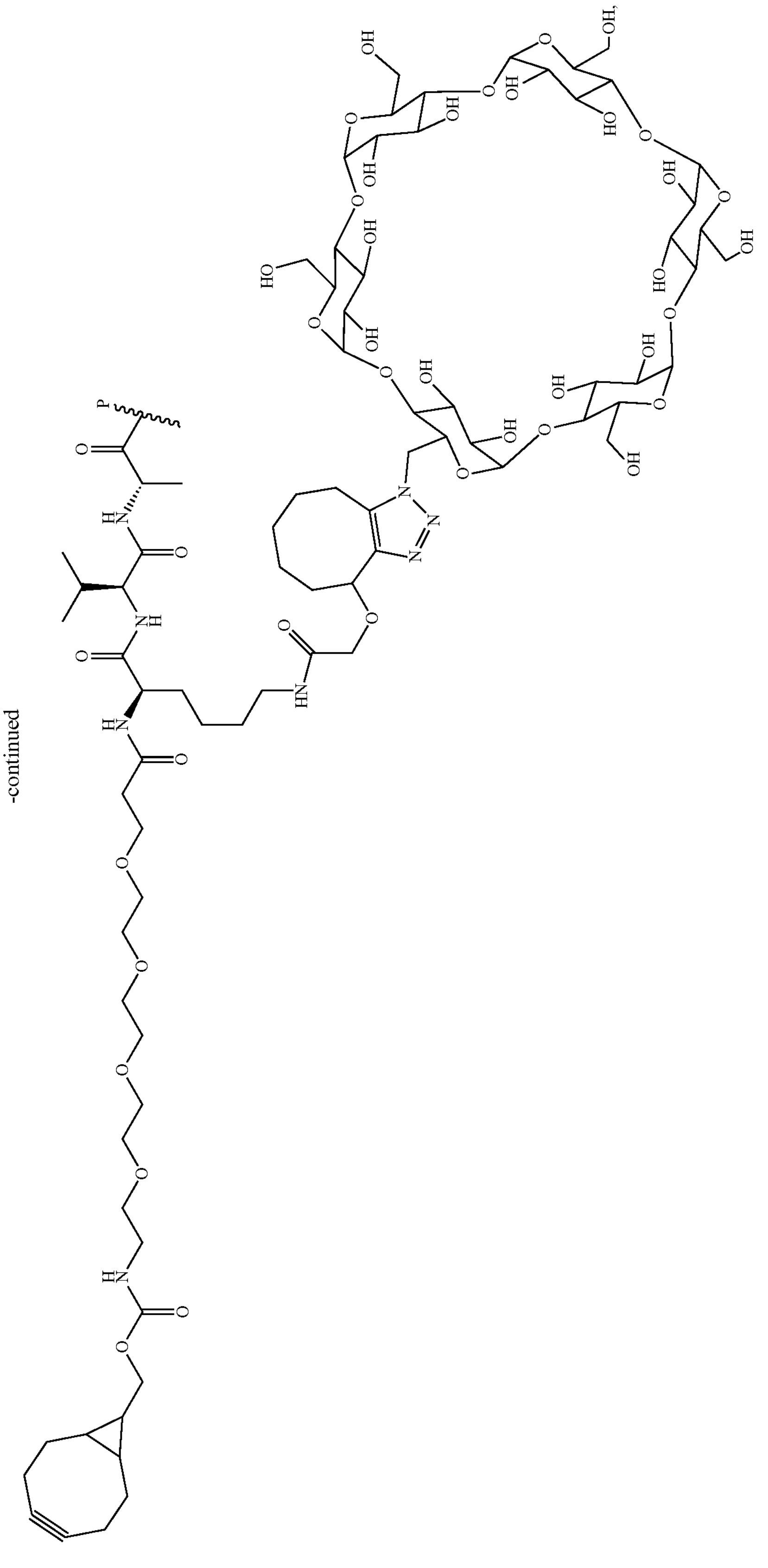

-continued
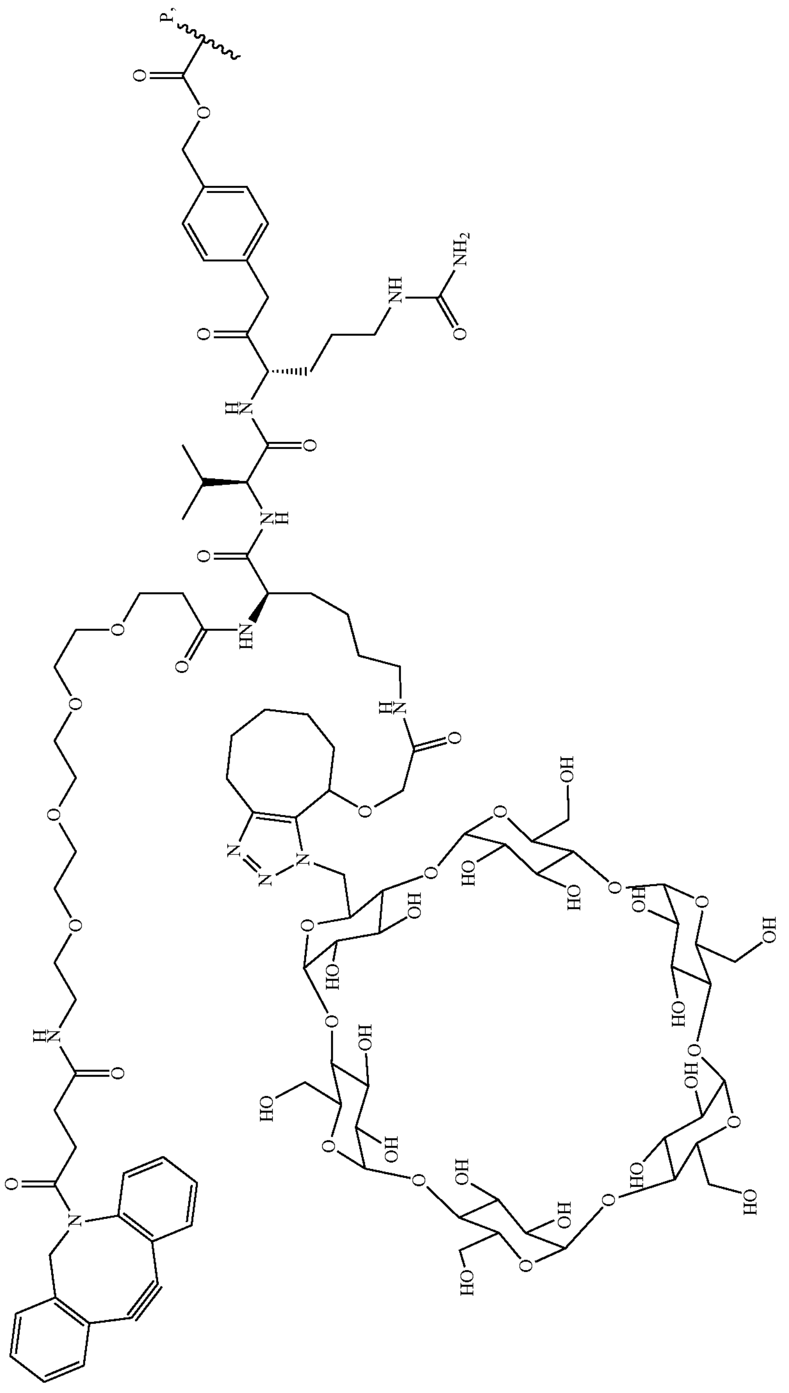

-continued
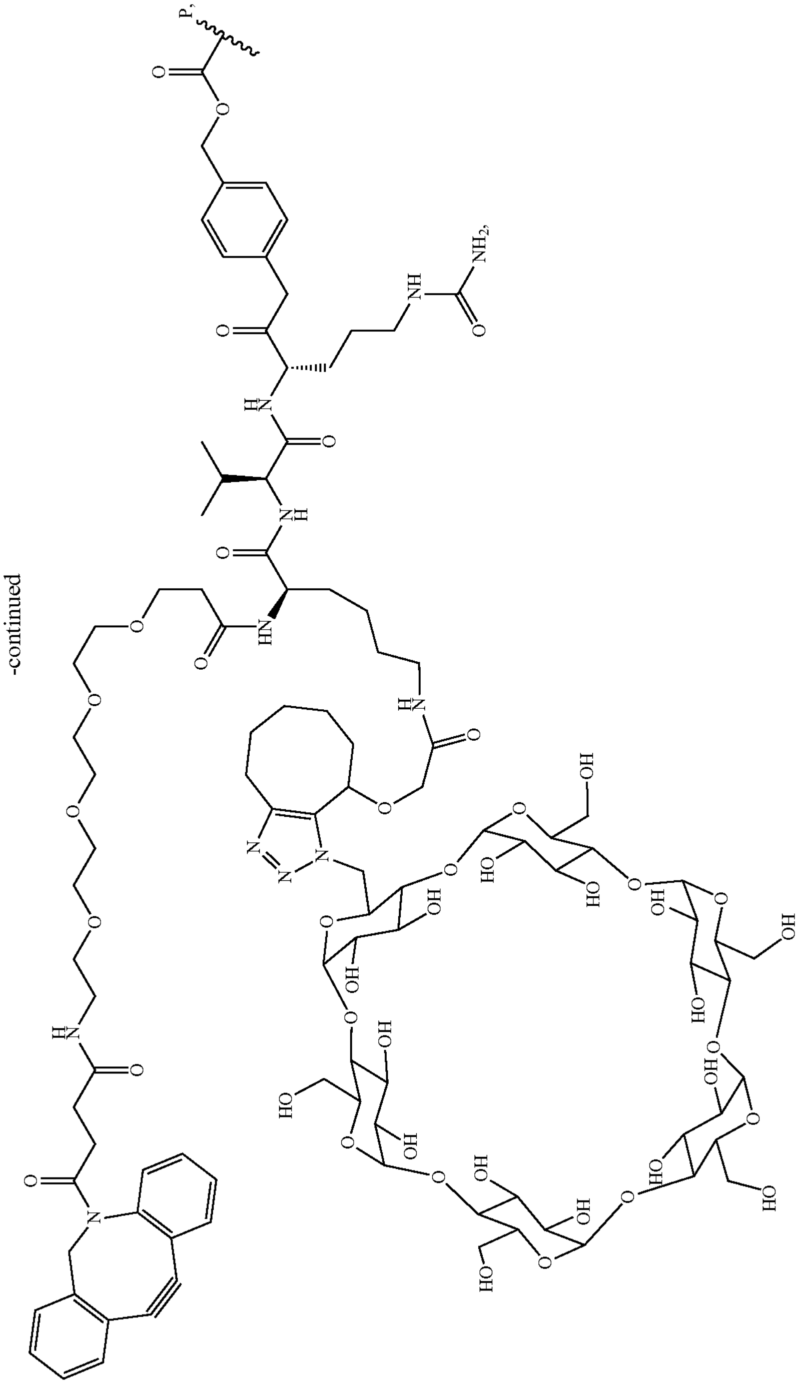

-continued
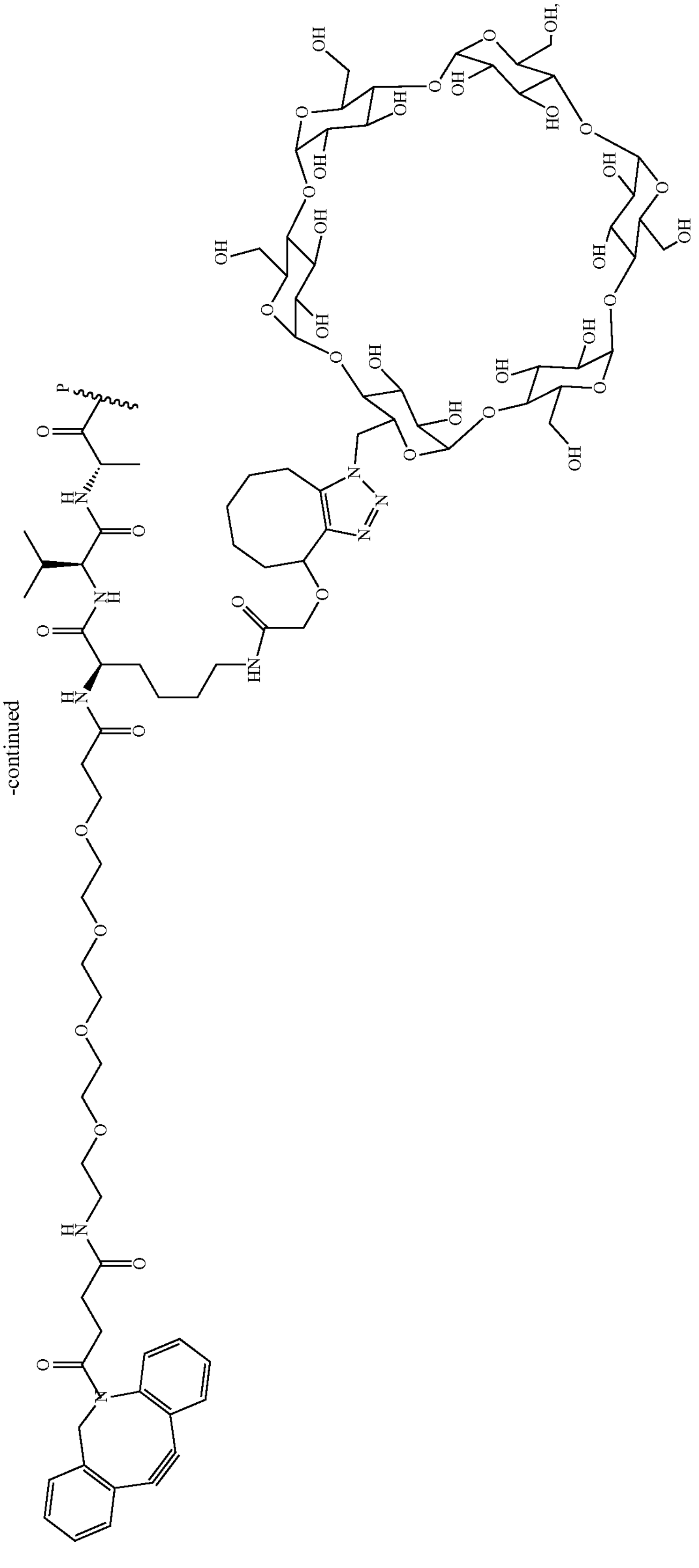

or a salt, solvate, stereoisomeric form thereof, a regioisomer thereof, or mixture of regioisomers thereof, wherein each

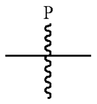

is a bond to the payload.

In some examples, -LL- is according to the formula (LL1)

(LL1)

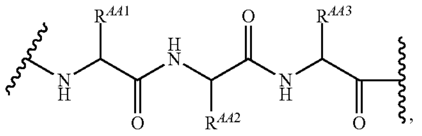

wherein $R^{AA1}$, $R^{AA2}$, and $R^{AA3}$ are each, independently, amino acid side chains, at least one of which is bonded directly or indirectly to —SP-RG-SP-CD. In some examples, $R^{AA1}$ is a lysine amino acid side chain. In some examples, $R^{AA2}$ is a valine amino acid side chain. In some examples, $R^{AA3}$ is an alanine amino acid side chain. In some examples, $R^{AA3}$ is a citrulline amino acid side chain. In certain examples, $R^{AA1}$ is a lysine amino acid side chain bonded directly or indirectly to CD and $R^{AA2}$ and $R^{AA3}$ are, independently, valine and alanine amino acid side chains. In certain examples, $R^{AA1}$ is a lysine amino acid side chain bonded directly or indirectly to CD and $R^{AA2}$ and $R^{AA3}$ are, independently, valine and citrulline amino acid side chains.

In some examples, including any of the foregoing, $R^{AA1}$ is a lysine side chain bonded directly or indirectly to CD and $R^{AA2}$ and $R^{AA3}$ are either lysine and valine or valine and lysine side chains, respectively.

In some examples, including any of the foregoing, CD is, independently in each instance, a cyclodextrin. In some examples, the CD is an α-cyclodextrin. In some examples, the CD is a β-cyclodextrin. In some examples, the CD is a γ-cyclodextrin. In any of these examples, the α-, β-, or γ-cyclodextrin is optionally substituted.

In some examples, including any of the foregoing, CD is, independently in each instance, selected from:

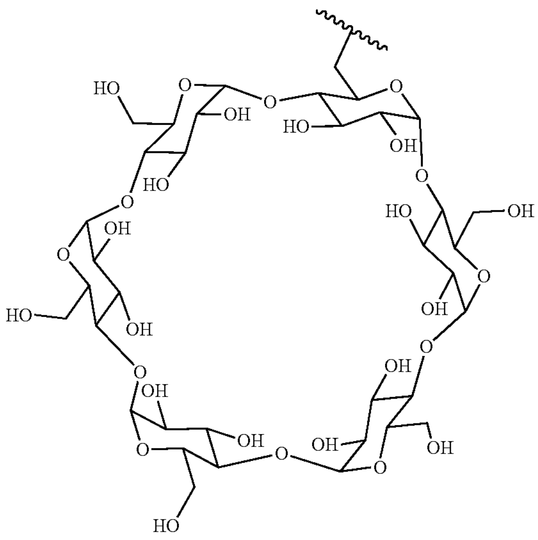

and

-continued

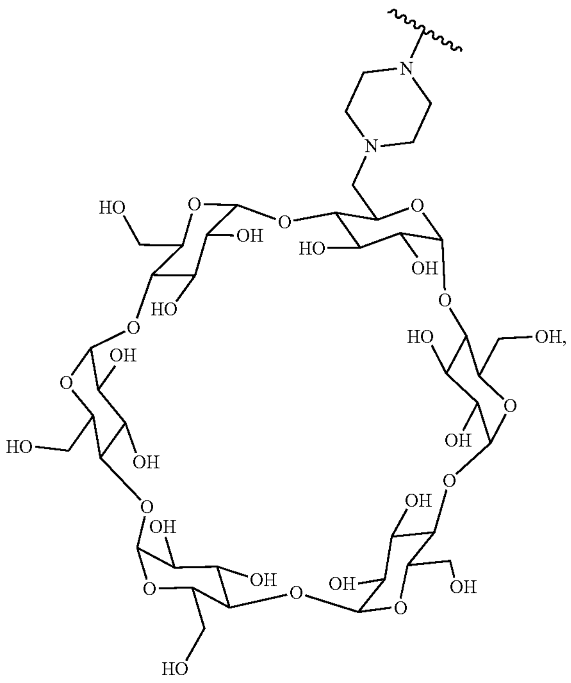

wherein the

indicates the atom through which the CD is bonded to the adjacent groups in the formula. In certain examples, the CD is

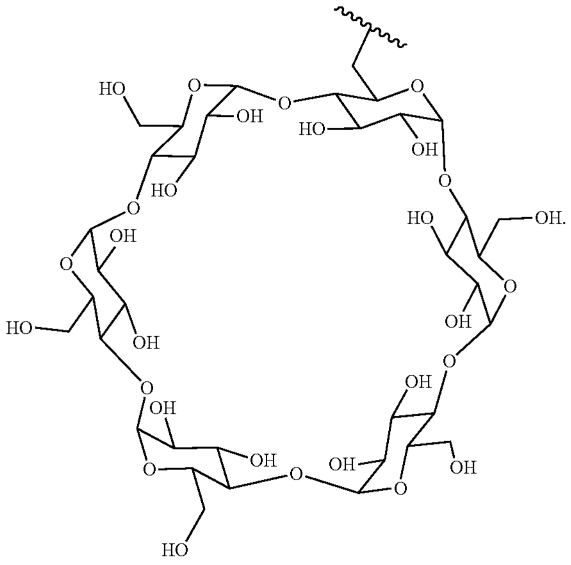 [SMILES: *CC1OC2OC3C(CO)OC(OC4C(CO)OC(OC5C(CO)OC(OC6C(CO)OC(OC7C(CO)OC(OC1C(O)C2O)C(O)C7O)C(O)C6O)C(O)C5O)C(O)C4O)C(O)C3O]

In certain examples, the CD is

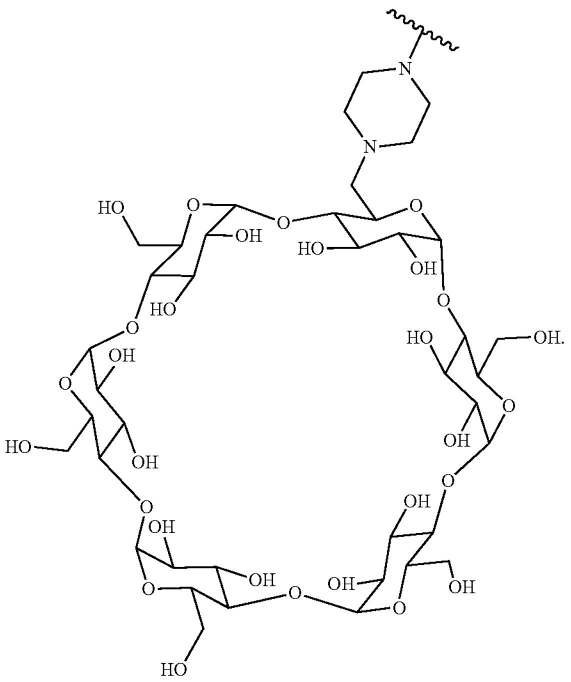 [SMILES: *N1CCN(CC2OC3OC4C(CO)OC(OC5C(CO)OC(OC6C(CO)OC(OC7C(CO)OC(OC8C(CO)OC(OC2C(O)C3O)C(O)C8O)C(O)C7O)C(O)C6O)C(O)C5O)C(O)C4O)CC1]

In some examples, including any of the foregoing, -$AA^2$- is

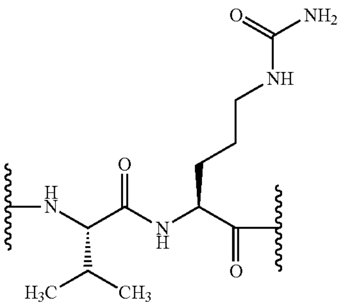

or

-continued

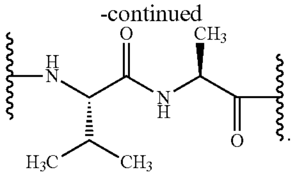

In some examples, including any of the foregoing, the spacer group is, independently in each instance, selected from the group consisting of $C_{1-6}$ alkylene, —NH—, —C(O)—, $(—CH_2—CH_2—O)_e$, $—NH—CH_2—CH_2—(—O—CH_2—CH_2)_e—C(O)—$.

In some examples, including any of the foregoing, subscript m, q, or e is 1. In some examples, including any of the foregoing, subscript m is 1. In some examples, including any of the foregoing, subscript q is 1. In some examples, including any of the foregoing, subscript e is 1.

In some examples, including any of the foregoing, subscript m, q, or e is 2. In some examples, including any of the foregoing, subscript m is 2. In some examples, including any of the foregoing, subscript q is 2. In some examples, including any of the foregoing, subscript e is 2.

In some examples, including any of the foregoing, subscript m, q, or e is 3. In some examples, including any of the foregoing, subscript m is 3. In some examples, including any of the foregoing, subscript q is 3. In some examples, including any of the foregoing, subscript e is 3.

In some examples, including any of the foregoing, subscript m, q, or e is 4. In some examples, including any of the foregoing, subscript m is 4. In some examples, including any of the foregoing, subscript q is 4. In some examples, including any of the foregoing, subscript e is 4.

In some examples, including any of the foregoing, subscript p is 1.

In some examples, including any of the foregoing, PA is the residue of a group selected from the group consisting of a dolastatin, an auristatin, a maytansinoid, a plant alkaloid, a taxane, and a vinca alkaloid. In some examples, PA is any compound set forth in FIG. 1.

In some examples, the compound of Formula (II) is selected from:

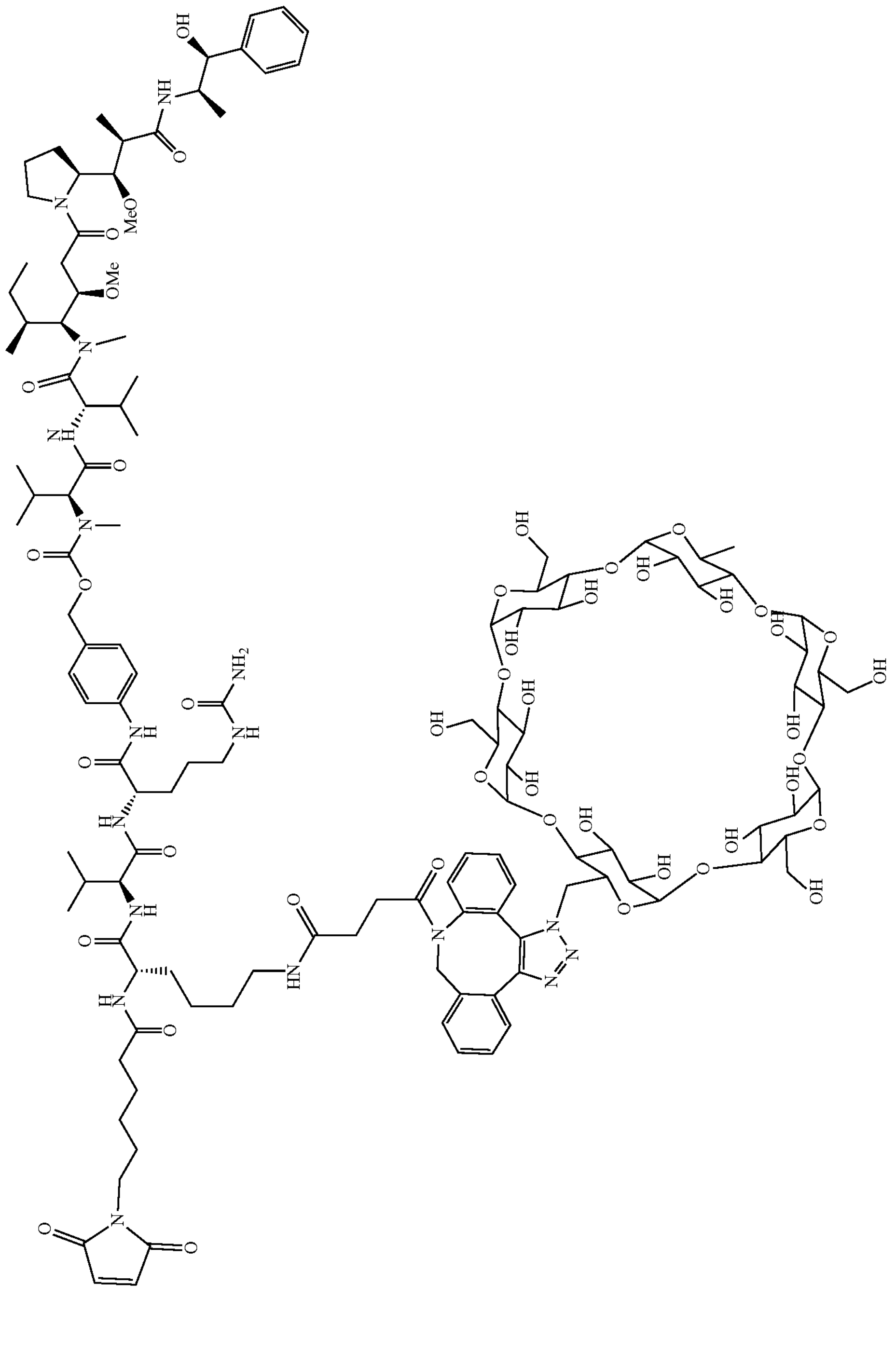

-continued
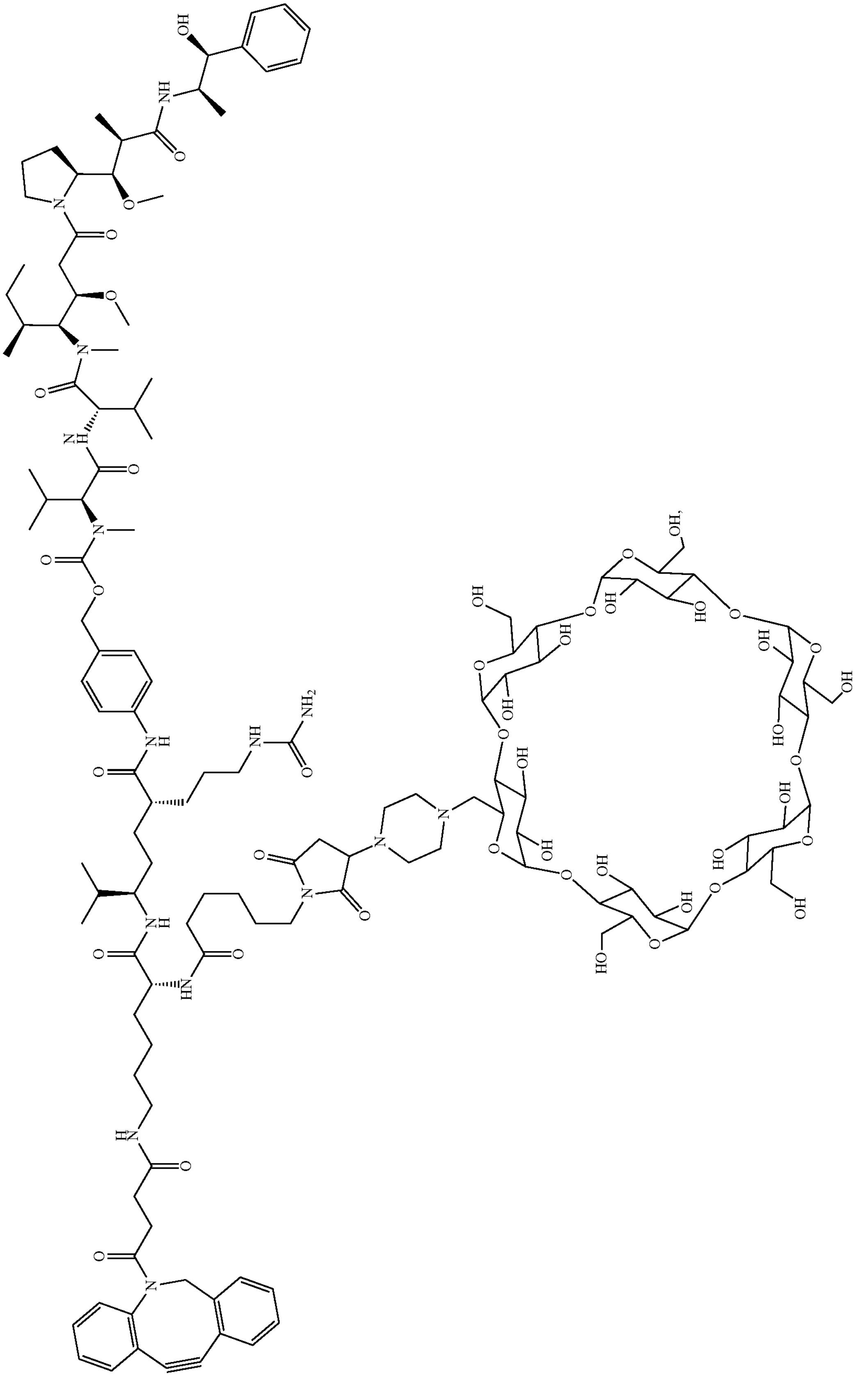

-continued
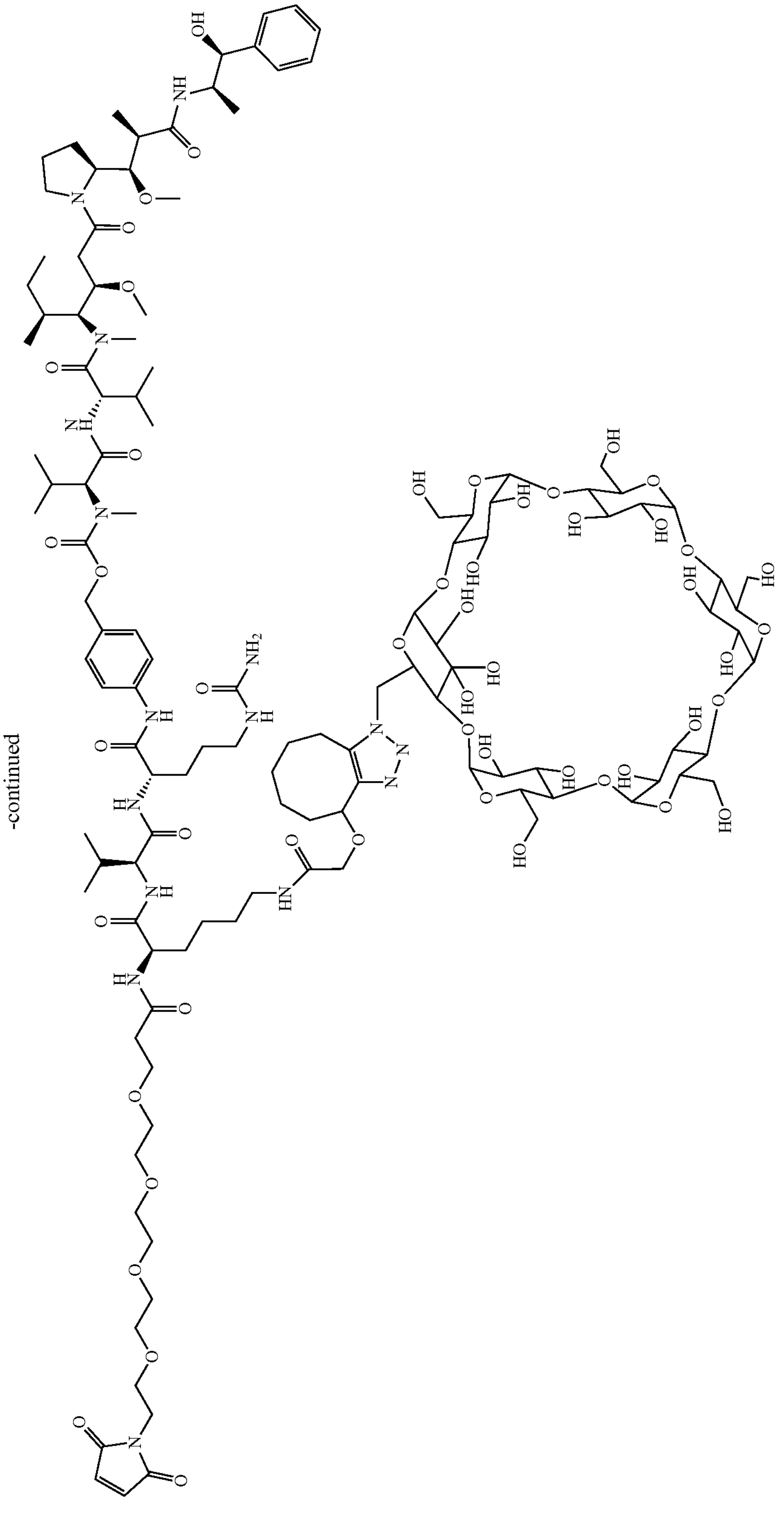

-continued
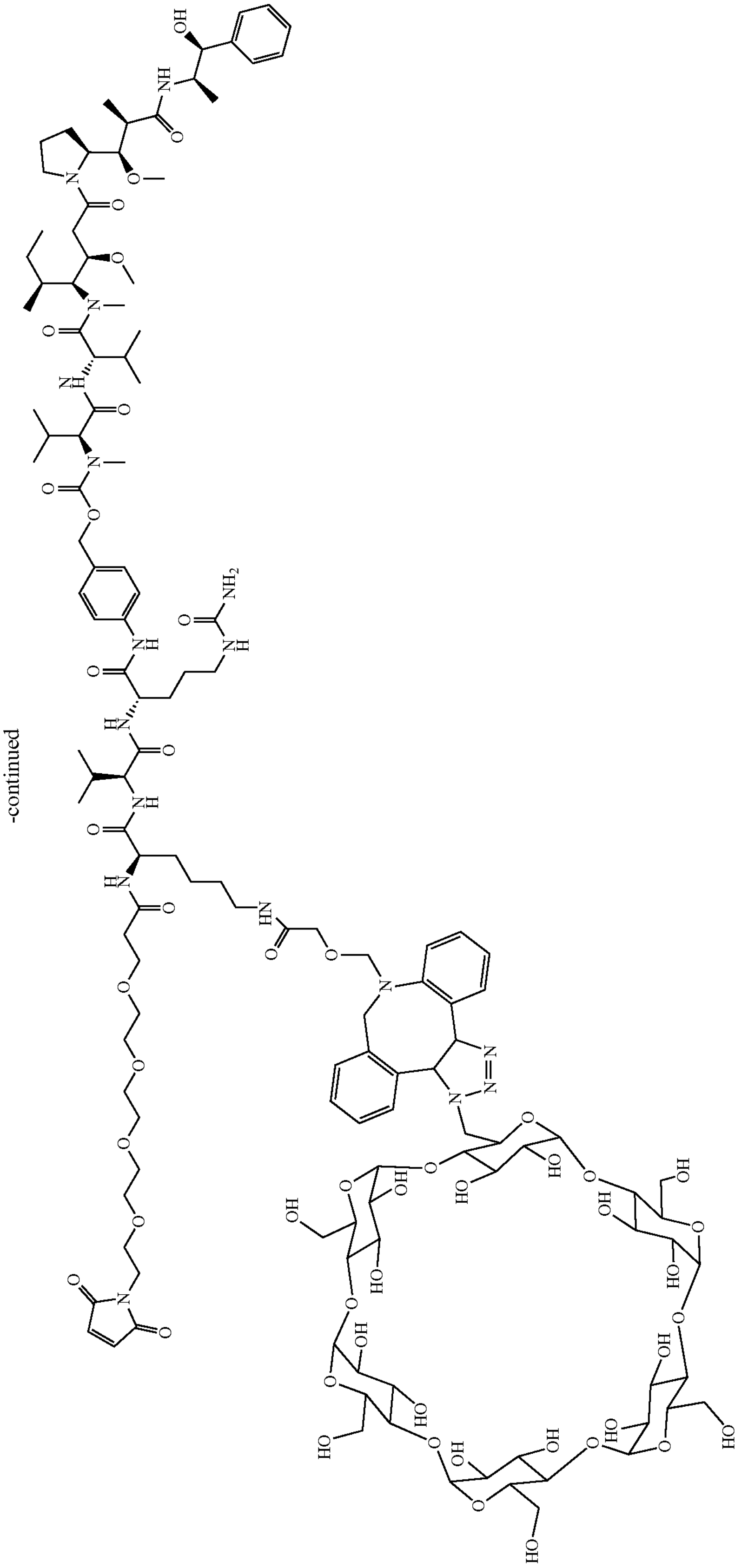

-continued
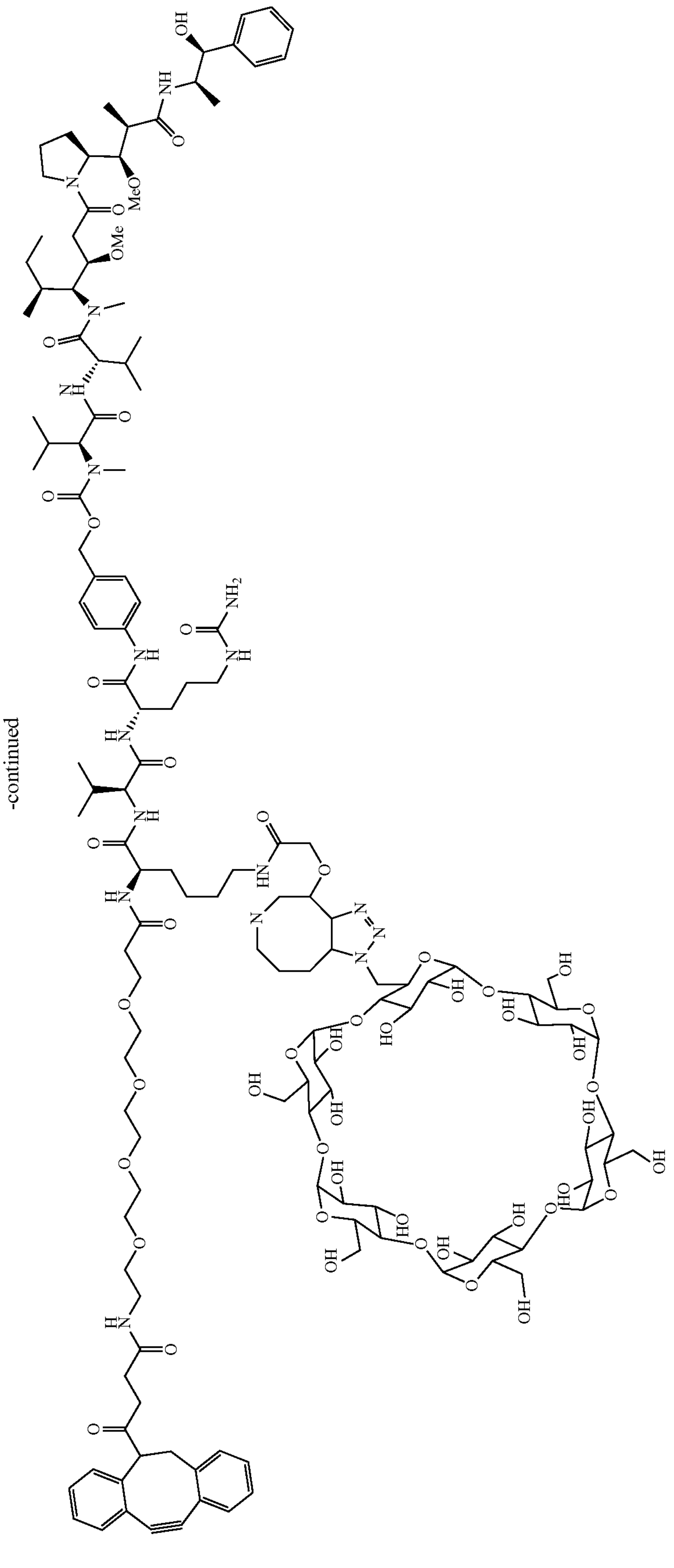

-continued
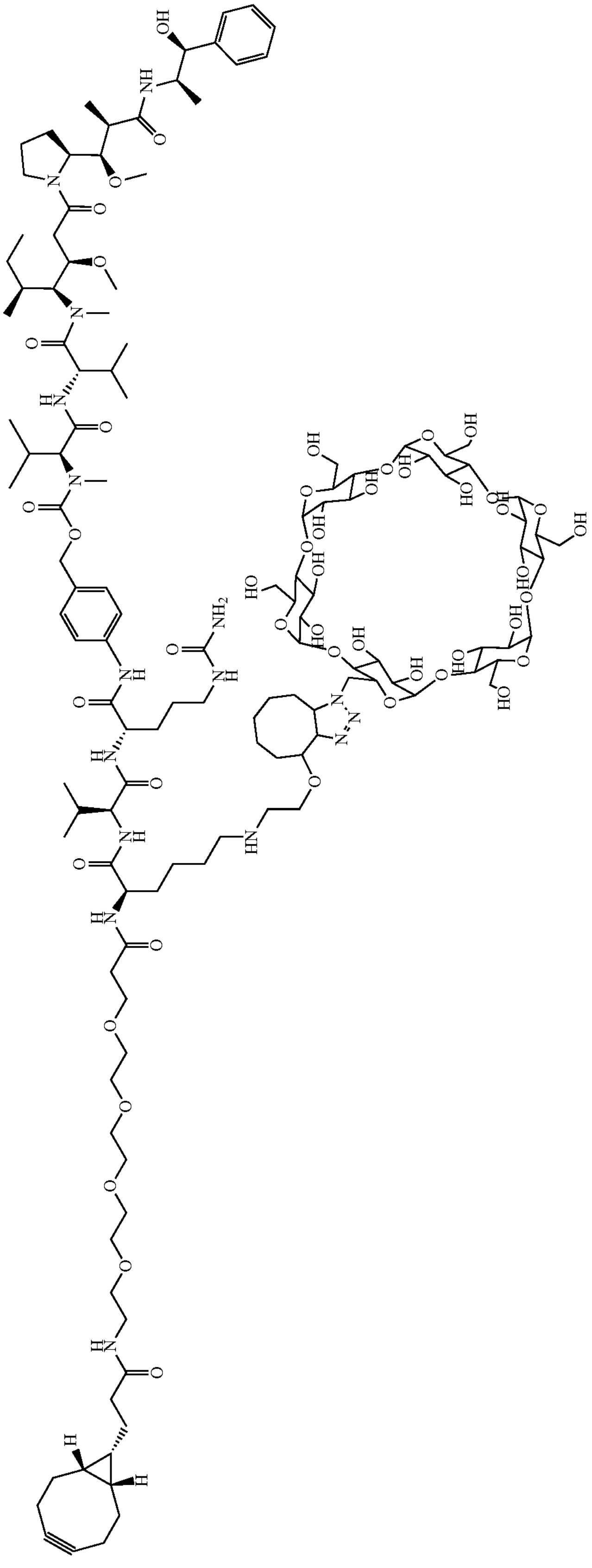

-continued
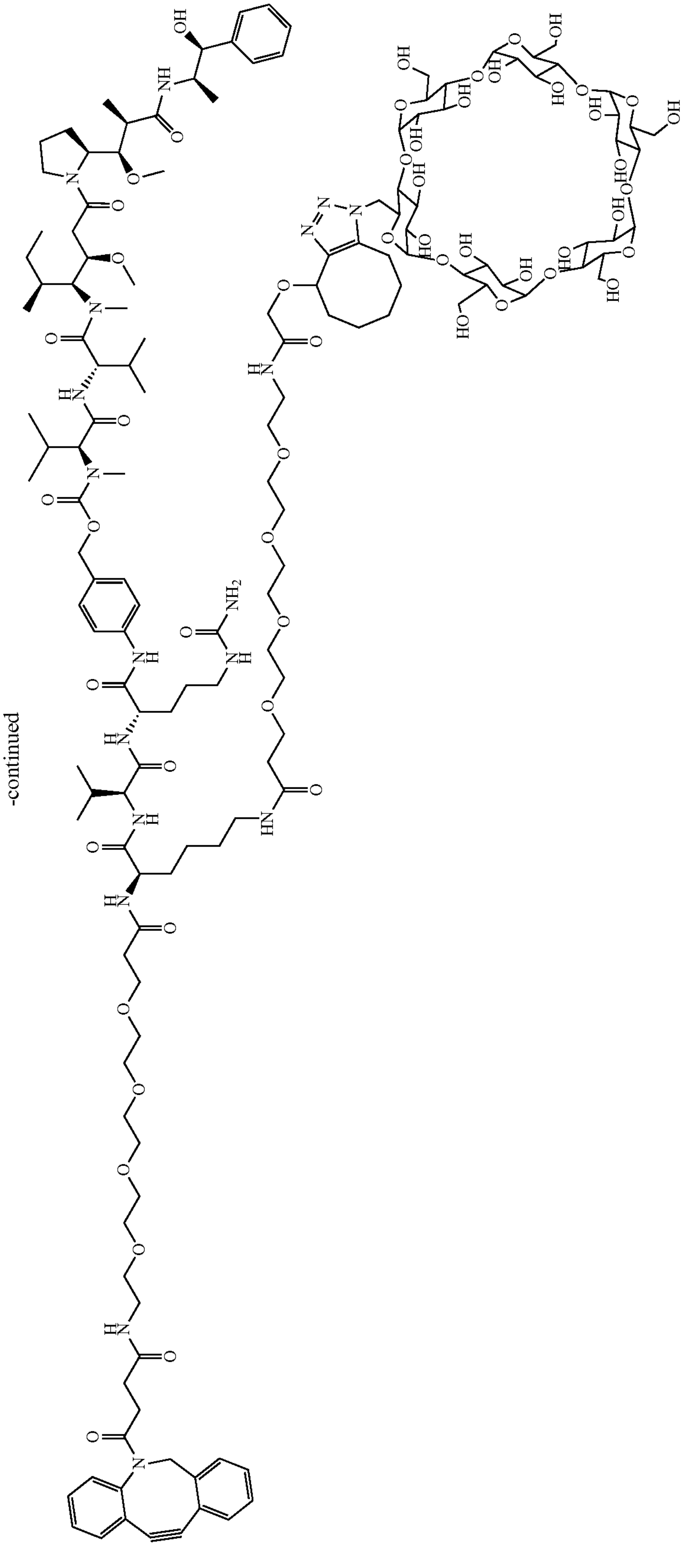

-continued
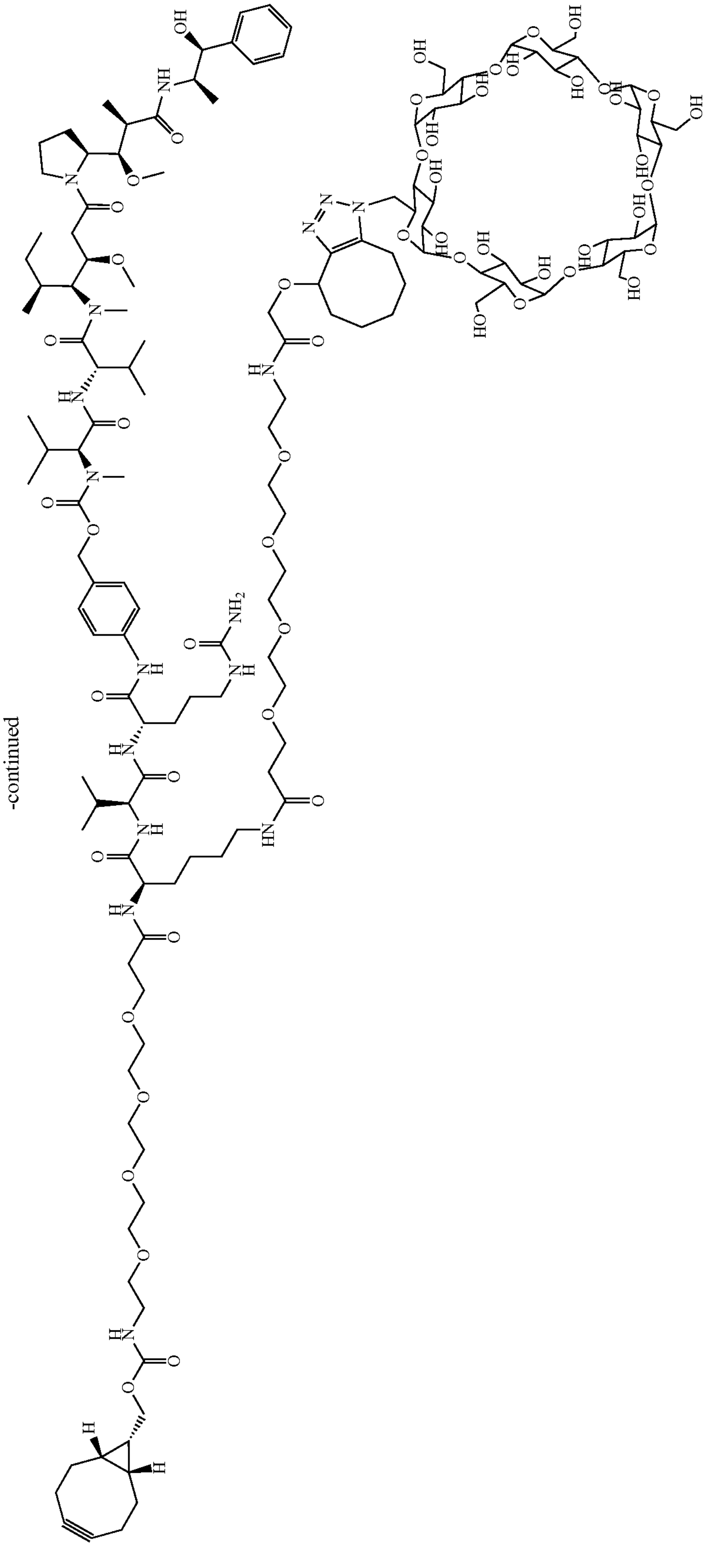

-continued
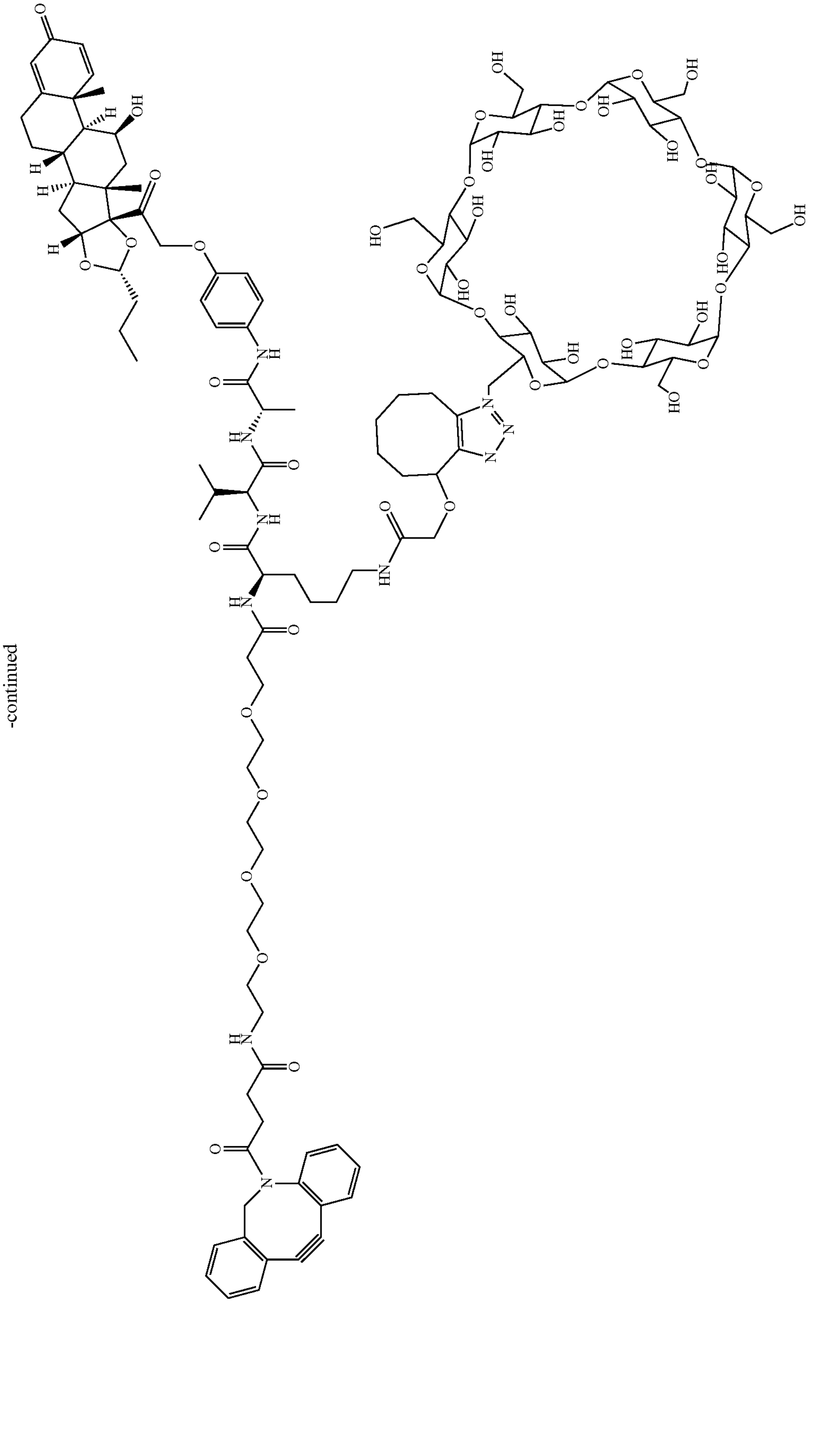

-continued
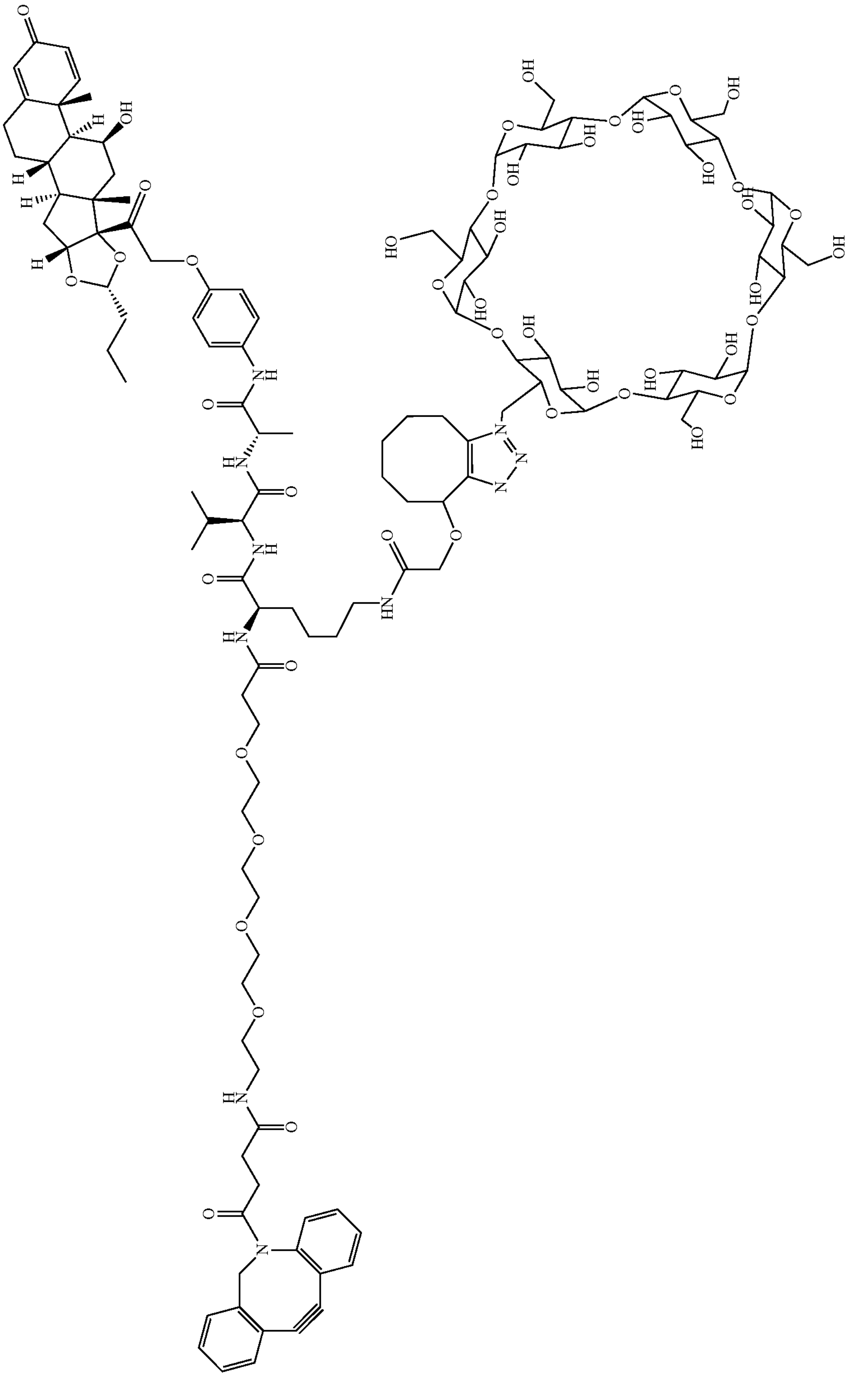

-continued
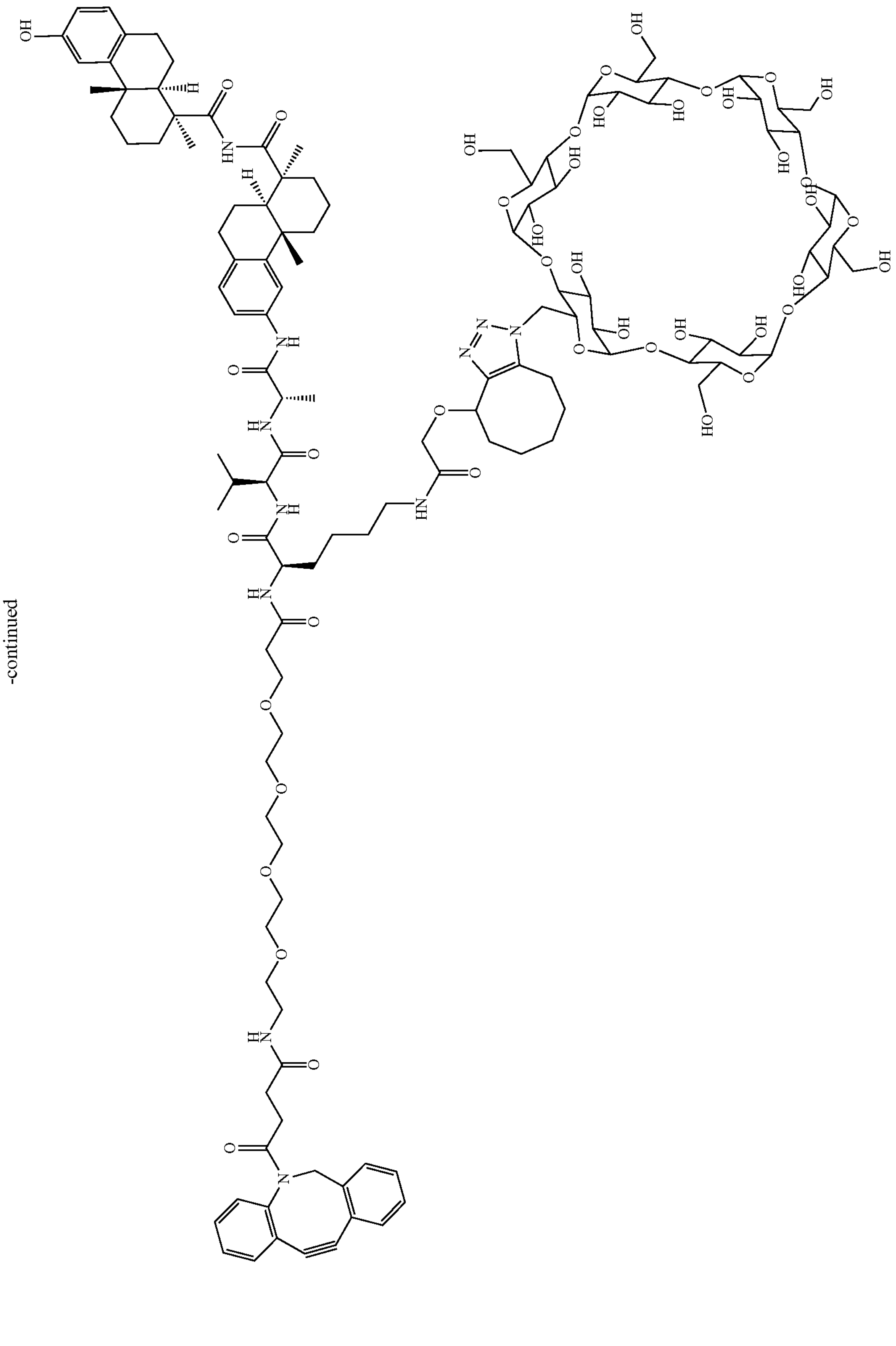

-continued
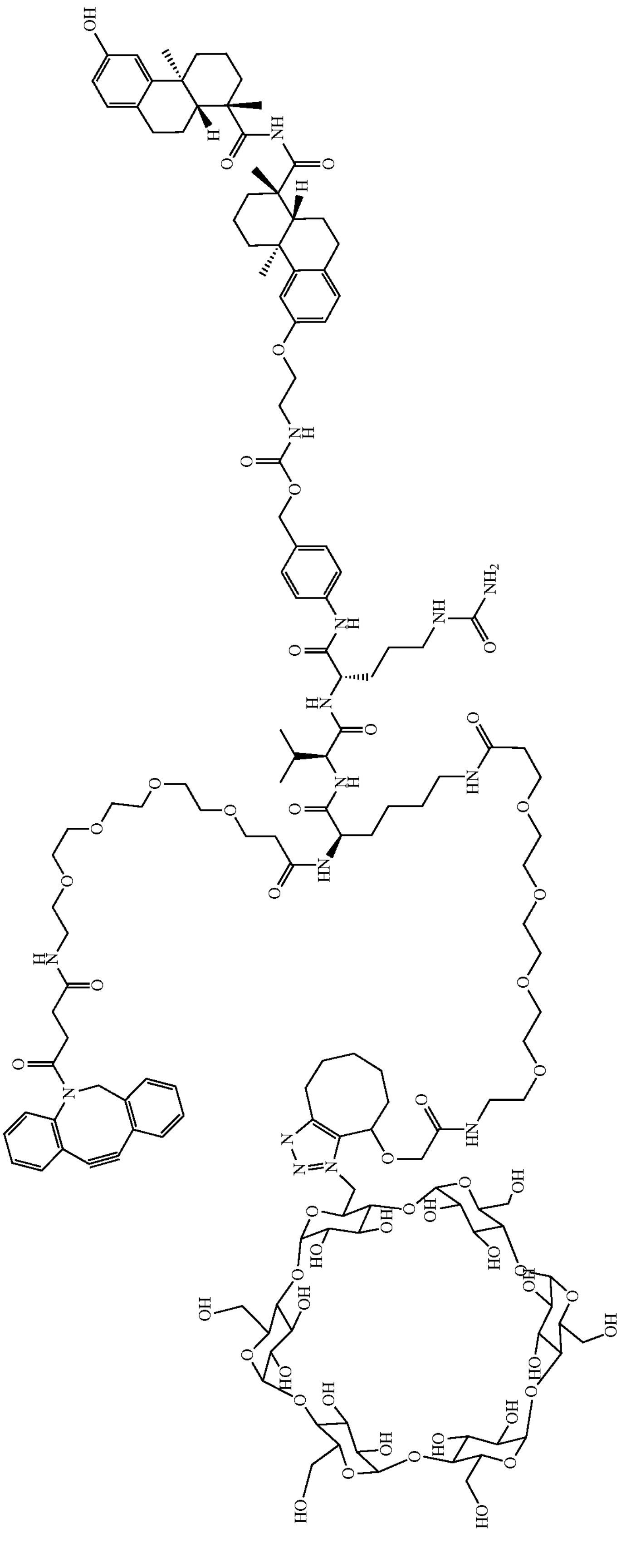

-continued
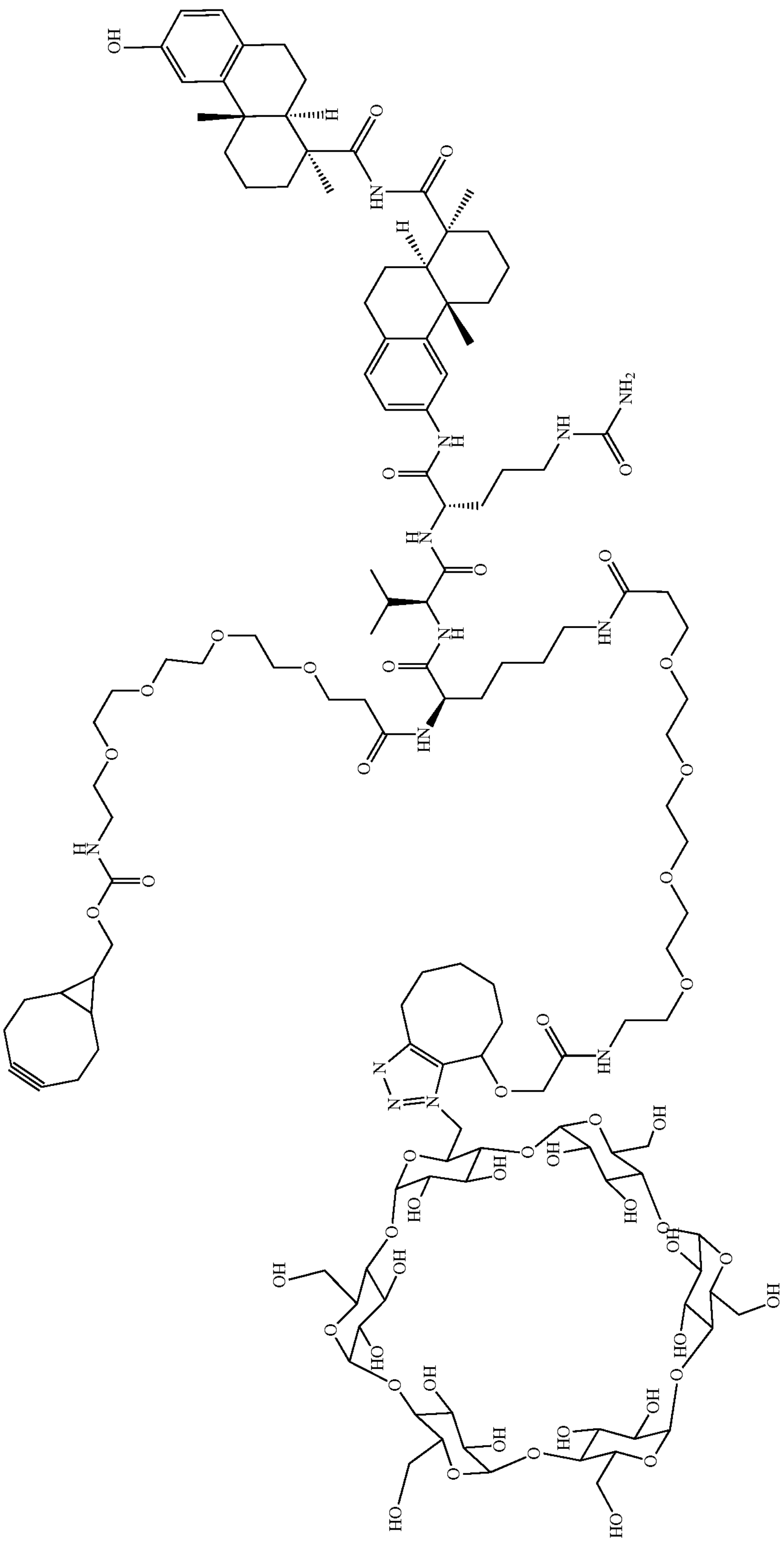

-continued
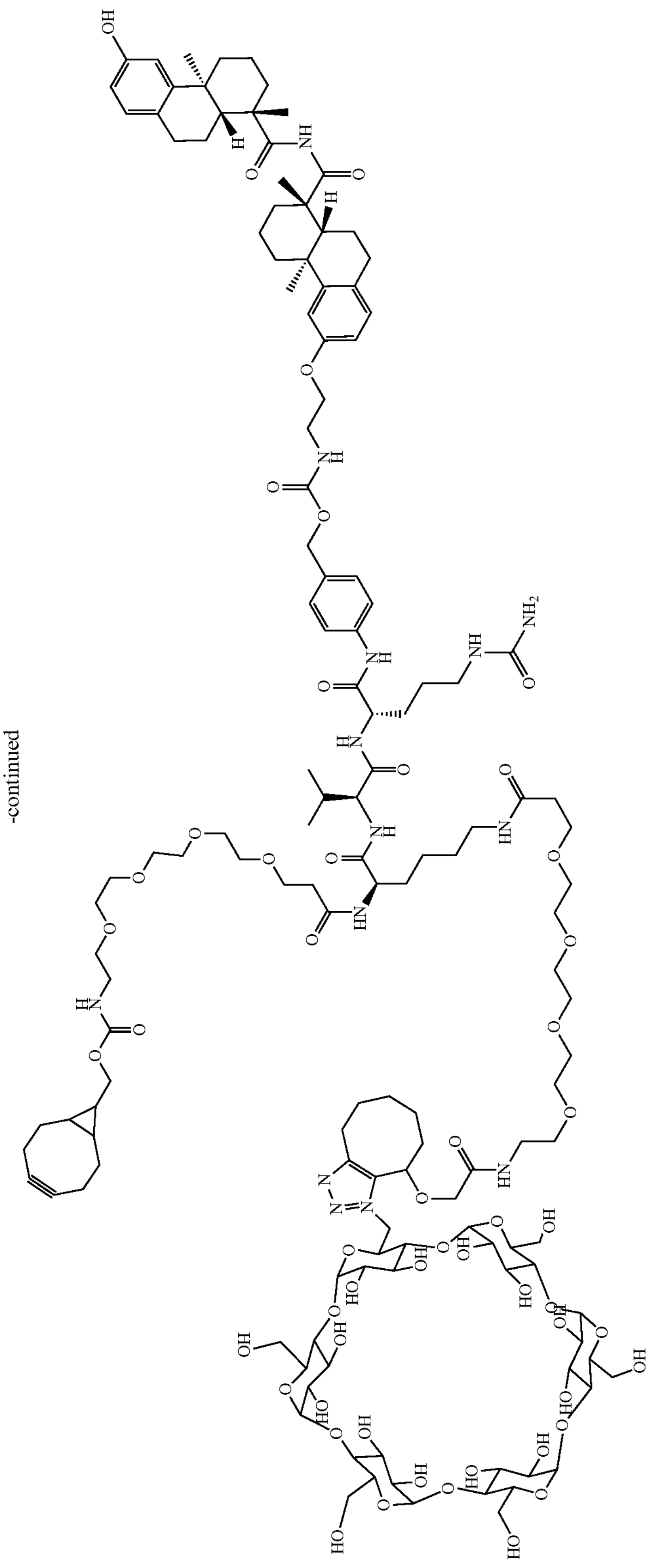

-continued
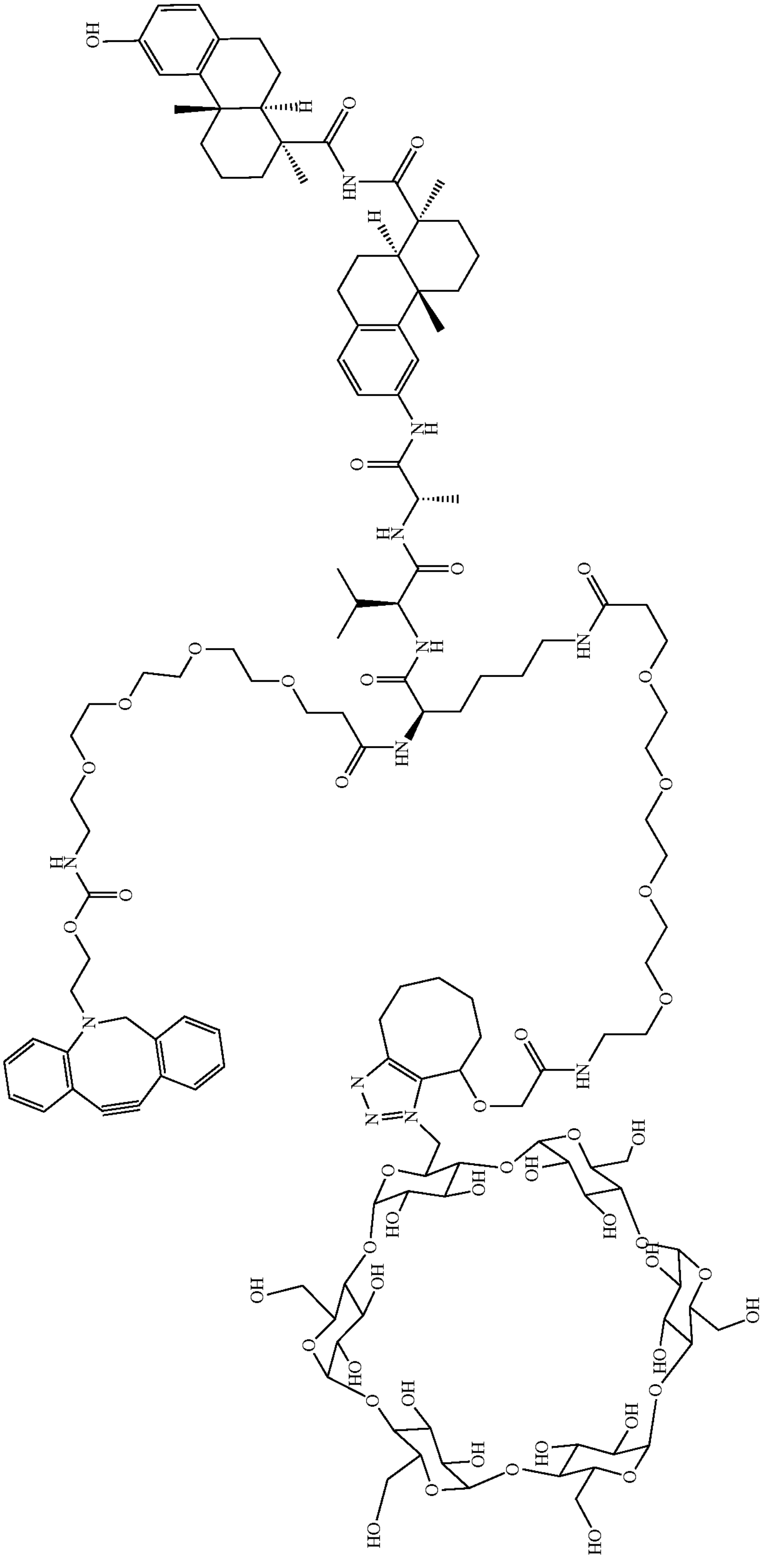

-continued
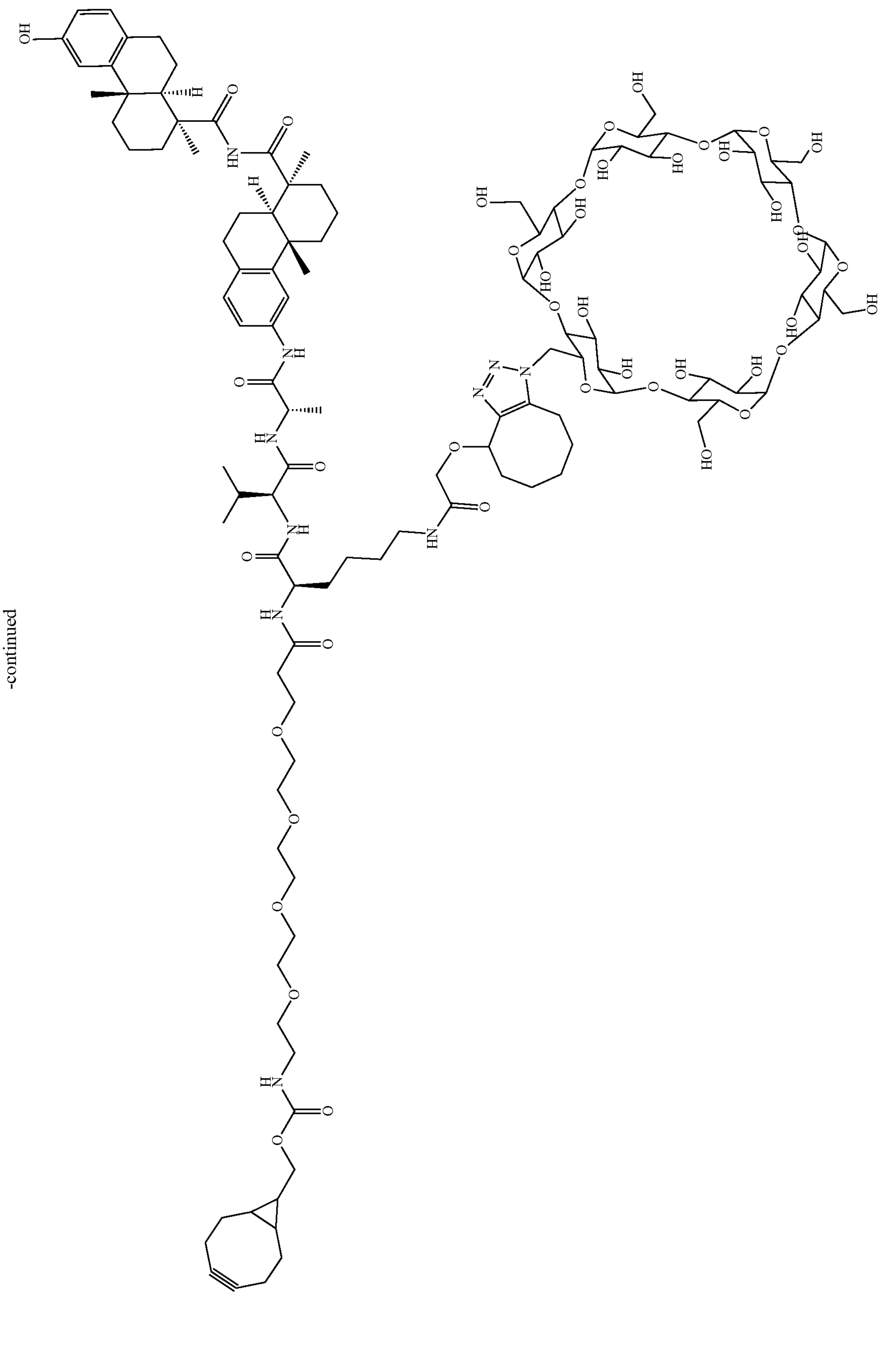

-continued
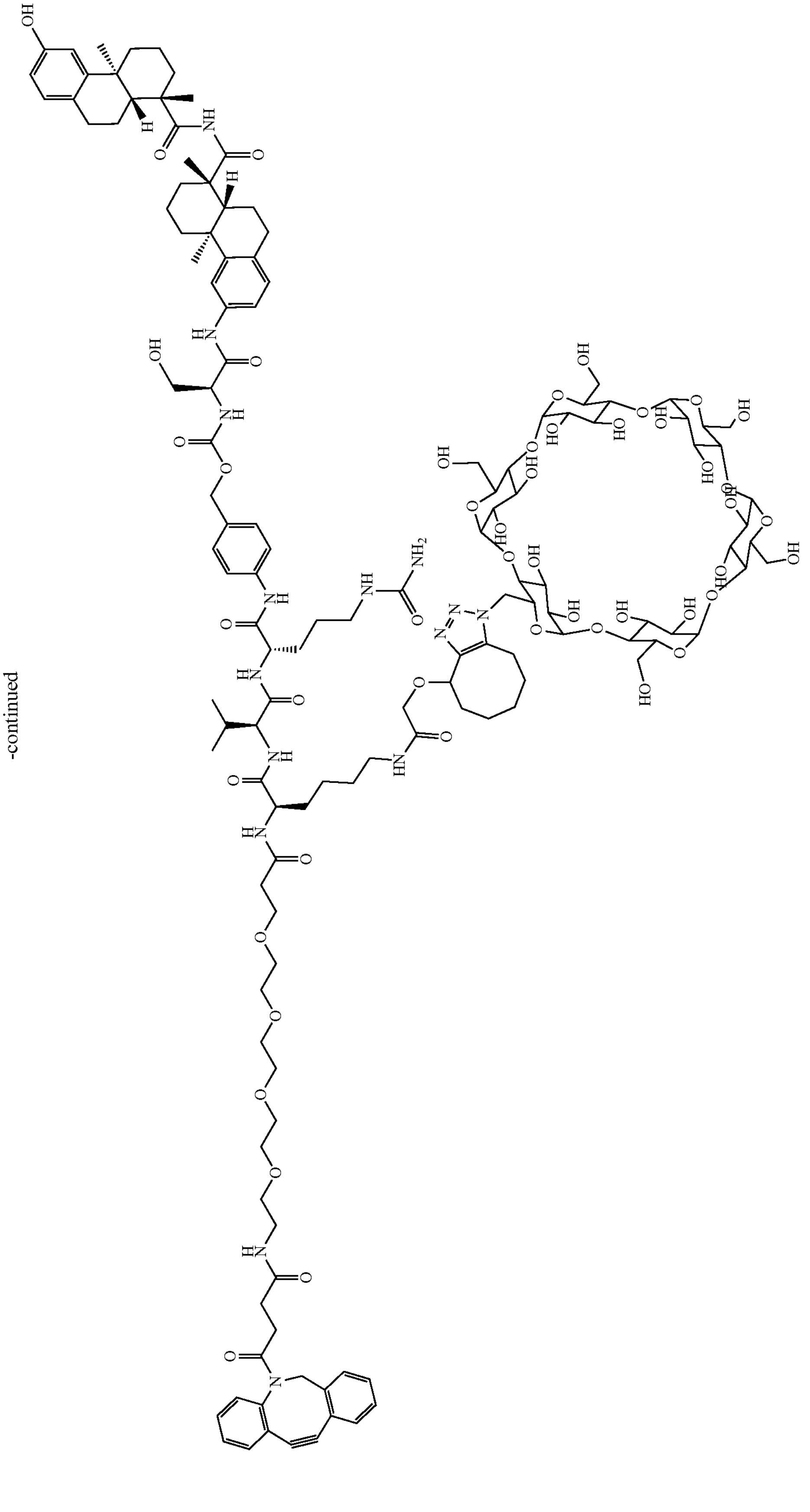

-continued
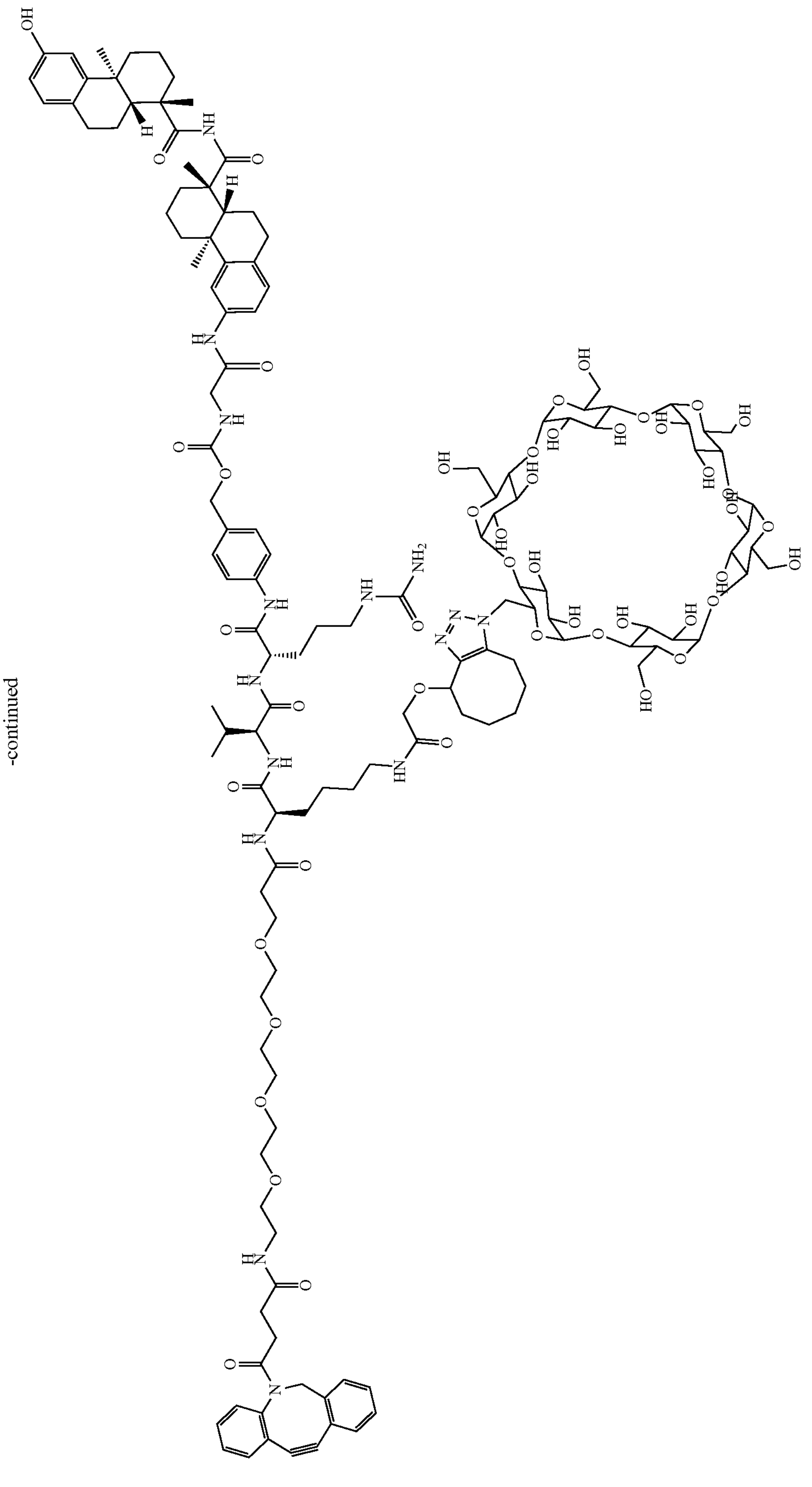

-continued
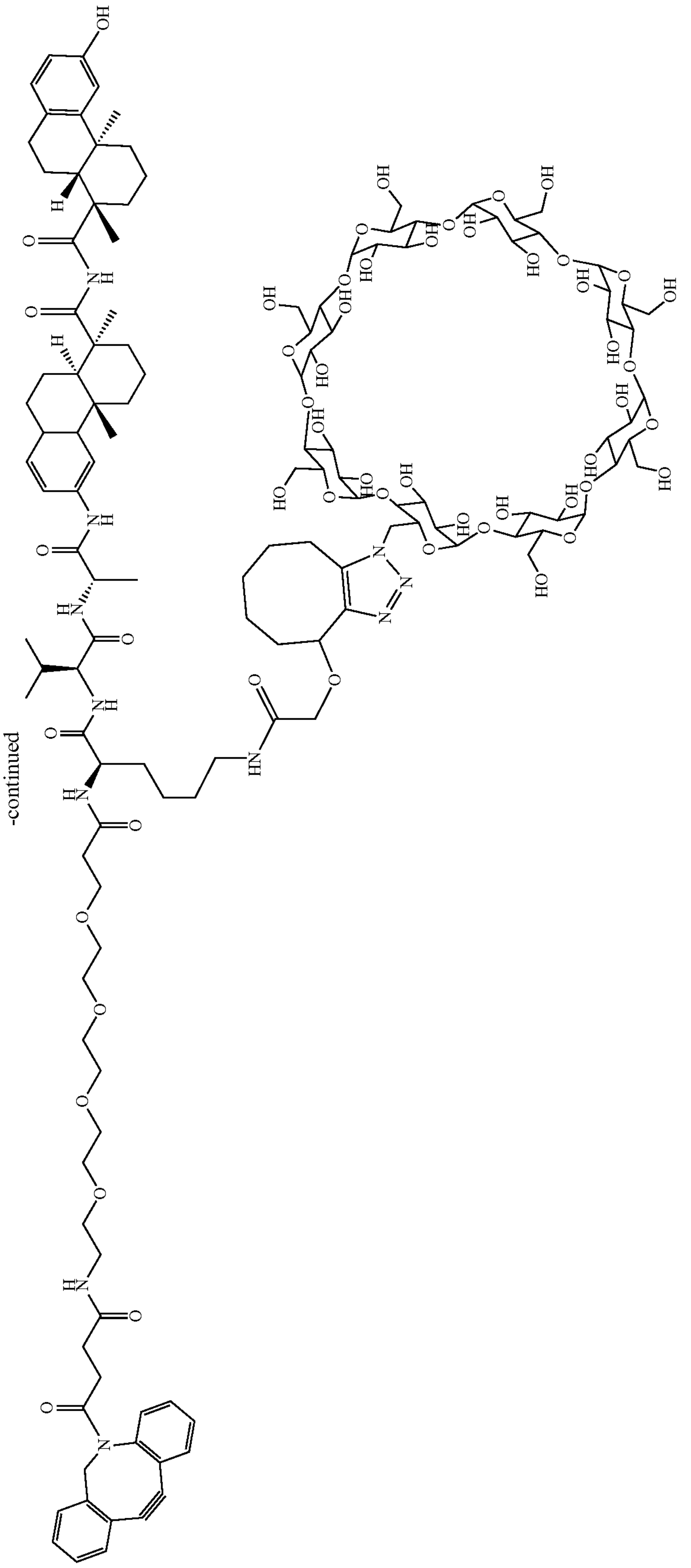

-continued
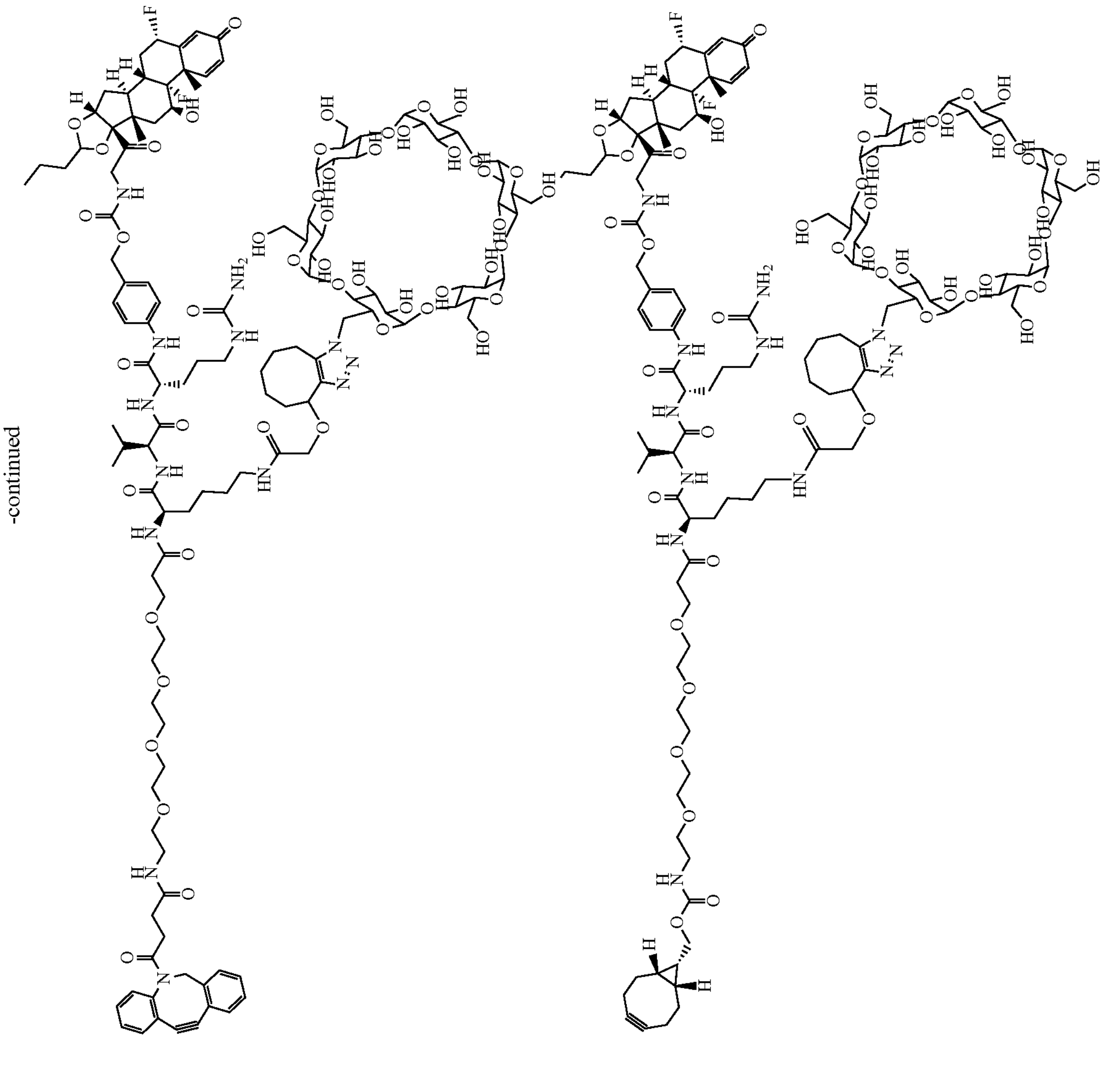

-continued
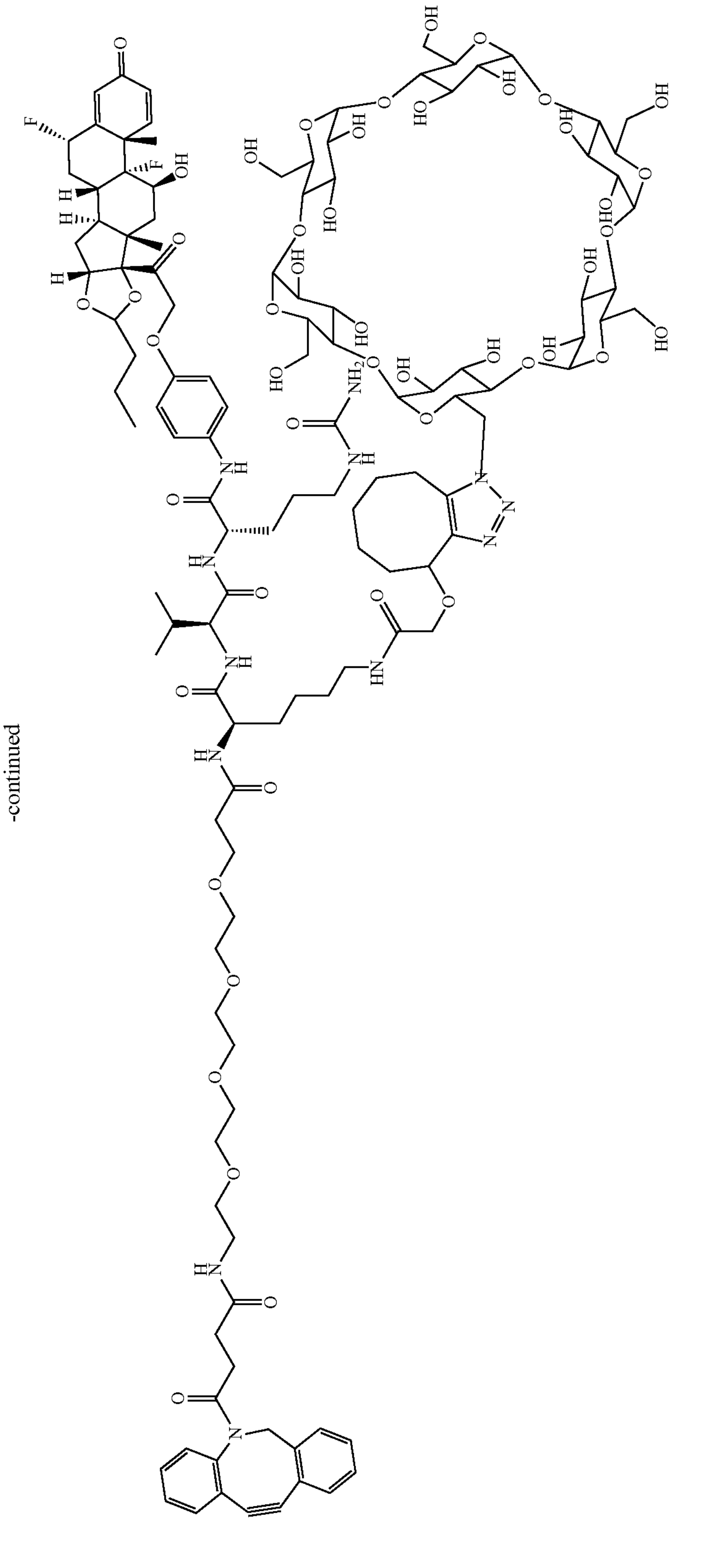

-continued
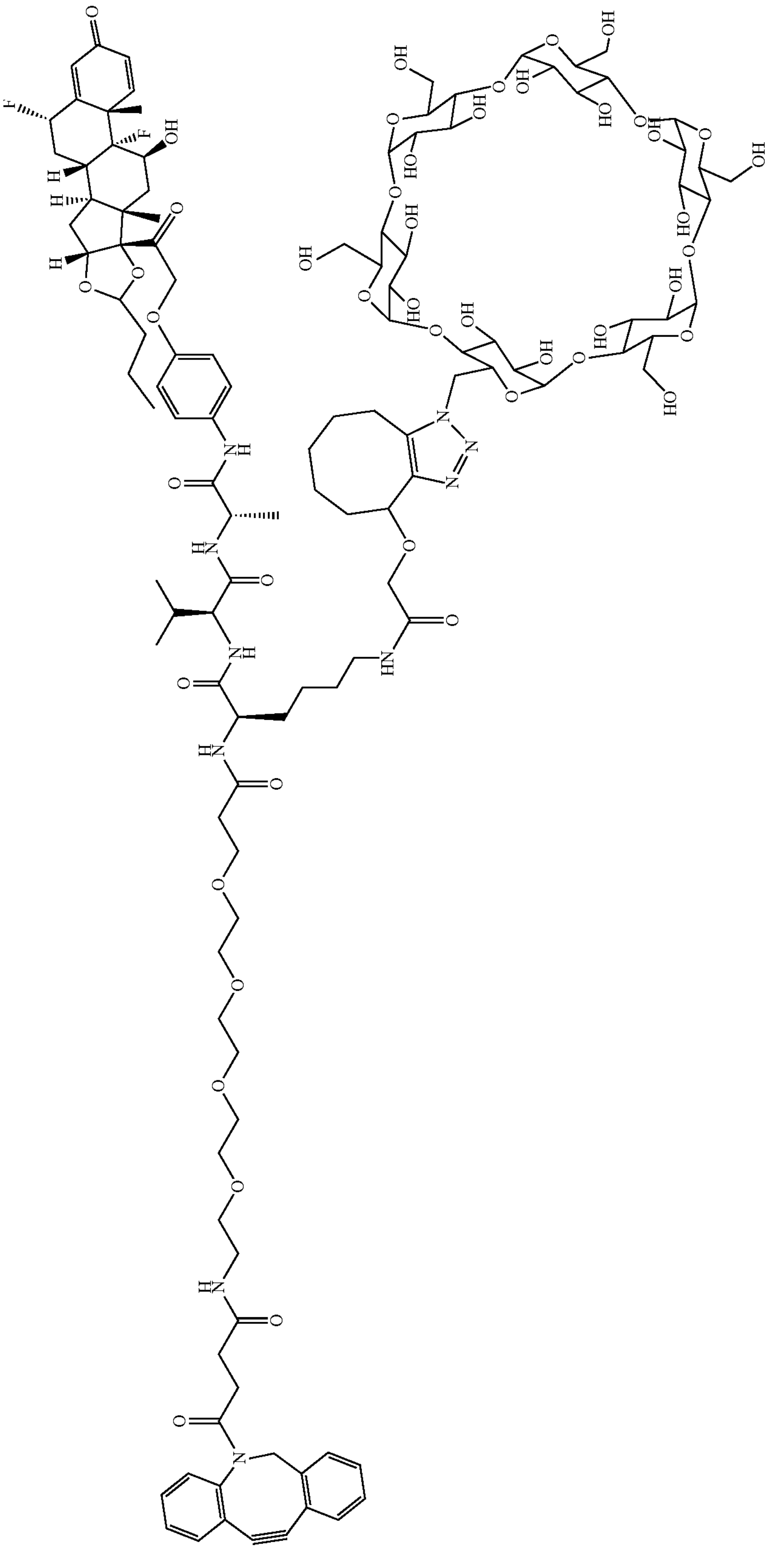

or stereoisomeric form thereof, or a regioisomer thereof, or mixture of regioisomers thereof.

In some examples, set forth herein is a linker-payload comprising a compound set forth herein.

In some examples, set forth herein is a linker-payload comprising a compound set forth herein bonded to an oxygen or a primary or secondary nitrogen of any compound described herein.

In some examples, set forth herein is an antibody-drug-conjugate comprising the compound or linker-payload set forth herein bonded to an antibody, or an antigen binding fragment thereof.

Methods of Preparing Compounds

The compounds provided herein can be prepared, isolated, or obtained by any method apparent to those of skill in the art. Exemplary methods of preparation are described in detail in the examples below. In certain embodiments, compounds provided herein can be prepared according to FIGS. 1-11, and 13-14.

The conjugates described herein can be synthesized by coupling the linker-payloads described herein with a binding agent, for example, an antibody under standard conjugation conditions (see, e.g., Doronina et al. *Nature Biotechnology* 2003, 21, 7, 778, which is incorporated herein by reference in its entirety). When the binding agent is an antibody, the antibody may be coupled to a linker-payload via one or more cysteine or lysine residues of the antibody. Linker-payloads can be coupled to cysteine residues, for example, by subjecting the antibody to a reducing agent, for example, dithiotheritol, to cleave the disulfide bonds of the antibody, purifying the reduced antibody, for example, by gel filtration, and subsequently treating the antibody with a linker-payload containing a suitable reactive moiety, for example, a maleimido group. Suitable solvents include, but are not limited to water, DMA, DMF, and DMSO. Linker-payloads containing a reactive group, for example, an activated ester or acid halide group, can be coupled to lysine residues of the antibody. Suitable solvents include, but are not limited to water, DMA, DMF, and DMSO. Conjugates can be purified using known protein techniques, including, for example, size exclusion chromatography, dialysis, and ultrafiltration/diafiltration.

Binding agents, for example antibodies, can also be conjugated via click chemistry reactions. In some embodiments of said click chemistry reactions, the linker-payload includes a reactive group, for example an alkyne, that is capable of undergoing a 1,3-cycloaddition reaction with an azide. Such suitable reactive groups are described above. The antibody includes one includes one or more azide groups. Such antibodies include antibodies functionalized with, for example, azido-polyethylene glycol groups. In certain embodiments, such a functionalized antibody is derived by treating an antibody having at least one glutamine residue, for example, heavy chain Gln295 and/or Gln55, with a primary amine compound in the presence of the enzyme transglutaminase. Such antibodies may also include Asn297Gln (N297Q) mutants. In certain embodiments, such functionalized antibody is derived by treating an antibody having at least two glutamine residues, for example, heavy chain Gln295 and heavy chain Gln297, with a primary amine compound in the presence of the enzyme transglutaminase. Such antibodies include Asn297Gln (N297Q) mutants. In certain embodiments, the antibody has two heavy chains as described in this paragraph for a total of two or a total of four glutamine residues. In certain instances, antibodies to be conjugated contain one or more additional naturally occurring glutamine residues in their variable regions, which can be accessible to transglutaminase and therefore are able to be conjugated, for instance Gln55. In these instances, the antibodies after conjugation via transglutaminase may have a DAR value higher than 4. Such antibodies include Asn297Gln (N297Q) mutants. In some embodiments, the antibody has two heavy chains as described in this paragraph for a total of two or a total of four or a total of five or six glutamine residues.

In certain embodiments, the antibody comprises a glutamine residue at one or more heavy chain positions numbered 295 in the EU numbering system. In the present disclosure, this position is referred to as glutamine 295, or as Gln295, or as Q295. Those of skill will recognize that this is a conserved glutamine residue in the wild type sequence of many antibodies. In other useful embodiments, the antibody can be engineered to comprise a glutamine residue. Techniques for modifying an antibody sequence to include a glutamine residue are within the skill of those in the art (see, e.g., Ausubel et al. *Current Protoc. Mol. Biol.*).

In certain embodiments, the antibody comprises two glutamine residues, one in each heavy chain. In particular embodiments, the antibody comprises a Q295 residue in each heavy chain. In further embodiments, the antibody comprises one, two, three, four, five, six, seven, eight, or more glutamine residues. These glutamine residues can be in heavy chains, light chains, or in both heavy chains and light chains. These glutamine residues can be wild-type residues, or engineered residues. The antibodies can be prepared according to standard techniques. In certain embodiments, the antibody comprises or further comprises a Q55 residue.

Those of skill will recognize that antibodies are often glycosylated at residue N297, near residue Q295 in a heavy chain sequence. Glycosylation at residue N297 can interfere with a transglutaminase at residue Q295 (Dennler et al., supra). Accordingly, in advantageous embodiments, the antibody is not glycosylated. In certain embodiments, the antibody is deglycoslated or aglycosylated. In particular embodiments, an antibody heavy chain has an N297 mutation. Alternatively stated, the antibody is mutated to no longer have an asparagine residue at position 297. In particular embodiments, an antibody heavy chain has an N297Q mutation. Such an antibody can be prepared by site-directed mutagenesis to remove or disable a glycosylation sequence or by site-directed mutagenesis to insert a glutamine residue at a site apart from any interfering glycosylation site or any other interfering structure. Such an antibody also can be isolated from natural or artificial sources.

The antibody without interfering glycosylation is then treated with a primary amine compound. In certain embodiments, an aglycosylated antibody is treated with a primary amine compound to produce a glutaminyl-modified antibody. In certain embodiments, a deglycosylated antibody is reacted with a primary amine compound to produce a glutaminyl-modified antibody.

The primary amine can be any primary amine that is capable of forming a covalent bond with a glutamine residue in the presence of a transglutaminase. Useful primary amines are described herein. The transglutaminase can be any transglutaminase deemed suitable by those of skill in the art. In certain embodiments, the transglutaminase is an enzyme that catalyzes the formation of an isopeptide bond between a free amine group on the primary amine compound and the acyl group on the side chain of a glutamine residue. Transglutaminase is also known as protein-glutamine-γ-glutamyltransferase. In particular embodiments, the transglutaminase is classified as EC 2.3.2.13. The transglutaminase can be from any source deemed suitable. In certain embodiments, the transglutaminase is microbial. Useful transglutaminases have been isolated from *Streptomyces mobaraense, Streptomyces cinnamoneum, Streptomyces griseo-carneum, Streptomyces lavendulae*, and *Bacillus subtilis*. Non-microbial transglutaminases, including mammalian transglutaminases, can also be used. In certain embodiments, the transglutaminase can be produced by any technique or obtained from any source deemed suitable by the practitioner of skill. In particular embodiments, the transglutaminase is obtained from a commercial source.

In particular embodiments, the primary amine compound comprises a reactive group capable of further reaction after transglutamination. In these embodiments, the glutaminyl-modified antibody can be reacted or treated with a reactive payload compound or a reactive linker-payload compound to form an antibody-payload conjugate. In certain embodiments, the primary amine compound comprises an azide as described herein.

In certain embodiments, the glutaminyl-modified antibody is reacted or treated with a reactive linker-payload to form an antibody-payload conjugate. The reaction can proceed under conditions deemed suitable by those of skill in the art. In certain embodiments, the glutaminyl-modified antibody is contacted with the reactive linker-payload compound under conditions suitable for forming a bond between the glutaminyl-modified antibody and the linker-payload compound. Suitable reaction conditions are well known to those in the art.

Exemplary reactions are provided in the Examples below.

In some examples, set forth herein is a method of making a conjugate comprising treating or contacting a compound with a binding agent under coupling conditions, wherein the compound comprises a reactive linker bonded to at least one payload moiety and linked to at least one cyclodextrin moiety via a covalent linker, wherein said covalent linker is bonded directly or indirectly to each of the reactive linker, the payload moiety, the cyclodextrin moiety. In some examples, the compound which reacts with a binding agent is a compound according to Formula (II):

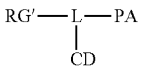

(II)

In Formula (II), RG' is a reactive group, L is a trivalent linker, CD is a cyclodextrin residue; and PA is a payload residue.

In some examples, the binding agent that reacts with a compound of Formula (II) is an antibody or an antigen binding fragment thereof.

In some examples, herein, the D-Lys can be replaced with a reagent set forth in FIG. 20.

In some examples, the cyclodextrin-containing moieties may react in a bioorthogonal reaction selected from a [3+2] click reaction, a Diels-Alder reaction, a reductive-amination, a photoclick reaction, or other reactions.

Other useful bioorthogonal reactions suitable for use with the methods herein include, but are not limited to, the Staudinger ligation, a click reaction, a tetrazine ligation, and a photoclick reaction.

The following reference shows example reactions and reagents that may be used with the bioorthogonal reactions set forth herein: Zheng, Mengmeng, et al., *Molecules* 2015, 20, 3190-3205, the contents of which are herein incorporated by reference in their entirety for all purposes.

Pharmaceutical Compositions and Methods of Treatment

Provided herein are methods of treating and preventing diseases, conditions, or disorders comprising administering a therapeutically or prophylactically effective amount of one or more of the compounds disclosed herein, for example, one or more of the compounds of a formula provided herein. A person of skill will appreciate that the diseases, disorders, and/or conditions include, but are not limited to, those associated with the antigens listed herein.

The compounds described herein can be administered alone or together with one or more additional therapeutic agents. The one or more additional therapeutic agents can be administered just prior to, concurrent with, or shortly after the administration of the compounds described herein. The present disclosure also includes pharmaceutical compositions comprising any of the compounds described herein in combination with one or more additional therapeutic agents, and methods of treatment comprising administering such combinations to subjects in need thereof.

Suitable additional therapeutic agents include, but are not limited to: a second glucocorticoid, an autoimmune therapeutic agent, a hormone, a biologic, or a monoclonal antibody. Suitable therapeutic agents also include, but are not limited to any pharmaceutically acceptable salts, acids, or derivatives of a compound set forth herein.

In some embodiments of the methods described herein, multiple doses of a compound described herein (or a pharmaceutical composition comprising a combination of a compound described herein and any of the additional therapeutic agents mentioned herein) may be administered to a subject over a defined time course. The methods according to this aspect of the disclosure comprise sequentially administering to a subject multiple doses of a compound described herein. As used herein, "sequentially administering" means that each dose of the compound is administered to the subject at a different point in time, e.g., on different days separated by a predetermined interval (e.g., hours, days, weeks or months). The present disclosure includes methods which comprise sequentially administering to the patient a single initial dose of a compound described herein, followed by one or more secondary doses of the compound, and optionally followed by one or more tertiary doses of the compound.

The terms "initial dose," "secondary doses," and "tertiary doses," refer to the temporal sequence of administration of the compounds described herein. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses can all contain the same amount the compound described herein, but generally can differ from one another in terms of frequency of administration. In certain embodiments, the amount of the compound contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present disclosure, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose the compound which is administered to a patient prior to the administration of the very next dose in the sequence with no intervening doses.

The methods according to this aspect of the disclosure may comprise administering to a patient any number of secondary and/or tertiary doses of the compound. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient. The administration regimen may be carried out indefinitely over the lifetime of a particular subject, or until such treatment is no longer therapeutically needed or advantageous.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the disclosure, the frequency at which the secondary and/or tertiary doses are administered to a patient can vary over the course of the treatment regimen. The frequency of administration may also be adjusted during the course of treatment by a physician depending on the needs of the individual patient following clinical examination.

The present disclosure includes administration regimens in which 2 to 6 loading doses are administered to a patient at a first frequency (e.g., once a week, once every two weeks, once every three weeks, once a month, once every two months, etc.), followed by administration of two or more maintenance doses to the patient on a less frequent basis. For example, according to this aspect of the disclosure, if the loading doses are administered at a frequency of once a month, then the maintenance doses may be administered to the patient once every six weeks, once every two months, once every three months, etc.

The present disclosure includes pharmaceutical compositions of the compounds and/or conjugates described herein, e.g., the compounds of Formula I, Ia, Ib, e.g., compositions comprising a compound described herein, a salt, stereoisomer, polymorph thereof, and a pharmaceutically acceptable carrier, diluent, and/or excipient. Examples of suitable carriers, diluents and excipients include, but are not limited to, buffers for maintenance of proper composition pH (e.g., citrate buffers, succinate buffers, acetate buffers, phosphate buffers, lactate buffers, oxalate buffers, and the like), carrier proteins (e.g., human serum albumin), saline, polyols (e.g., trehalose, sucrose, xylitol, sorbitol, and the like), surfactants (e.g., polysorbate 20, polysorbate 80, polyoxolate, and the like), antimicrobials, and antioxidants.

In some examples, set forth herein is a method of treating a disease, disorder or condition comprising administering to a patient having said disorder a therapeutically effective amount of a compound of Formula (I), (Ia), (Ib), (Ib1), (Ib2), (b3), (Ib4), (Ib5), (Ib6), (Ic), (I1), (Id), (Ie), (Ie1), (1e2), (If) or a pharmaceutical composition thereof.

In some examples, set forth herein is a method of preventing a disease, disorder or condition comprising administering to a patient having said disorder a prophylactically effective amount of a compound of Formula (I), (Ia), (Ib), (Ib1), (Ib2), (b3), (Ib4), (Ib5), (Ib6), (Ic), (I1), (Id), (Ie), (Ie1), (1e2), (If) or a pharmaceutical composition thereof.

In some examples, set forth herein is a method of treating or preventing a disease, disorder, or condition selected from the group consisting of a proliferative disorder, a neurodegenerative disorder, an immunological disorder, an autoimmune disease, an inflammatory disorder, a dermatological disease, a metabolic disease, cardiovascular disease, and a gastrointestinal disease.

Provided herein are methods for modulating LDLR (low-density lipoprotein receptor) protein expression or cholesterol efflux in a cell comprising contacting said cell with an antibody drug conjugate (ADC), wherein the ADC comprises an antibody targeting said cell, cyclodextrin, and LXR agonist.

The proliferative disorder can be any proliferative disorder known to those of skill. In certain embodiments, proliferative disorders include, without limitation, oncology disorders, where the oncology disorder can be any cancer disorder known to those of skill. In certain embodiments, provided herein are methods of treating or preventing a melanoma. In certain embodiments, provided herein are methods of treating or preventing metastatic melanoma. In certain embodiments, provided herein are methods of treating or preventing lung cancer. In certain embodiments, provided herein are methods of treating or preventing EGFR-tyrosine kinase inhibitor resistant lung cancer. In certain embodiments, provided herein are methods of treating or preventing oral cancer. In certain embodiments, provided herein are methods of treating or preventing oral squamous cell carcinoma. In certain embodiments, provided herein are methods of treating or preventing prostate cancer. In certain embodiments, provided herein are methods of treating or preventing Hodgkin's lymphoma. In certain embodiments, provided herein are methods of treating or preventing breast cancer.

The neurodegenerative disorder can be any neurodegenerative disorder known to those of skill. In certain embodiments, provided herein are methods of treating or preventing Alzheimer's disease. In certain embodiments, provided herein are methods of treating or preventing Parkinson's disease. In certain embodiments, provided herein are methods of treating or preventing Huntington's disease. In certain embodiments, provided herein are methods of treating or preventing amyotrophic lateral sclerosis. In certain embodiments, provided herein are methods of treating or preventing myelin gene expression. In certain embodiments, provided herein are methods of treating or preventing myelination and remyelination conditions, diseases, or disorders.

The immunological disorder can be any immunological disorder known to those of skill. In certain embodiments, provided herein are methods of treating or preventing inflammatory bowel disease. In certain embodiments, provided herein are methods of treating or preventing ulcerative colitis. In certain embodiments, provided herein are methods of treating or preventing Crohn's disease.

The inflammatory disorder can be any inflammatory disorder known to those of skill. In certain embodiments, provided herein are methods of treating or preventing arthritis. In certain embodiments, provided herein are methods of treating or preventing rheumatoid arthritis.

The metabolic disease can be any metabolic disease known to those of skill. In certain embodiments, dyslipidemia is selected from the group consisting of hyperlipidemia, hypercholesterolemia, hypertriglyceridemia, hyperlipoproteinemia, HDL deficiency, ApoA-I deficiency, and cardiovascular disease such as coronary artery disease (including, for example, treatment and prevention of angina, myocardial infarction and sudden cardiac death); atherosclerosis (including, for example, treatment and prevention of atherosclerosis); and restenosis (including, for example, preventing or treating atherosclerotic plaques which develop as a consequence of medical procedures such as balloon angioplasty). In certain embodiments, provided herein are methods of treating or preventing diabetes.

The cardiovascular disease can be any cardiovascular disease known to those of skill. In certain embodiments, provided herein are methods of treating or preventing atherosclerosis. In certain embodiments, provided herein are methods of treating or preventing atherosclerosis derived from abnormal macrophage processing. In certain embodiments, provided herein are methods of treating or preventing atherosclerosis derived from the formation of oxidized low-density lipoproteins (oxLDLs), where marcrophages fail to process oxLDLs. In certain embodiments, provided herein are methods of treating or preventing ischemic heart disease. In certain embodiments, provided herein are methods of treating or preventing stroke. In certain embodiments, provided herein are methods of treating or preventing hypertensive heart disease. In certain embodiments, provided herein are methods of treating or preventing aortic aneurysm. In certain embodiments, provided herein are methods of treating or preventing endocarditis. In certain embodiments, provided herein are methods of treating or preventing peripheral artery disease. In certain embodiments, provided herein are methods of treating or preventing combinations of any of the diseases provided in this paragraph.

In some examples, set forth herein is a method for modulating the function of a nuclear receptor. By way of non-limiting example, the function may be selected from expression/secretion of inflammatory mediators (e.g. cytokines, chemokines), cholesterol regulation, cholesterol intake, cholesterol efflux, cholesterol oxidation, migration, chemotaxis, apoptosis and necrosis, an inflammatory activity, lipid regulation, apoptosis, migration, chemotaxis, gene transcription, and protein expression.

In some examples, set forth herein is a method of treating a disease or disorder in a patient in need thereof comprising administering to the patient a compound or pharmaceutical composition set forth herein. In some examples, the administered compound is an antibody-drug conjugate set forth herein.

In some examples, set forth herein is a method of an antibody-drug conjugate comprising the step of contacting a binding agent with a linker-payload compound under conditions suitable for forming a bond between the binding agent and the compound.

In some examples, set forth herein is a method of treating a proliferative disease, a metabolic disease, inflammation, or a neurodegenerative disease in a subject comprising administering to the subject of an effective treatment amount of a compound or pharmaceutical composition set forth herein. In some examples, the administered compound is an antibody-drug conjugate set forth herein.

In some examples, set forth herein is a method of treating a disease, disorder, or condition in a subject comprising administering to the subject of an effective treatment amount of a compound or pharmaceutical composition set forth herein. In some examples, the administered compound is an antibody-drug conjugate set forth herein.

In some examples, set forth herein is a method of treating a proliferative disease in a subject comprising administering to the subject of an effective treatment amount of a compound or pharmaceutical composition set forth herein. In some examples, the administered compound is an antibody-drug conjugate set forth herein.

In some examples, set forth herein is a method of treating a metabolic disease in a subject comprising administering to the subject of an effective treatment amount of a compound or pharmaceutical composition set forth herein. In some examples, the administered compound is an antibody-drug conjugate set forth herein.

In some examples, set forth herein is a method of treating inflammation in a subject comprising administering to the subject of an effective treatment amount of a compound or pharmaceutical composition of set forth herein. In some examples, the administered compound is an antibody-drug conjugate set forth herein.

In some examples, set forth herein is a method of treating a neurodegenerative disease in a subject comprising administering to the subject of an effective treatment amount of a compound or pharmaceutical composition set forth herein. In some examples, the administered compound is an antibody-drug conjugate set forth herein.

EXAMPLES

Set forth in the Examples are cyclodextrin-$(PEG)_n$ linkers that link antibodies with at least three types of payloads (see FIG. 1). Two antibodies, anti-HER2 antibody and anti-PRLR (Anti-PRLR Ab) antibody, were used in the conjugations. The antibodies were bonded either directly to maleimide-linker-payloads (see FIG. 13) or through an azido functional group to DIBAC-Linker-payloads via [3+2] click reactions (see FIG. 14).

Compared to those without cyclodextrin moieties, the conjugates with the cyclodextrin-(PEG)A linkers showed lower calculated Log P/Log D values, shorter retention times on reverse HPLC, and better aqueous solubility, indicating better hydrophilicity (Table 8). These new linker-payloads were also cleavable in Cathepsin B assays (Table 8). In addition, those ADCs showed comparable bio-activities to those without CD-moieties in in vitro assays (Tables 10, 11, 12).

As used herein, the symbols and conventions used in the processes, and Examples, herein, are consistent with those used in the contemporary scientific literature, for example, the Journal of the American Chemical Society or the *Journal of Biological Chemistry* unless specified otherwise to the contrary. Specifically, but without limitation, the following abbreviations may be used in the Examples and throughout the specification:

| Abbreviation | Term |
|---|---|
| ADC | Antibody-drug conjugate |
| Aglycosylated antibody | Antibody does not have any glycan |
| API | Atmospheric pressure ionization |
| aq | Aqueous |
| Boc | N-tert-butoxycarbonyl |

| Abbreviation | Term |
|---|---|
| BupH ™ | Thermo Scientific Prod# 28372, containing 100 mM sodium phosphate and 150 mM sodium chloride, potassium free, pH was adjusted from 7.2 to 7.6-7.8 MQ, unless otherwise noted. |
| capB | Cathepsin B |
| CD | Cyclodextrin |
| COT | Cyclooctynol |
| Da | Dalton |
| DAD | Diode array detector |
| DAR | Drug to antibody ratio |
| DCM | Dichloromethane |
| DIBAC | 11,12-didehydro-5,6-dihydro-Dibenz[b,f]azocine |
| DIBAC-Suc | 11,12-didehydro-5,6-dihydro-Dibenz[b,f]azocine succinamic acid |
| DIBAC-Suc-PEG4-VC-pAB-PNP | {4-[(2S)-2-[(2S)-2-[1-(4-{2-azatricyclo[10.4.0.0$^{4,9}$]hexadeca-1(12),4(9),5,7,13,15-hexane-10-yn-2-yl}-4-oxobutanamido)-3,6,9,12-tetraoxapentadecan-15-amido]-3-methylbutanamido]-5-(carbamoylamino)pentanamido]phenyl}methyl 4-nitrophenyl carbonate |
| DIBACT | 3H-Benzo[c]-1,2,3-triazolo[4,5-e][1]benzazocine, 8,9-dihydro- |
| DIPEA | Diisopropylethylamine |
| D-Lys | D-Lysine |
| DMF | N,N-dimethylformamide |
| DMSO | Dimethylsulfoxide |
| EC | Enzyme commission |
| ELSD | Evaporative light scattering detector |
| ESI | Electrospray ionization |
| Fmoc | Fluorenylmethyloxycarbonyl |
| Fmoc-vcPAB-PNP | N-Fmoc-L-valine-L-citrulline-p-aminobenzyl alcohol p-nitrophenyl carbonate |
| g | Gram |
| HATU | 2-(7-Aza-1H-benzotriazole-1-yl)-1,1,3,3-tetramethyluronium hexafluorophosphate |
| HC | Heavy chain of immunoglobulin |
| HEK | Human embryonic kidney (cells) |
| HPLC | High performance liquid chromatography |
| hr, h, or hrs | hours |
| LC | Light chain of immunoglobulin |
| LCh | Liquid chromatography |
| MAL | Maleimide |
| MALDI | Matrix-assisted laser desorption/ionization |
| MC | Maleimidocaproyl |
| mg | milligrams |
| min | minutes |
| mL | milliliters |
| mmh | myc-myc-hexahistidine tag |
| μL | microliters |
| mM | millimolar |
| μM | micromolar |
| MMAE | Monomethyl auristatin E |
| MS | Mass spectrometry |
| MsCl | Methanesulfonyl chloride |
| MSD | Mass-selective detector |
| MTG | Microbial transglutaminase (MTG EC 2.3.2.13, Zedira, Darmstadt, Germany) |
| MW | Molecular weight |
| ncADC | Non-Cytotoxic antibody-drug conjugate |
| NHS | N-hydroxy succinimide |
| nM | nanomolar |
| NMR | Nuclear magnetic resonance |
| NOESY | Nuclear Overhauser effect spectroscopy |
| PAB | Para-aminobenzyloxy(carbonyl) |
| PBS | 10 mM sodium phosphate buffer and 150 mM sodium chloride |
| PBSg | 10 mM sodium phosphate buffer, 150 mM sodium chloride, and 5% glycerol |
| PEG | Polyethyleneglycol |
| PNP | p-nitrophenyl |
| MC-VC-PAB-PNP | Maleimidocaproyl-L-valine-L-citrulline-Para-aminobenzyloxy(carbonyl)-p-nitrophenyl carbonate |
| ppm | Parts per million (chemical shift, δ) |
| RP | Reversed phase |
| $R_t$ | Retention time |
| rt | room temperature |

| Abbreviation | Term |
|---|---|
| SDS—PAGE | Sodium dodecylsulfate polyacrylamide gel electrophoresis |
| SEC | Size exclusion chromatography |
| Suc or SC | Succinic acid |
| TCEP | Tris(2-carboxyethyl)phosphine hydrochloride |
| TEA | Triethylamine |
| TMS | tetramethylsilane |
| TFA | Trifluoroacetic acid |
| TG | Transglutaminase |
| THF | Tetrahydrofuran |
| TOF | Time-of-flight |
| TsCl | 4-toluenesulfonyl chloride |
| UPLC | Ultra Performance Liquid Chromatography |
| UV | Ultraviolet |
| VA | Valine-alanine |
| VC or vc | Valine-citrulline |
| VC-PAB or vc-PAB | Valine-citrulline-para-aminobenzyloxy(carbonyl) |

Certain embodiments of the invention are illustrated by the following non-limiting examples.

Reagents and solvents were obtained from commercial sources such as Sinopharm Chemical Reagent Co. (SCRC), Sigma-Aldrich, Alfa, or other vendors, unless explicitly stated otherwise.

$^1$H NMR and other NMR spectra were recorded on a Bruker AVIII 400 or Bruker AVIII 500. The data were processed with Nuts software or MestReNova software, measuring proton shifts in parts per million (ppm) downfield from an internal standard (e.g., tetramethylsilane (TMS)).

HPLC-MS measurements were run on an Agilent 1200 HPLC/6100 SQ System using the follow conditions:

Method A for HPLC-MS measurement included, as the Mobile Phase: A: Water (0.01% trifluoroacetic acid (TFA)), B: acetonitrile (0.01% TFA); Gradient Phase: 5% of B increased to 95% of B within 15 minutes (min); Flow Rate: 1.0 mL/min; Column: SunFire C18, 4.6×50 mm, 3.5 μm; Column Temperature: 50° C. Detectors: Analog to Digital Converter (ADC) Evaporative Light-scattering Detector (ELSD), Diode array detector (DAD) (214 nm and 254 nm), electrospray ionization-atmospheric ionization (ES-API).

Method B for HPLC-MS measurements included, as the Mobile Phase: A: Water (10 mM $NH_4HCO_3$), B: acetonitrile; Gradient Phase: 5% to 95% of B within 15 min; Flow Rate: 1.0 mL/min; Column: XBridge C18, 4.6×50 mm, 3.5 μm; Column Temperature: 50° C. Detectors: ADC ELSD, DAD (214 nm and 254 nm), mass selective detector (MSD) (ES-API).

LC-MS measurement was run on an Agilent 1200 HPLC/6100 SQ System using the following conditions:

Method A for LC-MS measurement included, as the Instrument: WATERS 2767; column: Shimadzu Shim-Pack, PRC-ODS, 20×250 mm, 15 μm, two connected in series; Mobile Phase: A: Water (0.01% TFA), B: acetonitrile (0.01% TFA); Gradient Phase: 5% of B increased to 95% of B within 3 min; Flow Rate: 1.8-2.3 mL/min; Column: SunFire C18, 4.6×50 mm, 3.5 μm; Column Temperature: 50° C. Detectors: ADC ELSD, DAD (214 nm and 254 nm), ES-API.

Method B for LC-MS measurement included, as the Instrument: Gilson GX-281; column: Xbridge Prep C18 10 μm OBD, 19×250 mm; Mobile Phase: A: Water (10 mM $NH_4HCO_3$), B: Acetonitrile; Gradient Phase: 5% to 95% of B within 3 min; Flow Rate: 1.8-2.3 mL/min; Column: XBridge C18, 4.6×50 mm, 3.5 μm; Column Temperature: 50° C. Detectors: ADC ELSD, DAD (214 nm and 254 nm), MSD (ES-API).

Preparative high-pressure liquid chromatography (Prep-HPLC) in an acidic (Method A) or basic (Method B) solvent system was utilized on a Gilson GX-281 instrument. The acidic solvent system used a Waters SunFire 10 μm C18 column (100 Å, 250×19 mm), and solvent A for prep-HPLC was water/0.05% TFA and solvent B was acetonitrile. The elution conditions were a linear gradient increase of solvent B from 5% to 100% over a time period of 20 min at a flow rate of 30 mL/min. The basic solvent system included a Waters Xbridge 10 μm C18 column (100 Å, 250×19 mm), and solvent A used for prep-HPLC was water/10 mM ammonium bicarbonate ($NH_4HCO_3$) and solvent B was acetonitrile. The elution conditions were a linear gradient increase of solvent B from 5% to 100% over a time period of 20 min at a flow rate of 30 mL/min.

Flash chromatography was performed on a Biotage instrument, with Agela Flash Column silica-CS cartridges; Reversed phase flash chromatography was performed on Biotage instrument, with Boston ODS or Agela C18 cartridges.

TABLE 1

LIST OF LINKER-PAYLOADS.

| Linker-Payload | Linker | Payload |
|---|---|---|
| Ex36 | DIBAC-suc-PEG4-vc-PAB | MMAE (1a) |
| Ex37 | MAL-Lys(suc-DIBAC-CD)-vc-PAB | MMAE (1a) |
| Ex38 | DIBAC-suc-Lys(mc-pip-CD)-vc-PAB | MMAE (1a) |
| Ex39 | MAL-$PEG_4$-Lys(COT-CD)-vc-PAB | MMAE (1a) |
| Ex40 | MAL-$PEG_4$-N(suc-DIBAC-CD)Lys-vc-PAB | MMAE (1a) |
| Ex41 | DIBAC-Suc-$PEG_4$-N(CD-COT)Lys-vc-PAB | MMAE (1a) |
| Ex42 | BCN-$PEG_4$-Lys(COT-CD)-vc-PAB | MMAE (1a) |
| Ex43 | DIBAC-Suc-$PEG_4$-D-Lys($PEG_4$-COT-CD)-vc-PAB | MMAE (1a) |
| Ex44 | BCN-$PEG_4$-D-Lys($PEG_4$-COT-CD)-vc-PAB | MMAE (1a) |
| Ex45 | DIBAC-suc-$PEG_4$-Val-Ala | 1c in FIG. 1 |
| Ex46 | DIBAC-suc-$PEG_4$-D-Lys(COT-CD)-Val-Ala | 1b in FIG. 1 |
| Ex47 | DIBAC-suc-$PEG_4$-D-Lys(COT-CD)-Val-Ala | 1c in FIG. 1 |
| Ex48 | DIBAC-suc-$PEG_4$-Val-Ala | 1d in FIG. 1 |
| Ex49 | DIBAC-suc-$PEG_4$-D-Lys(COT-CD)-Val-Ala | 1d in FIG. 1 |
| Ex50 | DIBAC-suc-$PEG_4$-D-Lys(PEG4-COT-CD)-vcPAB | 1d in FIG. 1 |
| Ex51 | BCN-$PEG_4$-D-Lys($PEG_4$-COT-CD)-Val-Ala | 1d in FIG. 1 |
| Ex52 | BCN-$PEG_4$-D-Lys($PEG_4$-COT-CD)-vcPAB | 1e in FIG. 1 |
| Ex53 | DIBAC-suc-$PEG_4$-D-Lys($PEG_4$-COT-CD)-Val-Ala | 1d in FIG. 1 |
| Ex54 | BCN-$PEG_4$-D-Lys(COT-CD)-Val-Ala | 1d in FIG. 1 |
| Ex55 | DIBAC-suc-$PEG_4$-D-Lys(COT-CD)-vcPAB | 1f in FIG. 1 |
| Ex56 | DIBAC-suc-$PEG_4$-D-Lys(COT-CD)-vcPAB | 1g in FIG. 1 |
| Ex57 | DIBAC-suc-$PEG_4$-D-Lys(COT-CD)-vcPAB | 1d in FIG. 1 |
| Ex58 | DIBAC-suc-$PEG_4$-vcPAB | 1h in FIG. 1 |
| Ex59 | DIBAC-suc-$PEG_4$-dLys(COT-CD)-vc-PAB | 1h in FIG. 1 |
| Ex60 | BCN-$PEG_4$-dLys(COT-CD)-vc-PAB | 1h in FIG. 1 |
| Ex61 | DI BAC-suc-$PEG_4$-vc-PAB | 1i in FIG. 1 |
| Ex62 | DIBAC-suc-$PEG_4$-dLys(COT-CD)-vc-PAB | 1i in FIG. 1 |
| Ex63 | DIBAC-suc-$PEG_4$-dLys(COT-CD)-Val-Ala | 1i in FIG. 1 |

TABLE 2A
| STRUCTURES OF LINKER-PAYLOADS. | |
|---|---|
| Ex | Structures of Linker-Payload |
| 36 | 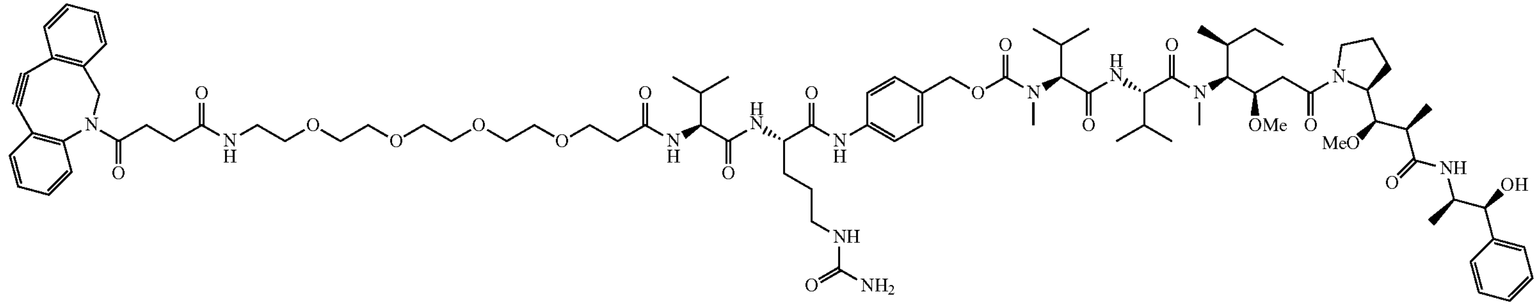 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCOCCOCCOCCOCCNC(=O)CCC(=O)N2Cc3ccccc3C#Cc3ccccc32)C(C)C)cc1)C(C)C] |

TABLE 2A-continued
| STRUCTURES OF LINKER-PAYLOADS. | |
|---|---|
| Ex | Structures of Linker-Payload |
| 37 | 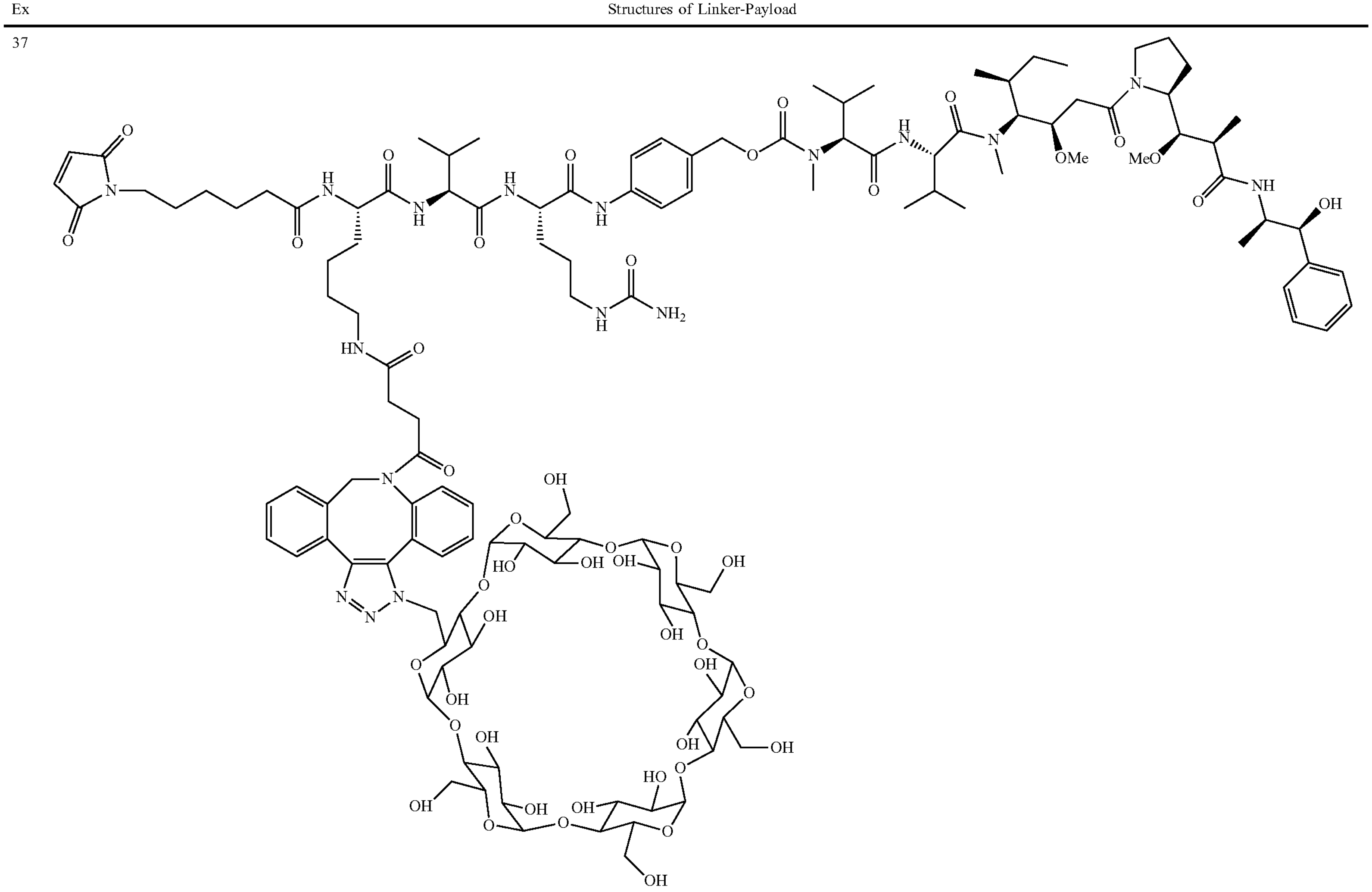 |

TABLE 2A-continued
| STRUCTURES OF LINKER-PAYLOADS. | |
|---|---|
| Ex | Structures of Linker-Payload |
| 38 | 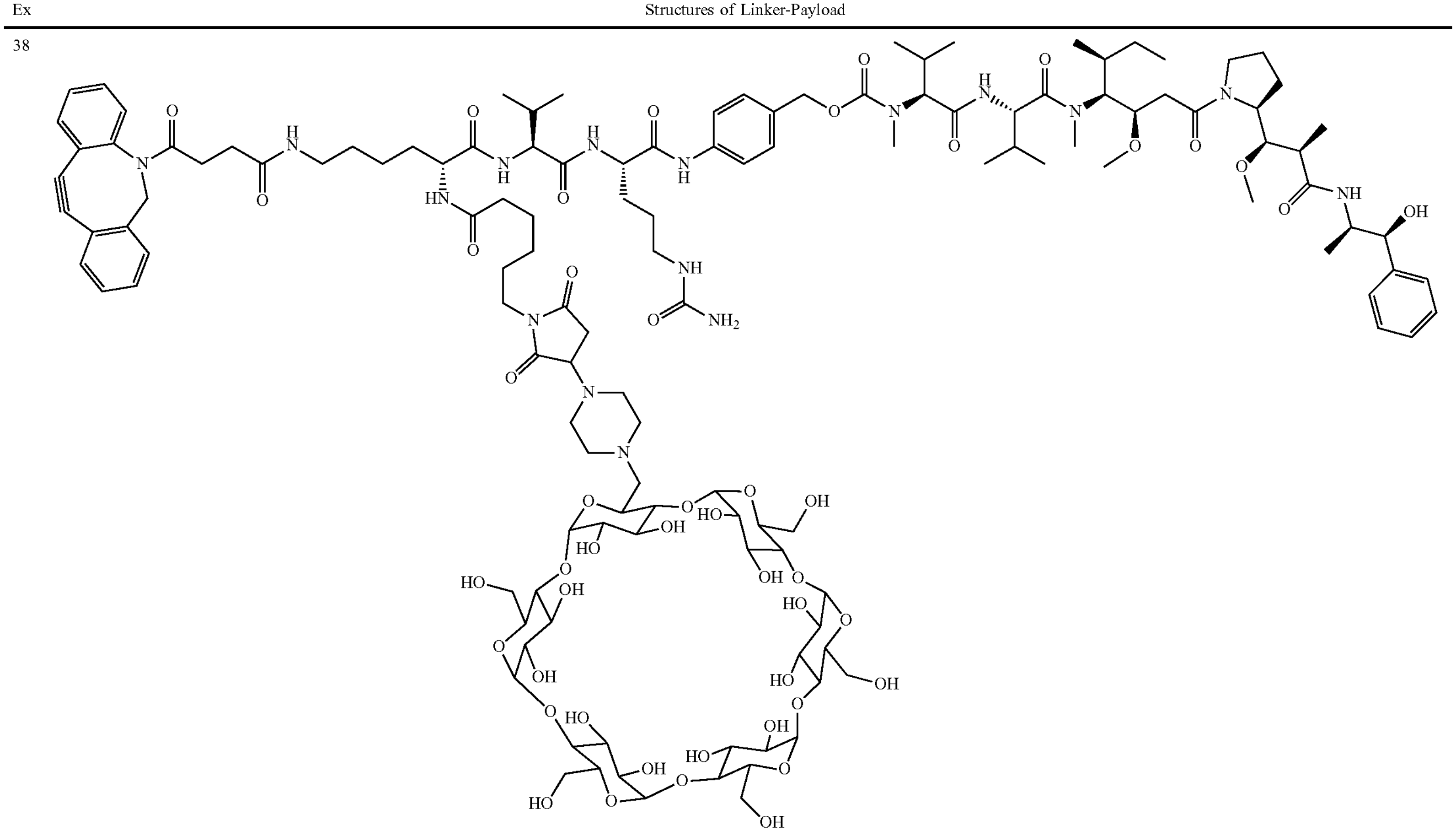 |

TABLE 2A-continued
| STRUCTURES OF LINKER-PAYLOADS. | |
|---|---|
| Ex | Structures of Linker-Payload |
| 39 | 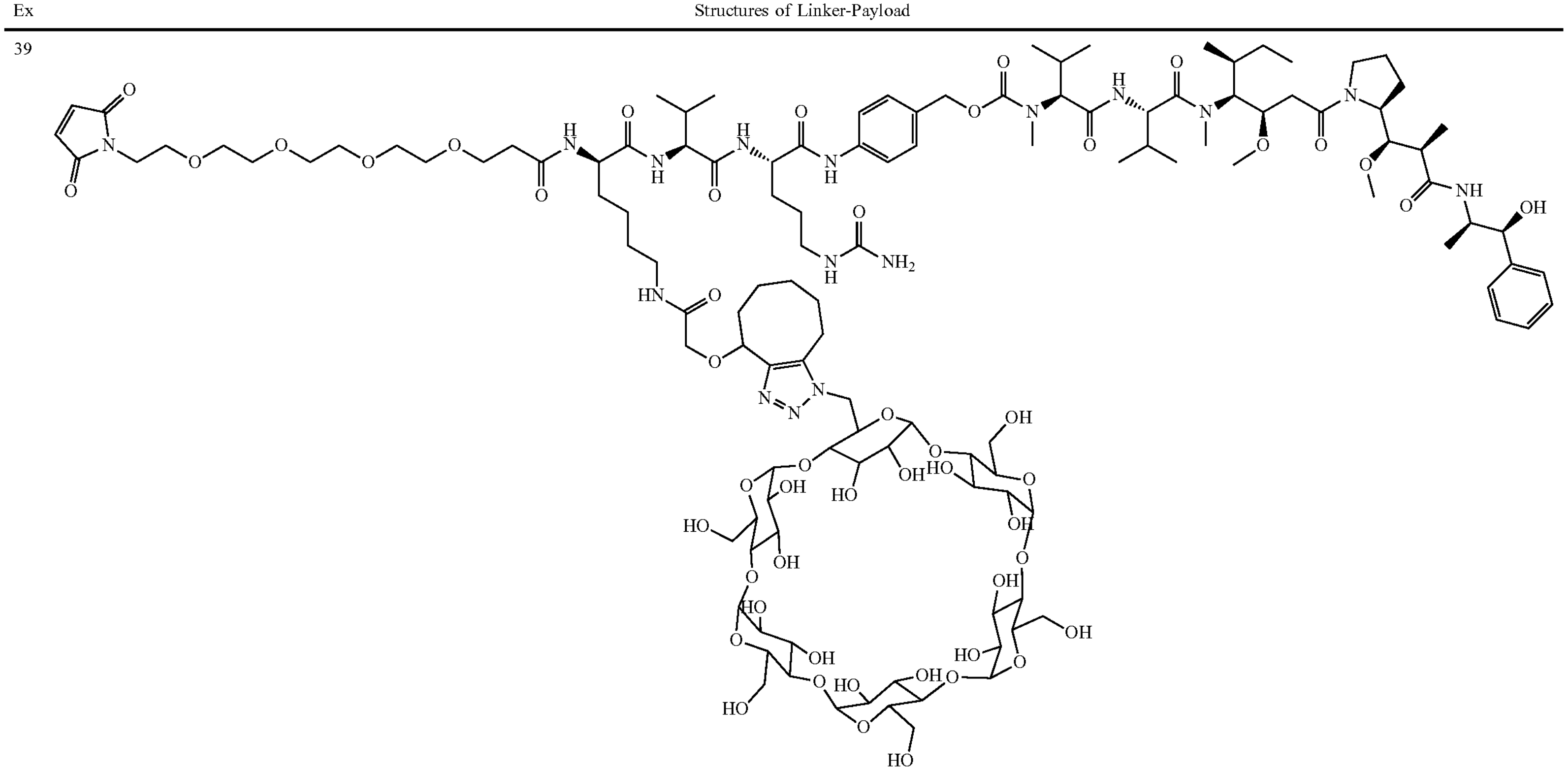 |

TABLE 2A-continued
| STRUCTURES OF LINKER-PAYLOADS. | |
|---|---|
| Ex | Structures of Linker-Payload |
| 40 | 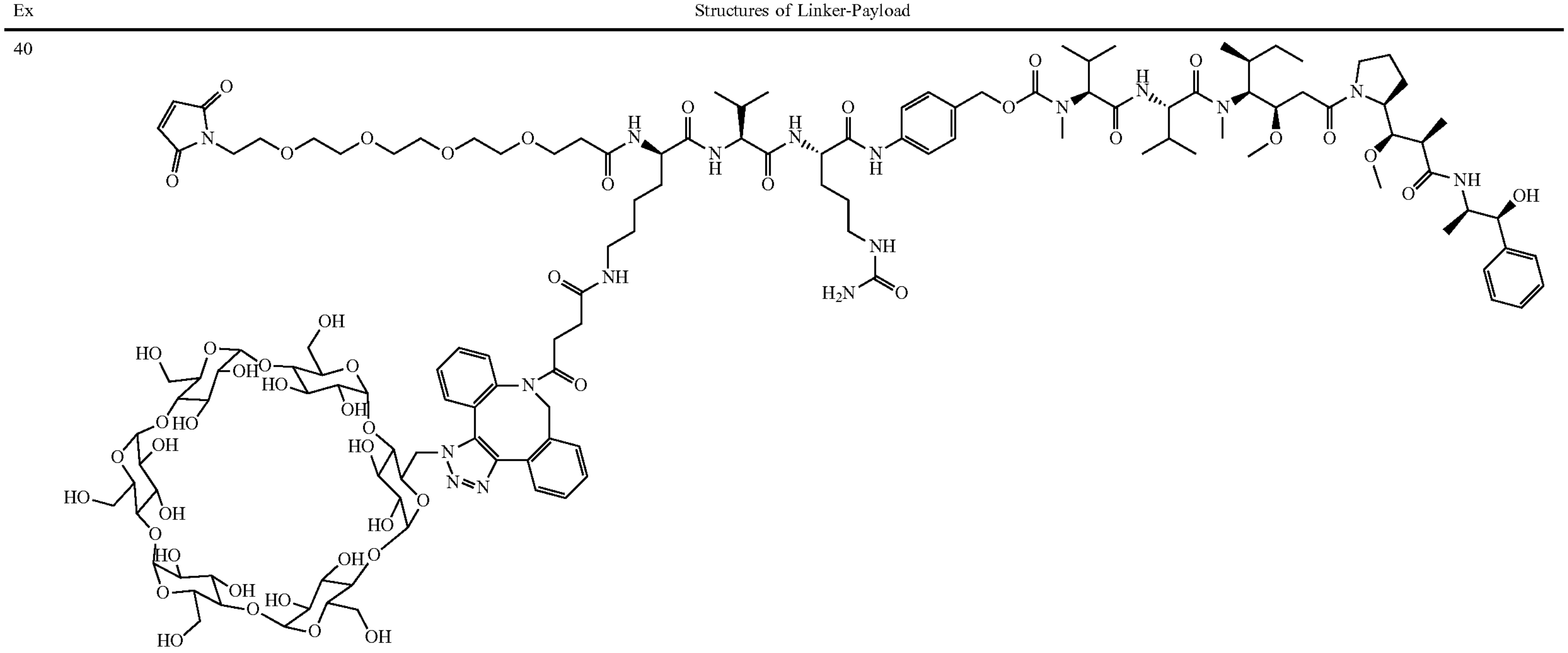 |

TABLE 2A-continued
| STRUCTURES OF LINKER-PAYLOADS. | |
|---|---|
| Ex | Structures of Linker-Payload |
| 41 | 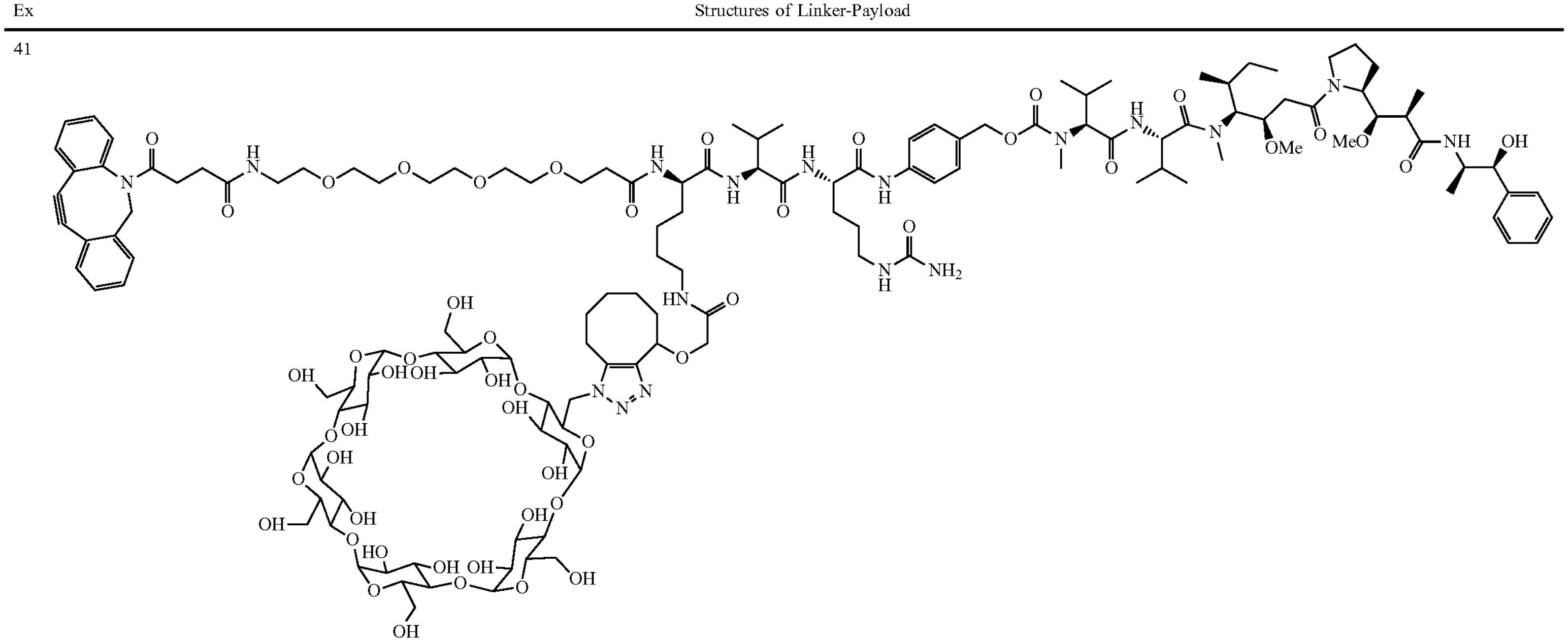 |

TABLE 2A-continued
| STRUCTURES OF LINKER-PAYLOADS. | |
|---|---|
| Ex | Structures of Linker-Payload |
| 42 | 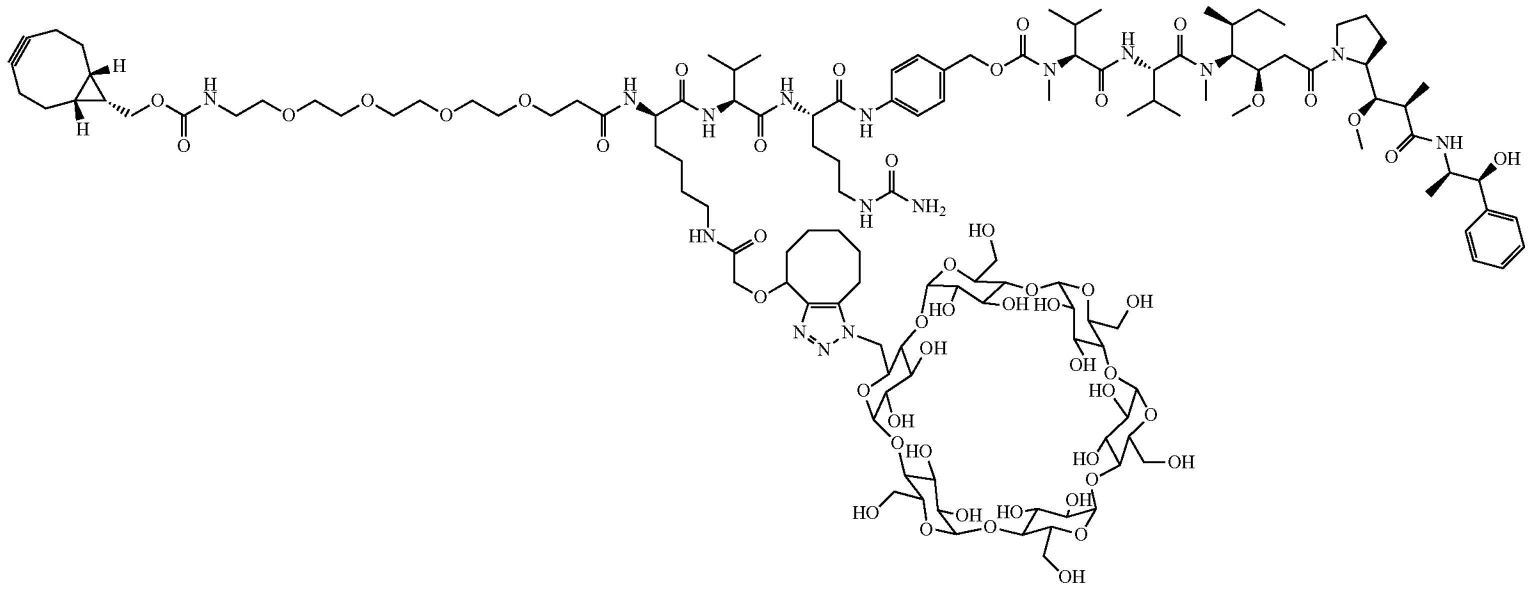 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)[C@@H](CCCCNC(=O)COC2CCCCCc3c2nnn3CC2OC3OC4C(CO)OC(OC5C(CO)OC(OC6C(CO)OC(OC7C(CO)OC(OC8C(CO)OC(OC2C(O)C3O)C(O)C8O)C(O)C7O)C(O)C6O)C(O)C5O)C(O)C4O)NC(=O)CCOCCOCCOCCOCCNC(=O)OC[C@@H]2[C@@H]3CCC#CCC[C@@H]32)C(C)C)cc1)C(C)C] |

TABLE 2A-continued
| STRUCTURES OF LINKER-PAYLOADS. | |
|---|---|
| Ex | Structures of Linker-Payload |
| 43 | 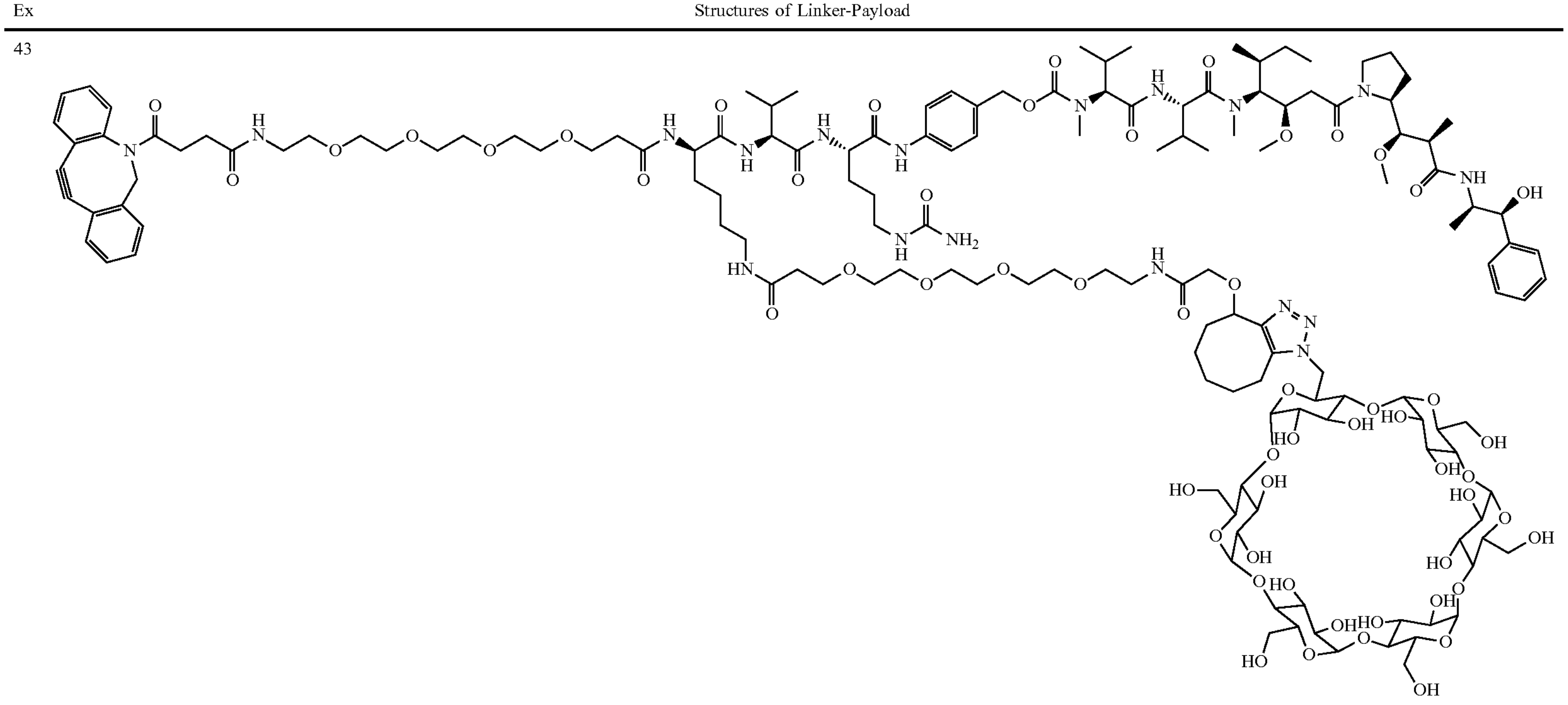 |

TABLE 2A-continued
| STRUCTURES OF LINKER-PAYLOADS. | |
|---|---|
| Ex | Structures of Linker-Payload |
| 44 | 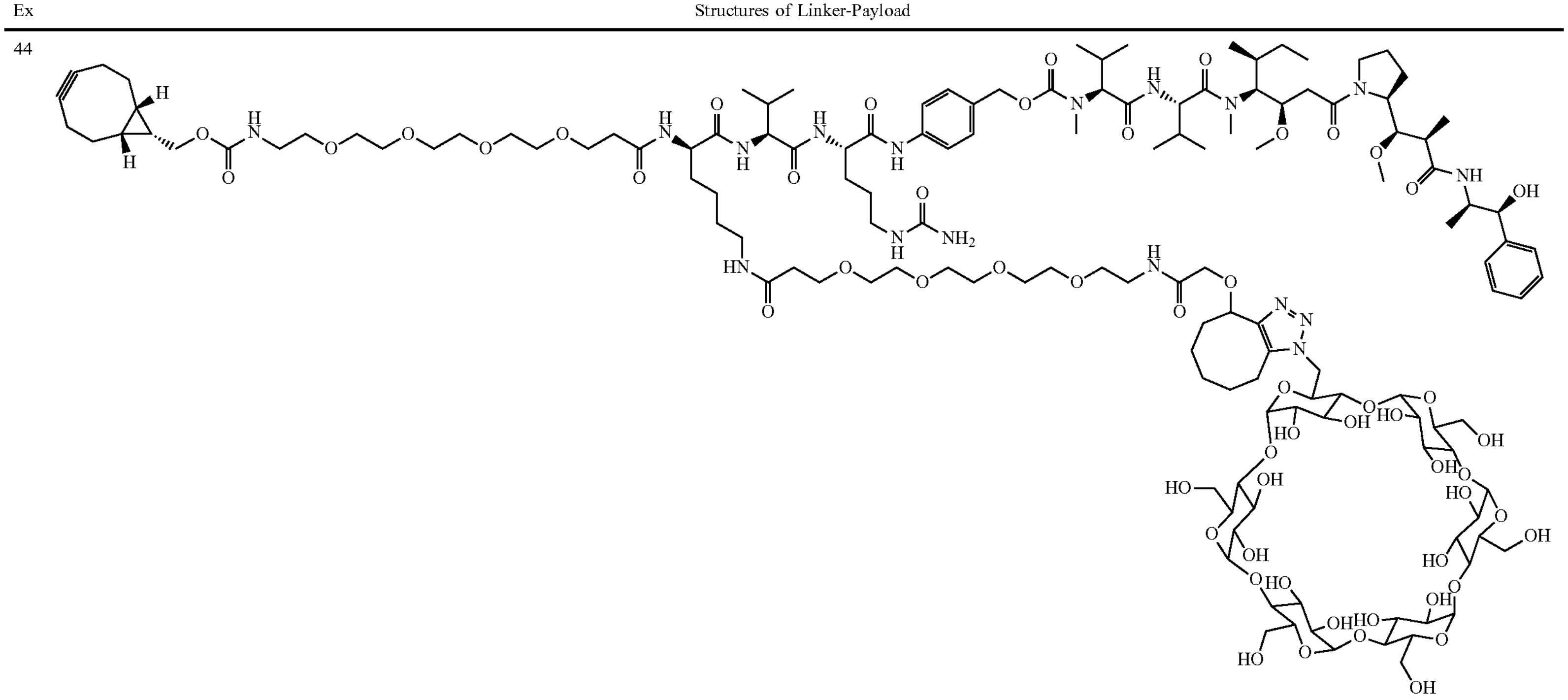 |

TABLE 2A-continued
| STRUCTURES OF LINKER-PAYLOADS. | |
|---|---|
| Ex | Structures of Linker-Payload |
| 45 | 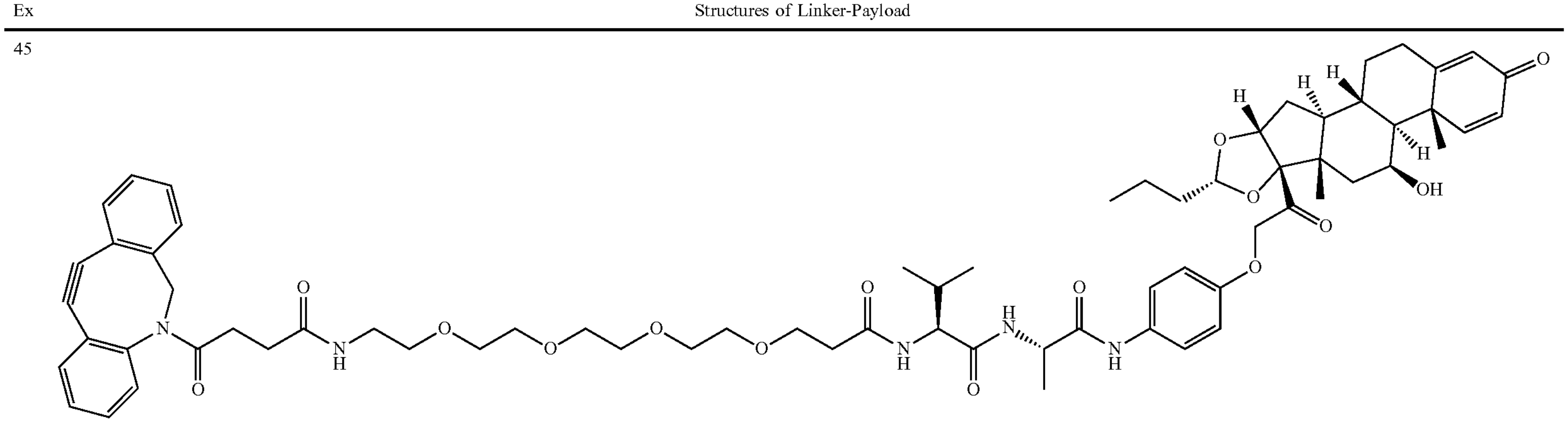 |

TABLE 2A-continued
| STRUCTURES OF LINKER-PAYLOADS. | |
|---|---|
| Ex | Structures of Linker-Payload |
| 46 | 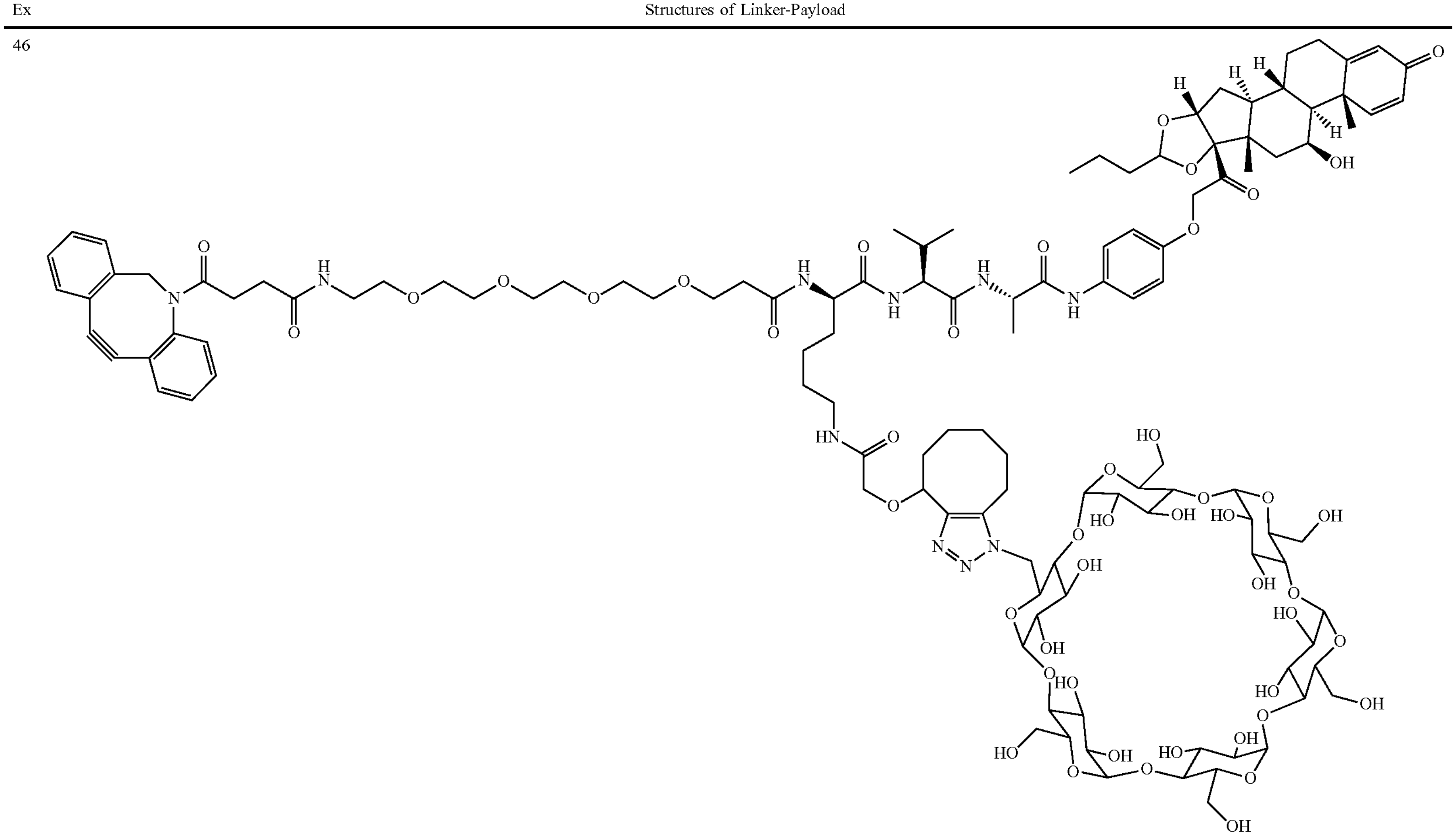 |

TABLE 2A-continued
| STRUCTURES OF LINKER-PAYLOADS. | |
|---|---|
| Ex | Structures of Linker-Payload |
| 47 | 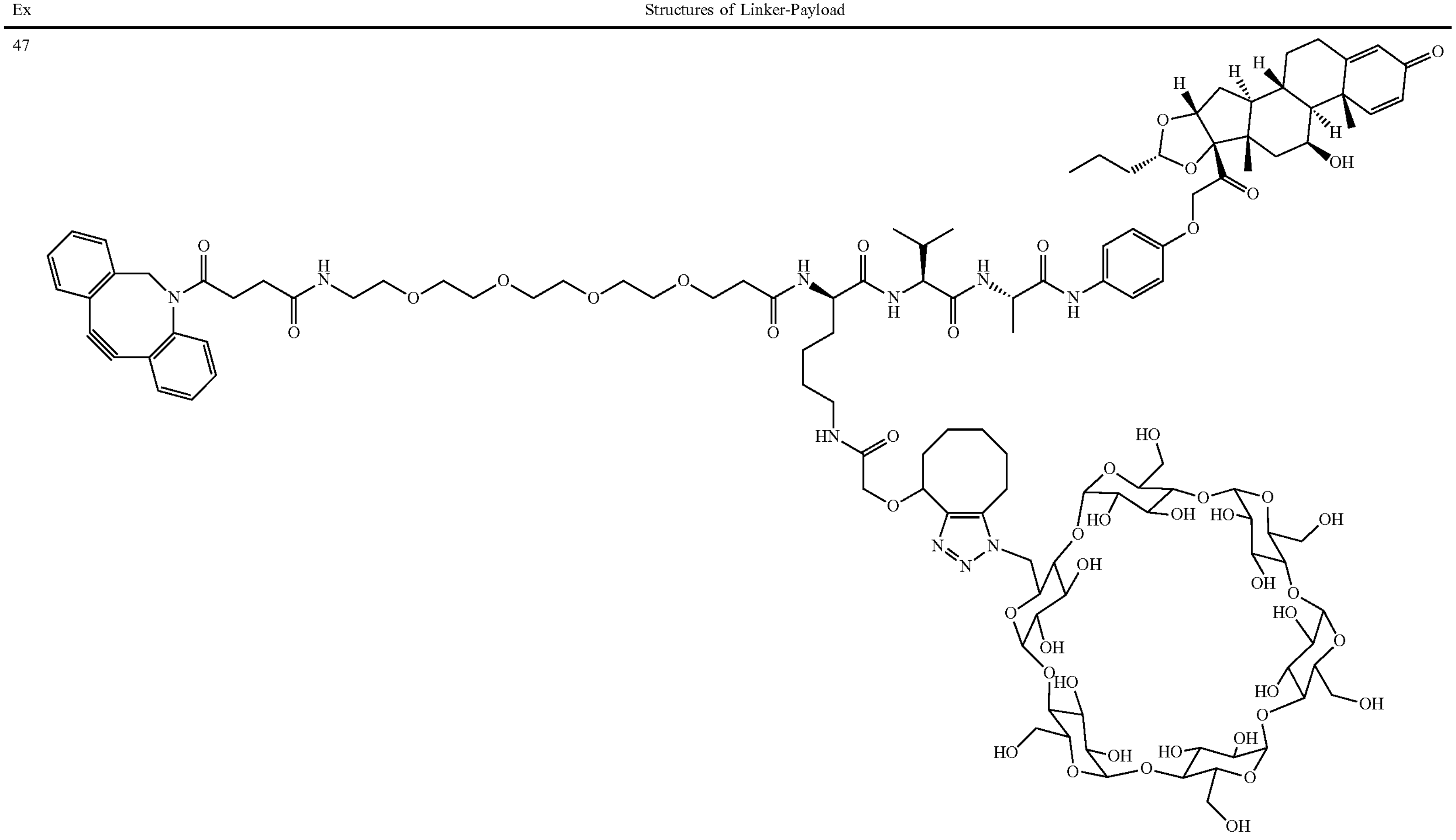 |

TABLE 2A-continued
| STRUCTURES OF LINKER-PAYLOADS. | |
|---|---|
| Ex | Structures of Linker-Payload |
| 48 | 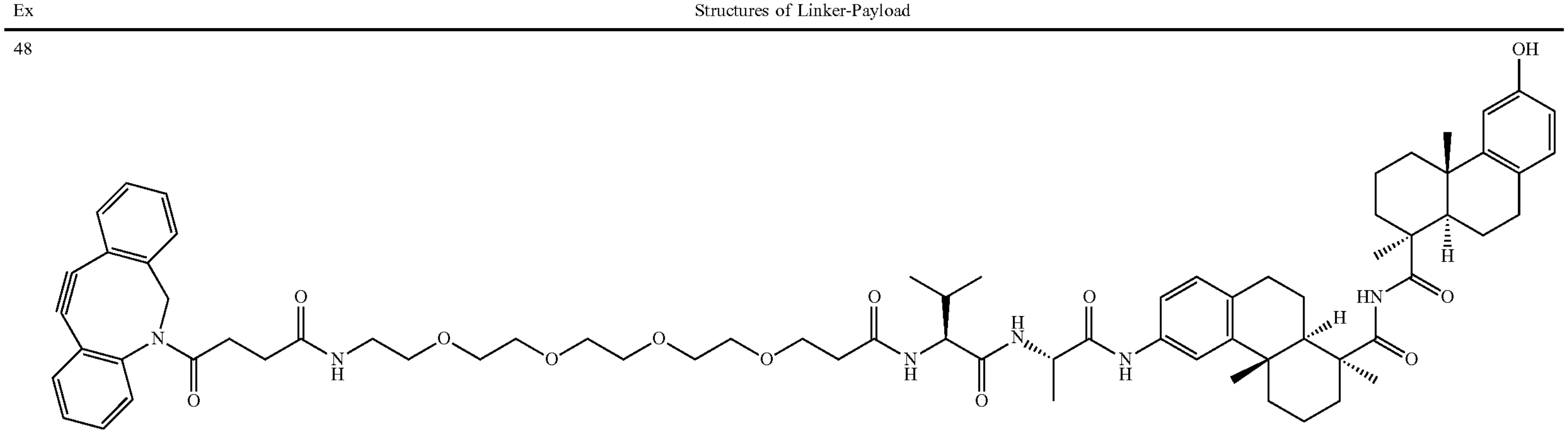 |

TABLE 2A-continued
| STRUCTURES OF LINKER-PAYLOADS. | |
|---|---|
| Ex | Structures of Linker-Payload |
| 49 | 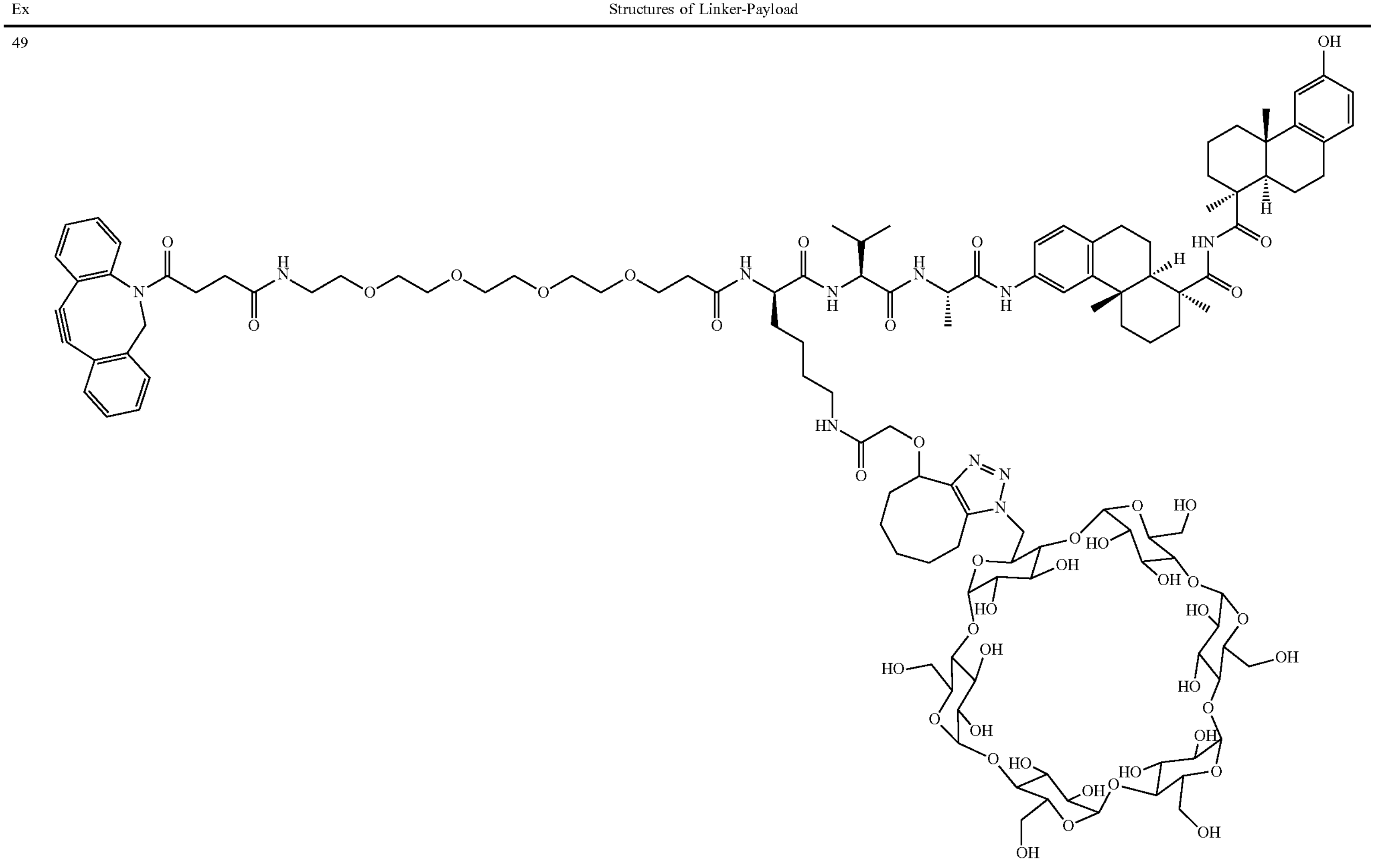 |

TABLE 2A-continued
| STRUCTURES OF LINKER-PAYLOADS. | |
| --- | --- |
| Ex | Structures of Linker-Payload |
| 50 | 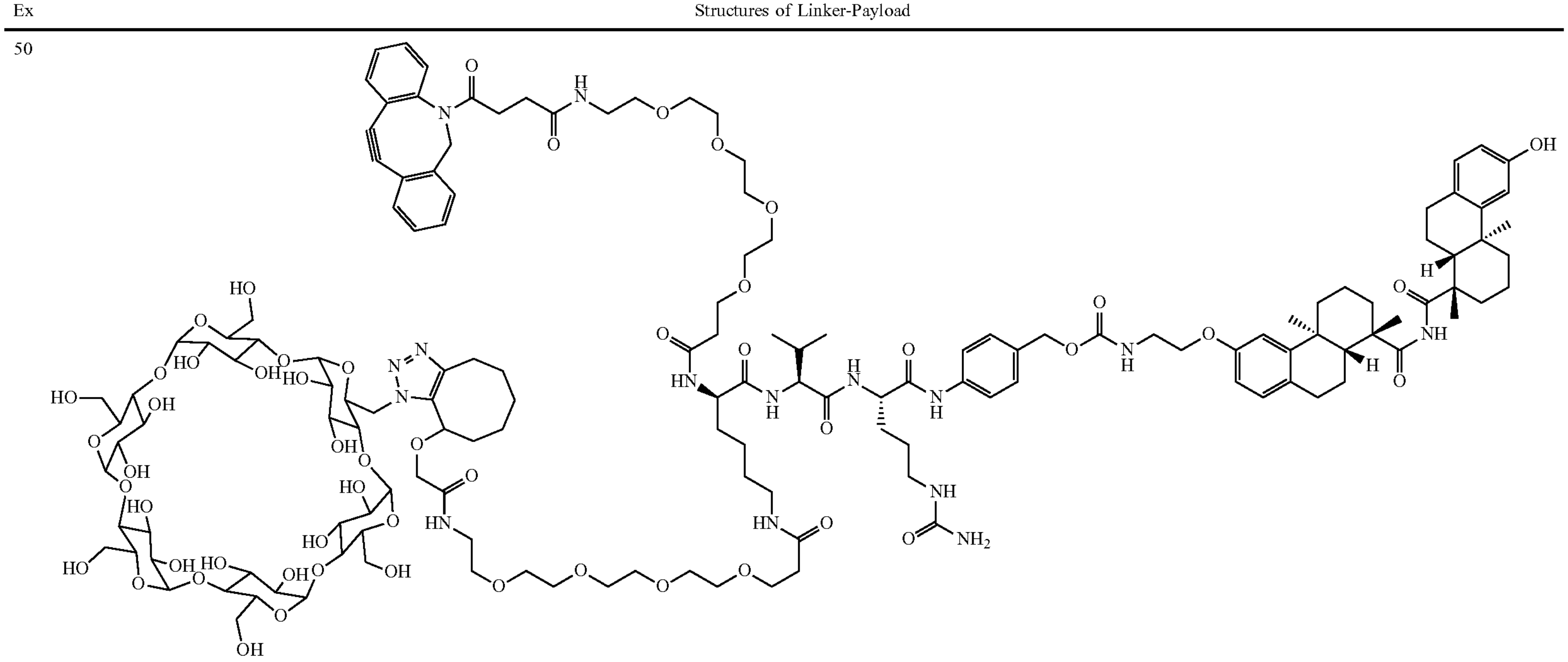 |

TABLE 2A-continued
| STRUCTURES OF LINKER-PAYLOADS. | |
|---|---|
| Ex | Structures of Linker-Payload |
| 51 | 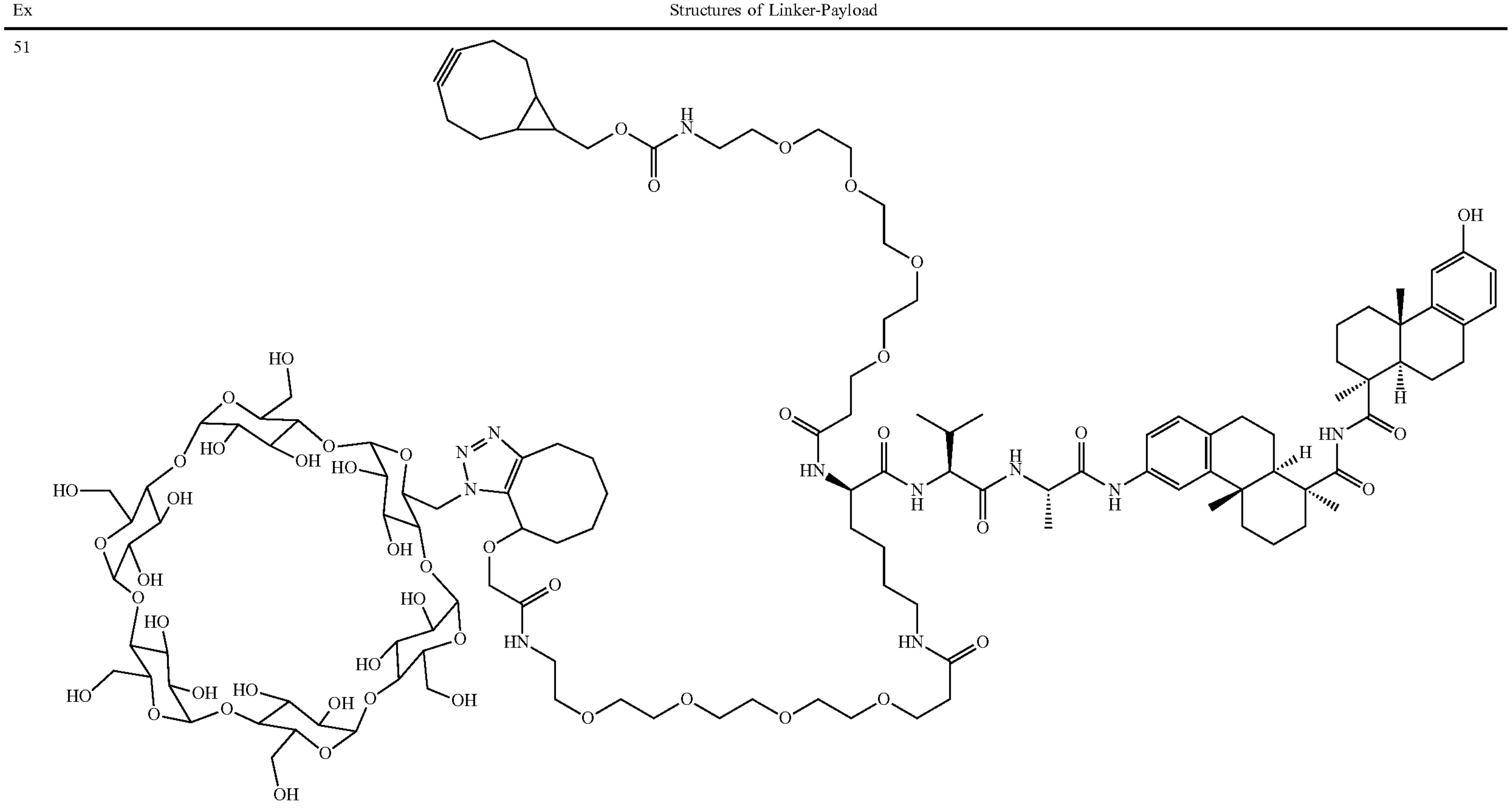 |

TABLE 2A-continued
| STRUCTURES OF LINKER-PAYLOADS. | |
|---|---|
| Ex | Structures of Linker-Payload |
| 52 | 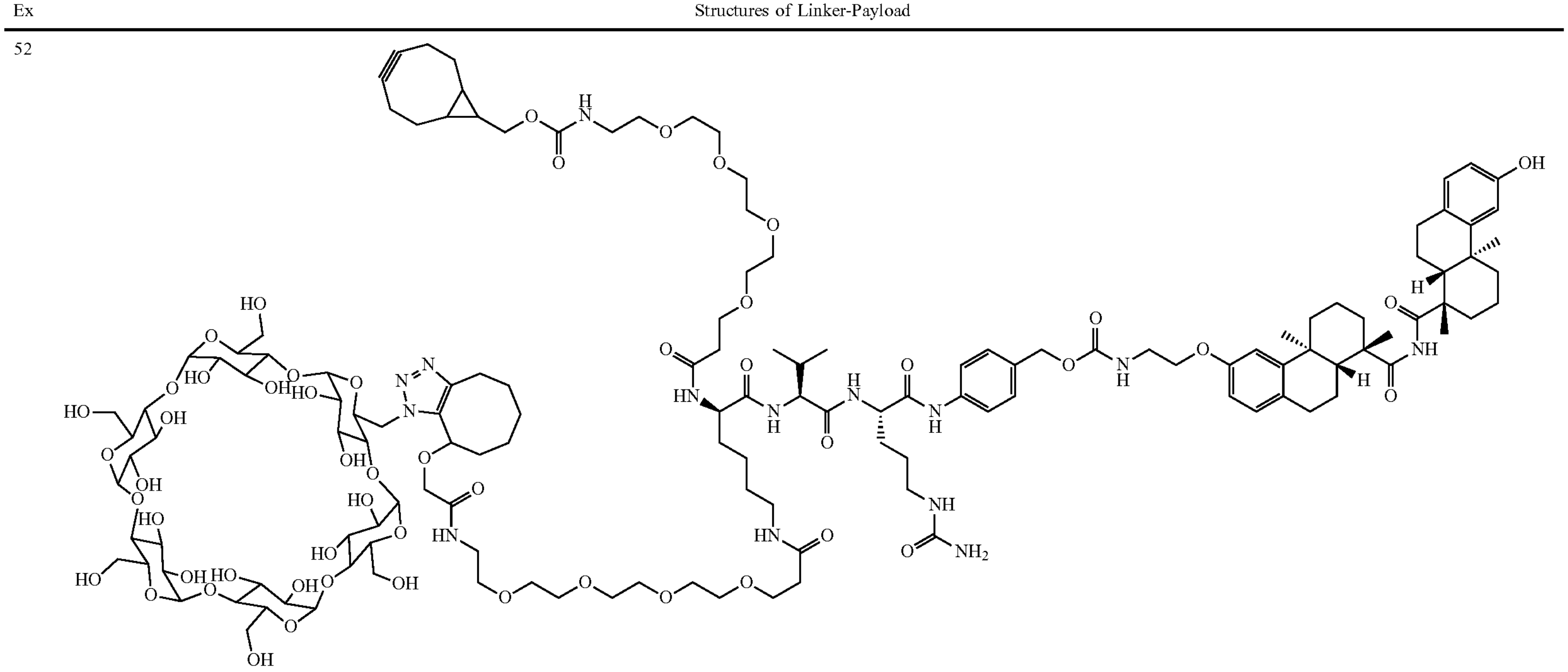 |

TABLE 2A-continued
| STRUCTURES OF LINKER-PAYLOADS. | |
|---|---|
| Ex | Structures of Linker-Payload |
| 53 | 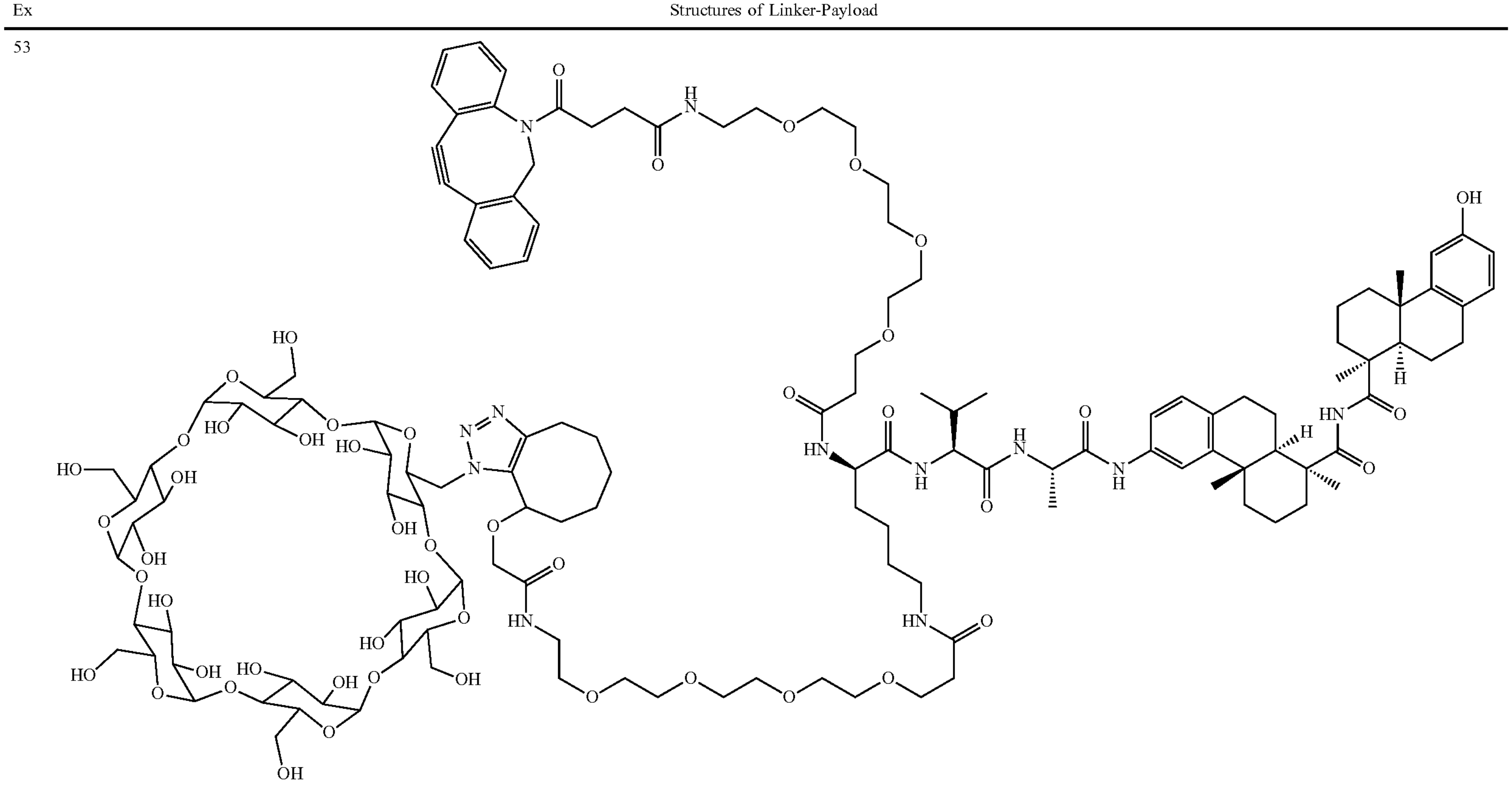 |

TABLE 2A-continued
| STRUCTURES OF LINKER-PAYLOADS. | |
|---|---|
| Ex | Structures of Linker-Payload |
| 54 | 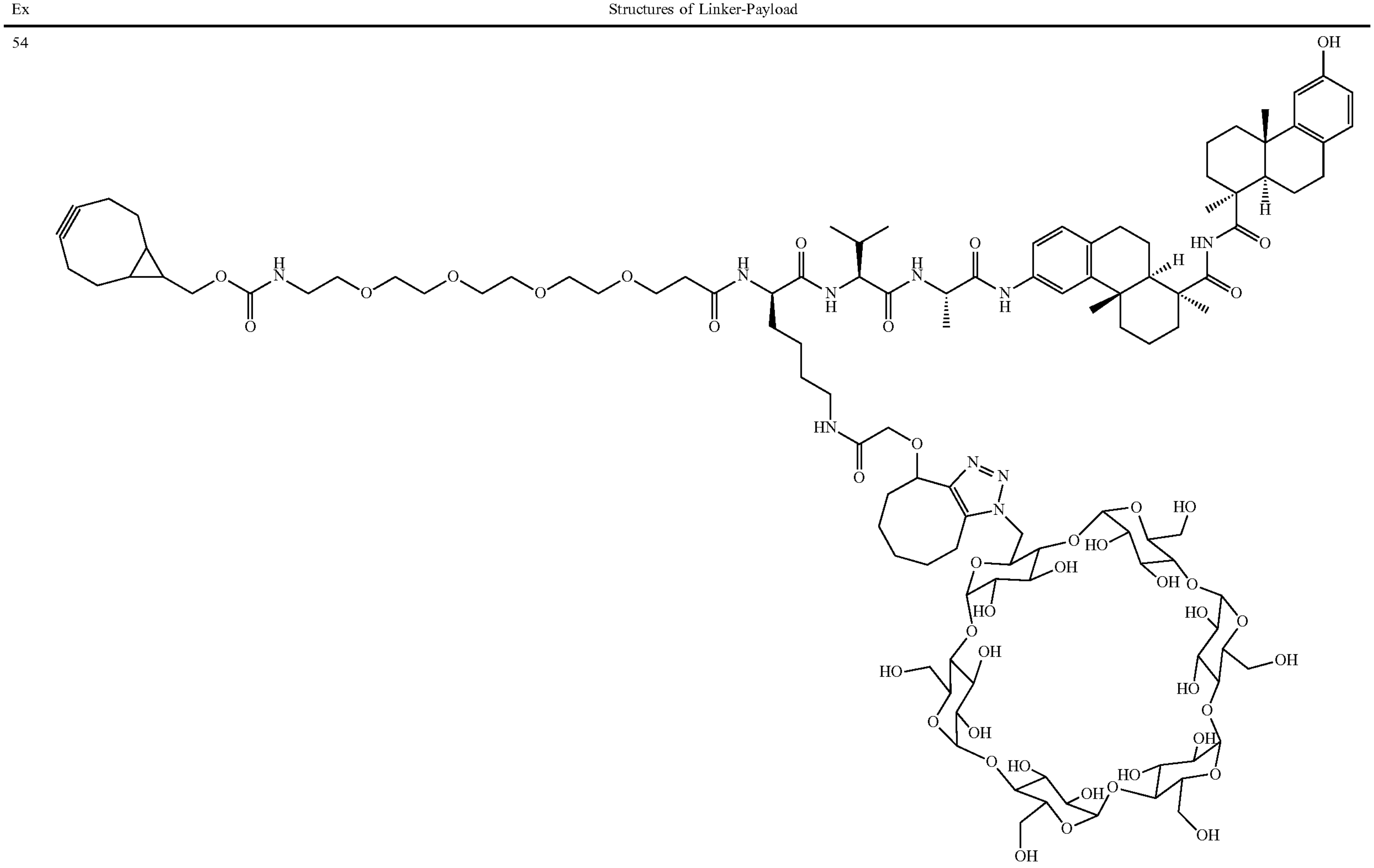 |

TABLE 2A-continued
| STRUCTURES OF LINKER-PAYLOADS. | |
|---|---|
| Ex | Structures of Linker-Payload |
| 55 | 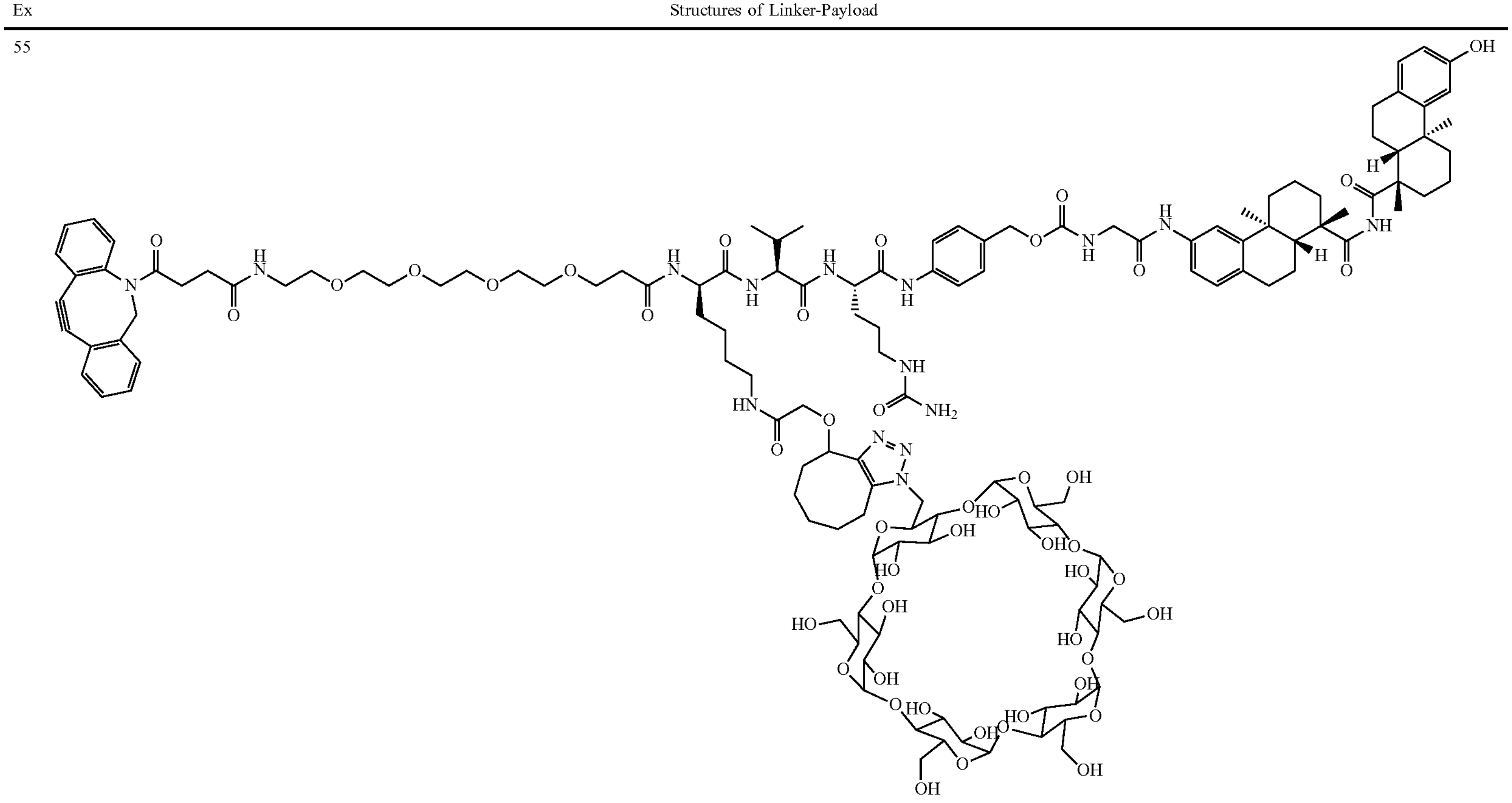 |

TABLE 2A-continued
| STRUCTURES OF LINKER-PAYLOADS. | |
| --- | --- |
| Ex | Structures of Linker-Payload |
| 56 | 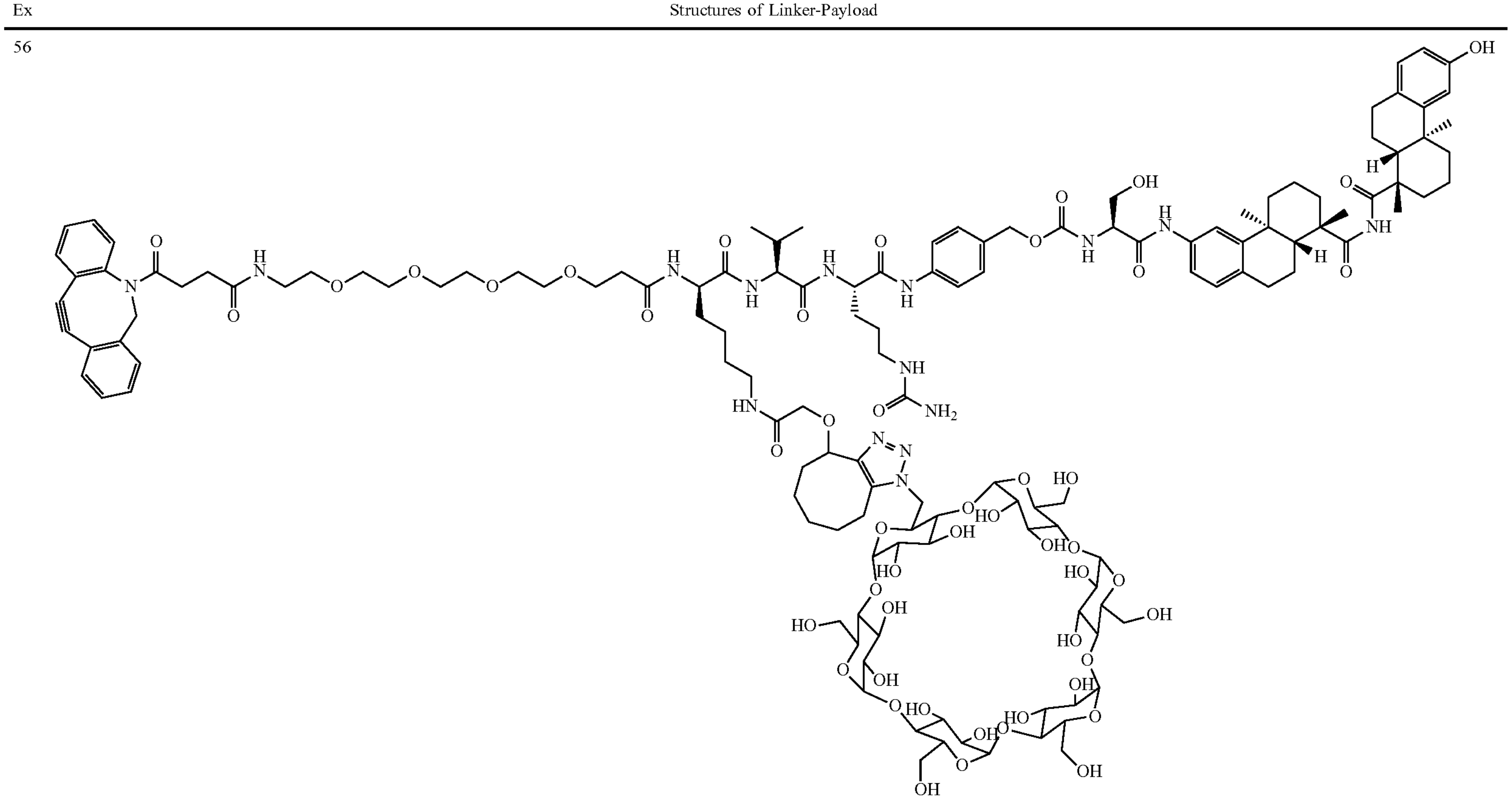 |

TABLE 2A-continued
| STRUCTURES OF LINKER-PAYLOADS. | |
|---|---|
| Ex | Structures of Linker-Payload |
| 57 | 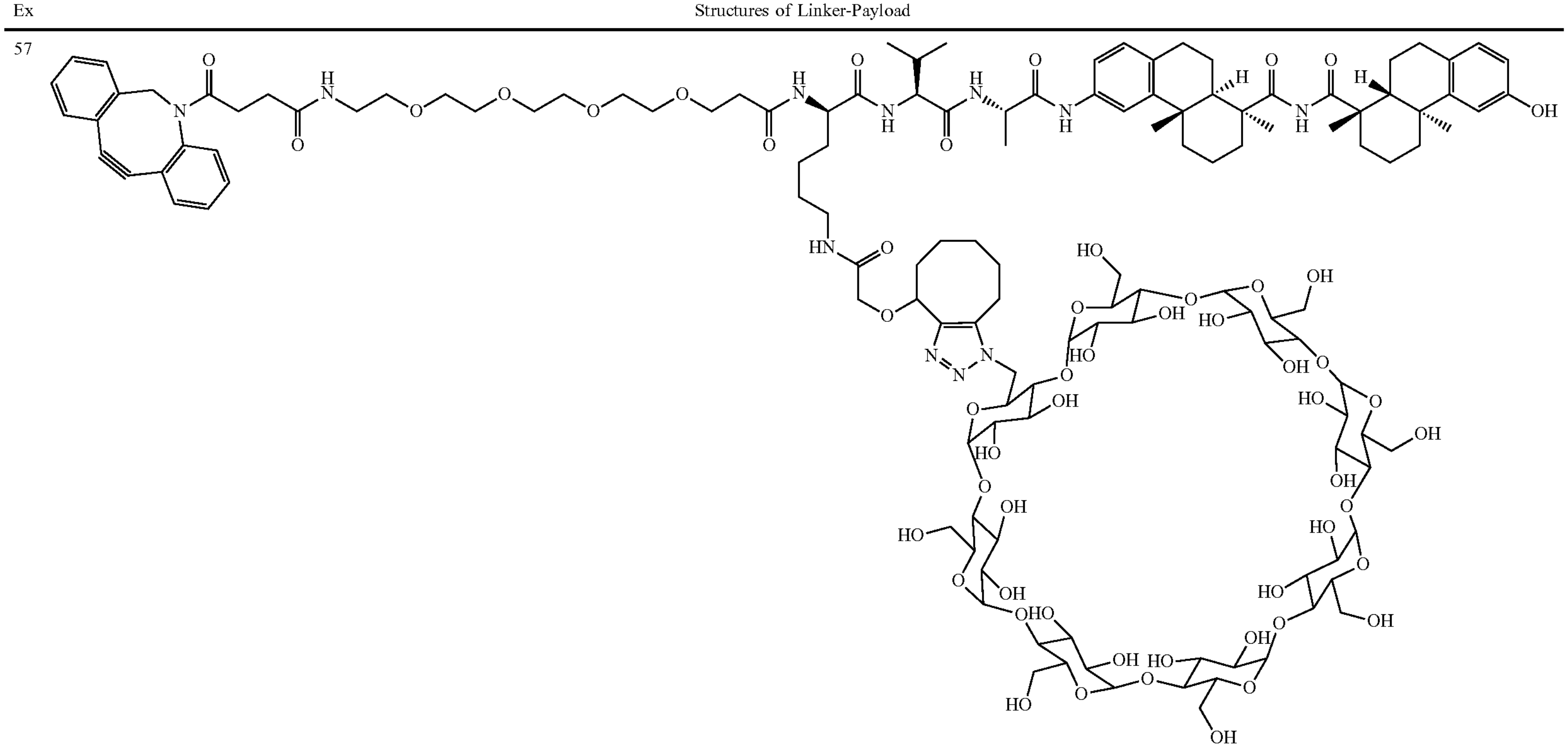 |

TABLE 2A-continued
| STRUCTURES OF LINKER-PAYLOADS. | |
|---|---|
| Ex | Structures of Linker-Payload |
| 58 | 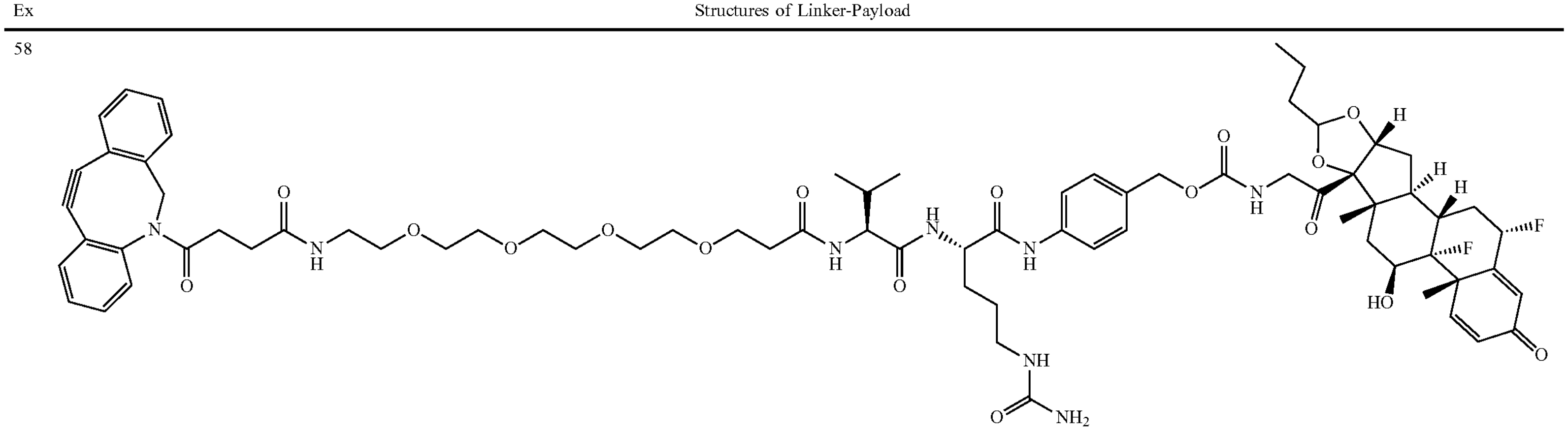 |

TABLE 2A-continued
| STRUCTURES OF LINKER-PAYLOADS. | |
|---|---|
| Ex | Structures of Linker-Payload |
| 59 | 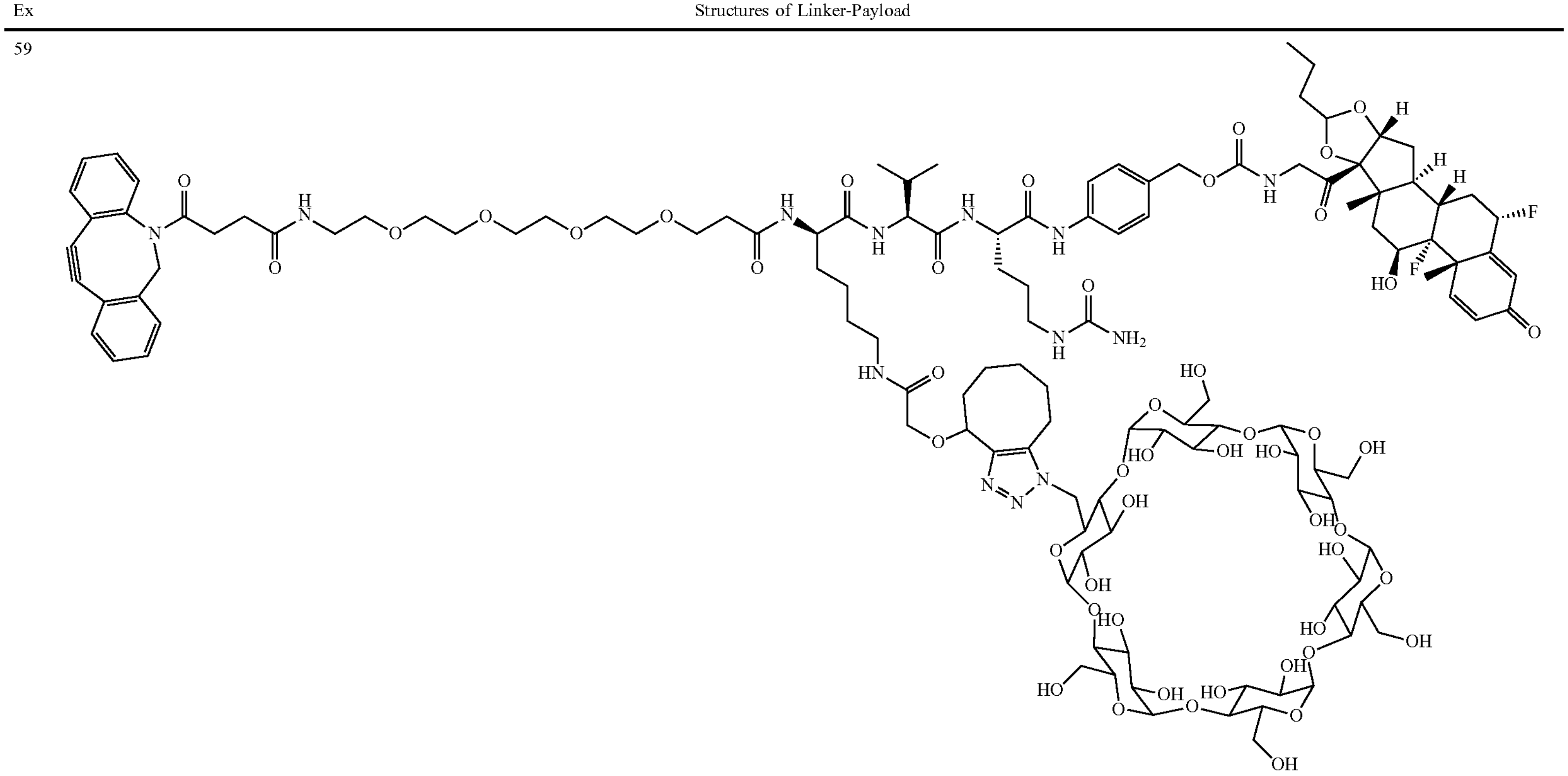 |

TABLE 2A-continued
| STRUCTURES OF LINKER-PAYLOADS. | |
|---|---|
| Ex | Structures of Linker-Payload |
| 60 | 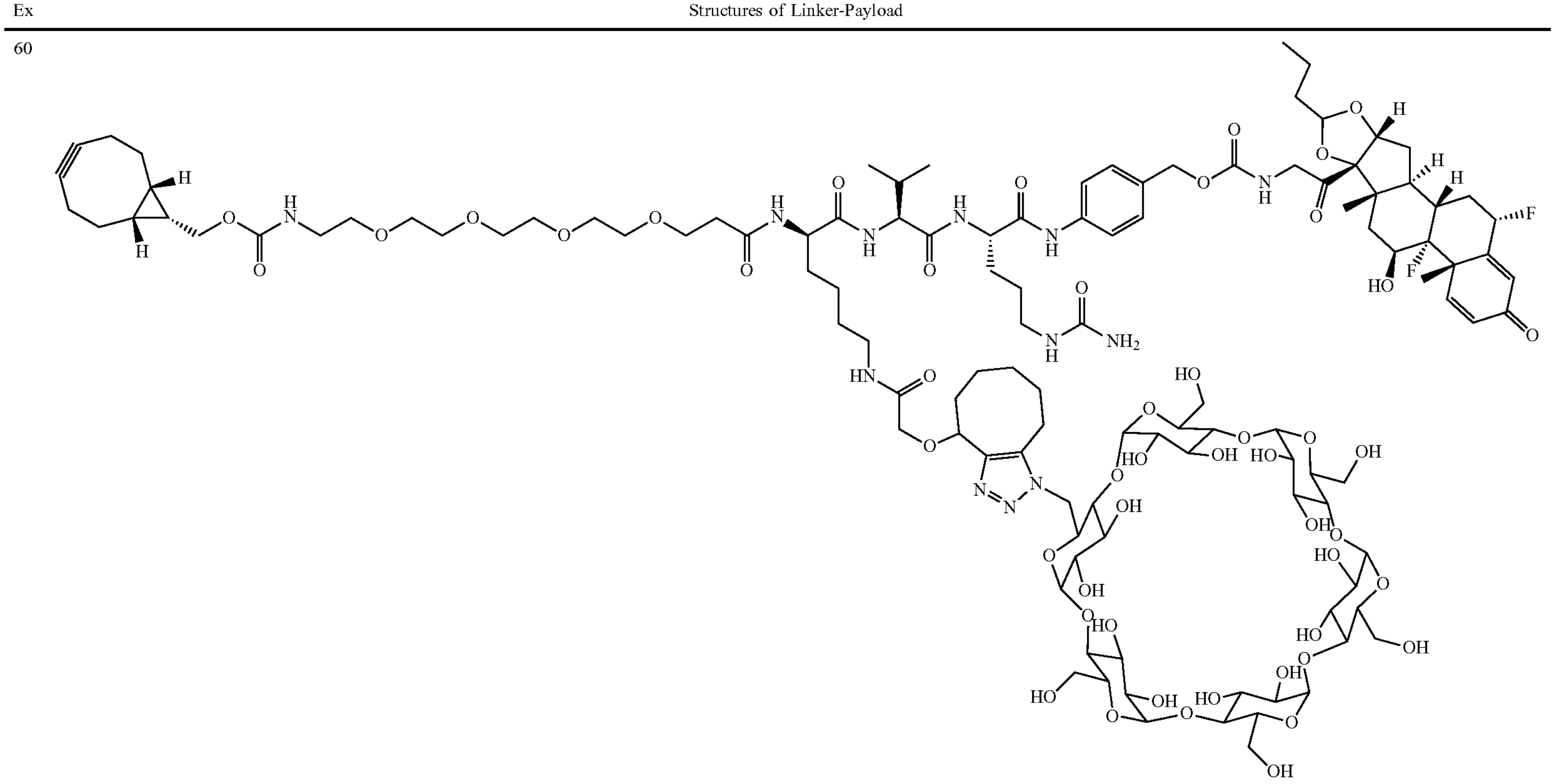 |

TABLE 2A-continued
| STRUCTURES OF LINKER-PAYLOADS. | |
|---|---|
| Ex | Structures of Linker-Payload |
| 61 | 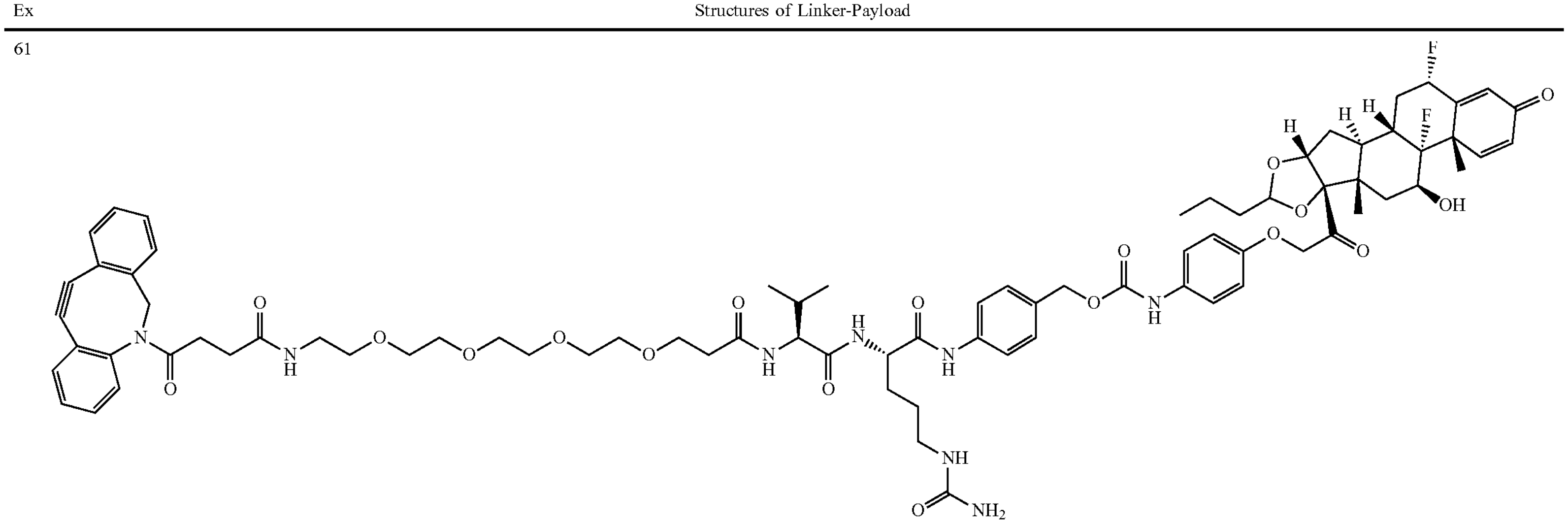 |

TABLE 2A-continued
| STRUCTURES OF LINKER-PAYLOADS. | |
|---|---|
| Ex | Structures of Linker-Payload |
| 62 | 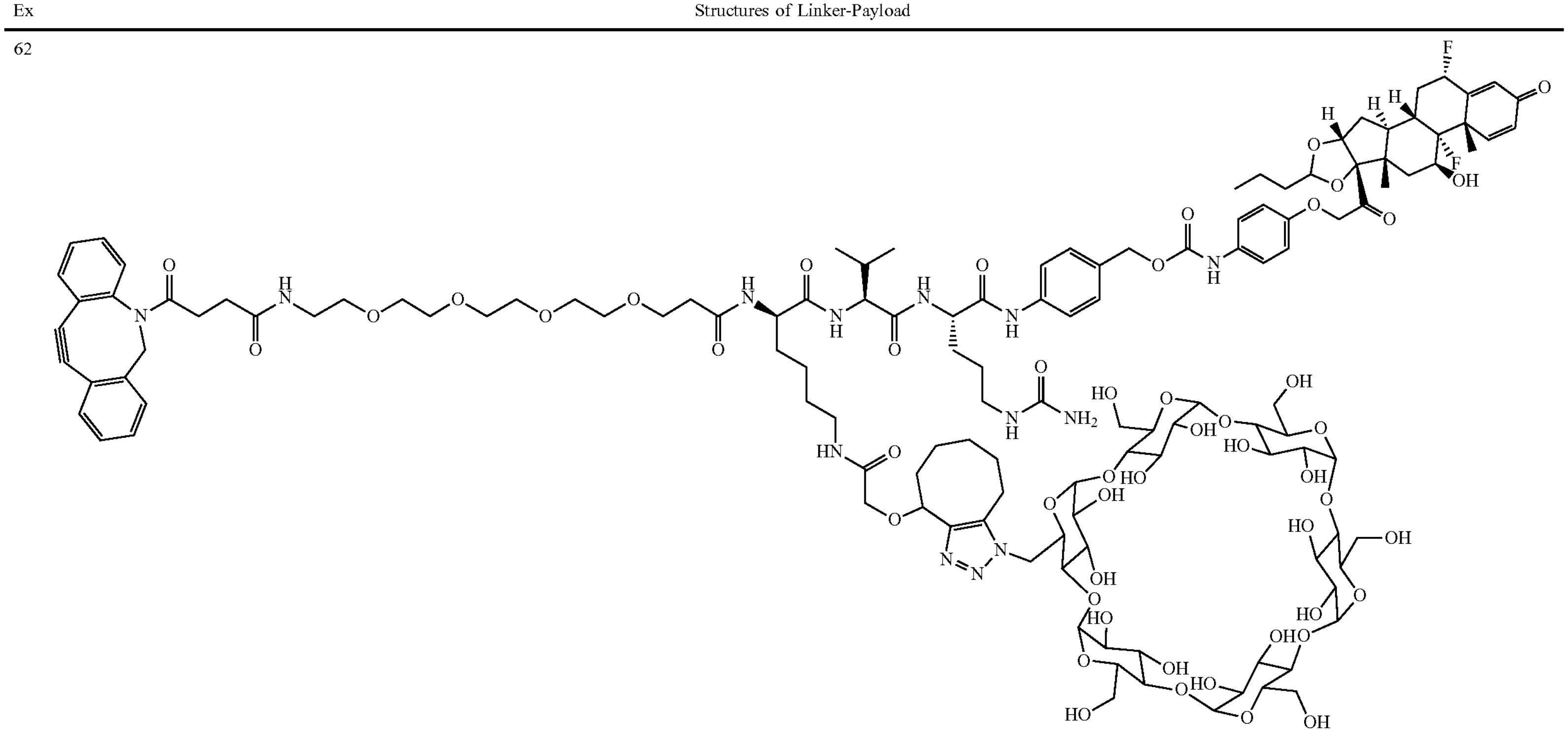 |

TABLE 2A-continued
| STRUCTURES OF LINKER-PAYLOADS. | |
|---|---|
| Ex | Structures of Linker-Payload |
| 63 | 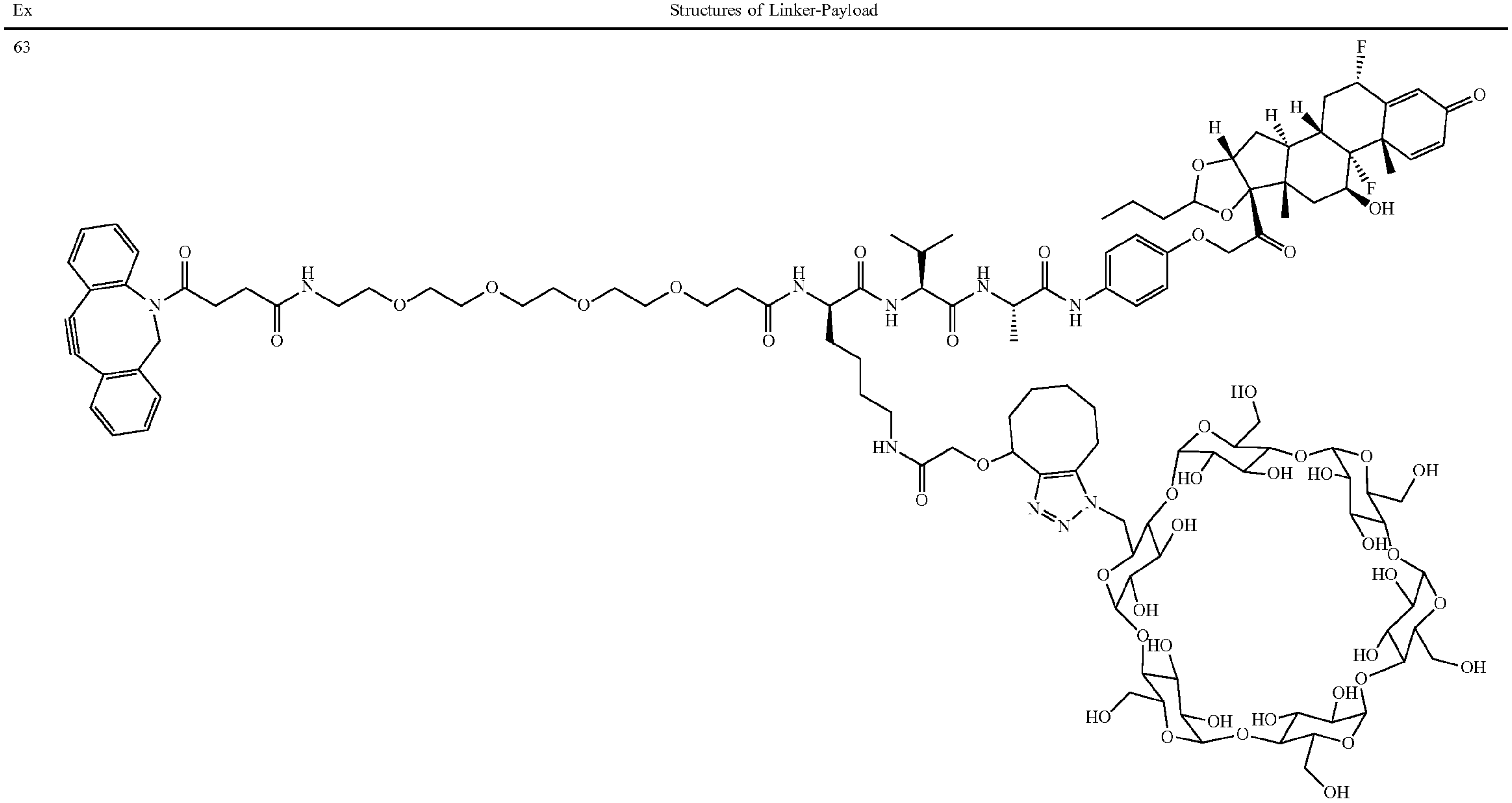 |

TABLE 2B

| LINKER-PAYLOAD cLogP . | | |
|---|---|---|
| Example | cLogP | Linker name |
| Ex36 | +++++ | DIBAC-suc-PEG4-vc-PAB-MMAE |
| Ex37 | ++ | mc-Lys(suc-DIBAC-CD)-vc-PAB-MMAE |
| Ex38 | ++ | DIBAC-suc-Lys(mc-pip-CD)-vc-PAB-MMAE |
| Ex39 | + | MAL-PEG4-Lys(COT-CD)-vc-PAB-MMAE |
| Ex40 | ++ | MAL-PEG4-N(suc-DIBAC-CD) Lys-vc-PAB-MMAE |
| Ex41 | ++ | DIBAC-Suc-PEG4-N(CD-COT)Lys-vc-PAB-MMAE |
| Ex42 | ++ | BCN-PEG4-Lys(COT-CD)-vc-PAB-MMAE |
| Ex43 | ++ | DIBAC-Suc-PEG4-D-Lys (PEG4-COT-CD)-vc-PAB-MMAE |
| Ex44 | ++ | BCN-PEG4-D-Lys(PEG4-COT-CD)-vc-PAB-MMAE |
| Ex45 | +++++ | DIBAC-suc-$PEG_4$-Val-Ala-1c |
| Ex46 | ++ | DIBAC-suc-$PEG_4$-D-Lys(CD-COT)-Val-Ala-1b |
| Ex47 | ++ | DIBAC-suc-$PEG_4$-D-Lys(CD-COT)-Val-Ala-1c |
| Ex48 | +++++ | DIBAC-suc-$PEG_4$-Val-Ala-1d |
| Ex49 | +++ | DIBAC-suc-$PEG_4$-D-Lys(CD-COT)-Val-Ala-1d |
| Ex50 | +++ | DIBAC-suc-PEG4-D-Lys (PEG4-COT-CD)-vcPAB-1d |
| Ex51 | +++ | BCN-PEG4-D-Lys(PEG4-COT-CD)-Val-Ala-1d |
| Ex52 | +++ | BCN-PEG4-D-Lys(PEG4-COT-CD)-vcPAB-1e |
| Ex53 | +++ | DIBAC-suc-PEG4-D-Lys(PEG4-COT-CD)-Val-Ala-1d |
| Ex54 | +++ | BCN-PEG4-D-Lys(COT-CD)-Val-Ala-1d |
| Ex55 | +++ | DIBAC-suc-PEG4-D-Lys(COT-CD)-vcPAB-1f |
| Ex56 | +++ | DIBAC-suc-PEG4-D-Lys(COT-CD)-vcPAB-1g |
| Ex57 | ++ | DIBAC-suc-$PEG_4$-D-Lys(COT-CD)-vcPAB-1d |
| Ex58 | ++++ | DIBAC-suc-$PEG_4$-vcPAB-1h |
| Ex59 | ++ | DIBAC-suc-$PEG_4$-dLys(COT-CD)-vcPAB-1h |
| Ex60 | ++ | BCN-$PEG_4$-dLys(COT-CD)-vcPAB-1h |
| Ex61 | +++++ | DIBAC-suc-$PEG_4$-vcPAB-1i |
| Ex62 | ++ | DIBAC-suc-$PEG_4$-dLys(COT-CD)-vcPAB-1i |
| Ex63 | ++ | DIBAC-suc-$PEG_4$-dLys(COT-CD)-Val-Ala-1i |

+ ≤−6; −6< ++ ≤−3; −3< +++ ≤1; 1< ++++ ≤5; 5< +++++ ≤9.5

TABLE 3A

| ANALYTICAL RESULTS OF LINKER-PAYLOADS | | | |
|---|---|---|---|
| | Payload | MF | MW |
| Ex36 | MMAE | $C_{88}H_{128}N_{12}O_{19}$ | 1658.0 |
| Ex37 | | $C_{133}H_{198}N_{16}O_{47}$ | 2773.1 |
| Ex38 | | $C_{129}H_{189}N_{17}O_{47}$ | 2730.0 |
| Ex39 | | $C_{134}H_{199}N_{17}O_{51}$ | 2864.1 |
| Ex40 | | $C_{125}H_{198}N_{16}O_{51}$ | 2741.0 |
| Ex41 | | $C_{140}H_{211}N_{17}O_{51}$ | 2948.3 |
| Ex42 | | $C_{132}H_{210}N_{16}O_{51}$ | 2837.2 |
| Ex43 | | $C_{151}H_{232}N_{18}O_{56}$ | 3195.5 |
| Ex44 | | $C_{143}H_{231}N_{17}O_{56}$ | 3084.4 |
| Ex45 | 1c in FIG. 1 | $C_{69}H_{87}N_5O_{15}$ | 1226.5 |
| Ex46 | 1b in FIG. 1 | $C_{121}H_{170}N_{10}O_{47}$ | 2516.7 |
| Ex47 | 1c in FIG. 1 | $C_{121}H_{170}N_{10}O_{47}$ | 2516.7 |
| Ex48 | 1d in FIG. 1 | $C_{72}H_{92}N_6O_{12}$ | 1233.5 |
| Ex49 | | $C_{124}H_{175}N_{11}O_{44}$ | 2523.8 |
| Ex50 | | $C_{148}H_{213}N_{15}O_{53}$ | 3050.3 |
| Ex51 | | $C_{127}H_{195}N_{11}O_{49}$ | 2660.0 |
| Ex52 | 1e in FIG. 1 | $C_{140}H_{212}N_{14}O_{53}$ | 2939.2 |
| Ex53 | 1d in FIG. 1 | $C_{135}H_{196}N_{12}O_{49}$ | 2771.1 |
| Ex54 | 1d in FIG. 1 | $C_1I_6H_{174}N_{10}O_{44}$ | 2412.7 |
| Ex55 | 1f in FIG. 1 | $C_{137}H_{191}N_{15}O_{48}$ | 2816.1 |
| Ex56 | 1g in FIG. 1 | $C_{138}H_{193}N_{15}O_{49}$ | 2846.1 |
| Ex57 | 1d in FIG. 1 | $C_{136}H_{195}N_{11}O_{54}$ | 2846.3 |
| Ex58 | 1h in FIG. 1 | $C_{74}H_{94}F_2N_8O_{17}$ | 1405.6 |
| Ex59 | 1h in FIG. 1 | $C_{126}H_{177}F_2N_{13}O_{49}$ | 2695.8 |
| Ex60 | 1h in FIG. 1 | $C_{118}H_{176}F_2N_{12}O_{49}$ | 2584.7 |
| Ex61 | 1i in FIG. 1 | $C_{80}H_{98}F_2N_8O_{18}$ | 1497.67 |
| Ex62 | 1i in FIG. 1 | $C_{132}H_{181}F_2N_{13}O_{50}$ | 2787.9 |
| Ex63 | 1i in FIG. 1 | $C_{121}H_{168}F_2N_{10}O_{47}$ | 2552.7 |

TABLE 3B

| ANALYTICAL RESULTS OF LINKER-PAYLOADS | | | | |
|---|---|---|---|---|
| | MS | | HPLC | |
| | m/z(100%) | m/z (highest MS) | Purity (%) | $R_t$ (min) |
| Ex36 | 829.7 (M/2 + H) | 1659.7 (M + H) | 98 | 8.25 (B) |
| Ex37 | 925.1 (M/3 + H) | 1387.2 (M/2 + H) | 96 | 7.22 (B) |
| Ex38 | 910.6 (M/3 + H) | 1365.8 (M/2 + H) | 100 | 7.19 (A) |
| Ex39 | 1432.6 (M/2 + H) | 1432.6 (M/2 + H) | 100 | 5.88 (A) |
| Ex40 | 1371.1 (M/2 + H) | 1371.1 (M/2 + H) | 100 | 5.78 (A) |
| Ex41 | 983.4 (M/3 + H) | 1475.0 (M/2 + H) | 100 | 7.29 (B) |
| Ex42 | 946.3 (M/3 + H) | 1418.9 (M/2 + H) | 100 | 7.33 (B) |
| Ex43 | 1065.9 (M/3 + H) | 1598.4 (M/2 + H) | 98 | 5.79 (B) |
| Ex44 | 1028.7 (M/3 + H) | 1541.8 (M/2 + H) | 100 | 5.66 (B) |
| Ex45 | 1226.6 (M + H) | 1226.6 (M + H) | 99 | 8.55 (B) |
| Ex46 | 839.5 (M/3 + H) | 1259.1 (M/2 + H) | 97 | 6.62(A), 6.67(B) |
| Ex47 | 839.5 (M/3 + H) | 1258.6 (M/2 + H) | 98 | 6.61(A), 6.73(B) |
| Ex48 | 617.3 (M/2 + H) | 1233.6 (M + H) | 100 | 9.21 (B) |
| Ex49 | 841.8 (M/3 + H) | 1262.4 (M/2 + H) | 98 | 6.45(A) 6.55(B) |
| Ex50 | 1017.3 (M/3 + H) | 1017.3 (M/3 + H) | 96 | 6.68 (B) |
| Ex51 | 837.2 [(M − BCN)/3 + H] | 1330.3 (M/2 + H) | 100 | 6.33 (B) |
| Ex52 | 980.3 (M/3 + H) | 1470.2 (M/2 + H) | 100 | 6.62 (B) |
| Ex53 | 924.5 (M/3 + H) | 1385.2 (M/2 + H) | 98 | 6.42 (B) |
| Ex54 | 1215.2 (M + $H_2O$)/2 + H] | 1207.1 (M/2 + H) | 100 | 6.37 (B) |
| Ex55 | 939.5 (M/3 + H) | 1408.7 (M/2 + H) | 99 | 6.33(A), 6.44(B) |
| Ex56 | 949.0 (M/3 + H) | 1423.3 (M/2 + H) | 100 | 6.11(A), 6.21(B) |
| Ex57 | 1424.2 $(M/2 + H)^+$. | 1424.2 $(M/2 + H)^+$ | 99 | 7.54 (B) |
| Ex58 | 703.5 (M/2 + H) | 1405.7 (M + H) (5%) | 100 | 7.40 (B) |
| Ex59 | 899.2 (M/3 + H) | 1348.6 (M/2 + H) (40%) | 100 | 6.23 (B) |
| Ex60 | 1293.6 (M/2 + H) | 1293.6 (M/2 + H) | 100 | 7.37, 7.41 (B) |
| Ex61 | 749.5 (M/2 + H) | 1497.7 (M + H) (5%) | 100 | 7.99 (B) |
| Ex62 | 930.3 (M/3 + H) | 1394.2 (M/2 + H) (33%) | 100 | 7.94, 8.02 (B) |
| Ex63 | 851.4 (M/3 + H) | 1276.8 (M/2 + H) (83%) | 100 | 7.76 (B) |

Examples 1-6 describe the preparation of certain compounds useful for, among other things, synthetic intermediates towards the synthesis of the linkers, linker-payloads, and/or conjugates described herein.

Example 1

Figure 2:
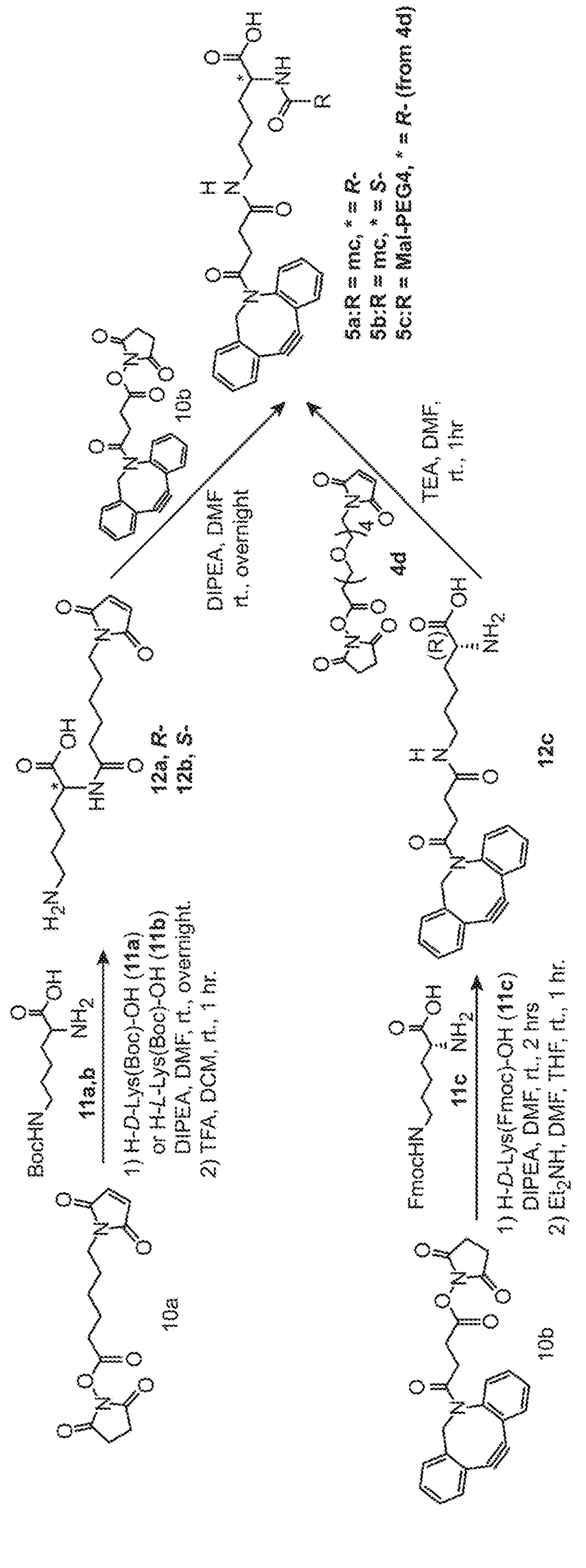
FIG. 2 shows a synthetic process for preparing intermediate compounds 5a-c.

Preparation of Intermediate 5a (See FIG. 2)

(2R)-6-(4-{2-Azatricyclo[10.4.0.0$^{4,9}$]hexadeca-1(12),4,6,8,13,15-hexaen-10-yn-2-yl}-4-oxobutanamido)-2-[6-(2,5-dioxo-2,5-dihydro-1H-pyrrol-1-yl)hexanamido]hexanoic acid (5a)

To a mixture of H-D-Lys(Boc)-OH (11a, 0.25 g, 1.0 mmol) in DMF (10 mL) were added 6-Maleimidocaproic acid-NHS (10a, 0.31 g, 1.0 mmol) and DIPEA (0.26 g, 2.0 mmol) successively at room temperature. The reaction was stirred at room temperature overnight until compound 11a was totally consumed, which was monitored by LCMS. The mixture was directly separated by reversed phase flash chromatography (0-100% acetonitrile in water (0.05% TFA)) to give intermediate Boc-12a (ESI m/z: 440 $(M+H)^+$) as colorless oil, which was dissolved in DCM (5 mL). To the solution was added TFA (0.5 mL) dropwise at 0° C., and the mixture was stirred at room temperature for an hour. The reaction was monitored by LCMS until intermediate Boc-12a was totally consumed. The volatiles were removed in vacuo to give crude 12a (ESI m/z: 340 $(M/2+H)^+$), which was used for the next step without further purification. To the mixture of crude compound 12a (0.21 g, 0.62 mmol) in DMF (5 mL) was added activated ester 10b (0.20 g, 0.50 mmol) and DIPEA (50 mg, 0.39 mmol) successively at room temperature. After the reaction mixture was stirred at room temperature overnight, compound 12a was totally consumed, which was monitored by LCMS. The reaction mixture was then directly separated by reversed phase flash chromatography (0-100% acetonitrile in water) to give compound 5a (0.10 g, 20% yield in 3 steps from 10a) as a white solid. ESI m/z: 627 $(M+H)^+$. $^1H$ NMR ($DMSO_{d6}$, 400 MHz): δ 7.89 (d, J=13.2 Hz, 1H), 7.69-7.62 (m, 3H), 7.48-7.47 (m, 3H), 7.36-7.28 (m, 3H), 6.99 (s, 2H), 5.03 (d, J=13.6 Hz, 1H), 4.09-4.04 (m, 1H), 3.60 (d, J=13.6 Hz, 1H), 3.38-3.34 (m, 1H), 2.90-2.87 (m, 2H), 2.61-2.55 (m, 1H), 2.25-2.17 (m, 1H), 2.08-1.51 (m, 5H), 1.46-1.15 (m, 12H) ppm.

Example 2

Preparation of Intermediate 5b (See FIG. 2)

(2S)-6-(4-{2-Azatricyclo[10.4.0.0$^{4,9}$]hexadeca-1(12),4,6,8,13,15-hexaen-10-yn-2-yl}-4-oxobutanamido)-2-[6-(2,5-dioxo-2,5-dihydro-1H-pyrrol-1-yl)hexanamido]hexanoic acid (5b)

Following the procedures in Example 1 for intermediate 5a except substituting H-L-Lys(Boc)-OH (11b) for H-D-Lys(Boc)-OH (11a), intermediate 5b was obtained (0.16 g, 19% yield from 11b) as a white solid. ESI m/z: 627 $(M+H)^+$. $^1H$ NMR ($DMSO_{d6}$, 400 MHz) δ 7.94-7.15 (m, 10H), 6.99 (s, 2H), 5.02 (d, J=14.0 Hz, 1H), 4.09-4.04 (m, 1H), 3.60 (d, J=14.0 Hz, 1H), 3.38-3.34 (m, 1H), 2.91-2.86 (m, 2H), 2.58-2.54 (m, 1H), 2.23-2.18 (m, 1H), 2.07-2.04 (m, 2H), 1.98-1.92 (m, 1H), 1.77-1.73 (m, 1H), 1.63-1.58 (m, 1H), 1.47-1.12 (m, 12H) ppm.

Example 3

Preparation of Intermediate 5c (See FIG. 2)

(2R)-2-Amino-6-(4-{2-azatricyclo[10.4.0.0$^{4,9}$]hexadeca-1(12),4,6,8,13,15-hexaen-10-yn-2-yl}-4-oxobutanamido)hexanoic acid (12c)

To a mixture of commercially available H-D-Lys(Fmoc)-OH (11c, 0.55 g, 1.5 mmol) in dry DMF (3.0 mL) were added DIPEA (0.38 g, 3.0 mmol) and compound 10b (See, *Accounts of Chemical Research,* 2011, 805-815) (0.60 g, 1.5 mmol) successively at room temperature. The resulting solution was stirred at room temperature for 2 hours until compound 11c was totally consumed, as monitored by LCMS. The mixture was then purified by reversed phase flash chromatography (0-80% acetonitrile in water) to give intermediate Fmoc-12c (0.48 g, 49% yield) as a white solid. ESI m/z: 656.3 $(M+H)^+$. To the mixture of intermediate Fmoc-12c (0.15 g, 0.23 mmol) in DMF (3 mL) was added diethylamine (0.1 mL). The mixture was stirred at room temperature for an hour and LCMS showed that Fmoc-12c was totally consumed. The mixture was filtered and the filtrate was purified by prep-HPLC (method B) to give compound 12c (42 mg, 42% yield) as a white solid. ESI m/z: 434 $(M+H)^+$. $^1H$ NMR ($DMSO_{d6}$, 400 MHz) δ 7.71-7.60 (m, 3H), 7.50-7.42 (m, 3H), 7.39-7.27 (m, 3H), 5.02 (d, J=14.0 Hz, 1H), 3.60 (d, J=14.0 Hz, 1H), 3.08-3.07 (m, 1H), 2.89-2.88 (m, 2H), 2.61-2.52 (m, 1H), 2.25-2.17 (m, 1H), 2.00-1.96 (m, 1H), 1.80-1.72 (m, 1H), 1.65-1.62 (m, 1H), 1.52-1.44 (m, 1H), 1.23-1.21 (m, 5H) ppm.

(2R)-6-(4-{2-Azatricyclo[10.4.0.0$^{4,9}$]hexadeca-1(12),4,6,8,13,15-hexaen-10-yn-2-yl}-4-oxobutanamido)-2-[1-(2,5-dioxo-2,5-dihydro-1H-pyrrol-1-yl)-3,6,9,12-tetraoxapentadecan-15-amido]hexanoic acid (5c)

To a mixture of compound 12c (40 mg, 92 μmol) in DMF (2 mL) were added compound 4d (41 mg, 0.11 mmol) and TEA (18 mg, 0.18 mmol) in DMF successively at room temperature. After the mixture was stirred at room temperature for an hour, most of compound 4d was consumed, as monitored by LCMS. The resulting mixture was then directly separated by reversed phase flash chromatography (0-100% acetonitrile in water) to give intermediate 5c (33 mg, 47% yield) as light yellow oil. ESI m/z: 761 $(M+H)^+$. $^1H$ NMR ($CDCl_3$, 400 MHz) δ 7.96 (d, J=12.8 Hz, 1H), 7.69-7.62 (m, 3H), 7.51-7.30 (m, 6H), 7.02 (s, 2H), 5.04 (d, J=14.4 Hz, 1H), 4.06 (m, 1H), 3.62-3.46 (m, 18H), 2.89 (m, 2H), 2.63-2.57 (m, 4H), 2.39-2.19 (m, 3H), 2.01-1.20 (m, 6H) ppm.

Example 4

Figure 3:
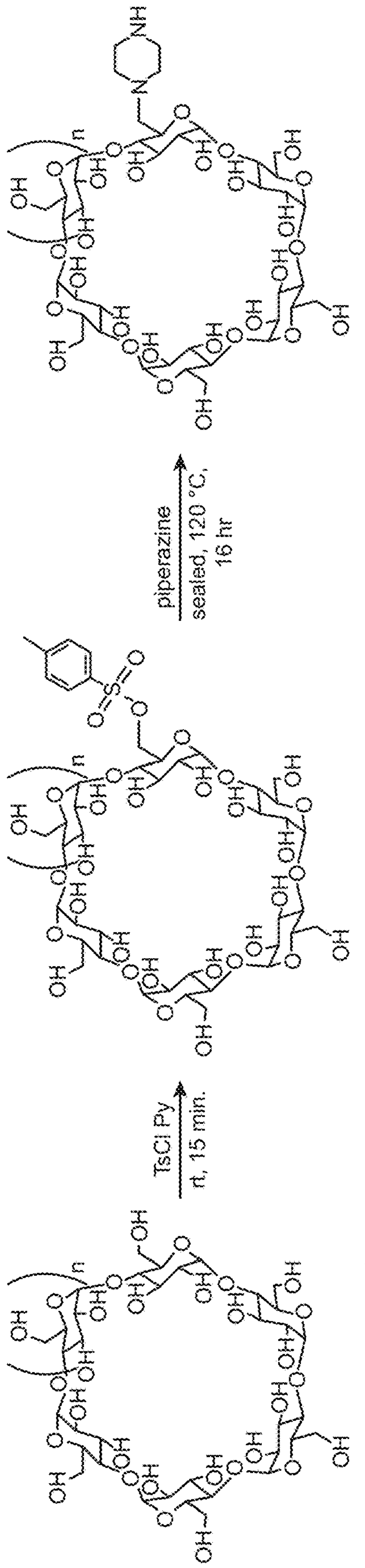
FIG. 3 shows a synthetic process for preparing intermediate compound 6b.

Preparation of Intermediate 6b (See FIG. 3)

[31,32,33,34,35,36,37,38,39,40,41,42-Dodecahydroxy-10,15,20,25,30-pentakis(hydroxymethyl)-2,4,7,9,12,14,17,19,22,24,27,29-dodecaoxaheptacyclo[26.2.2.2$^{3,6}$2$^{8,11}$.2$^{13,16}$.2$^{18,21}$.2$^{23,26}$]dotetracontan-5-yl]methyl 4-methylbenzene-1-sulfonate (14)[2]

To a solution of α-cyclodextrin (13, 10 g, 10 mmol) in dry pyridine (Py) (0.32 L) was added 4-toluenesulfonyl chloride (TsCL) (20 g, 0.10 mol) at room temperature. The mixture was stirred at this temperature for 15 minutes and was quenched with water (60 mL) immediately. The reaction mixture was concentrated under reduce pressure to remove the volatiles (pyridine and water). The residue was purified by reversed phase flash chromatography (0-25% of acetonitrile in water) to give product 14 (1.1 g, 10% yield) as a white solid. ESI m/z: 1127 $(M+H)^+$.

5,10,15,20,25-Pentakis(hydroxymethyl)-30-(piperazin-1-ylmethyl)-2,4,7,9,12,14,17,19,22,24,27,29-dodecaoxaheptacyclo[26.2.2.2$^{3,6}$.28$^{11}$.2$^{13,16}$.2$^{18,21}$.2$^{23,26}$]dotetracontane-31,32,33,34,35,36,37,38,39,40,41,42-dodecol (6b)

A mixture of compound 14 (1.2 g, 1.0 mmol) in piperazine (1.7 g, 20 mmol) was sealed and stirred at 120° C. for 16 hours. After the reaction was cooled to room temperature, the mixture was diluted with DMF (3 mL) and acetonitrile (30 mL). The precipitates were collected by filtration, and the crude product was then purified by Prep-HPLC (method B) to give intermediate 6b (0.32 g, 30% yield) as a white solid. ESI m/z: 1041 $(M+H)^+$.

Example 5

Figure 4:
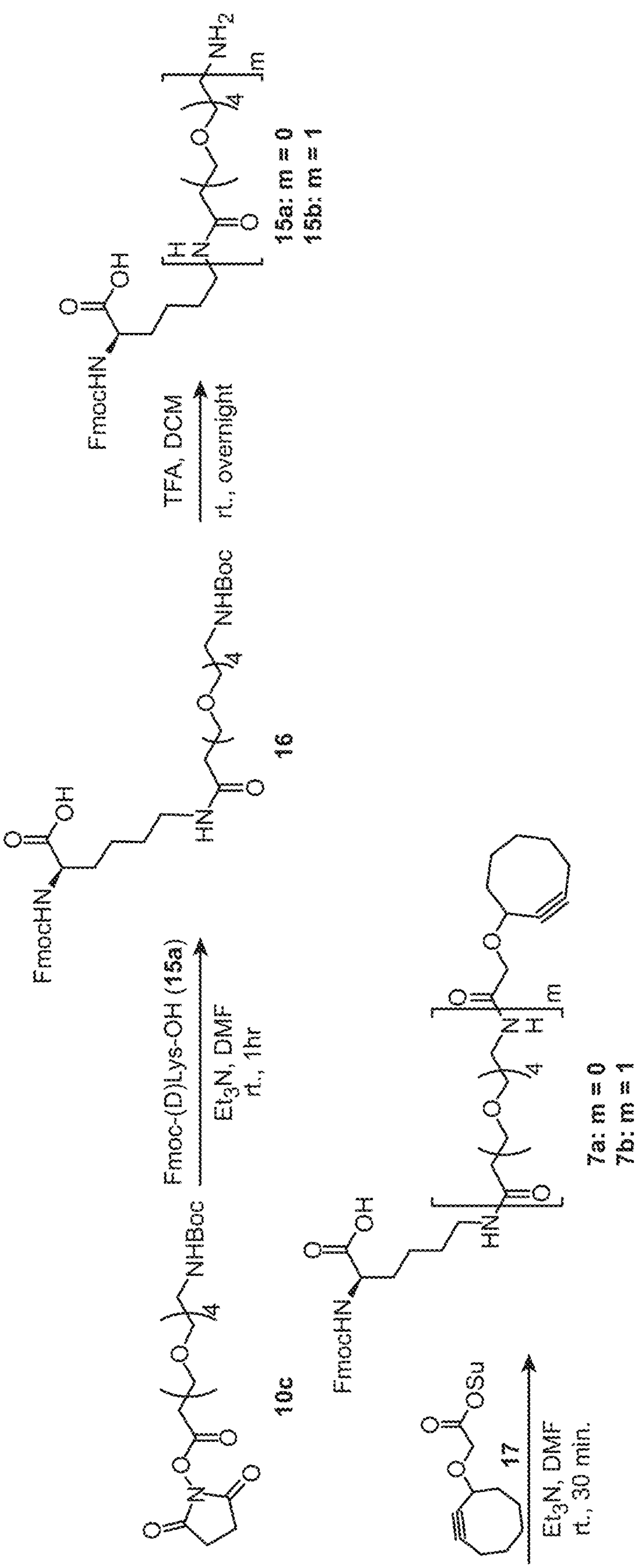
FIG. 4 shows a synthetic process for preparing intermediate compound 7a and 7b.

Preparation of Intermediate 7a (See FIG. 4)

(2R)-6-[2-(Cyclooct-2-yn-1-yloxy)acetamido]-2-{[(9H-fluoren-9-ylmethoxy)carbonyl]amino}hexanoic acid (7a)

To a mixture of commercial compound 17 (65 mg, 0.23 mmol, CAS: 1425803-45-7) in DMF (2 mL) were added Fmoc-D-Lys-OH (15a, 85 mg, 0.23 mmol) and triethylamine (52 mg, 0.51 mmol). The reaction mixture was stirred at room temperature for 30 minutes. The mixture was directly separated by reversed phase flash chromatography (0-100% acetonitrile in water (0.05% TFA)) to give intermediate 7a (85 mg, yield 70%) as a white solid. ESI m/z: 533 $(M+H)^+$. $^1H$ NMR ($MeOD_{d4}$, 500 MHz): δ 7.70 (d, J=7.5 Hz, 2H), 7.59 (t, J=8.0 Hz, 2H), 7.30 (t, J=7.5 Hz, 2H), 7.22 (t, J=7.4 Hz, 2H), 4.35-4.22 (m, 2H), 4.22-4.09 (m, 2H), 4.09-3.99 (m, 1H), 3.94-3.81 (m, 1H), 3.79-3.67 (m, 1H), 3.15 (t, J=6.9 Hz, 2H), 2.17-1.96 (m, 3H), 1.96-1.86 (m, 1H), 1.85-1.66 (m, 4H), 1.66-1.41 (m, 5H), 1.41-1.25 (m, 3H) ppm.

Example 6

Preparation of Intermediate 7b (See FIG. 4)

(R)-26-(((9H-Fluoren-9-yl)methoxy)carbonylamino)-2,2-dimethyl-4,20-dioxo-3,8,11,14,17-pentaoxa-5,21-diazaheptacosan-27-oic acid (16)

To a mixture of compound 10c (4.6 g, 10 mmol, CAS: 859230-20-9) in DMF (10 mL) were added 15a (3.6 g, 10 mmol) and triethylamine (2.0 g, 20 mmol). The reaction mixture was stirred at 25° C. for an hour until compound 15a was totally consumed which was monitored by TLC. The mixture was diluted with DCM and washed with water and brine. The organic layer was dried over anhydrous sodium sulfate and concentrated in vacuo. The residue was purified by silica gel column chromatography (0-5% methanol in DCM) to give the 16 (5.5 g, 77% yield) as colorless oil. ESI m/z: 716.2 $(M+H)^+$. $^1H$ NMR ($DMSO_{d6}$, 500 MHz) δ 7.89 (d, J=7.5 Hz, 2H), 7.84-7.80 (m, 1H), 7.74-7.72 (d, J=7.5 Hz, 2H), 7.61-7.59 (m, 1H), 7.42 (t, J=7.5 Hz, 2H), 7.33 (t, J=7.5 Hz, 2H), 6.76-6.74 (m, 1H), 4.28-4.21 (m, 3H), 3.93-3.85 (m, 1H), 3.58 (t, J=6.5 Hz, 2H), 3.48-3.47 (m, 12H), 3.16 (d, J=5.5 Hz, 1H), 3.07-2.97 (m, 3H), 2.28 (t, J=6.5 Hz, 2H), 2.02-1.94 (m, 1H), 1.71-1.56 (m, 2H), 1.36 (s, 9H), 1.23-1.15 (m, 6H) ppm.

(24R)-24-(((9H-Fluoren-9-yl)methoxy)carbonylamino)-1-(cyclooct-2-ynyloxy)-2,18-dioxo-6,9,12,15-tetraoxa-3,19-diazapentacosan-25-oic acid (7b)

To a solution of compound 16 (0.60 g, 0.84 mmol) in DCM (10 mL) was added trifluoroacetic acid (2.0 mL) at 0° C. The reaction solution was warmed and stirred at 25° C. overnight until compound 16 was totally consumed, which was monitored by LCMS (ESI m/z: 616.3 $(M+H)^+$). The volatiles were removed in vacuo to give crude 15b which was used for the next step directly.

Following the procedure in Example 5 for making intermediate 7a except substituting 15b for 15a, the title compound 7b was obtained (0.38 g, 49% yield) as colorless oil after purification by silica gel column chromatography (0-5% methanol in DCM). ESI m/z: 780.3 $(M+H)^+$. $^1H$ NMR ($CDCl_3$, 400 MHz) δ 7.75 (d, J=7.6 Hz, 2H), 7.61 (t, J=7.6 Hz, 2H), 7.39 (t, J=7.6 Hz, 2H), 7.32-7.27 (m, 2H), 7.05-7.01 (m, 1H), 6.86-6.83 (m, 1H), 5.85 (d, J=7.6 Hz, 1H), 4.38-4.37 (m, 3H), 4.27-4.15 (m, 2H), 4.11-4.05 (m, 1H), 3.91-3.87 (m, 1H), 3.69 (t, J=5.6 Hz, 2H), 3.62-3.47 (m, 17H), 3.28-3.19 (m, 2H), 2.46 (t, J=5.6 Hz, 2H), 2.27-2.01 (m, 3H), 1.91-1.72 (m, 5H), 1.66-1.55 (m, 4H), 1.42-1.34 (m, 3H) ppm.

Example 7

General Procedure A (See FIG. 5):

To a solution of Fmoc-vc-PAB-PNP (2a, 0.68-1.0 equiv.) and a compound 1 (1e, 1f, 1g, 1h, 1i or 1m, 1.0 equiv.) in DMF was added with DIPEA (5 equiv.) at RT by syringe. The mixture was stirred at 25° C. for 16-24 hours and most of 2a was consumed according to LCMS. To the resulting mixture was added piperidine (0.1-1 mL, excess) and it was stirred at 25° C. for 2 hours until Fmoc was totally removed, which was monitored by LCMS. After filtering through a membrane, the filtrate was directly purified by prep-HPLC (method B) to give a compound 3 (32-73% yield) as a white solid. Table 4 provides specific reaction conditions for making compounds 3e-3g, 3H and 31.

TABLE 4

| Prod. | Payload 1 | mg (mmol) | Fmoc-vcPAB-PNP (2a) (mmol) | Step 1 Base: DIPEA (mmol) | Step 1 DMF (mL) | Step 1 Temp (° C.) | Step 1 Time (hr) | Step 2 Pip.* (mL) | Step 2 Temp (° C.) | Step 2 Time (hr) | Purif.* | Yield mg, % | m/z (M + H) |
|---|---|---|---|---|---|---|---|---|---|---|---|---|---|
| 3e | 1e in FIG. 1 | 18 (0.031) | 0.021 | 0.16 | 5 | 25 | 24 | 0.1 | 25 | 2 | B | 14 68% | 978 |
| 3f | 1f in FIG. 1 | 160 (0.27) | 0.27 | 1.4 | 10 | 25 | 24 | 1 | 25 | 2 | B | 85 32% | 990 |
| 3g | 1g in FIG. 1 | 33 (0.054) | 0.054 | 0.27 | 5 | 25 | 24 | 0.1 | 25 | 2 | B | 22 40% | 1021 |
| 3H | (1h) | 93 (0.20) | 0.22 | 0.40 | 3 | 25 | 3 | 0.3 | 25 | 1 | B | 127 73% | 871 |
| 3I | (1i) | 87 (0.15) | 0.13** | 0.52 | 5 | 25 | 3 | 1 | 25 | 1 | B | 80 64% | 963 |

Pip.* = Piperidine; Purification*Prep-HPLC method; **with same equivalent of HOBt.

Example 8

General Procedure B (See FIG. 6):

To a solution of acid (Fmoc-Val-Ala-OH (2b), Fmoc-dLys(COT)-OH (7a) or Fmoc-dLys(PEG4-COT)-OH (7b), 1.0-1.8 equiv.) in DMF (or DCM/THF for 8a) were added HATU (1.0-2.8 equiv.) and DIPEA or TEA (2.0-5.0 equiv.) at 25° C. After the mixture was stirred at 25° C. for 30 minutes, a solution of amine (1b-d, 1i or 3a-l, 1.0 equiv.) in DMF (1 mL) was added by syringe. The resulting mixture was stirred at 25° C. for 2-24 hours until the amine was mostly consumed according to LCMS. To the mixture was then added piperidine or diethylamine (excess), and the mixture was stirred at 25° C. for 1-20 hours until Fmoc was totally removed, which was monitored by LCMS. The reaction mixture was filtered through a membrane and the filtrate was directly purified by prep-HPLC (method B) or reversed phase flash chromatography to give compound 3b-d or 8a-J (23-80% yield) as a white solid.

TABLE 5

REACTION CONDITIONS FOR SYNTHESIZING COMPOUNDS 3B-D, 3J AND 8A-L FOLLOWING GENERAL PROCEDURE B

| | | | | | Step 1 | | | | Step 2 | | | | |
|---|---|---|---|---|---|---|---|---|---|---|---|---|---|
| | Amine | | Acid | | HATU | DIPEA | | | | | | | |
| Product | | mg (mmol) | | mg (mmol) | mg (mmol) | mg (mmol) | DMF (mL) | Time (hr) | Piperidine (mL) | Time (hr) | Purification* | % Yield mg | m/z $(M + 1)^+$ |
| 3b | 1b | 0.20 (0.38) | 2b | 190 (0.46) | 200 (0.54) | 150 (1.1) | 4 | 2 | 0.5 | 2 | B | 60, 23% | 692 |
| 3c | 1c | 100-0.19 | 2b | 94 (0.23) | 100 (0.27) | 74 (0.57) | 2 | 2 | 0.25 | 2 | B | 36, 28% | 692 |
| 3d | 1d | 1000 (1.9) | 2b | 930 (2.3) | 860 (2.3) | 490 (3.8) | 10 | 2 | $Et_2NH$, 0.5 | 2 | RP-B | 880, 67% | 699 |
| 8a | 3a | 38 (0.034) | 7a | 34 (0.064) | 36 (0.096) | TEA 19 (0.19) | S** | 2 | $Et_2NH$, 0.2 | 16 | RP-A | 17, 35% | 1415 |
| 8b | 3b | 60 (0.087) | 7a | 55 (0.10) | 46 (0.12) | 34 (0.26) | 1 | 2 | 0.1 | 1 | RP | 50, 49% | 984 |
| 8c | 3c | 100 (0.15) | 7a | 92 (0.173) | 77 (0.20) | 56 (0.44) | 2 | 2 | 0.1 | 1 | B | 80, 56% | 984 |
| 8d | 3d | 45 (0.064) | 7a | 35 (0.064) | 24 (0.064) | 41 (0.32) | 1 | 16 | 0.1 | 3 | B | 30, 47% | 991 |
| 8e | 3f | 80 (0.064) | 7a | 53 (0.097) | 37 (0.097) | 41 (0.32) | 2 | 16 | 0.1 | 3 | RP-B | 65, 62% | 1283 |
| 8f | 3g | 35 (0.034) | 7a | 19 (0.034) | 13 (0.034) | 22 (0.17) | 1 | 16 | 0.1 | 3 | B | 15, 33% | 1313.6 |
| 8g | 3a | 85 (0.076) | 7b | 69 (0.088) | 69 (0.18) | TEA 18 (0.18) | 3 | 2 | $Et_2NH$, 0.5 | 16 | RP | 17, 43% | 832.2 $(M/2 + H)^+$ |
| 8h | 3d | 60 (0.086) | 7b | 67 (0.086) | 33 (0.086) | 55 (0.43) | 2 | 16 | 0.1 | 3 | B | 54, 50% | 620 $(M/2 + 1)^+$ |
| 8i | 3e | 85 (0.087) | 7b | 68 (0.087) | 69 (0.18) | 55 (0.43) | 2 | 16 | 0.1 | 3 | B | 40, 30% | 759 $(M/2 + 1)^+$ |
| 8J | 3H | 174 (0.20) | 7a | 117 (0.22) | 114 (0.30) | 77 (0.60) | 10 | 3 | 1 | 0.5 | RP-B | 120 52% | 1163 |
| 8K | 3I | 185 (0.19) | 7a | 120 (0.23) | 110 (0.29) | 74 (0.57) | 10 | 4 | 1 | 4 | RP-B | 192 80% | 1256 |
| 8L | 3J | 699 (0.96) | 7a | 562 (1.06) | 511 (1.34) | 372 (2.88) | 10 | 16 | $Et_2NH$, 225 mg* | 3 | B | 205 46%* | 1021 |

For Purification-B: Prep-HPLC method B; A: Prep-HPLC method A; RP: RP-flash; RP-B: RP-flash method B; RP-A: RP-flash method A. S**: DCM/THF = 4/8 (mL)
*40% of product in step 1 was used in step 32.

Example 9

Preparation of Compound 3a (See FIG. 6 and Table 5)

{4-[(2S)-2-[(2S)-2-Amino-3-methylbutanamido]-5-(carbamoylamino)pentanamido]phenyl}methyl N-[(1S)-1-{[(1S)-1-{[(3R,4S,5S)-1-[(2S)-2-[(1R,2R)-2-{[(1 S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate (3a)

(See WO2012/166560, incorporated herein by reference in its entirety)

To a 25 mL-round-bottom flask was added Fmoc-vc-PAB-PNP (2a) (0.33 g, 0.43 mmol) and anhydrous DMF (5 mL). To the solution were added MMAE (1a, 0.21 g, 0.21 mmol), HOBt (38 mg, 0.28 mmol) and DIPEA (74 mg, 0.57 mmol) were added at 25° C. successively. The mixture was stirred at 25-30° C. for 16 hours until MMAE was totally consumed according to LCMS. The reaction mixture was filtered through membrane and the filtrate was purified by prep-HPLC (method A) to give Fmoc-3a as a white solid, which was dissolved in DMF (5 mL). To the solution was added diethylamine (0.3 mL). The reaction mixture was stirred at 30° C. for an hour until Fmoc was removed according to LCMS. The reaction mixture was filtered through membrane and the filtrate was purified by prep-HPLC (method A) to give vcPAB-MMAE (3a) (0.20 g, 58% yield) as a white solid. ESI m/z: 562.5 $(M/2+H)^+$.

Example 10

Preparation of Compound 3b (See FIG. 6 and Table 5)

(2S)-2-Amino-N-[(1S)-1-[(4-{2-[(1S,2S,4R,8S,9S,11 S,12S,13R)-11-hydroxy-9,13-dimethyl-16-oxo-6-propyl-5,7-dioxapentacyclo[$10.8.0.0^{2,9}.0^{4,8}.0^{13,18}$]icosa-14,17-dien-8-yl]-2-oxoethoxy}phenyl)carbamoyl]ethyl]-3-methylbutanamide (3b)

Following the general procedure B, compound 3b (60 mg, 23% yield) was obtained as a white solid. ESI m/z: 692 $(M+H)^+$. $^1H$ NMR (500 MHz, $CDCl_3$) δ 8.90-8.77 (m, 1H), 7.87 (t, J=7.9 Hz, 1H), 7.48-7.36 (m, 2H), 7.26-7.20 (m, 1H), 6.88-6.81 (m, 2H), 6.30-6.25 (m, 1H), 6.05-6.00 (m, 1H), 5.21-5.17 (m, 1H), 5.06-5.00 (m, 0.5H), 4.96-4.90 (m, 1H), 4.73-4.54 (m, 2.5H), 4.53-4.46 (m, 1H), 3.33-3.28 (m, 1H), 2.95-2.90 (m, 1H), 2.62-2.52 (m, 1H), 2.39-2.28 (m, 2H), 2.22-2.03 (m, 4H), 1.85-1.51 (m, 10H), 1.48-1.34 (m, 5H), 1.21-1.10 (m, 2H), 1.03-0.89 (m, 9H), 0.86-0.75 (m, 3H) ppm.

Example 11

Preparation of Compound 3c (See FIG. 6 and Table 5)

(2S)-2-Amino-N-[(1S)-1-[(4-{2-[(1S,2S,4R,6R,8S,9S,11 S,12S,13R)-11-hydroxy-9,13-dimethyl-16-oxo-6-propyl-5,7-dioxapentacyclo[$10.8.0.0^{2,9}.0^{4,8}.0^{13,18}$]icosa-14,17-dien-8-yl]-2-oxoethoxy}phenyl) carbamoyl]ethyl]-3-methylbutanamide (3c)

Following the general procedure B, compound 3c (36 mg, 28% yield) was obtained as a white solid. ESI m/z: 692 $(M+H)^+$. $^1$H NMR (500 MHz, $CDCl_3$) δ 8.94-8.83 (m, 1H), 7.93-7.84 (m, 1H), 7.49-7.38 (m, 2H), 7.24 (d, J=10.1 Hz, 1H), 6.89-6.80 (m, 2H), 6.30-6.24 (m, 1H), 6.03 (s, 1H), 4.99-4.88 (m, 2H), 4.74-4.55 (m, 3H), 4.51 (s, 1H), 3.31 (t, J=3.9 Hz, 1H), 3.02-2.96 (m, 1H), 2.62-2.52 (m, 1H), 2.38-2.28 (m, 2H), 2.21-2.03 (m, 4H), 1.80-1.55 (m, 10H), 1.48-1.38 (m, 5H), 1.21-1.09 (m, 2H), 1.03-0.92 (m, 9H), 0.86-0.76 (m, 3H) ppm.

Example 12

Preparation of Compound 3d (See FIG. 6 and Table 5)

(1S,4aS,10aR)-6-((S)-2-((S)-2-Amino-3-methylbutanamido)propanamido)-N-((1S,4aS,10aR)-6-hydroxy-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (3d)

Following the general procedure B, compound 3d (0.88 g, 67% yield) was obtained as a white solid. ESI m/z: 699 $(M+H)^+$. $^1$H NMR (500 MHz, methanol$_{d4}$) δ 8.40 (s, 1H), 7.47 (s, 1H), 7.32 (d, J=8.0 Hz, 1H), 7.03 (d, J=8.3 Hz, 1H), 6.88 (d, J=8.2 Hz, 1H), 6.72 (d, J=2.4 Hz, 1H), 6.56 (dd, J=8.3, 2.4 Hz, 1H), 4.60-4.48 (m, 1H), 3.22-3.11 (m, 1H), 3.02-2.93 (m, 1H), 2.92-2.76 (m, 3H), 2.74-2.70 (m, 1H), 2.43-2.31 (m, 3H), 2.28 (d, J=14.1 Hz, 3H), 2.16-1.96 (m, 3H), 1.81 (s, 1H), 1.78-1.65 (m, 4H), 1.53-1.42 (m, 4H), 1.38 (d, J=5.3 Hz, 6H), 1.33-1.22 (m, 2H), 1.14 (d, J=6.6 Hz, 6H), 1.09 (d, J=18.6 Hz, 6H) ppm.

Example 13

Preparation of Compound 3e (See FIG. 5 and Table 4)

4-((S)-2-((S)-2-Amino-3-methylbutanamido)-5-ureidopentanamido)benzyl 2-((4bS,8S,8aR)-8-((1S,4aS,10aR)-6-hydroxy-1,4a-dimethyl-1,2,3,4,4a,9,10,10a-octahydrophenanthrene-1-carbonylcarbamoyl)-4b,8-dimethyl-4b,5,6,7,8,8a,9,10-octahydrophenanthren-3-yloxy)ethylcarbamate (3e)

Following the general procedure A, compound 3e (14 mg, 68% yield) was obtained as a white solid. ESI m/z: 978 $(M+1)^+$. $^1$H NMR (500 MHz, DMSO$_{d6}$) δ 10.22 (s, 1H), 9.04 (s, 1H), 8.71 (d, J=7.5 Hz, 1H), 8.12 (s, 2H), 7.59 (d, J=8.3 Hz, 2H), 7.42 (t, J=5.4 Hz, 1H), 7.29 (d, J=8.2 Hz, 2H), 6.94 (d, J=8.5 Hz, 1H), 6.84-6.76 (m, 2H), 6.67 (d, J=8.4 Hz, 1H), 6.64 (s, 1H), 6.51 (dd, J=8.1, 2.0 Hz, 1H), 6.12 (s, 1H), 5.52 (s, 2H), 4.96 (s, 2H), 4.51 (d, J=5.1 Hz, 1H), 3.92 (s, 2H), 3.66 (d, J=5.7 Hz, 1H), 3.32 (d, J=5.6 Hz, 2H), 3.13-2.63 (m, 6H), 2.26 (d, J=7.2 Hz, 2H), 2.22-2.03 (m, 4H), 1.89-1.82 (m, 4H), 1.79-1.69 (m, 1H), 1.68-1.53 (m, 4H), 1.46-1.40 (m, 2H), 1.27 (d, J=3.3 Hz, 8H), 1.19-1.08 (m, 4H), 1.03-0.89 (m, 12H) ppm.

Example 14

Preparation of Compound 3f (See FIG. 5 and Table 4)

{4-[(2S)-2-[(2S)-2-Amino-3-methylbutanamido]-5-(carbamoylamino)pentanamido]phenyl}methyl N-({[(4bS,8S,8aR)-8-{[(1S,4aS,10aR)-6-hydroxy-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}methyl) carbamate (3f)

Following the general procedure A, compound 3f (85 mg, 32% yield) was obtained as a white solid. ESI m/z: 991 $(M+1)^+$. $^1$H NMR (500 MHz, methanol$_{d4}$) δ 8.40 (s, 1H, NH of imidine), 7.58 (d, J=8.5 Hz, 2H), 7.50 (s, 1H), 7.37 (d, J=8.5 Hz, 2H), 7.30 (d, J=7.5 Hz, 1H), 7.02 (d, J=8.3 Hz, 1H), 6.88 (d, J=8.3 Hz, 1H), 6.72 (d, J=2.4 Hz, 1H), 6.56 (dd, J=8.2, 2.5 Hz, 1H), 5.10 (s, 2H), 4.66-4.52 (m, 1H), 3.92 (s, 2H), 3.75 (d, J=5.7 Hz, 1H), 3.26-2.75 (m, 6H), 2.42-2.22 (m, 7H), 2.14-1.59 (m, 11H), 1.40 (t, J=15.9 Hz, 8H), 1.34-1.27 (m, 3H), 1.16-1.12 (m, 6H), 1.10 (d, J=6.9 Hz, 3H), 1.07 (d, J=6.9 Hz, 3H) ppm.

Example 15

Preparation of Compound 3g (See FIG. 5 and Table 4)

{4-[(2S)-2-[(2S)-2-Amino-3-methylbutanamido]-5-(carbamoylamino)pentanamido]phenyl}methyl N-[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}-2-hydroxyethyl]carbamate (3g)

Following the general procedure A, compound 3g (22 mg, 40% yield) was obtained as a white solid. ESI m/z: 1021 $(M+1)^+$. $^1$H NMR (400 MHz, DMSO$_{d6}$) δ 10.02 (s, 1H), 9.82 (s, 1H), 9.00 (s, 1H), 8.69-8.65 (m, 1H), 8.11-8.00 (m, 4H), 7.65-7.53 (m, 3H), 7.40-7.30 (m, 3H), 7.30-7.20 (m, 1H), 6.96 (d, J=8.0 Hz, 1H), 6.81 (d, J=8.0 Hz, 1H), 6.65-6.61 (m, 1H), 6.50 (dd, J=8.0 Hz, 2.0 Hz, 1H), 6.00-5.95 (m, 1H), 5.48 (s, 2H), 5.00-4.95 (m, 3H), 4.60-4.40 (m, 1H), 4.25-4.20 (m, 1H), 3.65-3.55 (m, 4H), 3.15-2.55 (m, 10H), 2.40-2.20 (m, 3H), 2.20-2.00 (m, 5H), 2.00-1.80 (m, 4H), 1.86-1.55 (m, 6H), 1.27 (d, J=4.8 Hz, 9H), 1.20-1.10 (m, 2H), 0.97-0.90 (m, 6H) ppm Example 15-A Preparation of Compound 3H—See FIG. 5 and Table 4

{4-[(2S)-2-[(2S)-2-Amino-3-methylbutanamido]-5-(carbamoylamino)pentanamido]phenyl}methyl N-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl}carbamate (3H)

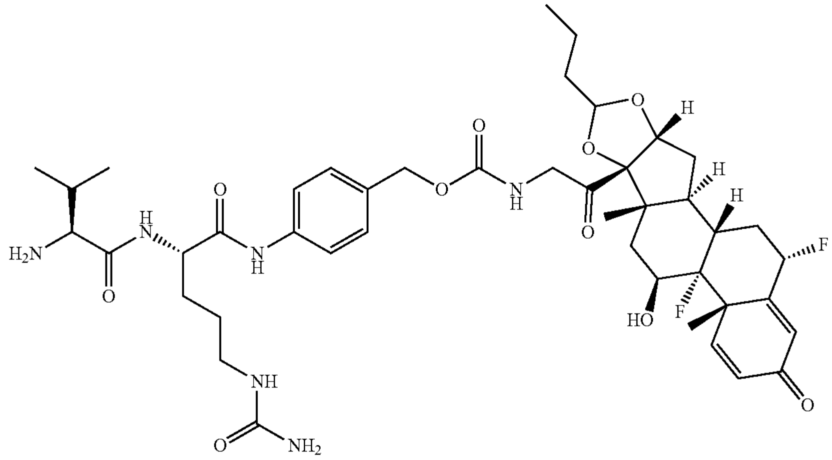 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)CNC(=O)OCc2ccc(NC(=O)[C@H](CCCNC(N)=O)NC(=O)[C@@H](N)C(C)C)cc2)O1]

Following the general procedure as described in example 7, compound 3H (127 mg, 73% yield) was obtained as a white solid. ESI m/z: 871 $(M+1)^+$.

Example 15-B

Preparation of Compound 31—See FIG. 5 and Table 4

{4-[(2S)-2-[(2S)-2-Amino-3-methylbutanamido]-5-(carbamoylamino)pentanamido]phenyl}methyl N-(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamate (31)

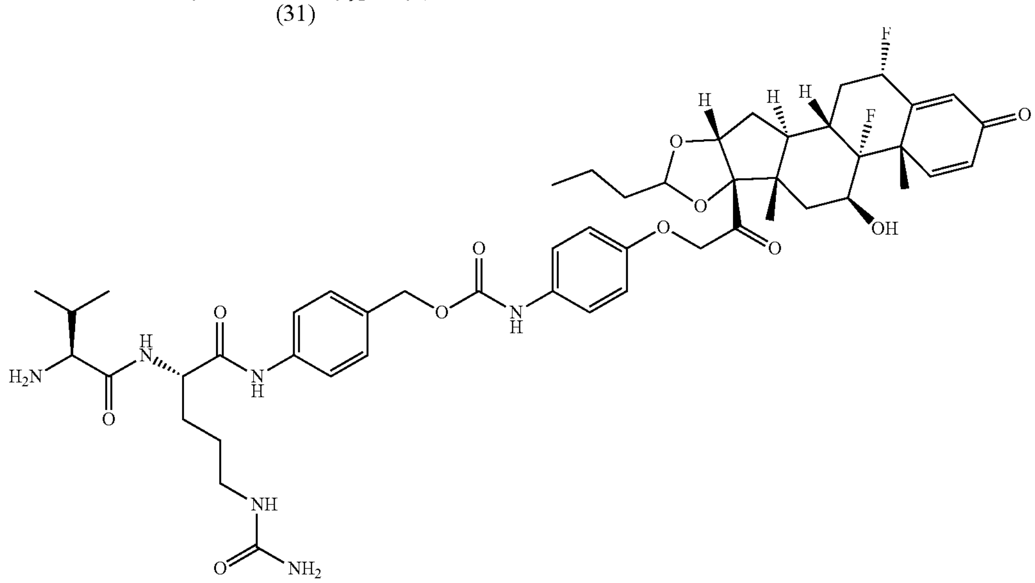

Following the general procedure described in example 7, compound 31 (80 mg, 64% yield) was obtained as a white solid. ESI m/z: 963 $(M+1)^+$. $^1H$ NMR (500 MHz, $DMSO_{d6}$) δ 10.22 (s, 1H), 9.57 (s, 1H), 8.69 (d, J=7.5 Hz, 1H), 8.08 (s, 3H), 7.61 (d, J=6.8 Hz, 2H), 7.36 (d, J=6.8 Hz, 3H), 7.27 (d, J=8.0 Hz, 1H), 7.22-7.00 (m, 1H), 6.84 (d, J=7.2 Hz, 2H), 6.30 (dd, J=8.0 Hz, 1.6 Hz, 1H), 6.11 (s, 1H), 6.10-6.00 (m, 1H), 5.72-5.55 (m, 1H), 5.52 (s, 1H), 5.48 (s, 1H), 5.16-5.05 (m, 3H), 4.88-4.80 (m, 1H), 4.80-4.76 (m, 1H), 4.75-4.70 (m, 1H), 4.55-4.48 (m, 1H), 4.25-4.20 (m, 1H), 3.70-3.60 (m, 1H), 3.12-2.90 (m, 2H), 2.70-2.55 (m, 1H), 2.40-2.20 (m, 1H), 2.15-2.00 (m, 3H), 1.86-1.75 (m, 1H), 1.75-1.65 (m, 1H), 1.64-1.54 (m, 5H), 1.49 (s, 4H), 1.46-1.34 (m, 4H), 0.97-0.91 (m, 5H), 0.90-0.85 (m, 4H), 0.85-0.80 (m, 3H) ppm.

Example 15-C

Preparation of Compound 3J—See FIG. 6

(2S)-2-Amino-N-[(1S)-1-[(4-{2-[(1S,2S,4R,8S,9S,11 S,12R,13S,19S)-12,19-difluoro-11-hydroxy-9,13-dimethyl-16-oxo-6-propyl-5,7-dioxapentacyclo[10.8.0.$0^{2,9}$.$0^{4,8}$.$0^{13,18}$]icosa-14,17-dien-8-yl]-2-oxoethoxy}phenyl)carbamoyl]ethyl]-3-methylbutanamide TFA salt (3J)

Example 16

Preparation of Compound 8a (See FIG. 6 and Table 5)

{4-[(2S)-2-[(2S)-2-[(2R)-2-Amino-6-[2-(cyclooct-2-yn-1-yloxy)acetamido]hexanamido]-3-methylbutanamido]-5-(carbamoylamino)pentanamido]phenyl}methyl N-[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate (8a)

Following the general procedure B, compound 8a (17 mg, 35% yield) was obtained as a white solid after purification by reversed phase flash chromatography (0-100% acetonitrile in water (0.05% TFA)). ESI m/z: 1415 $(M+H)^+$. $^1H$ NMR ($DMSO_{d6}$, 400 MHz) δ 10.09-10.02 (m, 1H), 8.54 (d, J=8.4 Hz, 1H), 8.38 (d, J=7.5 Hz, 1H), 8.35-8.26 (m, 0.5H), 8.12-8.02 (m, 3H), 7.94-7.85 (m, 0.5H), 7.66-7.54 (m, 3H), 7.34-7.23 (m, 6H), 7.20-7.13 (m, 1H), 6.08-5.97 (m, 1H), 5.54-5.37 (m, 3H), 5.13-4.94 (m, 2H), 4.52-4.21 (m, 6H), 4.03-3.70 (m, 4H), 3.63-3.51 (m, 1H), 3.25-3.17 (m, 8H), 3.13-2.82 (m, 10H), 2.31-1.91 (m, 10H), 1.85-1.64 (m, 9H), 1.64-1.25 (m, 15H), 1.07-0.96 (m, 6H), 0.90-0.74 (m, 26H) ppm.

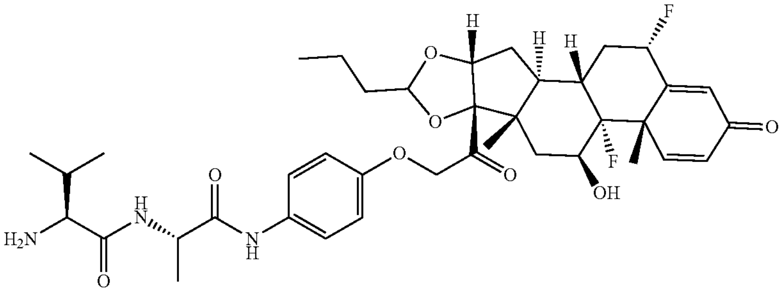 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COc2ccc(NC(=O)[C@H](C)NC(=O)[C@@H](N)C(C)C)cc2)O1]

To a solution of Boc-Val-Ala-OH (2d, 0.31 g, 1.1 mmol) in DMF (15 mL) were added HATU (0.48 g, 1.3 mmol) and DIPEA (0.35 g, 2.7 mmol) at 10° C. After the mixture was stirred at 10° C. for 30 minutes, amine (1i, 0.50 g, 0.90 mmol) was added into the mixture. The reaction mixture was stirred at 10° C. for an hour until the amine was totally consumed. The mixture was quenched with water and extracted with ethyl acetate. The combined organic solution was washed with brine, dried over sodium sulfate and concentrated in vacuo. The residue was purified by silica gel column chromatography (50% ethyl acetate in petroleum ether) to give Boc-3J, which was dissolved in DCM (9 mL). To the solution was added TFA (3 mL) at 10° C. The reaction mixture was stirred at 10° C. for 2 hours and then concentrated in vacuo to give compound 3J (0.53 g, 84% yield) as TFA salt, which was used for the next step without further purification. ESI m/z: 728 $(M+1)^+$.

Example 17

Preparation of Compound 8b (See FIG. 6 and Table 5)

(2R)-2-Amino-6-[2-(cyclooct-2-yn-1-yloxy)acetamido]-N-[(1S)-1-{[(1S)-1-[(4-{2-[(1S,2S,4R,8S,9S,11S,12S,13R)-11-hydroxy-9,13-dimethyl-16-oxo-6-propyl-5,7-dioxapentacyclo[10.8.0.$0^{2,9}$.$0^{4,8}$.$0^{13,18}$]icosa-14,17-dien-8-yl]-2-oxoethoxy}phenyl)carbamoyl]ethyl]carbamoyl}-2-methylpropyl]hexanamide (8b)

Following the general procedure B, compound 8b (50 mg, 49% yield) was obtained as a white solid. ESI m/z: 984 $(M+1)^+$.

Example 18

Preparation of Compound 8c (See FIG. 6 and Table 5)

(2R)-2-Amino-6-[2-(cyclooct-2-yn-1-yloxy)acetamido]-N-[(1S)-1-{[(1S)-1-[(4-{2-[(1S,2S,4R,6R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamoyl]ethyl]carbamoyl}-2-methylpropyl]hexanamide (8c)

Following the general procedure B, compound 8c (80 mg, 56% yield) was obtained as a white solid. ESI m/z: 984 $(M+1)^+$. $^1$H NMR (500 MHz, DMSO$_{d6}$) δ 10.08 (s, 0.5H), 9.46 (s, 0.5H), 8.43 (d, J=7.5 Hz, 0.5H), 8.22 (d, J=7.0 Hz, 0.5H), 8.07-7.91 (m, 1H), 7.61 (dd, J=13.1, 6.2 Hz, 1H), 7.56 (d, J=9.0 Hz, 1H), 7.51 (d, J=9.0 Hz, 1H), 7.32 (d, J=10.1 Hz, 1H), 6.85 (d, J=7.0 Hz, 2H), 6.18 (d, J=10.0 Hz, 1H), 5.93 (s, 1H), 5.10 (d, J=18.4 Hz, 1H), 4.85-4.66 (m, 4H), 4.46-4.08 (m, 4H), 3.85-3.17 (m, 3H), 3.09-3.00 (m, 2H), 2.40-1.69 (m, 15H), 1.66-1.48 (m, 8H), 1.45-1.15 (m, 15H), 1.05-0.94 (m, 2H), 0.91-0.79 (m, 12H) ppm.

Example 19

Preparation of Compound 8d (See FIG. 6 and Table 5)

(1S,4aS,10aR)-6-((2S)-2-((2S)-2-((2R)-2-Amino-6-(2-(cyclooct-2-ynyloxy)acetamido)hexanamido)-3-methylbutanamido)propanamido)-N-((1S,4aS,10aR)-6-hydroxy-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (8d)

Following the general procedure B, compound 8d (30 mg, 47% yield) was obtained as a white solid. ESI m/z: 991 $(M+1)^+$. $^1$H NMR (500 MHz, methanol$_{d4}$) 67.51 (d, J=1.5 Hz, 1H), 7.37 (dd, J=8.3, 2.0 Hz, 1H), 7.02 (d, J=8.3 Hz, 1H), 6.89 (d, J=8.4 Hz, 1H), 6.72 (d, J=2.4 Hz, 1H), 6.56 (dd, J=8.3, 2.5 Hz, 1H), 4.64-4.57 (m, 1H), 4.48 (q, J=7.1 Hz, 1H), 4.33-4.27 (m, 1H), 4.20 (d, J=6.7 Hz, 1H), 3.93 (m, 2H), 3.43 (t, J=6.6 Hz, 1H), 3.24 (t, J=6.9 Hz, 2H), 3.02-2.93 (m, 2H), 2.92-2.76 (m, 3H), 2.40-2.32 (m, 2H), 2.33-2.23 (m, 4H), 2.22-2.12 (m, 3H), 2.12-2.00 (m, 5H), 1.99-1.91 (m, 1H), 1.91-1.81 (m, 2H), 1.78-1.66 (m, 6H), 1.66-1.58 (m, 1H), 1.58-1.49 (m, 2H), 1.45 (d, J=7.1 Hz, 6H), 1.38 (d, J=4.0 Hz, 6H), 1.34-1.22 (m, 4H), 1.14 (d, J=7.0 Hz, 6H), 1.06-0.98 (m, 6H) ppm.

Example 20

Preparation of Compound 8e (See FIG. 6 and Table 5)

{4-[(2S)-2-[(2S)-2-[(2R)-2-Amino-6-[2-(cyclooct-2-yn-1-yloxy)acetamido]hexanamido]-3-methylbutanamido]-5-(carbamoylamino)pentanamido]phenyl}methyl N-({[(4bS,8S,8aR)-8-{[(1S,4aS,10aR)-6-hydroxy-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}methyl) carbamate (8e)

Following the general procedure B, compound 8e (65 mg, 62% yield) was obtained as a white solid. ESI m/z: 1283 $(M+1)^+$. $^1$H NMR (500 MHz, methanol$_{d4}$) δ 7.53-7.33 (m, 3H), 7.28-7.14 (m, 3H), 6.89 (d, J=8.4 Hz, 1H), 6.76 (d, J=8.3 Hz, 1H), 6.60 (d, J=2.5 Hz, 1H), 6.43 (dd, J=8.3, 2.5 Hz, 1H), 4.97 (s, 2H), 4.53-4.46 (m, 2H), 4.41 (dd, J=8.9, 5.0 Hz, 1H), 4.18 (t, J=6.0 Hz, 1H), 4.09 (d, J=7.1 Hz, 1H), 3.92-3.72 (m, 4H), 3.31 (t, J=6.6 Hz, 1H), 3.16-3.05 (m, 3H), 3.06-2.97 (m, 1H), 2.90-2.62 (m, 4H), 2.27-2.09 (m, 7H), 2.09-1.87 (m, 7H), 1.86-1.68 (m, 4H), 1.66-1.40 (m, 12H), 1.36-1.22 (m, 10H), 1.20-1.09 (m, 3H), 1.01 (s, 3H), 1.01 (s, 3H), 0.89 (t, J=7.0 Hz, 6H) ppm.

Example 21

Preparation of Compound 8f (See FIG. 6 and Table 5)

{4-[(2S)-2-[(2S)-2-[(2R)-2-Amino-6-[2-(cyclooct-2-yn-1-yloxy)acetamido]hexanamido]-3-methylbutanamido]-5-(carbamoylamino)pentanamido]phenyl}methyl N-[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}-2-hydroxyethyl]carbamate (8f)

Following the general procedure B, compound 8f (15 mg, 33% yield) was obtained as a white solid. ESI m/z: 1313.6 $(M+H)^+$. $^1$H NMR (500 MHz, methanol$_{d4}$) δ 7.59 (d, J=8.5 Hz, 2H), 7.51 (s, 1H), 7.36-7.26 (m, 3H), 7.01 (d, J=8.5 Hz, 1H), 6.88 (d, J=8.0 Hz, 1H), 6.72-6.71 (m, 1H), 6.57-6.54 (m, 1H), 5.09 (s, 2H), 4.64-4.52 (m, 1H), 4.35-4.28 (m, 2H), 4.21 (d, J=7.0 Hz, 1H), 4.01-3.98 (m, 1H), 3.88-3.84 (m, 3H), 3.43 (t, J=6.5 Hz, 1H), 3.26-3.10 (m, 4H), 3.00-2.76 (m, 3H), 2.38-2.24 (m, 7H), 2.19-2.02 (m, 9H), 1.98-1.78 (m, 4H), 1.74-1.54 (m, 12H), 1.45-1.26 (m, 14H), 1.13 (s, 6H), 1.00 (t, J=7.5 Hz, 6H) ppm.

Example 22

Preparation of Compound 8g (See FIG. 6 and Table 5)

{4-[(2S)-2-[(2S)-2-[(2R)-2-Amino-6-{1-[2-(cyclooct-2-yn-1-yloxy)acetamido]-3,6,9,12-tetraoxapentadecan-15-amido}hexanamido]-3-methylbutanamido]-5-(carbamoylamino)pentanamido]phenyl}methyl N-[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate (8g)

Following the general procedure B, compound 8g (17 mg, 43% yield) was obtained as a white solid. ESI m/z: 832.2 $(M/2+H)^+$. $^1$H NMR (methanol$_{d4}$, 500 MHz): δ 7.61 (d, J=8.0 Hz, 2H), 7.41-7.30 (m, 6H), 7.25-7.22 (m, 1H), 5.23-5.08 (m, 2H), 4.78-4.50 (m, 3H), 4.33-4.10 (m, 5H), 4.04-3.88 (m, 2H), 3.74 (t, J=6.0 Hz, 3H), 3.65-3.57 (m, 15H), 3.46-3.29 (m, 9H), 3.24-3.12 (m, 6H), 3.01-2.88 (m, 3H), 2.56-2.44 (m, 4H), 2.30-2.10 (m, 6H), 2.07-1.67 (m, 14H), 1.63-1.32 (m, 13H), 1.21-1.13 (m, 6H), 1.07-0.78 (m, 26H) ppm.

Example 23

Preparation of Compound 8h (See FIG. 6 and Table 5)

N-[(5R)-5-Amino-5-{[(1S)-1-{[(1S)-1-{[(4bS,8S,8aR)-8-{[(1S,4aS,10aR)-6-hydroxy-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}ethyl]carbamoyl}-2-methylpropyl]carbamoyl}pentyl]-1-[2-(cyclooct-2-yn-1-yloxy)acetamido]-3,6,9,12-tetraoxapentadecan-15-amide (8h)

Following the general procedure B, compound 8h (54 mg, 50% yield) was obtained as a white solid. ESI m/z: 620 $(M/2+1)^+$. $^1$H NMR (500 MHz, methanol$_{d4}$) δ 7.61-7.48 (m, 1H), 7.35-7.29 (m, 1H), 7.02 (d, J=8.3 Hz, 1H), 6.88 (d, J=8.3 Hz, 1H), 6.71 (d, J=1.8 Hz, 1H), 6.56 (dd, J=8.2, 1.7 Hz, 1H), 4.52-4.44 (m, 1H), 4.27 (dd, J=21.9, 7.2 Hz, 2H), 4.03 (dd, J=15.1, 2.4 Hz, 1H), 3.96 (dt, J=22.5, 6.5 Hz, 1H), 3.89 (dd, J=15.1, 3.1 Hz, 1H), 3.75 (t, J=5.8 Hz, 2H), 3.64 (t, J=8.6 Hz, 12H), 3.60-3.54 (m, 3H), 3.44 (dd, J=11.7, 5.9 Hz, 2H), 3.23 (t, J=6.7 Hz, 2H), 3.02-2.91 (m, 1H), 2.91-2.74 (m, 3H), 2.46 (t, J=5.9 Hz, 2H), 2.40-2.31 (m, 3H), 2.26-2.22 (m, 5H), 2.21-1.79 (m, 12H), 1.77-1.65 (m, 6H), 1.62-1.53 (m, 3H), 1.47-1.43 (m, 5H), 1.38 (s, 3H), 1.37 (s, 3H), 1.33-1.22 (m, 3H), 1.14 (s, 3H), 1.12 (s, 3H), 1.06-0.95 (m, 6H) ppm.

Example 24

Preparation of Compound 8i (See FIG. 6 and Table 5)

{4-[(2S)-2-[(2S)-2-[(2R)-2-Amino-6-{1-[2-(cyclooct-2-yn-1-yloxy)acetamido]-3,6,9,12-tetraoxapentadecan-15-amido}hexanamido]-3-methylbutanamido]-5-(carbamoylamino)pentanamido]phenyl}methyl N-(2-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]oxy}ethyl)carbamate (8i)

Following the general procedure B, compound 8i (40 mg, 30% yield) was obtained as a white solid. ESI m/z: 759 $(M/2+1)^+$, $^1$H NMR (500 MHz, DMSO$_{d6}$) δ 10.01 (s, 1H), 9.00 (s, 1H), 8.24-8.09 (m, 1H), 8.06-7.74 (m, 1H), 7.64-7.36 (m, 3H), 7.28 (d, J=8.3 Hz, 2H), 6.94 (d, J=8.5 Hz, 1H), 6.82 (d, J=8.4 Hz, 2H), 6.68 (d, J=7.6 Hz, 1H), 6.64 (s, 1H), 6.51 (d, J=6.4 Hz, 1H), 6.00 (s, 1H), 5.42 (s, 1H), 4.96 (s, 2H), 4.39 (s, 1H), 4.28-2.21 (m, 2H), 4.05 (s, 2H), 3.93 (t, J=5.6 Hz, 2H), 3.86-3.79 (m, 2H), 3.59 (t, J=6.5 Hz, 2H), 3.53-3.47 (m, 11H), 3.43 (t, J=5.9 Hz, 2H), 3.36 (s, 6H), 3.24 (dt, J=12.8, 6.1 Hz, 3H), 3.10-2.91 (m, 4H), 2.85 (t, J=17.2 Hz, 2H), 2.75-2.69 (m, 2H), 2.34-2.10 (m, 10H), 2.10-1.66 (m, 12H), 1.67-1.54 (m, 8H), 1.47-1.24 (m, 16H), 1.14 (t, J=13.3 Hz, 2H), 1.01 (d, J=11.8 Hz, 6H), 0.88 (s, 3H) 0.84 (s, 3H) ppm.

Example 24A

Preparation of Compound 8J—(See FIG. 6 and Table 5)

{4-[(2S)-2-[(2S)-2-[(2R)-2-Amino-6-[2-(cyclooct-2-yn-1-yloxy)acetamido]hexanamido]-3-methylbutanamido]-5-(carbamoylamino)pentanamido]phenyl}methyl N-{2-[(1S,2S,4R,8S,9S,11 S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl}carbamate (8J)

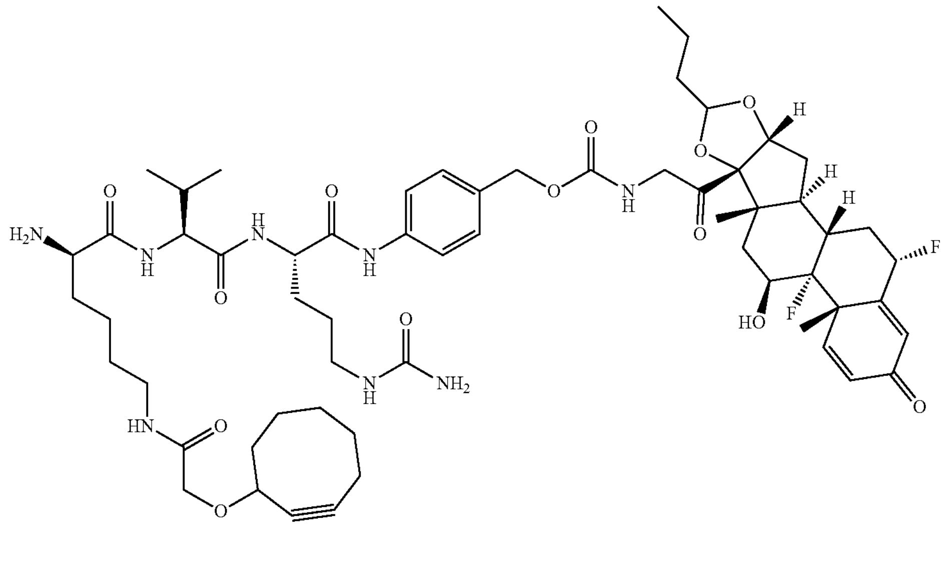 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)CNC(=O)OCc2ccc(NC(=O)[C@H](CCCNC(N)=O)NC(=O)[C@@H](NC(=O)[C@H](N)CCCCNC(=O)COC3C#CCCCCC3)C(C)C)cc2)O1]

Following the general procedure described in example 8, compound 8J (120 mg, 52% yield) was obtained as a white solid. ESI m/z: 1163 $(M+1)^+$. $^1H$ NMR (400 MHz, $MeOD_{d4}$) δ 7.65-7.55 (m, 2H), 7.40-7.26 (m, 3H), 6.39-6.27 (m, 2H), 5.65-5.45 (m, 1H), 5.13-5.01 (m, 2H), 4.71-4.50 (m, 2H), 4.40-4.14 (m, 4H), 4.11-3.82 (m, 3H), 3.46-3.39 (m, 1H), 3.29-3.09 (m, 4H), 2.76-2.54 (m, 1H), 2.41-2.10 (m, 7H), 2.09-1.99 (m, 1H), 1.96-1.80 (m, 5H), 1.78-1.21 (m, 23H), 1.06-0.82 (m, 12H) ppm.

Example 24B

Preparation of Compound 8K—(See FIG. 6 and Table 5)

{4-[(2S)-2-[(2S)-2-[(2R)-2-Amino-6-[2-(cyclooct-2-yn-1-yloxy)acetamido]hexanamido]-3-methylbutanamido]-5-(carbamoylamino)pentanamido]phenyl}methyl N-(4-{2-[(1S,2S,4R,8S,9S,11 S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl) carbamate (8K)

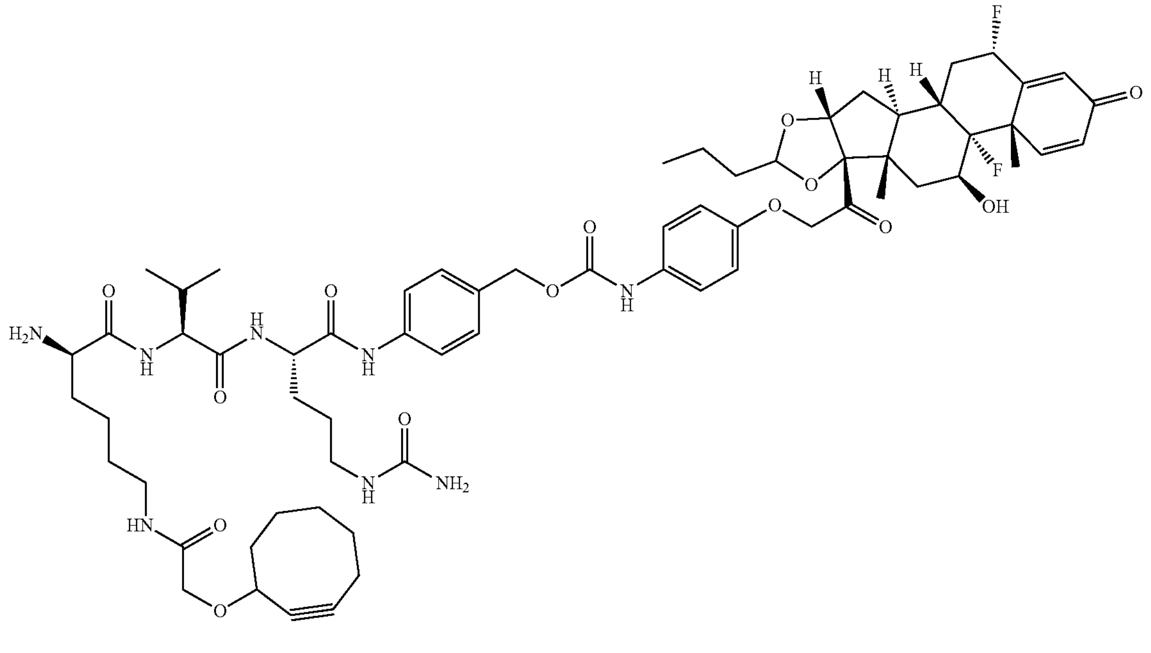 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COc2ccc(NC(=O)OCc3ccc(NC(=O)[C@H](CCCNC(N)=O)NC(=O)[C@@H](NC(=O)[C@H](N)CCCCNC(=O)COC4C#CCCCCC4)C(C)C)cc3)cc2)O1]

Following the general procedure described in example 8, compound 8K (192 mg, 80% yield) was obtained as a white solid. ESI m/z: 1256 $(M+1)^+$.

Example 24C

Preparation of Compound 8L—See (FIG. 6 and Table 5)

(2R)-2-Amino-6-[2-(cyclooct-2-yn-1-yloxy)acetamido]-N-[(1S)-1-{[(1S)-1-[(4-{2-[(1S,2S,4R,8S,9S,11 S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamoyl]ethyl]carbamoyl}-2-methylpropyl]hexanamide (8L)

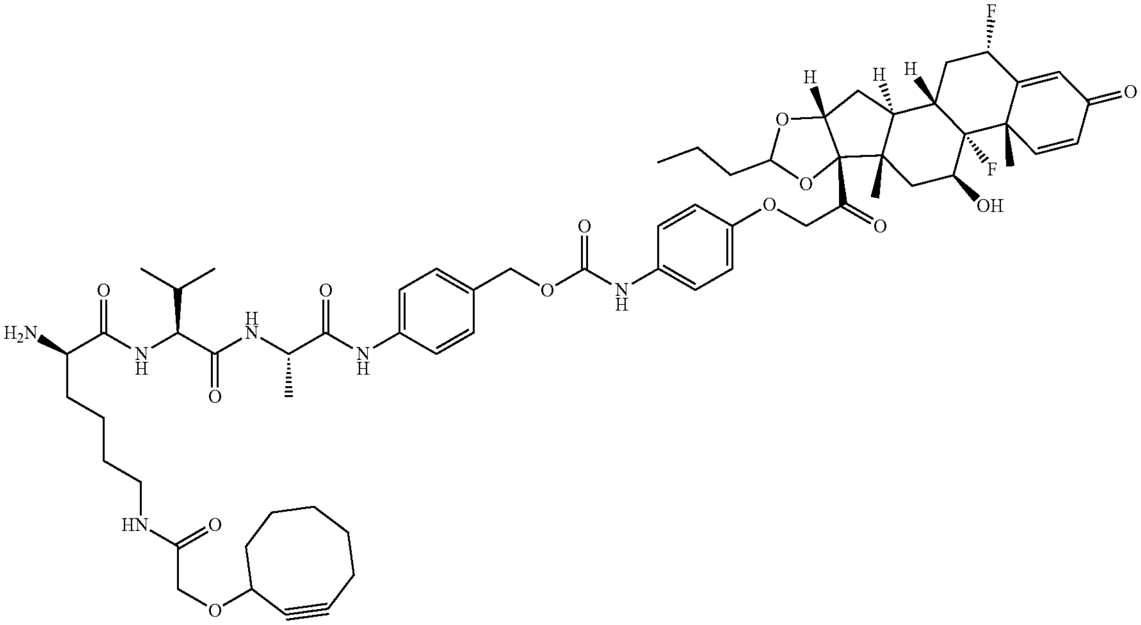 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COc2ccc(NC(=O)OCc3ccc(NC(=O)[C@H](C)NC(=O)[C@@H](NC(=O)[C@H](N)CCCCNC(=O)COC4C#CCCCCC4)C(C)C)cc3)cc2)O1]

Following the general procedure described in example 8, compound 8L (0.21 g, 46% yield) was obtained as a white solid. ESI m/z: 1021 $(M+1)^+$. ESI m/z: 1021.5 $(M+H)^+$. $^1$H NMR (400 MHz, $MeOD_{d4}$) δ 7.33-7.60 (m, 3H), 6.87-6.91 (m, 2H), 6.32-6.37 (m, 2H), 5.47-5.65 (m, 1H), 5.07-5.30 (m, 1H), 4.72-4.86 (m, 3H), 4.34-4.51 (m, 3H), 3.83-4.20 (m, 3H), 3.33-3.49 (m, 1H), 3.14-3.27 (m, 3H), 2.59-2.75 (m, 1H), 1.31-2.39 (m, 33H), 0.93-1.05 (m, 12H) ppm.

Example 25

General Procedure C for making compounds 9a-i and J-L. (See FIG. 7).

To a solution of alkyne 8a-i, J-L (1.0 equiv.) in corresponding solvent(s) was added α-cyclodextrin-azide 6a (See *Synth. Commun.*, 2002, 32(21), 3367-3372; *J. Am. Chem. Soc.*, 2012, 134(46), 19108-19117; *J. Med. Chem.*, 1997, 40(17), 2755-2761; *J. Am. Chem. Soc.*, 1993, 115(12), 5035-5040) (1.5-3.0 equiv.). The resulting mixture was then stirred at 20-30° C. for 16 hours to 3 days until the compound 8 was mostly consumed and the desired intermediate mass was detected, as monitored by LCMS. After filtration, the resulting mixture was directly purified by prep-HPLC (or used directly) to give compound 9 (9a-i, J-L) (16-78% yield) as a white solid (with triazole regioisomers).

TABLE 6

REACTION CONDITIONS FOR SYNTHESIZING COMPOUNDS 9A-I FOLLOWING GENERAL PROCEDURE C.

| Product | Alkyne mg (mmol) | | 6a mg (mmol) | Solvent (mL) | Temp. (° C.) | Time (hr) | Purification | Yield | m/z |
|---|---|---|---|---|---|---|---|---|---|
| 9a | 8a | 20 (0.014) | 28 (0.028) | DMSO (1) | 25 | 16 | A | 9.6 mg, 25% | 1207 $(M/2 + H)^+$ |
| 9bA 9bB | 8b | 30 (0.030) | 76 (0.076) | DMF (2) | 30 | 40 | B | A: 13 mg, 22% B: 19 mg, 32% | 991 $(M + H)^+$ |
| 9c | 8c | 80 (0.081) | 120 (0.12) | DMF (4) | 30 | 24 | B | 80 mg, 40% | 991 $(M + H)^+$ |
| 9d | 8d | 310 (0.31) | 620 (0.63) | DMF (6) | 20-25 | 72 | B | 0.38 g, 60% | 995 $(M/2 + H)^+$ |
| 9e | 8e | 60 (0.047) | 95 (0.095) | DMF (1) | 20-25 | 72 | RP-B | 67 mg, 64% | 1141 $(M/2 + 1)^+$ |
| 9f | 8f | 20 (0.015) | 30 (0.03) | DMF (0.5) | 20-25 | 72 | B | 20 mg, 57% | 1156 $(M/2 + 1)^+$ |
| 9g | 8g | 50 (0.030) | 60 (0.06) | DMSO (2) | 25 | 48 | RP-B | 46 mg, 58% | 887.9 $(M/3 + H)^+$. |
| 9h | 8h | 23 (0.019) | 40 (0.04) | DMF (0.5) | 20-25 | 72 | RP-B | 30 mg, 72% | 1118 $(M/2 + 1)^+$ |
| 9i | 8i | 40 (0.026) | 52 (0.052) | DMF (1) | 20-25 | 72 | RP-B | 51 mg, 78% | 1258 $(M/2 + 1)^+$ |
| 9J | 8J | 120 (0.10) | 300 (0.30) | DMF (5) | 50 | 3 | RP-B | 110 mg, 51% | 1081 $(M/2 + 1)^+$ |
| 9K | 8K | 100 (0.080) | 160 (0.16) | DMF (10) | 50 | 3 | RP-B | 105 mg, 58% | 751 $(M/3 + 1)^+$ |
| 9L | 8L | 60 (0.059) | 117 (0.12) | DMF (3) | 50 | 6 | B | 40 mg, 34% | 1009.5 $(M/2 + 1)^+$ |

*9bA and 9bB are two triazole regioisomers. For Purification-B: Prep-HPLC method B; A: Prep-HPLC method A; RP: RP-flash; RP-B: RP-flash method B; RP-A: RP-flash method A.

Example 26

Preparation of Compound 9a (See FIG. 7 and Table 6)

{4-[(2S)-2-[(2S)-2-[(2R)-2-Amino-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.$2^{3,6}$.$2^{8,11}$.$2^{13,16}$.$2^{18,21}$.$2^{23,26}$]dotetracontan-5-yl]methyl}-1H,4H,5H,6H,7H,8H,9H-cycloocta[d][1,2,3]triazol-4-yl)oxy]acetamido}hexanamido]-3-methylbutanamido]-5-(carbamoylamino)pentanamido]phenyl}methyl N-[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate (9a)

Following the general procedure C, compound 9a (9.6 mg, 25% yield) was obtained as a white solid. ESI m/z: 1207 $(M/2+H)^+$. $^1$H NMR (methanol$_{d4}$, 500 MHz): δ 7.64-7.55 (m, 2H), 7.50-7.39 (m, 3H), 7.39-7.29 (m, 3H), 7.26-7.20 (m, 1H), 5.22-4.93 (m, 11H), 4.70-4.54 (m, 6H), 4.25-4.20 (m, 4H), 4.09-3.78 (m, 21H), 3.69-3.42 (m, 18H), 3.38-3.36 (s, 6H), 3.28 (s, 4H), 3.24-3.12 (m, 5H), 2.97-2.94 (m, 6H), 2.73-2.47 (m, 3H), 2.28-1.77 (m, 12H), 1.71-1.37 (m, 12H), 1.35-1.28 (m, 1H), 1.21-1.14 (m, 6H), 1.03-0.78 (m, 24H) ppm.

Example 27

Preparation of Compound 9b (See FIG. 7 and Table 6)

(2R)-2-Amino-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.$2^{3,6}$.$2^{8,11}$.$2^{13,16}$.$2^{18,21}$.$2^{23,26}$]dotetracontan-5-yl]methyl}-1H,4H,5H,6H,7H,8H,9H-cycloocta[d][1,2,3]triazol-4-yl)oxy]acetamido}-N-[(1S)-1-{[(1S)-1-[(4-{2-[(1S,2S,4R,8S,9S,11 S,12S,13R)-11-hydroxy-9,13-dimethyl-16-oxo-6-propyl-5,7-dioxapentacyclo[10.8.0.$0^{2,9}$.$0^{4,8}$.$0^{13,18}$]icosa-14,17-dien-8-yl]-2-oxoethoxy}phenyl)carbamoyl]ethyl]carbamoyl}-2-methylpropyl]hexanamide (9b)

Following the general procedure C, triazole regioisomers 9bA (the first peak in LCMS, 13 mg, 22% yield) and 9bB (the second peak in LCMS, 19 mg, 32% yield) were separated and obtained as white solids. ESI m/z for both compounds: 991 $(M+H)^+$.

Example 28

Preparation of Compound 9c (See FIG. 7 and Table 6)

(2R)-2-Amino-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.$2^{3,6}$.$2^{8,11}$.$2^{13,16}$ $2^{18,21}$.$2^{23,26}$]dotetracontan-5-yl]methyl}-1H,4H,5H,6H,7H,8H,9H-cycloocta[d][1,2,3]triazol-4-yl)oxy]acetamido}-N-[(1S)-1-{[(1S)-1-[(4-{2-[(1S,2S,4R,6R,8S,9S,11 S,12S,13R)-11-hydroxy-9,13-dimethyl-16-oxo-6-propyl-5,7-dioxapentacyclo [10.8.0.$0^{2,9}$.$0^{4,8}$.$0^{13,18}$]icosa-14,17-dien-8-yl]-2-oxoethoxy}phenyl)carbamoyl]ethyl]carbamoyl}-2-methylpropyl]hexanamide (9c)

Following the general procedure C, compound 9c (80 mg, 40% yield) was obtained as a white solid. ESI m/z: 991 $(M+H)^+$. $^1H$ NMR (500 MHz, $DMSO_{d6}$) δ 9.92-9.73 (m, 1H), 8.52-8.19 (m, 2H), 8.11-7.93 (m, 1H), 7.90-7.76 (m, 1H), 7.70-7.47 (m, 3H), 7.32 (d, J=10.0 Hz, 1H), 7.03-6.77 (m, 3H), 6.49-6.29 (m, 1H), 6.18 (d, J=10.0 Hz, 1H), 5.93 (s, 1H), 5.71-5.53 (m, 5H), 5.51-5.33 (m, 5H), 5.21-3.51 (m, 42H), 3.50-2.64 (m, 19H), 2.43-2.26 (m, 3H), 2.16-1.93 (m, 4H), 1.90-1.78 (m, 3H), 1.74-1.11 (m, 24H), 1.07-0.72 (m, 16H) ppm.

Example 29

Preparation of Compound 9d (See FIG. 7 and Table 6)

(1S,4aS,10aR)-N-{[(1S,4aS,10aR)-6-[(2S)-2-[(2S)-2-[(2R)-2-Amino-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.$2^{3,6}$.$2^{8,11}$.$2^{13,16}$.$2^{18,21}$.$2^{23,26}$]dotetracontan-5-yl]methyl}-1H,4H,5H,6H,7H,8H,9H-cycloocta[d][1,2,3]triazol-4-yl)oxy]acetamido}hexanamido]-3-methylbutanamido]propanamido]-1,4a-dimethyl-1,2,3,4,4a,9,10,10a-octahydrophenanthren-1-yl]carbonyl}-6-hydroxy-1,4a-dimethyl-1,2,3,4,4a,9,10,10a-octahydrophenanthrene-1-carboxamide (9d)

Following the general procedure C, compound 9d (0.38 g, 60% yield) was obtained as a white solid. ESI m/z: 995 $(M/2+1)^+$. $^1H$ NMR (500 MHz, $methanol_{d4}$) δ 8.40 (s, 1H, imidine-H), 7.56-7.52 (m, 1H), 7.32 (t, J=7.7 Hz, 1H), 7.03 (d, J=8.4 Hz, 1H), 6.88 (d, J=8.3 Hz, 1H), 6.72 (d, J=2.4 Hz, 1H), 6.56 (dd, J=8.2, 2.3 Hz, 1H), 5.24-5.16 (m, 1H), 5.01-4.95 (m, 6H), 4.65-3.43 (m, 40H), 3.14-2.72 (m, 7H), 2.55-1.26 (m, 44H), 1.16 (s, 3H), 1.13 (s, 3H), 1.09-0.93 (m, 6H) ppm.

Example 30

Preparation of Compound 9e (See FIG. 7 and Table 6)

{4-[(2S)-2-[(2S)-2-[(2R)-2-Amino-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.$2^{3,6}$.$2^{8,11}$.$2^{13,16}$$2^{18,21}$.$2^{23,26}$]dotetracontan-5-yl]methyl}-1H,2H,3H,4H,5H,6H,7H,8H,9H-cycloocta[d][1,2,3]triazol-4-yl)oxy]acetamido}hexanamido]-3-methylbutanamido]-5-(carbamoylamino)pentanamido]phenyl}methyl N-({[(4bS,8S,8aR)-8-{[(1S,4aS,10aR)-6-hydroxy-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}methyl)carbamate (9e)

Following the general procedure C, compound 9e (67 mg, 64% yield) was obtained as a white solid. ESI m/z: 1141 $(M/2+1)^+$. $^1H$ NMR (500 MHz, $methanol_{d4}$) δ 8.40 (s, 1H), 7.65-7.45 (m, 3H), 7.40-7.26 (m, 3H), 7.02 (d, J=8.3 Hz, 1H), 6.88 (d, J=8.3 Hz, 1H), 6.72 (d, J=2.4 Hz, 1H), 6.56 (dd, J=8.3, 2.4 Hz, 1H), 5.24-5.16 (m, 1H), 5.10 (s, 2H), 5.02-4.93 (m, 4H), 4.66-4.51 (m, 2H), 4.43-4.22 (m, 2H), 4.15-3.73 (m, 22H), 3.64-3.42 (m, 12H), 3.37 (s, 3H), 3.24-3.03 (m, 4H), 3.01-2.75 (m, 6H), 2.42-2.25 (m, 6H), 2.18-1.98 (m, 8H), 1.94-1.58 (m, 15H), 1.56-1.50 (m, 3H), 1.47-1.40 (m, 3H), 1.38 (s, 3H), 1.37 (s, 3H), 1.34-1.25 (m, 4H), 1.16-1.10 (m, 6H), 1.09-0.93 (m, 7H) ppm.

Example 31

Preparation of Compound 9f (See FIG. 7 and Table 6)

{4-[(2S)-2-[(2S)-2-[(2R)-2-Amino-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.$2^{3,6}$.$2^{8,11}$.$2^{13,16}$.$2^{18,21}$.$2^{23,26}$]dotetracontan-5-yl]methyl}-1H,4H,5H,6H,7H,8H,9H-cycloocta[d][1,2,3]triazol-4-yl)oxy]acetamido}hexanamido]-3-methylbutanamido]-5-(carbamoylamino)pentanamido]phenyl}methyl N-[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}-2-hydroxyethyl]carbamate (9f)

Following the general procedure C, compound 9f (20 mg, 57% yield) was obtained as a white solid. ESI m/z: 1156.0 $(M/2+1)^+$.

Example 32

Preparation of Compound 9g (See FIG. 7 and Table 6)

{4-[(2S)-2-[(2S)-2-[(2R)-2-Amino-6-(1-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}-3,6,9,12-tetraoxapentadecan-15-amido)hexanamido]-3-methylbutanamido]-5-(carbamoylamino)pentanamido]phenyl}methyl N-[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate (9g)

Following the general procedure C, compound 9g (46 mg, 58% yield) was obtained as a white solid. ESI m/z: 887.9 $(M/3+H)^+$. $^1$H NMR (methanol$_{d4}$, 500 MHz) δ 7.61 (d, J=6.5 Hz, 2H), 7.46-7.27 (m, 6H), 7.23 (t, J=7.2 Hz, 1H), 5.38-5.02 (m, 3H), 5.00-4.91 (m, 6H), 4.72-4.50 (m, 5H), 4.44-4.15 (m, 5H), 4.12-3.78 (m, 21H), 3.77-3.69 (m, 5H), 3.68-3.41 (m, 30H), 3.39-3.35 (m, 4H), 3.30-3.26 (m, 3H), 3.24-2.84 (m, 12H), 2.59-2.40 (m, 4H), 2.31-1.86 (m, 11H), 1.84-1.69 (m, 5H), 1.67-1.50 (m, 8H), 1.48-1.37 (m, 4H), 1.36-1.29 (m, 3H), 1.22-1.11 (m, 6H), 1.06-0.76 (m, 24H) ppm.

Example 33

Preparation of Compound 9h (See FIG. 7 and Table 6)

N-[(5R)-5-Amino-5-{[(1S)-1-{[(1S)-1-{[(4bS,8S,8aR)-8-{[(1S,4aS,10aR)-6-hydroxy-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}ethyl]carbamoyl}-2-methylpropyl]carbamoyl}pentyl]-1-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-9-yl)oxy]acetamido}-3,6,9,12-tetraoxapentadecan-15-amide (9h)

Following the general procedure C, compound 9h (30 mg, 72% yield) was obtained as a white solid. ESI m/z: 1118 $(M/2+1)^+$. $^1$H NMR (500 MHz, DMSO$_{d6}$) δ 9.91-9.85 (m, 1H), 9.13-8.90 (m, 1H), 8.58 (t, J=9.3 Hz, 2H), 8.50-8.47 (m, 1H), 8.17-8.00 (m, 6H), 7.88-7.78 (m, 2H), 7.53-7.49 (m, 1H), 7.36-7.30 (m, 1H), 6.97 (d, J=8.5 Hz, 1H), 6.82 (d, J=8.3 Hz, 1H), 6.63 (s, 1H), 6.51 (d, J=8.3 Hz, 1H), 5.52-5.50 (m, 11H), 5.14 (s, 1H), 4.86-4.67 (m, 10H), 4.54 (d, J=12.9 Hz, 2H), 4.46-4.32 (m, 5H), 4.06-3.94 (m, 3H), 3.89-3.76 (m, 4H), 3.73-3.61 (m, 5H), 3.57 (t, J=6.5 Hz, 3H), 3.53-3.34 (m, 12H), 3.33-3.19 (m, 4H), 3.17-3.08 (m, 3H), 3.00 (dd, J=12.6, 6.2 Hz, 3H), 2.91-2.68 (m, 8H), 2.31-2.22 (m, 5H), 2.18-2.07 (m, 6H), 1.93-1.78 (m, 6H), 1.74-1.35 (m, 15H), 1.28 (d, J=6.6 Hz, 17H), 1.19-1.06 (m, 5H), 1.01-0.94 (m, 9H), 0.89-0.79 (m, 6H) ppm.

Example 34

Preparation of Compound 9i (See FIG. 7 and Table 6)

{4-[(2S)-2-[(2S)-2-[(2R)-2-Amino-6-(1-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-9-yl)oxy]acetamido}-3,6,9,12-tetraoxapentadecan-15-amido)hexanamido]-3-methylbutanamido]-5-(carbamoylamino)pentanamido]phenyl}methyl N-(2-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]oxy}ethyl)carbamate (9i)

Following the general procedure C, compound 9i (51 mg, 78% yield) was obtained as a white solid. ESI m/z: 1258 $(M/2+1)^+$. $^1$H NMR (500 MHz, DMSO$_{d6}$) δ 10.08 (s, 1H), 9.09-8.91 (m, 1H), 8.56 (d, J=8.7 Hz, 1H), 8.39 (d, J=7.3 Hz, 1H), 8.12 (s, 1H), 8.07 (s, 1H), 7.85-7.78 (m, 2H), 7.58 (d, J=8.5 Hz, 2H), 7.41 (s, 1H), 7.29 (d, J=8.5 Hz, 2H), 6.94 (d, J=8.5 Hz, 1H), 6.85-6.78 (m, 2H), 6.68 (d, J=8.3 Hz, 1H), 6.63 (s, 1H), 6.51 (d, J=8.2 Hz, 1H), 6.06 (s, 1H), 5.50 (br s, 25H), 5.15 (s, 1H), 4.96 (s, 3H), 4.85-4.78 (m, 12H), 4.70 (s, 3H), 4.56 (s, 3H), 4.39 (s, 5H), 3.89-3.75 (m, 14H), 3.74-3.56 (m, 8H), 3.54-3.39 (m, 8H), 3.38-3.29 (m, 7H), 3.14 (s, 2H), 3.01 (d, J=5.5 Hz, 5H), 2.86-2.8 (m, 2H), 2.74 (s, 4H), 2.32-2.23 (m, 5H), 2.16 (d, J=11.2 Hz, 3H), 2.00 (d, J=6.6 Hz, 2H), 1.93-1.86 (m, 5H), 1.77-1.54 (m, 10H), 1.46-1.42 (m, 6H), 1.30-1.27 (m 11H), 1.14 (s, 3H), 1.00 (d, J=12.5 Hz, 6H), 0.88 (s, 3H) 0.84 (s, 3H) ppm.

Example 34A

Preparation of Compound 9J—(See FIG. 7 and Table 6)

{4-[(2S)-2-[(2S)-2-[(2R)-2-Amino-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}hexanamido]-3-methylbutanamido]-5-(carbamoylamino)pentanamido]phenyl}methyl N-{2-[(1S,2S,4R,8S,9S,11 S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl}carbamate (9J)

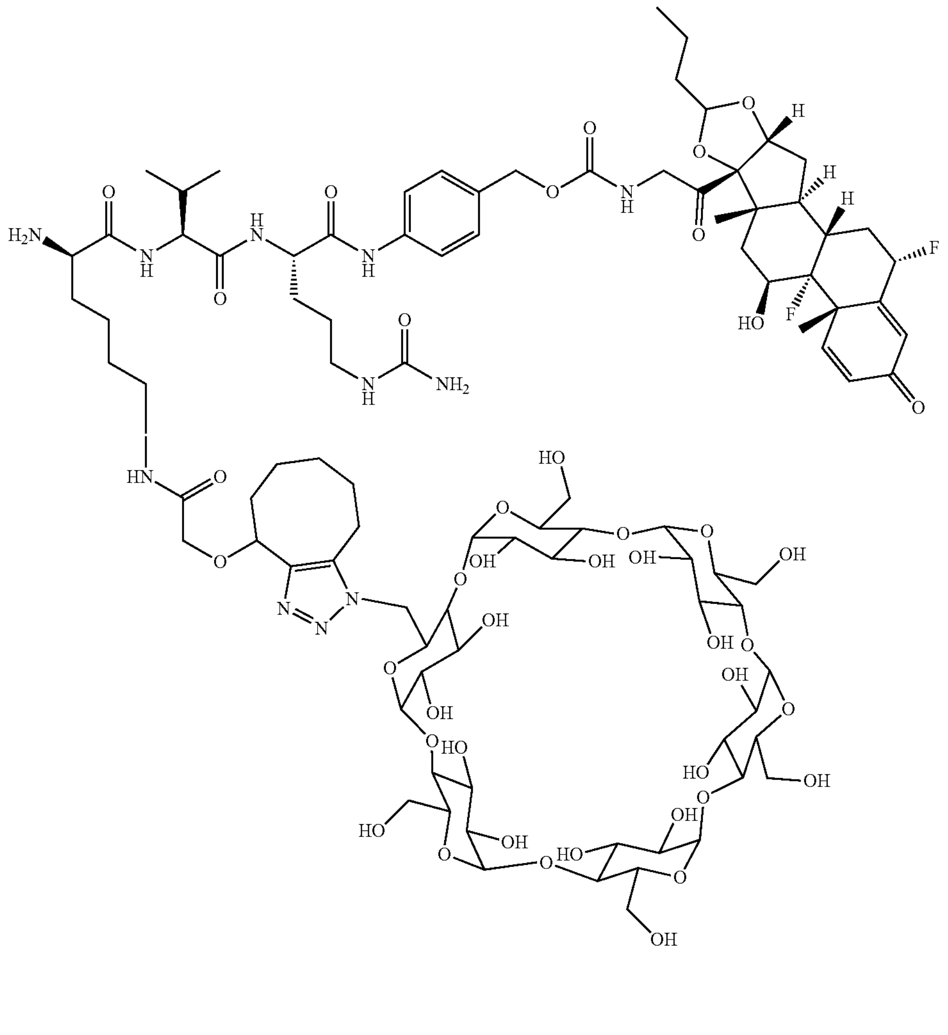 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)CNC(=O)OCc2ccc(NC(=O)[C@H](CCCNC(N)=O)NC(=O)[C@@H](NC(=O)[C@H](N)CCCCNC(=O)COC3CCCCCc4c3nnn4CC3OC4OC5C(CO)OC(OC6C(CO)OC(OC7C(CO)OC(OC8C(CO)OC(OC9C(CO)OC(OC3C(O)C4O)C(O)C9O)C(O)C8O)C(O)C7O)C(O)C6O)C(O)C5O)C(C)C)cc2)O1]

Following the general procedure as described in example 25, compound 9J (0.11 g, 51% yield) was obtained as a white solid. ESI m/z: 1081 $(M/2+1)^+$. $^1$H NMR (500 MHz, DMSO$_{d6}$) δ 10.05 (s, 1H), 8.30-7.80 (m, 3H), 7.80-7.55 (m, 2H), 7.50-7.40 (m, 1H), 7.40-7.25 (m, 3H), 6.30 (d, J=12.5 Hz, 1H), 6.11 (s, 1H), 6.00 (s, 1H), 5.80-5.35 (m, 16H), 5.25-5.05 (m, 1H), 4.97 (s, 2H), 4.90-4.50 (m, 13H), 4.50-4.00 (m, 5H), 3.95-3.55 (m, 22H), 3.30-3.20 (m, 8H), 3.20-3.00 (m, 4H), 3.00-2.85 (m, 5H), 2.25-2.20 (m, 2H), 2.10-1.95 (m, 4H), 1.80-1.00 (m, 30H), 1.00-0.90 (m, 4H), 0.90-0.80 (m, 14H) ppm.

Example 34B

Preparation of Compound 9K—(See FIG. 7 and Table 6)

{4-[(2S)-2-[(2S)-2-[(2R)-2-Amino-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.$2^{3,6}$.$2^{8,11}$.$2^{13,16}$.$2^{18,21}$.$2^{23,26}$]dotetracontan-5-yl]methyl}-1H,4H,5H,6H,7H,8H,9H-cycloocta[d][1,2,3]triazol-4-yl)oxy]acetamido}hexanamido]-3-methylbutanamido]-5-(carbamoylamino)pentanamido]phenyl}methyl N-(4-{2-[(1S,2S,4R,8S,9S,11 S,12R,13S,19S)-12,19-difluoro-11-hydroxy-9,13-dimethyl-16-oxo-6-propyl-5,7-dioxapentacyclo[10.8.0.$0^{2,9}$.$0^{4,8}$.$0^{13,18}$]icosa-14,17-dien-8-yl]-2-oxoethoxy}phenyl)carbamate (9K)

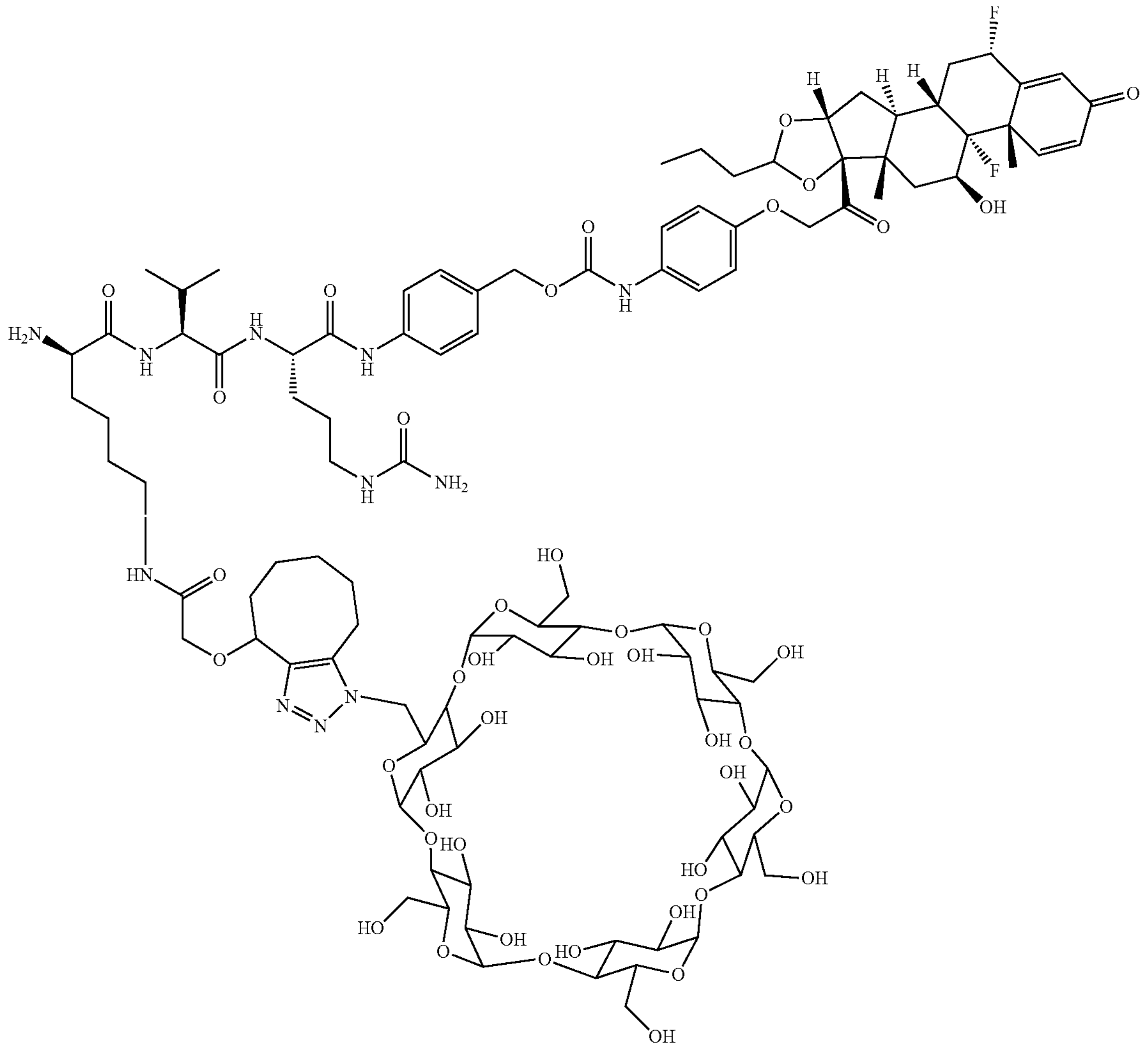 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COc2ccc(NC(=O)OCc3ccc(NC(=O)[C@H](CCCNC(N)=O)NC(=O)[C@@H](NC(=O)[C@H](N)CCCCNC(=O)COC4CCCCCc5c4nnn5CC4OC5OC6C(CO)OC(OC7C(CO)OC(OC8C(CO)OC(OC9C(CO)OC(OC%10C(CO)OC(OC4C(O)C5O)C(O)C%10O)C(O)C9O)C(O)C8O)C(O)C7O)C(O)C6O)C(C)C)cc3)cc2)O1]

Following the general procedure as described in example 25, compound 9K (0.11 g, 58% yield) was obtained as a white solid. ESI m/z: 751 $(M/3+1)^+$.

Example 34C

Preparation of Compound 9L—(See FIG. 7 and Table 6)

(2R)-2-Amino-N-[(1S)-1-{[(1S)-1-[(4-{2-[(1S,2S,4R,8S,9S,11 S,12R,13S,19S)-12,19-difluoro-11-hydroxy-9,13-dimethyl-16-oxo-6-propyl-5,7-dioxa-pentacyclo[10.8.0.0$^{2,9}$.0$^{4,8}$.0$^{13,18}$]icosa-14,17-dien-8-yl]-2-oxoethoxy}phenyl)carbamoyl]ethyl]carbamoyl}-2-methylpropyl]-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo [26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}hexanamide (9L)

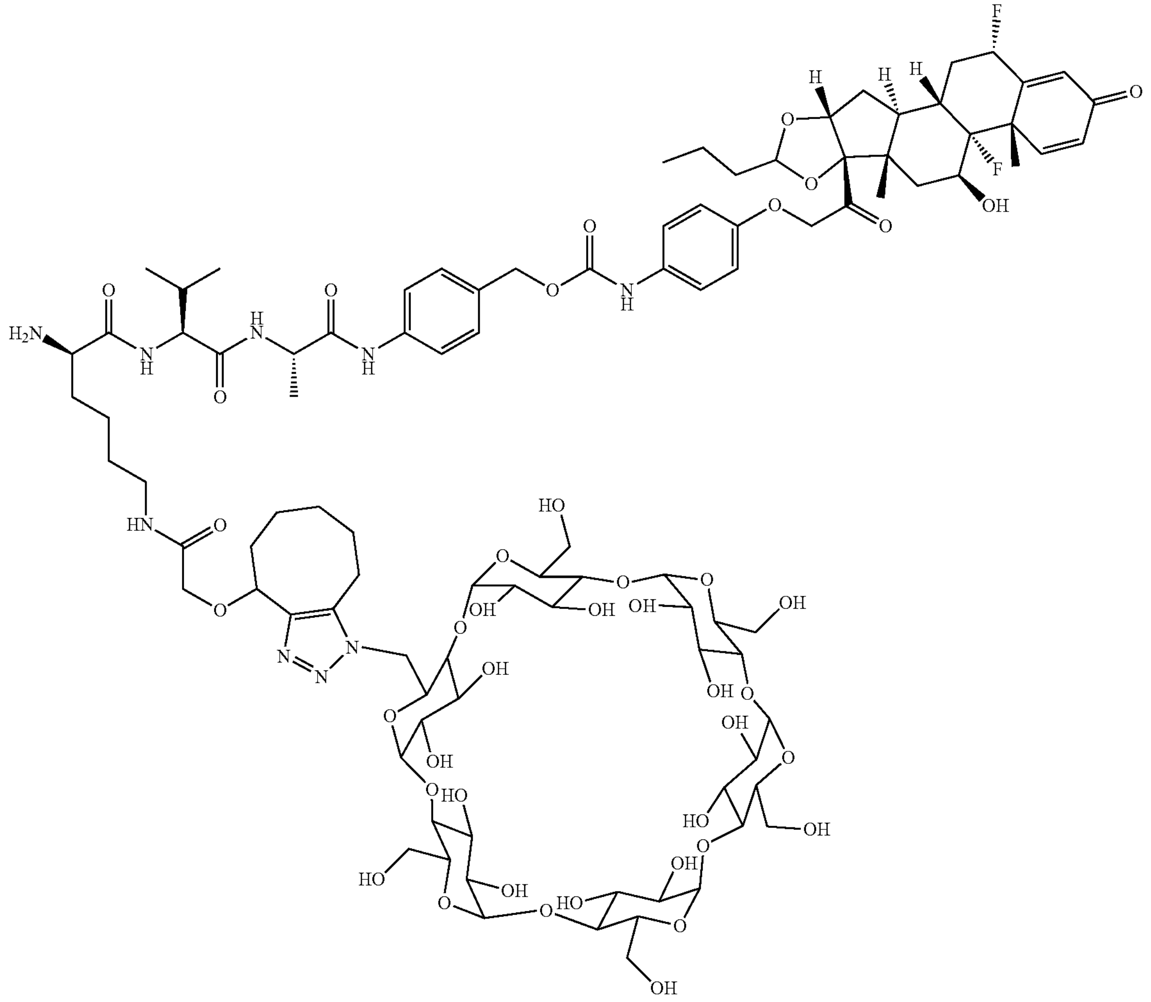 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COc2ccc(NC(=O)OCc3ccc(NC(=O)[C@H](C)NC(=O)[C@@H](NC(=O)[C@H](N)CCCCNC(=O)COC4CCCCCc5c4nnn5CC4OC5OC6C(CO)OC(OC7C(CO)OC(OC8C(CO)OC(OC9C(CO)OC(OC%10C(CO)OC(OC4C(O)C5O)C(O)C%10O)C(O)C9O)C(O)C8O)C(O)C7O)C(O)C6O)C(C)C)cc3)cc2)O1]

Following the general procedure as described in example 25, compound 9L (40 mg, 34% yield) was obtained as a white solid. ESI m/z: 1009.5 $(M/2+1)^+$.

Example 35

Certain linker-payloads were synthesized following the following procedure (General Procedure D (see FIG. 8).

General Procedure D: To a solution of acid 4a or 4c (1.0-2.5 equiv.) in DMF (or DCM/DMF) were added DIPEA (1.5-10 equiv.) and HATU (2.5-4.0 equiv.) at room temperature successively. The resulting mixture was stirred at this temperature for 0.5-1 hour before the amine (3a, 3c, 3d, 3H, 3I or 9a-i, 9J-L) (1.0 equiv.) was added. The reaction mixture was stirred at room temperature for 2-16 hours until the amine was totally consumed, as monitored by LCMS. The reaction mixture was filtered through a membrane and the filtrate was then separated by prep-HPLC to give the example compound (20-69% yield) as a white solid.

TABLE 7

REACTION CONDITIONS FOR EX. 36 AND 41-61-GENERAL PROCEDURE D.

| LP of EX # | Amine mg (µmol) | Acid mg (µmol) | Step 1 HATU mg (µmol) | Step 1 DIPEA mg (µmol) | Step 1 DMF (mL) | Step 1 Temp. (° C.) | Step 1 Time (hr) | purification | mg % Yield | MS m/z |
|---|---|---|---|---|---|---|---|---|---|---|
| Ex 36 | 3a 6.9 (6.1) | 4a 5.1 (9.2) | 3.5 (9.2) | 1.7 (13) | 1 | 25 | 16 | B | 2.0 20% | 829.7 (M/2 + H)+ |
| Ex 41 | 9a 11 (4.7) | 4a 2.6 (4.7) | 2.7 (7.1) | 1.2 (9.4) | 2 | 25 | 16 | B | 6.0 25% | 983.4 (M/3 + H)+ |
| Ex 42 | 9a 11 (4.7) | 4c 3.0 (6.9) | 4.0 (10) | 2.0 (16) | 1 | 25 | 2 | B | 4.0 31% | 946.3 (M/3 + H)+ |
| Ex 43 | 9g 15 (5.6) | 4a 3.4 (6.2) | 4.0 (10) | 1.5 (11) | DCM/ DMF (1:1, 2 mL) | 25 | 2 | B | 7.5 42% | 1065.9 (M/3 + H)+ |
| Ex 44 | 9g 21 (7.9) | 4c 9.0 (20) | 7.8 (20) | 0.04 mL, excess | DCM/ DMF (1:1, 2 mL) | 25 | 2 | B | 8.5 35% | 1028.7 (M/3 + H)+ |
| Ex 45 | 3c 30 (43) | 4a 48 (87) | 40 (105) | 17 (132) | 1 | 25 | 16 | B | 30 56% | 1226 (M + H)+ |
| Ex 46 | 9bB 13 (6.0) | 4a 20 (36) | 15 (39) | 4.0 (31) | 2 | 25 | 2 | B | 6.0 36% | 1258 (M/2 + H)+ |
| Ex 47 | 9c 30 (15) | 4a 10 (18) | 8.0 (21) | 6.0 (47) | 1 | 15-20 | 16 | B | 18 47% | 1258 (M/2 + H)+ |
| Ex 48 | 3d 20 (29) | 4a 18 (33) | 33 (87) | 33 (87) | 1 | 15-20 | 16 | B | 10 28% | 1234 (M + H)+ |
| Ex 49 | 9d 300 (150) | 4a 82 (150) | 57 (0.15) | 38 (0.30) | 8 | 15 | 3 | B | 260 v 69% | 1262 (M/2 + H)+ |
| Ex 51 | 9h 12 (5.4) | 4c 3.0 (6.7) | 6.2 (16) | 2.1 (16) | 1 | 15-20 | 16 | B | 2.0 14% | 1330 (M/2 + H)+ |
| Ex 52 | 9i 20 (8.0) | 4c 5.3 (12) | 4.6 (12) | 4.1 (32) | 1 | 15-20 | 16 | B | 5.0 21% | 1470 (M/2 + H)+ |
| Ex 53 | 9h 28 (13) | 4a 8.9 (16) | 6.1 (16) | 5.2 (40) | 1 | 15-20 | 16 | B | 8.0 32% | 1386 (M/2 + H)+ |
| Ex 54 | 9d 30 (15) | 4c 10 (22) | 8.4 (22) | 7.7 (60) | 1 | 15-20 | 16 | B | 16 43% | 1206 (M/2 + H)+ |
| Ex 55 | 9e 65 (28) | 4a 18 (34) | 33 (87) | 33 (87) | 1 | 15-20 | 16 | B | 28 35% | 1409 (M/2 + H)+ |
| Ex 56 | 9f 15 (6.5) | 4a 4.3 (7.8) | 7.6 (20) | 26 (20) | 1 | 15-20 | 16 | B | 10 42% | 1424.3 (M/2 + H)+ |
| Ex 57 | 3H 43 (50) | 4a 30 (54) | 31 (81) | 13 (100) | 5 | 25 | 3 | B | 16 23% | 1406 (M + H)+ |
| Ex 58 | 9J 100 (46) | 4a 30 (54) | 26 (69) | 18 (138) | 5 | 25 | 4 | B | 26 22% | 1349 (M/2 + H)+ |
| Ex 59 | 9J 22 (10) | 4c 4.5 (10) | 6.0 (16) | 3 (23) | 1.5 | 20 | 2 | B | 10 38% | 1293 (M/2 + H)+ |
| Ex 60 | 3I 58 (60) | 4a 37 (67) | 34 (90) | 15 (120) | 5 | 25 | 3 | B | 20 22% | 1499 (M + H)+ |
| Ex 61 | 9K 100 (44) | 4a 30 (54) | 26 (69) | 18 (138) | 5 | 25 | 4 | B | 29 24% | 1394 (M/2 + H)+ |
| Ex 62 | 100 (44) | 4a 30 (54) | 26 (69) | 18 (138) | 5 | 25 | 4 | B | 29 24% | 1394 (M/2 + H) |

| LP of EX # | Amine mg (µmol) | NHS mg (µmol) | Step 1 DIPEA mg (µmol) | Step 1 DMF (mL) | Step 1 Temp. (° C.) | Step 1 Time (hr) | purification | mg % Yield | MS m/z |
|---|---|---|---|---|---|---|---|---|---|
| Ex 63 | 9L 19 (9.4) | 4b 7.0 (11) | 2.3 (18) | 2 | 25 | 16 | B | 7 29% | 1276.8 (M/2 + H)+ |

For Purification-B: Prep-HPLC method B.

Example 36

Preparation of Linker-MMAE (See FIG. 8 and Table 7)

{4-[(2S)-2-[(2S)-2-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl N-[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate mg, 4.7 μmol) and DIPEA (0.8 mg, 6.2 μmol) at room temperature successively. The mixture was stirred at room temperature for 30 minutes before a solution of compound 3a (3.6 mg, 3.1 μmol) in dry THF (1 mL) was added into the reaction mixture. The resulting mixture was stirred at room temperature for 16 hours until the reaction was deemed complete by LCMS. The volatiles were removed in vacuo and the residue 8j (ESI m/z: 866.3 (M/2+H)$^+$) was dissolved in acetonitrile (1 mL). To the solution was added a solution of αCD-azide 6a (4.6 mg, 4.7 μmol) in water (1 mL). The reaction mixture was stirred at room temperature for 16 hours, and monitored by LCMS. The mixture was directly purified by prep-HPLC (method A) to give the linker payload compound recited in this Example (2 mg, 25% yield) as a white solid. ESI m/z: 910.8 (M/3+H)$^+$ (100%), 1365.4 (M/2+H)$^+$ (20%).

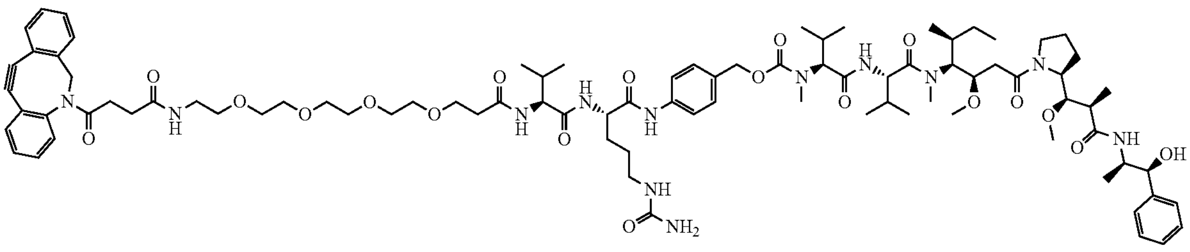 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCOCCOCCOCCOCCNC(=O)CCC(=O)N2Cc3ccccc3C#Cc3ccccc32)C(C)C)cc1)C(C)C]

ESI m/z: 829.7 (M/2+H)$^+$ (100%), 1659.7 (M+H)$^+$ (20%). $^1$H NMR (DMSO$_{d6}$, 500 MHz): δ 9.98 (s, 1H), 8.29 (s, 1H), 8.11 (d, J=7.3 Hz, 1H), 8.04 (s, 1H), 7.92-7.82 (m, 2H), 7.75 (t, J=5.1 Hz, 1H), 7.68 (d, J=7.2 Hz, 1H), 7.65-7.53 (m, 3H), 7.53-7.42 (m, 3H), 7.41-7.22 (m, 9H), 7.22-7.10 (m, 1H), 6.06-5.91 (m, 1H), 5.75 (s, 1H), 5.40 (s, 2H), 5.33 (d, J=4.8 Hz, 1H), 5.15-4.91 (m, 3H), 4.79-4.57 (m, 1H), 4.54-4.17 (m, 5H), 4.08-3.88 (m, 2H), 3.67-3.40 (m, 16H), 3.27-2.80 (m, 18H), 2.62-2.53 (m, 1H), 2.41-1.27 (m, 21H), 1.07-0.95 (m, 6H), 0.90-0.67 (m, 26H) ppm.

Anal. HPLC: 98%, Retention time: 8.25 min (method B).

Solubility: <0.1 mg/mL water.

Example 37

This Example provides a representative synthetic route for making certain linker-payloads (See FIG. 9).

{4-[(2S)-5-(Carbamoylamino)-2-[(2S)-2-[(2S)-2-[6-(2,5-dioxo-2,5-dihydro-1H-pyrrol-1-yl)hexanamido]-6-[4-(3-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-3,4,5,13-tetraazatetracyclo[13.4.0.0$^{2,6}$.0$^{7,12}$]nonadeca-1(19),2(6),4,7(12),8,10,15,17-octaen-13-yl)-4-oxobutanamido]hexanamido]-3-methylbutanamido]pentanamido]phenyl}methyl N-[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate To a solution of Mc-(L) D-Lys(suc-DIBAC)—OH (5b, 2.0 mg, 3.1 μmol) in dry THF (1 mL) were added HATU (1.8

Anal. HPLC: >99.9%, Retention time: 6.97 min (method B).

Example 38

Preparation of {4-[(2S)-2-[(2S)-2-[(2R)-6-(4-{2-Azatricyclo[10.4.0.0$^{4,9}$]hexadeca-1(12),4,6,8,13,15-hexaen-10-yn-2-yl}-4-oxobutanamido)-2-{6-[3-(4-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}piperazin-1-yl)-2,5-dioxopyrrolidin-1-yl]hexanamido}hexanamido]-3-methylbutanamido]-5-(carbamoylamino)pentanamido]phenyl}methyl N-[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate (See FIG. 10)

A mixture of intermediate 5a (15 mg, 24 μmol) and HATU (15 mg, 39 μmol) in THF (1 mL) was stirred at room temperature for half an hour. Then a solution of vc-PAB-MMAE (I, 26 mg, 23 μmol) in DMF (2 mL) and DIPEA (8.9 mg, 69 μmol) subsequently were added. The mixture was stirred at room temperature overnight. The reaction was monitored by LCMS until vc-PAB-MMAE was consumed and desired compound was detected. The volatiles were removed in vacuo and the residue was purified by reversed phase flash chromatography (0-100% acetonitrile in water) to give Ex38-Int (18 mg, 26% yield) as a white solid. ESI m/z: 1732 (M+H)$^+$. $^1$H NMR (DMSO$_{d6}$, 400 MHz): δ 9.61 (s, 1H), 8.31-7.87 (m, 6H), 7.68-7.61 (m, 5H), 7.49-7.37 (m, 4H), 7.30-7.12 (m, 13H), 6.98 (s, 2H), 5.95 (m, 1H), 5.38-5.33 (m, 4H), 5.12-5.02 (m, 2H), 4.76-4.26 (m, 7H), 4.16-4.14 (m, 2H), 4.04-3.94 (m, 3H), 3.79-3.43 (m, 5H), 3.3 (s, 6H), 3.24-3.23 (m, 5H), 3.20 (s, 3H), 3.17 (s, 2H), 3.11 (m, 2H), 3.04-2.84 (m, 8H), 2.64-2.57 (m, 2H), 2.43-2.36 (m, 2H), 2.29-2.14 (m, 2H), 2.04-1.94 (m, 5H), 1.80-1.72 (m, 3H), 1.57-1.24 (m, 5H), 1.11-0.97 (m, 6H), 0.89-

0.75 (m, 24H) ppm. The above intermediate was dissolved in DMF (0.7 mL). To the solution were added TEA (0.5 mg, 5.0 μmol) and αCD-pip 6b (9.6 mg, 9.4 μmol) at room temperature successively. The resulting mixture was stirred at room temperature for 16 hours until the reaction was completed according to LCMS. The mixture was directly purified by prep-HPLC (method B) to give the linker payload compound recited in this Example (3 mg, 23% yield) as a white solid.

ESI m/z: 925.1 $(M/3+H)^+$ (100%), 1387 $(M/2+H)^+$ (10%).

$^1$H NMR ($DMSO_{d6}$, 500 MHz): δ 9.68 (s, 1H), 8.34-7.83 (m, 4H), 7.72-7.56 (m, 5H), 7.55-7.24 (m, 12H), 7.21-7.12 (m, 1H), 5.97 (s, 1H), 5.69-5.26 (m, 14H), 5.25-4.70 (m, 9H), 4.69-4.38 (m, 7H), 4.36-4.21 (m, 3H), 4.17 (s, 1H), 4.06-3.88 (m, 2H), 3.87-3.53 (m, 25H), 3.52-3.35 (m, 14H), 3.32-3.08 (m, 21H), 3.08-2.80 (m, 7H), 2.79-2.52 (m, 9H), 2.46-1.88 (m, 11H), 1.87-1.10 (m, 21H), 1.07-0.96 (m, 6H), 0.90-0.74 (m, 24H) ppm.

Anal. HPLC: 96%, Retention time: 7.22 min (method B).

Solubility: 0.25 mg/mL water.

Example 39

This Example provides a representative synthetic route for making certain linker-payloads (See FIG. 11).

{4-[(2S)-5-(Carbamoylamino)-2-[(2S)-2-[(2R)-2-[1-(2,5-dioxo-2,5-dihydro-1H-pyrrol-1-yl)-3,6,9,12-tetraoxapentadecan-15-amido]-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}hexanamido]-3-methylbutanamido]pentanamido]phenyl}methyl N-[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate To a mixture of compound 8a (10 mg, 7.1 μmol) and compound 4d (6.2 mg, 14 μmol) in DMF (0.5 mL) was added TEA (2.1 mg, 21 μmol) at 25° C. by syringe. The mixture was stirred at 20-25° C. for 16 hours until most of 8a was consumed, as monitored by LCMS. The reaction mixture was purified by reversed phase flash chromatography (0-100% acetonitrile in water (with 0.03% TFA)) to give a white solid (ESI m/z: 1743 $(M+H)^+$), which was dissolved into DMF (1 mL) and water (1 mL). To the solution was added azide 6a (3.0 mg, 3.0 μmol) at 25° C. and the mixture was stirred at this temperature for 3 days. The reaction was then deemed complete by LCMS. The volatiles were removed in vacuo and the residue was purified by prep-HPLC (method A) to give the linker payload compound recited in this Example (1.5 mg, 9% yield) as a white solid.

ESI m/z: 1371 $(M/2+H)^+$.

$^1$H NMR ($DMSO_{d6}$, 500 MHz): δ 9.70 (s, 1H), 8.36-7.54 (m, 8H), 7.37-7.09 (m, 8H), 7.01 (s, 2H), 6.55 (s, 1H), 6.05-5.94 (m, 1H), 5.76 (s, 3H), 5.64-5.29 (m, 16H), 5.24-4.91 (m, 3H), 4.89-4.67 (m, 8H), 4.62-4.14 (m, 13H), 4.07-3.89 (m, 3H), 3.87-3.53 (m, 28H), 3.53-3.15 (m, 15H), 3.15-3.03 (m, 9H), 3.01-2.80 (m, 10H), 2.43-2.35 (m, 3H), 2.31-2.22 (m, 2H), 2.16-1.94 (m, 5H), 1.90-1.11 (m, 23H), 1.07-0.94 (m, 8H), 0.92-0.68 (m, 28H) ppm.

Anal. HPLC: >99.9%, Retention time: 5.78 min (method A).

Example 40

Preparation of {4-[(2S)-5-(Carbamoylamino)-2-[(2S)-2-[(2R)-2-[1-(2,5-dioxo-2,5-dihydro-1H-pyrrol-1-yl)-3,6,9,12-tetraoxapentadecan-15-amido]-6-[4-(3-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-3,4,5,13-tetraazatetracyclo[13.4.0.0$^{2,6}$.0$^{7,12}$]nonadeca-1(19),2(6),4,7(12),8,10,15,17-octaen-13-yl)-4-oxobutanamido]hexanamido]-3-methylbutanamido]pentanamido]phenyl}methyl N-[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate (See FIG. 9)

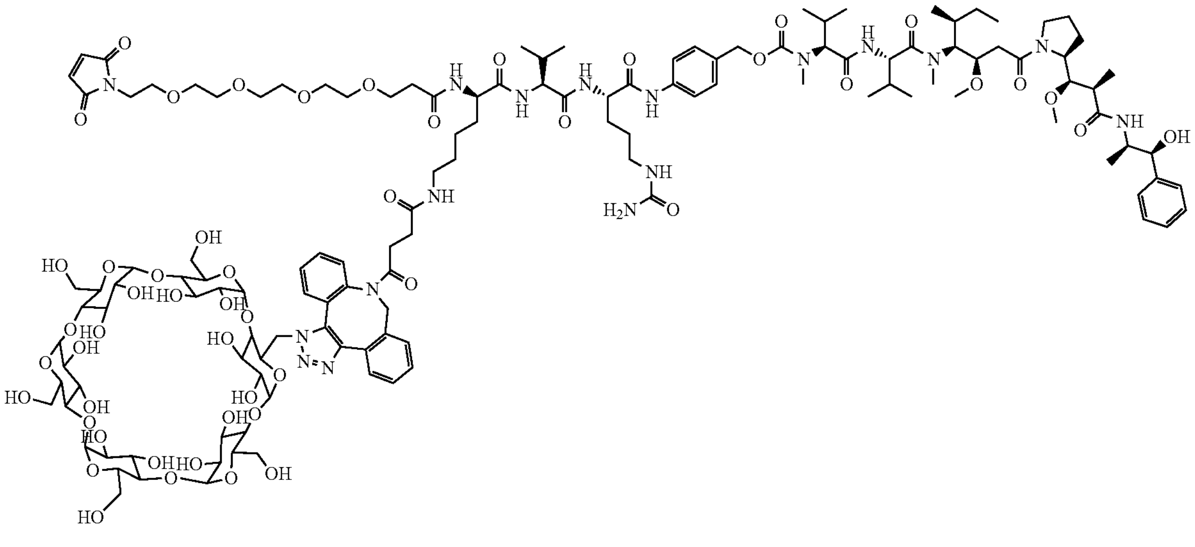 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)[C@@H](CCCCNC(=O)CCC(=O)N2Cc3ccccc3-c3nnn(CC4OC5OC6C(CO)OC(OC7C(CO)OC(OC8C(CO)OC(OC9C(CO)OC(OC%10C(CO)OC(OC4C(O)C5O)C(O)C%10O)C(O)C9O)C(O)C8O)C(O)C7O)C(O)C6O)c3-c3ccccc32)NC(=O)CCOCCOCCOCCOCCN2C(=O)C=CC2=O)C(C)C)cc1)C(C)C]

See the synthetic route in Example 37. Following the procedure of Example 37, except substituting compound 5c for 5b, the linker payload compound recited in this Example (8.0 mg, 36% yield) was obtained as a white solid.

ESI m/z: 1432 $(M/2+H)^+$.

$^1H$ NMR ($DMSO_{d6}$, 500 MHz): δ 9.68 (s, 1H), 8.10-8.07 (m, 4H), 7.89-7.81 (m, 1H), 7.67-7.39 (m, 10H), 7.31-7.10 (m, 12H), 7.01 (s, 2H), 5.98-5.87 (m, 1H), 5.67-5.22 (m, 14H), 5.05-4.67 (m, 11H), 4.49-4.16 (m, 13H), 4.04-3.69 (m, 12H), 3.68-2.85 (m, 54H), 2.71-1.29 (m, 28H), 1.05-0.97 (m, 7H), 0.89-0.68 (m, 29H) ppm.

Anal. HPLC: >99.9%, Retention time: 6.84 min (method B).

Solubility: 0.33 mg/mL water.

Example 41

Preparation of {4-[(2S)-2-[(2S)-2-[(2R)-2-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}hexanamido]-3-methylbutanamido]-5-(carbamoylamino)pentanamido]phenyl}methyl N-[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate (See FIG. 8 and Table 7)

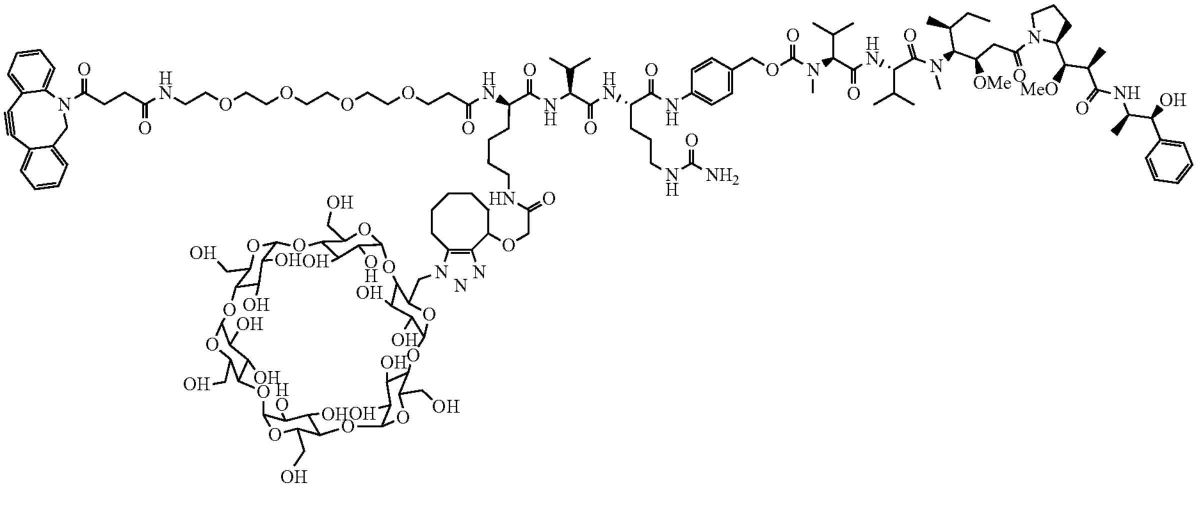 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)[C@@H](CCCCN2C(=O)COC3c4nnn(CC5OC6OC7C(CO)OC(OC8C(CO)OC(OC9C(CO)OC(OC%10C(CO)OC(OC%11C(CO)OC(OC5C(O)C6O)C(O)C%11O)C(O)C%10O)C(O)C9O)C(O)C8O)C(O)C7O)c4CCCCC32)NC(=O)CCOCCOCCOCCOCCNC(=O)CCC(=O)N2Cc3ccccc3C#Cc3ccccc32)C(C)C)cc1)C(C)C]

ESI m/z: 983.4 $(M/3+H)^+$ (100%), 1475 $(M/2+H)^+$ (5%).

$^1H$ NMR ($DMSO_{d6}$, 500 MHz): δ 9.70 (s, 1H), 8.39-7.09 (m, 24H), 5.97 (s, 1H), 5.79-5.30 (m, 15H), 5.22-4.92 (m, 4H), 4.90-4.64 (m, 8H), 4.64-4.14 (m, 13H), 4.06-3.90 (m, 4H), 3.90-2.81 (m, 77H), 2.65-2.55 (m, 2H), 2.44-1.93 (m, 9H), 1.89-1.59 (m, 8H), 1.57-1.40 (m, 8H), 1.35-1.18 (m, 7H), 1.07-0.95 (m, 6H), 0.90-0.67 (m, 24H) ppm.

Anal. HPLC: >99.9%, Retention time: 7.29 min (method B).

Solubility: 0.25 mg/mL water.

Example 42

Preparation of (1R,8S,9S)-bicyclo[6.1.0]non-4-yn-9-ylmethyl N-(14-{[(1R)-1-{[(1S)-1-{[(1S)-4-(carbamoylamino)-1-({4-[({[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl](methyl)carbamoyl}oxy)methyl]phenyl}carbamoyl)butyl]carbamoyl}-2-methylpropyl]carbamoyl}-5-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.$2^{3,6}$.$2^{8,11}$.$2^{13,16}$.$2^{18,21}$.$2^{23,26}$]dotetracontan-5-yl]methyl}-1H,4H,5H,6H,7H,8H,9H-cycloocta[d][1,2,3]triazol-4-yl)oxy]acetamido}pentyl]carbamoyl}-3,6,9,12-tetraoxatetradecan-1-yl)carbamate (See FIG. 8 and Table 7)

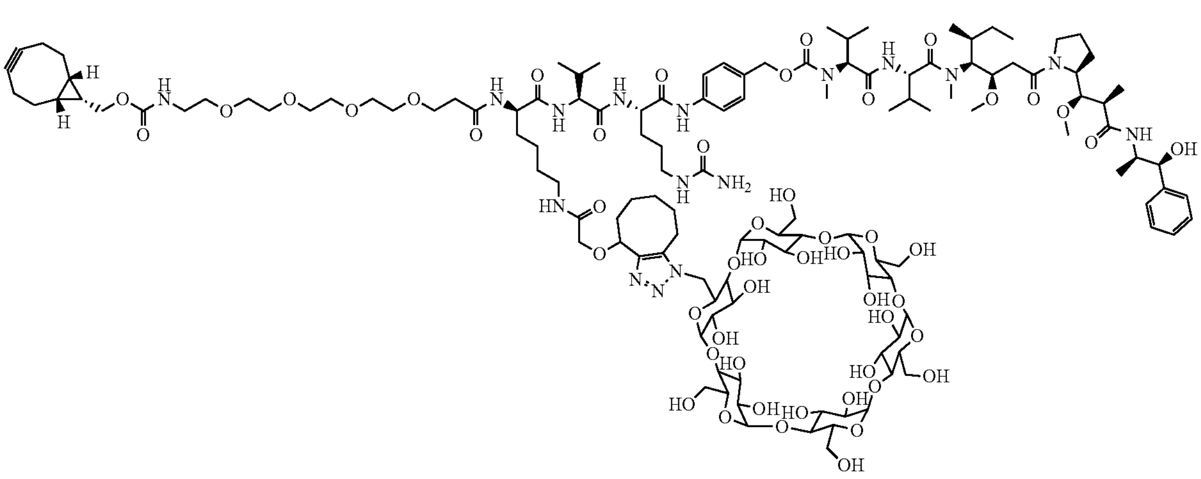 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)[C@@H](CCCCNC(=O)COC2CCCCCc3c2nnn3CC2OC3OC4C(CO)OC(OC5C(CO)OC(OC6C(CO)OC(OC7C(CO)OC(OC8C(CO)OC(OC2C(O)C3O)C(O)C8O)C(O)C7O)C(O)C6O)C(O)C5O)C(O)C4O)NC(=O)CCOCCOCCOCCOCCNC(=O)OC[C@@H]2[C@@H]3CCC#CCC[C@@H]32)C(C)C)cc1)C(C)C]

ESI m/z: 946.3 $(M/3+H)^+$ (100%), 1418.9 $(M/2+H)^+$ (20%).

$^1$H NMR (methanol$_{d4}$, 500 MHz): δ 7.59-7.58 (m, 2H), 7.29-7.10 (m, 7H), 5.25-4.98 (m, 4H), 4.86-4.81 (m, 5H), 4.58-4.31 (m, 4H), 4.22-4.03 (m, 6H), 3.92-3.61 (m, 21H), 3.53-3.32 (m, 36H), 3.26-3.25 (m, 5H), 3.18-2.83 (m, 13H), 2.56-2.54 (m, 1H), 2.44-1.43 (m, 33H), 1.35-1.01 (m, 15H), 0.91-0.69 (m, 29H) ppm.

Anal. HPLC: >99.9%, Retention time: 7.33 min (method B).

Solubility: 1.0 mg/mL water.

Example 43

Preparation of {4-[(2S)-2-[(2S)-2-[(2R)-2-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-6-(1-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}-3,6,9,12-tetraoxapentadecan-15-amido)hexanamido]-3-methylbutanamido]-5-(carbamoylamino)pentanamido]phenyl}methyl N-[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate (See FIG. 8 and Table 7)

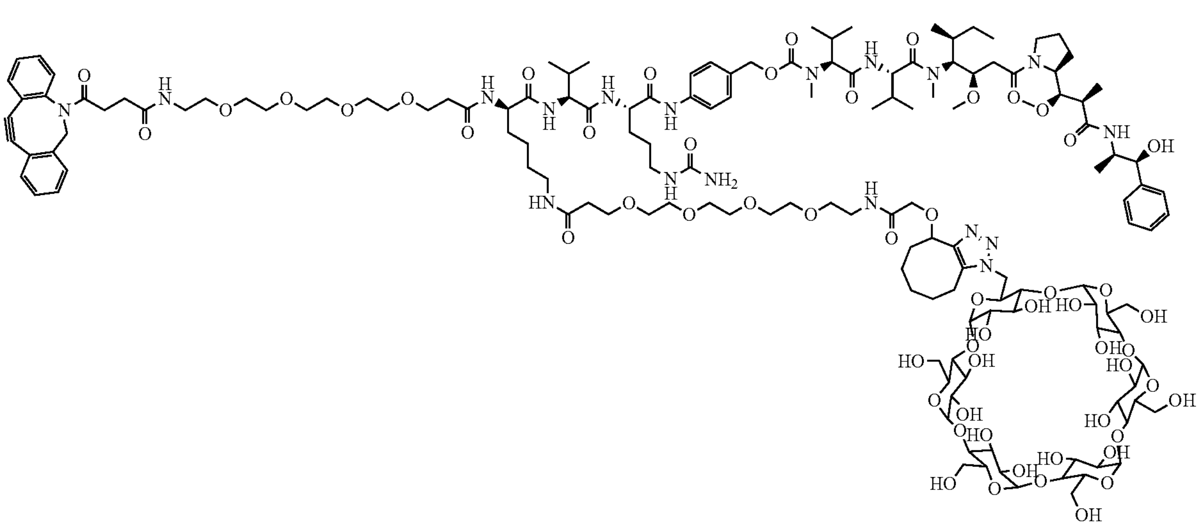

ESI m/z: 1065.9 (M/3+H)$^+$ (100%), 1598.4 (M/2+H)$^+$ (20%).

$^1$H NMR (500 MHz, methanol$_d$4) b 7.67-7.04 (m, 17H), 5.24 (t, J=4.7 Hz, 1H), 5.13-4.82 (m, 10H), 4.60-4.41 (m, 5H), 4.37-4.31 (m, 1H), 4.22-4.04 (m, 5H), 3.99-3.66 (m, 18H), 3.65-3.57 (m, 4H), 3.55-3.29 (m, 40H), 3.29-2.65 (m, 24H), 2.64-2.55 (m, 1H), 2.45-1.12 (m, 46H), 1.09-1.00 (m, 6H), 0.94-0.66 (m, 24H) ppm.

Anal. HPLC: 98.2%, Retention time: 5.79 min (method B).

Solubility: 0.5 mg/mL water.

Example 44

Preparation of [(1R,8S,9S)-Bicyclo[6.1.0]non-4-yn-9-yl]methyl N-(14-{[(1R)-1-{[(1S)-1-{[(1S)-4-(carbamoylamino)-1-({4-[({[(1 S)-1-{[(1 S)-1-{[(3R,4S,5S)-1-[(2S)-2-[(1R,2R)-2-{[(1 S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl](methyl)carbamoyl}oxy)methyl]phenyl}carbamoyl)butyl]carbamoyl}-2-methylpropyl]carbamoyl}-5-(1-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}-3,6,9,12-tetraoxapentadecan-15-amido)pentyl]carbamoyl}-3,6,9,12-tetraoxatetradecan-1-yl)carbamate (See FIG. 8 and Table 7)

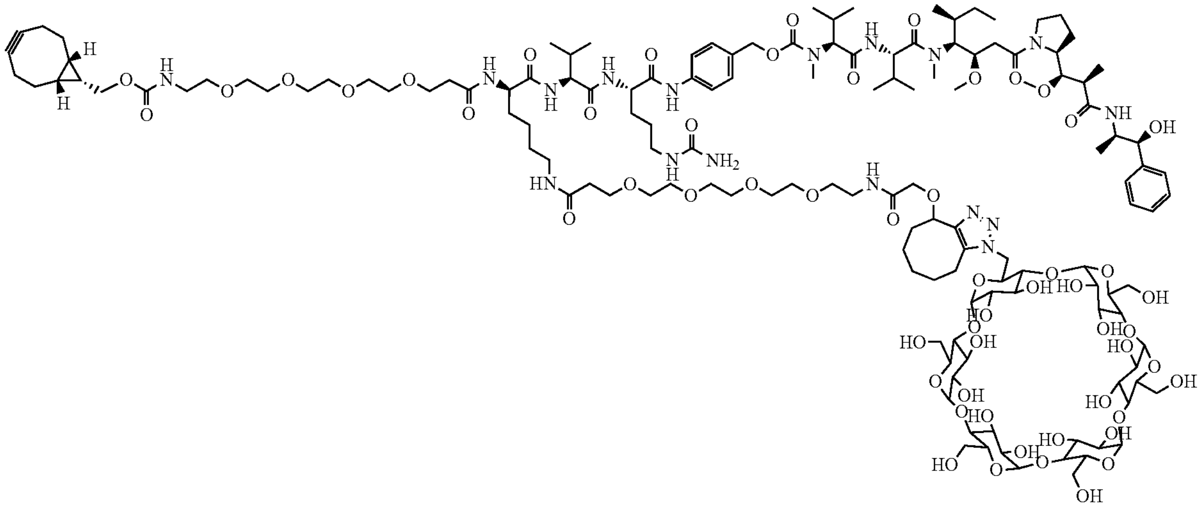

ESI m/z: 1028.7 $(M/3+H)^+$ (100%), 1541.5 $(M/2+H)^+$ (5%).

$^1$H NMR (500 MHz, methanol$_{d4}$): 67.58 (d, J=8.0 Hz, 2H), 7.29-7.09 (m, 7H), 5.26-4.98 (m, 4H), 4.87-4.85 (m, 3H), 4.54-4.43 (m, 3H), 4.35-4.32 (m, 1H), 4.19-4.03 (m, 10H), 3.93-3.71 (m, 19H), 3.65-3.47 (m, 30H), 3.39-3.25 (m, 32H), 3.24-3.17 (m, 5H), 3.10-2.90 (m, 5H), 2.89-2.69 (m, 4H), 2.50-2.34 (m, 7H), 2.23-1.97 (m, 13H), 1.97-1.34 (m, 16H), 1.22-1.20 (m, 7H), 1.08-0.91 (m, 7H), 0.82-0.67 (m, 26H) ppm.

Anal. HPLC: >99.9%, Retention time: 7.02 min (method B).

Solubility: 1.0 mg/mL water.

Example 45

This Example provides the synthesis of a linker-glucocorticoid (GC) Steroid (See FIG. 8 and Table 7).

1-(4-{2-azatricyclo[10.4.0.0$^{4,9}$]hexadeca-1(12),4(9),5,7,13,15-hexaen-10-yn-2-yl}-4-oxobutanamido)-N-[(1S)-1-{[(1S)-1-[(4-{2-[(1S,2S,4R,6R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamoyl]ethyl]carbamoyl}-2-methylpropyl]-3,6,9,12-tetraoxapentadecan-15-amide

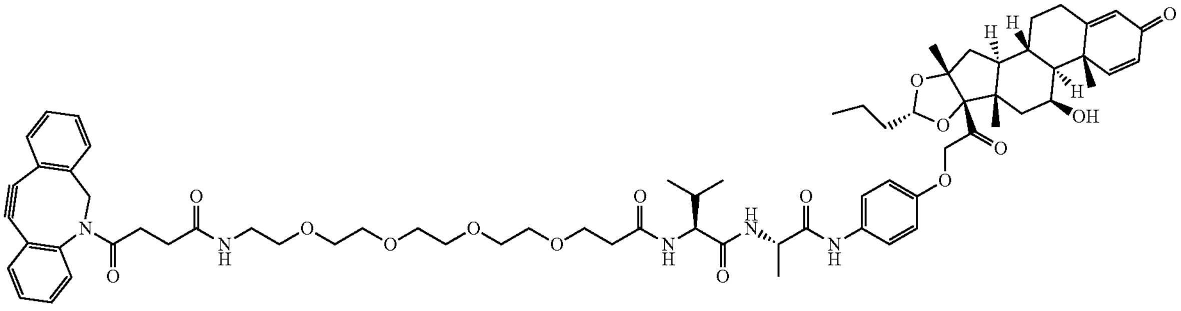 [SMILES: CCC[C@H]1O[C@]2(C(=O)COc3ccc(NC(=O)[C@H](C)NC(=O)[C@@H](NC(=O)CCOCCOCCOCCOCCNC(=O)CCC(=O)N4Cc5ccccc5C#Cc5ccccc54)C(C)C)cc3)[C@@](C)(C[C@H]3[C@@H]4CCC5=CC(=O)C=C[C@]5(C)[C@H]4[C@@H](O)C[C@@]32C)O1]

ESI m/z: 1227 $(M+H)^+$.

$^1$H NMR (500 MHz, DMSO$_{d6}$) (rotamers) δ 9.79 (s, 0.5H), 9.70 (s, 0.5H), 8.41 (d, J=7.5 Hz, 0.5H), 8.17 (d, J=7.0 Hz, 0.5H), 8.02 (d, J=8.0 Hz, 0.5H), 7.89 (d, J=8.6 Hz, 0.5H), 7.77 (t, J=4.8 Hz, 1H), 7.68 (d, J=7.3 Hz, 1H), 7.62 (d, J=7.3 Hz, 1H), 7.58 (d, J=9.0 Hz, 1H), 7.53-7.43 (m, 4H), 7.40-7.28 (m, 4H), 6.88-6.82 (m, 2H), 6.18 (d, J=9.1 Hz, 1H), 5.93 (s, 1H), 5.10 (d, J=18.4 Hz, 1H), 5.03 (d, J=14.0 Hz, 1H), 4.83-4.67 (m, 4H), 4.45-4.29 (m, 2H), 4.23-4.17 (m, 0.5H), 4.11 (t, J=7.7 Hz, 0.5H), 3.64-3.40 (m, 15H), 3.31-3.26 (m, 2H), 3.13-3.03 (m, 2H), 2.65-2.52 (m, 2H), 2.47-1.26 (m, 24H), 1.06-0.93 (m, 2H), 0.90-0.80 (m, 12H) ppm.

Anal. HPLC: 99%, Retention time: 8.55 min (method B).

Solubility: <0.1 mg/mL water; 0.06 mg/mL 20% DMSO in water; 0.07 mg/mL 30% DMSO in water.

Example 46

Preparation of 1-(4-{2-Azatricyclo[10.4.0.0$^{4,9}$]hexadeca-1(12),4(9),5,7,13,15-hexaen-10-yn-2-yl}-4-oxobutanamido)-N-[(1R)-5-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}-1-{[(1S)-1-{[(1S)-1-[(4-{2-[(1S,2S,4R,8S,9S,11S,12S,13R)-11-hydroxy-9,13-dimethyl-16-oxo-6-propyl-5,7-dioxapentacyclo[10.8.0.0$^{2,9}$.0$^{4,9}$.0$^{13,11}$]icosa-14,17-dien-8-yl]-2-oxoethoxy}phenyl)carbamoyl]ethyl]carbamoyl}-2-methylpropyl]carbamoyl}pentyl]-3,6,9,12-tetraoxapentadecan-15-amide (See FIG. 8 and Table 7)

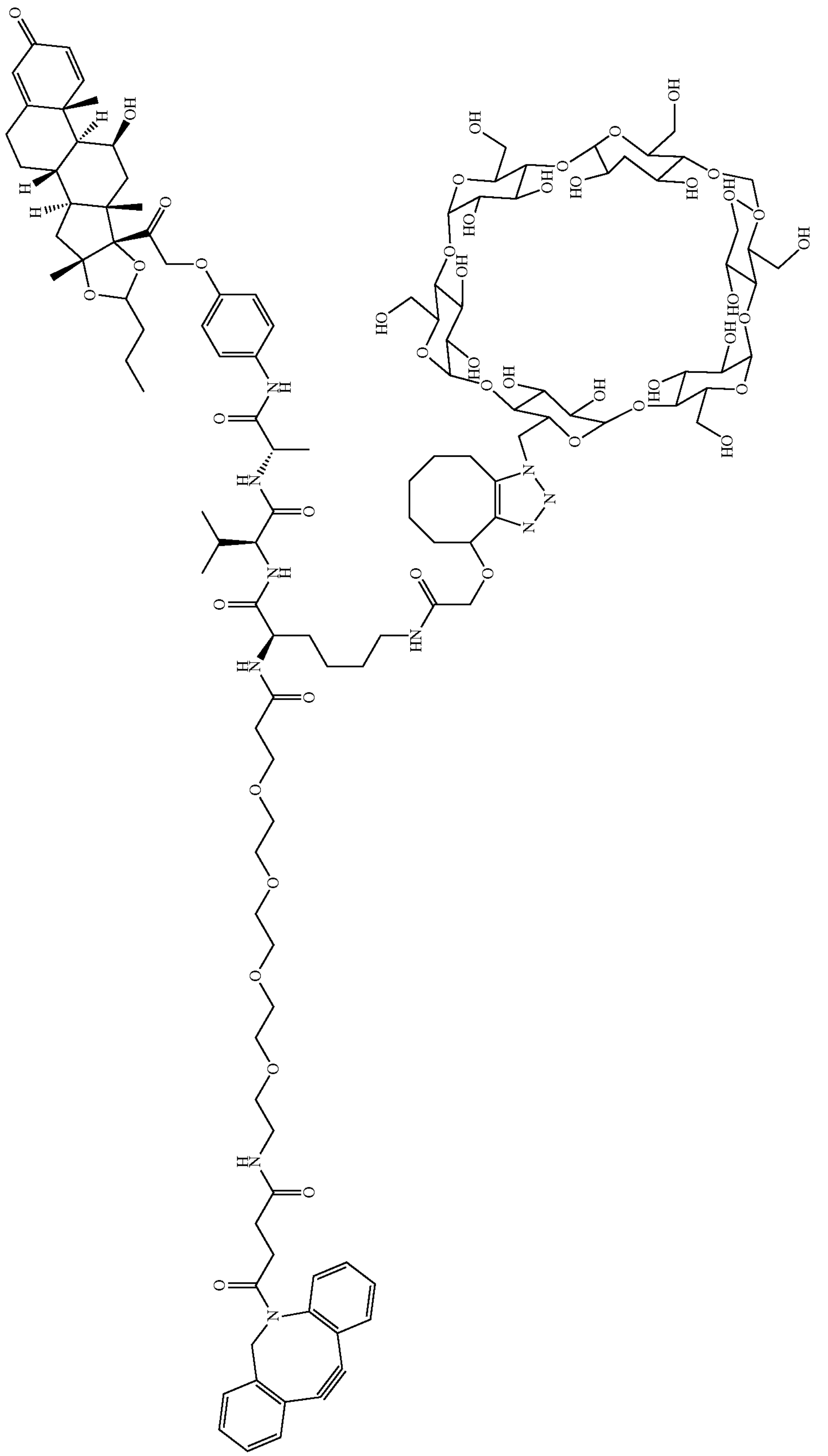

ESI m/z: 1259 $(M/2+H)^+$.

$^1$H NMR (500 MHz, $DMSO_{d6}$) (rotamers) δ 9.84 (s, 1H), 8.34 (s, 0.5H), 8.15 (d, J=7.3 Hz, 1H), 8.04 (d, J=6.6 Hz, 1H), 7.90-7.84 (m, 1H), 7.81-7.74 (m, 1.5H), 7.72-7.56 (m, 4H), 7.56-7.27 (m, 11H), 6.89-6.79 (m, 2H), 6.17 (d, J=10.0 Hz, 1H), 5.93 (s, 1H), 5.64-5.44 (m, 12H), 5.24-5.00 (m, 5H), 4.86-4.51 (m, 16H), 4.40-4.16 (m, 5H), 4.05-3.96 (m, 1H), 3.86-3.73 (m, 10H), 3.67-2.88 (m, 35H), 2.80-2.69 (m, 1H), 2.62-2.55 (m, 1H), 2.41-2.20 (m, 6H), 2.10-1.71 (m, 10H), 1.66-1.07 (m, 26H), 1.05-0.79 (m, 17H) ppm.

Anal. HPLC: 97%, Retention time: 6.62 and 6.67 min (method B).

Example 47

Preparation of 1-(4-{2-Azatricyclo[10.4.0.0$^{4,9}$]hexadeca-1(12),4(9),5,7,13,15-hexaen-10-yn-2-yl}-4-oxobutanamido)-N-[(1R)-5-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}-1-{[(1S)-1-{[(1S)-1-[(4-{2-[(1S,2S,4R,6R,8S,9S,11 S,12S,13R)-11-hydroxy-9,13-dimethyl-16-oxo-6-propyl-5,7-dioxapentacyclo[10.8.0.0$^{2,9}$.0$^{4,9}$.0$^{13,18}$]icosa-14,17-dien-8-yl]-2-oxoethoxy}phenyl)carbamoyl]ethyl]carbamoyl}-2-methylpropyl]carbamoyl}pentyl]-3,6,9,12-tetraoxapentadecan-15-amide (See FIG. 8 and Table 7)

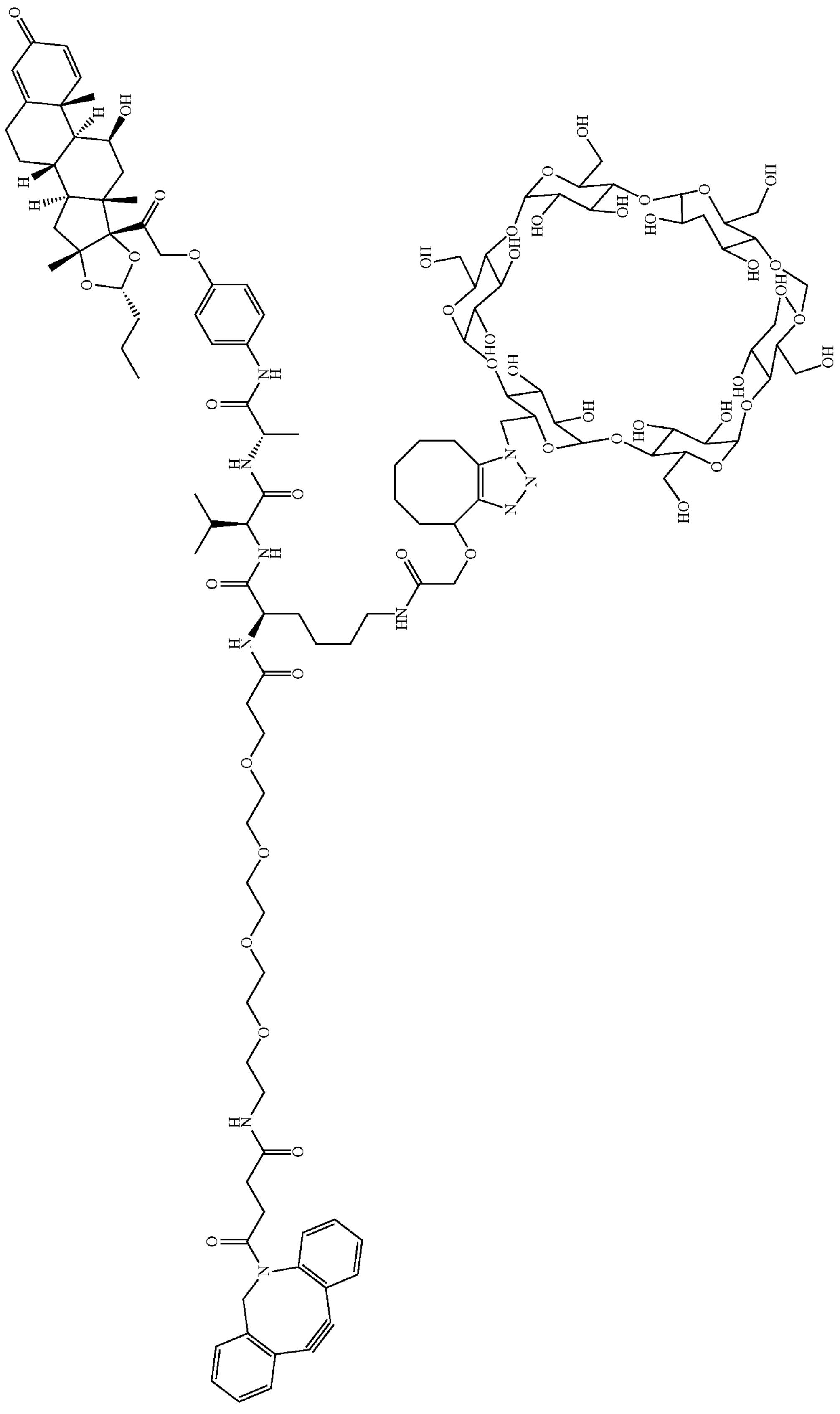

ESI m/z: 839.5 $(M/3+H)^+$, 1259 $(M/2+H)^+$ (60%).

$^1$H NMR (500 MHz, $DMSO_{d6}$) (with triazole regioisomer) δ 9.77-9.42 (m, 1H), 8.27-8.20 (m, 0.5H), 8.17-8.01 (m, 2H), 7.86-7.74 (m, 2.5H), 7.70-7.60 (m, 4H), 7.57-7.43 (m, 7H), 7.39-7.28 (m, 6H), 6.88-6.81 (m, 2H), 6.21-6.14 (m, 1H), 5.93 (s, 1H), 5.61-5.42 (m, 10H), 5.16-4.97 (m, 4H), 4.89-4.48 (m, 17H), 4.40-4.28 (m, 4H), 4.16-4.10 (m, 1H), 4.04-3.94 (m, 1H), 3.83-3.74 (m, 7H), 3.65-3.56 (m, 9H), 3.48-3.21 (m, 23H), 3.15-3.06 (m, 4H), 2.97-2.89 (m, 1H), 2.81-2.69 (m, 1H), 2.61-2.53 (m, 2H), 2.40-2.20 (m, 6H), 2.14-2.06 (m, 2H), 2.03-1.95 (m, 4H), 1.91-1.70 (m, 5H), 1.64-1.52 (m, 9H), 1.49-1.25 (m, 14H), 1.13-0.81 (m, 19H) ppm.

Anal. HPLC: 98%, Retention time: 6.61 (59%) and 6.73 (39%) min (method B).

Solubility: 0.1 mg/mL 10% DMSO in water.

Example 48

Preparation of 1-(4-{2-Azatricyclo[10.4.0.0$^{4,9}$]hexadeca-1(12),4(9),5,7,13,15-hexaen-10-yn-2-yl}-4-oxobutanamido)-N-[(1S)-1-{[(1 S)-1-{[(4bS,8S,8aR)-8-{[(1S,4aS,10aR)-6-hydroxy-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}ethyl]carbamoyl}-2-methylpropyl]-3,6,9,12-tetraoxapentadecan-15-amide (See FIG. 8 and Table 7)

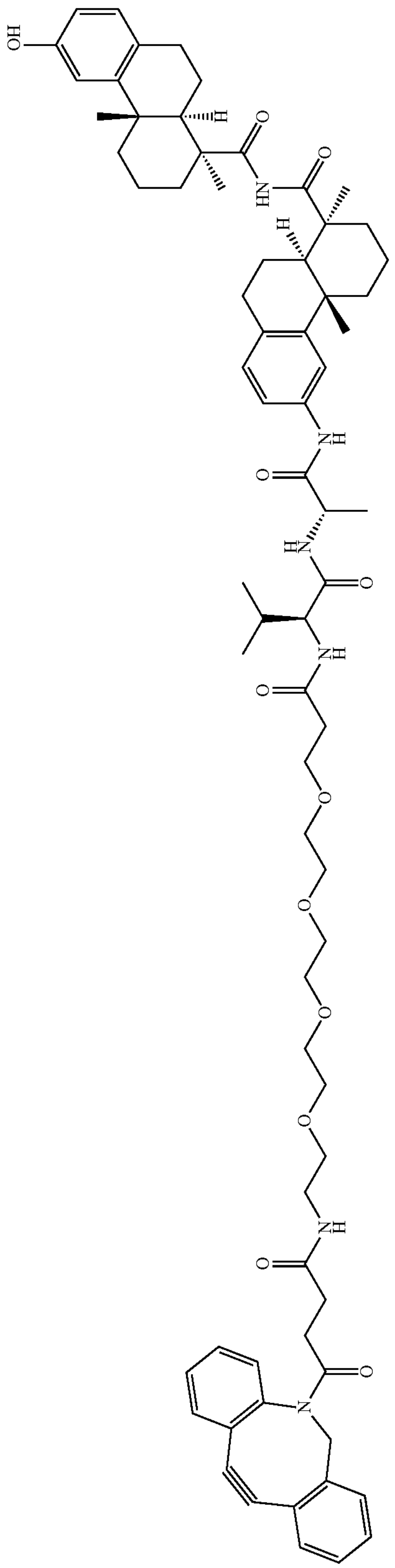

ESI m/z: 1234 $(M+H)^+$.

$^1H$ NMR (500 MHz, $methanol_{d4}$) δ 7.65 (d, J=7.4 Hz, 1H), 7.62-7.51 (m, 2H), 7.48-7.28 (m, 6H), 7.27-7.21 (m, 1H), 7.00 (d, J=8.5 Hz, 1H), 6.88 (d, J=8.0 Hz, 1H), 6.72 (d, J=2.4 Hz, 1H), 6.56 (dd, J=8.3, 2.4 Hz, 1H), 5.15-5.10 (m, 1H), 4.52-4.43 (m, 1H), 4.20 (d, J=6.5 Hz, 0.5H), 4.04 (d, J=7.9 Hz, 0.5H), 3.77-3.64 (m, 3H), 3.63-3.49 (m, 12H), 3.47-3.39 (m, 2H), 3.24 (t, J=5.5 Hz, 2H), 2.99-2.66 (m, 5H), 2.57-2.42 (m, 2H), 2.42-1.94 (m, 14H), 1.76-1.63 (m, 4H), 1.48-1.21 (m, 13H), 1.14-1.10 (m, 6H), 1.05-0.97 (m, 6H) ppm.

Anal. HPLC: >99%, Retention time: 9.21 min (method B).

Solubility: <0.1 mg/mL water.

Example 49

Preparation of 1-(4-{2-Azatricyclo[10.4.0.0$^{4,9}$]hexadeca-1(12),4(9),5,7,13,15-hexaen-10-yn-2-yl}-4-oxobutanamido)-N-[(1R)-1-{[(1S)-1-{[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}ethyl]carbamoyl}-2-methylpropyl]carbamoyl}-5-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}pentyl]-3,6,9,12-tetraoxapentadecan-15-amide (See FIG. 8 and Table 7)

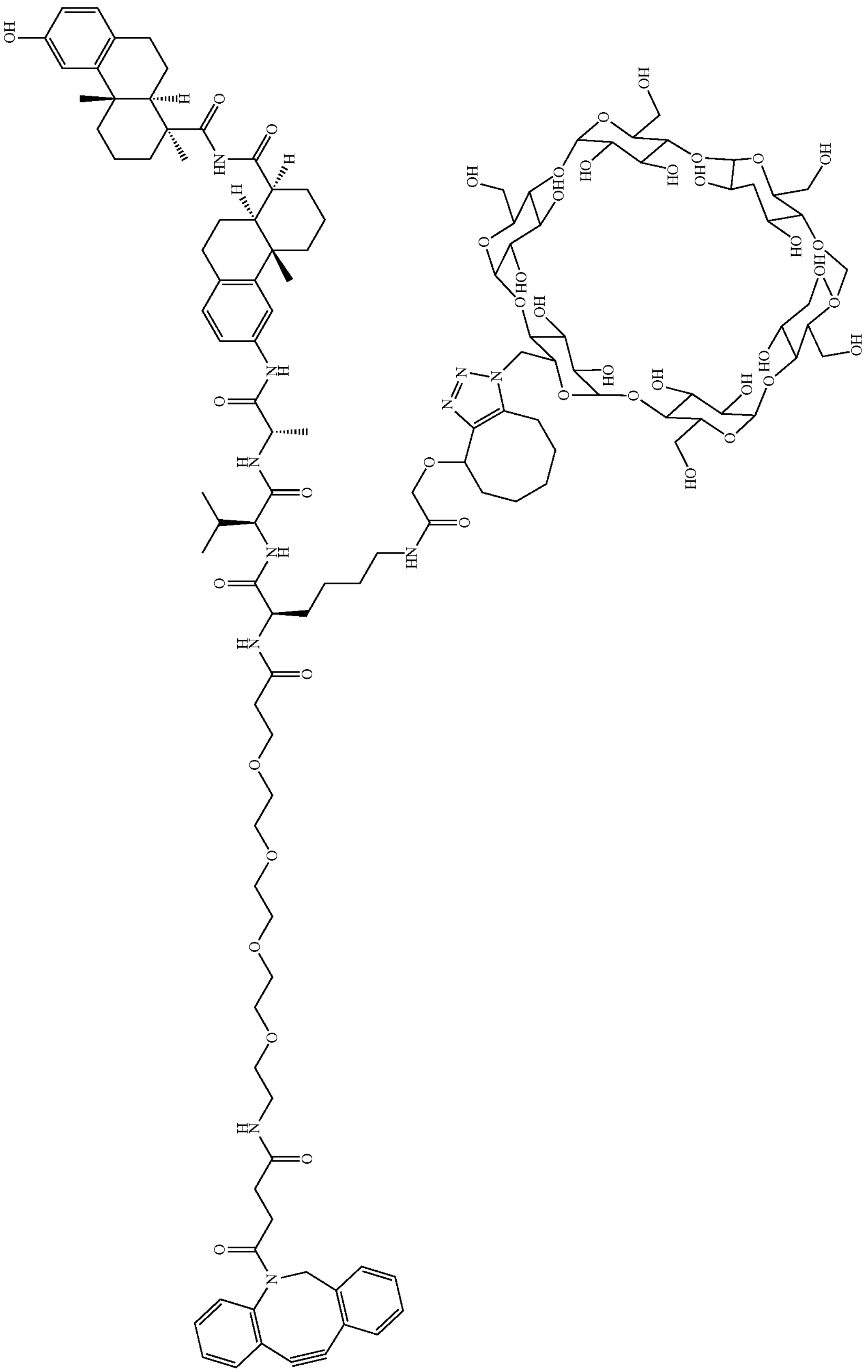

ESI m/z: 1261 $(M/2+H)^+$.

$^1H$ NMR (500 MHz, methanol$_{d4}$) δ 7.69-7.44 (m, 6H), 7.41-7.30 (m, 3H), 7.26 (d, J=6.8 Hz, 1H), 7.04-6.96 (m, 1H), 6.88 (d, J=8.4 Hz, 1H), 6.72 (d, J=1.9 Hz, 1H) 6.56 (dd, J=8.3, 2.4 Hz, 1H), 5.25-4.94 (m, 6H), 4.75-4.55 (m, 16H), 4.53-3.41 (m, 49H), 3.33-1.20 (m, 53H), 1.18-1.10 (m, 6H), 1.06-0.94 (m, 6H) ppm.

Anal. HPLC: 99%, Retention time: 6.55 min (method B).

Solubility: 0.05 mg/mL water.

Example 50

Preparation of {4-[(2S)-2-[(2S)-2-[(2R)-2-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-6-(1-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-9-yl)oxy]acetamido}-3,6,9,12-tetraoxapentadecan-15-amido)hexanamido]-3-methylbutanamido]-5-(carbamoylamino)pentanamido]phenyl}methyl N-(2-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]oxy}ethyl)carbamate (See FIG. 8 and Table 7)

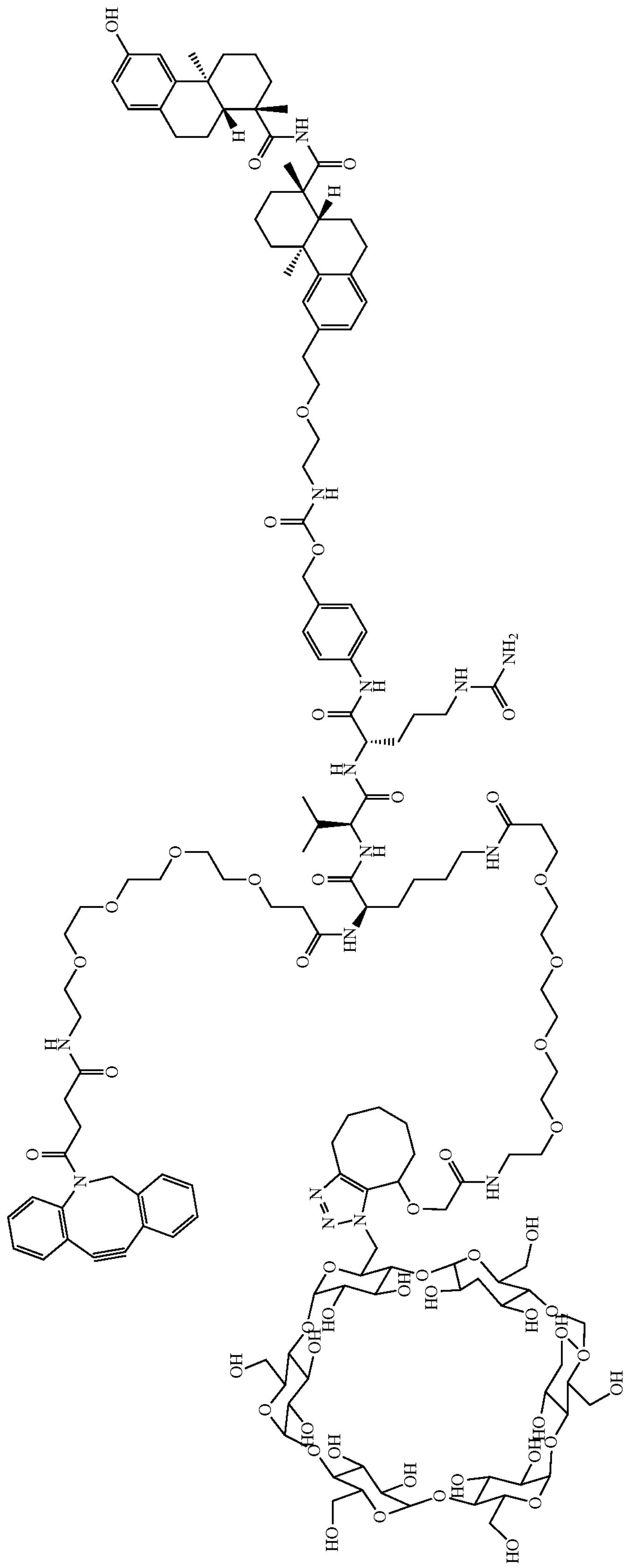

To a solution of compound 9i (25 mg, 9.9 μmol) and DIBAC-Suc-$PEG_4$-OSu 4b (6.8 mg, 12 μmol) in DMF (1 mL) was added triethylamine (2.0 mg, 20 μmol) and the mixture was stirred at 20-25° C. for 16 hours. The reaction was then deemed complete according to LCMS. Most of the volatiles were removed in vacuo and the residue was purified by prep-HPLC (method B) to give (12 mg, 39% yield) as a white solid.

ESI m/z: 1017 $(M/3+H)^+$.

$^1$H NMR (500 MHz, $DMSO_{d6}$) δ 9.68 (s, 1H), 8.21-8.04 (m, 3H), 7.88-7.74 (m, 2H), 7.71-7.56 (m, 3H), 7.52-7.21 (m, 8H), 6.93 (d, J=8.6 Hz, 1H), 6.84-6.77 (m, 1H), 6.70-6.58 (m, 2H), 6.51 (d, J=8.1 Hz, 1H), 6.01 (s, 1H), 5.78-5.33 (m, 12H), 5.22-4.51 (m, 14H), 4.43-4.12 (m, 4H), 4.07-3.55 (m, 35H), 3.53-3.33 (m, 38H), 3.33-2.52 (m, 32H), 2.43-1.21 (m, 41H), 1.20-0.77 (m, 14H) ppm.

Anal. HPLC: 96%, Retention time: 6.68 min (method B).

Solubility: 0.33 mg/mL water.

Example 51

Preparation of {Bicyclo[6.1.0]non-4-yn-9-yl}methyl N-(14-{[(1R)-1-{[(1S)-1-{[(1S)-1-{[(4bS,8S,8aR)-8-{[(1S,4aS,10aR)-6-hydroxy-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}ethyl]carbamoyl}-2-methylpropyl]carbamoyl}-5-(1-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.$2^{3,6}$.$2^{8,11}$.$2^{13,16}$.$2^{18,21}$.$2^{23,26}$]dotetracontan-5-yl]methyl}-1H,4H,5H,6H,7H,8H,9H-cycloocta[d][1,2,3]triazol-9-yl)oxy]acetamido}-3,6,9,12-tetraoxapentadecan-15-amido)pentyl]carbamoyl}-3,6,9,12-tetraoxatetradecan-1-yl)carbamate (See FIG. 8 and Table 7)

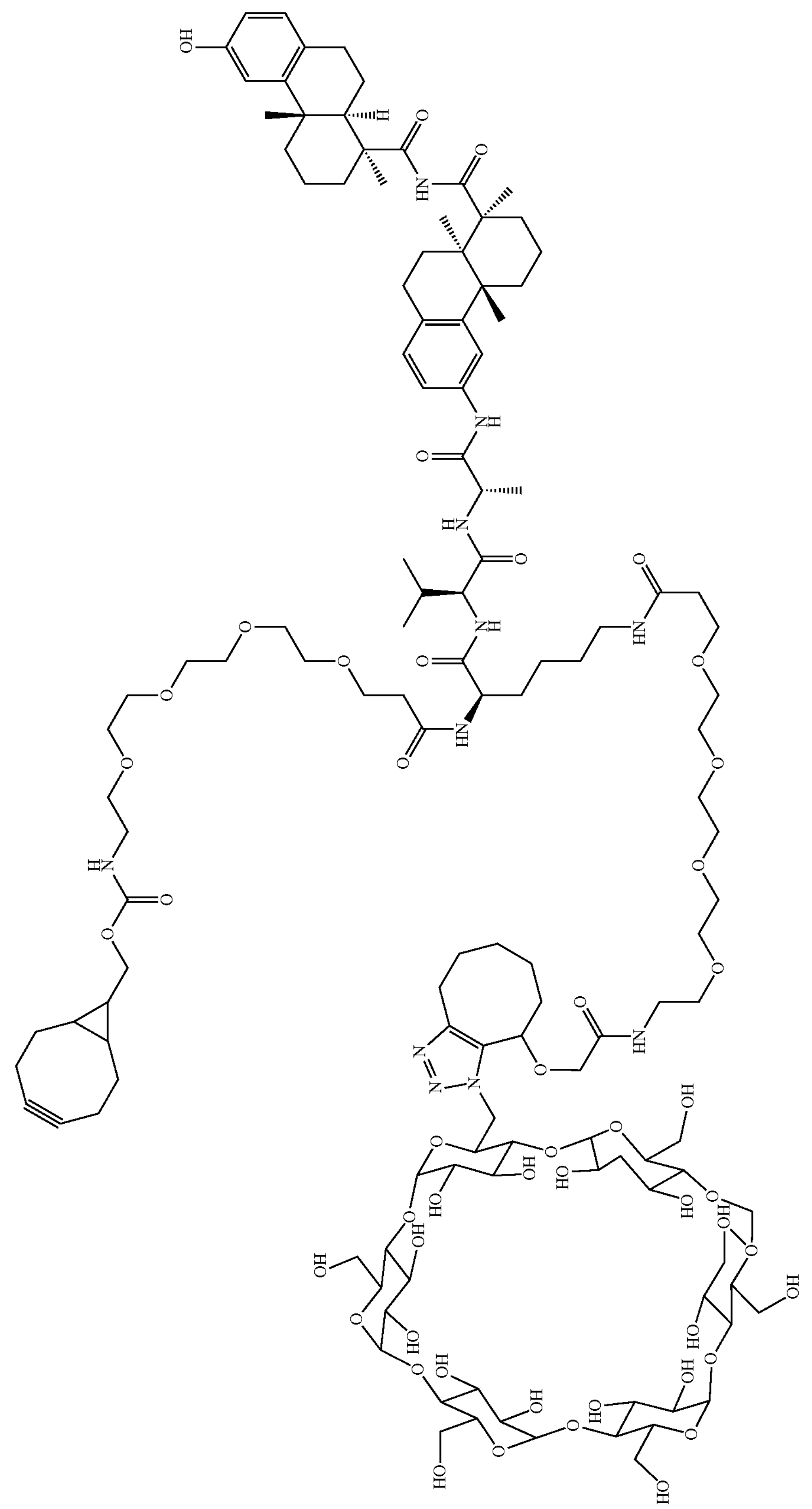

ESI m/z: 1330 $(M/2+H)^+$.

$^1H$ NMR (500 MHz, $DMSO_{d6}$) δ 9.70 (br s, 0.6H), 9.28 (br s, 0.4), 9.00 (s, 1H), 8.26-7.75 (m, 5H), 7.56-7.35 (m, 2H), 7.16-7.03 (m, 1H), 7.01-6.86 (m, 1H), 6.81 (d, J=8.3 Hz, 1H), 6.63 (s, 1H), 6.50 (d, J=8.8 Hz, 1H), 5.71-5.32 (m, 12H), 4.87-4.49 (m, 12H), 4.42-3.93 (m, 8H), 3.90-3.54 (m, 25H), 3.52-3.33 (m, 28H), 3.33-2.66 (m, 17H), 2.33-1.20 (m, 58H), 1.19-0.77 (m, 21H) ppm.

Anal. HPLC: >99%, Retention time: 6.33 min (method B).

Solubility: 0.33 mg/mL water.

Example 52

Prepared according to FIG. 8 and Table 7

Preparation of {Bicyclo[6.1.0]non-4-yn-9-yl}methyl N-(14-{[(1R)-1-{[(1S)-1-{[(1S)-1-{[4-({[(2-{[(4bS, 8S,8aR)-8-({[(1 S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8, 8a,9,10-octahydrophenanthren-3-yl]oxy}ethyl)carbamoyl]oxy}methyl)phenyl]carbamoyl}-4-(carbamoylamino)butyl]carbamoyl}-2-methylpropyl]carbamoyl}-5-(1-{2-[(1-{[31,32,33, 34,35,36,37,38,39,40,41,42-dodecahydroxy-10,15, 20,25,30-pentakis(hydroxymethyl)-2,4,7,9,12,14,17, 19,22,24,27,29-dodecaoxaheptacyclo[26.2.2. $2^{3,6}.2^{8,11}.2^{13,16}.2^{18,21}.2^{23,26}$]dotetracontan-5-yl] methyl}-1H,4H,5H,6H,7H,8H,9H-cycloocta[d][1,2, 3]triazol-9-yl)oxy]acetamido}-3,6,9,12-tetraoxapentadecan-15-amido)pentyl]carbamoyl}-3,6,9,12-tetraoxatetradecan-1-yl)carbamate (See FIG. 8 and Table 7)

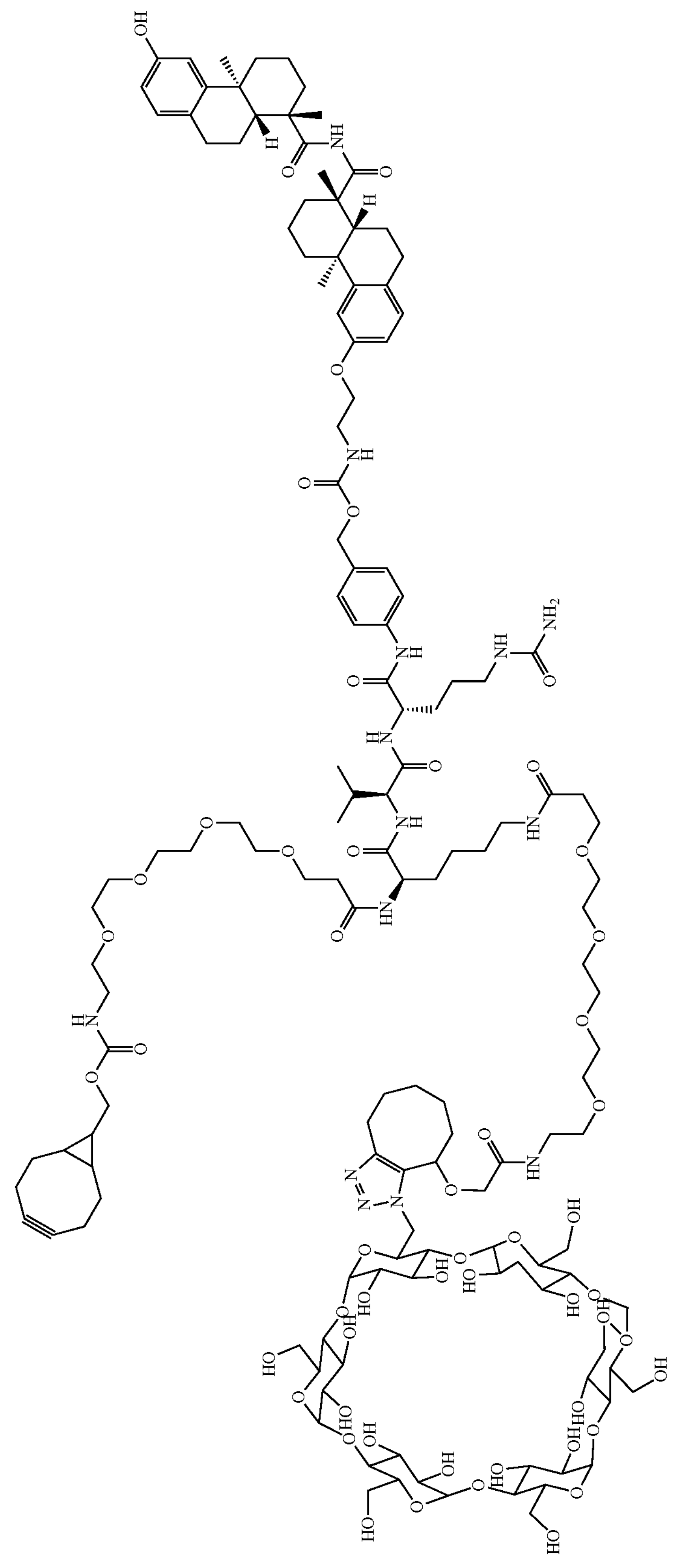

ESI m/z: 1470 $(M/2+H)^+$.

$^1H$ NMR (500 MHz, $DMSO_{d6}$) 69.68 (s, 1H), 9.00 (s, 1H), 8.21-8.03 (m, 2H), 7.62 (d, J=8.4 Hz, 2H), 7.27 (d, J=8.3 Hz, 2H) 6.93 (d, J=8.8 Hz, 1H) 6.81 (d, J=8.4 Hz, 1H), 6.80 (s, 1H), 6.67 (d, J=8.6 Hz, 1H), 6.63 (s, 1H), 6.50 (d, J=7.9 Hz, 1H), 5.99 (s, 1H), 5.64-5.37 (m, 12H), 5.14 (s, 1H), 5.00-4.50 (m, 13H), 4.38-4.29 (m, 3H), 4.20-4.13 (m, 1H), 4.09-3.97 (m, 10H), 3.95-3.89 (m, 2H), 3.86-3.54 (m, 23H), 3.52-3.33 (m, 28H), 3.16-2.61 (m, 17H), 2.45-1.20 (m, 66H), 1.18-0.80 (m, 21H) ppm.

Anal. HPLC: >99%, Retention time: 6.62 min (method B).

Solubility: 0.29 mg/mL water.

Example 53

Preparation of 1-(4-{2-Azatricyclo[10.4.0.0$^{4,9}$]hexadeca-1(12),4(9),5,7,13,15-hexaen-10-yn-2-yl}-4-oxobutanamido)-N-[(1R)-1-{[(1S)-1-{[(1S)-1-{[(4bS,8S,8aR)-8-{[(1S,4aS,10aR)-6-hydroxy-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}ethyl]carbamoyl}-2-methylpropyl]carbamoyl}-5-(1-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-9-yl)oxy]acetamido}-3,6,9,12-tetraoxapentadecan-15-amido)pentyl]-3,6,9,12-tetraoxapentadecan-15-amide (See FIG. 8 and Table 7)

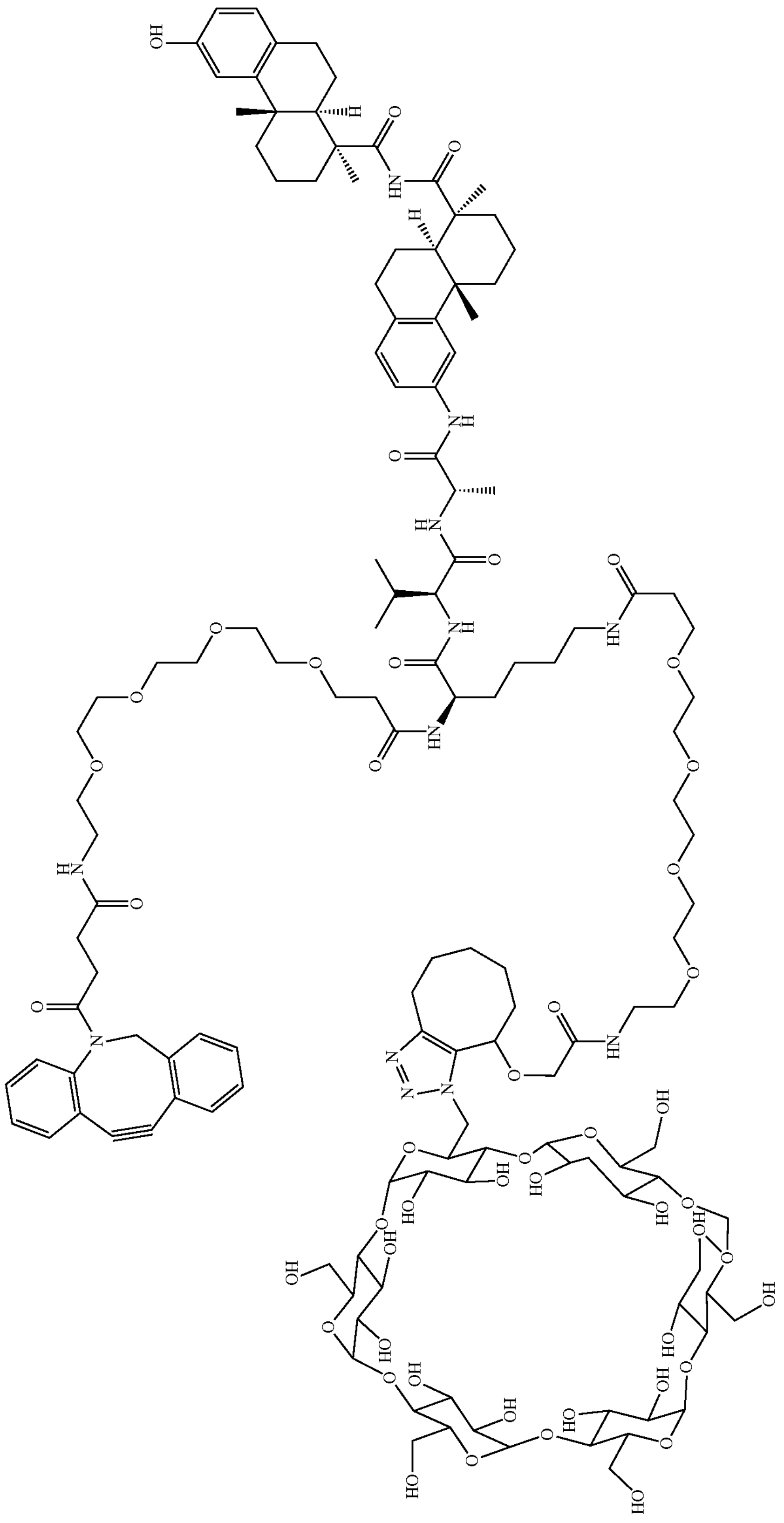

ESI m/z: 1385.9 $(M/2+H)^+$.

$^1H$ NMR (500 MHz, $DMSO_{d6}$) δ 9.71 (br s, 0.6H), 9.30 (brs, 0.4H), 9.01 (s, 1H), 8.29-7.99 (m, 4H), 7.89-7.76 (m, 3H), 7.74-7.60 (m, 2H), 7.58-7.27 (m, 7H), 7.01-6.92 (m, 1H), 6.82 (d, J=8.1 Hz, 1H), 6.68-6.48 (m, 2H), 5.71-5.45 (m, 12H), 5.17-4.69 (m, 2H), 4.90-4.50 (m, 12H), 4.44-3.54 (m, 33H), 3.54-3.41 (m, 38H), 3.33-2.54 (m, 15H), 2.43-1.19 (m, 44H), 1.18-0.66 (m, 18H) ppm.

Anal. HPLC: 98%, Retention time: 6.42 min (method B).

Solubility: 0.18 mg/mL water.

Example 54

Preparation of {Bicyclo[6.1.0]non-4-yn-9-yl}methyl N-(14-{[(1R)-1-{[(1S)-1-{[(1S)-1-{[(4bS,8S,8aR)-8-{[(1S,4aS,10aR)-6-hydroxy-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}ethyl]carbamoyl}-2-methylpropyl]carbamoyl}-5-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}pentyl]carbamoyl}-3,6,9,12-tetraoxatetradecan-1-yl)carbamate (See FIG. 8 and Table 7)

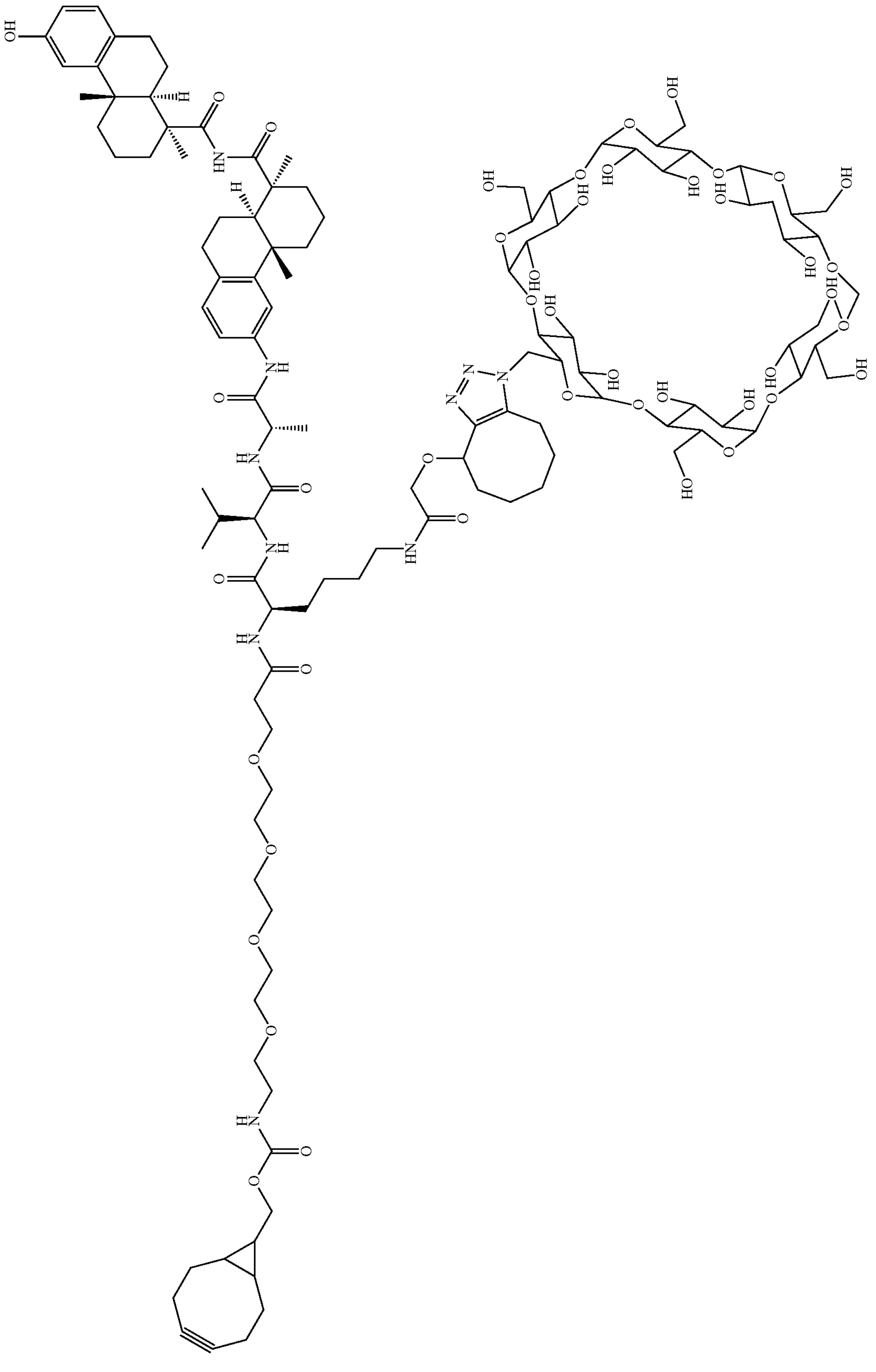

ESI m/z: 1207 $(M/2+H)^+$.

$^1H$ NMR (500 MHz, methanol$_{d4}$) δ 7.62 (s, 1H) 7.39 (d, J=8.2 Hz, 1H), 7.03 (d, J=8.4 Hz, 1H), 6.89 (d, J=8.3 Hz, 1H), 6.72 (d, J=2.3 Hz, 1H), 6.56 (dd, J=8.2, 2.4 Hz, 1H), 5.21 (t, J=2.8 Hz, 1H), 4.99-4.95 (m, 4H), 4.65-3.43 (m, 57H), 3.31-2.74 (m, 11H), 2.55-1.22 (m, 55H), 1.16 (s, 3H), 1.13 (s, 3H), 1.06-0.87 (m, 9H) ppm.

Anal. HPLC: >99%, Retention time: 6.37 min (method B).

Example 55

Preparation of 1-(4-{2-Azatricyclo[10.4.0.0$^{4,9}$]hexadeca-1(12),4(9),5,7,13,15-hexaen-10-yn-2-yl}-4-oxobutanamido)-N-[(1R)-1-{[(1S)-1-{[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}ethyl]carbamoyl}-2-methylpropyl]carbamoyl}-5-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}pentyl]-3,6,9,12-tetraoxapentadecan-15-amide (See FIG. 8 and Table 7)

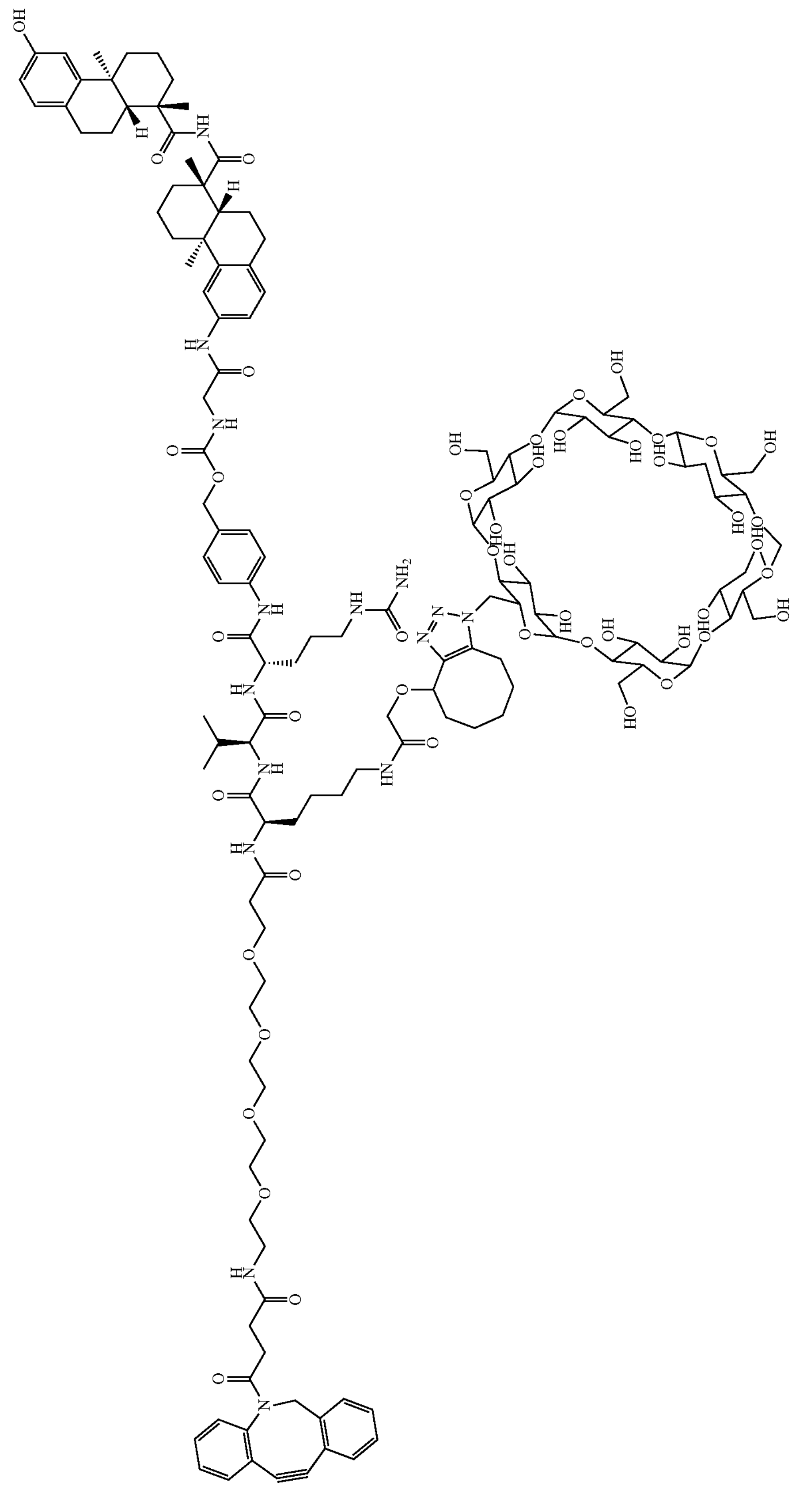

ESI m/z: 1409 $(M/2+H)^+$.

$^1H$ NMR (500 MHz, $DMSO_{d6}$) δ 9.79 (s, 1H), 9.68 (s, 1H), 8.99 (s, 1H), 8.24-8.05 (m, 3H), 7.86-7.73 (m, 2H), 7.71-7.58 (m, 3H), 7.54-7.42 (m, 4H), 7.42-7.25 (m, 5H), 6.96 (d, J=8.5 Hz, 1H), 6.81 (d, J=8.4 Hz, 1H), 6.63 (s, 1H), 6.57-6.45 (m, 1H), 5.99 (s, 1H), 5.69-5.31 (m, 12H), 5.17-4.49 (m, 14H), 4.39-3.95 (m, 5H), 3.90-3.51 (m, 25H), 3.50-3.33 (m, 32H), 3.33-2.53 (m, 21H), 2.44-1.20 (m, 41H), 1.21-0.77 (m, 16H) ppm.

Anal. HPLC: 99%, Retention time: 6.33 and 6.44 min (method B).

Example 56

Preparation of {4-[(2S)-2-[(2S)-2-[(2R)-2-[1-(4-{2-Azatricyclo[10.4.0.$0^{4,9}$]hexadeca-1(12),4(9),5,7,13,15-hexaen-10-yn-2-yl}-4-oxobutanamido)-3,6,9,12-tetraoxapentadecan-15-amido]-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.$2^{3,6}$.$2^{8,11}$.$2^{13,16}$.$2^{18,21}$.$2^{23,26}$]dotetracontan-5-yl]methyl}-1H,4H,5H,6H,7H,8H,9H-cycloocta[d][1,2,3]triazol-4-yl)oxy]acetamido}hexanamido]-3-methylbutanamido]-5-(carbamoylamino)pentanamido]phenyl}methyl N-[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}-2-hydroxyethyl]carbamate (See FIG. 8 and Table 7)

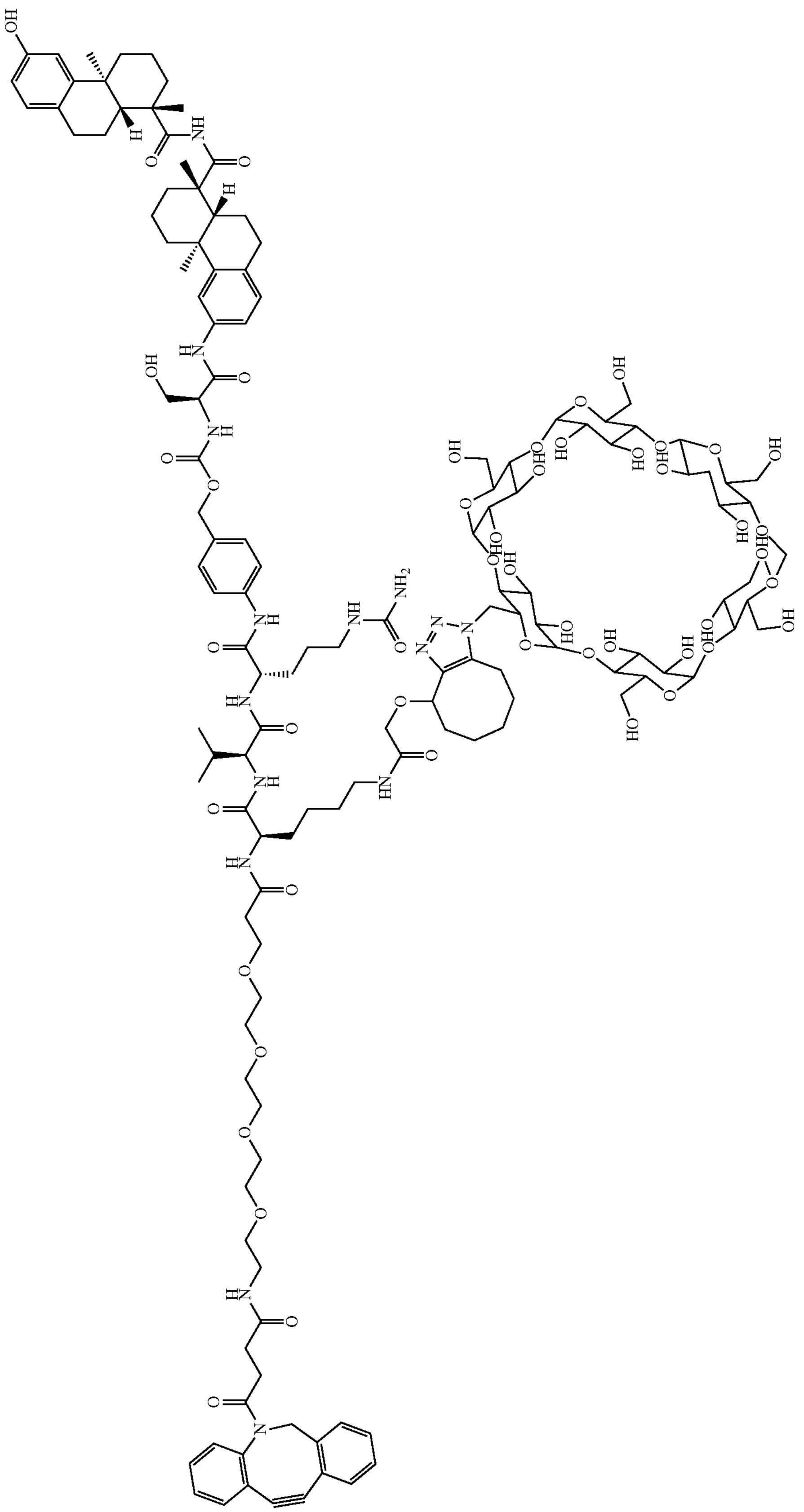

ESI m/z: 1424.3 $(M/2+H)^+$.

$^1H$ NMR (500 MHz, $DMSO_{d6}$) δ 9.81 (s, 1H), 9.65 (s, 1H), 8.97 (s, 1H), 8.28-8.04 (m, 3H), 7.91-7.73 (m, 2H), 7.73-7.16 (m, 12H), 6.95 (d, J=8.8 Hz, 1H), 6.81 (d, J=7.8 Hz, 1H), 6.73-6.59 (m, 1H), 6.59-6.44 (m, 1H), 5.98 (s, 1H), 5.71-5.27 (m, 12H), 5.23-4.48 (m, 14H), 4.43-3.93 (m, 5H), 4.09-3.50 (m, 24H), 3.51-3.33 (m, 31H), 3.33-2.53 (m, 17H), 2.42-1.08 (m, 51H), 1.06-0.67 (m, 14H) ppm.

Anal. HPLC: >99%, Retention time: 6.11 and 6.21 min (method B).

Solubility: <0.1 mg/mL water.

Example 57

Preparation of 1-(4-{2-Azatricyclo[10.4.0.0+]hexadeca-1(12),4(9),5,7,13,15-hexaen-10-yn-2-yl}-4-oxobutanamido)-N-[(1R)-1-{[(1S)-1-{[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}ethyl]carbamoyl}-2-methylpropyl]carbamoyl}-5-{2-[(1-{[41,42,43,44,45,46,47,48,49,50,51,52,53,54,55,56-hexadecahydroxy-10,15,20,25,30,35,40-heptakis(hydroxymethyl)-2,4,7,9,12,14,17,19,22,24,27,29,32,34,37,39-hexadecaoxanonacyclo[26.2.2.2$^{3,6}$.2$^{8,11}$.2$^{13,16}$.2$^{18,21}$.2$^{23,26}$]hexapentacontan-5-yl]methyl}-1H,4H,5H,6H,7H,8H,9H-cycloocta[d][1,2,3]triazol-4-yl)oxy]acetamido}pentyl]-3,6,9,12-tetraoxapentadecan-15-amide (See FIG. 9 and Table 7)

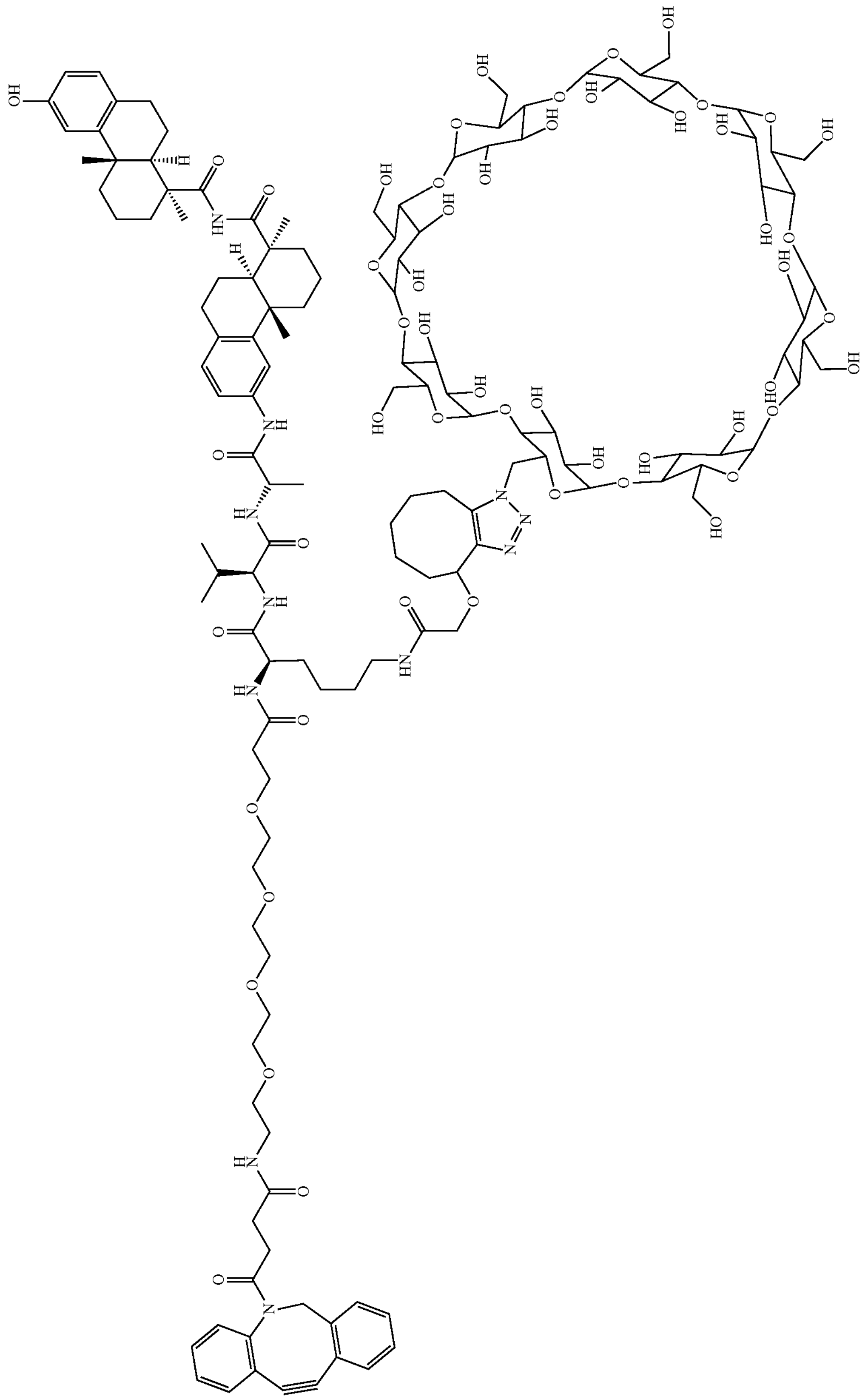

$C_{136}H_{195}N_{11}O_{54}$, Exact mass: 2846.3

ESI m/z: 1424.2 $(M/2+H)^+$. $^1H$ NMR (500 MHz, $DMSO_{d6}$) δ 9.26 (s, 1H), 8.95 (s, 1H), 8.24-7.98 (m, 4H), 7.81 (d, J=5.6 Hz, 1H), 7.72 (t, J=5.5 Hz, 1H), 7.67 (d, J=8.1 Hz, 1H), 7.61 (d, J=7.4 Hz, 1H), 7.55 (s, 1H), 7.53-7.25 (m, 7H), 6.95 (d, J=8.5 Hz, 1H), 6.81 (d, J=8.4 Hz, 1H), 6.63 (d, J=2.1 Hz, 1H), 6.50 (dd, J=8.2, 2.1 Hz, 1H), 5.94-5.58 (m, 15H), 5.39-4.43 (m, 17H), 4.37-4.24 (m, 3H), 4.13-4.08 (m, 1H), 3.98-3.33 (m, 52H), 3.26-2.52 (m, 18H), 2.40-1.18 (m, 48H), 1.18-0.63 (m, 19H) ppm.

Example 58

Prepared according to FIG. 8 and Table 7.

{4-[(2S)-2-[(2S)-2-[1-(4-{2-Azatricyclo[10.4.0.$0^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl N-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.$0^{2,9}$.$0^{4,8}$.$0^{13,18}$]icosa-14,17-dien-8-yl]-2-oxoethyl}carbamate

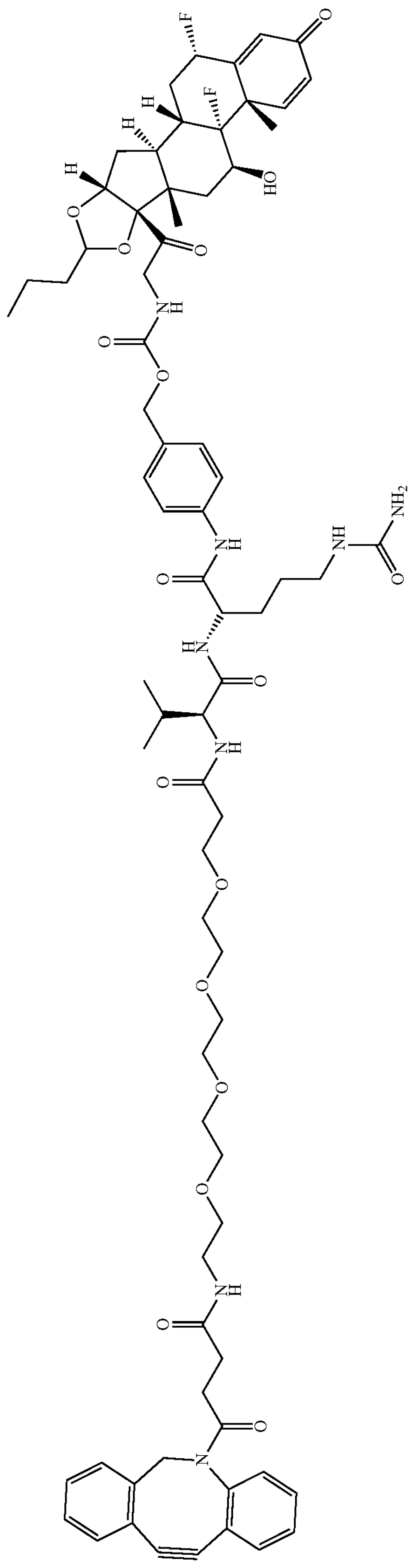

$C_{74}H_{94}F_2N_8O_{17}$, Exact mass: 1404.7

ESI m/z: 1406 $(M+H)^+$. $^1H$ NMR (500 MHz, $DMSO_{d6}$) δ 9.99 (s, 1H), 8.11 (d, J=7.5 Hz, 1H), 7.88 (d, J=8.5 Hz, 1H), 7.80-7.75 (m, 1H), 7.70-7.66 (m, 1H), 7.65-7.60 (m, 3H), 7.53-7.33 (m, 6H), 7.33-7.28 (m, 3H), 6.30 (dd, J=10.0 Hz, 1.5 Hz, 1H), 6.11 (s, 1H), 6.10-6.00 (m, 1H), 5.72-5.55 (m, 2H), 5.41 (s, 2H), 5.05-5.01 (m, 1H), 4.97 (s, 2H), 4.80-4.72 (m, 1H), 4.60-4.58 (m, 1H), 4.43-4.33 (m, 1H), 4.25-4.10 (m, 3H), 3.88-3.80 (m, 1H), 3.65-3.55 (m, 3H), 3.50-3.40 (m, 12H), 3.30-3.25 (m, 2H), 3.12-2.90 (m, 4H), 2.70-2.55 (m, 2H), 2.48-2.35 (m, 2H), 2.30-2.20 (m, 2H), 2.15-1.95 (m, 4H), 1.86-1.65 (m, 3H), 1.64-1.54 (m, 5H), 1.49 (s, 4H), 1.46-1.34 (m, 5H), 0.90-0.80 (m, 12H) ppm.

Anal. HPLC: 100%, Retention time: 7.40 min (method B).

Solubility: 0.02 mg/mL water.

Example 59

Prepared according to FIG. 8 and Table 7.

{4-[(2S)-2-[(2S)-2-[(2R)-2-[1-(4-{2-Azatricyclo[$10.4.0.0^{4,9}$]hexadeca-1(12),4(9),5,7,13,15-hexaen-10-yn-2-yl}-4-oxobutanamido)-3,6,9,12-tetraoxa-pentadecan-15-amido]-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[$26.2.2.2^{3,6}.2^{8,11}.2^{13,16}.2^{18,21}.2^{23,26}$]dotetracontan-5-yl]methyl}-1H,4H,5H,6H,7H,8H,9H-cycloocta[d][1,2,3]triazol-4-yl)oxy]acetamido}hexanamido]-3-methylbutanamido]-5-(carbamoylamino)pentanamido]phenyl}methyl N-{2-[(1S,2S,4R,8S,9S,11 S,12R,13S,19S)-12,19-difluoro-11-hydroxy-9,13-dimethyl-16-oxo-6-propyl-5,7-dioxapentacyclo[$10.8.0.0^{2,9}.0^{4,8}.0^{13,18}$]icosa-14,17-dien-8-yl]-2-oxoethyl}carbamate

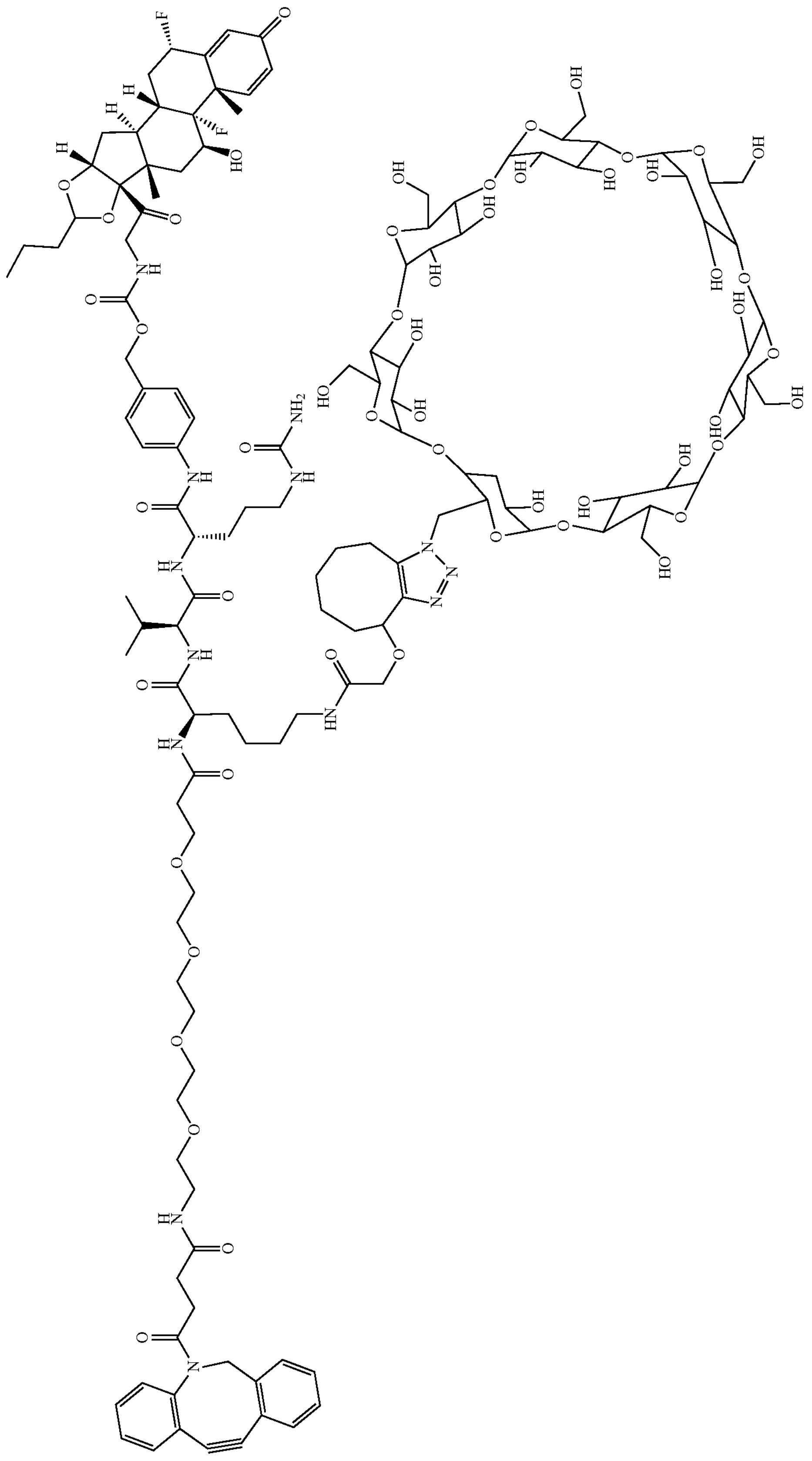

$C_{126}H_{177}F_2N_{13}O_{49}$, Exact mass: 2694.2

ESI m/z: 1349 $(M+H)^+$. $^1H$ NMR (500 MHz, $DMSO_{d6}$) δ 9.71 (s, 1H), 8.30-8.00 (m, 3H), 8.00-7.74 (m, 2H), 7.70-7.58 (m, 5H), 7.52-7.20 (m, 12H), 6.35-6.20 (m, 2H), 6.15-5.85 (m, 3H), 5.80-5.35 (m, 18H), 5.25-4.90 (m, 6H), 4.90-4.50 (m, 14H), 4.40-4.25 (m, 4H), 4.25-4.10 (m, 3H), 4.10-3.95 (m, 2H), 3.95-3.55 (m, 22H), 3.55-3.40 (m, 22H), 3.20-3.00 (m, 6H), 3.00-2.85 (m, 3H), 2.65-2.55 (m, 1H), 2.25-2.20 (m, 4H), 2.10-1.95 (m, 6H), 1.80-1.70 (m, 5H), 1.70-1.50 (m, 10H), 1.50-1.45 (m, 9H), 0.90-0.80 (m, 14H) ppm.

Anal. HPLC: 100%, Retention time: 6.23 min (method B).

Solubility: 0.026 mg/mL water.

Example 60

Prepared according to FIG. 8 and Table 7.

(1R,8S,9S)-Bicyclo[6.1.0]non-4-yn-9-ylmethyl N-(14-{[(1R)-1-{[(1S)-1-{[(1S)-4-(carbamoylamino)-1-[(4-{[({2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl}carbamoyl)oxy]methyl}phenyl)carbamoyl]butyl]carbamoyl}-2-methylpropyl]carbamoyl}-5-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}pentyl]carbamoyl}-3,6,9,12-tetraoxatetradecan-1-yl)carbamate

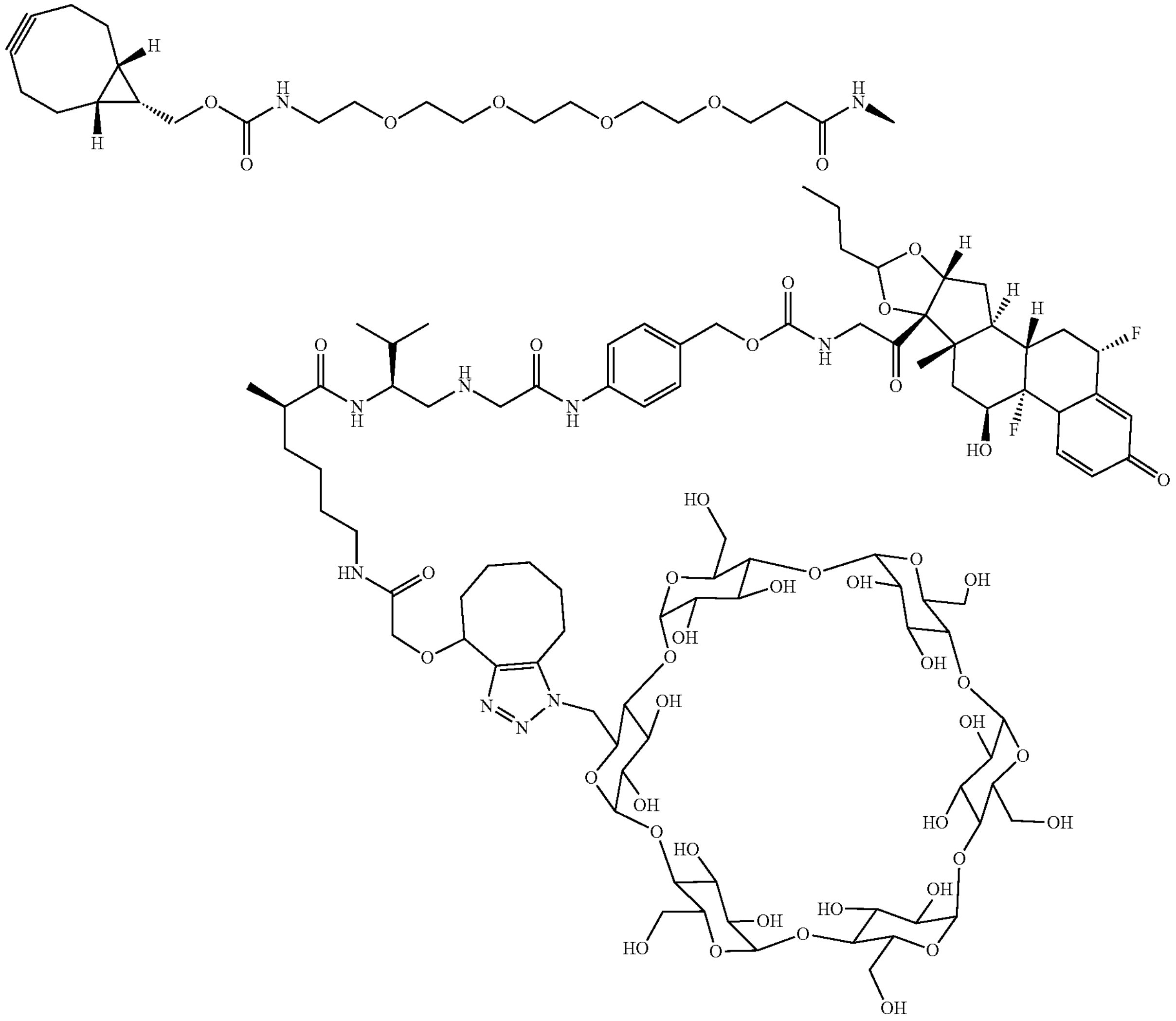

$C_{118}H_{176}F_2N_{12}O_{49}$, Exact mass: 2583.2

ESI m/z: 1292.8 $(M/2+1)^+$. $^1H$ NMR (500 MHz, $DMSO_{d6}$) δ 9.68 (s, 1H), 8.14-7.08 (m, 11H), 6.30 (d, J=10.0 Hz, 1H), 6.11 (s, 1H), 5.99 (s, 1H), 5.67-5.31 (m, 15H), 5.21-3.33 (m, 61H), 3.13-2.60 (m, 22H), 2.30-1.96 (m, 46H), 0.95-0.80 (m, 17H) ppm.

Anal. HPLC (with triazole region-isomers): 48%, Retention time: 7.31 min and 52%, Retention time: 7.41 min (method B).

Example 61

Prepared according to FIG. 8 and Table 7.

{4-[(2S)-2-[(2S)-2-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl N-(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamate

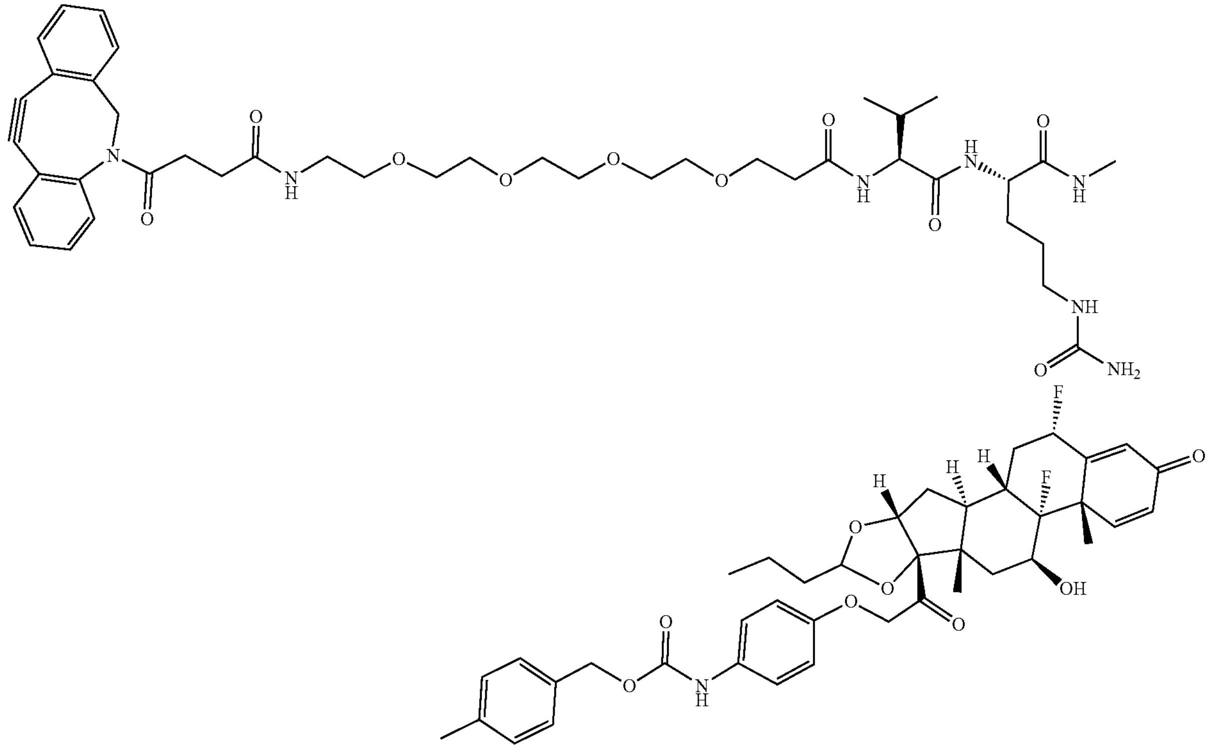

$C_{80}H_{98}F_2N_8O_{18}$, Exact mass: 1496.7

ESI m/z: 1499 $(M+H)^+$. $^1H$ NMR (400 MHz, $DMSO_{d6}$) δ 10.02 (s, 1H), 9.59 (s, 1H), 8.14 (d, J=7.6 Hz, 1H), 7.88 (d, J=8.8 Hz, 1H), 7.80-7.75 (m, 1H), 7.70-7.66 (m, 1H), 7.65-7.60 (m, 3H), 7.53-7.45 (m, 3H), 7.40-7.28 (m, 7H), 6.84 (d, J=9.2 Hz, 2H), 6.30 (dd, J=10.4 Hz, 1.6 Hz, 1H), 6.11 (s, 1H), 6.10-6.00 (m, 1H), 5.72-5.55 (m, 1H), 5.52 (s, 1H), 5.43 (s, 2H), 5.16-5.05 (m, 4H), 4.88-4.70 (m, 3H), 4.43-4.33 (m, 1H), 4.25-4.20 (m, 2H), 3.65-3.55 (m, 3H), 3.50-3.40 (m, 12H), 3.30-3.25 (m, 2H), 3.12-2.90 (m, 4H), 2.70-2.55 (m, 2H), 2.48-2.43 (m, 1H), 2.40-2.35 (m, 1H), 2.30-2.20 (m, 2H), 2.15-1.95 (m, 4H), 1.86-1.75 (m, 2H), 1.64-1.54 (m, 5H), 1.49 (s, 4H), 1.46-1.34 (m, 4H), 1.23 (s, 2H), 0.90-0.80 (m, 12H) ppm.

Anal. HPLC: 100%, Retention time: 7.99 min (method B).

Solubility: <0.01 mg/mL water.

Example 62

Prepared according to FIG. 8 and Table 7.

{4-[(2S)-2-[(2S)-2-[(2R)-2-[1-(4-{2-Azatricyclo [10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}hexanamido]-3-methylbutanamido]-5-(carbamoylamino)pentanamido]phenyl}methyl N-(4-{2-[(1S,2S,4R,8S,9S,11 S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamate

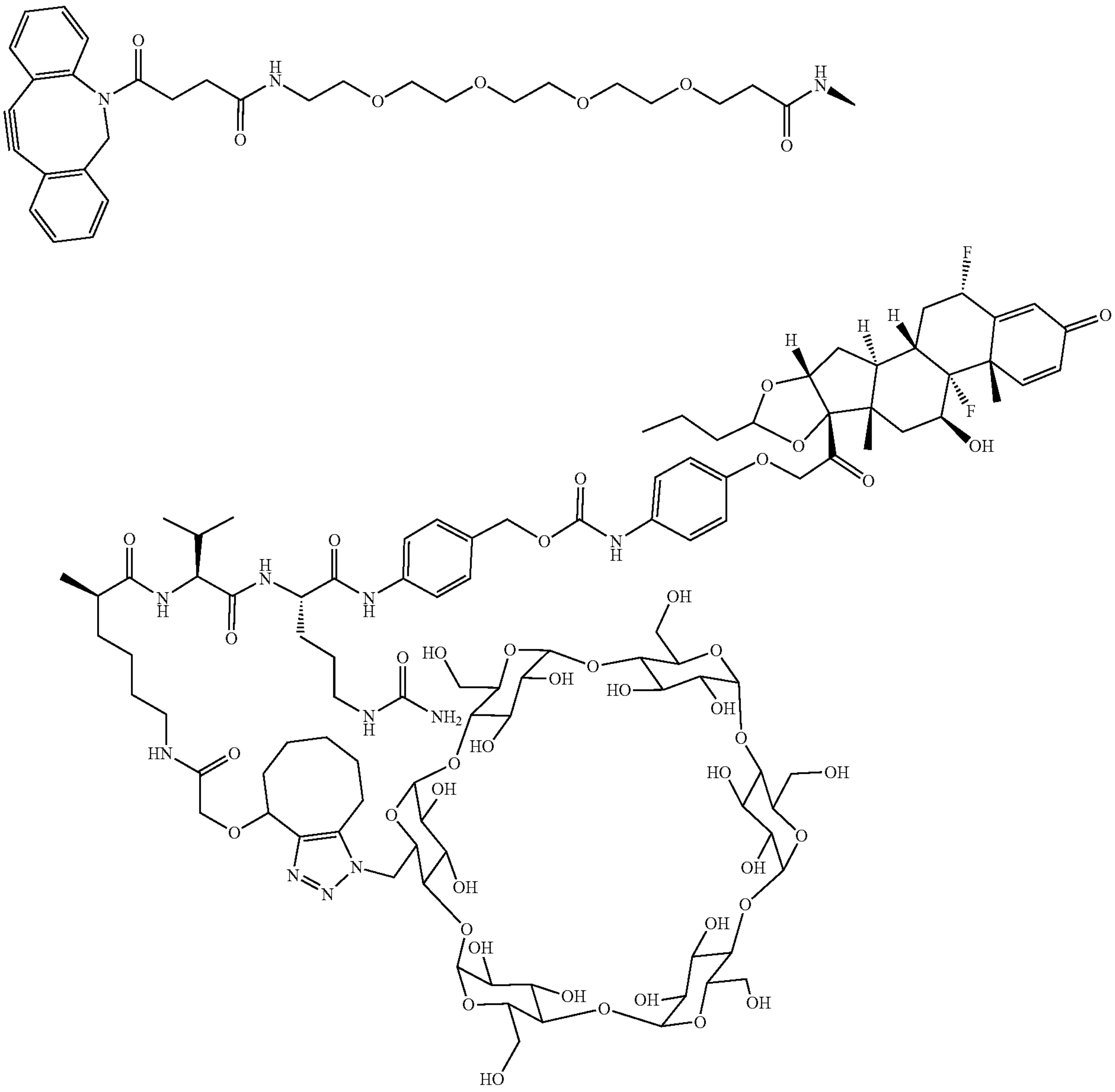

$C_{132}H_{181}F_2N_{13}O_{50}$, Exact Mass: 2786.2

ESI m/z: 1394 $(M/2+H)^+$. $^1$H NMR (500 MHz, $DMSO_{d4}$) δ 9.67 (s, 1H), 9.56 (s, 1H), 8.20-8.05 (m, 2H), 7.85-7.70 (m, 2H), 7.70-7.60 (m, 4H), 7.50-7.25 (m, 12H), 6.90-6.80 (m, 2H), 6.30 (d, J=12.5 Hz, 1H), 6.11 (s, 1H), 6.0 (s, 1H), 5.80-5.35 (m, 16H), 5.25-5.00 (m, 6H), 4.90-4.65 (m, 10H), 4.65-4.45 (m, 4H), 4.40-4.00 (m, 6H), 3.95-3.55 (m, 22H), 3.50-3.30 (m, 22H), 3.20-2.85 (m, 12H), 2.65-2.55 (m, 2H), 2.45-2.35 (m, 2H), 2.35-2.20 (m, 3H), 2.15-1.95 (m, 5H), 1.90-1.70 (m, 4H), 1.70-1.50 (m, 10H), 1.50-1.00 (m, 18H), 0.90-0.80 (m, 12H) ppm.

Anal. HPLC (with triazole region-isomers): 82%, Retention time: 7.93 min; 18%, Retention time: 8.02 min (method B).

Solubility: 0.02 mg/mL water.

Example 63

Prepared according to FIG. 8 and Table 7.

1-(4-{2-Azatricyclo[10.4.0.04,]hexadeca-1(12),4(9),5,7,13,15-hexaen-10-yn-2-yl}-4-oxobutanamido)-N-[(1R)-1-{[(1S)-1-{[(1S)-1-[(4-{2-[(1S,2S,4R,8S,9S,11 S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamoyl]ethyl]carbamoyl}-2-methylpropyl]carbamoyl}-5-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}pentyl]-3,6,9,12-tetraoxapentadecan-15-amide

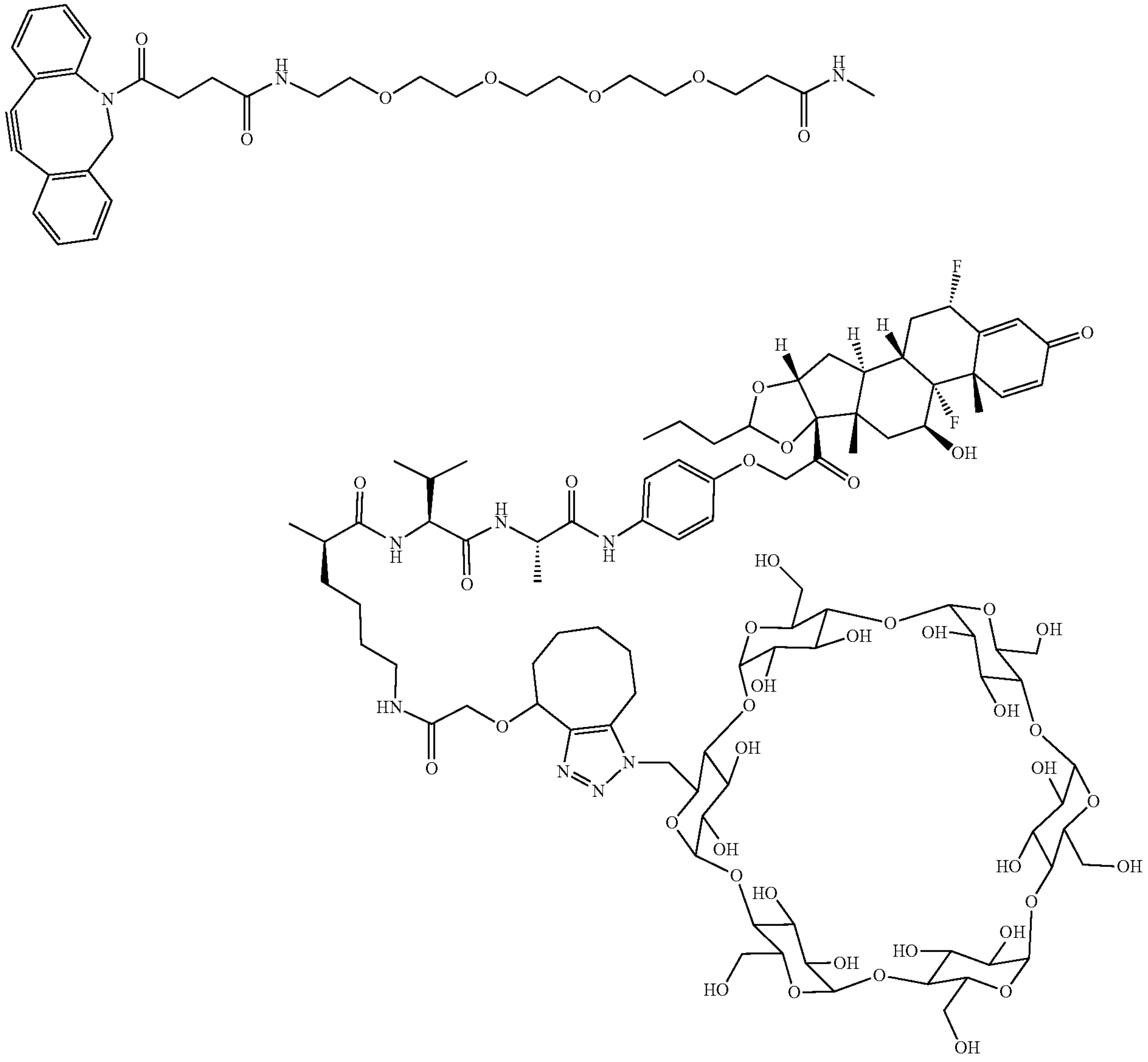

To a solution of compound 9L (19 mg, 9.4 μmol) in DMF (2 mL) were added DIBAC-Suc-PEG$_4$-OSu 4b (7.0 mg, 11 μmol) and DIPEA (2.3 mg, 18 μmol). After stirred at room temperature overnight, the resulting mixture was directly purified by prep-HPLC (method B) to give Ex105 (7 mg, 29% yield) as a white solid.

$C_{121}H_{168}F_2N_{10}O_{47}$, Exact Mass: 2551.1

ESI m/z: 1276.8 (M/2+H)$^+$. $^1$H NMR (400 MHz, DMSO$_{d6}$) δ 9.80-9.47 (m, 1H), 8.23-7.91 (m, 3H), 7.83-7.11 (m, 13H), 6.87-6.66 (m, 2H), 6.32-6.11 (m, 2H), 5.85-5.23 (m, 14H), 5.14-5.01 (m, 3H), 4.86-3.99 (m, 19H), 3.85-3.40 (m, 38H), 3.27-2.87 (m, 13H), 2.76-2.55 (m, 3H), 2.33-2.20 (m, 4H), 2.12-1.91 (m, 6H), 1.83-1.72 (m, 4H), 1.59-0.98 (m, 31H), 0.89-0.84 (m, 12H) ppm.

Anal. HPLC: 100%, Retention time: 7.76 min (method B).

Example 64

Figure 1A:
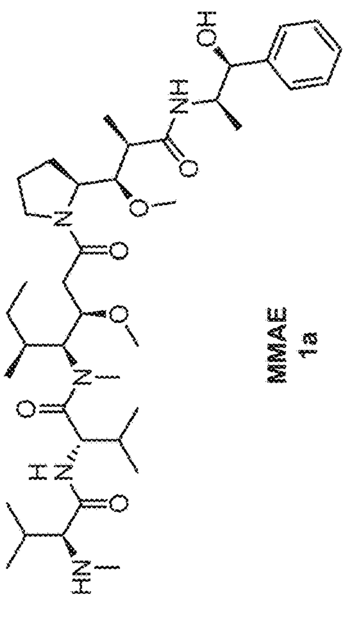
FIG. 1A shows three different types of payload compounds.
Figure 1A:
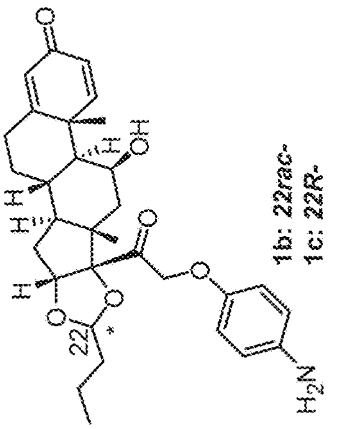
Figure 1A:
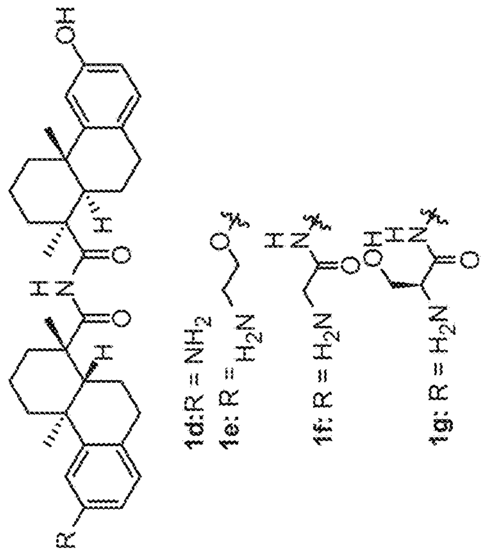
Figure 1A:
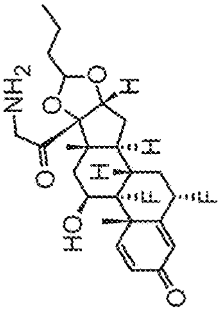
Figure 1A:
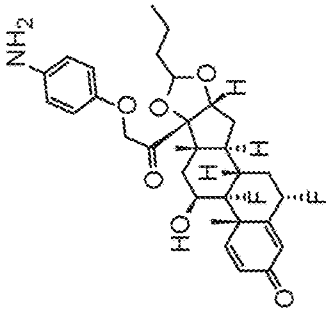
Figure 1B:
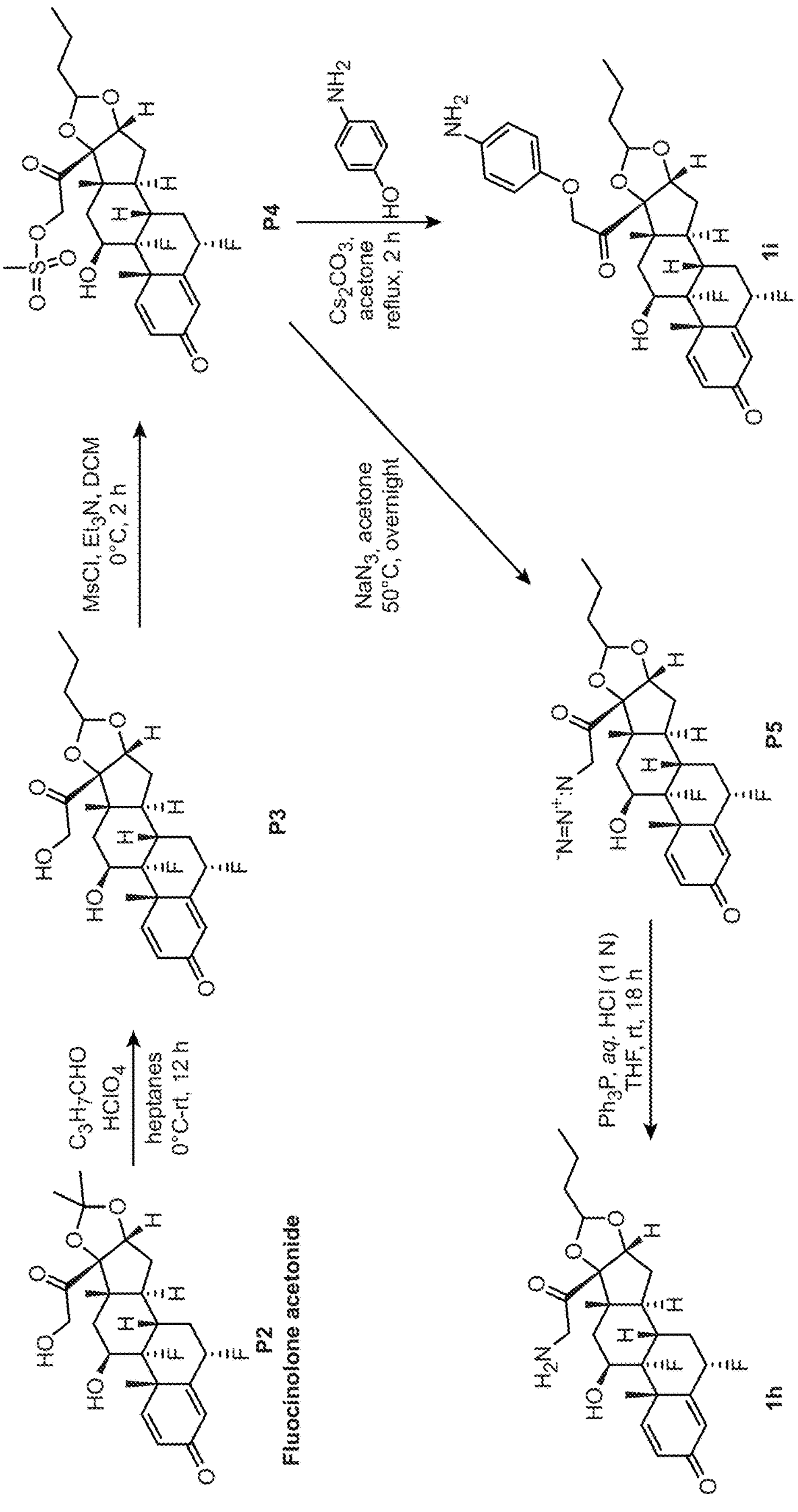
FIG. 1B shows a synthetic process for preparing payload compound 1h or 1i.

Synthesis of Payloads 1h and 1i, See FIG. 1B

Steroidal payloads 1h and 1i were prepared according to scheme 1 starting from commercial fluocinolone acetonide P2 (CAS: 67-73-2). Compound P3, obtained from P2 by ketal-exchange with butyraldehyde in the presence of perchloric acid, was converted to mesylate P4 followed by replacement of the mesylate group with azide moiety to form P5 that were further reduced to amine 1h. Otherwise, the mesylate moiety in P4 was also replaced by 4-aminophenol to afford aniline 1i.

(1S,2S,4R,8S,9S,11S,12R,13S,19S)-12,19-Difluoro-11-hydroxy-8-(2-hydroxyacetyl)-9,13-dimethyl-6-propyl-5,7-dioxapentacyclo[10.8.0.0$^{2,9}$.0$^{4,8}$.0$^{13,18}$]icosa-14,17-dien-16-one (P3)

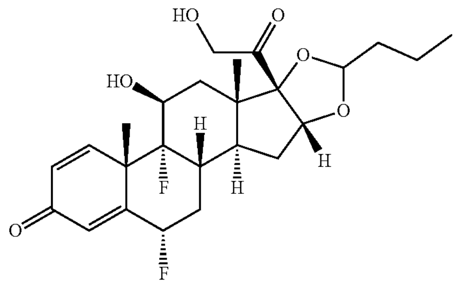

To a mixture of fluocinolone acetonide (P2, 0.90 g, 2.0 mmol) and silica gel (18 g) in heptanes (90 mL) was added butyraldehyde (0.27 mL, 3.0 mmol) at 10° C. and the suspension was stirred at 10-20° C. for 10 minutes. To the mixture was added perchloric acid (70%, 0.68 mL, 8.3 mmol) dropwise at 0° C. The reaction mixture was then stirred at 10-20° C. overnight. Most of fluocinolone acetonide P2 was consumed according to TLC and LCMS. The reaction mixture was diluted with petroleum ether and quenched with sat. aq. $Na_2CO_3$. The suspension was filtered and the solid was washed with DCM/methanol (v/v=1). The combined filtrate was concentrated in vacuo. The residue was purified by flash chromatography on silica gel (0-100% ethyl acetate in petroleum ether) to give compound P3 (0.15 g, 16% yield) as a white solid. ESI m/z: 467.1 (M+H)$^+$.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl methanesulfonate (P4)

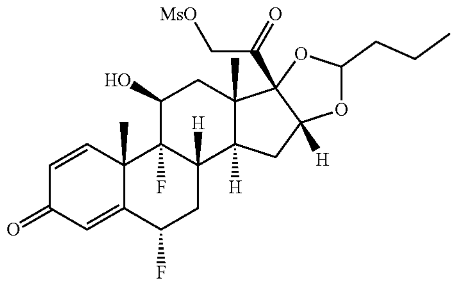

To a solution of compound P3 (0.28 g, 0.65 mmol)) and triethylamine (0.13 g, 1.3 mmol) in DCM (3 mL) was added methanesulfonyl chloride (89 mg, 0.78 mmol) at 0° C. After stirred at 0° C. for 0.5 h, the reaction mixture was diluted with DCM (20 mL). The mixture was washed with $H_2O$ (20 mL×2), dried over anhydrous $Na_2SO_4$, filtered and concentrated in vacuo. The residue was purified by silica gel column chromatography on silica gel (0-50% ethyl acetate in petroleum ether) to give compound P4 (0.26 g, >99% yield) as a white solid. ESI m/z: 545 (M+H)$^+$.

(1S,2S,4R,8S,9S,11S,12R,13S,19S)-8-(2-Azido-acetyl)-12,19-difluoro-11-hydroxy-9,13-dimethyl-6-propyl-5,7-dioxapentacyclo[10.8.0.0$^{2,9}$.0$^{4,8}$.0$^{13,18}$]icosa-14,17-dien-16-one (P5)

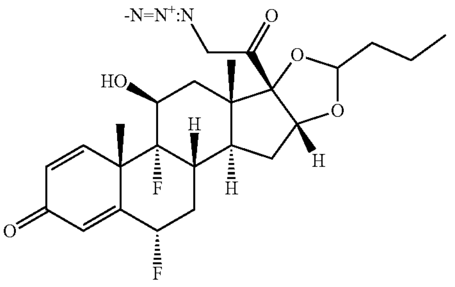

A suspension of compound P4 (1.0 g, 1.8 mmol) and sodium azide (1.2 g, 18 mmol) in acetone (15 mL) was stirred at 50° C. overnight. The mixture was cooled to RT and poured into water (80 mL). The aqueous mixture was extracted with ethyl acetate (50 mL×3). The combined organic layer was washed with brine (30 mL), dried over anhydrous $Na_2SO_4$, filtered and concentrated in vacuo to afford crude compound P5 (0.90 g, >99% yield) as a yellow solid, which was used for the next step without further purification. ESI m/z: 492 $(M+H)^+$.

Payload 1h, (1S,2S,4R,6R,8S,9S,11 S,12R,13S,19S)-8-(2-Aminoacetyl)-12,19-difluoro-11-hydroxy-9,13-dimethyl-6-propyl-5,7-dioxapentacyclo[10.8.0.0$^{2,9}$.0$^{4,8}$.0$^{13,88}$]icosa-14,17-dien-16-one; trifluoroacetic acid salt (1h)

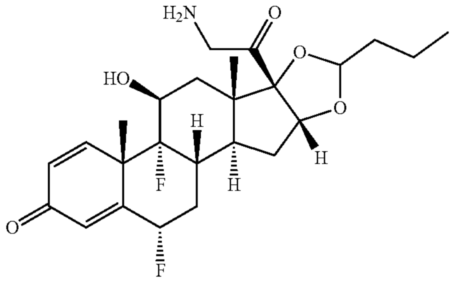

To a solution of compound P5 (0.85 g, 1.7 mmol) in THF (20 mL) was added aq. hydrochloride (1 N, 10 mL). The mixture was stirred at 28-32° C. until it turned clear, to the mixture was then added triphenylphosphine (0.68 g, 2.6 mmol). The resulting yellow clear solution was stirred at RT for 18 h. The mixture was concentrated in vacuo and the residue was purified by reversed phase flash chromatography (0-50% acetonitrile in aq. TFA (0.05%)) to give compound 1h (0.56 g, 57% yield, TFA salt) as an off-white solid. ESI m/z: 466 $(M+H)^+$. $^1H$ NMR (400 MHz, $MeOD_{d4}$) δ 7.33 (d, J=9.9 Hz, 1H), 6.40-6.29 (m, 2H), 5.69-5.45 (m, 1H), 4.93-4.92 (m, 1H), 4.71 (t, J=4.3 Hz, 1H), 4.35-4.27 (m, 2H), 3.90-3.84 (m, 1H), 2.81-2.54 (m, 1H), 2.42-2.06 (m, 3H), 1.82-1.32 (m, 11H), 1.09-0.87 (m, 6H) ppm. $^{19}F$ NMR (376 MHz, $CD_3OD$) δ−77.01, −166.24, −166.92, −188.81, −188.83 ppm. Anal. HPLC: 100%, Retention time: 6.86 min (method A).

Payload 1i, (1S,2S,4R,8S,9S,11 S,12R,13S,19S)-8-[2-(4-Aminophenoxy)acetyl]-12,19-difluoro-11-hydroxy-9,13-dimethyl-6-propyl-5,7-dioxapentacyclo[10.8.0.0$^{2,9}$.0$^{4,8}$.0$^{13,18}$]icosa-14,17-dien-16-one (ii)

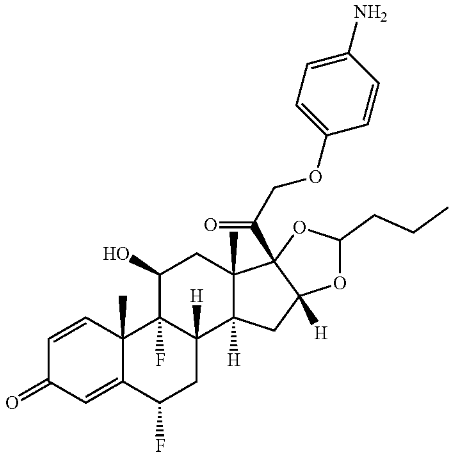

A mixture of compound P4 (93 mg, 0.17 mmol), 4-aminophenol (37 mg, 0.34 mmol) and cesium carbonate (0.11 g, 0.34 mmol) in acetone (0.5 mL) was refluxed for 2 hours. The mixture was cooled to RT and diluted with $H_2O$ (10 mL). The mixture was extracted with ethyl acetate (10 mL×3). The combined organic layer was washed with water (20 mL) and brine (20 mL), dried over $Na_2SO_4$, filtered and concentrated in vacuo. The residue was purified by prep-HPLC to give payload 1i (6.0 mg, 6.3% yield) as a white solid. ESI m/z: 298 $(M/2+H)^+$, 558 $(M+H)^+$ (10%). $^1H$ NMR (500 MHz, $MeOD_{d4}$) δ 7.34 (d, J=10.0 Hz, 1H), 6.78-6.71 (m, 4H), 6.37-6.33 (m, 2H), 5.63-5.49 (m, 1H), 5.10-4.99 (m, 1H), 4.77-4.63 (m, 2H), 4.33 (d, J=9.1 Hz, 1H), 2.74-2.57 (m, 1H), 2.39-2.13 (m, 3H), 1.98-1.31 (m, 12H), 1.03-0.93 (m, 6H) ppm. Anal. HPLC: purity 97.4%, Retention time: 7.55 min (method B).

Figure 1C:
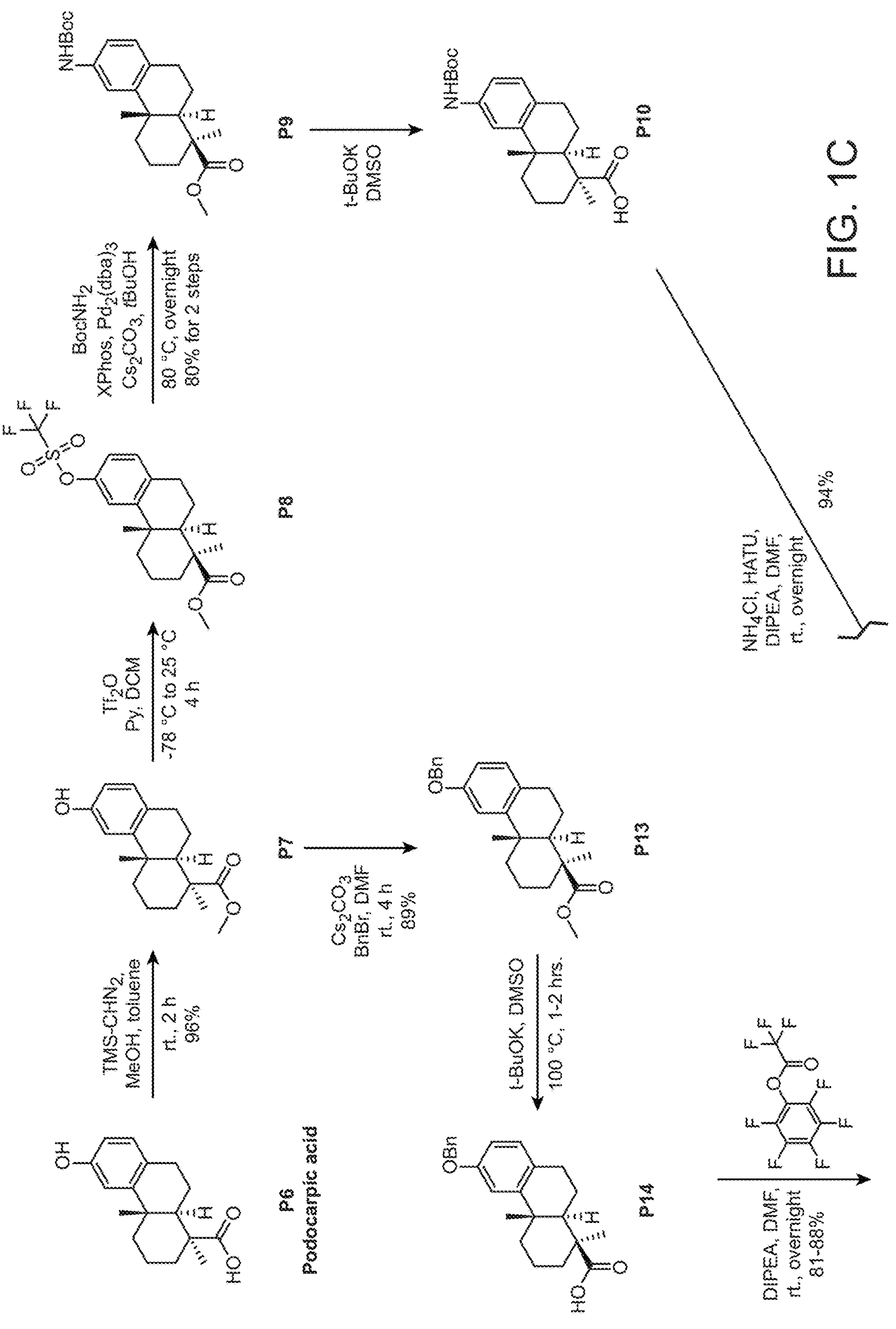
FIG. 1C shows a synthetic process for preparing payload compound 1d.
Figure 1C:
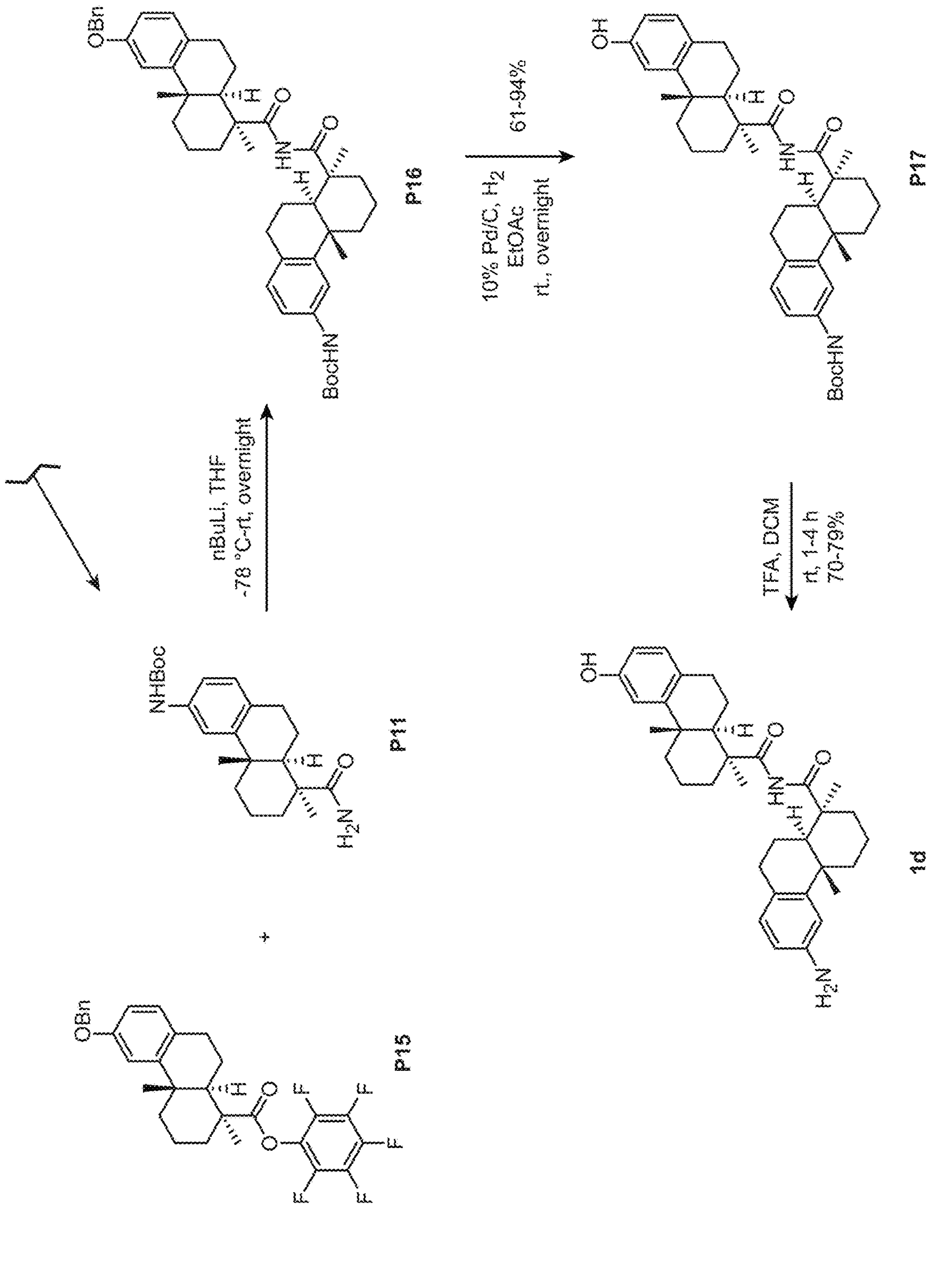

Synthesis of Payload 1d, See FIG. 1C

Methyl (1S,4aS,10aR)-6-hydroxy-1,4a-dimethyl-1,2,3,4,4a,9,10,10a-octahydrophenanthrene-1-carboxylate (P7)

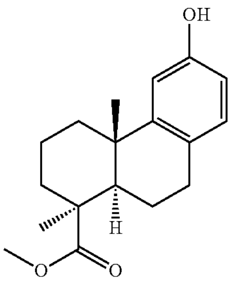 [SMILES: COC(=O)[C@@]1(C)CCC[C@]2(C)c3cc(O)ccc3CC[C@@H]12]

To a solution of podocarpic acid (P6, 90 g, 0.33 mol) in methanol (200 mL) and toluene (600 mL) was added with (trimethylsilyl)diazomethane (2 M in hexane, 200 mL). The reaction mixture was stirred at room temperature for 2 hours. The podocarpic acid was then totally consumed according to LCMS. The volatiles were removed in vacuo, and the residue was triturated from petroleum ether (2 L) to give compound P7 (91 g, 96% yield) as a white solid. ESI m/z: 289 $(M+H)^+$. $^1H$ NMR (400 MHz, $DMSO_{d6}$) δ 8.95 (s, 1H), 6.79 (d, J=8.2 Hz, 1H), 6.63 (d, J=2.4 Hz, 1H), 6.48 (dd, J=8.2, 2.4 Hz, 1H), 3.58 (s, 3H), 2.80-2.55 (m, 2H), 2.20-2.02 (m, 3H), 1.96-1.71 (m, 2H), 1.56-1.45 (m, 2H), 1.27 (t, J=13.5 Hz, 1H), 1.21 (s, 3H), 1.09 (td, J=13.5, 4.1 Hz, 1H), 0.91 (s, 3H) ppm.

Methyl (1S,4aS,10aR)-1,4a-dimethyl-6-(trifluoromethanesulfonyloxy)-1,2,3,4,4a,9,10,10a-octahydrophenanthrene-1-carboxylate (P8)

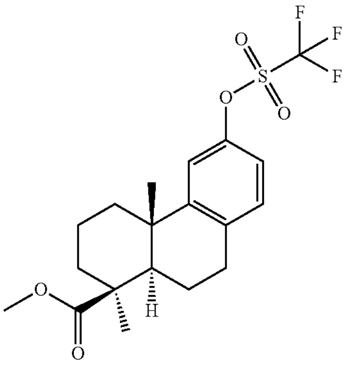 [SMILES: COC(=O)[C@@]1(C)CCC[C@]2(C)c3cc(OS(=O)(=O)C(F)(F)F)ccc3CC[C@@H]12]

To a solution of compound P7 (10 g, 35 mmol) in methylene chloride (200 mL) were added pyridine (3.3 g, 42 mmol) and DMAP (0.84 g, 6.9 mmol) under nitrogen atmosphere. The mixture was cooled to −78° C. and was added triflic anhydride (12 g, 42 mmol), and the resulting mixture was allowed to warm to 25° C. and stirred at 25° C. for another 4 hours. The reaction mixture was diluted with DCM (500 mL), washed with water (100 mL), aq. hydrochloride (1 N, 150 mL) and brine (100 mL), dried over sodium sulfate and concentrated in vacuo to give crude compound P8 (14 g, 97% crude yield) as viscous oil, which was pure enough for the next step. The crude compound P8 could be purified by flash chromatography (0-10% ethyl acetate in petroleum ether) to give pure product as viscous oil. ESI m/z: 421.2 $(M+1)^+$. $^1H$ NMR (400 MHz, $CDCl_3$) δ 7.12 (d, J=2.5 Hz, 1H), 7.10 (d, J=8.5 Hz, 1H), 6.97 (dd, J=8.5, 2.5 Hz, 1H), 3.67 (s, J=3.4 Hz, 3H), 2.93 (dd, J=17.2, 4.4 Hz, 1H), 2.85-2.71 (m, 1H), 2.29 (d, J=13.5 Hz, 1H), 2.25-2.14 (m, 2H), 2.03-1.89 (m, 2H), 1.71-1.61 (m, 1H), 1.56-1.48 (m, 1H), 1.40 (td, J=13.4, 4.2 Hz, 1H), 1.30-1.22 (m, 3H), 1.09 (td, J=13.6, 4.2 Hz, 1H), 1.02 (s, 3H) ppm.

Methyl (1S,4aS,10aR)-6-((tert-butoxycarbonyl)amino)-1,4a-dimethyl-1,2,3,4,4a,9,10,10a-octahydrophenanthrene-1-carboxylate (P9)

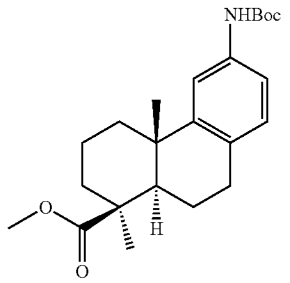 [SMILES: COC(=O)[C@@]1(C)CCC[C@]2(C)c3cc(NC(=O)OC(C)(C)C)ccc3CC[C@@H]12]

To a solution of compound P8 (14 g, 34 mmol) and tert-butyl carbamate ($BocNH_2$, 7.9 g, 68 mmol) in tert-butanol (100 mL) were added successively cesium carbonate (22 g, 68 mmol), tris(dibenzylideneacetone)dipalladium(0) ($Pd_2(dba)_3$, 1.8 g, 2.0 mmol) and X-Phos (1.8 g, 4.0 mmol) at room temperature. The mixture was de-gassed and fulfilled with argon for 3 times and was then stirred at 80° C. under argon protection (balloon) overnight until compound P8 was totally consumed, which was monitored by TLC. After cooled to room temperature, the reaction mixture was diluted with ethyl acetate and filtered through Celite. The solid was washed with ethyl acetate for 3 times. The combined filtrate was concentrated in vacuo and the residue was purified by silica gel column chromatography (0-6.25% ethyl acetate in petroleum ether) to give compound P9 (11 g, 82% yield) as a white solid. ESI m/z: 410 $(M+23)^+$. $^1H$ NMR (500 MHz, $DMSO_{d6}$) δ 9.07 (s, 1H), 7.39 (s, 1H), 7.13 (d, J=8.5 Hz, 1H), 6.87 (d, J=8.3 Hz, 1H), 3.59 (s, 3H), 2.76 (dd, J=16.4, 4.5 Hz, 1H), 2.70-2.61 (m, 1H), 2.16-2.05 (m, 3H), 2.00-1.75 (m, 2H), 1.65-1.50 (m, 2H), 1.45 (s, 9H), 1.31-1.25 (m, 1H), 1.21 (s, 3H), 1.10 (td, J=13.5, 4.1 Hz, 1H), 0.92 (s, 3H) ppm.

(1S,4aS,10aR)-6-{[(tert-Butoxy)carbonyl]amino}-1,4a-dimethyl-1,2,3,4,4a,9,10,10a-octahydrophenanthrene-1-carboxylic acid (P10)

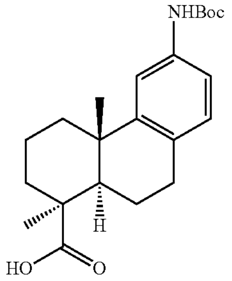 [SMILES: CC(C)(C)OC(=O)Nc1ccc2c(c1)[C@@]1(C)CCC[C@](C)(C(=O)O)[C@@H]1CC2]

To a solution of compound P9 (4.9 g, 13 mmol) in DMSO was added potassium tert-butoxide (15 g, 0.13 mol) in one portion at room temperature. The reaction mixture was stirred at 60° C. for 3 hours under argon protection until the reaction was completed according to LCMS. After cooled to room temperature, the reaction mixture was poured into ice and acidified slowly with aq. hydrochloride (0.5 M) to pH 5, during which the temperature was not allowed to higher than 25° C. The precipitates were collected by filtration was washed with water several times. The crude product was further purified by silica gel column chromatography (0-20% ethyl acetate in petroleum ether) to give compound P10 (4.5 g, 93% yield) as a white solid. ESI m/z: 318 $(M-55)^+$. $^1H$ NMR (500 MHz, $DMSO_{d6}$) δ 12.08 (s, 1H), 9.08 (s, 1H), 7.40 (s, 1H), 7.11 (s, 1H), 6.87 (d, J=8.3 Hz, 1H), 2.79-2.68 (m, 1H), 2.65 (d, J=12.6 Hz, 1H), 2.17-2.03 (m, 4H), 1.94-1.76 (m, 2H), 1.53 (d, J=13.7 Hz, 1H), 1.46 (d, J=7.4 Hz, 9H), 1.29-1.14 (m, 5H), 1.04 (s, 3H) ppm.

tert-Butyl N-[(4bS,8S,8aR)-8-carbamoyl-4b,8-dimethyl-4b,5,6,7,8,8a,9,10-octahydrophenanthren-3-yl]carbamate (P11)

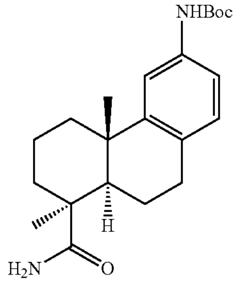

To a solution of P10 (4.5 g, 12 mmol) and HATU (4.9 g, 13 mmol) in DMF (50 mL) was added diisopropylethylamine (20 mL, 0.12 mol), and the mixture was stirred at 25° C. for an hour. To the mixture was then added ammonium chloride (16 g, 0.30 mol) and the mixture was stirred at room temperature overnight. The resulting mixture was diluted with ethyl acetate, washed with water and brine, dried over sodium sulfate and concentrated in vacuo. The residue was purified by flash chromatography (0-20% ethyl acetate in petroleum ether) to give compound P11 (4.2 g, 94% yield) as a white solid. ESI m/z: 373.3 $(M+1)^+$. $^1H$ NMR (500 MHz, $MeOD_{d4}$) δ 7.20 (s, 1H), 6.97 (d, J=7.7 Hz, 1H), 6.80

(d, J=8.3 Hz, 1H), 2.77-2.68 (m, 2H), 2.66-2.55 (m, 1H), 2.20 (d, J=12.9 Hz, 1H), 2.13 (dd, J=13.2, 5.3 Hz, 1H), 2.08 (d, J=14.0 Hz, 1H), 2.03-1.86 (m, 2H), 1.54 (d, J=11.1 Hz, 1H), 1.40 (s, 9H), 1.26 (t, J=26.7 Hz, 1H), 1.18 (s, 3H), 1.14-1.03 (m, 4H) ppm.

Methyl (1S,4aS,10aR)-6-(benzyloxy)-1,4a-dimethyl-1,2,3,4,4a,9,10,10a-octahydrophenanthrene-1-carboxylate (P13)

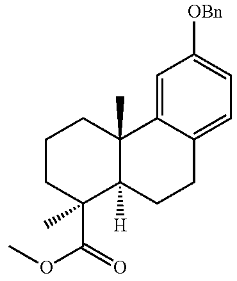 [SMILES: COC(=O)[C@@]1(C)CCC[C@]2(C)c3cc(OCc4ccccc4)ccc3CC[C@@H]12]

A mixture of compound P7 (12 g, 40 mmol) and cesium carbonate (14 g, 44 mmol) in DMF (100 mL) was stirred at 20-25° C. for 15 minutes. To the mixture was added benzyl bromide (7.1 mL, 60 mmol) at room temperature. After stirred at room temperature for 4 hours, the resulting mixture was poured into cold water and extracted with ethyl acetate. The combined organic solution was washed with water and brine, dried over sodium sulfate and concentrated in vacuo. The crude product was purified by flash chromatography (0-10% ethyl acetate in petroleum ether) to give the title compound P13 (13 g, 89% yield) as a white solid. ESI m/z: 379 $(M+H)^+$. $^1H$ NMR (500 MHz, $MeOD_{d4}$) δ 7.60-7.20 (m, 5H), 7.00-6.82 (m, 2H), 6.73 (d, J=7.1 Hz, 1H), 5.03 (s, 2H), 3.66 (s, 3H), 2.95-2.58 (m, 2H), 2.36-2.10 (m, 3H), 2.10-1.85 (m, 2H), 1.70-1.48 (m, 2H), 1.44-1.21 (m, 4H), 1.15 (t, J=17.2 Hz, 1H), 1.01 (s, 3H) ppm.

(1S,4aS,10aR)-6-(Benzyloxy)-1,4a-dimethyl-1,2,3,4,4a,9,10,10a-octahydrophenanthrene-1-carboxylic acid (P14)

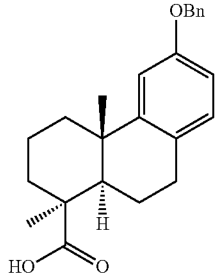 [SMILES: C[C@]1(C(=O)O)CCC[C@]2(C)c3cc(OCc4ccccc4)ccc3CC[C@@H]12]

A mixture of compound P13 (11 g, 29 mmol) and potassium tert-butoxide (33 g, 0.29 mol) in DMSO (0.19 L) was stirred at 100° C. for an hour until the methyl group was totally removed, which was monitored by LCMS and TLC. After cooled to 25° C., the mixture was quenched with aqueous hydrochloride (1 N) and extracted with ethyl acetate. The combined organic solution was washed with brine, dried over sodium sulfate and concentrated in vacuo.

The residue was purified by silica gel column chromatography (0-24% ethyl acetate in petroleum ether) to give compound P14 (7.5 g, 71% yield) as a white solid. ESI m/z: 365 $(M+H)^+$. $^1H$ NMR (500 MHz, $MeOD_{d4}$) δ 7.42 (d, J=7.4 Hz, 2H), 7.36 (t, J=7.5 Hz, 2H), 7.30 (t, J=7.3 Hz, 1H), 6.92 (d, J=8.4 Hz, 1H), 6.87 (d, J=2.5 Hz, 1H), 6.72 (dd, J=8.4, 2.5 Hz, 1H), 5.02 (s, 2H), 2.82 (dd, J=16.3, 4.4 Hz, 1H), 2.77-2.65 (m, 1H), 2.24 (d, J=13.2 Hz, 2H), 2.19 (dd, J=13.8, 6.0 Hz, 1H), 2.11-1.96 (m, 2H), 1.64-1.56 (m, 1H), 1.53 (d, J=11.0 Hz, 1H), 1.35 (td, J=13.3, 3.7 Hz, 1H), 1.30 (s, 3H), 1.13 (s, 3H), 1.11-1.05 (m, 1H) ppm.

Pentafluorophenyl (1S,4aS,10aR)-6-(benzyloxy)-1,4a-dimethyl-1,2,3,4,4a,9,10,10a-octahydrophenanthrene-1-carboxylate (P15)

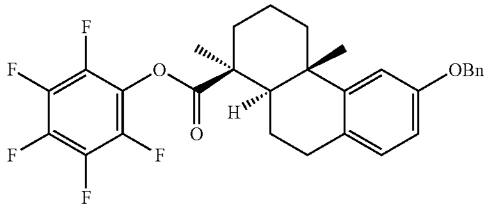 [SMILES: C[C@]1(C(=O)Oc2c(F)c(F)c(F)c(F)c2F)CCC[C@]2(C)c3cc(OCc4ccccc4)ccc3CC[C@@H]12]

To a solution of P14 (9.6 g, 26 mmol) in DMF (100 mL) was added DIPEA (14 mL, 79 mmol), and perfluorophenyl 2,2,2-trifluoroacetate (15 g, 53 mmol). This mixture was stirred at room temperature overnight, which was monitored by LCMS. The reaction mixture was then diluted with ether (200 mL) and washed with water (300 mL) and brine (200 mL). The organic solution was dried over sodium sulfate, and concentrated in vacuo. The residue was purified by flash chromatography (0-10% ethyl acetate in petroleum ether) to give compound P15 (12 g, 88% yield) as a white solid. ESI m/z: 531 $(M+H)^+$. $^1H$ NMR (500 MHz, $DMSO_{d6}$) δ 7.43 (d, J=7.1 Hz, 2H), 7.38 (t, J=7.4 Hz, 2H), 7.31 (t, J=7.2 Hz, 1H), 6.93 (dd, J=10.2, 5.5 Hz, 2H), 6.76 (dd, J=8.4, 2.5 Hz, 1H), 5.05 (s, 2H), 2.81 (dd, J=16.3, 4.5 Hz, 1H), 2.77-2.68 (m, 1H), 2.28-2.19 (m, 2H), 2.18 (dd, J=13.4, 5.6 Hz, 1H), 2.00-1.83 (m, 2H), 1.74 (d, J=11.8 Hz, 1H), 1.65 (d, J=14.1 Hz, 1H), 1.47 (s, 3H), 1.38-1.27 (m, 2H), 1.08 (s, 3H) ppm.

tert-Butyl N-[(4bS,8S,8aR)-8-({[(1S,4aS,10aR)-6-(benzyloxy)-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamate (P16)

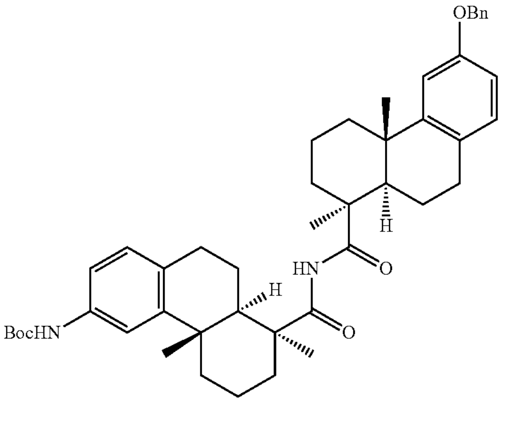 [SMILES: CC(C)(C)OC(=O)Nc1ccc2c(c1)[C@@]1(C)CCC[C@](C)(C(=O)NC(=O)[C@@]3(C)CCC[C@]4(C)c5cc(OCc6ccccc6)ccc5CC[C@@H]34)[C@@H]1CC2]

To a solution of compound P11 (2.3 g, 6.2 mmol) in THF (20 mL) was added dropwise n-BuLi (2.5 M in hexane, 5.5 mL, 14 mmol) at −78° C. The reaction was stirred at this temperature for 1 hour. To the mixture was added a solution of P15 (3.0 g, 5.6 mmol) in THF (20 mL), and the resulting mixture was then stirred at 10-20° C. overnight until compound P15 was consumed, which was monitored by LCMS. The reaction was quenched with sat. aq. ammonium chloride and extracted with ethyl acetate. The combined organic solution was washed with water and brine, dried over sodium sulfate and concentrated in vacuo. The residue was purified by flash chromatography (0-30% ethyl acetate in petroleum ether) to give compound P16 (1.59 g, 51% yield) as a white solid. ESI m/z: 719 $(M+1)^+$.

tert-Butyl N-[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamate (P17)

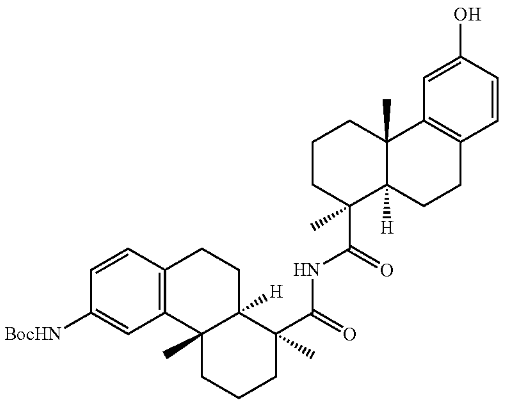 [SMILES: CC(C)(C)OC(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2]

To a solution of P16 (2.0 g, 2.78 mmol) in ethyl acetate (40 mL) was added wet palladium on carbon (10% Pd, 0.9 g) under nitrogen protection. The mixture was degassed and fulfilled with hydrogen and stirred at room temperature under hydrogen balloon overnight until P16 was totally consumed, which was monitored by LCMS. The mixture was filtered through Celite and the filtration was concentrated in vacuo. The residue was purified by silica gel column chromatography (0-55% ethyl acetate in petroleum ether) to give P17 (1.06 g, 61% yield) as a white solid. ESI m/z: 629 $(M+H)^+$. $^1H$ NMR (500 MHz, $DMSO_{d6}$) δ 9.10 (s, 1H), 8.98 (s, 1H), 8.11 (s, 1H), 7.40 (s, 1H), 7.15 (d, J=7.5 Hz, 1H), 6.90 (d, J=8.4 Hz, 1H), 6.81 (d, J=8.3 Hz, 1H), 6.63 (d, J=2.3 Hz, 1H), 6.50 (dd, J=8.2, 2.4 Hz, 1H), 2.84 (td, J=16.3, 3.8 Hz, 2H), 2.77-2.64 (m, 2H), 2.30-2.22 (m, 2H), 2.14 (t, J=10.9 Hz, 4H), 2.00-1.80 (m, 4H), 1.65-1.54 (m, 4H), 1.45 (s, 9H), 1.34-1.28 (m, 2H), 1.27 (d, J=2.5 Hz, 6H), 1.15-1.08 (m, 2H), 0.99 (s, 6H) ppm.

Payload 1d, (1S,4aS,10aR)-N-[(1S,4aS,10aR)-6-Amino-1,4a-dimethyl-1,2,3,4,4a,9,10,10a-octahydro-phenanthrene-1-carbonyl]-6-hydroxy-1,4a-dimethyl-1,2,3,4,4a,9,10,10a-octahydrophenanthrene-1-carboxamide (1d)

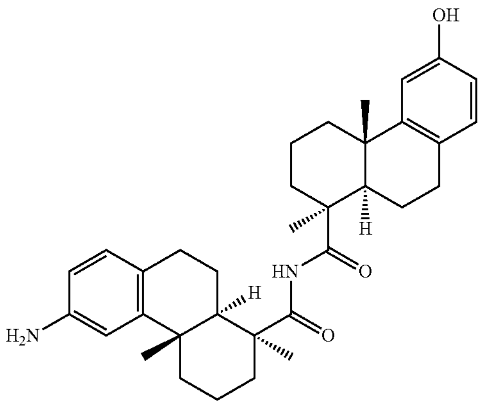 [SMILES: C[C@]1(C(=O)NC(=O)[C@@]2(C)CCC[C@]3(C)c4cc(O)ccc4CC[C@@H]23)CCC[C@]2(C)c3cc(N)ccc3CC[C@@H]12]

To the solution of compound P17 (0.17 g, 0.27 mmol) in DCM (10 mL) was added dropwise TFA (3 mL) at room temperature. The reaction mixture was stirred at room temperature for an hour until Boc was removed according to LCMS. The volatiles were removed in vacuo and the residue was purified by prep-HPLC (method B) to give 1d (0.10 g, 70% yield) as a white solid.

ESI m/z: 529.3 $(M+1)^+$.

$^1H$ NMR (400 MHz, $CDCl_3$) δ 8.14 (s, 1H), 6.92 (d, J=8.3 Hz, 1H), 6.86 (d, J=8.1 Hz, 1H), 6.73 (d, J=2.5 Hz, 1H), 6.65-6.57 (m, 2H), 6.50 (dd, J=8.1, 2.3 Hz, 1H), 4.75 (s, 1H), 3.49 (s, 1H), 2.99-2.85 (m, 2H), 2.79 (tt, J=11.6, 5.8 Hz, 2H), 2.34-2.14 (m, 6H), 2.15-1.95 (m, 4H), 1.74-1.51 (m, 5H), 1.46-1.34 (m, 2H), 1.30 (s, 6H), 1.21-1.06 (m, 8H) ppm.

$^1H$ NMR (400 MHz, $DMSO_{d6}$) δ 8.99 (s, 1H), 8.09 (s, 1H), 6.81 (d, J=8.0 Hz, 1H), 6.68 (d, J=8.0 Hz, 1H), 6.63 (d, J=2.5 Hz, 1H), 6.50 (dd, J=8.0, 2.5 Hz, 1H), 6.48 (d, J=2.5 Hz, 1H), 6.34 (dd, J=8.0, 2.5 Hz, 1H), 4.69 (s, 2H), 2.86-2.60 (m, 4H), 2.28-2.10 (m, 6H), 1.94-1.75 (m, 4H), 1.65-1.53 (m, 4H), 1.35-1.20 (m, 8H), 1.20-1.06 (m, 2H), 0.98 (s, 6H) ppm.

$^{13}C$ NMR (100 MHz, $DMSO_{d6}$) δ 174.03, 173.92, 155.34, 148.39, 147.63, 146.43, 129.56, 129.09, 124.60, 121.65, 113.23, 112.58, 111.81, 110.77, 52.32, 52.09, 45.56, 45.52, 39.20, 39.36, 38.23, 38.17, 37.18, 37.12, 31.08, 31.00, 27.65, 27.64, 23.08, 23.03, 21.43, 21.27, 19.64, 19.61 ppm.

HPLC (method B): Retention time: 8.92 min, purity: 99.4%. chiral HPLC: >99.9% (in column AD, AS, OD and OJ).

Optical rotation (α): +2.53° (1.7 g/100 mL THF, 25° C.).

Example 65

This Example describes an analysis of certain linker-payloads.

The linker-payloads were evaluated in several physio-chemical assays and enzymatic assays prior to conjugations with the antibodies to compare the linker-payloads with a cyclodextrin moiety with the linker-payloads without a cyclodextrin moiety.

The following test assays the solubility of the linker-payloads with a cyclodextrin moiety and the linker-payloads without a cyclodextrin moiety.

The test compounds were dissolved in DMSO to build a standard curve using LC-MS method A or B. The test sample was dissolved in water and sonicated for 10 minutes, and then centrifuged. The upper clear solution was analyzed using the same method A or B and the solubility was calculated based on its peak area. Shown in FIG. 12 is the solubility result of Ex49. The corresponding Linker-payload (Ex47) had an aqueous solubility below detectable levels.

See FIG. 12. Solubility of Example 49 compound.

| Example 49 Compound solutions | X: Concentration (mg/mL) | Con-centration (mM) | Y: Area in LCMS |
|---|---|---|---|
| A | 0.100 | 0.040 | 288.06 |
| B | 0.050 | 0.020 | 131.96 |
| C | 0.025 | 0.0099 | 66.15 |
| D | 0.O10 | 0.0040 | 25.73 |
| Sat. | 0.048 | 0.019 | 132.96 |

Detailed test procedures were as follows:

1. 0.5 mg of testing compound was dissolved into 0.5 mL DMSO.
   The DMSO solution (1 mg/mL, 0.5 mL, 0.5 mg) was diluted with water (4.5 mL) to give solution A (0.1 mg/mL, 5 mL, 0.5 mg).
   0.5 mL of solution A (0.1 mg/mL, 0.5 mL, 0.05 mg) was diluted with water (0.5 mL) to give solution B (0.05 mg/mL, 2 mL, 0.05 mg).
   0.5 mL of solution A (0.1 mg/mL, 0.5 mL, 0.05 mg) was diluted with water (1.5 mL) to give solution C (0.025 mg/mL, 2 mL, 0.05 mg).
   0.5 mL of solution A (0.1 mg/mL, 0.5 mL, 0.05 mg) was diluted with water (4.5 mL) to give solution D (0.01 mg/mL, 5 mL, 0.05 mg).
   0.5 mL of solution D (0.01 mg/mL, 0.5 mL, 5 μg) was diluted with water (4.5 mL) to give solution E (1 μg/mL, 5 mL, 0.5 μg)
2. 0.05 mg of compound was suspended in water (1 mL) and sonicated for 10 minutes. After centrifugation, the clear solution above was collected to provide the saturated sample solution.
3. All the standard solutions A, B, C, D, E and sample solution were analyzed by LCMS (using the same method and same injection volume) to obtain the peak areas.
4. Calculate the standard curve according to the data of A-D (X=concentration, Y=peak areas).
5. Calculate to obtain the concentration of saturated sample solution according to the functions obtained above.

Example 66

Cathepsin B cleavage rate of linker-payloads with vs. without cyclodextrin

The procedure for the Cathepsin B assay follows, and the test results were summarized in Table 8.

Step 1: Preparation of Cathepsin B buffer: 0.1 M NaOAc/0.01M DTT (pH5.0) Dissolve 8.3 g/L NaOAc, 1.54 g/L DTT in deionized water. Adjust pH to 5.0 with HCl/sodium hydroxide.

Step 2: Test Cleavage Rate

1. Prepare 25 μM of testing sample: To a 2-mL-tube was added 0.5 mg of testing sample, followed by the addition of 0.2 mL of DMSO. The solution was added dropwise into 0.8 mL of 0.1 M NaOAc/0.01 M DTT buffer. The obtained mixtures were sonicated for 5 minutes to obtain clear and colorless solutions. The pH value of the solution was around 5 according to pH test strip.
2. Preheat assay buffer: 0.1 M NaOAc/0.01 M DTT (pH 5.0)
3. Spiking solutions for test compounds: 25 μM Spiking solutions for test compounds: Add 2 μL of 5 mM stock solution into 398 μL of 0.1 M NaOAc/0.01 M DTT buffer (pH 5.0).
4. Prepare 0.47 μg/μL Cathepsin B in 50 mM NaOAc/1 mM EDTA (pH 5.0). Put on ice.
5. Without CA074 samples: Add 4 μL of 0.47 μg/μL Cathepsin B into 196 μL of 25 μM Spiking solutions (from step 2), incubate the tubes at 37° C.
6. With CA074 samples: Add 4 μL of 0.47 μg/μL Cathepsin B with 4 μL of 10 mM Inhibitor (CA074) into 196 μL of 25 μM Spiking solutions (from step 2), incubate the tubes.
7. After quenching, shake the plate and centrifuge them at 14000 rpm.
8. Transfer 50 μL of the supernatant from each well into a 96-well sample plate containing 50 μL of ultra pure water (Millipore, $ZMQS50F_{01}$) for LC/MS analysis.

Step 3: Test reference compounds:

9. Preheat assay buffer: 100 mM Na/K phosphate, pH 6.0, with 1.33 mM EDTA and 2 mM DTT.
10. Prepare 0.024 μg/μL Cathepsin B: Add 1 μL of 0.47 μg/μL Cathepsin B stock into 19 μL of assay buffer (from step 11).
11. Add 2 μL of 0.024 μg/μL Cathepsin B (from step 12) to a opaque 96-well plate.
12. Add 96 μL of assay buffer to each sample.
13. Add 2 μL of the 10 mM substrate Z-RR-MNA (200 μM final concentration).
14. For negative control (With inhibitor), add 2 μL of 10 mM Inhibitor (CA074): Immediately read the samples in a kinetic mode at excitation of 340 nm/emission of 425 nm (Read the plate every 30 Second for 3 min).

Step 4: Stability of Cathepsin B in incubation samples:

15. Take 5 μL of incubation samples into 93 μL of assay buffer (from step 11), and then add 2 μL of 10 mM substrate (Z-RR-MNA).
16. Incubate the samples at 37° C. for 2 min.
17. Read the samples at excitation of 340 nm/emission of 425 nm.

In general most conjugates with vcPAB-moiety can be cleaved by capB with cleavage rate>50%.

In general, the insertion of cyclodextrin into the linkers increased the Cathepsin B cleavage rates, such as from 14% (Ex47) to 62% (Ex48).

The other samples were tested and summarized in the Table 8. In general, most testing compounds have retention time (RT) on HPLC in the range from 6 to 7 minutes. If RT>7 min, c Log P is larger than 5 and their aqueous solubility was poor.

TABLE 8

SOLUBILITY AND CAPB CLEAVAGE RATE OF LINKER-PAYLOADS WITH CYCLODEXTRIN

| Cpd | Payload | cLogP | CapB (%) | HPLC* RT (min) | Aq. Solubility (mg/mL) |
|---|---|---|---|---|---|
| Ex36 | MMAE | +++++ | % % % | 8.25 (B) | <0.1 |
| Ex37 | | ++ | — | 7.22 (B) | 0.25 |

TABLE 8-continued

SOLUBILITY AND CAPB CLEAVAGE RATE OF LINKER-PAYLOADS WITH CYCLODEXTRIN

| Cpd | Payload | cLogP | CapB (%) | HPLC* RT (min) | Aq. Solubility (mg/mL) |
|---|---|---|---|---|---|
| Ex39 | | ++ | — | 7.19 (A) | — |
| Ex40 | | ++ | — | 5.88 (A) | 0.33 |
| Ex38 | | + | — | 5.78 (A) | 0.5 |
| Ex41 | | ++ | % % % % | 7.29 (B) | 0.14 |
| Ex42 | | ++ | % % % | 7.33 (B) | >1 |
| Ex43 | | ++ | % % | 5.79 (B) | 0.5 |
| Ex44 | | ++ | % % | 5.66 (B) | >1 |
| Ex45 | 1c in FIG. 1 | +++++ | % | 8.55 (B) | <0.1** |
| Ex46 | 1b in FIG. 1 | ++ | — | 6.62 (A); 6.67 (B) | — |
| Ex47 | 1c in FIG. 1 | ++ | % | 6.61 (A); 6.73 (B) | <0.1 |
| Ex48 | 1d in FIG. 1 | +++++ | % | 9.21 (B) | <0.1** |
| Ex49 | | +++ | % % % | 6.45 (A); 6.55 (B) | 0.05 |
| Ex50 | | +++ | % | 6.68 (B) | — |
| Ex51 | | +++ | | 6.33 (B) | 0.18 |
| Ex52 | 1e in FIG. 1 | +++ | | 6.62 (B) | 0.3 |
| Ex53 | 1d in FIG. 1 | +++ | % % | 6.42 (B) | 0.33 |
| Ex54 | 1d in FIG. 1 | +++ | | 6.37 (B) | 0.3 |
| Ex55 | 1f in FIG. 1 | +++ | | 6.33 (A); 6.44 (B) | |
| Ex56 | 1g in FIG. 1 | +++ | | 6.11 (A); 6.21 (B) | <0.1 |

TABLE 8-continued

SOLUBILITY AND CAPB CLEAVAGE RATE OF LINKER-PAYLOADS WITH CYCLODEXTRIN

| Cpd | Payload | cLogP | CapB (%) | HPLC* RT (min) | Aq. Solubility (mg/mL) |
|---|---|---|---|---|---|
| Ex57 | 1d in FIG. 1 | ++ | | 7.54 (B) | — |
| Ex58 | 1h in FIG. 1 | ++++ | % | 7.40 (B) | <0.02 |
| Ex59 | | ++ | % | 6.23 (B) | 0.026 |
| Ex60 | | ++ | % | 7.37, 7.41 (B) | — |
| Ex61 | 1i in FIG. 1 | +++++ | % | 7.99 (B) | 0.01 |
| Ex62 | | ++ | % | 7.94, 8.02 (B) | 0.02 |
| Ex63 | | ++ | % | 7.76 (B) | — |

*A and B: see HPLC method A and method B, respectively, in general procedure.

**Aqueous Solubility in other solvents For Example 44 compound: 0.06 mg/mL in 20% DMSO in water; 0.07 mg/mL in 30% DMSO in water. For Example 46 compound: 0.10 mg/mL in 10% DMSO/$H_2O$.

+ ≤−6 cLogP

−6< ++ ≤−3 cLogP

−3< +++ ≤1 cLogP

1< ++++ ≤5 cLogP

5< +++++ ≤9.5 cLogP

% ≤50 CapB (%)

50< % % ≤60 CapB (%)

60< % % % ≤70 CapB (%)

70< % % % % ≤80 CapB (%)

80< % % % % %

TABLE 8A
COMPARISON OF SOLUBILITY AND CAPB CLEAVAGE RATE OF LINKER-PAYLOADS WITH CYCLODEXTRIN VS WITHOUT CYCLODEXTRIN
| Linker-payload | Structures | Linker | Pay-load | Solu-bility | Sta-bil-ity | capB |
|---|---|---|---|---|---|---|
| Ex61 | 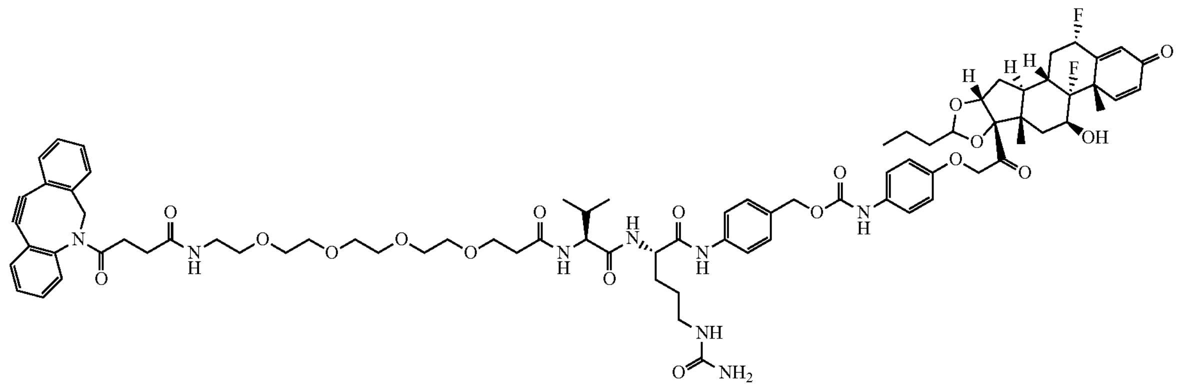 | DIBAC-suc-$PEG_4$-vcPAB | 1i | 0.01 mg/mL | Y | <5% |

TABLE 8A-continued
COMPARISON OF SOLUBILITY AND CAPB CLEAVAGE RATE OF LINKER-PAYLOADS WITH CYCLODEXTRIN VS WITHOUT CYCLODEXTRIN
| Linker-payload | Structures | Linker | Payload | Solubility | Stability | capB |
| --- | --- | --- | --- | --- | --- | --- |
| Ex62 | 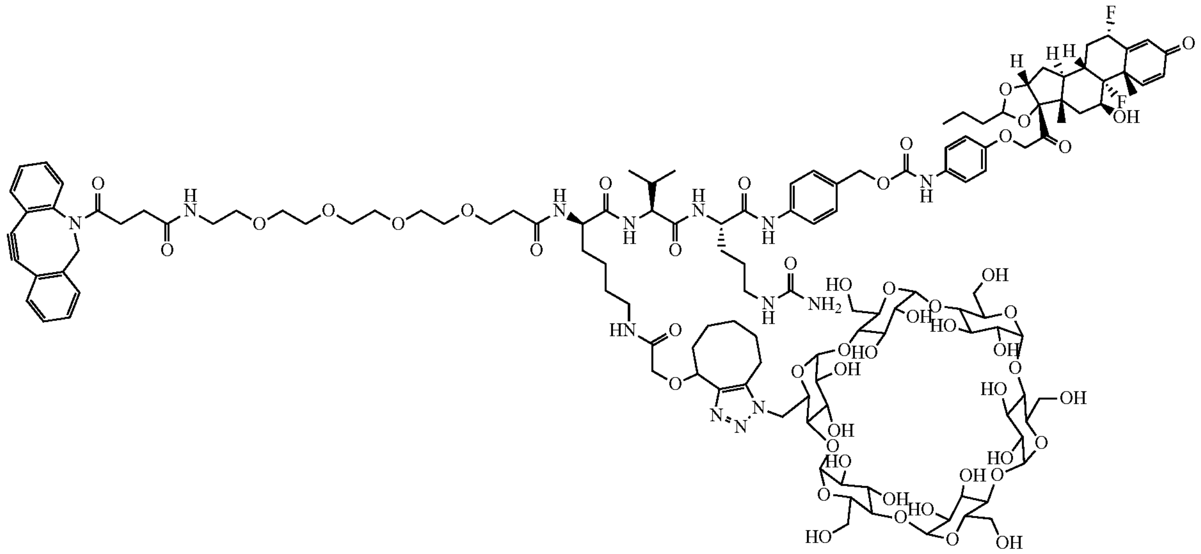 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COc2ccc(NC(=O)OCc3ccc(NC(=O)[C@H](CCCNC(N)=O)NC(=O)[C@@H](NC(=O)[C@@H](CCCCNC(=O)COC4CCCCCc5c4nnn5CC4OC5OC6C(CO)OC(OC7C(CO)OC(OC8C(CO)OC(OC9C(CO)OC(OC%10C(CO)OC(OC4C(O)C5O)C(O)C%10O)C(O)C9O)C(O)C8O)C(O)C7O)C(O)C6O)NC(=O)CCOCCOCCOCCOCCNC(=O)CCC(=O)N4Cc5ccccc5C#Cc5ccccc54)C(C)C)cc3)cc2)O1] | DIBAC-suc-$PEG_4$-dLys(COT-CD)-vcPAB | 1i | 0.02 mg/mL | Y | 12.8% |
| E58 | 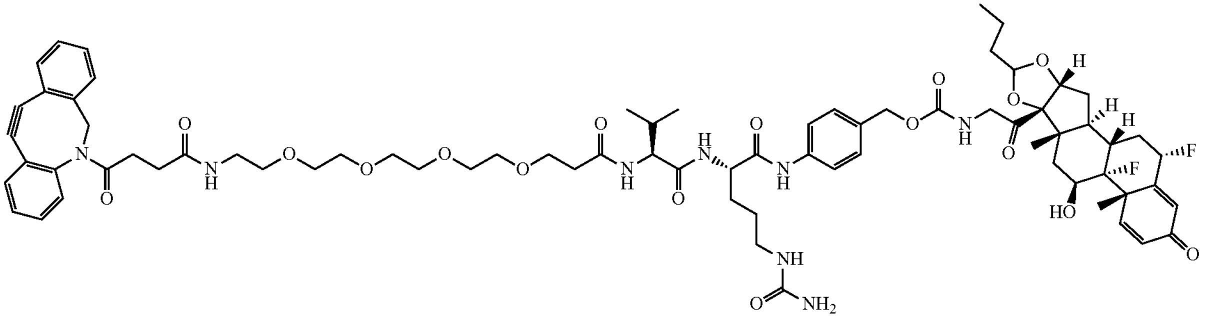 | DIBAC-suc-$PEG_4$-vcPAB | 1h | <0.02 mg/mL | Y | 20.8% |

TABLE 8A-continued
COMPARISON OF SOLUBILITY AND CAPB CLEAVAGE RATE OF LINKER-PAYLOADS WITH CYCLODEXTRIN VS WITHOUT CYCLODEXTRIN
| Linker-payload | Structures | Linker | Payload | Solubility | Stability | capB |
|---|---|---|---|---|---|---|
| Ex59 | 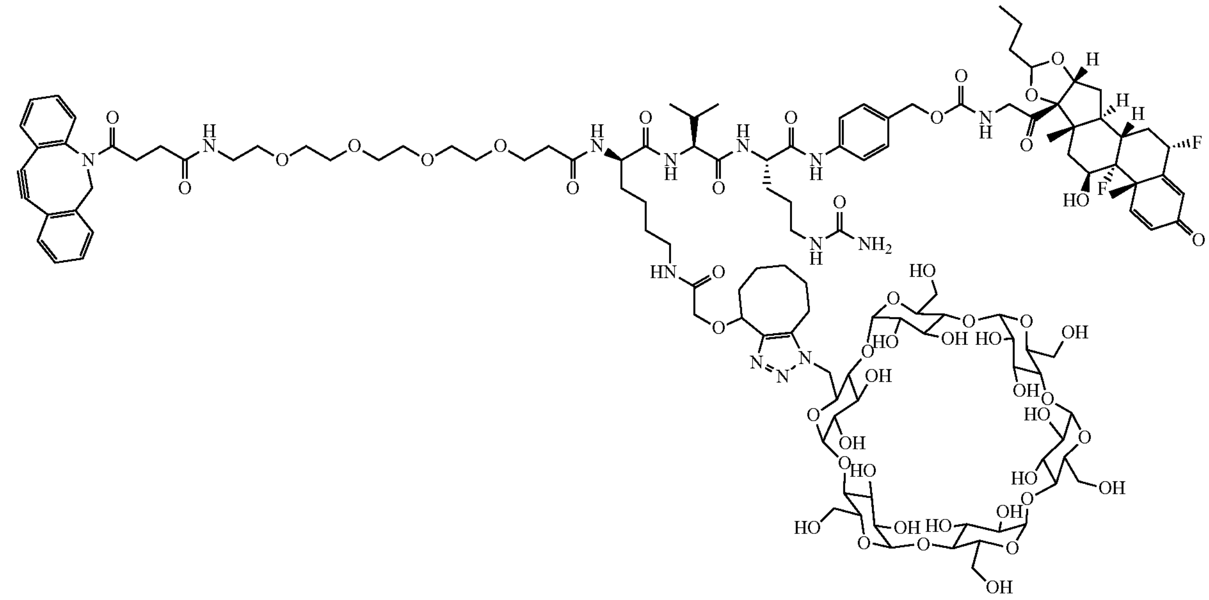 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)CNC(=O)OCc2ccc(NC(=O)[C@H](CCCNC(N)=O)NC(=O)[C@@H](NC(=O)[C@@H](CCCCNC(=O)COC3CCCCCc4c3nnn4CC3OC4OC5C(CO)OC(OC6C(CO)OC(OC7C(CO)OC(OC8C(CO)OC(OC9C(CO)OC(OC3C(O)C4O)C(O)C9O)C(O)C8O)C(O)C7O)C(O)C6O)C(O)C5O)NC(=O)CCOCCOCCOCCOCCNC(=O)CCC(=O)N3Cc4ccccc4C#Cc4ccccc43)C(C)C)cc2)O1] | DIBAC-suc-$PEG_4$-dLys(C-OT-CD)-vcPAB | 1h | 0.026 mg/mL | Y | 29% |
| Ex48 | 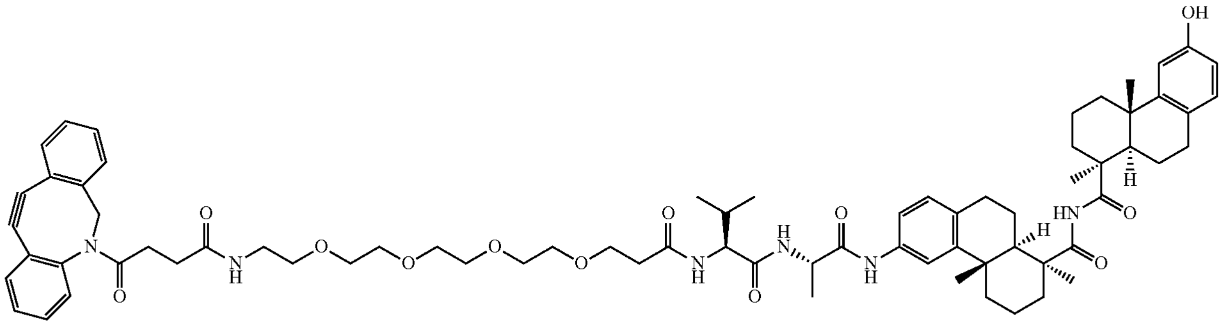 [SMILES: CC(C)[C@H](NC(=O)CCOCCOCCOCCOCCNC(=O)CCC(=O)N1Cc2ccccc2C#Cc2ccccc21)C(=O)N[C@@H](C)C(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2] | DIBAC-suc-PEG4-VA | 1d | <0.1 mg/mL | Y | 13.6% |

TABLE 8A-continued
COMPARISON OF SOLUBILITY AND CAPB CLEAVAGE RATE OF LINKER-PAYLOADS WITH CYCLODEXTRIN VS WITHOUT CYCLODEXTRIN
| Linker-payload | Structures | Linker | Payload | Solubility | Stability | capB |
|---|---|---|---|---|---|---|
| Ex49 | 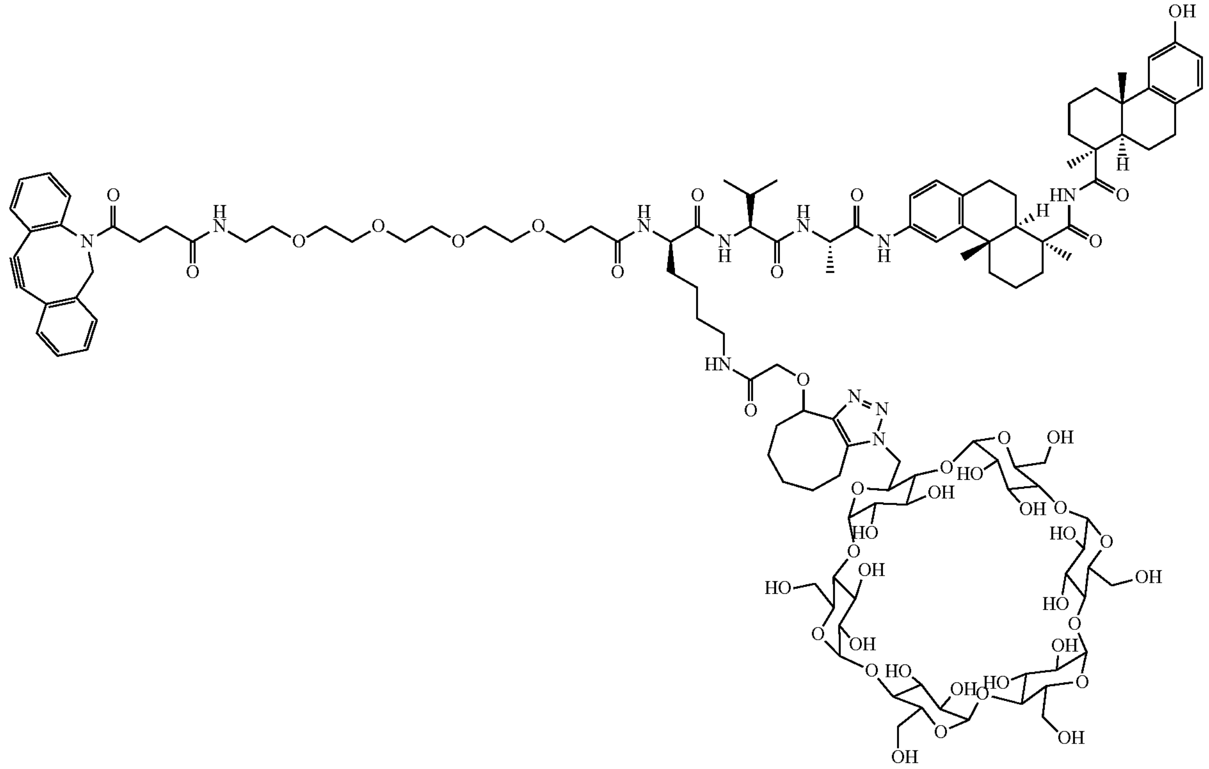 [SMILES: CC(C)[C@H](NC(=O)[C@@H](CCCCNC(=O)COC1CCCCCc2c1nnn2CC1OC2OC3C(CO)OC(OC4C(CO)OC(OC5C(CO)OC(OC6C(CO)OC(OC7C(CO)OC(OC1C(O)C2O)C(O)C7O)C(O)C6O)C(O)C5O)C(O)C4O)C(O)C3O)NC(=O)CCOCCOCCOCCOCCNC(=O)CCC(=O)N1Cc2ccccc2C#Cc2ccccc21)C(=O)N[C@@H](C)C(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2] | DIBAC-suc-PEG4-dLys(COT-CD)-VA | 1d | 0.05 mg/mL | Y | 38.5% [1] |

TABLE 8A-continued
| COMPARISON OF SOLUBILITY AND CAPB CLEAVAGE RATE OF LINKER-PAYLOADS WITH CYCLODEXTRIN VS WITHOUT CYCLODEXTRIN | | | | | | |
|---|---|---|---|---|---|---|
| Linker-payload | Structures | Linker | Payload | Solubility | Stability | capB |
| Ex57 | 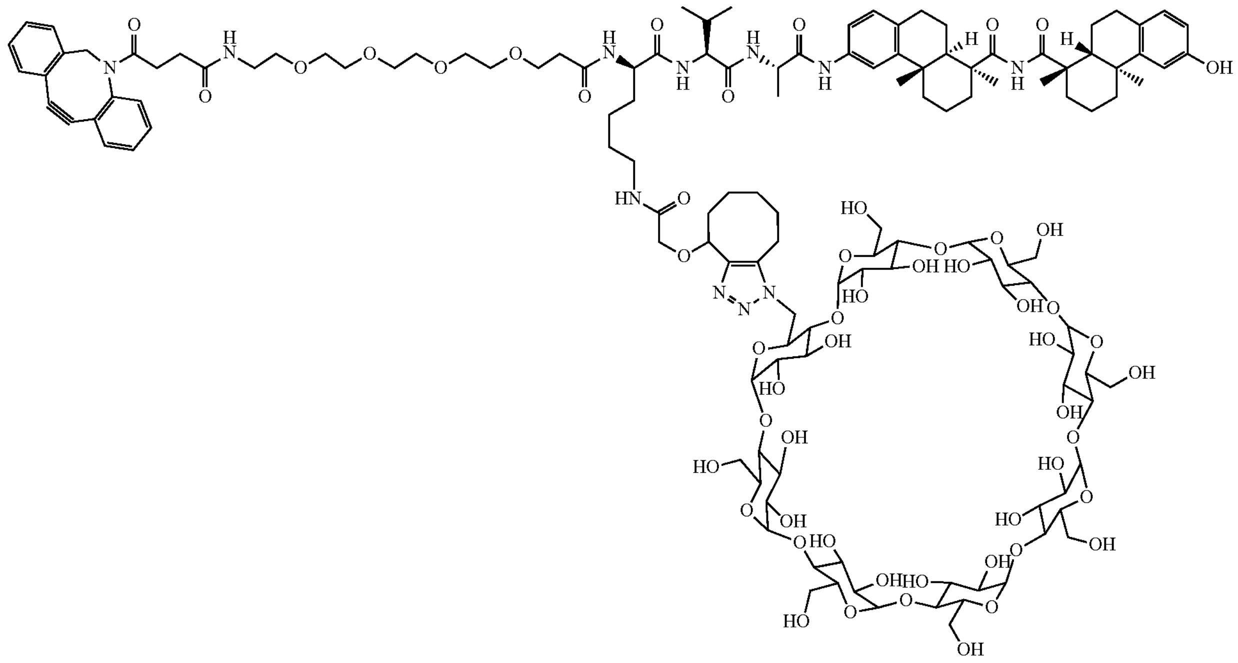 [SMILES: CC(C)[C@H](NC(=O)[C@@H](CCCCNC(=O)COC1CCCCCc2c1nnn2CC1OC2OC3C(CO)OC(OC4C(CO)OC(OC5C(CO)OC(OC6C(CO)OC(OC7C(CO)OC(OC8C(CO)OC(OC9C(CO)OC(OC1C(O)C2O)C(O)C9O)C(O)C8O)C(O)C7O)C(O)C6O)C(O)C5O)C(O)C4O)C(O)C3O)NC(=O)CCOCCOCCOCCOCCNC(=O)CCC(=O)N1Cc2ccccc2C#Cc2ccccc21)C(=O)N[C@@H](C)C(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2] | DIBAC-suc-PEG4-dLys(COT-yCD)-VA | 1d | 0.075 mg/mL | Y | 8.3% |

Example 67

Stability of Linker-payloads with vs. without cyclodextrin under different pH buffers The testing samples were dissolved in in 0.5 mg/mL of 20% DMSO+80% PBS buffers at pH 5.0, 7.4 or 8.0. The buffers were prepared as follows:

1. 0.05 M sodium phosphate and 0.07 M NaCl buffer, pH 7.4:

Dissolve 14.505 g/L Na2HPO4_12H2O, 1.483 g/L NaH2PO4_2H2O and 4.095 g/L NaCl in deionized water. Adjust pH to 7.40 with phosphate acid/sodium hydroxide.

2. PBS with 0.5% BSA:

Dissolve 0.5 g BSA into 100 mL buffer1

The results indicated that the DIBAC-hydrophilic linkers-payloads are quite stable at pH 6-8, >95% remained at testing time. Increased hydrophilicity of the linker results in increasing the aqueous stability of the linker-payloads over time.

Example 68

ADC Conjugation

The conjugations of Maleimide-Linker-payload to an antibody (FIG. 13) and DIBAC-Linker-payload to the azido-functionalized antibody via [3+2] click reaction (FIG. 14) were outlined in FIGS. 13 and 14, respectively.

General Procedure E for non site-specific maleimide-linker-payload conjugated to antibody This example demonstrates a method for conjugation of a linker-payload non-site-specifically to an antibody or antigen-binding fragment via a Michael addition or thiol-maleimide bond formation. This example refers the compounds depicted in FIG. 13. Conjugation through antibody-cysteines was performed in two steps using the methods similar to those for making Adcetris®-like ADCs (See, *Mol. Pharm.* 2015, 12(6), 1863-71). A monoclonal antibody (mAb) (10 mg/mL in 50 mM HEPES, 150 mM NaCl) at pH 7-8 was reduced with 1 mM dithiothreitol (0.006 mg per mg of antibody) or TCEP (2.5 molar equivalents to antibody) at 37° C. for 30 min. After gel filtration (G-25, pH 4.5 sodium acetate), Example 38 compound at the concentration of 1-10 mg/mL in DMSO was added to the reduced antibody, and the reaction was allowed to stir for 3-14 h. The resulting mixture was purified by SEC to generate pure conjugate. The DAR (UV) values were determined using the measured absorbances of the ADC and the extinction coefficients of the antibody and Example 38 compound. The conjugation results were summarized in the following Table 9.

Conjugation via Michael addition represented by Ab-Ex.38. See FIG. 13

TABLE 9

EXAMPLE OF CONJUGATION VIA MICHAEL ADDITION

| | ADC Name | Anti-PRLR Ab ADC | DAR |
|---|---|---|---|
| Ex. 61-1 | Ab-SC-PEG$_4$-VC-PAB-MMAE | L17 | 3 |
| Ex. 62-2 | Ab-SC-N$^5$-(α-CD-DIBACT-Suc) D-Lys-VC-PAB-MMAE | L18 | 1.5 |
| Ex. 62-4 | Ab-SC-PEG$_4$-N$^5$-(α-CD-COT) D-Lys-VC-PABC-MMAE | L34 | 2.0 |
| Ex. 62-5 | Ab-SC-PEG$_4$-N-(α-CD-DIBACT-Suc)D-Lys-VC-PABC-MMAE | L37 | 1.5 |

TABLE 9-continued

EXAMPLE OF CONJUGATION VIA MICHAEL ADDITION

| | ADC Name | Anti-PRLR Ab ADC | DAR |
|---|---|---|---|
| | | Isotype control (Control ADC) | |
| Ex. 62-1 | Ab-SC-PEG$_4$-VC-PAB-MMAE | L93 | 2.9 |
| Ex. 62-2 | Ab-SC-N$^5$-(α-CD-DIBACT-Suc) D-Lys-VC-PAB-MMAE | L126 | 2.9 |
| Ex. 62-4 | Ab-SC-PEG$_4$-N$^5$-(α-CD-COT) D-Lys-VC-PABC-MMAE | L120 | 3.2 |
| Ex. 62-5 | Ab-SC-PEG$_4$-N-(α-CD-DIBACT-Suc)D-Lys-VC-PABC-MMAE | L129 | 1.0 |

Example 69

General Procedure F for Site-Specific Conjugation of Alkyne-Linker-Payload Conjugated to Antibody This example demonstrates a method for site-specific conjugation, generally, for a linker-payload to an antibody or antigen-binding fragment thereof. This example refers to the compounds depicted in FIG. 14.

In this example, the site-specific conjugates were produced in two steps. The first step is Microbial transglutaminase (MTG)-based enzymatic attachment of a small molecule, such as azide-PEG$_3$-amine (supra), to the antibody having a Q-tag (references for the Qtag) (hereinafter "MTG-based" conjugation). The second step employed the attachment of a linker-payload to the azido-functionalized antibody via a [2+3] cycloaddition, for example, the 1,3-dipolar cycloaddition between the azides and the cyclooctynes (aka copper-free click chemistry). See, Baskin, J. M.; Prescher, J. A.; Laughlin, S. T.; Agard, N. J.; Chang, P. V.; Miller, I. A.; Lo, A.; Codelli, J. A.; Bertozzi, C. R. *PNAS* 2007, 104 (43), 16793-7. Shown in FIG. 14 is an example of a linker-payload having a DIBAC moiety conjugated with an azido-functionalized antibody via a [2+3] cycloaddition. This process provided the site-specific and stoichiometric conjugates in about 50-80% isolated yield.

Scheme 10. ADC conjugation via [2+3] click reaction represent by Ab-Ex49 now FIG. 14.

Step 1: Preparation of an Azido-Functionalized Antibody

Aglycosylated human antibody IgG (IgG1, IgG4, etc.) or a human IgG1 isotype with N297Q mutation, in PBS (pH 6.5-8.0) was mixed with >200 molar equivalents of azido-dPEG$_3$-amine (MW=218.26 g/mol). The resulting solution was mixed with MTG (EC 2.3.2.13 from Zedira, Darmstadt, Germany, or Modernist Pantry [L #210115A]—ACTIVA TI contains Maltodextrin from Ajinomoto, Japan) (25 U/mL; 5 U MTG per mg of antibody) resulting in a final concentration of the antibody at 0.5-5 mg/mL, and the solution was then incubated at 37° C. for 4-24 h while gently shaking. The reaction was monitored by ESI-MS. Upon reaction completion, the excess amine and MTG were removed by SEC or protein A column chromatography, to generate the azido-functionalized antibody. This product was characterized by SDS-PAGE (FIG. 15) and ESI-MS (FIG. 16). The azido-dPEG$_3$-amine added to two sites of the antibody resulting in a 204 Da increase for the 2DAR antibody-PEG$_3$-azide conjugate.

In a specific experimental, the N-terminal Q tag antibody (24 mg) in 7 mL potassium-free PBS buffer (pH 7.3) was incubated with >200 molar equivalent of the azido-$PEG_3$-amine (MW 218.26) in the presence of MTG (0.350 mL, 35 U, mTGase, Zedira, Darmstadt, Germany). The reaction was incubated at 37° C. overnight while gently mixing. Excess azido-$PEG_3$-amine and mTGase were removed by size exclusion chromatography (SEC, Superdex 200 PG, GE Healthcare).

Step 2: Preparation of Site-Specific Conjugates of a Drug to an Antibody Using Click Chemistry Reactions The site-specific antibody drug conjugates with a human IgG (IgG1, IgG4, etc.) in Table 10 were prepared by a [2+3] click reaction between azido-functionalized antibodies and an alkyne containing linker-payload. The detailed conjugation procedure follows. A site-specific antibody conjugate with linker-payload (LP) was prepared by incubating mAb-$PEG_3$-$N_3$ (1-3 mg/mL) in an aqueous medium (e.g., PBS, PBS containing 5% glycerol, HBS) with >6 molar equivalents of an LP dissolved in a suitable organic solvent, such as DMSO, DMF or DMA (i.e., the reaction mixture contains 5-20% organic solvent, v/v) at 24° C. to 37° C. for over 6 h. The progress of the reaction was monitored by ESI-MS and the absence of mAb-$PEG_3$-$N_3$ indicated the completion of the conjugation. The excess amount of the LP and organic solvent were removed by SEC via elution with PBS, or via protein A column chromatography via elution with acidic buffer followed by neutralization with Tris (pH8.0).

In a specific example, the azido-functionalized antibody (1 mg) in 0.800 mL PBSg (PBS, 5% glycerol, pH 7.4) was treated with six molar equivalents of DIBAC-$PEG_4$-D-Lys (COT-∞-CD)-VC-PABC-payload (conc. 10 mg/mL in DMSO) for 6-12 hours at room temperature and the excess linker payload (LP) was removed by size exclusion chromatography (SEC, Superdex 200 HR, GE Healthcare).

The final product was concentrated by ultra centrifugation and characterized by UV, SEC, SOS-PAGE and ESI-MS.

Shown in Table 10 is a list of non-cytotoxic steroid antibody conjugates (ncADCs) from the corresponding LPs, their molecular weights of the naked antibodies, the azido-functionalized antibodies, the LPs, and the ncADCs, as well as the ESI-DAR values. In the table, Ab refers to an antibody, Ab-$N_3$ refers to an azido-functionalized antibody, and ncADC refers to a non-cytotoxic antibody drug conjugate.

TABLE 10

LIST OF SITE-SPECIFIC CONJUGATES WITH CD-CONTAINING LINKER-PAYLOAD

| LP | | Ab, Ab-N3, or Ab-Steroid conjugates | | |
|---|---|---|---|---|
| EX | MS m/z | Name | MW (Da) | DAR |
| | | Anti-PRLR Ab | 144588 | — |
| $PEG_3$-$N_3$ | 218.26 | Anti-PRLR Ab-HN-$PEG_3$-$N_3$ | 145389 | 4 |
| Ex36 | 1656.9 | Anti-PRLR Ab-Ex36 | 152564 | 3.9 |
| Ex48 | 2773.1 | Anti-PRLR Ab-Ex48 | 156508 | 3.9 |
| Ex41 | 2946.4 | Anti-PRLR Ab-Ex41 | 157185 | 4 |
| Ex42 | 2837.2 | Anti-PRLR Ab-Ex42 | 156744 | 3.9 |
| Ex43 | 3195.5 | Anti-PRLR Ab-Ex43 | 158194 | 3.9 |
| Ex44 | 3082.6 | Anti-PRLR Ab-Ex44 | 157753 | 3.9 |
| | | Anti-Her2 Ab | 145137 | |
| PEGa-azido | 218.26 | Anti-Her2 Ab-HN-$PEG_3$-$N_3$ | 145939 | 4 |
| Ex36 | 1656.94 | Anti-Her2 Ab-Ex36 | 152566 | 4 |
| Ex41 | 2948.3 | Anti-Her2 Ab-Ex41 | 157746 | 4 |

TABLE 10-continued

LIST OF SITE-SPECIFIC CONJUGATES WITH CD-CONTAINING LINKER-PAYLOAD

| | | | | |
|---|---|---|---|---|
| Ex42 | 2837.2 | Anti-Her2 Ab-Ex42 | 157302 | 4 |
| Ex43 | 3195.5 | Anti-Her2 Ab-Ex43 | 158714 | 4 |
| Ex44 | 3082.6 | Anti-Her2 Ab-Ex44 | 157340 | 3.9 |
| | | Anti-PRLR Ab | 144588 | |
| $PEG_3$-azido | 218 | Anti-PRLR Ab-M404 | 145389 | 4 |
| Ex45 | 1225.6 | Anti-PRLR Ab-Ex45 | 150311 | 3.9 |
| Ex46 | 2515.1 | Anti-PRLR Ab-Ex46 | 155460 | 3.9 |
| Ex47 | 2515.1 | Anti-PRLR Ab-Ex47 | 155486 | 3.9 |
| | | Isotype control Ab | 145441 | |
| PEG3-azido | | Isotype control Ab-HN-$PEG_3$-$N_3$ | 146235 | 4 |
| Ex45 | 1225.6 | Isotype control Ab-Ex47 | 151156 | 3.9 |
| Ex46 | 2515.1 | Isotype control Ab-Ex46 | 156332 | 3.9 |
| Ex48 | 2515.1 | Isotype control Ab-Ex48 | 156316 | 3.9 |
| EX | MS m/z | Name | MW (DA) | DAR |
| | | Anti-PRLR Ab | 144588 | |
| PEG3-azido | 218.26 | Anti-PRLR Ab-HN-$PEG_3$-$N_3$ | 145389 | |
| Ex49 | 2523.8 | Anti-PRLR Ab-Ex49 | 155484 | 4 |
| Ex50 | 3048.3 | Anti-PRLR Ab-Ex50 | 157589 | 4 |
| Ex51 | 2658.3 | Anti-PRLR Ab-Ex51 | 156052 | 4 |
| Ex52 | 2937.4 | Anti-PRLR Ab-Ex52 | 157169 | 4 |
| Ex53 | 2769.3 | Anti-PRLR Ab-Ex53 | 156474 | 4 |
| | | Isotype control Ab | 145441 | |
| PEG3-azido | 218.26 | Isotype control Ab-HN-PEGs-Na | 146235 | |
| Ex54 | 2816.1 | Isotype control Ab-Ex54 | 157514 | 3.9 |
| Ex55 | 2846.1 | Isotype control Ab-Ex55 | 157636 | 4 |
| | | Anti-Her2 Ab | 145137 | |
| PEG3-azido | 218.26 | Anti-Her2 Ab-HN-$PEG_3$-$N_3$ | 145939 | |
| Ex49 | 2523.8 | Anti-Her2 Ab-Ex49 | 156047 | 4 |
| 50 | 3048.3 | Anti-Her2 Ab-Ex50 | 158153 | 4 |
| Ex51 | 2658.3 | Anti-Her2 Ab-Ex51 | 156602 | 4 |
| Ex52 | 2937.4 | Anti-Her2 Ab-Ex52 | 157715 | 4 |
| Ex53 | 2769.3 | Anti-Her2 Ab-Ex53 | 157040 | 4 |
| Ex54 | 2816.1 | Anti-Her2 Ab-Ex54 | 157212 | 3.9 |
| Ex55 | 2846.1 | Anti-Her2 Ab-Ex55 | 157340 | 3.9 |

Example 70

General Procedure G for Characterization of Antibody and Antibody-Drug-Conjugates The purified conjugates were analyzed by SEC, SDS-PAGE, and ESI-MS. Anti-Her2-LP conjugate in Table 10 was generated from the anti-Her2 antibody via click reactions of the azido-functionalized antibody (anti-Her2-$PEG_3$-$N_3$) with LPs in Table 10. The ADCs were characterized by SEC (FIG. 15), ESI-MS, and SEC (FIG. 16).

Characterization of ADC by SDS-PAGE

In one method, SDS-PAGE conditions included non-reduced and reduced samples (2-4 μg) along with BenchMark Pre-Stained Protein Ladder (Invitrogen, cat #10748-010; L #1671922.) were loaded per lane in (1.0 mm×10 well) Novex 4-20% Tris-Glycine Gel and were ran at 180 V, 300 mA, for 80 min. An analytic sample was prepared using Novex Tris-Glycine SDS buffer (2×) (Invitrogen, Cat #LC2676) and the reducing sample was prepared with SDS sample buffer (2×) containing 10% 2-mecaptoethanol.

In FIG. 15 is shown a representative gel, indicating slight shift of the molecular weights of the antibodies and ADCs on SDS-PAGE performed under reducing conditions. The mass shifts were not observed on the light chain. However, the masses of the ADC heavy chains were increased when compared to that of the naked antibody. There was no detectable cross-linked material and no detectable aggregation.

FIG. 15. Coomassie-stained SDS-PAGE Gel of anti-Her2 antibody, anti-Her2-PEG$_3$-N$_3$, and anti-Her2-EX49. In FIG. 15, the lanes are labeled according to the following legend:

| Lane | Sample |
|---|---|
| 1 | Standards (Bench Mark 10 μL) |
| 2 | Anti Her2 mAb |
| 3 | Anti Her2 mAb-NH-PEG$_3$-N$_3$ |
| 4 | Anti Her2 mAb-Ex49 |
| 7 | Anti Her2 mAb (reduced) |
| 8 | Anti Her2 mAb-NH-PEG$_3$-N$_3$ (reduced) |
| 9 | Anti Her2 mAb-Ex50 (reduced) |

~2 μg of non-reduced/reduced sample/lane. Novex 4-20% Tris-Glycine Gel; 1.0 mm × 10 well; 180 V, 300 mA, 80 min. BenchMark Pre-Stained Protein Ladder, Invitrogen, cat# 10748-010; L# 1671922.

Characterization of ADC by LC-ESI-MS.

Measurement of intact masses for the ncADC samples by LC-ESI-MS was performed to determine drug-payload distribution profiles and to calculate the average DAR. Each testing sample (20-50 ng, 5 uL) was loaded onto an Acquity UPLC Protein BEH C4 column (10K psi, 300 Å, 1.7 μm, 75 μm×100 mm; Cat No. 186003810). After 3 min desalting, the protein was eluted and mass spectra were acquired using a Waters Synapt G2-Si mass spectrometer.

The deconvoluted mass spectra exhibited a predominant peak for the aglycosylated anti-Her2 antibody with a molecular weight of 145126.0 Da, and a predominant peak for the azido functionalized anti-Her2 antibody with a molecular weight of 145932.0 Da, indicating a 806 Da increase compared to its aglycosylated parent antibody (i.e., corresponding to 4 amino-PEG$_3$-azide conjugations to each aglycosylated antibody). Also, the predominant peak for anti-Her2-LP conjugate had a molecular weight of 152166.0 Da, indicating a 6234 Da increase compared to its aglycosylated parent antibody (i.e., corresponding to 4 LPs (MW=1558.5 Da) conjugations to each aglycosylated antibody). As summarized in Table 3, most site-specific ADCs in this document have 4DAR.

Example 71

This Example shows the characterization of ADC by SEC.

Analytical SEC experiments were run using a Waters 600 instrument, on a Superdex 200 (1.0×30 cm) column, at flow rate of 0.80 mL/min using PBS pH 7.4, and monitored at λ=280 nm using a Waters 2998 PDA. An analytic sample was composed of 200 μL PBS (pH 7.4) with 30-100 μL of test sample. Preparative SEC purifications were performed using an AKTA instrument from GE Healthcare, on Superdex 200 PG (2.6×60 cm) column, at a flow rate 2 mL/min eluting with PBS pH 7.4, and monitored at A=280 nm. The SEC results in FIG. 16 indicate typical retention times for monomeric mAb and its conjugates and there was no detectable aggregation or degradation.

FIG. 16. SEC of anti-Her2 Ab, anti-Her2-PEG$_3$-N$_3$, and anti-Her2-Ex49.

Example 72

This Example shows bioactivity of cytotoxic ADCs with and without Cyclodextrin linkers (FIG. 17).

To assess the comparability of ADCs with and without CDs containing cytotoxic payloads, a cytotoxicity assay used SKBR3 cells. SKBR3 cells have been commonly used to assess aHer2 ADC activity. An aPRLR ADC has been used as a control mAb ADC in the SKBR3 cytotoxicity assay. For the assay, in vitro cytotoxicity of anti-Her2 ADCs or PRLR ADCs were evaluated using the CellTiter-Glo Assay Kit (Promega, Cat #G7573), in which the quantity of ATP present is used to determine the number of viable cells in culture. For the assay, SKBR3 cells were seeded at 6000 cells/well on Nunclon white 96 well plates in complete growth medium and grown overnight at 37° C. in 5% $CO_2$. For cell viability curves, 1:4 serially diluted ADCs or free payload MMAE were added to the cells at concentrations starting at 100 nM including a no treatment control and were then incubated for 5 days. After the 5-day incubation, cells were incubated at room temperature with 100 μL of Cell-Titer-Glo reagents for 5 minutes. Relative luminescence units (RLU) were determined on a Victor plate reader (PerkinElmer). The $IC_{50}$ values were determined from a four-parameter logistic equation over a 10-point response curve (GraphPad Prism). All curves and $EC_{50}$ values were corrected for payload equivalents. All $IC_{50}$s are expressed in nM concentration and percentage of cells killed (% kill) is reported for the highest concentration tested.

As shown in Table 11 and FIG. 17, anti-Her2 Ab ADCs containing CD (Ex38, Ex40, Ex41, Ex48, Ex42, Ex39) have similar efficacy and potency in killing SKBR3 cells as anti-Her2 Ab ADCs that do not contain CD (Anti-Her2 Ab-Ex36). Both sets of anti-HER2 ADCs displayed greater than 90 percent killing at the highest concentration tested. In this assay, unconjugated antibodies did not demonstrate any effect. Isotype control ADCs, regardless of whether they contain CD or not, do not demonstrate any effect in this assay.

TABLE 11

CYTOTOXICITY OF ADCS WITH OR WITHOUT CYCLODEXTRIN LINKERS IN SKBR3 CELLS

| Molecule tested | % kill | $EC_{50}$ (nM) |
|---|---|---|
| Anti-Her2 Ab-Ex36 | ≥90 | 0.06 |
| Anti-Her2 Ab-Ex38 | ≥90 | 0.10 |
| Anti-Her2 Ab-Ex41 | ≥90 | 0.10 |
| Anti-Her2 Ab-Ex43 | ≥90 | 0.08 |
| Anti-Her2 Ab-Ex42 | ≥90 | 0.11 |
| Anti-Her2 Ab-Ex44 | ≥90 | 0.11 |
| MMAE | ≥90 | 0.19 |
| Anti-Her2 Ab | ≥20 | 0.42 |
| Anti-PRLR Ab-Ex36 | <10 | NA |
| Anti-PRLR Ab-Ex38 | <10 | NA |
| Anti-PRLR Ab-Ex41 | <10 | NA |
| Anti-PRLR Ab-Ex43 | <10 | NA |
| Anti-PRLR Ab-Ex42 | <20 | NA |
| Anti-PRLR Ab-Ex44 | <10 | NA |
| MMAE | ≥90 | 0.19 |
| Anti-PRLR Ab | <10 | NA |

NA = not-applicable

Bioactivity of Steroid ADCs with and without Cyclodextrin Linkers is Shown in FIG. 18.

To test the comparability of ADCs with and without CDs containing steroid payloads, their activity in the 293/PRLR/GRE-Luc cells was studied at 72 hours of incubation. For this assay, 20,000 cells were seeded in 96-well plates in media containing DMEM supplemented with 10% FBS and pencillin/streptomycin (complete media) and grown overnight at 37° C. in 5% $CO_2$. For the free drug or ADC dose response curves, serially diluted reagents ranging from 100 nM to 5.1 μM were added to the cells and incubated for 72 hours at 37° C. Luciferase activity was determined by addition of One-Glo™ reagent (Promega, Cat #E6130) and relative light units (RLUs) were measured on a Victor luminometer (Perkin Elmer). The $EC_{50}$ values were determined from a four-parameter logistic equation over a 10-point response curve using GraphPad Prism. Delivery of the steroids will result in an activation of the Luc reporter in 293/PRLR/GRE-Luc cells. Full activation in this assay is defined between 90 and 100% of the maximal activation measured with the free payload. Partial activation in this assay is defined as activation that is between 10% and 90% of the maximal activation measured with the free payload. Minimal activation in this assay is defined as less than 10% of the maximal activation measured with the free payload.

As shown in Table 12 and FIG. 18, anti-PRLR Ab ADCs containing CD (Anti-PRLR Ab-Ex46, Anti-PRLR Ab-Ex47) have similar efficacy and potency in activating GRE-Luc reporter in 293/PRLR/GRE-Luc cells as anti-PRLR Ab ADC that do not contain CD (Anti-PRLR Ab-Ex45). In this assay, isotype control ADCs, regardless of whether they contain CD or not, as well as the unconjugated antibody did not demonstrate any significant effects in this assay.

TABLE 12

GR ACTIVATION OF STEROID ADCS WITH OR WITHOUT CYCLODEXTRIN LINKERS IN 293/PRLR/GRE-LUC CELLS

| Molecule tested | Maximal Activation | $EC_{50}$ (nM) |
|---|---|---|
| Anti-PRLR Ab-Ex46 | Partial | 8.6 |
| Anti-PRLR Ab-Ex45 | Partial | 9.5 |
| Free payload (compound 1c) | Full | 8.4 |
| Isotype control Ab-Ex46 | Minimal | NA |
| Isotype control Ab-Ex45 | Minimal | NA |
| Anti-PRLR Ab | Minimal | NA |

NA = not-applicable

Bioactivity of LXR Agonist ADCs with and without Cyclodextrin Linkers. See FIG. 19.

To test the comparability of ADCs with and without CDs containing LXR agonists anti-HER2 Ab ADC with and without CD were tested for their ability to activate LXR in a THP1/LXR-Luc/Her2 bioassay. In the assay, either THP1/LXR-Luc cells or THP1/LXR-Luc/Her2 cells were seeded onto white 96 well plates at 30,000 cells/well in media containing RPMI supplemented with 10% FBS and pencillin/streptomycinin (complete media). Subsequently 3-fold serial dilutions of antibody drug conjugates, unconjugated antibodies, or free payloads were added to the cells at final concentration ranging from 100 nM to 0.01 nM. After a 48-hour incubation, luciferase activity was determined after the addition of One-Glo™ reagent (Promega, E6130) to each well of cells. Relative light units (RLUs) were measured on a Victor luminometer (PerkinElmer) and the $EC_{50}$ values were determined using a four-parameter logistic equation over a 10-point dose response curve (GraphPad Prism). The $EC_{50}$ values of LXR agonists of the invention and reference compounds are shown in Table 13. The $EC_{50}$ values of the ncADCs and the corresponding LXR agonists are shown in Table 13. Full activation in this assay is defined as between 95% to over 100% of the maximal activation measured with the free payload 1d. Partial activation in this assay is defined as between 10% and 94.9% of the maximal activation measured with the free payload 1d. Minimal activation in this assay is defined as less than 10% of the maximal activation measured with the free payload 1d.

As shown in Table 13 and FIG. 19, the anti-Her2 Ab ADC containing CD and that releases payload 1d (anti Her2 Ab-Ex49) has similar efficacy and potency in activating LXR in THP1/Her2/LXR-Luc cells as an anti-Her2 Ab ADC that does not contain CD and that releases payload 1d (anti Her2 Ab-Ex48). Another anti-Her2 Ab ADC containing CD that releases payload if also demonstrates full activation as compared to the free payload 1d. In this assay, the unconjugated antibody did not demonstrate any effect. Isotype control ADCs, regardless of whether they contain CD or not, showed no significant effect at most of the concentrations tested. Some isotype controls did show some partial activation at the highest concentration tested.

TABLE 13

ACTIVATION IN THP1/LXR-LUC/HER2 ASSAY BY LXR AGONISTS AND NCADCS

| Molecule tested | Maximal activation | $EC_{50}$ (nM) |
|---|---|---|
| 1d derived ncADCs and free payload | | |
| 1d, payload of Ex48 and 49 | Full activation | 2.8 |
| Anti Her2 Ab-Ex48 | Full activation | 0.8 |
| Isotype control Ab-Ex48 | Partial activation | NA |
| Anti Her2 Ab-Ex49 | Full activation | 0.7 |
| Isotype control Ab-Ex49 | Minimal activation | NA |
| 1f derived ncADCs and free payload | | |
| 1f, payload of Ex55 | Full activation | 0.7 |
| Anti Her2 Ab-Ex55 | Full activation | 0.5 |
| Isotype control Ab-Ex55 | Partial activation | NA |
| Anti Her2 Ab | Minimal activation | NA |

NA = not applicable

See, also, *J. Am. Chem. Soc.*, 2012, 134(46), 19108-19117*; Org. Biomol. Chem.*, 2009, 7(8), 1680-1688 and US2015/284416A1*; Angew. Chem. Int. Ed.*, 2011, 50(47), 11117-11120*; J. Am. Chem. Soc.*, 2012, 134 (46), 18886-18888; Synthesis (Germany), 2014 46(5), 669-677.

Example 73

To determine the effect on the cleavage efficiency on a steroid or LXR agonist payload when a cyclodextrin moiety was added in the linker, a Cathepsin B cleavage assay was performed. For the assay, the linker-payload stock solution (10 mM of linker-payload in DMSO) was added into a solution of 100 mM NaOAc, 10 mM dithiothreitol, at pH5 to obtain a 50 μM substrate solution. Human liver Cathepsin B (Athens Research & Technology, Cat #16-12-030102) in 50 mM NaOAc, 1 mM EDTA, at pH 5, was added to the substrate solution. The Cathepsin B and substrate solution was mixed with and without 10 mM of a Cathepsin B inhibitor (CA074; APE Bio, Cat #A1926), and incubated at 37° C. for 4 hours. Following the 4 hour incubation, acetic acid and then acetonitrile were added to stop the reaction. The quenched samples then underwent centrifugation at 14,000 rpm. Aliquots of the resultant supernatants were then diluted with equal volume of water and analyzed by LC/MS to determine the amount of payload released. The stability and activity of Cathepsin B was confirmed by incubating with 200 μM fluorogenic substrate for Cathepsin B (Santa Cruz Biotechnology, Cat #207975) (fluorescence at excitation of 340 nm/emission of 425 nm).

As shown in Table 14, the LXR agonist linker payload without cyclodextrin had 13.6% of the free payload release when treated with Cathepsin B for 4 hours, whereas the LXR agonist linker payload with cyclodextrin had 38.5% of the free payload release when treated with Cathepsin B for 4 hours. The steroid linker payload without cyclodextrin had between 7.5-17.2% of the free payload release when treated with Cathepsin B for 4 hours, whereas the steroid linker payload with cyclodextrin had 28.9% of the free payload release when treated with Cathepsin B for 4 hours.

TABLE 14

AMOUNT OF PAYLOAD RELEASED FROM LINKER-PAYLOADS WITH AND WITHOUT CYCLODEXTRIN MOIETY IN CATHEPSIN B ASSAY

| Payload | Payload Type | Linker-Payload (LP) | Linker Modification | Percent of payload released at 4 hrs |
|---|---|---|---|---|
| 1d | LXR Agonist | Ex 48 | No cyclodextrin | 13.6% |
| | | Ex 49 | Cyclodextrin | 38.5% |
| 1h | Steroid | Ex 58 | No cyclodextrin | 7.5-17.2% |
| | | Ex 59 | Cyclodextrin | 28.9% |

Example 74

To determine the effect of the addition of a cyclodextrin linker to the activity of anti-MSR1 antibody LXR agonist non-cytotoxic ADCs, an in vitro, a cell based LXR responsive luciferase reporter assay was developed. To generate the assay cell line, a LXR regulated luciferase reporter gene [Cignal Lenti LXR Reporter (luc) kit (Qiagen, Cat #CLS-001L)] was transduced into THP1 cells and the cells were selected for two weeks in puromycin. The lentivirus expresses the firefly luciferase gene under the control of a minimal CMV promoter and tandem repeats of the LXR transcriptional response element. The resulting cell line is referred to as THP1/LXR-Luc cells.

For the assay, THP1/LXR-Luc cells were seeded onto 96 well plates at 40,000 cells/well in media containing RPMI supplemented with 10% FBS and pencillin/streptomycin, and were subsequently differentiated with 200 nM Phorbol Myristate Acetate for 3 days. After the 3 day differentiation, three-fold serial dilutions of antibody drug conjugates in fresh media were added to the cells at final concentration ranging from 100 nM to 0.01 nM. The last well in the plate served as blank control containing only the media. Forty-eight hours later, luciferase activity was determined after the addition of One-Glo™ reagent (Promega, Cat #E6130) to each well. Relative light units (RLUs) were measured on a Victor luminometer (PerkinElmer) and $EC_{50}$ values were determined using a four-parameter logistic equation over a 10-point dose response curve (GraphPad Prism). The $EC_{50}$ value of each molecule tested is shown in the Table 15. The signal to noise (S/N) was determined by calculating the RLU of standard one over the RLU of standard eight for each of the anti-MSR1 antibodies.

As shown in Table 15, H1H21234N-N297Q conjugated with the LXR agonist linker payload without cyclodextrin (H1H21234N-N297Q-Ex 48) demonstrated stimulation of the THP1/LXR-Luc cells with an $EC_{50}$ value of 1.77 nM and a S/N value of 16. H1H21234N-N297Q conjugated with the LXR agonist linker payload with cyclodextrin (H1H21234N-N297Q-Ex 49) stimulation of the THP1/LXR-Luc cells with an $EC_{50}$ value of 1.99 nM and a S/N value of 17.

TABLE 15

ACTIVITY OF ANTI-MSR1 AB-LXR AGONIST NCADCS IN THP1/LXR-LUC CELL BASED ASSAY

| Payload | Payload Type | Linker-Payload (LP) | ncADC | 48 hour $EC_{50}$ (M) | S/N |
|---|---|---|---|---|---|
| 1d | LXR Agonist | Ex 48 | H1H21234N-N297Q-Ex48 | 1.77E−09 | 16 |
| | | Ex 49 | H1H21234N-N297Q-Ex49 | 1.99E−09 | 17 |

Example 75

To determine if there was any effect of the addition of a cyclodextrin linker to the activity of anti-MSR1 antibody steroid non-cytotoxic ADCs, an in vitro lipopolysaccharide (LPS) mediated IL-1p release assay was performed. For the assay, THP-1 cells were seeded onto 96 well plates at 40,000 cells/well in media containing RPMI supplemented with 10% FBS and pencillin/streptomycinin, and were differentiated with 200 nM Phorbol Myristate Acetate (PMA) for 3 days. After the 3 day differentiation, three-fold serial dilutions of antibody drug conjugates, in fresh media were added to the cells at final concentration ranging from 100 nM to 0.01 nM. The last well was left as blank control containing only the media. Seventy-two hours later, cells were treated with 5 μg/mL of LPS (InVivoGen, Cat #tIrl-eklps) for 5 hours. The cell media was then collected and the IL-1p was measured using a V-PLEX Proinflammatory Panel 1 human kit (Meso Scale Diagnostics, Cat #15049D-2) as per manufacturer's instructions. Subsequently, the plate was read on a MSD plate reader (Meso Scale Discovery). The $IC_{50}$ values were determined from a four-parameter logistic equation over a 10-point response curve (GraphPad Prism). All $IC_{50}$ values are expressed in molar (M) concentration.

As shown in Table 16, H1H21234N-N297Q conjugated with the steroid linker payload without cyclodextrin (H1H21234N-N297Q-Ex 58) demonstrated inhibition of LPS mediated IL-13 release from THP1 cells with an $IC_{50}$ value of 1.73 nM and having a reduction of IL-1p released down to 97.2 μg/mL. H1H21234N-N297Q conjugated with the steroid linker payload without cyclodextrin (H1H21234N-N297Q-Ex 59) demonstrated similar inhibition of LPS mediated IL-13 release from THP1 cells with an $IC_{50}$ value of 1.33 nM and having a reduction of IL-1p released down to 126.46 μg/mL. The unconjugated antibody demonstrated inhibition of LPS mediated IL-13 release from THP1 cells with an $IC_{50}$ value of 22.9 nM and having a reduction of IL-1p released down to 343.7 μg/mL showing the lack of efficacy compared to the conjugated antibodies.

TABLE 16

ACTIVITY OF ANTI-MSR1 AB-STEROID NCADCS ON LPS-INDUCED IL-1β RELEASE FROM THP1 CELLS

| Payload | Payload Type | Linker-Payload (LP) | ncADC | 72 hour $IC_{50}$ (M) | IL1beta released at max concentration tested (pg/mL) |
|---|---|---|---|---|---|
| 1h | Steroid | Ex 58 | H1H21234N-N297Q-Ex58 | 1.73E−09 | 97.24 |
| | | Ex 59 | H1H21234N-N297Q-Ex59 | 1.33E−09 | 126.46 |

TABLE 16-continued

| ACTIVITY OF ANTI-MSR1 AB-STEROID NCADCS ON LPS-INDUCED IL-1β RELEASE FROM THP1 CELLS | | | | | |
|---|---|---|---|---|---|
| Payload | Payload Type | Linker-Payload (LP) | ncADC | 72 hour $IC_{50}$ (M) | IL1beta released at max concentration tested (pg/mL) |
| N/A | N/A | N/A | H1H21234N-N297Q (unconjugated Ab) | 2.29E−08 | 343.7 |

The embodiments and examples described above are intended to be merely illustrative and non-limiting. Those skilled in the art will recognize or will be able to ascertain using no more than routine experimentation, numerous equivalents of specific compounds, materials and procedures. All such equivalents are considered to be within the scope and are encompassed by the appended claims.

What is claimed is:

1. A method for the treatment of a disease or disorder in a patient in need thereof comprising administering a compound or a pharmaceutically acceptable salt thereof to the patient, wherein the disease or disorder is selected from the group consisting of a proliferative disorder, a neurodegenerative disorder, an immunological disorder, an autoimmune disease, an inflammatory disorder, a dermatological disease, a metabolic disease, a cardiovascular disease, and a gastrointestinal disease, and wherein the compound is according to:

(i) Formula (Ib1), Formula (Ib2), or Formula (Ic1):

(Ib1)

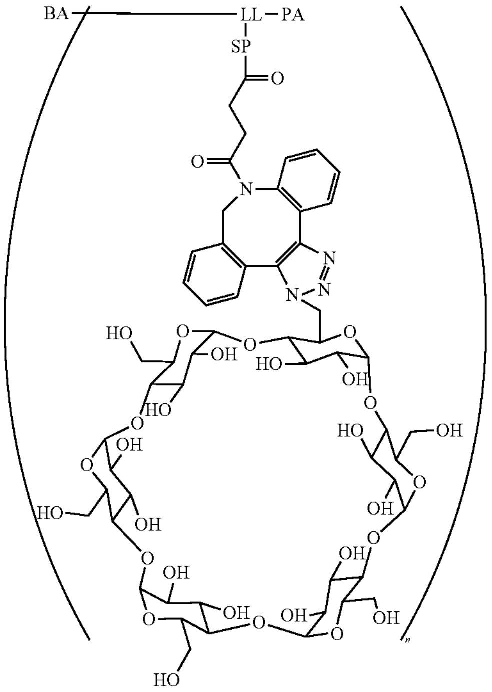

,

-continued (Ib2)

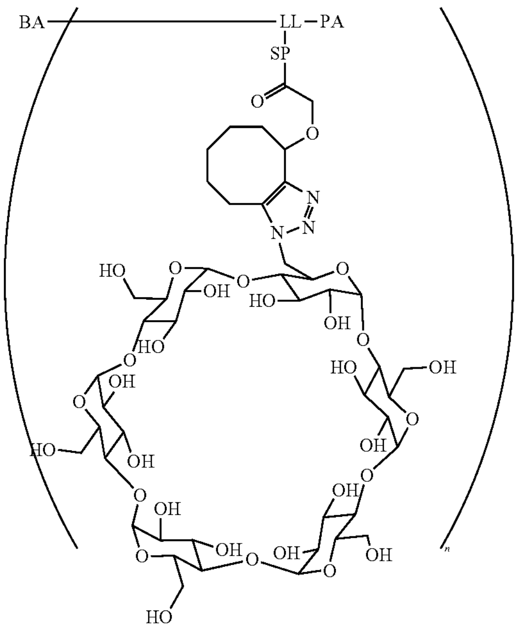

, (Ic1)

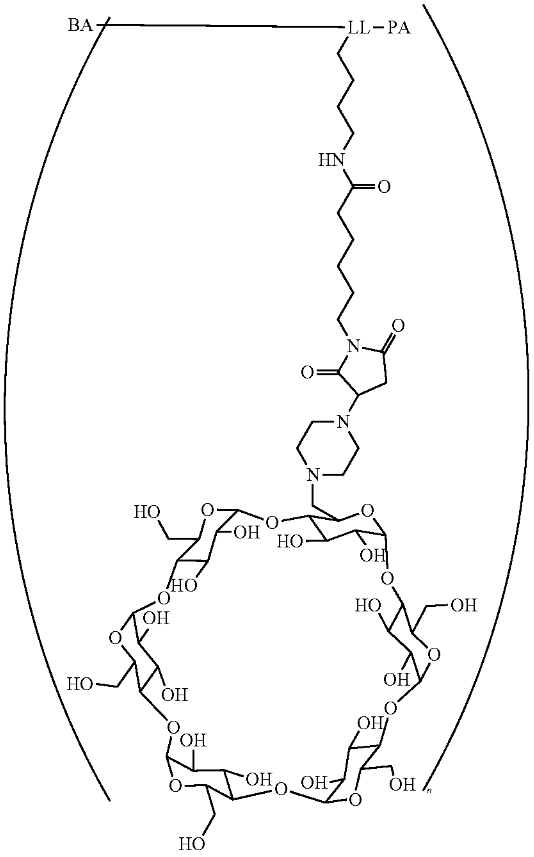

;

(ii) a Formula selected from the group consisting of:
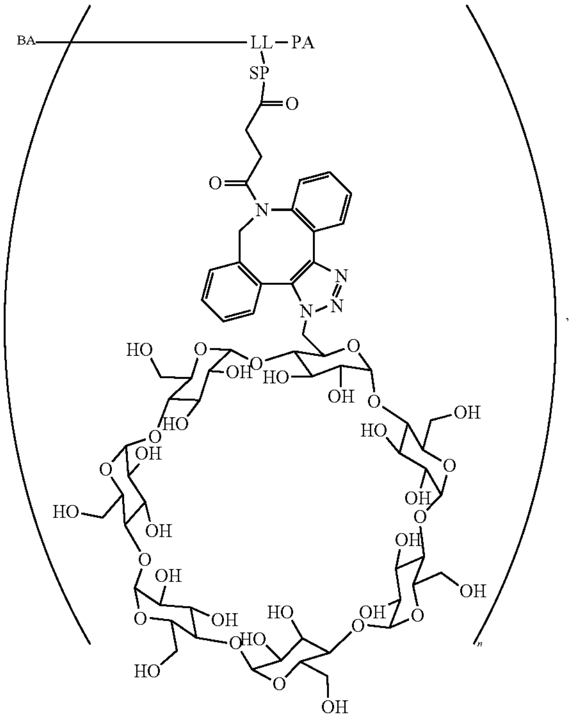
,
-continued
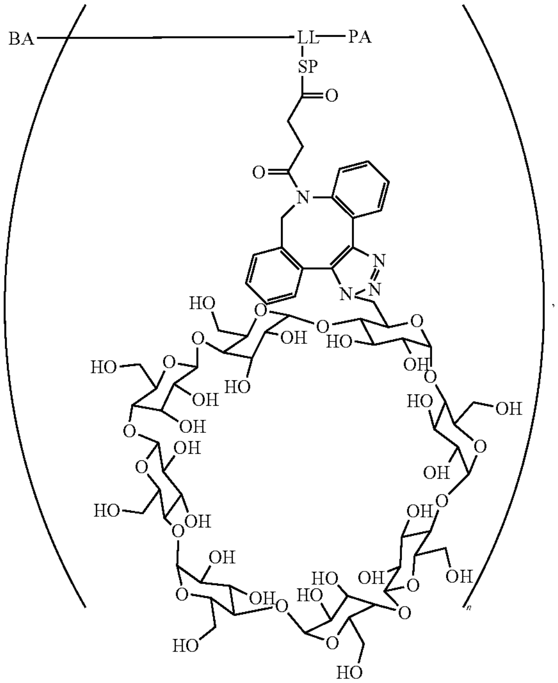
,
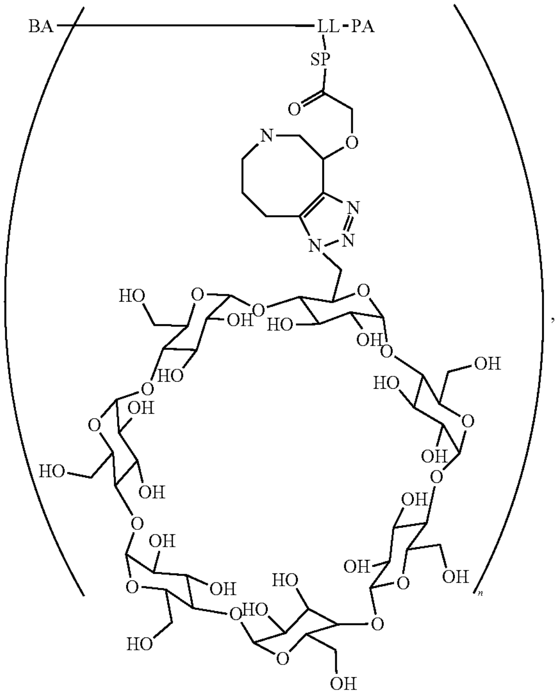
,
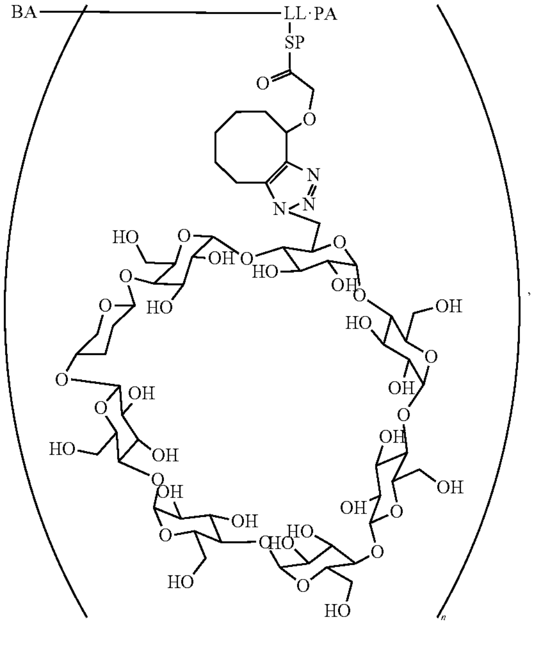
, -continued

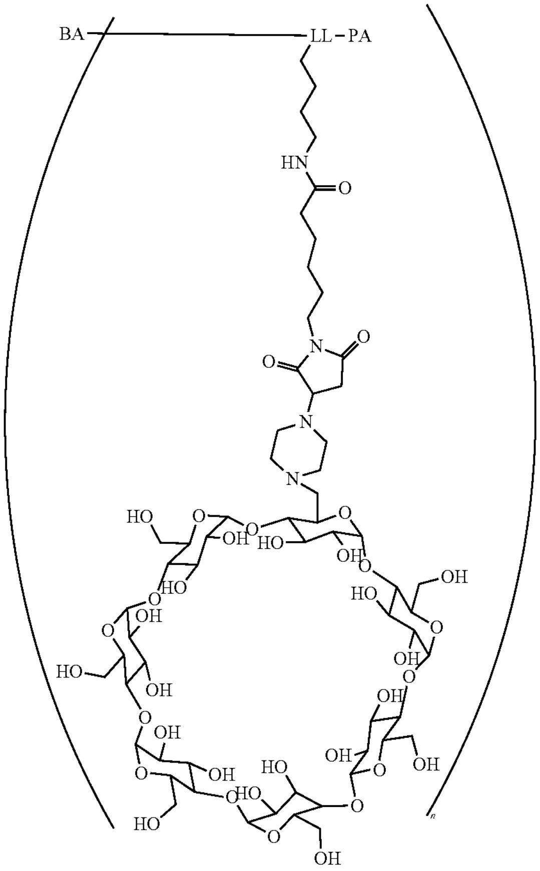

, and

-continued

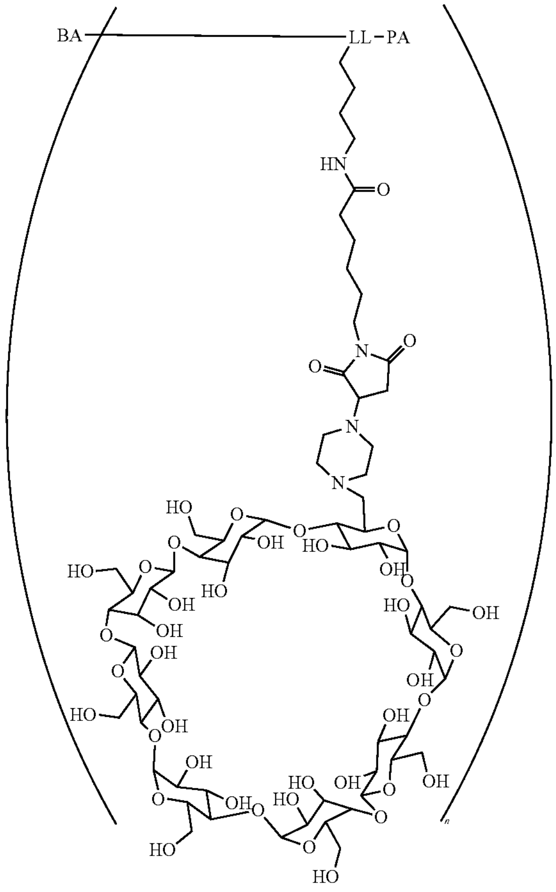

;

wherein BA is an antibody or an antigen binding fragment thereof;

LL is a trivalent linker;

SP is, independently in each instance, absent or is a spacer;

n is an integer from 1 to 30; and

PA is a payload moiety; or a regioisomer and/or stereoisomer thereof;

(iii) Formula (Id):

(Id)

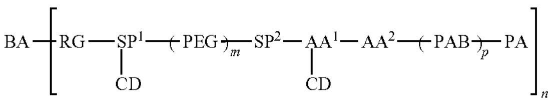

wherein:

BA is an antibody or antigen binding fragment thereof;

RG is a reactive group residue independently selected from the group consisting of

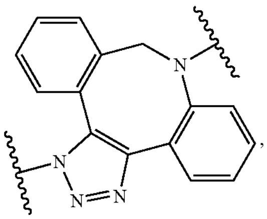
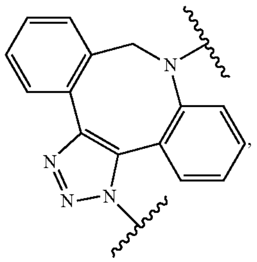
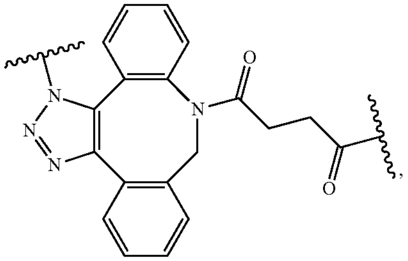
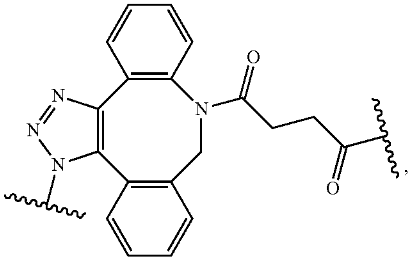
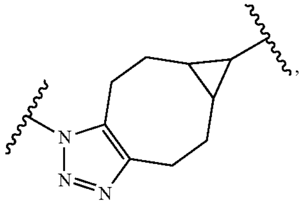
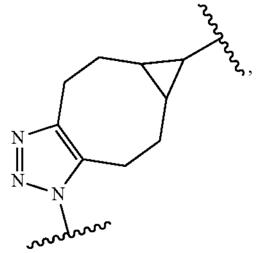
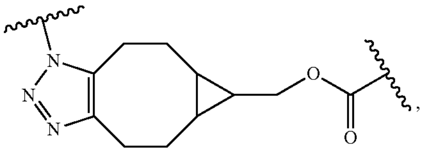
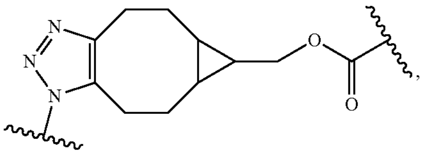
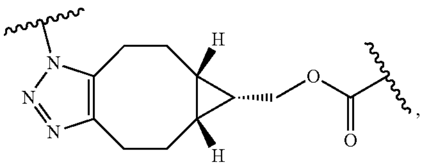
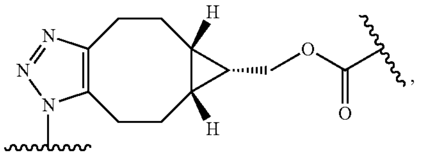

-continued

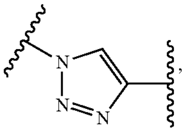
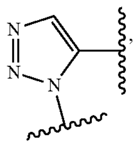
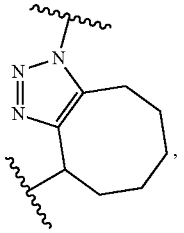
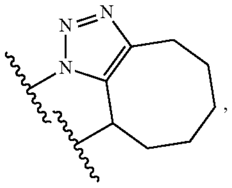
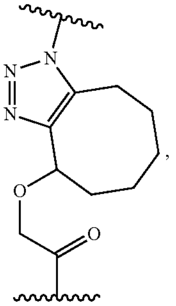
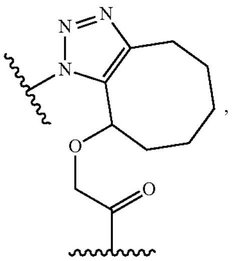
and
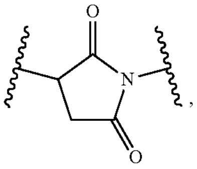

wherein the

indicates the atom through which the RG is bonded to the adjacent groups in the formula;

$SP^1$ and $SP^2$ are each, independently in each instance, a spacer group residue, and wherein $SP^1$ comprises a trivalent linker when attached to -CD, or $SP^1$-CD or $SP^2$ are independently, in each instance, absent;

$AA^1$ is a trivalent linker comprising an amino acid residue;

$AA^2$ is a di-peptide residue;

PEG is a polyethylene glycol residue;

PAB is

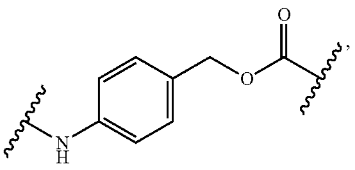 [SMILES: *Nc1ccc(COC(*)=O)cc1]

wherein the

indicates the atom through which the PAB is bonded to the adjacent groups in the formula;

CD is, independently in each instance, absent, a cyclodextrin, or a modified cyclodextrin wherein the modified cyclodextrin is $-SP^3$-RG-cyclodextrin; and, wherein at least one of CD is present;

$SP^3$ is, independently in each instance, absent or a spacer group residue;

cyclodextrin is selected from the group consisting of

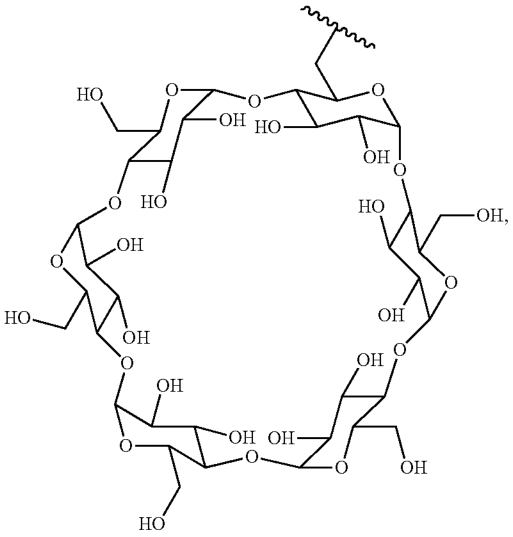

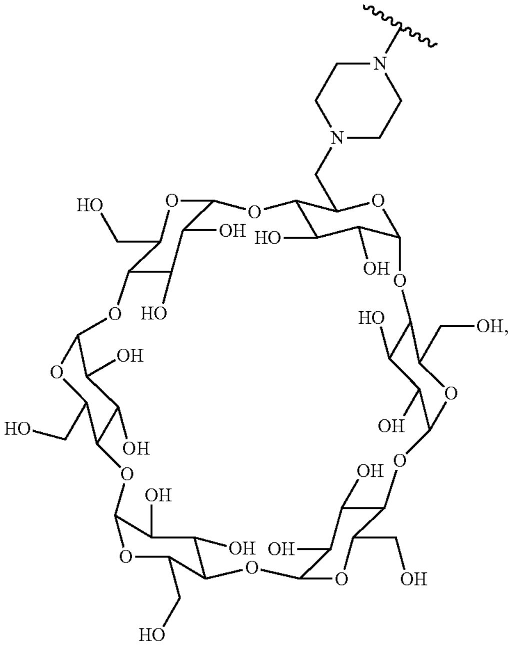

-continued

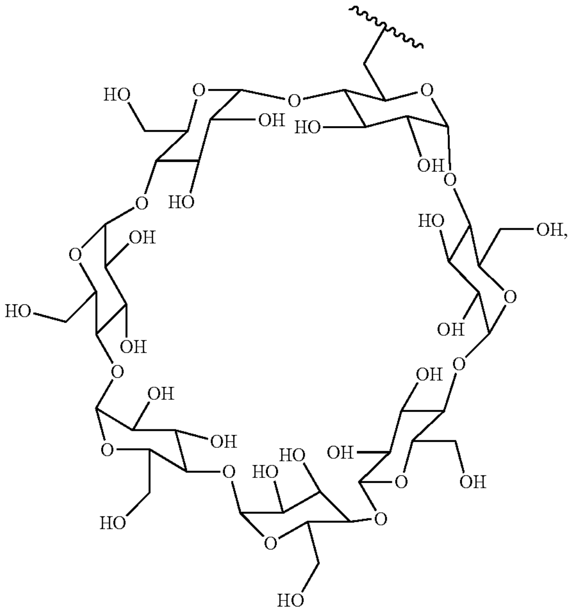

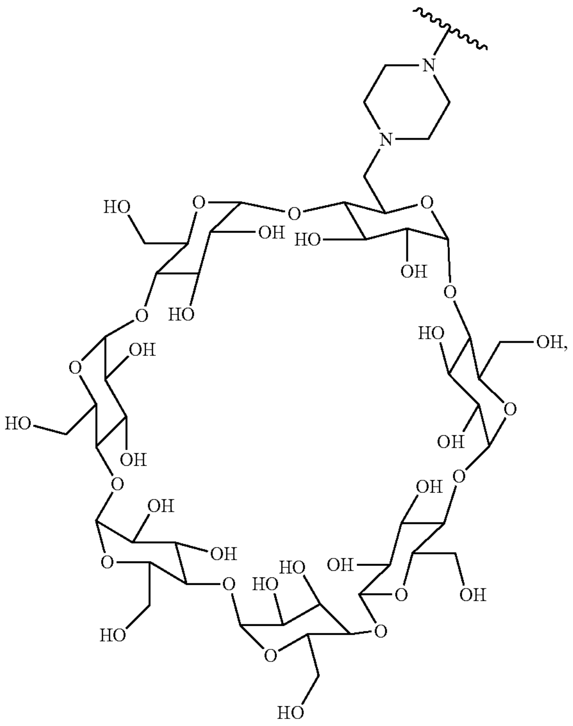

-continued

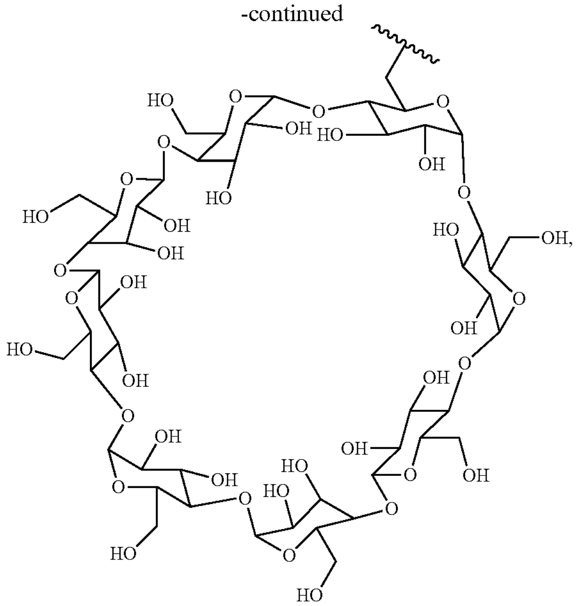

and

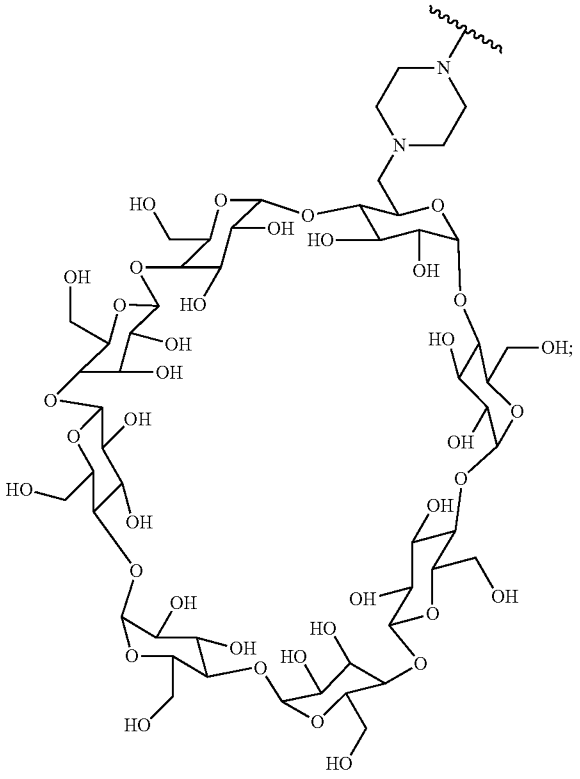 [SMILES: *N1CCN(CC2OC3OC4C(CO)OC(OC5C(CO)OC(OC6C(CO)OC(OC7C(CO)OC(OC8C(CO)OC(OC9C(CO)OC(OC%10C(CO)OC(OC2C(O)C3O)C(O)C%10O)C(O)C9O)C(O)C8O)C(O)C7O)C(O)C6O)C(O)C5O)C(O)C4O)CC1]

wherein the

indicates the atom through which the cyclodextrin is bonded to the adjacent groups in the formula;

subscript n is an integer from 1 to 30;

subscript m is an integer from 0 to 5;

subscript p is 0 or 1; and

PA is a payload moiety; or a regioisomer and/or stereoisomer thereof; or (iv) Formula (Ie):

(Ie)

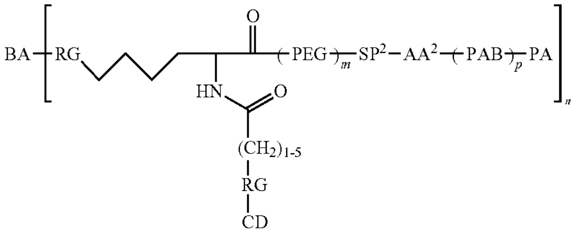

wherein:

BA is an antibody or antigen binding fragment thereof;

RG is, independently in each instance, a reactive group residue;

$SP^2$ is, independently in each instance, absent or a spacer group residue;

$AA^1$ is a trivalent linker comprising an amino acid residue;

$AA^2$ is a di-peptide residue;

PEG is a polyethylene glycol residue;

PAB is

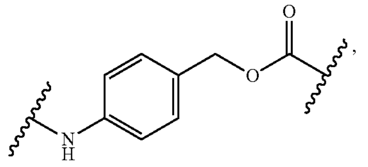 [SMILES: *Nc1ccc(COC(*)=O)cc1]

wherein the

indicates the atom through which the PAB is bonded to the adjacent groups in the formula;

CD is a cyclodextrin residue;

subscript n is an integer from 1 to 30;

subscript m is an integer from 0 to 5;

subscript p is 0 or 1; and

PA is a payload moiety; or a regioisomer and/or stereoisomer thereof.

2. The method of claim 1, wherein the compound is according to Formula (Ib1) or Formula (Ib2):

(Ib1)
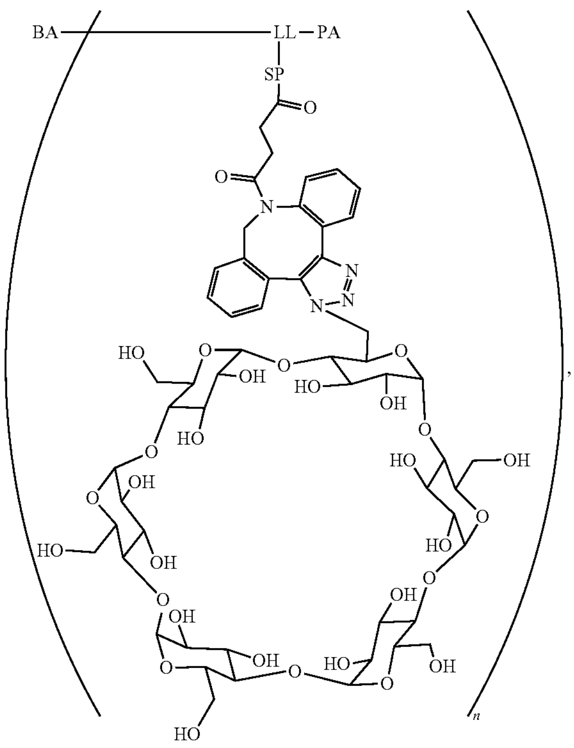
,
(Ib2)
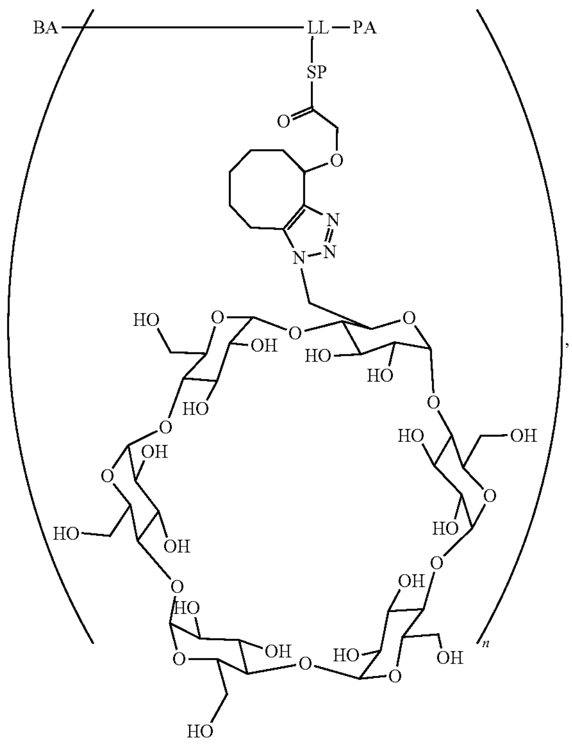
,
or a regioisomer and/or stereoisomer thereof.
3. The method of claim 1, wherein the compound is according to Formula (Ib3), Formula (Ib4), Formula (Ib5), or Formula (Ib6):

(Ib3)
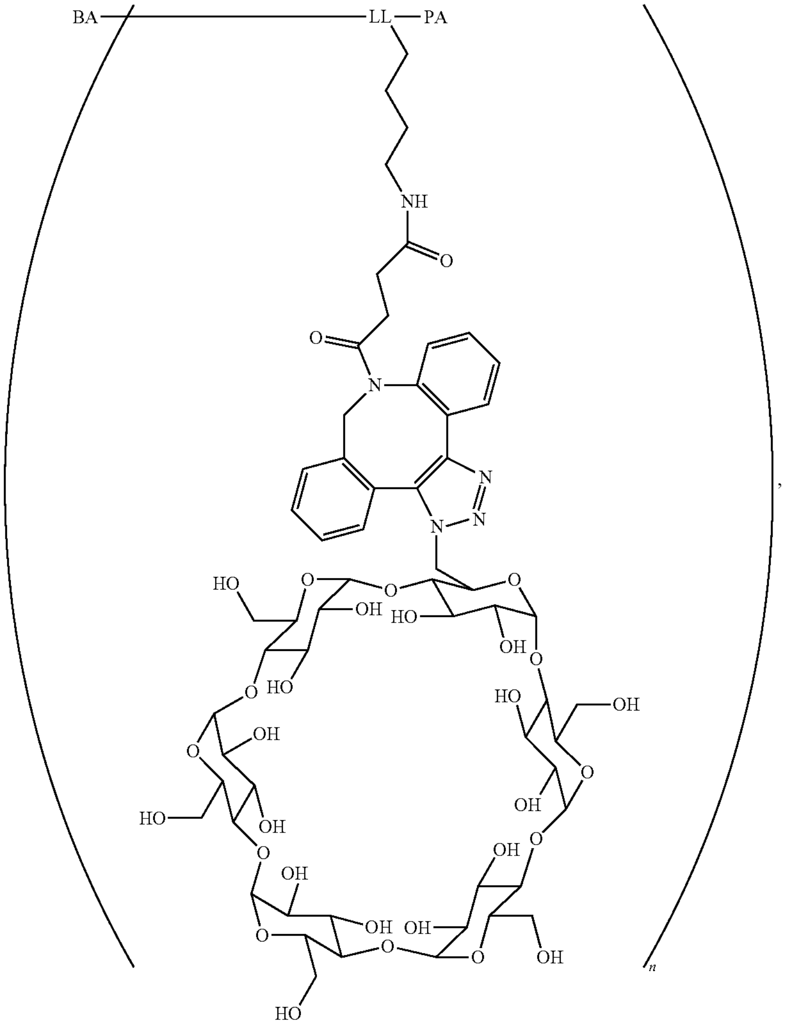
,

-continued
(Ib4)
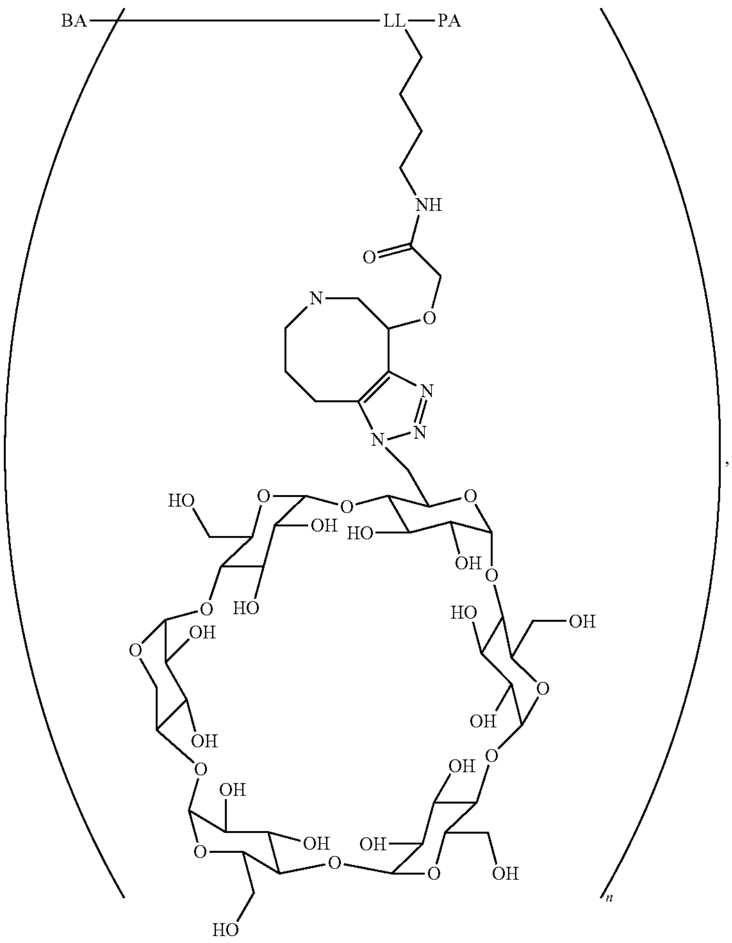
,

-continued
(Ib5)
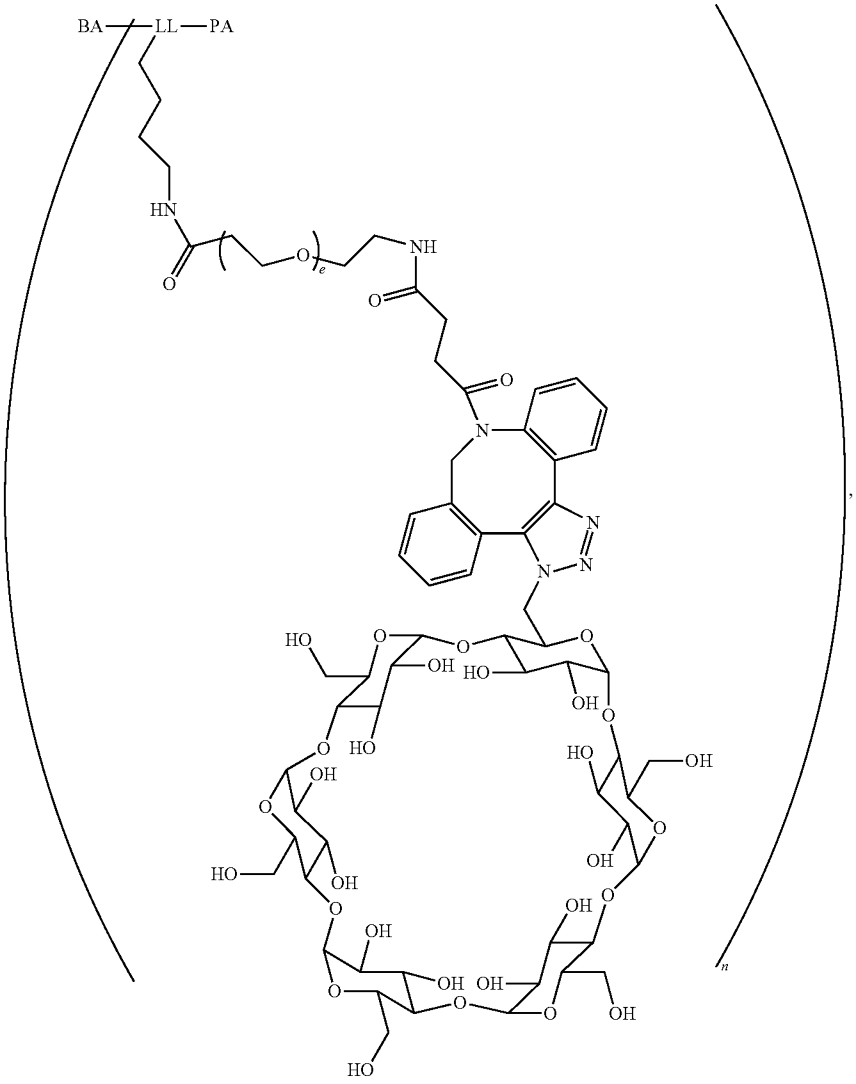
,

-continued
(Ib6)
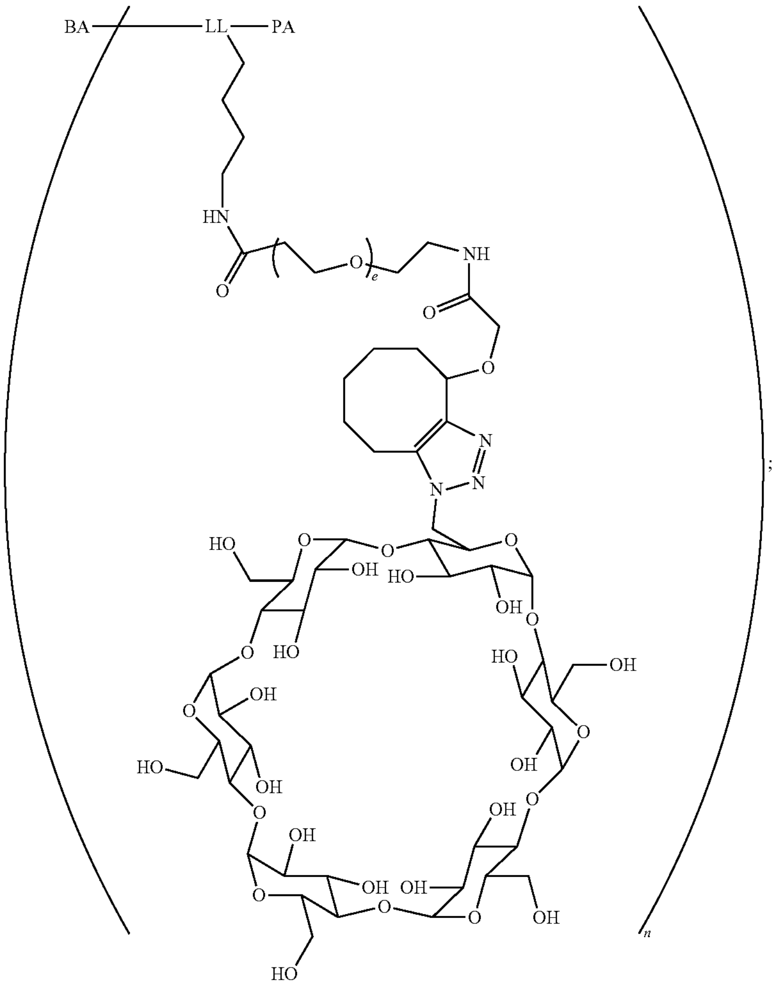
;
or a regioisomer and/or stereoisomer thereof.
4. The method of claim 1, wherein the compound is according to Formula (Ic1):

(Ic1)
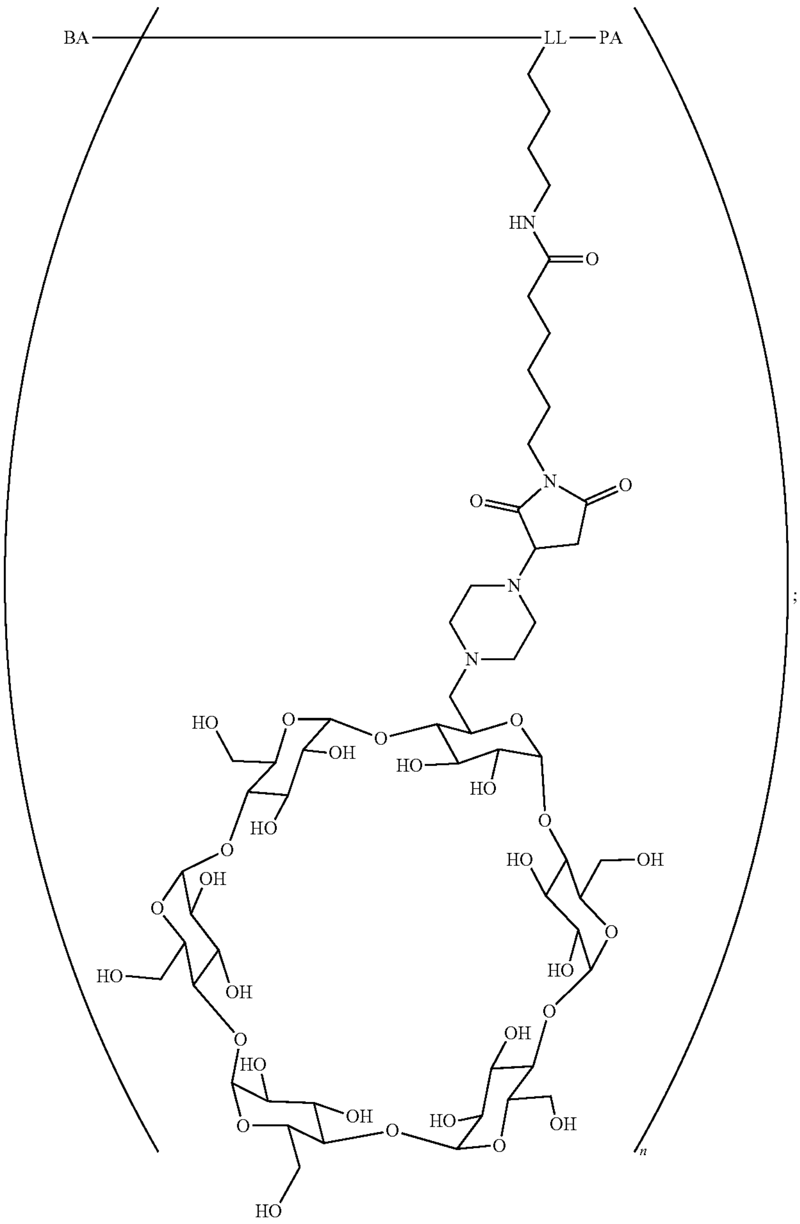
;
or a regioisomer and/or stereoisomer thereof.
5. The method of claim 1, wherein the compound is according to Formula (Id):
(Id)
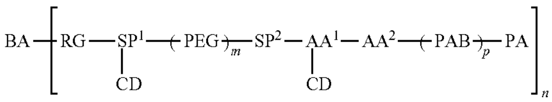
or a regioisomer and/or stereoisomer thereof.
6. The method of claim 1, wherein the compound is according to Formula (Ie):
(Ie)
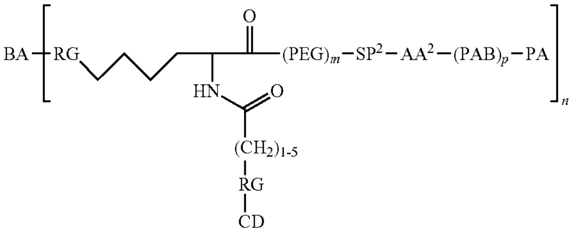
or a regioisomer and/or stereoisomer thereof.
7. The method of claim 6, wherein the compound is according to Formula (Ie1):

(Ie1)

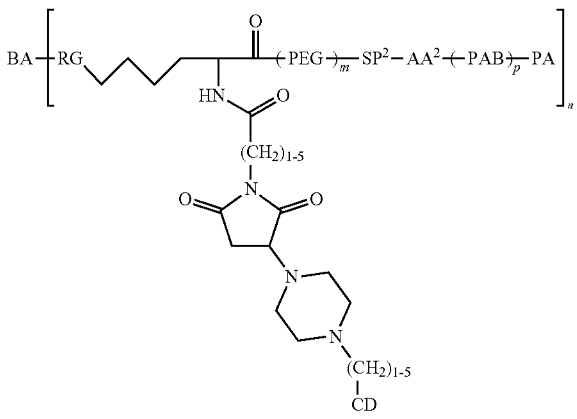

or a regioisomer and/or stereoisomer thereof.

8. The method of claim 7, wherein the compound is according to Formula (Ie2):

(Ie2)

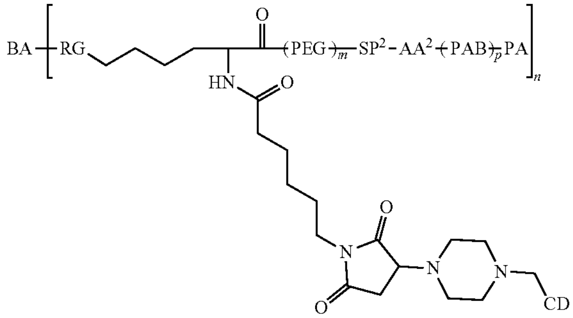

or a regioisomer and/or stereoisomer thereof.

9. The method of claim 1, wherein the compound is according to Formula (If):

(If)

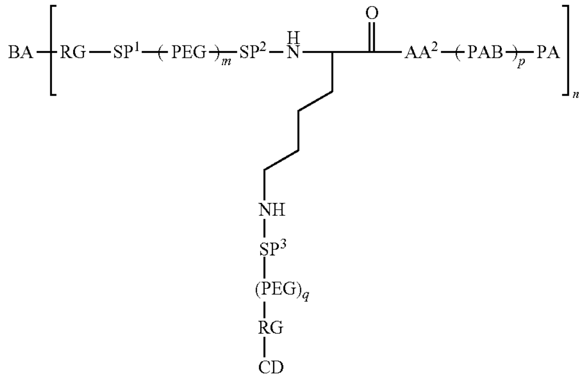

or a regioisomer and/or stereoisomer thereof;

wherein subscript q is an integer from 0 to 5.

10. The method of claim 1, wherein CD is, independently in each instance, selected from the group consisting of:

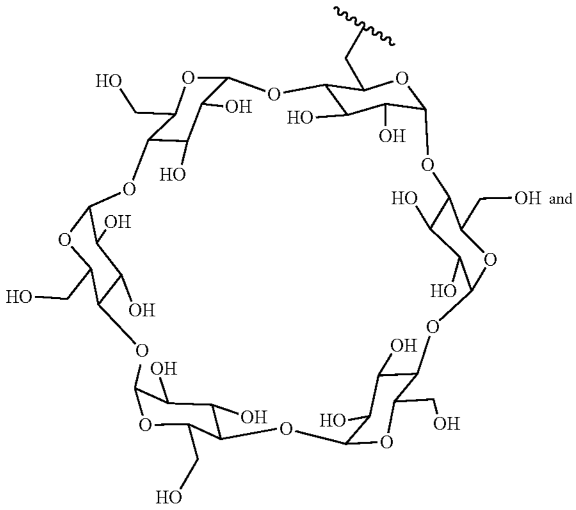

and

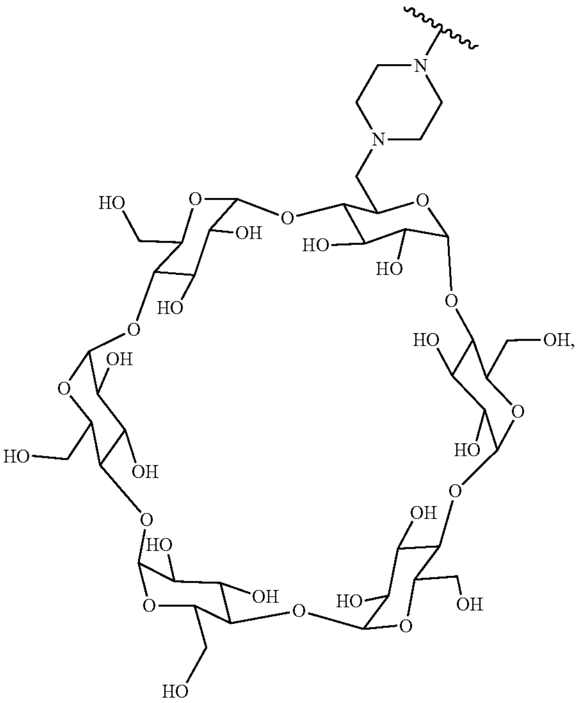

wherein the

indicates the atom through which the CD is bonded to the adjacent groups in the formula.

11. The method of claim 1, wherein CD is, independently in each instance, selected from the group consisting of:

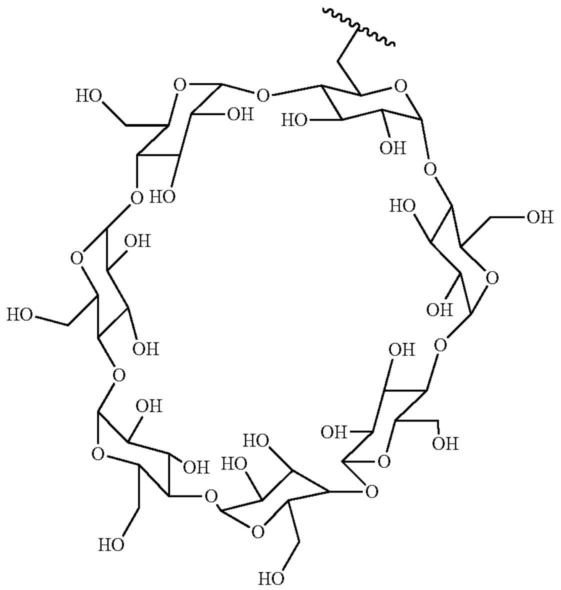

and

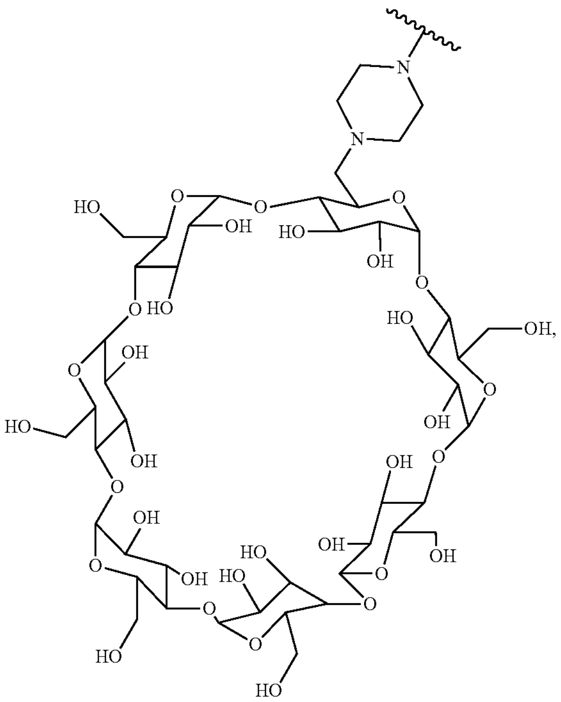

wherein the

indicates the atom through which the CD is bonded to the adjacent groups in the formula.

12. The method of claim 1, wherein CD is, independently in each instance, selected from the group consisting of:

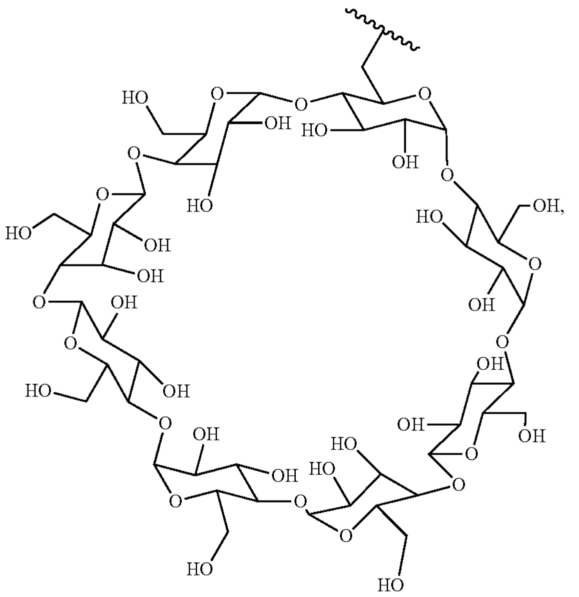

and

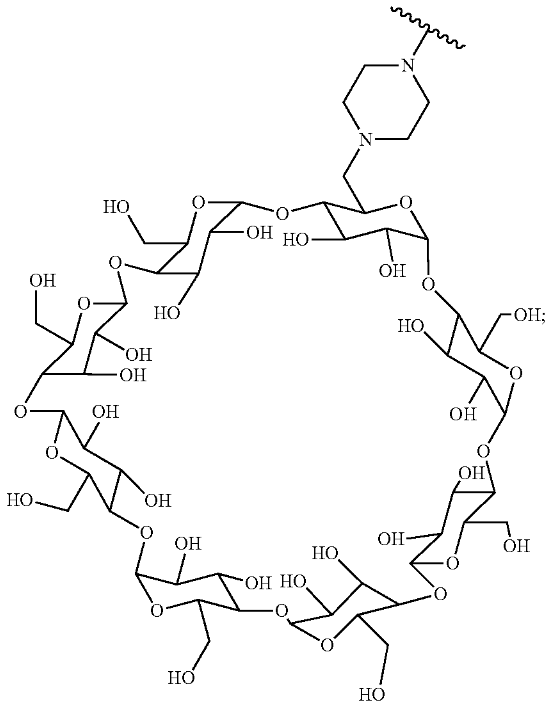

wherein the

indicates the atom through which the CD is bonded to the adjacent groups in the formula.

13. The method of claim 1, wherein RG is, independently in each instance, a click chemistry residue.

14. The method of claim 1, wherein RG, independently in each instance, comprises a triazole or a fused triazole.

15. The method of claim 1, wherein RG is, independently in each instance, selected from the group consisting of
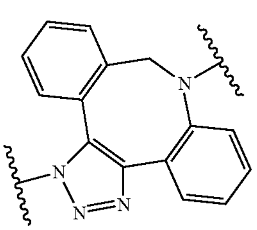,
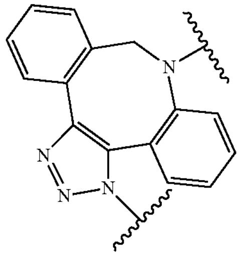,
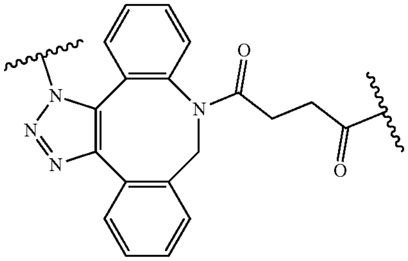,
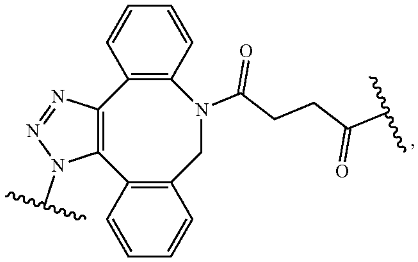,
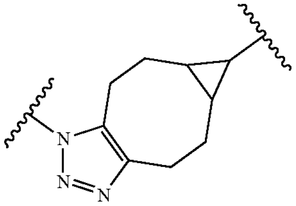,
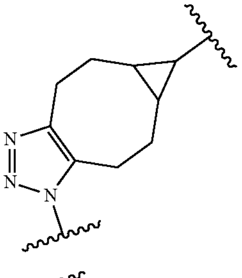,
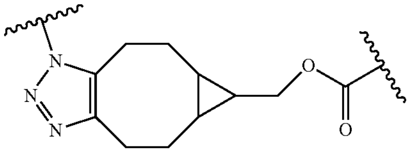,
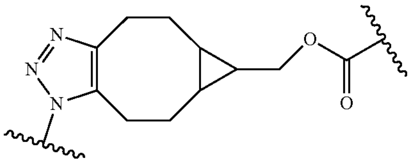,
-continued
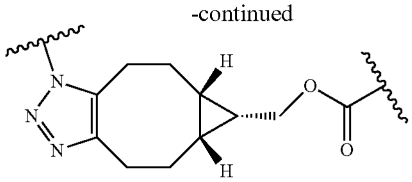,
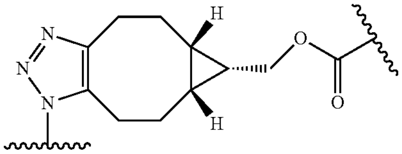,
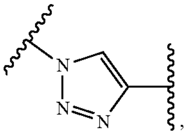,
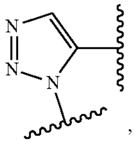,
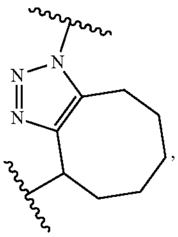,
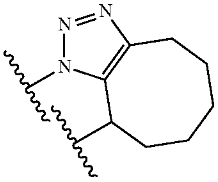,
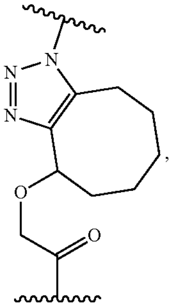,
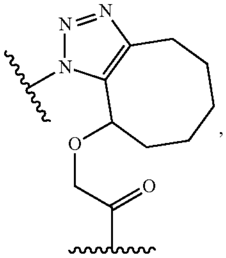, and
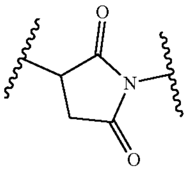,
wherein the
indicates the atom through which the RG is bonded to the adjacent groups in the formula.
16. The method of claim 5, wherein the compound according to Formula (Id):
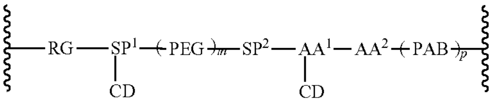

is selected from the group consisting of
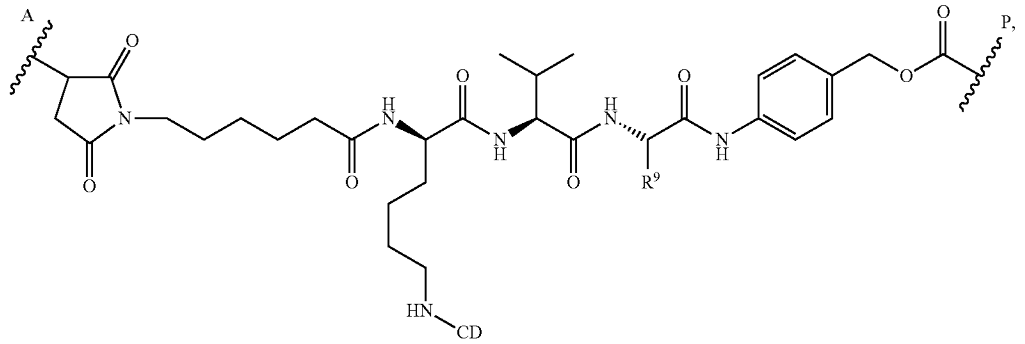
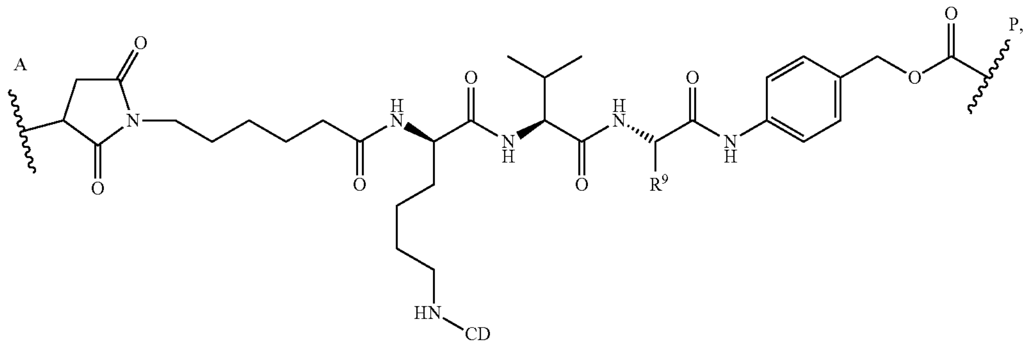
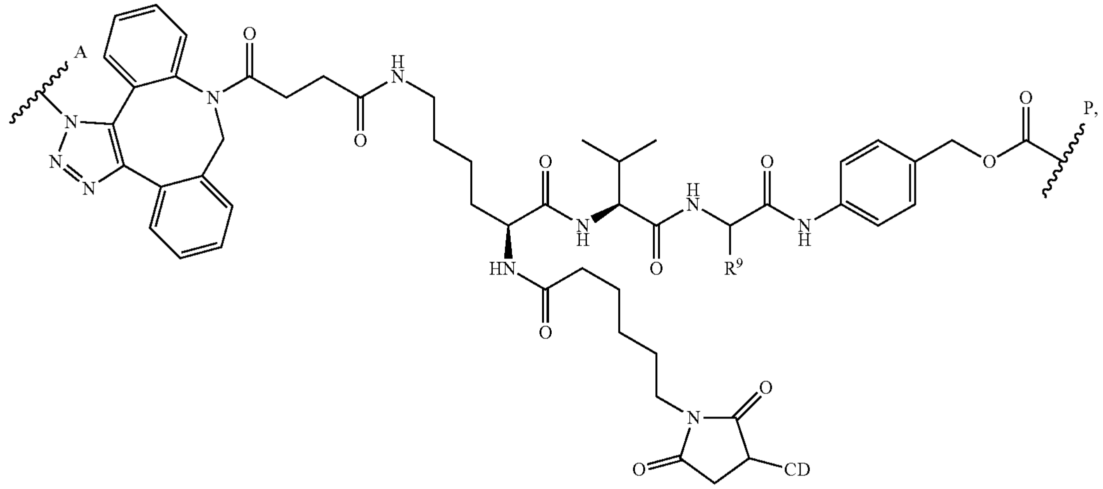

-continued
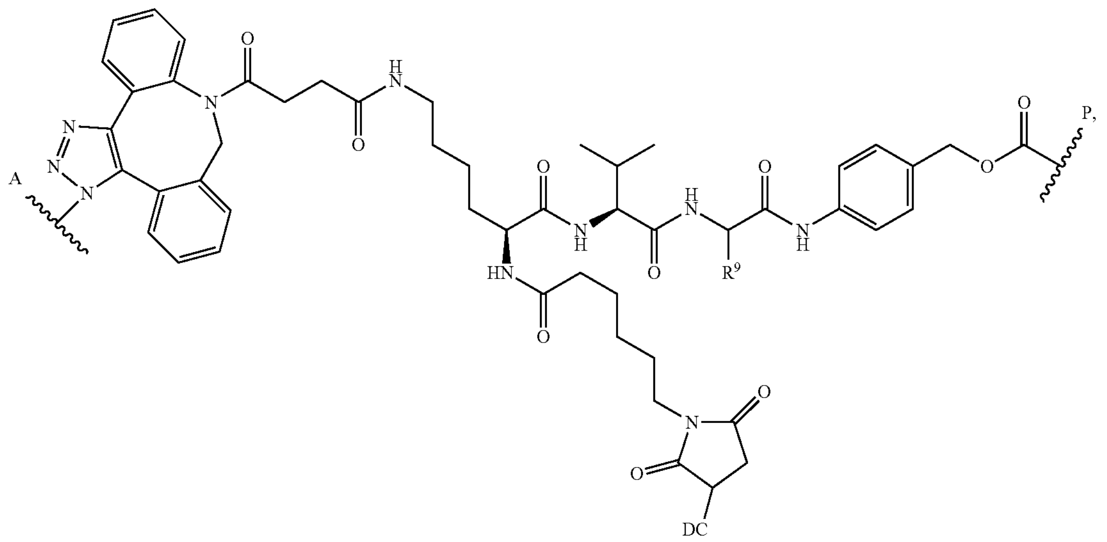
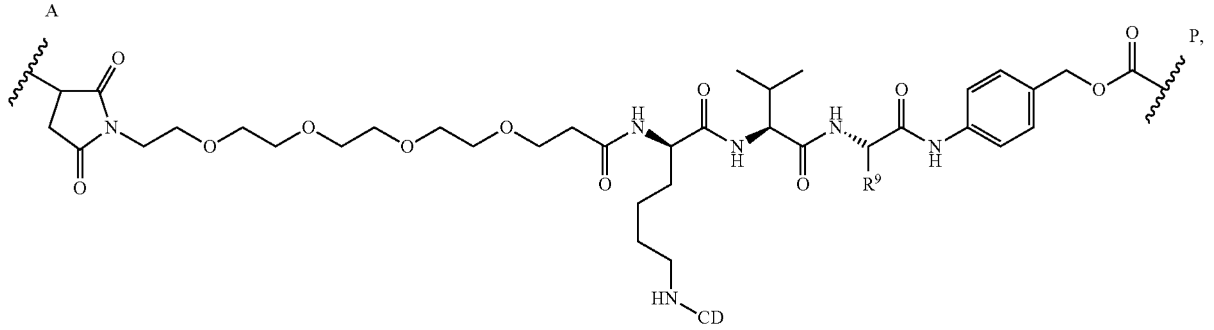
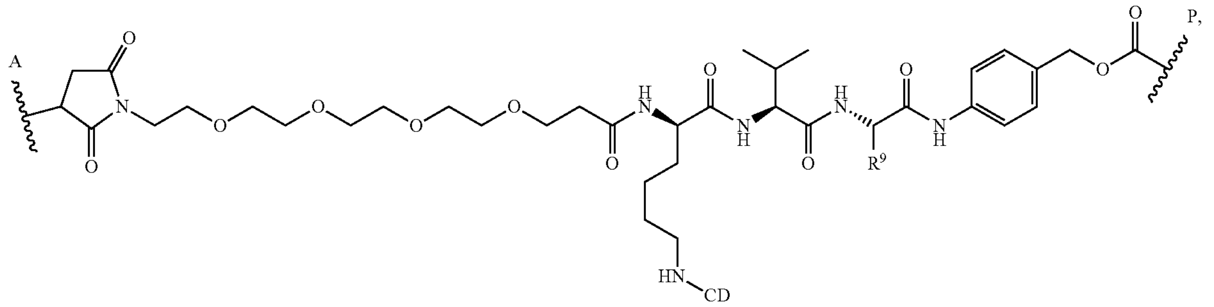
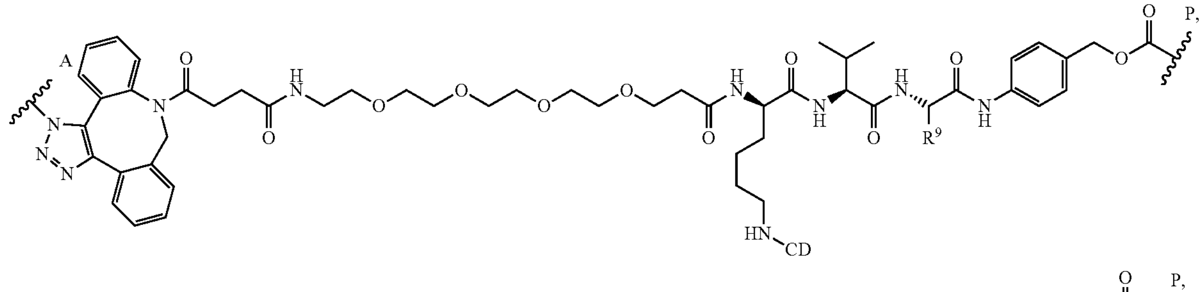
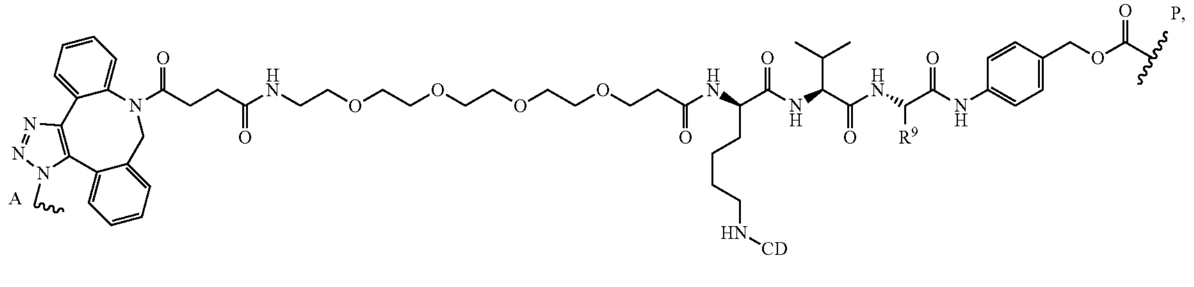

-continued
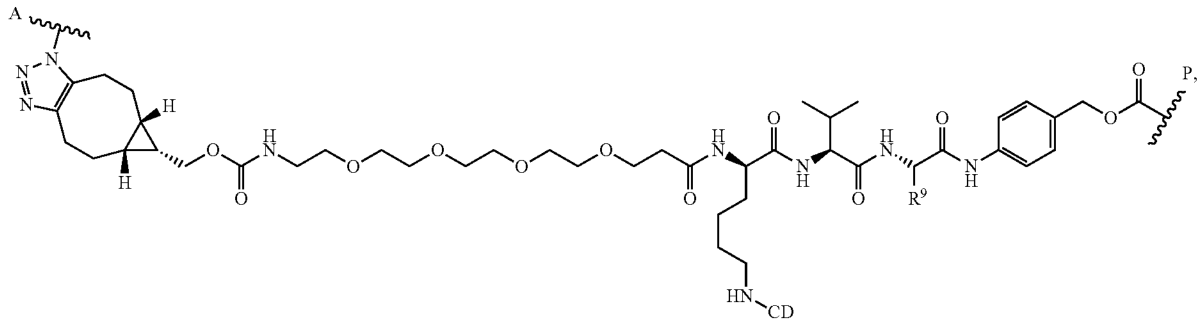
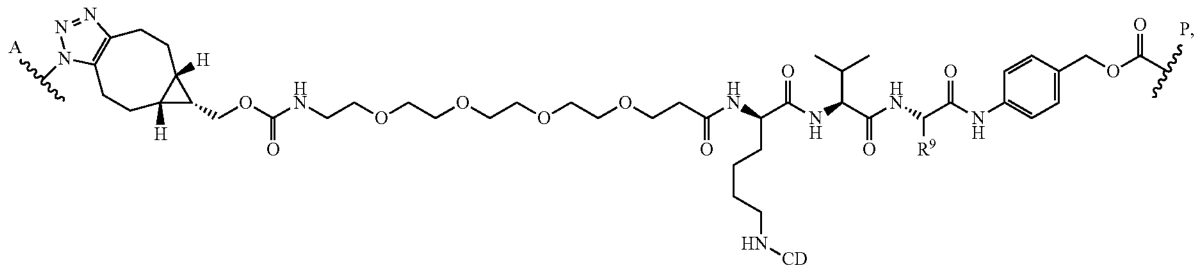
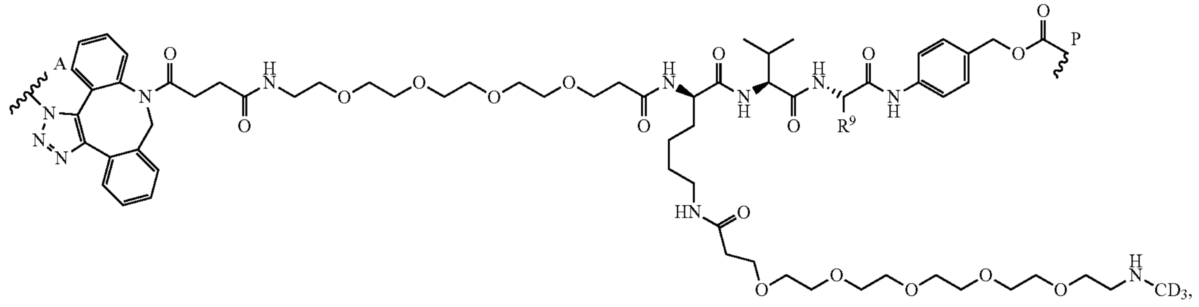
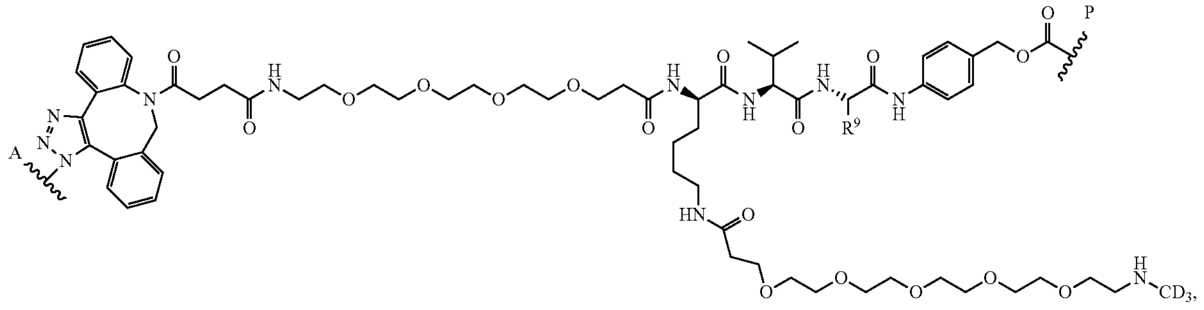
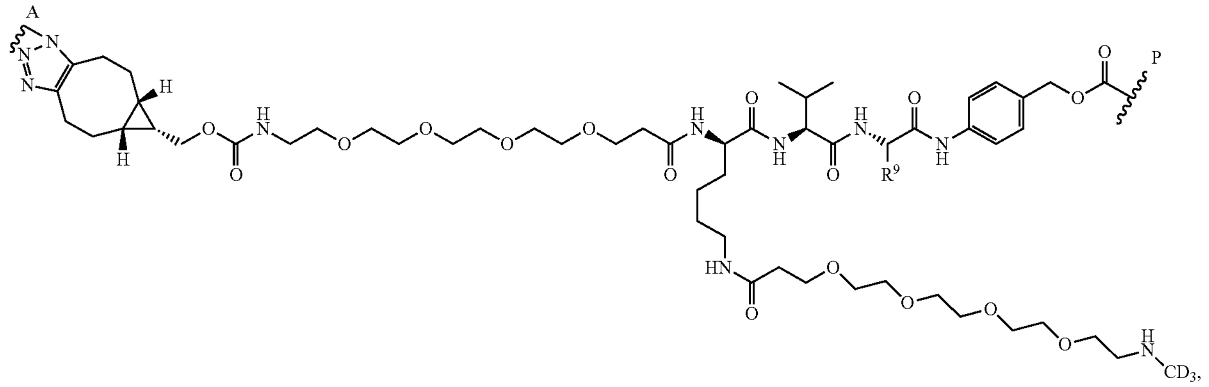

-continued
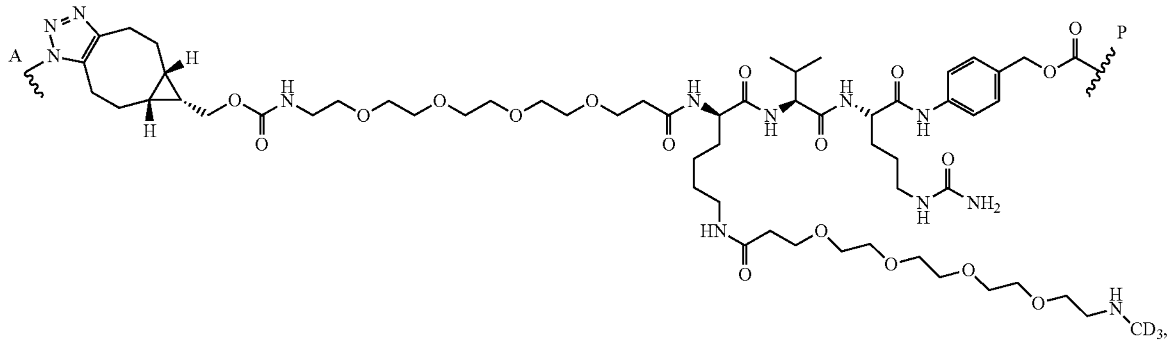
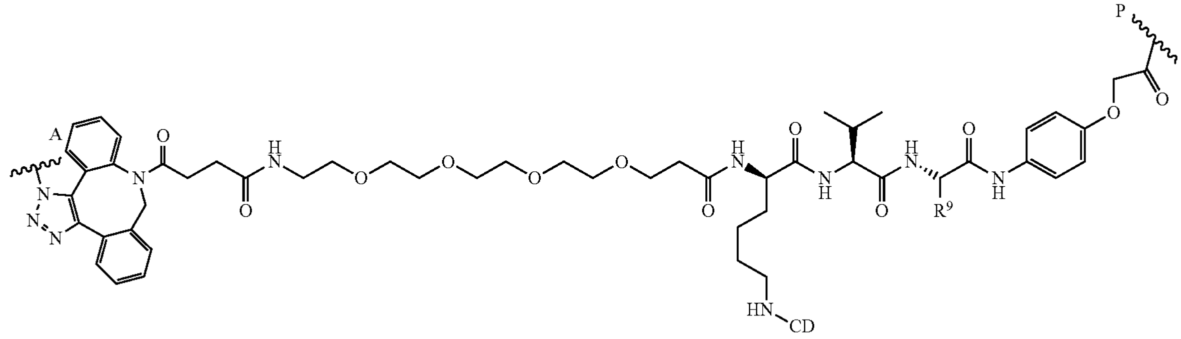
,
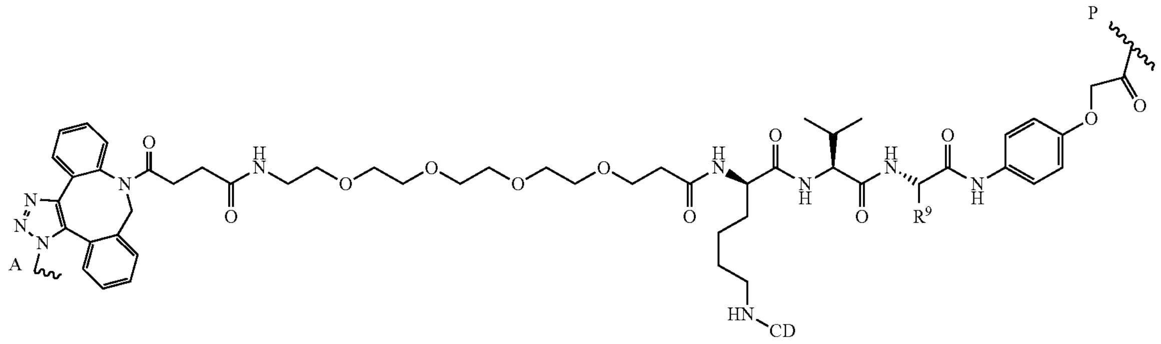
,
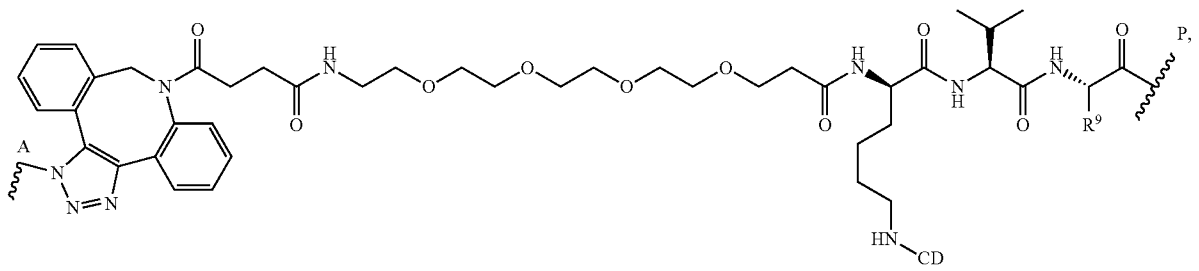
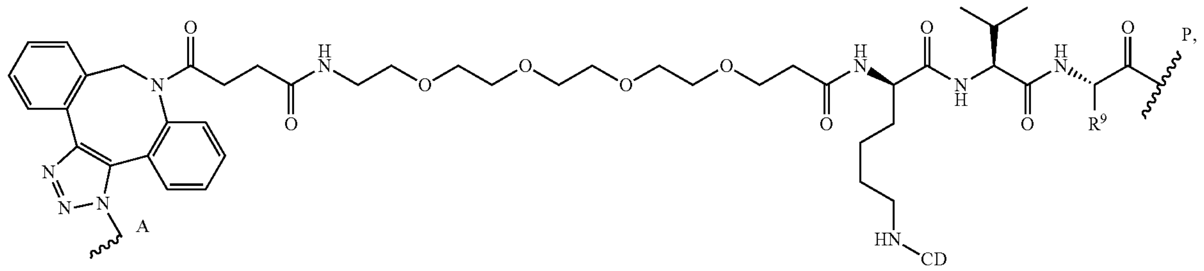

-continued
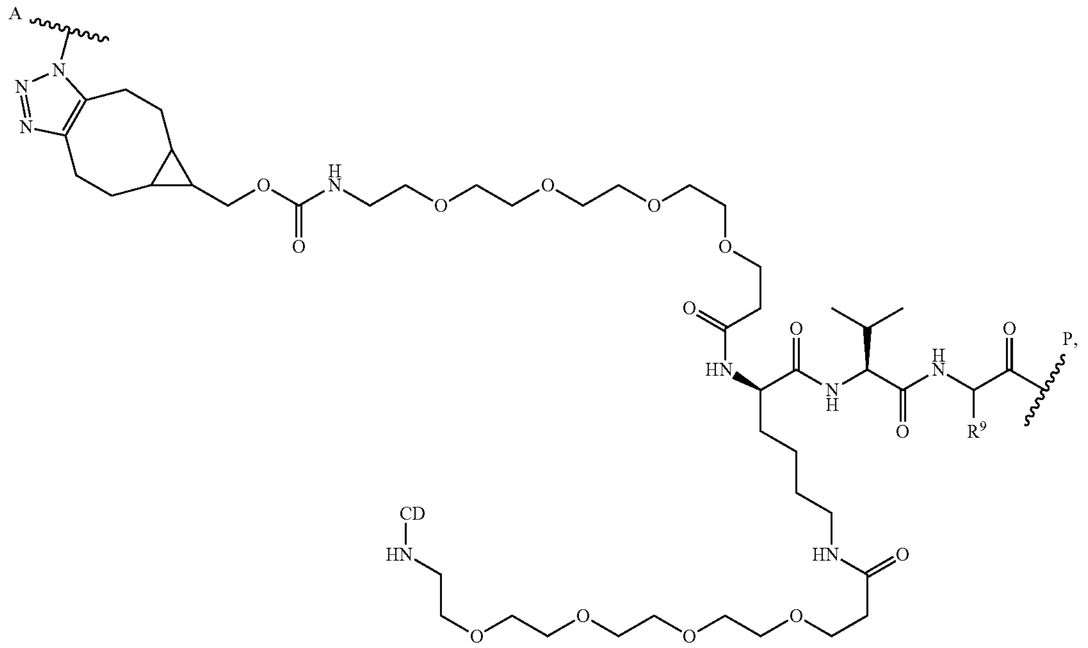
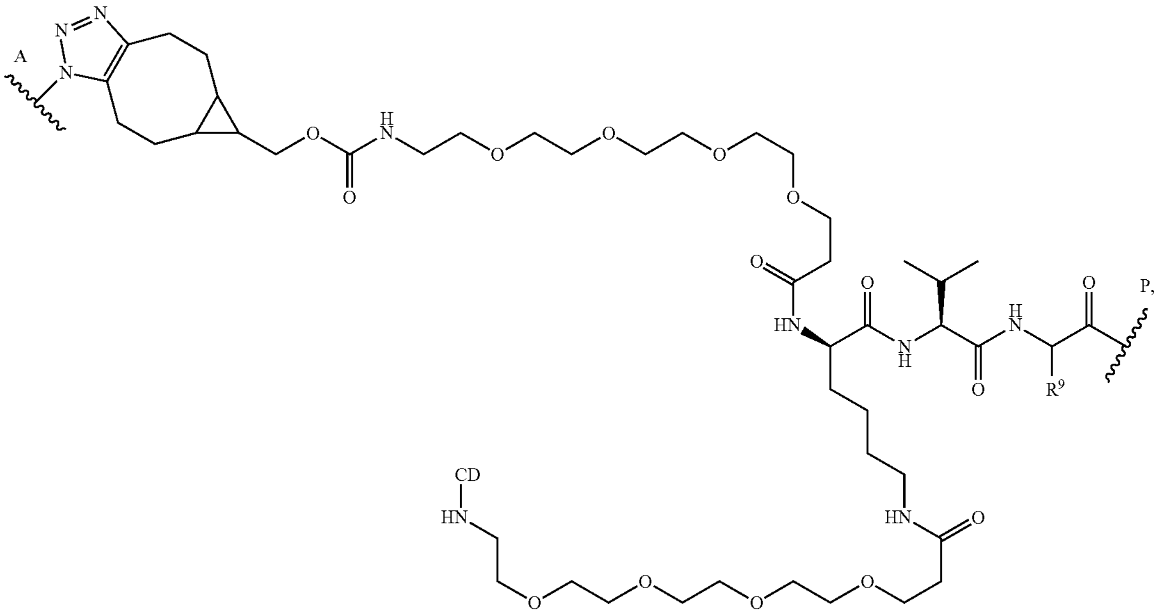

-continued
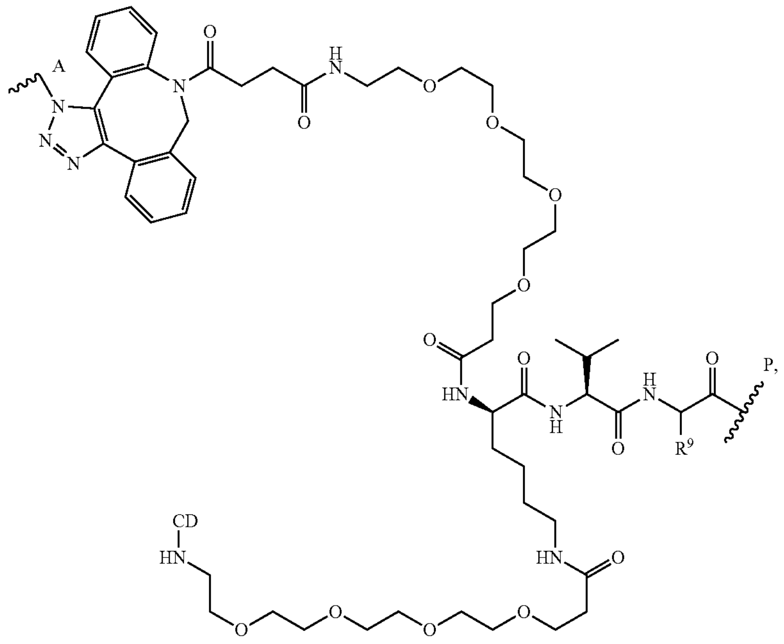
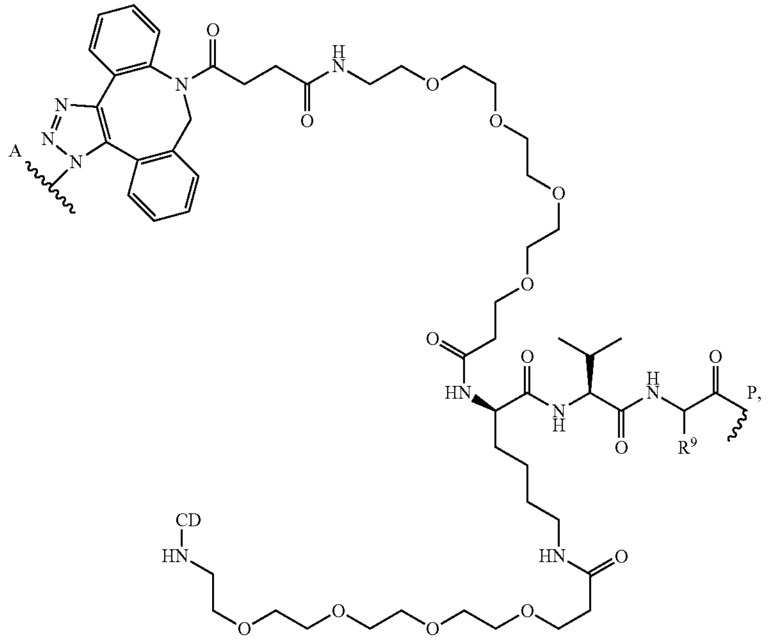
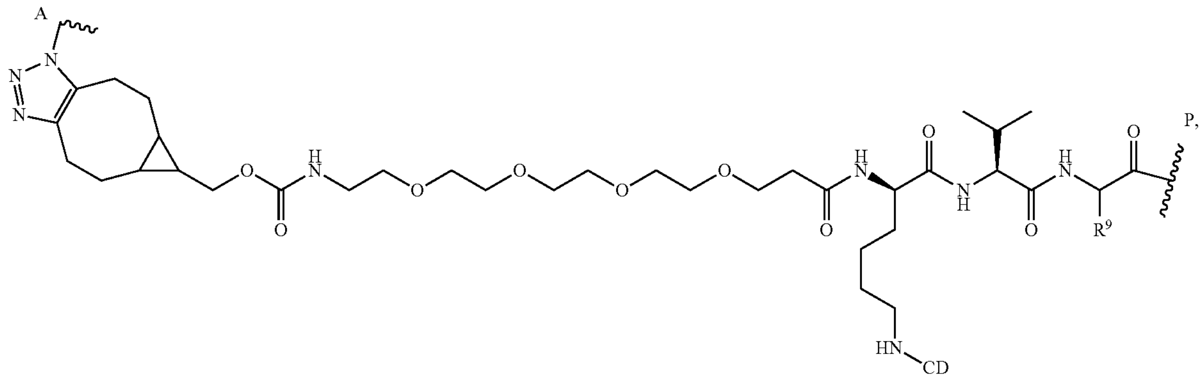

-continued
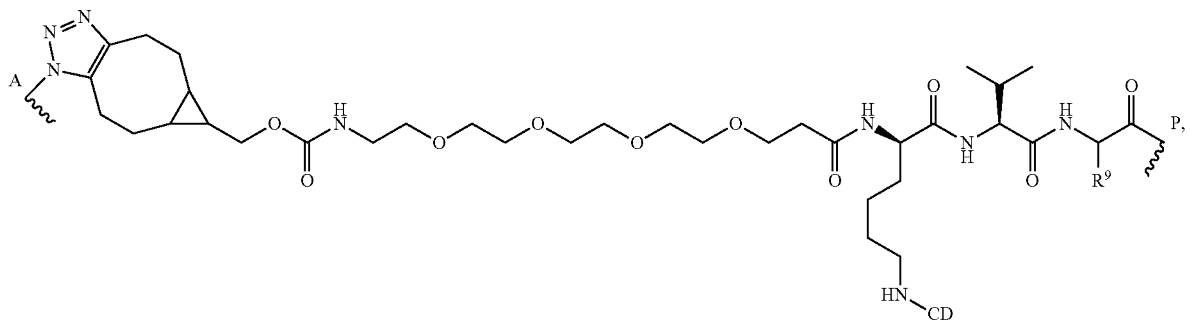
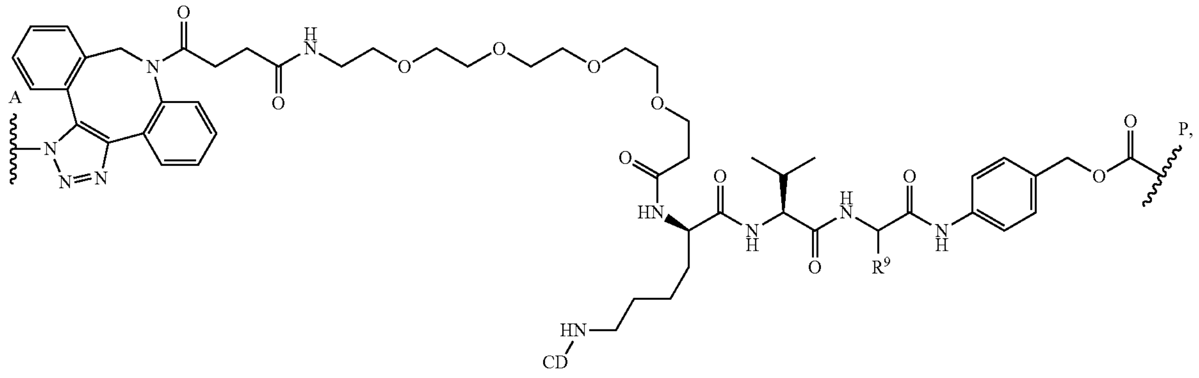
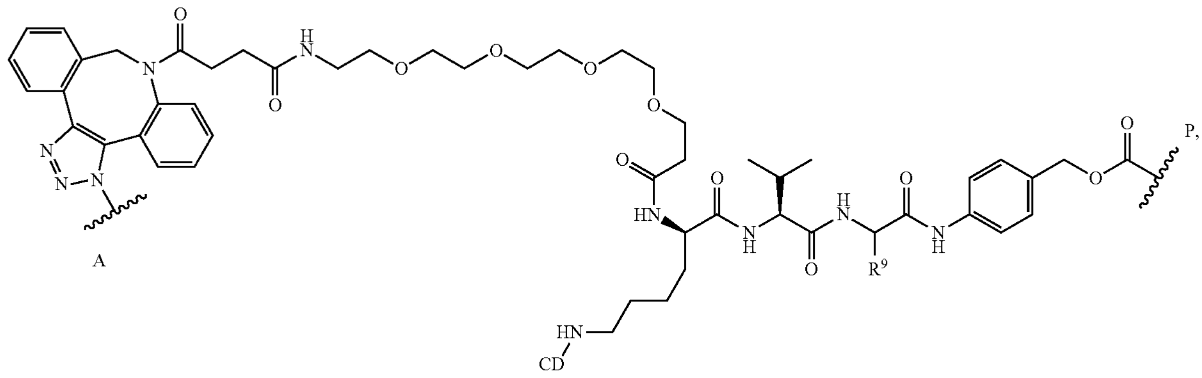
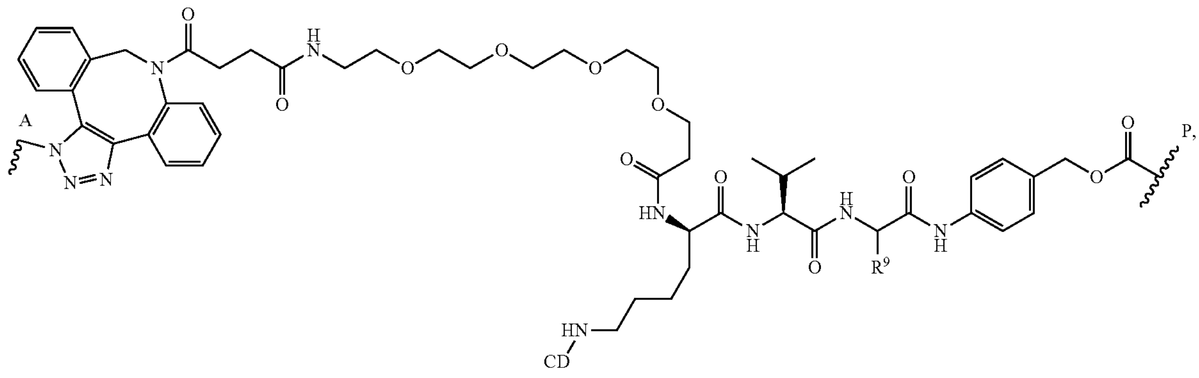
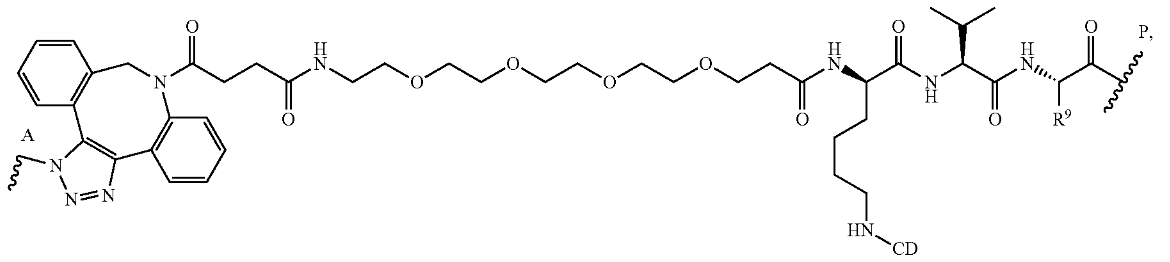
and

-continued

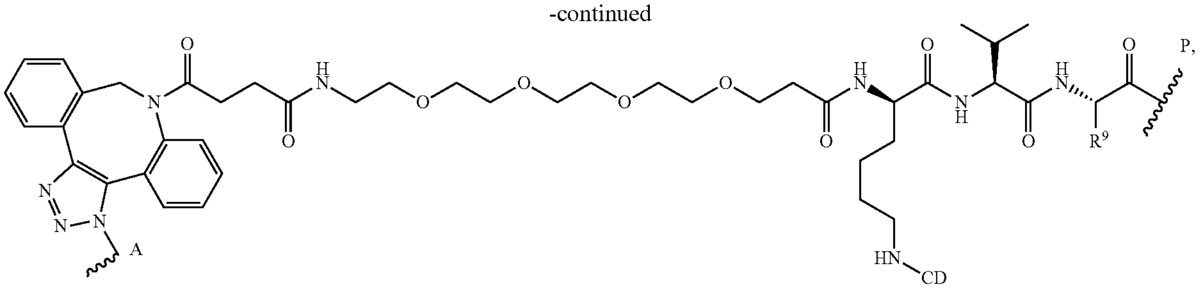

or a pharmaceutically acceptable salt, or stereoisomeric form thereof, or a regioisomer thereof, or mixture of regioisomers thereof, wherein:

each

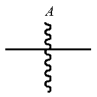

is a bond to the antibody or an antigen binding fragment thereof;

each

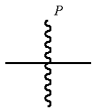

is a bond to the payload moiety; and $R^9$ is —$CH_3$ or —$(CH_2)_3N(H)C(O)NH_2$.

17. The method of claim 16, wherein the compound according to Formula (Id):

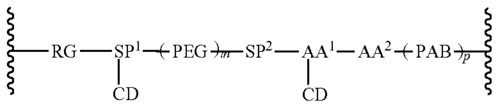

is selected from the group consisting of

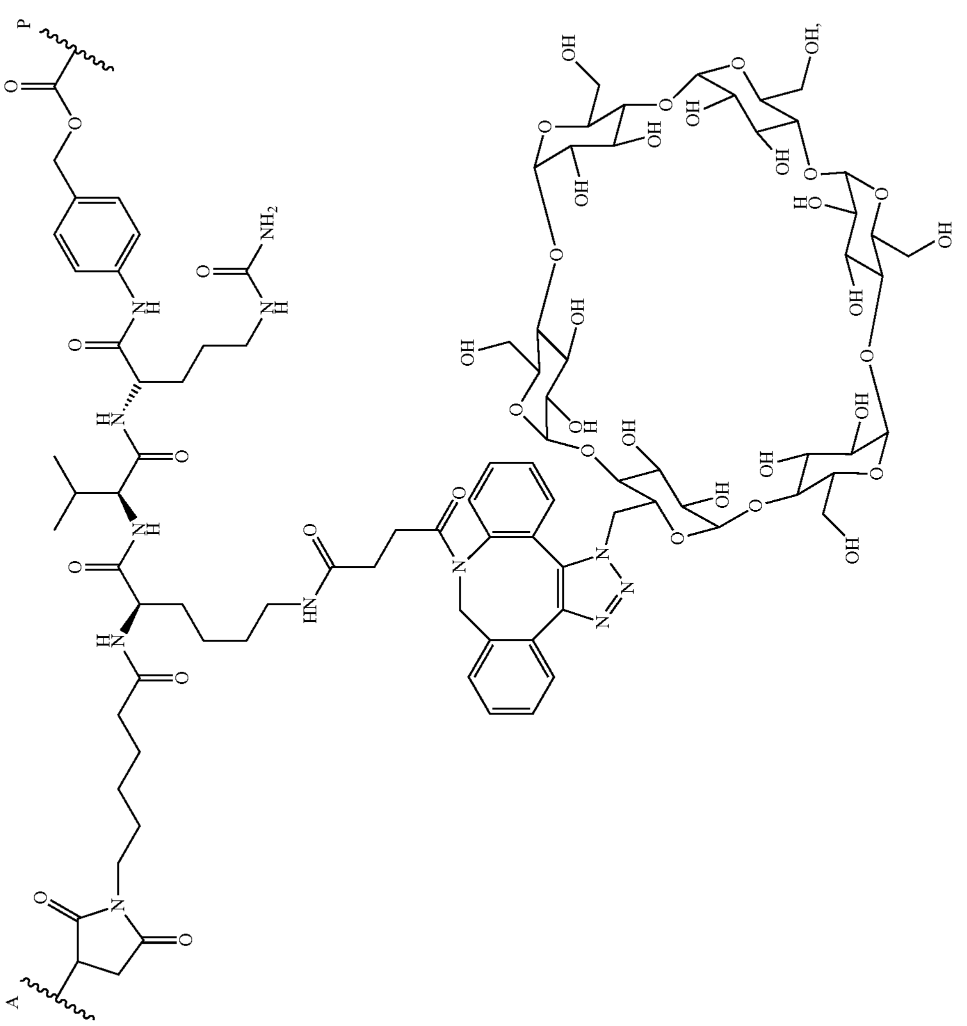

-continued
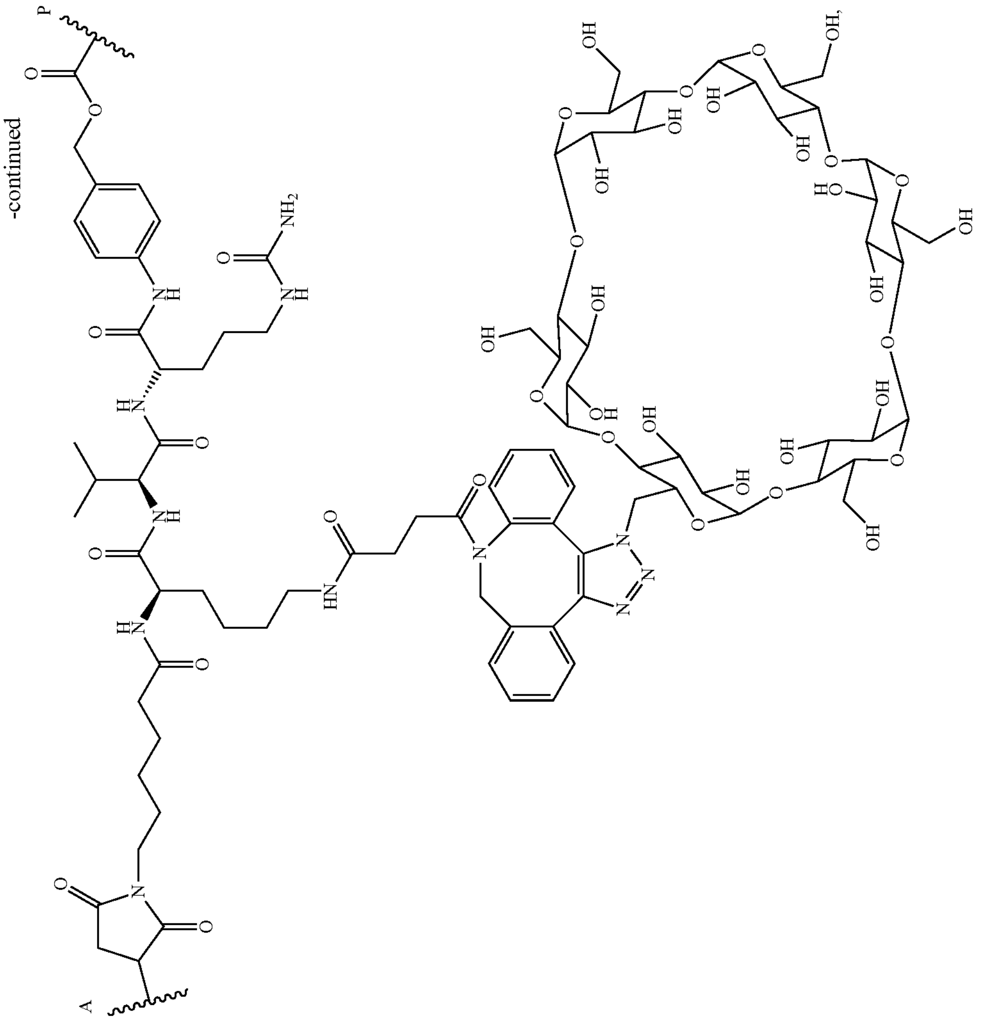

-continued
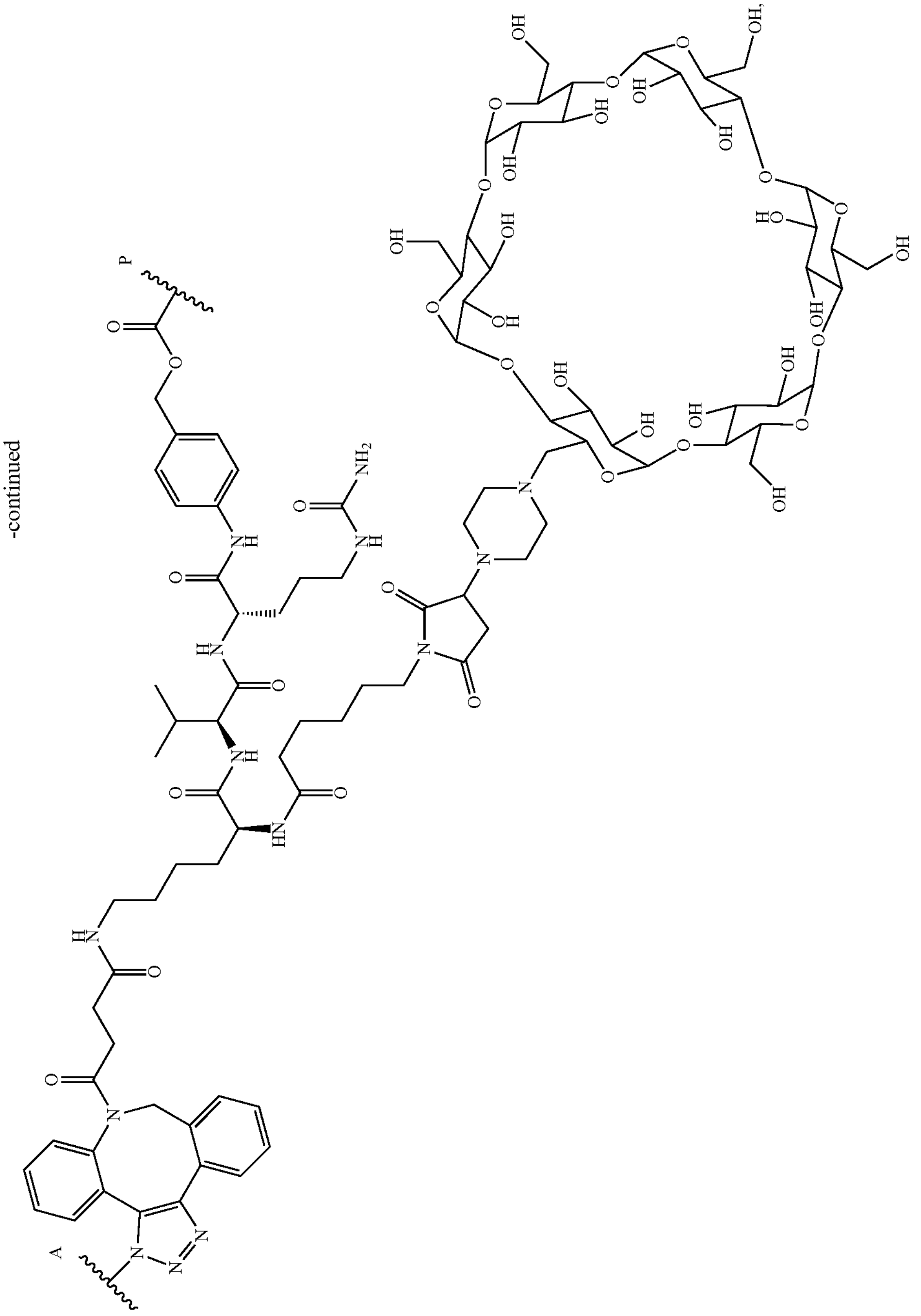

-continued
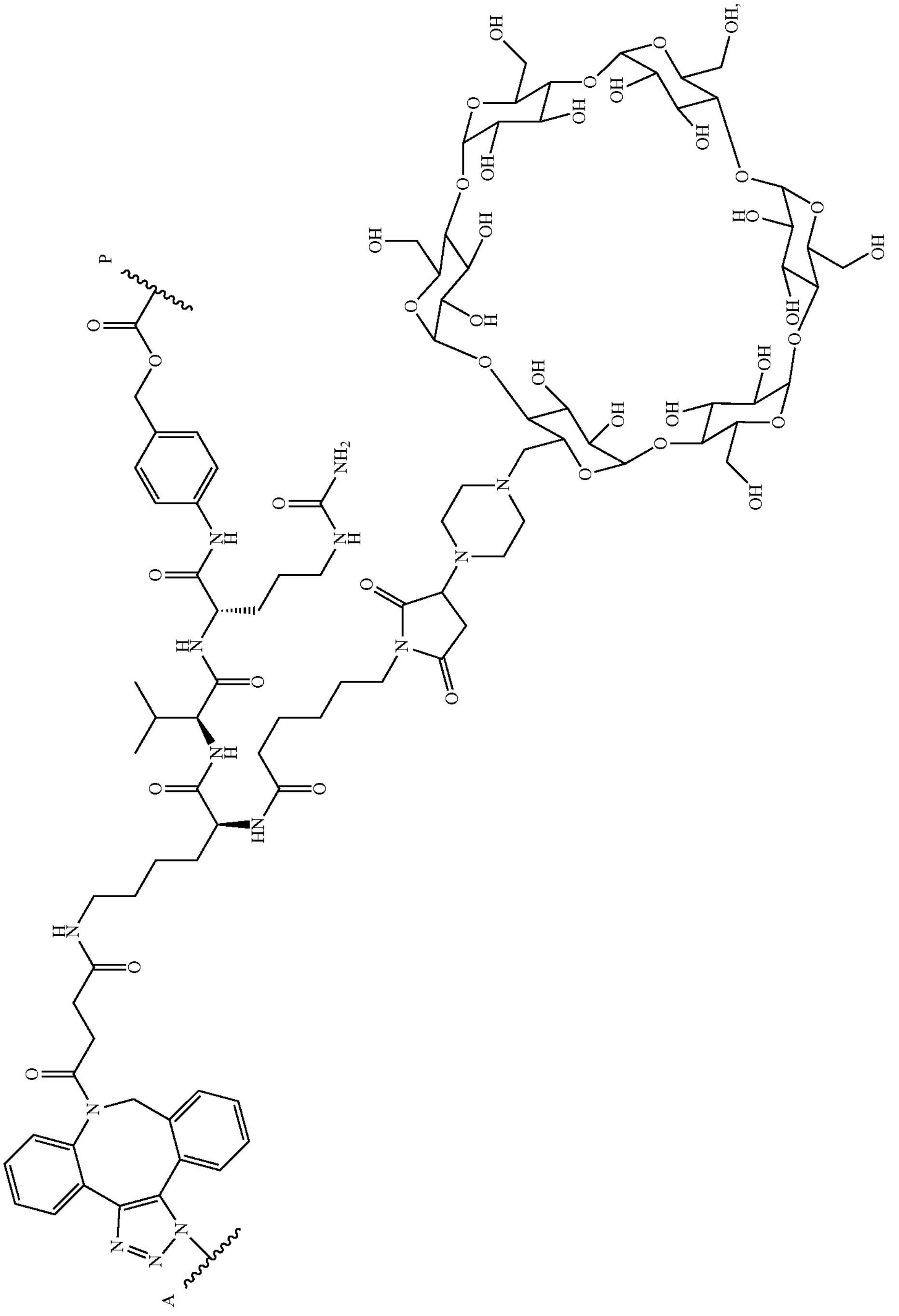

-continued
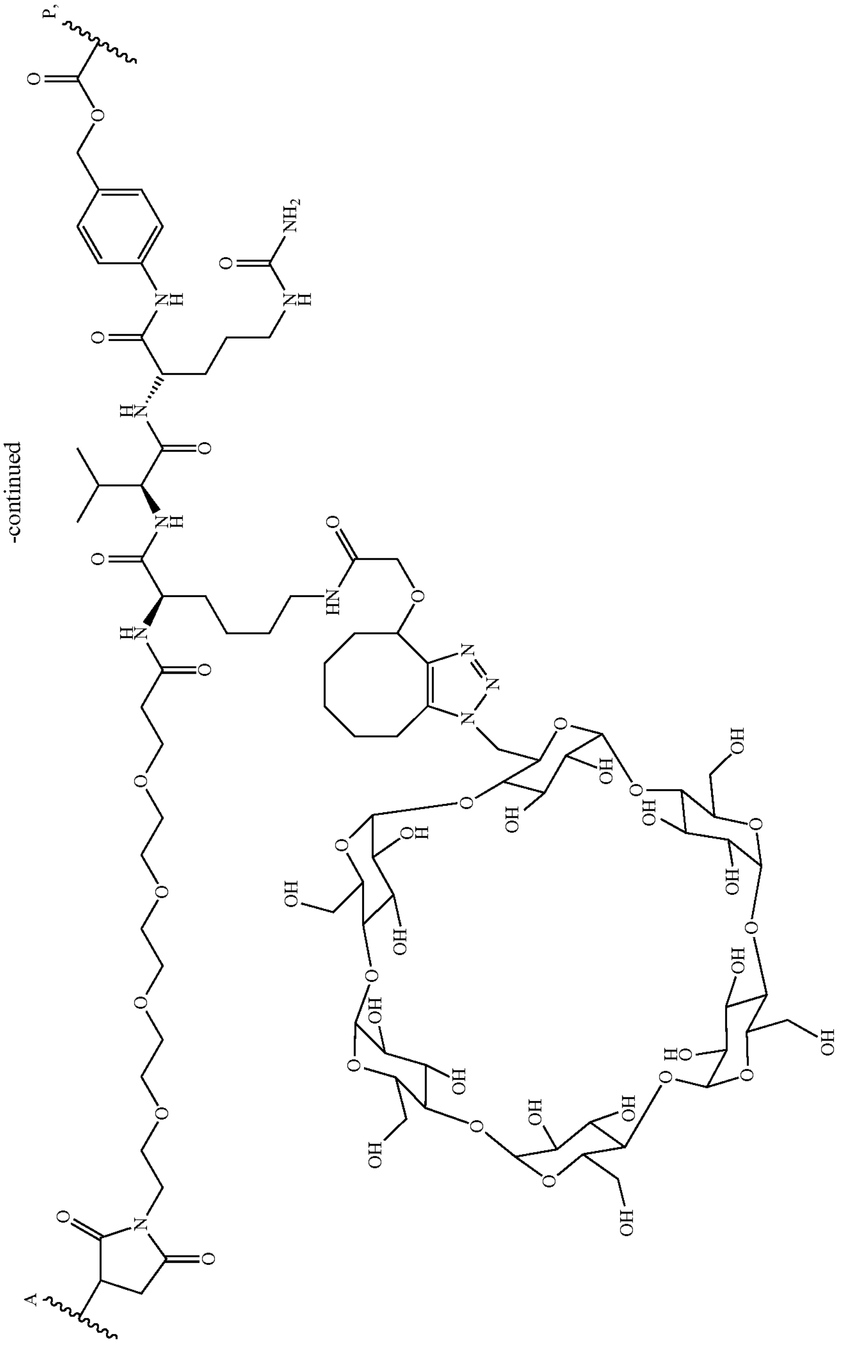

-continued
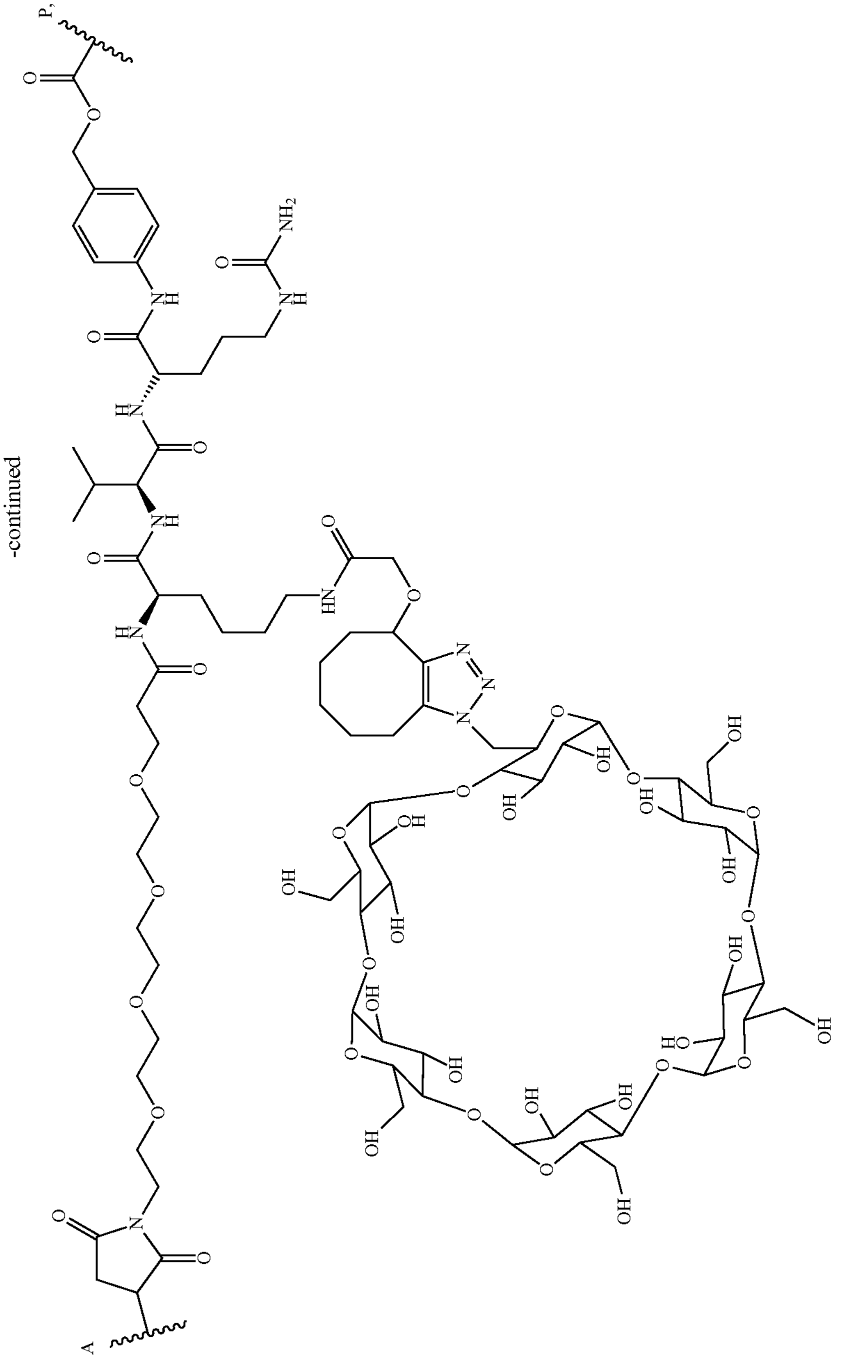

-continued
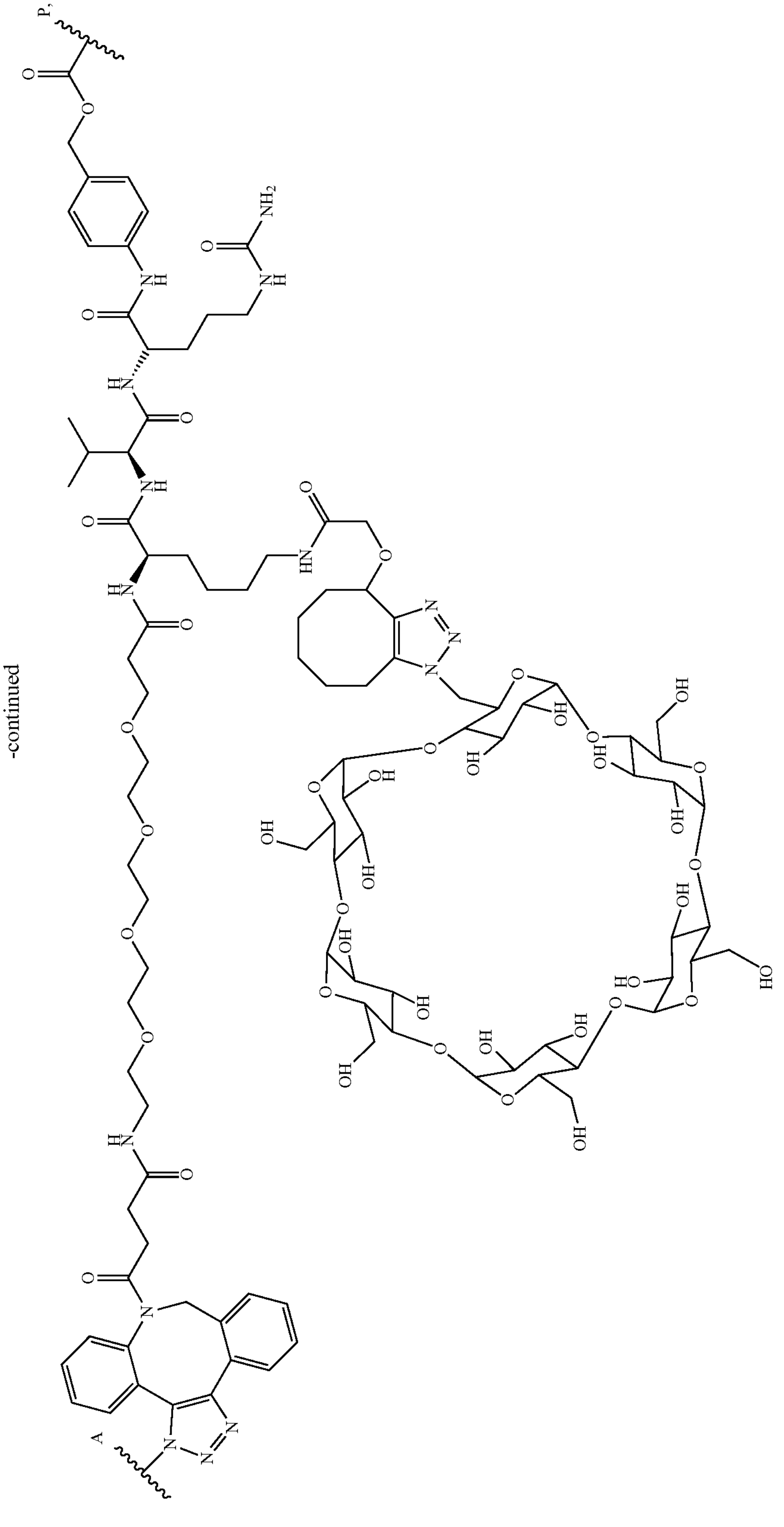

-continued
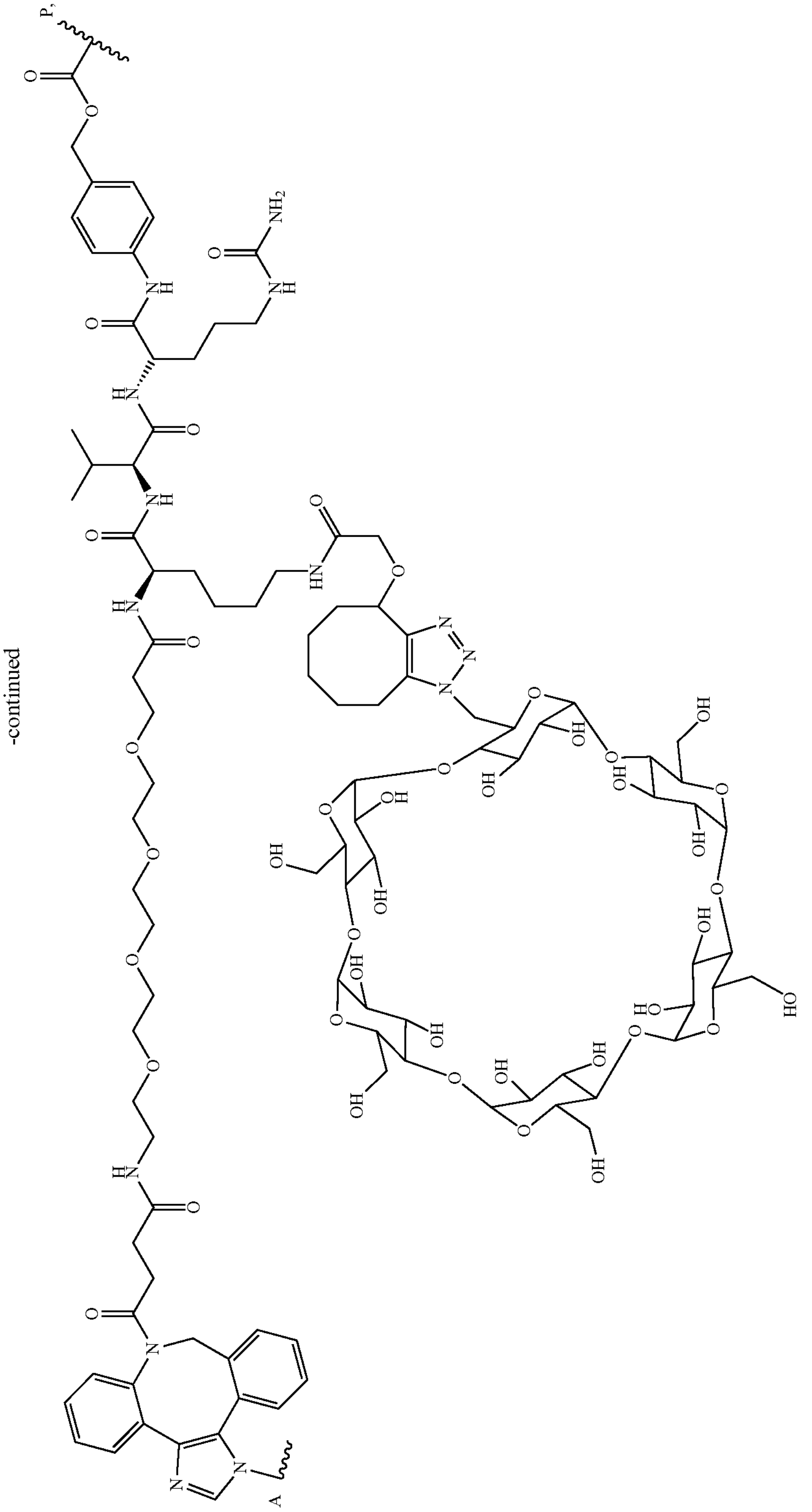

-continued
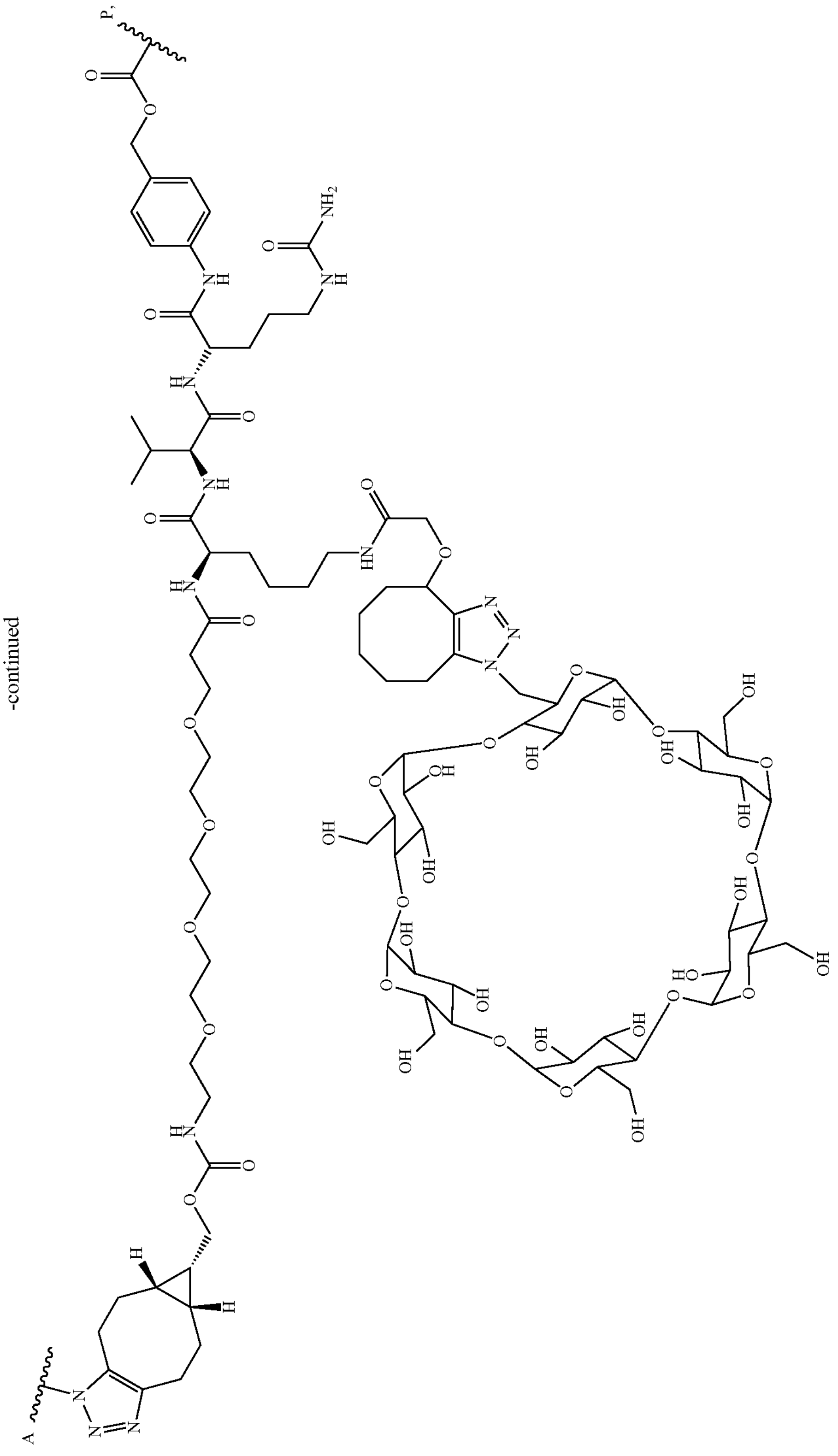

-continued
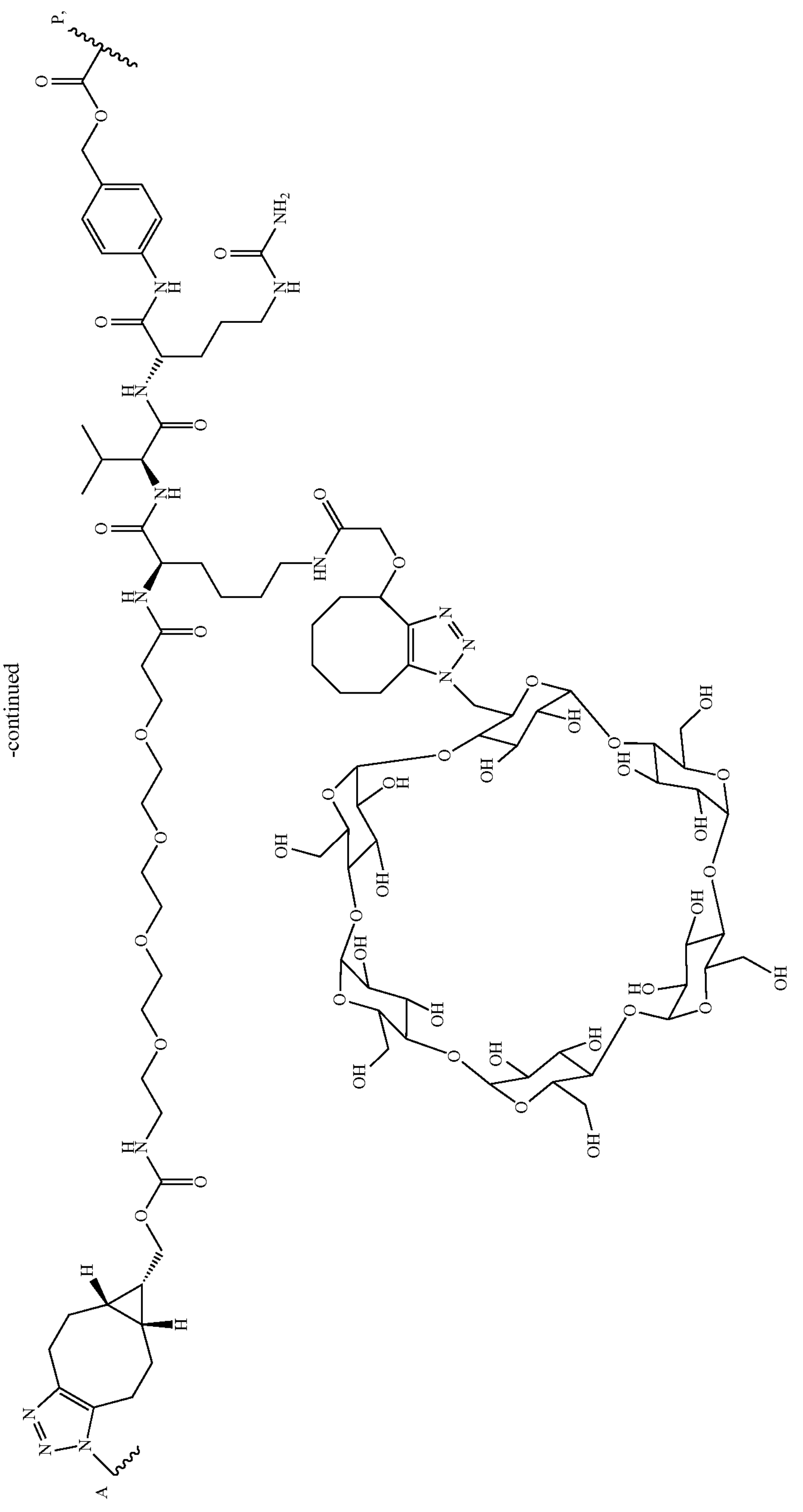

-continued
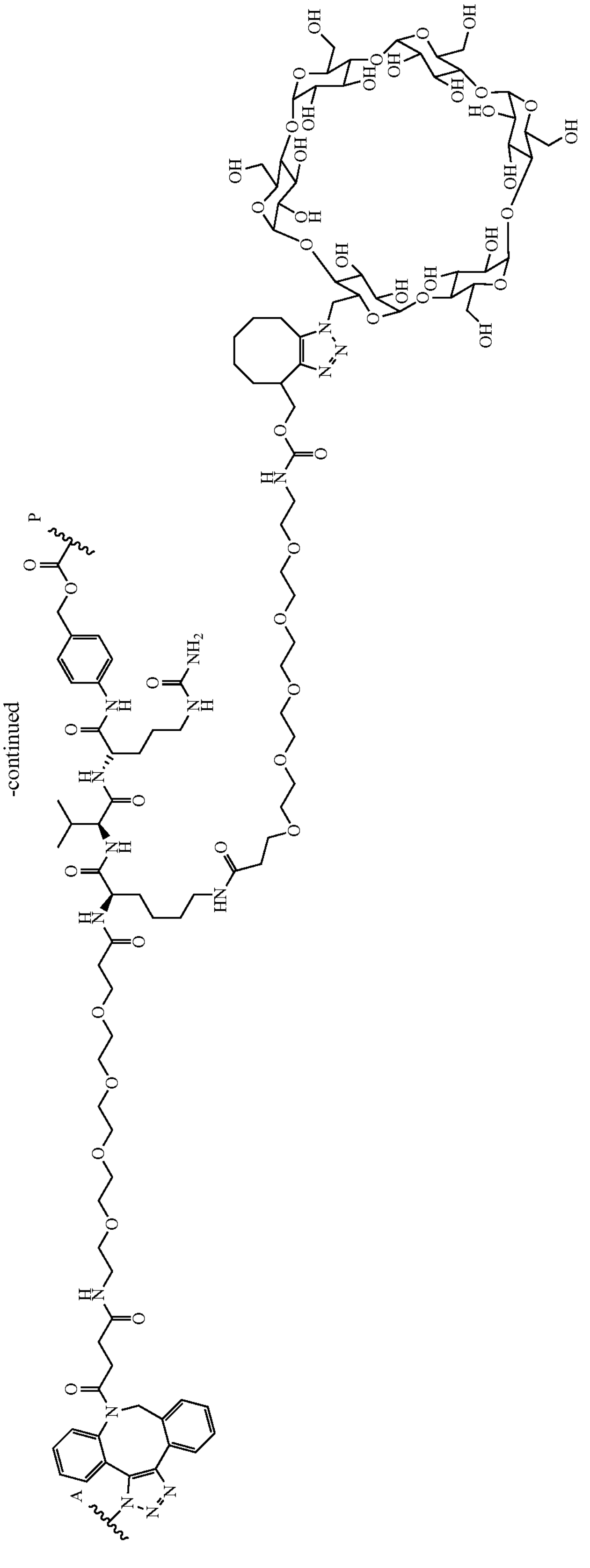

-continued
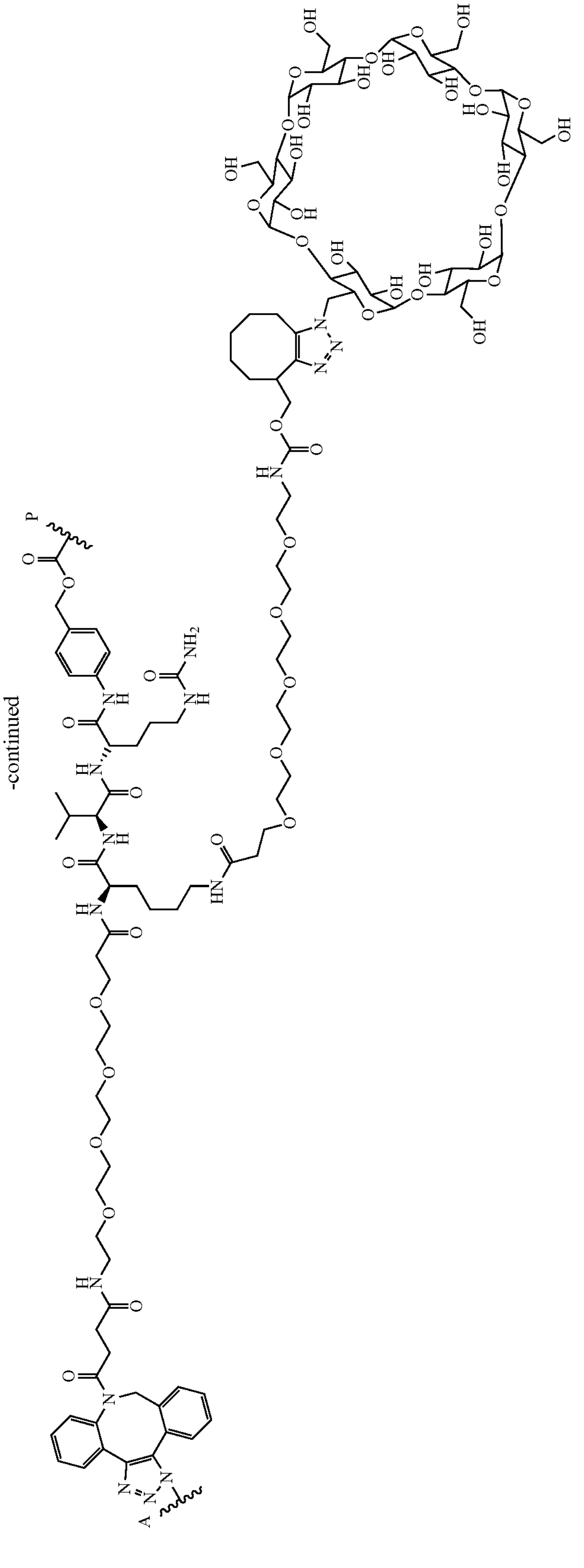

-continued
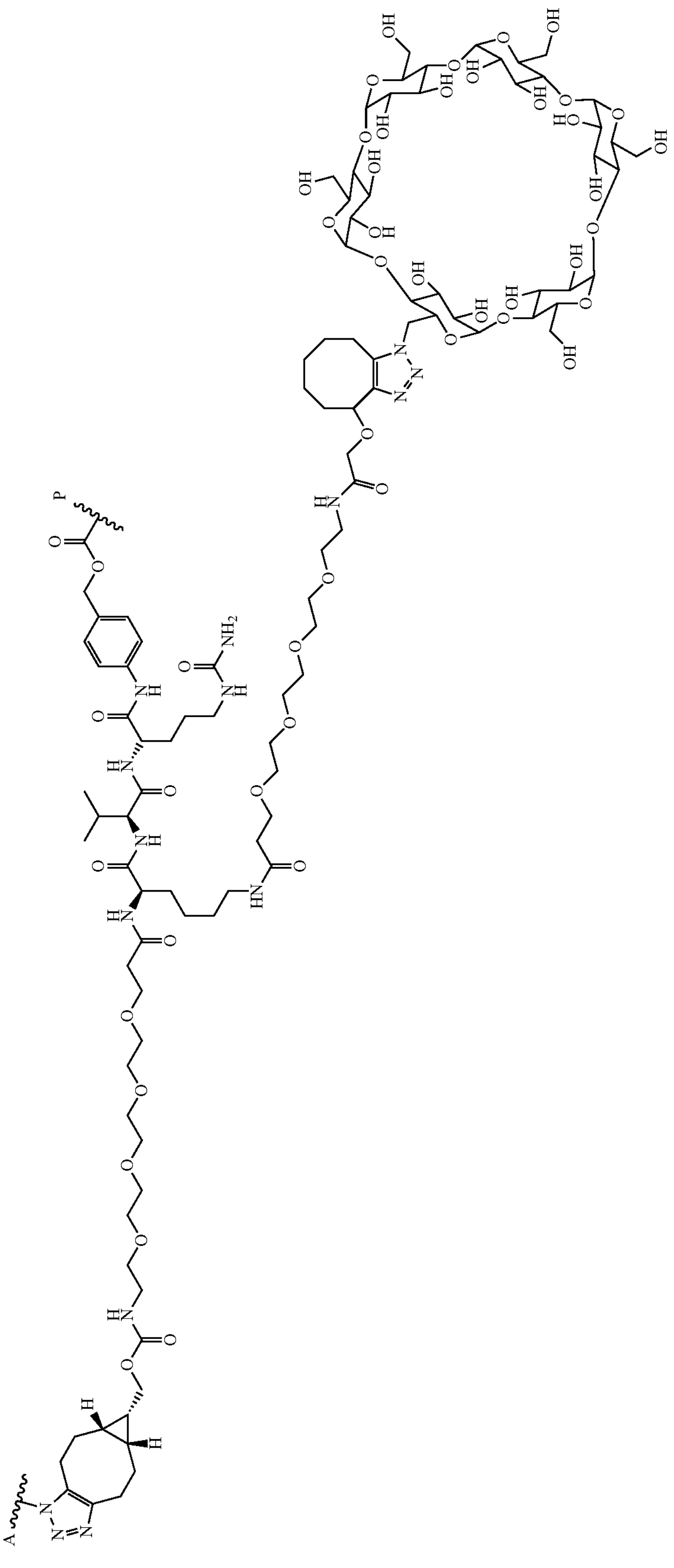

-continued
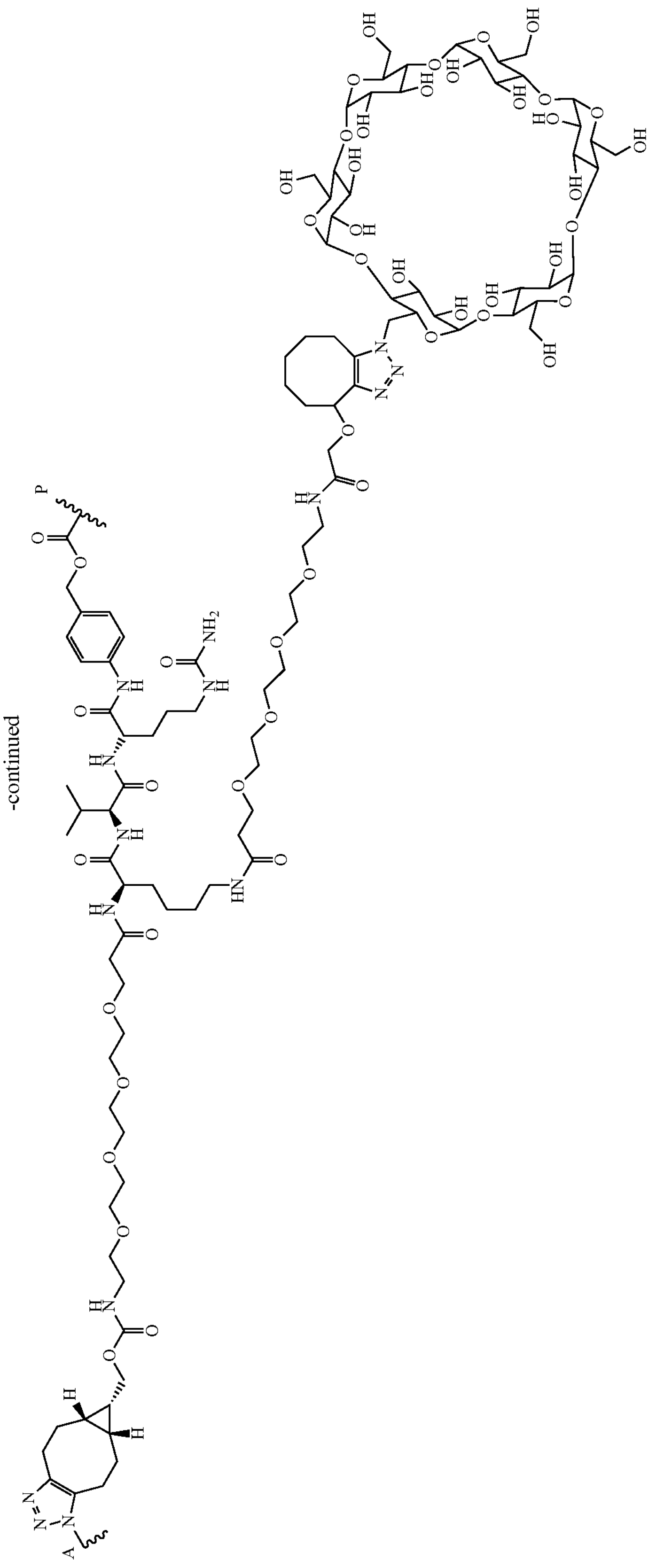

-continued
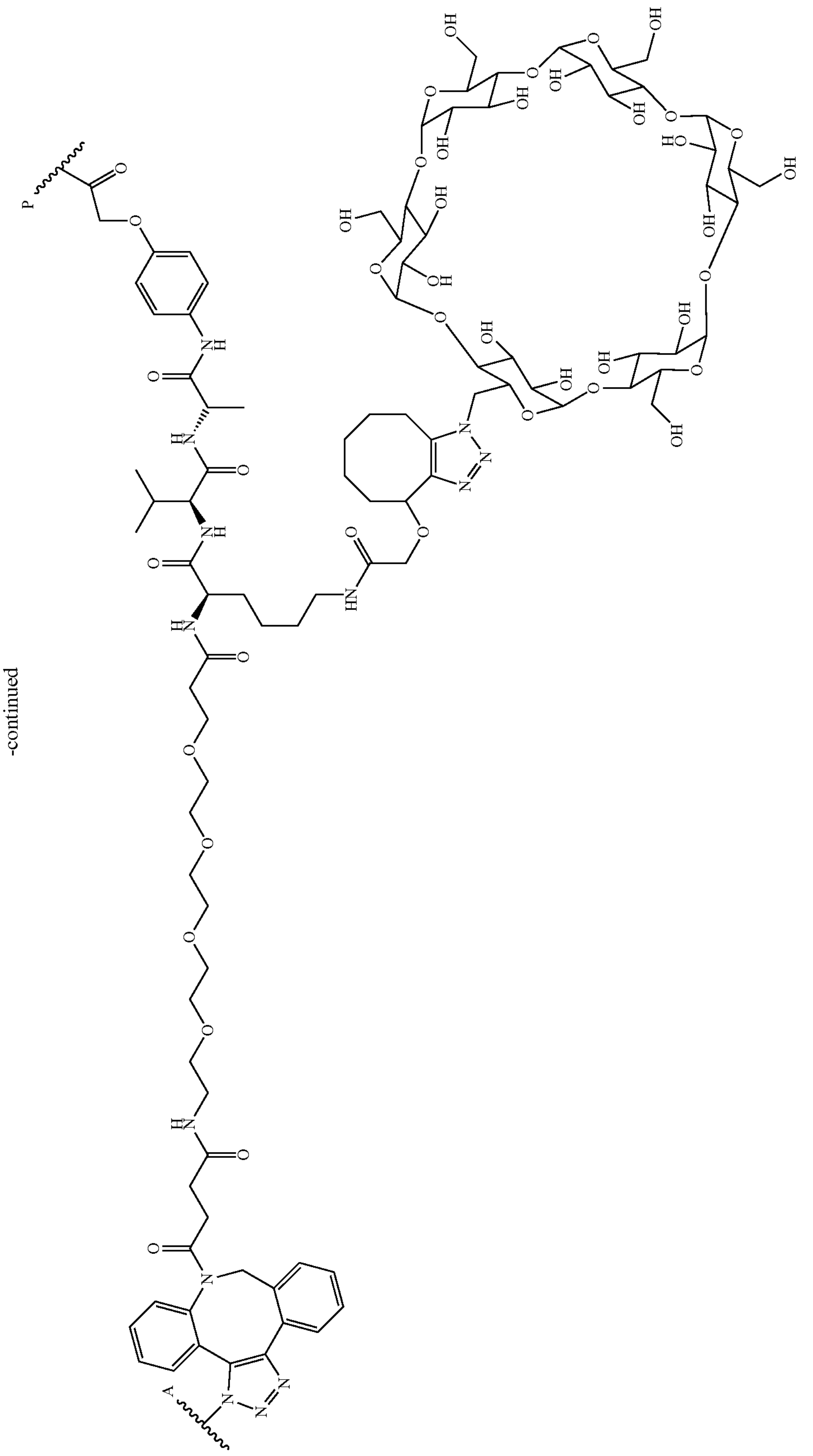

-continued
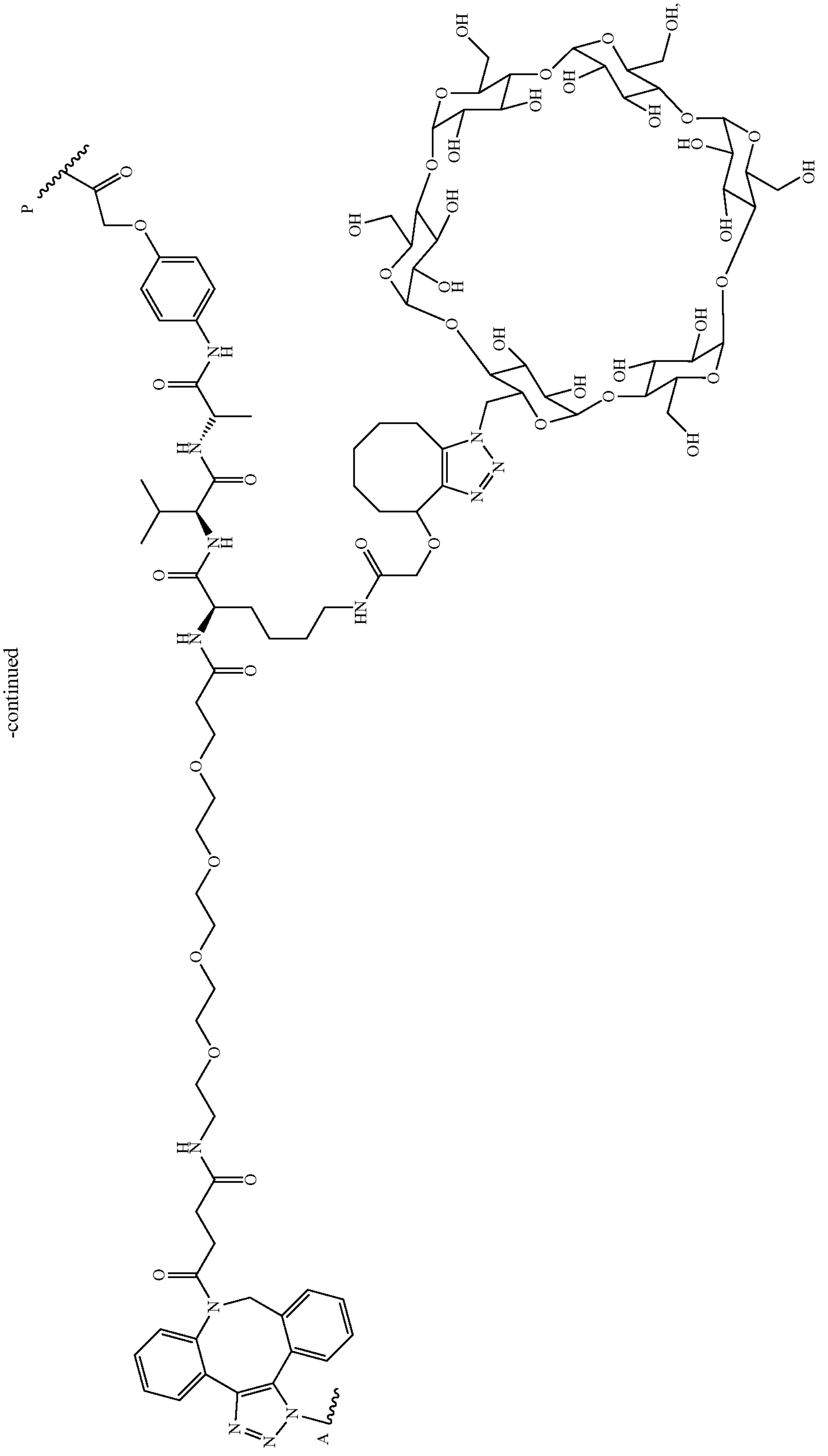

-continued
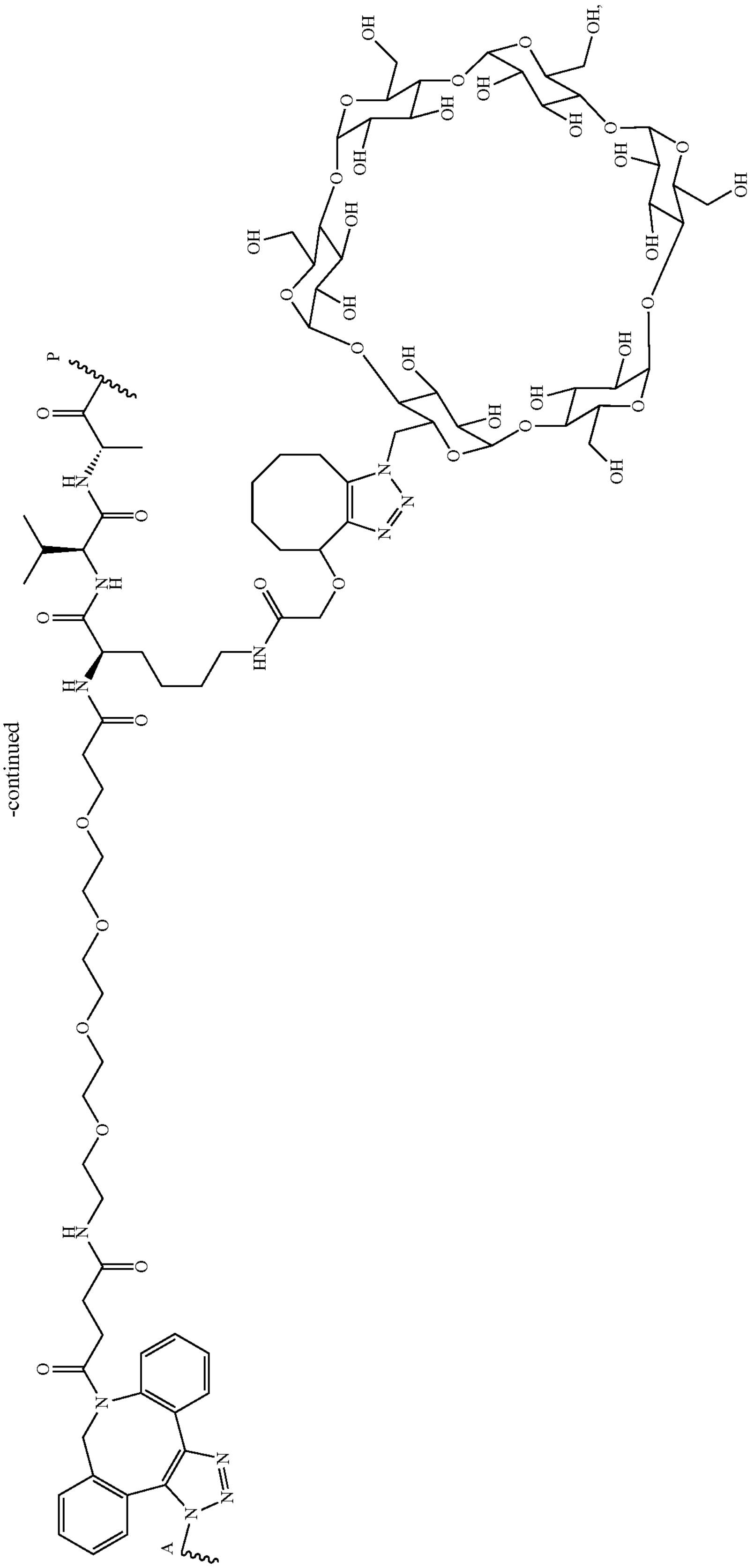

-continued
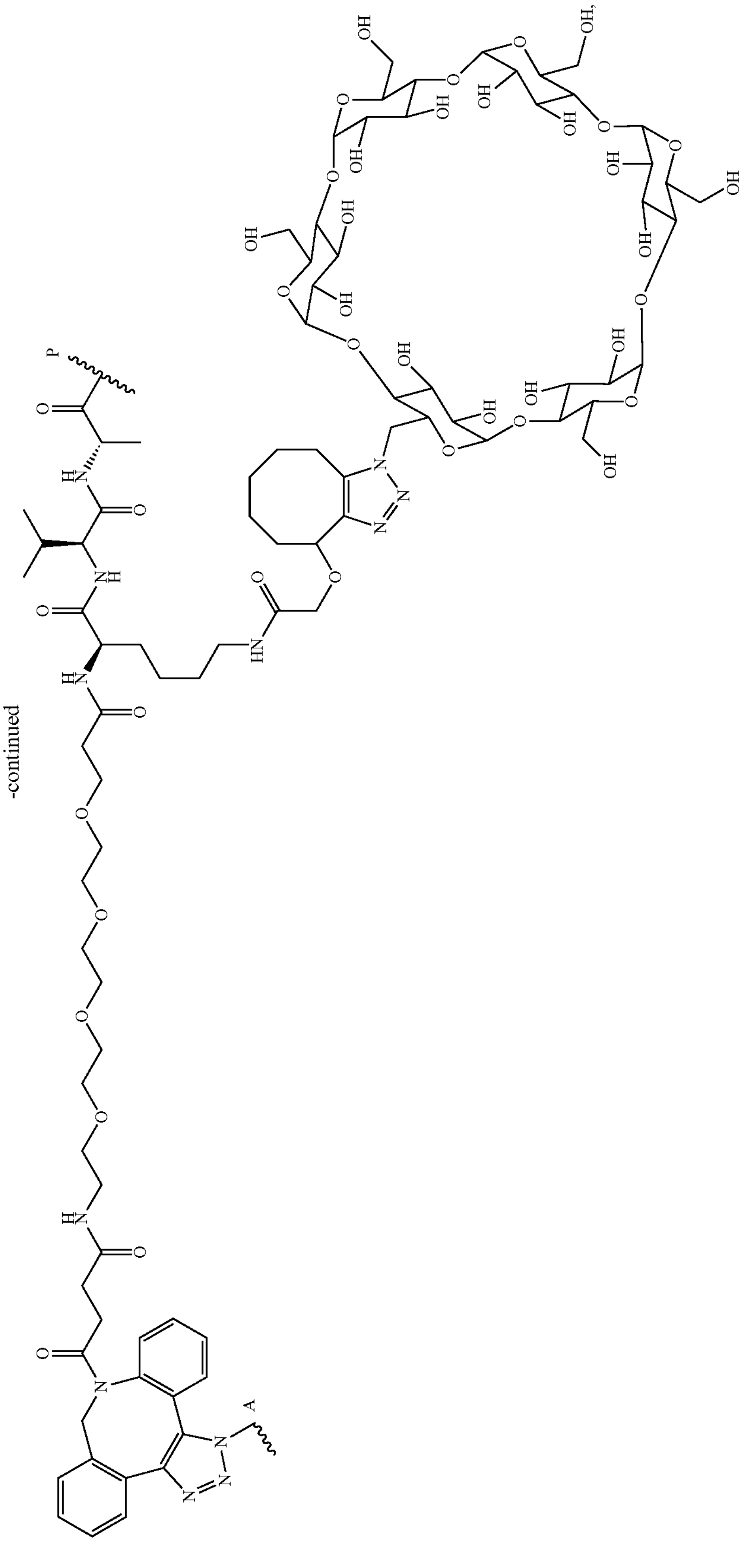

-continued
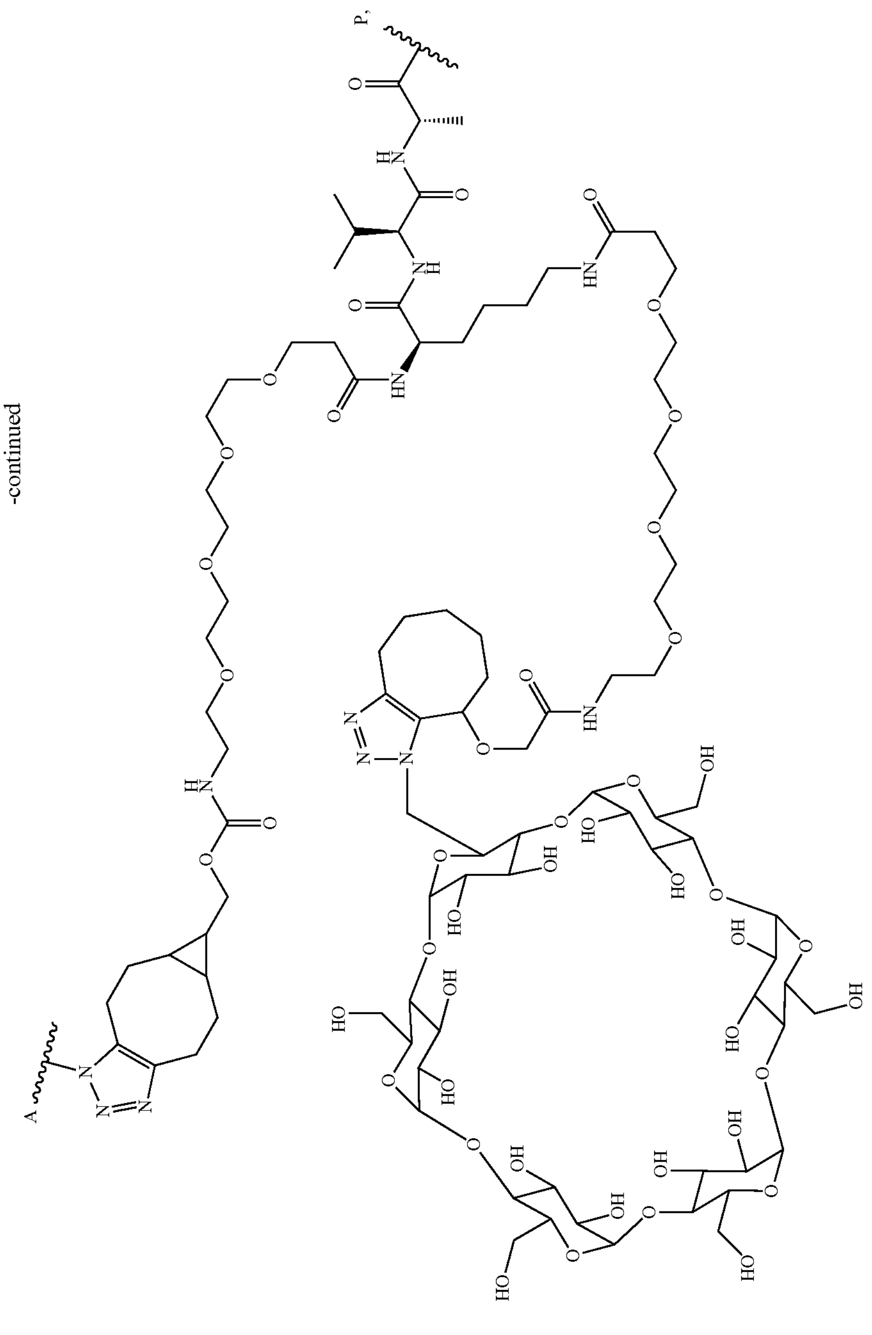

-continued
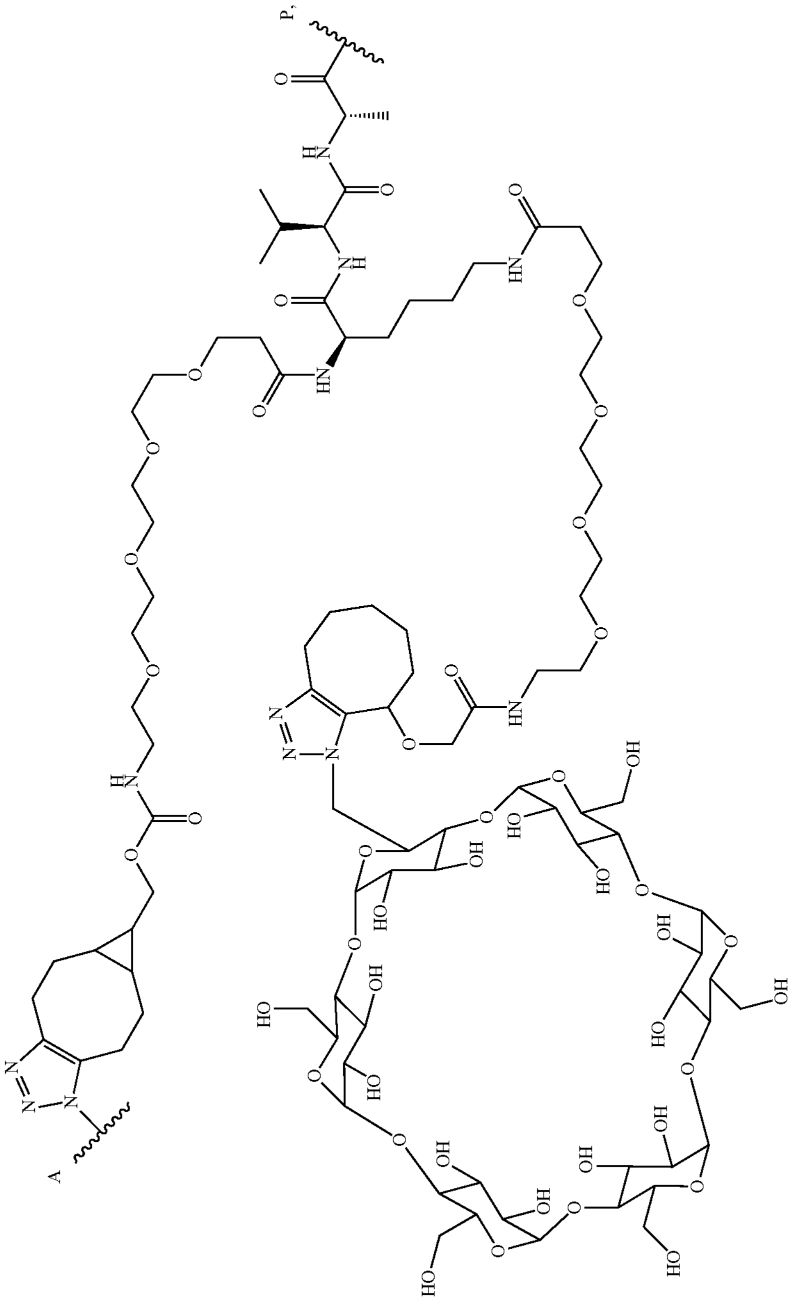

-continued
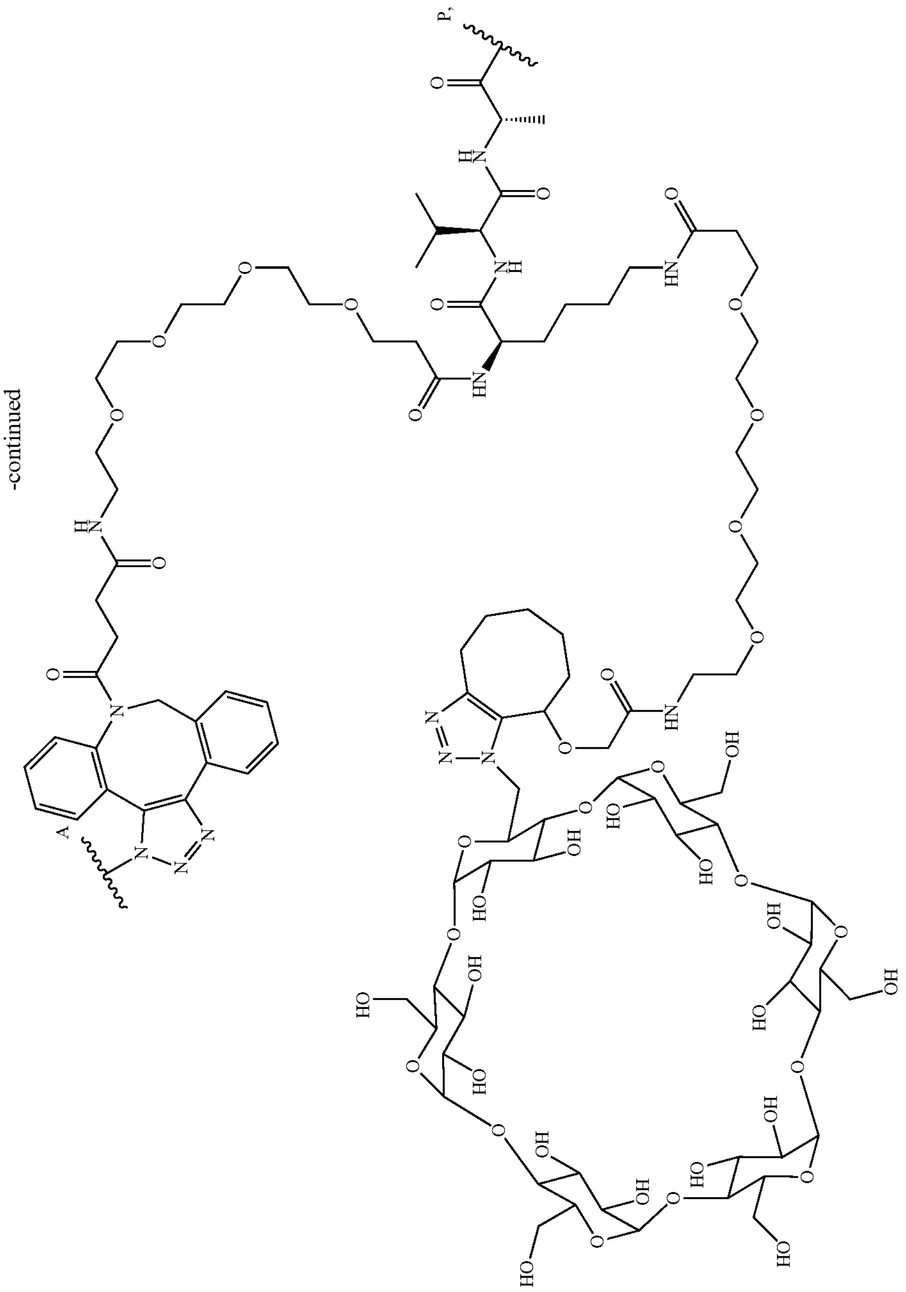

-continued
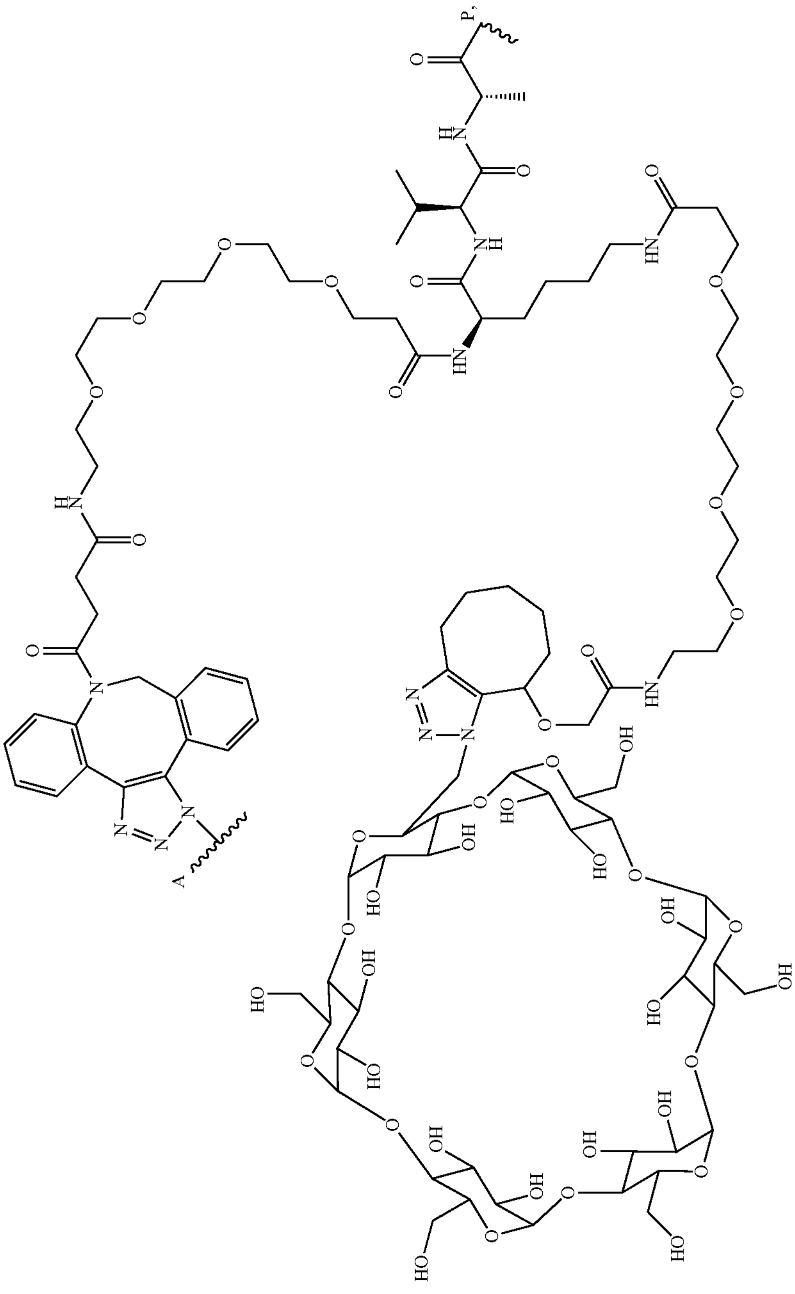

-continued
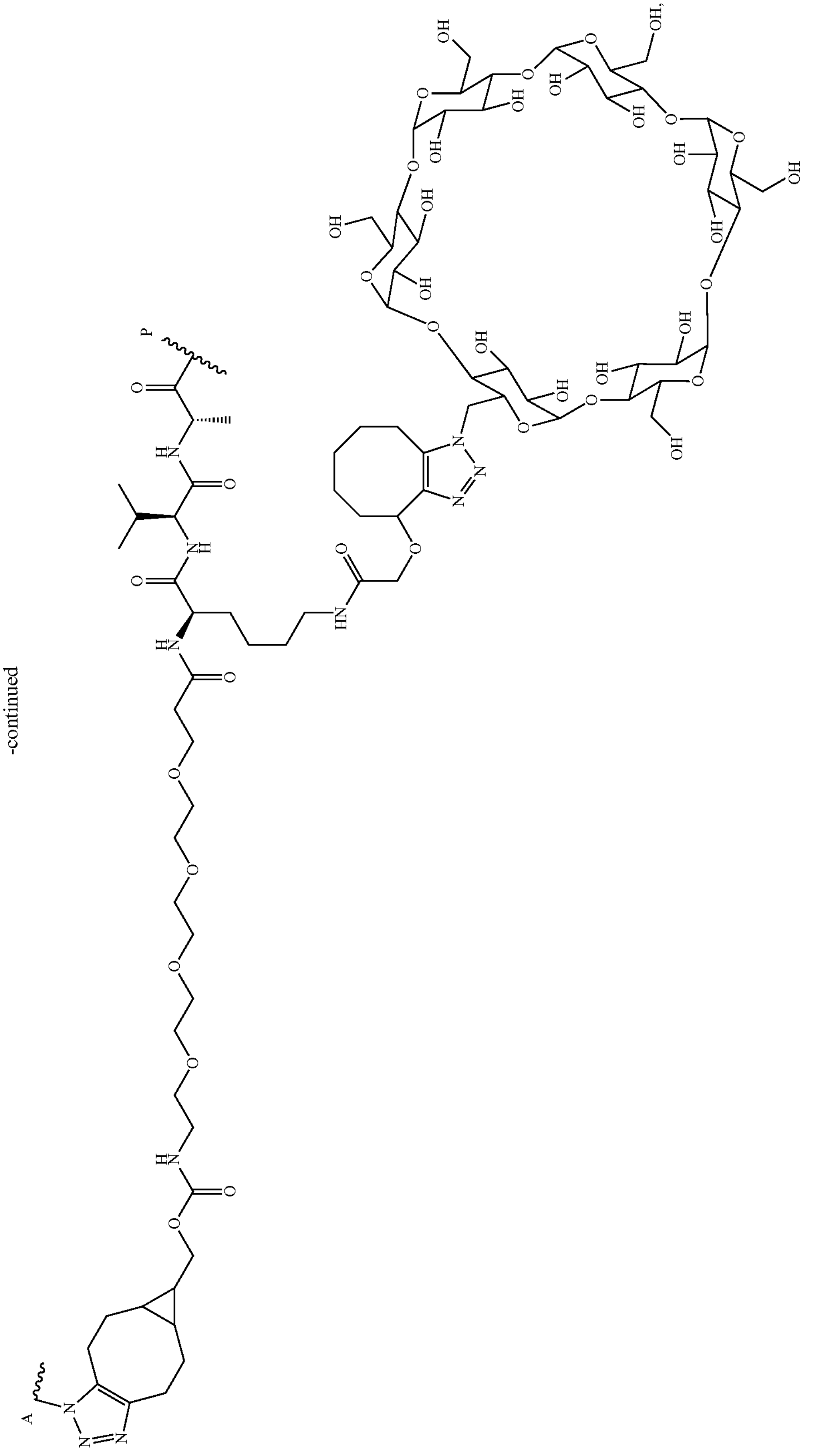

-continued
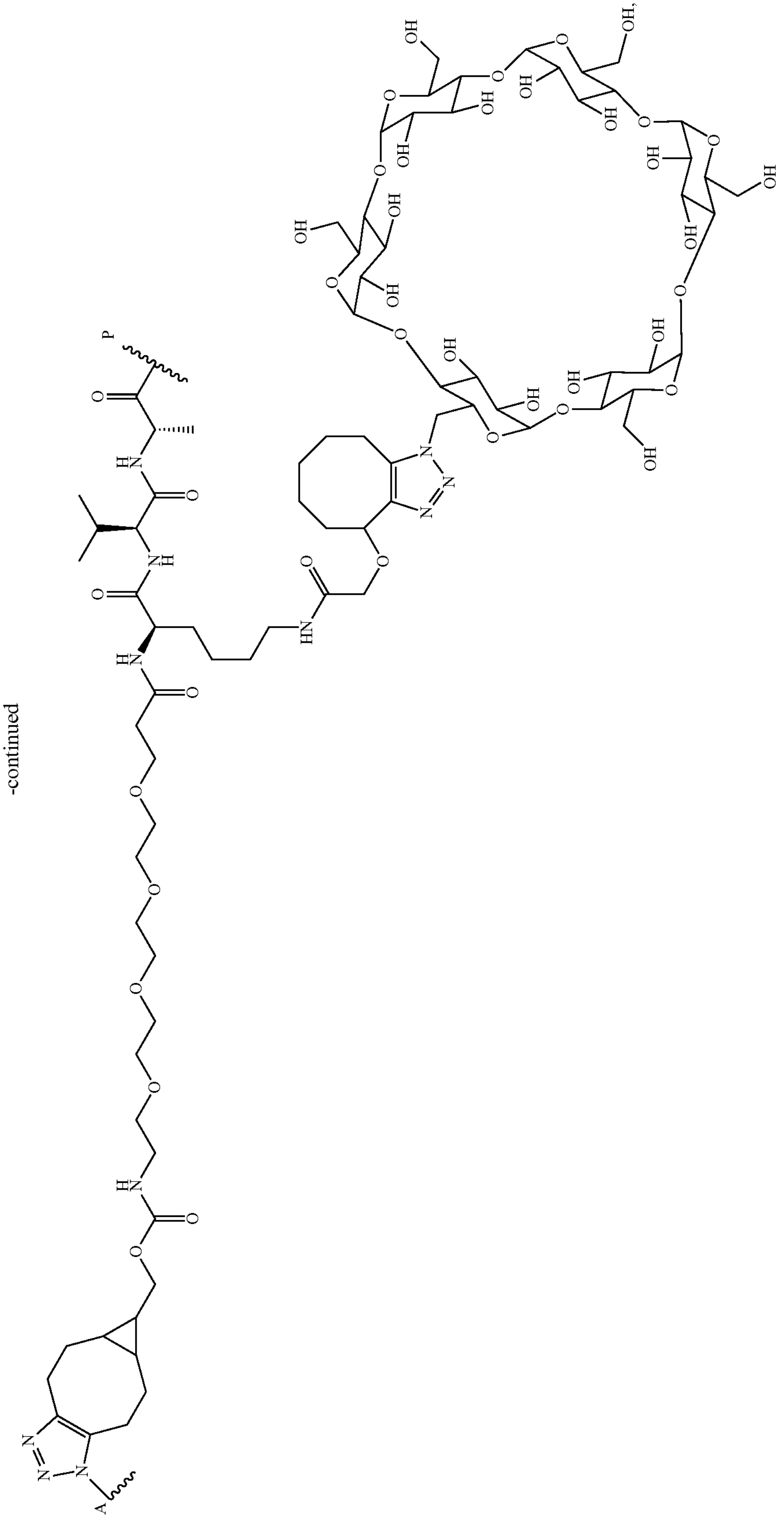

-continued
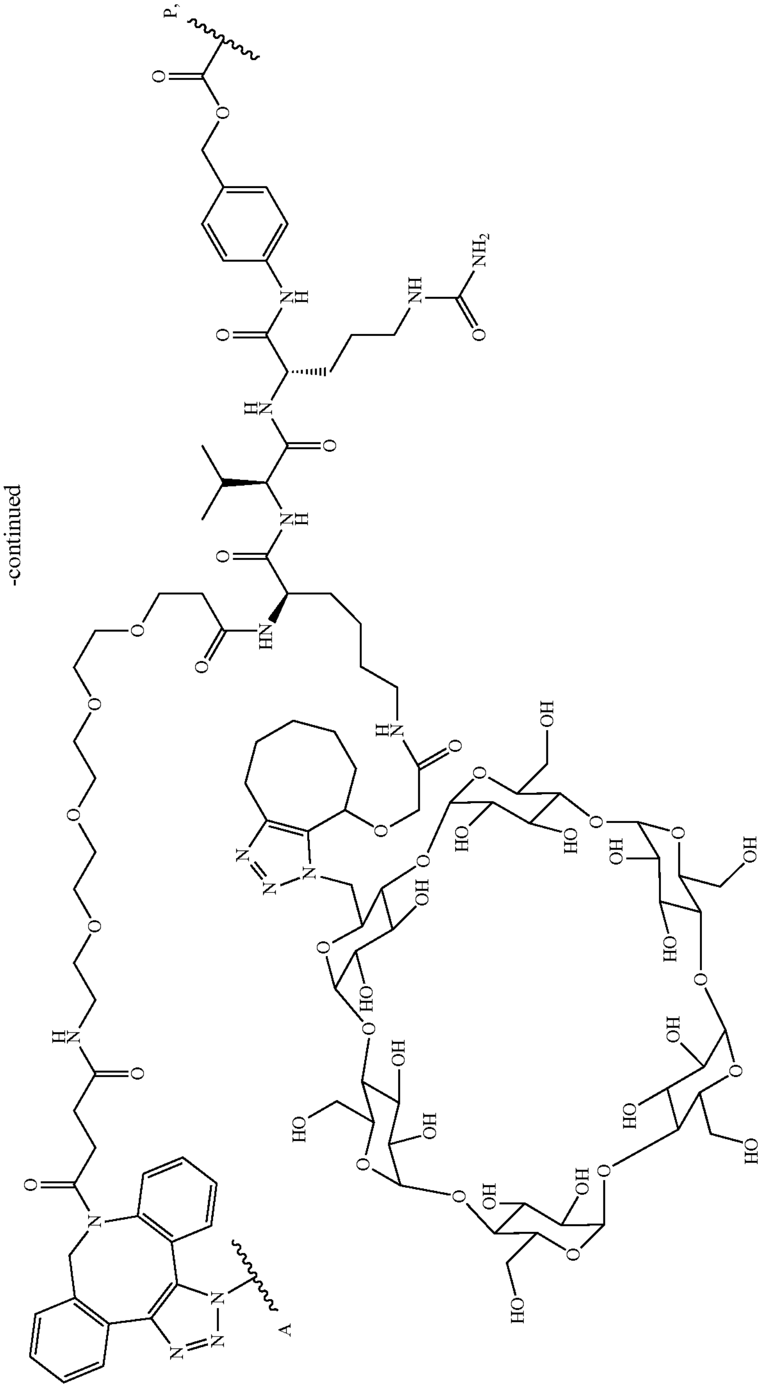

-continued
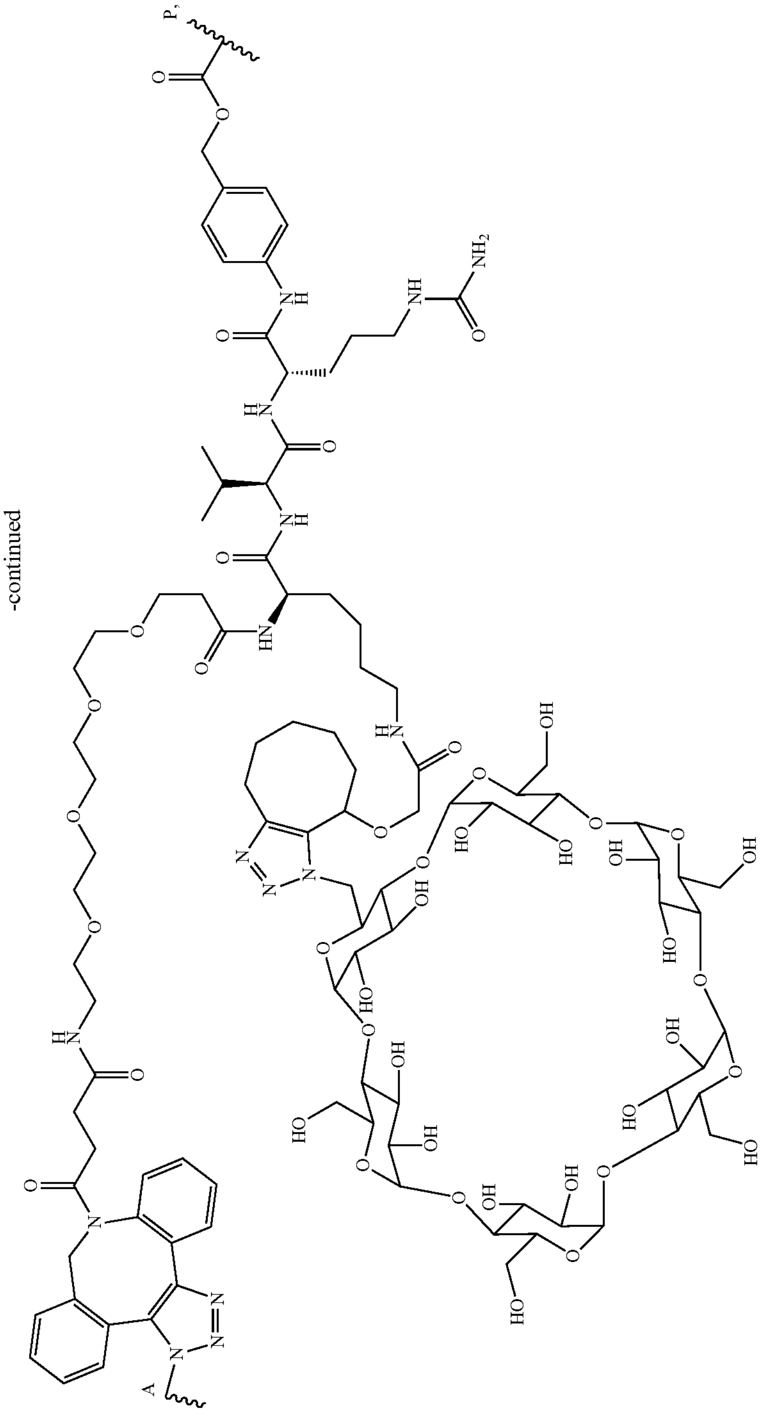

-continued
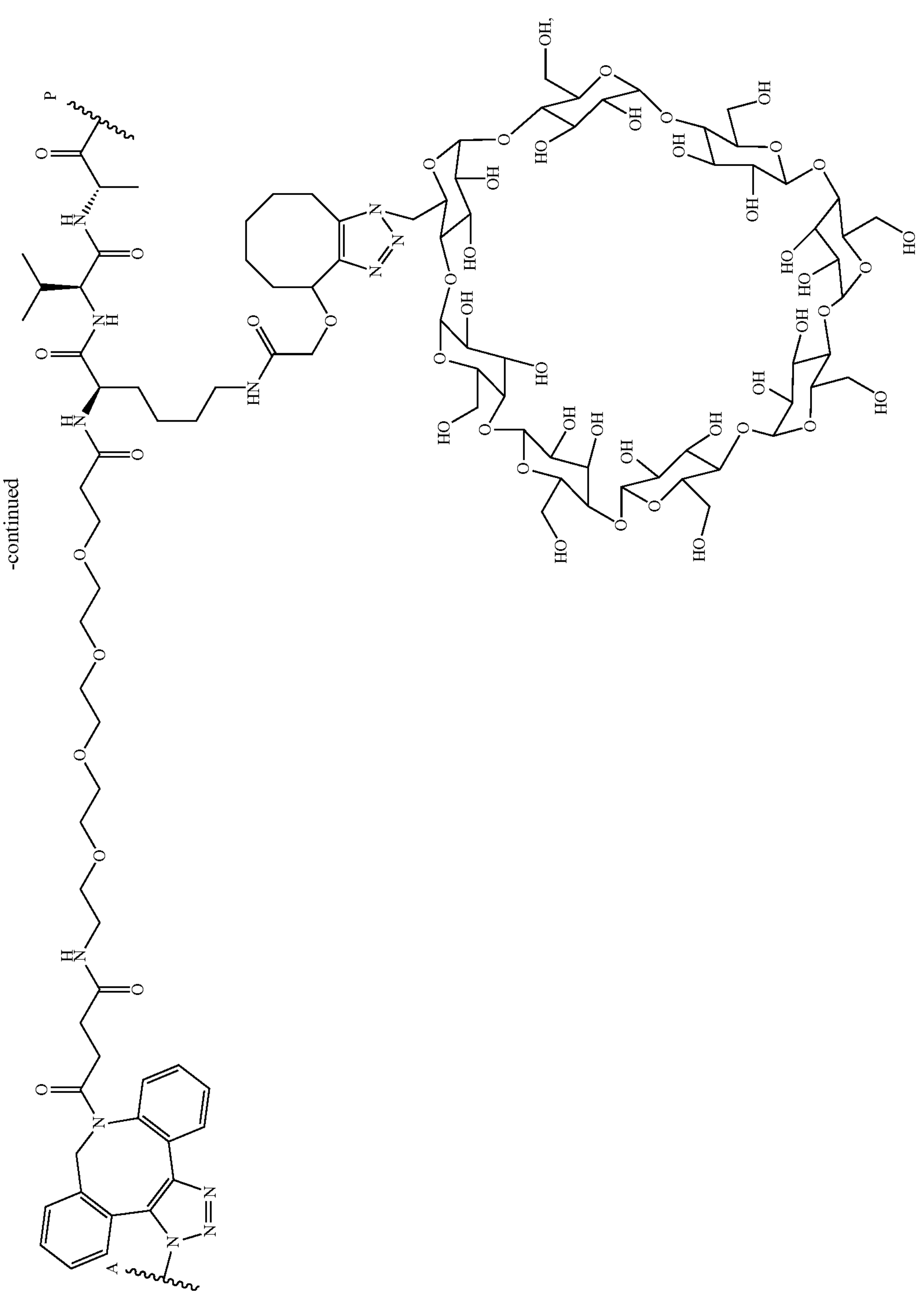
and

-continued
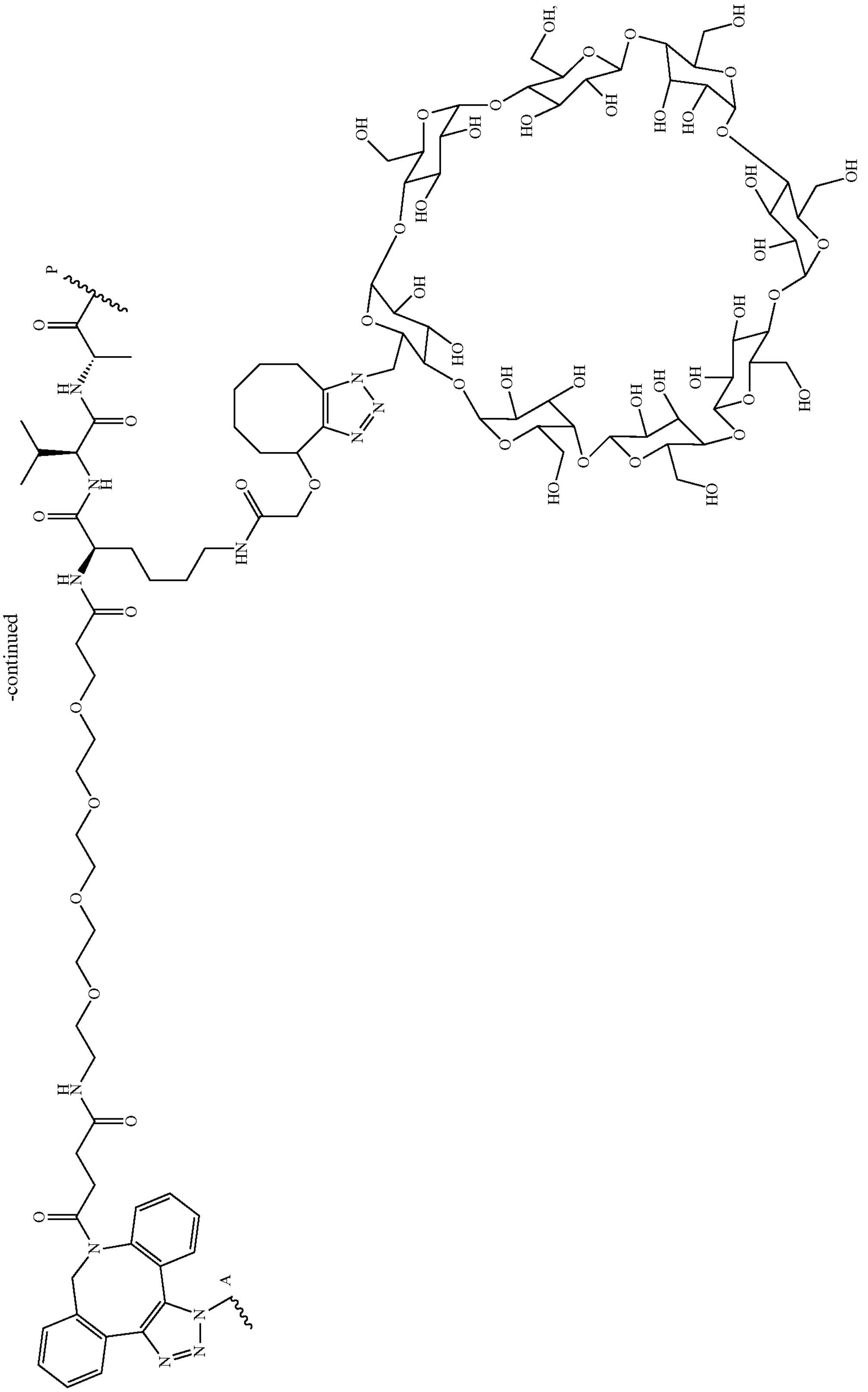

or a pharmaceutically acceptable salt, or stereoisomeric form thereof, or a regioisomer thereof, or mixture of regioisomers thereof, wherein:

each

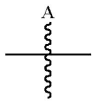

is a bond to the antibody or an antigen binding fragment thereof; and each

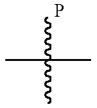

is a bond to the payload moiety.

18. The method of claim 1, wherein -LL- is according to the Formula (LL1):

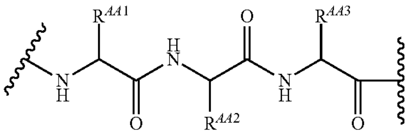

(LL1)

wherein $R^{AA1}$, $R^{AA2}$, and $R^{AA3}$ are each, independently, amino acid side chains, at least one of which is bonded directly or indirectly to CD.

19. The method of claim 18, wherein $R^{AA1}$ is a lysine side chain bonded directly or indirectly to CD and $R^{AA2}$ and $R^{AA3}$ taken together, are either valine and citrulline or valine and alanine side chains, respectively.

20. The method of claim 18, wherein $R^{AA2}$ and $R^{AA3}$, taken together, are:

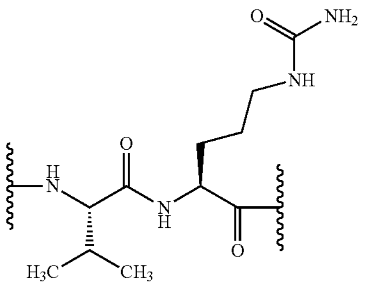

or

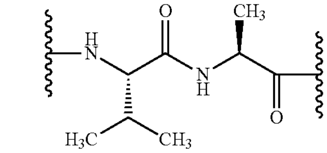

.

21. The method of claim 1, wherein the spacer group is, independently in each instance, selected from the group consisting of $C_{1-6}$ alkylene, —NH—, —C(O)—, (—$CH_2$—$CH_2$—O) e, —$NHCH_2$—$CH_2$—(—O—$CH_2$—$CH_2$)e-C(O)—, —C(O)—($CH_2$)u-C(O)—, —C(O)—NH—($CH_2$)v-, and combinations thereof, wherein subscript e is an integer from 0 to 4, subscript u is an integer from 1 to 8, and subscript v is an integer from 1 to 8.

22. The method of claim 21, wherein e is 4.

23. The method of claim 22, wherein subscript p is 1.

24. The method of claim 1, wherein subscript n is 2-4.

25. The method of claim 1, wherein the antibody or antigen-binding fragment thereof is selective for an antigen selected from the group consisting of AXL, BAFFR, BCMA, BCR-list components, BDCA2, BDCA4, BTLA, BTNL2, BTNL3, BTNL8, BTNL9, C10 or f54, CCR1, CCR3, CCR4, CCR5, CCR6, CCR7, CCR9, CCR10, CD11c, CD137, CD138, CD14, CD168, CD177, CD19, CD20, CD209, CD209L, CD22, CD226, CD248, CD25, CD27, CD274, CD276, CD28, CD30, CD300A, CD33, CD37, CD38, CD4, CD40, CD44, CD45, CD46, CD48, CDS, CD52, CD55, CD56, CD59, CD62E, CD68, CD69, CD70, CD74, CD79a, CD79b, CD8, CD80, CD86, CD90.2, CD96, CLEC12A, CLEC12B, CLEC7A, CLEC9A, CR1, CR3, CRTAM, CSF1R, CTLA4, CXCR1/2, CXCR4, CXCR5, DDR1, DDR2, DEC-205, DLL4, DR6, FAP, FCamR, FCMR, FeR's, Fire, GITR, HHLA2, HLA class II, HVEM, ICOSLG, IFNLR1, IL10R1, IL10R2, IL12R, IL13RA1, IL13RA2, IL15R, IL17RA, IL17RB, IL17RC, IL17RE, IL20R1, IL20R2, IL21R, IL22R1, IL22RA, IL23R, IL27R, IL29R, IL2Rg, IL31R, IL36R, IL3RA, IL4R, IL6R, ILSR, IL7R, IL9R, Integrins, LAG3, LIFR, MAG/Siglec-4, MMR, MSR1, NCR3LG1, NKG2D, NKp30, NKp46, PDCD1, PROKR1, PVR, PVRIG, PVRL2, PVRL3, RELT, SIGIRR, Siglec-1, Siglec-10, Siglec-5, Siglec-6, Siglec-7, Siglec-8, Siglec-9, SIRPA, SLAMF7, TACI, TCR-list components/assoc, PTCRA, TCRb, CD3z, CD3, TEK, TGFBR1, TGFBR2, TGFBR3, TIGIT, TLR2, TLR4, TROY, TSLPR, TYRO, VLDLR, VSIG4, and VTCN1.

26. The method of claim 1, wherein the antibody or the antigen-binding fragment thereof is coupled to a primary amine compound by a transglutaminase-mediated coupling.

27. The method of claim 26, wherein the glutaminyl-modified antibody is an antibody modified with an azido-polyethylene glycol compound.

28. The method of claim 1, wherein the antibody is conjugated to a reactive group compound at a glutamine residue, and LL is bonded to BA through said reactive group compound.

29. The method of claim 28, wherein the reactive group compound comprises a divalent polyethylene glycol group.

30. The method of claim 1, wherein PA is a residue of a group selected from the group consisting of a dolastatin, an auristatin, a maytansinoid, a taxane, a *vinca* alkaloid, a steroid, an LXR modulator, a pyrrolobenzodiazepine, a tubulysin, and a camptothecin.

31. The method of claim 30, wherein PA is selected from the group consisting of

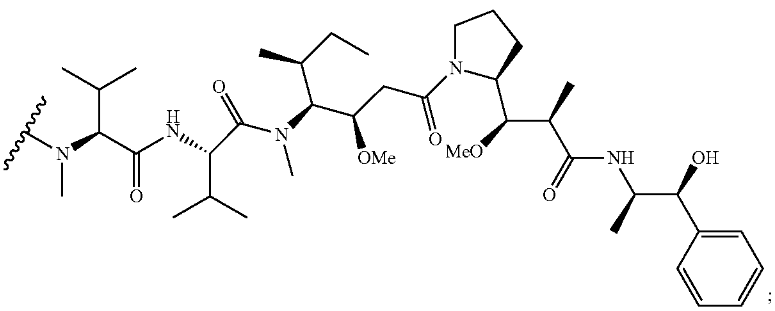
;
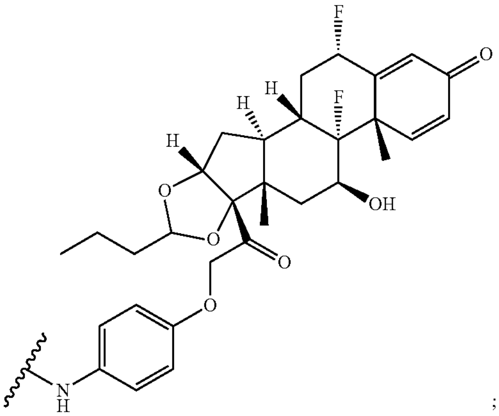
;
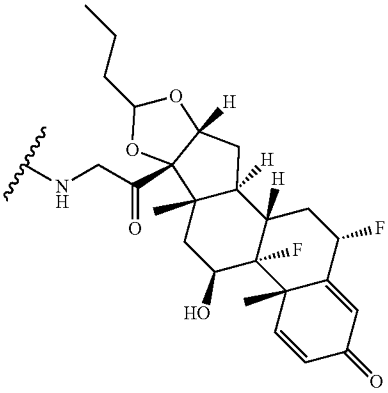
;
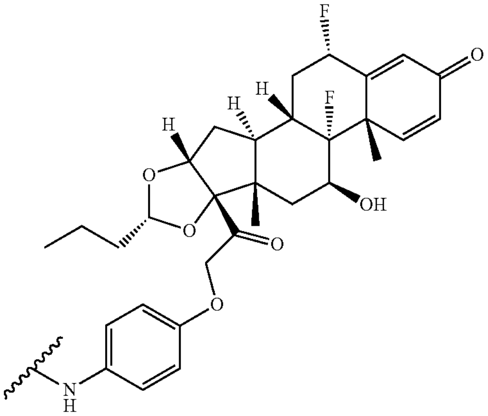
;
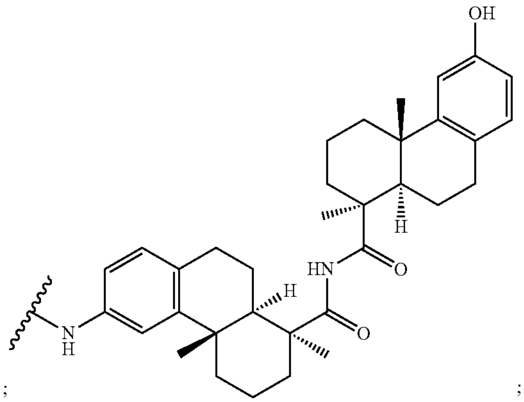
;
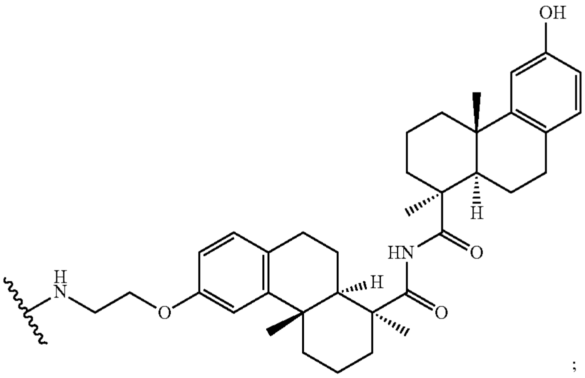
;
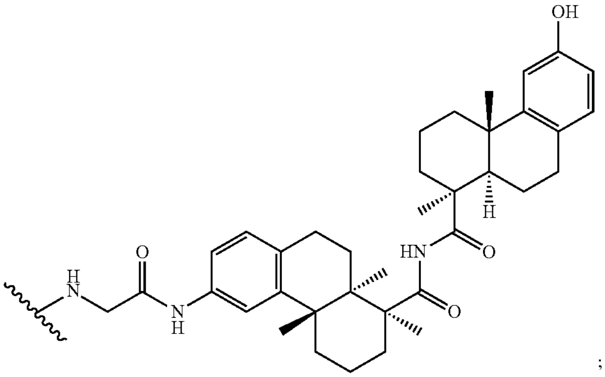
;
and -continued

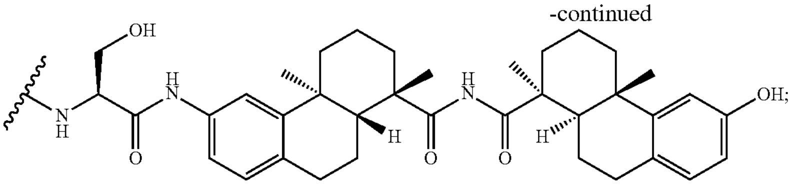

wherein the

indicates the atom through which the PA is bonded to the adjacent groups in the formula.

32. The method of claim 30, wherein PA is a residue of a maytansinoid, steroid, LXR modulator, pyrrolobenzodiezepine, tubulysirr, or camptothecin.

33. The method of claim 32, wherein PA is a residue of an auristatin.

34. The method of claim 32, wherein PA is a residue of a maytansinoid.

35. The method of claim 32, wherein PA is a residue of a glucocorticoid.

36. The method of claim 32, wherein PA is a residue of a liver X receptor modulator.

37. The method of claim 17, wherein the compound is selected from the group consisting of:

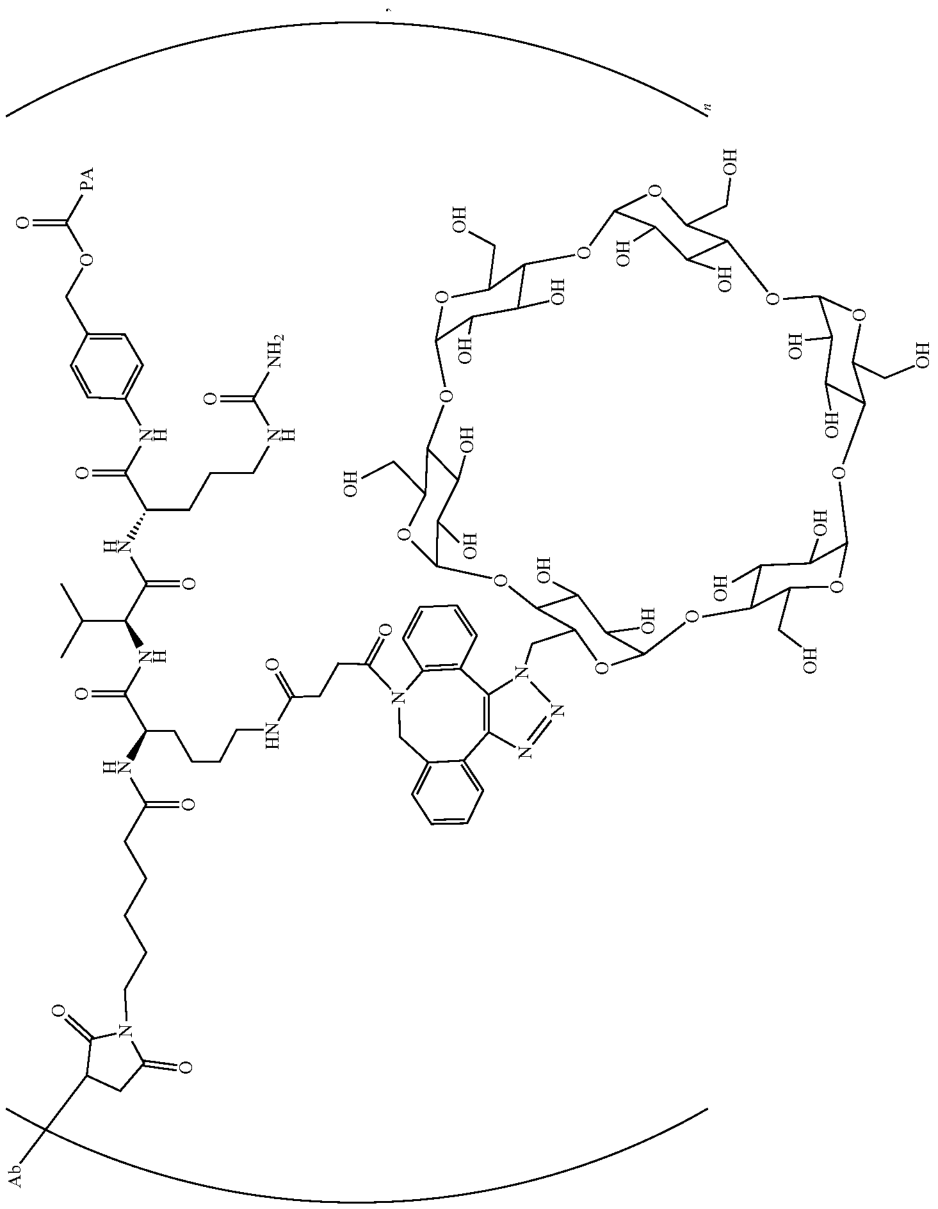

-continued
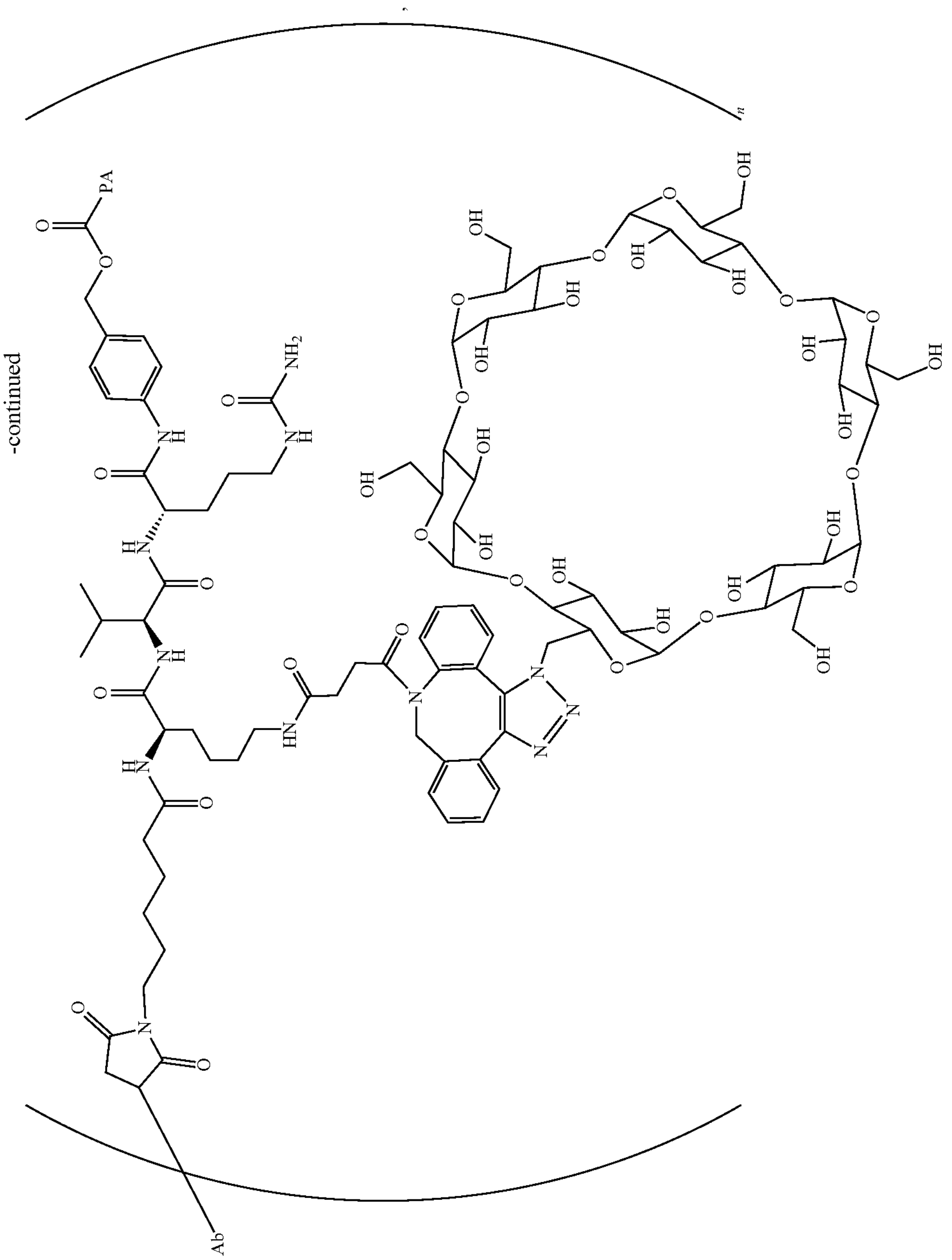

-continued
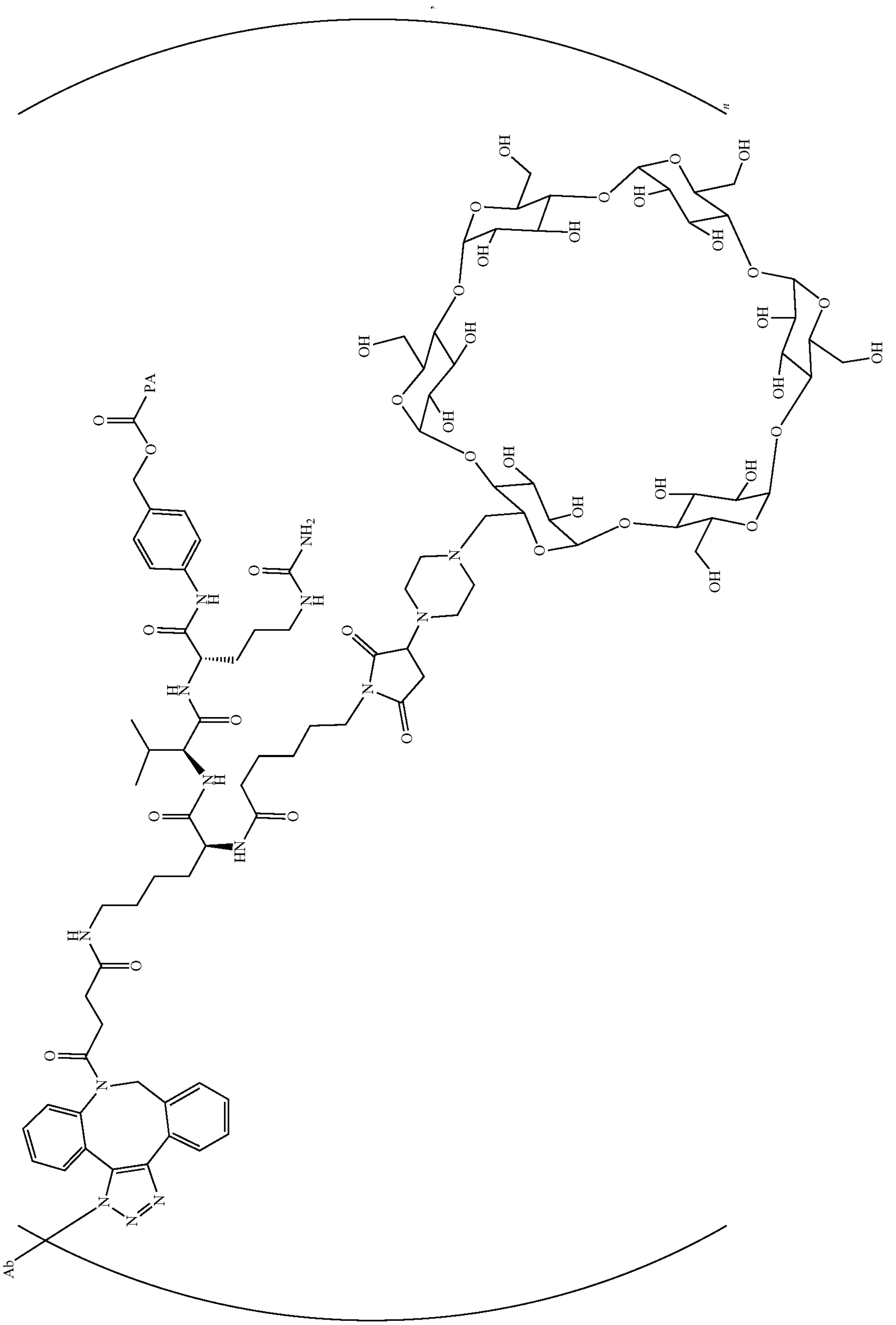

-continued
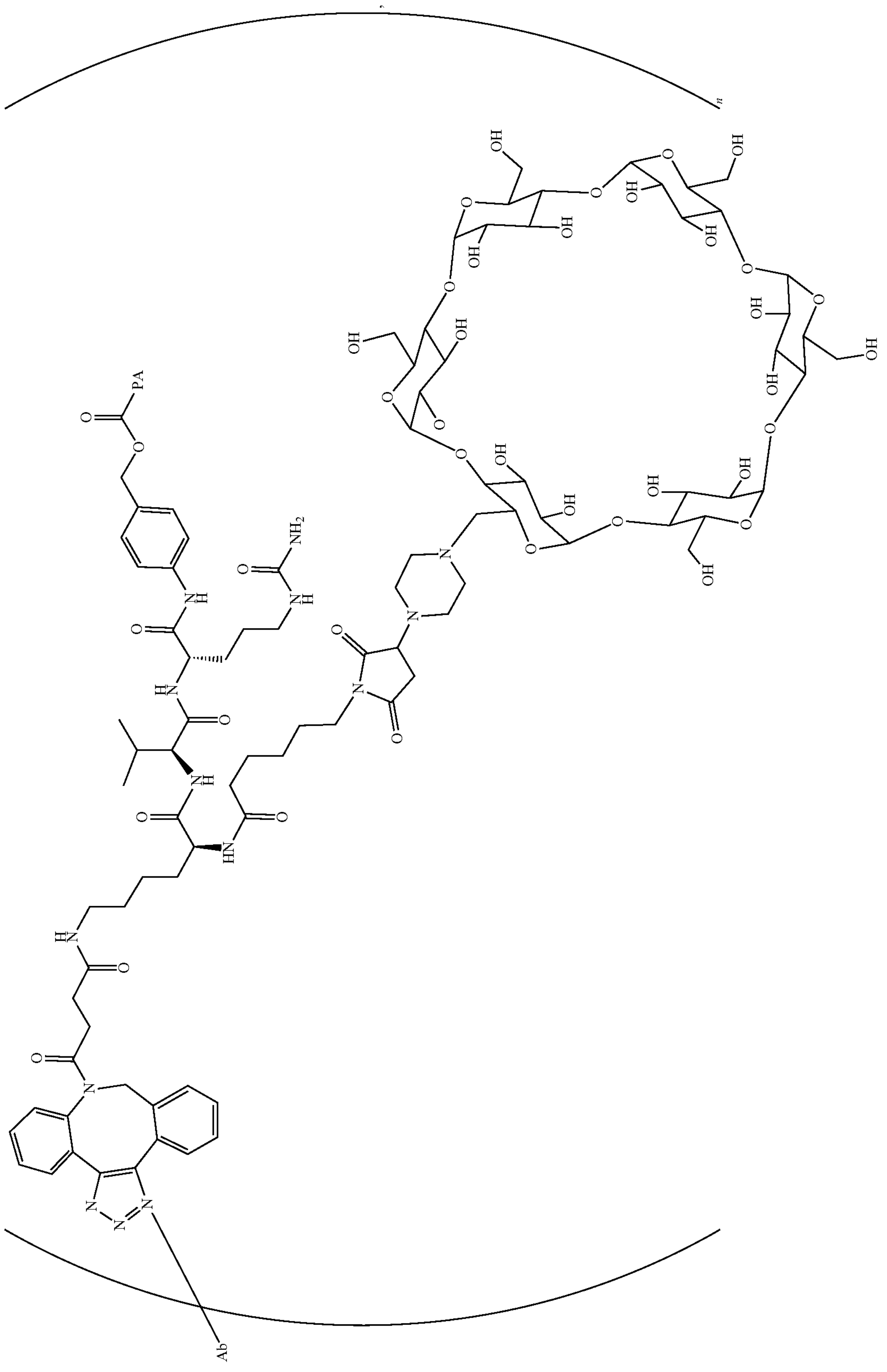

-continued
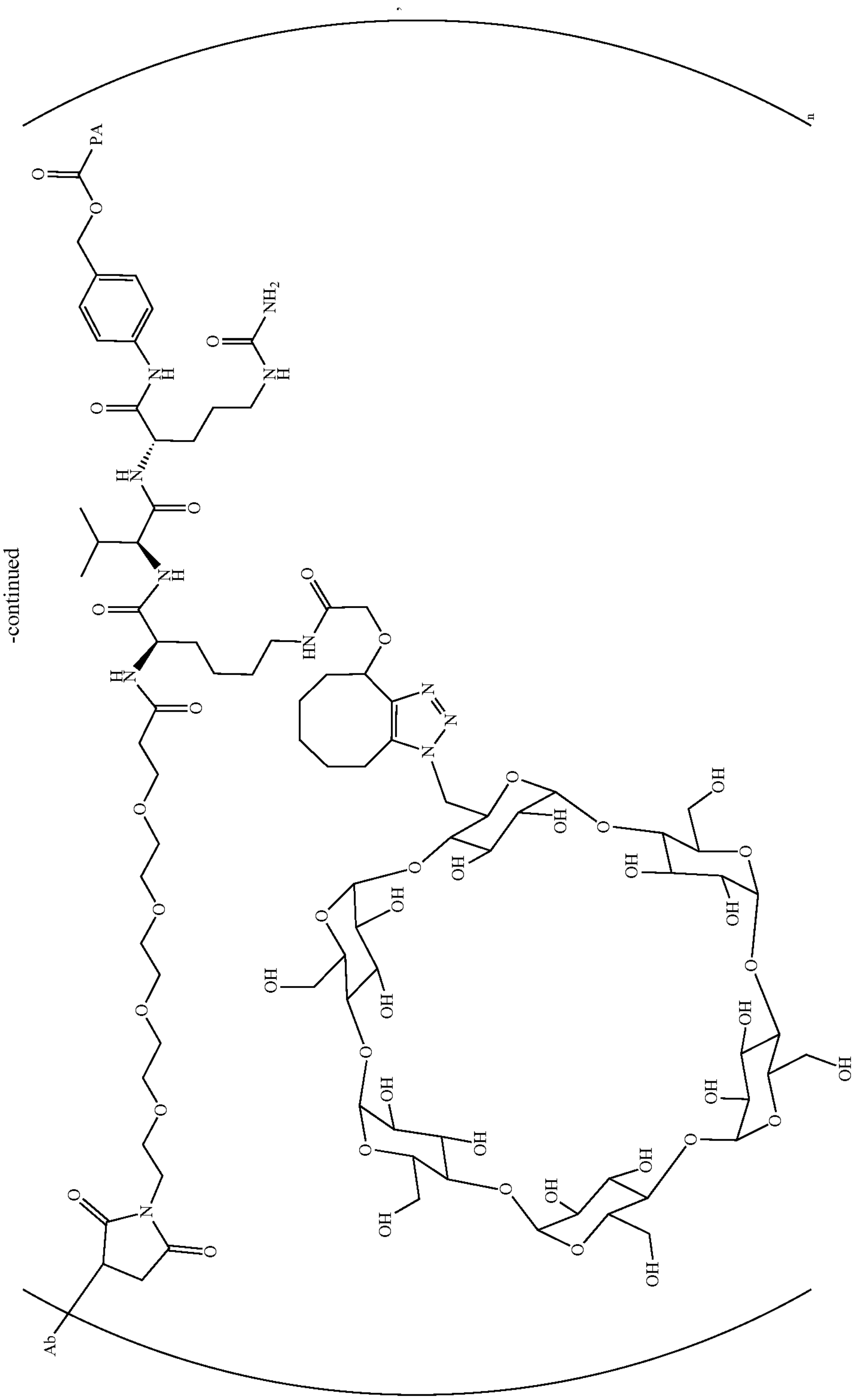

-continued
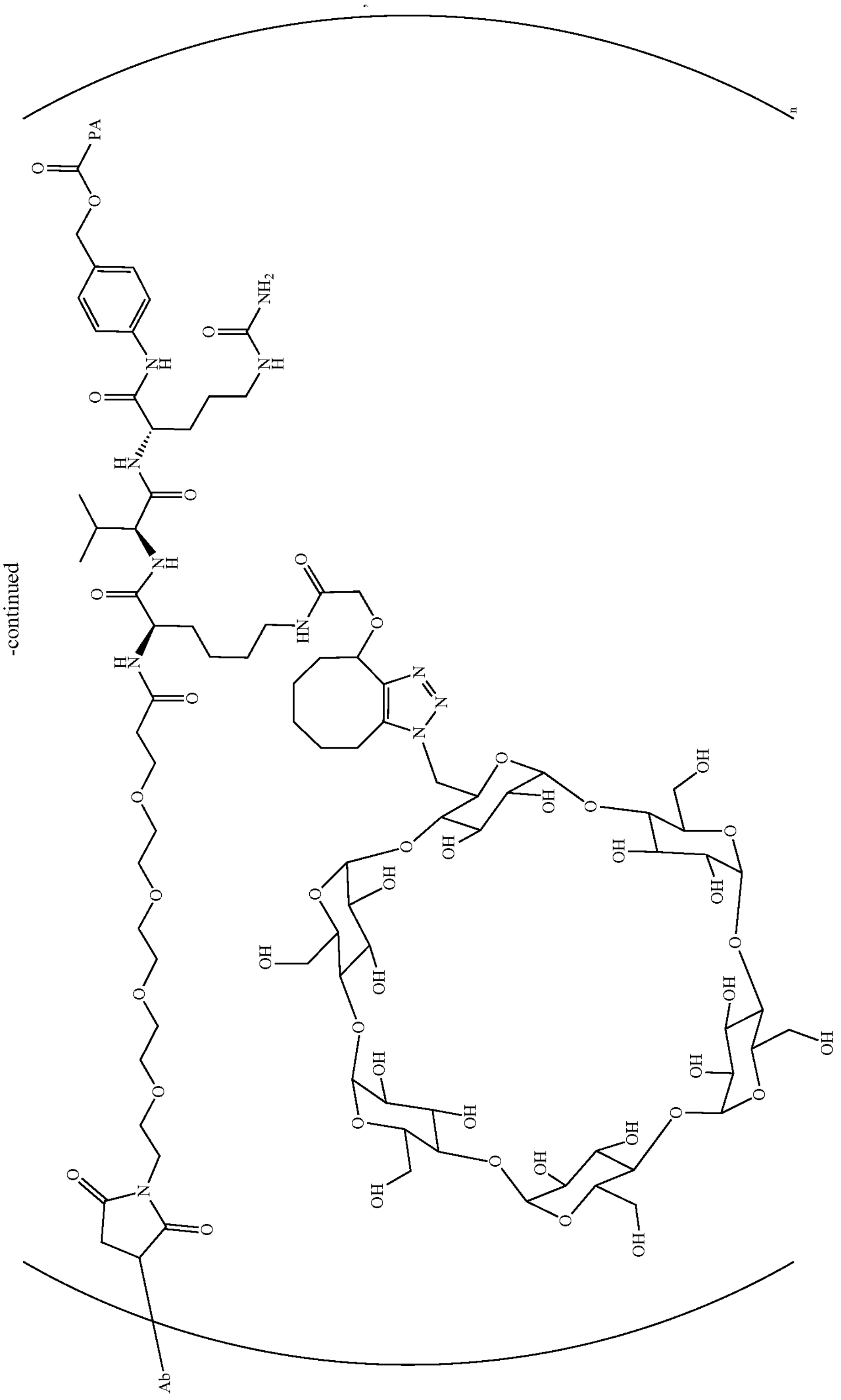

-continued
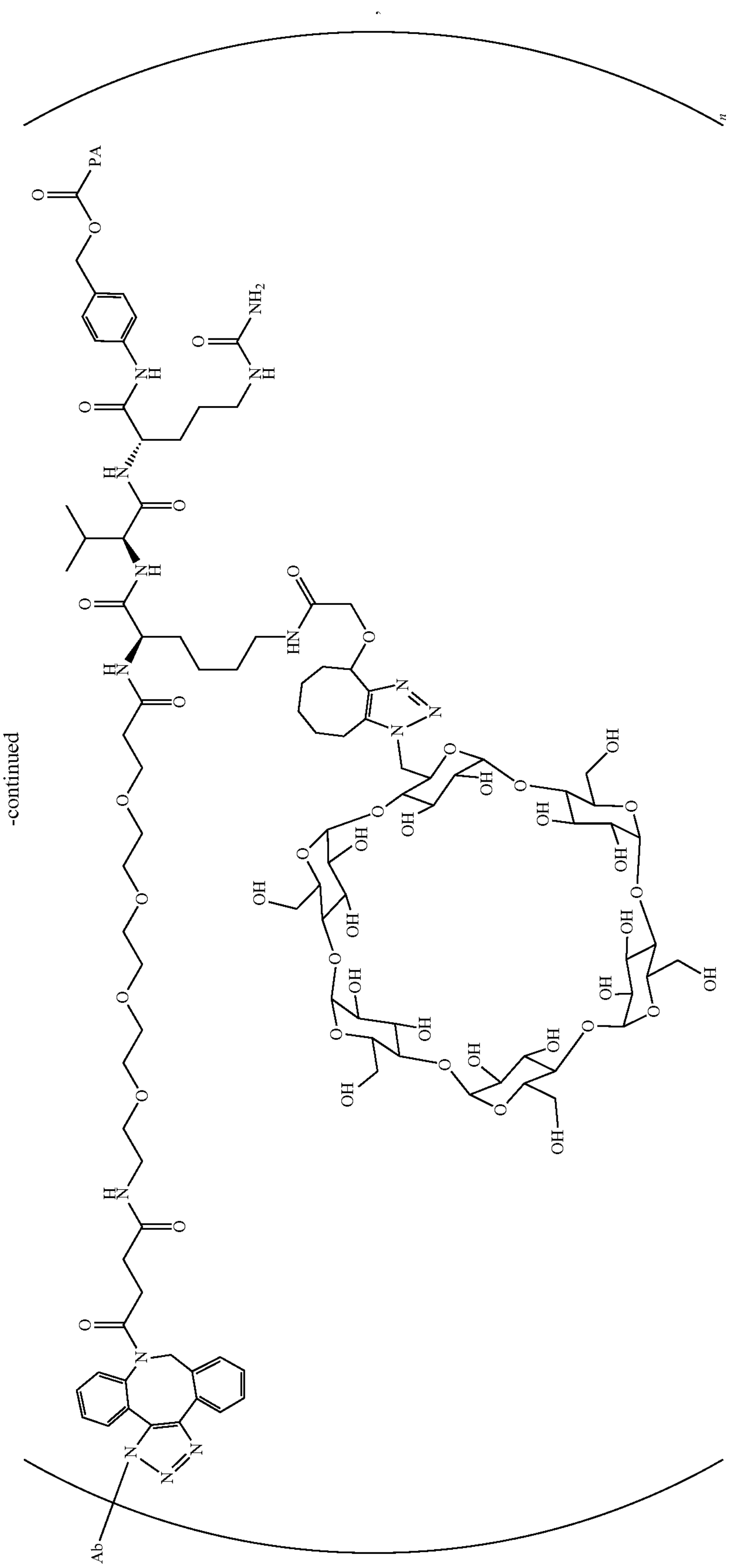

-continued
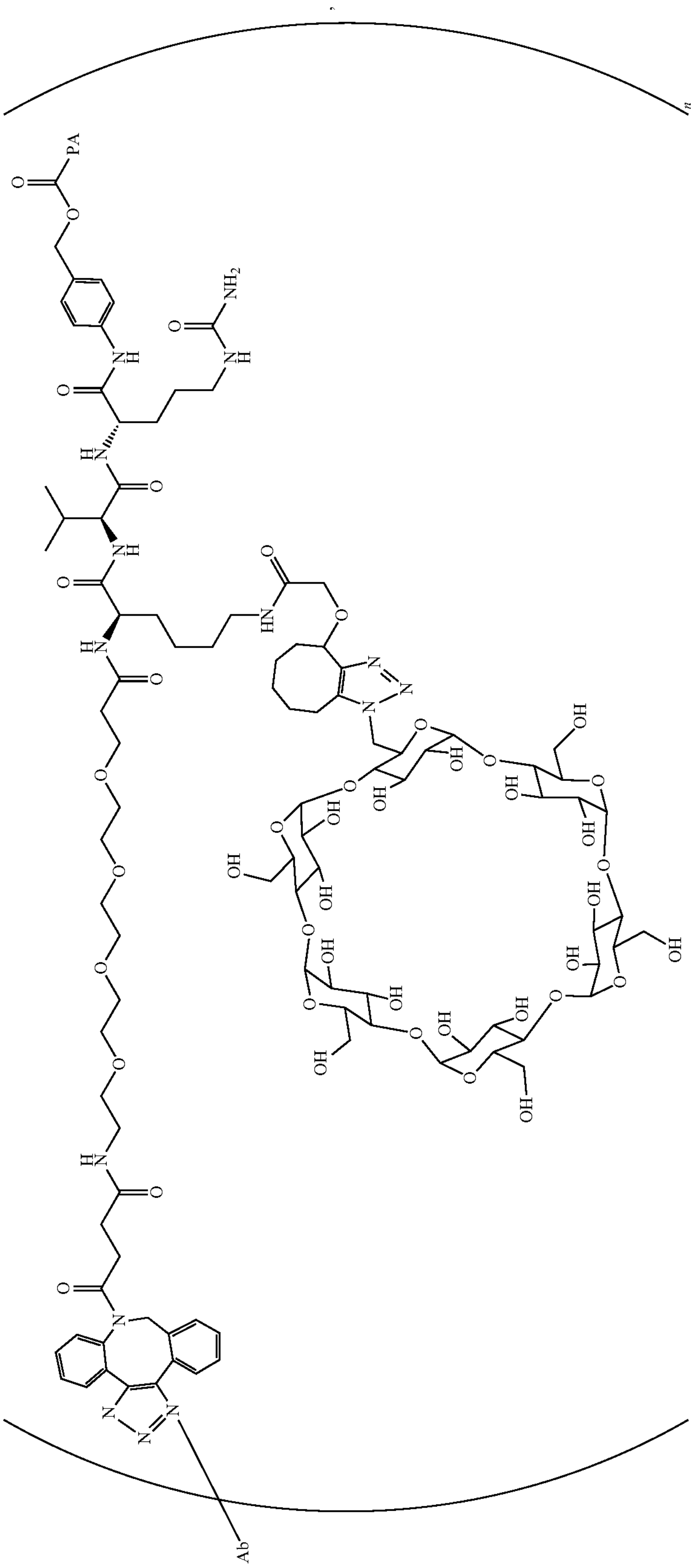

-continued
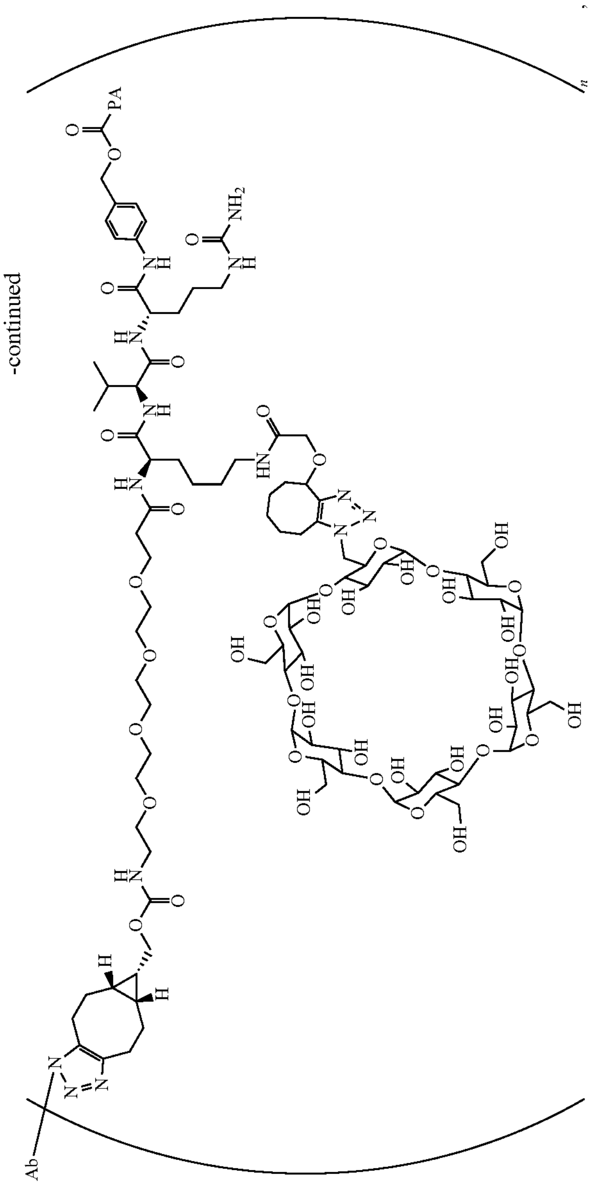

-continued
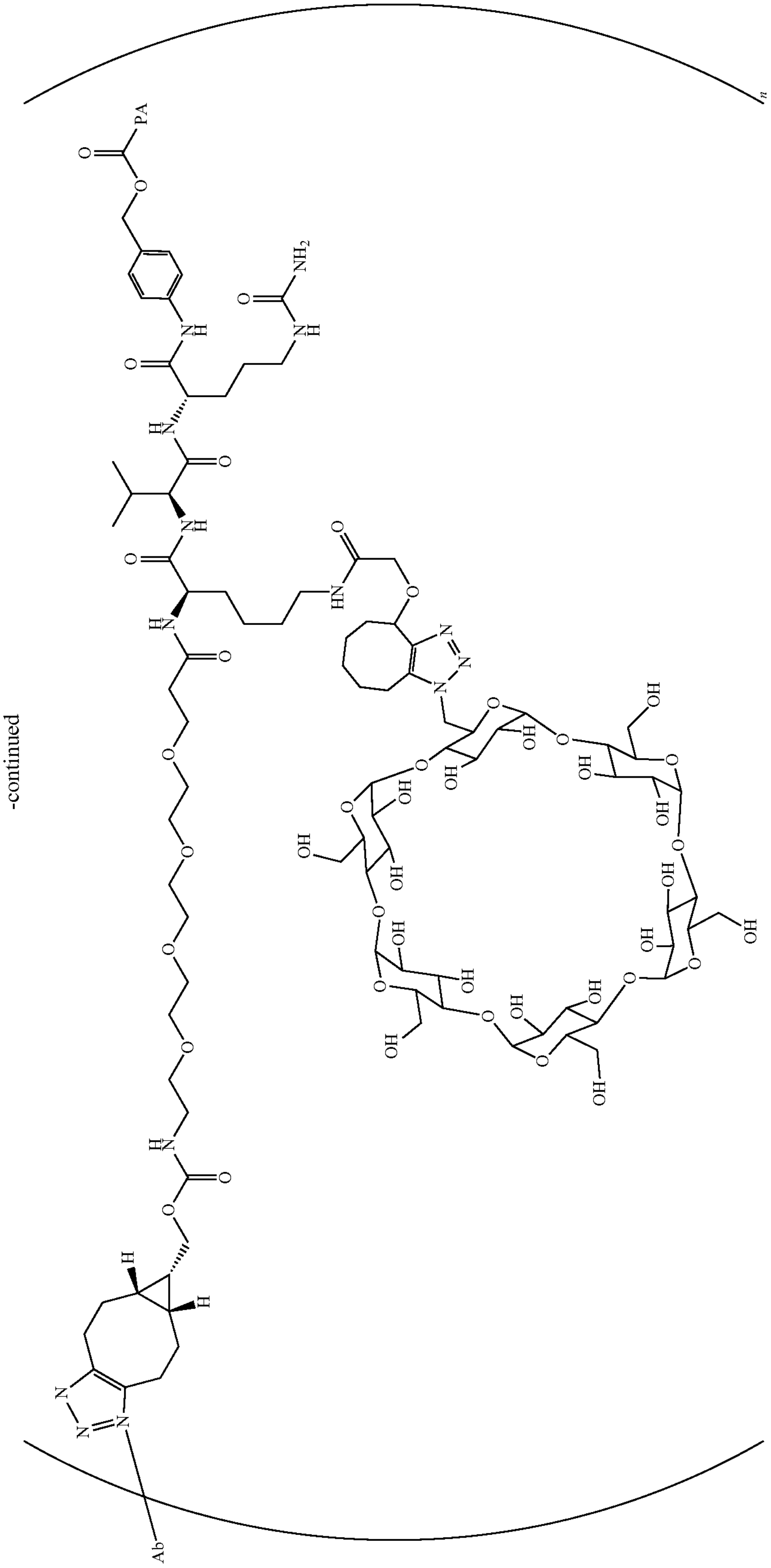

-continued
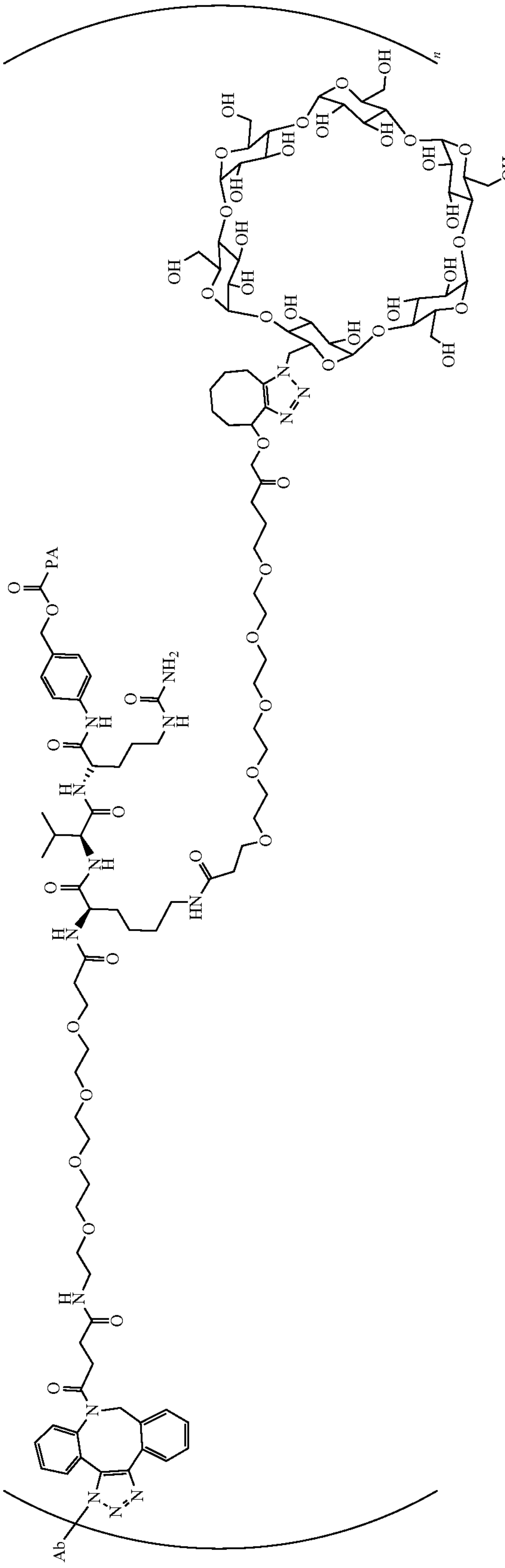
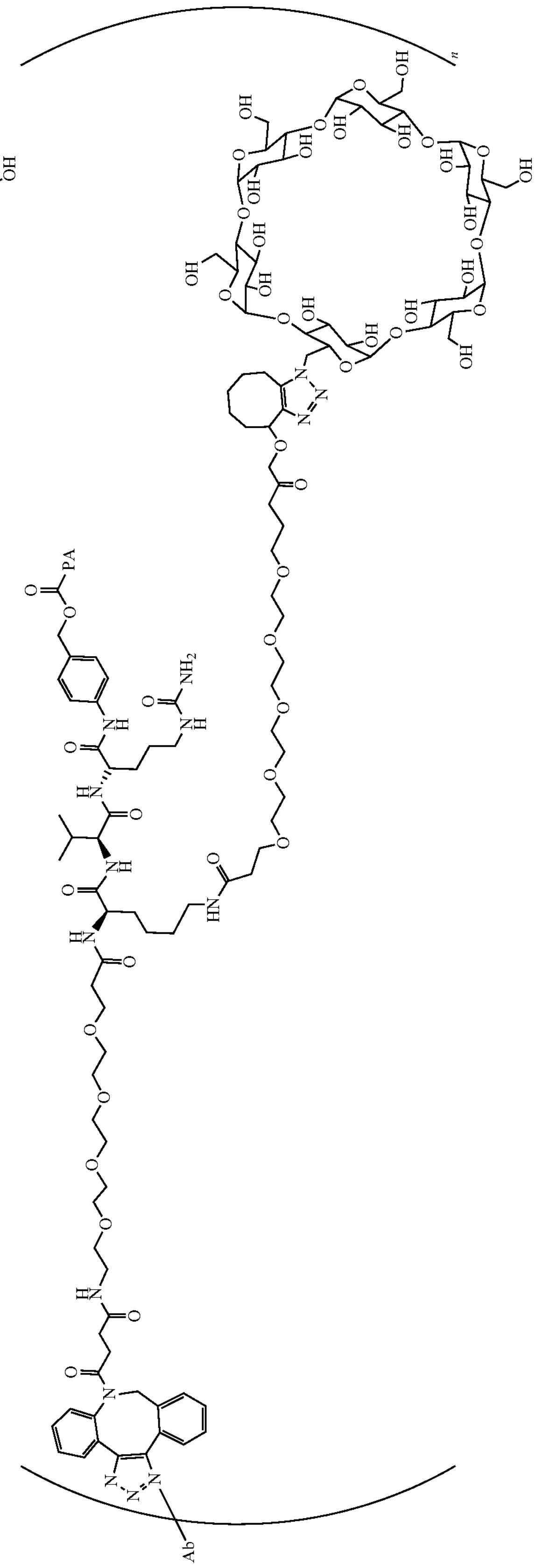

-continued
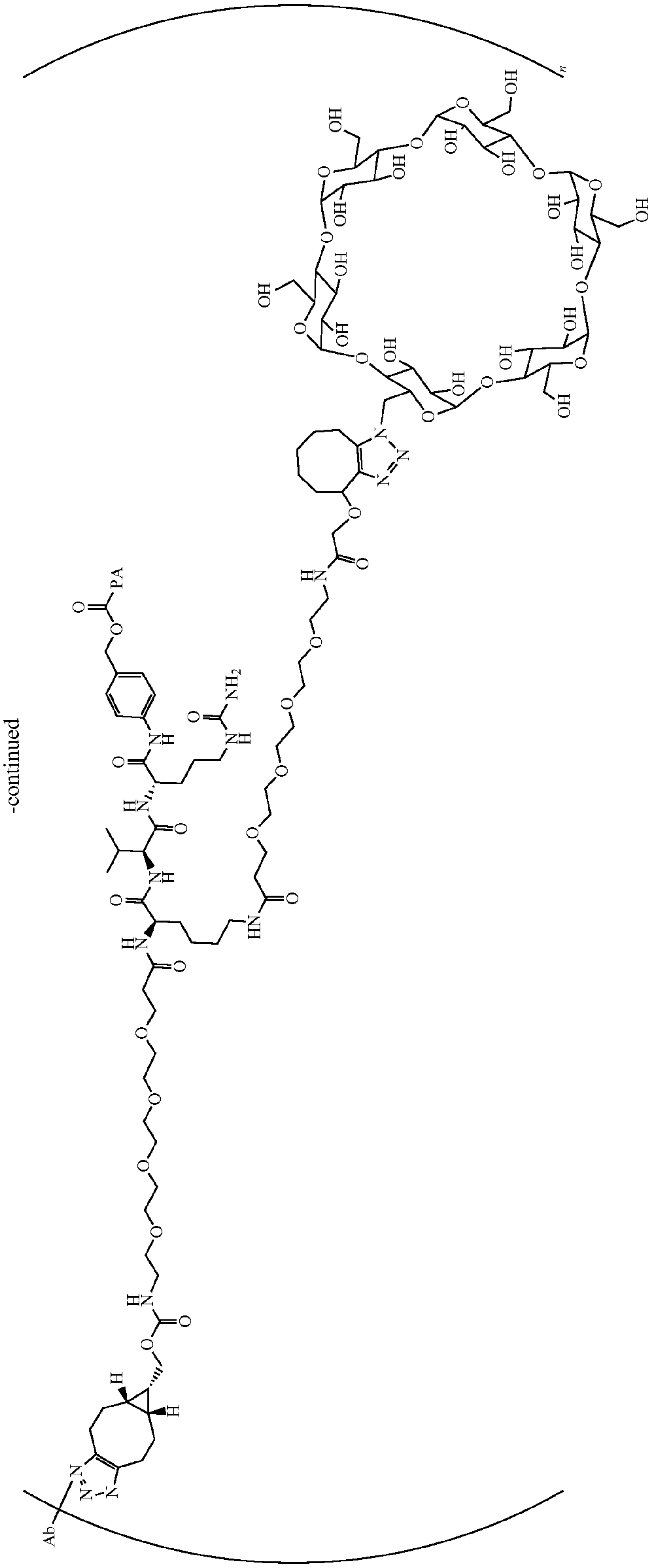

-continued
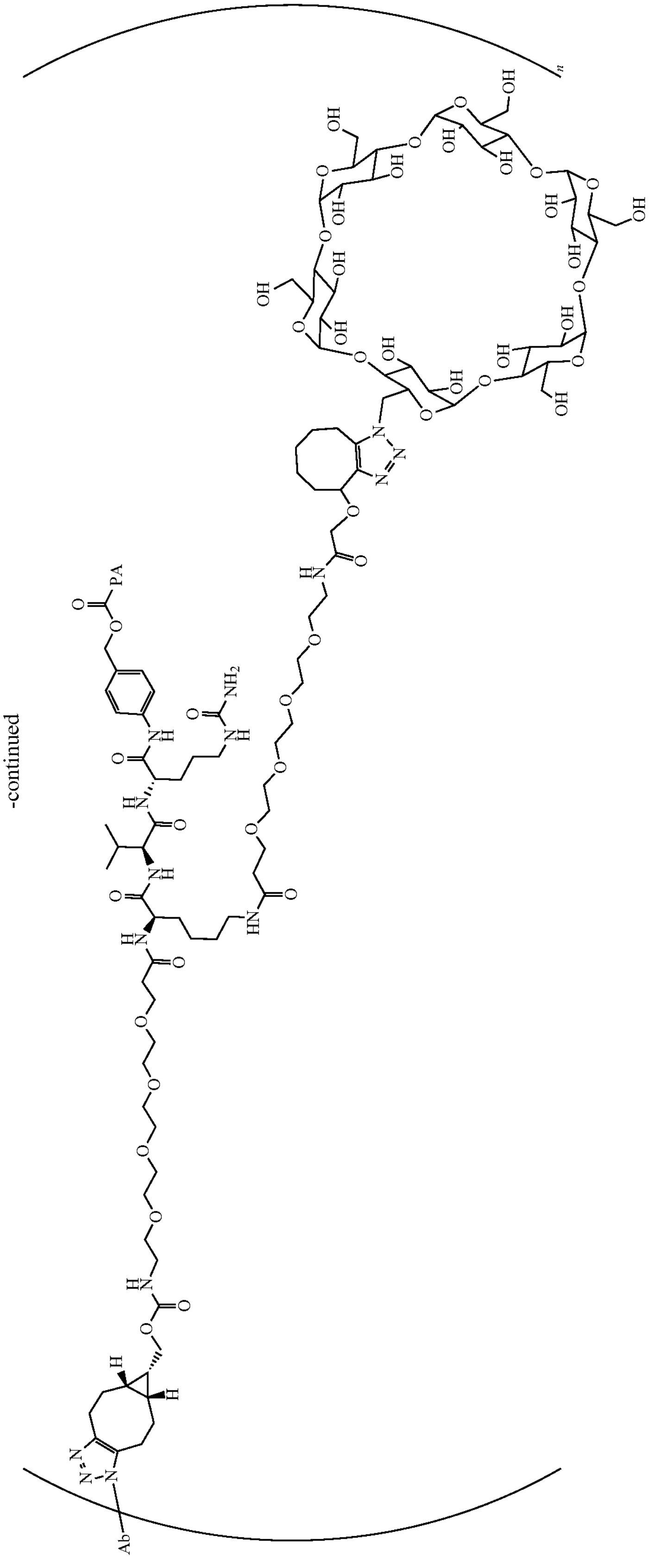

-continued
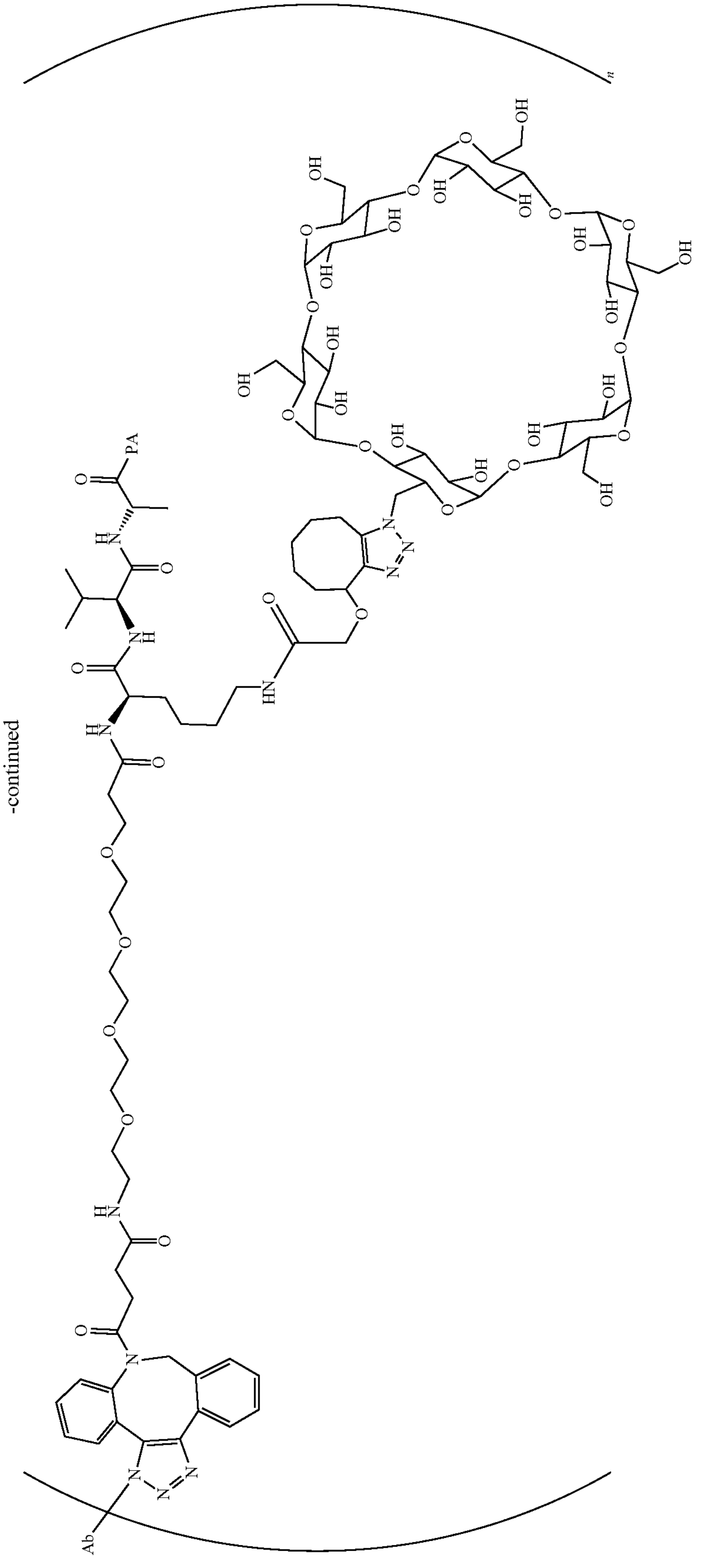

-continued
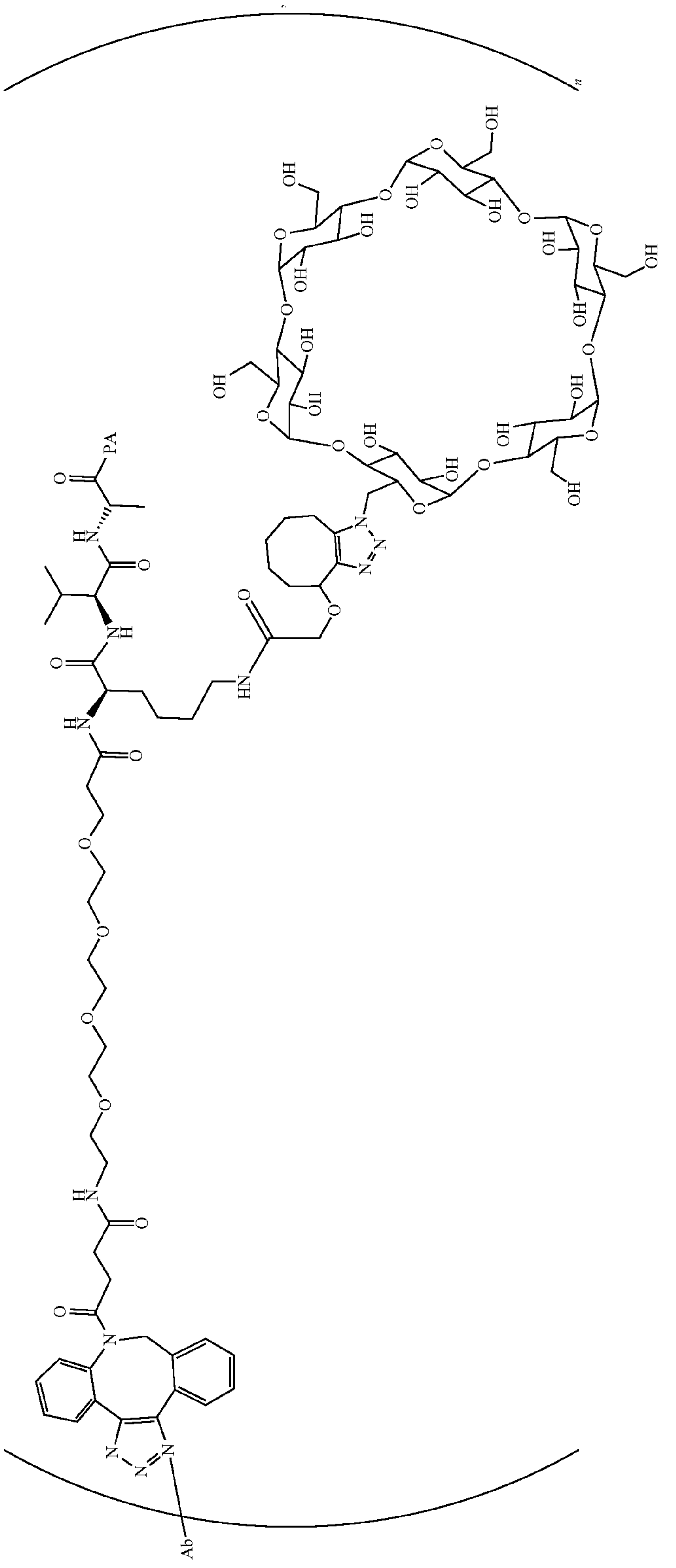

-continued
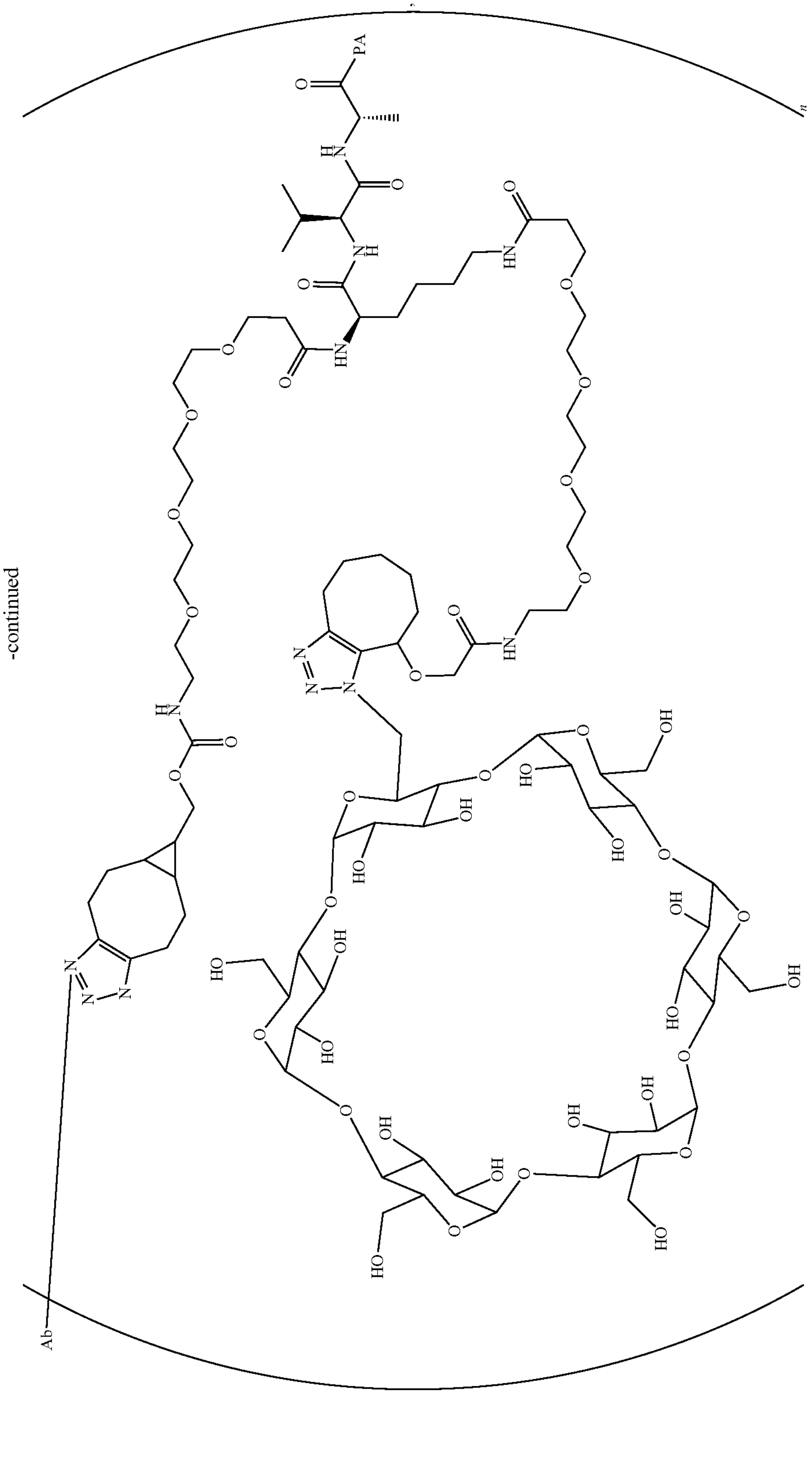

-continued
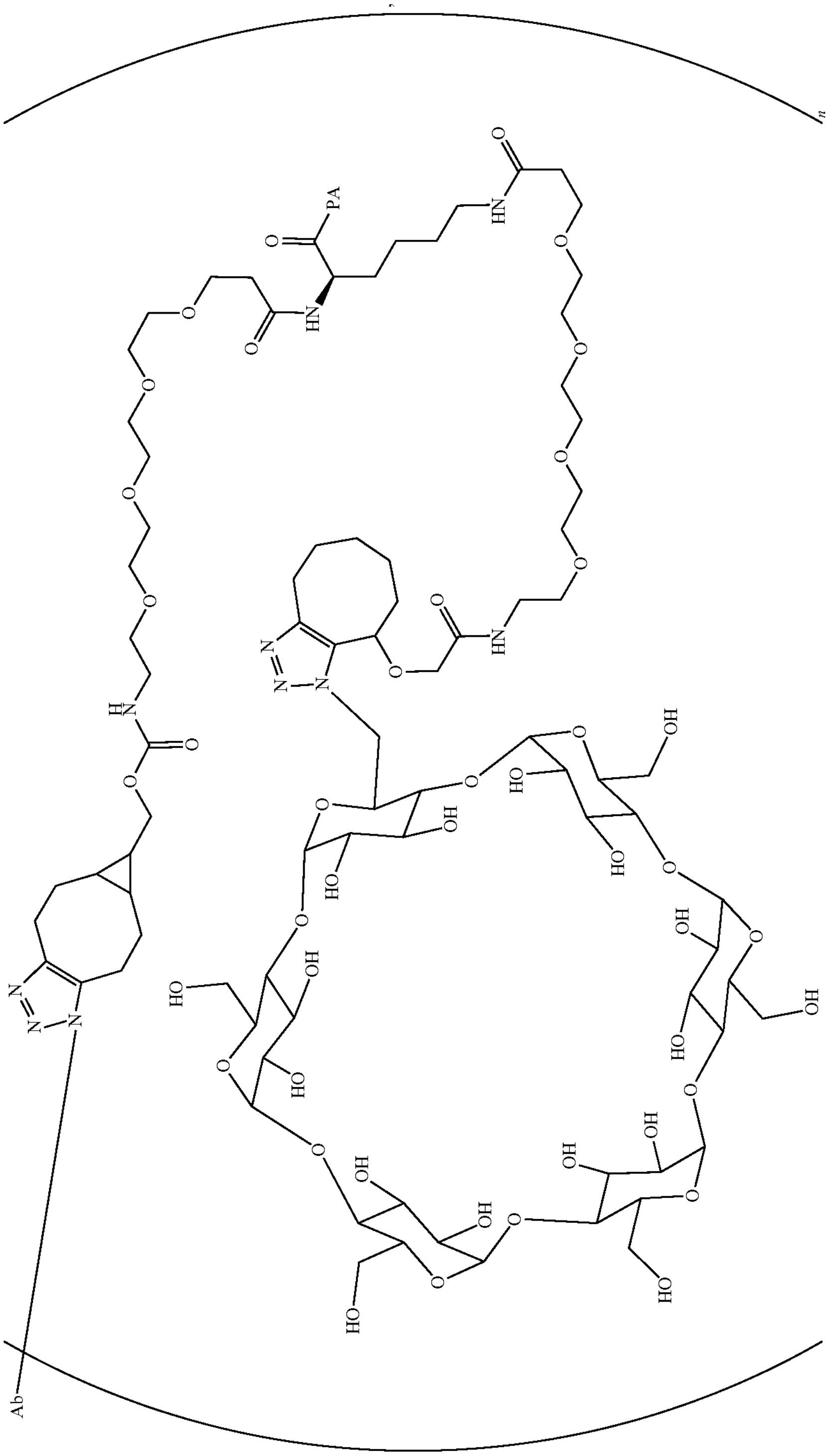

-continued
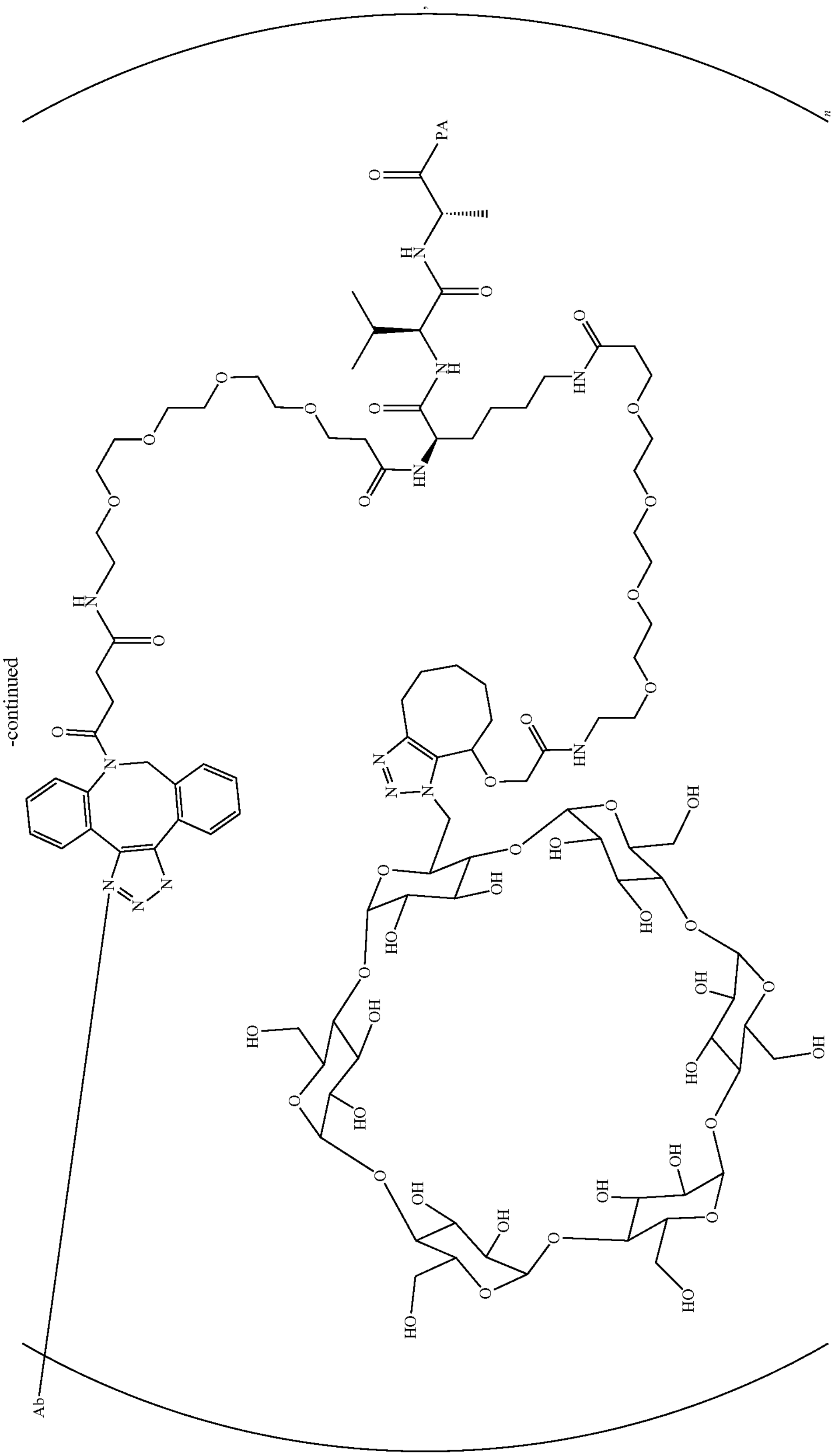

-continued
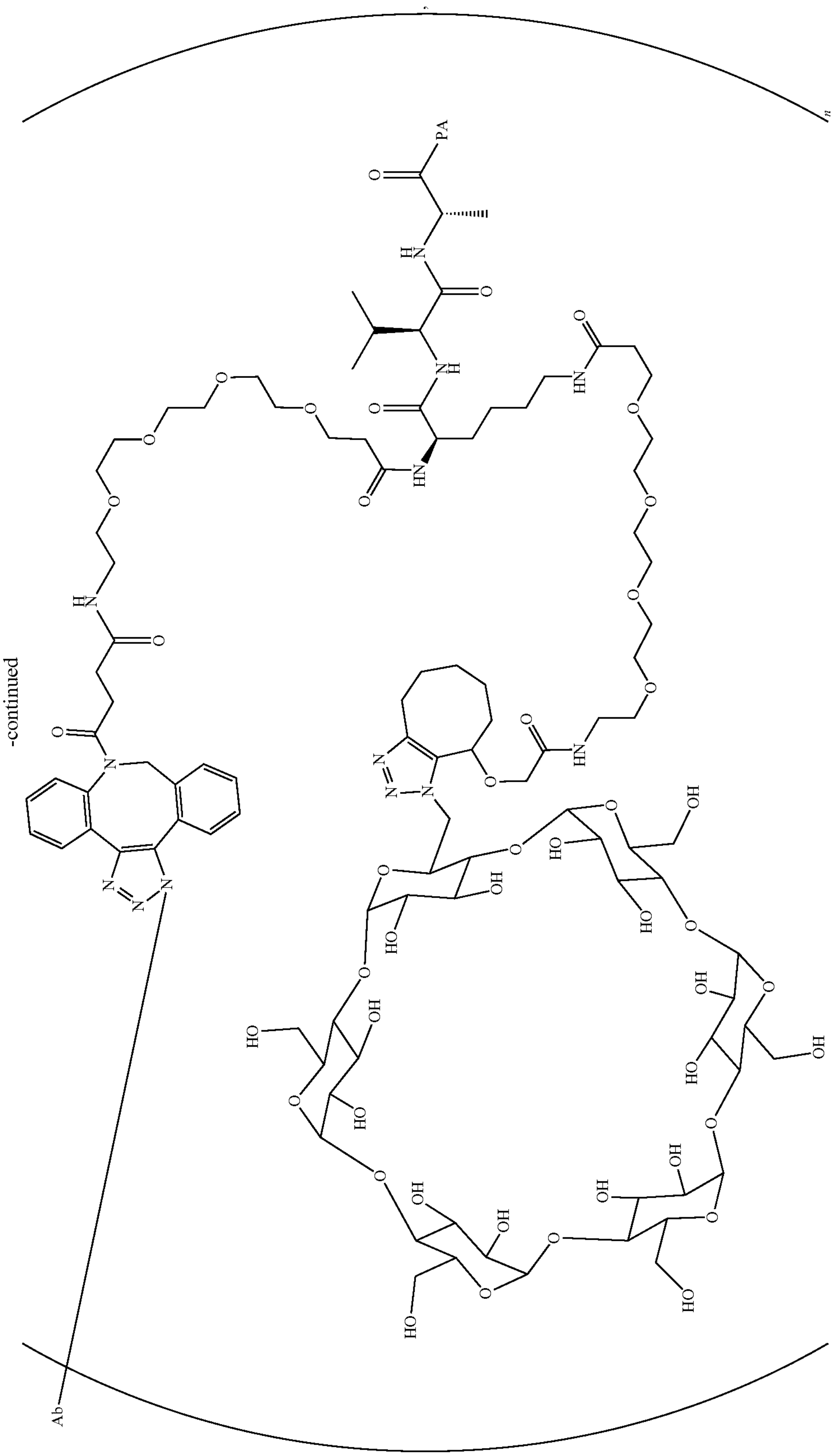

-continued
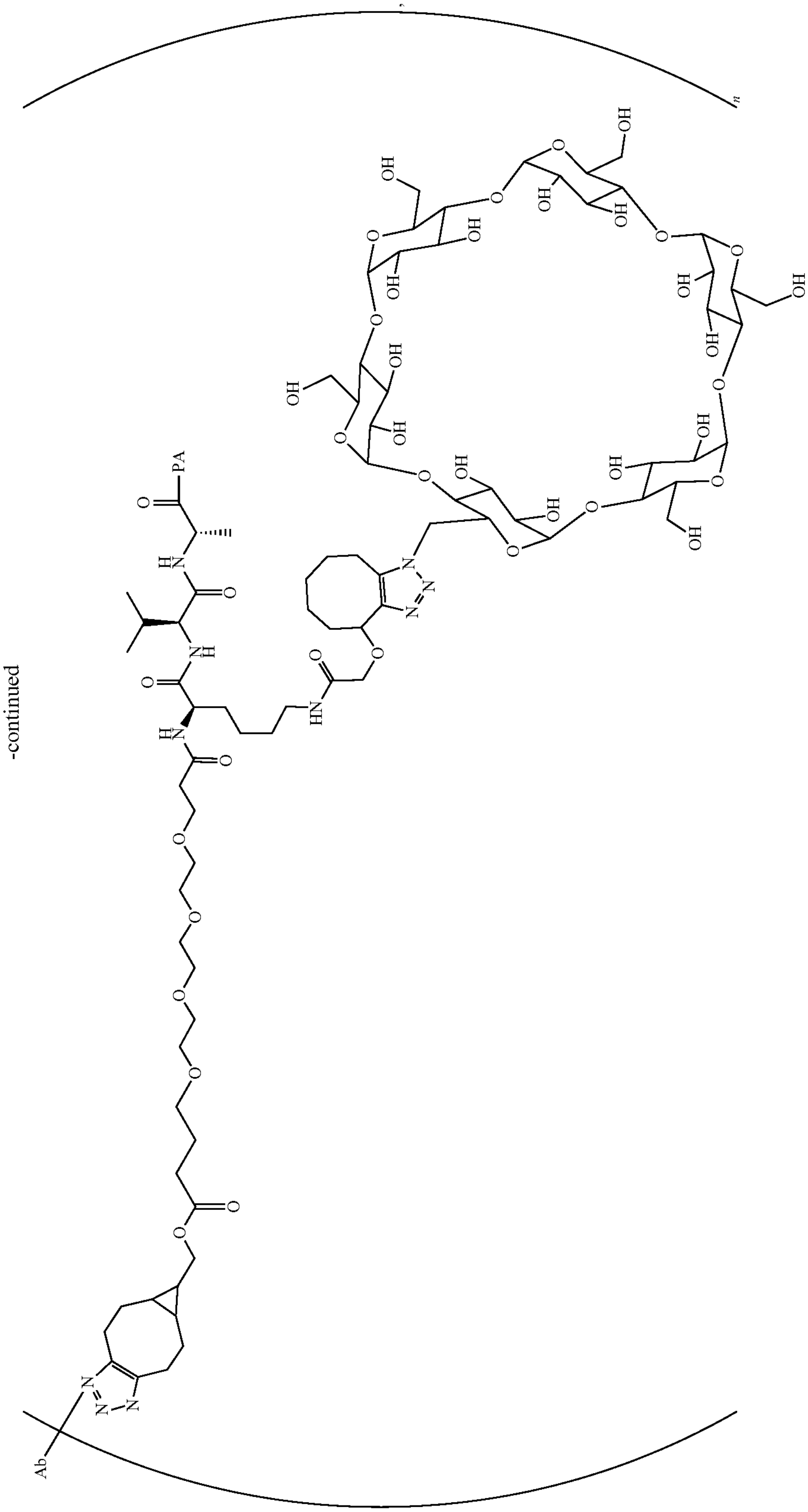
, and

-continued
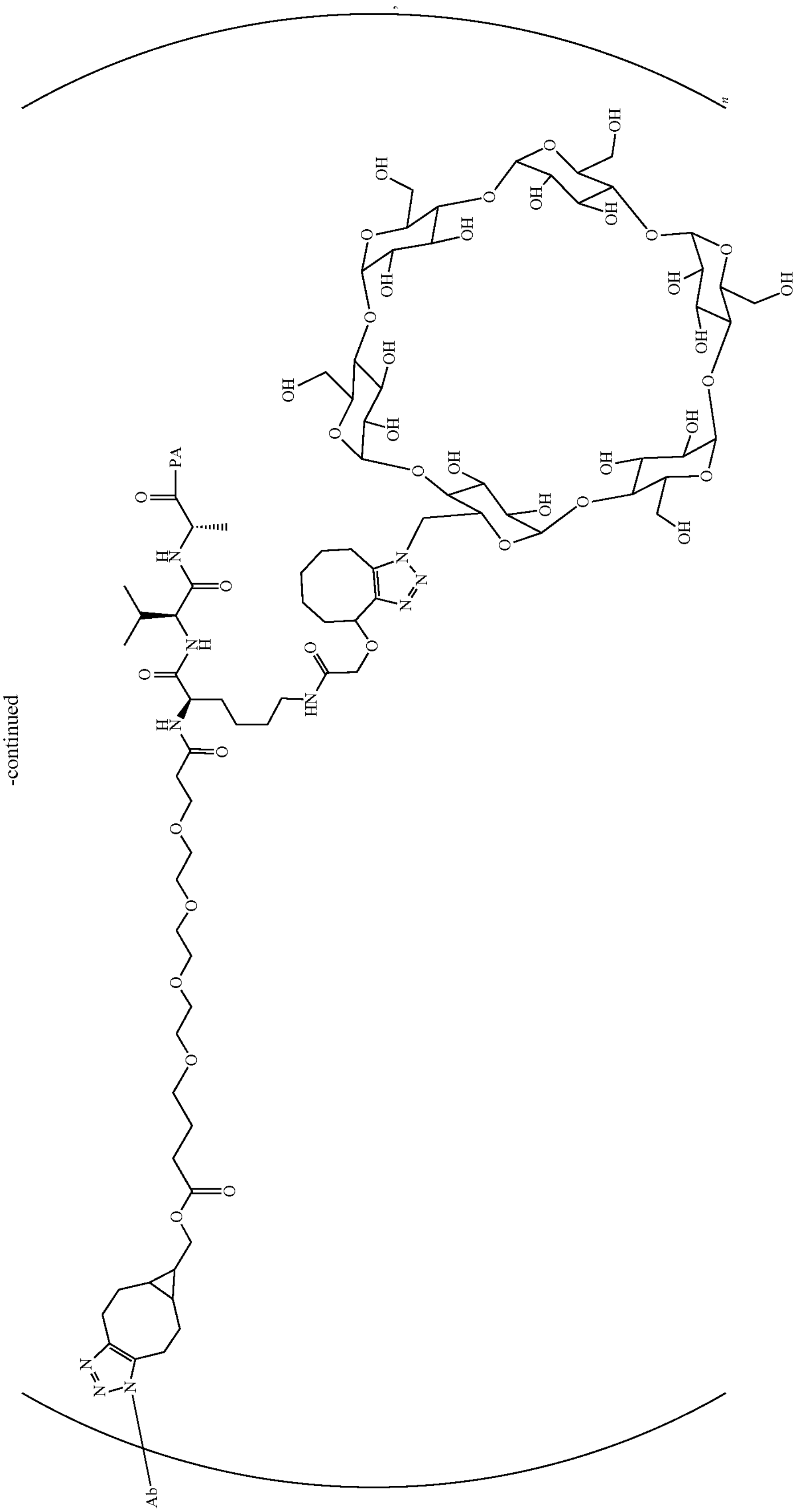

or a stereoisomeric form, or a pharmaceutically acceptable salt thereof, or a regioisomer thereof, or mixture of regioisomers thereof; wherein Ab is an antibody or antigen-binding fragment thereof;

PA is a payload moiety; and n is an integer from 1 to 30.

38. The method of claim 17, wherein the compound is selected from the group consisting of:

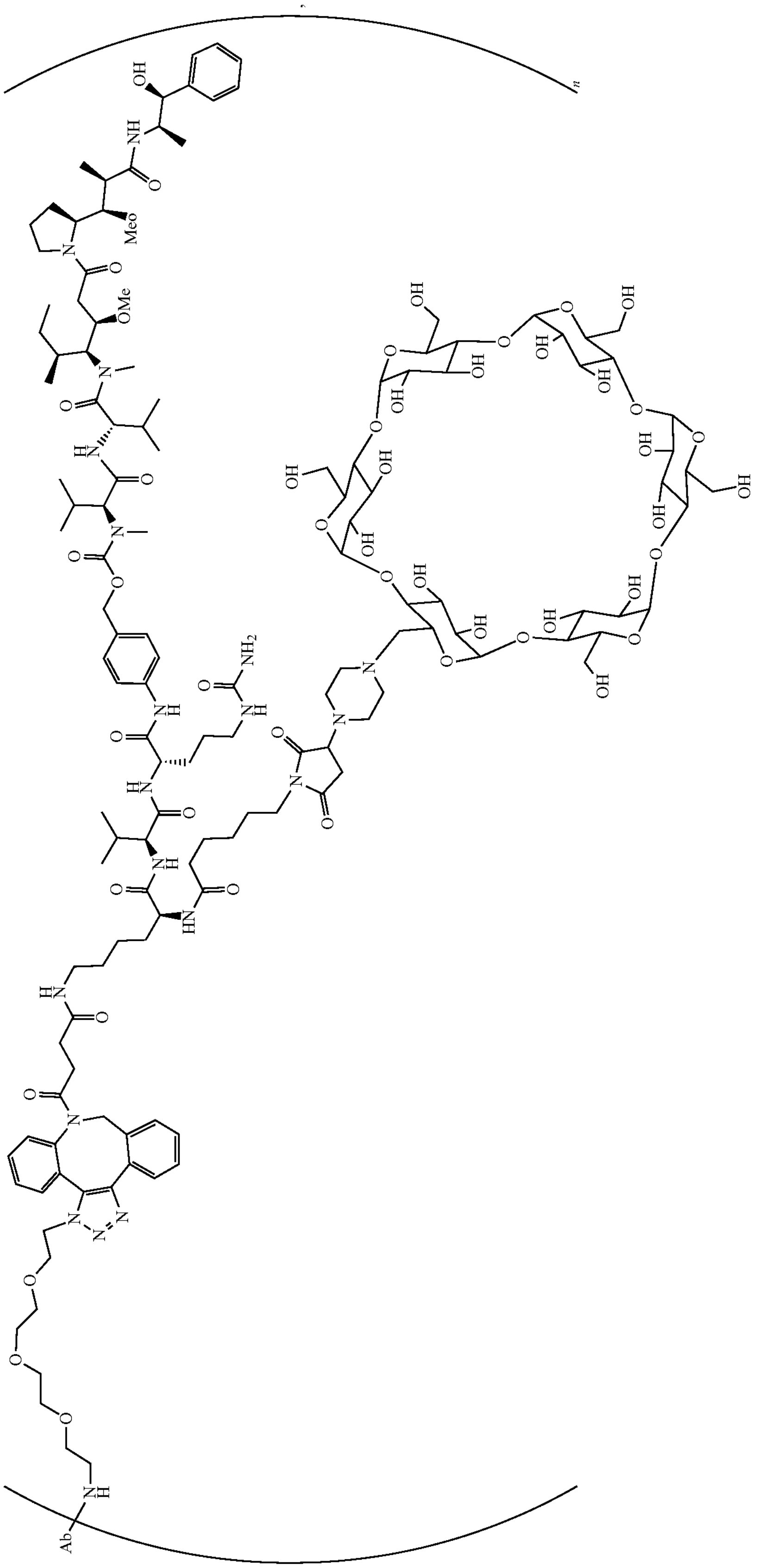

-continued
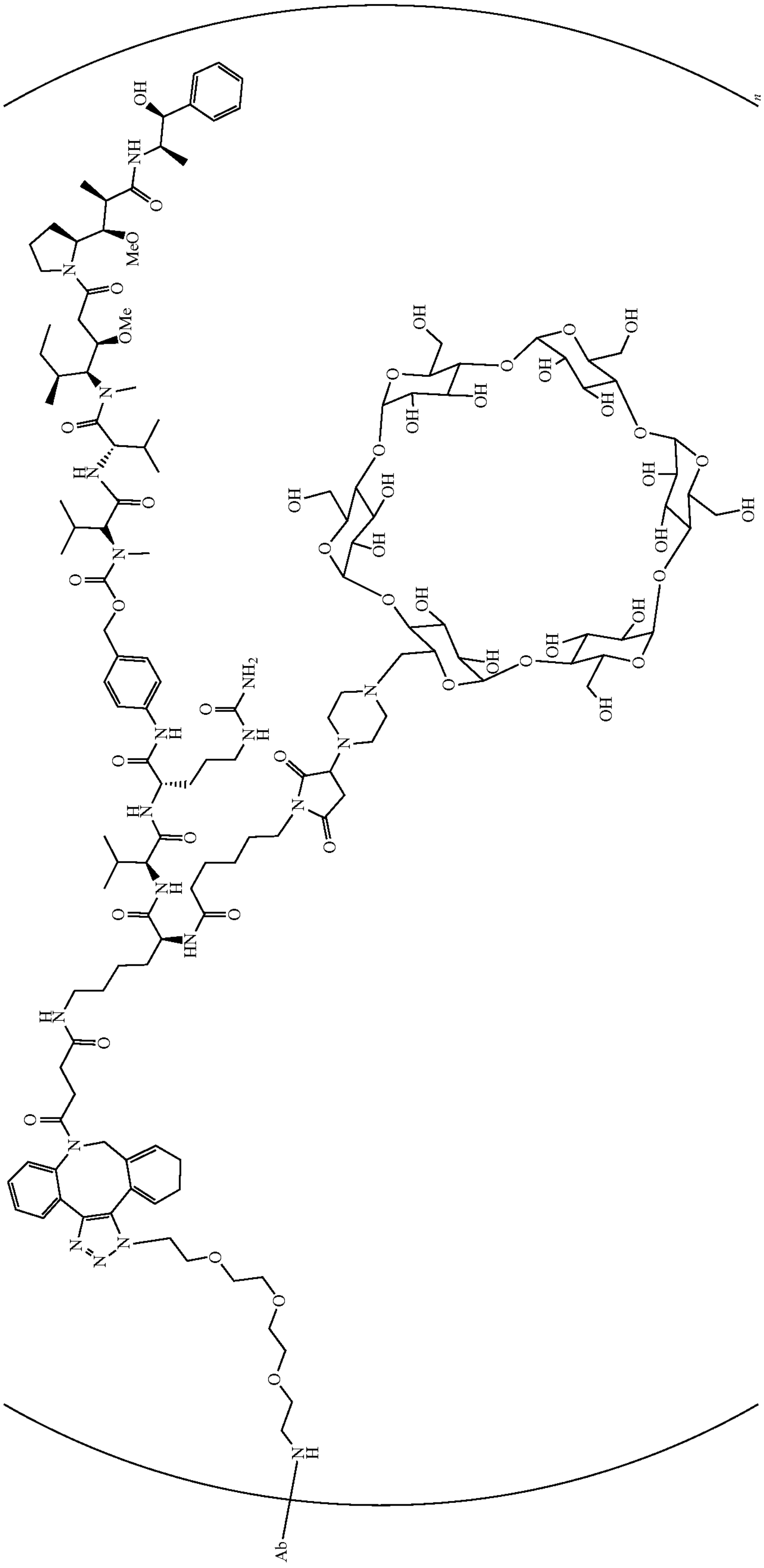

-continued
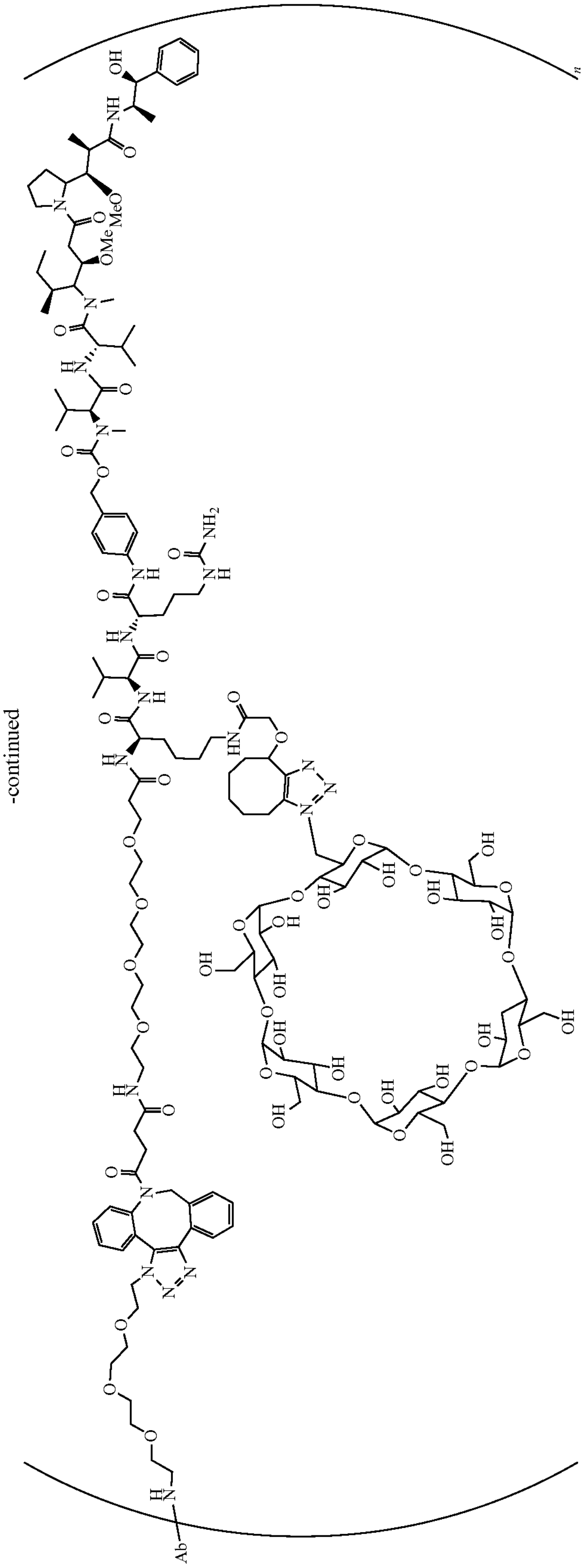

-continued
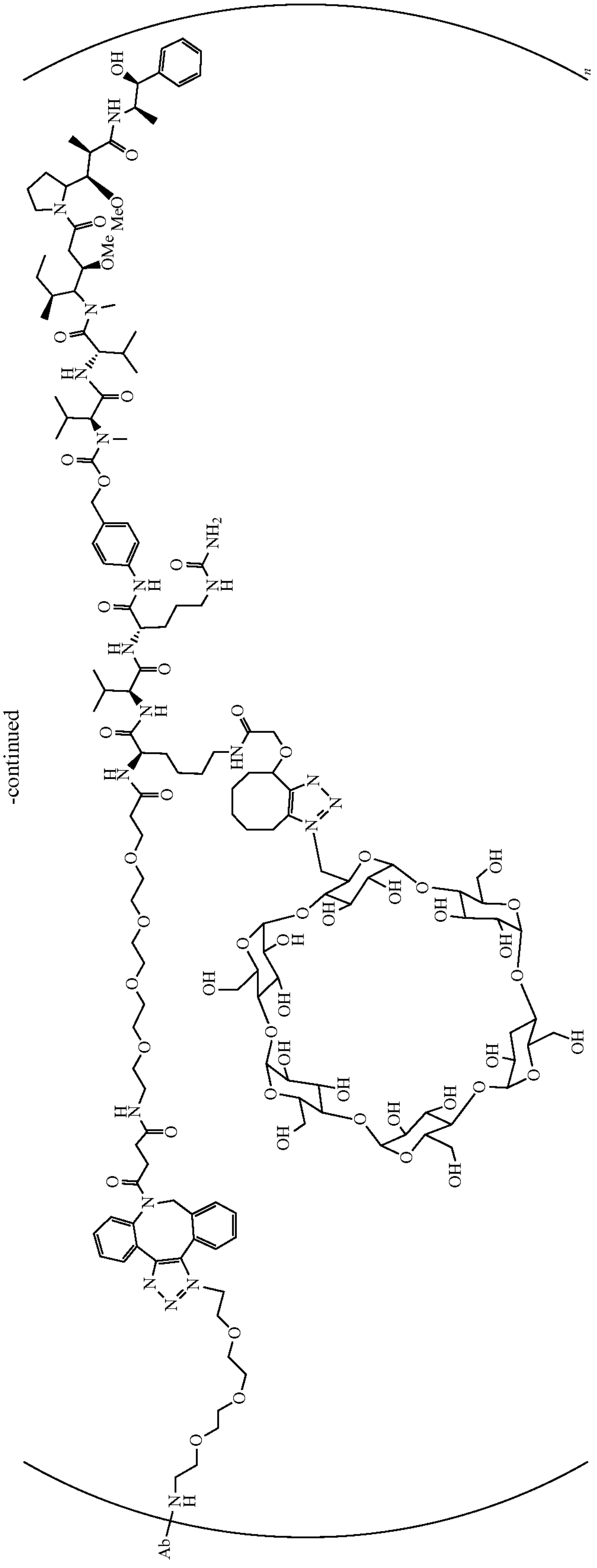

-continued
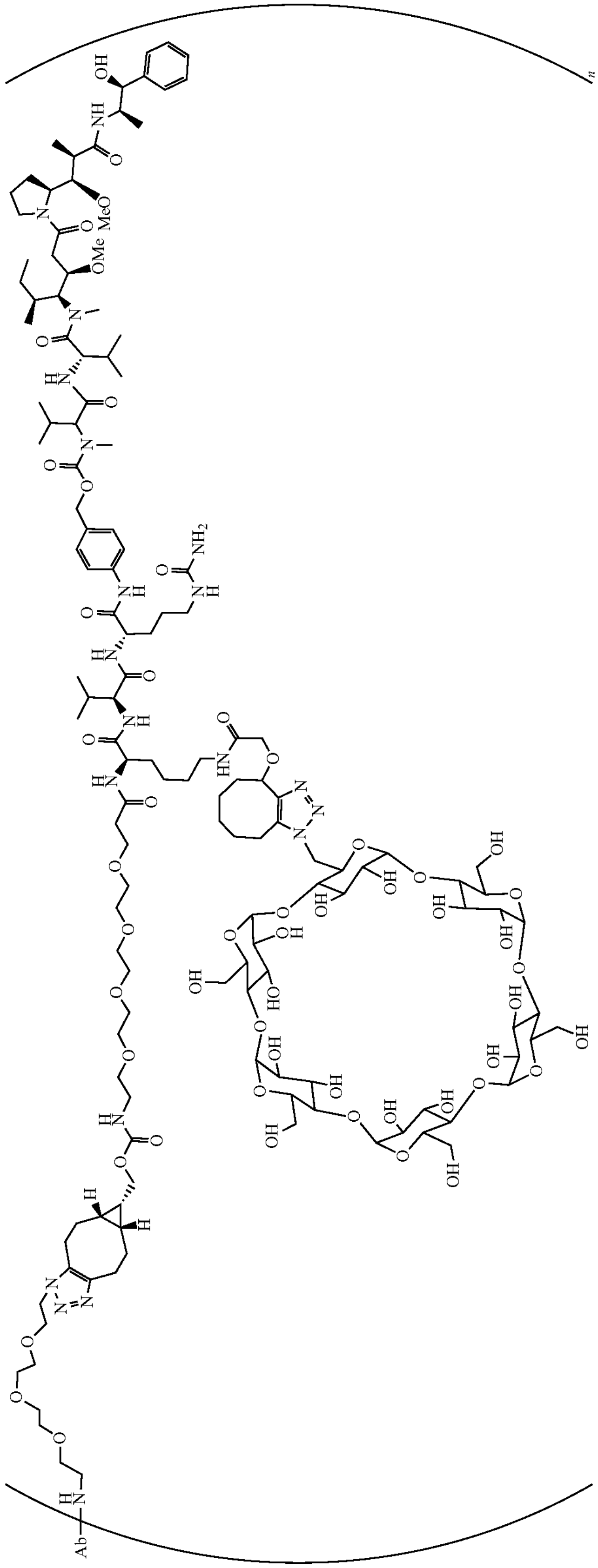

-continued
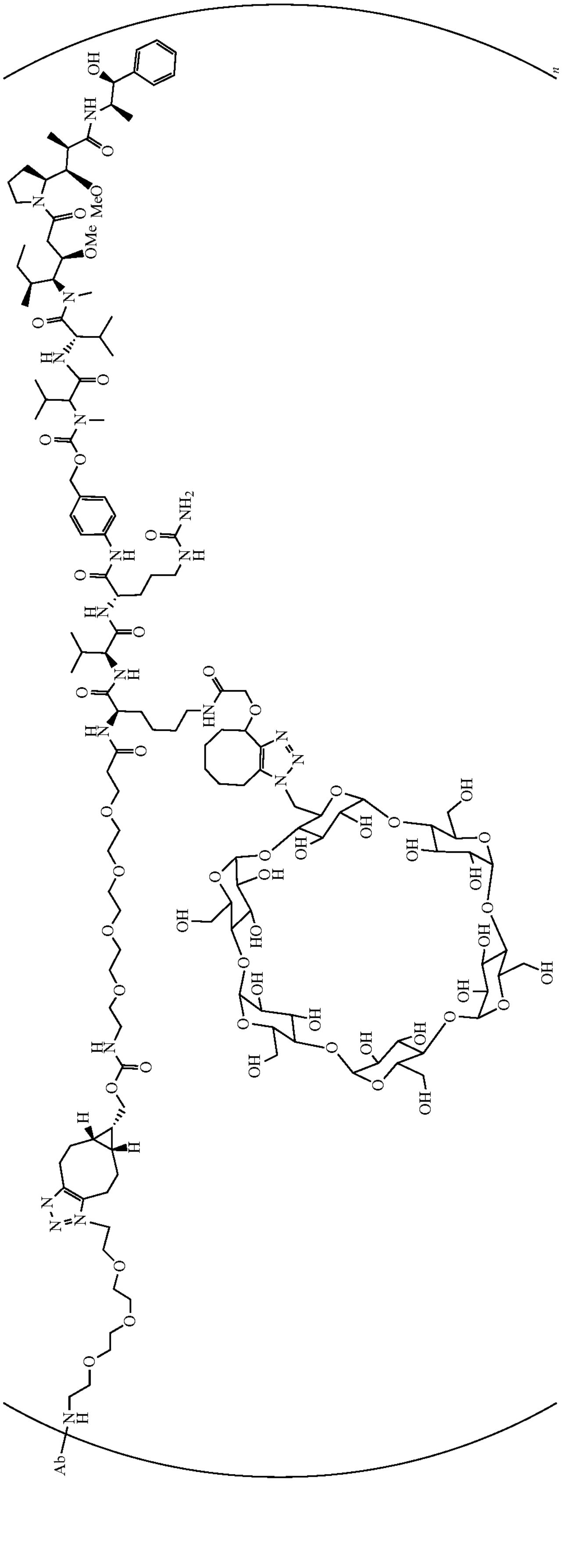

-continued
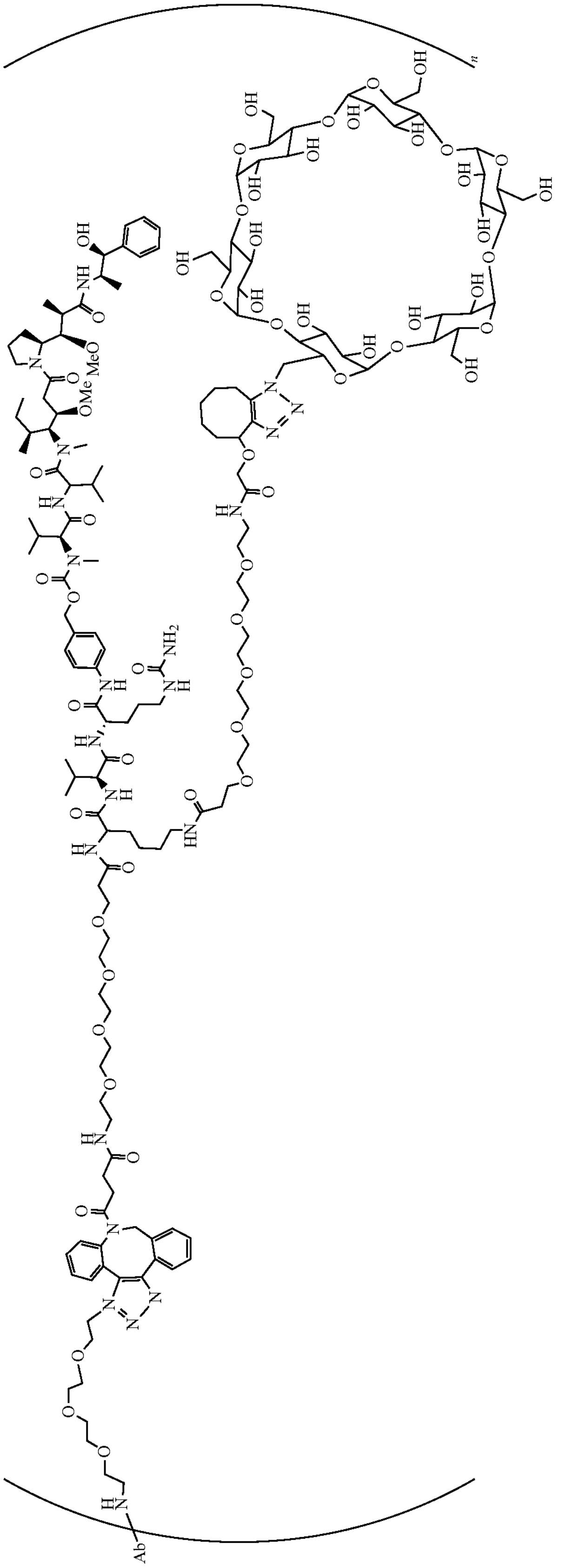

-continued
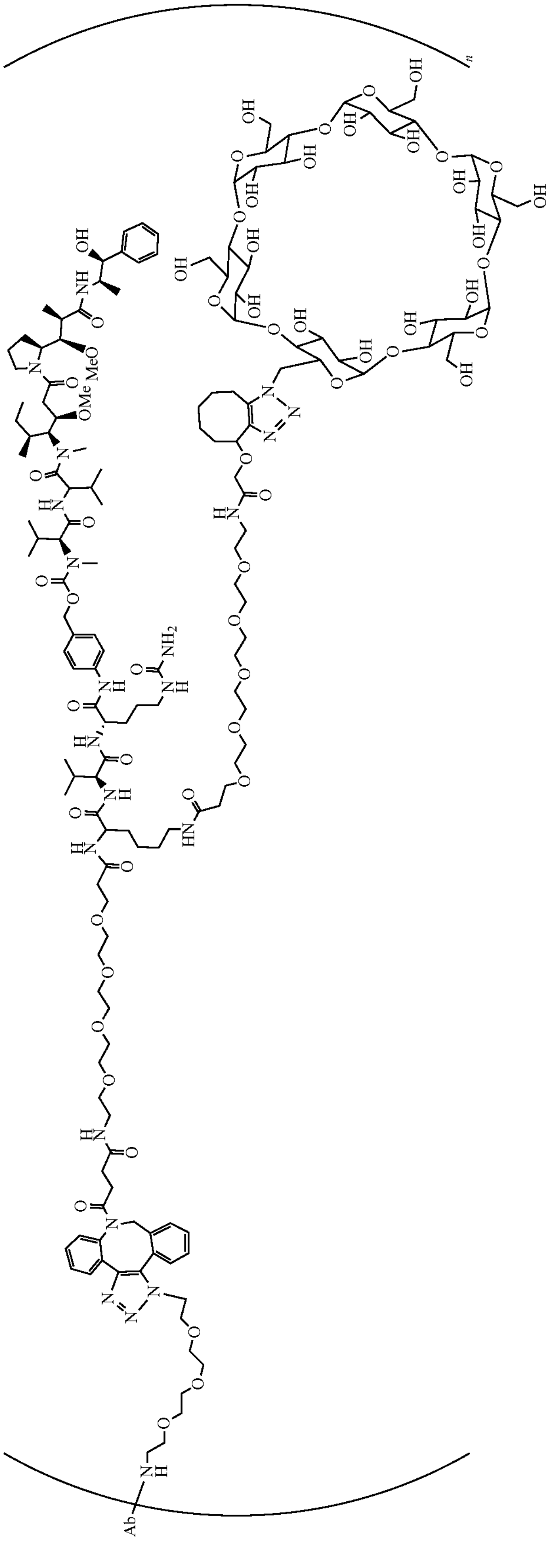

-continued
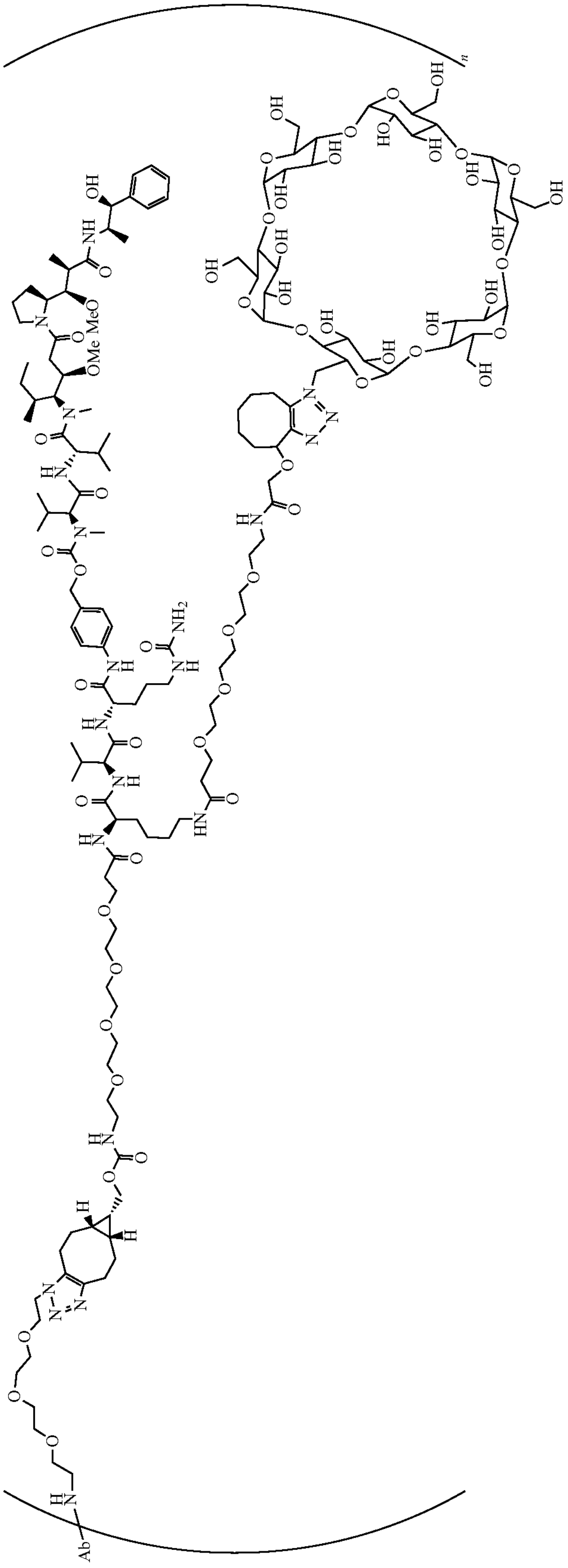

-continued
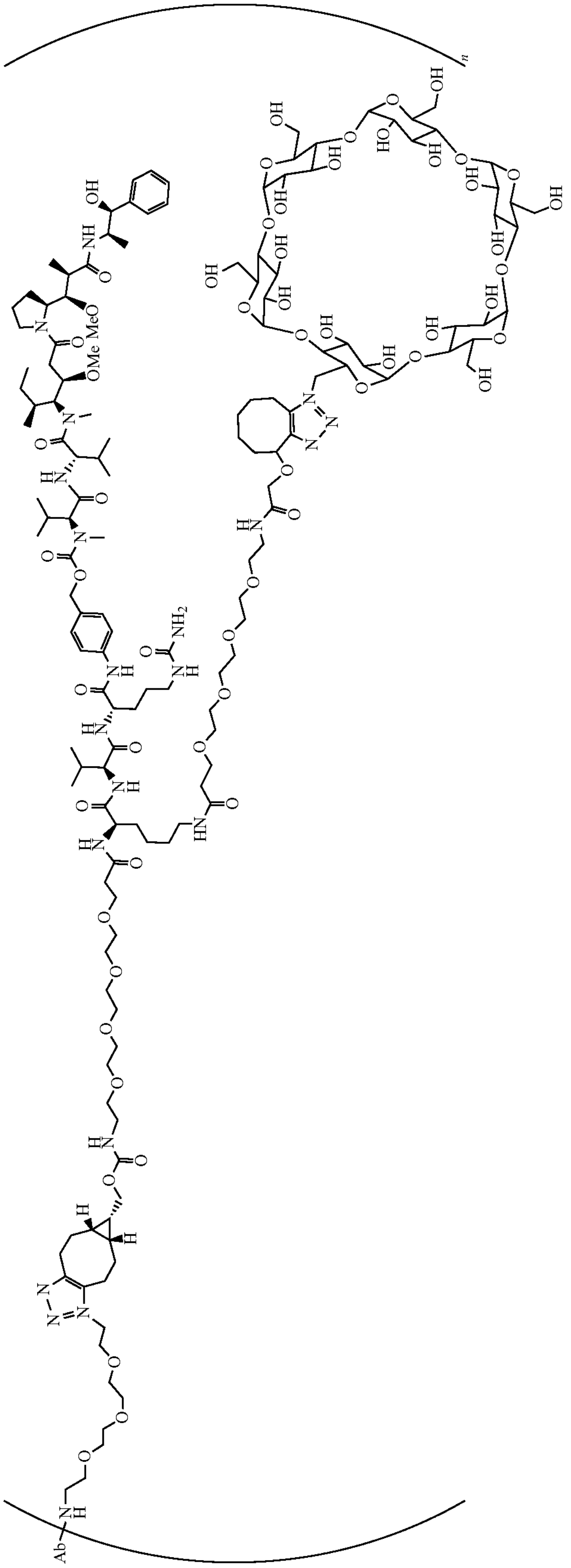

-continued
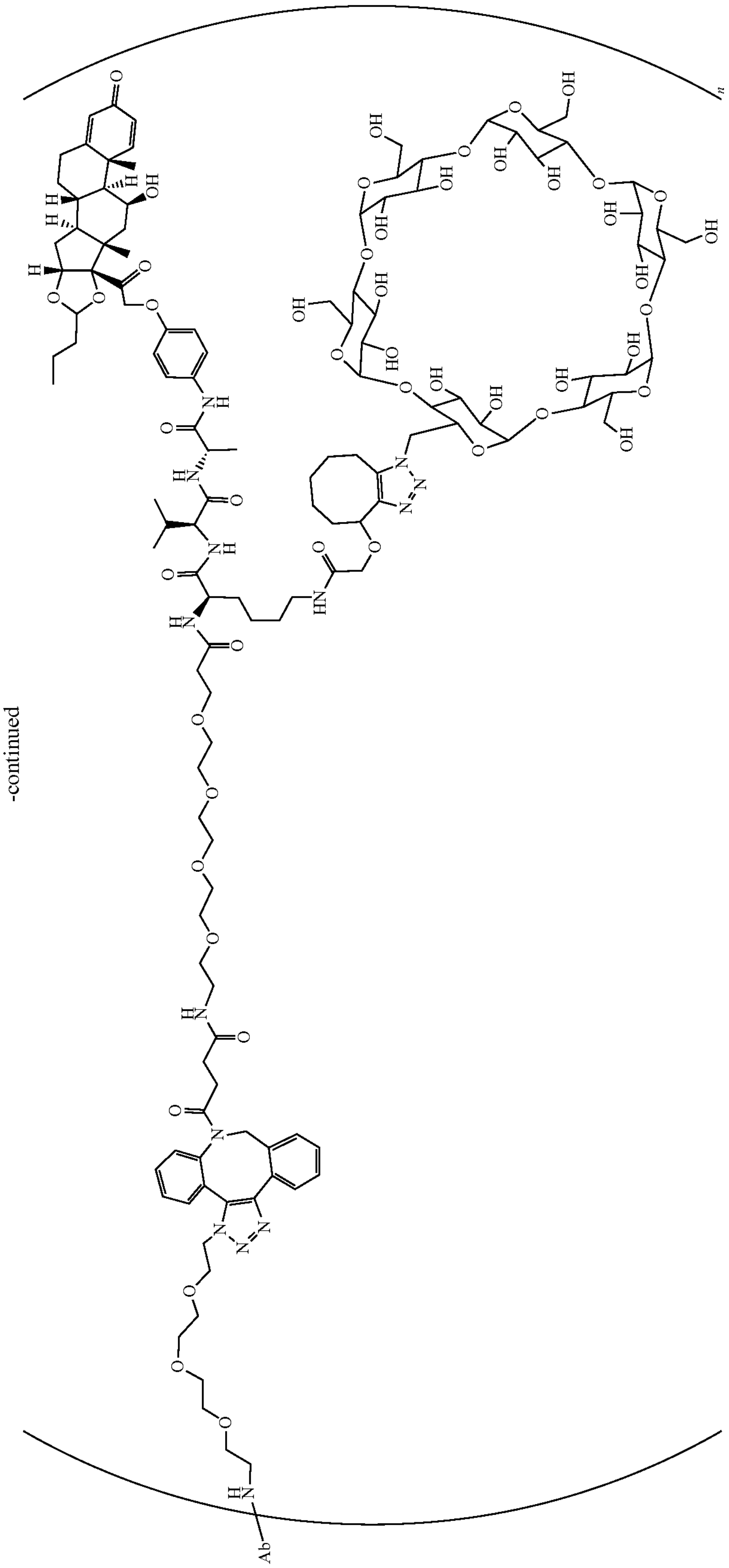

-continued
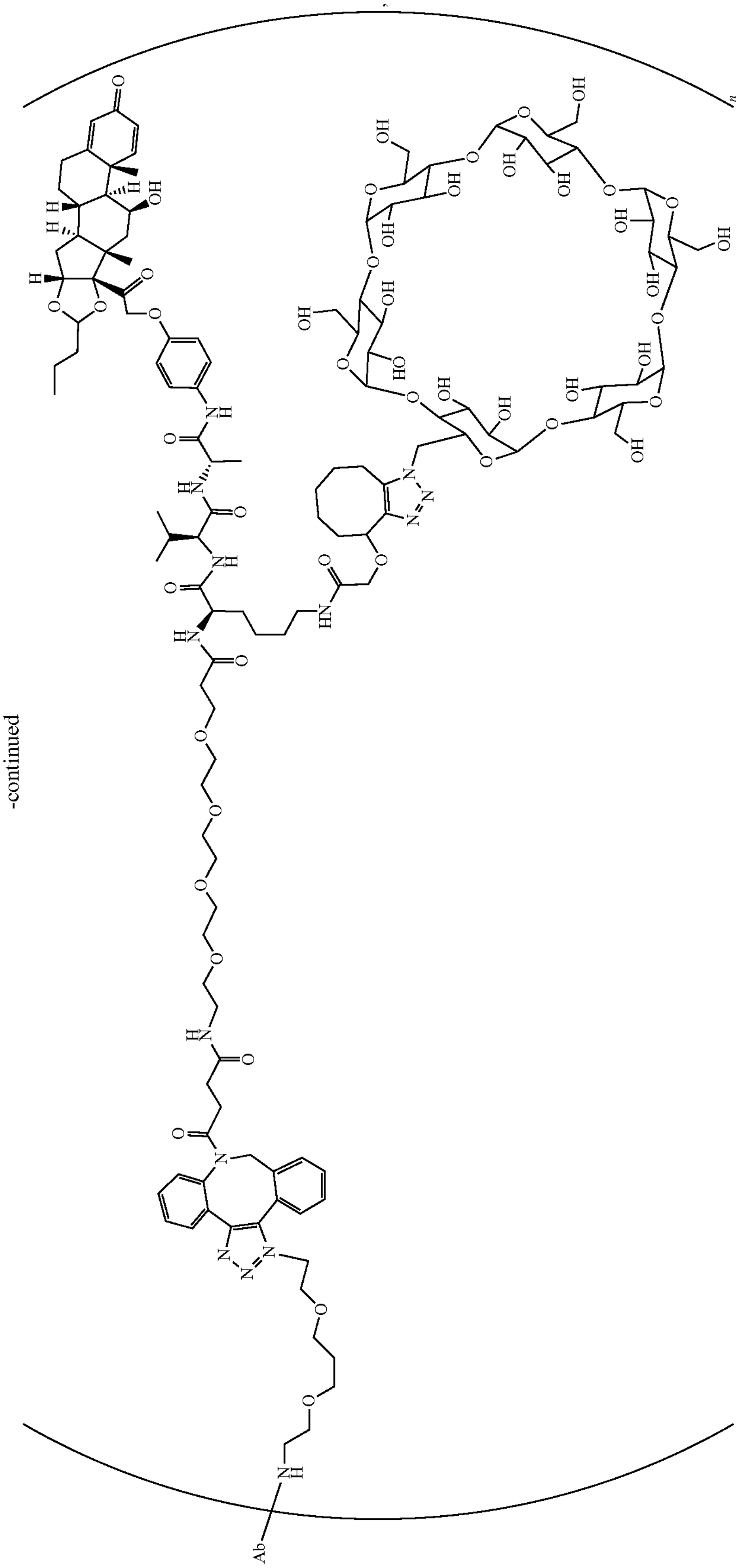

-continued
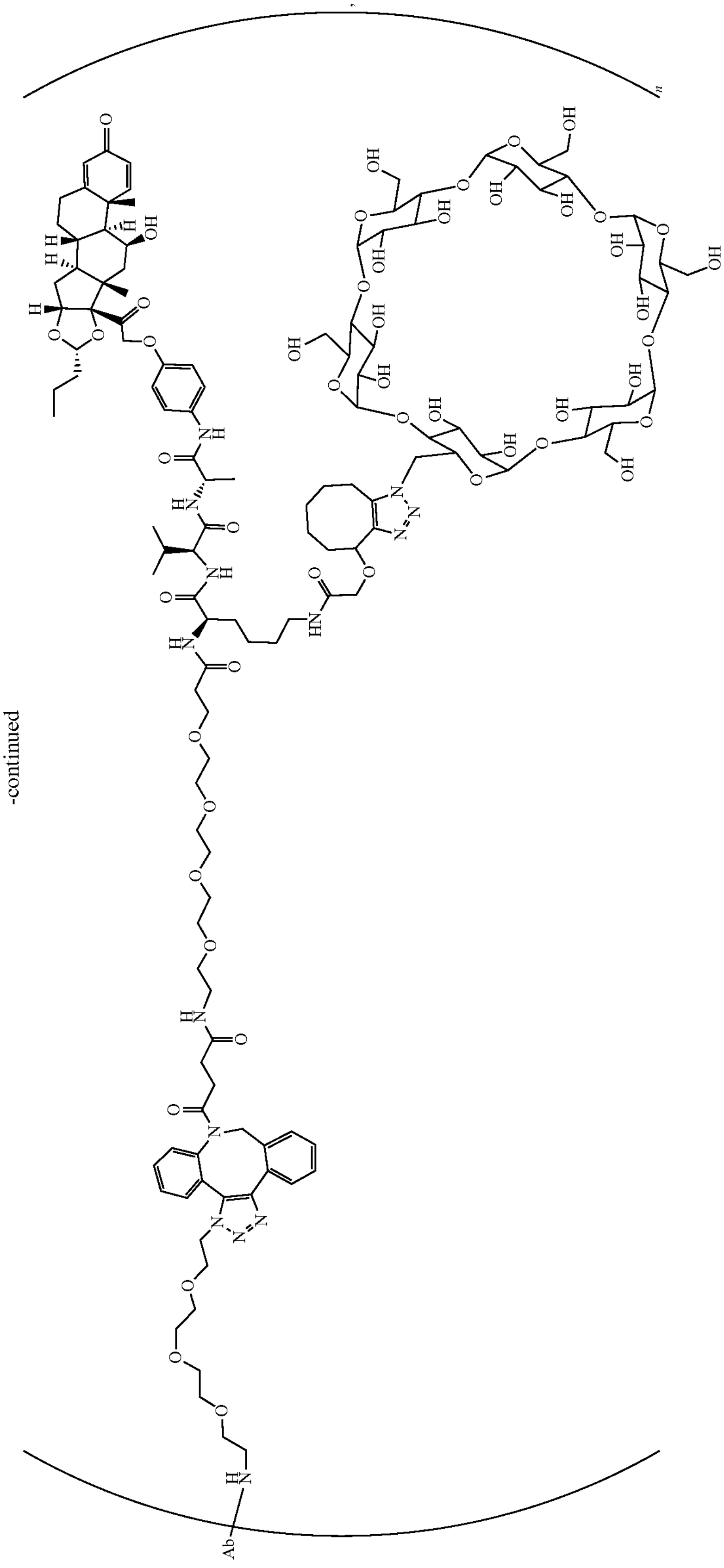

-continued
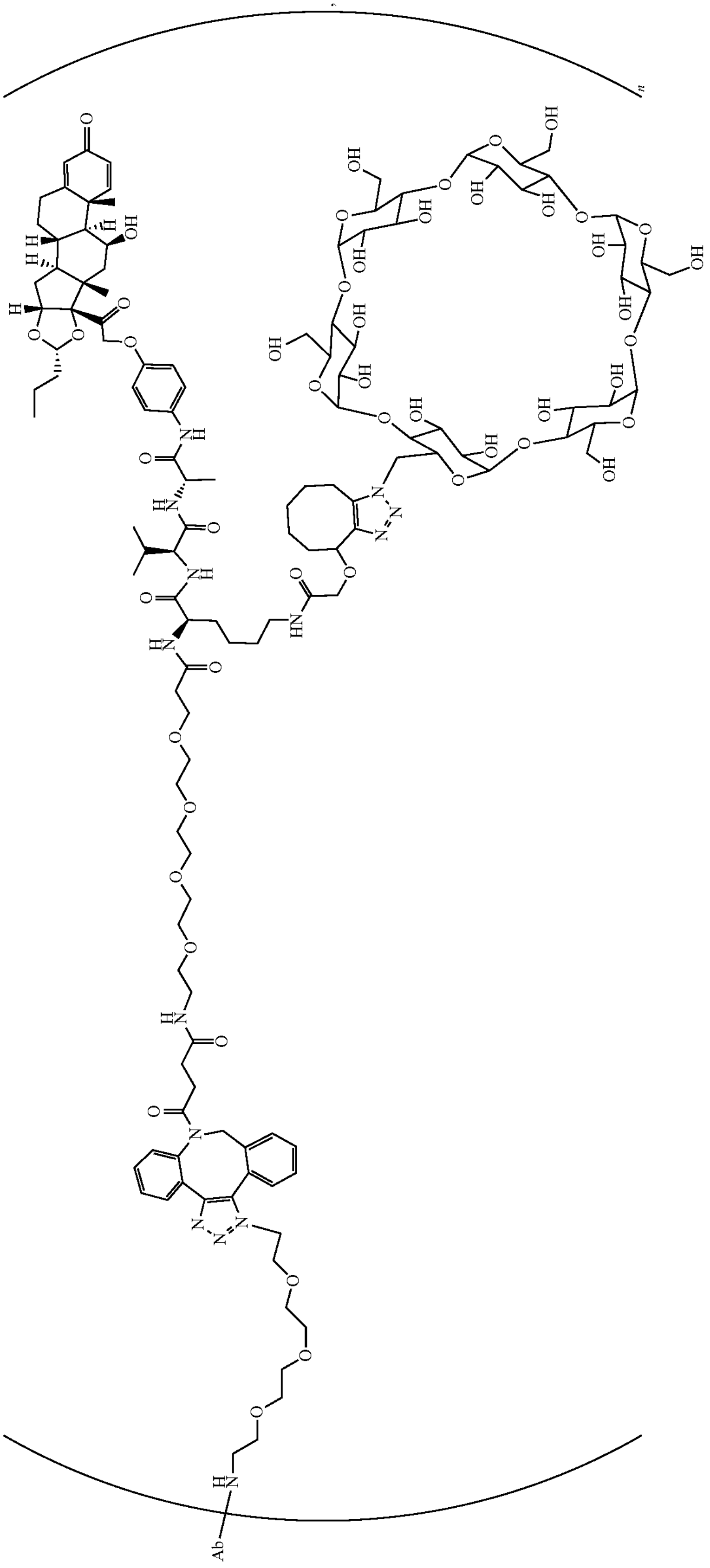

-continued
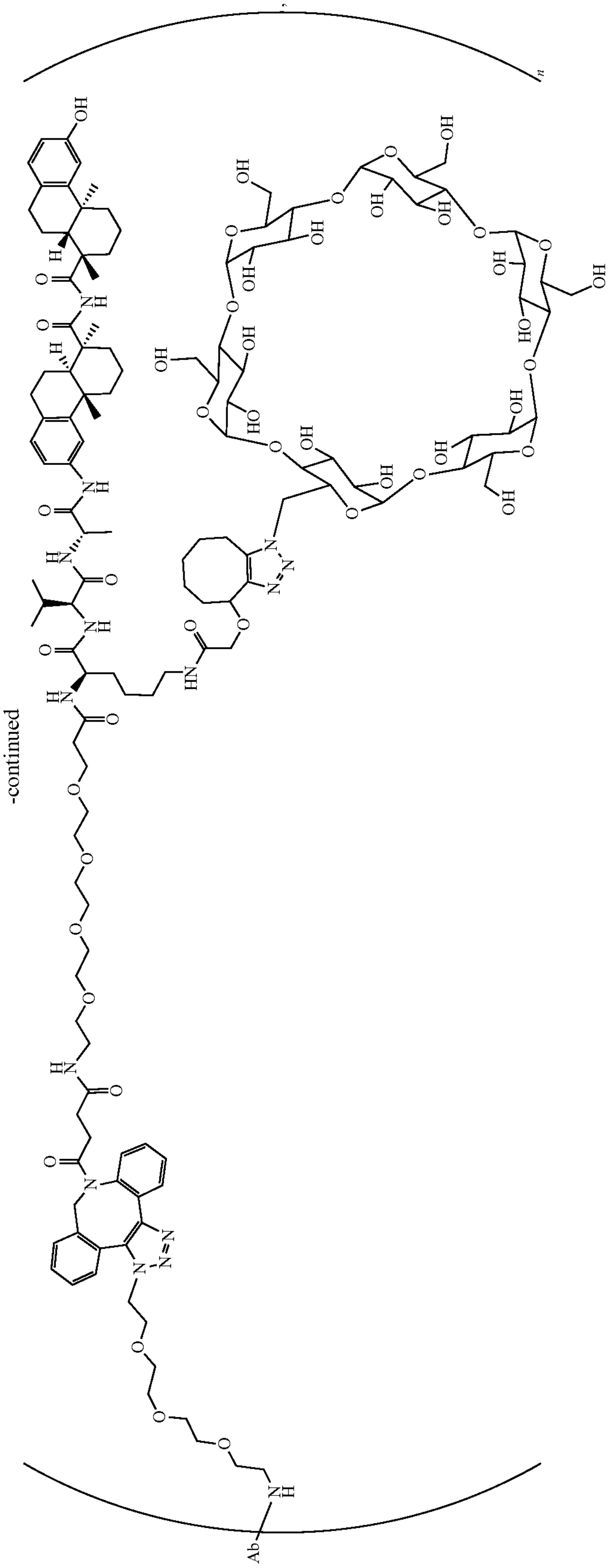

-continued
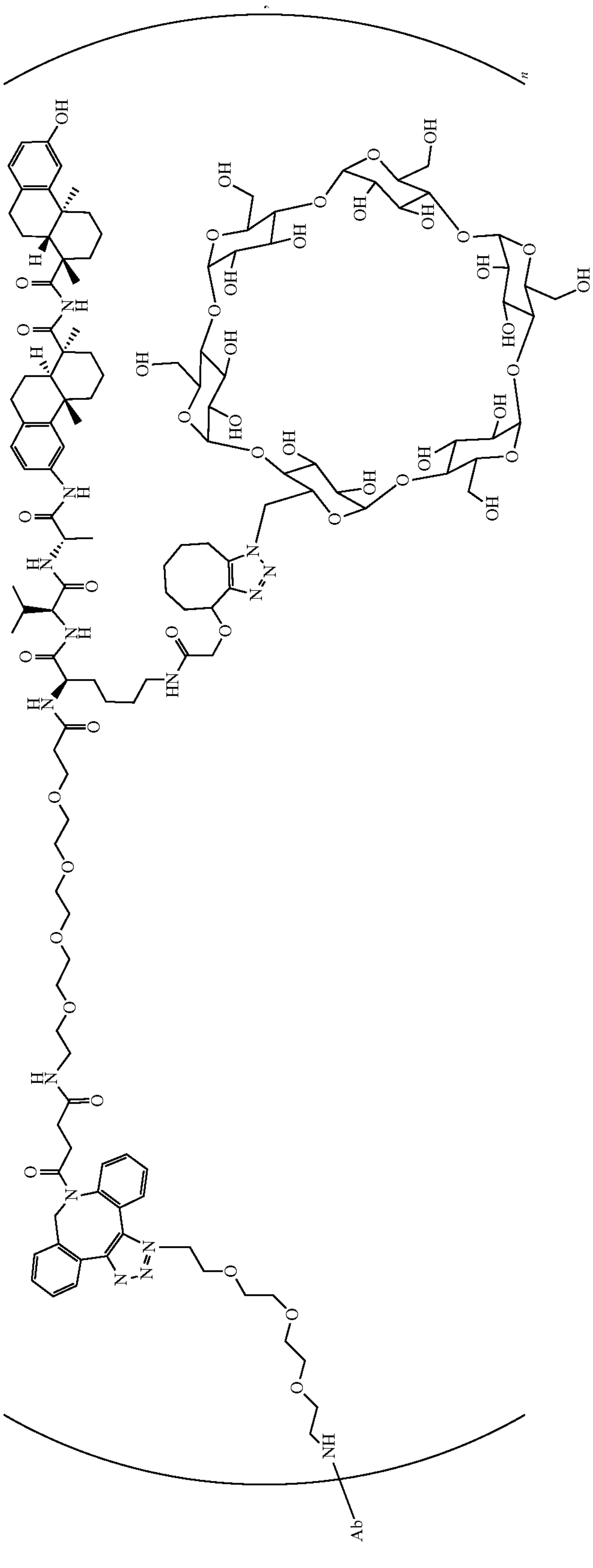

-continued
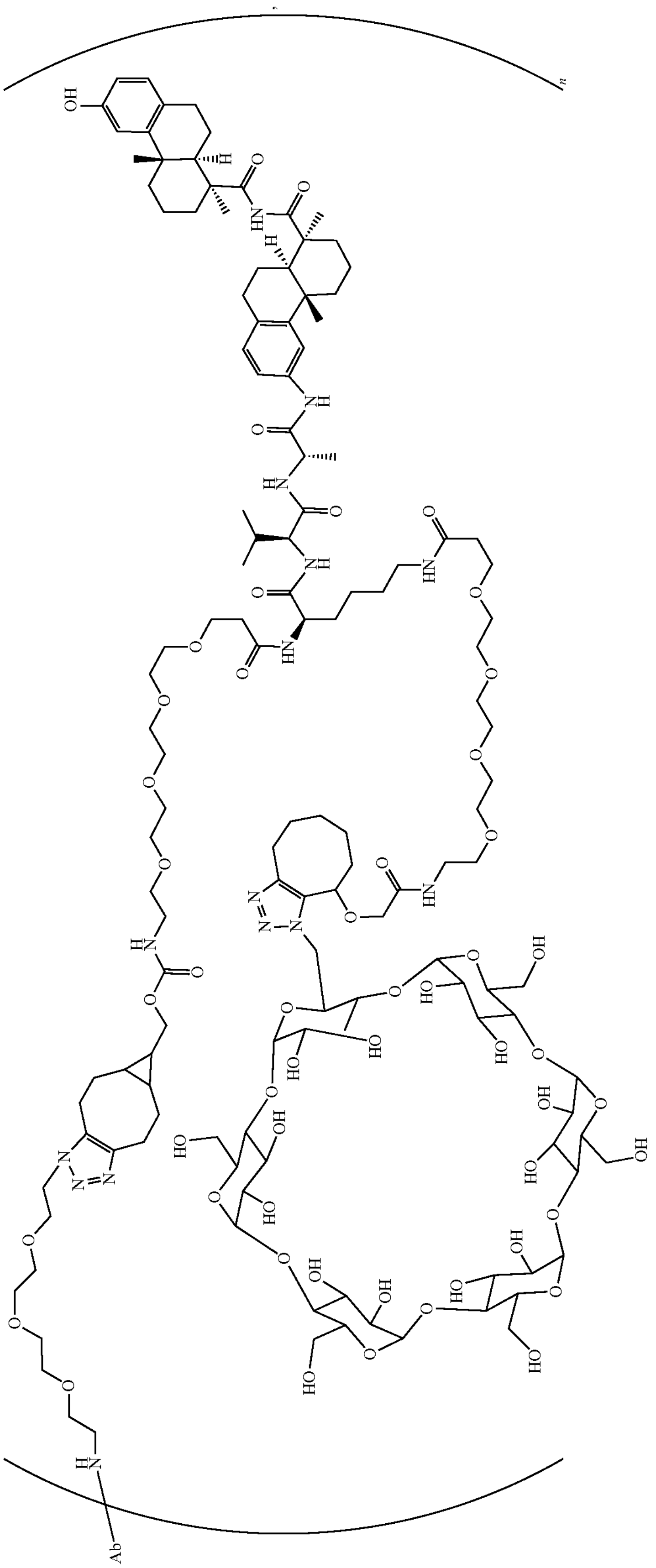

-continued
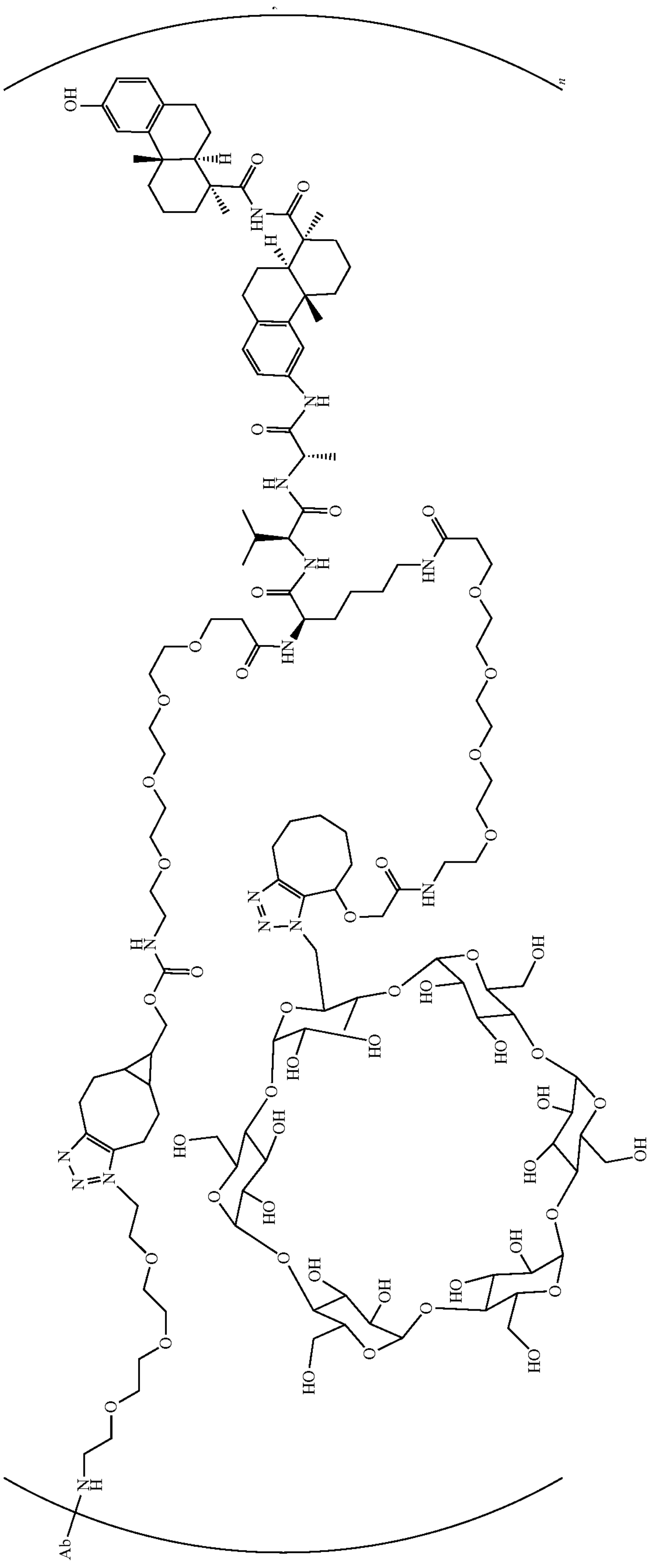

-continued
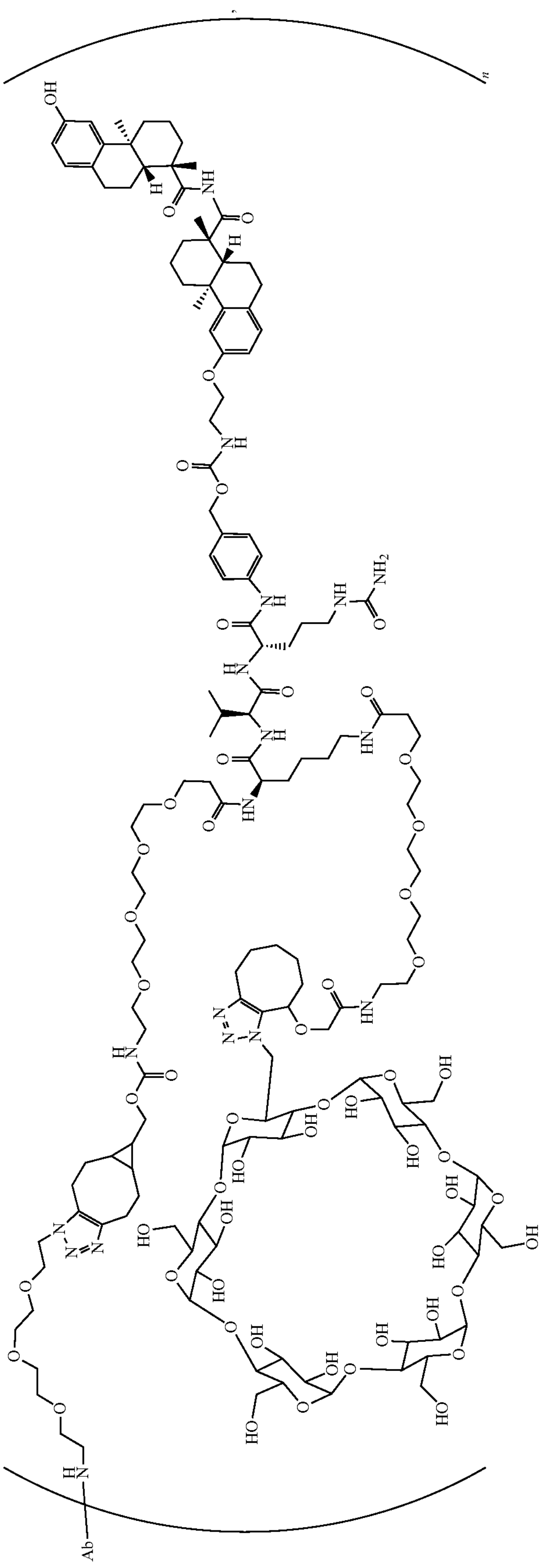

-continued
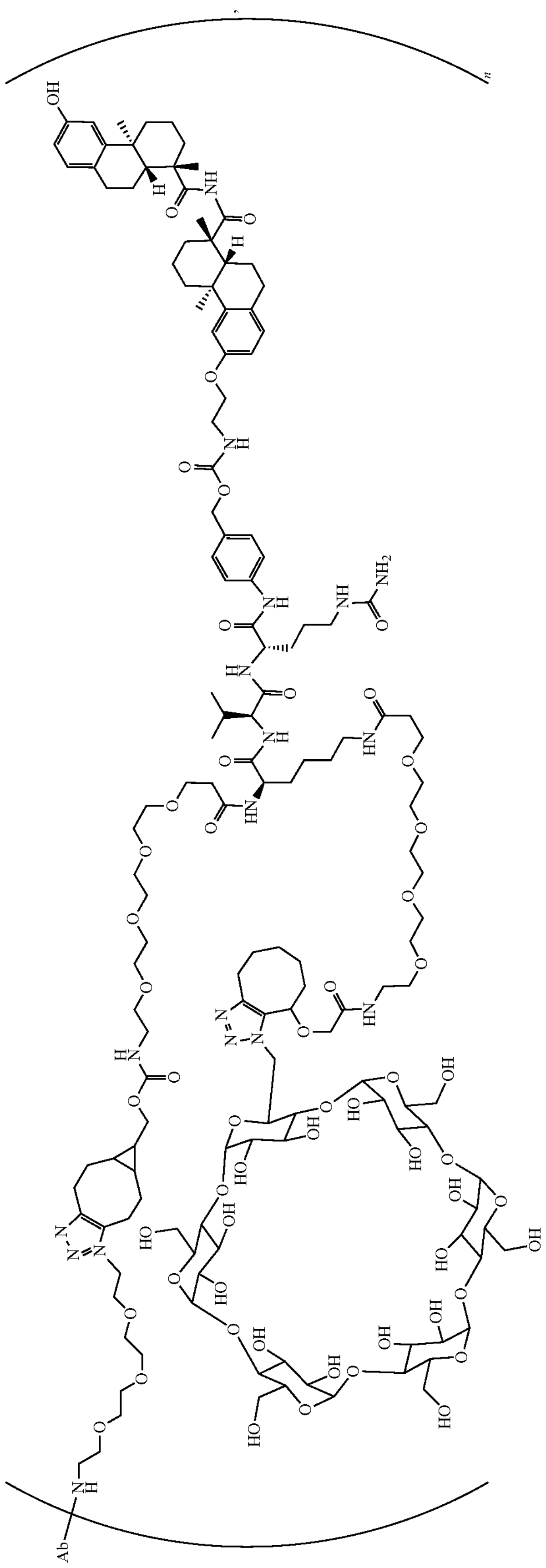

-continued
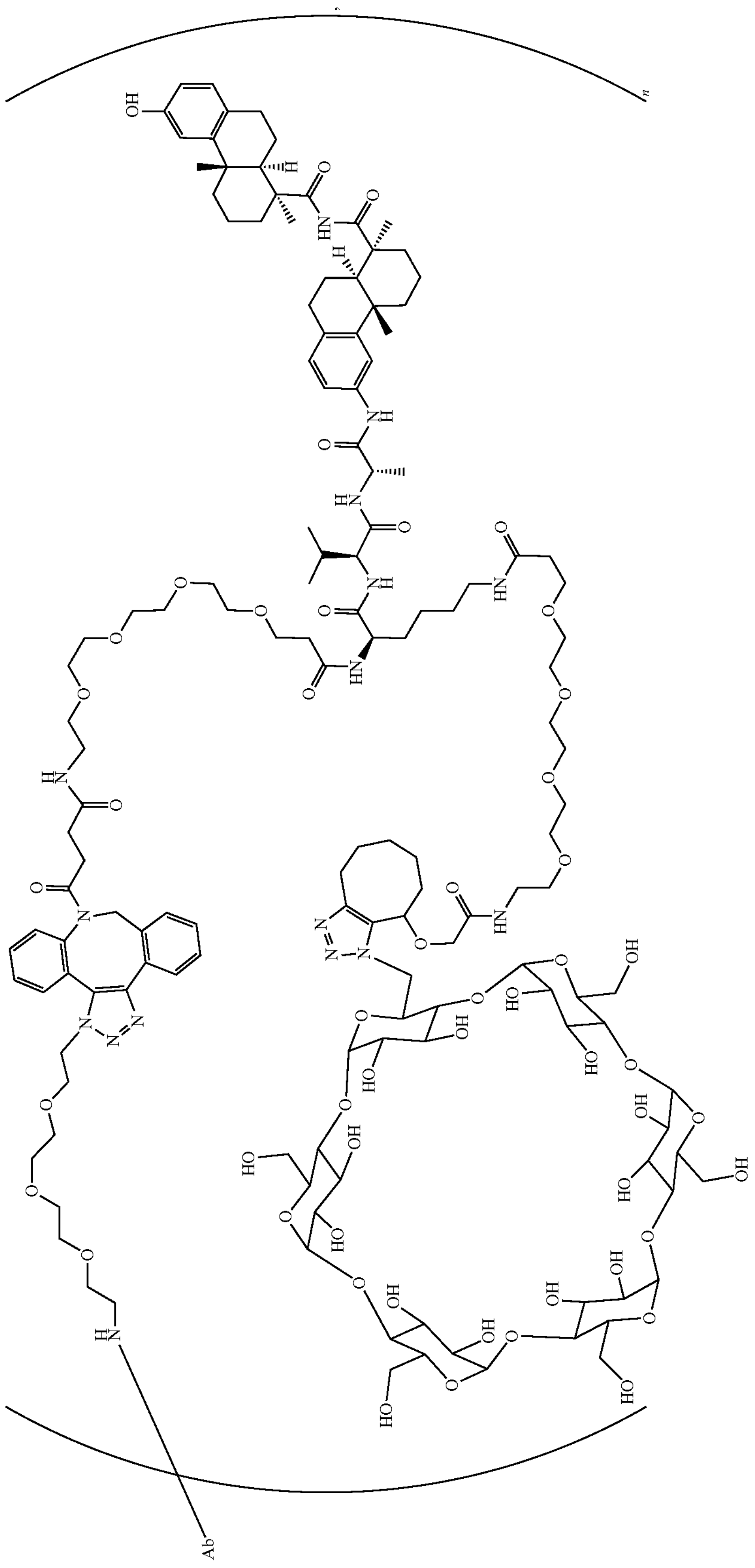

-continued
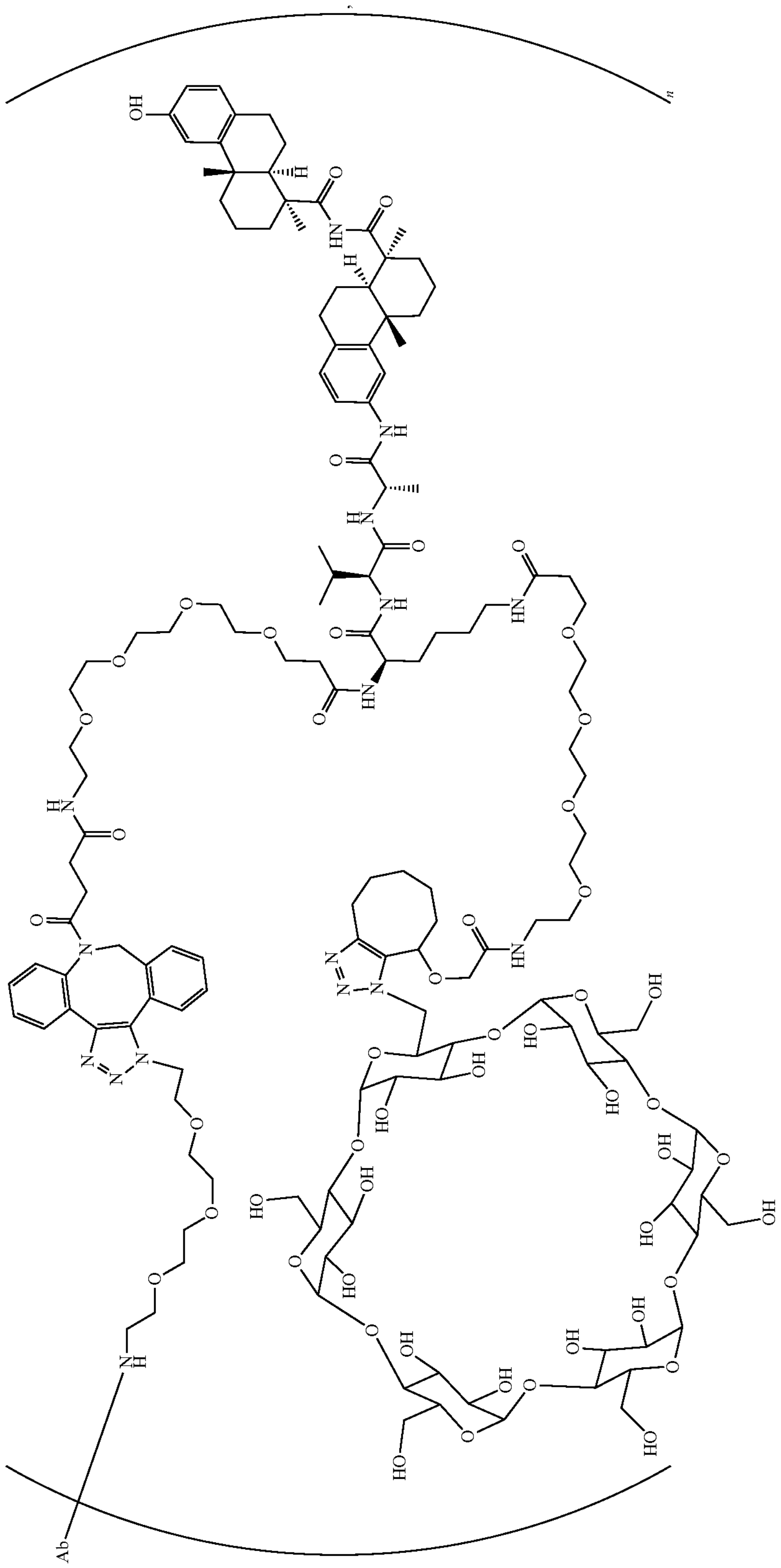

-continued
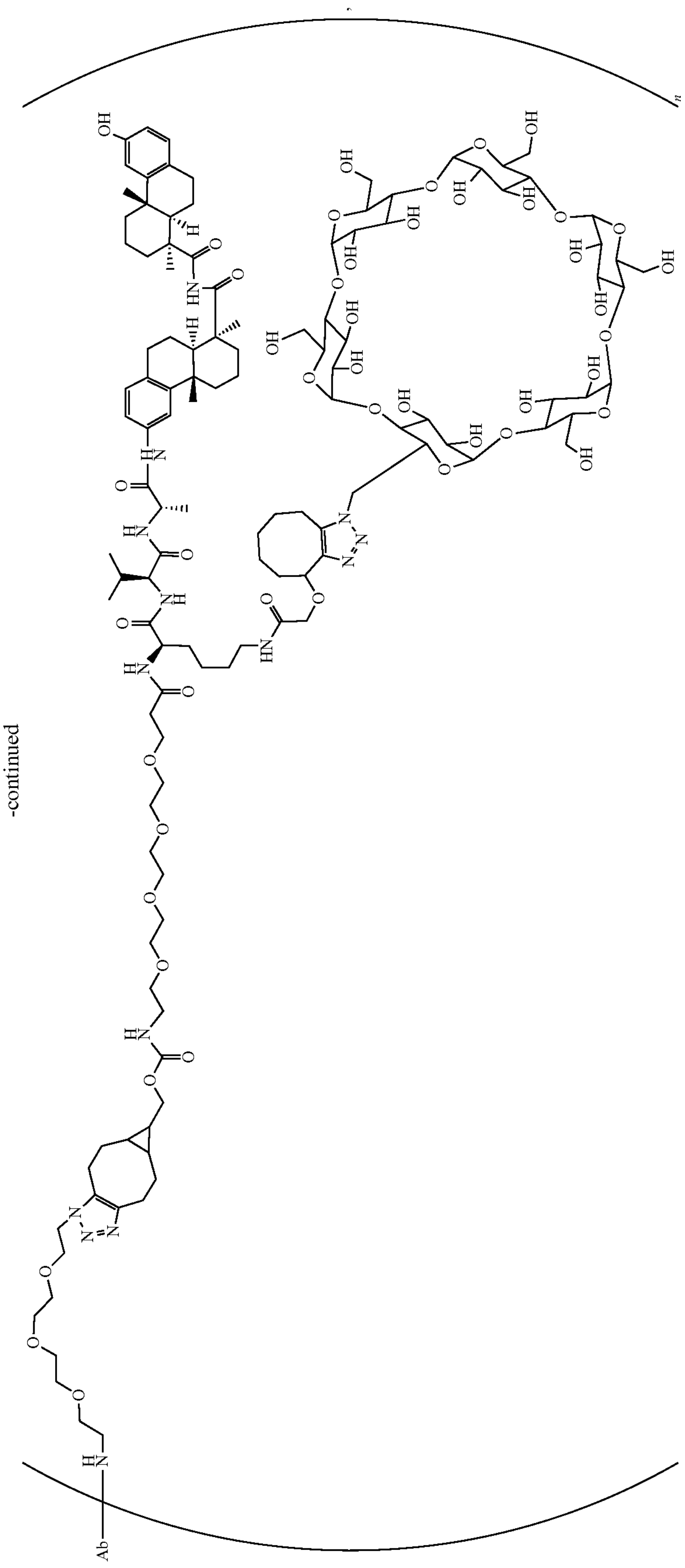

-continued
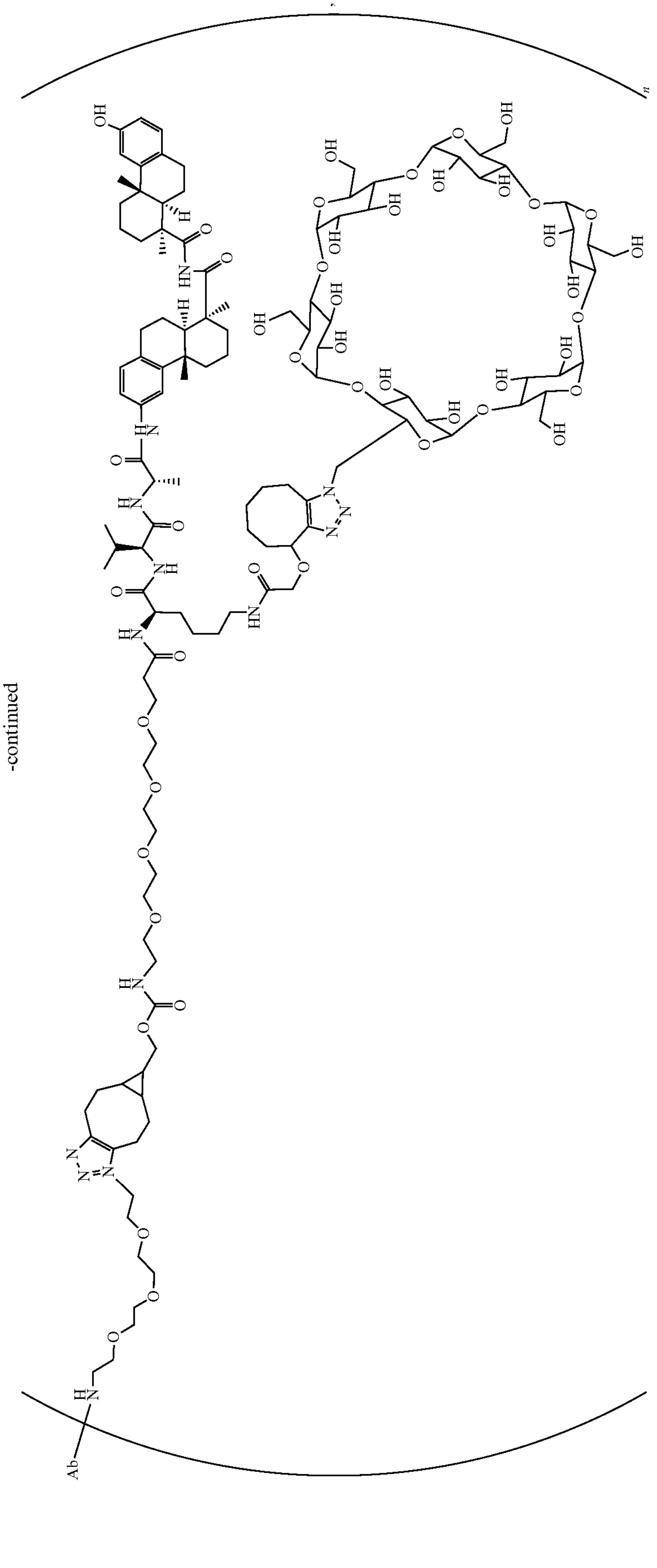

-continued
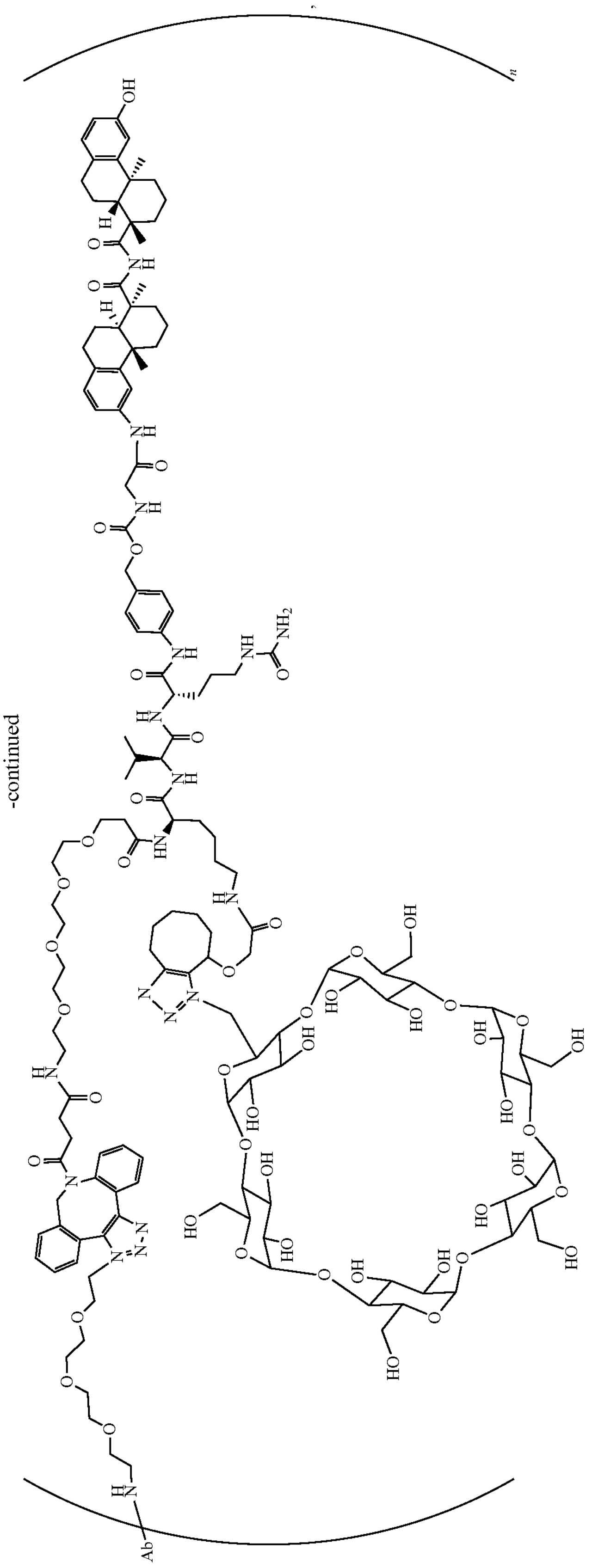

-continued
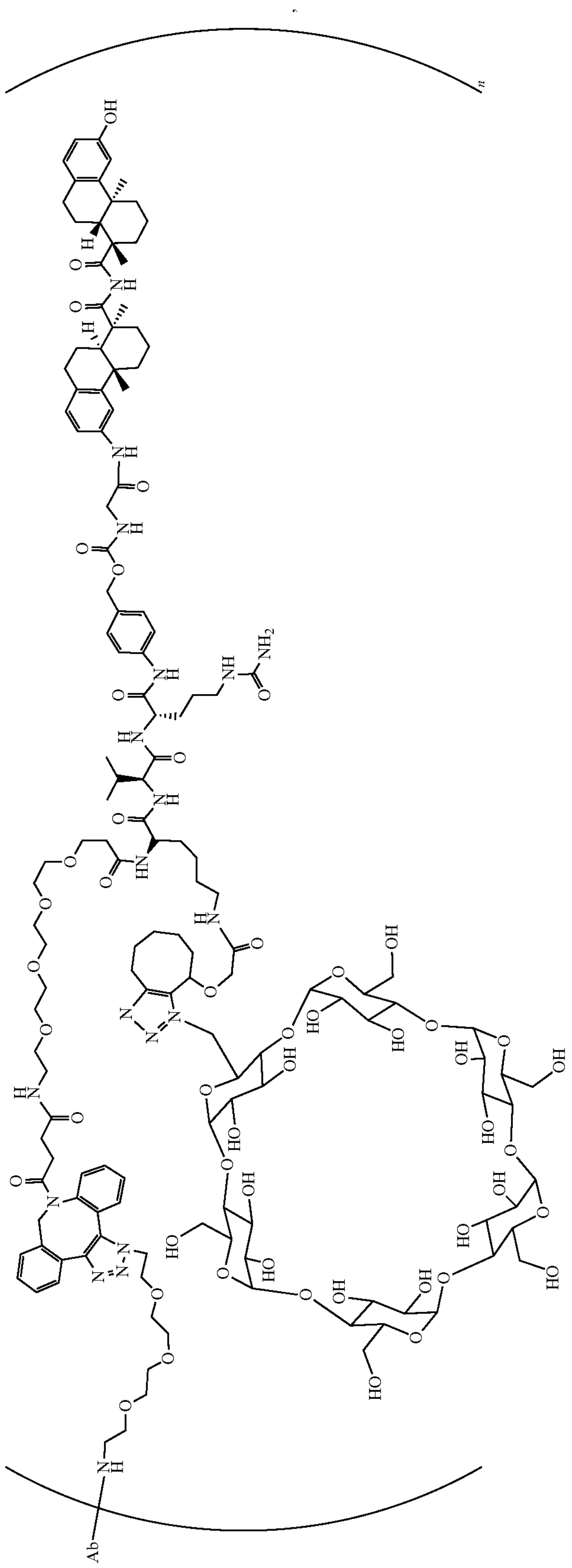

-continued
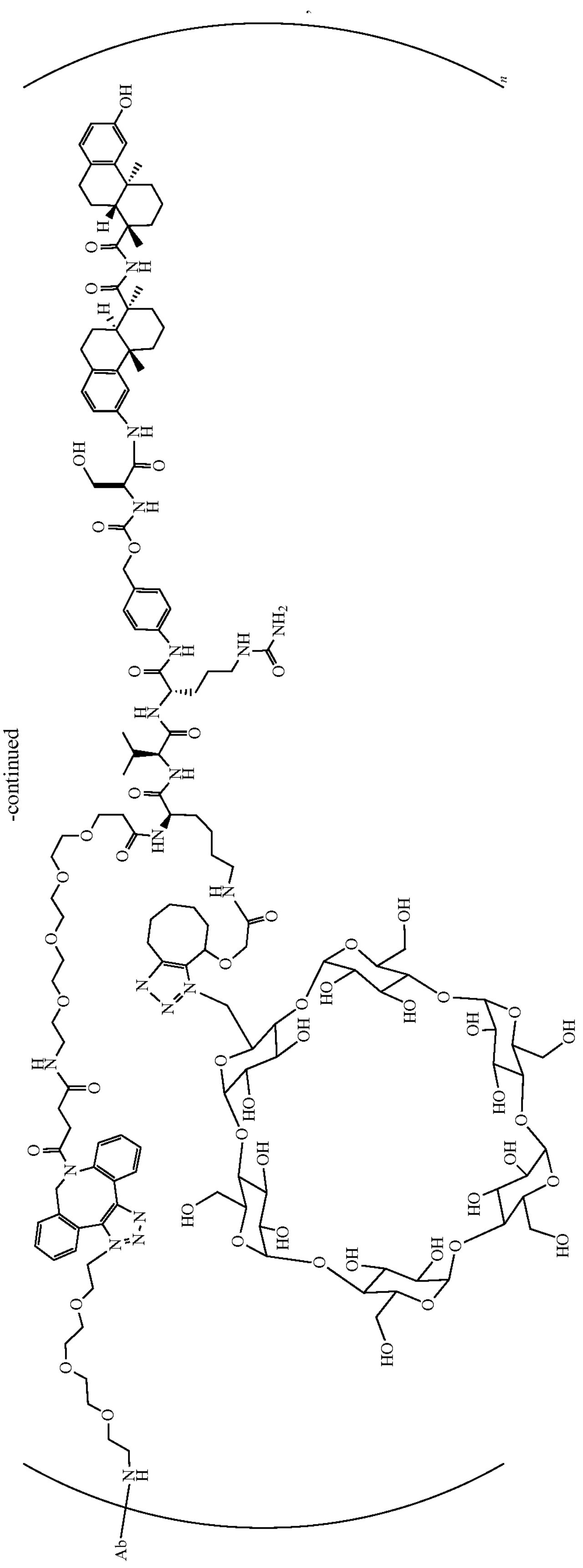

-continued
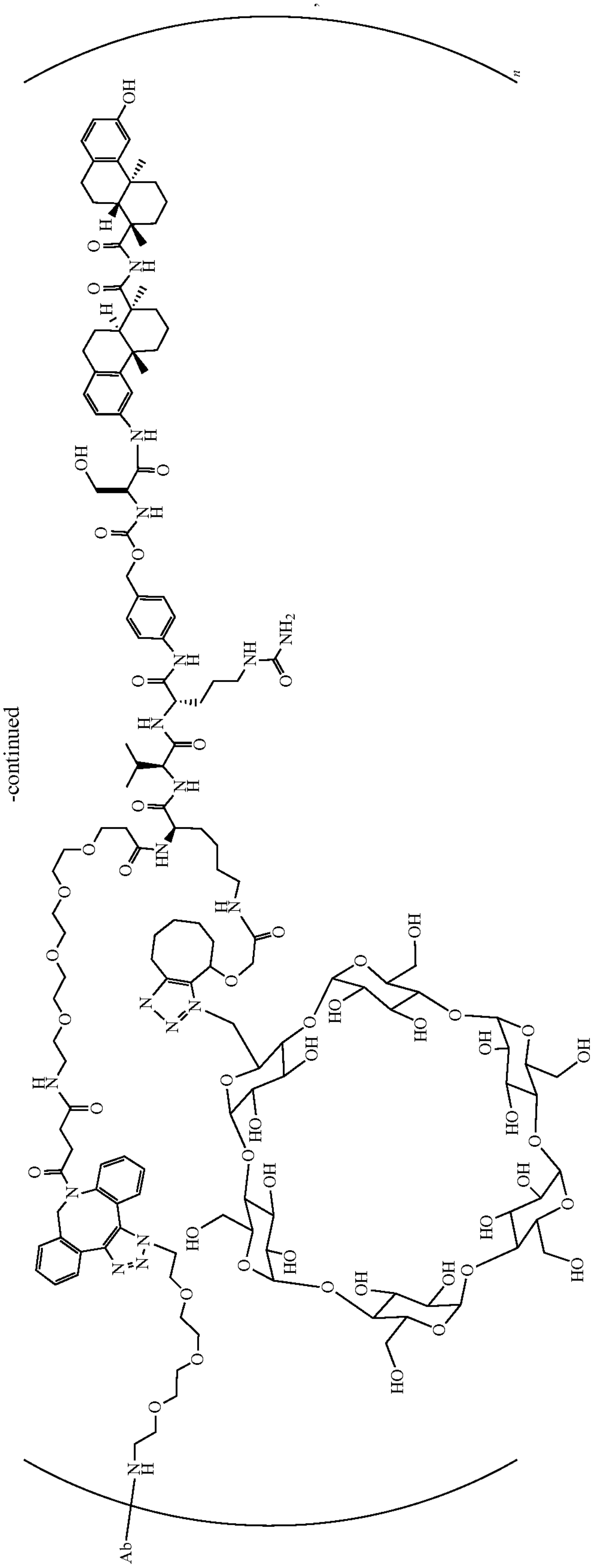

-continued
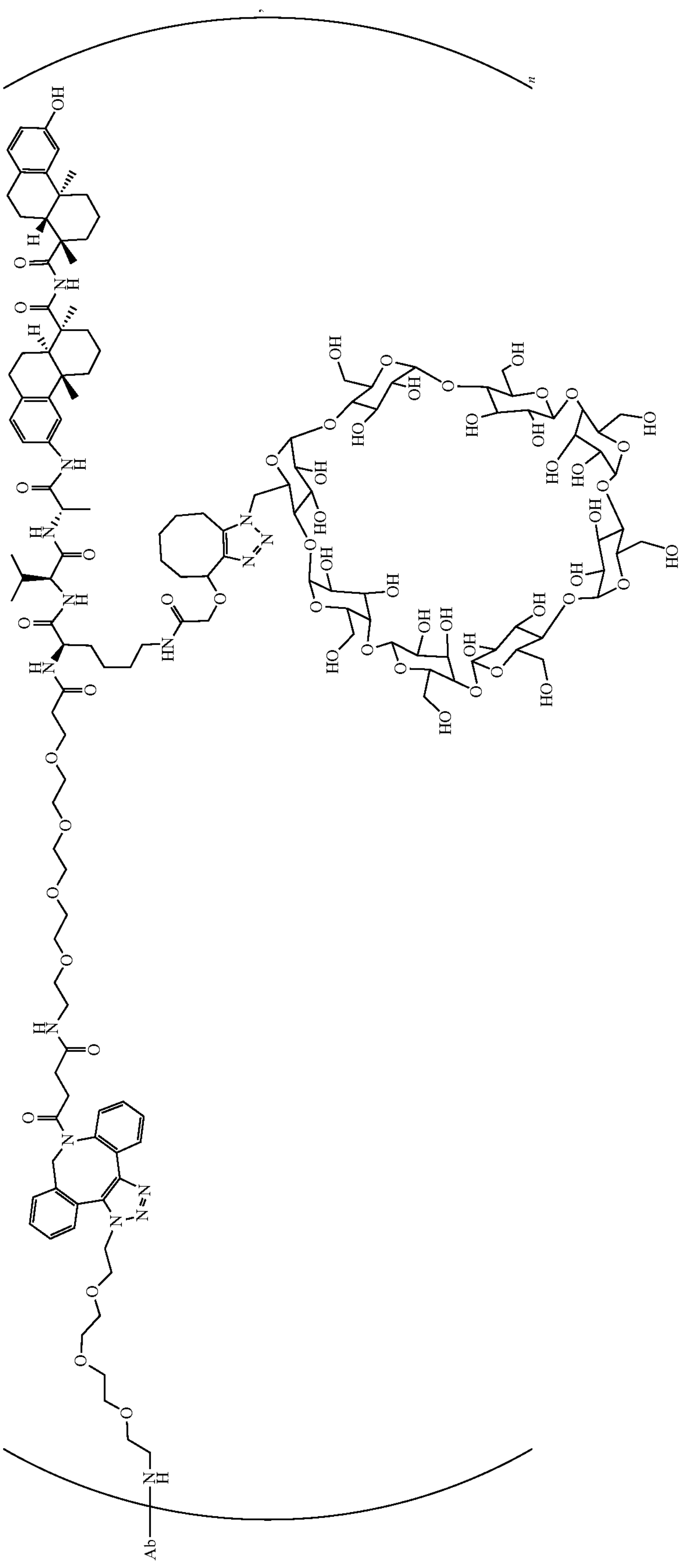

-continued
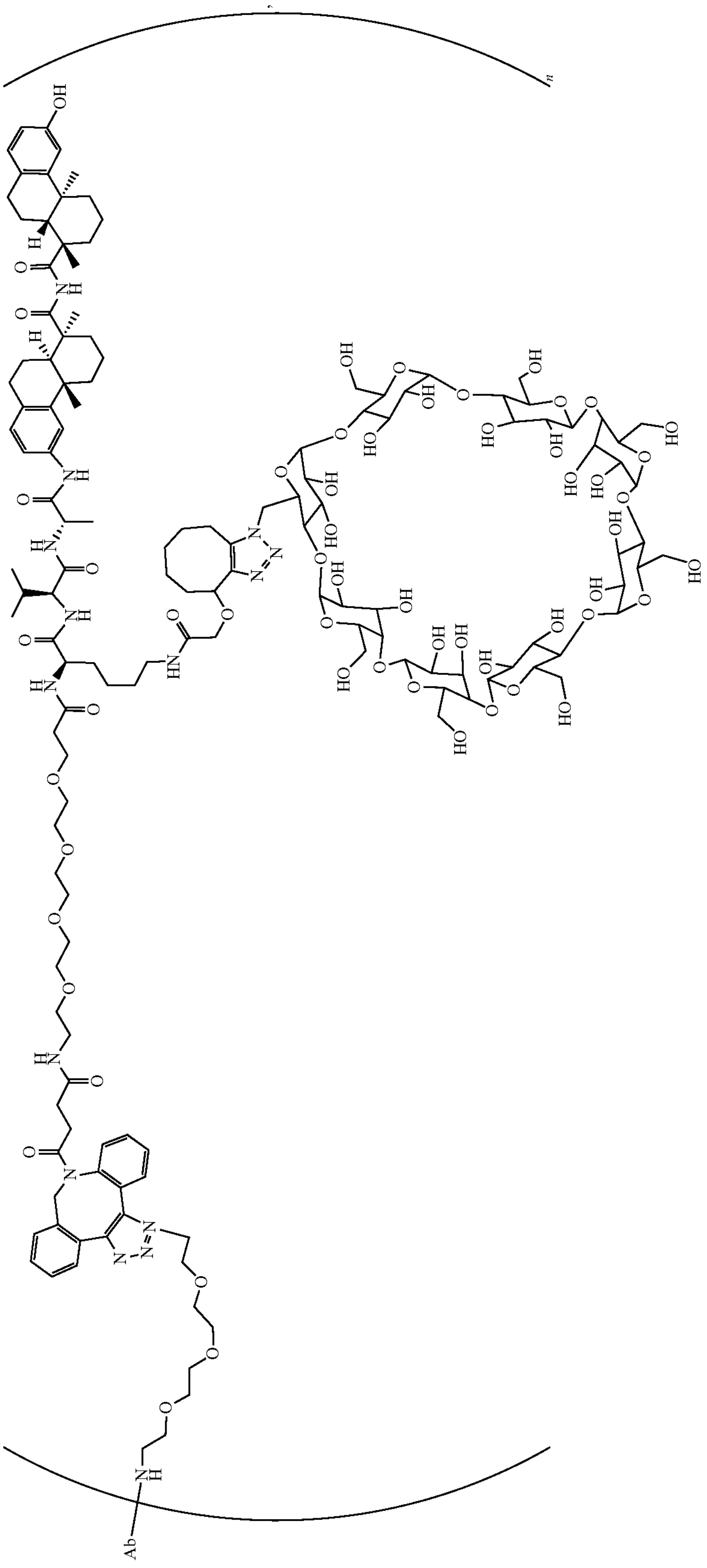

-continued
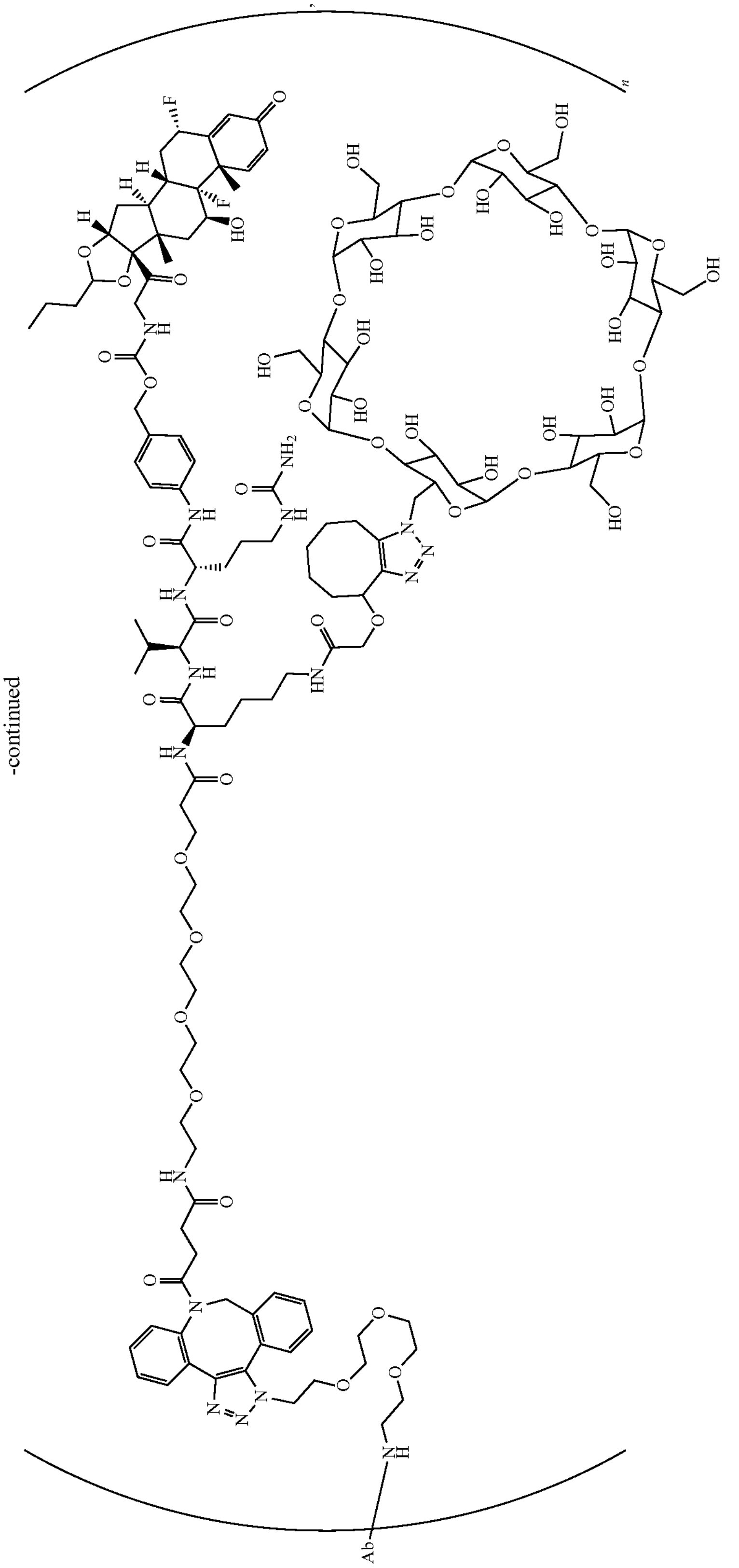

-continued
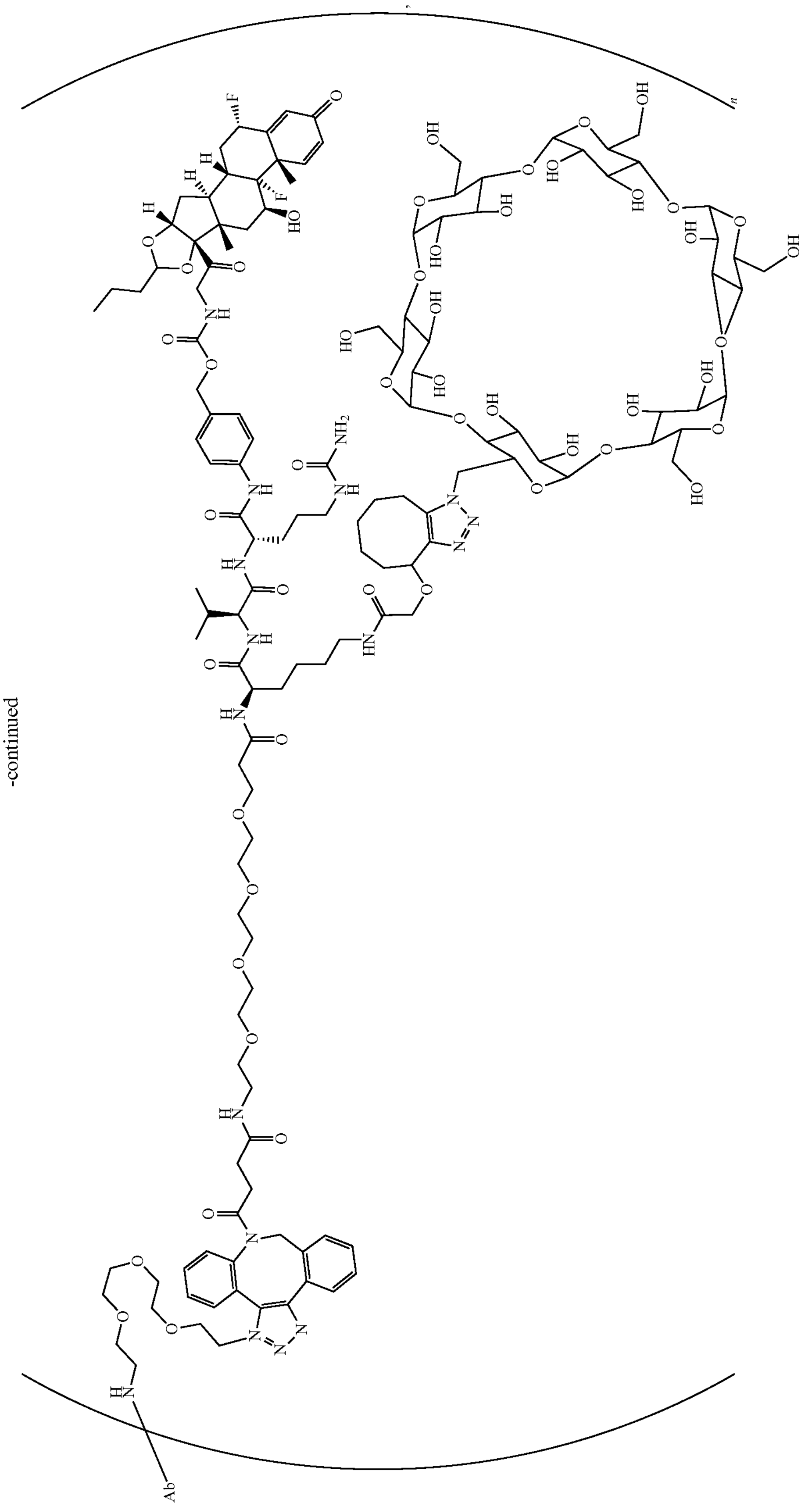

-continued
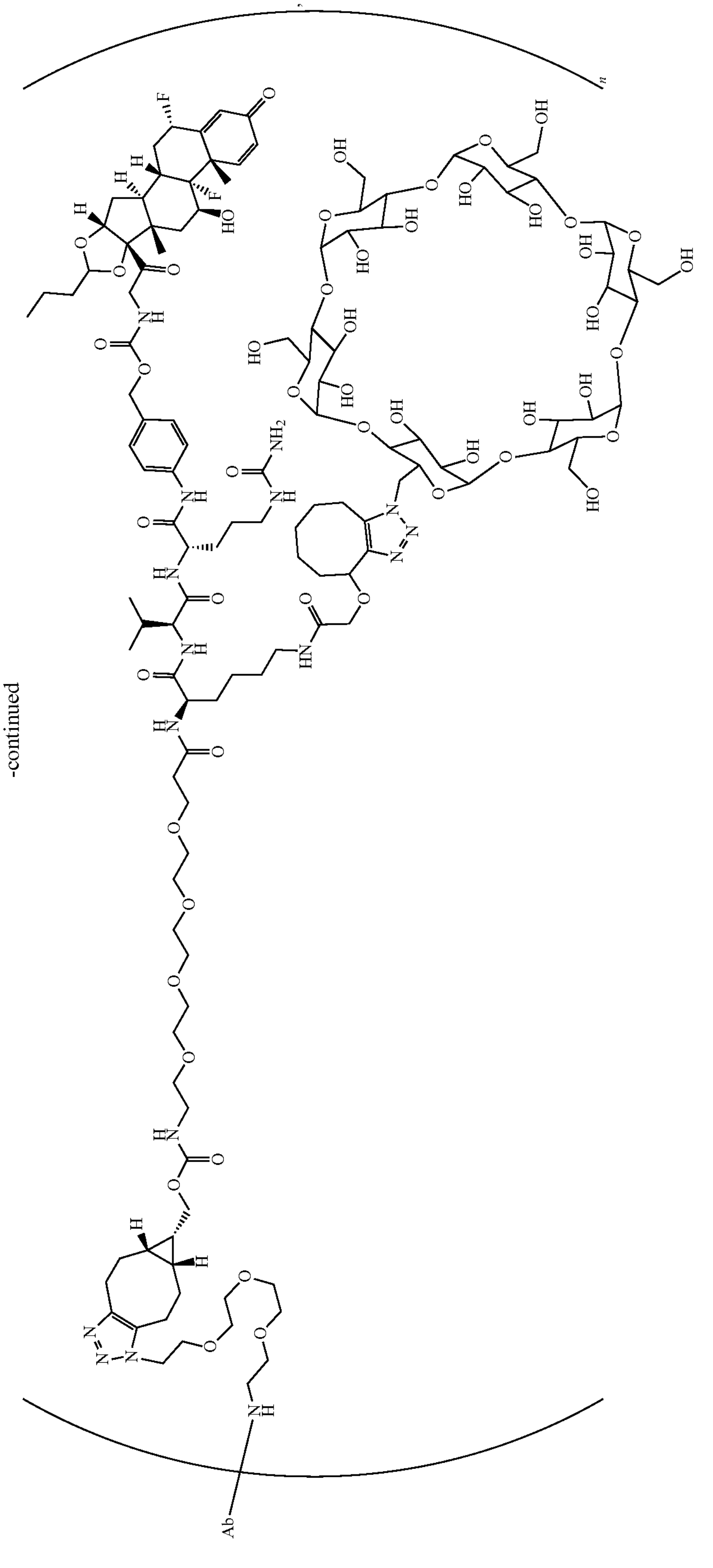

-continued
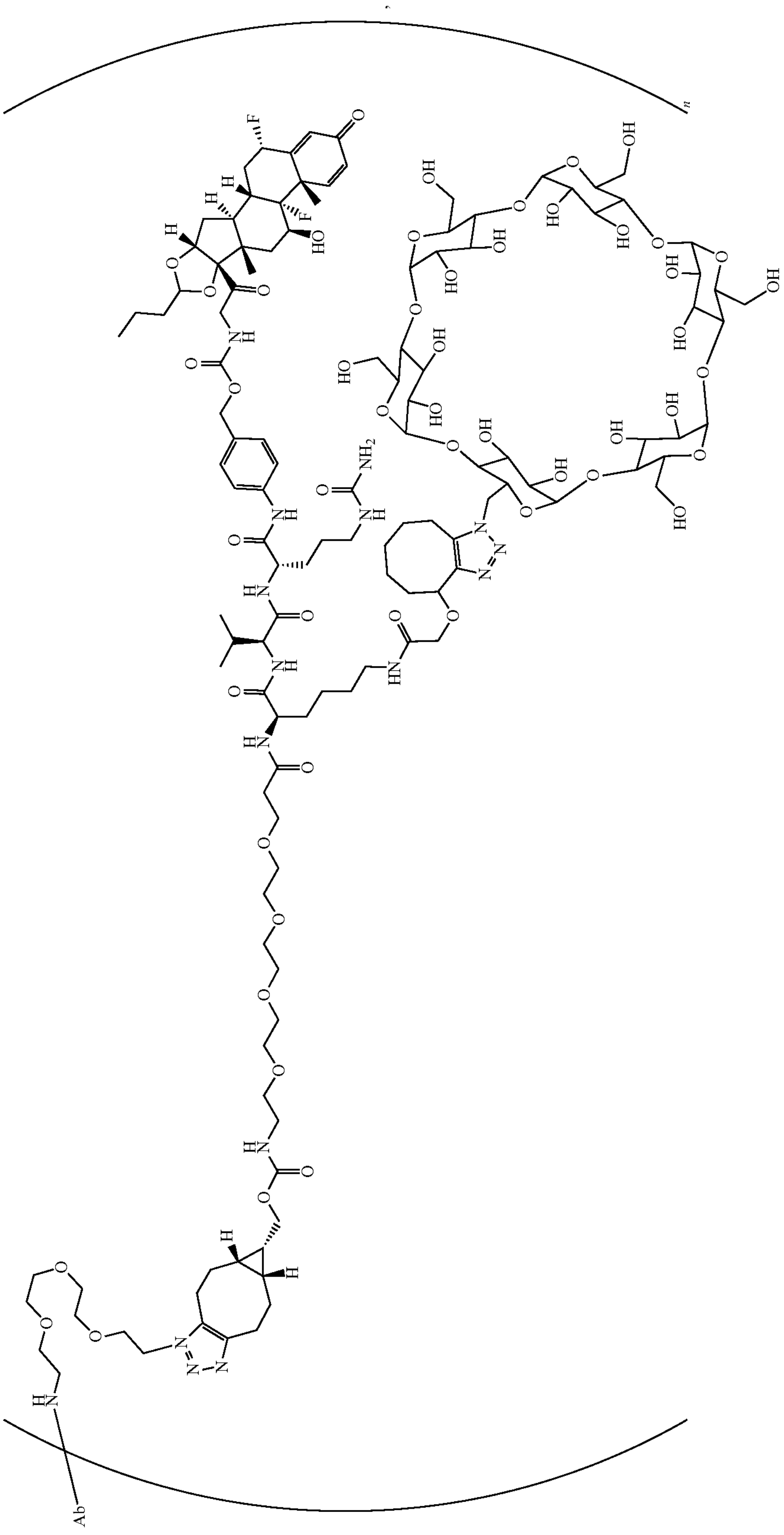

-continued
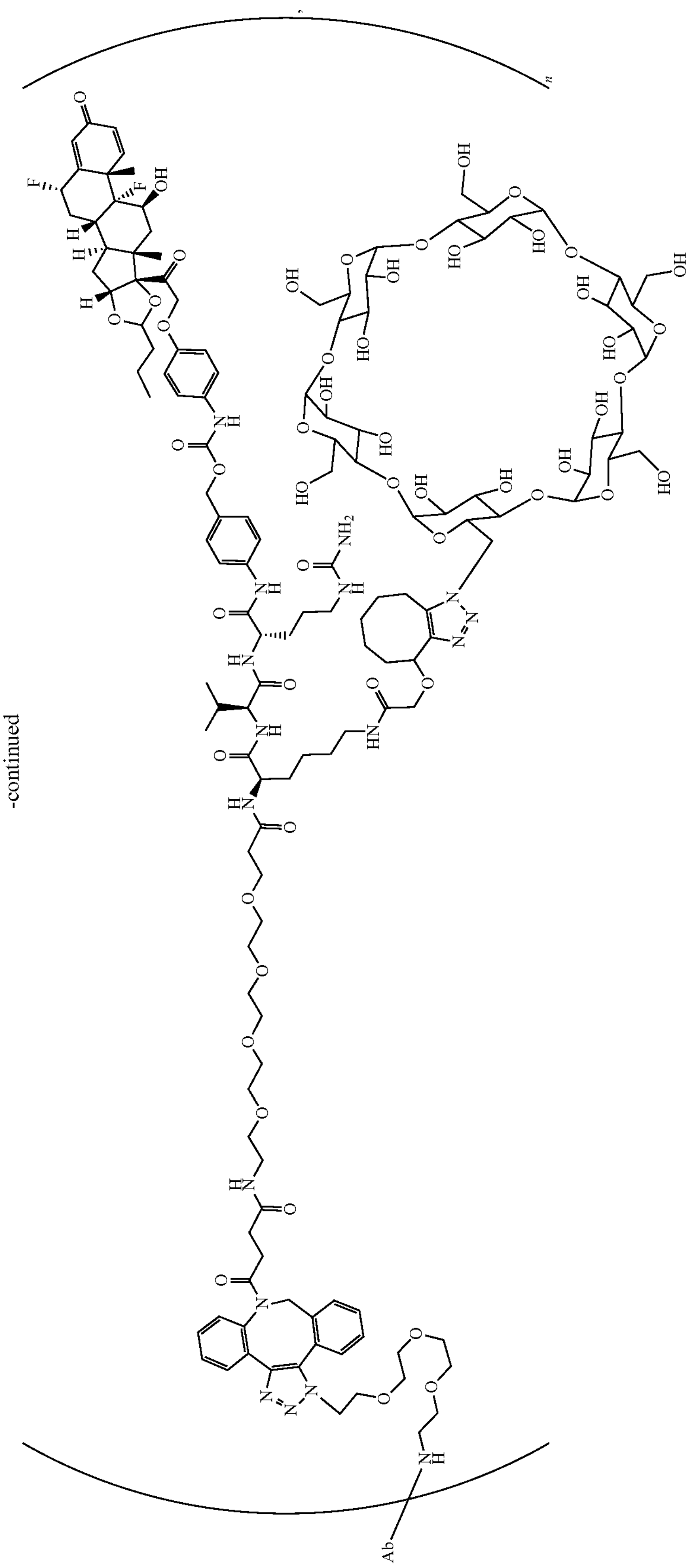

-continued
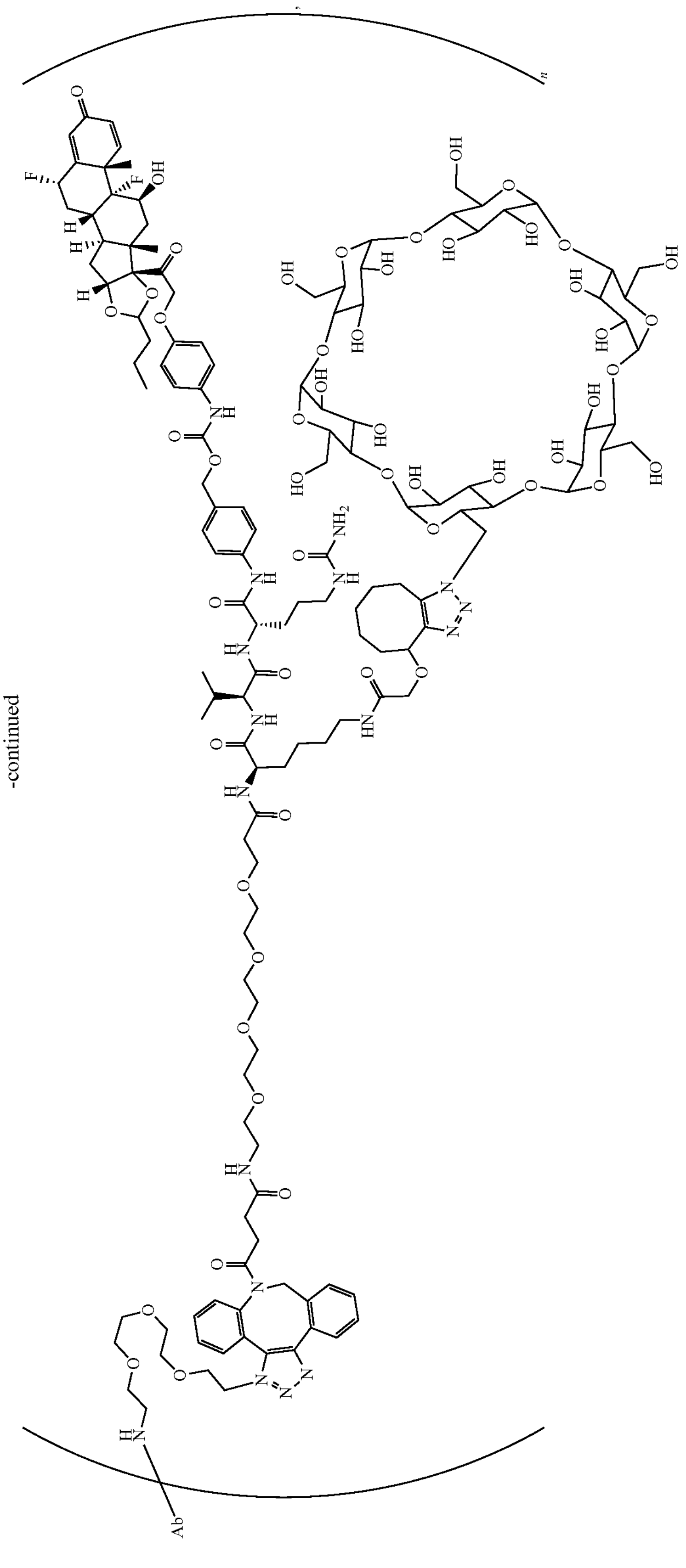

-continued
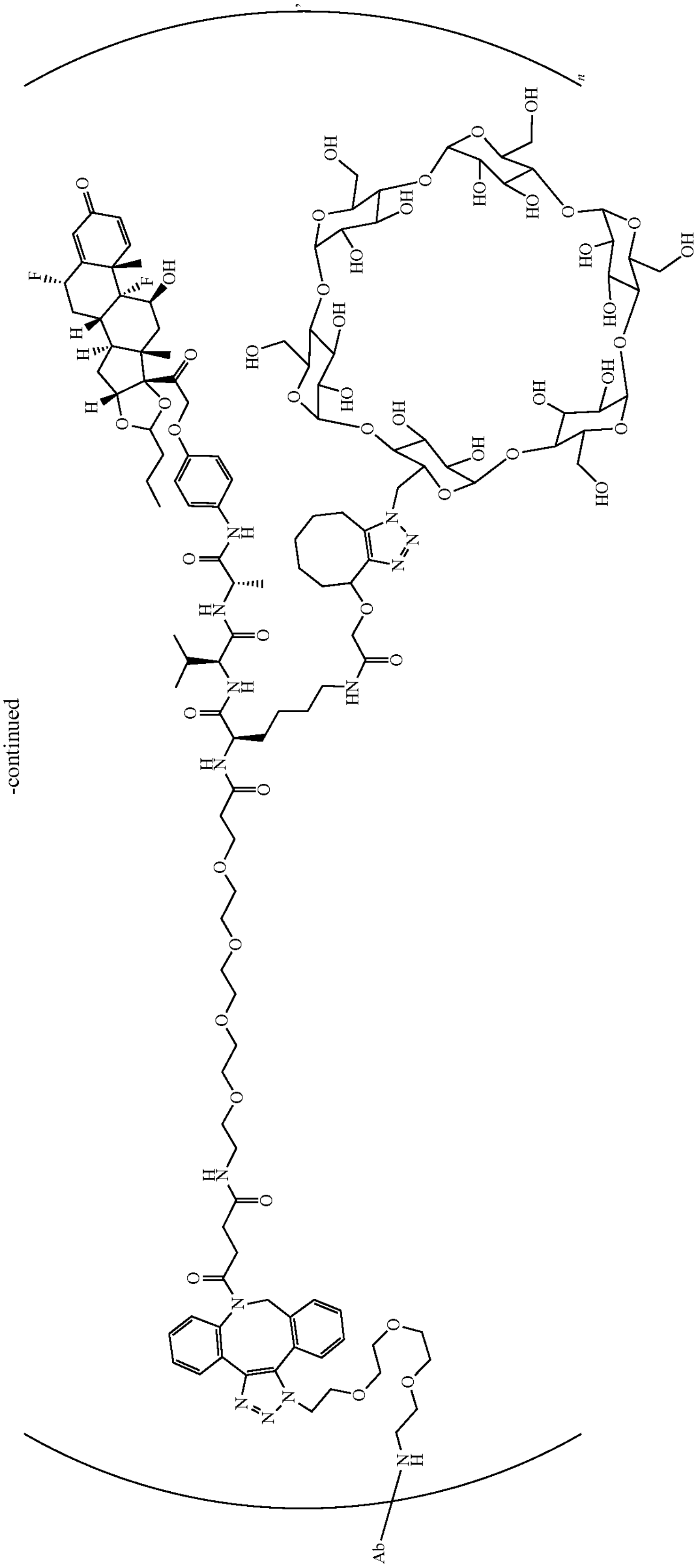
, and

-continued
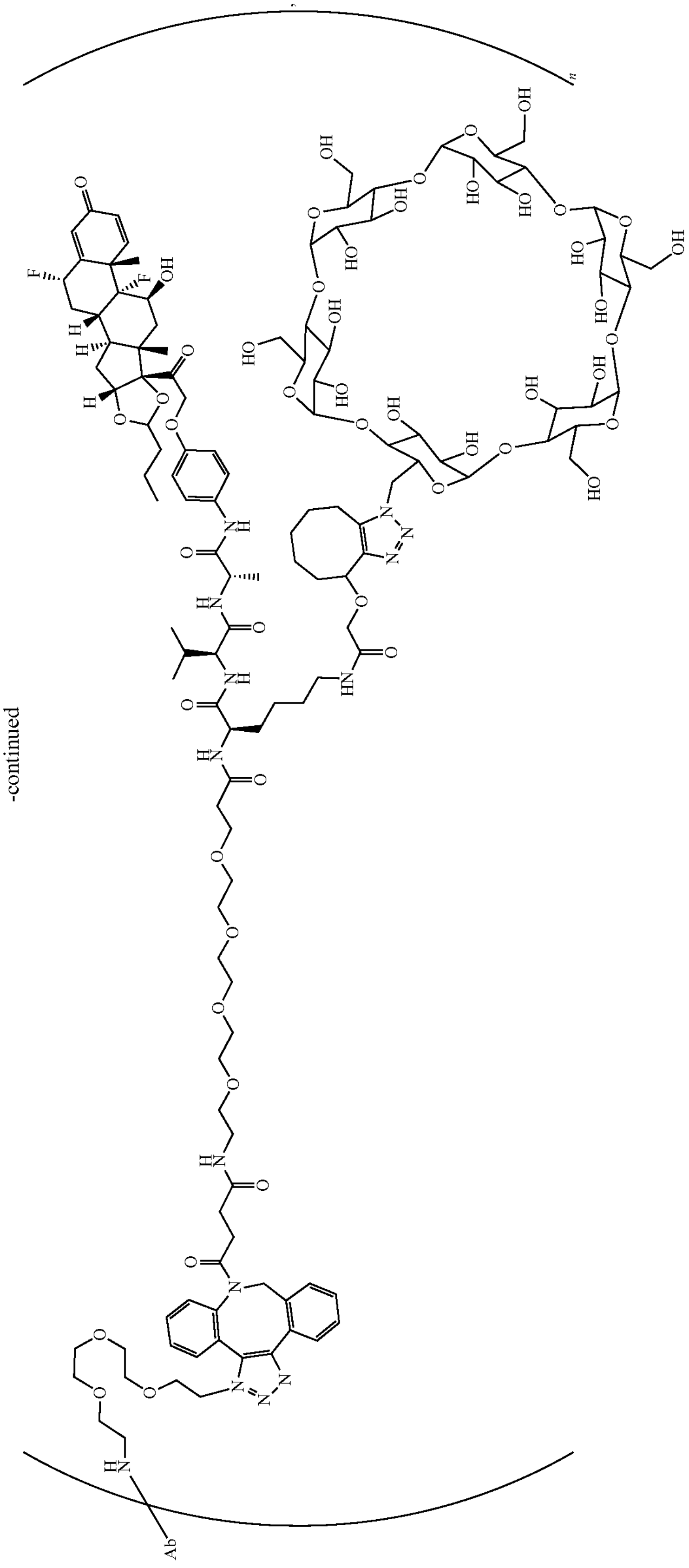

or a stereoisomeric form, or a pharmaceutically acceptable salt thereof, or a regioisomer thereof, or mixture of regioisomers thereof; wherein Ab is an antibody or antigen-binding fragment thereof; and n is an integer from 1 to 30.

39. The method of claim 1, wherein the disease or disorder is a proliferative disorder.

40. The method of claim 1, wherein the disease or disorder is an inflammatory disorder.

41. The method of claim 1, wherein the disease or disorder is a metabolic disease.

* * * * *